(12) United States Patent
Kawada et al.

(10) Patent No.: US 7,101,915 B1
(45) Date of Patent: Sep. 5, 2006

(54) P-TERPHENYL COMPOUNDS

(75) Inventors: Kenji Kawada, Osaka (JP); Mitsuaki Ohtani, Nara (JP); Ryuji Suzuki, Nara (JP); Akinori Arimura, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 09/214,277

(22) PCT Filed: Jul. 30, 1997

(86) PCT No.: PCT/JP97/02635

§ 371 (c)(1),
(2), (4) Date: Mar. 1, 2000

(87) PCT Pub. No.: WO98/04508

PCT Pub. Date: Feb. 5, 1998

(30) Foreign Application Priority Data

| Jul. 31, 1996 | (JP) | .................................. 8-201859 |
| Oct. 30, 1996 | (JP) | .................................. 8-287782 |
| Mar. 18, 1997 | (JP) | .................................. 9-086085 |

(51) Int. Cl.
C07C 43/205 (2006.01)
C07C 43/225 (2006.01)
C07C 43/23 (2006.01)
A61K 31/075 (2006.01)
A61K 31/09 (2006.01)

(52) U.S. Cl. ...................... 514/650; 514/717; 514/721; 568/642; 568/643; 544/224; 544/242; 544/336; 544/182; 546/134; 546/285; 548/215; 548/304.4

(58) Field of Classification Search ................. 568/642; 514/717, 721, 650
See application file for complete search history.

(56) References Cited

U.S. PATENT DOCUMENTS

| 3,624,142 | A |   | 11/1971 | Shen et al. ................. 260/515 |
| 4,495,202 | A |   | 1/1985  | Matsumoto et al. ......... 568/643 |
| 4,594,465 | A | * | 6/1986  | Kam Ming Chan et al. ..... 568/642 |
| 4,728,670 | A |   | 3/1988  | Haslanger et al. ........... 560/160 |
| 5,417,885 | A | * | 5/1995  | Suzuki et al. .......... 252/299.65 |
| 5,487,845 | A | * | 1/1996  | Reiffenrath et al. .... 252/299.63 |
| 5,494,605 | A | * | 2/1996  | Kurihara et al. ............ 568/642 |
| 5,560,864 | A | * | 10/1996 | Goulding ............... 252/299.01 |
| 5,750,051 | A |   | 5/1998  | Goulding et al. ...... 252/299.01 |
| 5,871,665 | A |   | 2/1999  | Coates et al. .......... 252/299.01 |
| 5,968,980 | A |   | 10/1999 | Kawashima et al. .......... 560/34 |

FOREIGN PATENT DOCUMENTS

| EP | 0769299 A1 |   | 4/1997 |
| GB | 2 198 743 A | * | 6/1988 |
| GB | 2 200 912 A | * | 8/1988 |
| GB | 2 240 778 A | * | 8/1991 |
| JP | 4319935 |   | 8/1943 |
| JP | 6013730 |   | 1/1985 |
| JP | 62294650 |   | 12/1987 |
| JP | 525145 |   | 2/1993 |
| JP | 6507987 |   | 9/1994 |
| JP | 8277247 |   | 10/1996 |
| WO | WO-93/22397 A1 | * | 11/1993 |
| WO | WO 9610012 |   | 4/1996 |
| WO | WO 9618606 |   | 6/1996 |

OTHER PUBLICATIONS

West, Anthony R., Solid State Chemistry and its Applications, Wiley, New York, 1988, pp. 358 & 365.*

Akihide, K. :A Prototype Drug for Ice Antibody Synthesis Modulation, Agents and Actions Supplements, 1991, vol. 34, p. 369-378.

Kallitsis, J.K., Synthesis and Characterization of Soluble Aromatic Polyesters Containing Oligophenyl Moieties in the Main Chain., Macromolecules, 1994, vol. 27, p. 4509-4515.

Kakali, F. et al. Synthesis and Characterization of Soluble Aromatic Polyesters Derived from Substituted Terphenyl and Quinquephenyl Diols, J. Polymer Science part A Polymer Chemistry, Jun. 1996, vol. 34, No. 2, p. 1581-1587.

Wagner, Gabriele et al. Ferrocene derivatives containing anthracene linked by spacers, J. Organomet. Chem., Jun. 1996, vol. 516, p. 225-232.

(Continued)

Primary Examiner—Venkataraman Balasubramanian
(74) Attorney, Agent, or Firm—Birch, Stewart, Kolasch & Birch, LLP

(57) ABSTRACT

The present invention provides a selective suppressor of the IgE production comprising a compound which suppresses the IgE production in a process from a differentiation of a mature B cell into an antibody-producing cell to the production of an antibody and which does not suppress or weakly suppresses the production of IgG, IgM and/or IgA which are produced at the same time, a compound of the formula (I):

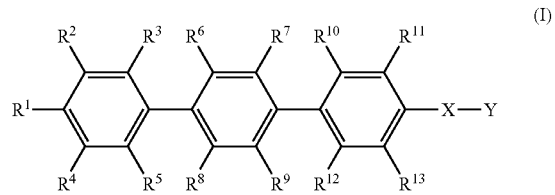

wherein $R^1$–$R^{13}$ are hydrogen, halogen, lower alkyl, lower alkoxy or the like, X is —O—, $CH_2$—, —$NR^{14}$— or —$S(O)_p$— and Y is lower alkyl, lower alkenyl or the like, a process for producing the same and a pharmaceutical composition comprising the same.

27 Claims, 2 Drawing Sheets

OTHER PUBLICATIONS

Akira Suzuki et al., New Synthetic Reactions of Organoboron Compounds By Transition Metal Catalysts (in Japanese) The Journal of Synthetic Organic Chemistry Japan, 1993, vol. 51, No. 11, pp. 91 to 100.

Tringali, C. et al. Previously unreported p-terphenyl derivatives with anti-biotic properties from the fruiting bodies of Sarcodon leucopus (Basidiomycetes)., Can. J. Chem., 1987, vol. 65, p. 2369-2372.

Yanagihara et al., "Suppression of IgE Production by IPD-1151T (Suplatast Tosilate), a New Dimethylsulfonium Ager (2) Regulation of Human IgE Response," Japan J. Pharmacol. (1993), vol. 61, pp. 31-39.

Loh et al., "Disodium Cromoglycate Inhibits Sµ → Sε Deletional Switch Recombination and IgE Synthesis in Human B Cells," J. Exp. Med. (1994), vol. 180, pp. 663-671.

Loh et al. "Mechanisms of inhibition of IgE synthesis by nedocromil sodium: Nedocromil sodium inhibits deletional switch recombination in human B cells," J. Allergy Clin. Immunol. (1996), vol. 97, pp. 1141-1150.

Hasegawa et al. "Novel Naphthalene Derivatives as Inhibitors of Human Immunoglobulin E Antibody Production," J. Med. Chem. (1997), vol. 40, pp. 395-407.

Li et al., "Novel Terphenyl as Selective Cyclooxygenase-2 Inhibitors and Orally Active Anti-inflammatory Agents," J. Med. Chem. (1996), vol. 39, pp. 1846-1856.

Takahashi et al. "The Structures of Toxic Metabolites of *Aspergillus candidus*. 1. The Compounds A and E, Cytotoxic p-Terphenyls," Chem. Pharm. Bulletin (1976), vol. 24, No. 4, pp. 613-620.

Vining et al. "3-Hydroxyterphenyllin, A New Metabolite of *Aspergillus Candidus*," The Journal of Antibiotics (1979), vol. 32, No. 6, pp. 559-564.

Kobayashi et al. "p-Terphenyls with Cytotoxic Activity toward Sea Urchin Embryos," Agric. Biol. Chem. (1985), Vo. 49, No. 3, pp. 867-868.

Brune, K. :A Prototype Drug for Ice Antibody Synthesis Modulation, Agents and Actions Supplements, 1991, vol. 34, p. 369-378.

Kallitsis, J. K., Synthesis and Characterization of Soluble Aromatic Polyesters Containing Oligophenyl Moieties in the Main Chain., Macromolecules, 1994, vol. 27, p. 4509-4515.

Kakali, F. et al. Synthesis and Characterization of Soluble Aromatic Polyesters Derived from Substituted Terphenyl and Quinquephenyl Diols, J. Polymer Science part A Polymer Chemistry, Jun. 1996, vol. 34, No. 2, p. 1581-1587.

Wagner, Gabriele et al. Ferrocene derivatives containing anthracene linked by spacers, J. Organomet. Chem., Jun. 1996, vol. 516, p. 225-232.

Akira Suzuki, Norio Miyaura, Reactions of Organoboron Compounds in the Presence of Transition Metal Catalysts (in Japanese) The Journal of Synthetic Organic Chemistry Japan, 1993, vol. 51, No. 11, pp. 91 to 100.

Tringali, C. et al. Previously unreported p-terphenyl derivatives with anti-biotic properties from the fruiting bodies of Sarcodon leucopus (Basidiomycetes)., Can. J. Chem., 1987, vol. 65, p. 2369-2372.

* cited by examiner

P-TERPHENYL COMPOUNDS

This application is the national phase under 35 U.S.C. §371 of prior PCT International Application No. PCT/JP97/02635 which has an International filing date of Jul. 30, 1997 which designated the United States of America.

TECHNICAL FIELD

The present invention relates to a novel para-terphenyl compound, a process for producing the same, a selective suppressor of the IgE production, an immunosuppressor and an anti-allergic agent.

BACKGROUND ART

A serious problem of a transplantation of a tissue or an organ which is frequently performed in recent years is a rejection symptom for excluding a transplanted part after an operation. Prevention of the rejection symptom is very important for a success of the transplantation.

Various immunosuppressors such as azathioprine, corticoid, Cyclosporin A, Tacrolimus and the like are developed and come into practical use for prevention and a treatment of a rejection symptom against a transplantation of an organ or a tissue or a graft-versus-host reaction which is caused by a bone marrow transplantation. But they are not so satisfactory in view of their effects and side effects.

Allergic diseases such as atopic dermatitis, allergic rhinitis, bronchial asthma, allergic conjunctivitis and the like globally tend to increase in recent years and become serious problems. The conventional antiinflammatory agents are suppressors of releasing chemical mediators from mast cells, receptor inhibitors of the chemical mediators released, suppressors of allergic inflammation reaction or the like. All of these are agents for symptomatic therapy and are not fundamental therapeutic agents for allergic diseases.

As an fundamental therapeutic agent for allergic diseases, a suppressor of the IgE antibody production has been expected.

One of compounds which have a suppressive effect on the IgE production is Suplatast Tosilate (IPD c-1151-T). This is reported to act on T cell of type 2 (Th2 cell) to suppress the IL-4 production and to suppress a differentiation of B cells to IgE antibody-producing cells (Jpn. Pharmacol. (1993) 61, 31–39).

As compounds which directly act on B cells to suppress the IgE antibody production, for example, DSCG (Intal) or Nedcromil sodium which are degranulation inhibitors of mast cells are exemplified. These are reported to inhibit a class-switch of B cells (J. Exp. Med. (1994)180: 663–671, J. Allergy Clin. Immunol.(1996) 97: 1141–1150). In J. Med. Chem. (1997) 40: 395–407, a compound which directly acts on B cells to suppress the IgE production is described.

Because immune globulins are necessary for phylaxis and a suppression of immune globulins other than IgE antibody is not preferable, an inhibitor which has a high selectivity to IgE and a potent effect has been desired.

The compounds which have an antiinflammatory effect and ortho-terphenyl structure are described in JP-A 60-13730, J. Med. Chem.(1996) 39: 1846-1856 and WO96/10012, and the compounds which have the same effect and biphenyl structure are described in JP-B 43-19935, JP-A 62-294650 and WO96/18606.

The compounds which have para-terphenyl structure are described in Chemical & Pharmaceutical Bulletin, 24 (4), 613–620 (1976), The Journal of Antibiotics, 32 (6), 559–564 (1979) and Agricultural Biological Chemistry, 49 (3), 867–868 (1985) but an immunosuppressive or antiinflammatory effect of these compounds is not described at all.

DISCLOSURE OF INVENTION

An object of the present invention is to provide a selective suppressor of the IgE production, an immunosuppressor, and/or an anti-allergic agent which has a potent suppressive effect on the IgE production, an immunosuppressive effect and/or an antiallergic effect. Other object of the present invention is to provide novel compounds which have the above effects and a process for producing the same.

The present invention provides a selective suppressor of the IgE production, an immunosuppressor and/or an anti-allergic agent comprising a compound which suppresses the IgE production in a process from a differentiation of a mature B cell into an antibody-producing cell to the production of an antibody and which does not suppress or weakly suppresses the production of IgG, IgM and/or IgA which are produced at the same time. The present invention provides a method for selectively suppressing the IgE production or for suppressing an immune reaction or a method for treating and/or preventing allergic diseases comprising administering the compound. In another embodiment, the present invention provides use of the compound for the manufacture of a medicament for selectively suppressing the IgE production, suppressing the immune reaction or treating and/or preventing allergic diseases.

The present invention provides a compound of the formula (I) as an example of the compounds which has the above effects:

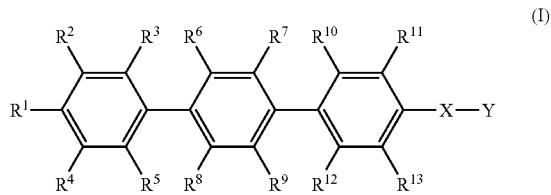

(I)

wherein $R^1$, $R^2$, $R^3$, $R^4$, $R^5$, $R^6$, $R^7$, $R^8$, $R^9$, $R^{10}$, $R^{11}$, $R^{12}$ and $R^{13}$ are each independently hydrogen, hydroxy, halogen, carboxy, optionally substituted lower alkyl, optionally substituted lower alkoxy, optionally substituted lower alkenyl, optionally substituted lower alkenyloxy, optionally substituted lower alkylthio, optionally substituted lower alkoxycarbonyl, optionally substituted acyloxy, optionally substituted lower alkylsulfonyl, optionally substituted lower alkylsulfonyloxy, optionally substituted lower alkylsulfinyl, nitro, cyano, formyl, optionally substituted amino, optionally substituted carbamoyl, optionally substituted sulfamoyl or optionally substituted heterocyclyl, X is —O—, —CH$_2$—, —NR$^{14}$— wherein R$^{14}$ is hydrogen, optionally substituted lower alkyl, optionally substituted lower alkenyl or acetyl, or —S(O)$_p$— wherein p is an integer of 0 to 2, Y is optionally substituted lower alkyl, optionally substituted lower alkenyl, optionally substituted lower alkynyl, optionally substituted acyl, optionally substituted cycloalkyl, optionally substituted cycloalkenyl, optionally substituted aryl or optionally substituted heterocyclyl, and Y may optionally be substituted lower alkoxy when X is —CH$_2$— and may optionally be substituted lower alkoxycarbonyl, optionally substituted lower alkylsulfonyl or optionally substituted arylsulfonyl when X is —O— or —NR$^{14}$—, R$^1$ and R$^4$, R$^1$ and R$^2$, R$^2$ and R$^3$, R$^4$ and R$^5$, R$^6$ and R$^7$, R$^8$ and R$^9$, R$^{10}$ and R$^{11}$ R$^{12}$ and R$^{13}$, R$^{11}$ and —X-Y, or R$^{13}$ and —X-Y taken together may form a 5- or 6-membered ring which may contain one or more of O, S or NR$^{15}$ wherein R$^{15}$ is hydrogen, optionally substituted lower alkyl, optionally substituted lower alkenyl, optionally substituted arylsulfonyl and which may optionally be substituted, excluding compounds wherein one or more of R$^6$, R$^7$, R$^8$ and R$^9$ are halogen and the others are hydrogen, all of R$^6$, R$^7$, R$^8$ and R$^9$ are halogen and all of R$^2$–R$^{13}$ are hydrogen, halogen or cyano, provided that R$^1$ is not hydrogen, fluorine, optionally substituted lower alkyl or optionally substituted lower alkoxy, all of R$^2$, R$^3$, R$^4$, R$^5$ and R$^{12}$ are hydrogen, or R$^{13}$ is not hydrogen or halogen when R$^6$, R$^7$, R$^8$ and R$^9$ are all simultaneously hydrogen, and further provided that R$^1$ is not methyl or acetyloxy, R$^{13}$ is not hydrogen, optionally substituted lower alkoxycarbonyl or optionally substituted carbamoyl, or —X—Y is not methoxy when at least one of R$^6$, R$^7$, R$^8$ and R$^9$ is a substituent other than hydrogen, and excluding a compound of the formula (I'):

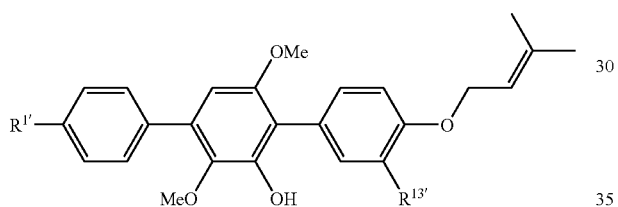

(I')

wherein R$^{1'}$ is hydrogen or hydroxy and R$^{13'}$ is hydroxy or methoxy, pharmaceutically acceptable salt, hydrate or prodrug thereof.

The present invention provides a pharmaceutical composition, more specifically a selective suppressor of the IgE production, an immunosuppressor or an anti-allergic agent, comprising the compound (I), pharmaceutically acceptable salt, hydrate or prodrug thereof.

The present invention provides a selective suppressor of the IgE production, an immunosuppressor and/or an anti-allergic agent comprising a compound of the formula (I"):

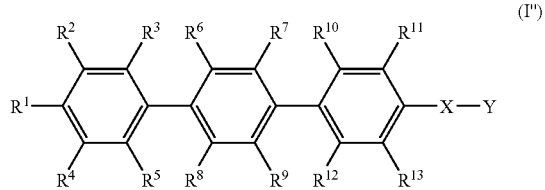

(I")

wherein R$^1$ R$^2$, R$^3$, R$^4$, R$^5$, R$^6$, R$^7$, R$^8$, R$^9$, R$^{10}$, R$^{11}$, R$^{12}$ and R$^{13}$ are each independently hydrogen, hydroxy, halogen, carboxy, optionally substituted lower alkyl, optionally substituted lower alkoxy, optionally substituted lower alkenyl, optionally substituted lower alkenyloxy, optionally substituted lower alkylthio, optionally substituted lower alkoxycarbonyl, optionally substituted acyloxy, optionally substituted lower alkylsulfonyl, optionally substituted lower alkylsulfonyloxy, optionally substituted lower alkylsulfinyl, nitro, cyano, formyl, optionally substituted amino, optionally substituted carbamoyl, optionally substituted sulfamoyl or optionally substituted heterocyclyl, X is —O—, —CH$_2$—, —NR$^{14}$— wherein R$^{14}$ is hydrogen, optionally substituted lower alkyl, optionally substituted lower alkenyl or acetyl, or —S(O)$_p$— wherein p is an integer of 0 to 2, Y is optionally substituted lower alkyl, optionally substituted lower alkenyl, optionally substituted lower alkynyl, optionally substituted acyl, optionally substituted cycloalkyl, optionally substituted cycloalkenyl, optionally substituted aryl or optionally substituted heterocyclyl, and Y may optionally be substituted lower alkoxy when X is —CH$_2$— and may optionally be substituted lower alkoxycarbonyl, optionally substituted lower alkylsulfonyl or optionally substituted arylsulfonyl when X is —O— or —NR$^{14}$—, R$^1$ and R$^4$, R$^1$ and R$^2$, R$^2$ and R$^3$, R$^4$ and R$^5$, R$^6$ and R$^7$, R$^8$ and R$^9$, R$^{10}$ and R$^{11}$, R$^{12}$ and R$^{13}$, R$^{11}$ and —X—Y, or R$^{13}$ and —X—Y taken together may form a 5- or 6-membered ring which may contain one or more of O, S or NR$^{15}$ wherein R$^{15}$ is hydrogen, optionally substituted lower alkyl, optionally substituted lower alkenyl or optionally substituted arylsulfonyl and which may optionally be substituted, excluding a compound of the formula (I'):

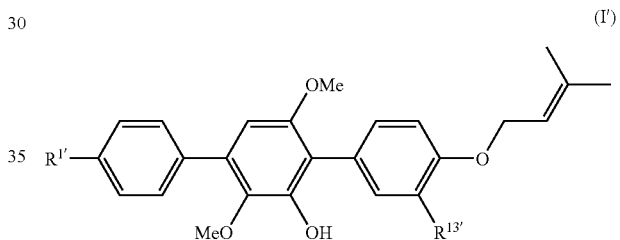

(I')

wherein R$^{1'}$ is hydrogen or hydroxy and R$^{13'}$ is hydroxy or methoxy, pharmaceutically acceptable salt, hydrate or prodrug thereof.

The present invention provides a method for selectively suppressing the IgE production, suppressing an immune reaction or treating or preventing allergic diseases comprising administering the compound (I) or (I"). In another embodiment, the present invention provides use of the compound (I) or (I") for manufacturing of a medicament for selectively suppressing the IgE production, suppressing the immune reaction or treating or preventing allergic diseases.

In one of the other embodiments, the present invention provides a process for producing a compound of the formula (I'''):

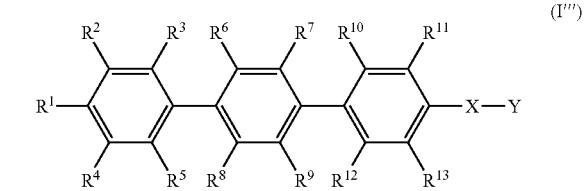

(I''')

the compound of the above formula (I) or (I'), pharmaceutically acceptable salt or hydrate thereof wherein $R^1, R^2, R^3, R^4, R^5, R^6, R^7, R^8, R^9, R^{10}, R^{11}, R^{12}$ and $R^{13}$ are each independently hydrogen, hydroxy, halogen, carboxy, optionally substituted lower alkyl, optionally substituted lower alkoxy, optionally substituted lower alkenyl, optionally substituted lower alkenyloxy, optionally substituted lower alkylthio, optionally substituted lower alkoxycarbonyl, optionally substituted acyloxy, optionally substituted lower alkylsulfonyl, optionally substituted lower alkylsulfonyloxy, optionally substituted lower alkylsulfinyl, nitro, cyano, formyl, optionally substituted amino, optionally substituted carbamoyl, optionally substituted sulfamoyl or optionally substituted heterocyclyl, X is —O—, —CH$_2$—, —NR$^{14}$— wherein R$^{14}$ is hydrogen, optionally substituted lower alkyl, optionally substituted lower alkenyl or acetyl, or —S(O)p— wherein p is an integer of 0 to 2, Y is optionally substituted lower alkyl, optionally substituted lower alkenyl, optionally substituted lower alkynyl, optionally substituted acyl, optionally substituted cycloalkyl, optionally substituted cycloalkenyl, optionally substituted aryl or optionally substituted heterocyclyl, and Y may optionally be substituted lower alkoxy when X is —CH$_2$— and may optionally be substituted lower alkoxycarbonyl, optionally substituted lower alkylsulfonyl or optionally substituted arylsulfonyl when X is —O— or —NR$^{14}$—, $R^1$ and $R^4$, $R^1$ and $R^2$, $R^2$ and $R^3$, $R^4$ and $R^5$, $R^6$ and $R^7$, $R^8$ and $R^9$, $R^{10}$ and $R^{11}$, $R^{12}$ and $R^{13}$, $R^{11}$ and —X—Y, or $R^{13}$ and —X—Y taken together may form a 5- or 6-membered ring which may contain one or more of O, S or NR$^{15}$ wherein R$^{15}$ is hydrogen, optionally substituted lower alkyl, optionally substituted lower alkenyl, optionally substituted arylsulfonyl, and which may optionally be substituted, excluding a compound wherein one or more of $R^6$, $R^7$, $R^8$ and $R^9$ are halogen and the others are hydrogen, all of $R^6$, $R^7$, $R^8$ and $R^9$ are halogen and all of $R^2$–$R^{13}$ are hydrogen, halogen or cyano, provided that $R^1$ is not hydrogen, fluorine, optionally substituted lower alkyl or optionally substituted lower alkoxy, all of $R^2$, $R^3$, $R^4$, $R^5$ and $R^{12}$ are hydrogen or $R^{13}$ is not hydrogen or halogen when $R^6$, $R^7$, $R^8$ and $R^9$ are all simultaneously hydrogen, and further provided that $R^1$ is not methyl or acetyloxy, $R^{13}$ is not hydrogen, optionally substituted lower alkoxycarbonyl or optionally substituted carbamoyl or —X—Y is not methoxy when at least one of $R^6$, $R^7$, $R^8$ and $R^9$ is a substituent other than hydrogen, pharmaceutically acceptable salt or hydrate thereof, which comprises reacting a compound of the formula (II):

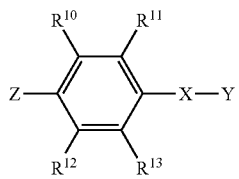

(II)

with a compound of the formula (III):

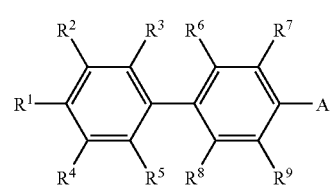

(III)

wherein, in the formulas (II) and (III), $R^1$–$R^{13}$, X and Y are the same as defined in the above formula (I), either of A and Z is dihydroxyborane, di(lower)alkoxyborane, di(lower)alkylborane,

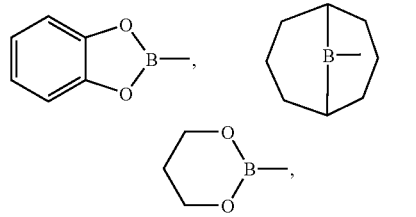

or

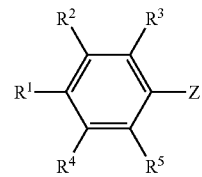

and the other is halogen or —OSO$^2$(C$_q$F$_{2q+1}$)—wherein q is an integer of 0 to 4, or reacting a compound of the formula (II'):

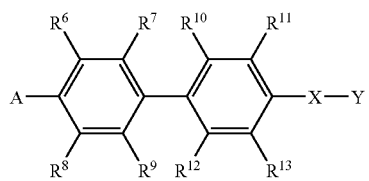

(II')

with a compound of the formula (III'):

(III')

wherein, in the formulas (II') and (III'), $R^1$–$R^{13}$, X and Y are the same as defined in the above formula (I) and A and Z are the same as defined in the above formulas (II) and (III). As another process, the present invention provides a process for producing the compound of the above formula (I'''), (I) or (I'), pharmaceutically acceptable salt or hydrate thereof comprising the reaction of a compound of the formula (IV):

(IV)

with a compound of the formula (V):

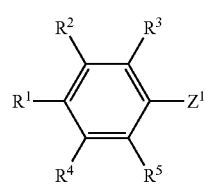

(V)

wherein, in the formulas (IV) and (V), $R^1$–$R^9$ are the same as defined in the above formula (I), $Z^1$ is the same as Z defined in the above formula (II), $A^1$ and $A^2$ are each independently the same as A defined in the above formula (III) and the reactivity of $A^1$ is higher than or equal to that of $A^2$, followed by the reaction with a compound of the formula (VI):

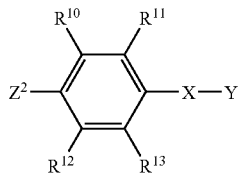

(VI)

wherein $R^{10}$–$R^{13}$, X and Y are the same as defined in the above formula (I) and $Z^2$ is the same as Z defined in the above formula (II) and a process for producing the compound of the above formula (I'''), (I) or (I'), pharmaceutically acceptable salt, hydrate thereof comprising the reaction of a compound of the formula (IV'):

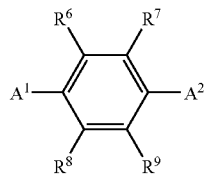

(IV')

wherein $R^6$–$R^9$ is the same as defined in the above formula (I), $A^1$ and $A^2$ are each independently the same as A defined in the above formula (III) and the reactivity of $A^2$ is higher than or equal to that of $A^1$,
with a compound of the above formula (VI), followed by the reaction with a compound of the above formula (V).

BEST MODE FOR CARRYING OUT THE INVENTION

Figure 1:
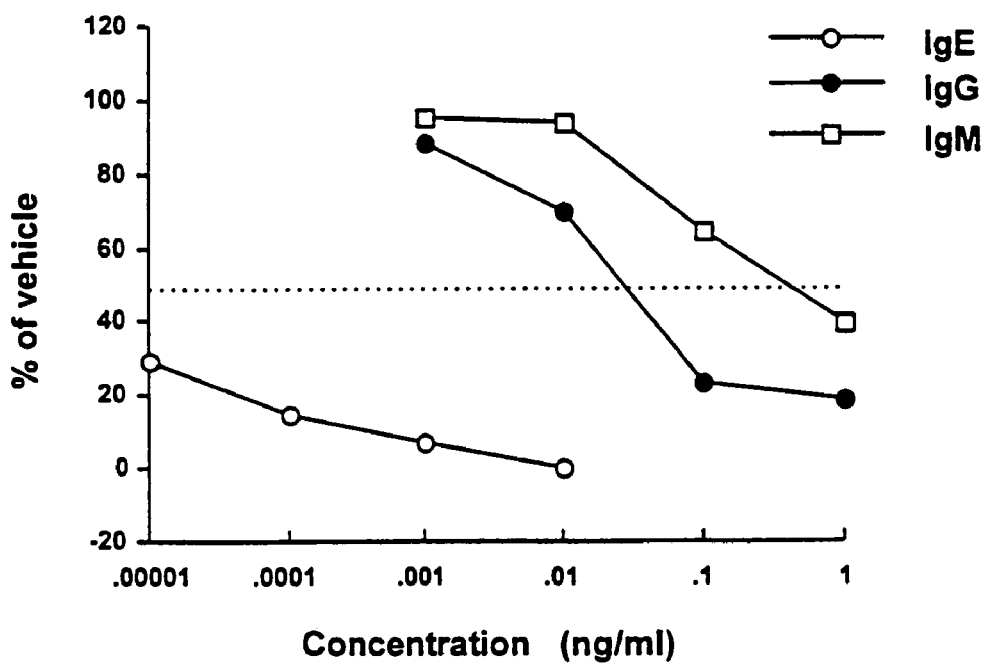
FIG. 1 shows an antibody production-suppressive effect on human peripheral lymphocytes of the compound (I-839) of the present invention. The ordinate represents a percentage of the amount of antibodies to that of antibodies which are produced in the absence of the compound. The abscissa represents a concentration of the compound.

In the present specification, the term "halogen" includes fluorine, chlorine, bromine and iodine. Fluorine or chlorine is preferable. The halogen in the term "halogeno(lower)alkyl", "halogeno(lower)alkenyl" and "halogenoaryl" is the same as above.

The term "lower alkyl" represents straight or branched chain alkyl having 1 to 10 carbon atoms, preferably 1 to 8 carbon atoms, more preferably 1 to 6 carbon atoms and most preferably 1 to 4 carbon atoms. For example, included are methyl, ethyl, n-propyl, isopropyl, n-butyl, isobutyl, sec-butyl, tert-butyl, n-pentyl, isopentyl, neopentyl, hexyl, isohexyl, n-heptyl, isoheptyl, n-octyl, isooctyl, n-nonyl, n-decyl and the like.

As substituents of the "optionally substituted lower alkyl" in $R^1$–$R^{13}$, $R^{14}$ and $R^{15}$ exemplified are halogen; hydroxy; lower alkoxy optionally substituted with lower alkoxy; carboxy; lower alkoxycarbonyl; acyloxy and the like and the lower alkyl may be substituted with one or more of these substituents at any possible positions.

As substituents for "optionally substituted lower alkyl" in Y exemplified are halogen; hydroxy; carboxy; lower alkoxycarbonyl; lower alkoxy optionally substituted with lower alkoxy; acyl; acyloxy; amino optionally substituted with hydroxy or lower alkyl; imino optionally substituted with hydroxy, lower alkoxy, carboxy(lower)alkoxy, aryl(lower)alkoxy or heterocyclyl; hydrazono optionally substituted with carbamoyl or lower alkoxycarbonyl; cycloalkyl optionally substituted with lower alkyl; cycloalkenyl optionally substituted with lower alkyl; cyano; carbamoyl optionally substituted with lower alkyl or amino; thiocarbamoyl optionally substituted with lower alkyl;

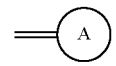

wherein ring A represents cycloalkyl or heterocyclyl; aryl optionally substituted with lower alkyl, halogeno(lower)alkyl, carboxy(lower)alkyl, lower alkoxycarbonyl(lower)alkyl, halogen, hydroxy, lower alkoxy, carboxy, lower alkoxycarbonyl, lower alkenyloxycarbonyl, acyloxy, nitro, cyano, amino, lower alkoxycarbonylamino, acylamino, lower alkylsulfonylamino, lower alkylamino or guanidino; or heterocyclyl optionally substituted with lower alkyl (optionally substituted with heterocyclyl), halogen, hydroxy, carboxy, lower alkoxycarbonyl, lower alkylsulfonyl, lower alkylarylsulfonyl, mercapto, lower alkylthio or heterocyclyl optionally substituted with aryl.

The alkyl part of "halogeno(lower)alkyl", "hydroxy(lower)alkyl", "carboxy(lower)alkyl", "lower alkoxycarbonyl(lower)alkyl", "lower alkylthio", "lower alkylamino", "lower alkylsulfonyl", "lower alkylsulfonyloxy", "lower alkylsulfonylamino", "lower alkylsulfinyl", "lower alkylaryl", "lower alkylarylsulfonyl", "di(lower)alkylcarbamoyl", "di(lower)alkylborane, "lower alkoxy", "carboxy(lower)alkoxy", "aryl(lower)alkoxy", "lower alkoxy(lower)alkoxy", "lower alkoxyaryl" or "di(lower)alkoxyborane" is the same as defined in the above "lower alkyl". As substituents in the case of being "optionally substituted" exemplified are halogen; hydroxy; lower alkoxy; carboxy; lower alkoxycarbonyl; acyloxy; cycloalkyl; aryl optionally substituted with lower alkyl; heterocyclyl and the like. These substituents may substitute at one or more of any possible positions.

The part of lower alkyl in "lower alkoxycarbonyl" is the same as the above defined "lower alkyl" and substituents for "optionally substituted lower alkoxycarbonyl" are the same as those for the above "optionally substituted lower alkoxy".

The part of "lower alkoxycarbonyl" in "lower alkoxycarbonyl(lower)alkyl", "lower alkoxycarbonyl(lower)alkenyl" or "lower alkoxycarbonylamino" is the same as the above defined "lower alkoxycarbonyl".

The term "lower alkenyl" represents straight or branched chain alkenyl having 2 to 10 carbon atoms, preferably 2 to 8 carbon atoms and more preferably 3 to 6 carbon atoms. For example, included are vinyl, propenyl, isopropenyl, butenyl, isobutenyl, butadienyl, pentenyl, isopentenyl, pentadienyl, hexenyl, isohexenyl, hexadienyl, heptenyl, octenyl, nonenyl, decenyl and the like and these have one or more double bonds at any possible positions. Substituents for "optionally substituted lower alkenyl" are the same as that for the above "optionally substituted lower alkoxy".

The part of lower alkenyl in "lower alkoxycarbonyl (lower)alkenyl", "halogeno(lower)alkenyl", "lower alkenyloxy", "lower alkenyloxycarbonyl" or "lower alkenylamino" is the same as the above defined "lower alkenyl".

Substituents for "optionally substituted lower alkenyloxy" are the same as those for the above "optionally substituted lower alkoxy".

The term "lower alkynyl" represents straight or branched chain alkynyl having 2 to 10 carbon atoms, preferably 2 to 8 carbon atoms and more preferably 3 to 8 carbon atoms. Specifically, included are ethynyl, propynyl, butynyl, pentynyl, hexynyl, heptynyl, octynyl, nonyl, decynyl and the like. These have one or more triple bonds at any possible positions and may further have a double bond. Substituents for "optionally substituted lower alkynyl" are the same as those for the above "optionally substituted lower alkoxy".

The term "acyl" represents aliphatic acyl which includes chain acyl having 1 to 10 carbon atoms, preferably 1 to 8 carbon atoms, more preferably 1 to 6 carbon atoms, most preferably 1 to 4 carbon atoms and cyclic acyl having 3 to 8 carbon atoms, preferably 3 to 6 carbon atoms, and aroyl. Specifically, included are formyl, acetyl, propionyl, butyryl, isobutyryl, valeryl, pivaloyl, hexanoyl, acryloyl, propioloyl, methacryloyl, crotonoyl, cyclohexanecarbonyl, benzoyl and the like. Substituents for "optionally substituted acyl" are the same as those for "optionally substituted lower alkoxy" and aroyl may further be substituted with lower alkyl.

The part of acyl in "acyloxy" or "acylamino" is the same as the above identified "acyl" and substituents for "optionally substituted acyloxy" are the same as those for the above "optionally substituted acyl".

The term "cycloalkyl" represent cyclic hydrocarbon having 3 to 6 carbon atoms and includes, for example, cyclopropyl, cyclobutyl, cyclopentyl cyclohexyl and the like. As substituents for "optionally substituted cycloalkyl" exemplified are lower alkyl, halogen, hydroxy, carboxy, lower alkoxycarbonyl, lower alkoxy, aryl, heterocyclyl and the like and the cycloalkyl may be substituted at any possible positions.

The term "cycloalkenyl" represents the group having one or more double bonds at any possible positions in the above cycloalkyl and included are, for example, cyclopropenyl, cyclobutenyl, cyclopentenyl, cyclohexenyl, cyclohexadienyl and the like. Substituents for "optionally substituted cycloalkenyl" are the same as those for the above identified "cycloalkyl".

The term "optionally substituted amino" includes substituted amino and unsubstituted amino and substituents exemplified are lower alkyl optionally substituted with lower alkylaryl etc.; lower alkenyl optionally substituted with halogen; lower alkylsulfonyl; lower alkylarylsulfonyl; lower alkoxycarbonyl; sulfamoyl; acyl optionally substituted with halogen; carbamoyl and the like.

The term "optionally substituted carbamoyl" includes substituted carbamoyl and unsubstituted carbamoyl and substituents exemplified are lower alkyl; lower alkylsulfonyl; sulfamoyl; acyl optionally substituted with halogen; amino and the like.

The term "optionally substituted sulfamoyl" includes substituted sulfamoyl and unsubstituted sulfamoyl and substituents exemplified are lower alkyl optionally substituted with aryl; lower alkenyl and the like.

The term "aryl" includes phenyl, naphthyl, anthryl, indenyl, phenanthryl and the like. Substituents for "optionally substituted aryl" exemplified are lower alkyl optionally substituted with halogen or carboxy; hydroxy; halogen; lower alkoxy; lower acyloxy; carboxy; lower alkoxycarbonyl; lower alkenyloxycarbonyl; amino optionally substituted with lower alkyl, lower alkylsulfonyl, lower alkoxycarbonyl or acyl; guanidino; nitro; aryl; heterocyclyl and the like and "optionally substituted aryl" may be substituted with one or more of these substituents at any possible positions.

The part of aryl in "lower alkylaryl", "halogenoaryl", "lower alkoxyaryl", "arylsulfonyl", "aryl(lower)alkoxy", "lower alkylarylsulfonyl", "heterocyclyl substituted with aryl", "aroyl" or "aroyloxy" is the same as the above "aryl" and the substituents for "optionally substituted" are also the same as those for in the above "optionally substituted aryl".

The term "heterocyclyl" represents a heterocyclic group which contains one or more of hetero atoms arbitrarily selected from a group of O, S and N and exemplified are 5- or 6- membered aromatic heterocyclyl such as pyrrolyl, imidazolyl, pyrazolyl, pyridyl, pyridazinyl, pyrimidinyl, pyrazinyl, triazolyl, triazinyl, isoxazolyl, oxazolyl, oxadiazolyl, isothiazolyl, thiazolyl, thiazolyl, furyl, thienyl etc., condensed aromatic heterocyclyl such as indolyl, carbazolyl, acridinyl, benzimidazolyl, indazolyl, indolizinyl, quinolyl, isoquinolyl, cinnolinyl, phthalazinyl, quinazolinyl, naphthyridinyl, quinoxalinyl, purinyl, pteridinyl, benzisoxazolyl, benzoxazolyl, benzoxadiazolyl, benzisothiazolyl, benzothiazolyl, benzothiaziazolyl, benzofuryl, benzothienyl, benzotriazolyl etc., and alicyclic heterocyclyl such as dioxanyl, thiiranyl, oxiranyl, oxathioranyl, azetidinyl, thianyl, pyrrolidinyl, pyrrolinyl, imidazolidinyl, imidazolinyl, pyrazolidinyl, pyrazolinyl, piperidyl, piperazinyl, morpholinyl etc. As substituents for "optionally substituted heterocyclyl" exemplified are lower alkyl, lower alkenyl, hydroxy, halogen, carboxy, lower alkoxycarbonyl, lower alkoxy, mercapto, lower alkylthio, lower alkylsulfonyl, aryl, heterocyclyl and the like and the heterocyclyl may be substituted with one or more of these substituents at any possible positions. The part of heterocycle in "heterocyclyl substituted with aryl" is the same as the above "heterocyclyl".

The term "5- or 6-membered ring which may contain one or more of O, S or $NR^{15}$ and may optionally be substituted" represents a 5- or 6-membered ring which is formed by $R^1$ and $R^4$, $R^1$ and $R^2$, $R^2$ and $R^3$, $R^4$ and $R^5$, $R^6$ and $R^7$, $R^8$ and $R^9$, $R^{10}$ and $R^{11}$, $R^{12}$ and $R^{13}$, $R^{11}$ and —X—Y, or $R^{13}$ and —X—Y with the two carbon atoms constituting phenyl to which the above substituents are attached. For example, the above substituents taken together form —$(CH_2)_3$—, —$(CH_2)_4$—, —$O(CH_2)_mO$—, —$O(CH_2)_n$—, —$(CH_2)_nO$—, —$S(CH_2)_mS$—, —$S(CH_2)_n$—, —$(CH_2)_nS$—, —$NR^{15}$ $(CH_2)_mNR^{15}$—, —$NR^{15}(CH_2)_n$—, —$(CH_2)_nNR^{15}$, —O $(CH_2)_mS$—, —$S(CH_2)_mO$—, —$S(CH_2)_mS$—, —$O(CH_2)_m$ $NR^{15}$—, —$NR^{15}(CH_2)_mO$—, —$S(CH_2)_mNR^{15}$—, —$NR^{15}$ $(CH_2)_n$—, —$NR^{15}$—CH=CH—, —CH=CH—$NR^{15}$—, —S—CH=N—, —N=CH—S—, —S—N=CH—, —CH═N—S—, —N═CH—O—, —O—N═CH—, —CH═N—O—, —NR$^{15}$—CH═N—, —N═CH—NR$^{15}$—, —NR$^{15}$—N═CH—, CH═N—NR$^{15}$—, —N═CH—, —CH═N—NR$^{15}$—, —N═CH—CH═CH—, —CH═CH—CH═N—, —N═N—CH═CH—, —CH═CH—N═N—, —N═CH═N—CH═N—CH—, —CH═N—CH═N—(m is 1 or 2 and n is 2 or 3) or the like and further these and the two carbon atoms constituting phenyl taken together form a 5- or 6- membered ring. These rings may be substituted with one or more of hydroxy; halogen; lower alkyl optionally substituted with lower alkoxycarbonyl or heterocyclyl; lower alkenyl optionally substituted with halogen; lower alkyliden optionally substituted with halogen; or the like. The substituents of "5- or 6-membered ring which may contain one or more of O or NR$^{15}$ and may optionally be substituted", "5- or 6- membered ring which contains one or more of O or NR$^{15}$ and may optionally be substituted" and "5- or 6- membered ring which contains one or more of O and may optionally be substituted" are the same as the above unless otherwise defined.

The term "lower alkylidene" represents straight or branched alkylidene having 1 to 6 carbon atoms, preferably 1 to 4 carbon atoms, more preferably 1 to 3 carbon atoms and includes, for example, methylene, ethylidene, isopropylidene, vinylidene, methylidyne and the like.

The term "all of R$^2$–R$^{13}$ are hydrogen, halogen or cyano" represents, for example, the case that R$^2$–R$^{13}$ are the same or different and hydrogen, halogen or cyano. For example, included are the case that all of R$^2$–R$^{13}$ are hydrogen, the case that all of them are halogen, the case that some are halogen and the others are hydrogen, the case that some are cyano and the others are hydrogen, the case that some are halogen, some are cyano and the others are hydrogen and the like.

The term "compound (I)", "compound (I")" or "compound (I'")" also includes formable and pharmaceutically acceptable salts of each compounds. As "the pharmaceutically acceptable salt", exemplified are salts with mineral acid such as hydrochloric acid, sulfuric acid, nitric acid, phosphoric acid, hydrofluoric acid, hydrobromic acid and the like; salts with organic acids such as formic acid, acetic acid, tartaric acid, lactic acid, citric acid, fumaric acid, maleic acid, succinic acid and the like; salts with organic bases such as ammonium, trimethylammonium, triethylammonium and the like; salts with alkaline metals such as sodium, potassium and the like and salts with alkaline earth metals such as calcium, magnesium and the like.

The compound of the present invention includes hydrates and all of stereoisomers, for example, atropisomers etc. thereof.

The compound of the present invention includes prodrugs thereof. The term "prodrug" means a group of compounds which are easily changeable to the compounds (I) or (I") which have activities in living bodies. The prodrug may be prepared by usual reactions. As usual methods for producing prodrugs exemplified is the substitution of hydroxy by acyloxy substituted with carboxy, sulfo, amino, lower alkylamino or the like, phosphonoxy or the like. The substitution of hydroxy attached to R$^1$ by —OCOCH$_2$CH$_2$COOH, —OCOCH═CHCOOH, —OCOCH$_2$SO$_3$H, —OPO$_3$H$_2$, —OCOCH$_2$NMe$_2$, —OCO-Pyr (Pyr is pyridine) or the like is preferable.

In the present specification, the term "compound (I)" represents a group comprising novel compounds excluding the compound (I'), the term "compound (I")" represents a group comprising the compound (I) and known compounds and the term "compound (I'")" represents a group comprising the compound (I) and the compound (I').

All of the compounds (I) and (I") have a suppressive effect on the IgE production, an immunosuppressive effect and/or an anti-allergic effect and the following compounds are specifically preferable.

In the formulas (I) and (I"),
1) a compound wherein R$^1$, R$^2$, R$^3$, R$^4$, R$^5$, R$^6$, R$^7$, R$^8$, R$^9$, R$^{10}$, R$^{11}$, R$^{12}$ and R$^{13}$ are each independently hydrogen, hydroxy, halogen, carboxy, optionally substituted lower alkyl, optionally substituted lower alkoxy, optionally substituted lower alkenyl, optionally substituted lower alkenyloxy, optionally substituted lower alkylthio, optionally substituted lower alkoxycarbonyl, optionally substituted acyloxy, optionally substituted lower alkylsulfonyloxy, formyl, optionally substituted amino, optionally substituted carbamoyl or optionally substituted sulfamoyl, X is —O—, —CH$_2$—, —NR$^{14}$— wherein R$^{14}$ is hydrogen or optionally substituted lower alkyl, or —S(O)$_p$— wherein p is an integer of 0 to 2, Y is optionally substituted lower alkyl, optionally substituted lower alkenyl, optionally substituted lower alkynyl, optionally substituted acyl or optionally substituted cycloalkenyl, and R$^1$ and R$^4$, R$^1$ and R$^2$, R$^8$ and R$^9$, R$^{11}$ and —X—Y, or R$^{13}$ and —X—Y taken together may form a 5- or 6-membered ring which may contain one or more of O or NR$^{15}$, 2) a compound wherein R$^1$ is hydrogen, hydroxy, halogen, carboxy, optionally substituted lower alkyl, optionally substituted lower alkoxy, optionally substituted lower alkenyloxy, optionally substituted lower alkylthio, optionally substituted lower alkoxycarbonyl, optionally substituted lower alkylsulfonyloxy, lower alkylsulfonyl, formyl, optionally substituted amino, lower alkylsulfinyl, acyloxy, nitro, cyano, optionally substituted sulfamoyl or heterocyclyl, R$^2$ is hydrogen, hydroxy, halogen, optionally substituted lower alkyl or optionally substituted lower alkylsulfonyloxy, R$^3$ is hydrogen, hydroxy, halogen or optionally substituted lower alkoxy, R$^4$ is hydrogen, optionally substituted lower alkyl, halogen, optionally substituted lower alkoxy, nitro or optionally substituted amino, R$^5$ is hydrogen, optionally substituted lower alkoxy, lower alkoxycarbonyl or carboxy, R$^6$ is hydrogen, halogen, optionally substituted lower alkyl, carboxy, lower alkoxycarbonyl, nitro, formyl, amino or lower alkylsulfonyloxy, R$^7$ and R$^8$ are each independently hydrogen, halogen, optionally substituted lower alkyl, optionally substituted lower alkoxy, formyl or optionally substituted amino, R$^9$ is hydrogen, hydroxy, carboxy, optionally substituted lower alkyl, optionally substituted lower alkoxy, optionally substituted lower alkenyl, optionally substituted lower alkoxycarbonyl, optionally substituted lower alkylsulfonyloxy, formyl, optionally substituted carbamoyl or optionally substituted amino, R$^{10}$ is hydrogen or lower alkoxy, R$^{11}$ is hydrogen, halogen, optionally substituted lower alkyl, carboxy, lower alkoxycarbonyl, optionally substituted lower alkylsulfonyloxy, formyl, nitro or amino, R$^{12}$ is hydrogen, R$^{13}$ is hydroxy, halogen, carboxy, optionally substituted lower alkyl, optionally substituted lower alkoxy, optionally substituted lower alkenyloxy, optionally substituted acyloxy, optionally substituted lower alkylsulfonyloxy, formyl, nitro or optionally substituted amino, and further R$^{13}$ may be hydrogen in the formula (I"), Y is optionally substituted lower alkyl, optionally substituted lower alkenyl, optionally substituted lower alkynyl, optionally substituted acyl or optionally substituted cycloalkenyl and Y may be optionally substituted lower alkoxycarbonyl, optionally substituted lower alkylsulfonyl or optionally substituted arylsulfonyl when X is —O— or —NR$^{14}$—, and $R^1$ and $R^2$, $R^1$ and $R^4$, $R^8$ and $R^9$, $R^{11}$ and —X—Y, or $R^{13}$ and —X—Y taken together may form a 5- or 6-membered ring which contains one or more of O or $NR^{15}$ wherein $R^{15}$ is the same as defined above and which may optionally be substituted, 3) a compound wherein $R^1$ is hydrogen, hydroxy, halogen, carboxy, optionally substituted lower alkyl, optionally substituted lower alkoxy, optionally substituted lower alkenyloxy, optionally substituted lower alkylthio, optionally substituted lower alkoxycarbonyl, optionally substituted lower alkylsulfonyloxy, lower alkylsulfonyl, formyl, optionally substituted amino, lower alkylsulfinyl, acyloxy, nitro, cyano, optionally substituted sulfamoyl or heterocyclyl (hereinafter referred to as "$R^1$ is R1-1") or $R^1$ and $R^2$ or $R^4$ taken together form a 5- or 6-membered ring which contains one or more of O or $NR^{15}$ wherein $R^{15}$ is the same as defined above and which may optionally be substituted, preferably $R^1$ is hydrogen, hydroxy, halogen, optionally substituted lower alkoxy, optionally substituted lower alkenyloxy, optionally substituted lower alkylsulfonyloxy, optionally substituted amino, optionally substituted sulfamoyl (hereinafter referred to as "$R^1$ is R1-2"), or $R^1$ and $R^2$ or $R^4$ taken together form a 5- or 6-membered ring which contains one or more of O or $NR^{15}$ wherein $R^{15}$ is the same as defined above and which may optionally be substituted, more preferably, $R^1$ is hydrogen, hydroxy, halogen, lower alkoxy(lower)alkoxy, aryl(lower)alkoxy, lower alkenyloxy, lower alkylsulfonyloxy, amino, lower alkylamino or lower alkenylamino (hereinafter referred to as "$R^1$ is R1-3"), or $R^1$ and $R^2$ or $R^4$ taken together form a 5- or 6-membered ring which contains one or more of O or $NR^{15}$ wherein $R^{15}$ is the same as defined above and which may optionally be substituted, most preferably, $R^1$ is hydrogen, hydroxy, chlorine, fluorine, methoxymethyloxy, benzyloxy, 3-methyl-2-butenyloxy, methanesulfonyloxy, amino, dimethylamino or 3-methyl-2-butenylamino (hereinafter referred to as "$R^1$ is R1-4"), or $R^1$ and $R^2$ or $R^4$ taken together form —OCH$_2$O— or —CH=CH—NH—, 4) a compound wherein $R^2$ is hydrogen, hydroxy, halogen, lower alkyl or optionally substituted lower alkylsulfonyloxy (hereinafter referred to as "$R^2$ is R2-1") or $R^1$ and $R^2$ taken together form a 5- or 6-membered ring which contains one or more of O or $NR^{15}$ wherein $R^{15}$ is the same as defined above and which may optionally be substituted, preferably $R^2$ is hydrogen, halogen or alkyl having 1 to 3 carbon atoms (hereinafter referred to as "$R^2$ is R2-2"), 5) a compound wherein $R^3$ is hydrogen, hydroxy, halogen or optionally substituted lower alkoxy (hereinafter referred to as "$R^3$ is R3-1"), preferably $R^3$ is hydrogen or halogen (hereinafter referred to as "$R^3$ is R3-2"), more preferably $R^3$ is hydrogen or fluorine (hereinafter referred to as "$R^3$ is R3-3"), 6) a compound wherein $R^4$ is hydrogen, optionally substituted lower alkyl, halogen, optionally substituted lower alkoxy, nitro or optionally substituted amino (hereinafter referred to as "$R^4$ is R4-1") or $R^4$ and $R^1$ taken together may form a 5- or 6-membered ring which contains one or more of O or $NR^{15}$ wherein $R^{15}$ is the same as defined above and which may optionally be substituted, preferably $R^4$ is hydrogen, lower alkyl, lower alkoxy or halogen (hereinafter referred to as "$R^4$ is R4-2"), or $R^4$ and $R^1$ taken together may form —OCH$_2$O—, 7) a compound wherein $R^5$ is hydrogen, optionally substituted lower alkoxy, lower alkoxycarbonyl or carboxy (hereinafter referred to as "$R^5$ is R5-1"), preferably $R^5$ is hydrogen, lower alkoxycarbonyl or carboxy (hereinafter referred to as "$R^5$ is R5-2"), more preferably $R^5$ is hydrogen (hereinafter referred to as "$R^5$ is R5-3"), 8) a compound wherein $R^6$ is hydrogen, halogen, optionally substituted lower alkyl, carboxy, lower alkoxycarbonyl, nitro, formyl, amino or lower alkylsulfonyloxy (hereinafter referred to as "$R^6$ is R6-1"), preferably $R^6$ is hydrogen or lower alkyl or halogen (hereinafter referred to as "$R^6$ is R6-2"), more preferably $R^6$ is hydrogen, alkyl having 1 to 3 carbon atoms or halogen (hereinafter referred to as "$R^6$ is R6-3"), 9) a compound wherein $R^7$ is hydrogen, halogen, optionally substituted lower alkyl, optionally substituted lower alkoxy, formyl or optionally substituted amino (hereinafter referred to as "$R^7$ is R7-1"), preferably $R^7$ is hydrogen, lower alkyl or lower alkoxy (hereinafter referred to as "$R^7$ is R7-2"), 10) a compound wherein $R^8$ is hydrogen, halogen, optionally substituted lower alkyl, optionally substituted lower alkoxy, formyl or optionally substituted amino (hereinafter referred to as "$R^8$ is R8-1") or $R^8$ and $R^9$ taken together may form a 5- or 6-membered ring which contains one or more of O and which may optionally be substituted, preferably $R^8$ is hydrogen, lower alkyl or lower alkoxy (hereinafter referred to as "$R^8$ is R8-2"), 11) a compound wherein $R^9$ is hydrogen, hydroxy, carboxy, optionally substituted lower alkyl, optionally substituted lower alkoxy, optionally substituted lower alkenyl, optionally substituted lower alkoxycarbonyl, optionally substituted lower alkylsulfonyloxy, formyl, optionally substituted carbamoyl or optionally substituted amino (hereinafter referred to as "$R^9$ is R9-1") or $R^9$ and $R^8$ taken together may form a 5- or 6-membered ring which contains one or more of O and which may optionally be substituted, preferably $R^9$ is hydrogen, hydroxy, carboxy, optionally substituted lower alkyl, optionally substituted lower alkoxy, optionally substituted lower alkenyl, optionally substituted lower alkoxycarbonyl, optionally substituted lower alkylsulfonyloxy, formyl, optionally substituted carbamoyl or optionally substituted amino (hereinafter referred to as "$R^9$ is R9-2"), more preferably $R^9$ is hydrogen, hydroxy, lower alkyl, hydroxy(lower)alkyl, lower alkoxycarbonyl(lower)alkenyl, lower alkoxy(lower)alkoxy, lower alkylsulfonyloxy, di(lower)alkylcarbamoyl, carboxy, lower alkoxycarbonyl or amino (hereinafter referred to as "$R^9$ is R9-3"), most preferably $R^9$ is hydrogen, hydroxy, methyl, hydroxymethyl, ethoxycarbonylvinyl, methoxymethyloxy, methanesulfonyl, dimethylcarbamoyl, carboxy, methoxycarbonyl or amino (hereinafter referred to as "$R^9$ is R9-4"), 12) a compound wherein $R^{10}$ is hydrogen or lower alkoxy (hereinafter referred to as "$R^{10}$ is R10-1"), preferably $R^{10}$ is hydrogen (hereinafter referred to as "$R^{10}$ is R10-2"), 13) a compound wherein $R^{11}$ is hydrogen, halogen, optionally substituted lower alkyl, carboxy, lower alkoxycarbonyl, optionally substituted lower alkylsulfonyloxy, formyl, nitro or amino (hereinafter referred to as "$R^{11}$ is R11-1") or $R^{11}$ and —X—Y taken together form a 5- or 6-membered ring which contains one or more of O or $NR^{15}$ wherein $R^{15}$ is the same as defined above and which may optionally be substituted with lower alkenyl, halogeno(lower)alkenyl or the like, preferably $R^{11}$ is hydrogen or halogen (hereinafter referred to as "$R^{11}$ is R11-2"), 14) a compound wherein $R^{12}$ is hydrogen, 15) a compound wherein $R^{13}$ is hydrogen, hydroxy, halogen, carboxy, optionally substituted lower alkyl, optionally substituted lower alkoxy, optionally substituted lower alkenyloxy, optionally substituted acyloxy, optionally substituted lower alkylsulfonyloxy, formyl, nitro or optionally substituted amino (hereinafter referred to as "$R^{13}$ is R13-1") or $R^{13}$ and —X—Y taken together form a 5- or 6-membered ring which contains one or more of O or $NR^{15}$ wherein $R^{15}$ is the same as defined above and which may optionally be substituted with lower alkenyl, halogeno(lower)alkenyl or the like, preferably $R^{13}$ is hydrogen, hydroxy, halogen, carboxy, optionally substituted lower alkyl, optionally substituted lower alkoxy, optionally substituted acyloxy, optionally substituted lower alkylsulfonyloxy, formyl or optionally substituted amino (hereinafter referred to as "$R^{13}$ is R13-2"), more preferably $R^{13}$ is hydroxy; halogen; lower alkyl optionally substituted with hydroxy or halogen; lower alkoxy optionally substituted with lower alkoxycarbonyl or lower alkoxy; lower alkenyloxy optionally substituted with halogen; aroyloxyl; lower alkylsulfonyloxy; formyl or amino (hereinafter referred to as "$R^{13}$ is R13-3"), most preferably $R^{13}$ is hydroxy, fluorine, methyl, hydroxymethyl, iodomethyl, methoxy, ethoxy, isopropyloxy, ethoxycarbonylmethyloxy, methoxymethyloxy, chlorobutenyloxy, bromopropenyloxy, chloropropenyloxy, bromobutenyloxy, dichloropropenyloxy, ethoxycarbonyl, benzoyloxy, methanesulfonyloxy, formyl or amino (hereinafter referred to as "$R^{13}$ is R13-4"), 16) a compound wherein X is —O—, —$NR^{14}$— or —S(O)$_p$— wherein p is an integer of 0 to 2 (hereinafter referred to as "X is X1"), or X, $R^{13}$ and Y taken together may form a 5- or 6-membered ring which contains one or more of O or $NR^{15}$ wherein $R^{15}$ is the same as defined above and may optionally be substituted, preferably X is —O—, —NH—, —NMe- or —SO$_2$— (hereinafter referred to as "X is X2"), more preferably X is —O—, —NH— or —NMe—(hereinafter referred to as "X is X3"), most preferably X is —O—, 17) a compound wherein Y is optionally substituted lower alkyl, optionally substituted lower alkenyl, optionally substituted lower alkynyl, optionally substituted cycloalkenyl, lower alkylsulfonyl, optionally substituted arylsulfonyl, lower alkoxycarbonyl or optionally substituted acyl (hereinafter referred to as "Y is Y1"), or Y, $R^{13}$ and X taken together may form a 5- or 6-membered ring which contains one or more of O or $NR^{15}$ wherein $R^{15}$ is the same as defined above and which may optionally be substituted, preferably Y is lower alkyl optionally substituted with halogen; hydroxy; amino optionally substituted with lower alkyl; lower alkoxy; carboxy; lower alkoxycarbonyl; acyl; cycloalkyl; cycloalkenyl; cyano; imino optionally substituted with hydroxy, lower alkoxy, carboxy(lower)alkoxy, aryl(lower)alkoxy or heterocyclyl; hydrazono optionally substituted with carbamoyl or lower alkoxycarbonyl; carbamoyl optionally substituted with lower alkyl or amino; thiocarbamoyl optionally substituted with lower alkyl; aryl optionally substituted with amino (optionally substituted with lower alkyl, acyl, lower alkoxycarbonyl or lower alkylsulfonyl), nitro, acyloxy, lower alkyl (optionally substituted with halogen or carboxy), halogen, lower alkoxy, carboxy, lower alkoxycarbonyl, lower alkenyloxycarbonyl or guanidino; or heterocyclyl optionally substituted with halogen or lower alkyl;

lower alkenyl optionally substituted with halogen, hydroxy, cycloalkyl, lower alkoxycarbonyl or aryl-substituted heterocyclyl; lower alkynyl optionally substituted with halogen; or cycloalkenyl (hereinafter referred to as "Y is Y2"), more preferably Y is lower alkyl optionally substituted with lower alkoxycarbonyl, aryl, lower alkylaryl, halogenoaryl, lower alkoxyaryl, heterocyclyl or acyl; or lower alkenyl optionally substituted with hydroxy, halogen or aryl (hereinafter referred to as "Y is Y3"), most preferably Y is isopropyl, ethoxycarbonylmethyl, benzyl, methylphenylmethyl, fluorophenylmethyl, dichlorophenylmethyl, methoxyphenylmethyl, pyridylmethyl, benzoylmethyl, propenyl, methylpropenyl, methylbutenyl, hydroxymethylbutenyl, pentenyl, methylpentenyl, dimethyloctadienyl, chloropropenyl, dichloropropenyl, bromopropenyl, dibromopropenyl, fluoropropenyl, difluoropropenyl, butenyl, bromobutenyl, chlorobutenyl or phenylpropenyl (hereinafter referred to as "Y is Y4"), 18) a compound wherein $R^1$ is R1-2, $R^2$ is R2-1, $R^3$ is R3-1, $R^4$ is R4-1, $R^5$ is R5-1, $R^6$ is R6-1, $R^7$ is R7-1, $R^8$ is R8-1, $R^9$ is R9-2, $R^{10}$ is R10-1, $R^{11}$ is R11-1, $R^{12}$ is hydrogen, $R^{13}$ is R13-1, X is X1 and Y is Y1, and $R^1$ and $R^2$, $R^1$ and $R^4$, $R^8$ and $R^9$, or $R^{13}$ and —XY taken together may form a 5- or 6-membered ring which contains one or more of O or $NR^{15}$ wherein $R^{15}$ is the same as defined above and which may optionally be substituted, 19) a compound wherein $R^1$ is R1-2, $R^2$ is R2-1, $R^3$ is R3-1, $R^4$ is R4-1, $R^5$ is R5-1, $R^6$ is R6-1, $R^7$ is R7-1, $R^8$ is R8-1, $R^9$ is R9-1, $R^{10}$ is R10-1, $R^{11}$ is R11-1, $R^{12}$ is hydrogen, $R^{13}$ is R13-2, X is X1 and Y is Y1, and $R^1$ and $R^2$, $R^1$ and $R^4$, $R^8$ and $R^9$, or $R^{13}$ and —XY taken together may form a 5- or 6-membered ring which contains one or more of O or $NR^{15}$ wherein $R^{15}$ is the same as defined above and which may optionally be substituted, 20) a compound wherein $R^1$ is R1-2, $R^2$ is R2-1, $R^3$ is R3-1, $R^4$ is R4-1, $R^5$ is R5-1, $R^6$ is R6-2, $R^7$ is R7-2, $R^8$ is R8-2, $R^9$ is R9-1, $R^{10}$ is R10-1, $R^{11}$ is R11-1, $R^{12}$ is hydrogen, $R^{13}$ is R13-1, X is X1 and Y is Y2, and $R^1$ and $R^2$, $R^1$ and $R^4$, $R^8$ and $R^9$, or $R^{13}$ and-X—Y taken together may form a 5- or 6-membered ring which contains one or more of O or $NR^{15}$ wherein $R^{15}$ is the same as defined above and which may optionally be substituted, 21) a compound wherein $R^1$ is R1-1, $R^2$ is R2-1, $R^3$ is R3-1, $R^4$ is R4-1, $R^5$ is R5-1, $R^6$ is R6-2, $R^7$ is R7-1, $R^8$ is R8-2, $R^9$ is R9-2, $R^{10}$ is R10-1, $R^{11}$ is R11-1, $R^{12}$ is hydrogen, $R^{13}$ is R13-2, X is X1 and Y is Y1, and $R^1$ and $R^2$, $R^1$ and $R^4$, $R^8$ and $R^9$, or $R^{13}$ and-X—Y taken together may form a 5- or 6-membered ring which contains one or more of O or $NR^{15}$ wherein $R^{15}$ is the same as defined above and which may optionally be substituted, 22) a compound wherein $R^1$ is R1-1, $R^2$ is R2-1, $R^3$ is R3-1, $R^4$ is R4-1, $R^5$ is R5-1, $R^6$ is R6-2, $R^7$ is R7-1, $R^8$ is R8-2, $R^9$ is R9-2, $R^{10}$ is R10-1, $R^{11}$ is R11-1, $R^{12}$ is hydrogen, $R^{13}$ is R13-1, X is X1 and Y is Y2, and $R^1$ and $R^2$, $R^1$ and $R^4$, $R^8$ and $R^9$, or $R^{13}$ and —XY taken together may form a 5- or 6-membered ring which contains one or more of O or $NR^{15}$ wherein $R^{15}$ is the same as defined above and which may optionally be substituted, 23) a compound wherein $R^1$ is R1-1, $R^2$ is R2-1, $R^3$ is R3-1, $R^4$ is R4-1, $R^5$ is R5-1, $R^6$ is R6-2, $R^7$ is R7-1, $R^8$ is R8-2, $R^9$ is R9-1, $R^{10}$ is R10-1, $R^{11}$ is R11-1, $R^{12}$ is hydrogen, $R^{13}$ is R13-2, X is X1 and Y is Y2, and $R^1$ and $R^2$, $R^1$ and $R^4$, $R^8$ and $R^9$ or $R^{13}$ and —XY taken together may form a 5- or 6-membered ring which contains one or more of O or $NR^{15}$ wherein $R^1$ is the same as defined above and which may optionally be substituted, 24) a compound wherein $R^1$ is R1-2, $R^2$ is R2-1, $R^3$ is R3-1, $R^4$ is R4-1, $R^5$ is R5-1, $R^6$ is R6-2, $R^7$ is R7-1, $R^8$ is R8-2, $R^9$ is R9-2, $R^{10}$ is R10-1, $R^{11}$ is R11-1, $R^{12}$ is hydrogen, $R^{13}$ is R13-2, X is X1 and Y is Y1, and $R^1$ and $R^2$, $R^1$ and $R^4$, $R^8$ and $R^9$, or $R^{13}$ and —XY taken together may form a 5- or 6-membered ring which contains one or more of O or $NR^{15}$ wherein $R^{15}$ is the same as defined above and which may optionally be substituted, 25) a compound wherein $R^1$ is R1-2, $R^2$ is R2-1, $R^3$ is R3-1, $R^4$ is R4-1, $R^5$ is R5-1, $R^6$ is R6-2, $R^7$ is R7-1, $R^8$ is R8-2, $R^9$ is R9-2, $R^{10}$ is R10-1, $R^{11}$ is R1-1, $R^{12}$ is hydrogen, $R^{13}$ is R13-1, X is X1 and Y is Y2, and $R^1$ and $R^2$, $R^1$ and $R^4$, $R^8$ and $R^9$, or $R^{13}$ and —X—Y taken together may form a 5- or 6-membered ring which contains one or more of O or $NR^{15}$ wherein $R^{15}$ is the same as defined above and which may optionally be substituted, 26) a compound wherein $R^1$ is R1-2, $R^2$ is R2-1, $R^3$ is R3-1, $R^4$ is R4-1, $R^5$ is R5-1, $R^6$ is R6-2, $R^7$ is R7-1, $R^8$ is R8-2, $R^9$ is R9-1, $R^{10}$ is R10-1, R11 is R11-1, $R^{12}$ is hydrogen, $R^{13}$ is R13-2, X is X1 and Y is Y2, and $R^1$ and $R^2$, $R^1$ and $R^4$, $R^8$ and $R^9$, or $R^{13}$ and —XY taken together may form a 5- or 6-membered ring which contains one or more of O or $NR^{15}$ wherein $R^{15}$ is the same as defined above and which may optionally be substituted, 27) a compound wherein $R^1$ is R1-1, $R^2$ is R2-1, $R^3$ is R3-1, $R^4$ is R4-1, $R^5$ is R5-1, $R^6$ is R6-2, $R^7$ is R7-1, $R^8$ is R8-2, $R^9$ is R9-2, $R^{10}$ is R10-1, $R^{11}$ is R11-1, $R^{12}$ is hydrogen, $R^{13}$ is R13-2, X is X1 and Y is Y2, and $R^1$ and $R^2$, $R^1$ and $R^4$, $R^8$ and $R^9$, or $R^{13}$ and —XY taken together may form a 5- or 6-membered ring which contains one or more of O or $NR^{15}$ wherein $R^{15}$ is the same as defined above and which may optionally be substituted, 28) a compound wherein $R^1$ is R1-2, $R^2$ is R2-2, $R^3$ is R3-2, $R^4$ is R4-2, $R^5$ is R5-2, $R^6$ is R6-2, $R^7$ is R7-2, $R^8$ is R8-2, $R^9$ is R9-2, $R^{10}$ is R10-2, $R^{11}$ is R11-2, $R^{12}$ is hydrogen, $R^{13}$ is R13-2, X is $X_2$ and Y is $Y_2$, and $R^1$ and $R^4$, or $R^8$ and $R^9$ taken together may form a 5- or 6-membered ring which contains one or more of O, 29) a compound wherein $R^1$ is R1-3, $R^2$ is R2-2, $R^3$ is R3-2, $R^4$ is R4-2, $R^5$ is R5-2, $R^6$ is R6-2, $R^7$ is R7-2, $R^8$ is R8-2, $R^9$ is R9-2, $R^{10}$ is R10-2, $R^{11}$ is R11-2, and $R^1$ and $R^4$, or $R^8$ and $R^9$ taken together may form a 5- or 6-membered ring which contains one or more of O, 30) a compound wherein $R^1$ is R1-4, $R^2$ is R2-2, $R^3$ is R3-2, $R^4$ is R4-2, $R^5$ is R5-2, $R^6$ is R6-2, $R^7$ is R7-2, $R^8$ is R8-2, $R^9$ is R9-2, $R^{10}$ is R10-2, $R^{11}$ is R11-2, $R^{12}$ is hydrogen, $R^{13}$ is R13-2, X is X2 and Y is Y2, and $R^1$ and $R^4$, or $R^8$ and $R^9$ taken together may form —$OCH_2O$—, 31) a compound wherein $R^1$ is R1-2, $R^2$ is R2-2, $R^3$ is R3-2, $R^4$ is R4-2, $R^5$ is R5-2, $R^6$ is R6-2, $R^7$ is R7-2, $R^8$ is R8-2, $R^9$ is R9-3, $R^{10}$ is R10-2, $R^{11}$ is R11-2, $R^{12}$ is hydrogen, $R^{13}$ is R13-2, X is X2 and Y is Y2, and $R^1$ and $R^4$, or $R^8$ and $R^9$ taken together may form a 5- or 6-membered ring which contains one or more of O, 32) a compound wherein $R^1$ is R1-2, $R^2$ is R2-2, $R^3$ is R3-2, $R^4$ is R4-2, $R^5$ is R5-2, $R^6$ is R6-2, $R^7$ is R7-2, $R^8$ is R8-2, $R^9$ is R9-4, $R^{10}$ is R10-2, $R^{11}$ is R11-2, $R^{12}$ is hydrogen, $R^{13}$ is R13-2, X is X2 and Y is Y2, and $R^1$ and $R^4$, or $R^8$ and $R^9$ taken together may form a 5- or 6-membered ring which contains one or more of O, 33) a compound wherein $R^1$ is R1-2, $R^2$ is R2-2, $R^3$ is R3-2, $R^4$ is R4-2, $R^5$ is R5-2, $R^6$ is R6-2, $R^7$ is R7-2, $R^8$ is R8-2, $R^9$ is R9-2, $R^{10}$ is R10-2, $R^{11}$ is R11-2, $R^{12}$ is hydrogen, $R^{13}$ is R13-3, X is X2 and Y is Y2, and $R^1$ and $R^4$, or $R^8$ and $R^9$ taken together may form a 5- or 6-membered ring which contains one or more of O, 34) a compound wherein $R^1$ is R1-2, $R^2$ is R2-2, $R^3$ is R3-2, $R^4$ is R4-2, $R^5$ is R5-2, $R^6$ is R6-2, $R^7$ is R7-2, $R^8$ is R8-2, $R^9$ is R9-2, $R^{10}$ is R10-2, $R^{11}$ is R11-2, $R^{12}$ is hydrogen, $R^{13}$ is R13-4, X is X2 and Y is Y2, and $R^1$ and $R^4$, or $R^8$ and $R^9$ taken together may form a 5- or 6-membered ring which contains one or more of O, 35) a compound wherein $R^1$ is R1-2, $R^2$ is R2-2, $R^3$ is R3-2, $R^4$ is R4-2, $R^5$ is R5-2, $R^6$ is R6-2, $R^7$ is R7-2, $R^8$ is R8-2, $R^9$ is R9-2, $R^{10}$ is R10-2, $R^{11}$ is R11-2, $R^{12}$ is hydrogen, $R^{13}$ is R13-2, X is $X_2$ and Y is $Y_3$, and $R^1$ and $R^4$, or $R^8$ and $R^9$ taken together may form a 5- or 6-membered ring which contains one or more of O, 36) a compound wherein $R^1$ is R1-3, $R^2$ is R2-2, $R^3$ is R3-2, $R^4$ is R4-2, $R^5$ is R5-2, $R^6$ is R6-2, $R^7$ is $R^{70-2}$, $R^8$ is R8-2, $R^9$ is R9-3, $R^{10}$ is R10-2, $R^{11}$ is R11-2, $R^{12}$ is hydrogen, $R^{13}$ is R13-2, X is $X_2$ and Y is $Y_2$, and $R^1$ and $R^4$, or $R^8$ and $R^9$ taken together may form a 5- or 6-membered ring which contains one or more of O, 37) a compound wherein $R^1$ is R1-3, $R^2$ is R2-2, $R^3$ is R3-2, $R^4$ is R4-2, $R^5$ is R5-2, $R^6$ is R6-2, $R^7$ is R7-2, $R^8$ is R8-2, $R^9$ is R9-2, $R^{10}$ is R10-2, $R^{11}$ is R11-2, $R^{12}$ is hydrogen, $R^{13}$ is R13-3, X is X2 and Y is Y2, and $R^1$ and $R^4$, or $R^8$ and $R^9$ taken together may form a 5- or 6-membered ring which contains one or more of O, 38) a compound wherein $R^1$ is R1-3, $R^2$ is R2-2, $R^3$ is R3-2, $R^4$ is R4-2, $R^5$ is R5-2, $R^6$ is R6-2, $R^7$ is R7-2, $R^8$ is R8-2, $R^9$ is R9-2, $R^{10}$ is R10-2, $R^{11}$ is R11-2, $R^{12}$ is hydrogen, $R^{13}$ is R13-2, X is X2 and Y is Y3, and $R^1$ and $R^4$, or $R^8$ and $R^9$ taken together may form a 5- or 6-membered ring which contains one or more of O, 39) a compound wherein $R^1$ is R1-2, $R^2$ is R2-2, $R^3$ is R3-2, $R^4$ is R4-2, $R^5$ is R5-2, $R^6$ is R6-2, $R^7$ is R7-2, $R^8$ is R8-2, $R^9$ is R9-3, $R^{10}$ is R10-2, $R^{11}$ is R11-2, $R^{12}$ is hydrogen, $R^{13}$ is R13-3, X is X2 and Y is Y2, and $R^1$ and $R^4$, or $R^8$ and $R^9$ taken together may form a 5- or 6-membered ring which contains one or more of O, 40) a compound wherein $R^1$ is R1-2, $R^2$ is R2-2, $R^3$ is R3-2, $R^4$ is R4-2, $R^5$ is R5-2, $R^6$ is R6-3, $R^7$ is R7-2, $R^8$ is R8-2, $R^9$ is R9-3, $R^{10}$ is R10-2, $R^{11}$ is R11-2, $R^{12}$ is hydrogen, $R^{13}$ is R13-2, X is X2 and Y is Y3, and $R^1$ and $R^4$, or $R^8$ and $R^9$ taken together may form a 5- or 6-membered ring which contains one or more of O, 41) a compound wherein $R^1$ is R1-2, $R^2$ is R2-2, $R^3$ is R3-2, $R^4$ is R4-2, $R^5$ is R5-2, $R^6$ is R6-2, $R^7$ is R7-2, $R^8$ is R8-2, $R^9$ is R9-2, $R^{10}$ is R10-2, $R^{11}$ is R11-2, $R^{12}$ is hydrogen, $R^{13}$ is R13-3, X is X2 and Y is Y3, and $R^1$ and $R^4$, or $R^8$ and $R^9$ taken together may form a 5- or 6-membered ring which contains one or more of O, 42) a compound wherein $R^1$ is R1-3, $R^2$ is R2-2, $R^3$ is R3-2, $R^4$ is R4-2, $R^5$ is R5-2, $R^6$ is R6-2, $R^7$ is R7-2, $R^8$ is R8-2, $R^9$ is R9-3, $R^{10}$ is R10-2, $R^{11}$ is R11-2, $R^{12}$ is hydrogen, $R^{13}$ is R13-3, X is X2 and Y is Y2, and $R^1$ and $R^4$, or $R^8$ and $R^9$ taken together may form —$OCH_2O$—, 43) a compound wherein $R^1$ is R1-3, $R^2$ is R2-2, $R^3$ is R3-2, $R^4$ is R4-2, $R^5$ is R5-2, $R^6$ is R6-2, $R^7$ is R7-2, $R^8$ is R8-2, $R^9$ is R9-3, $R^{10}$ is R10-2, $R^{11}$ is R11-2, $R^{12}$ is hydrogen, $R^{13}$ is R13-2, X is X2 and Y is Y3, and $R^1$ and $R^4$, or $R^8$ and $R^9$ taken together may form —$OCH_2O$—, 44) a compound wherein $R^1$ is R1-3, $R^2$ is R2-2, $R^3$ is R3-3, $R^4$ is R4-2, $R^5$ is R5-2, $R^6$ is R6-2, $R^7$ is R7-2, $R^8$ is R8-2, $R^9$ is R9-2, $R^{10}$ is R10-2, $R^{11}$ is R11-2, $R^{12}$ is hydrogen, $R^{13}$ is R13-3, X is X2 and Y is Y3, and $R^1$ and $R^4$, or $R^8$ and $R^9$ taken together may form —OCH$_2$O—, 45) a compound wherein $R^1$ is R1-2, $R^2$ is R2-2, $R^3$ is R3-3, $R^4$ is R4-2, $R^5$ is R5-3, $R^6$ is R6-2, $R^7$ is R7-2, $R^8$ is R8-2, $R^9$ is R9-3, $R^{10}$ is R10-2, $R^{11}$ is R11-2, $R^{12}$ is hydrogen, $R^{13}$ is R13-3, X is X2 and Y is Y3, and $R^1$ and $R^4$, or $R^8$ and $R^9$ taken together may form a 5- or 6-membered ring which contain one or more of O, 46) a compound wherein $R^1$ is R1-3, $R^2$ is R2-2, $R^3$ is R3-3, $R^4$ is R4-2, $R^5$ is R5-3, $R^6$ is R6-3, $R^7$ is R7-2, $R^8$ is R8-2, $R^9$ is R9-3, $R^{10}$ is R10-2, $R^{11}$ is R11-2, $R^{12}$ is hydrogen, $R^{13}$ is R13-3, X is X3 and Y is Y4, and $R^1$ and $R^4$, or $R^8$ and $R^9$ taken together may form —OCH$_2$O—, 47) a compound wherein $R^1$ is R1-4, $R^2$ is R2-2, $R^3$ is R3-3, $R^4$ is R4-2, $R^5$ is R5-3, $R^6$ is R6-3, $R^7$ is R7-2, $R^8$ is R8-2, $R^9$ is R9-4, $R^{10}$ is R10-2, $R^{11}$ is R11-2, $R^{12}$ is hydrogen, $R^{13}$ is R13-4, X is X3 and Y is Y4, $R^1$ and $R^4$ taken together may form —OCH$_2$O— and $R^8$ and $R^9$ taken together may form —OCH$_2$CH$_2$O—, 48) a compound wherein the benzene ring which is substituted with $R^1$–$R^5$ is

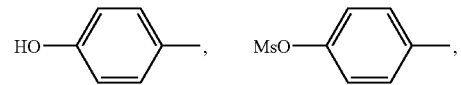,

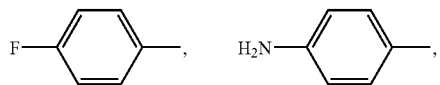,

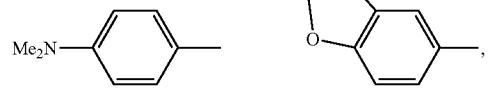,

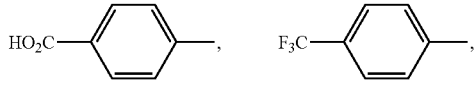,

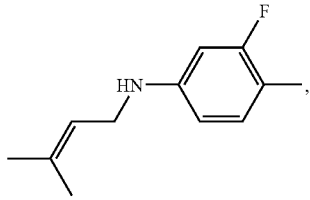,

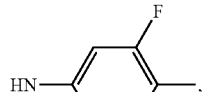,

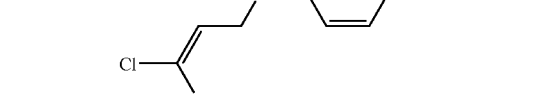,

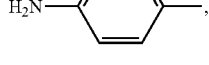, 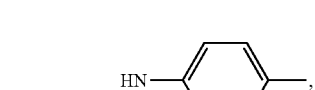,

-continued

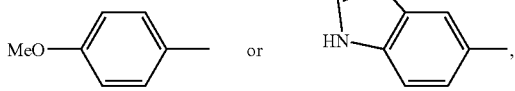

49) a compound wherein the benzene ring which is substituted with $R^6$–$R^9$ is

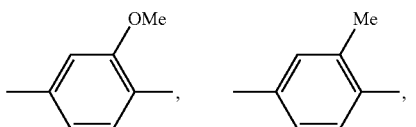,

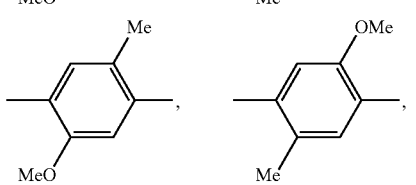,

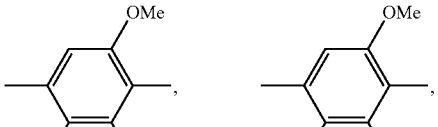,

,

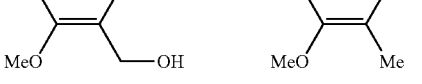,

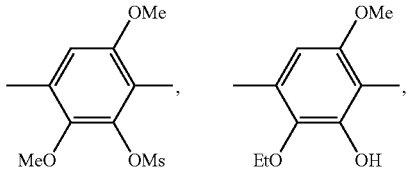,

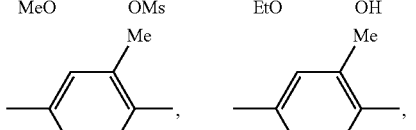,

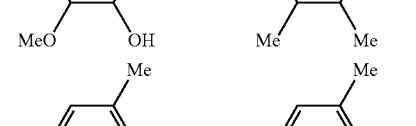,

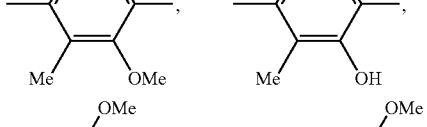,

-continued

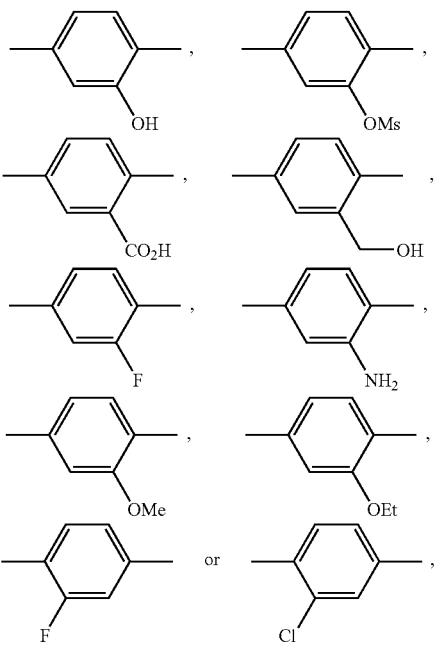

50) a compound wherein the benzene ring which is substituted with $R^{10}$–$R^{13}$ is 51) a compound wherein Y is —$CH_2CH=CMe_2$, —$(CH_2)_2CH=CMe_2$, —$CH_2CH=CCl_2$, —$CH_2CH=CBr_2$, —$CH_2CH=CF_2$, —$CH_2CH=CHMe$, —$CH_2CH=C(Me)CH_2OH$, —$CH_2C\equiv CMe$, —$CH_2C_6H_4$-4-Me, —$CH_2C_6H_5$, —$CH_2CH_2CHMe_2$ or —Me, 52) a compound wherein —X—Y is —$OCH_2CH=CMe_2$, —$O(CH_2)_2CH=CMe_2$, —$OCH_2CH=CCl_2$, —$OCH_2CH=CBr_2$, —$OCH_2CH=CF_2$, —$OCH_2C=CMe$, —$OCH_2C_6H_4$-4-Me, —$OCH_2C_6H_5$, —$NHCH_2CH=CMe_2$, —$N(Me)CH_2CH=CMe_2$, —$NHCH_2CH_2CHMe_2$, $NHCH_2C\equiv CH$, or —$NMe_2$, or 53) a compound wherein at least seven of the substituents of $R^1$–$R^{13}$ are hydrogen, preferably at least eight are hydrogen, more preferably at least nine are hydrogen, and their pharmaceutically acceptable salts, their hydrates and their prodrugs.

A process for producing the compound (I''') is as follows.

Process for Producing the Compound (I''') [Process a]

The compound (I''') can be produced by the reaction of a borane compound of the formula (II) and (II') coupled with a biphenyl derivative of the formula (III) and (III') respectively, as shown below.

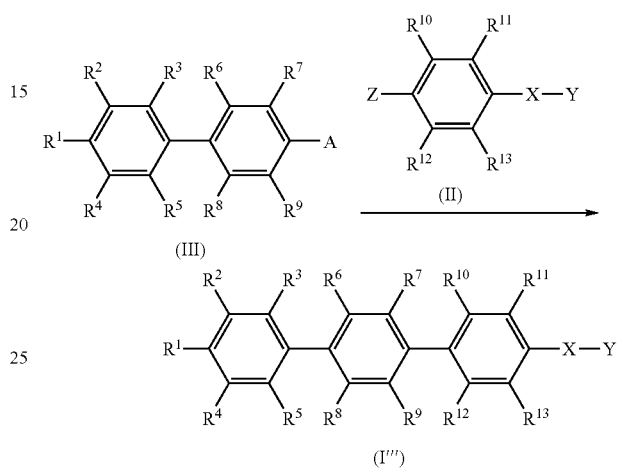

wherein $R^1$–$R^{13}$, X and Y are the same as defined in the above formula (I'''), and A and Z are the same as defined in the above formulas (II) and (III), or

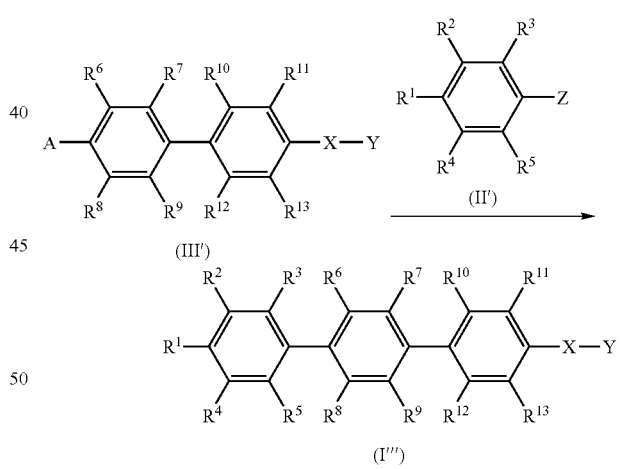

wherein $R^1$–$R^{13}$, X and Y are the same as defined in the above formula (I'''), and A and Z are the same as defined in the above formulas (II) and (III).

The compounds (II) and (II') are reacted with the compounds (III) and (III') respectively in a mixture system of an appropriate solvent such as benzene, toluene, dimethylformamide, dimethoxyethane, tetrahydrofuran, dioxane, ethanol, methanol or the like and water or in an anhydrous system in the presence of a palladium catalyst such as $Pd(PPh_3)_4$, $PdCl_2(PPh_3)_2$, $PdCl_2(OAc)_2$, $PdCl_2(CH_3CN)_2$ or the like, preferably $Pd(PPh_3)_4$, under a basic condition (for example, by $K_3PO_4$, $NaHCO_3$, NaOEt, $Na_2CO_3$, $Et_4NCl$, Ba(OH)$_2$, Cs$_2$CO$_3$, CsF, NaOH, Ag$_2$CO$_3$ or the like) at room temperature or with heating for several tens minutes to several tens hours to obtain the compound (I'").

One of substituents A and Z of the compounds to be reacted may be any of the borane groups which are applicable in the Suzuki Reaction (Chemical Communication 1979, 866, Journal of Synthetic Organic Chemistry, Japan, 1993, Vol.51, No.11, 91–100) and dihydroxyborane is preferable. The other may be any of the leaving groups which are applicable in the Suzuki Reaction, for example, halogen, —OSO$_2$(C$_q$F$_{2q+1}$) wherein q is an integer of 0 to 4, or the like. Specifically, halogen, trifluoromethanesulfonyloxy (hereinafter referred to as OTf) or the like is preferable and bromine, iodine or OTf is more preferable.

The substituents R$^1$–R$^{13}$ and —X—Y of the compounds (II), (III), (II') and (III') may be any of the groups which do not affect the Suzuki Reaction, for example, any groups other than halogen and —OSO$_2$(C$_q$F$_{2q+1}$) wherein q is an integer of 0 to 4.

For example, Y may be optionally substituted lower alkyl, optionally substituted lower alkenyl, optionally substituted lower alkynyl, optionally substituted acyl, optionally substituted cycloalkyl, optionally substituted cycloalkenyl, optionally substituted aryl or optionally substituted heterocyclyl, Y may be optionally substituted lower alkoxy when X is —CH$_2$— and Y may be optionally substituted lower alkoxycarbonyl, optionally substituted lower alkylsulfonyl or optionally substituted arylsulfonyl when X is —O— or —NR$^{14}$—. Even if R$^1$–R$^{13}$ or Y is halogen, these reactions can be carried out without difficulty when the reactivity of the substituent A with the substituent Z is higher than that of halogen with either of substituents A and Z.

Even if one of R$^1$–R$^{13}$ and —X—Y is hydroxy, the above reactions can be carried out preferably after the protection of hydroxy group with a usual hydroxy-protecting group (for example, metoxymethyl, benzyl, tert-butyldimethylsilyl, methansulfonyl, p-toluenesulfonyl or the like), followed by the removal of them by usual methods.

As processes for producing the compound (I'"), the above mentioned Suzuki Reaction is most preferable in view of the efficiency and easiness but silicon, zinc, tin or the like can be used in place of the borane group in the above scheme.

For example, in the case that one of A and Z is —SiR$^{17}$$_{3-r}$(Hal)$_r$ wherein R$^{17}$ is independently lower alkyl, Hal is halogen and r is an integer of 1 to 3 and the other is halogen or —OSO$_2$(C$_q$F$_{2q+1}$) wherein q is an integer of 0 to 4, the coupling reaction may be carried out using a usual palladium catalyst (Synlett (1991) 845-853, J. Org. Chem. 1996, 61, 7232–7233). Examples of preferable palladium catalysts are (i-Pr$_3$P)$_2$PdCl$_2$, [(dcpe)PdCl$_2$] (dcpe=Cy$_2$PCH$_2$CH$_2$PCy$_2$), ($\eta^3$-C$_3$H$_5$PdCl)$_2$ and the like.

Even in the case that one of A and Z is —SnR$^{18}$$_3$ wherein R$^{18}$ is each independently lower alkyl and the other is halogen, acetyloxy or —OSO$_2$(C$_q$F$_{2q+1}$) wherein q is an integer of 0 to 4, an objective compound can be obtained using a usual palladium catalyst (preferably Pd(PPh$_3$)$_4$ or the like) (Angew. Chem. Int. Ed. Engl. 25 (1986) 508–524).

In the case that one of A and Z is —Zn(Hal) wherein Hal is halogen and the other is halogen, an objective compound can be obtained (Acc. Chem. Res. 1982, 15, 340-348). Any usual palladium catalyst is applicable and Pd(PPh$_3$)$_4$, PdCl$_2$(dppf), PdCl$_2$(PPh$_3$)$_2$, PdCl$_2$(P(o-Tolyl)$_3$)$_2$, Pd(OAc)$_2$ and the like are exemplified as preferable examples.

All of these reactions may be carried out in a suitable solvent (for example, dimethylformamide, tetrahydrofuran or the like) at room temperature or with heating for several tens minutes to several tens hours.

Process for Producing the Compound (I'") [Process b]

As another easier processes for producing the compound (I'"), the following process wherein the compound of the formulas (IV), (V) and (VI) are coupled is also applicable.

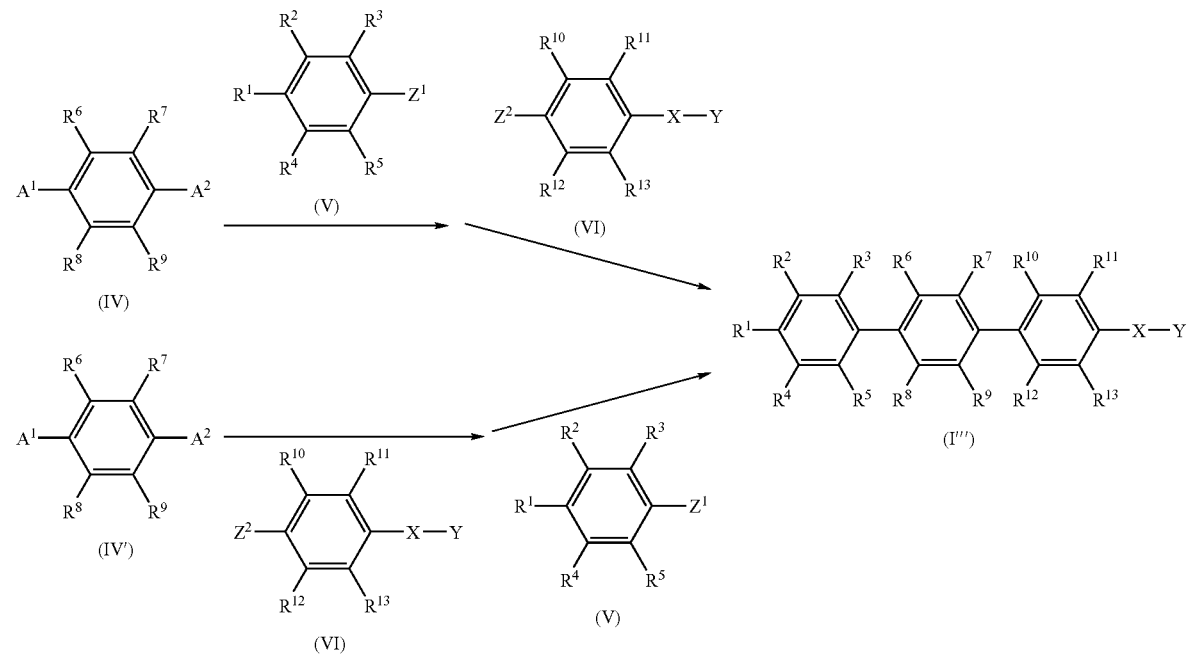

wherein $R^1$–$R^{13}$, X and Y are the same as defined in the above formulas (I), (II) and (III) and $A^1$, $A^2$, $Z^1$ and $Z^2$ are the same as defined in the above A and Z, respectively. The reactivity of $A^1$ is higher than or equal to that of $A^2$ in the compound (IV) and the reactivity of $A^2$ is higher than or equal to that of $A^1$ in the compound (IV').

For production of the compound (I''') by the above process the compound (IV) may be reacted with the compound (V), followed by the reaction with the compound (VI) without an isolation. The objective compound can be obtained also by a process wherein the compound (IV') is reacted with the compound (VI), followed by a reaction with the compound (V).

Because the reactions of the substituents $A^1$ and $Z^1$ and the substituents $A^2$ and $Z^2$ are necessary to obtain the objective compound, the reactivity of the substituent $A^1$ and that of $A^2$ should be different. A preferable example is the combination that $A^1$ is iodine and $A^2$ is bromine or —OTf in the compound (IV). Conversely in the compound (IV') iodine for $A^2$ and bromine or —OTf for $A^1$ are preferable. In the case that the compound (IV) or (IV') is a symmetry compound, the objective compound is obtained even if $A^1$ and $A^2$ are the same group.

The substituents $Z^1$ and $Z^2$ may be the same or different group.

Various other conditions in this process are the same as those in the "Process a".

In the above compounds, the substituents $R^1$–$R^{13}$ may be any of the groups which do not affect the reaction (for example, a group other than halogen and —OSO$_2$(C$_q$F$_{2q+1}$) wherein q is an integer of 0 to 4) or any of the groups which do not affect the reaction and are changeable to $R^1$–$R^{13}$ by a usual reaction. In the latter case the substituents may be changed to $R^1$–$R^{13}$ in suitable steps according to the reaction of each compound.

For example, in the case that a substituent is formyl and an objective substituent is hydroxy, after the substituent is changed to formyloxy by the Baeyer-Villiger reaction etc., a usual hydrolysis reaction may be carried out under an acidic or alkaline condition. Specifically, a compound which has formyl is reacted with a peroxy acid such as peracetic acid, perbenzoic acid, m-chloroperbenzoic acid, trifluoroperacetic acid, hydrogen peroxide or the like in a suitable solvent such as 1,2-dichloroethane, chloroform, dichloromethane, carbon tetrachloride, benzene or the like at –20° C. or with heating for several minutes to several tens hours, followed by the hydrolysis of the obtained compound which has formyloxy under an acidic condition (for example, with heating with hydrochloric acid) or under a basic condition (for example, with heating with sodium hydroxide).

In the case that a substituent is formyl and an objective substituent is hydroxymethyl, the compound which has formyl may be reacted with a reductant such as sodium borohydride, lithium borohydride, zinc borohydride, triethyllithium borohydride, alminium hydride, diisobutylalminium hydride or the like in a solvent (for example, methanol, ethanol, isopropanol, dimethylsulfoxide, diethylene glycol dimethoxyethane, tetrahydrofuran, benzene, toluene, cyclohexane or the like) which is suitable for the reductant at –20° C. to 80° C., preferably under ice-cooling or at room temperature, for several tens minutes to several hours.

In the case that a substituent is formyl and an objective substituent is alkenyl having additional carbon atoms, an objective compound can be obtained by the Wittig Reaction (Organic Reaction, 1965, vol.14, p. 270).

In the case that a substituent is formyl and an objective substituent is carboxy, the compound which has formyl may be reacted with an oxidizing agent such as sodium chlorite, the Jones Reagent, chromic anhydride or the like in a solvent such as tert-butanol, acetone or the like which is suitable for the oxidizing agent at 0° C. or with heating for several hours. The reaction is preferably carried out by addition of 2-methyl-2-buten, sodium dihydrogenphosphate or the like if needed.

In the case that a substituent is hydroxy and an objective substituent is substituted lower alkoxy, the compound which has hydroxy may be reacted with a proper alkylating agent in the presence of a base such as sodium carbonate, sodium bicarbonate, potassium carbonate, calcium hydroxide, barium hydroxide, calcium carbonate or the like in a suitable solvent such as tetrahydrofuran, acetone, dimethylformamide, acetonitrile or the like. Specifically, the reaction of a compound which has hydroxy with a proper halogenated compound such as methyl iodoacetate, ethyl chloroacetate, propyl chloroacetate or the like can give a compound of which substituent is alkoxycarbonyl(lower)alkoxy.

In the case that a substituent is carboxy and an objective substituent is carbamoyl, the compound which has carboxy may be carbamoylated with an amine such as ammonia, dimethylamine or the like at 0° C. or with heating for several minutes to several hours in a suitable solvent such as tetrahydrofuran, dimethylformamide, diethyl ether, dichloromethane or the like, if necessary after activation by an activating agent such as thionyl chloride, an acid halide, an acid anhydride, an activated ester or the like.

In the case that a substituent is hydrogen and an objective substituent is halogen, the compound which has hydrogen may be halogenated by a halogenating agent which is generally used (for example, bromine, chlorine, iodine, sulfuryl chloride, N-bromosuccinimide, N-iodosuccinimide or the like) in a suitable solvent such as chloroform, dichloromethane, carbon tetrachloride, acetonitrile, nitromethane, acetic acid, acetic anhydride or the like, if necessary in the presence of a catalyst such as the Lewis acid, hydrochloric acid, phosphoric acid or the like at –20° C. or with heating for several minutes to several tens hours.

The compound (I) can be obtained by a reaction of the compound (II) which has a substituent —X—Y with the compound (III) or a reaction of the compound (III') which has a substituent —X—Y with the compound (II'). Further, the compound (I) can also be obtained by a reaction of the compound (II) or (III') which has a substituent —W which is convertible into a substituent —X—Y with the compound (III) or (II'), followed by a conversion of a substituent —W into a substituent —X—Y.

For example, in the case of a compound wherein —W is hydroxy or protected hydroxy, an objective substituent such as lower alkyl, lower alkenyl, lower alkynyl, acyl, cycloalkyl, cycloalkenyl, aryl, heterocyclyl, lower alkoxy or the like may be introduced by a usual reaction.

Concretely, to obtain a compound wherein X is —O—, a compound wherein —W is hydroxy is synthesized and dissolved in a suitable solvent (for example, dimethylformamide, tetrahydrofuran, acetone, benzene, dioxane, acetonitrile or the like), followed by addition of a base such as hydroxides or carbonates of alkaline metals or alkaline-earth metals (for example, sodium carbonate, sodium bicarbonate, potassium carbonate, calcium hydroxide, barium hydroxide, calcium carbonate and the like) or tertiary amines such as triethylamine and the like. To the reactant is added a compound Y—V wherein V is halogen or —OSO$_2$(C$_q$F$_{2q+1}$) wherein q is an integer of 0–4 (for example, prenyl bromide, cyclohexenyl bromide, cinnamyl bromide, 1-bromo-2-penten, geranyl bromide, 5-bromo-2-methyl-2-penten, 1,3- dichloro-2-buten, 3-chloropropyne, prenyl triflate, cyclohexenyl triflate, 1,3-trichloropropene or the like) at 20° C. or with heating for several minutes to several tens hours to obtain an objective compound wherein —W has been converted into —O—Y.

To obtain a compound wherein X is —CH$_2$—, —NR$^{14}$- or —S—, a compound wherein —W is hydroxy is reacted with trifluoromethanesulfonic anhydride etc. in a solvent such as anhydrous dichloromethane, chloroform, carbon tetrachloride or the like in the presence of a base such as pyridine, triethylamine or the like to obtain a triflate. Then, the obtained compound is reacted with Y—V' wherein V' is —CH$_2$ZnI, —SH, —NHR$^{14}$ in the presence of a catalyst such as palladium, nickel or the like in a suitable solvent such as tetrahydrofuran, dimethylformamide, diethyl ether, dimethoxyethane or the like to give an objective compound.

In the case that X is NR$^{14}$, a compound wherein W is NH$_2$ may be reacted with a ketone or an aldehyde in a suitable solvent such as tetrahydrofuran, methanol or the like, followed by reduction with a suitable reductant such as sodium borohydride, sodium cyanoborohydride, zinc hydrochloride or the like or by catalytic reduction to obtain an objective compound.

A usual reaction of a compound wherein W is NH$_2$ with Y—V''' wherein Y is acyl, lower alkylsulfonyl optionally substituted or arylsulfonyl optionally substituted and V''' is a leaving group such as halogen gives a compound wherein —X—Y is —NH—Y.

To obtain a compound wherein X is —SO— or —SO$_2$—, a compound wherein X is —S—which is synthesized by the above mentioned process may be oxidized with a usual oxidizing agent such as m-chloroperbenzoic acid.

A compound of the present invention wherein —X—Y is lower alkenyloxy is dissolved in a solvent such as ethanol, ethyl acetate or the like and hydrogenated with a catalyst such as Pd-carbon powder, platinum, rhodium, ruthenium, nickel or the like to give a compound wherein —X—Y is lower alkoxy.

A reaction of a compound wherein —X—Y is lower alkenyloxy with m-chloroperbenzoic acid or the like in a solvent such as dichloromethane, chloroform, benzene, hexane, tert-butanol or the like gives a compound wherein —X—Y is epoxidated lower alkoxy.

In the case that a compound has a substituent interfering of a reaction, the substituent may be protected with a suitable protecting group in advance and the protecting group may be left in a suitable step by a usual method. For example, if hydroxy interferes the reaction, hydroxy may be protected with methoxymethyl, methanesulfonyl, benzyl, trifluoromethylsulfonyl, tert-butyldimethylsilyl or the like, followed by deprotection in a suitable step.

For example, for a protection of hydroxy with methanesulfonyl, a compound which has hydroxy may be reacted with methanesulfonyl chloride in a solvent such as dichloromethane, chloroform, carbon tetrachloride or the like in the presence of a base such as triethylamine, pyridine or the like under ice-cooling or at room temperature for several hours. The protected compound may be deprotected with 1-4 N sodium hydroxide, potassium hydroxide, aqueous solution thereof, sodium methoxide, ethyl magnesium bromide or the like in a solvent such as dimethylsulfoxide, dimethylformamide, tetrahydrofuran, dioxane, dimethoxyethane or the like at room temperature or with heating for several tens minutes to several hours.

When methoxymethyl is used as a protecting group of hydroxy, a compound which has hydroxy may be reacted with chloromethylmethylether in a solvent such as tetrahydrofuran, dioxane, dimethoxyethane or the like in the presence of sodium hydride, diisopropylethylamine or the like to obtain a compound which has a protected hydroxy group. The compound may be subjected to a usual deprotection reaction with hydrochloric acid, sulfuric acid or the like in a solvent such as methanol, tetrahydrofuran, acetic acid or the like for a deprotection.

When tert-butyldimethylsilyl is used as a protective group, a compound which has hydroxy may be reacted with tert-butyldimethylsilyl chloride, tert-butyldimethylsilyl triflate or the like in a solvent such as dimethylformamide, acetonitrile, tetrahydrofuran, dimethylformamide, dichloromethane or the like in the presence of imidazole, triethylamine, 2, 6-lutidine or the like. For a deprotection reaction the protected compound may be reacted with tetrabutylammonium fluoride or the like in a solvent such as tetrahydrofuran or the like.

Both of known compounds and the compounds which are produced by the following process may be used as the compounds (III) and (III') in the above scheme.

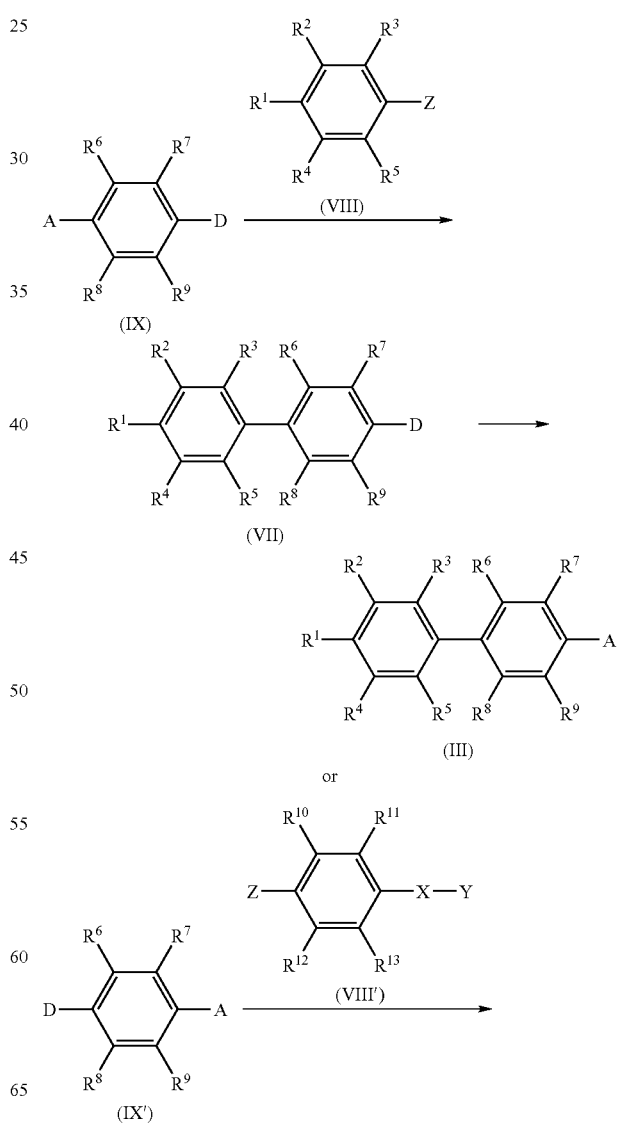

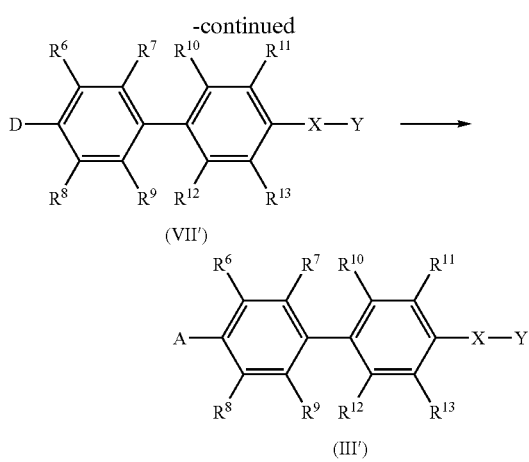

Known compounds (VIII) and (IX), or (VIII') and (IX') wherein A and Z are groups which can be subjected to a coupling reaction by the Suzuki Reaction with each other; for example, one is borane such as dihydroxyborane, di(lower)alkoxyborane or the like and the other is halogen or —OSO$_2$(CqF$_{2q+1}$) wherein q is an integer of 0–4; D is a group other than halogen and —OSO$_2$(CqF$_{2q+1}$) wherein q is the same as defined above are reacted by the same method as above to obtain a compound (VII) or (VII').

As described above, instead of a compound which has borane, a compound which has —SiR$^{17}$$_{3-r}$(Hal)$_r$ wherein R$^{17}$ is each independently lower alkyl, Hal is halogen and r is an integer of 1–3, —SnR$^{18}$$_3$ wherein R$^{18}$ is each independently lower alkyl or —Zn(Hal) wherein Hal is halogen may be used for a reaction to obtain an objective compound.

Then, a substituent D is converted into a substituent A which is applicable to the Suzuki Reaction.

For example, a compound wherein D is hydrogen may be reacted with a halogenating agent such as bromine, chlorine, iodine, sulfuryl chloride, N-bromosuccinimide or the like in a suitable solvent such as acetic acid, chloroform, dichloromethane, carbon tetrachloride, water, acetic acid-sodium acetate or the like at 20° C. or with heating for several minutes to several tens hours to give an objective compound wherein A is halogen.

A compound wherein D is protected hydroxy may be reacted with a trifluoromethanesulfonating agent such as trifluoromethanesulfonic anhydride, trifluoromethansulfonyl chloride or the like in a suitable solvent such as dichloromethane, chloroform, tetrahydrofuran or benzene in the presence of a base such as pyridine or triethylamine at −20° C. or with heating for several minutes to several tens hours to give an objective compound wherein A is OTf.

A compound of the present invention thus obtained can be converted into prodrug thereof. Any usual methods for conversion into a prodrug may be used. For example, hydroxy or amino which is attached a compound of the present invention at any position may be substituted with a usual group for a prodrug. An example of conversion into a prodrug is a substitution of hydroxy with acyloxy substituted with carboxy, sulfo, amino, lower alkylamino or the like, phosphonoxy etc. A substitution of hydroxy for R$^1$ with —OCOCH$_2$CH$_2$COOH, —OCOCH═CHCOOH, —OCOCH$_2$SO$_3$H, —OPO$_3$H$_2$, —OCOCH$_2$NMe$_2$, —OCO-Pyr wherein Pyr is pyridine or the like is preferable.

A selective suppressor of the IgE production of the present invention comprises a compound which suppresses the IgE production in a process from a differentiation of a mature B cell into an antibody-producing cell to the production of an antibody and which does not suppress or weakly suppresses the production of the immunoglobulins IgG, IgM and/or IgA which are produced at the same time.

The term "suppresses the IgE production in a process from a differentiation of a mature B cell into an antibody-producing cell to the production of an antibody" means to suppress the IgE production by inhibiting one of the following processes.

1) A process wherein mature B cells are activated by various factors such as cytokines, i.e., IL-4, IL-5, etc., anti-CD40 antibody or the like,
2) A process wherein the activated B cells differentiate into antibody-producing cells such as plasma cells etc. (concretely, a process of switching of the activated B cells to IgE class antibody-producing cells) and/or
3) A process wherein the antibody-producing cells produce immunoglobulins (specifically, a process of the IgE production)

An inhibition of "a process wherein a mature B cell is activated by various factors" in the process 1) does not include an inhibition of a process wherein the factors are produced from other cells and the like.

The term "suppresses the IgE production and does not suppress or weakly suppresses the production of the immunoglobulins IgG, IgM and/or IgA which are produced at the same time" means that the IgE production is suppressed enough to suppress allergy reactions and that the IgG, IgM and/or IgA production is not suppressed so potent as to badly affect an immune system concerning a living body protection under the condition that IgE and one or more of IgG, IgM and IgA can be produced at the same time. In other words, ① The suppression of the IgE production is 5,000 times, preferably 10,000 times, more preferably 15,000 times, most preferably 20,000 times or more as potent as those of the IgG, IgM and/or IgA production and/or ② The IgG, IgM and/or IgA production is not suppressed to less than 50% even at 5,000 times, preferably 10,000 times, more preferably 15,000 times, most preferably 20,000 times the concentration at which 50% of the IgE production is suppressed as compared with that in the absence of the suppressor.

The term "the concentration at which 50% of the IgE production is suppressed as compared with that in the absence of the suppressor" means a concentration at which the IgE production is limited to 50% of the production in the absence or without administration of the selective suppressor of the IgE production of the present invention under the condition that the IgE can be produced. The suppressor is useful as a medicament when it has a selectivity for the IgE as compared with at least one of IgG, IgM or IgA, preferably with all of them.

The selective suppressor of the IgE production of the present invention suppresses 90% or more of the IgE production as compared with that without administration of the suppressor at a dosage that the suppressor does not suppress or weakly suppresses the IgM, IgG and/or IgA production when the suppressor is administered to a mammal, which includes human, sensitized by an allergen. The term "allergen" means any substance that can induce the IgE production and an allergic reaction. Clinical examples are pollen, a acarid, house dust, albumin, milk, a soybean etc. and experimental examples are ovalbumin, bovine gamma globulin, bovine serum albumin, an antigen protein of cedar pollen (Cryj I and Cryj II), an antigen protein for acarid (Derf I and Derf II) etc. The term "a dosage that the suppressor does not suppress or weakly suppresses the IgM, IgG and/or IgA production" means the dosage at which the suppression rate of the IgG, IgM and/or IgA is 10% or less, preferably 5% or less, more preferably 3% or less as compared with those produced without administration of the selective suppressor of the IgE production of the present invention.

The selective suppressor of the IgE production of the present invention suppresses infiltration of an inflammatory cell to a tissue. The term "inflammatory cell" includes all of a lymphocyte, an eosinophil, a neutrophile and a macrophage, and an eosinophil and/or a neutrophile are preferable.

The effect of the selective suppressor on the IgE production of the present invention is potent for its direct action to B cells. Because the suppressor does not affect the humoral immunity concerning a biological protective reaction, it has many advantages, for example, little side effect such as infections etc., All of compounds that have the above effect are useful as an immunosuppressor regardless of the structure and one of the examples is the compound (I) or (I") of the present invention.

The compounds of the present invention also include ones which have the suppressive effect on a mitogen reaction and/or a cytokine reaction.

Specifically, the compounds have a potent antiproliferative effect on T and/or B cells and/or a suppressive effect on the IL-5 and/or IL-4 production. They selectively suppress the IL-4 and/or IL-5 production and do not suppress the IL-2 production.

The immunosuppressor or anti-allergic agent of the present invention is useful for prevention or a treatment of allergic diseases such as a rejection symptom against a transplantation of an organ or a tissue, a graft-versus-host reaction which is caused by a bone marrow transplantation, atopic allergic diseases (for example, a bronchial asthma, an allergic rhinitis, an allergic dermatitis and the like), a hypereosinophils syndrome, an allergic conjunctivitis, a systemic lupus erythematosus, a polymyositis, a dermatomyositis, a scleriasis, MCTD, a chronic rheumatoid arthritis, an inflammatory bowel disease, an injury caused by ischemia-reperfusion, a pollenosis, an allergic rhinitis, an urticaria, a psoriasis and the like.

When the compound of the present invention is administered as a immunosuppressor and/or anti-allergic agent, it can safely be administered both orally and parenterally. In the case of an oral administration, it may be in any usual forms such as tablets, granules, powders, capsules, pills, solutions, suspensions, syrups, buccal tablets, sublingual tablets and the like for the administration. When the compound is parenterally administered, any usual forms are preferable, for example, injections such as intravenous injections and intramuscular injections, suppositories, endermic agents, vapors and the like. An oral administration is particularly preferable.

A pharmaceutical composition may be manufactured by mixing an effective amount of the compound of the present invention with various pharmaceutical ingredients suitable for the administration form, such as excipients, binders, moistening agents, disintegrators, lubricants, diluents and the like. When the composition is of an injection, an active ingredient can be sterilized with a suitable carrier to give a pharmaceutical composition.

Specifically, examples of the excipients include lactose, saccharose, glucose, starch, calcium carbonate, crystalline cellulose and the like, examples of the binders include methylcellulose, carboxymethylcellulose, hydroxypropylcellulose, gelatin, polyvinylpyrrolidone and the like, examples of the disintegrators include carboxymethylcellulose, sodium carboxymethylcellulose, starch, sodium alginate, agar, sodium lauryl sulfate and the like, and examples of the lubricants include talc, magnesium stearate, macrogol and the like. Cacao oil, macrogol, methyl cellulose and the like may be used as base materials of suppositories. When the composition is manufactured as solutions, emulsified injections or suspended injections, dissolving accelerators, suspending agents, emulsifiers, stabilizers, preservatives, isotonic agents and the like may be added. For an oral administration, sweetening agents, flavors and the like may be added.

Although a dosage of the compound of the present invention as an immunosuppressor and/or anti-allergic agent should be determined in consideration of the patient's age and body weight, the type and degree of diseases, the administration route or the like, a usual oral dosage for human adults is 0.05–100 mg/kg/day and the preferable dosage is 0.1–10 mg/kg/day. In the case that it is parenterally administered, although the dosage highly varies with administration routes, a usual dosage is 0.005–10 mg/kg/day, preferably, 0.01–1 mg/kg/day. The dosage may be administered in one or some separate administrations.

The present invention is further explained by the following Examples and Experiments, which are not intended to limit the scope of the present invention.

EXAMPLE

The abbreviations which are used in EXAMPLE mean the following.

| | |
|---|---|
| Bn | benzyl |
| DME | 1,2-dimethoxyethane |
| DMF | N,N-dimethylformamide |
| DMSO | dimethylsulfoxide |
| MCPBA | m-chloroperbenzoic acid |
| MOM | methoxymethyl |
| Ms | methanesulfonyl |
| Py | pyridyl |
| TBS | tert-butyldimethylsilyl |
| Tf | trifluoromethanesulfonyl |
| Ts | p-toluenesulfonyl |

Example 1

Synthesis of the Compounds (I-1), (I-2) and (I-3)

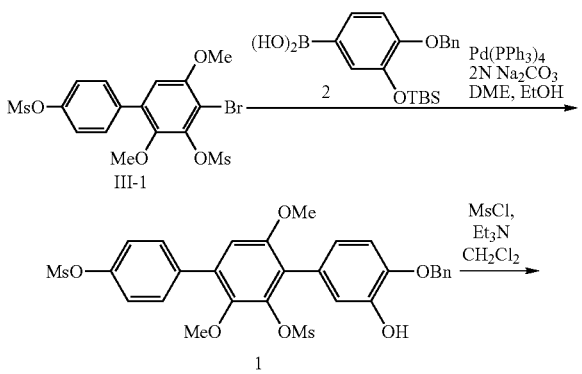

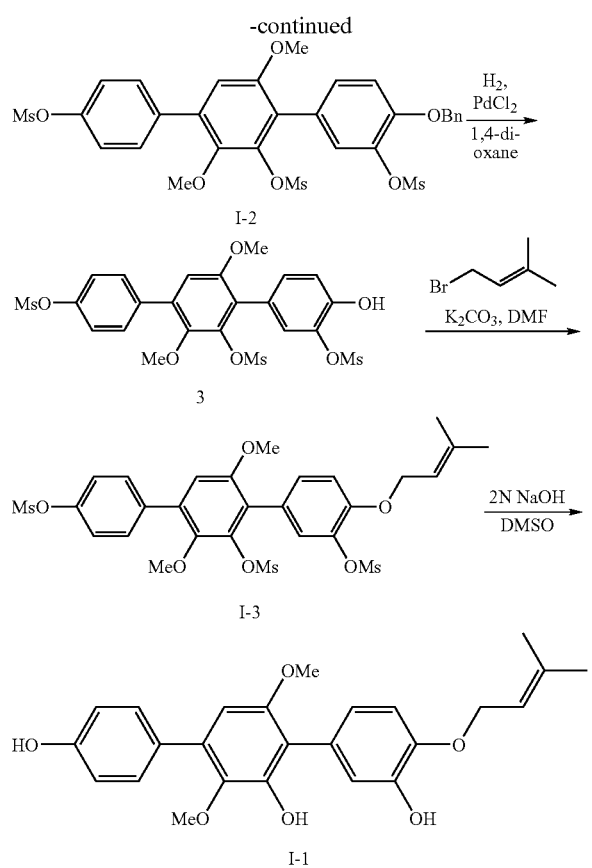

(Step 1) Synthesis of the Compound 1

To 300 ml of a solution of 10.63 g (22.08 mmol) of a compound (III-1) in 1,2-dimethoxyethane was added 3.60 g (3.12 mmol) of tetrakis(triphenylphosphine)palladium (0) at room temperature. To the mixture were added 80 ml of a solution of a compound 2 (9.50 g; 26.5 mmol) in 99% ethanol and 125 ml (250 mmol) of an aqueous solution of 2 M sodium carbonate and the reacted suspension was heated under refluxing in an argon atmosphere for 6 hours. After cooling, the reaction mixture was filtered off to remove an insoluble material and the filtrate was acidified with 2 N hydrochloric acid and extracted with ethyl acetate. The extract was washed with 5% aqueous solution of sodium bicarbonate and saturated brine successively, then dried and concentrated. After the residue was purified by silica gel chromatography (hexane-ethyl acetate 1:1), the obtained product was recrystallized from hexane-ethyl acetate to give the compound 1 (11.57 g; 87% yield) as colorless crystals.

(Step 2) Synthesis of the Compound (I-2)

To 60 ml of a suspension of the compound 1 (9.30 g; 15.48 mmol) in anhydrous dichloromethane was added 3.24 ml (23.22 mmol) of triethylamine, followed by addition of 1.80 ml (23.22 mmol) of methanesulfonyl chloride under ice-cooling and stirred for 2 hours at the same temperature. After the solvent was removed, the residue was acidified with 80 ml of 1 N hydrochloric acid and extracted with chloroform. The extract was washed with 1 N hydrochloric acid, 5% aqueous solution of sodium bicarbonate and saturated brine successively, and the obtained product was dried and concentrated. The obtained residue was recrystallized from hexane-ethyl acetate to give 9.93 g of the compound (I-2) (95% yield) as colorless crystals.

(Step 3) Synthesis of the Compound 3

Stirred were 300 ml of a solution of 9.76 g (14.38 mmol) of the compound (I-2) and 765 mg (4.31 mmol) of palladium chloride (II) in 1, 4-dioxane under a hydrogen atmosphere at room temperature for 15 hours. An insoluble material was removed off by filtration with celite and the obtained filtrate was concentrated. The residue was recrystallized from hexane-ethyl acetate to give the compound 3 (8.43 g; 100% yield) as colorless crystals.

(Step 4) Synthesis of the Compound (I-3)

To 40 ml of a solution of the compound 3 (4.01 g; 6.81 mmol) in anhydrous N, N-dimethylformamide were added successive, 1.45 g (10.5 mmol) of potassium carbonate and 1.21 ml (10.5 mmol) of prenyl bromide. After the mixture was stirred under a nitrogen atmosphere for 15 hours at room temperature, the reaction mixture was poured into 230 ml of 6% aqueous citric acid and extracted with ethyl acetate. The extract was washed with 5% citric acid, 5% aqueous solution of sodium bicarbonate and saturated brine successively, followed by being dried and concentrated. The residue was recrystallized from hexane-ethyl acetate to give 4.01 g of the compound (I-3) (90% yield) as colorless crystals.

(Step 5) Synthesis of the Compound (I-1)

To 38 ml of a solution of 3.80 g (5.79 mmol) of the compound (I-3) in dimethylsulfoxide was added 15 ml (60.0 mmol) of 4 N sodium hydroxide and the reaction mixture was warmed at 60° C. for 4 hours. After the mixture was cooled, 100 ml of 1 N hydrochloric acid was added to it and the obtained mixture was extracted with ethyl acetate. The extract was washed with 5% aqueous solution of sodium bicarbonate and saturated brine successively, then dried and concentrated. The residue was recrystallized from methanol to give 1.72 g of the compound (I-1) (70% yield) as colorless crystals.

Reference Example 1

Synthesis of the compound 2

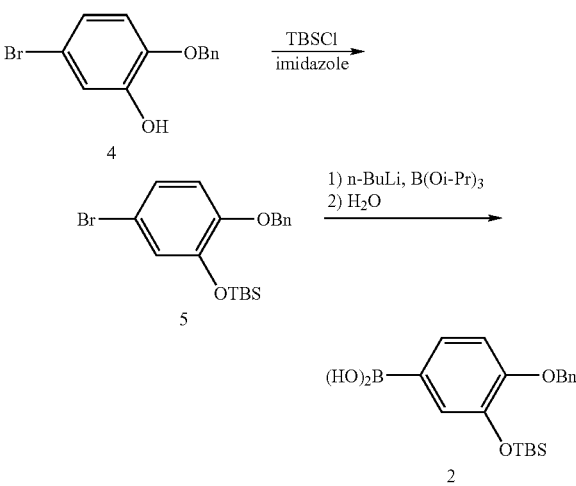

To a solution of the compound 4 (80.0 g; 0.287 mol) in 300 ml of N, N-dimethylformamide were added tert-butyldimethylsilyl chloride (45.87 g; 0.296 mol) and imidazole (21.46 g; 0.315 mol) and stirred at room temperature for 19 hours. The reaction mixture was poured into 1 L of water and extracted with ether. The extract was washed with water and saturated brine successively and then dried and concentrated. The residue was purified by silica gel chromatography (hexane-ethyl acetate 50:1) to give the compound 5 (97.20 g; 86% yield) as a colorless oil.

To 850 ml of a solution of the compound 5 (97.20 g; 0.247 mol) in anhydrous tetrahydrofuran was added 152 ml (0.252 mol) of a solution of 1.66 N n-butyllithium in hexane under a nitrogen atmosphere at −70° C. and stirred at the same temperature for 1.5 hours. To the mixture was added 171 ml (0.741 mol) of triisopropyl borate at −70° C. and stirred for 3 hours with gradually warming to room temperature. Under cooling with ice, 500 ml of water and 320 ml of 5% citric acid were added to the mixture and stirred at the same temperature for 30 minutes. The solution was extracted with ethyl acetate and the extract was washed with water and saturated brine successively, then dried and concentrated. The residue was purified by silica gel chromatography (hexane-ethyl acetate 2:1) to give the compound 2 (51.10 g; 58% yield) as colorless crystals.

Reference Example 2

Synthesis of the Compound (III-1)

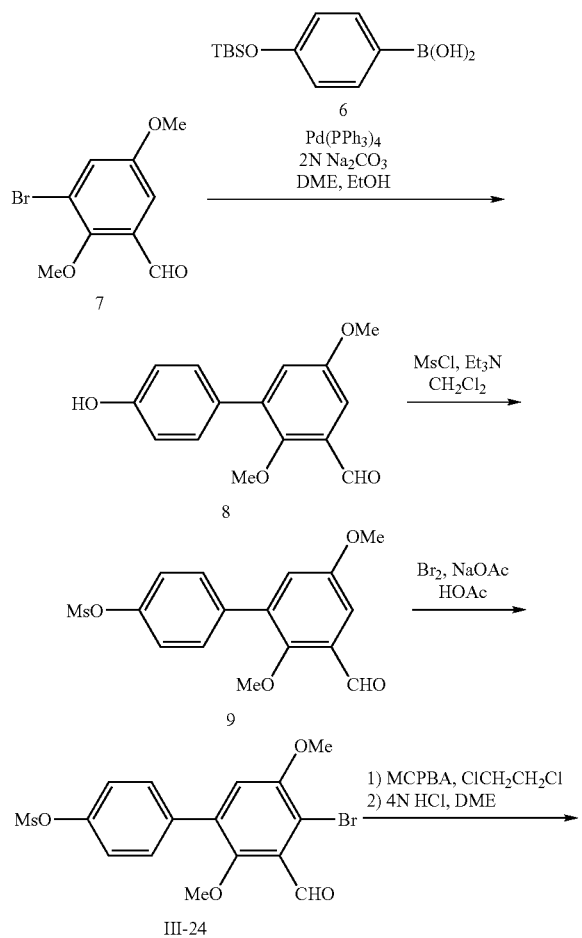

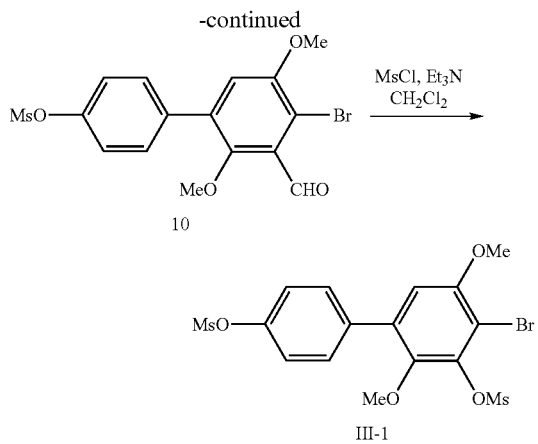

(Step 1) Synthesis of the Compound 8

To a solution of 15.30 g (62.4 mmol) of a compound 7 (Journal of Chemical Society, 1925, 1998) in 300 ml of 1,2-dimethoxyethane was added 3.60 g (3.12 mmol) of tetrakis(triphenylphosphine)palladium (0) at room temperature. To the mixture were added a solution of 18.89 g (74.9 mmol) of a compound 6 (GB-A No. 2276162) in 80 ml of 99% ethanol and 125 ml (250 mmol) of an aqueous solution of 2 M sodium carbonate and the reaction suspension was heated under refluxing in an argon atmosphere for 6 hours. After cooling, the reaction mixture was filtered off to remove an insoluble substance. The filtrate was acidified with 2 N hydrochloric acid and extracted with ethyl acetate. The extract was washed with 5% aqueous solution of sodium bicarbonate and saturated brine successively, then dried and concentrated. The residue was purified by silica gel chromatography (hexane-ethylacetate 1:1) and recrystallized from hexane-ethyl acetate to give the compound 8 (15.68 g; 97% yield) as colorless crystals.

(Step 2) Synthesis of the Compound 9

To a suspension of the compound 8 (15.34 g; 59.39 mmol) in 240 ml of anhydrous dichloromethane were added 16.6 ml (118.8 mmol) of triethylamine and 6.93 ml (89.09 mmol) of methanesulfonyl chloride under ice-cooling and stirred at the same temperature for 2 hours. After the solvent was removed, the residue was acidified with 1 N hydrochloric acid (100 ml) and extracted with ethyl acetate. The extract was washed with 1 N hydrochloric acid, 5% aqueous solution of sodium bicarbonate and saturated brine successively, then dried and concentrated. The residue was recrystallized from hexane-ethyl acetate to give the compound 9 (17.24 g; 86% yield) as colorless crystals.

(Step 3) Synthesis of the Compound (III-24)

To 210 ml of a suspension of the compound 9 (17.03 g; 50.63 mmol) in acetic acid were added 6.23 g (75.95 mmol) of sodium acetate and 3.91 ml (75.95 mmol) of bromine at room temperature and stirred at the same temperature for 16 hours. After 3.91 ml (75.95 mmol) of bromine was added to the reacted suspension and stirred at 50° C. for 4 hours, 3.91 ml (75.95 mmol) of bromine was added and stirred at 50° C. for 3 hours. The reaction mixture was poured into 1 L of 1 M aqueous sodium thiosulfate and stirred for 30 minutes. The precipitate was collected by filtration and washed with water. The obtained crystals were dissolved in 800 ml of chloroform, washed with 5% aqueous solution of sodium bicarbonate and saturated brine successively, then dried and concentrated. The residue was recrystallized from hexane-ethyl acetate to give the compound (III-24) (18.12 g; 86% yield) as colorless crystals.

(Step 4) Synthesis of the Compound 10

To a suspension of the compound (III-24) (15.80 g; 38.05 mmol) in 400 ml of 1,2-dichloroethane was added 12.30 g (57.05 mmol) of 80% m-chloroperoxybenzoic acid at room temperature and stirred at the same temperature for 17 hours. The reaction mixture was poured into 360 ml of 0.2 M aqueous sodium thiosulfate and extracted with chloroform. The extract was washed with 300 ml of 0.2 M sodium thiosulfate and 200 ml of 5% of sodium bicarbonate (×2) successively, then dried and concentrated. The residue (15.80 g) was dissolved in 330 ml of 1,2-dimethoxyethane and 30 ml (120 mmol) of 4 N hydrochloric acid was added. After the reaction mixture was stirred at 50° C. for 12 hours and cooled, the solvent was removed and the residue was extracted with ethyl acetate. The extract was washed with 5% aqueous solution of sodium bicarbonate and saturated brine successively, then dried and concentrated to give the compound 10 (14.35 g; 97% yield) as pale brown crystals.

(Step 5) Synthesis of the Compound (III-1)

Using an analogous procedure for the compound (I-4), 12.63 g of the compound (III-1) as colorless crystals (88% yield) was obtained from the compound 10 (12.0 g; 29.76 mmol).

Example 2

Synthesis of the Compound (I-4)

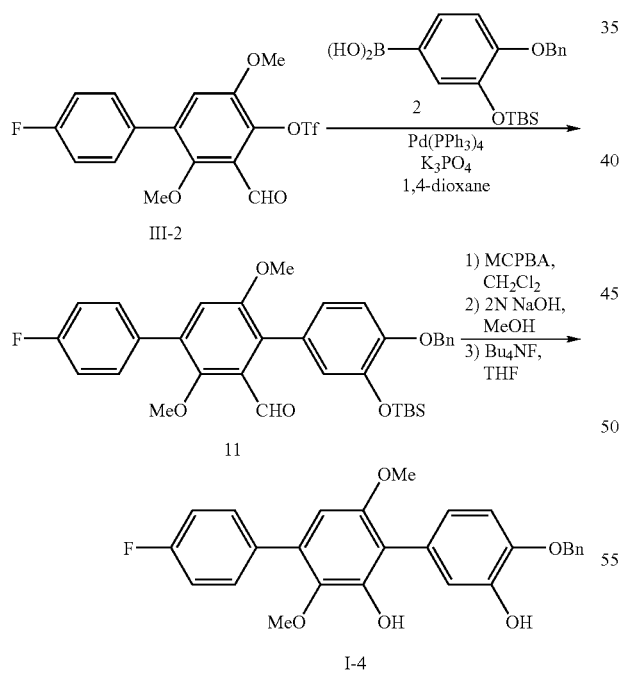

(Step 1) Synthesis of the Compound 11

To a solution of 816 mg (2 mmol) of a compound (III-2) in 40 ml of 1,4-dioxane were added 114 mg (0.1 mmol) of tetrakis(triphenylphosphine)palladium (0), 748 mg (2.09 mmol) of the compound 2 and 589 mg (2.77 mmol) of powders of anhydrous potassium phosphate at room temperature and heated in a nitrogen atmosphere at 85° C. for 23 hours. The reaction mixture was cooled and extracted with ethyl acetate. The extract was washed with 2 N hydrochloric acid, 5% aqueous sodium bicarbonate and saturated brine successively, then dried and concentrated. The residue was purified by silica gel chromatography (hexane-ethyl acetate 4:1) and crystallized from pentane to give the compound 11 (745 mg; 67% yield) as pale yellow crystals.

(Step 2) Synthesis of the Compound (I-4)

To a solution of the compound 11 (557 mg; 1 mmol) in 10 ml of dichloromethane was added 259 mg (1.2 mmol) of 80% m-chloroperbenzoic acid at room temperature and stirred for 15 hours. The reaction mixture was poured into 0.1 M aqueous sodium thiosulfate and extracted with ethyl acetate. The extract was washed with 0.1 M aqueous sodium thiosulfate, 5% aqueous sodium bicarbonate and saturated brine successively, then dried and concentrated. To a solution of 650 mg of the obtained residue in 5 ml of methanol was added a solution of 1 M sodium methoxide in 2 ml of methanol under ice-cooling and stirred for 30 minutes. After the reacted solution was acidified with 2 N hydrochloric acid and extracted with ethyl acetate, the extract was washed with saturated brine, then dried and concentrated. To a solution of 647 mg of the obtained residue in 10 ml of tetrahydrofuran was added 2 ml of 1 M tetrabutylammonium fluoride in tetrahydrofuran under ice-cooling and stirred for 30 minutes. The obtained reaction mixture was poured into 2 N aqueous hydrochloric acid under ice-cooling to acidify and extracted with ethyl acetate. The ethyl acetate layer was washed with water, 5% aqueous sodium bicarbonate and saturated brine successively, then dried and concentrated. The residue was purified by silica gel chromatography (hexane-ethyl acetate 2:1) to give 275 mg of the compound (I-4) (62% yield) as powders.

Reference Example 3

Synthesis of the Compound (III-2)

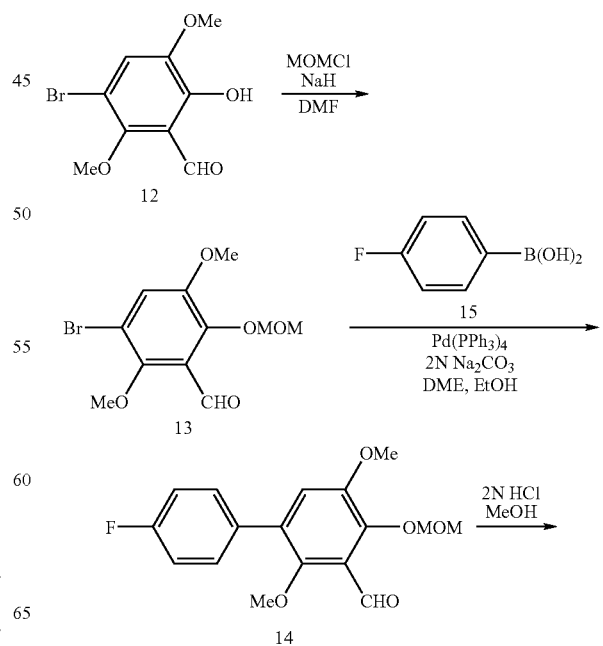

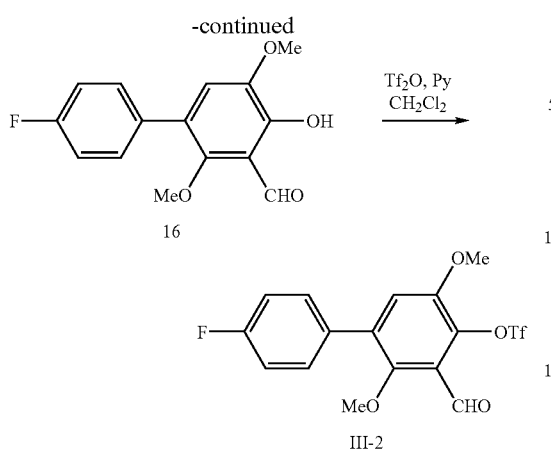

Example 3

Synthesis of the compounds (I-5), (I-6) and (I-7)

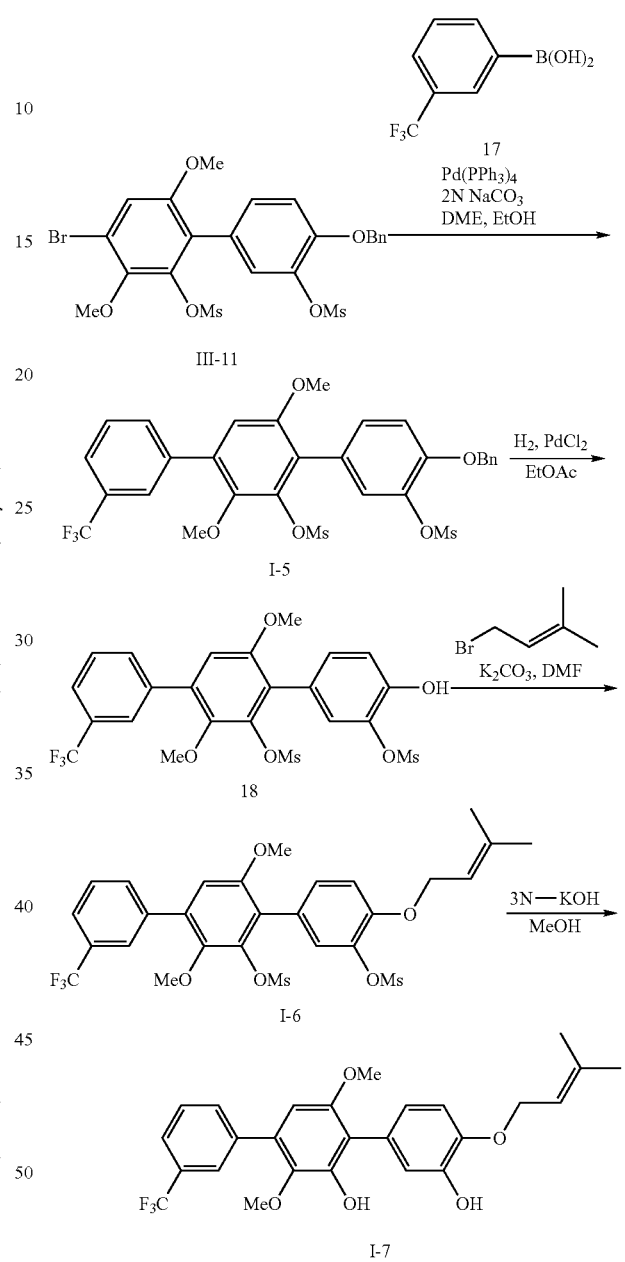

(Step 1) Synthesis of the Compound 13

To 26 ml of a solution of 2.61 g (10 mmol) of a compound 12 (Journal of Organic Chemistry, 1987, 52, 4485) in dimethylformamide were added 400 mg (10 mmol) of 60% sodium hydride dispersion in oil and 836 mg (11 mmol) of chloromethyl methyl ether under ice-cooling and stirred for 30 minutes. After warming to room temperature, it was further stirred for 1 hours. The reaction mixture was concentrated under reduced pressure and extracted with ethyl acetate. The extract was washed with 5% aqueous solution of sodium bicarbonate and saturated brine successively, then dried and concentrated. The residue was recrystallized from ethyl acetate-hexane-pentane to give the compound 13 (2.8 g; 92% yield).

(Step 2) Synthesis of the Compound 14

Using an analogous procedure for the compound 8, the compound 14 was obtained as a pale yellow oil (96% yield) from the compound 13 and the compound 15 (Tokyo Kasei Kogyo Co., Ltd.).

(Step 3) Synthesis of the Compound 16

To 16 ml of a suspension of 1.38 g (4.3 mmol) of the compound 14 in methanol was added 4 ml of 2 N aqueous hydrochloric acid and stirred for 1 hour under warming at 60° C. The reaction mixture was concentrated under reduced pressure and extracted with ethyl acetate. The extract was washed with 5% aqueous sodium bicarbonate and saturated brine successively, then dried and concentrated to give the compound 16 (1.12 g; 94% yield) as a yellow crystalline residue.

(Step 4) Synthesis of the Compound (III-2)

To 12 ml of a solution of the compound 16 (1.12 g; 4.05 mmol) in anhydrous dichloromethane was added 1.02 ml (6.08 mmol) of trifluoromethanesulfonic anhydride and then 980 ml (12.2 mmol) of pyridine under ice-cooling and stirred for 30 minutes. The reaction mixture was allowed to warm to room temperature and stirred for additional 2 hours and the solvent was removed. The residue was extracted with ethyl acetate, washed with 5% aqueous sodium bicarbonate and saturated brine successively, then dried and concentrated. The obtained crude product was purified by silica gel chromatography to give 1.23 g of the compound (III-2) (74% yield) as a white crystalline residue.

(Step 1) Synthesis of the Compound (I-5)

Using an analogous procedure for the compound 1 in Example 1, 634 mg (0.972 mmol) of the compound (I-5) was synthesized from 881 mg (1.50 mmol) of the compound (III-11) and 370 mg (1.95 mmol) of 3-trifluoromethyl boric acid. 65% yield.

(Step 2) Synthesis of the Compound 18

Using an analogous procedure for the compound 3 in Example 1, the compound 18 (360 mg; 0.640 mmol) was synthesized from 433 mg (0.664 mmol) of the compound (I-5). 96% yield.

(Step 3) Synthesis of the Compound (I-6)

Using an analogous procedure for the compound (I-3) in Example 1, 185 mg (0.293 mmol) of the compound (I-6) was synthesized from the compound 18 (170 mg; 0.302 mmol). 97% yield.

(Step 4) Synthesis of the Compound (I-7)

Using an analogous procedure for the compound (I-1) in Example 1, 85 mg (0.179 mmol) of the compound (I-7) was synthesized from 150 mg (0.238 mmol) of the compound (1–6). 75% yield.

Reference Example 4

Synthesis of the Compound (III-11)

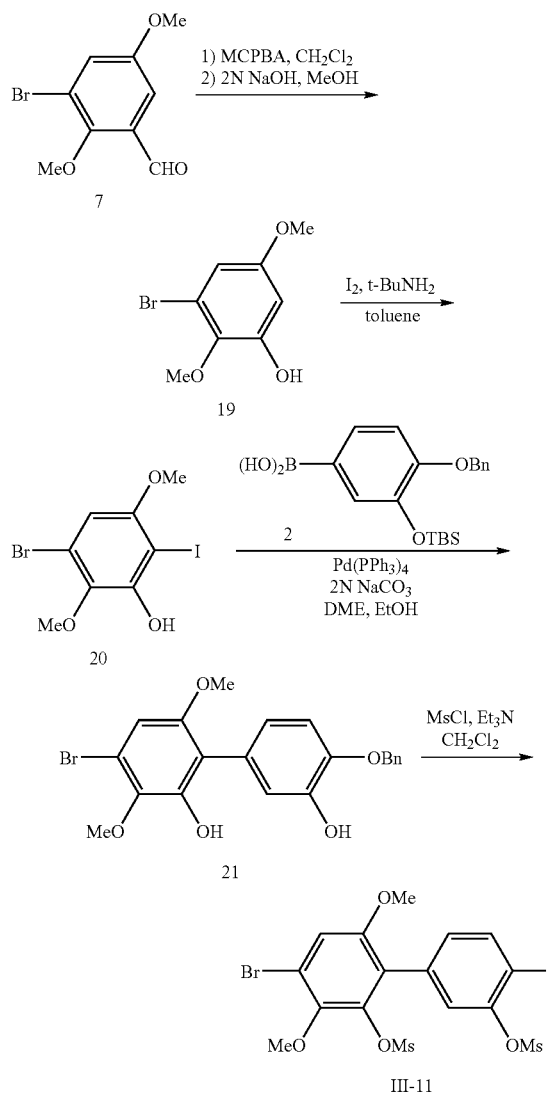

(Step 2) Synthesis of the Compound 20

To a solution of tert-butylamine (5.0 ml; 47.8 mmol) in 10 ml of toluene was added iodine (5.94 g; 23.39 mmol) under a nitrogen atmosphere and stirred for 50 minutes at room temperature. The compound 19 (5.46 g; 23.43 mmol) was added to the solution under ice-cooling, then warmed to room temperature and stirred for 6 days. The reaction mixture was poured into 1 M of aqueous sodium thiosulfate and extracted with ethyl acetate. The extract was washed with 1 M aqueous sodium thiosulfate and saturated brine successively, then dried and concentrated to give the compound 20 (8.30 g; 23.16 mmol). 99% yield.

(Step 3) Synthesis of the Compound 21

Using an analogous procedure for the compound 1 in Example 1, the compound 21 (2.10 g; 4.87 mmol) was synthesized from the compound 20 (8.70 g; 24.20 mmol). 20% yield.

(Step 4) Synthesis of the Compound (III-11)

Using an analogous procedure for the compound (I-2) in Example 1, 2.61 g (4.44 mmol) of the compound (III-11) was synthesized from the compound 21 (3.20 g; 7.42 mmol). 60% yield.

Example 4

Synthesis of the Compound (I-9)

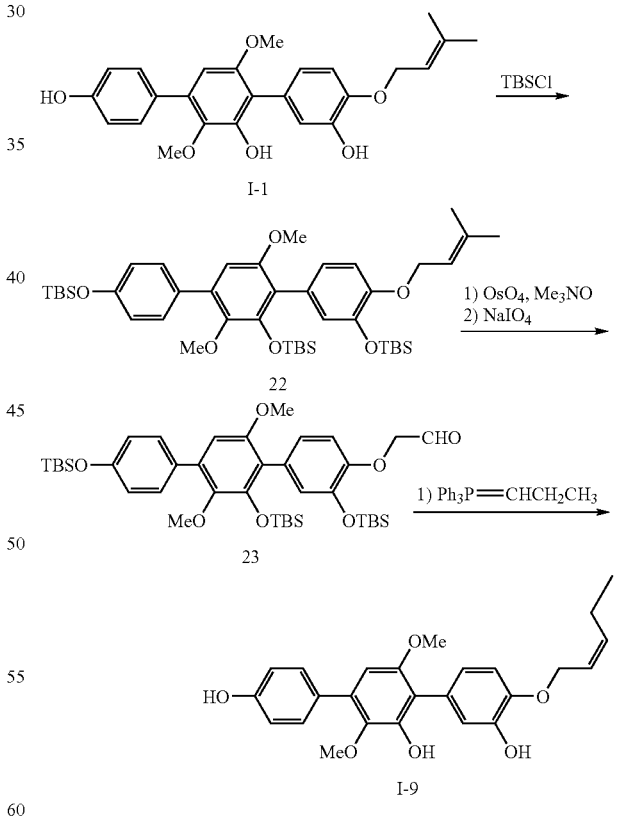

(Step 1) Synthesis of the Compound 19

Using an analogous procedure for the compound 10 in Reference Example 2, the compound 19 (24.04 g; 103 mmol) was synthesized from the compound 7 (40.03 g; 163 mmol). 63% yield.

(Step 1) Synthesis of the Compound 22

Using an analogous procedure described in Reference Example 1, 1.53 g (3.63 mmol) of the compound (I-1) was silylated and the obtained crude product was crystallized from methanol to obtain the compound 22 (2.62 g; 95% yield) as colorless crystals.

(Step 2) Synthesis of the Compound 23

To a solution of the compound 22 (2.38 g; 3.1 mmol) in 90 ml of acetone were added 415 mg (3.74 mmol) of trimethylamine-N-oxide dihydrate and 1.60 ml of 5% aqueous solution of osmium tetroxide (0.3 mmol) and stirred for 1 hour at room temperature. After 20 ml of water was added to the reaction mixture, 4.0 g of sodium bicarbonate and 4.0 g of sodium bisulfite were added and stirred for 30 minutes. The reaction mixture was concentrated under reduced pressure and the residue was extracted with ethyl acetate. The extract was washed with saturated brine, then dried and concentrated.

A solution of 1.96 g (9.16 mmol) of sodium periodate in 33 ml of water was added dropwise to a solution of 2.46 g of the residue obtained by the above method in 90 ml of ethanol with stirring at room temperature. After stirring for 2 hours, 100 ml of water was added to the reaction mixture and the precipitate was collected by filtration and dried to give the compound 23 (1.98 g; 87% yield) as powder.

(Step 3) Synthesis of the Compound (I-9)

To a suspension of 146 mg (0.38 mmol) of n-propyltriphenylphosphonium bromide in 2.5 ml of anhydrous tetrahydrofuran was added 32 mg (0.29 mmol) of potassium tert-butoxide in a nitrogen atmosphere at 0° C. and stirred at the same temperature for 1 hour. The reaction mixture was cooled to −78° C., a solution of the compound 23 (70 mg; 0.095 mmol) in 1.5 ml of anhydrous tetrahydrofuran was added and stirred for 30 minutes at the same temperature and for additional 1 hour at room temperature. The reaction mixture was poured into an ice-cooling aqueous solution of saturated ammonium chloride and extracted with ethyl acetate. The extract was washed with saturated brine, then dried and concentrated.

Using an analogous procedure described in Example 2 Step 2, 70 mg of the residue obtained by the above method was desilylated and the obtained crude product was purified by silica gel chromatography (toluene-ethyl acetate 4:1) to give 37 mg of the compound (I-9) as pale yellow crystals.

Example 5

Synthesis of the Compound (I-565)

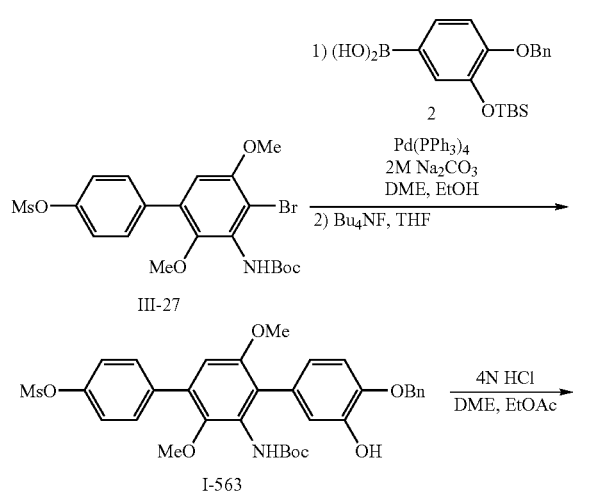

-continued

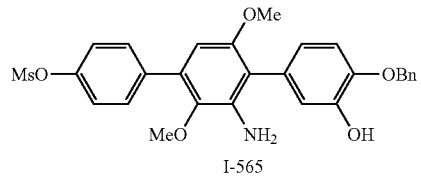

I-565

(Step 1) Synthesis of the Compound (I-563)

Using an analogous procedure for the compound 2 in Example 1, 850 mg of the compound (I-563) was obtained from a compound (III-27) (800 mg; 1.59 mmol) and the compound 2 (1.25 g; 3.50 mmol) as colorless crystals (86% yield).

(Step 2) Synthesis of the Compound (I-565)

To a solution of 120 mg (0.193 mmol) of the compound (I-563) in 3 ml dimethoxyethane and 1 ml of ethyl acetate was added 2.4 ml of 4 N hydrochloric acid at 40° C. and stirred at the same temperature for 2 hours 20 minutes. After cooling, the reaction mixture was neutralized with aqueous solution of saturated sodium bicarbonate and extracted with ethyl acetate. The extract was washed with saturated aqueous solution of sodium bicarbonate and saturate brine, then dried and concentrated. The obtained crude product was crystallized from hexane-ethyl acetate to give 93 mg of the compound (I-565) as pale yellow crystals (92% yield).

Reference Example 5

Synthesis of the Compound (III-27)

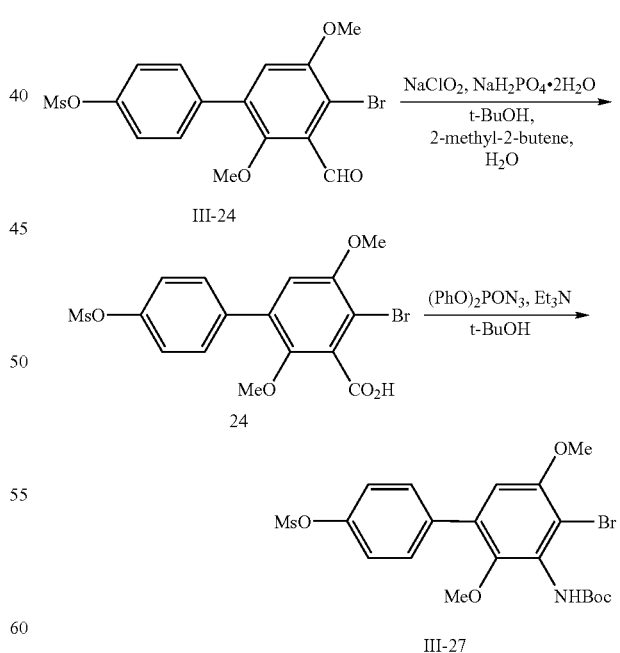

(Step 1) Synthesis of the Compound 24

In a mixture of 17.5 ml of tert-butanol and 5.3 ml of 2-methyl-2-butene was suspended 415 mg (1.00 mmol) of the compound (III-24), 6.7 ml of aqueous solution of 724 mg (8.00 mmol) of sodium chlorite and 968 mg (6.20 mmol) of sodium dihydrogen phosphate dihydrate was added and stirred at the same temperature for 4 hours 30 minutes. The solution of 1 M sodium thiosulfate was added to the reaction mixture and the mixture was extracted with ethyl acetate. Then, organic layer was extracted with aqueous solution of saturated sodium bicarbonate. Then the aqueous layer was acidified with conc. hydrochloric acid and extracted with ethyl acetate. The extract was washed with saturated brine, then dried and concentrated to give the compound 24 (384 mg; 89% yield) as colorless crystals.

(Step 2) Synthesis of the Compound (III-27)

To 10 ml of a suspension of the compound 24 (1.50 g; 3.48 mmol) in tert-butanol were added 0.533 ml (3.83 mmol) of triethylamine, followed by 0.825 ml (3.83 ml) of diphenyl phosphate azide, and the mixture was stirred at 100° C. for 23 hours. After the reaction mixture was cooled, water was added to it and the mixture was extracted with ethyl acetate. The extract was washed with saturated aqueous solution of sodium bicarbonate and saturated brine, then dried and concentrated. The residue was purified by silica gel chromatography (hexane-ethyl acetate 2.5:1) to give 1.43 g of the compound (III-27) as colorless form product (82% yield).

Example 6

Synthesis of the Compound (I-480)

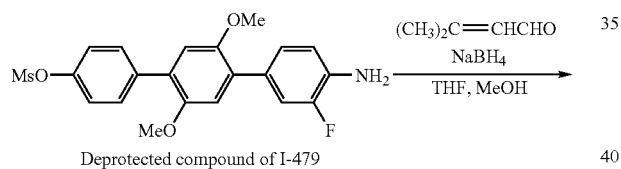

Deprotected compound of I-479

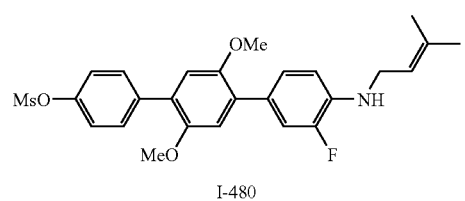

I-480

To a solution of 120 mg of a compound which was eliminated a Boc group of the compound (I-479) in 2 ml of tetrahydrofuran and 0.5 ml of methanol were added 33 ml (0.34 mmol) of 3-methyl-2-butenal and 90 ml (0.26 mmol) of 3 M aqueous solution of sulfuric acid at 0° C. and stirred for 10 minutes. Further, 19.6 mg of sodium borohydride was added in small portions to the mixture and stirred at room temperature for 1 hour. The saturated aqueous solution of sodium bicarbonate was added to the reaction mixture and extracted with ethyl acetate. The extract was washed with saturated brine, then dried and concentrated. The residue was purified by silica gel chromatography (hexane-ethyl acetate 3:1) to give 98 mg of the compound (I-480) as colorless crystals (78% yield).

Example 7

Synthesis of the Compound (I-628)

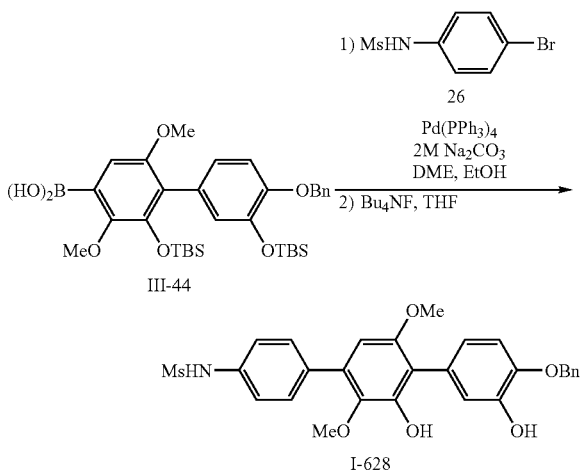

Using an analogous procedure for the compound 1 in Example 1, 1.2 g (2 mmol) of the compound (III-44) was reacted with 551 mg (2.2 mmol) of 4-bromomethanesulfonyl anilide were reacted, followed by desilylated by an analogous procedure described in Example 1 Step 2. The obtained crude product was crystallized from ethyl acetate-hexane to obtain 760 mg of the compound (I-628) as pale yellow crystals (73% yield).

Reference Example 6

Synthesis of the Compound (III-44)

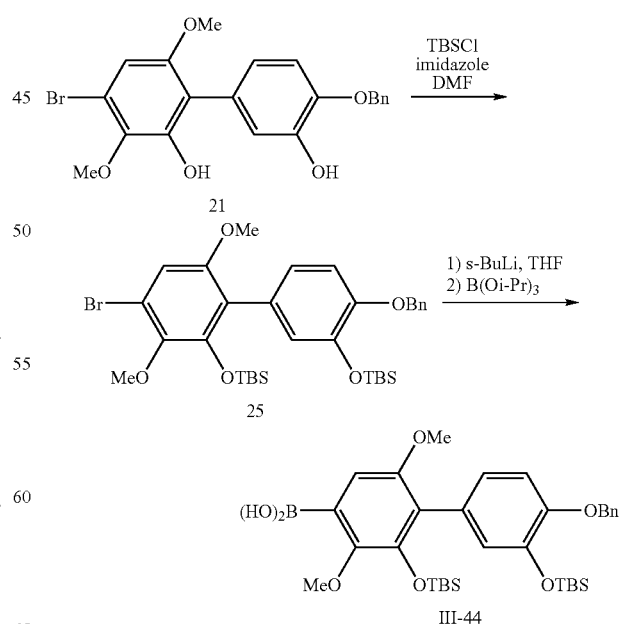

(Step 1) Synthesis of the Compound 25

Using an analogous procedure for the compound 5 in Reference Example 1, a crude product was synthesized by the reaction of 22.2 g (52.7 mmol) of the compound 21, 8.95 g (132 mmol) of imidazole and 17.5 g (1.16 mmol) of tert-butyldimethylsilyl chloride. The obtained product was purified by silica gel chromatography (ethyl acetate:hexane=1:20) and crystallized from ethyl acetate-hexane to give 29.7 g of the compound 25 as colorless crystals (85% yield).

(Step 2) Synthesis of the Compound (III-44)

Using an analogous procedure for the compound 2 in Reference Example 1, 402.7 g (610 mmol) of the compound 25 was reacted with 678 ml (814 mmol) of 1.08 N s-butyl lithium in cyclohexane, followed by addition of 282 ml (1.22 mol) of triisopropyl borate to give 246 g of the compound (III-44) as colorless powders (65% yield).

Example 8

Synthesis of the Compound (I-233)

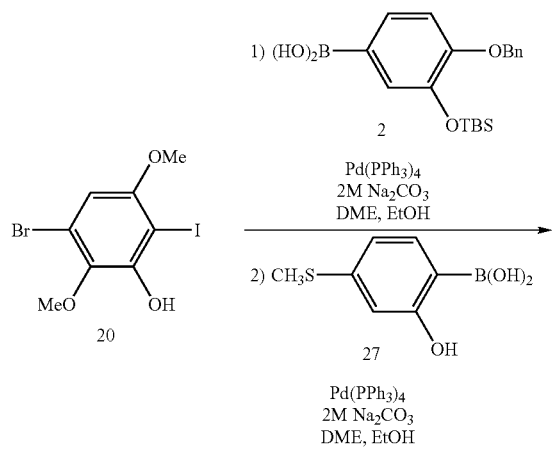

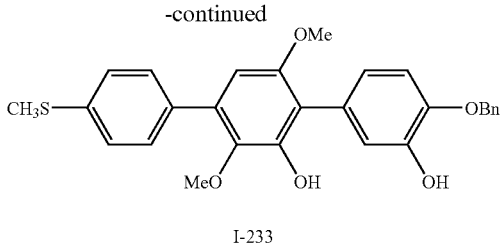

In an argon atmosphere, 2.87 g (8.0 mmol) of the compound 20 was dissolved in 32 ml of dimethoxyethane and 8 ml of ethanol, 3.01 g of the compound 2 and 16 ml of 2 M aqueous solution of sodium carbonate were added and the reaction mixture was degassed. To the mixture was added 462 mg (0.4 mmol) of palladium tetrakistriphenylphosphine and the mixture was heated under refluxing for 2 hours. After the reaction mixture was cooled to room temperature, 2.02 g (12.0 mmol) of 4-methylthiophenyl boronic acid, 462 mg (0.4 mmol) of palladium tetrakistriphenylphosphine, 16 ml of 2 M aqueous solution of sodium carbonate, 32 ml of dimethoxyethane and 8 ml of ethanol were added to it. Then, the reaction mixture was degassed again and heated under refluxing for 16 hours. After the reaction mixture was cooled to room temperature, 100 ml of 5% aqueous citric acid was added and stirred at the same temperature for 1 hour. Ethyl acetate was added to the reaction mixture and the organic layer was washed with 5% aqueous citric acid, water, saturated aqueous solution of sodium bicarbonate and saturated brine successively, then dried and concentrated. The residue was purified by silica gel chromatography (hexane-ethyl acetate 3:1) to obtain 2.13 g of crude crystals. The obtained crude crystals were recrystallized from hexane-ethyl acetate to give 1.66 g of the compound (I-233) as colorless crystals (44% yield).

Example 9

Synthesis of other Compounds

Following compounds (I) were synthesized by analogous procedures described above. The structures and physical constants of the compounds (III) and (I) are as follows.

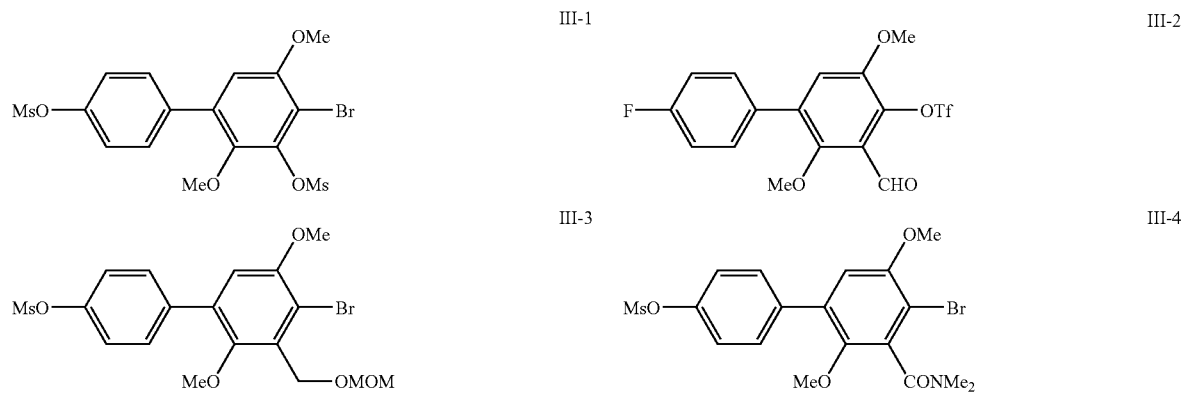

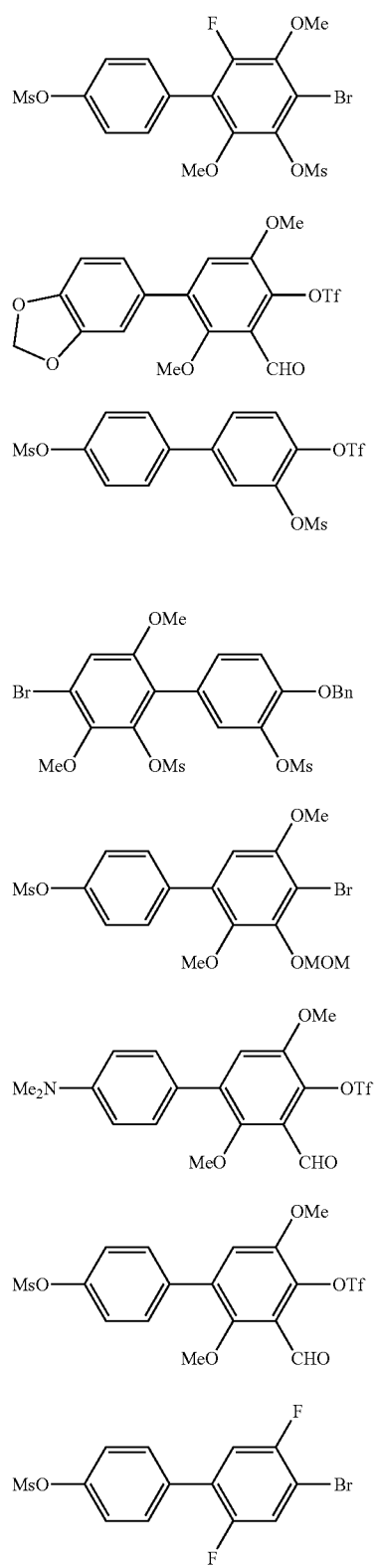
-continued
III-5 III-6 III-7 III-8 III-9 III-10 III-11 III-12 III-13 III-14 III-15 III-16 III-17 III-18 III-19 III-20

-continued
III-21 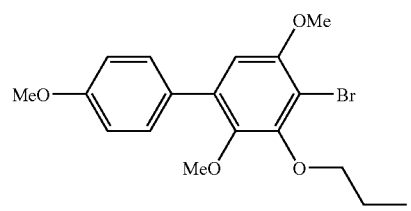
III-22 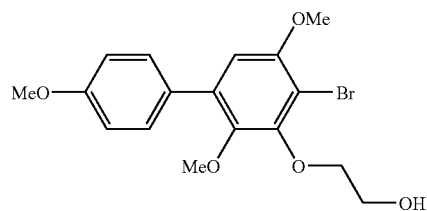
III-23 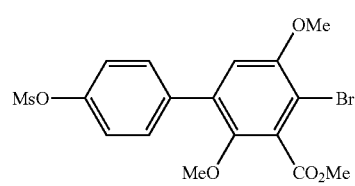
III-24 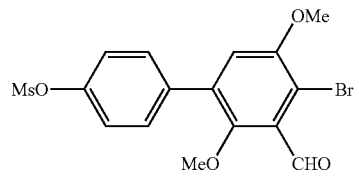
III-25 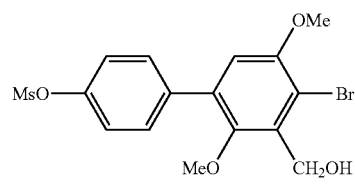
III-26 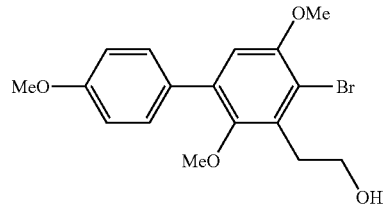
III-27 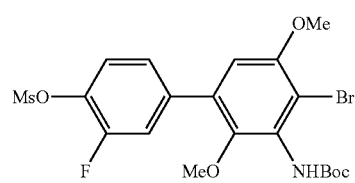
III-28 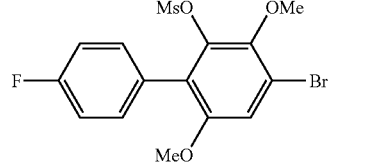
III-29 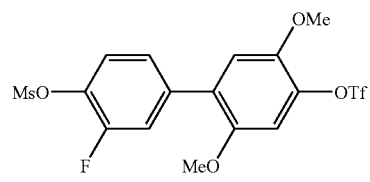
III-30 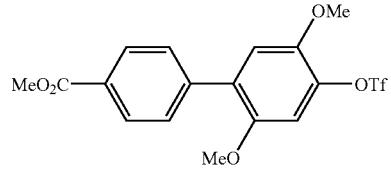
III-31 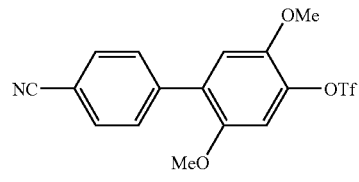
III-32 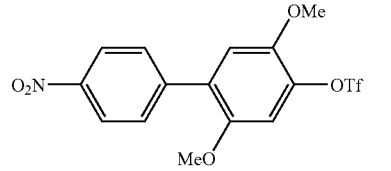
III-33 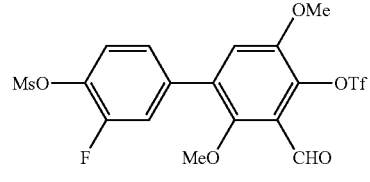
III-34 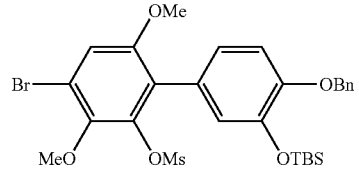
III-35 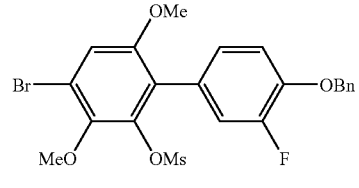
III-36 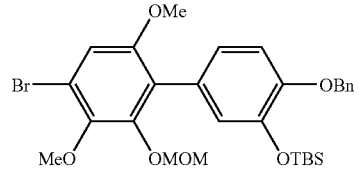

III-37 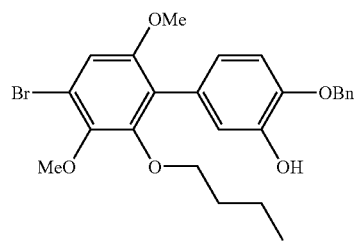
III-38 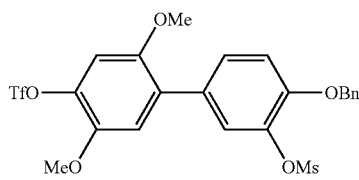
III-39 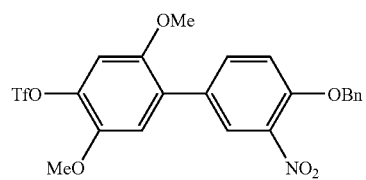
III-40 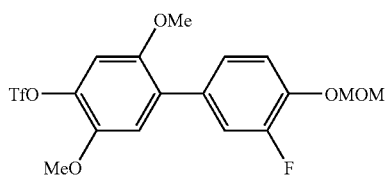
III-41 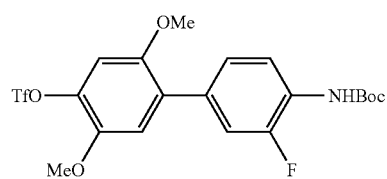
III-42 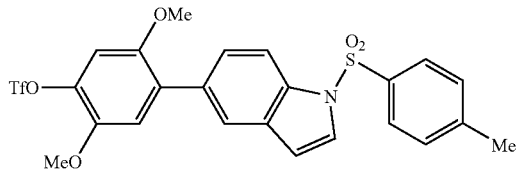
III-43 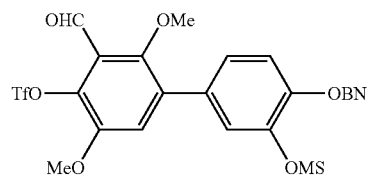
III-44 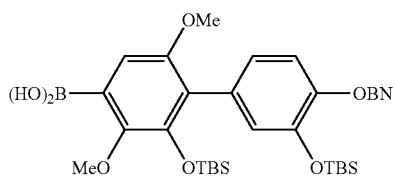
III-45 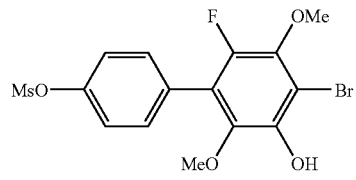
III-46 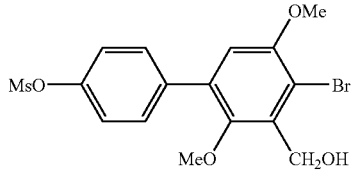
III-47 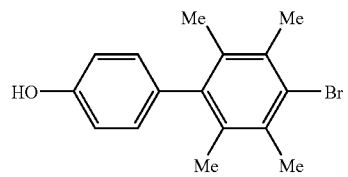
III-48 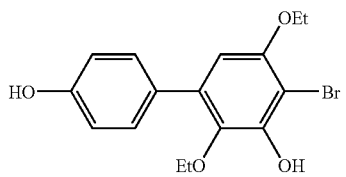
III-49 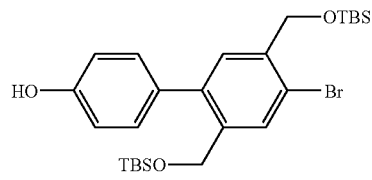
III-50 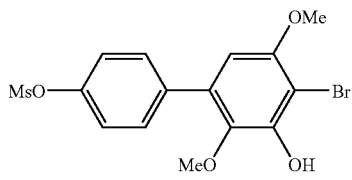
III-51 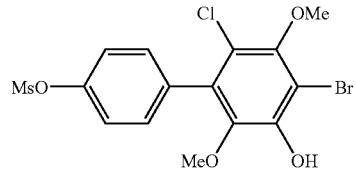
III-52 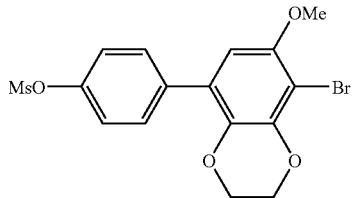

-continued
III-53 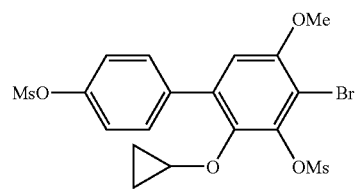
III-54 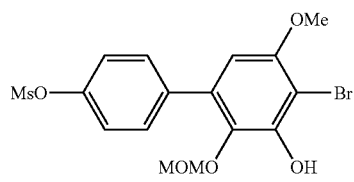
III-55 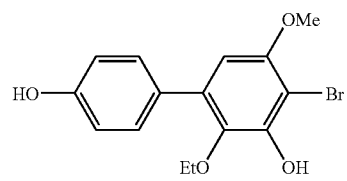
III-56 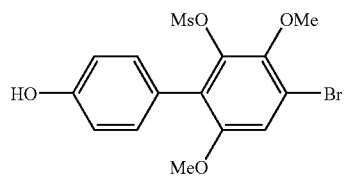
III-57 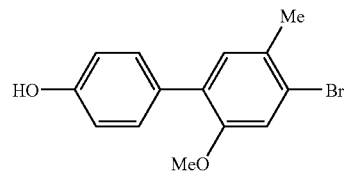
III-58 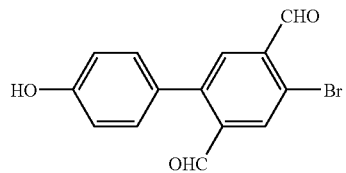
III-59 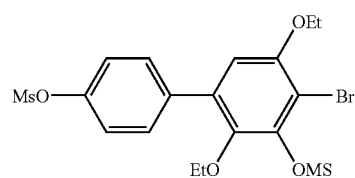
III-60 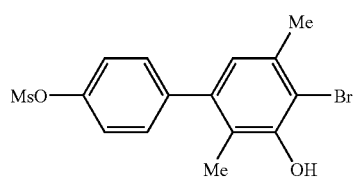
III-61 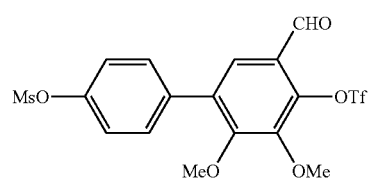
III-62 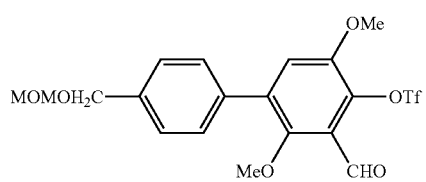
III-63 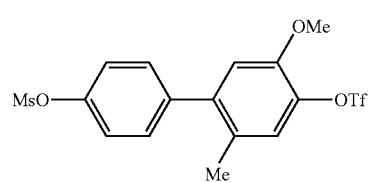
III-64 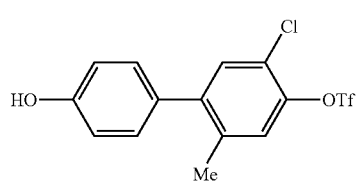
III-65 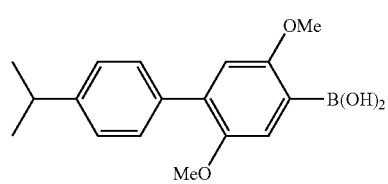
III-66 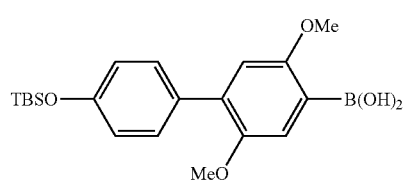
III-67 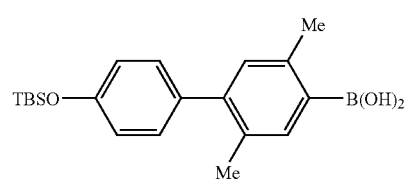
III-68 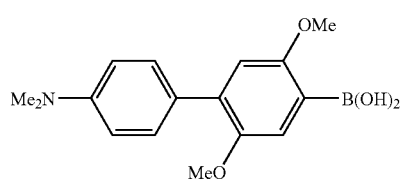

-continued
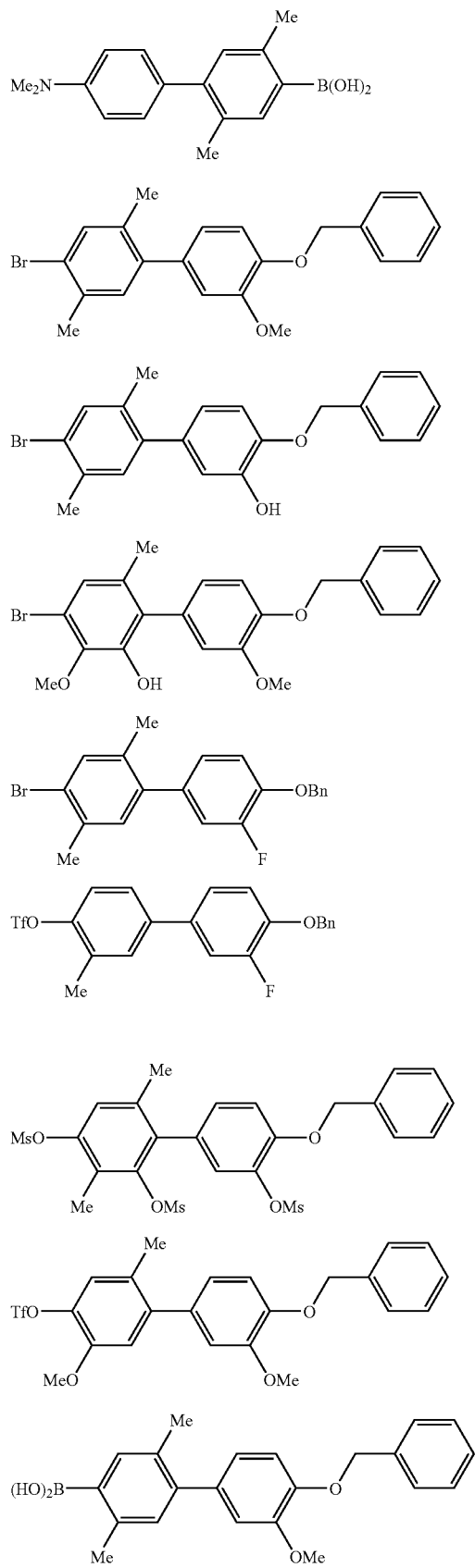
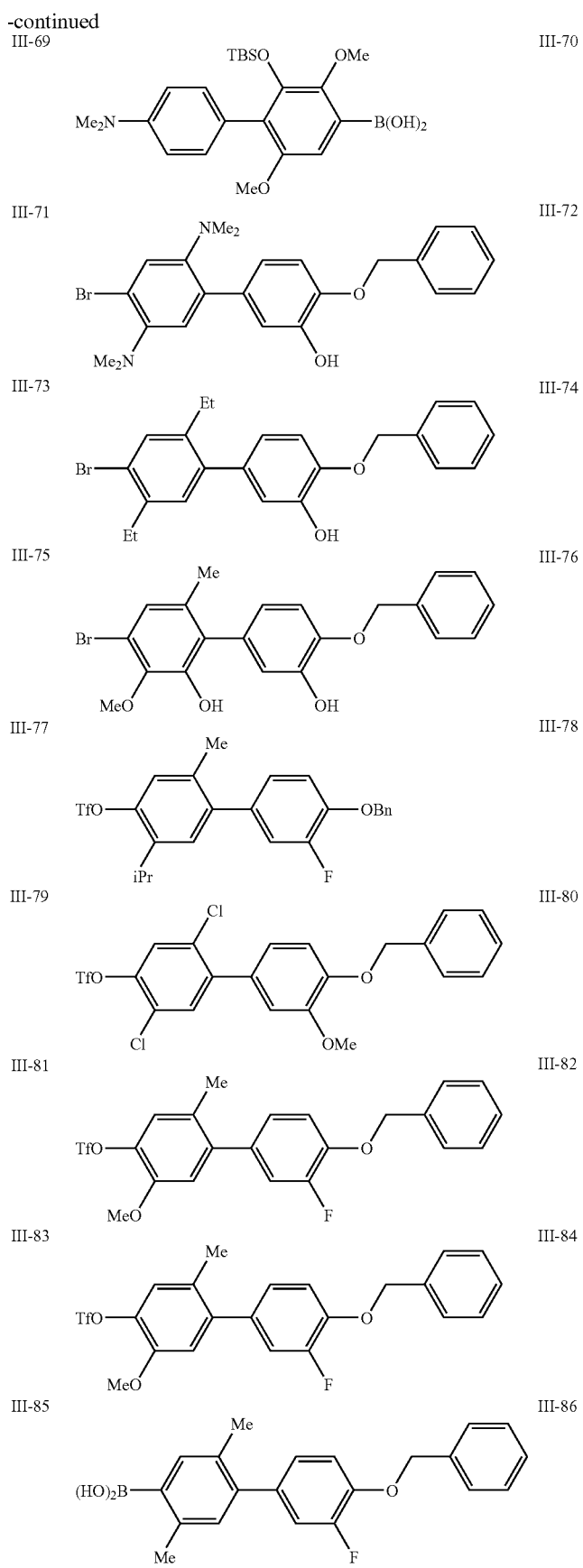

-continued
I-1
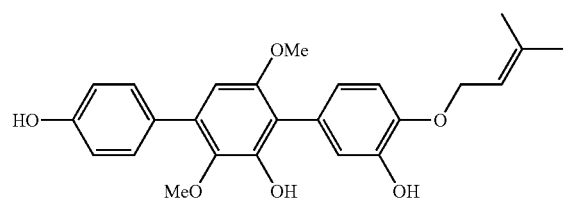
I-2
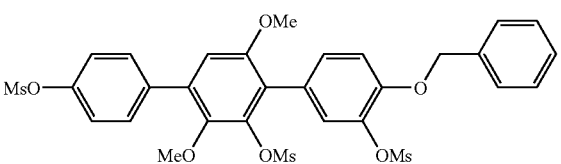
I-3
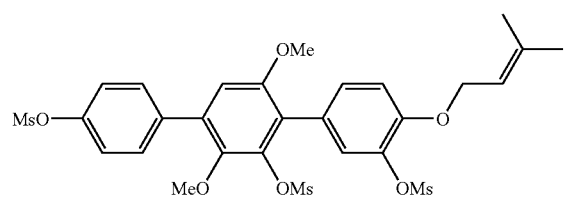
I-4
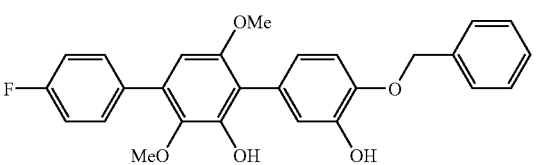
I-5
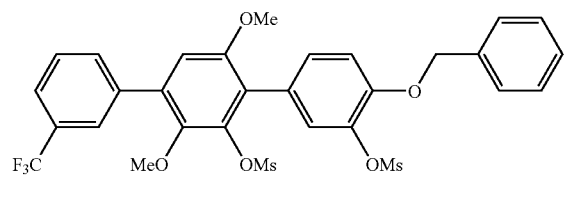
I-6
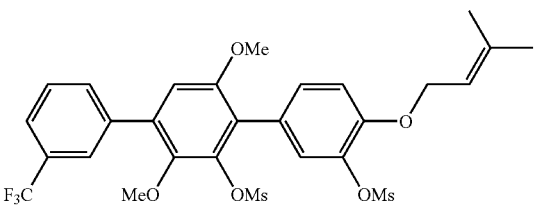
I-7
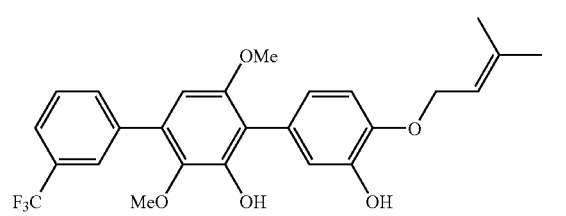
I-8
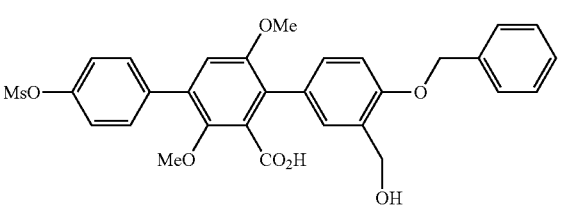
I-9
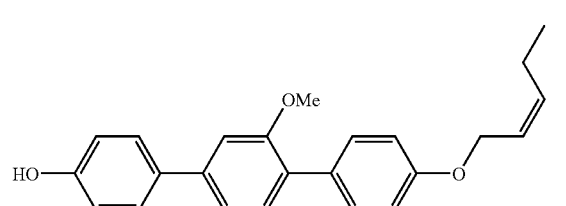
I-10
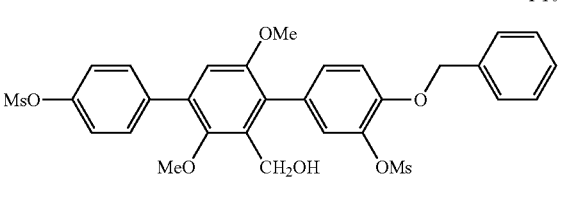
I-11
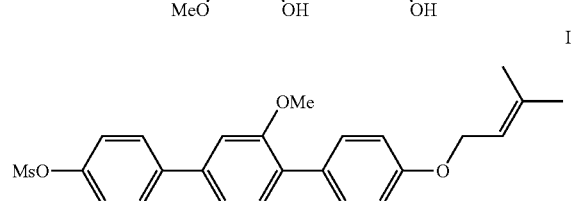
I-12
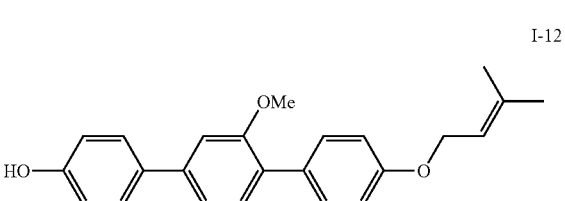
I-13
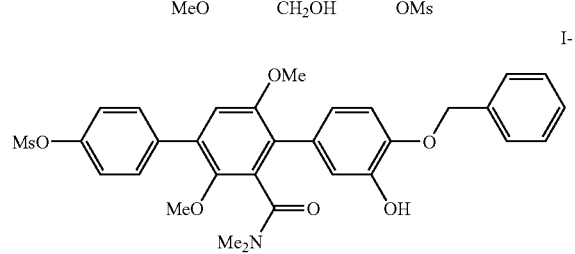
I-14
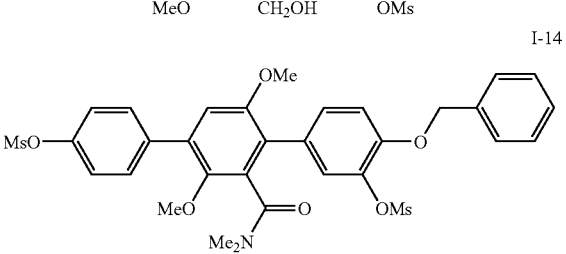

-continued
I-15
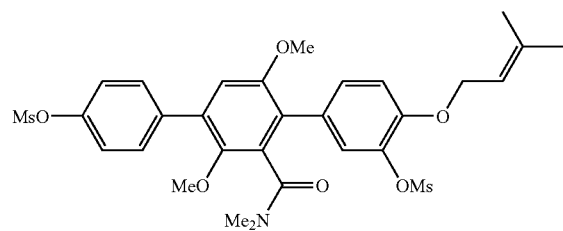
I-16
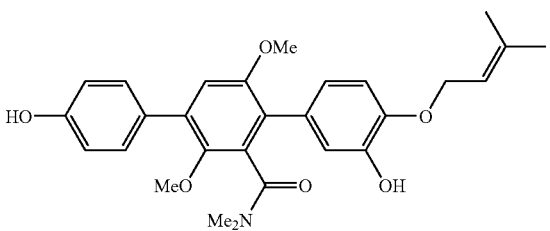
I-17
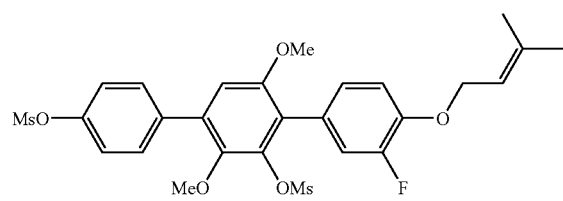
I-18
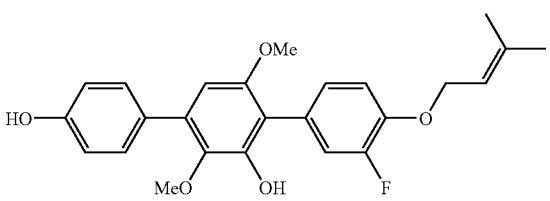
I-19
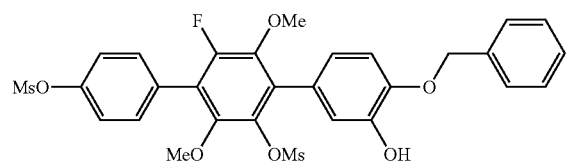
I-20
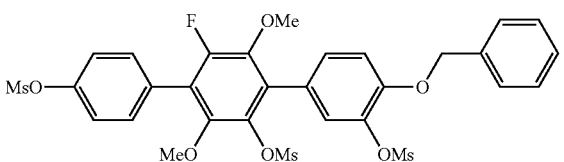
I-21
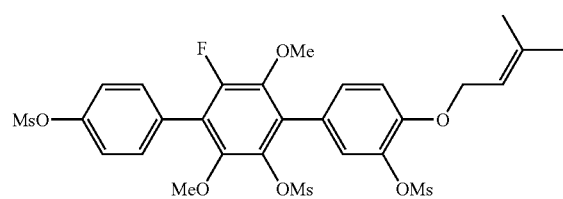
I-22
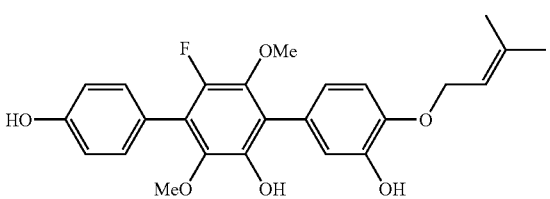
I-23
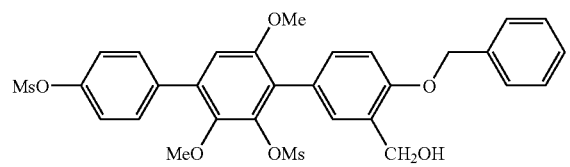
I-24
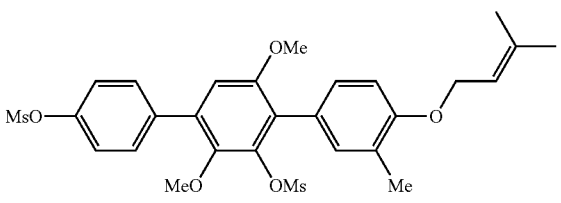
I-25
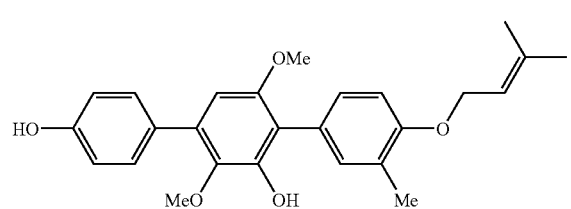
I-26
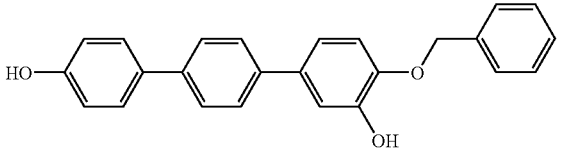
I-27
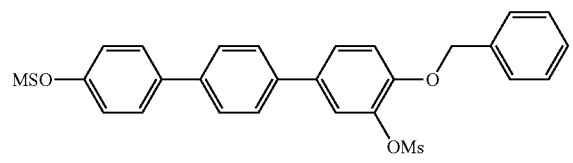
I-28
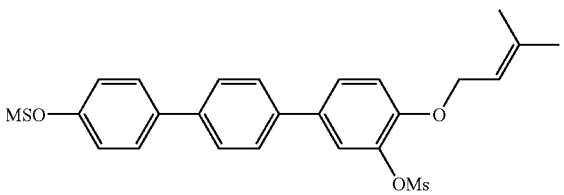

-continued
I-29
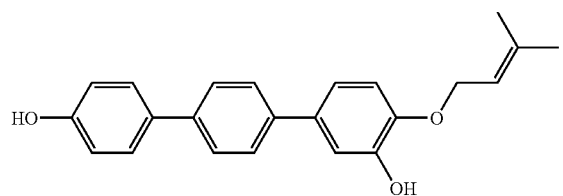
I-30
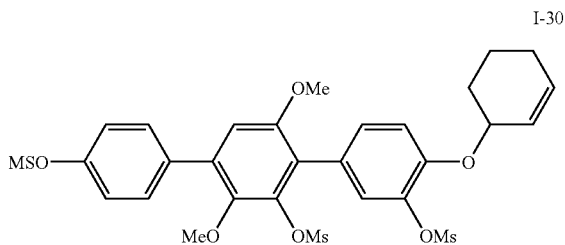
I-31
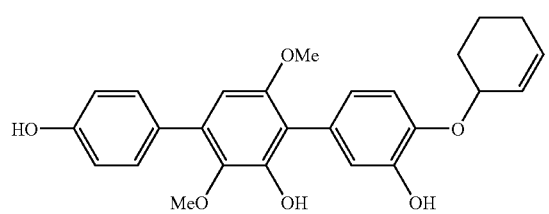
I-32
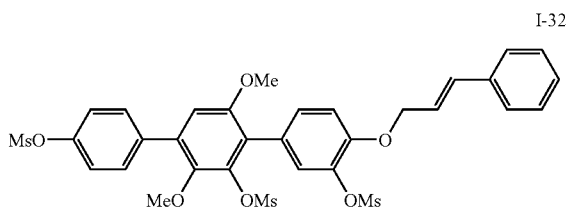
I-33
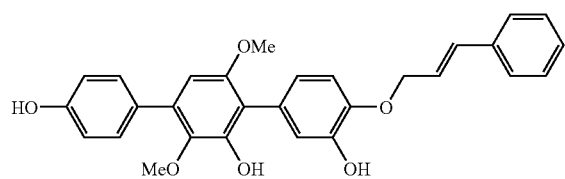
I-34
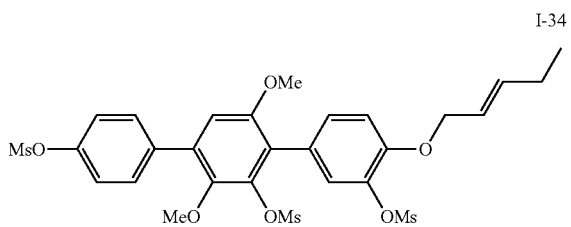
I-35
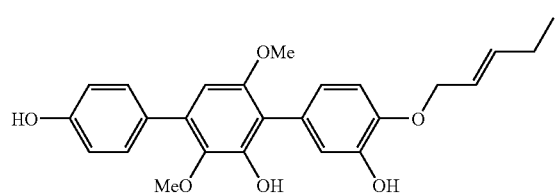
I-36
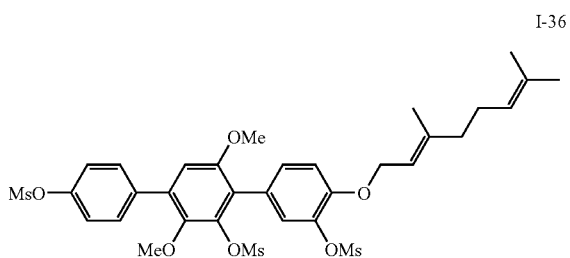
I-37
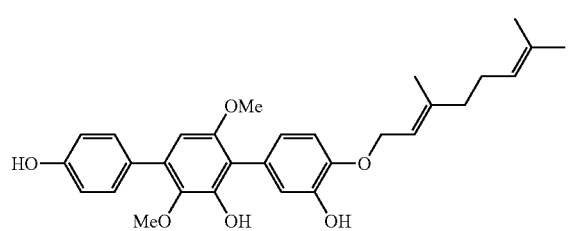
I-38
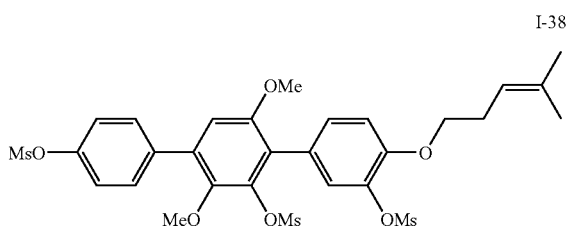
I-39
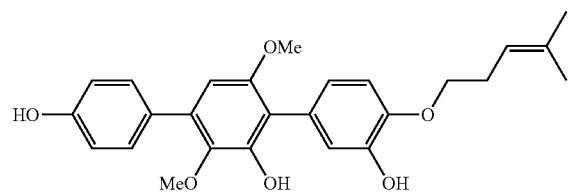
I-40
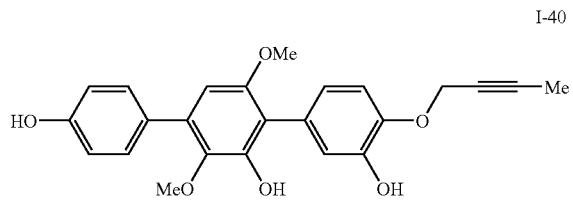
I-41
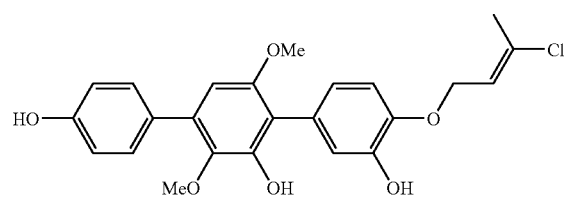
I-42
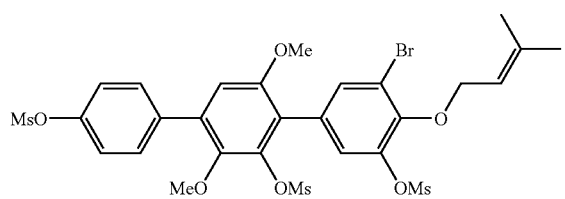

-continued
I-43
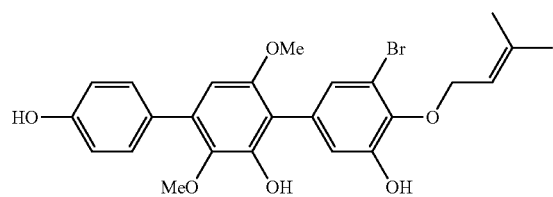
I-44
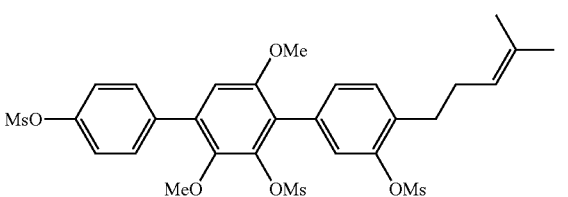
I-45
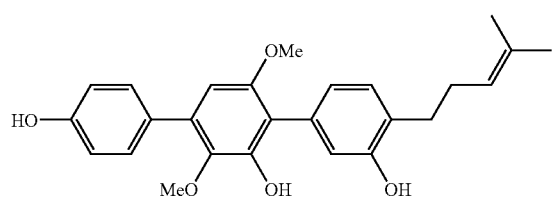
I-46
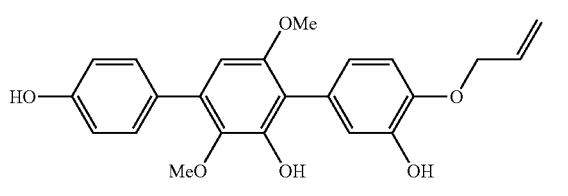
I-47
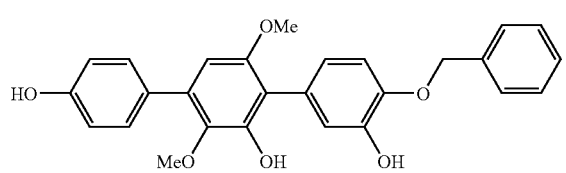
I-48
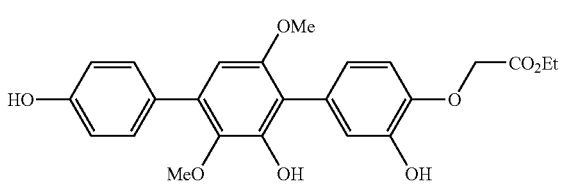
I-49
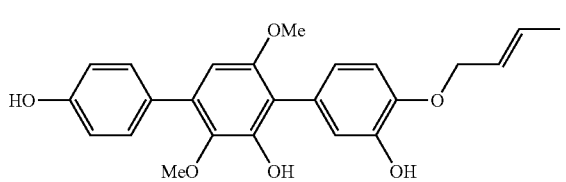
I-50
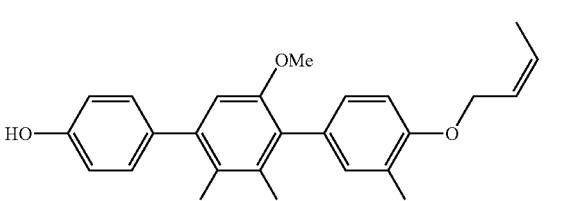
I-51
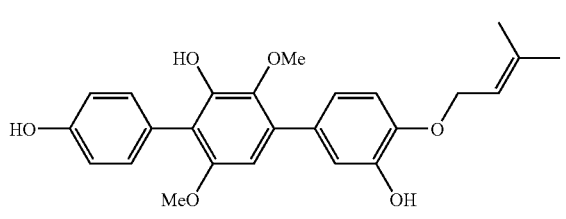
I-52
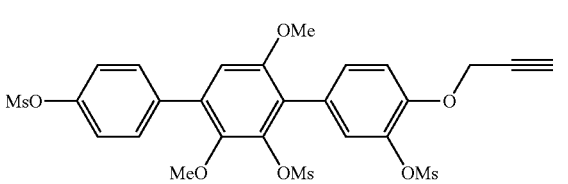
I-53
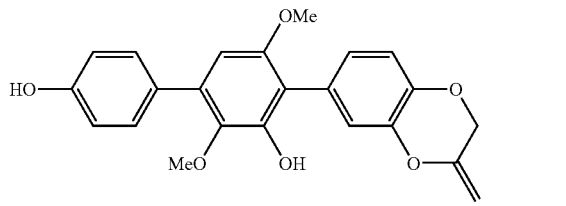
I-54
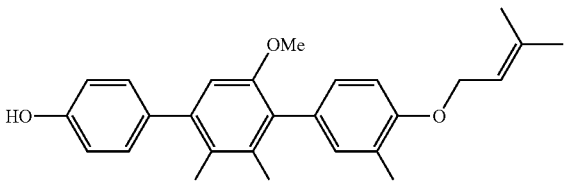
I-55
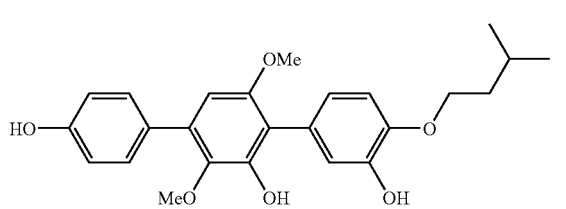
I-56
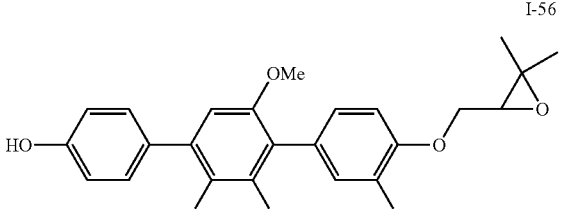

-continued
I-57
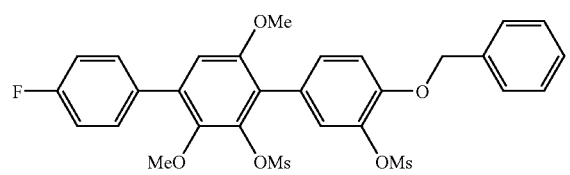
I-58
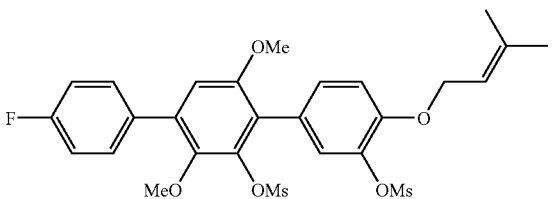
I-59
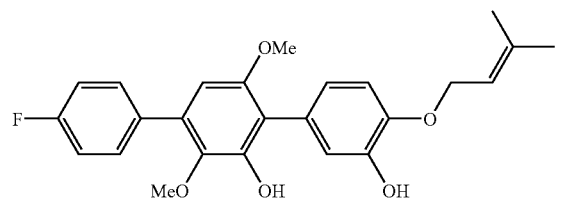
I-60
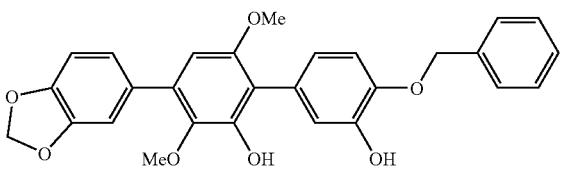
I-61
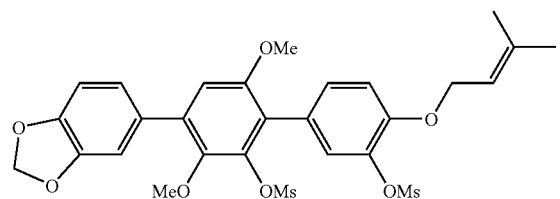
I-62
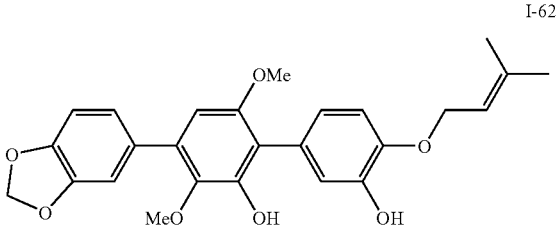
I-63
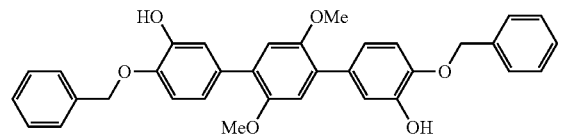
I-64
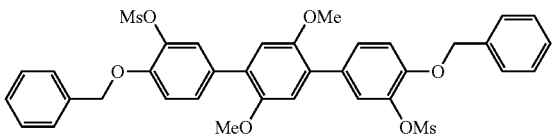
I-65
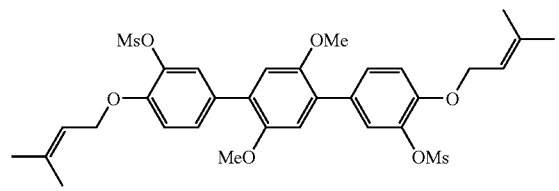
I-66
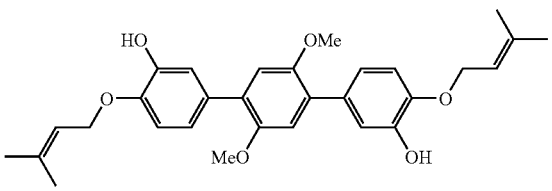
I-67
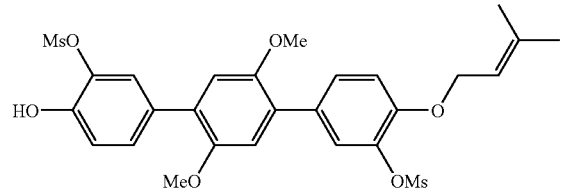
I-68
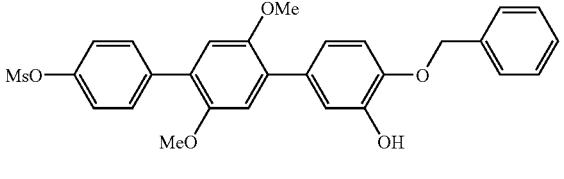
I-69
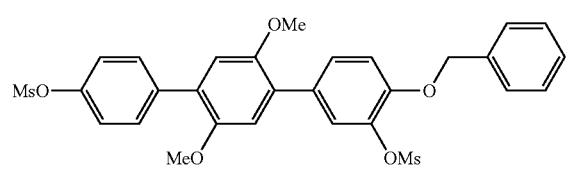
I-70
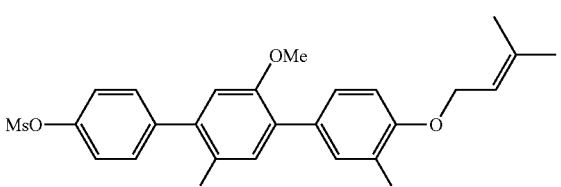

-continued
I-71
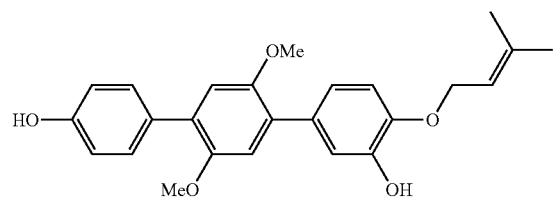
I-72
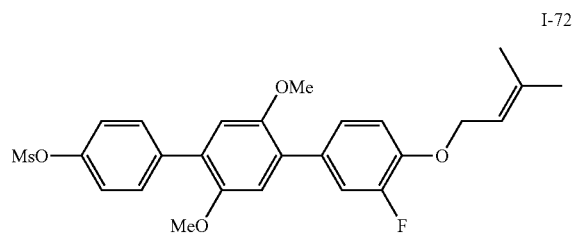
I-73
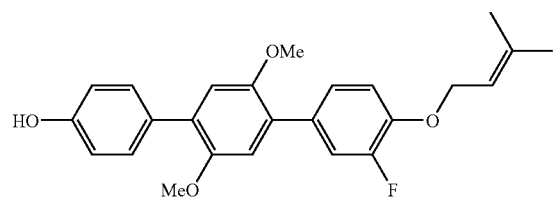
I-74
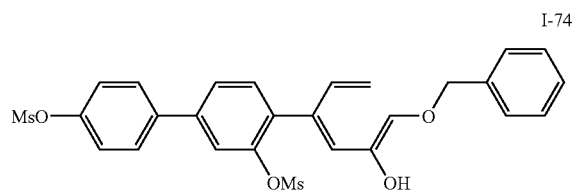
I-75
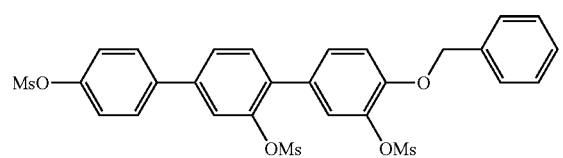
I-76
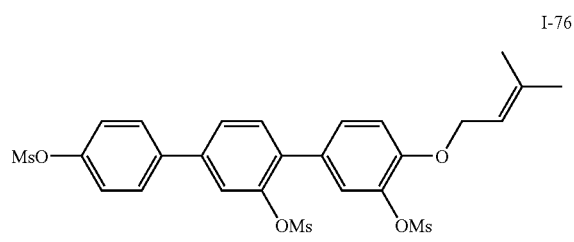
I-77
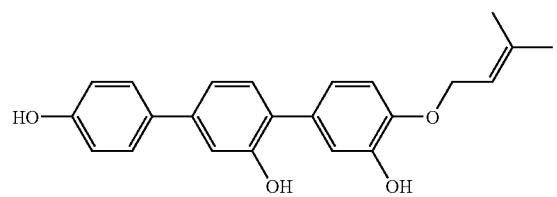
I-78
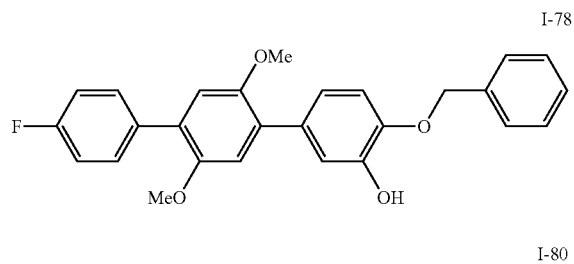
I-79
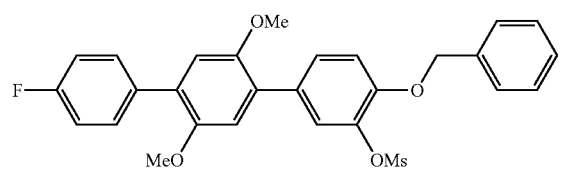
I-80
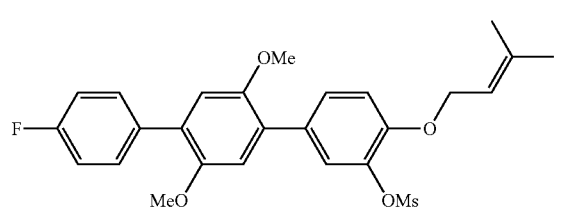
I-81
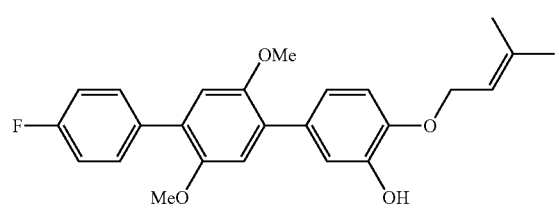
I-82
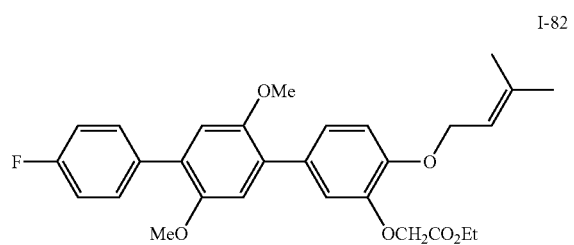
I-83
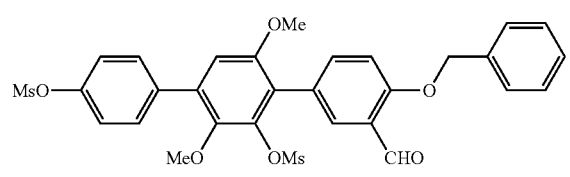
I-84
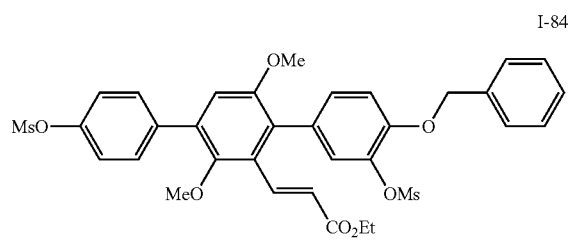

-continued
I-85
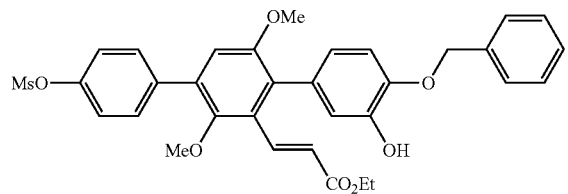
I-86
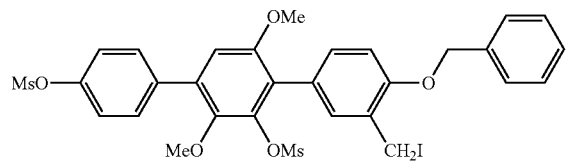
I-87
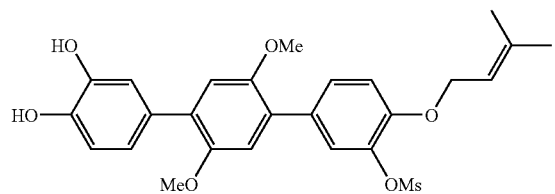
I-88
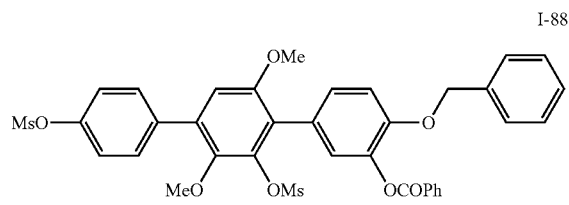
I-89
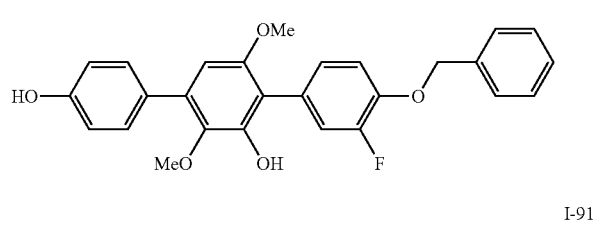
I-90
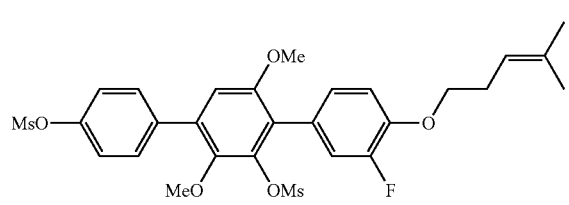
I-91
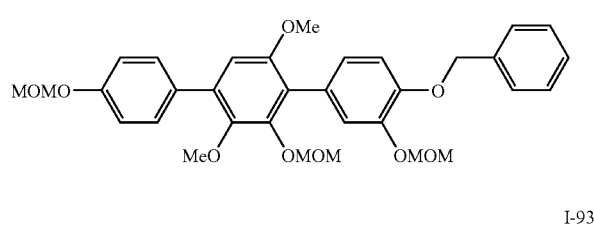
I-92
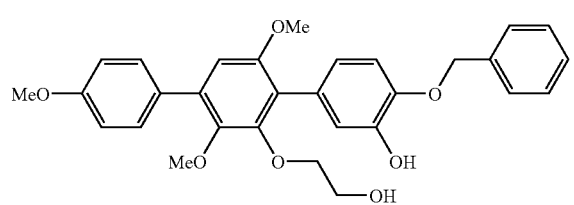
I-93
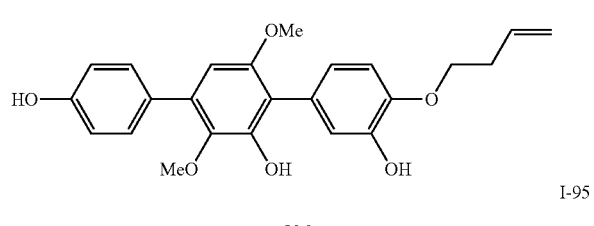
I-94
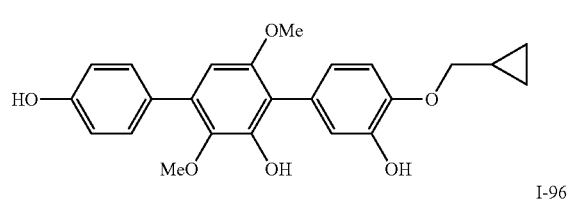
I-95
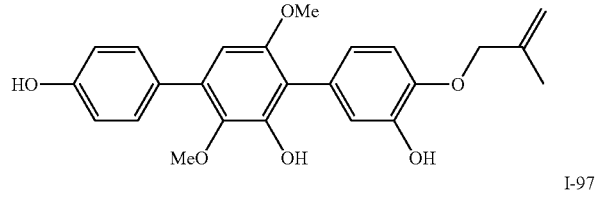
I-96
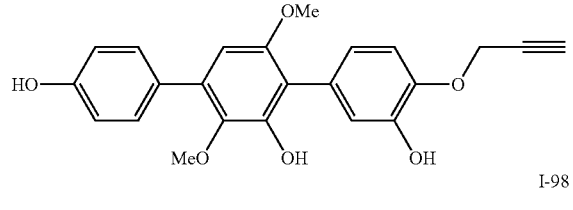
I-97
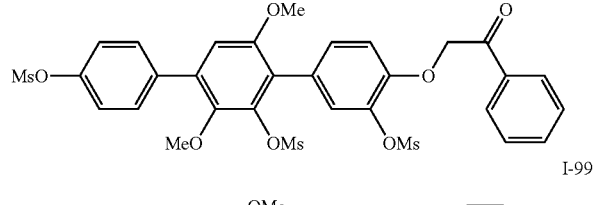
I-98
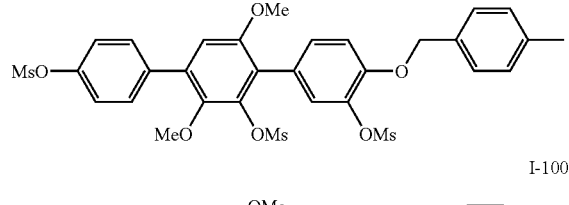
I-99
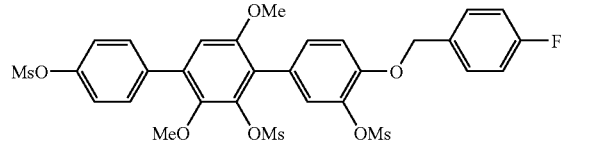
I-100
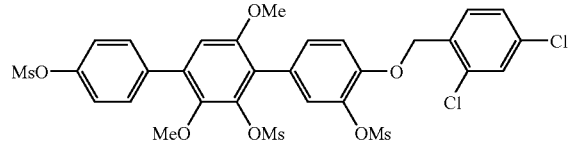

-continued
I-101
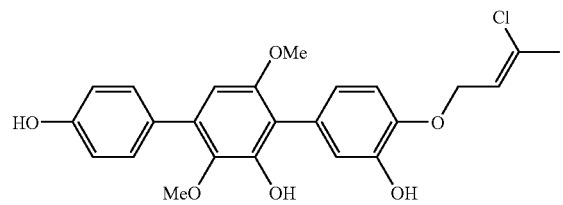
I-102
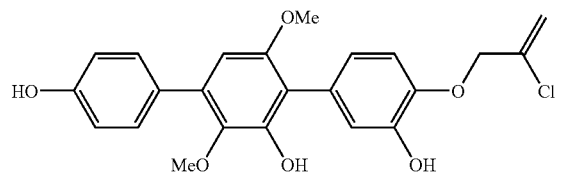
I-103
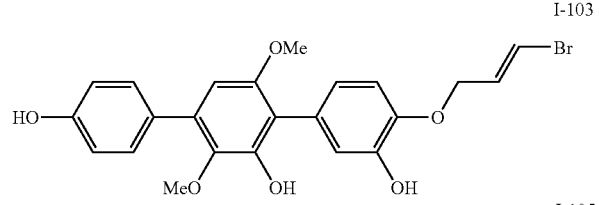
I-104
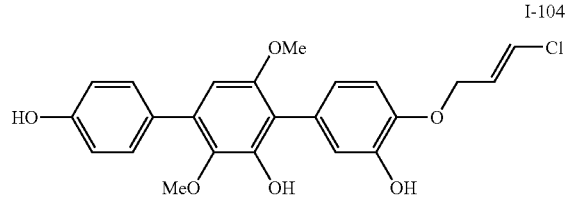
I-105
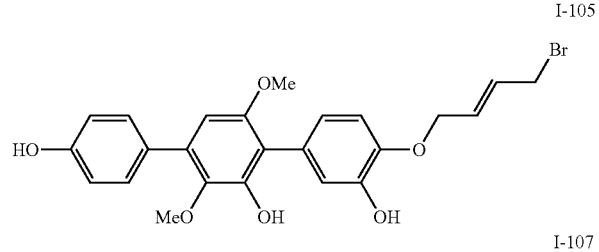
I-106
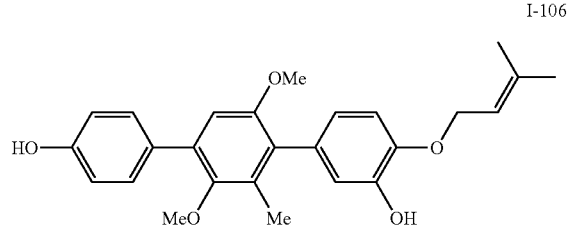
I-107
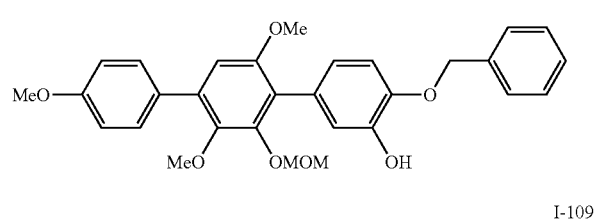
I-108
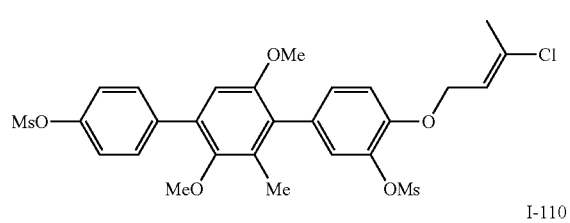
I-109
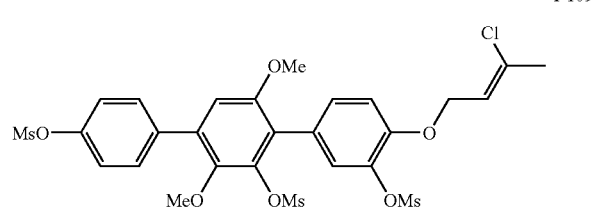
I-110
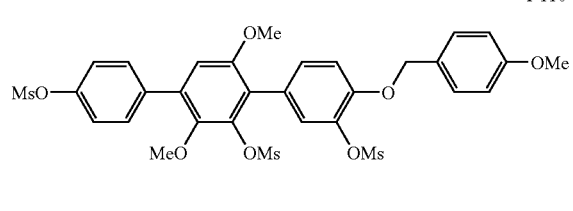
I-111
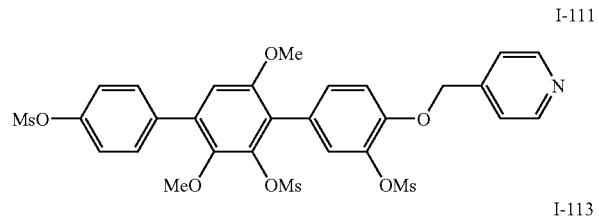
I-112
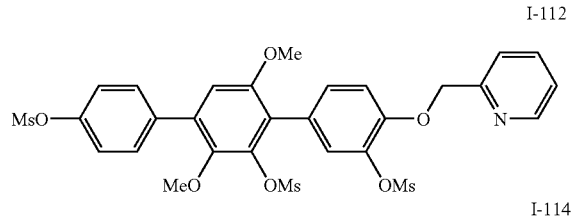
I-113
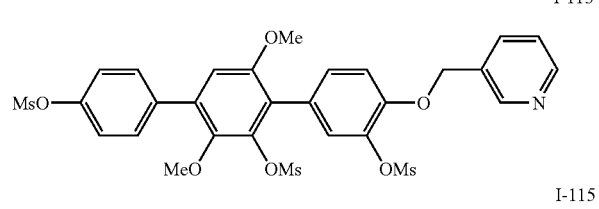
I-114
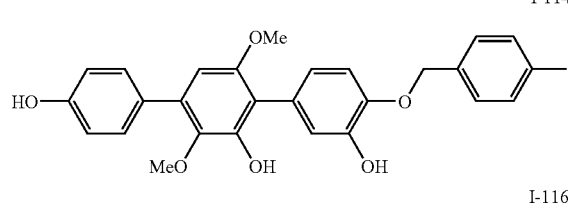
I-115
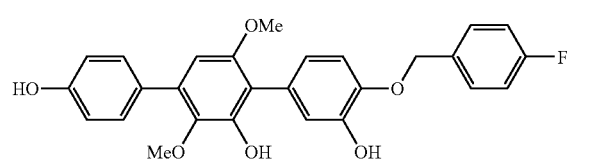
I-116
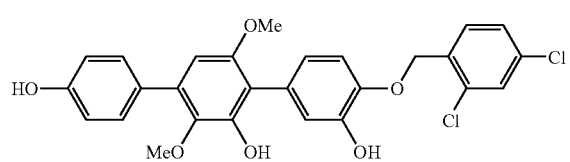

-continued
I-117
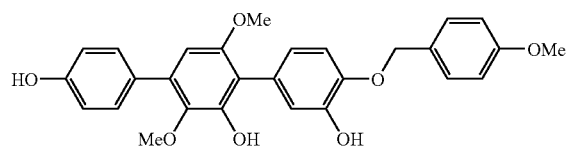
I-118
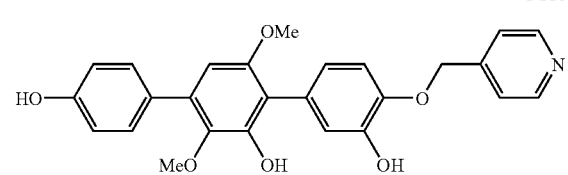
I-119
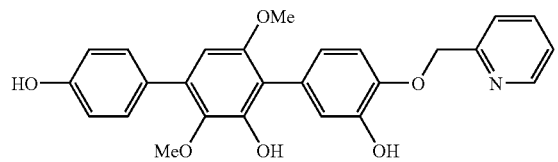
I-120
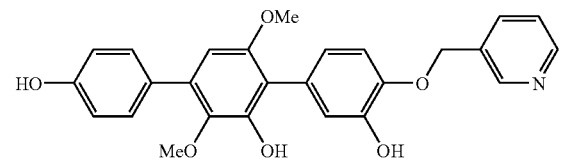
I-121
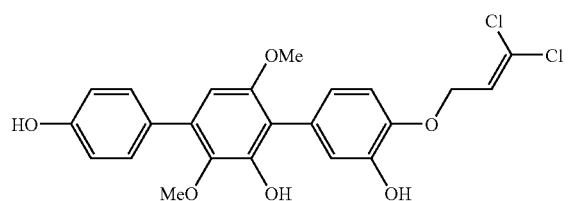
I-122
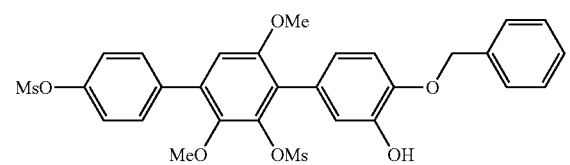
I-123
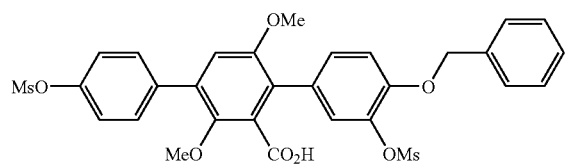
I-124
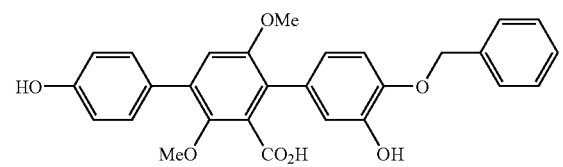
I-125
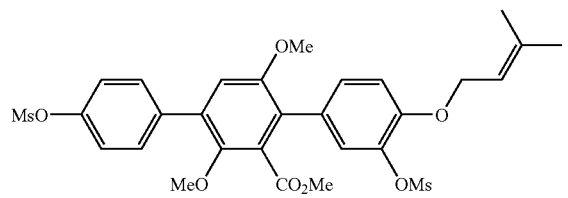
I-126
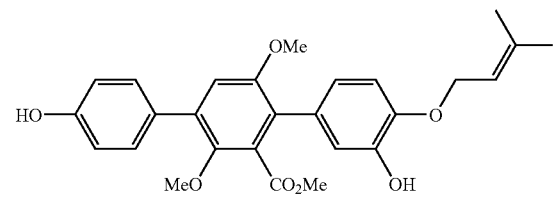
I-127
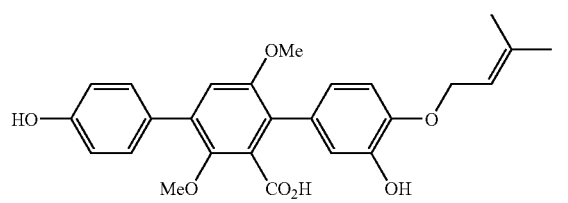
I-128
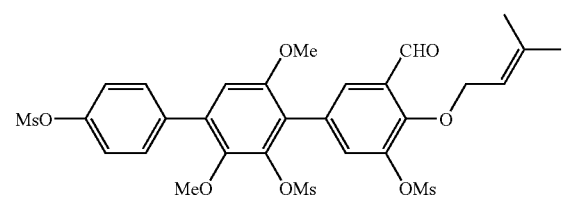
I-129
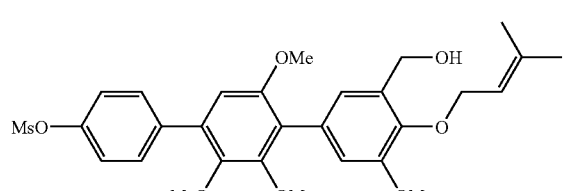
I-130
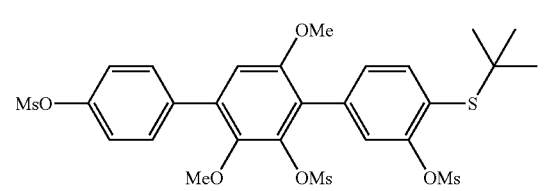

-continued
I-131
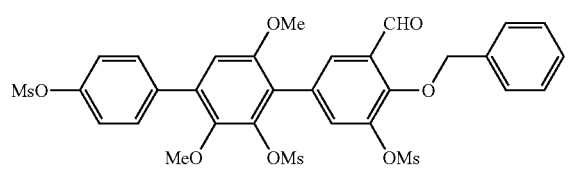
I-132
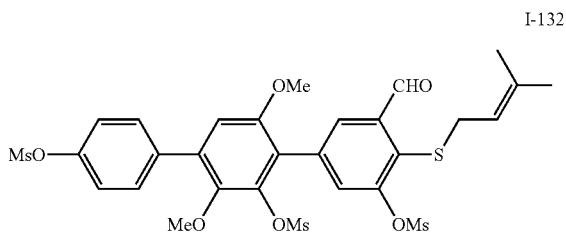
I-133
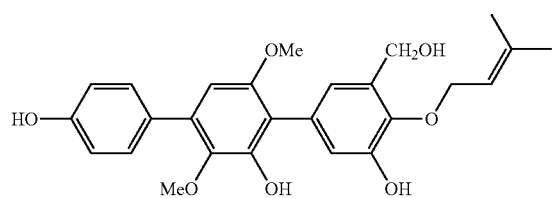
I-134
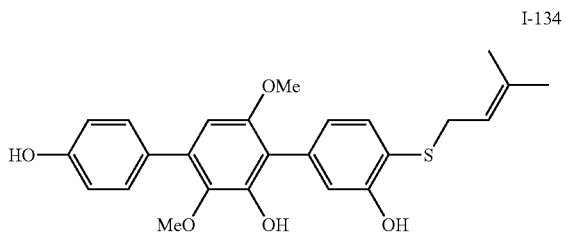
I-135
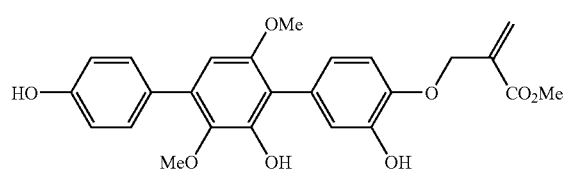
I-136
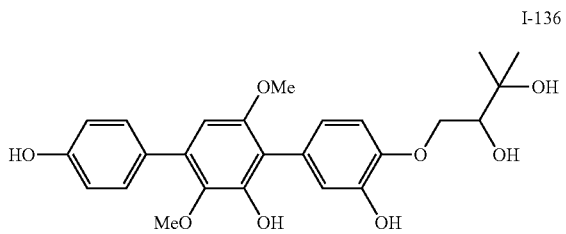
I-137
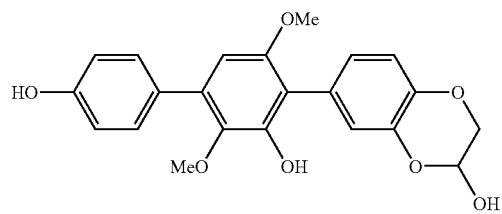
I-138
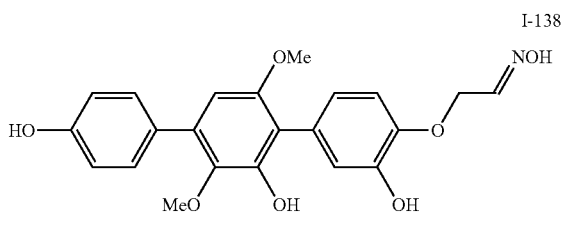
I-139
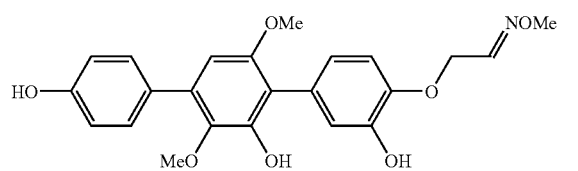
I-140
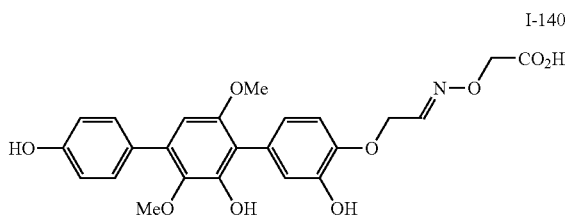
I-141
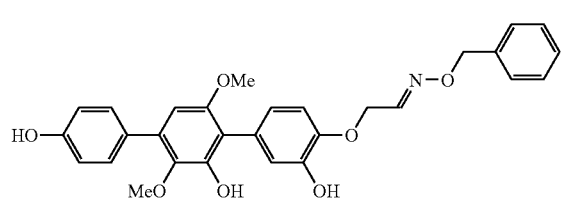
I-142
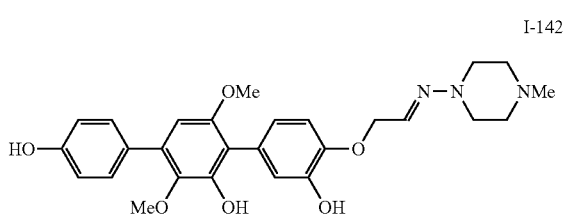
I-143
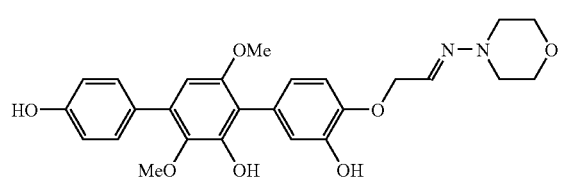
I-144
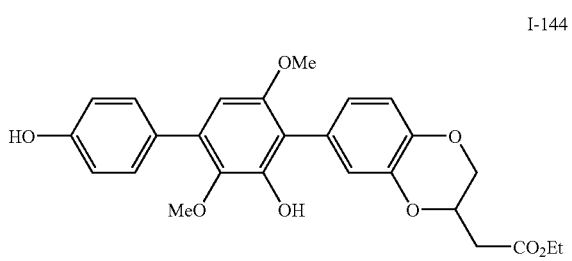

-continued
I-145
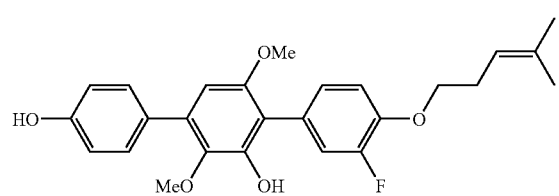
I-146
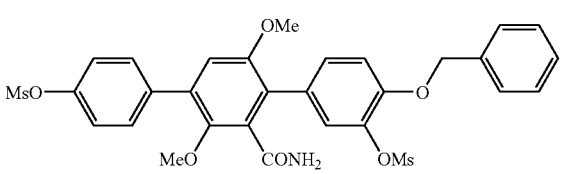
I-147
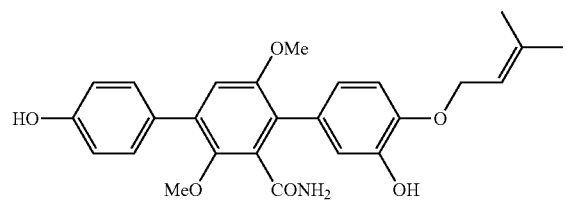
I-148
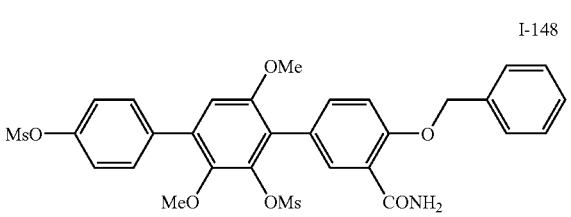
I-149
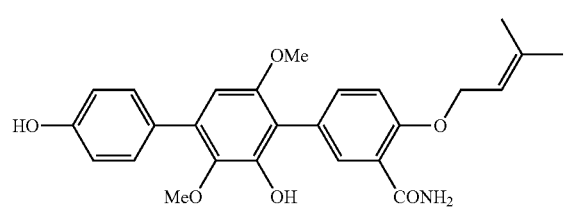
I-150
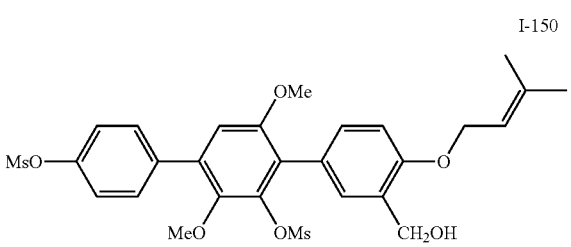
I-151
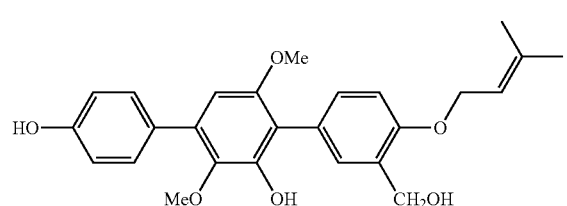
I-152
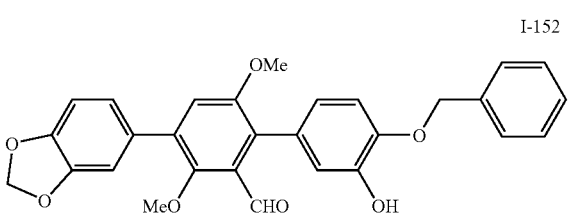
I-153
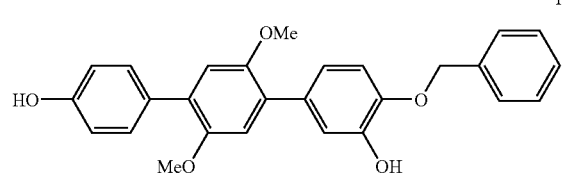
I-154
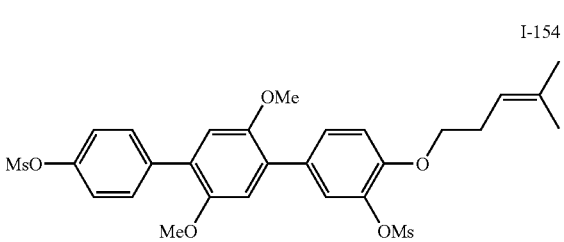
I-155
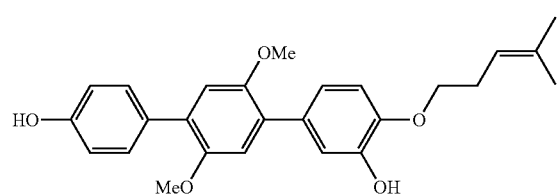
I-156
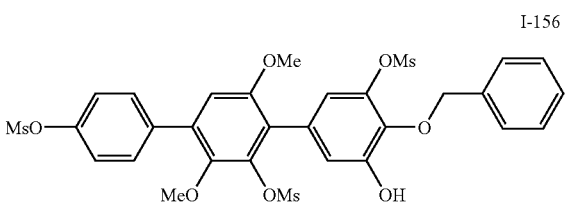
I-157
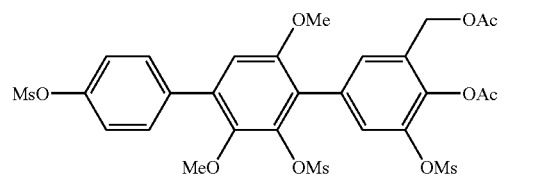
I-158
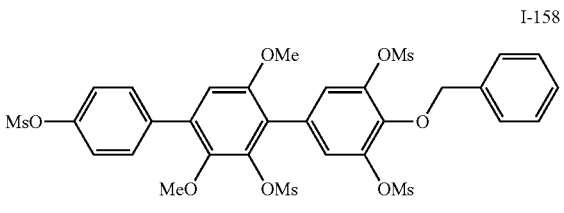

-continued
I-159
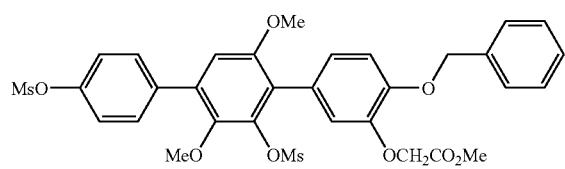
I-160
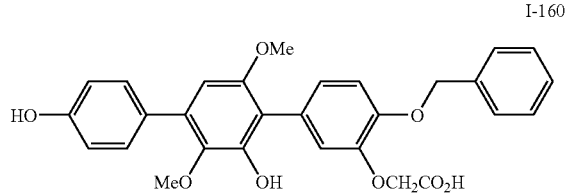
I-161
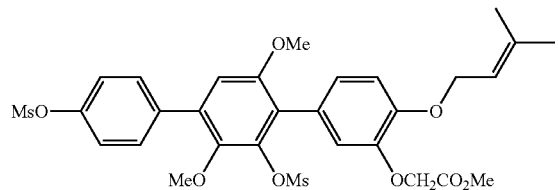
I-162
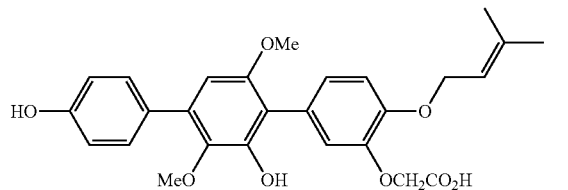
I-163
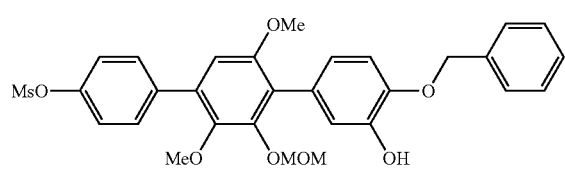
I-164
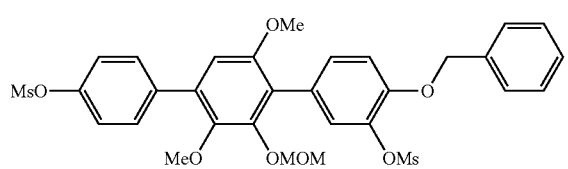
I-165
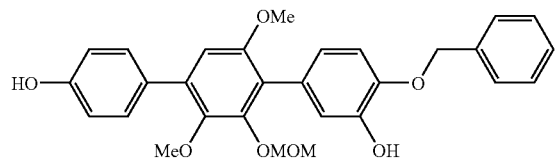
I-166
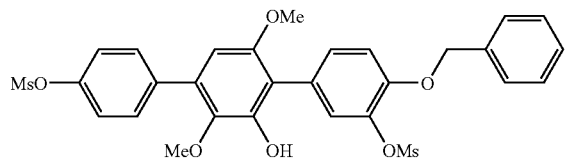
I-167
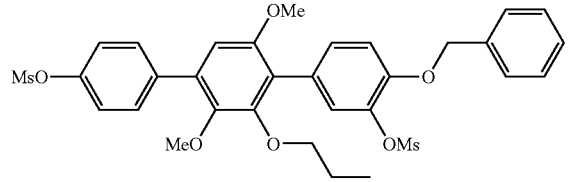
I-168
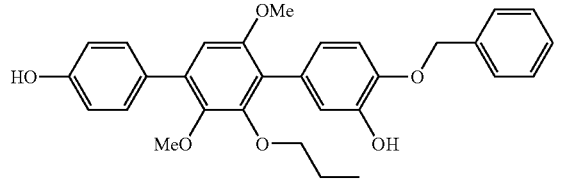
I-169
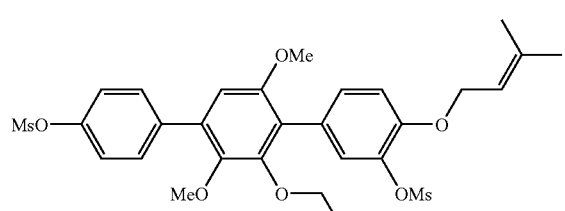
I-170
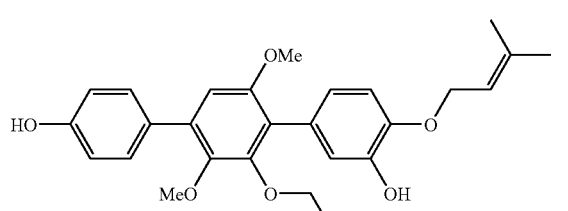
I-171
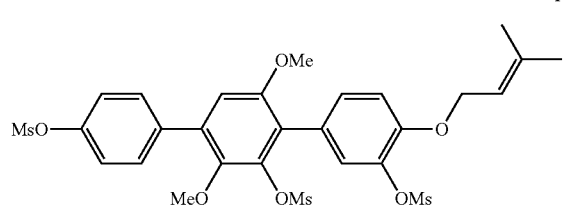
I-172
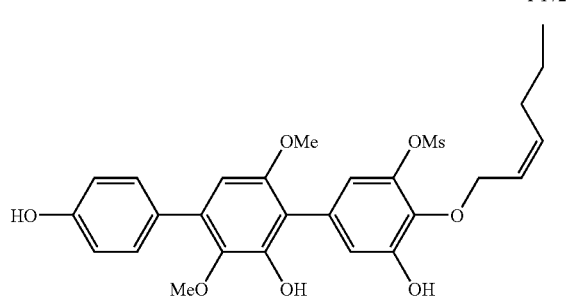

-continued
I-173
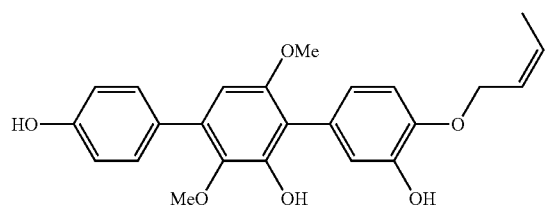
I-174
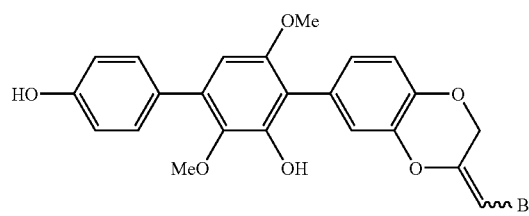
I-175
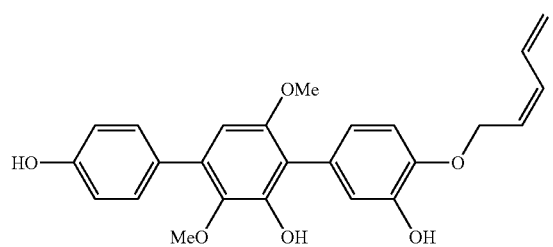
I-176
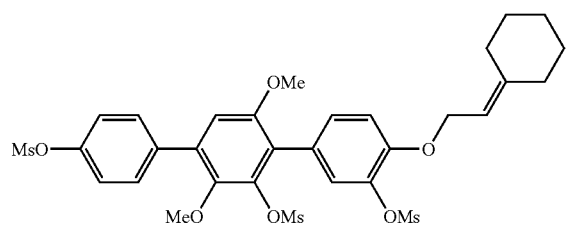
I-177
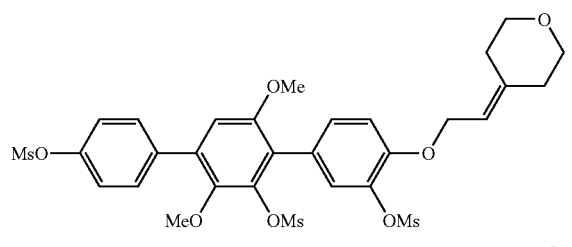
I-178
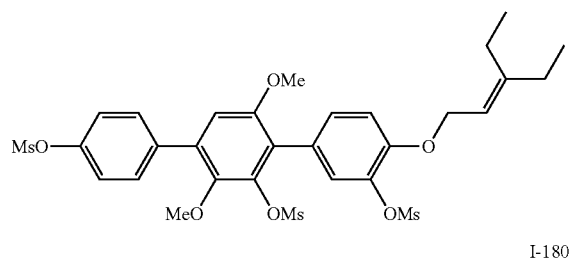
I-179
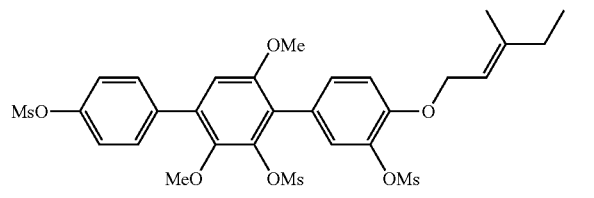
I-180
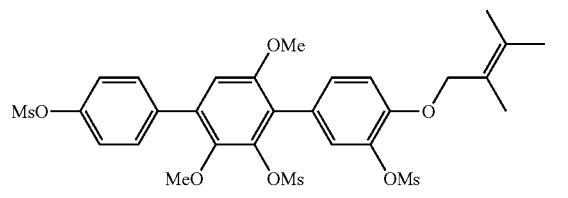
I-181
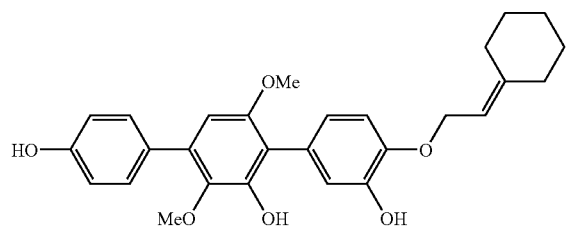
I-182
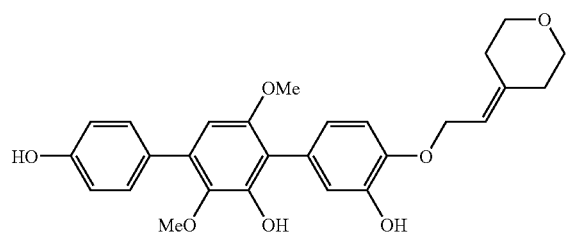
I-183
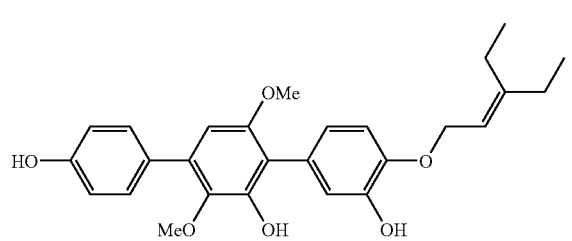
I-184
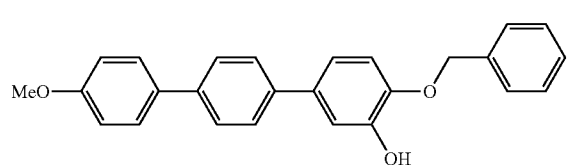

-continued
I-185
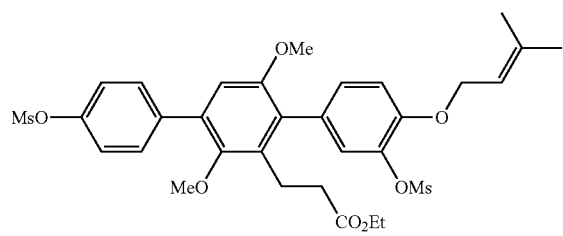
I-186
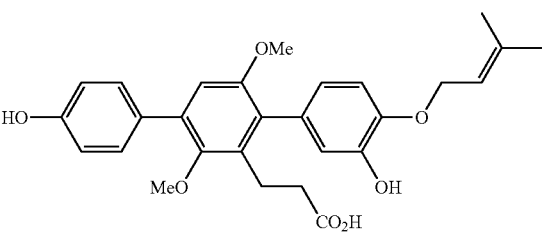
I-187
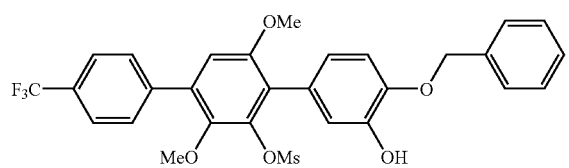
I-188
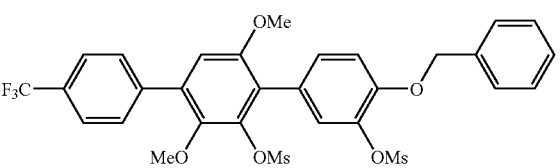
I-189
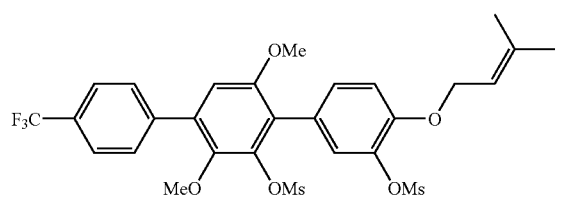
I-190
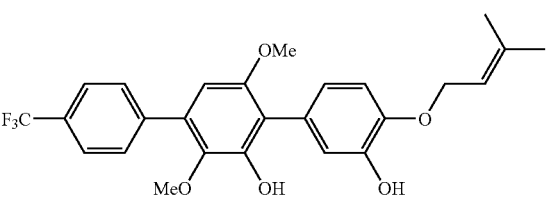
I-191
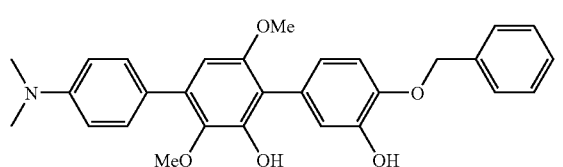
I-192
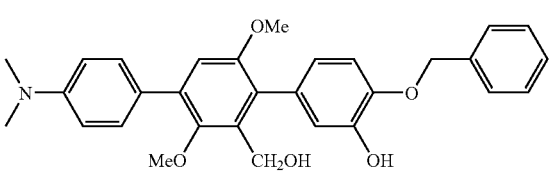
I-193
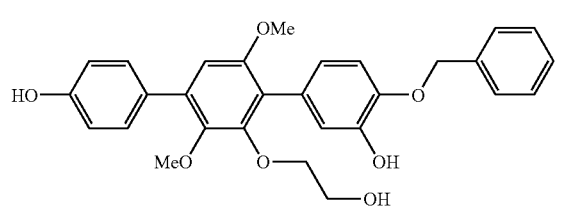
I-194
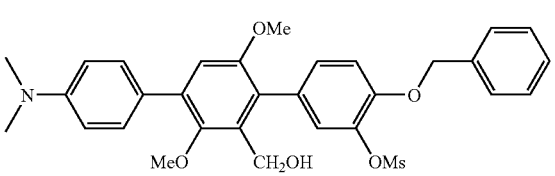
I-195
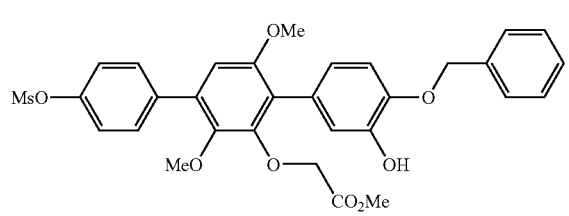
I-196
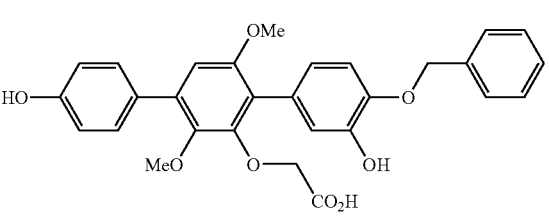
I-197
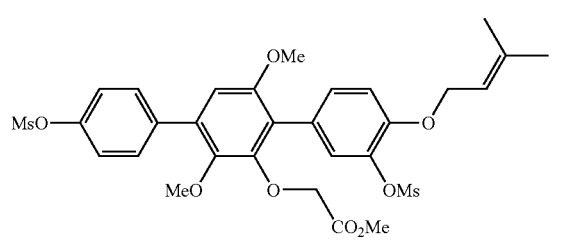
I-198
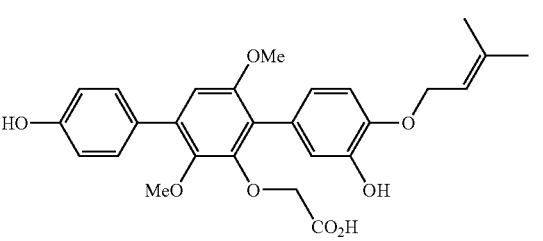

-continued
I-199
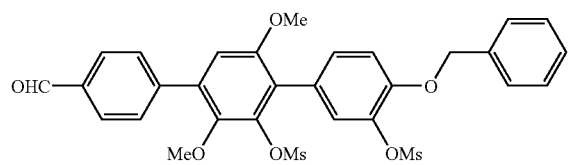
I-200
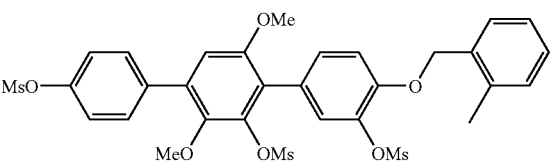
I-201
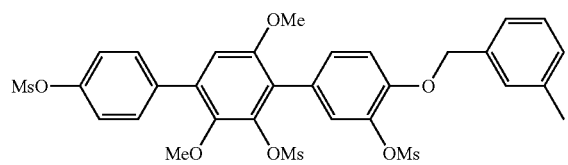
I-202
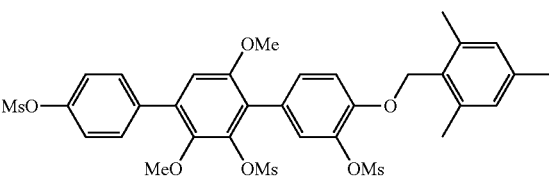
I-203
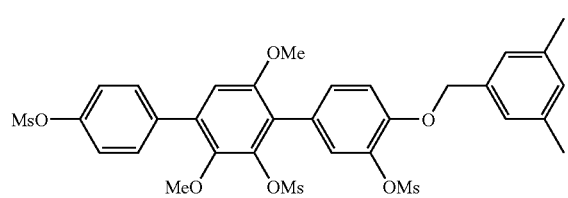
I-204
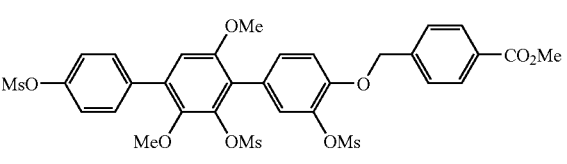
I-205
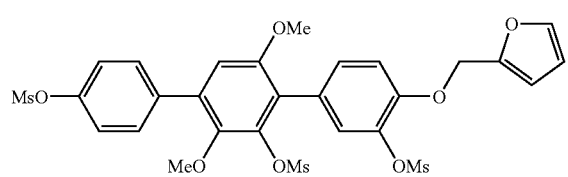
I-206
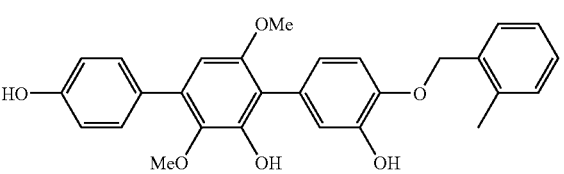
I-207
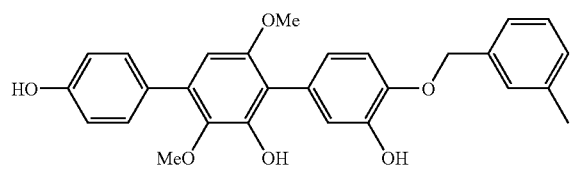
I-208
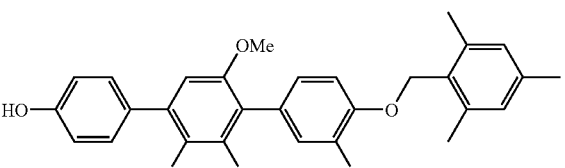
I-209
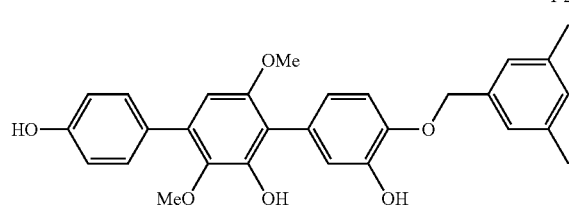
I-210
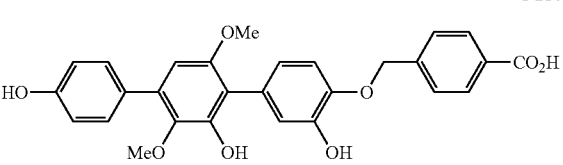
I-211
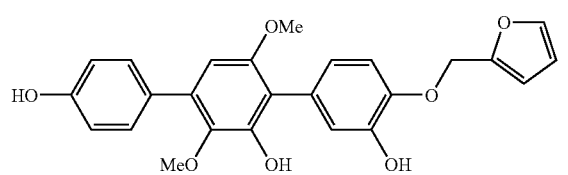
I-212
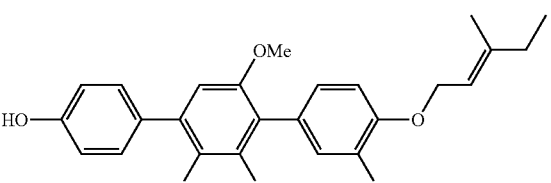

-continued
I-213
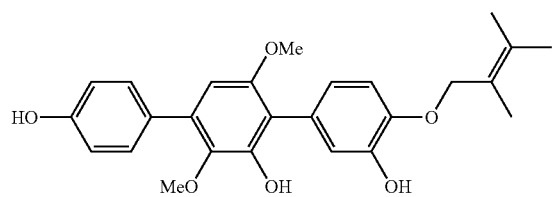
I-214
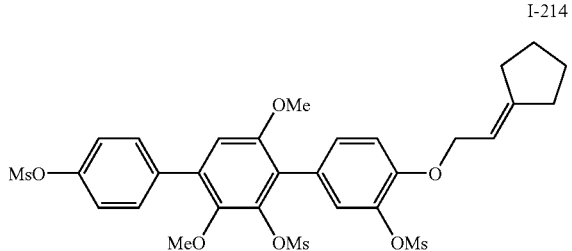
I-215
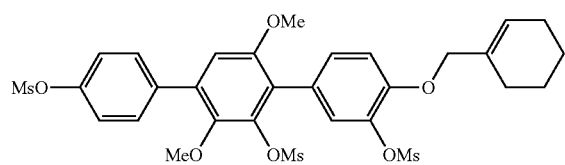
I-216
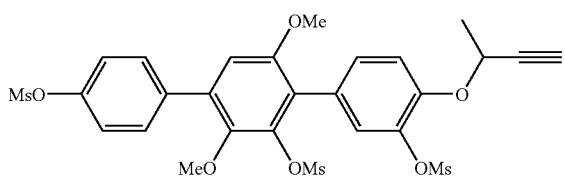
I-217
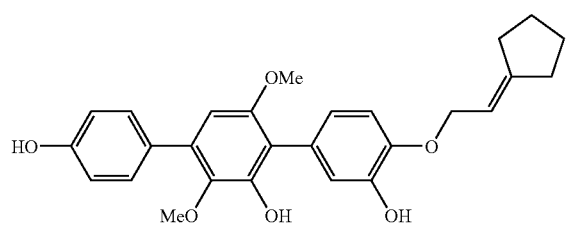
I-218
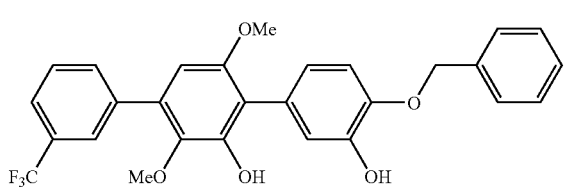
I-219
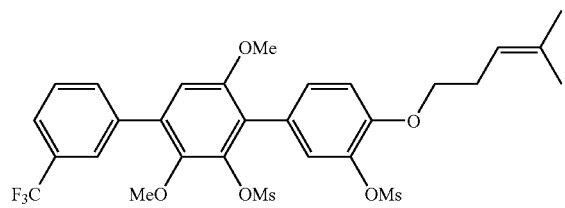
I-220
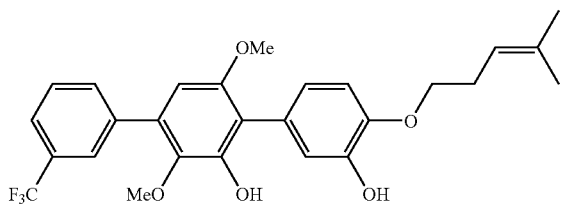
I-221
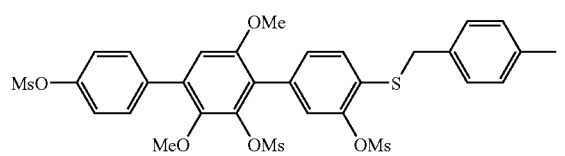
I-222
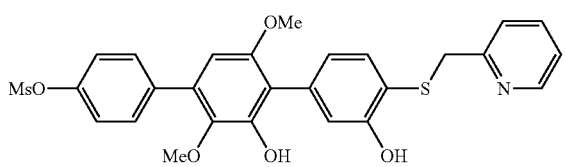
I-223
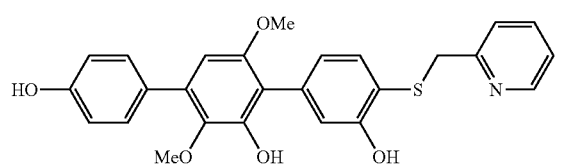
I-224
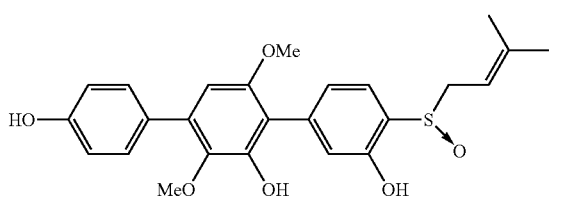
I-225
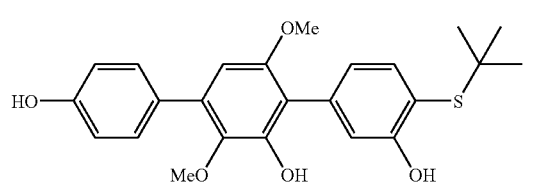
I-226
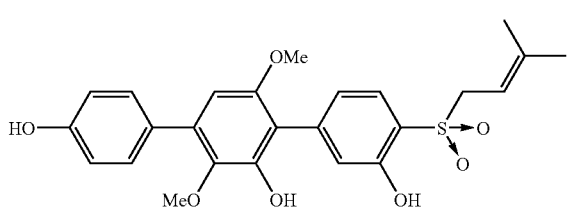

I-227 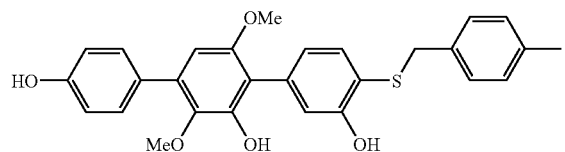
I-228 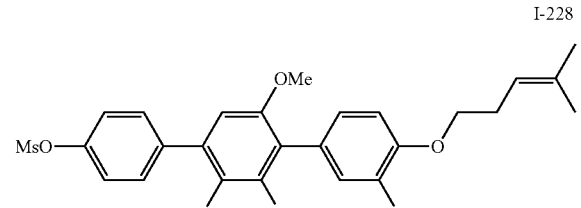
I-229 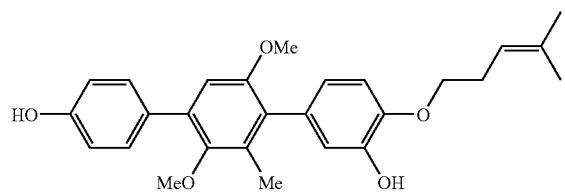
I-230 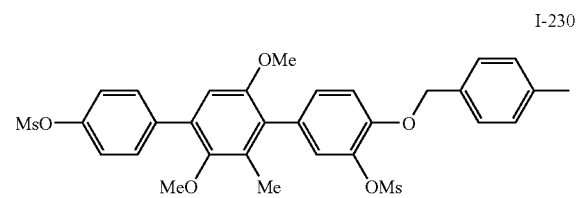
I-231 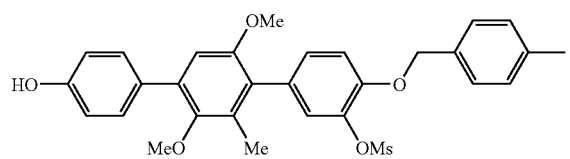
I-232 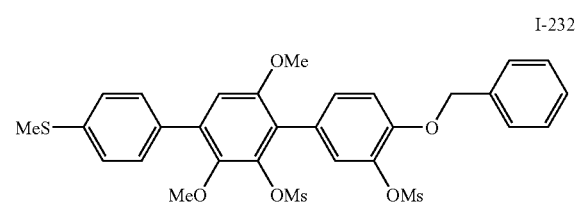
I-233 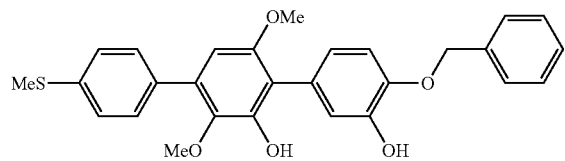
I-234 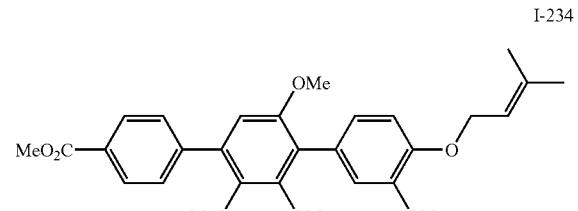
I-235 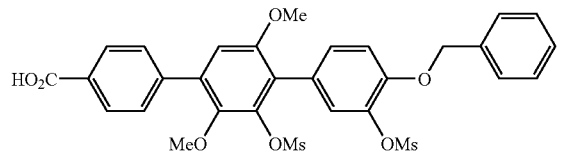
I-236 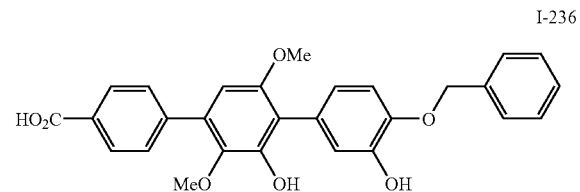
I-237 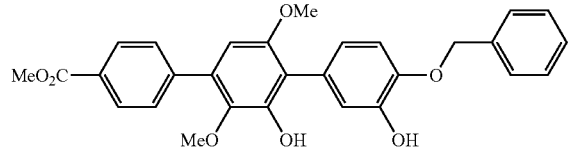
I-238 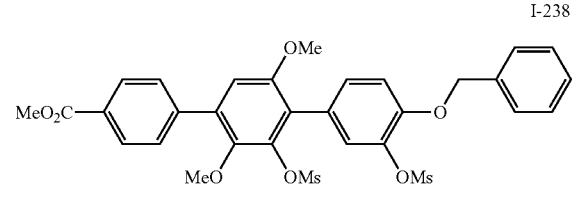
I-239 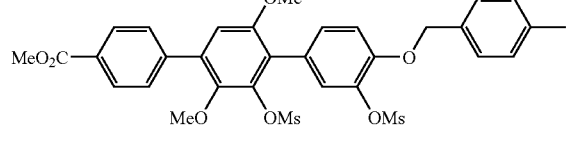
I-240 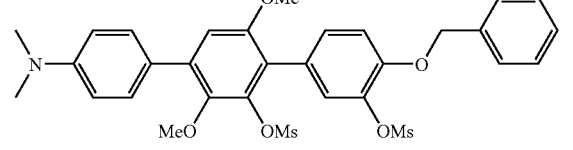
I-241 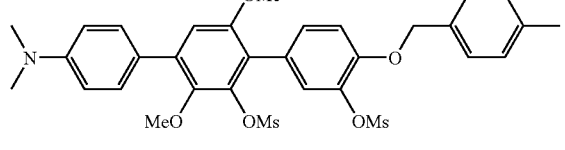
I-242 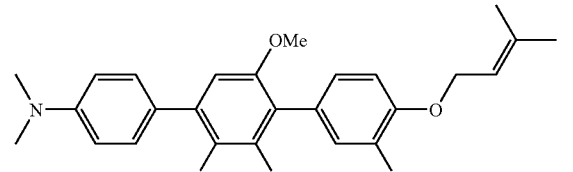

-continued
I-243
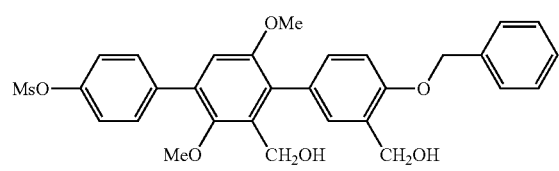
I-244
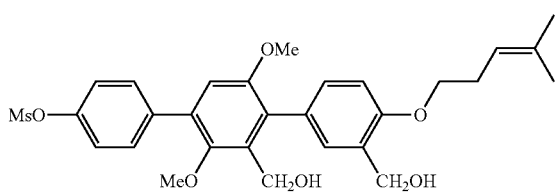
I-245
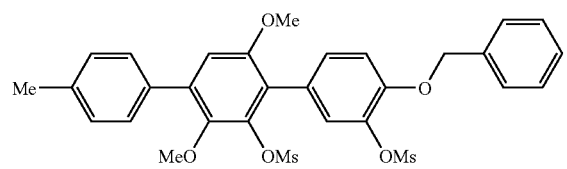
I-246
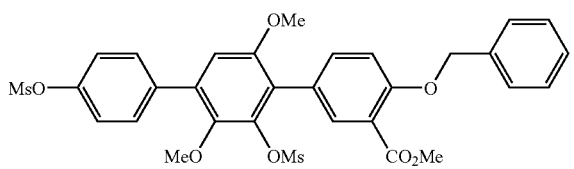
I-247
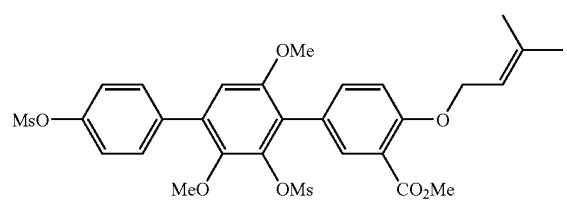
I-248
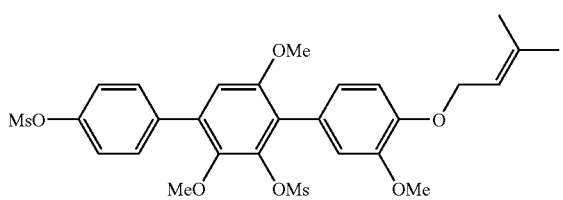
I-249
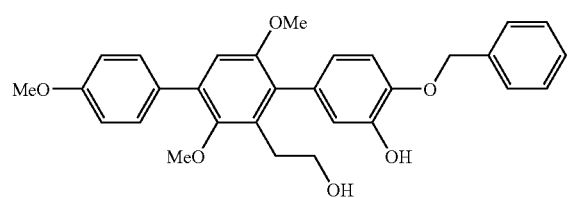
I-250
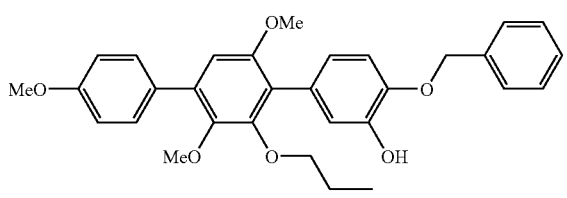
I-251
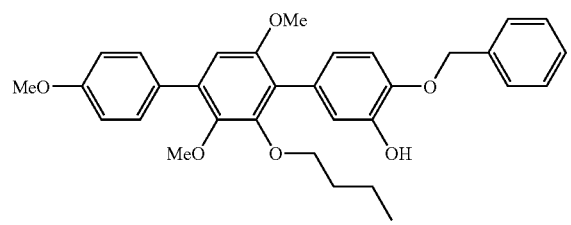
I-252
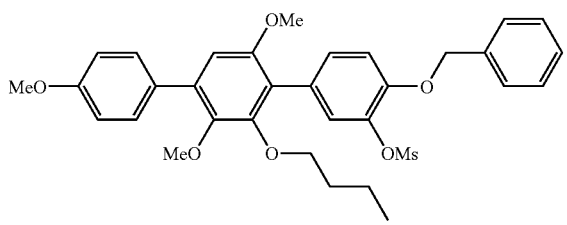
I-253
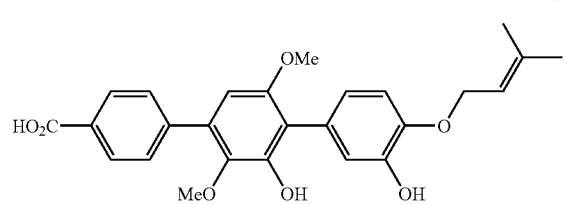
I-254
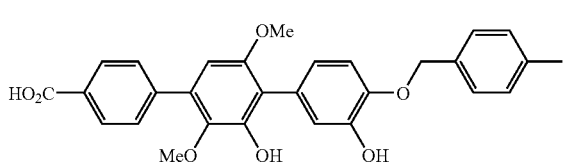
I-255
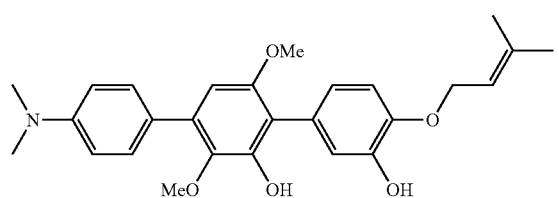
I-256
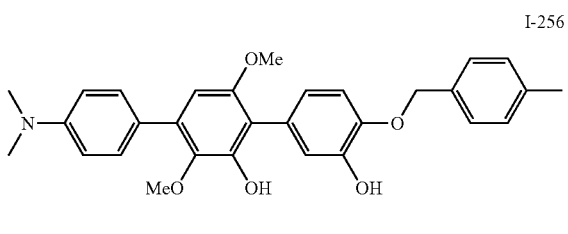

-continued
I-257
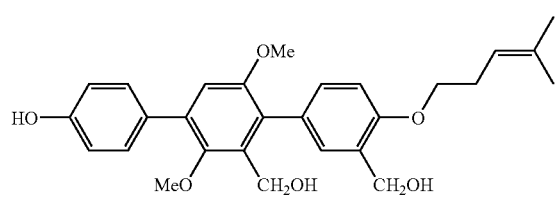
I-258
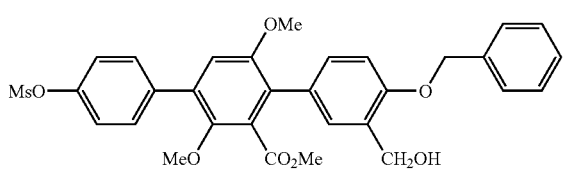
I-259
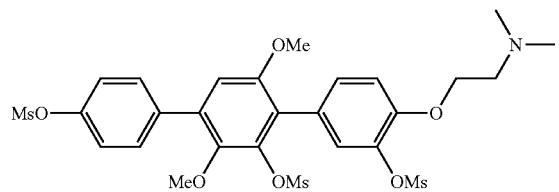
I-260
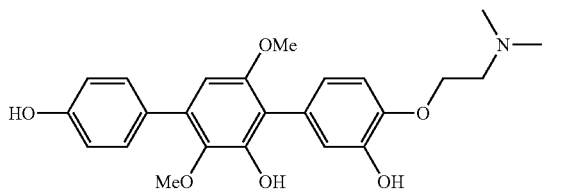
I-261
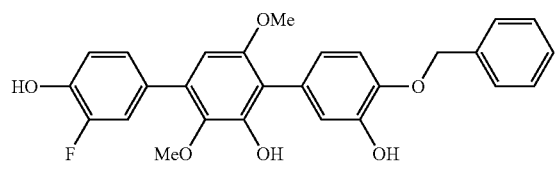
I-262
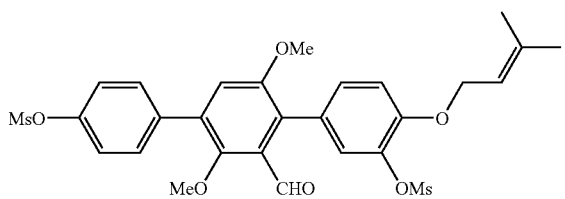
I-263
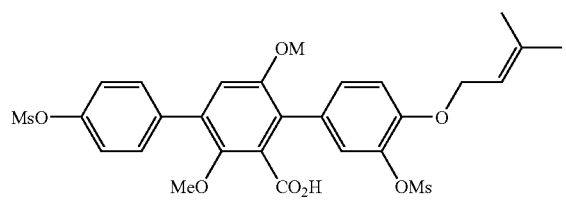
I-264
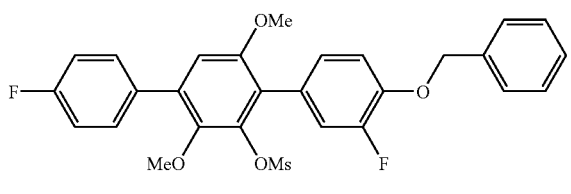
I-265
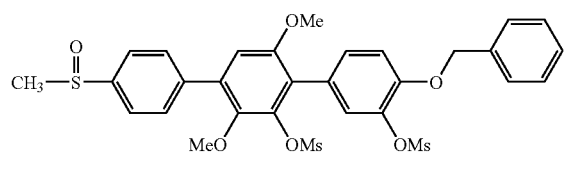
I-266
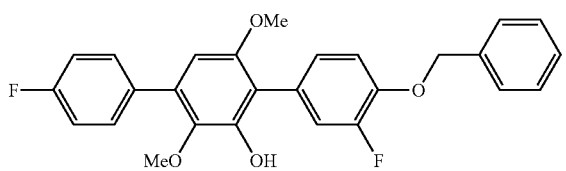
I-267
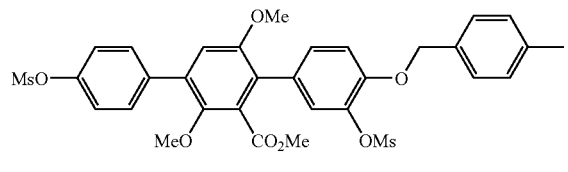
I-268
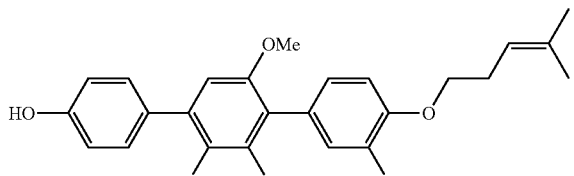
I-269
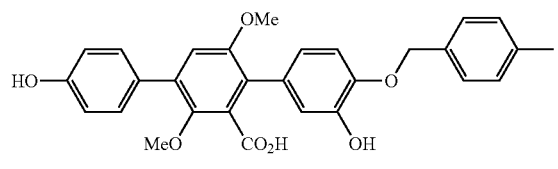
I-270
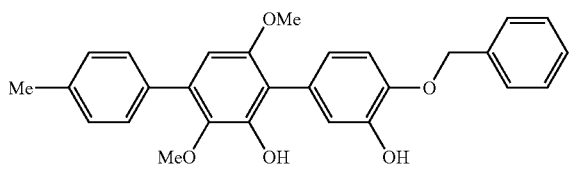

-continued
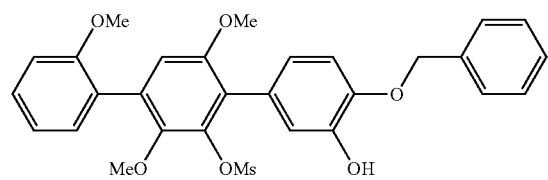
I-271
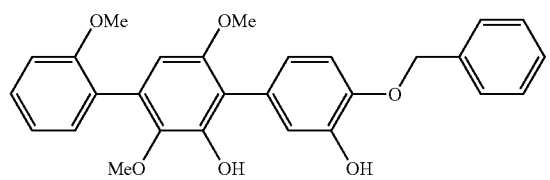
I-272
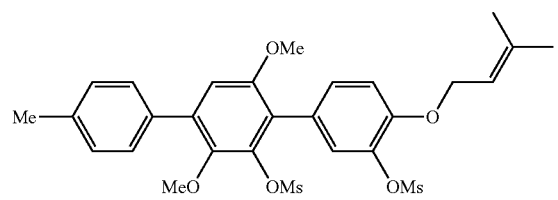
I-273
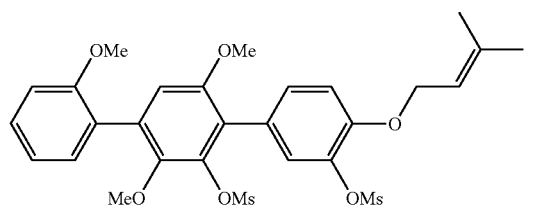
I-274
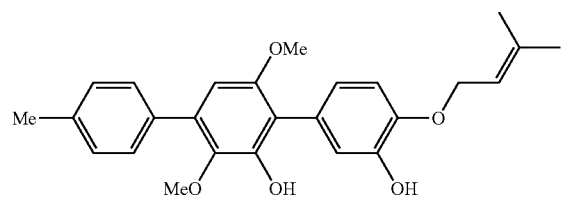
I-275
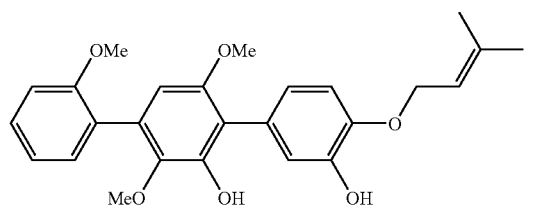
I-276
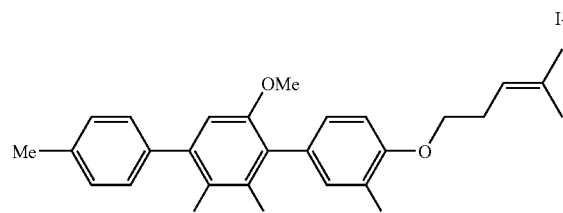
I-277
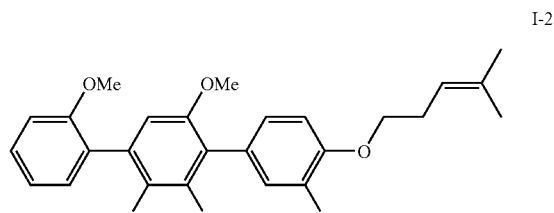
I-278
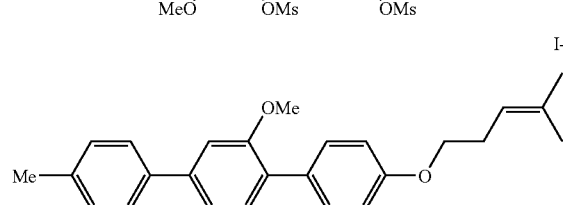
I-279
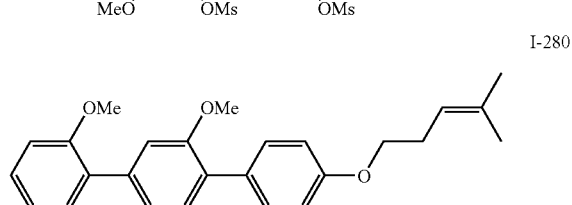
I-280
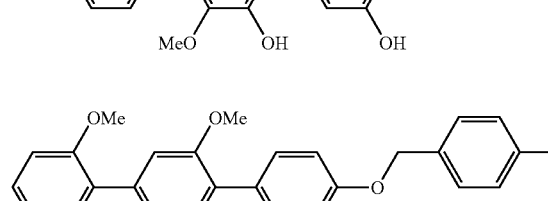
I-281
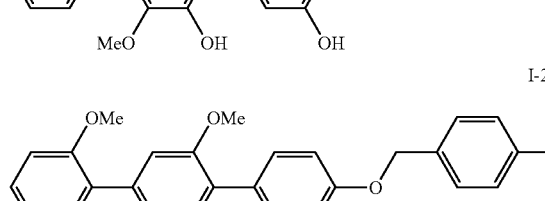
I-282
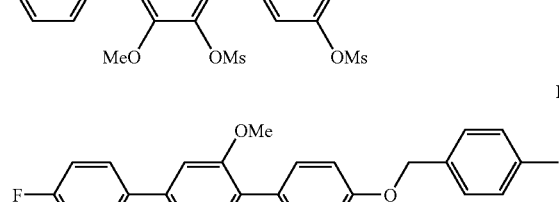
I-283
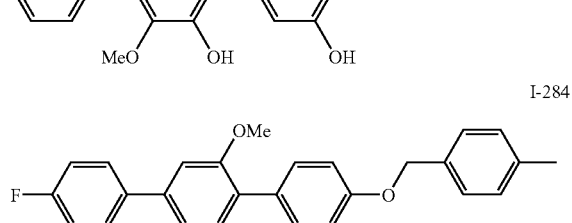
I-284
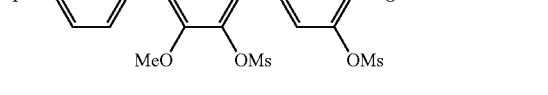

-continued
I-285
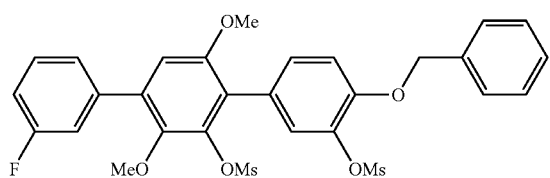
I-286
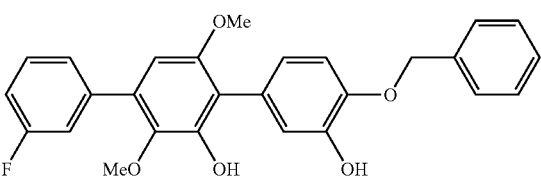
I-287
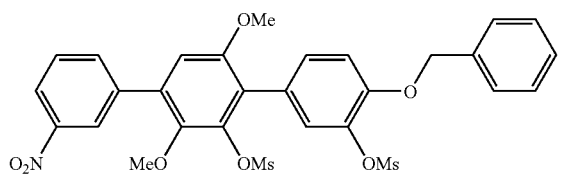
I-288
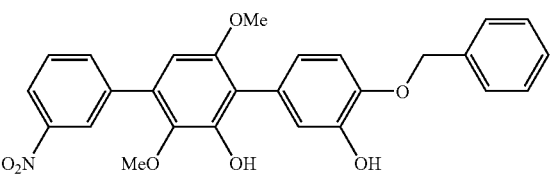
I-289
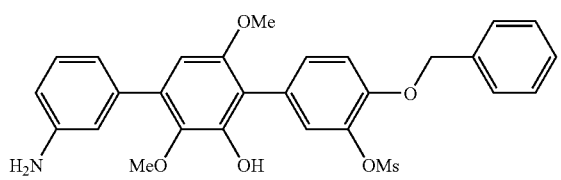
I-290
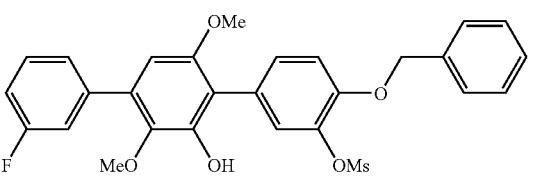
I-291
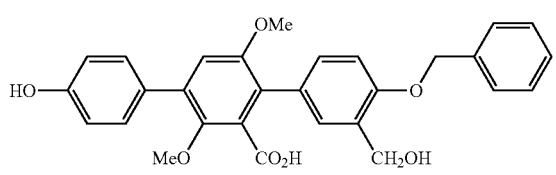
I-292
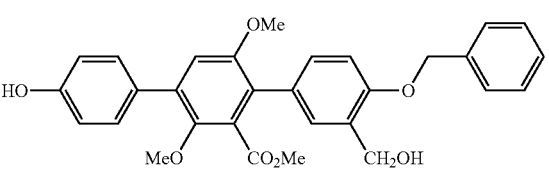
I-293
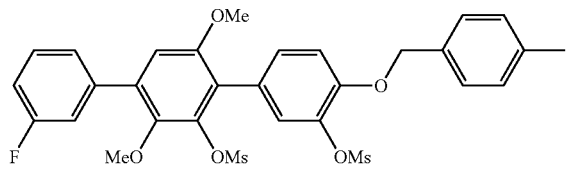
I-294
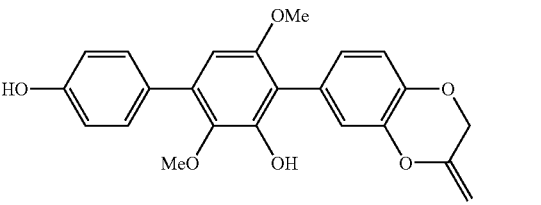
I-295
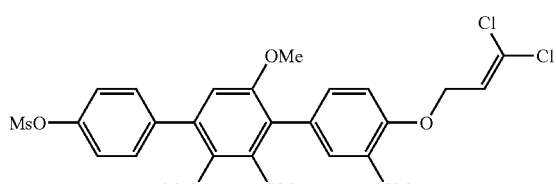
I-296
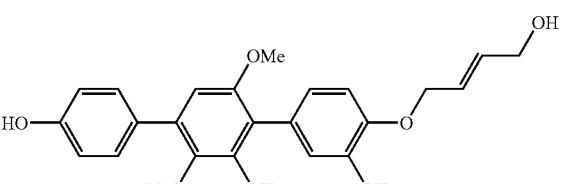
I-297
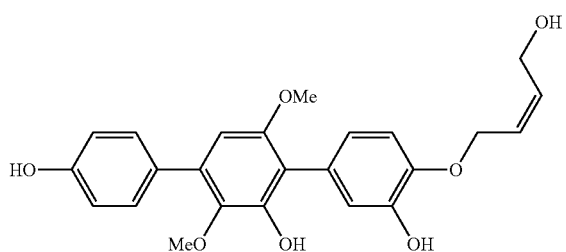
I-298
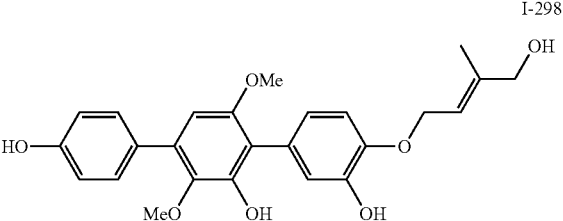

-continued
I-299
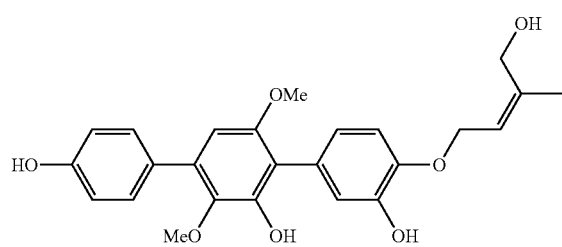
I-300
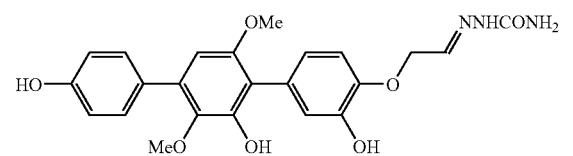
I-301
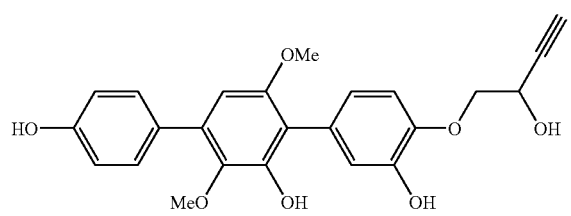
I-302
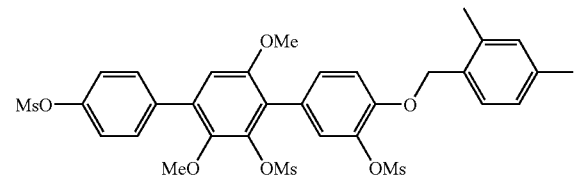
I-303
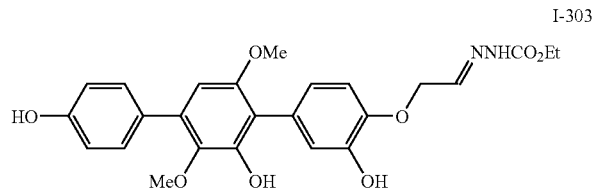
I-304
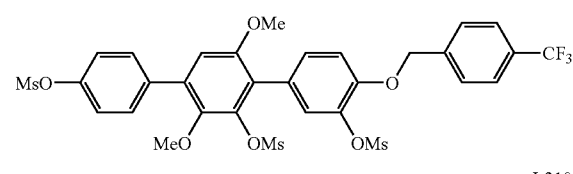
I-305
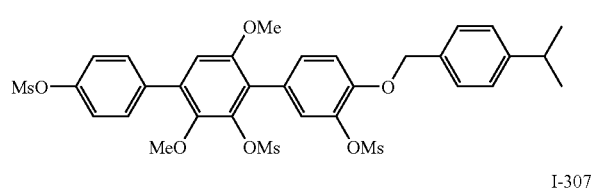
I-306
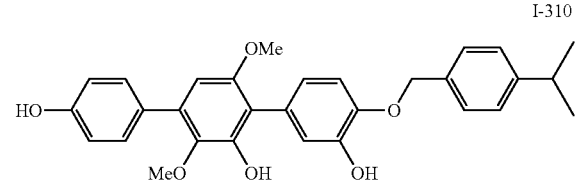
I-307
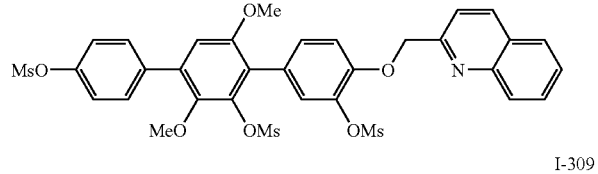
I-308
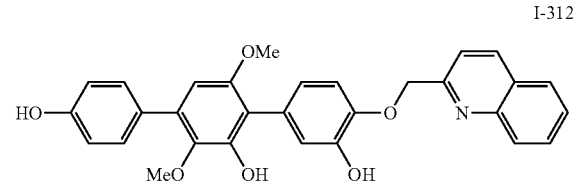
I-309
I-310
I-311
I-312

-continued
I-313
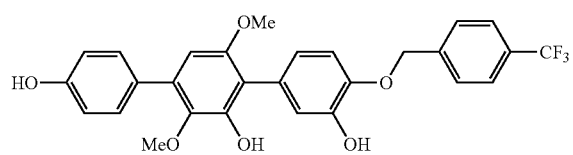
I-314
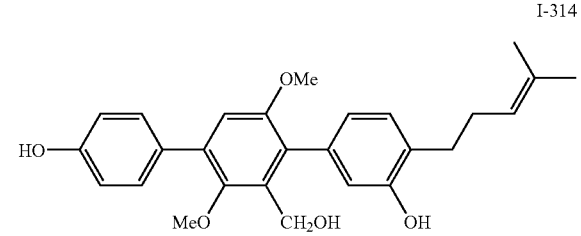
I-315
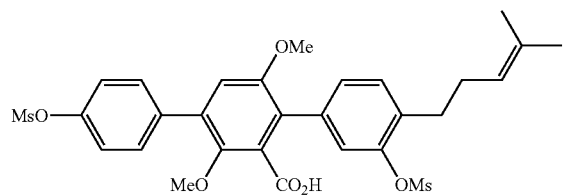
I-316
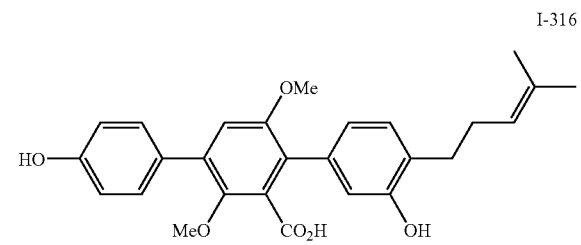
I-317
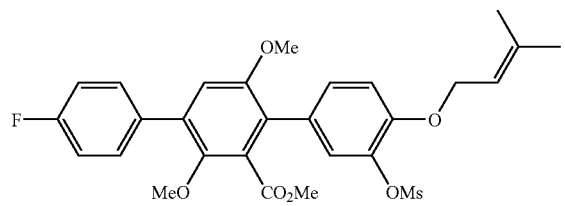
I-318
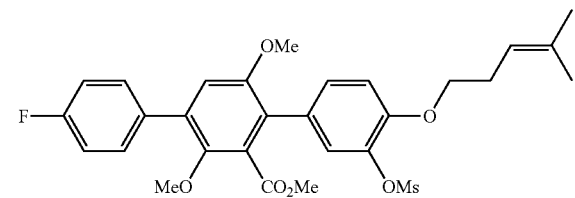
I-319
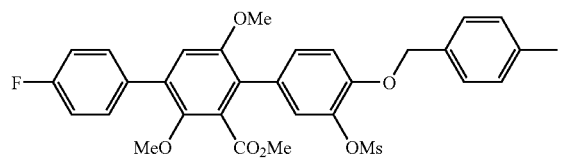
I-320
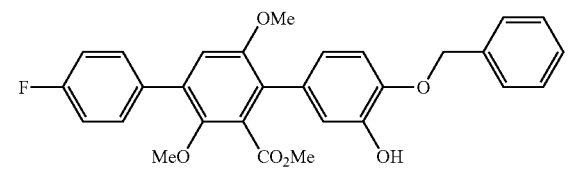
I-321
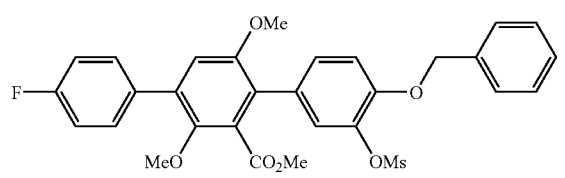
I-322
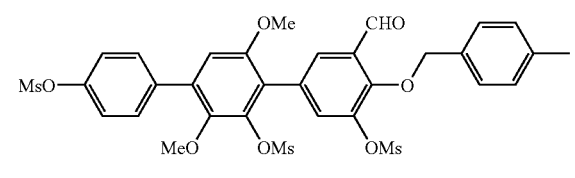
I-323
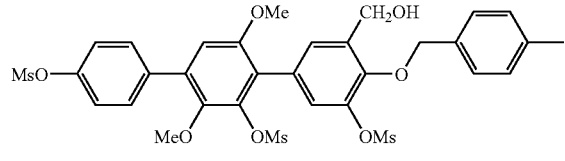
I-324
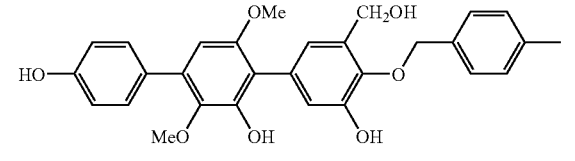
I-325
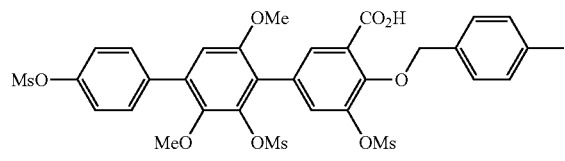
I-326
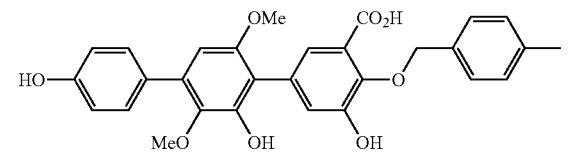

-continued
I-327
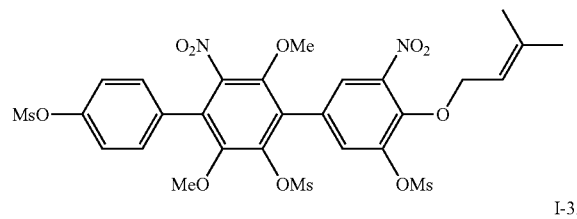
I-328
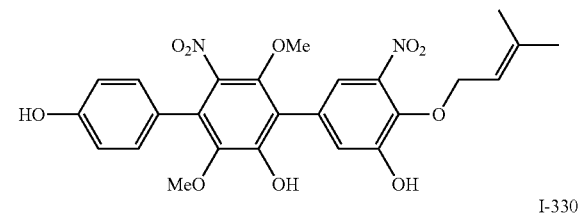
I-329
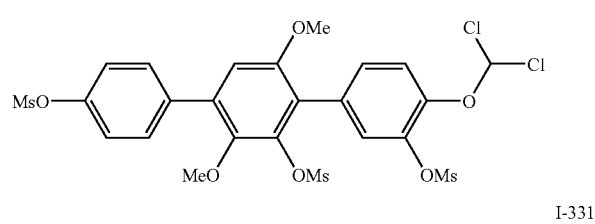
I-330
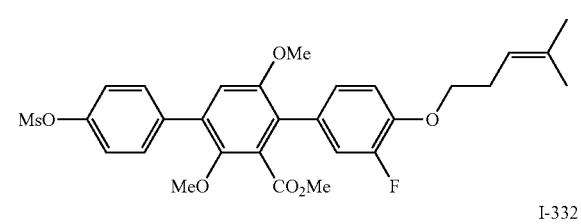
I-331
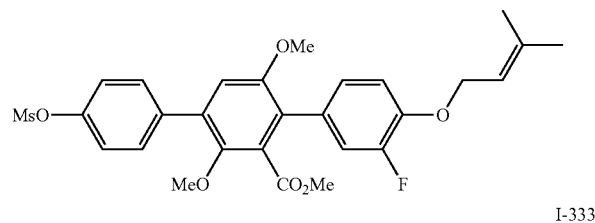
I-332
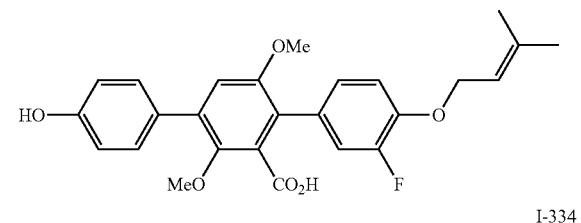
I-333
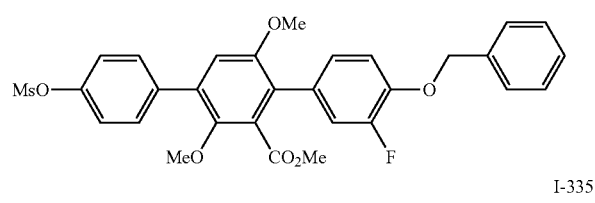
I-334
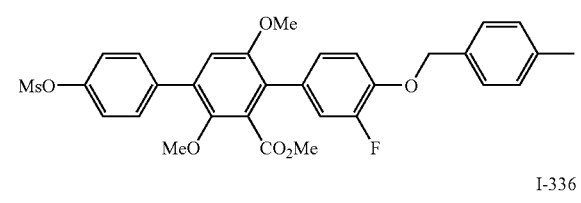
I-335
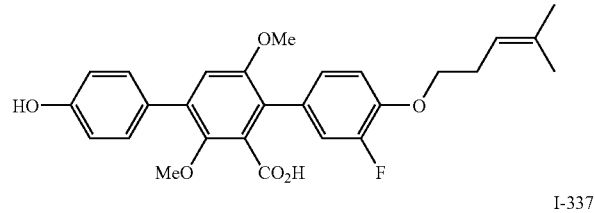
I-336
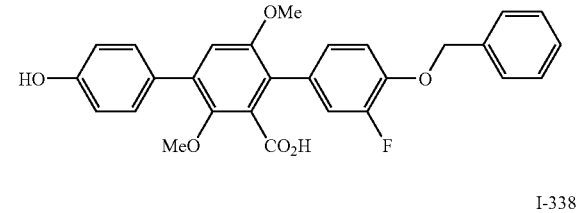
I-337
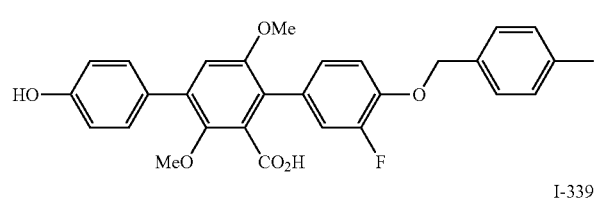
I-338
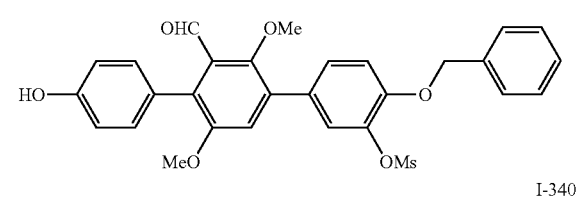
I-339
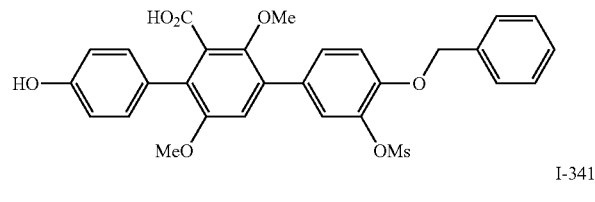
I-340
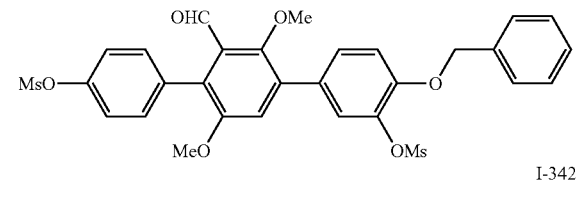

-continued
I-343
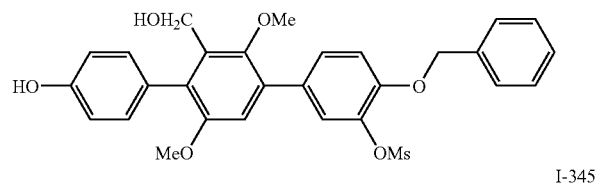
I-344
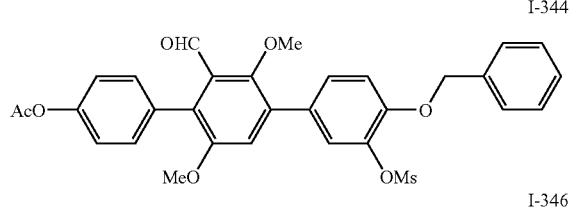
I-345
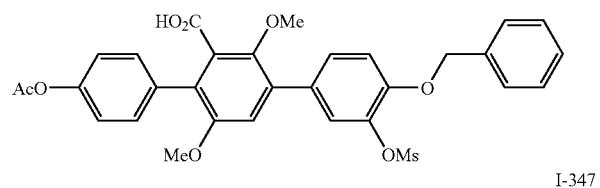
I-346
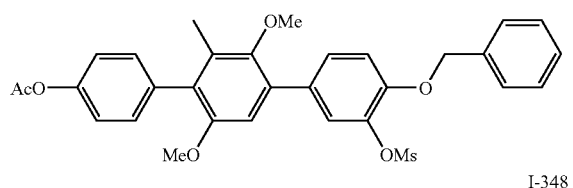
I-347
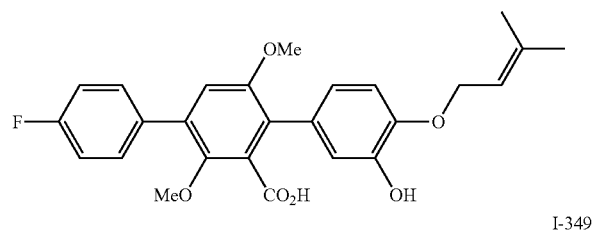
I-348
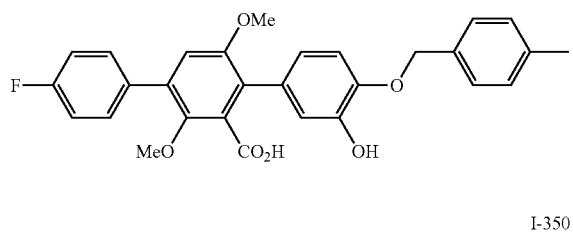
I-349
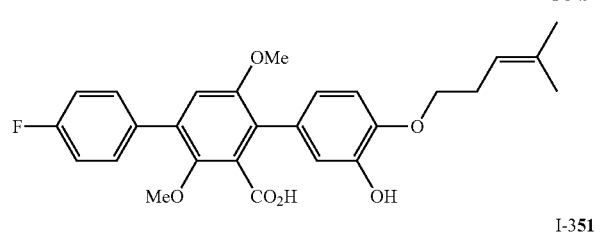
I-350
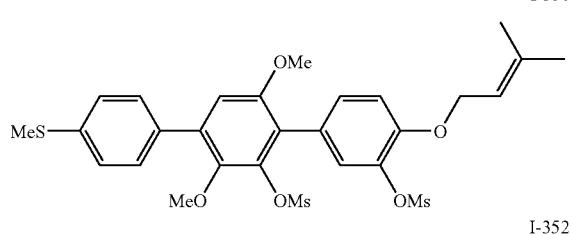
I-351
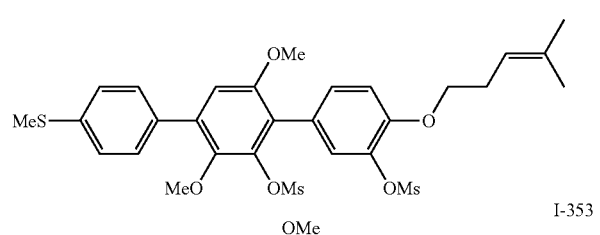
I-352
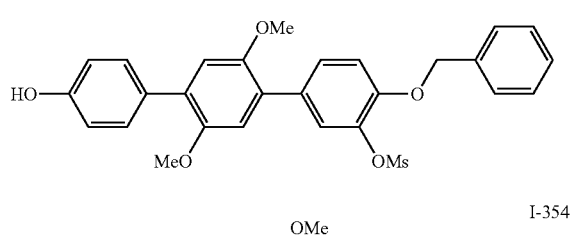
I-353
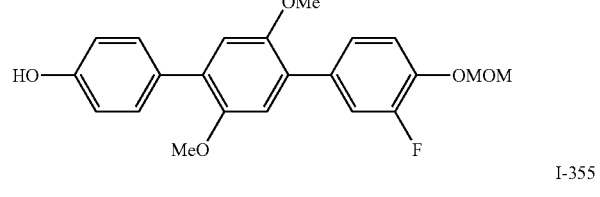
I-354
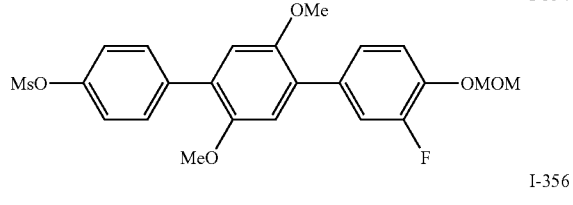
I-355
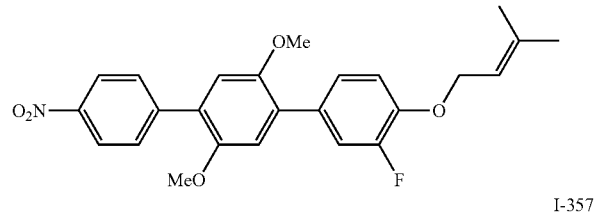
I-356
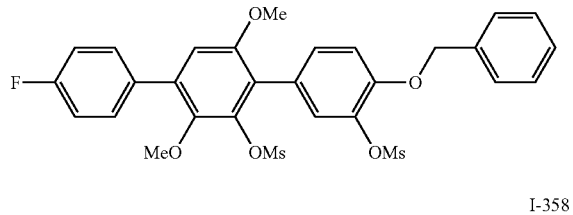
I-357
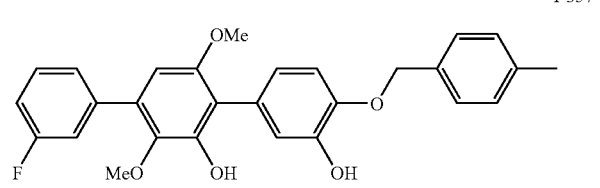
I-358
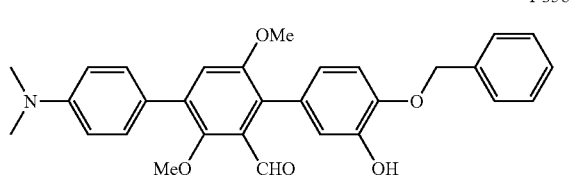

-continued
I-359
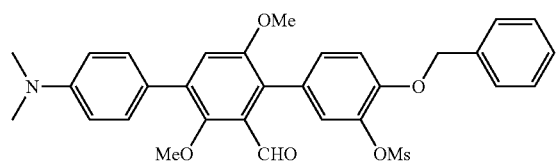
I-361
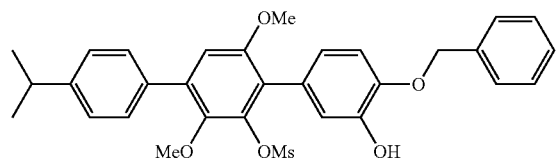
I-363
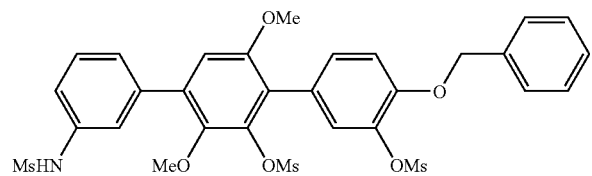
I-365
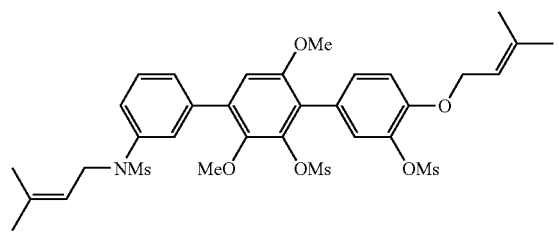
I-367
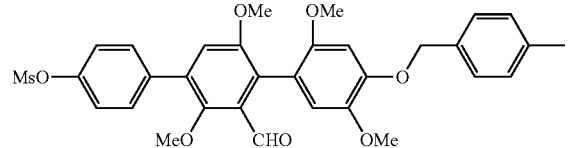
I-369
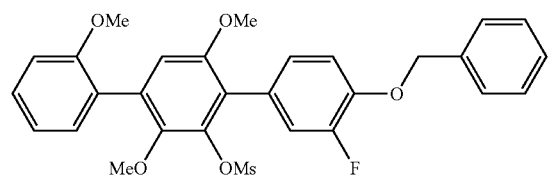
I-371
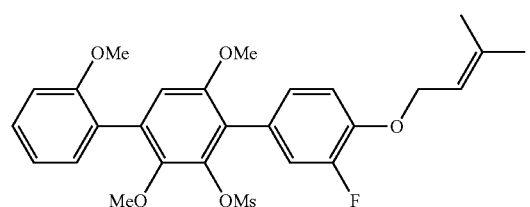
I-360
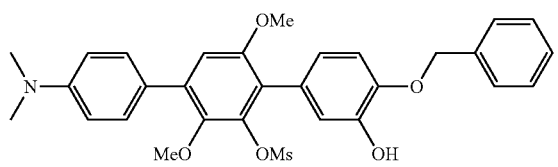
I-362
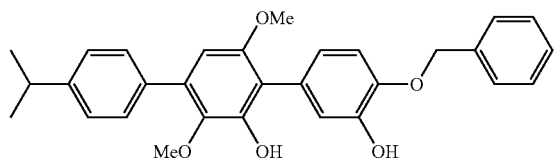
I-364
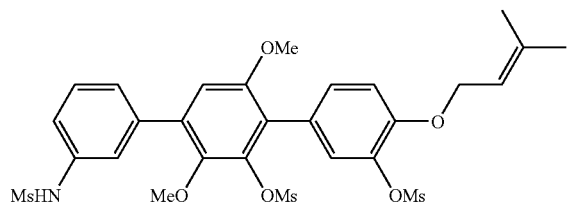
I-366
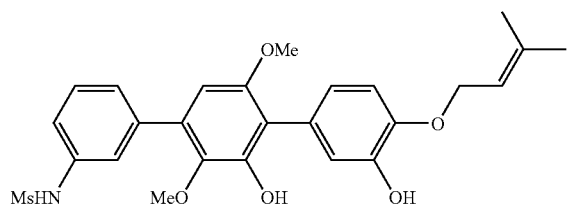
I-368
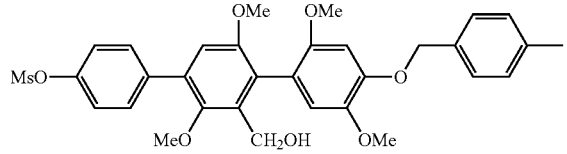
I-370
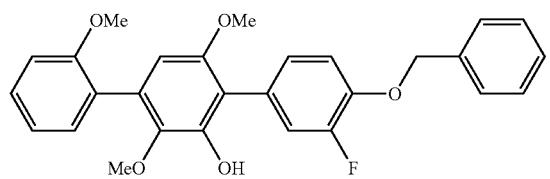

-continued
I-373
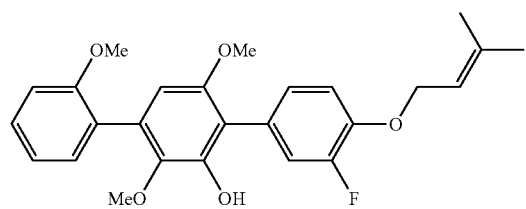
I-374
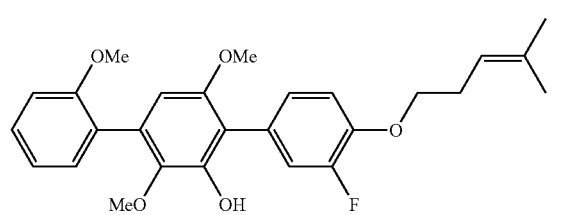
I-375
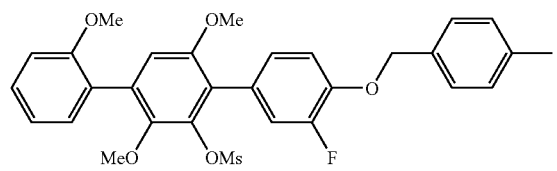
I-376
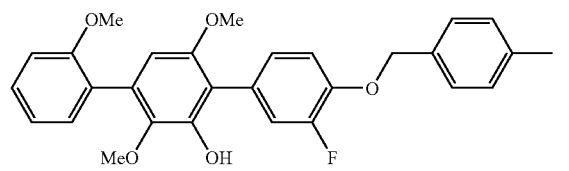
I-377
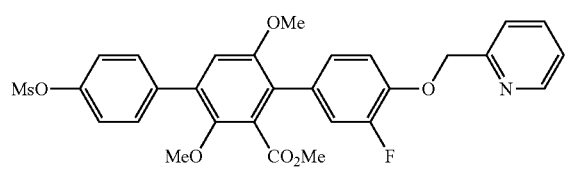
I-378
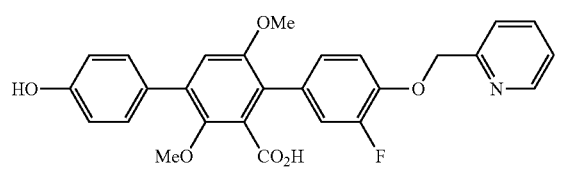
I-379
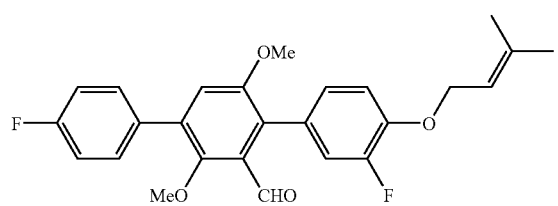
I-380
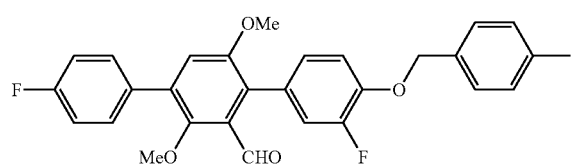
I-381
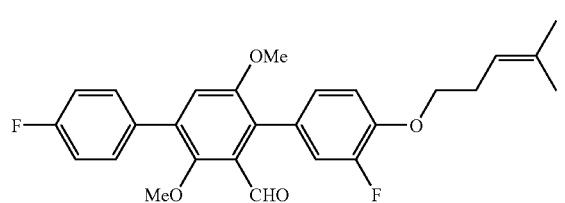
I-382
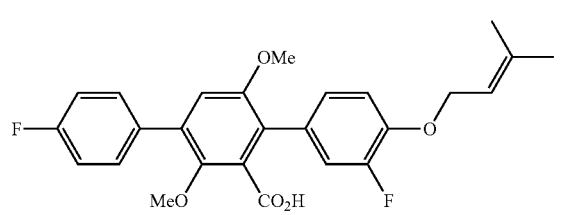
I-383
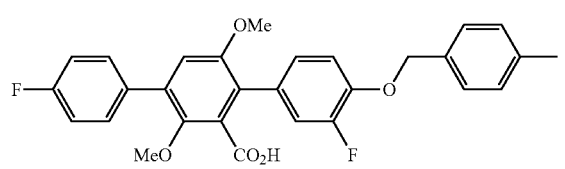
I-384
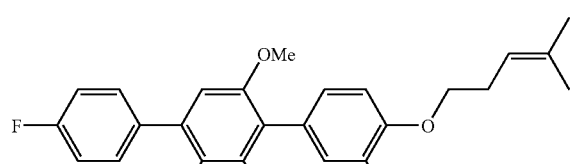
I-385
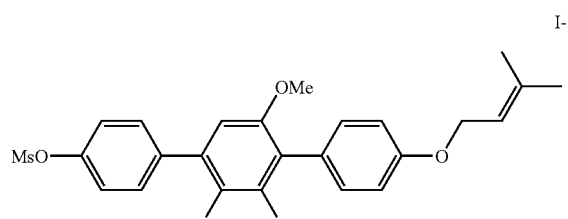
I-386
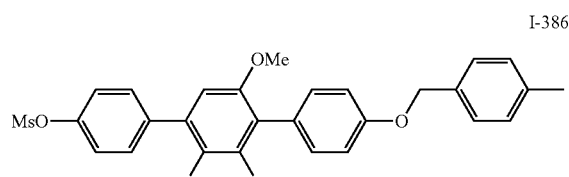

-continued
I-387
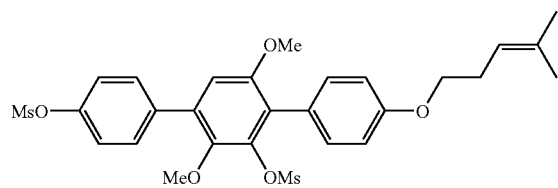
I-388
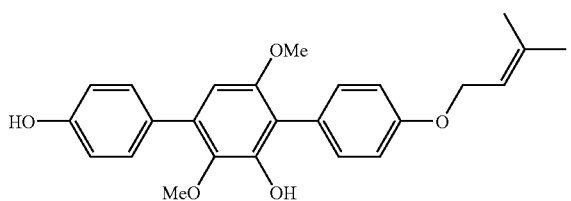
I-389
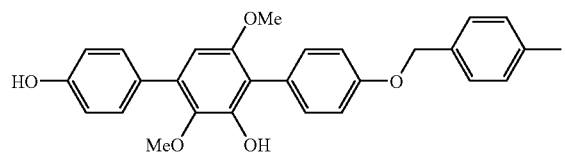
I-390
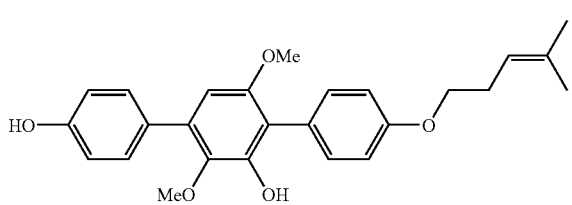
I-391
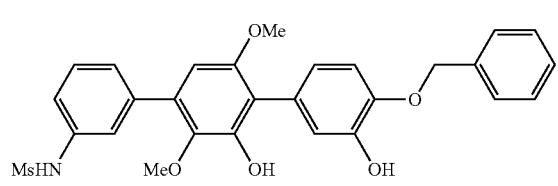
I-392
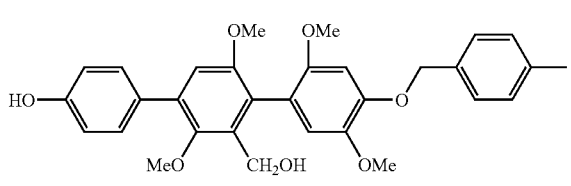
I-393
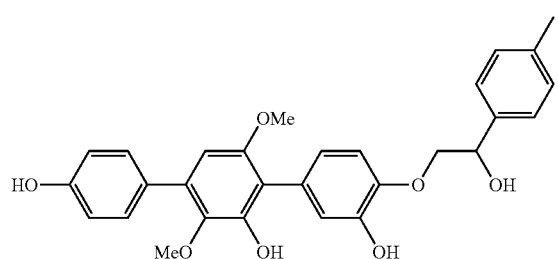
I-394
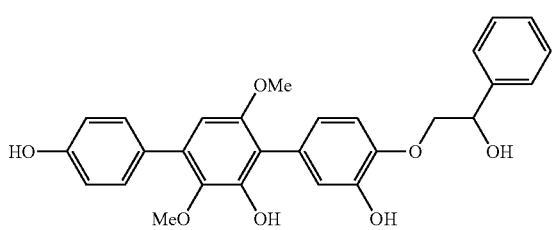
I-395
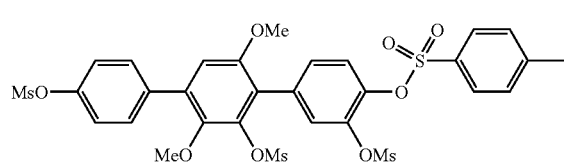
I-396
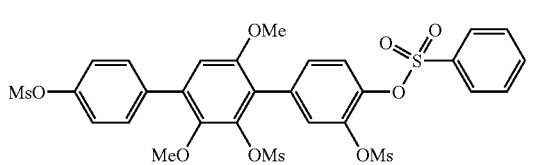
I-397
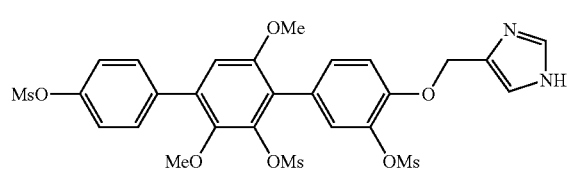
I-398
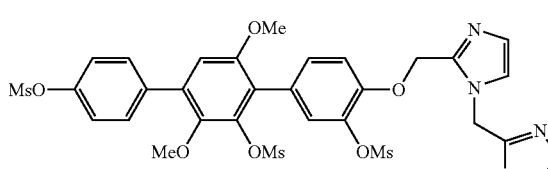
I-399
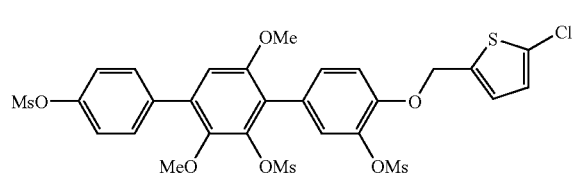
I-400
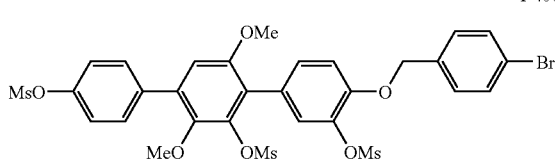

-continued
I-401
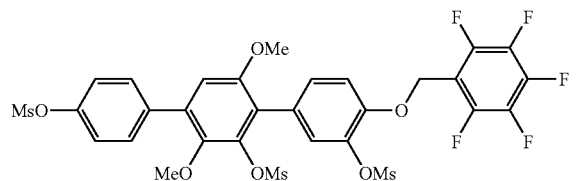
I-402
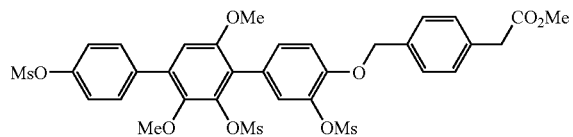
I-403
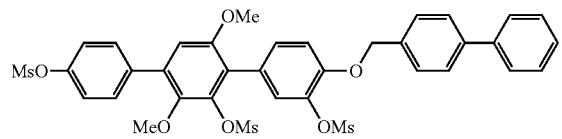
I-404
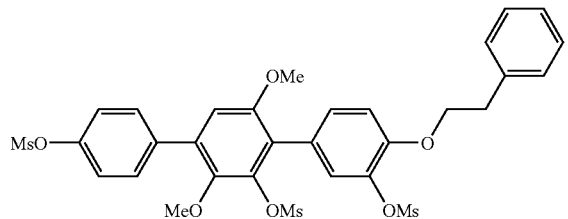
I-405
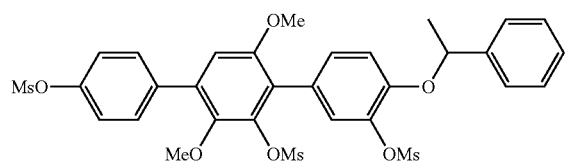
I-406
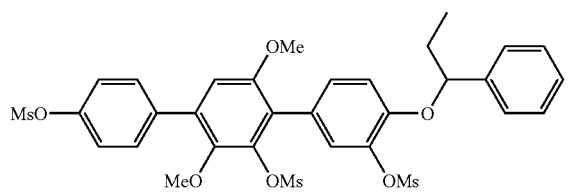
I-407
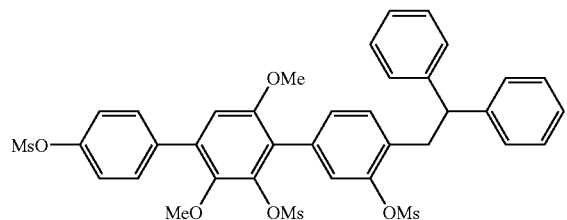
I-408
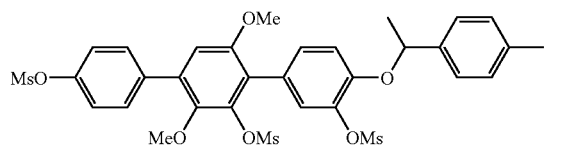
I-409
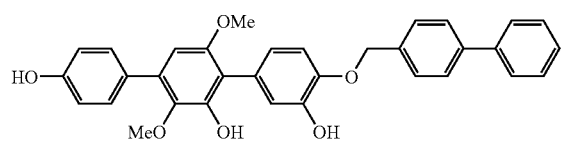
I-410
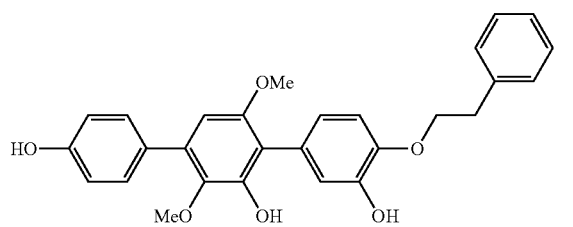
I-411
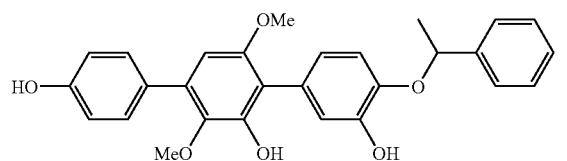
I-412
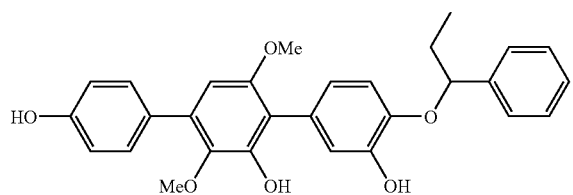
I-413
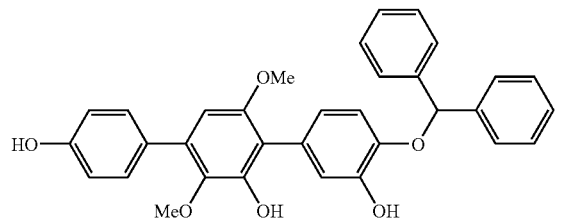
I-414

-continued
I-415
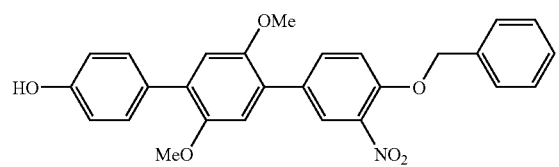
I-416
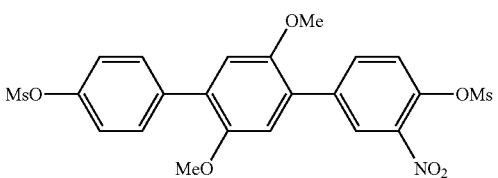
I-417
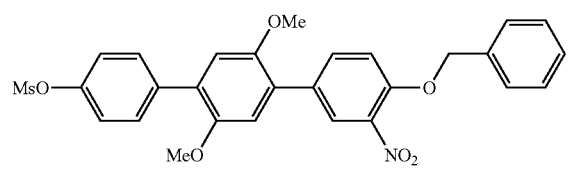
I-418
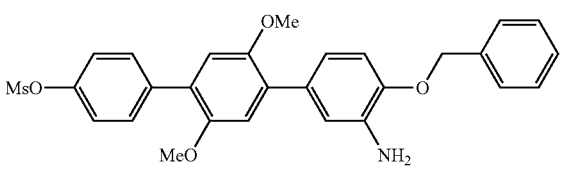
I-419
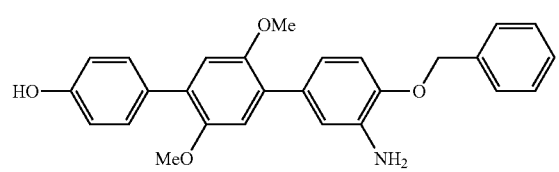
I-420
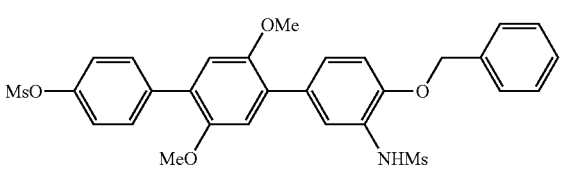
I-421
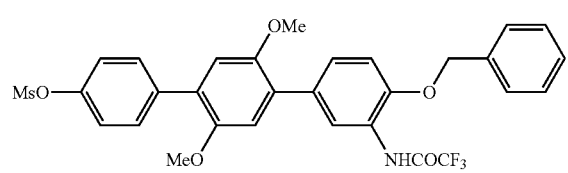
I-422
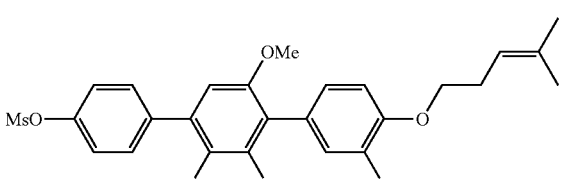
I-423
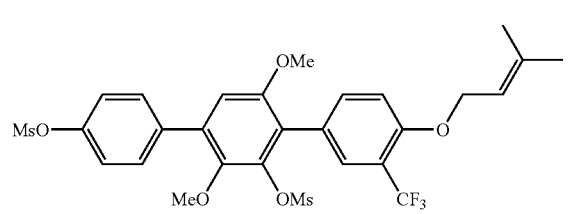
I-424
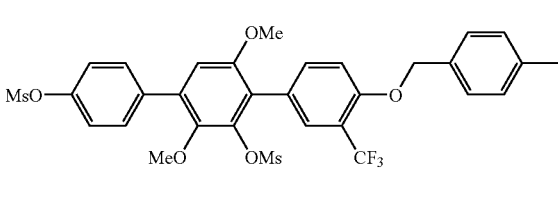
I-425
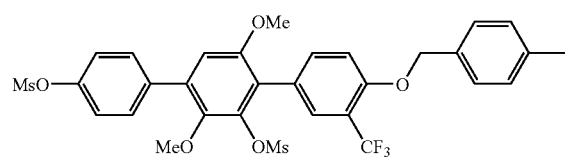
I-426
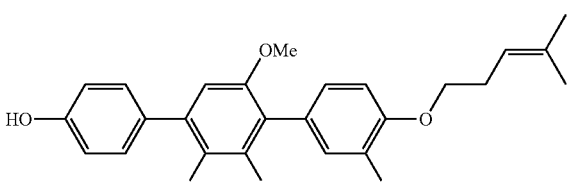
I-427
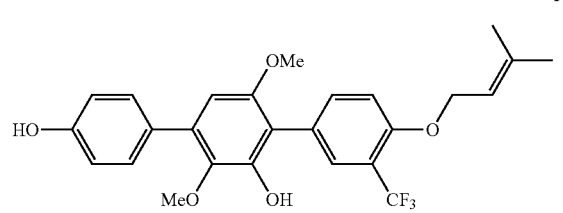
I-428
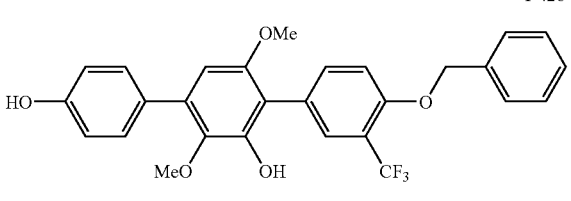

-continued
I-429
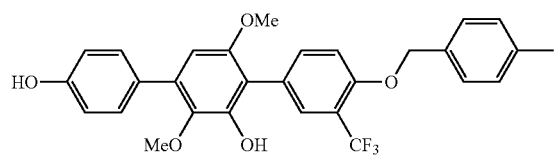
I-430
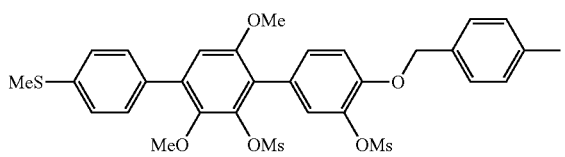
I-431
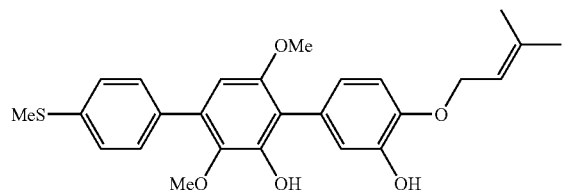
I-432
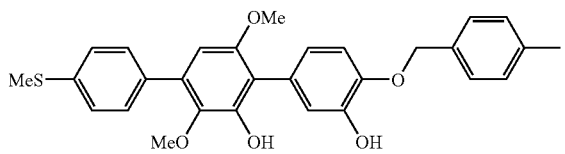
I-433
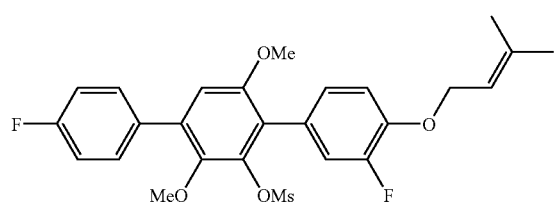
I-434
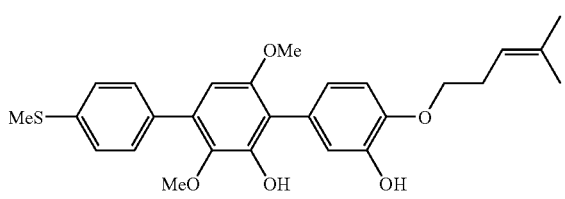
I-435
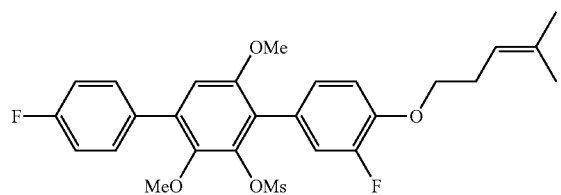
I-436
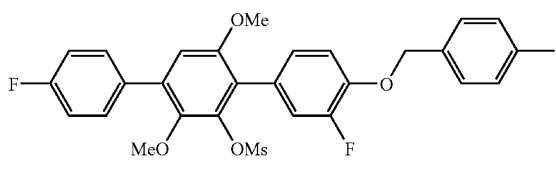
I-437
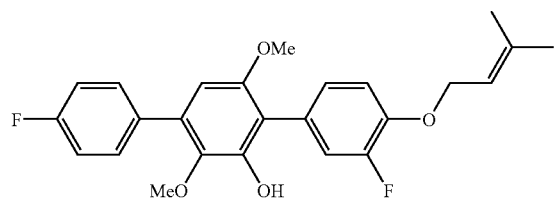
I-438
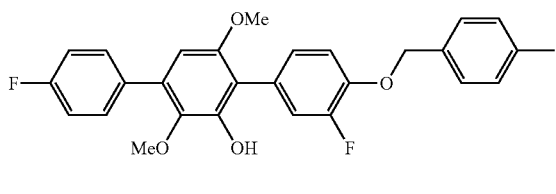
I-439
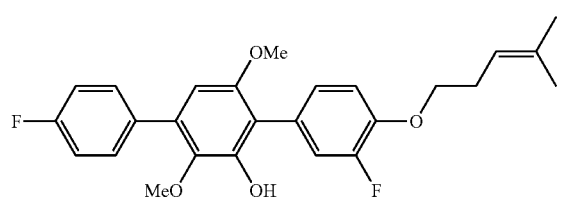
I-440
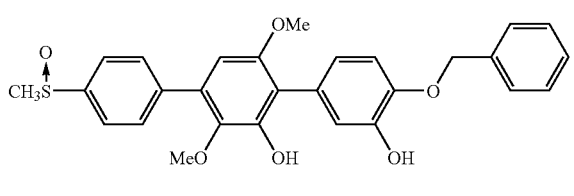
I-441
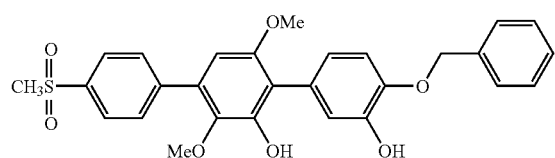
I-442
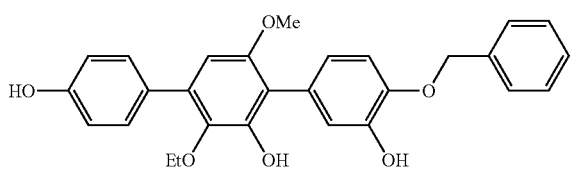

-continued
I-443
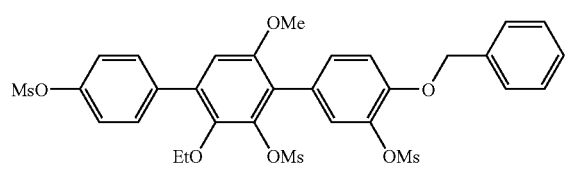
I-444
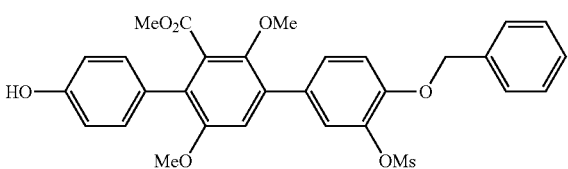
I-445
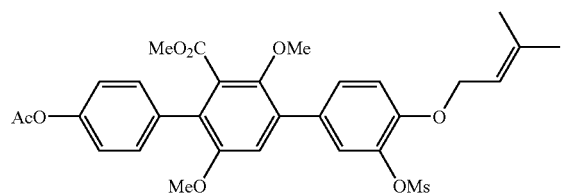
I-446
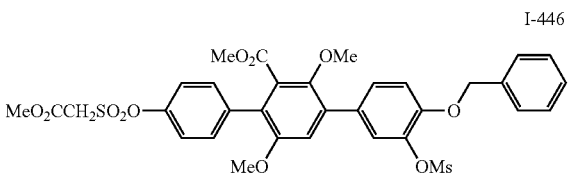
I-447
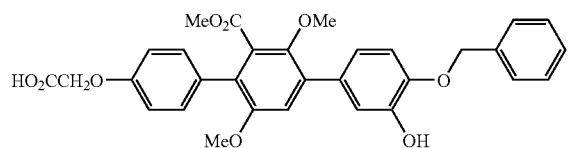
I-448
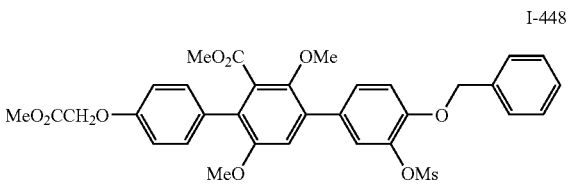
I-449
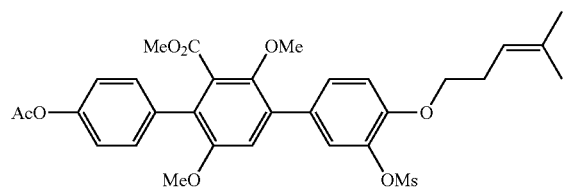
I-450
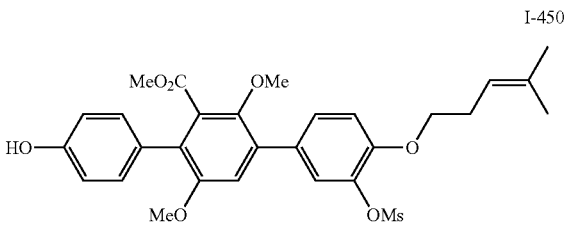
I-451
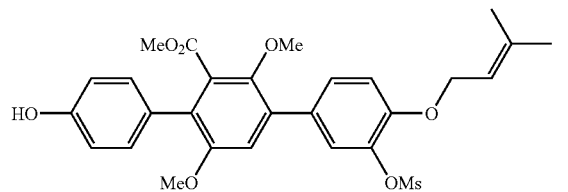
I-452
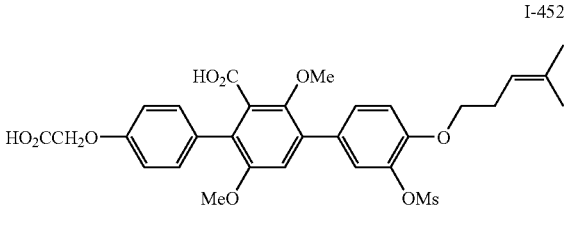
I-453
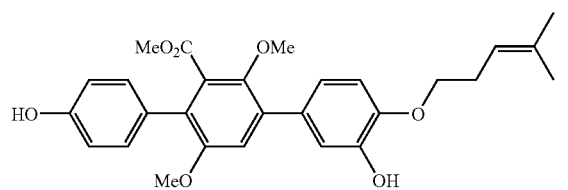
I-454
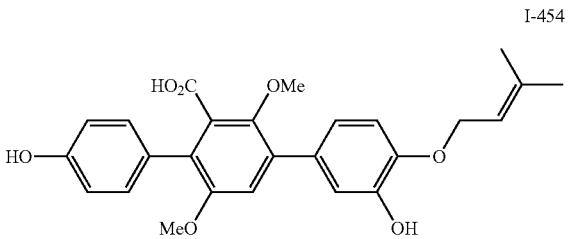
I-455
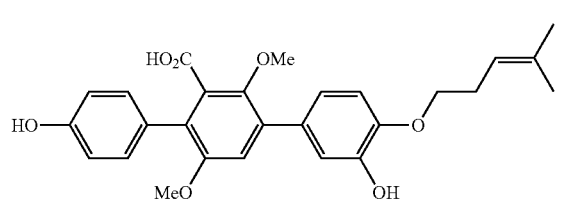
I-456
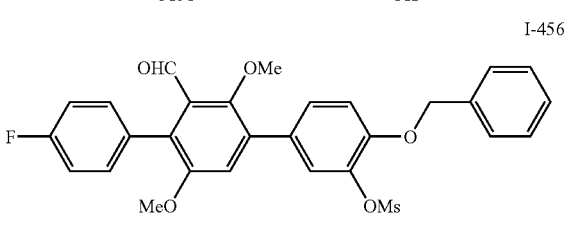

-continued
I-457
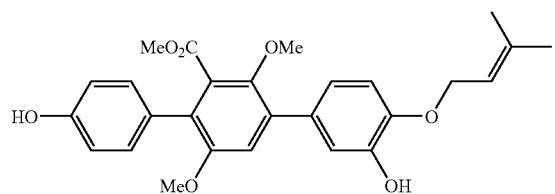
I-458
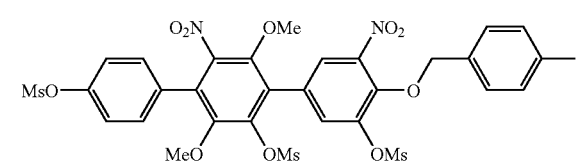
I-459
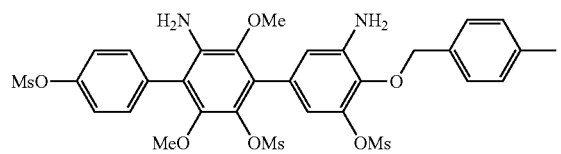
I-460
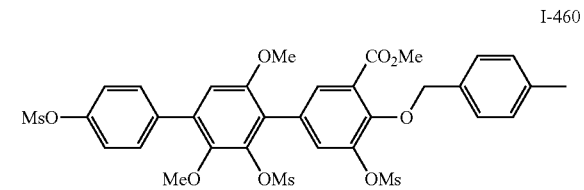
I-461
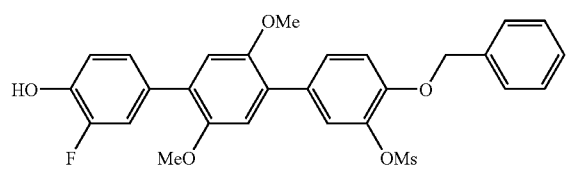
I-462
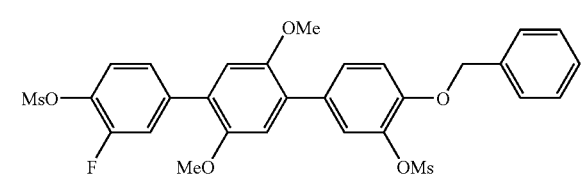
I-463
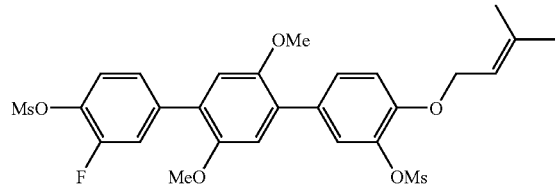
I-464
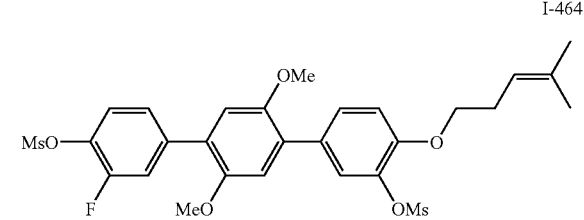
I-465
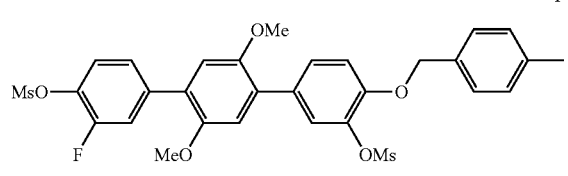
I-466
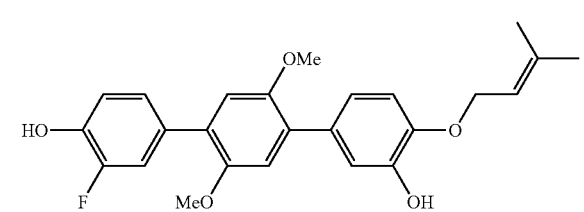
I-467
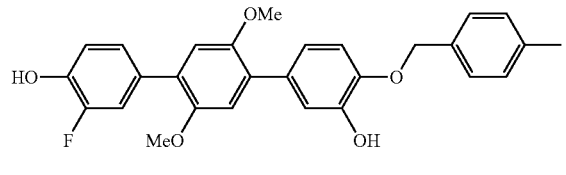
I-468
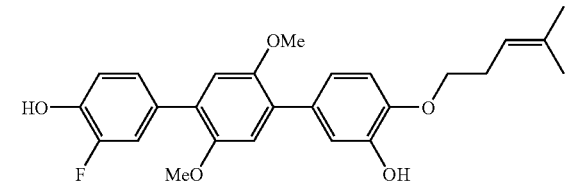
I-469
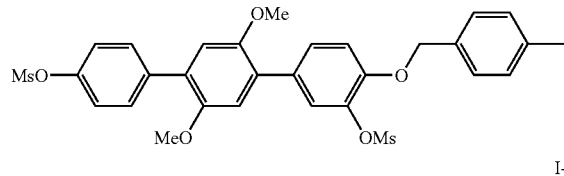
I-470
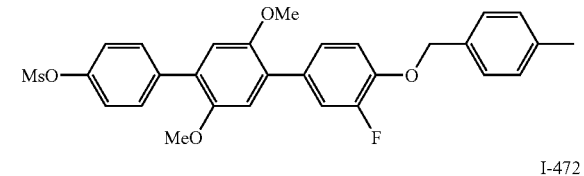
I-471
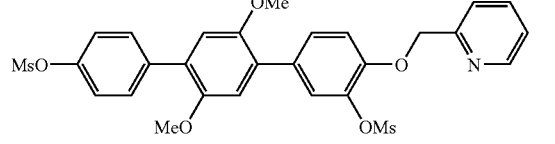
I-472

-continued
I-473
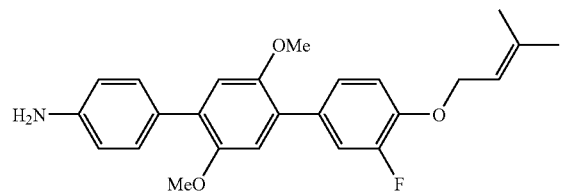
I-474
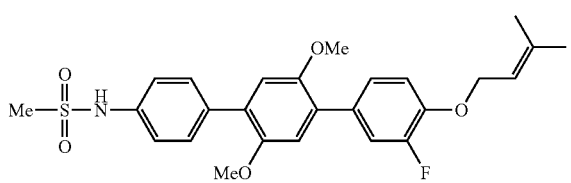
I-475
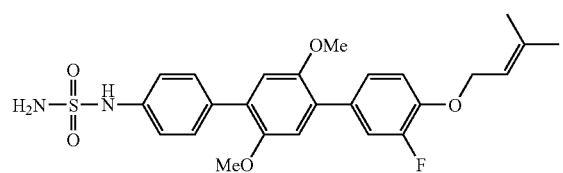
I-476
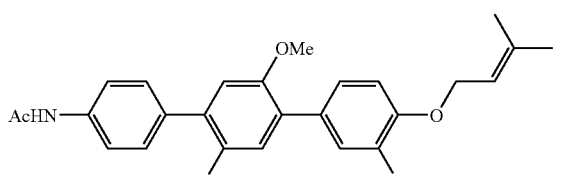
I-477
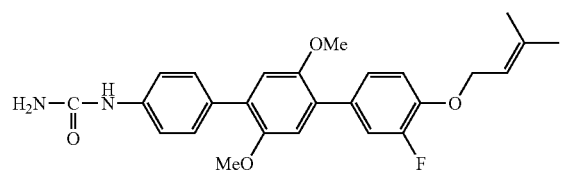
I-478
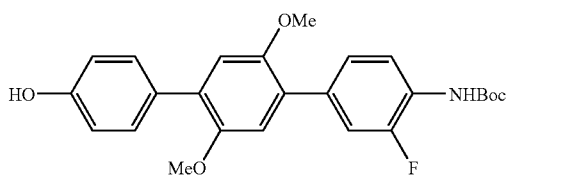
I-479
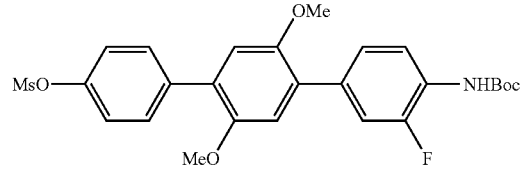
I-480
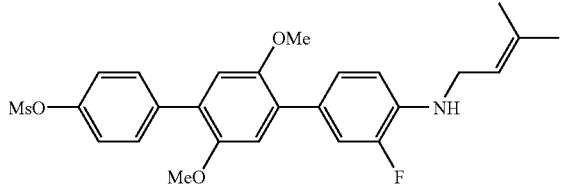
I-481
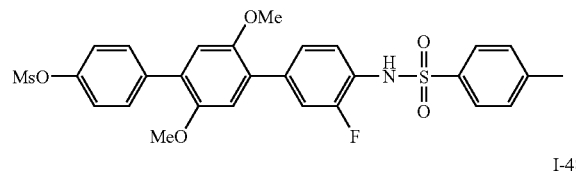
I-482
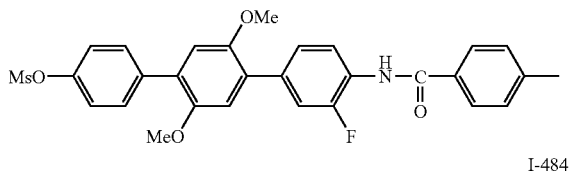
I-483
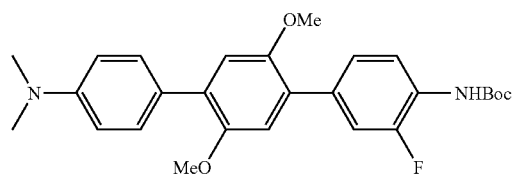
I-484
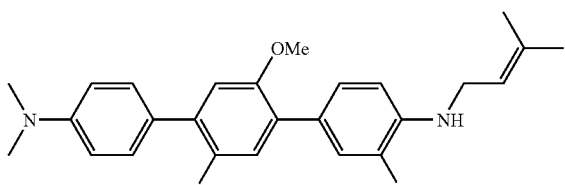
I-485
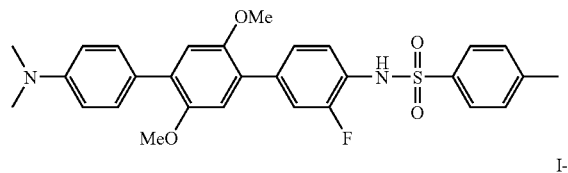
I-486
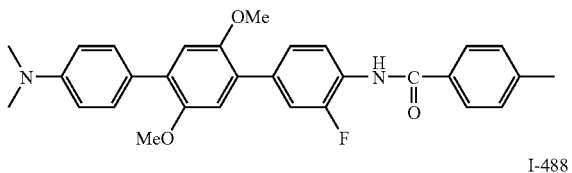
I-487
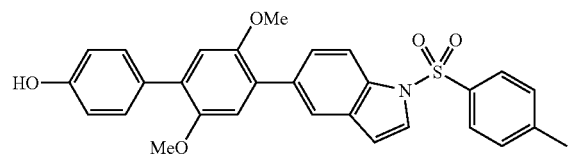
I-488

-continued
I-489
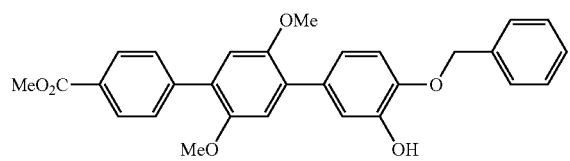
I-491
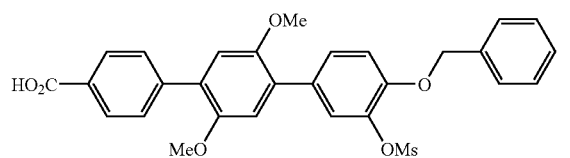
I-493
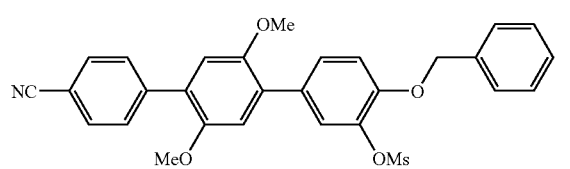
I-495
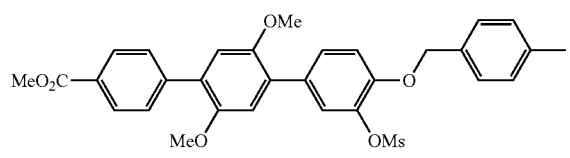
I-497
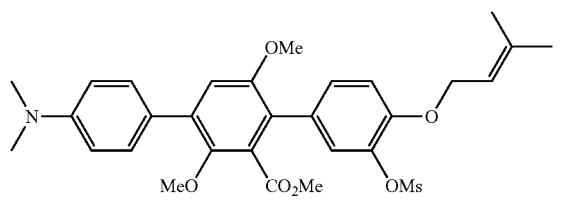
I-499
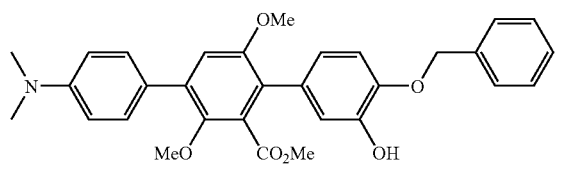
I-501
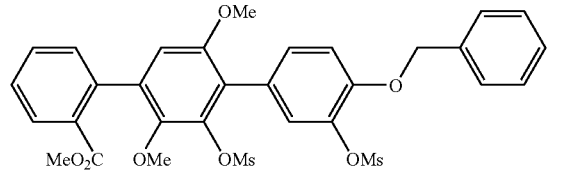
I-490
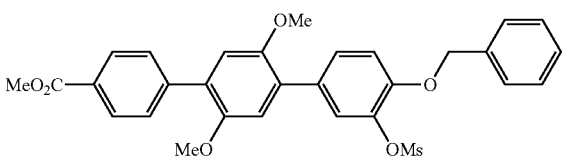
I-492
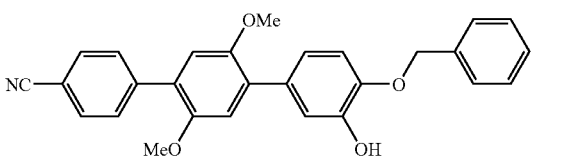
I-494
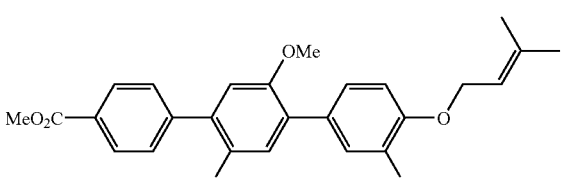
I-496
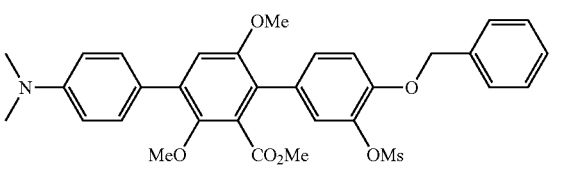
I-498
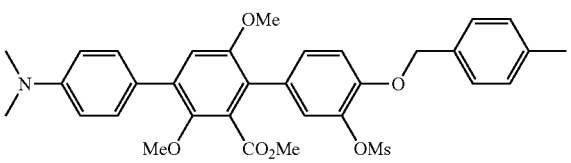
I-500
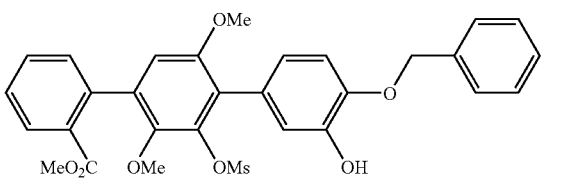
I-502
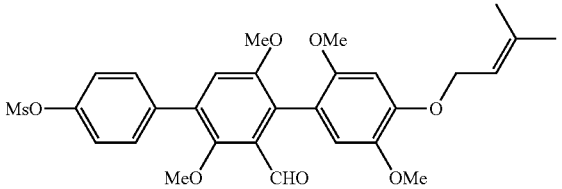

-continued
I-503
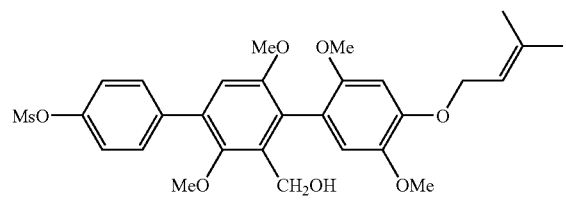
I-504
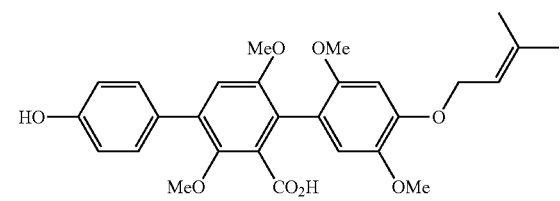
I-505
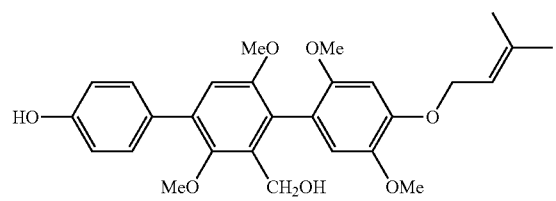
I-506
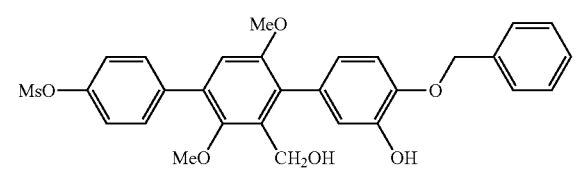
I-507
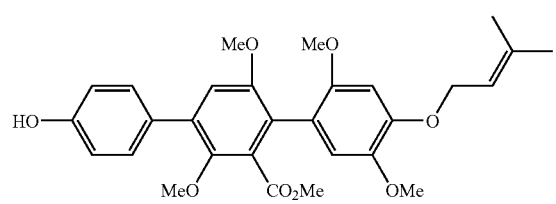
I-508
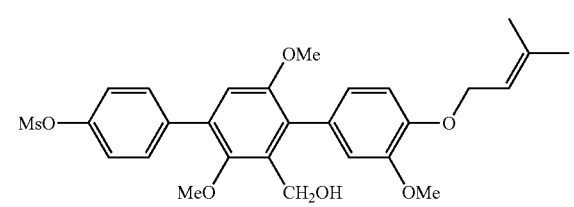
I-509
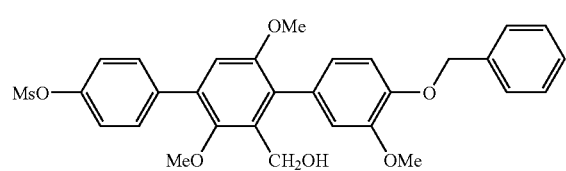
I-510
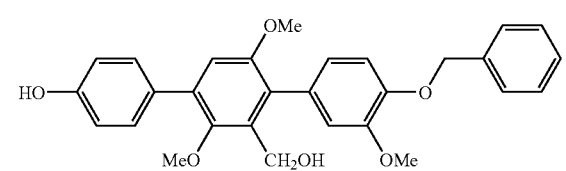
I-511
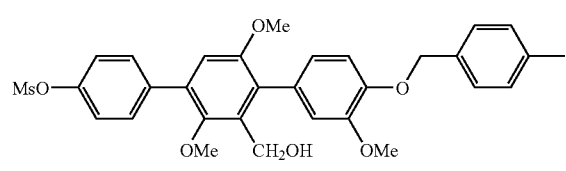
I-512
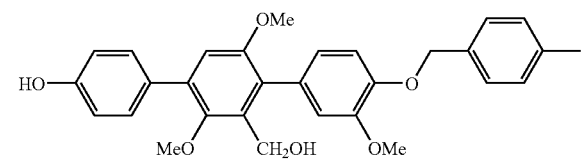
I-513
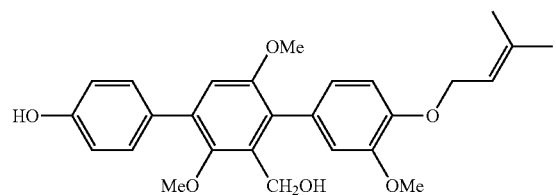
I-514
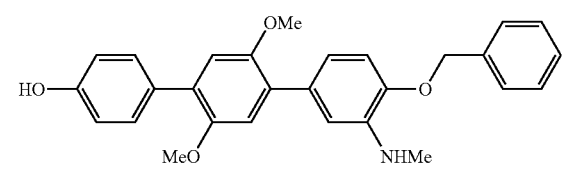
I-515
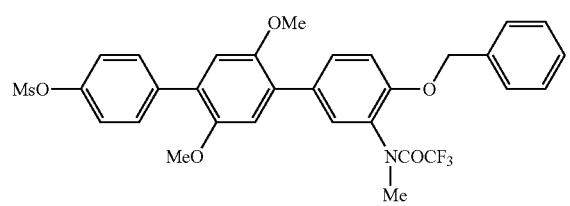
I-516

I-517
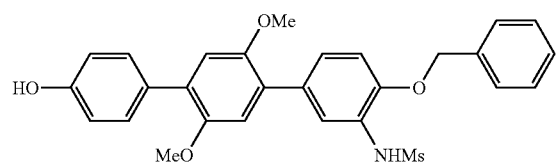
I-518
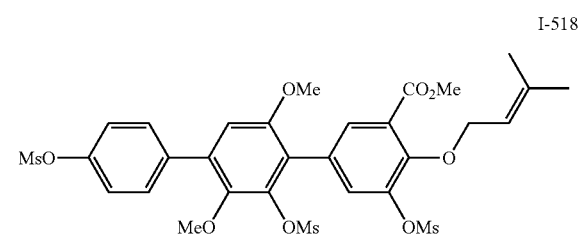
I-519
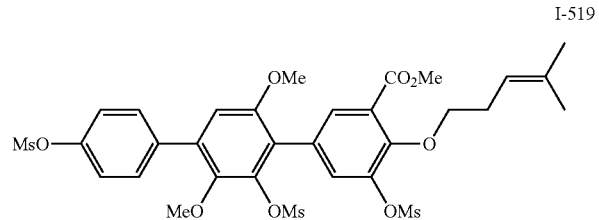
I-520
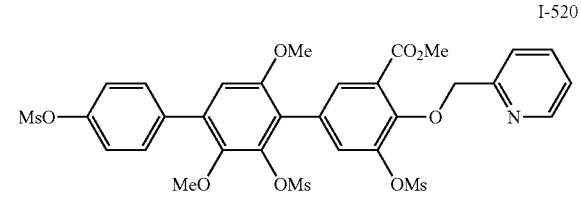
I-521
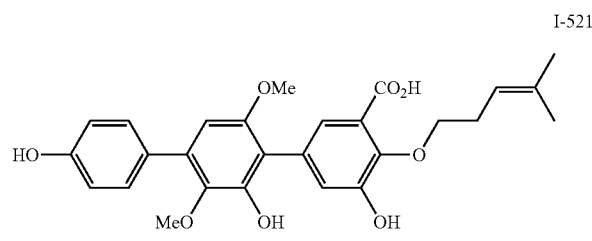
I-522
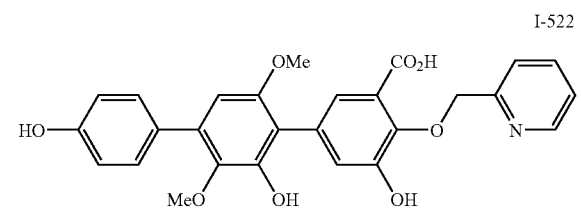
I-523
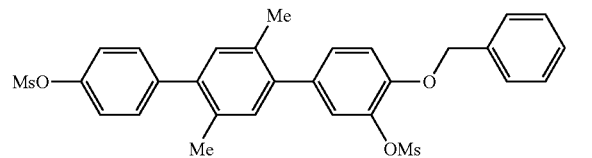
I-524
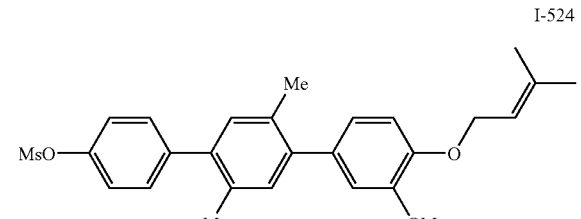
I-525
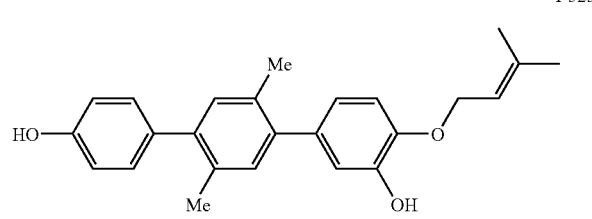
I-526
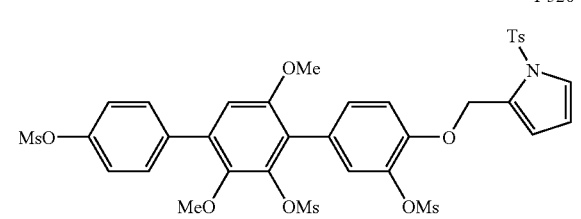
I-527
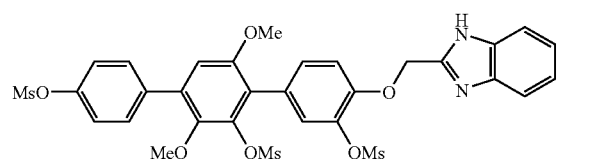
I-528
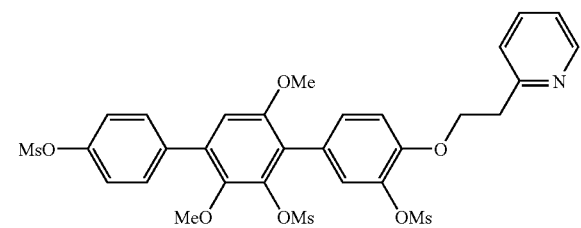
I-529
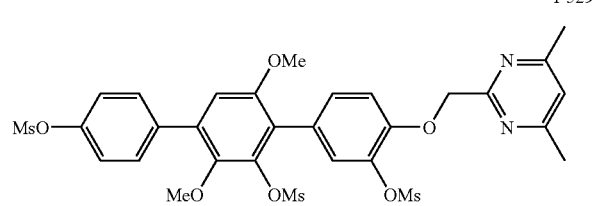
I-530
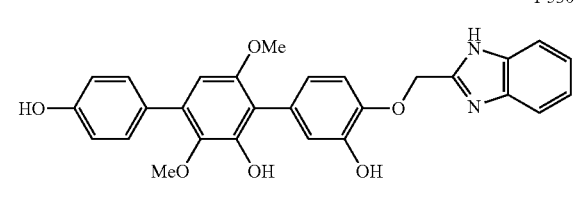

-continued
I-531
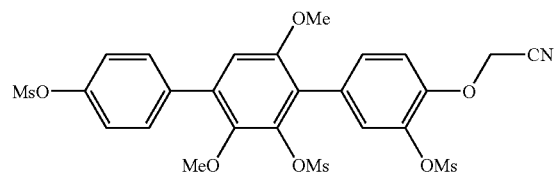
I-532
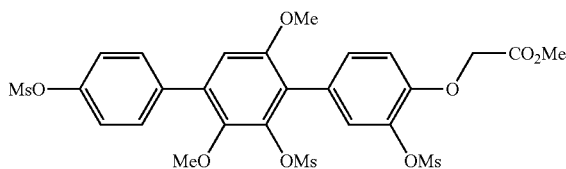
I-533
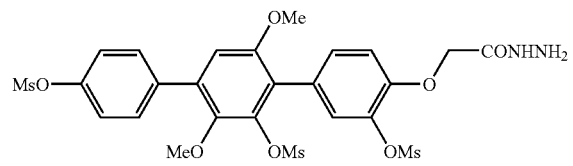
I-534
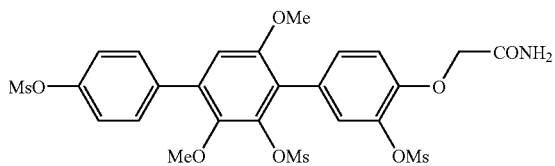
I-535
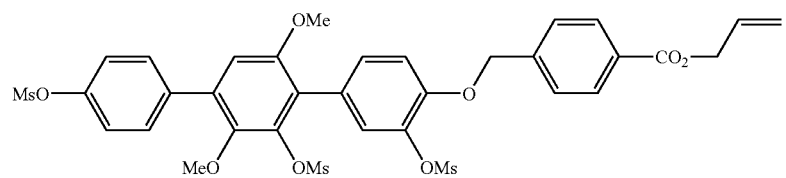
I-536
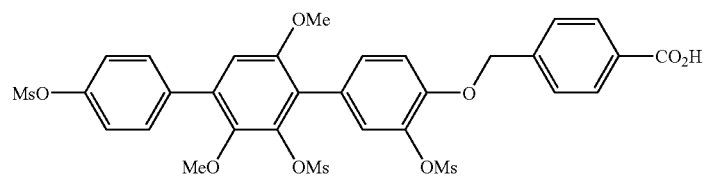
I-537
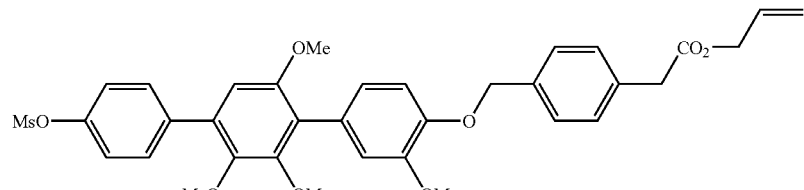
I-538
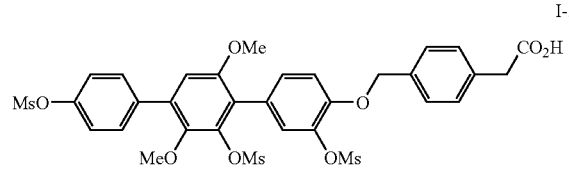
I-539
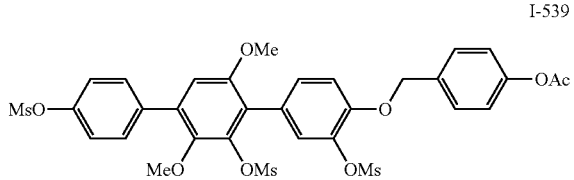
I-540
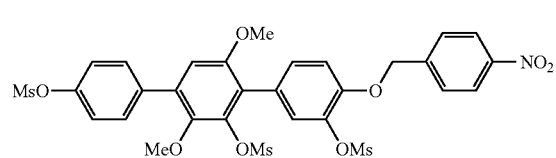
I-541
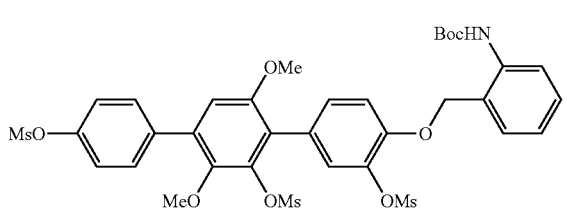
I-542
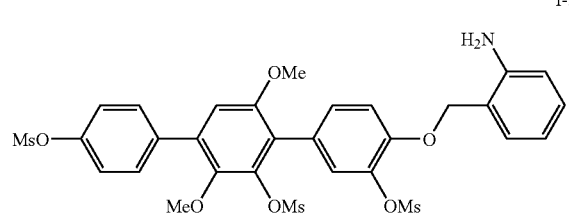
I-543

-continued
I-544
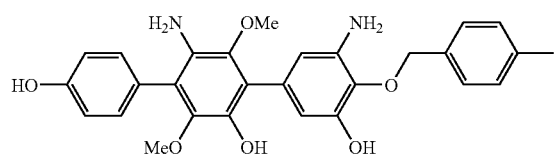
I-545
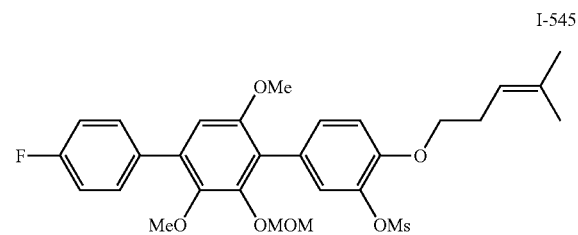
I-546
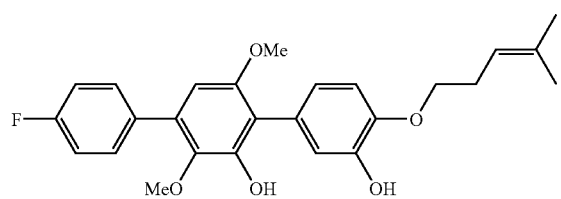
I-547
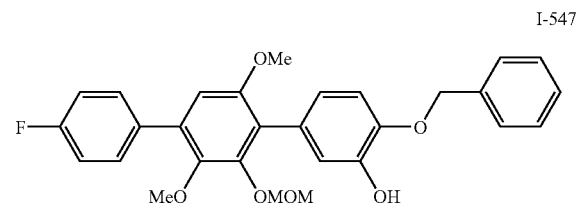
I-548
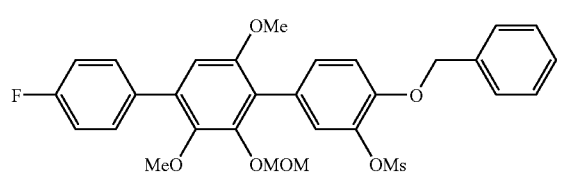
I-549
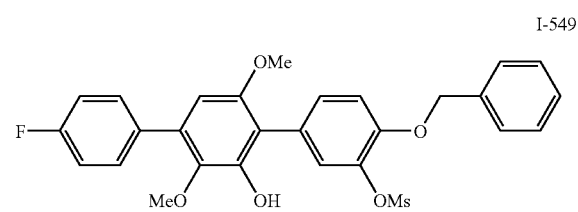
I-550
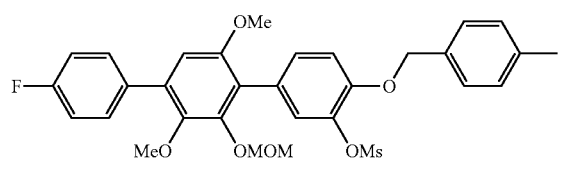
I-551
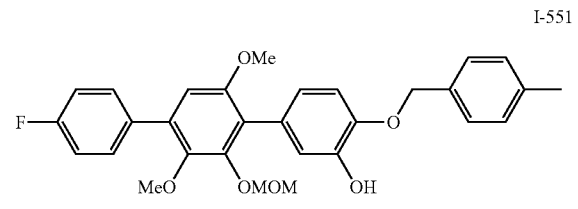
I-552
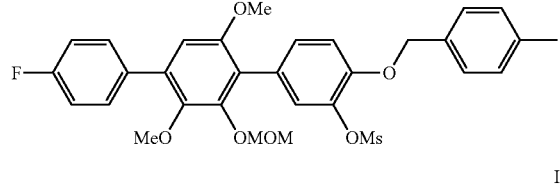
I-553
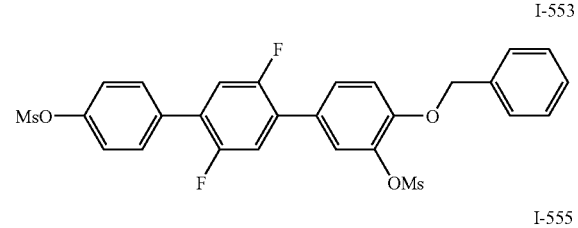
I-554
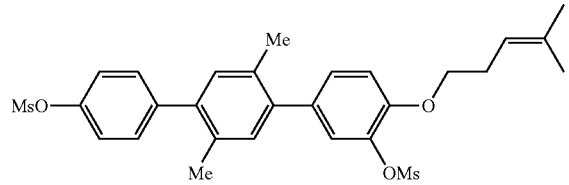
I-555
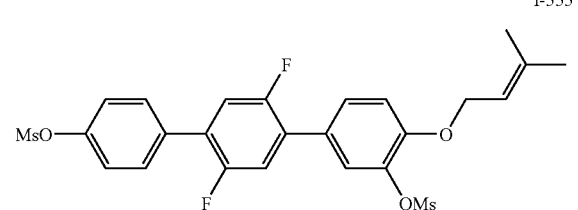
I-556
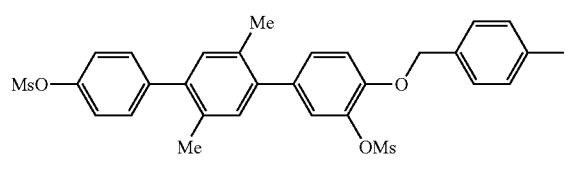
I-557
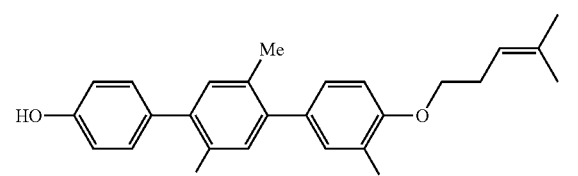

-continued
I-558
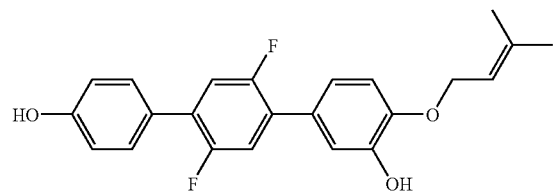
I-559
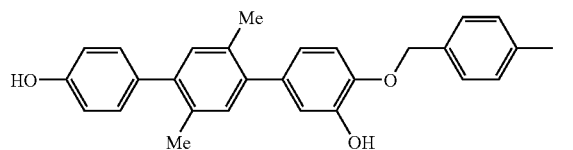
I-560
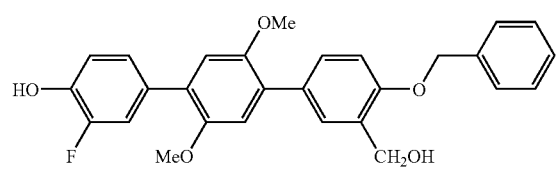
I-561
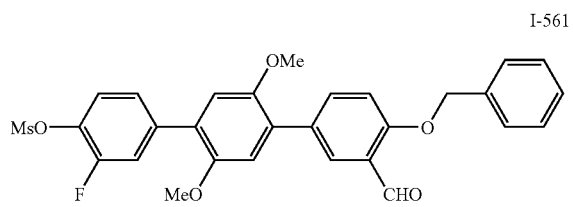
I-562
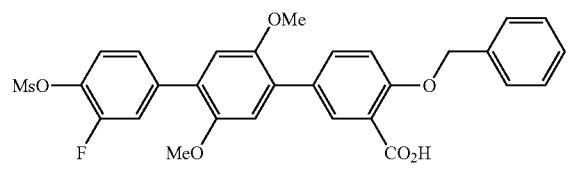
I-563
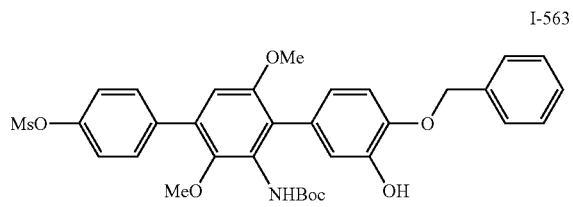
I-564
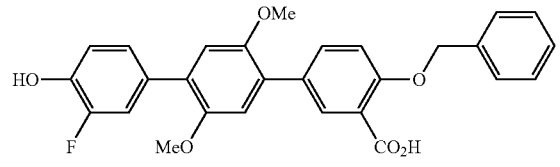
I-565
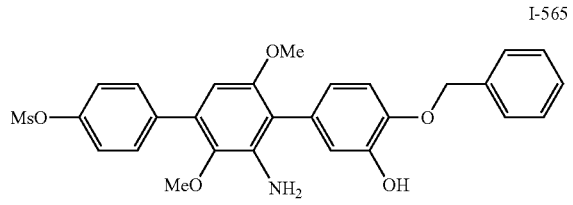
I-566
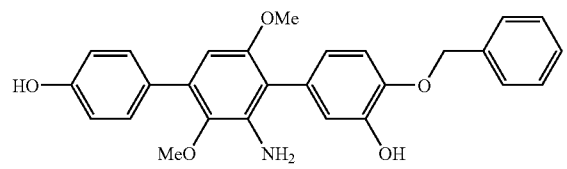
I-567
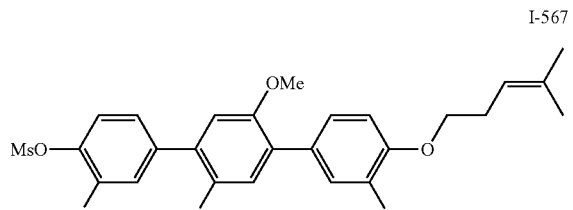
I-568
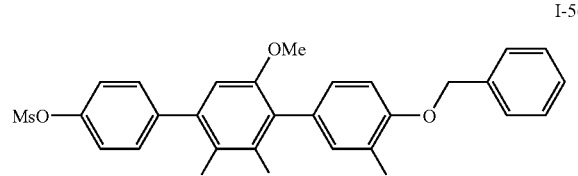
I-569
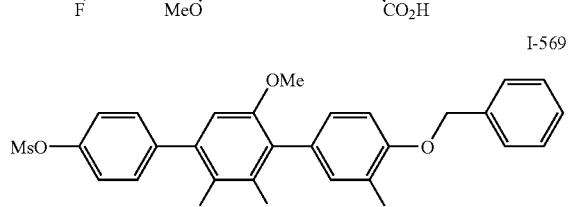
I-570
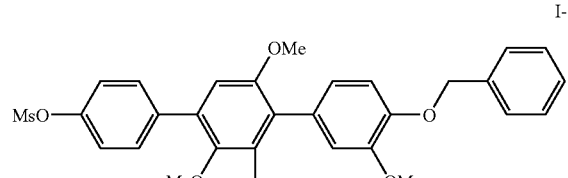
I-571
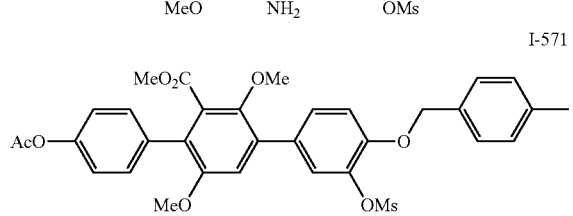
I-572
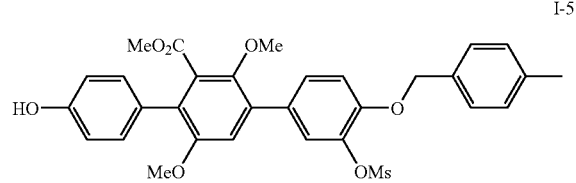
I-573
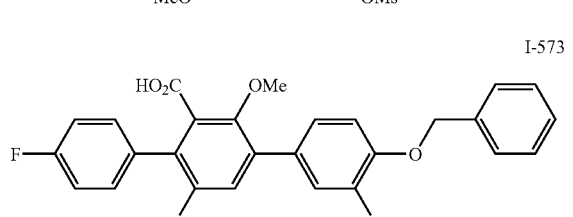

-continued
I-574
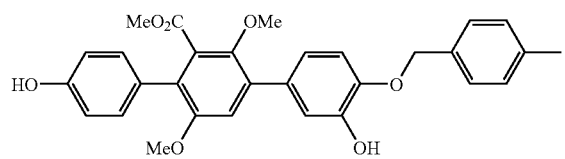
I-575
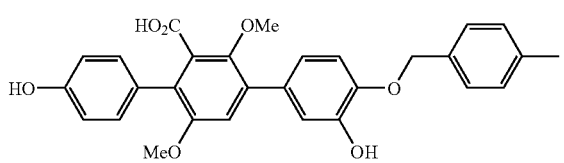
I-576
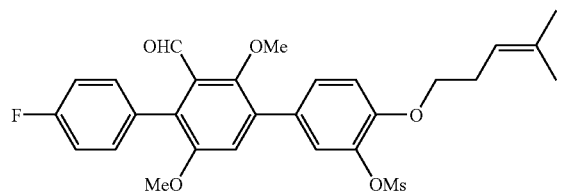
I-577
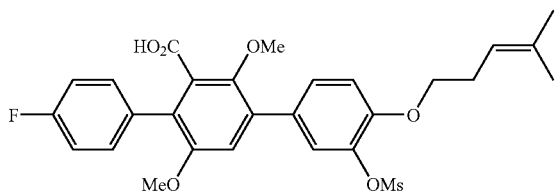
I-578
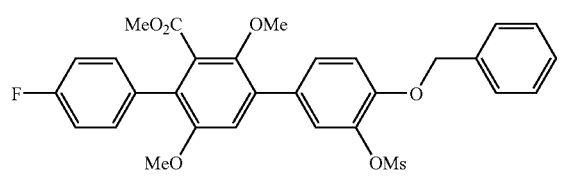
I-579
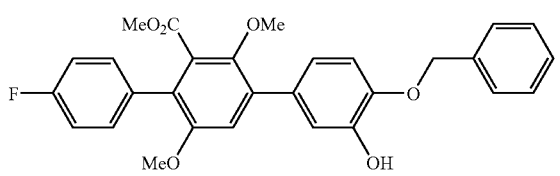
I-580
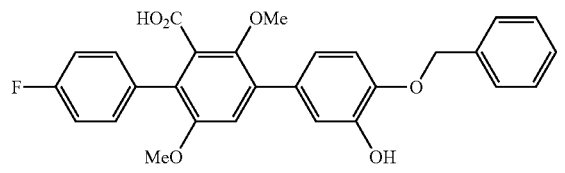
I-581
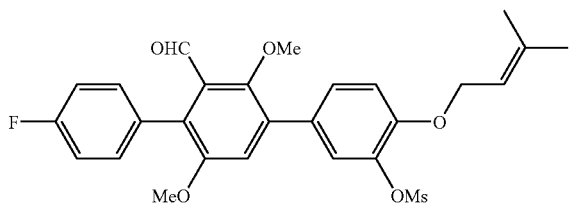
I-582
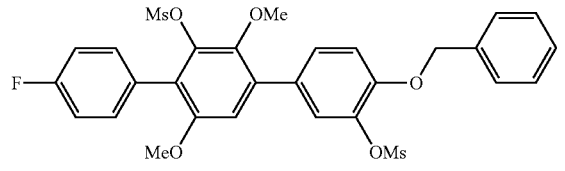
I-583
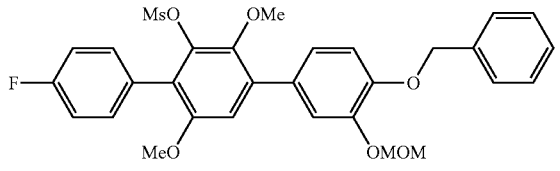
I-584
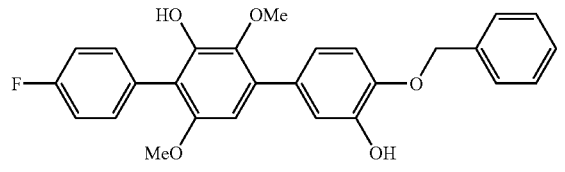
I-585
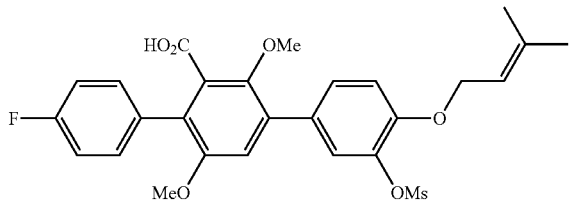
I-586
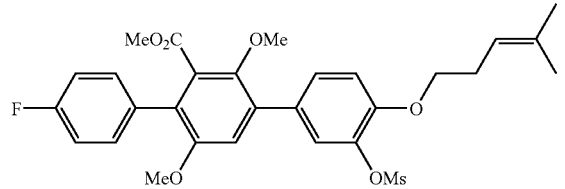
I-587
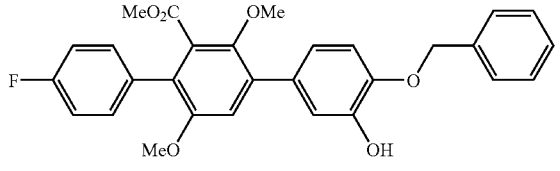

-continued
I-588
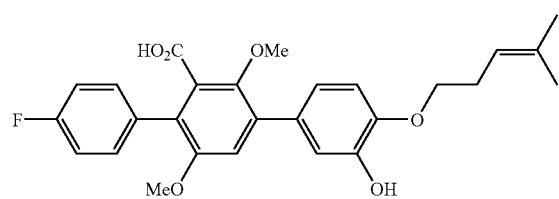
I-589
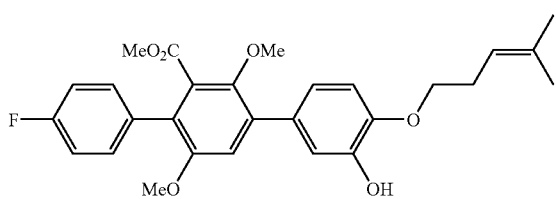
I-590
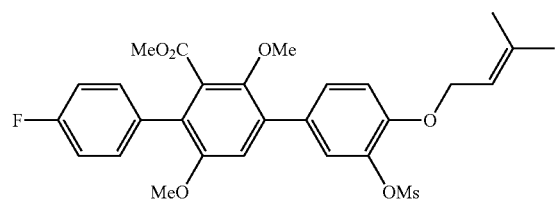
I-591
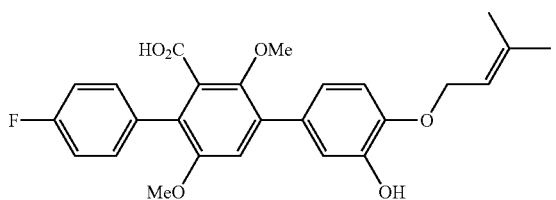
I-592
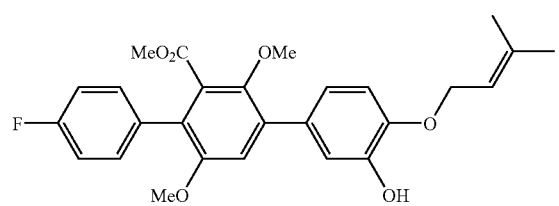
I-593
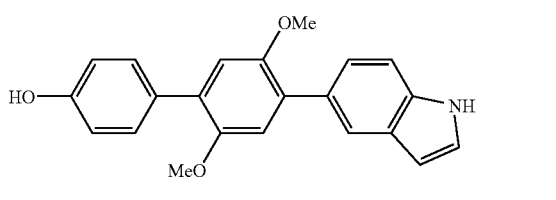
I-594
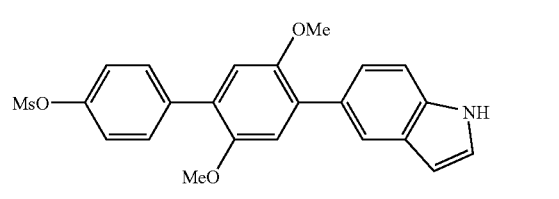
I-595
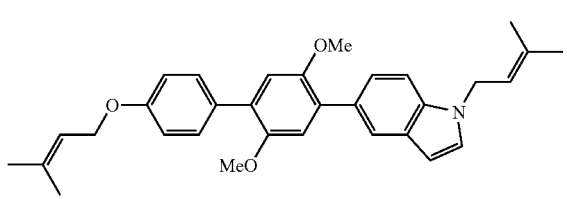
I-596
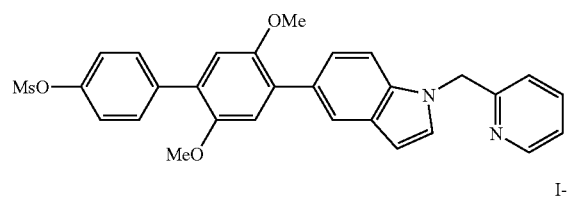
I-597
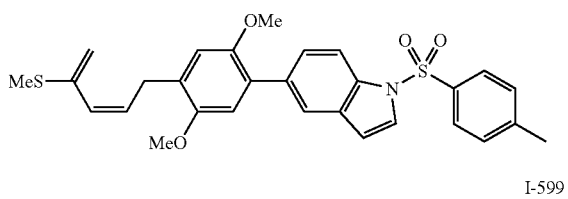
I-598
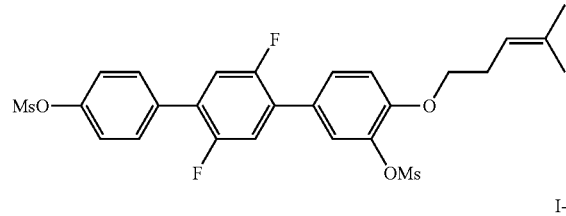
I-599
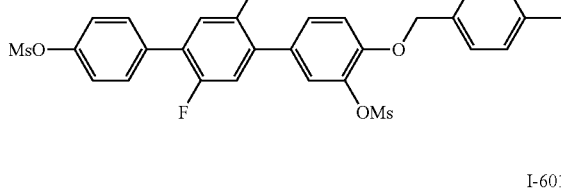
I-600
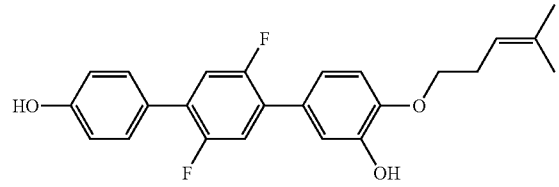
I-601
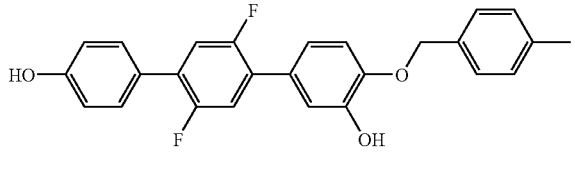

-continued
I-602
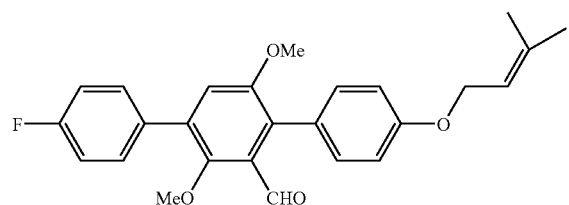
I-603
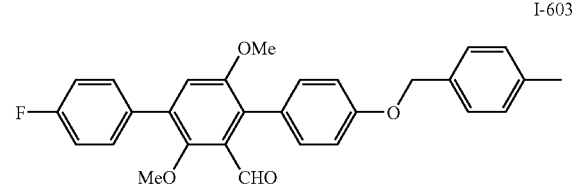
I-604
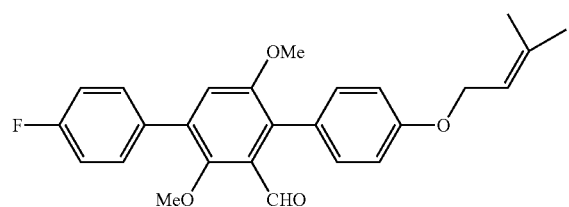
I-605
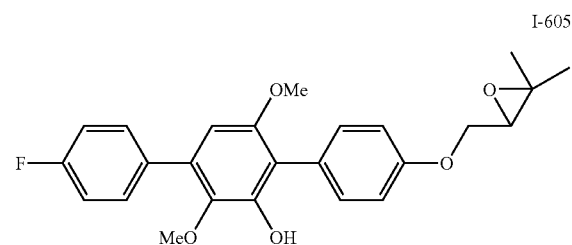
I-606
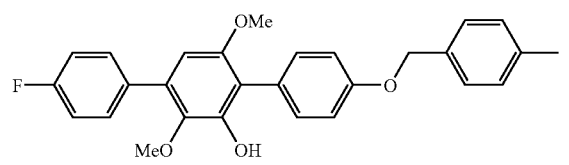
I-607
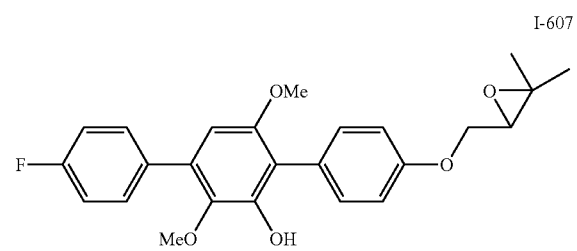
I-608
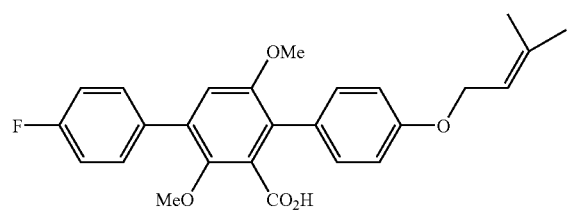
I-609
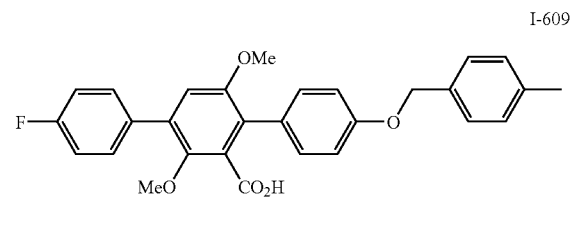
I-610
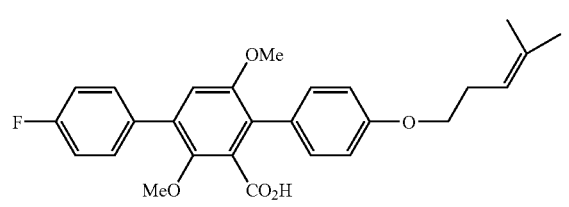
I-611
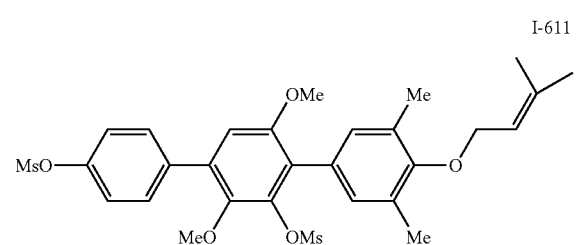
I-612
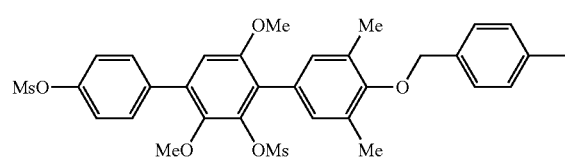
I-613
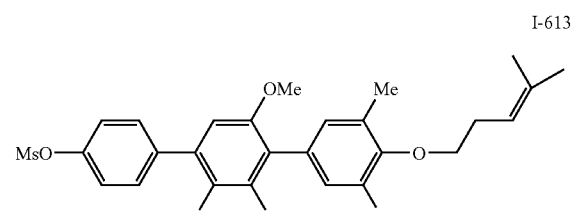
I-614
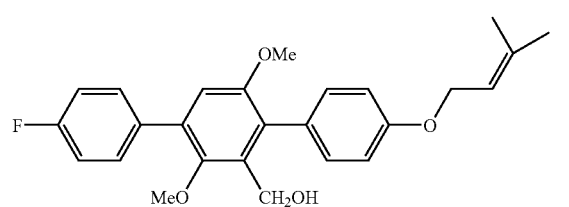
I-615
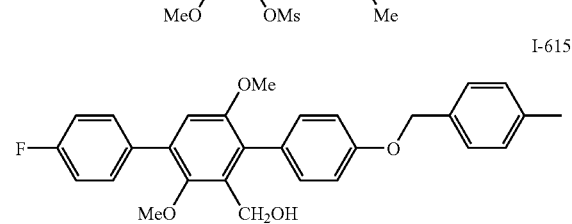

-continued
I-616
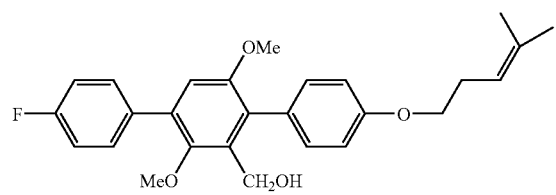
I-617
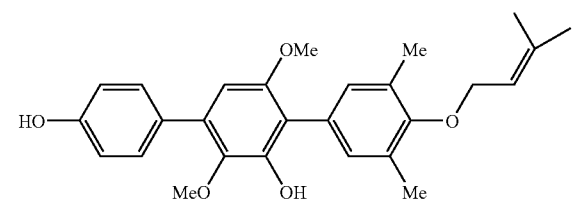
I-618
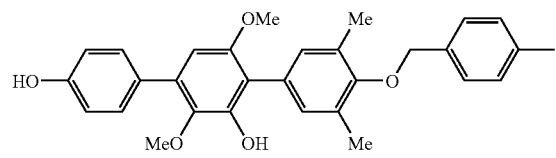
I-619
I-620
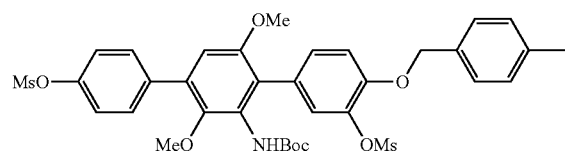
I-621
I-622
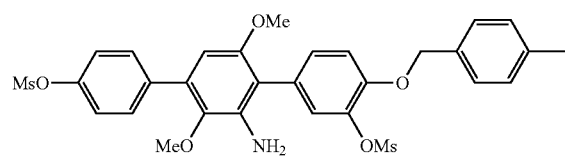
I-623
I-624
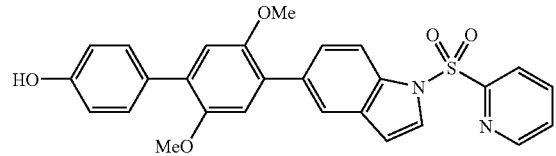
I-625
I-626
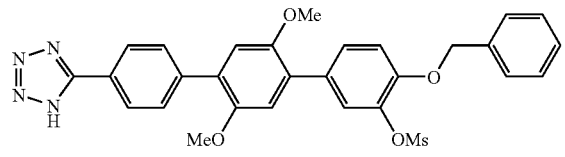
I-627
I-628
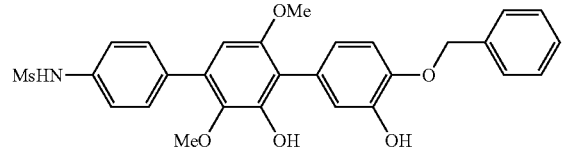
I-629
I-630
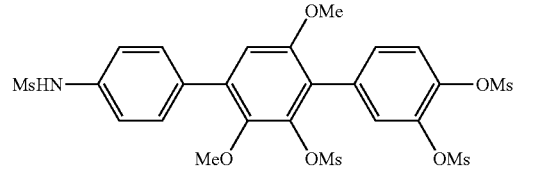
I-631
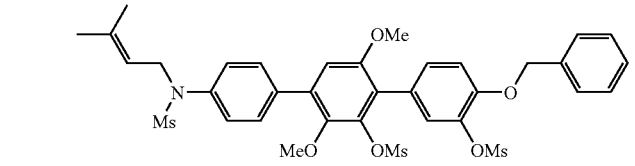

-continued
I-632
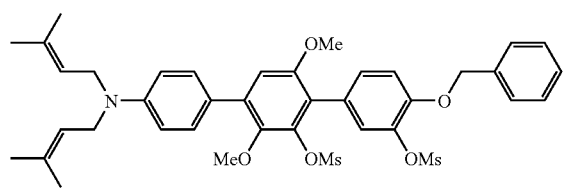
I-633
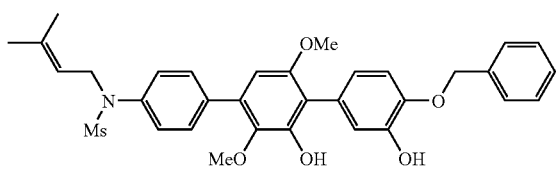
I-634
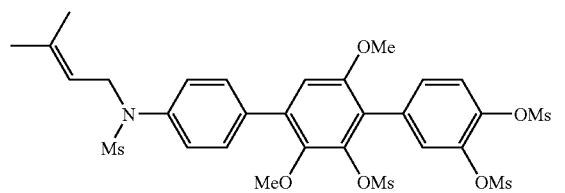
I-635
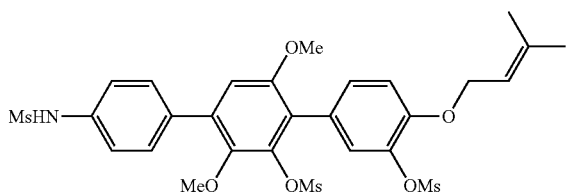
I-636
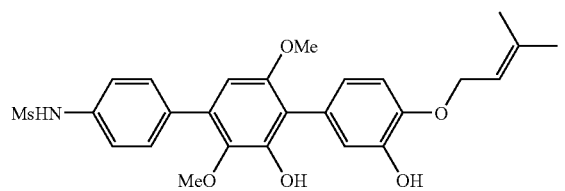
I-637
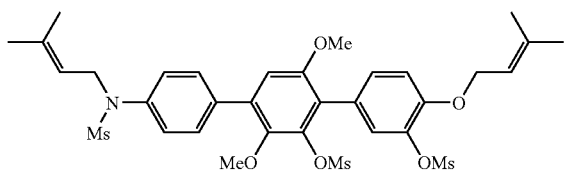
I-638
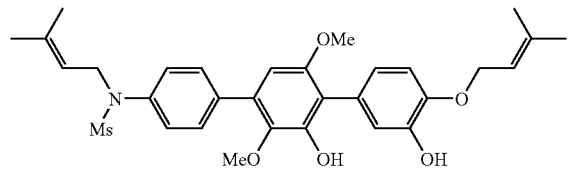
I-639
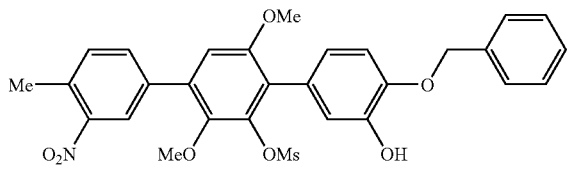
I-640
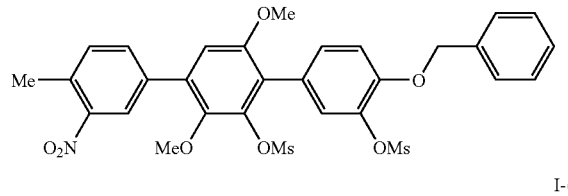
I-641
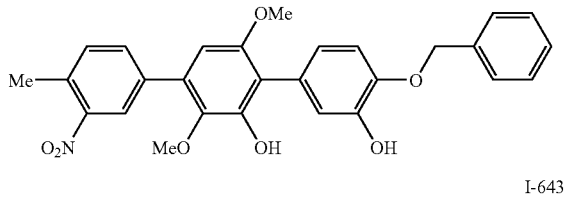
I-642
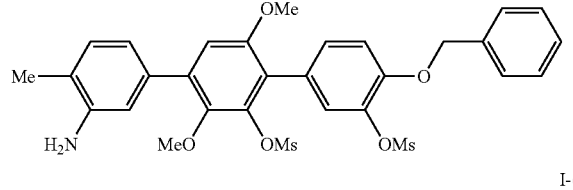
I-643
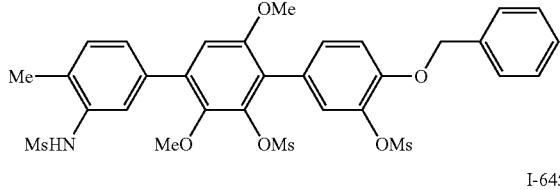
I-644
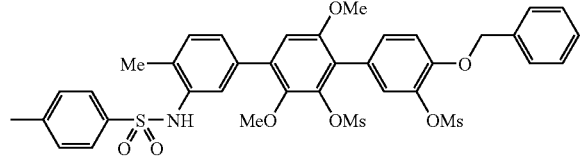
I-645
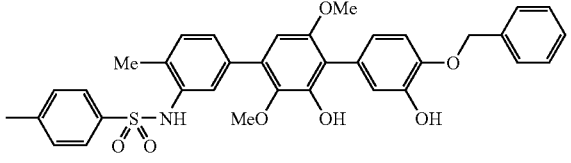

-continued
I-646
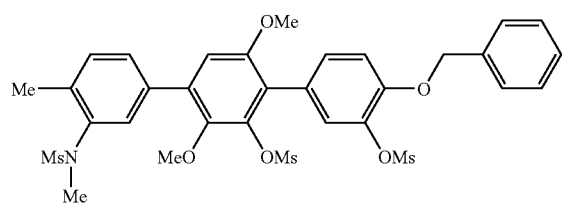
I-647
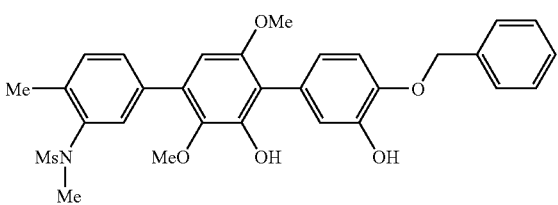
I-648
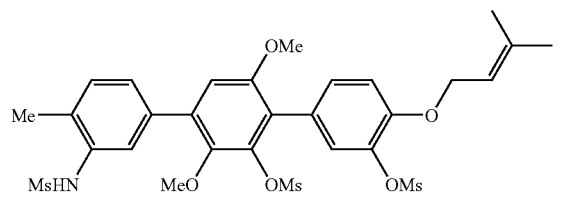
I-649
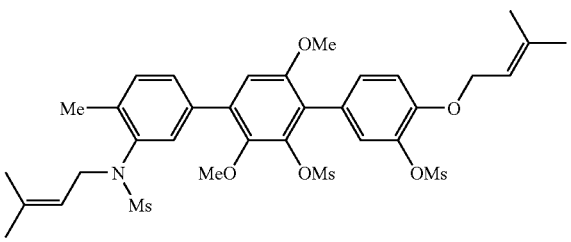
I-650
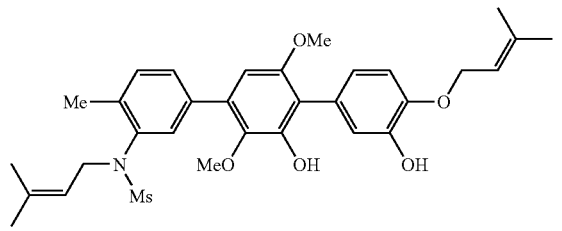
I-651
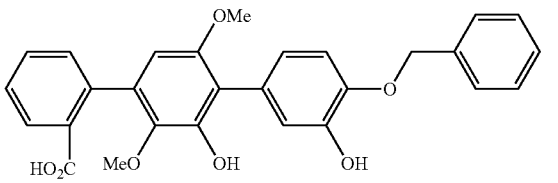
I-652
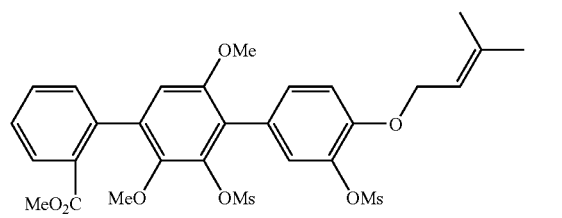
I-653
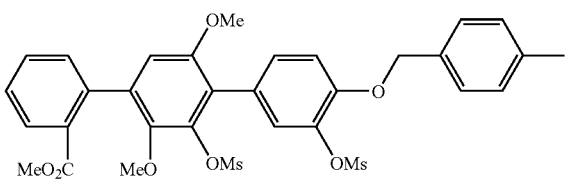
I-654
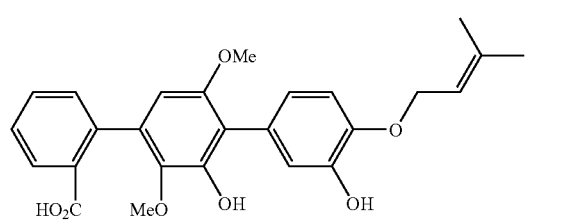
I-655
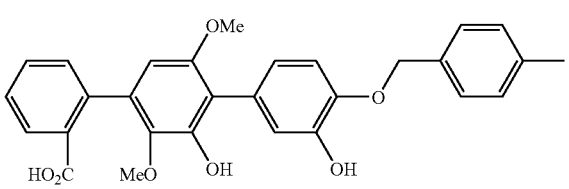
I-656
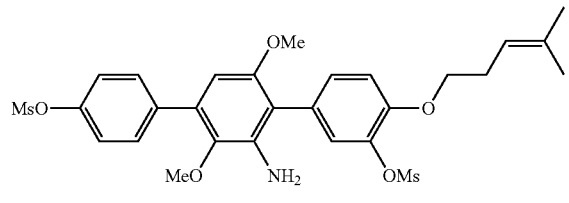
I-657
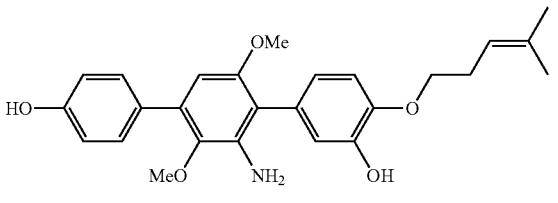

-continued
I-658
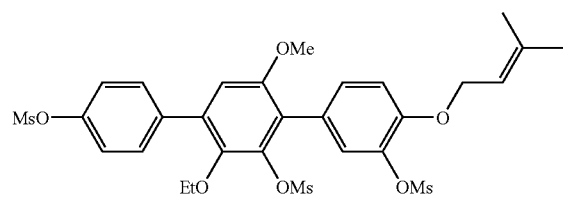
I-660
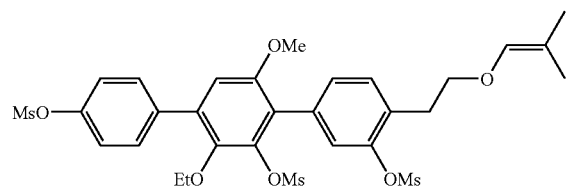
I-662
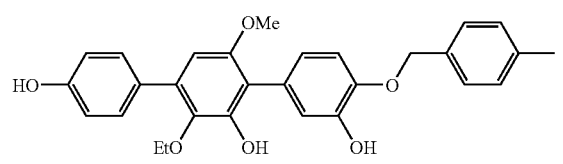
I-664
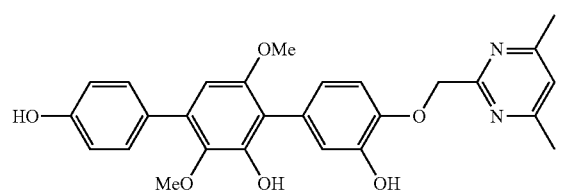
I-666
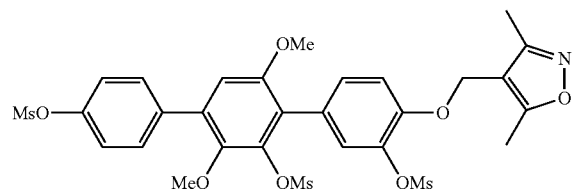
I-668
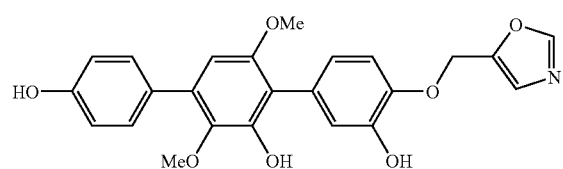
I-670
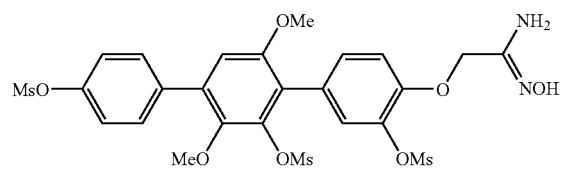
I-659
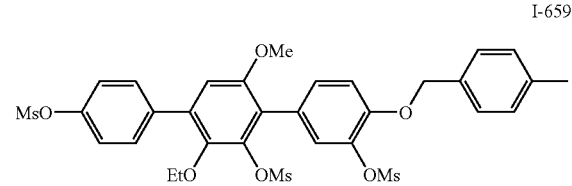
I-661
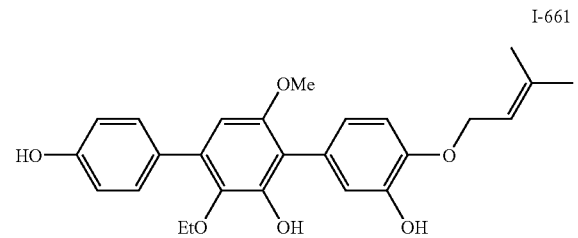
I-663
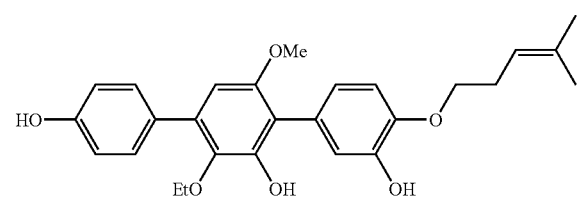
I-665
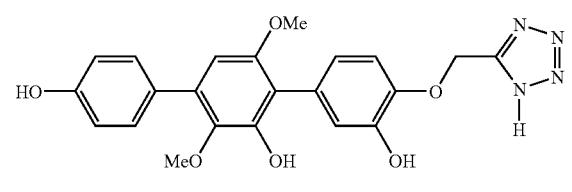
I-667
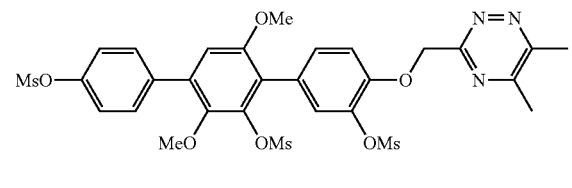
I-669
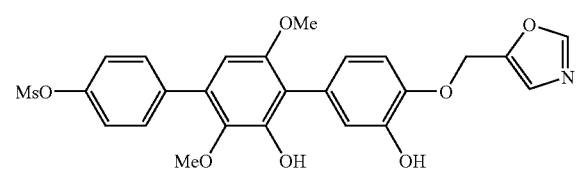
I-671
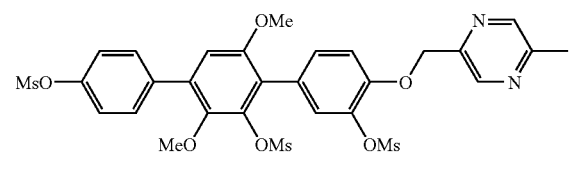

-continued
I-672
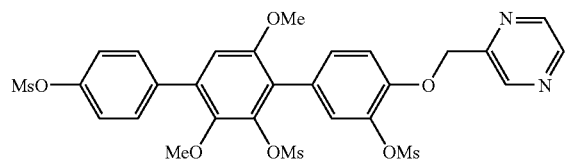
I-673
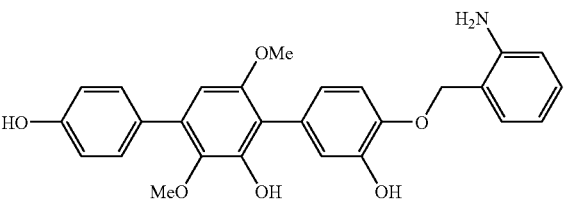
I-674
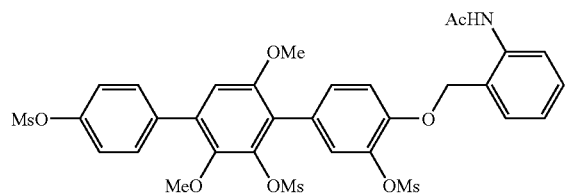
I-675
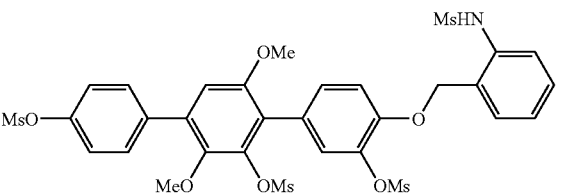
I-676
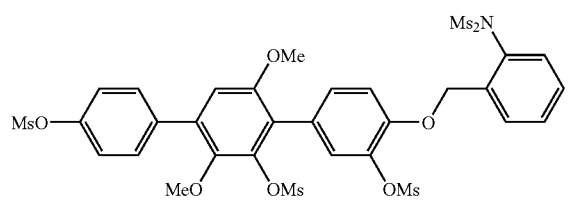
I-677
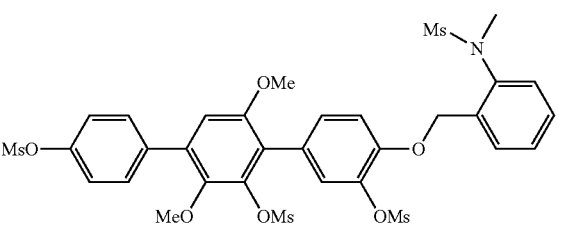
I-678
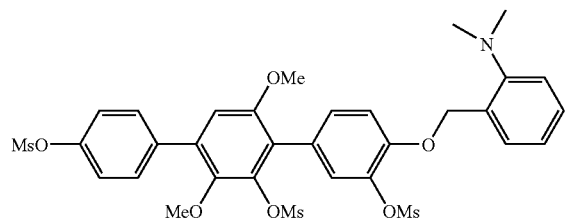
I-679
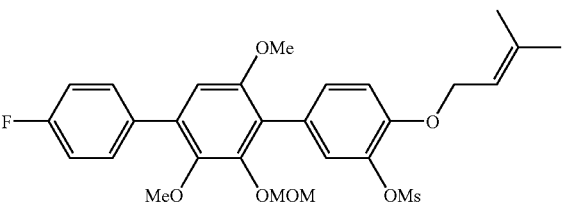
I-680
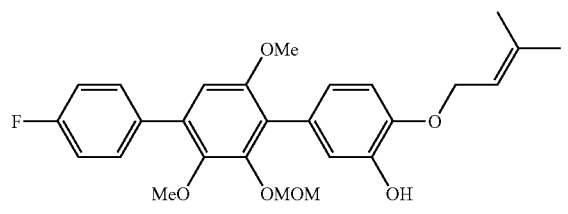
I-681
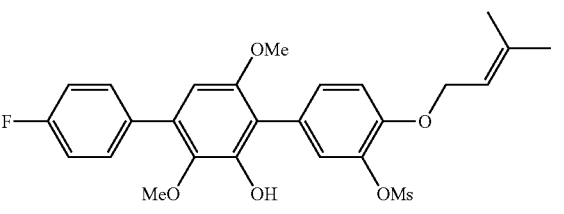
I-682
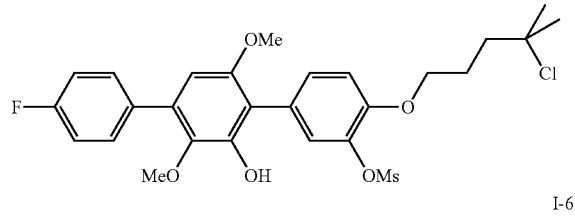
I-683
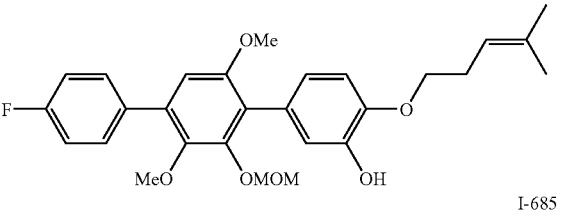
I-684
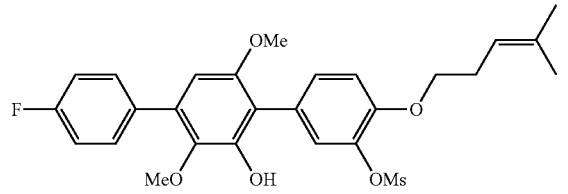
I-685
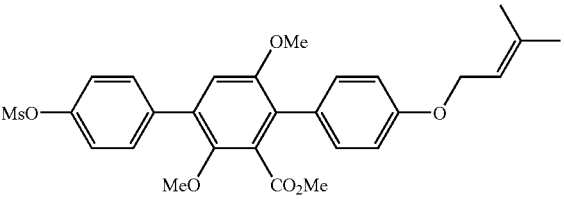

-continued
I-686
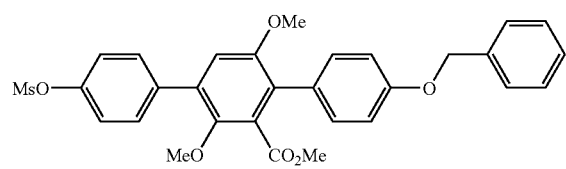
I-687
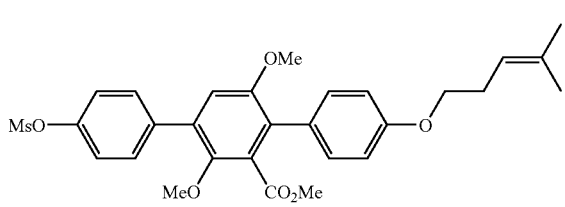
I-688
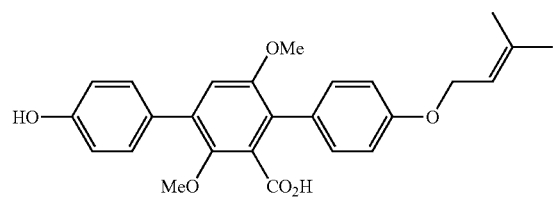
I-689
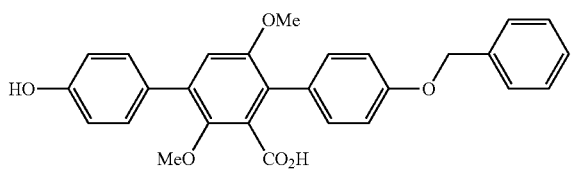
I-690
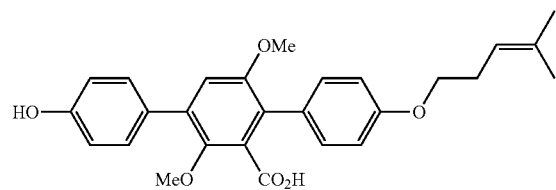
I-691
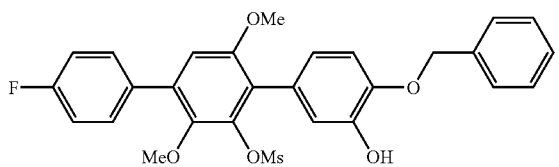
I-692
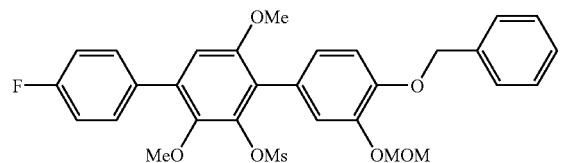
I-693
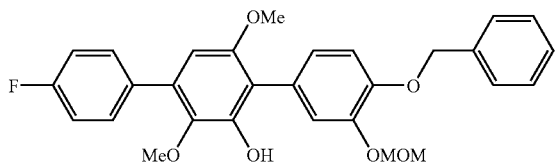
I-694
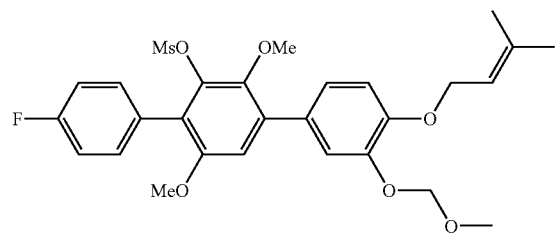
I-695
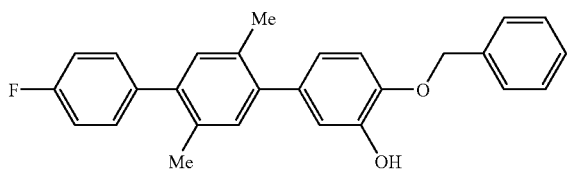
I-696
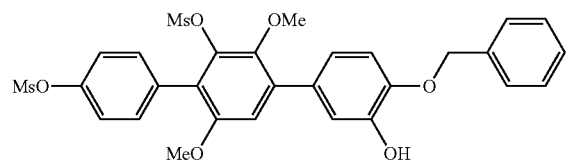
I-697
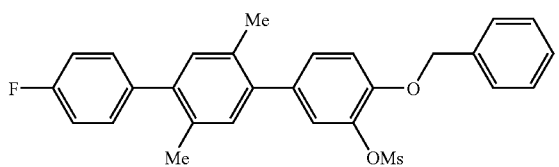
I-698
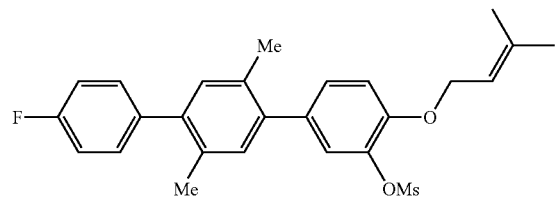
I-699
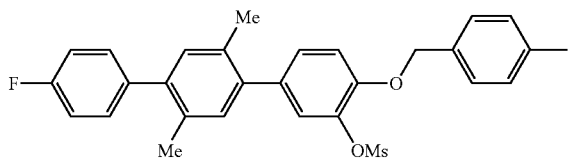

-continued
I-700
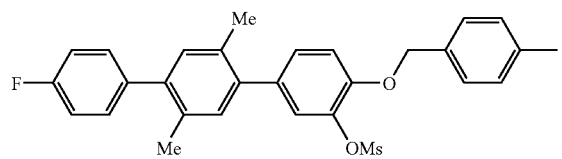
I-701
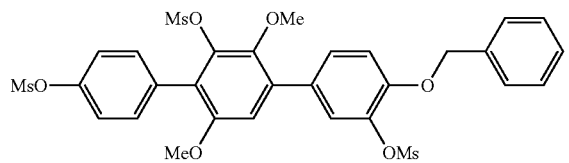
I-702
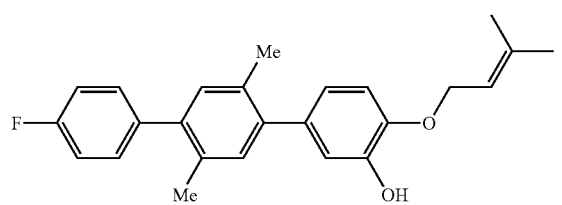
I-703
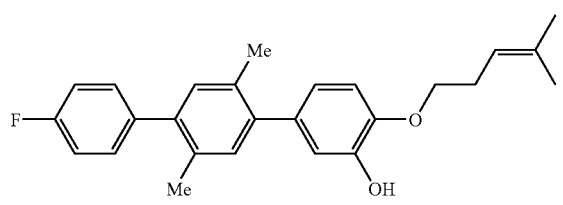
I-704
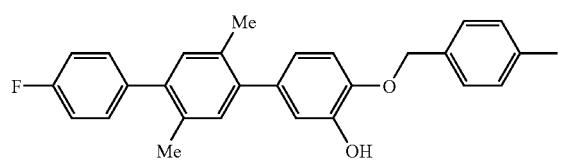
I-705
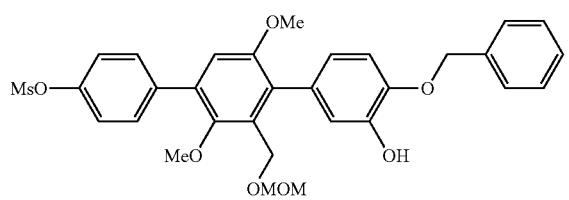
I-706
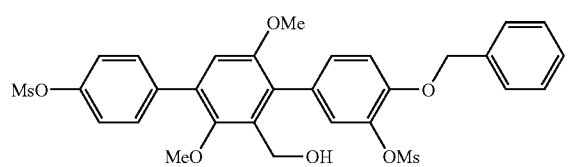
I-707
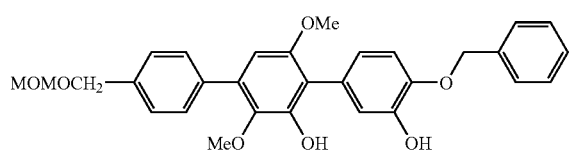
I-708
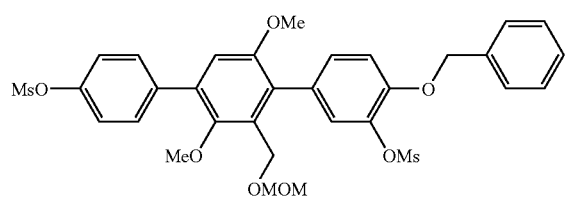
I-709
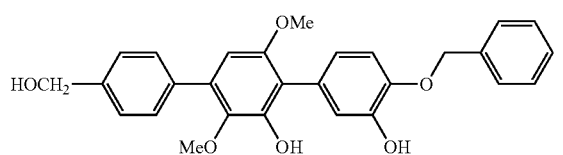
I-710
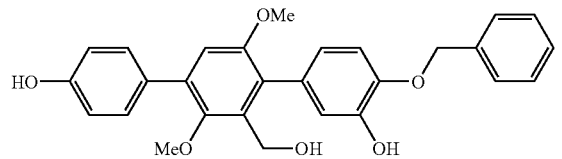
I-711
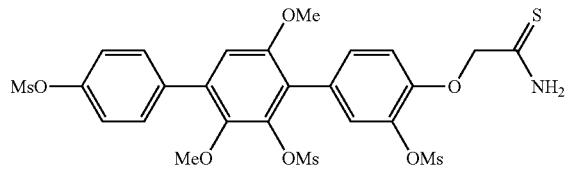
I-712
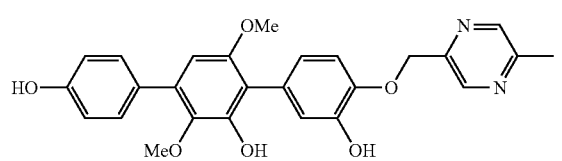
I-713
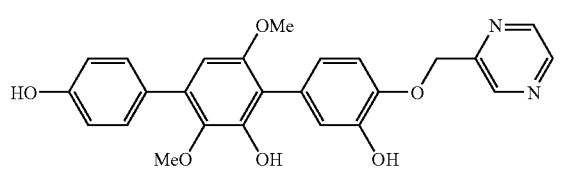
I-714
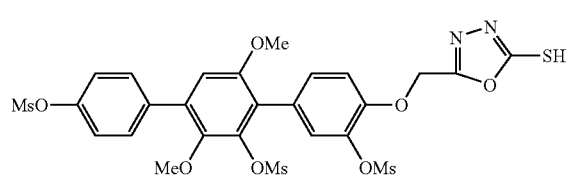
I-715
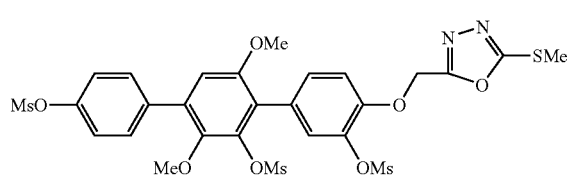

-continued
I-716 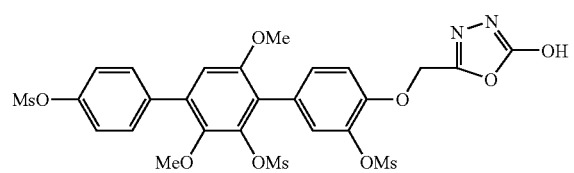
I-717 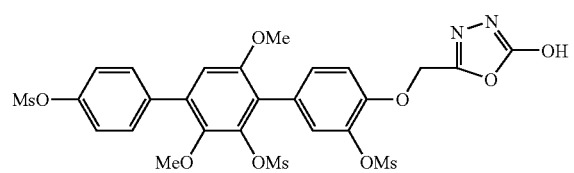
I-718 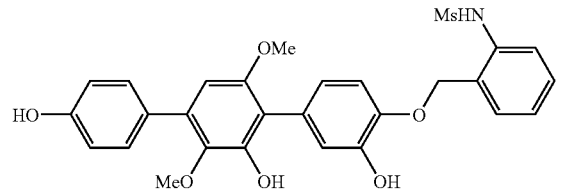
I-719 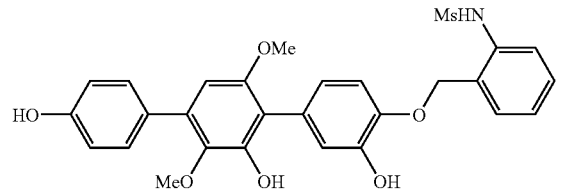
I-720 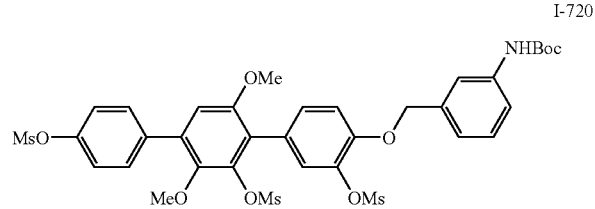
I-721 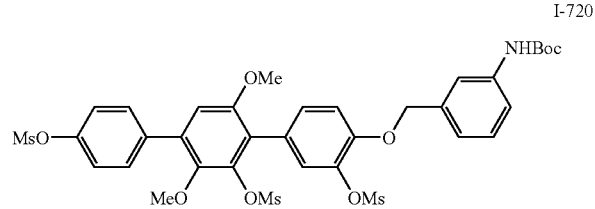
I-722 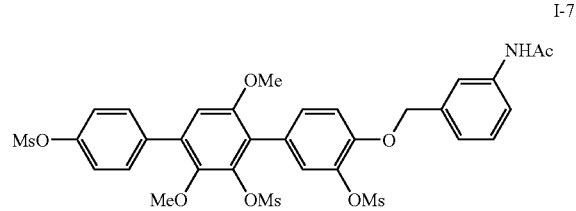
I-723 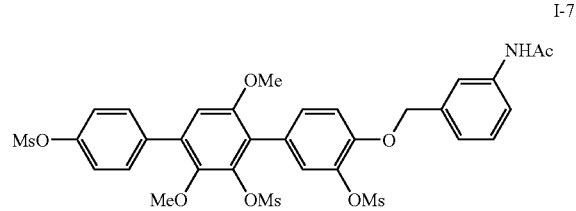
I-724 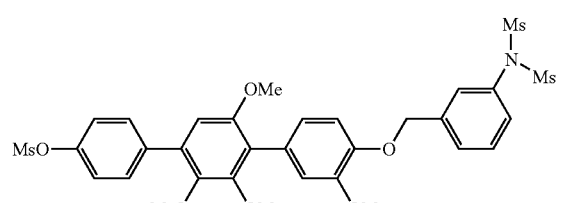
I-725 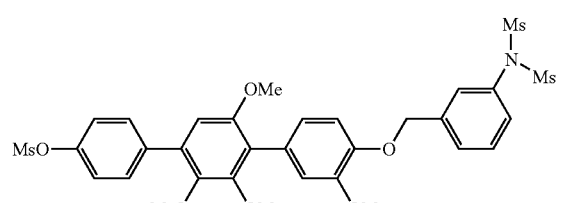
I-726 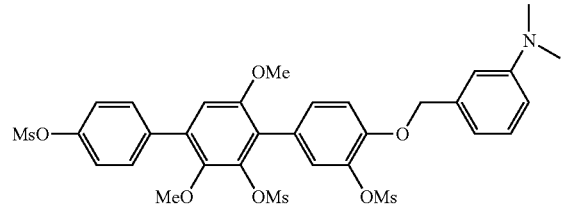
I-727 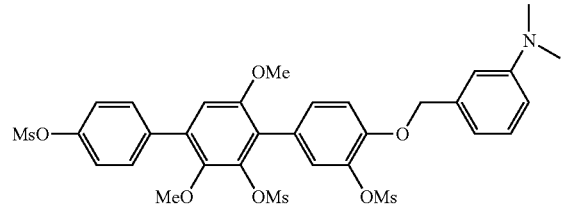
I-728 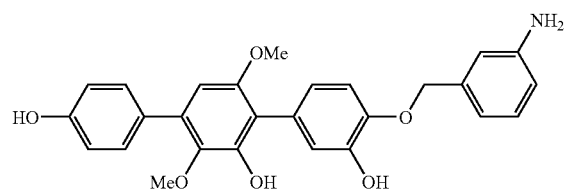
I-729 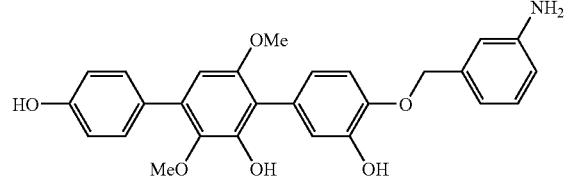

-continued
I-730
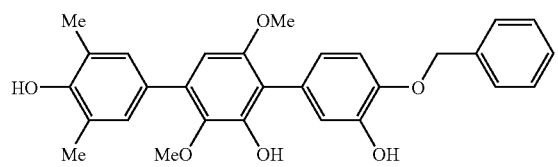
I-731
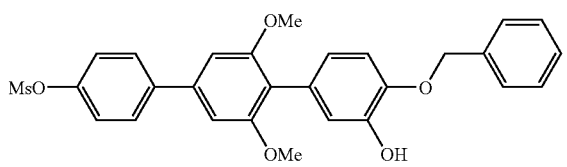
I-732
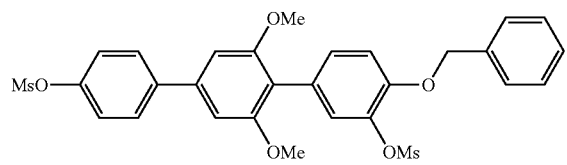
I-733
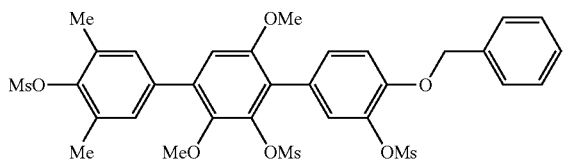
I-734
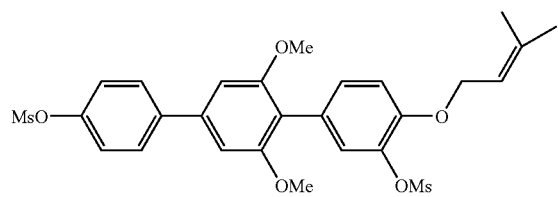
I-735
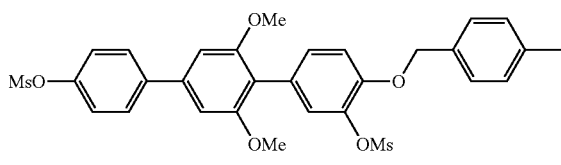
I-736
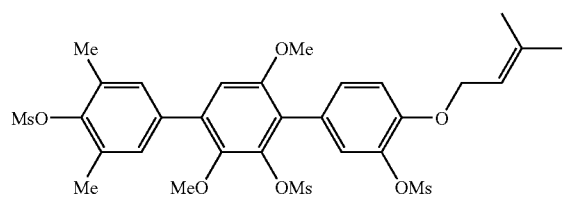
I-737
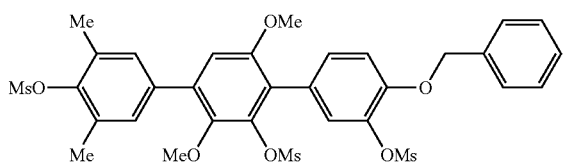
I-738
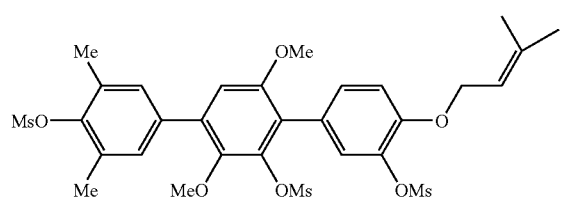
I-739
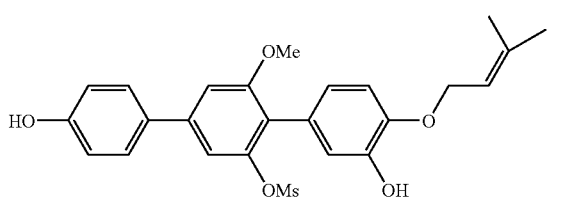
I-740
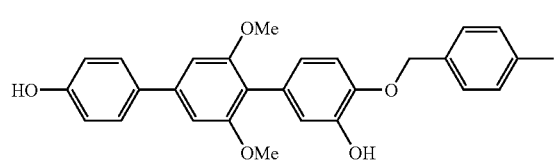
I-741
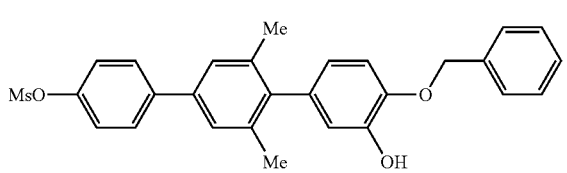
I-742
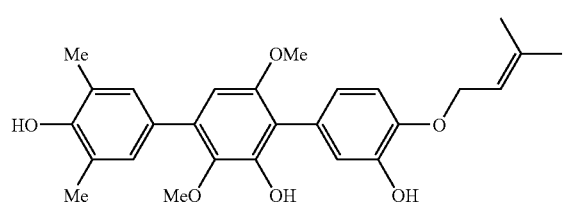
I-743
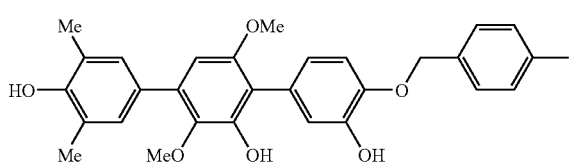

-continued
I-744
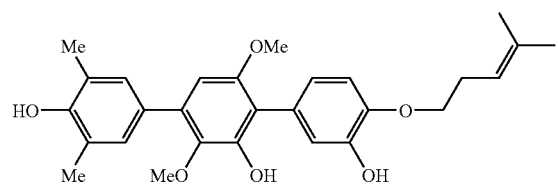
I-745
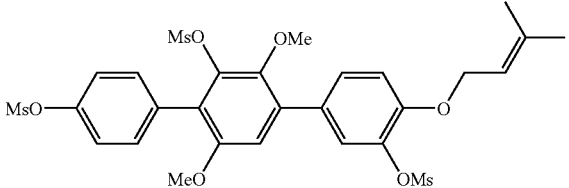
I-746
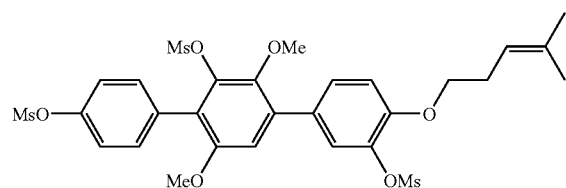
I-747
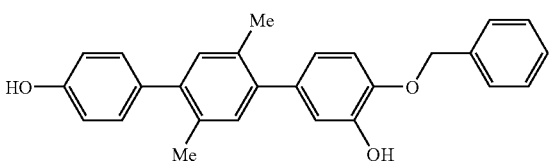
I-748
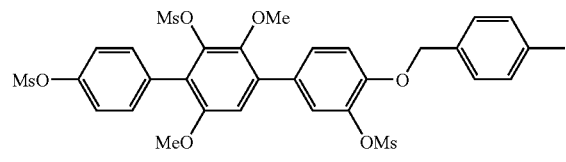
I-749
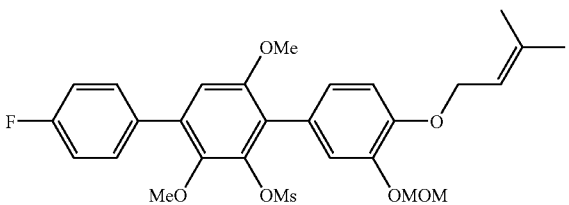
I-750
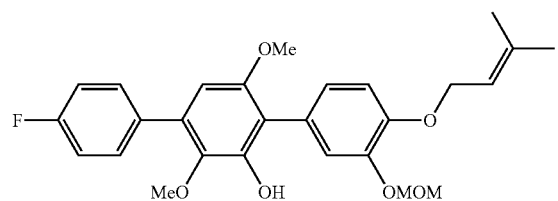
I-751
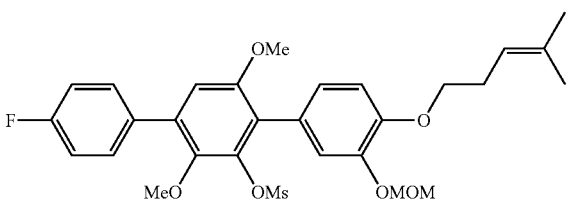
I-752
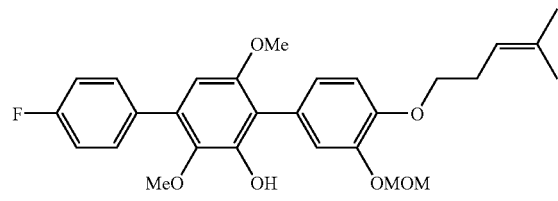
I-753
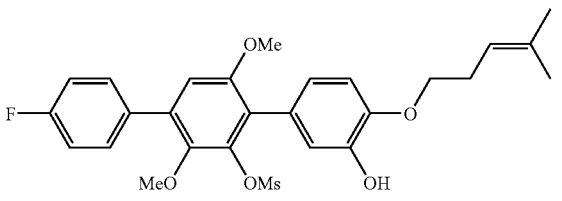
I-754
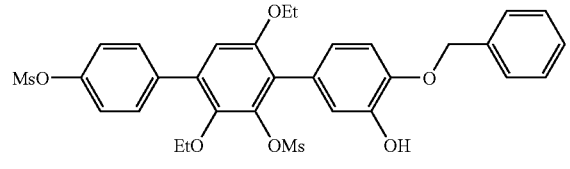
I-755
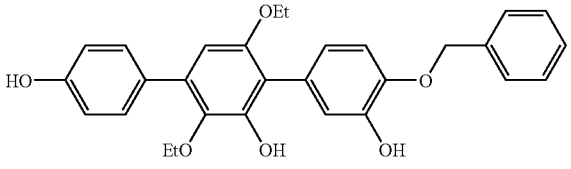
I-756
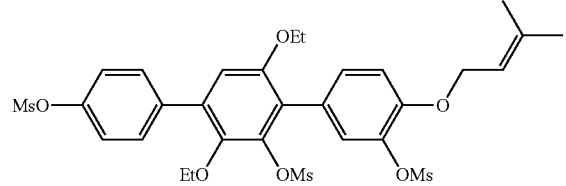
I-757
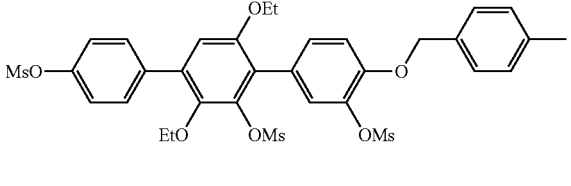

I-758
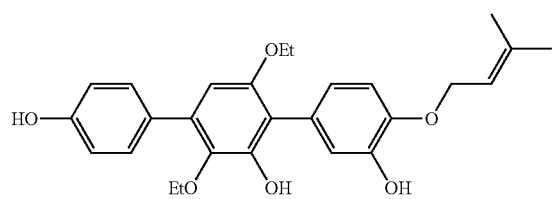
I-759
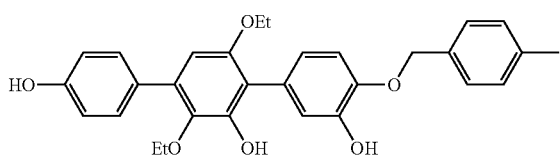
I-760
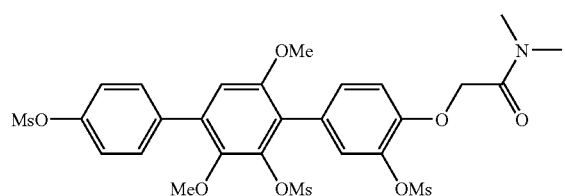
I-761
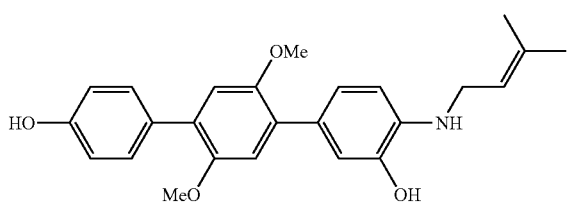
I-762
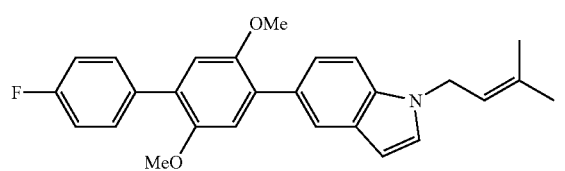
I-763
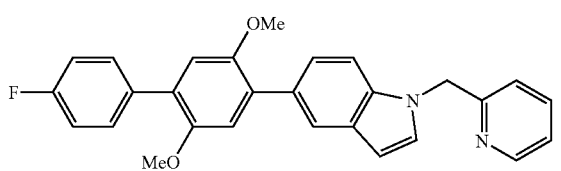
I-764
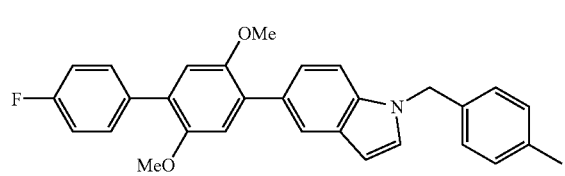
I-765
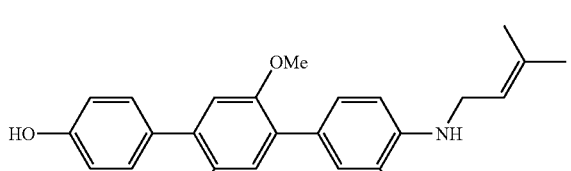
I-766
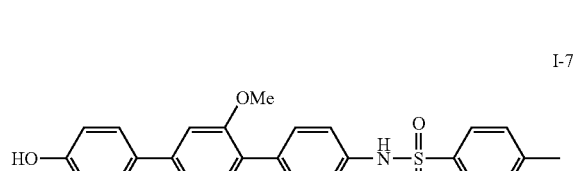
I-767
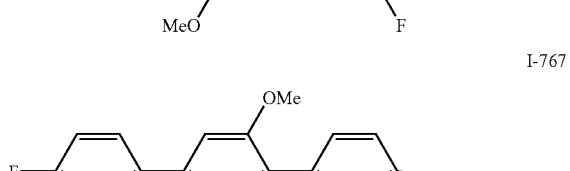
I-768
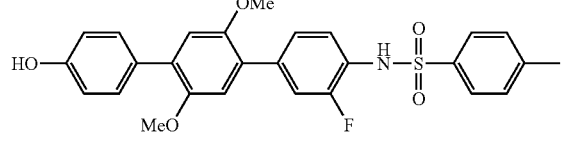
I-769
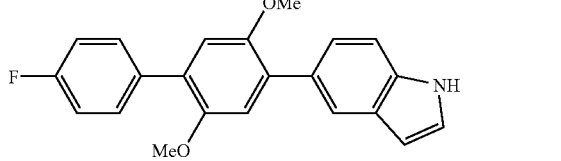
I-770
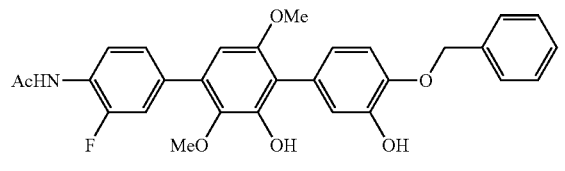
I-771
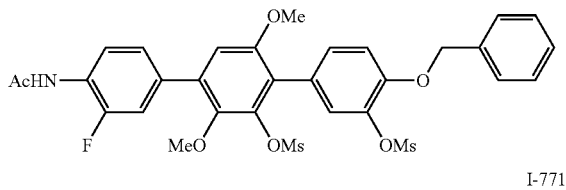
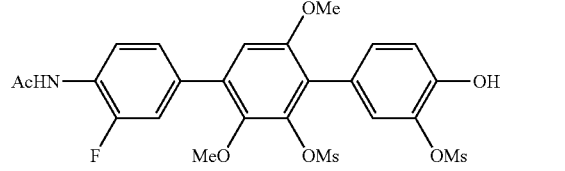

-continued
I-772
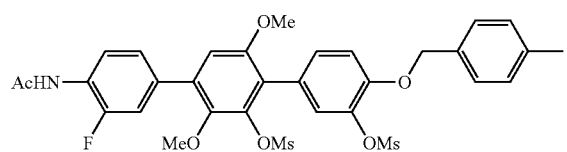
I-773
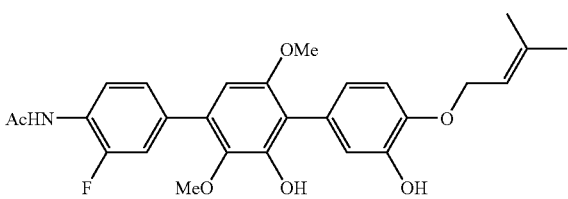
I-774
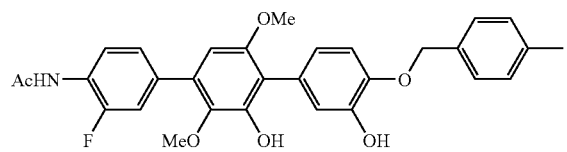
I-775
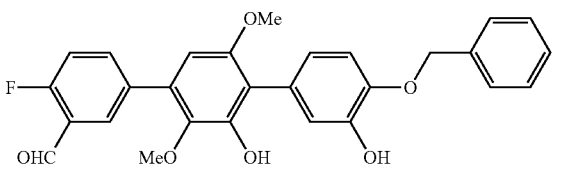
I-776
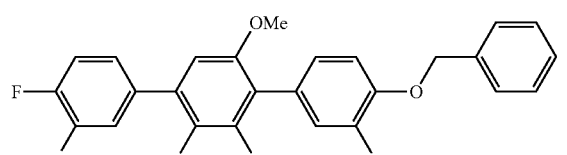
I-777
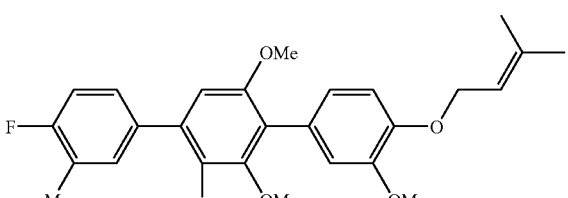
I-778
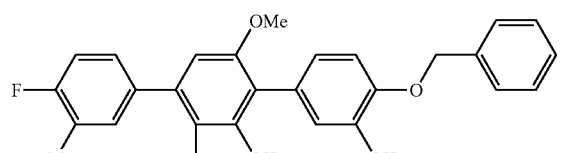
I-779
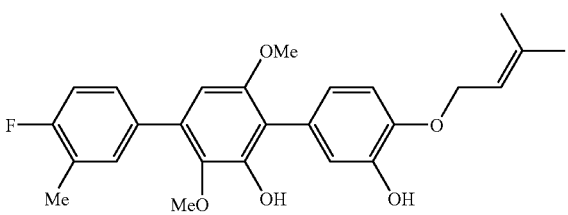
I-780
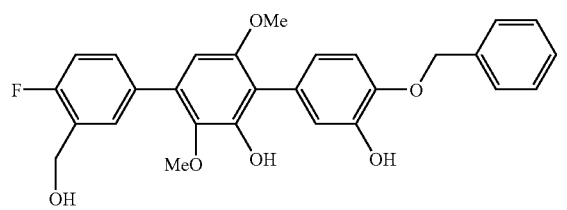
I-781
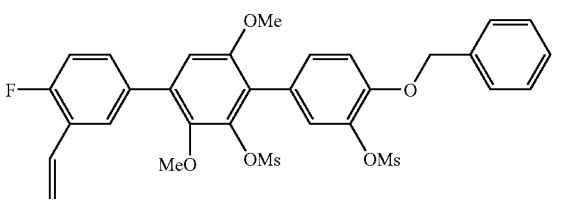
I-782
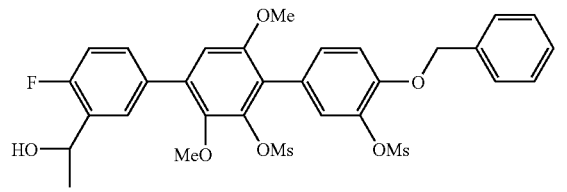
I-783
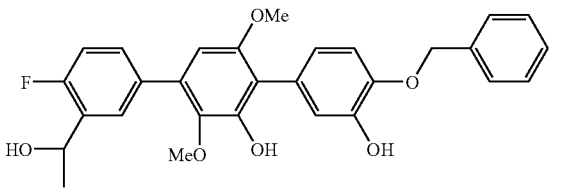
I-784
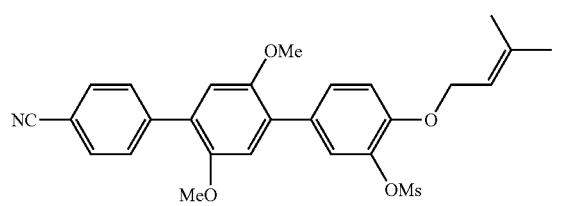
I-785
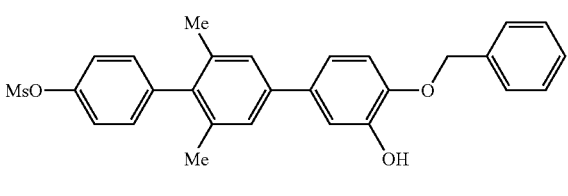

-continued
I-786
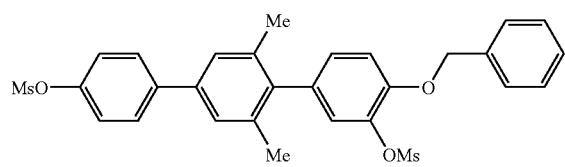
I-787
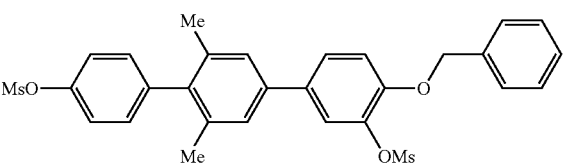
I-788
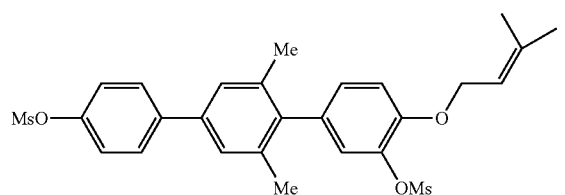
I-789
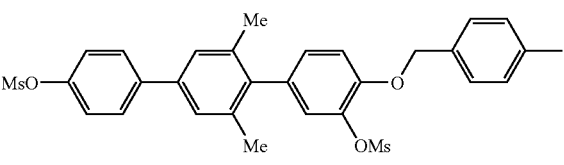
I-790
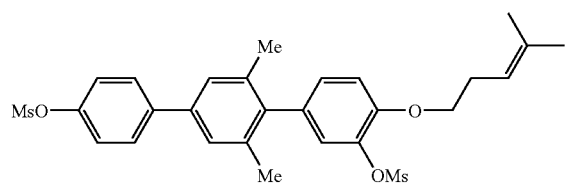
I-791
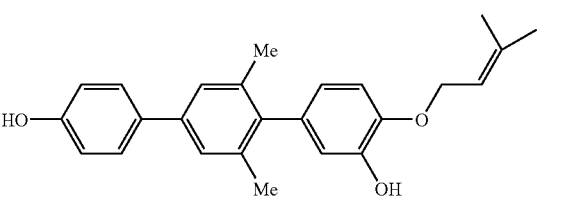
I-792
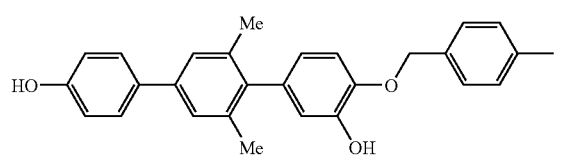
I-793
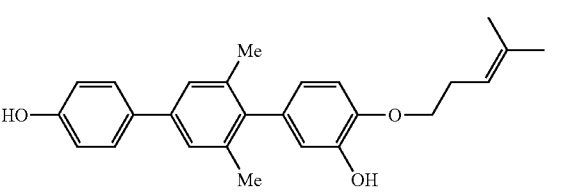
I-794
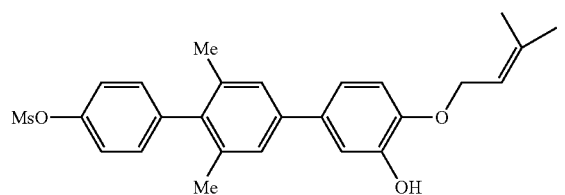
I-795
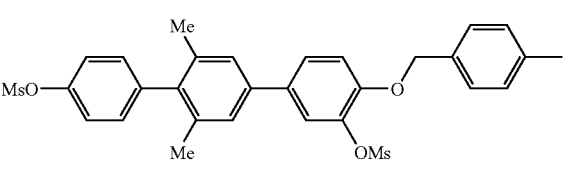
I-796
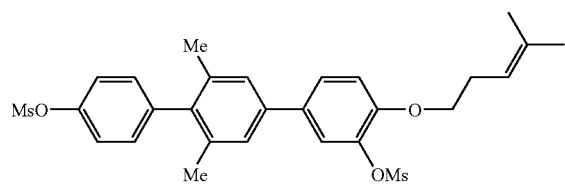
I-797
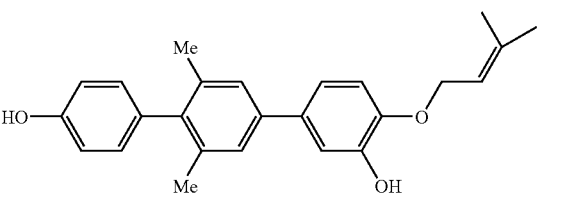
I-798
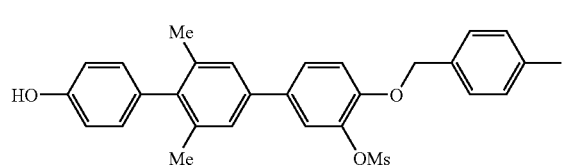
I-799

-continued
I-800
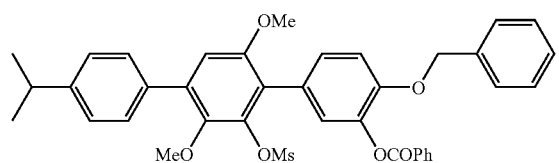
I-801
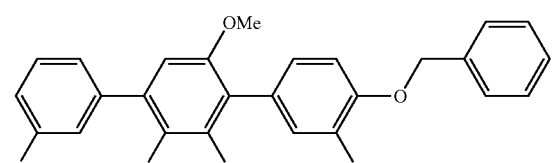
I-802
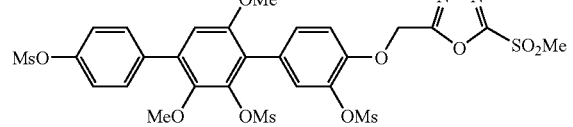
I-803
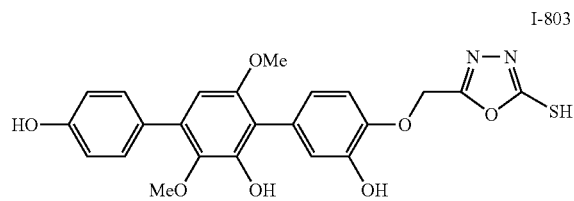
I-804
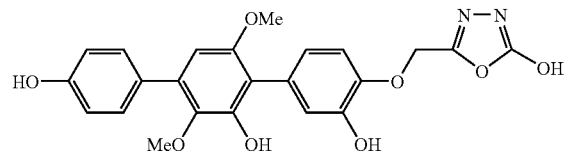
I-805
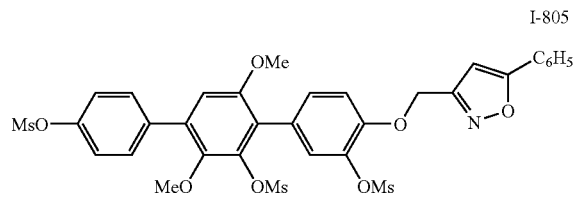
I-806
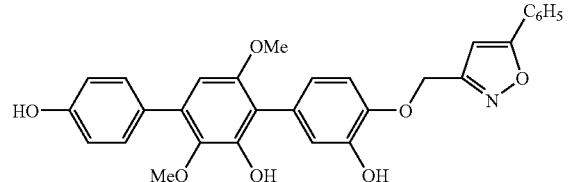
I-807
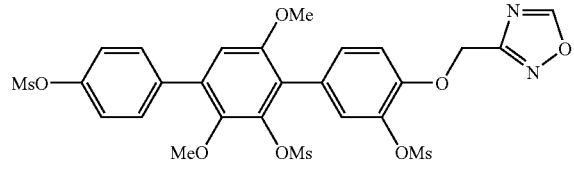
I-808
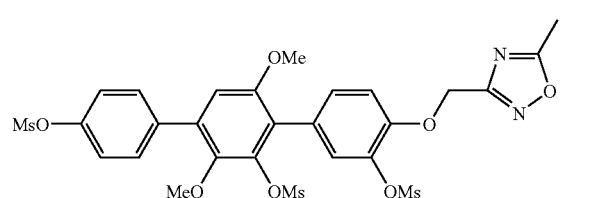
I-809
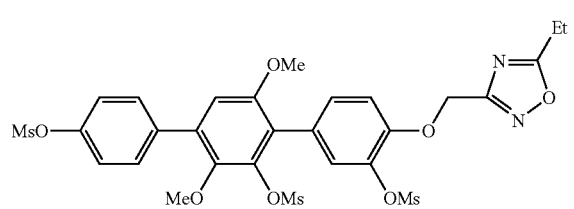
I-810
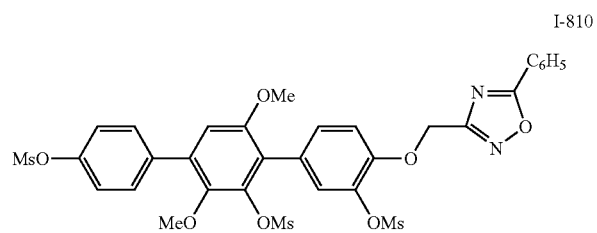
I-811
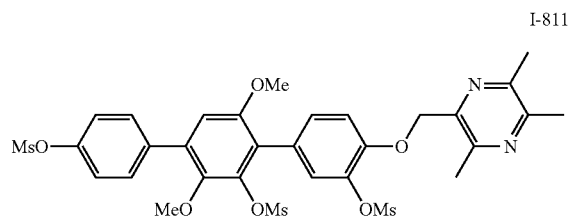
I-812
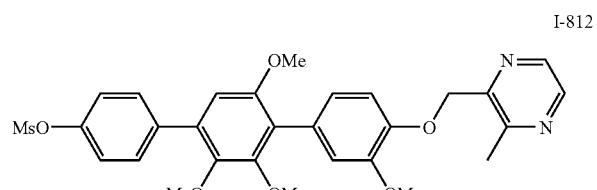
I-813
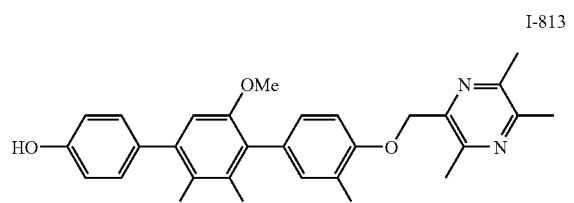

-continued
I-814
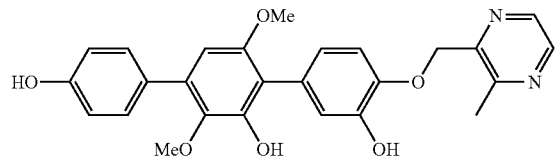
I-815
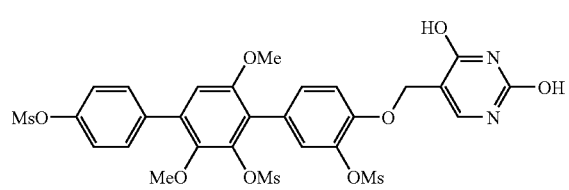
I-816
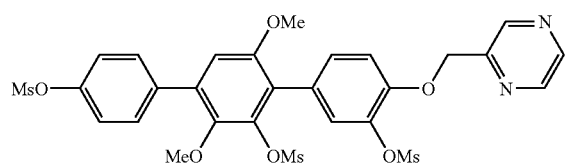
I-817
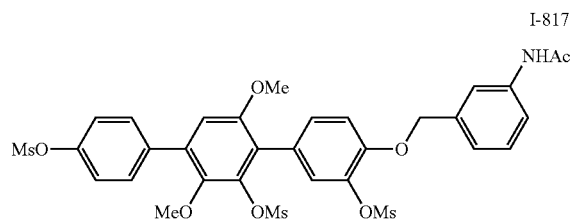
I-818
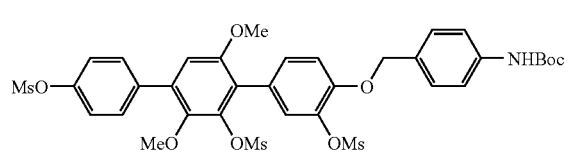
I-819
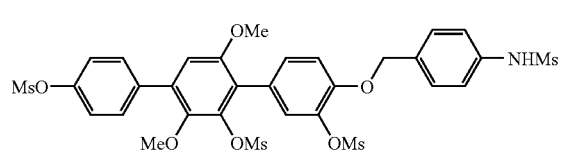
I-820
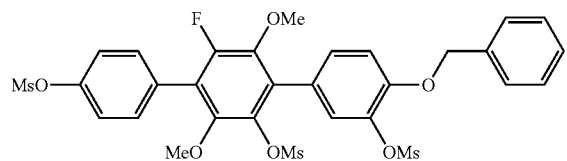
I-821
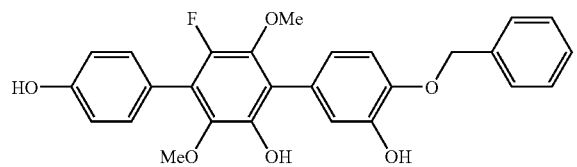
I-822
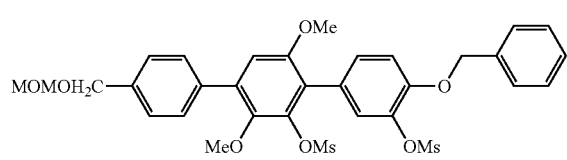
I-823
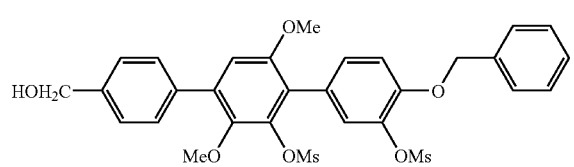
I-824
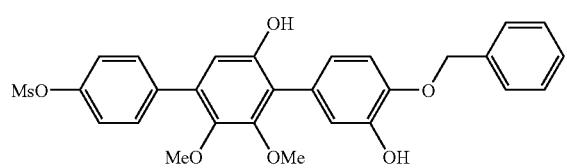
I-825
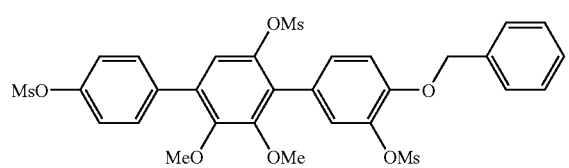
I-826
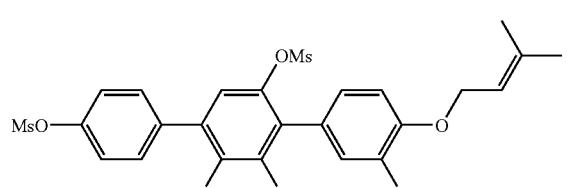
I-827
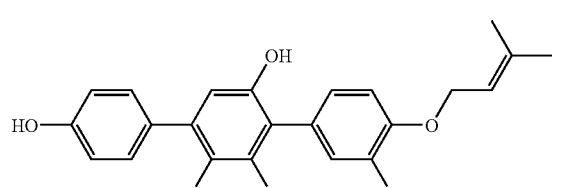
I-828
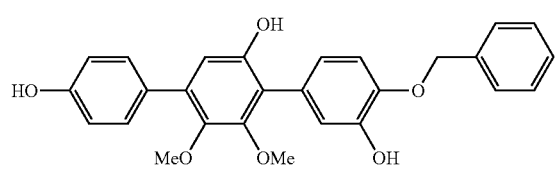
I-829
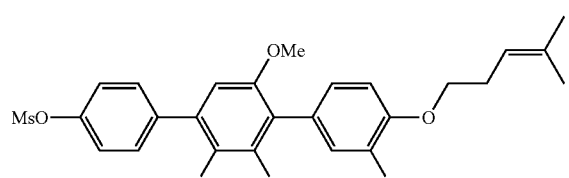

-continued
I-830
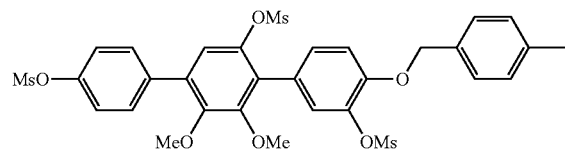
I-831
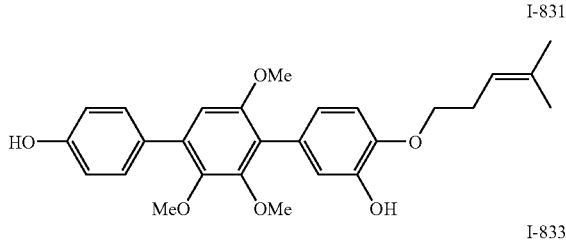
I-832
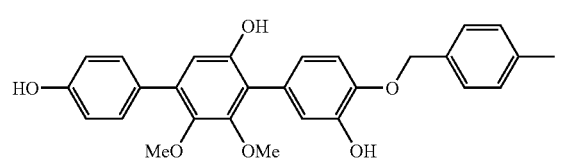
I-833
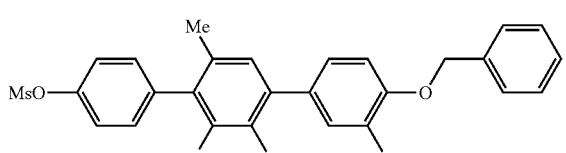
I-834
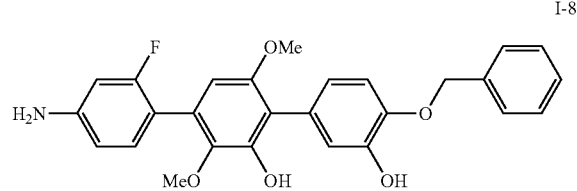
I-835
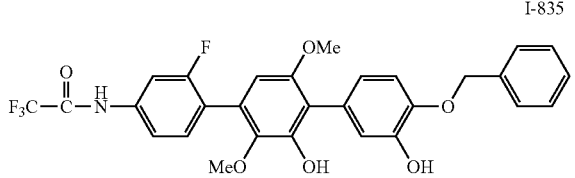
I-836
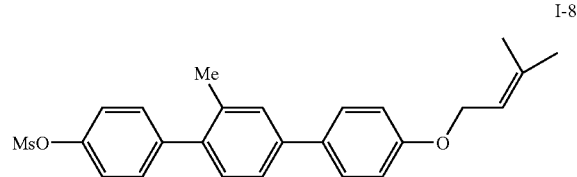
I-837
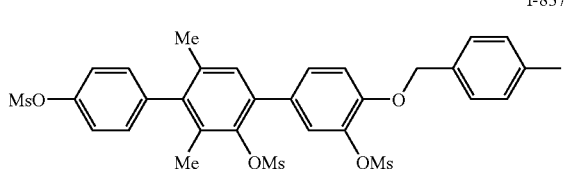
I-838
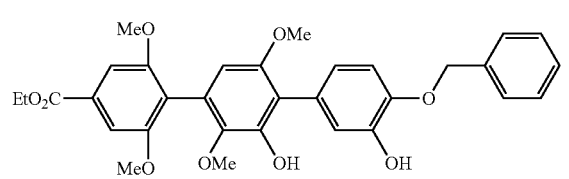
I-839
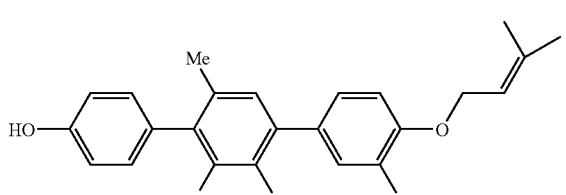
I-840
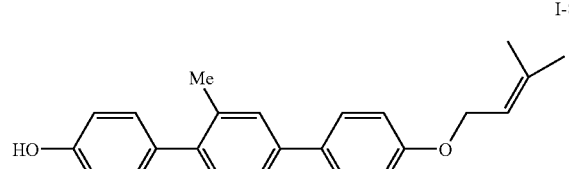
I-841
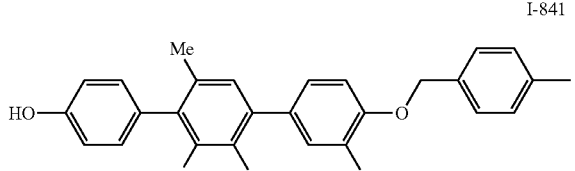
I-842
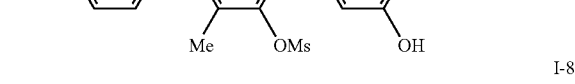
I-843
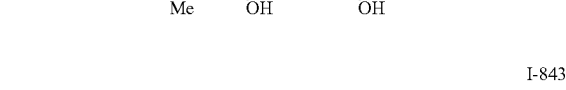
I-844
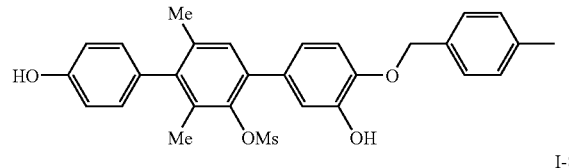
I-845
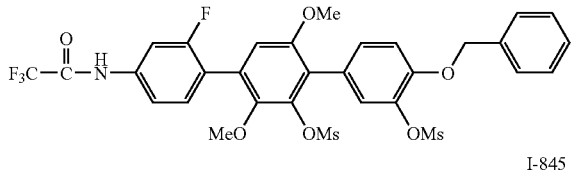
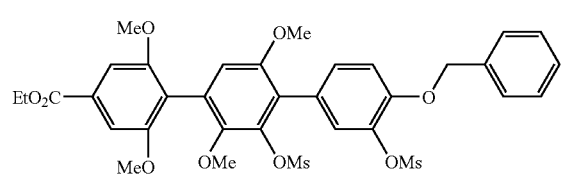
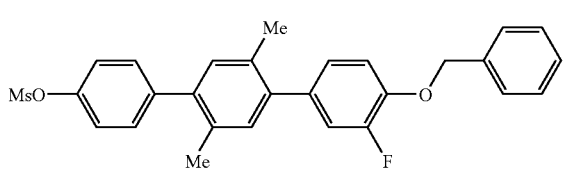

-continued
I-846
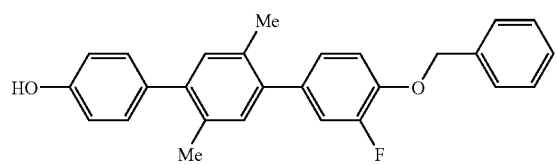
I-847
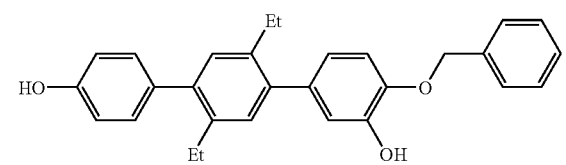
I-848
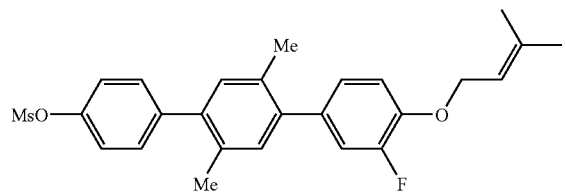
I-849
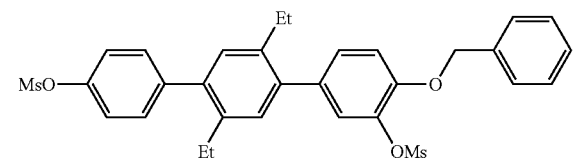
I-850
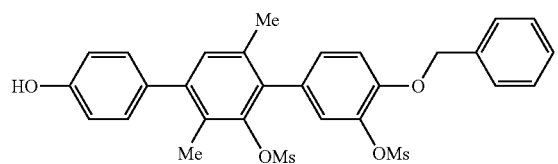
I-851
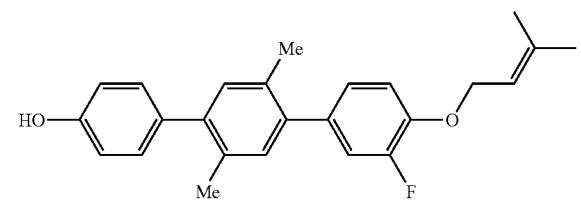
I-852
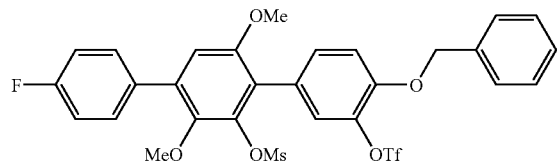
I-853
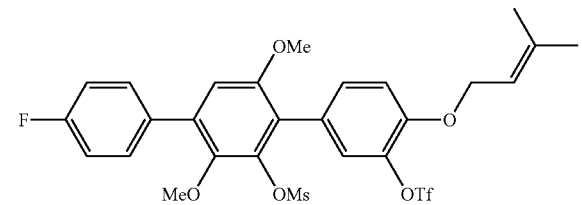
I-854
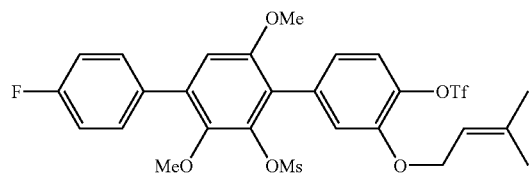
I-855
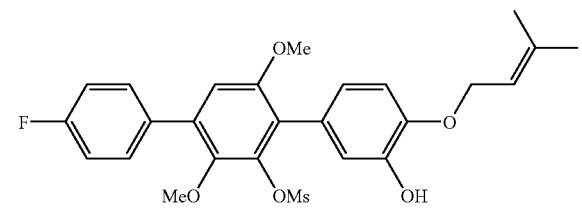
I-856
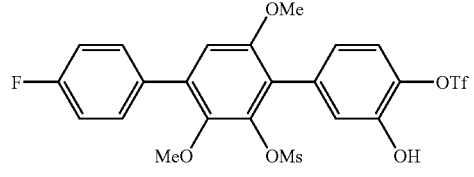
I-857
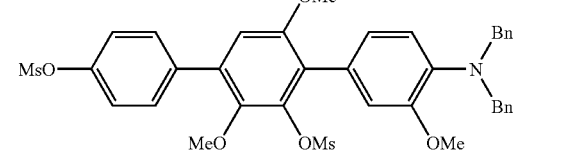
I-858
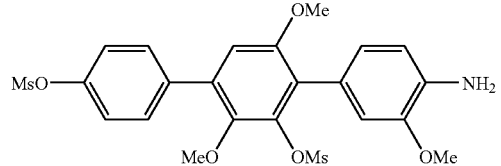
I-859
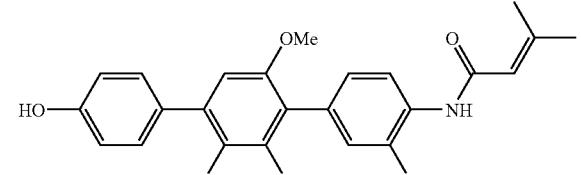

-continued
I-860
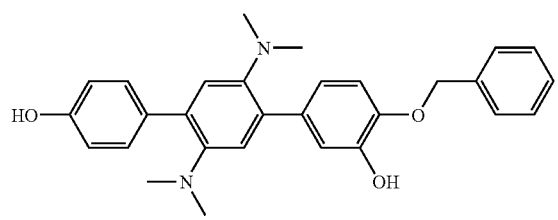
I-861
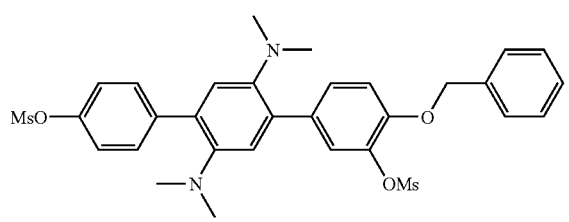
I-862
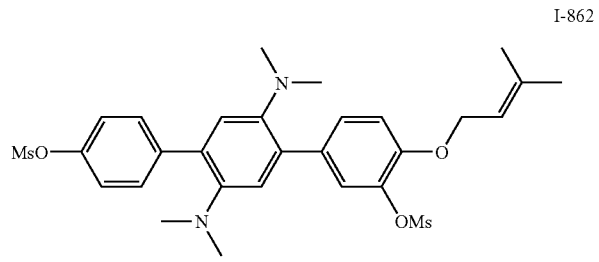
I-863
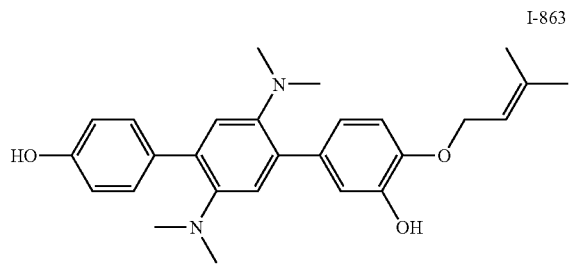
I-864
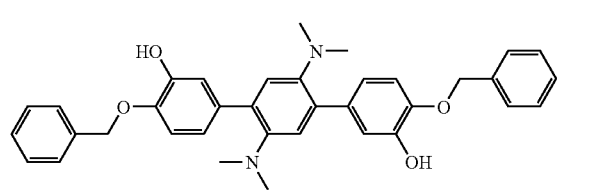
I-865
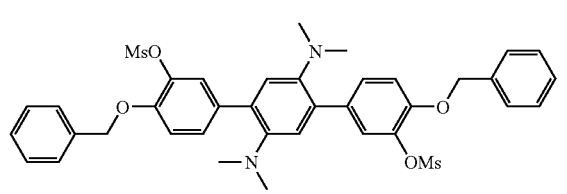
I-866
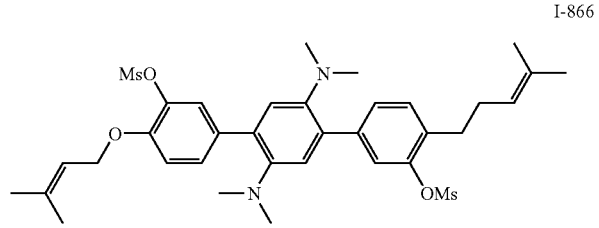
I-867
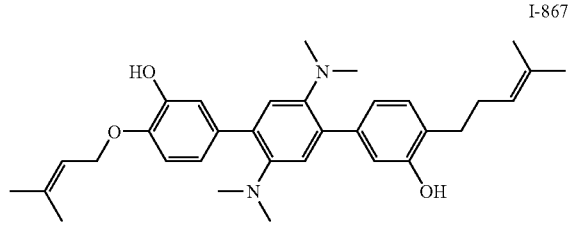
I-868
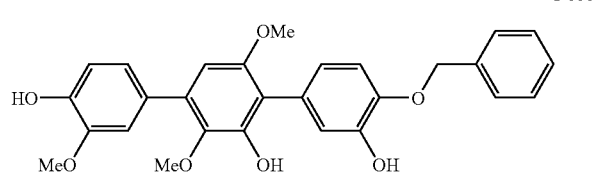
I-869
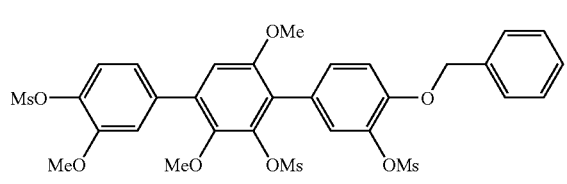
I-870
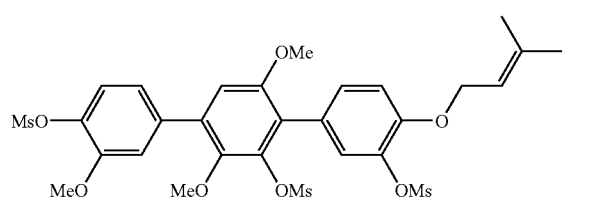
I-871
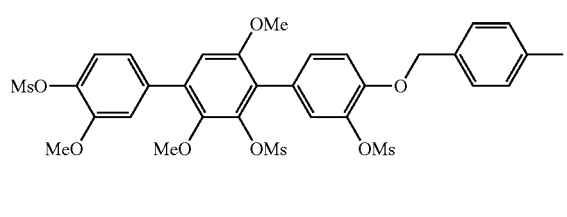
I-872
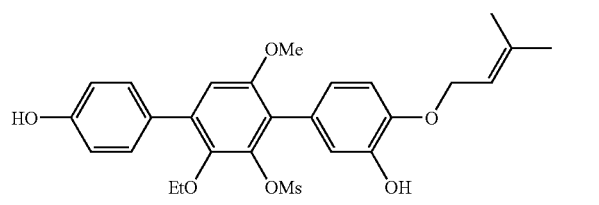
I-873
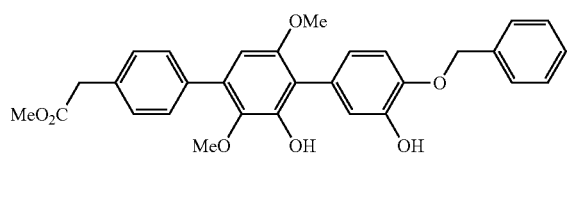

-continued
I-874
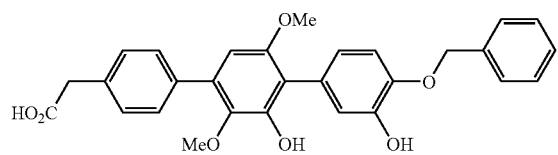
I-875
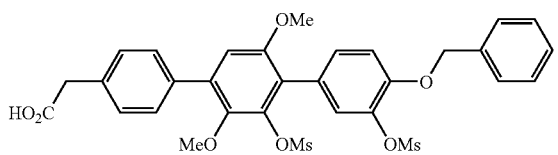
I-876
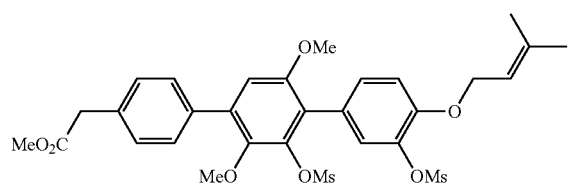
I-877
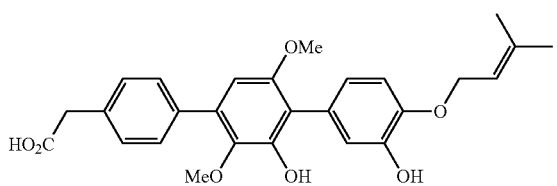
I-878
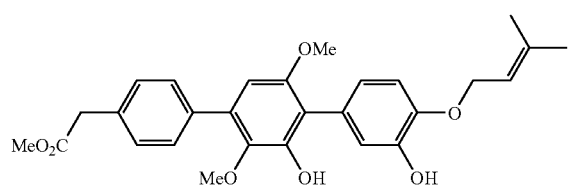
I-879
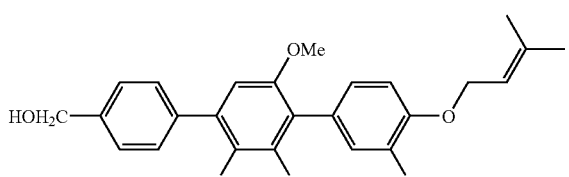
I-880
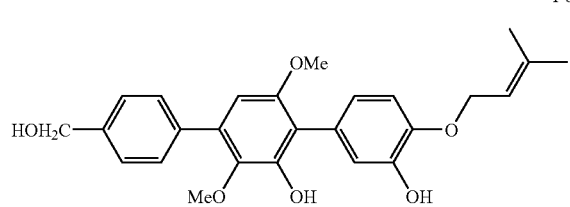
I-881
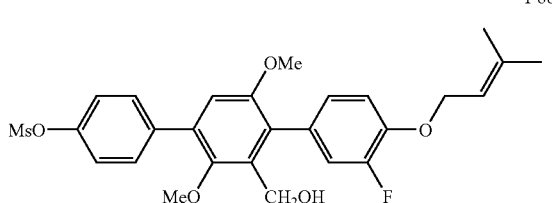
I-882
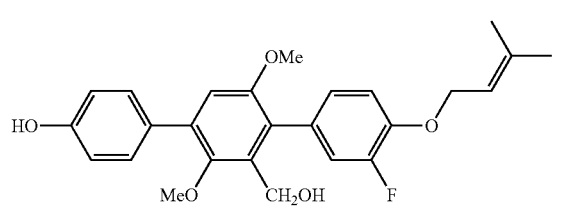
I-883
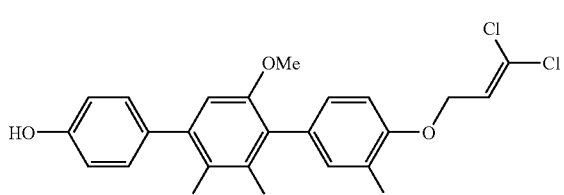
I-884
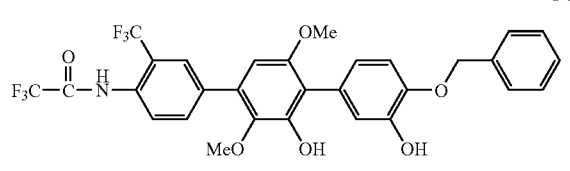
I-885
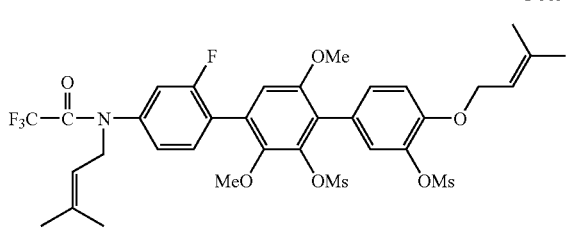
I-886
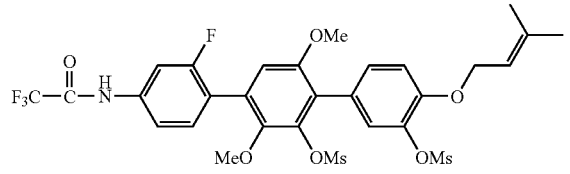
I-887
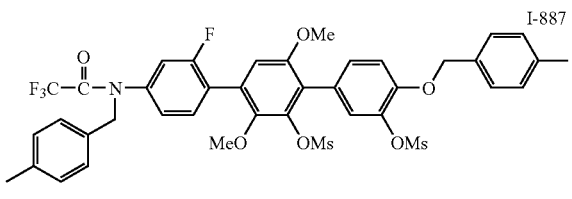

-continued
I-888
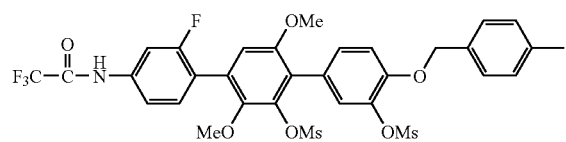
I-889
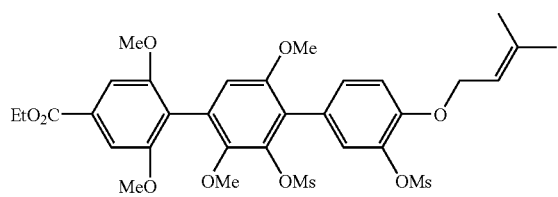
I-890
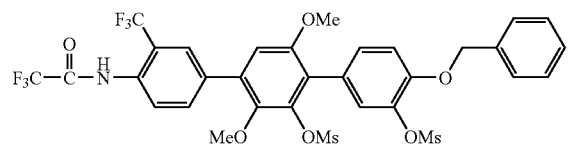
I-891
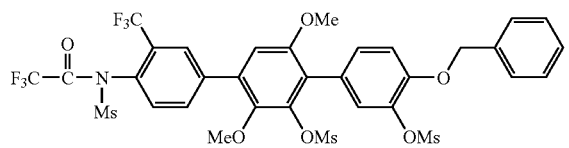
I-892
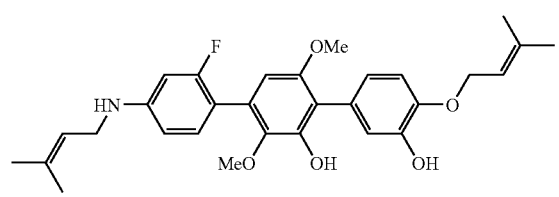
I-893
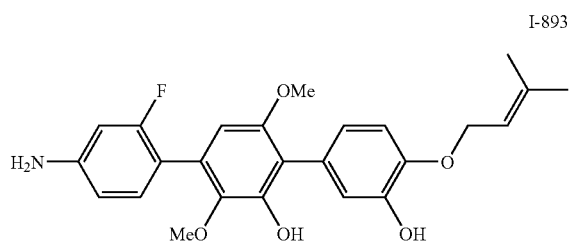
I-894
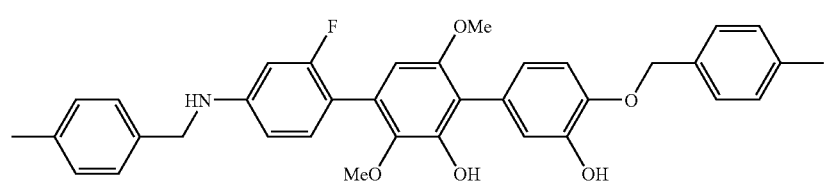
I-895
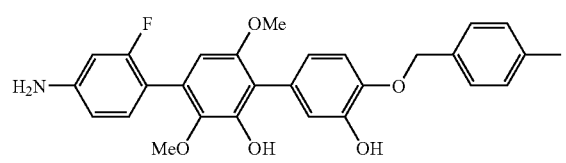
I-896
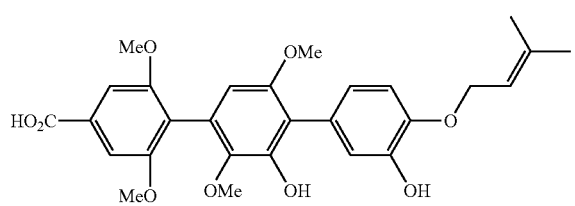
I-897
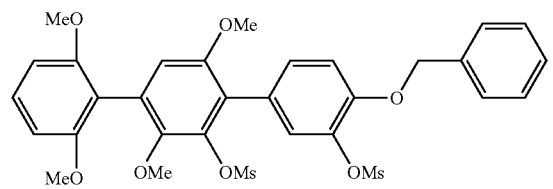
I-898
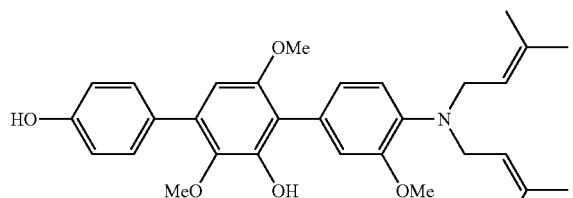
I-899
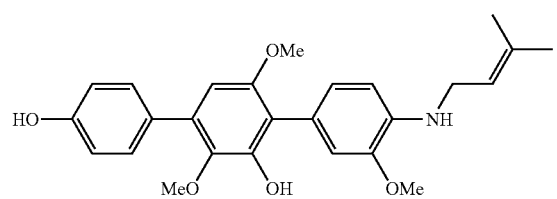
I-900
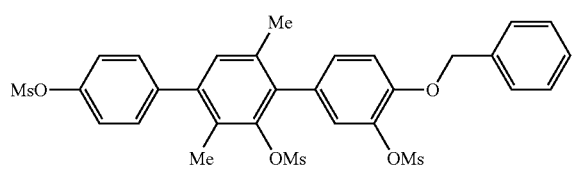

-continued
I-901
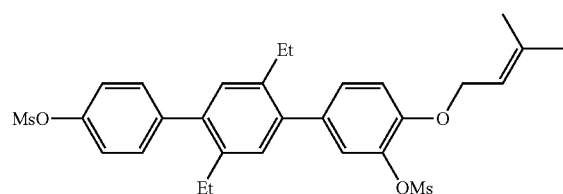
I-902
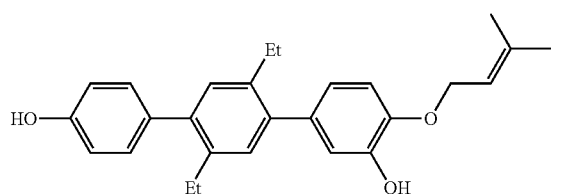
I-903
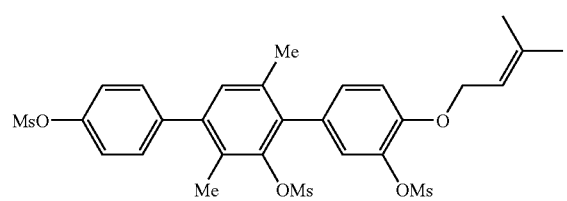
I-904
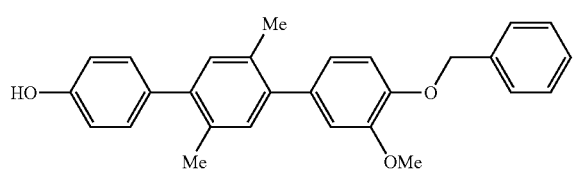
I-905
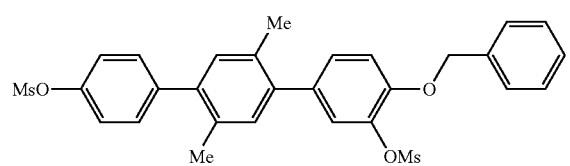
I-906
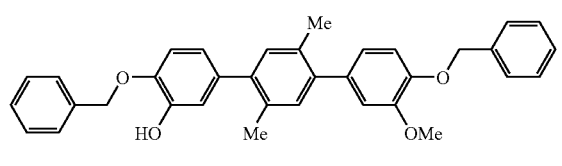
I-907
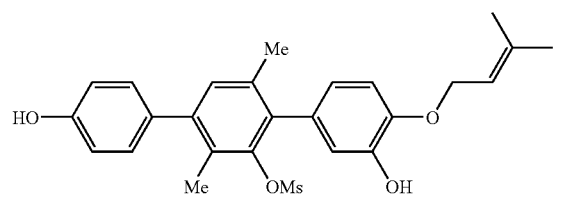
I-908
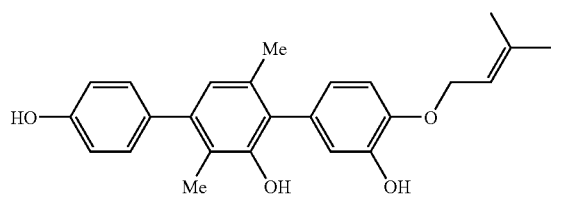
I-909
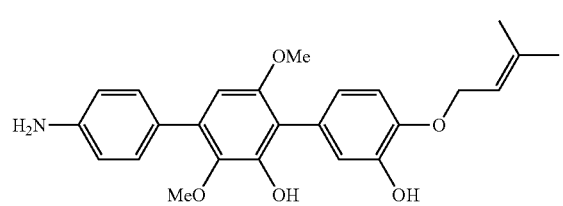
I-910
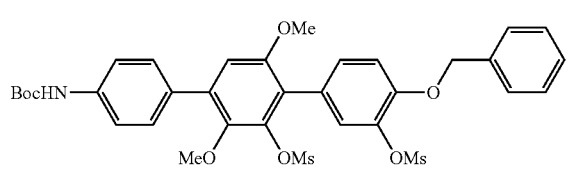
I-911
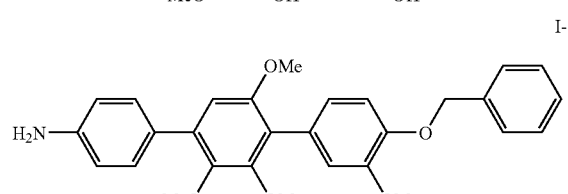
I-912
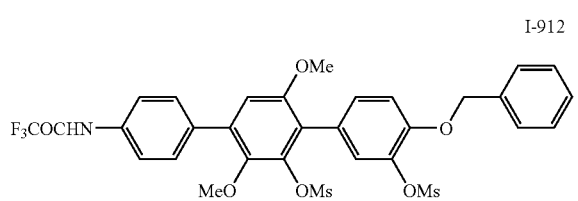
I-913
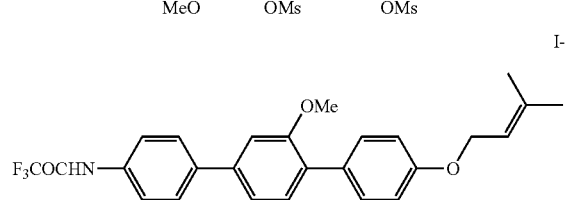
I-914
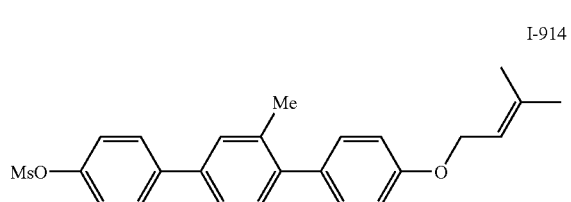

-continued
I-915
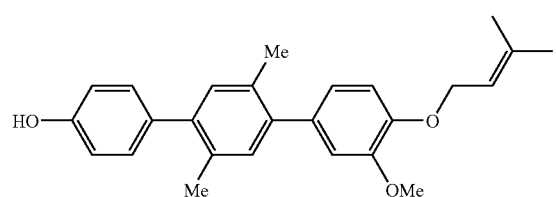
I-916
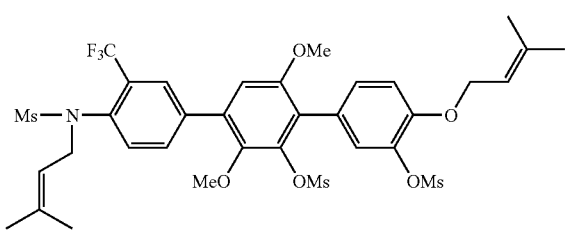
I-917
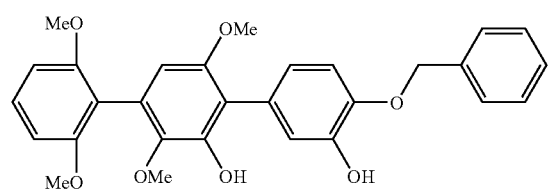
I-918
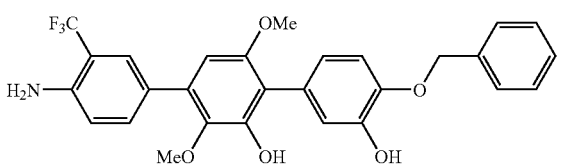
I-919
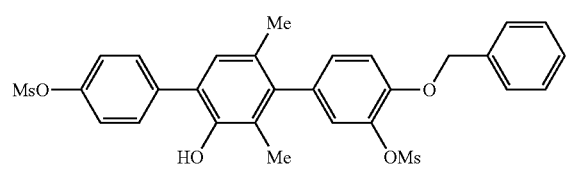
I-920
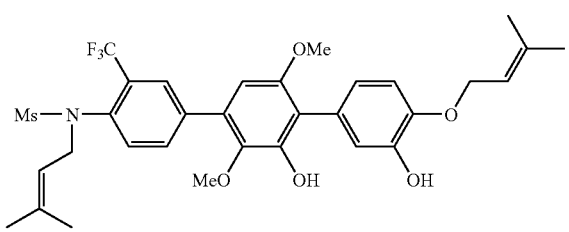
I-921
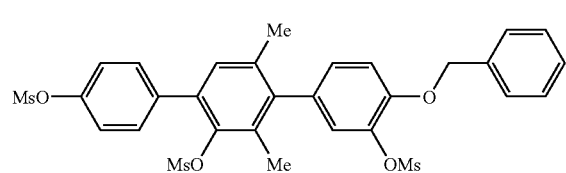
I-922
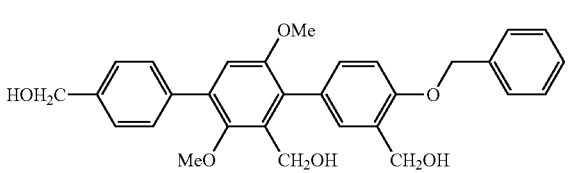
I-923
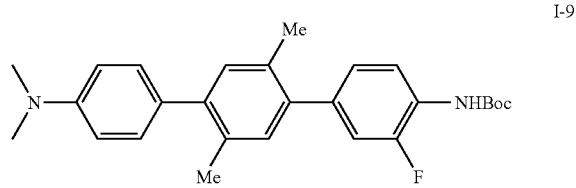
I-924
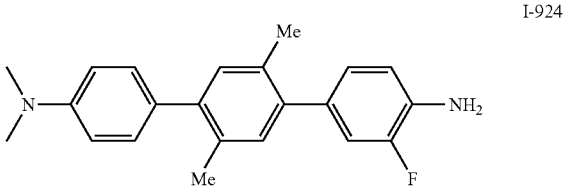
I-925
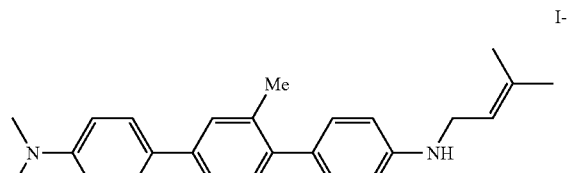
I-926
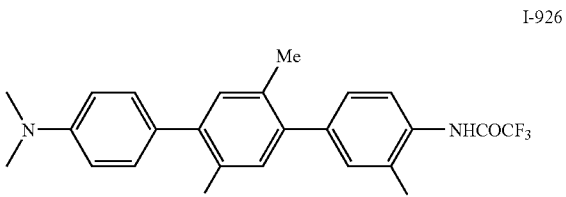
I-927
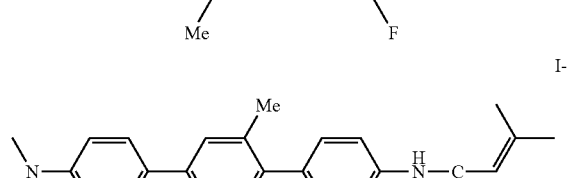
I-928
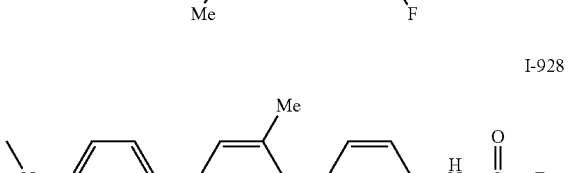

-continued
I-929
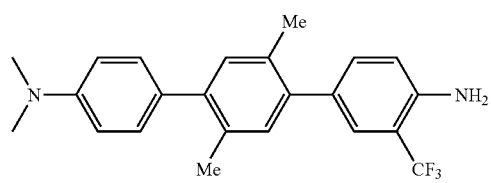
I-930
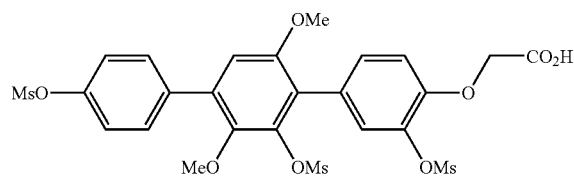
I-931
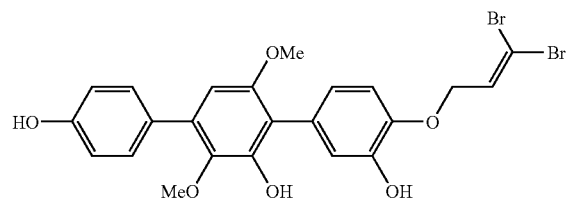
I-932
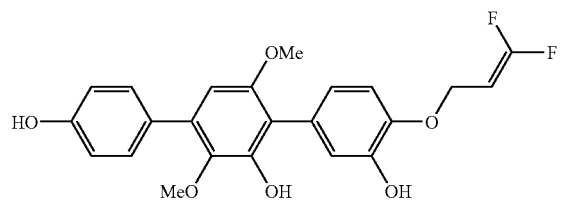
I-933
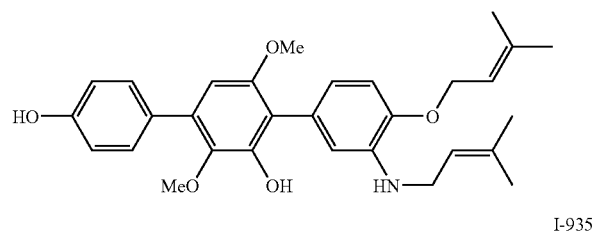
I-934
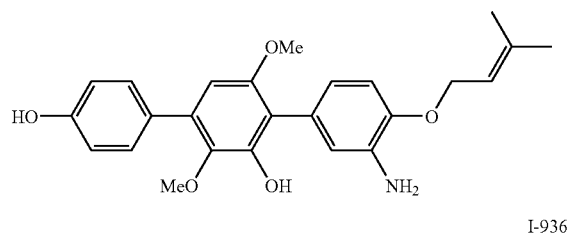
I-935
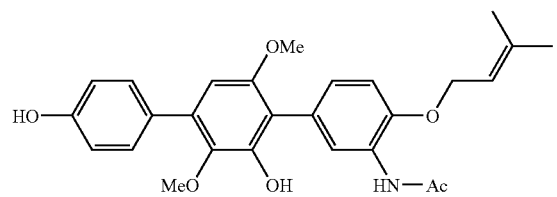
I-936
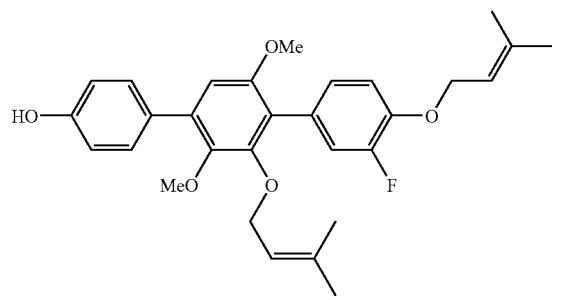
I-937
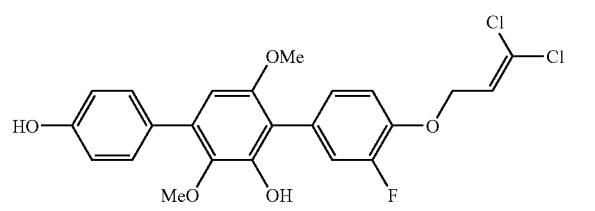
I-938
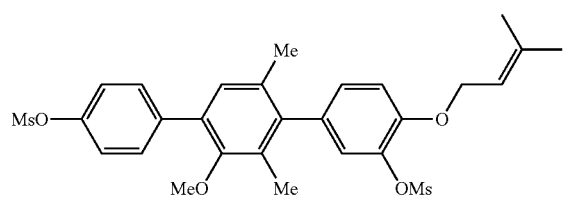
I-939
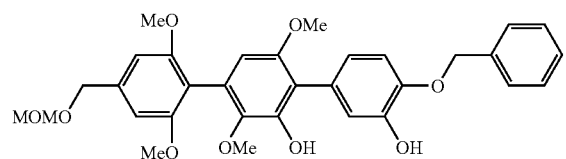
I-940
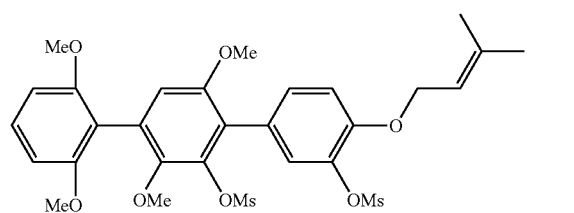

-continued
I-941
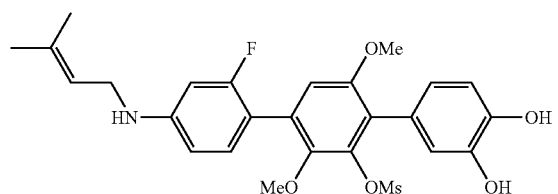
I-942
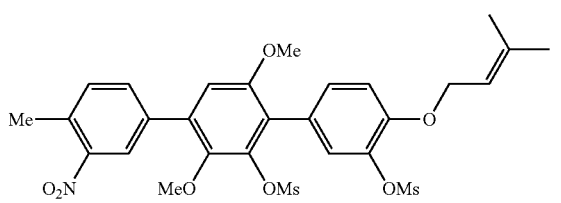
I-943
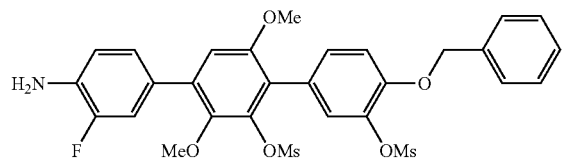
I-944
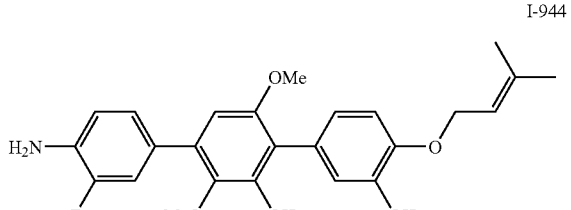
I-945
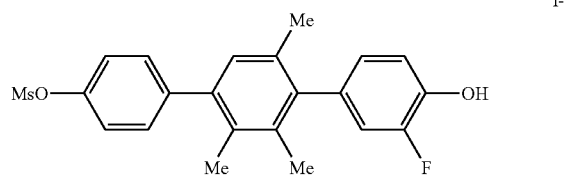
I-946
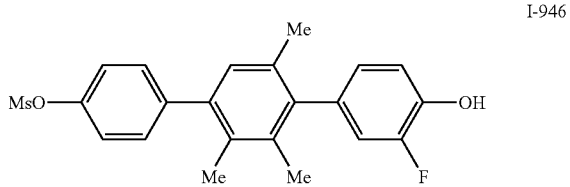
I-947
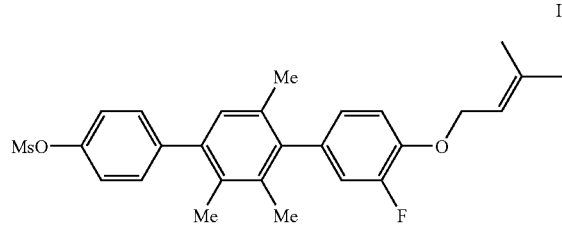
I-948
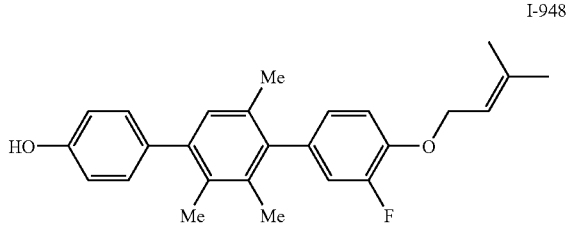
I-949
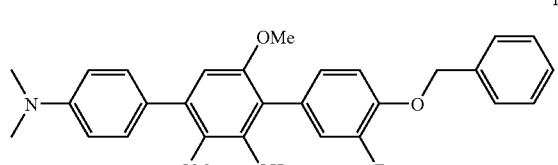
I-950
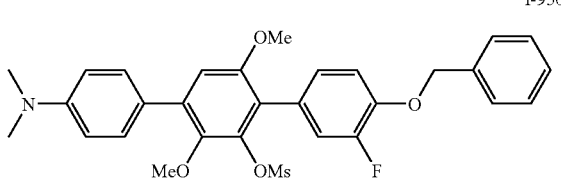
I-951
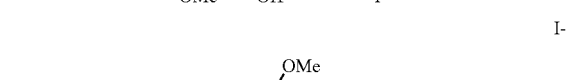
I-952
I-953
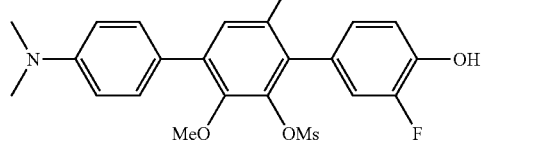
I-954
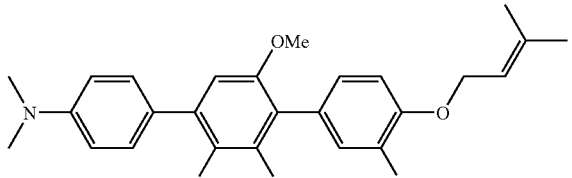
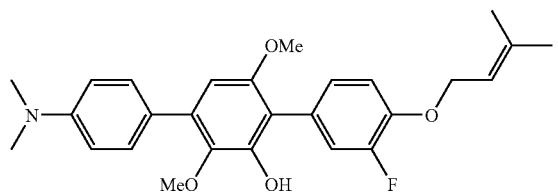
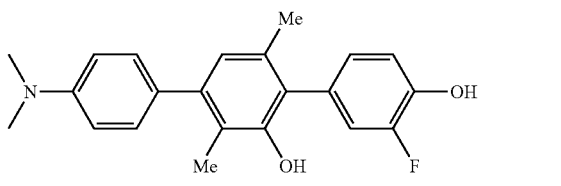

-continued
I-955
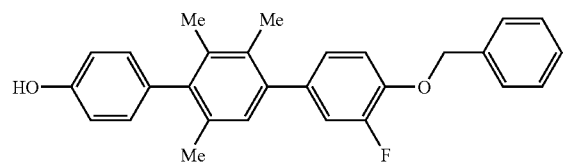
I-956
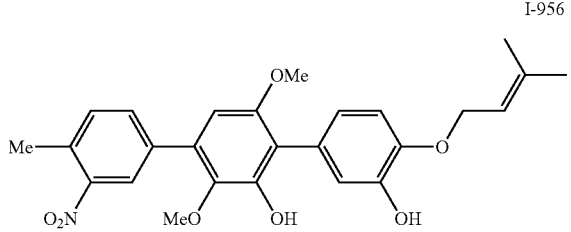
I-957
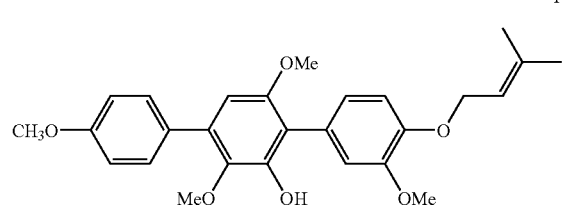
I-958
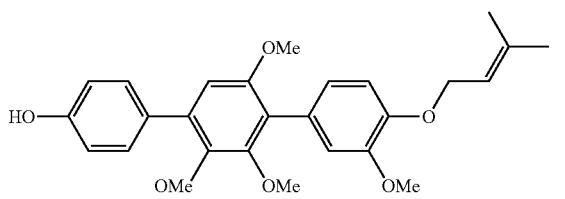
I-959
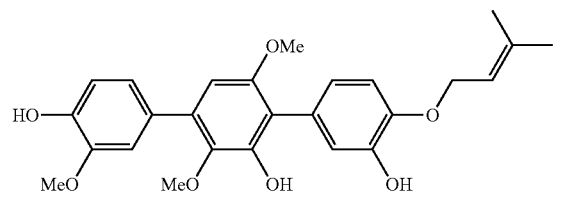
I-960
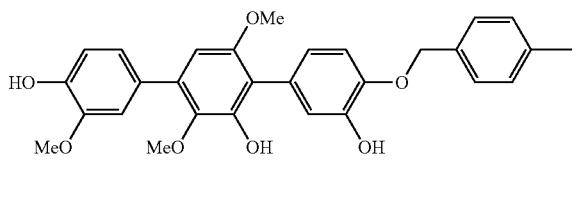
I-961
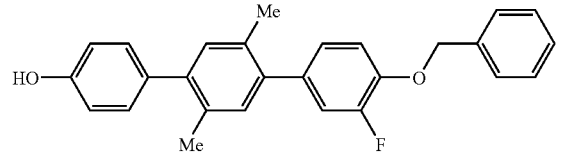
I-962
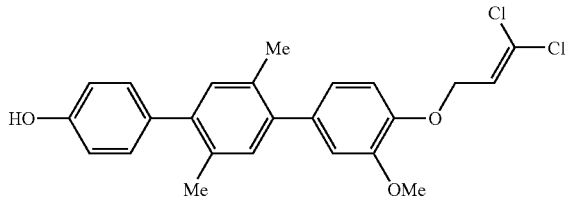
I-963
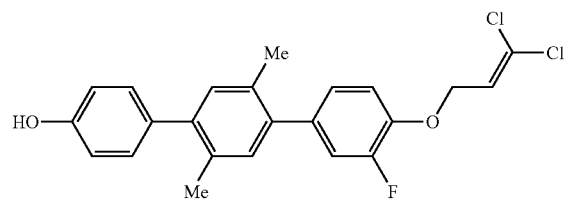
I-964
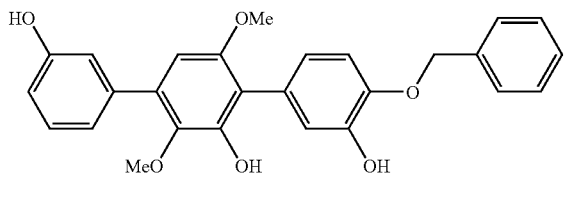
I-965
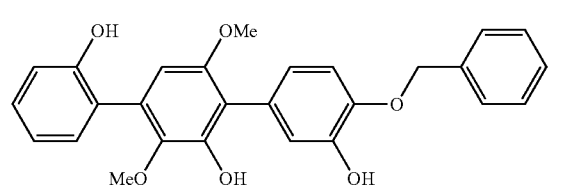
I-966
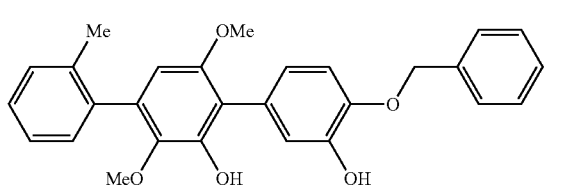
I-967
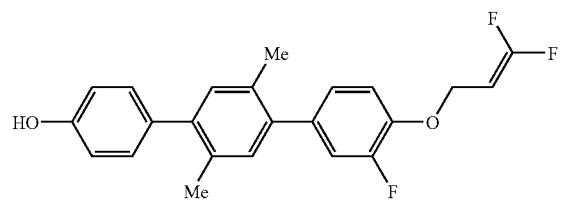

-continued
I-969
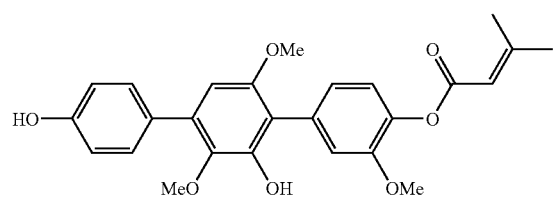
I-970
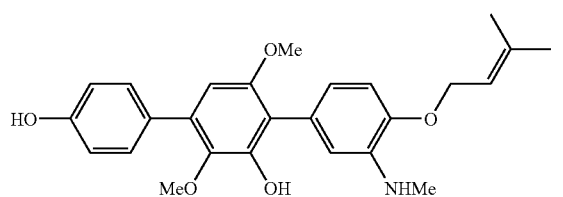
I-971
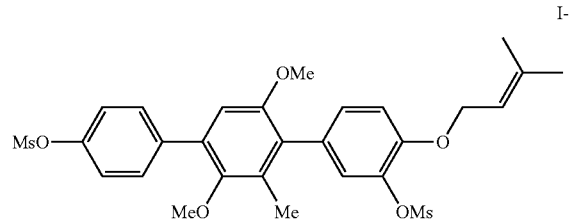
I-972
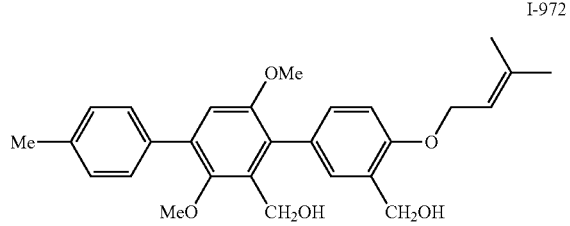
I-973
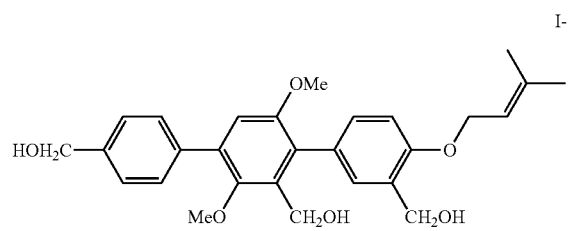
I-974
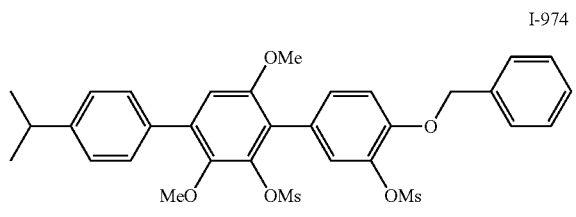
I-975
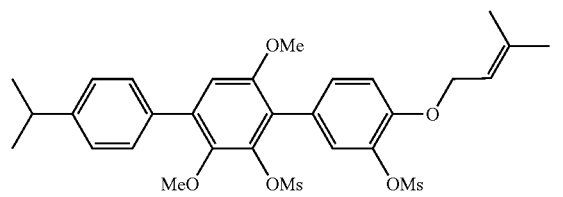
I-976
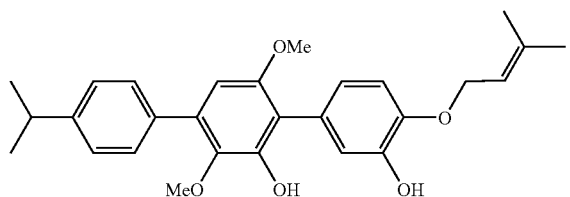
I-977
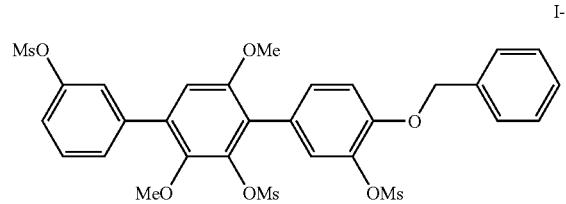
I-979
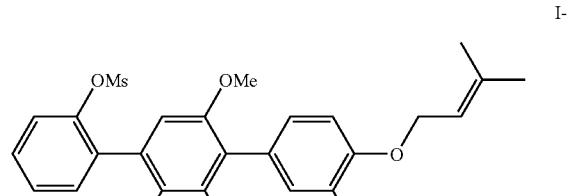
I-978
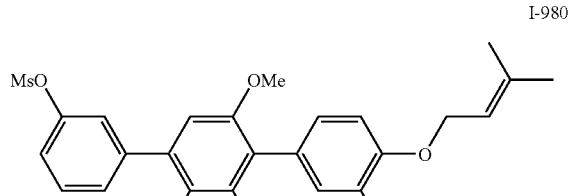
I-981
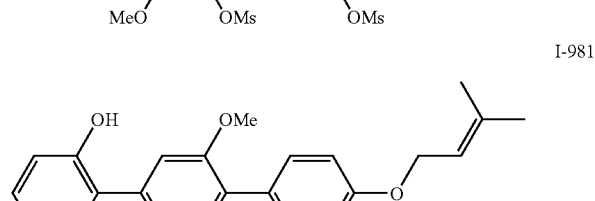
I-980
I-982
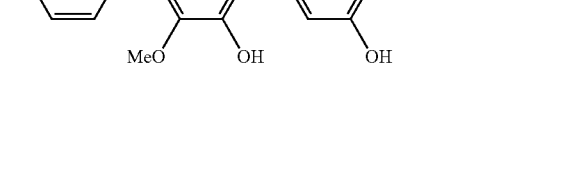

-continued
I-983
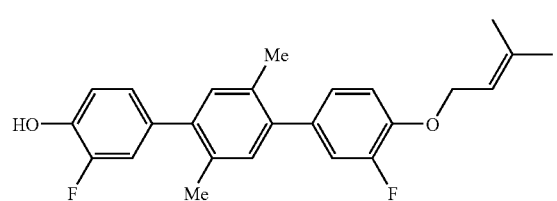
I-984
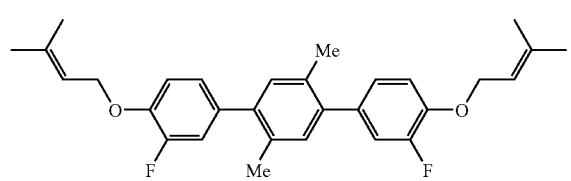
I-985
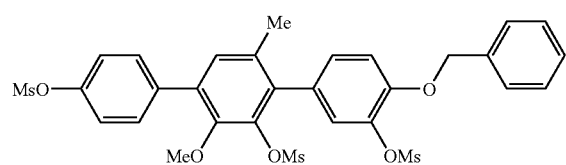
I-986
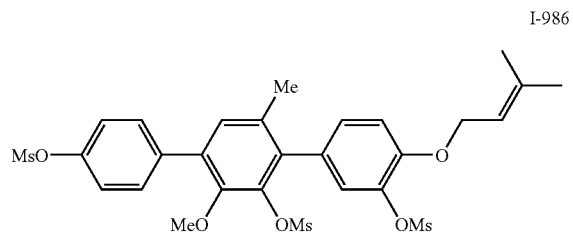
I-987
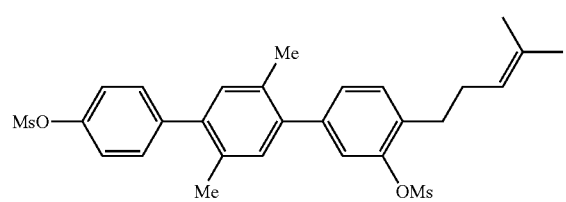
I-988
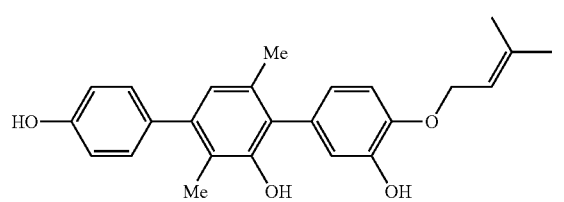
I-989
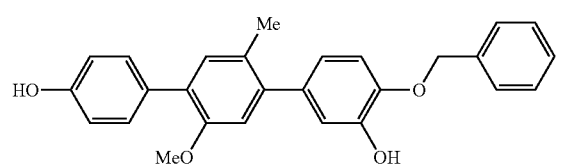
I-990
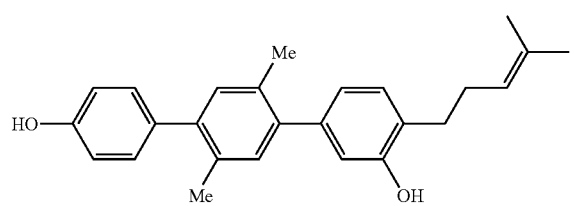
I-991
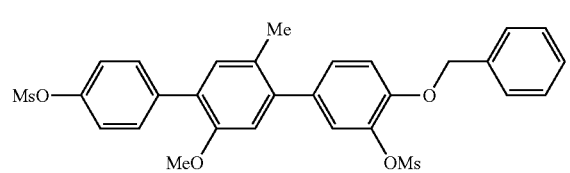
I-992
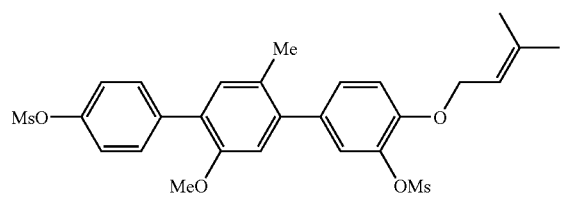
I-993
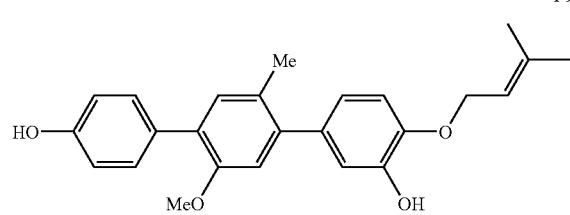
I-994
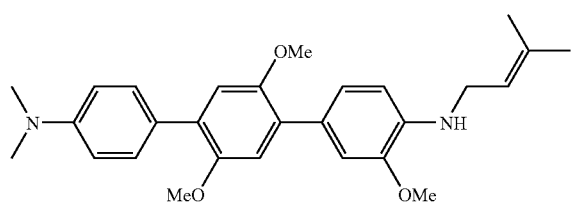
I-995
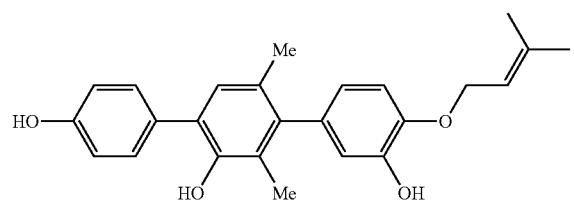
I-996
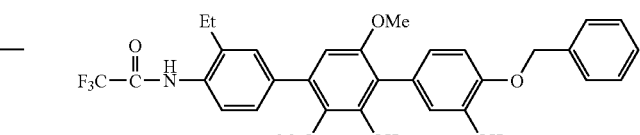

-continued
I-997
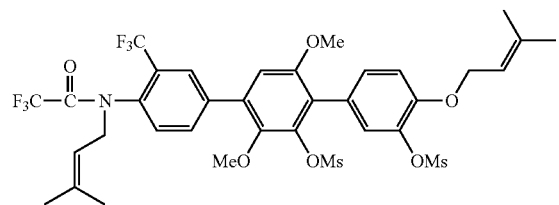
I-998
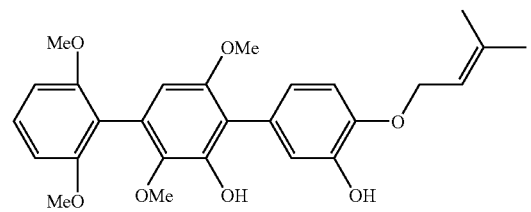
I-999
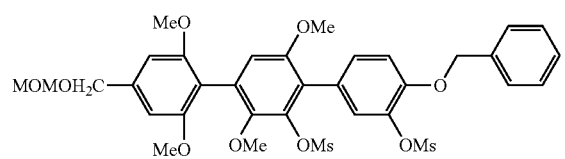
I-1000
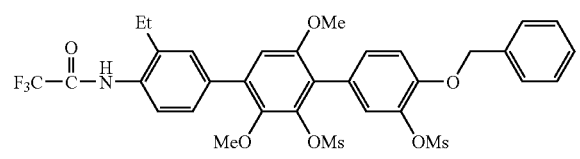
I-1001
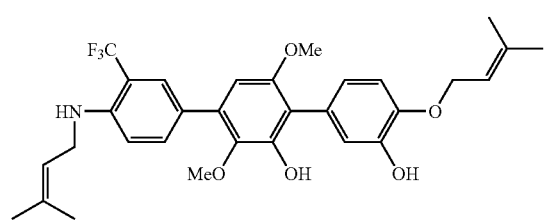
I-1002
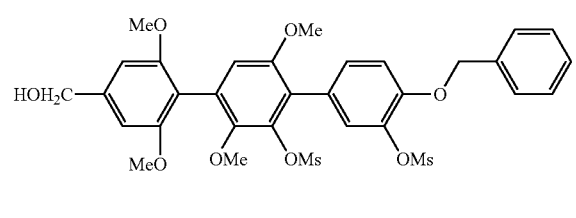
I-1003
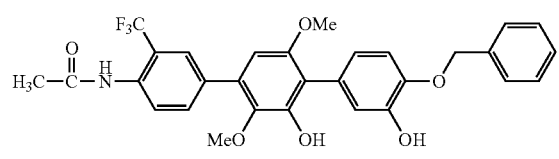
I-1004
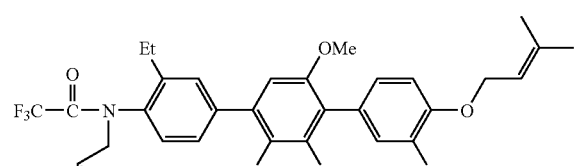
I-1005
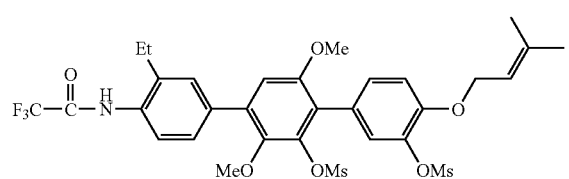
I-1006
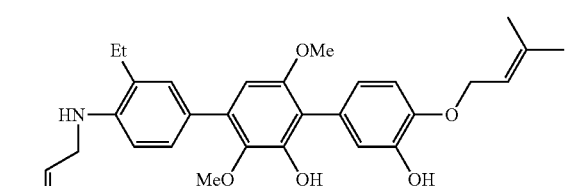
I-1007
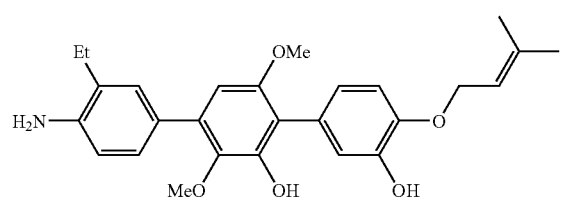
I-1008
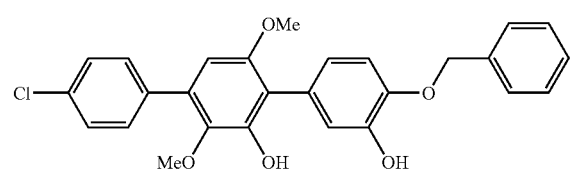
I-1009
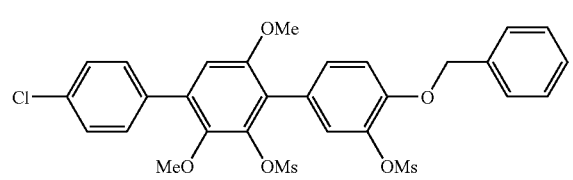
I-1010
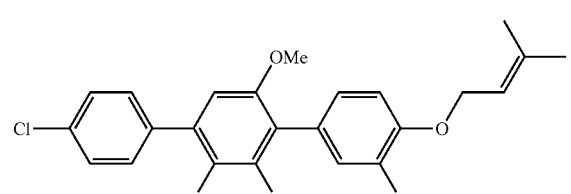

-continued
I-1011
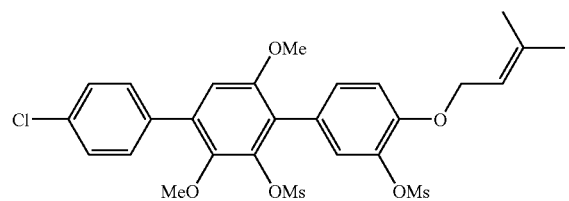
I-1012
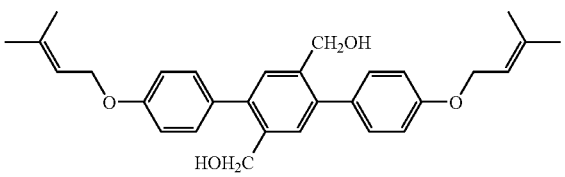
I-1013
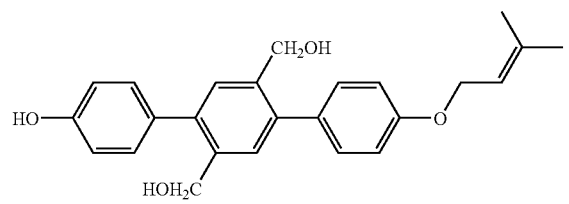
I-1014
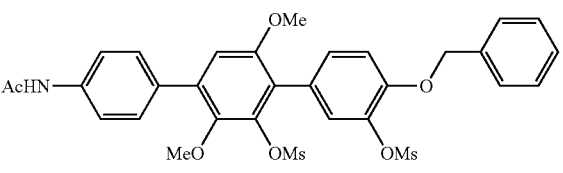
I-1015
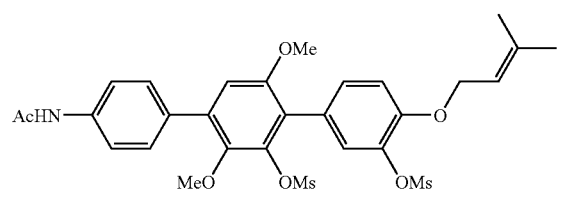
I-1016
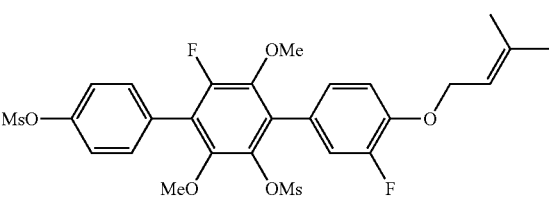
I-1017
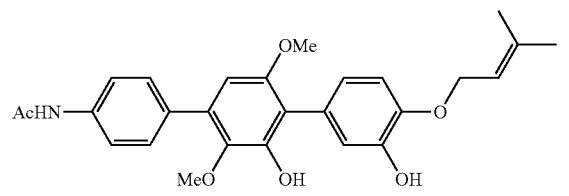
I-1018
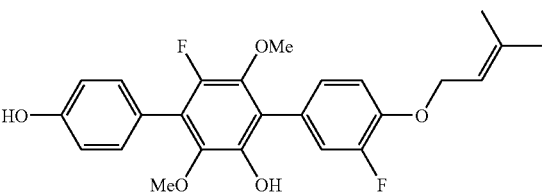
I-1019
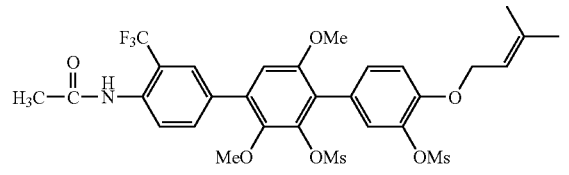
I-1020
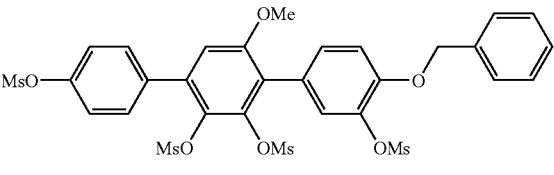
I-1021
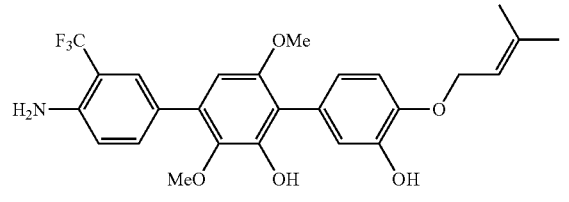
I-1022
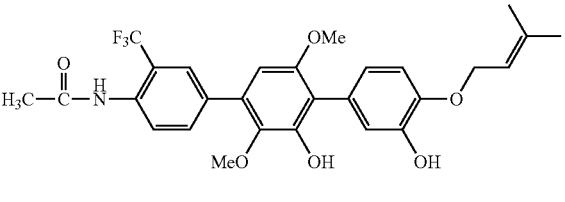
I-1023
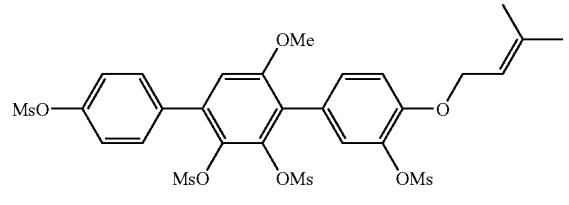
I-1024
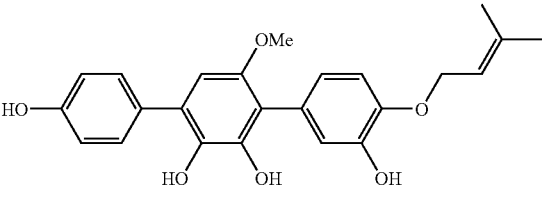

-continued
I-1025
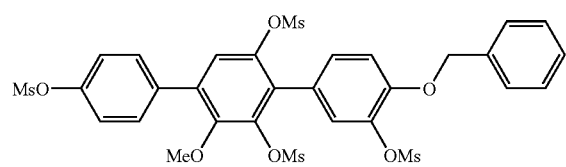
I-1027
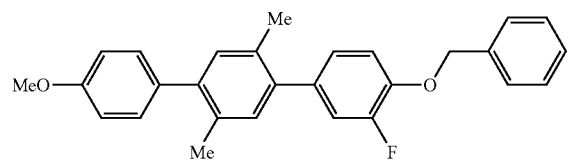
I-1029
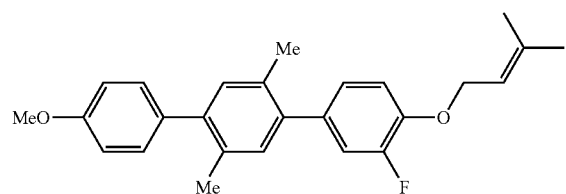
I-1031
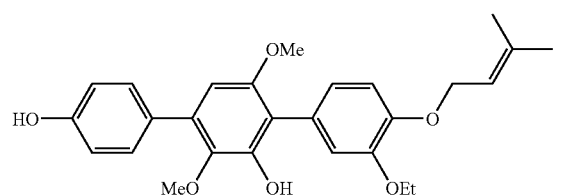
I-1033
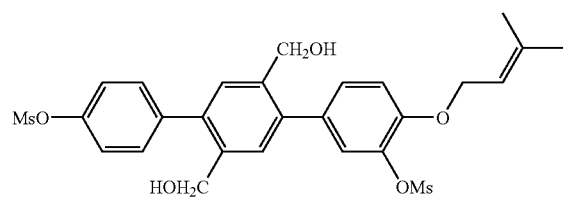
I-1035
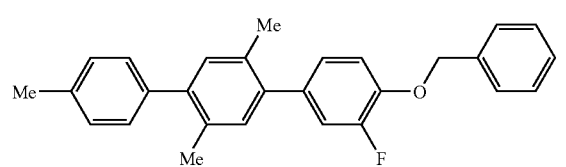
I-1037
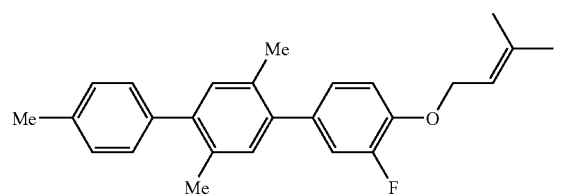
I-1026
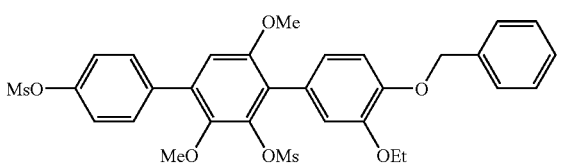
I-1028
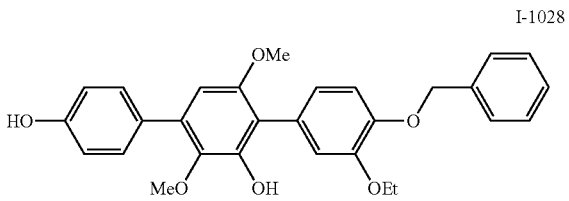
I-1030
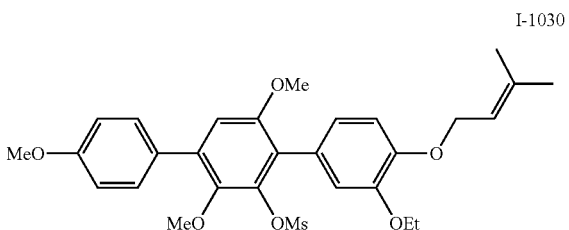
I-1032
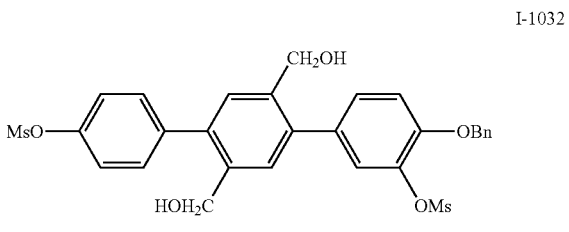
I-1034
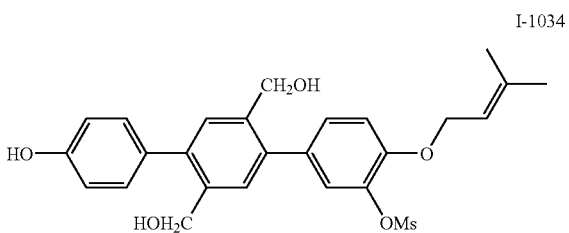
I-1036
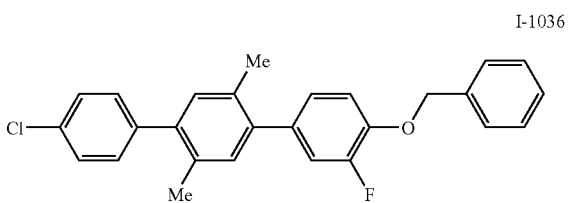
I-1038
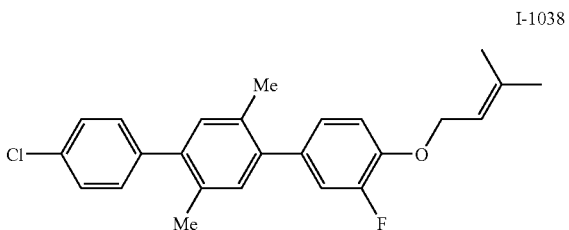

-continued
I-1039
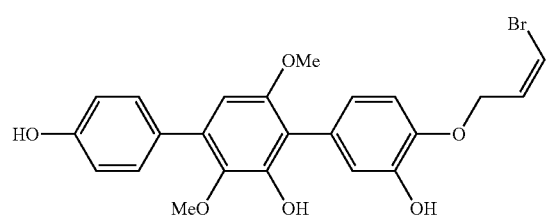
I-1040
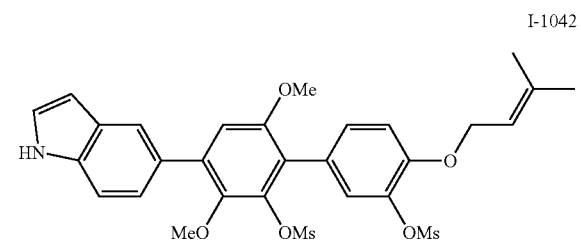
I-1041
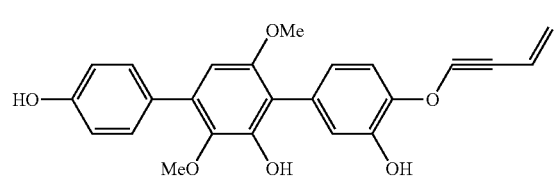
I-1042
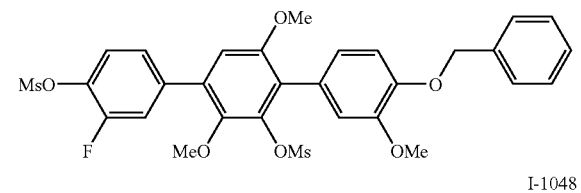
I-1043
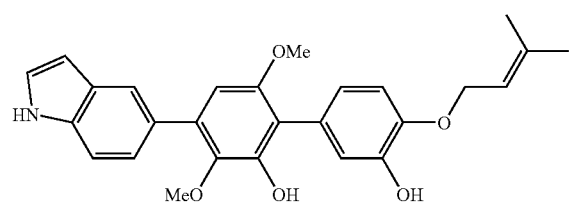
I-1044
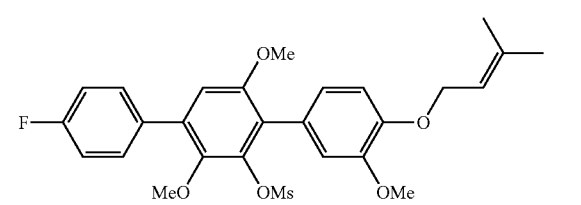
I-1045
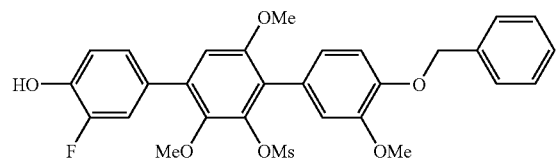
I-1046
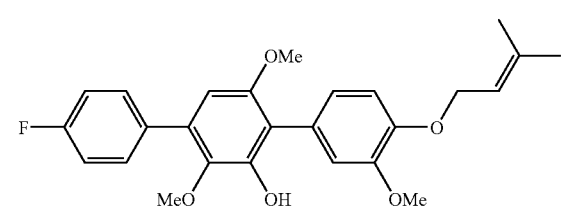
I-1047
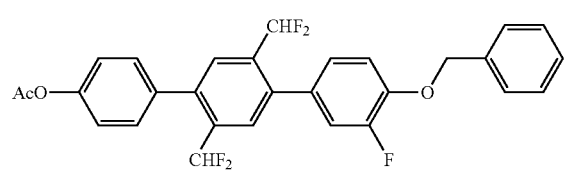
I-1048
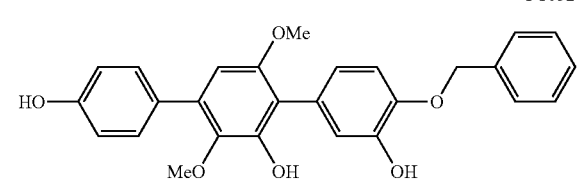
I-1049
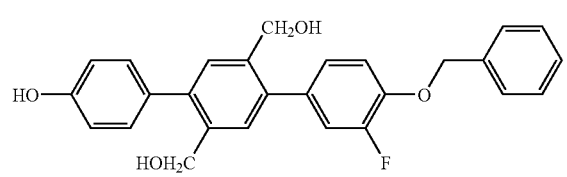
I-1050
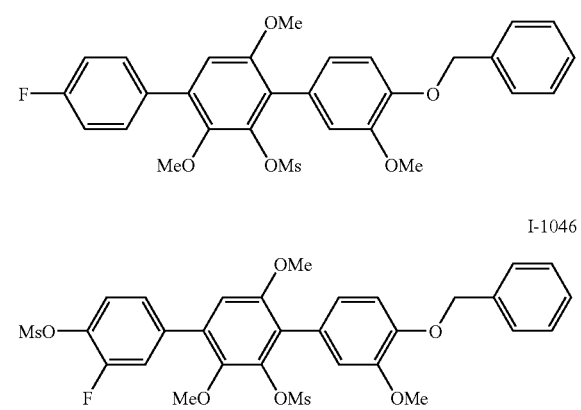
I-1051
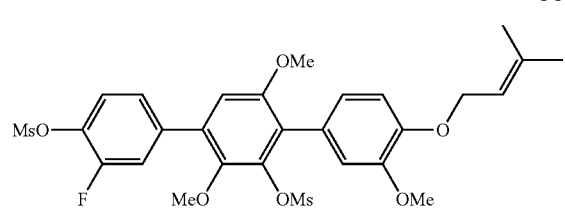
I-1052

-continued
I-1053
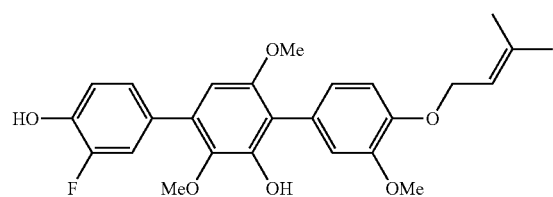
I-1054
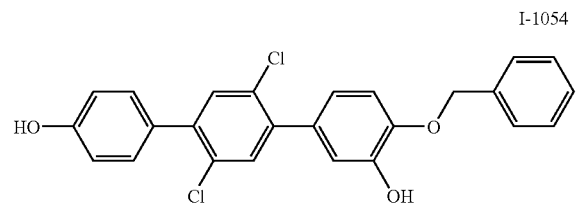
I-1055
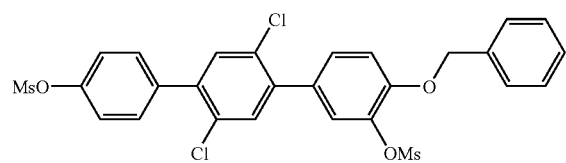
I-1056
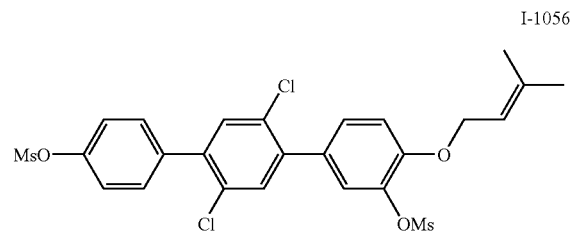
I-1057
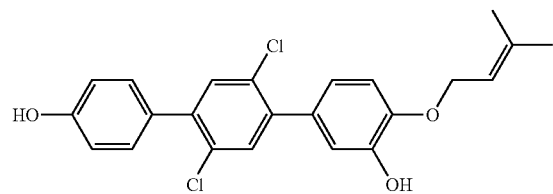
I-1058
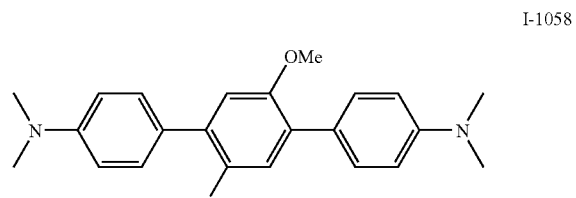
I-1059
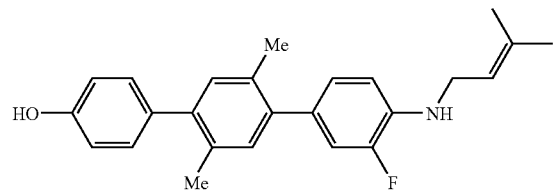
I-1060
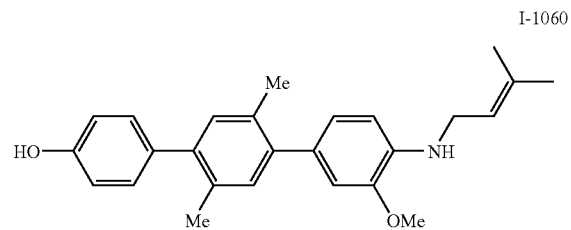
I-1061
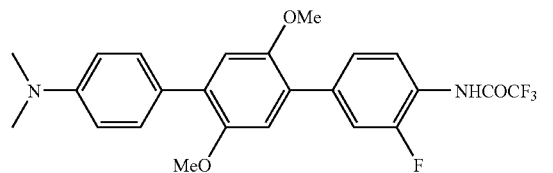
I-1062
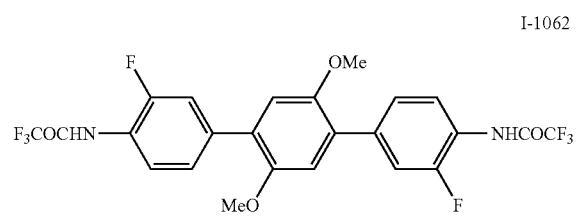
I-1063
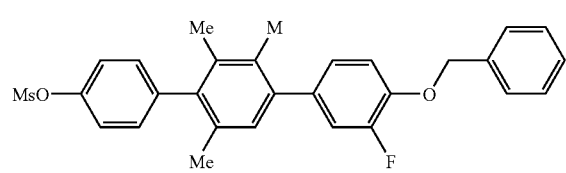
I-1064
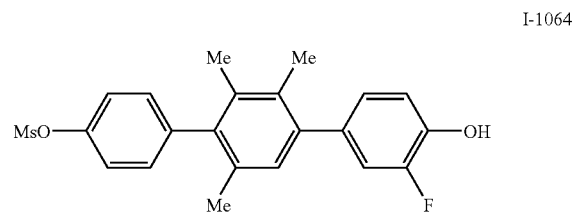
I-1065
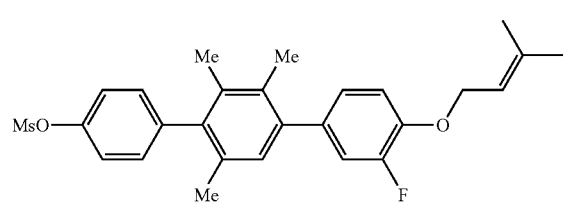
I-1066
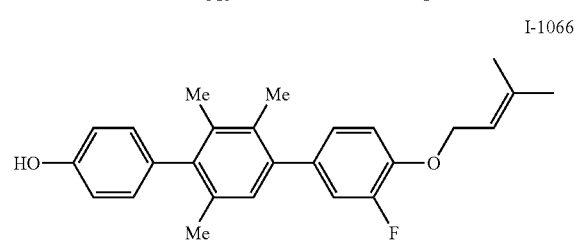

-continued
I-1067
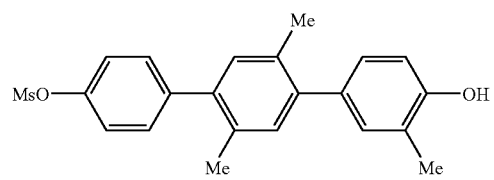
I-1068
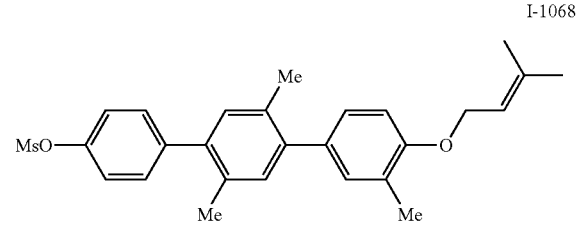
I-1069
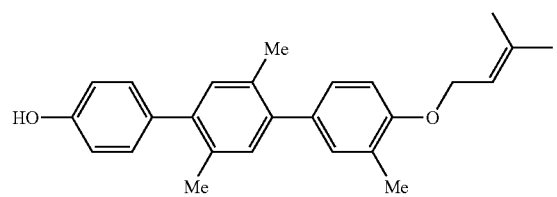
I-1070
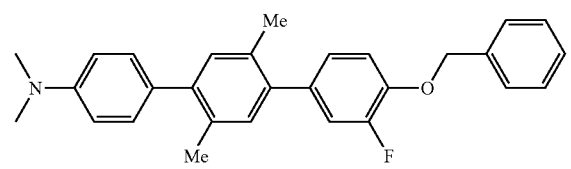
I-1071
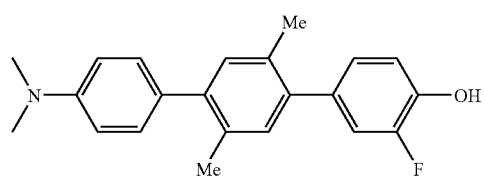
I-1072
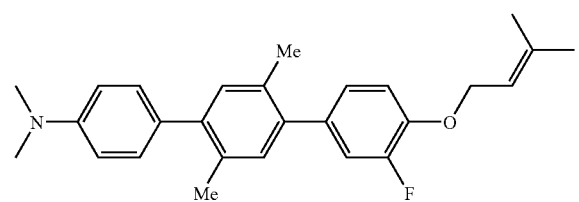
I-1073
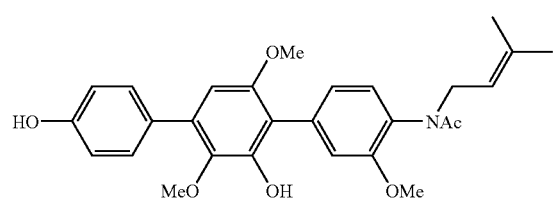
I-1074
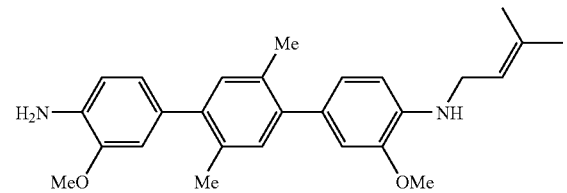
I-1075
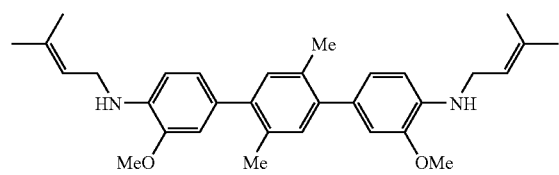
I-1076
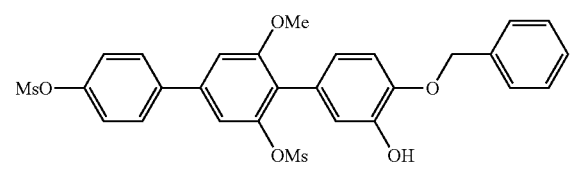
I-1077
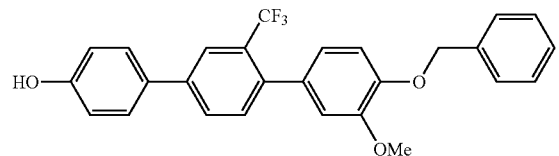
I-1078
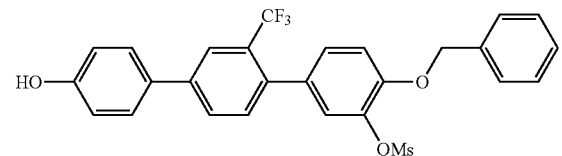
I-1079
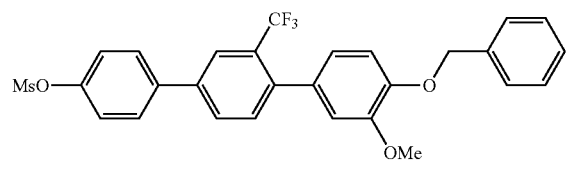
I-1080
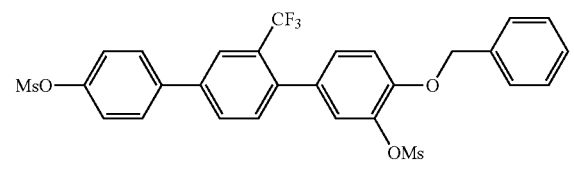

I-1081
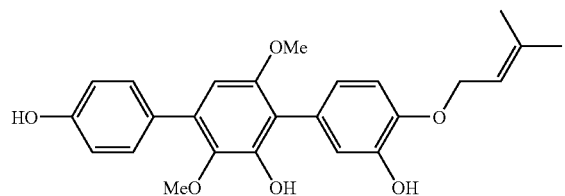
I-1082
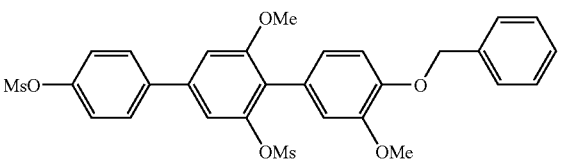
I-1083
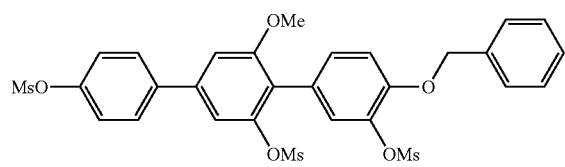
I-1084
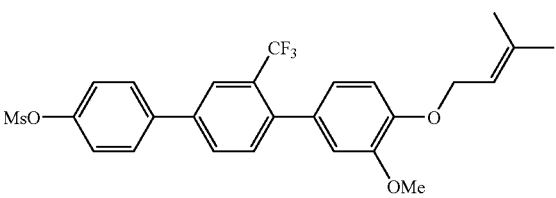
I-1085
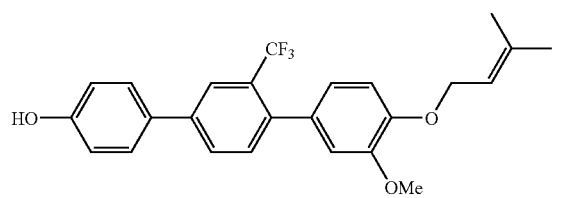
I-1086
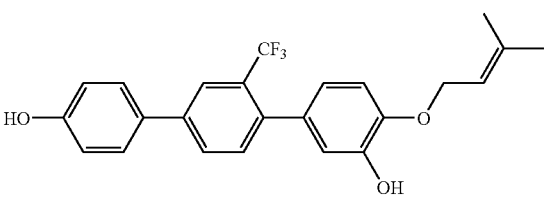
I-1087
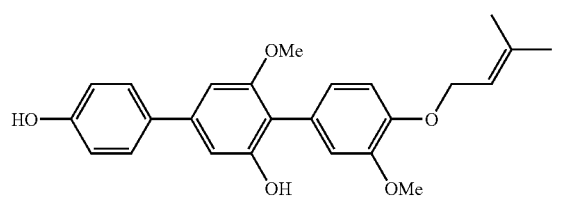
I-1088
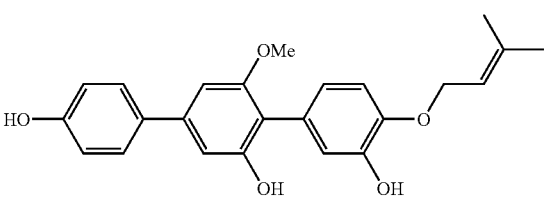
I-1089
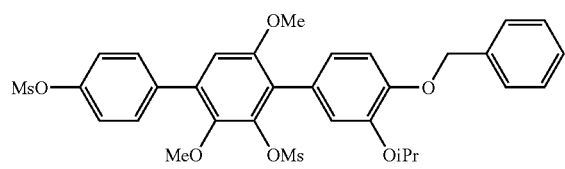
I-1090
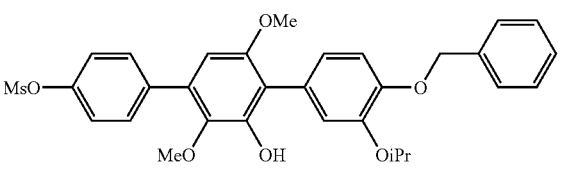
I-1091
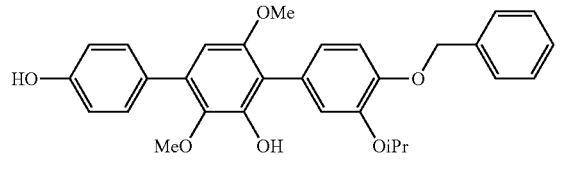
I-1092
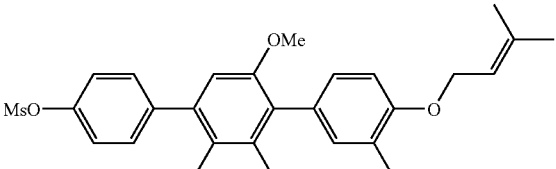
I-1093
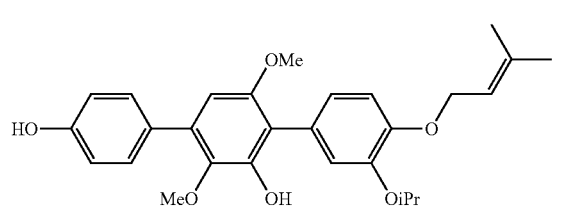
I-1094
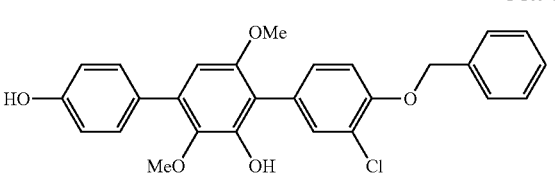

-continued
I-1095
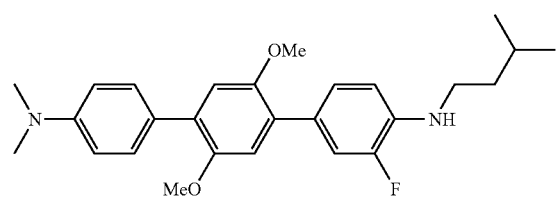
I-1096
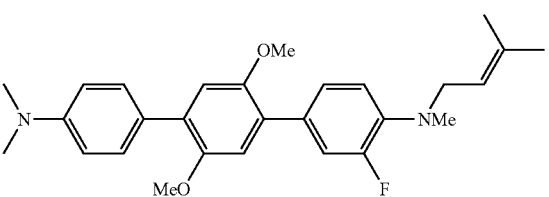
I-1097
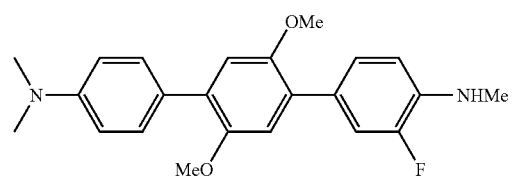
I-1098
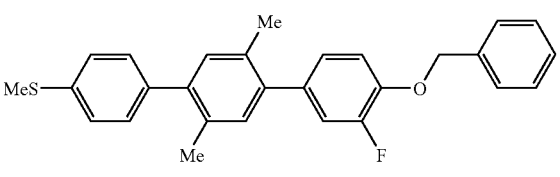
I-1099
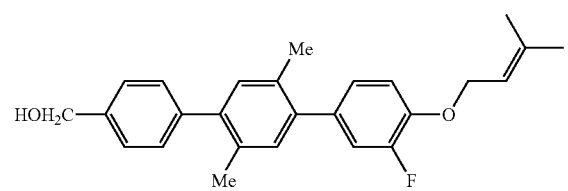
I-1100
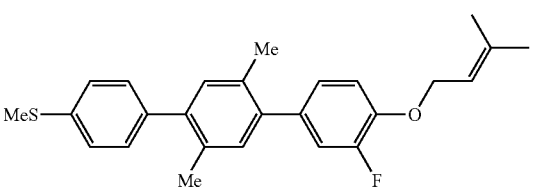
I-1101
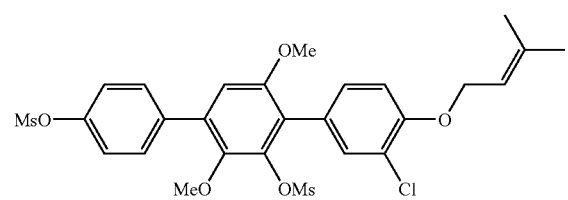
I-1102
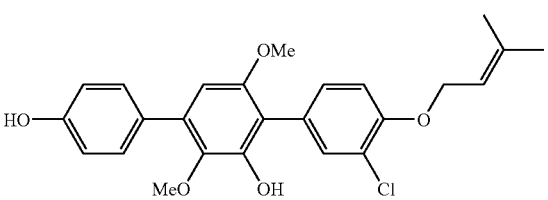
I-1103
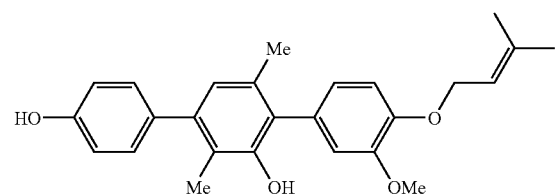
I-1104
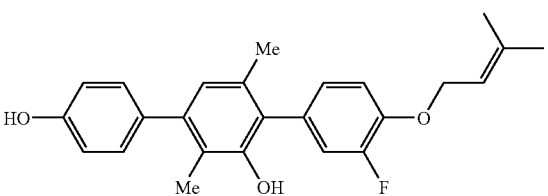
I-1105
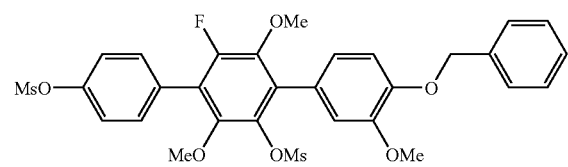
I-1106
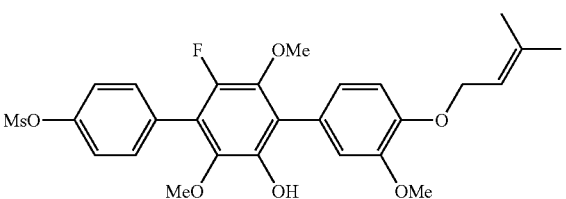
I-1107
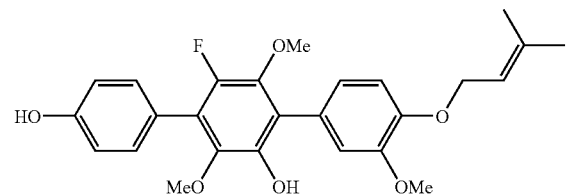
I-1108
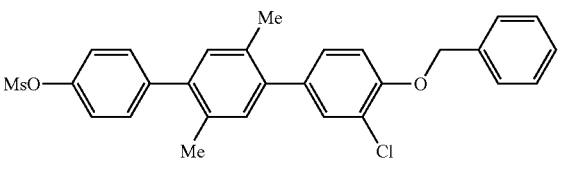

-continued
I-1109
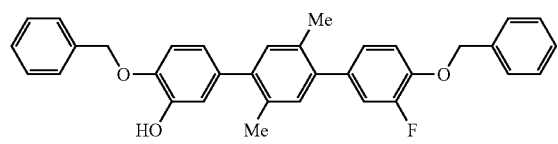
I-1110
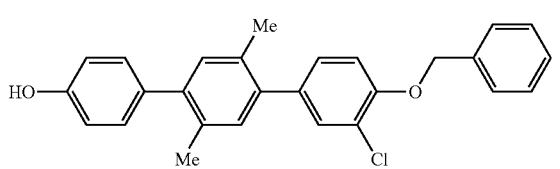
I-1111
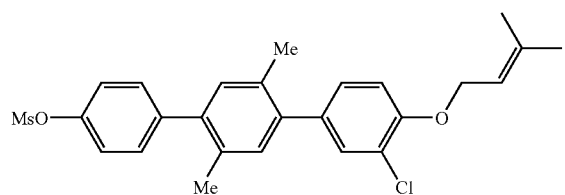
I-1112
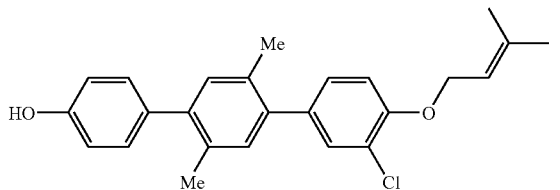
I-1113
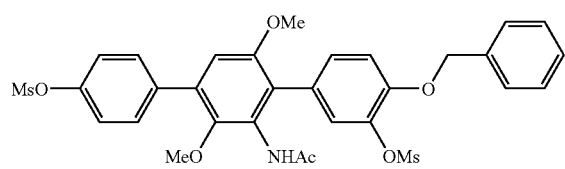
I-1114
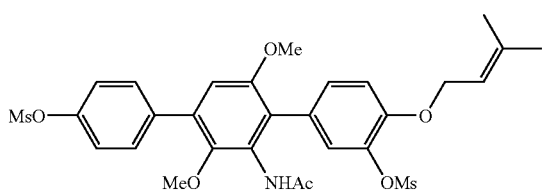
I-1115
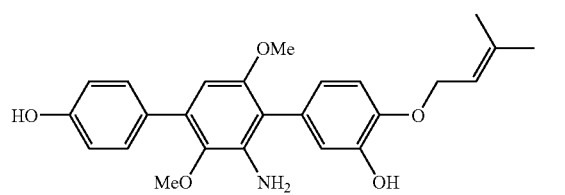
I-1116
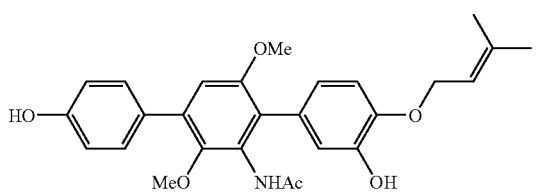
I-1117
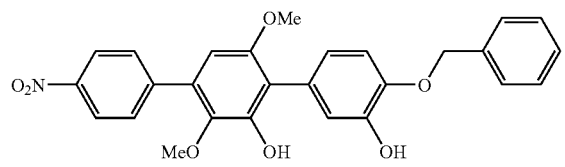
I-1118
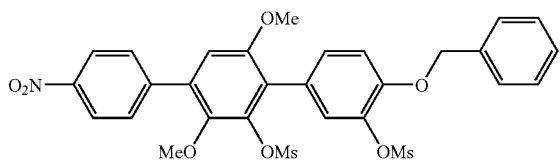
I-1119
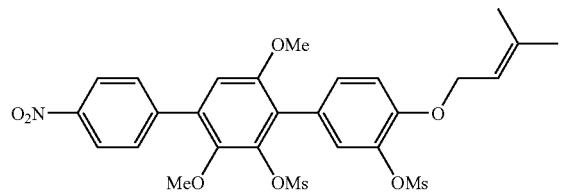
I-1120
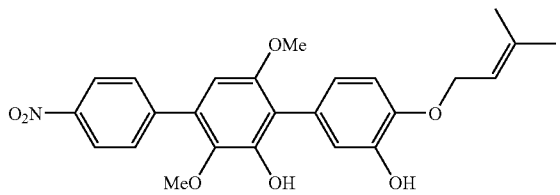
I-1121
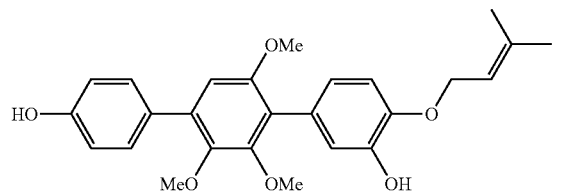
I-1122
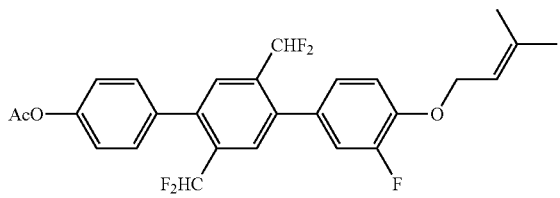

-continued
I-1123
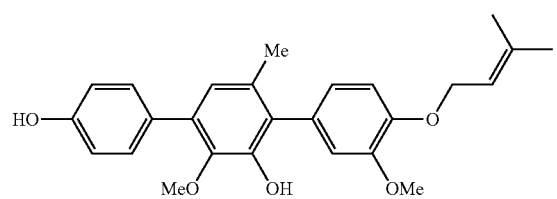
I-1124
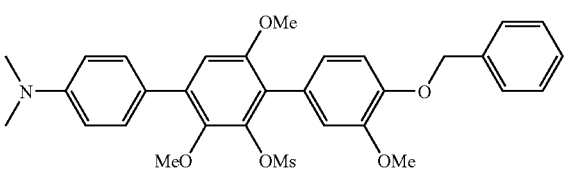
I-1125
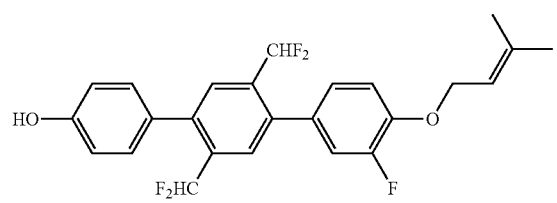
I-1126
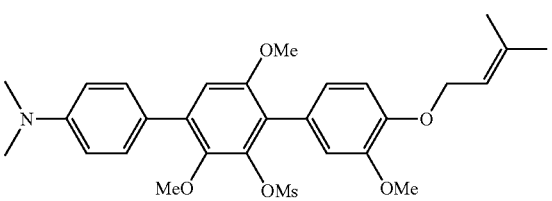
I-1127
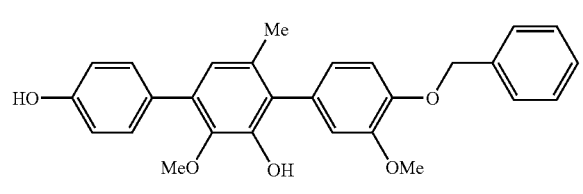
I-1128
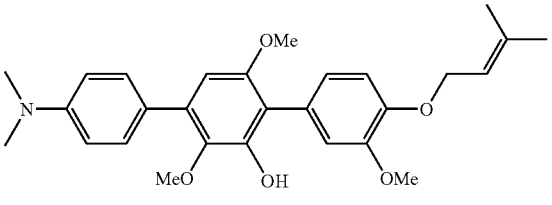
I-1129
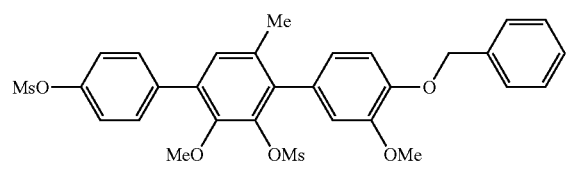
I-1130
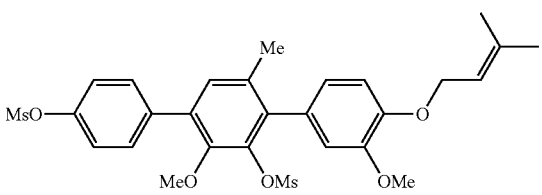
I-1131
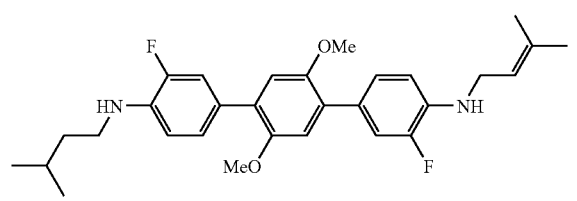
I-1132
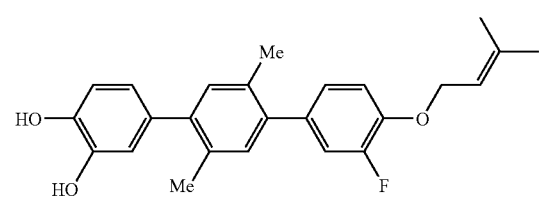
I-1133
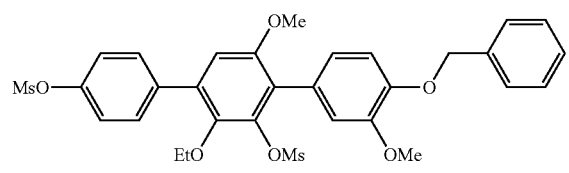
I-1134
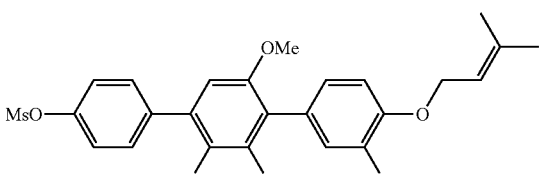
I-1135
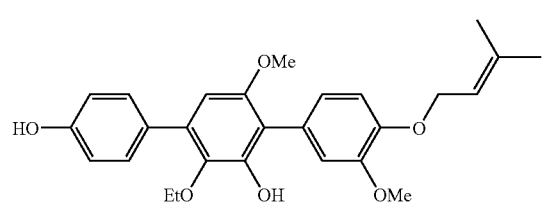
I-1136
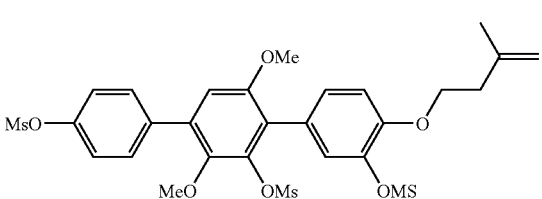

-continued
I-1137
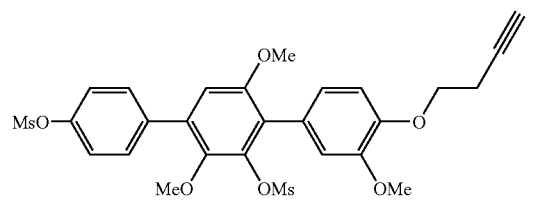
I-1138
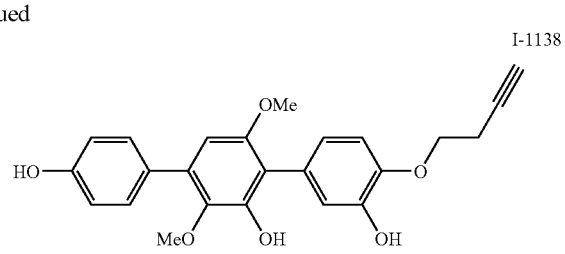
I-1139
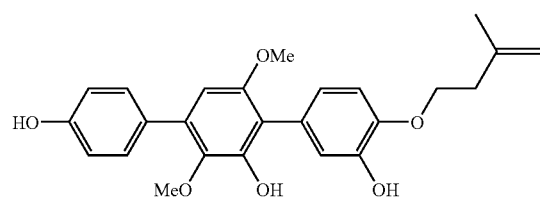
I-1140
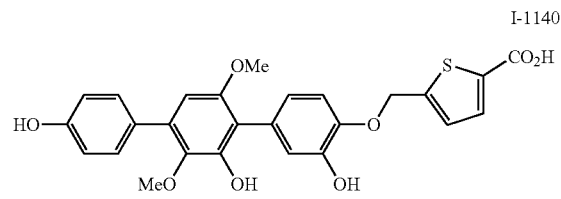
I-1141
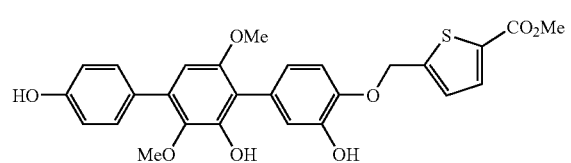
I-1142
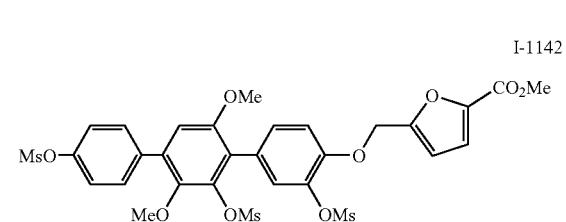
I-1143
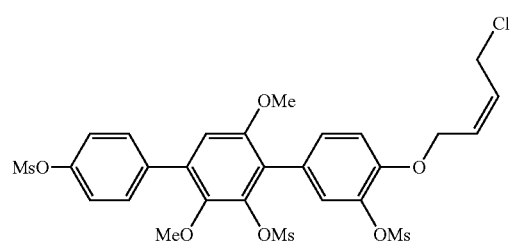
I-1144
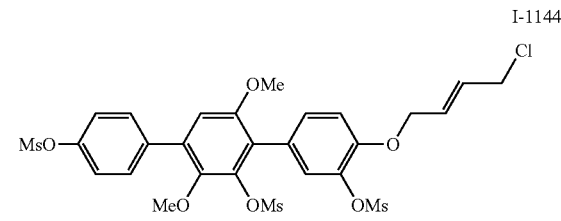
I-1145
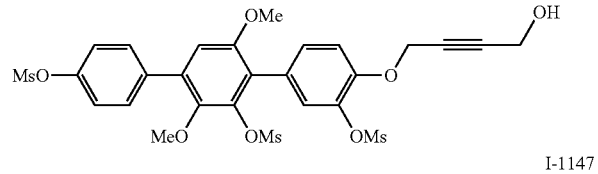
I-1146
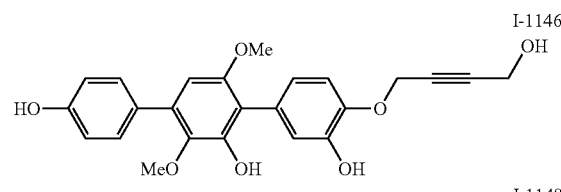
I-1147
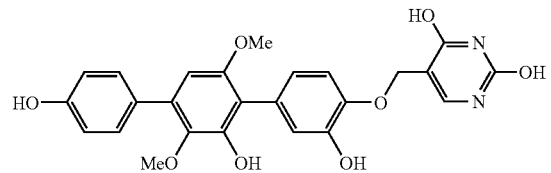
I-1148
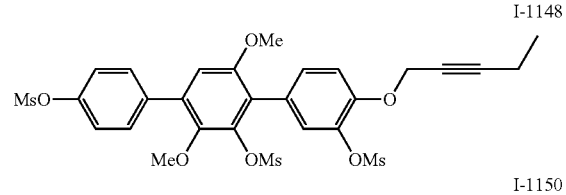
I-1149
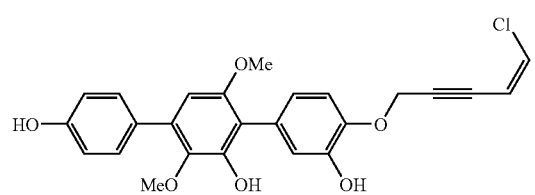
I-1150
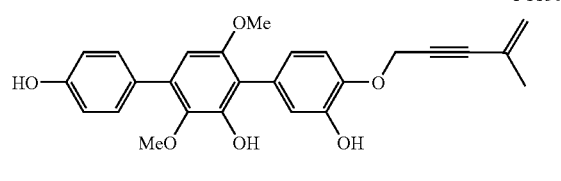
I-1151
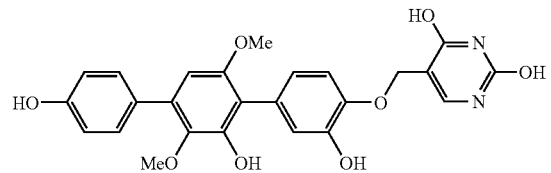
I-1152
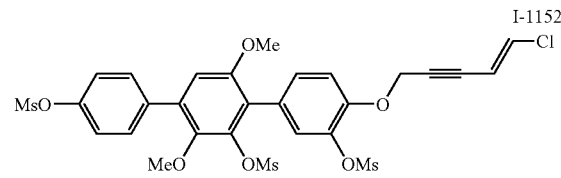

-continued
I-1153
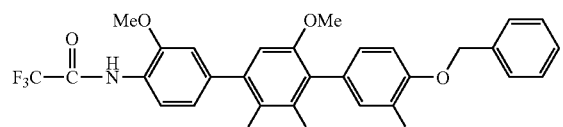
I-1154
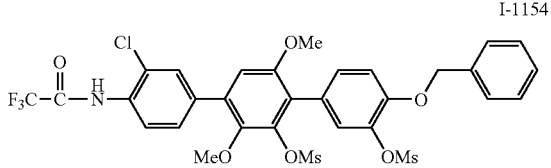
I-1155
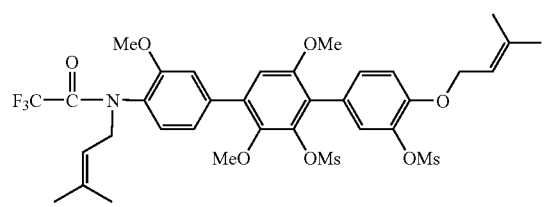
I-1156
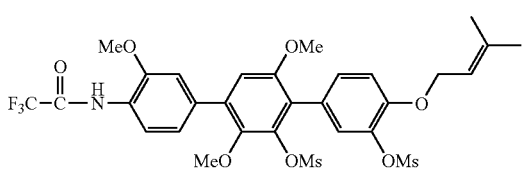
I-1157
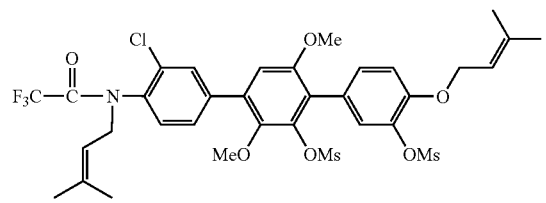
I-1158
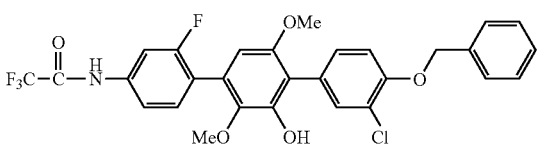
I-1159
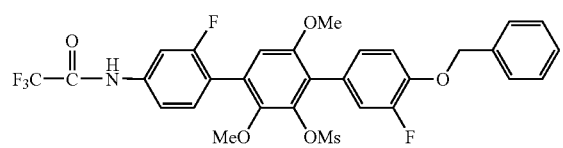
I-1160
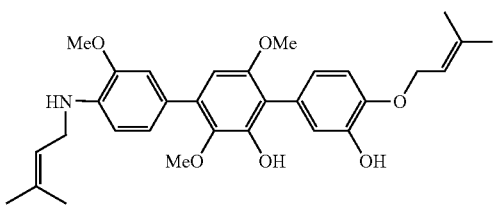
I-1161
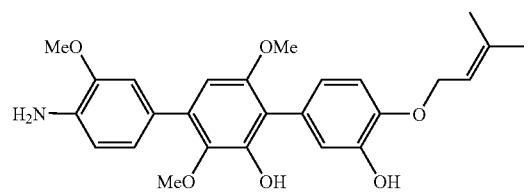
I-1162
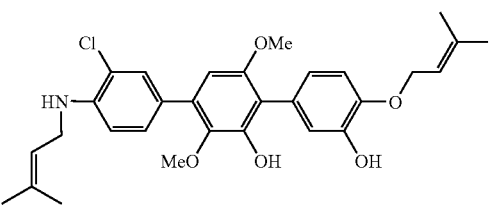
I-1163
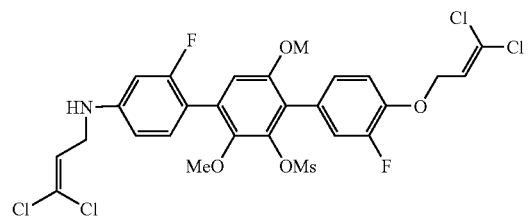
I-1164
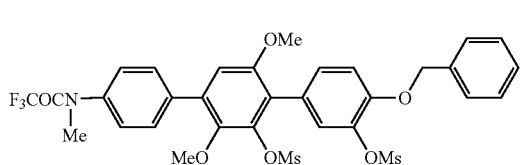
I-1165
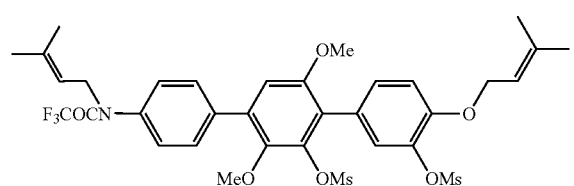
I-1166
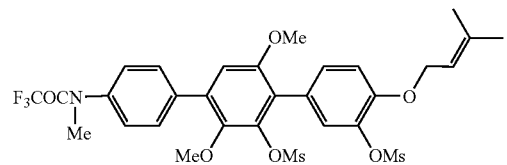

-continued
I-1167
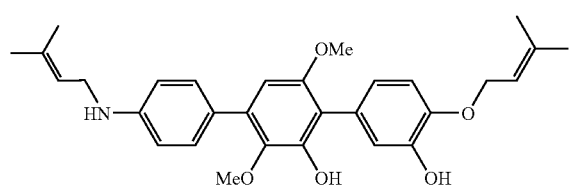
I-1168
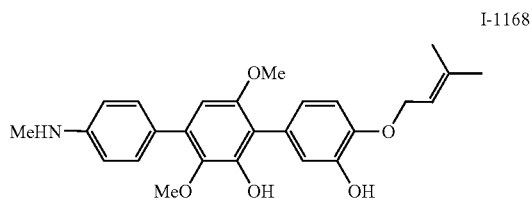
I-1169
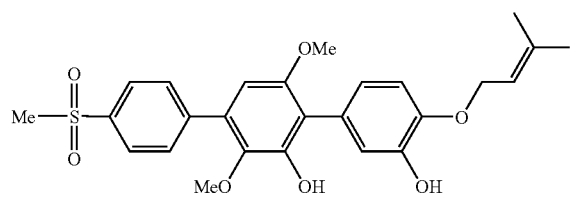
I-1170
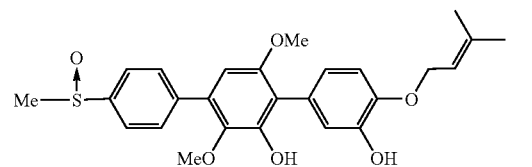
I-1171
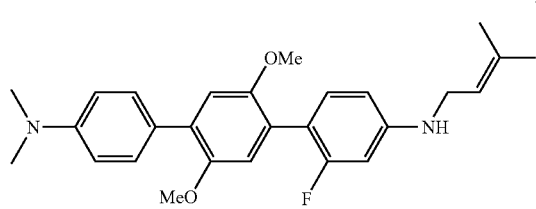
I-1172
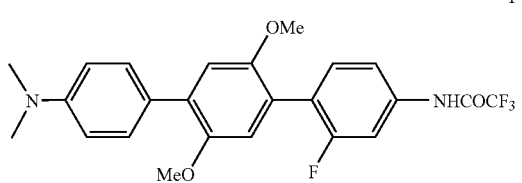
I-1173
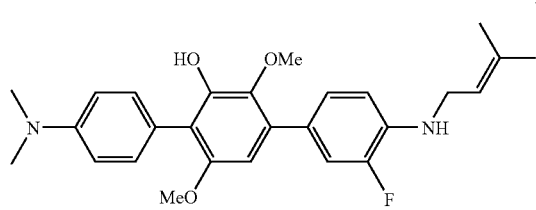
I-1174
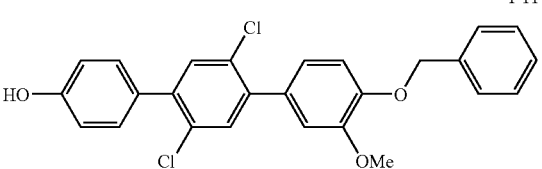
I-1175
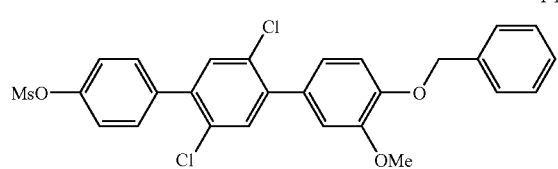
I-1176
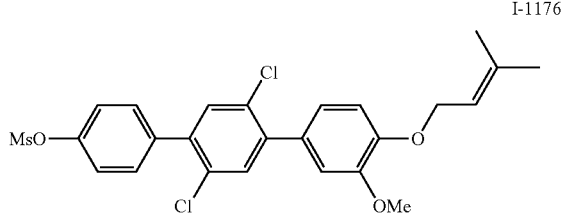
I-1177
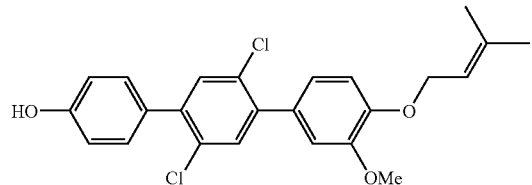
I-1178
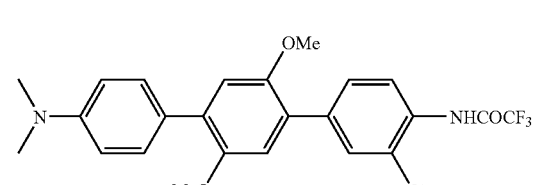
I-1179
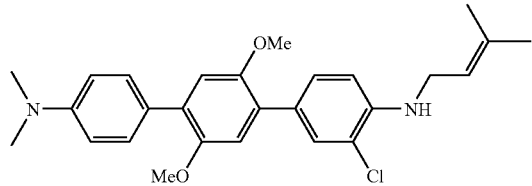
I-1180
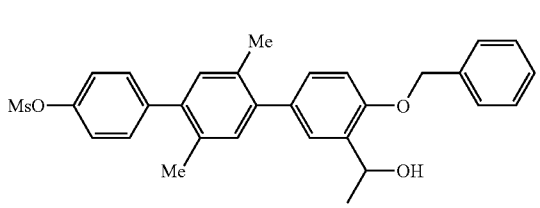

-continued
I-1181
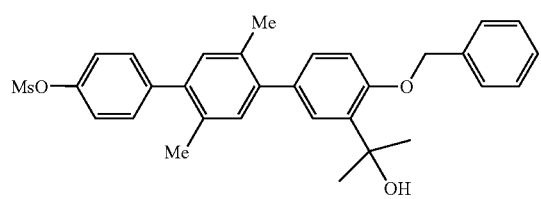
I-1182
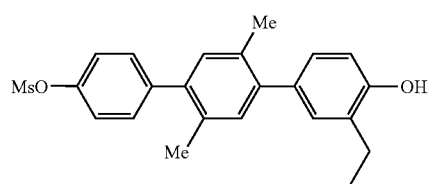
I-1183
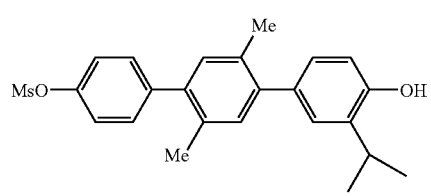
I-1184
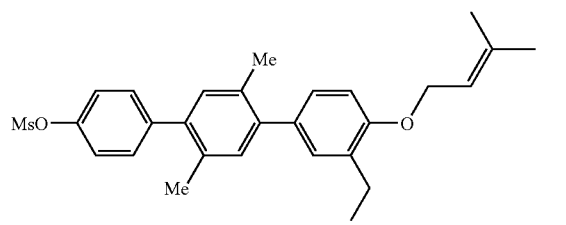
I-1185
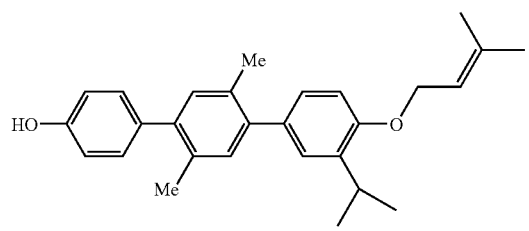
I-1186
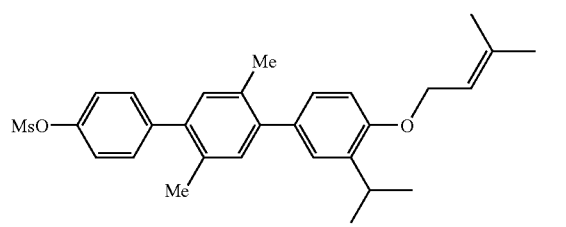
I-1187
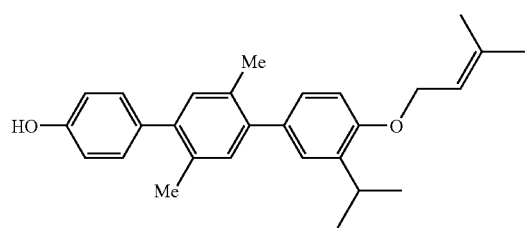
I-1188
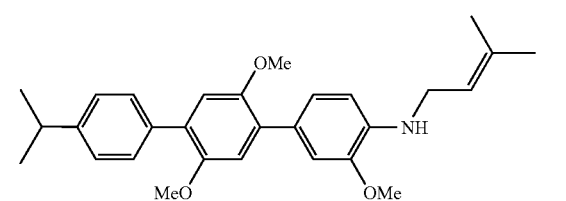
I-1189
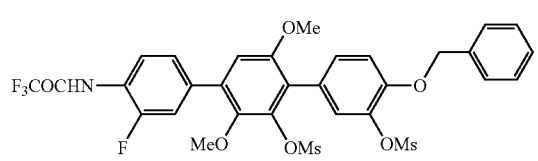
I-1190
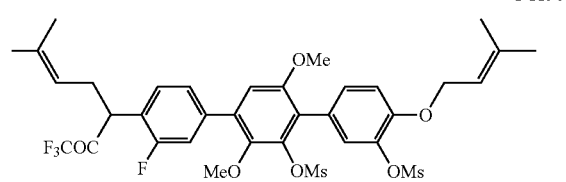
I-1191
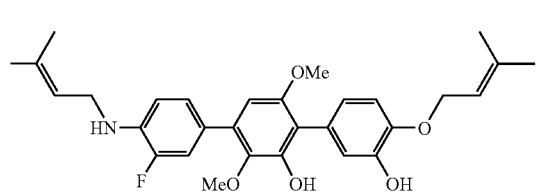
I-1192
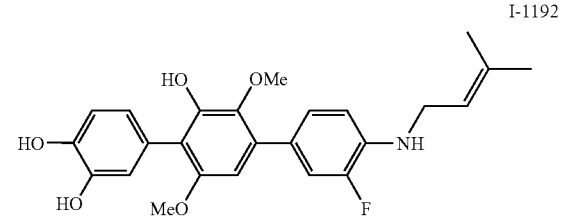
I-1193
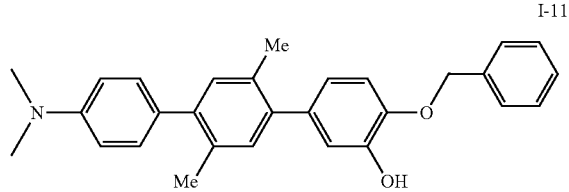
I-1194
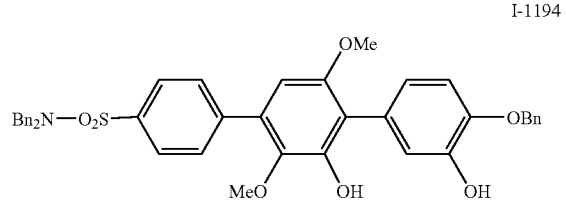

-continued
I-1195
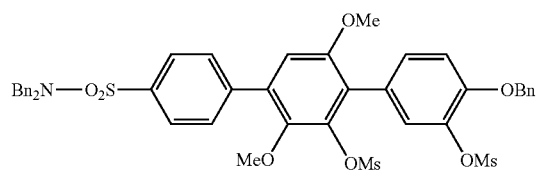
I-1196
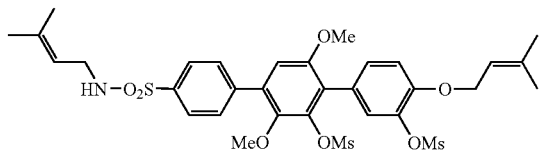
I-1197
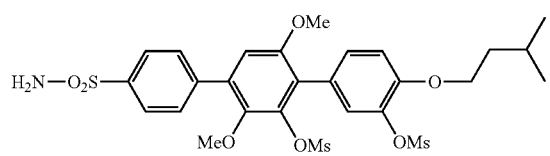
I-1198
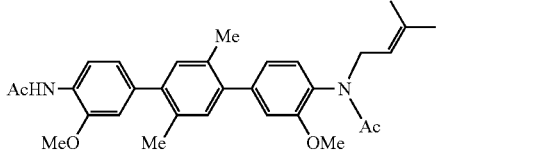
I-1199
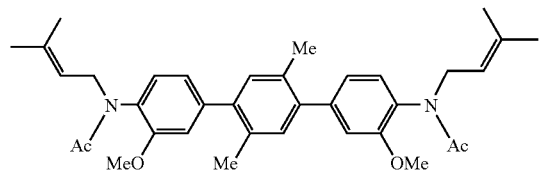
I-1200
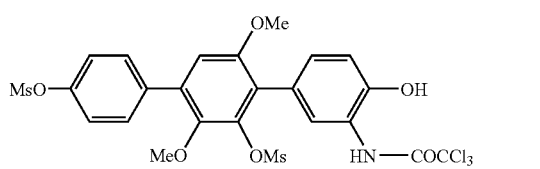
I-1201
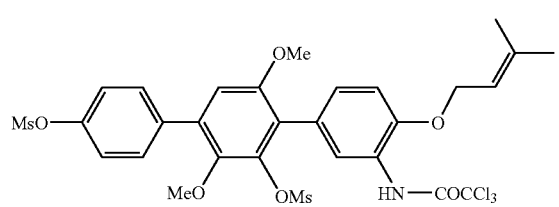
I-1202
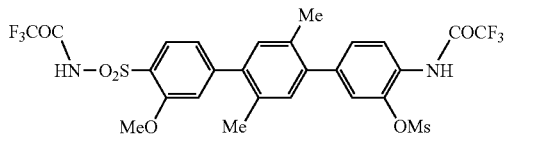
I-1203
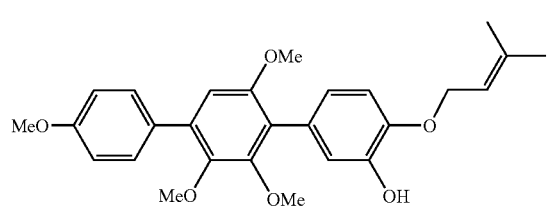
I-1204
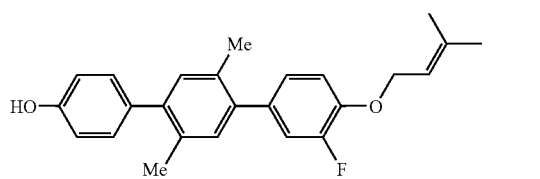
I-1205
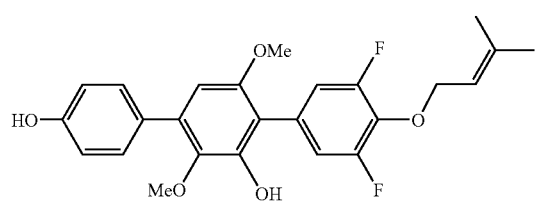
I-1206
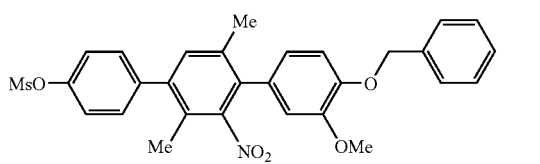
I-1207
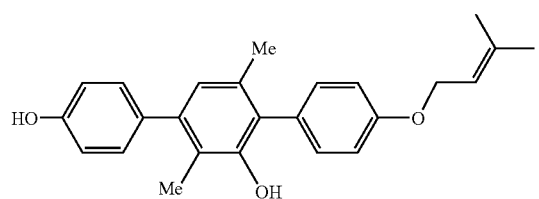
I-1208
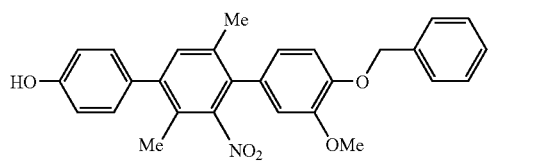

-continued

-continued
I-1225
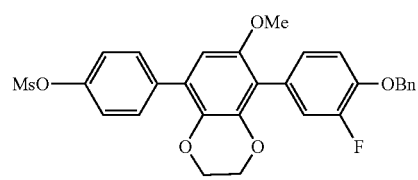
I-1226
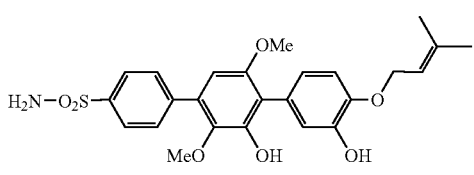
I-1227
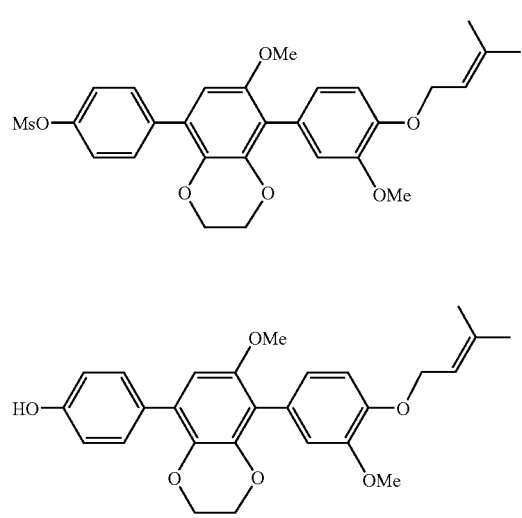
I-1228
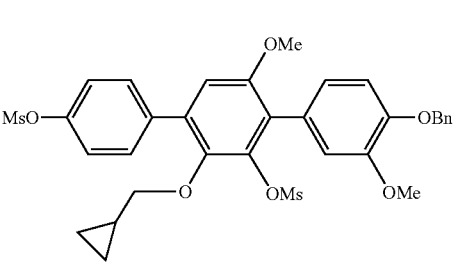
I-1229
I-1230
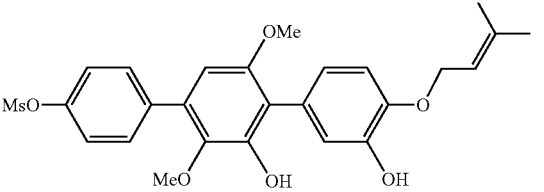
I-1231
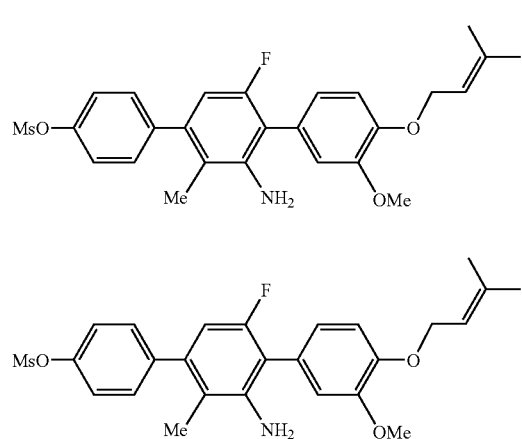
I-1232
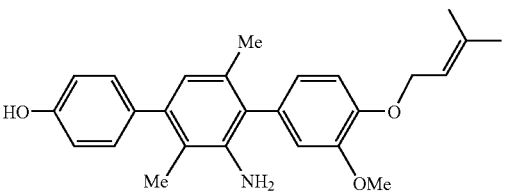
I-1233
I-1234
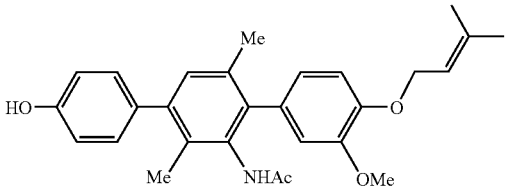
I-1235
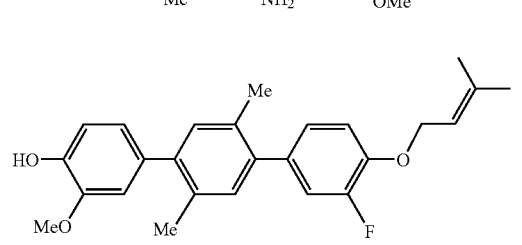
I-1236
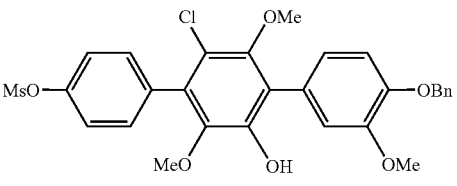
I-1237
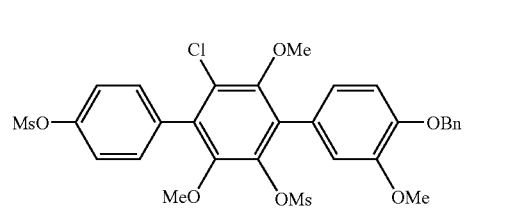
I-1238
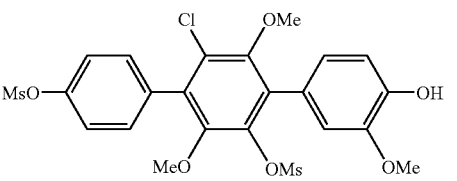

-continued
I-1239
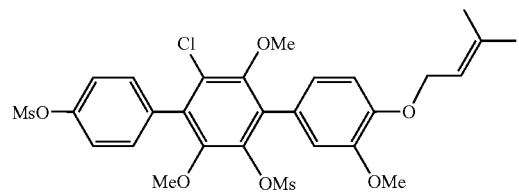
I-1240
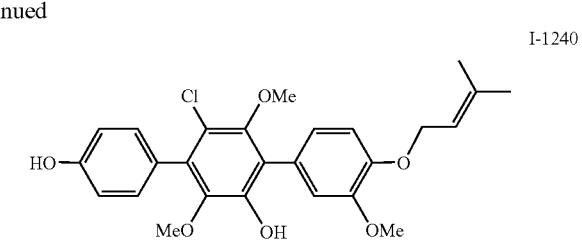
I-1241
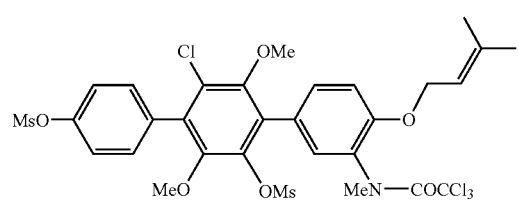
I-1242
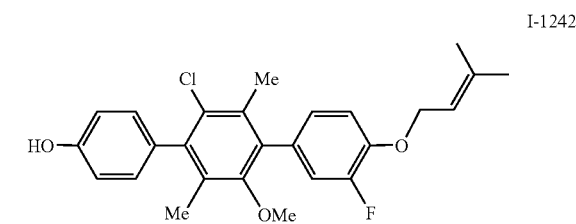
I-1243
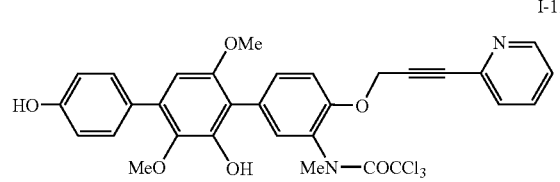
I-1244
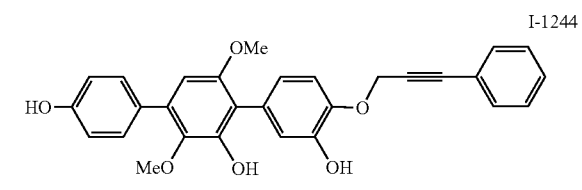
I-1245
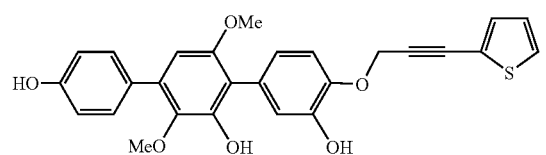
I-1246
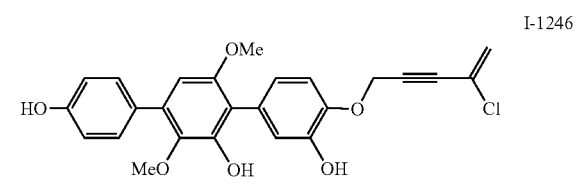
I-1245
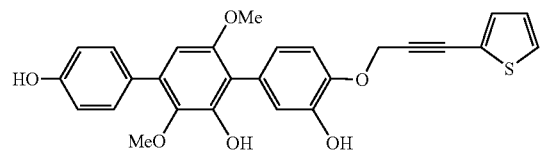
I-1246
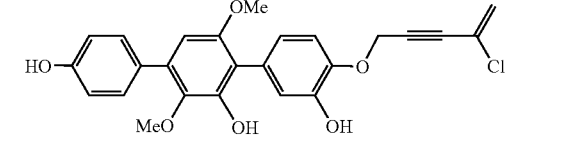
I-1247
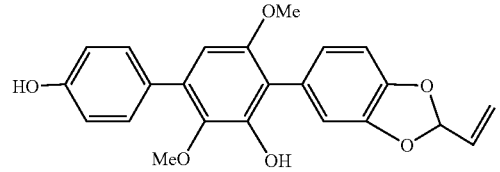
I-1248
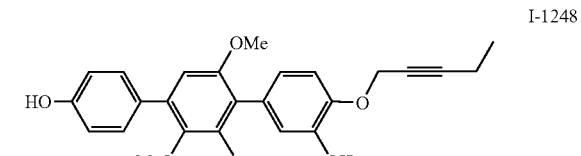
I-1249
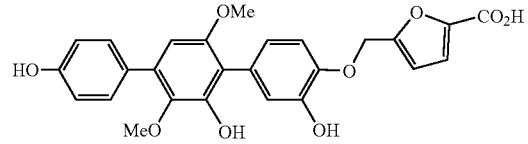
I-1250
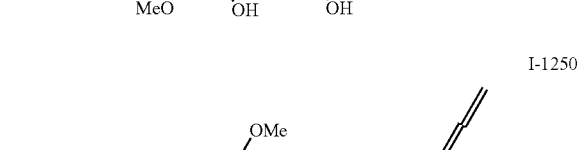
I-1251
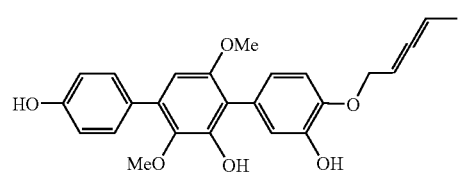
I-1252
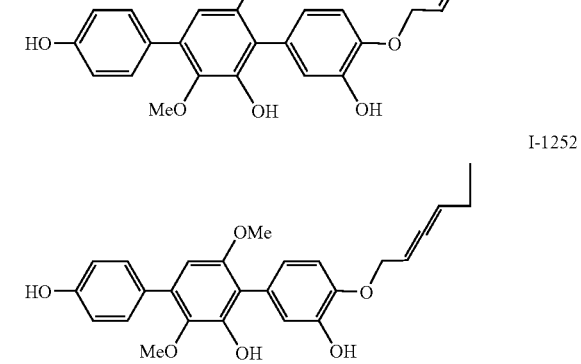

-continued
I-1253
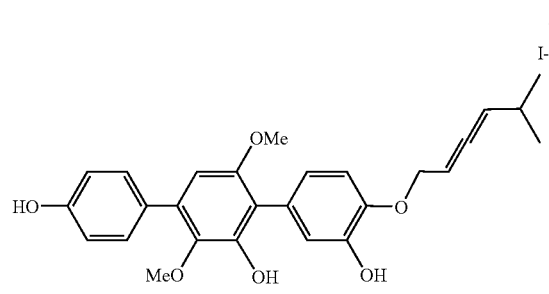
I-1254
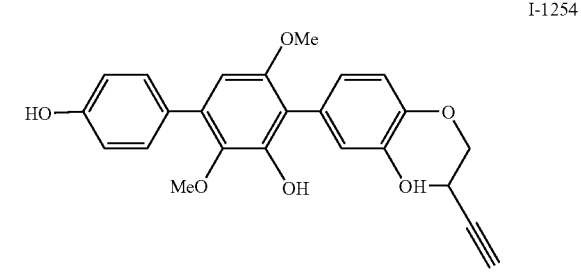
I-1255
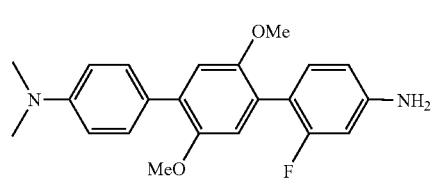
I-1256
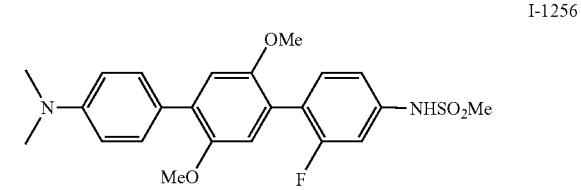
I-1257
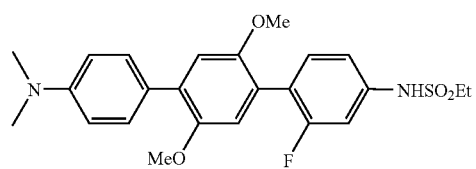
I-1258
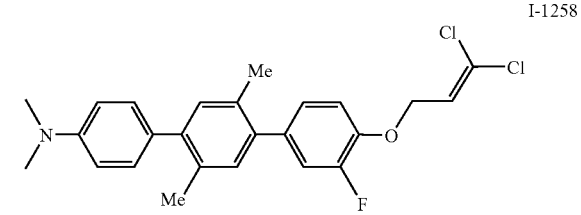
I-1259
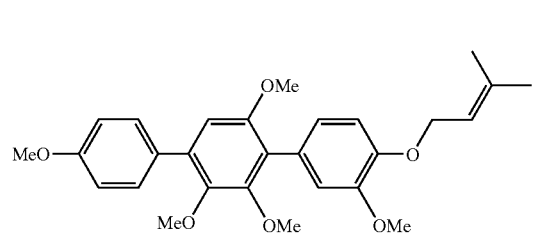
I-1260
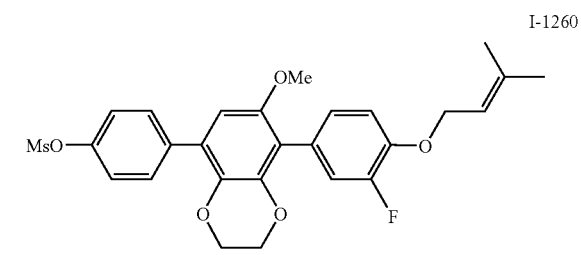
I-1261
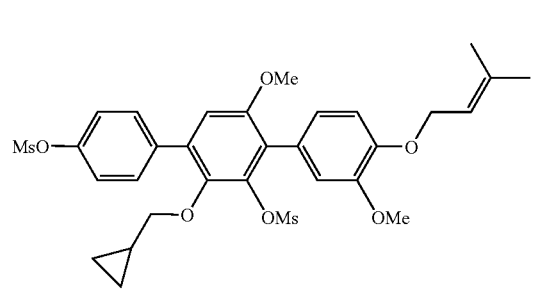
I-1262
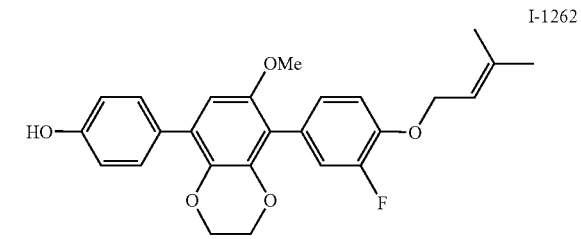
I-1263
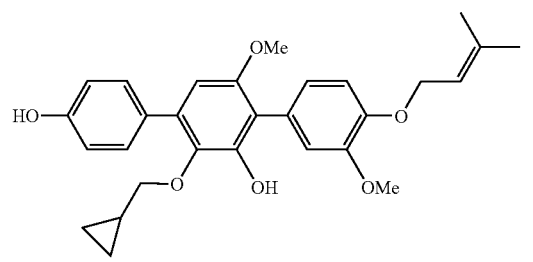
I-1264
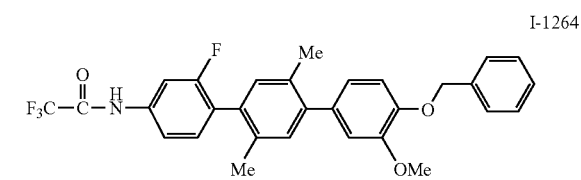

-continued
I-1265
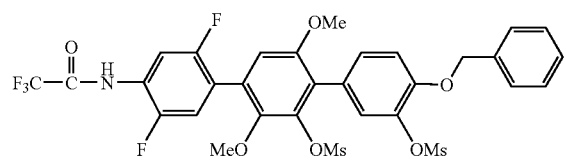
I-1266
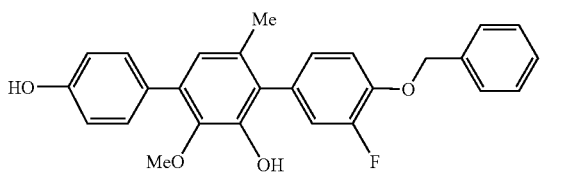
I-1267
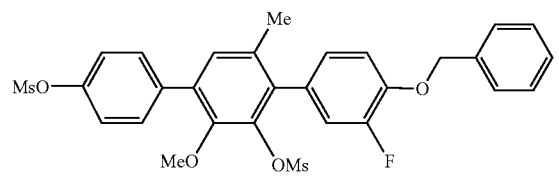
I-1268
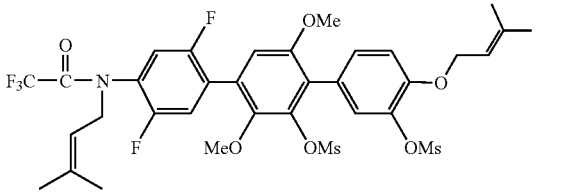
I-1269
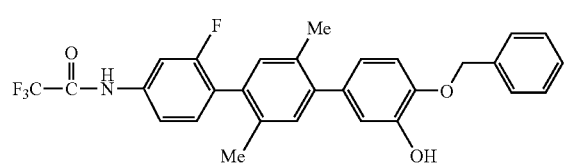
I-1270
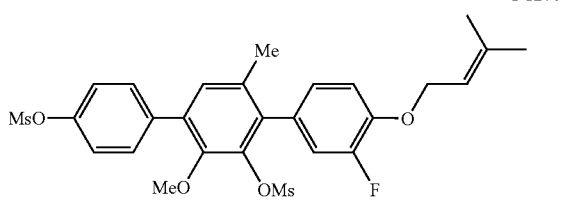
I-1271
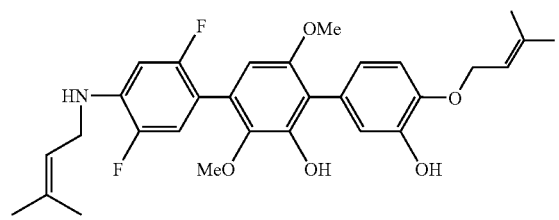
I-1272
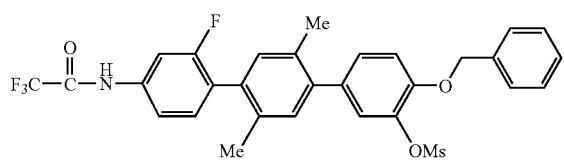
I-1273
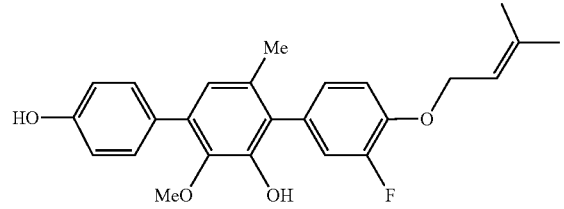
I-1274
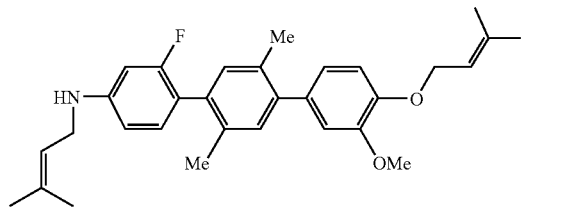
I-1275
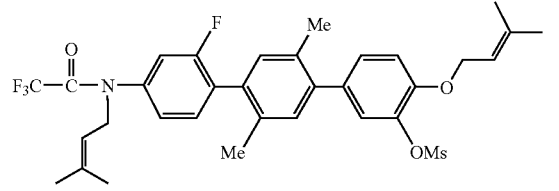
I-1276
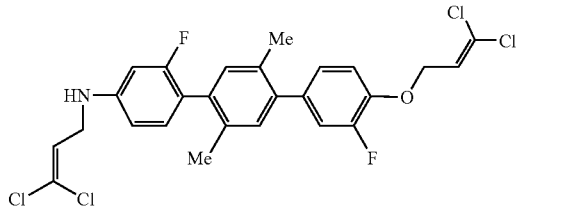
I-1277
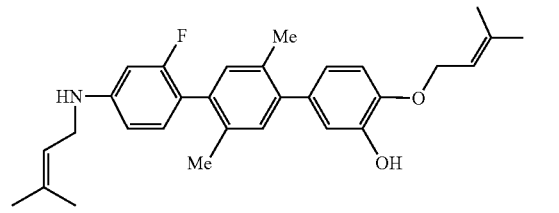
I-1278
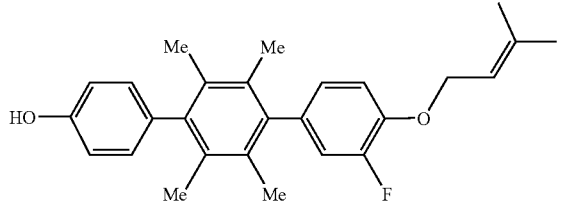

-continued
I-1279
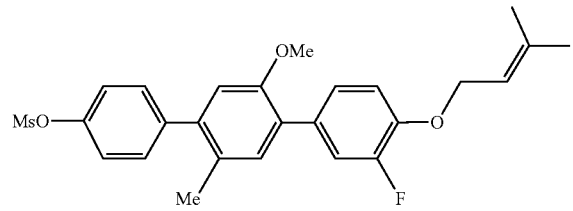
I-1280
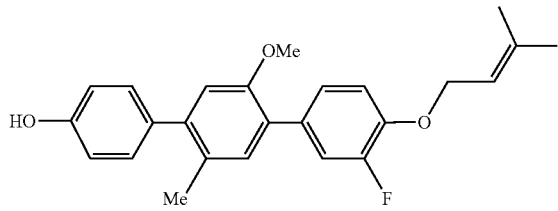
I-1281
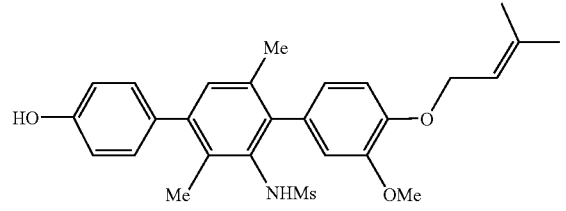
I-1282
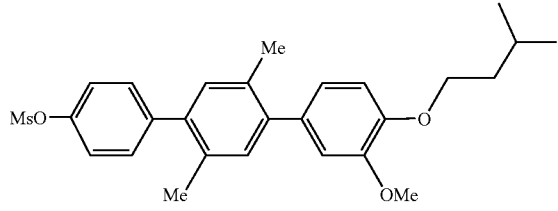
I-1283
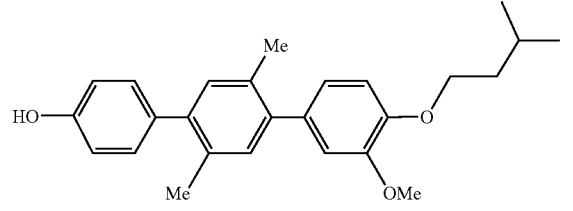
I-1284
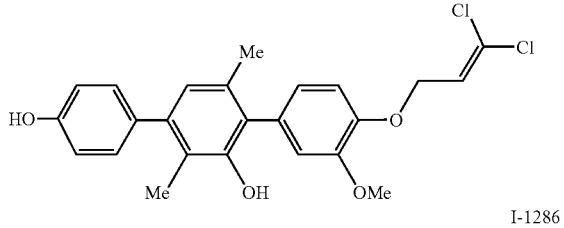
I-1285
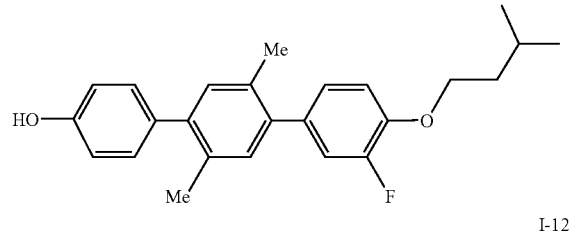
I-1286
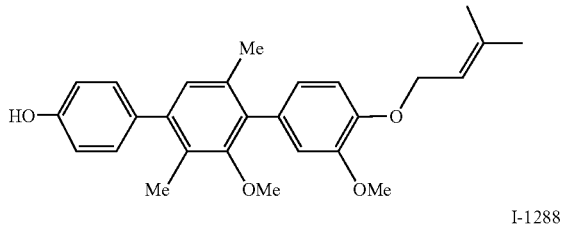
I-1287
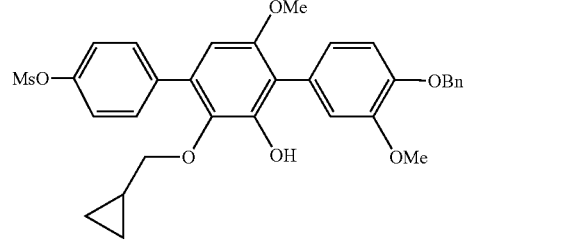
I-1288
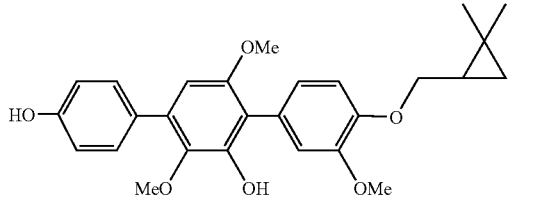
I-1289
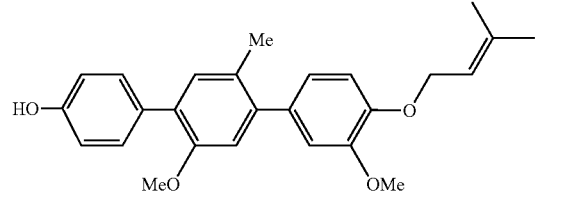
I-1290
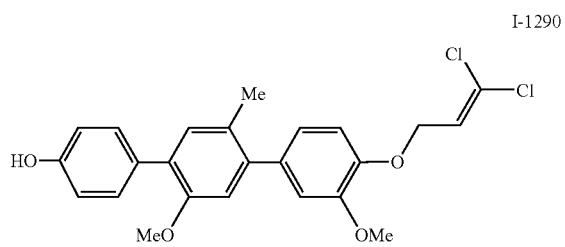
I-1291
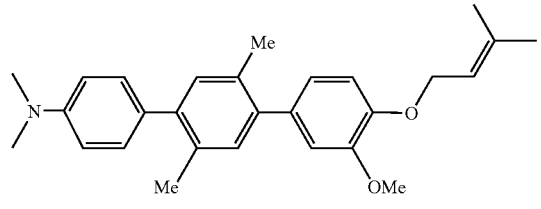
I-1292
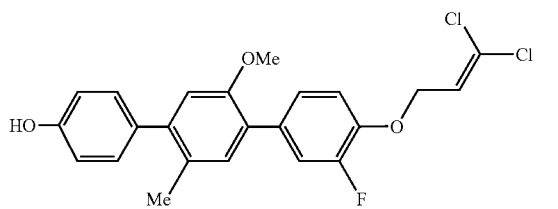

-continued
I-1293
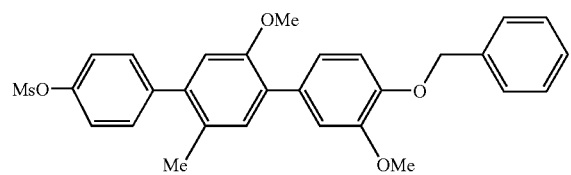
I-1294
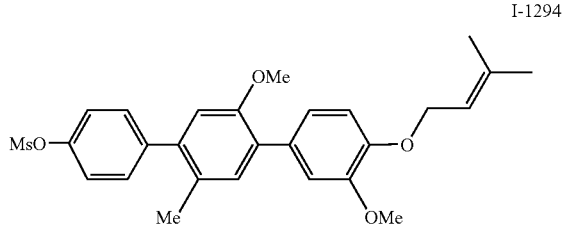
I-1295
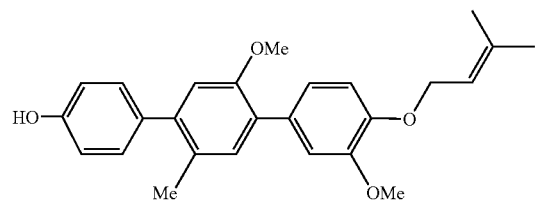
I-1296
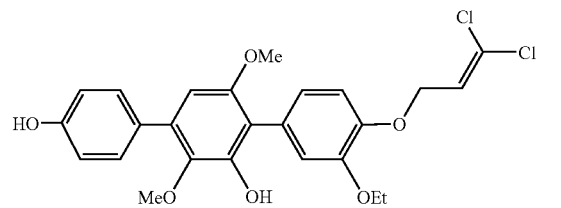
I-1297
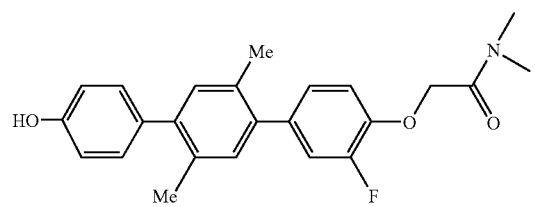
I-1298
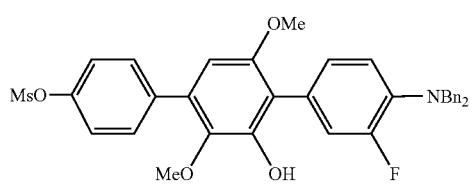
I-1299
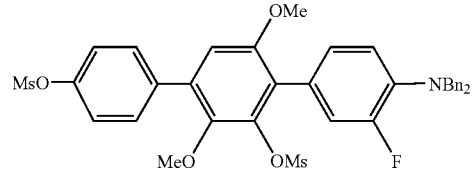
I-1300
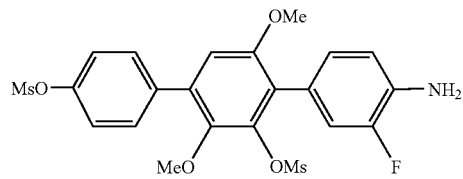
I-1301
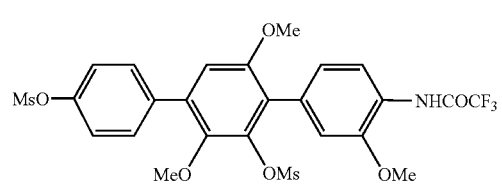
I-1302
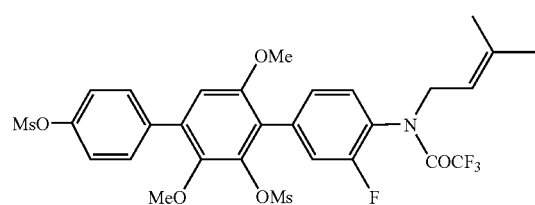
I-1303
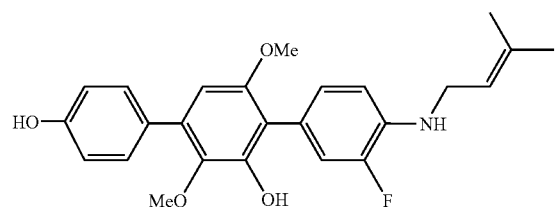
I-1304
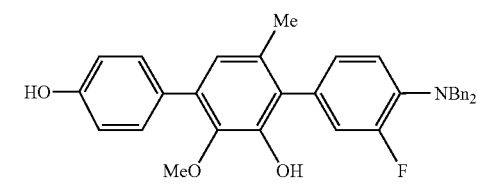
I-1305
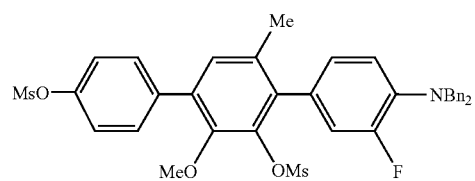
I-1306
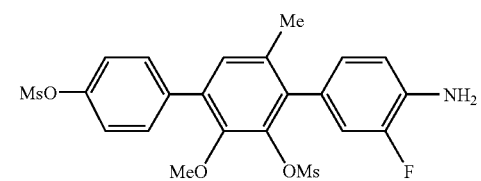

-continued
I-1307
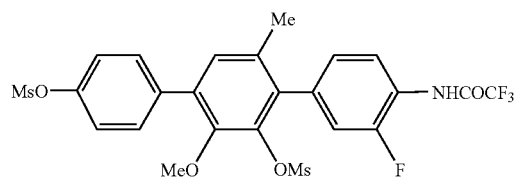
I-1308
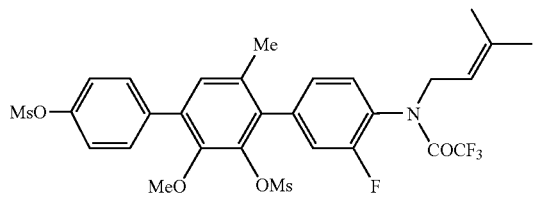
I-1309
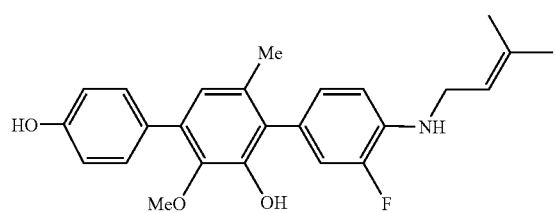
I-1310
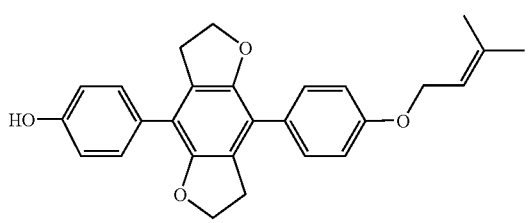
I-1311
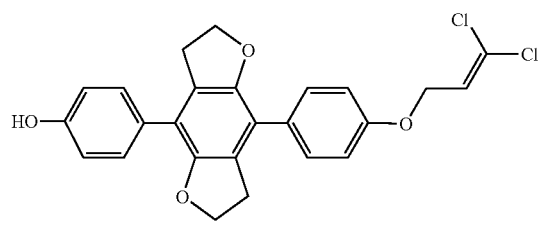
I-1312
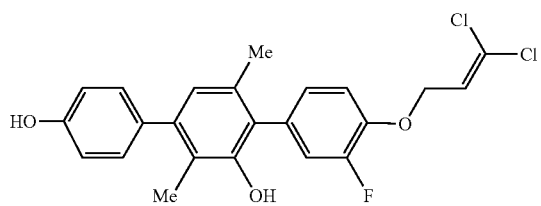
I-1313
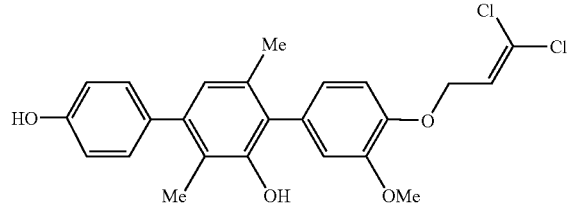
I-1314
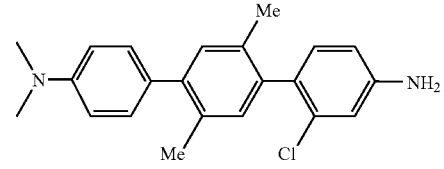
I-1315
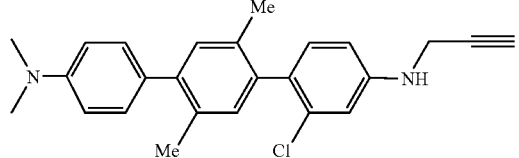
I-1316
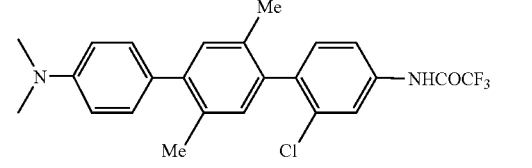
I-1317
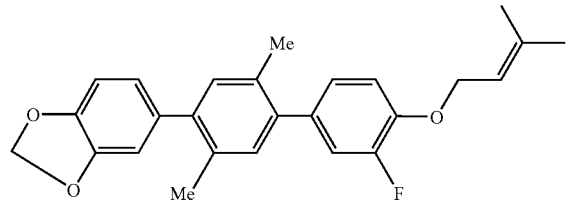
I-1318
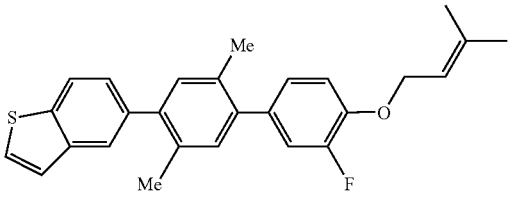
I-1319
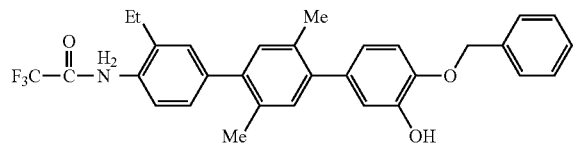
I-1320
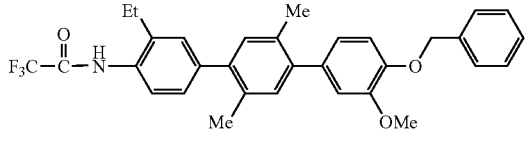

-continued
I-1321
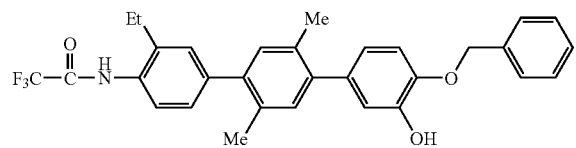
I-1322
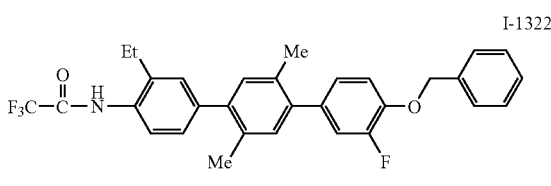
I-1323
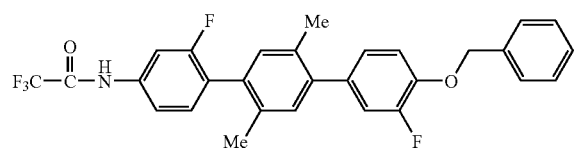
I-1324
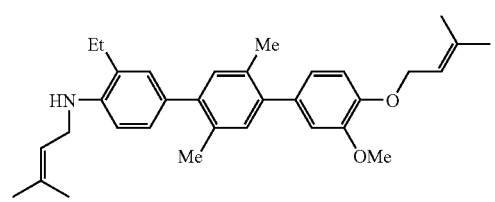
I-1325
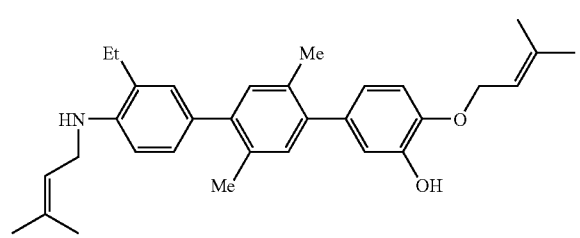
I-1326
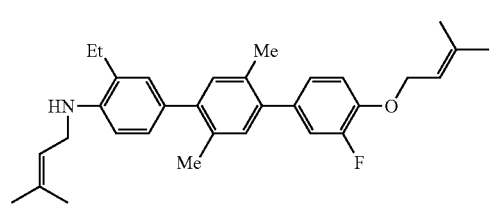
I-1327
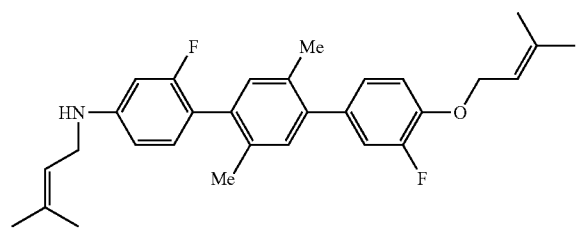
I-1328
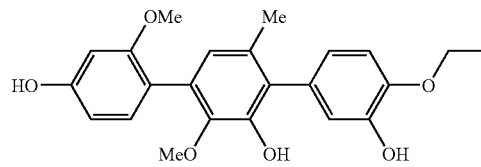
I-1329
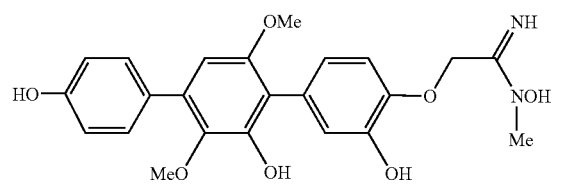
I-1330
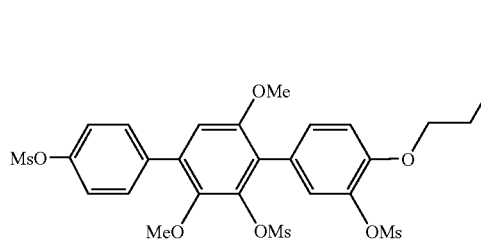
I-1331
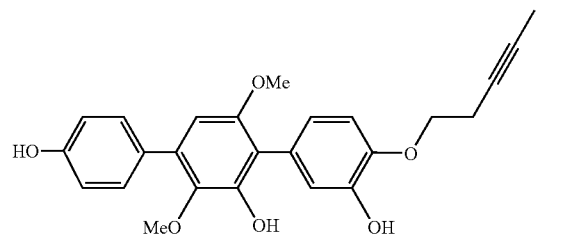
I-1332
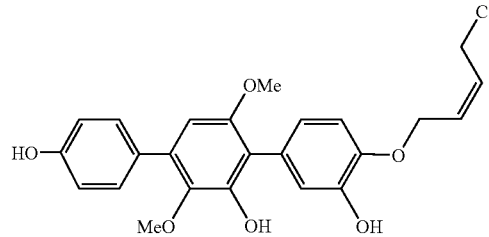

-continued
I-1333
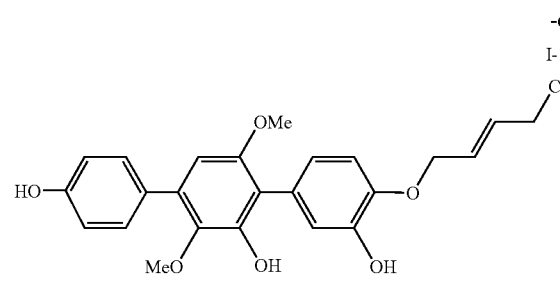
I-1334
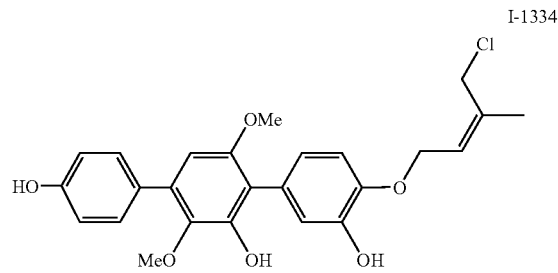
I-1335
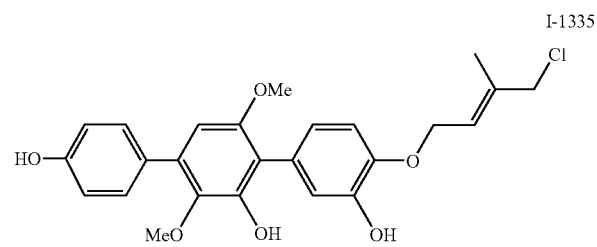
I-1336
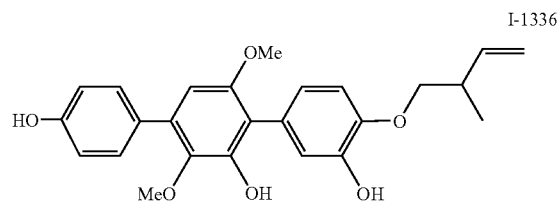
I-1337
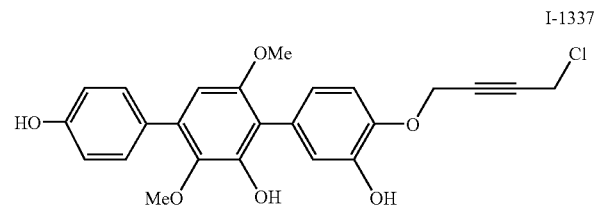
I-1338
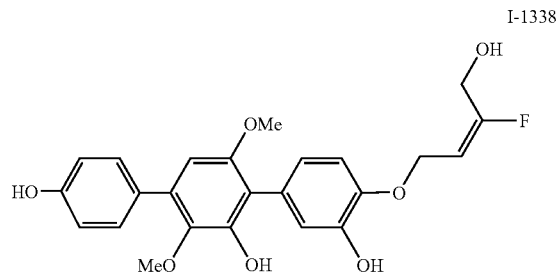
I-1339
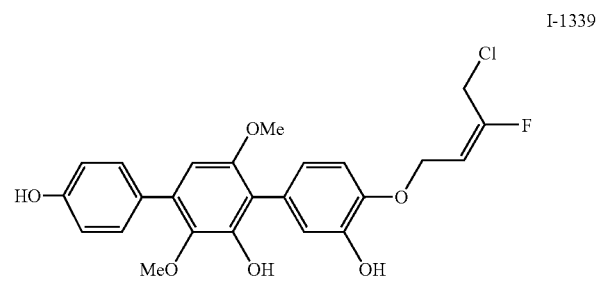
I-1340
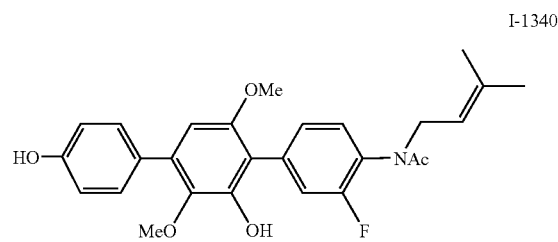
I-1341
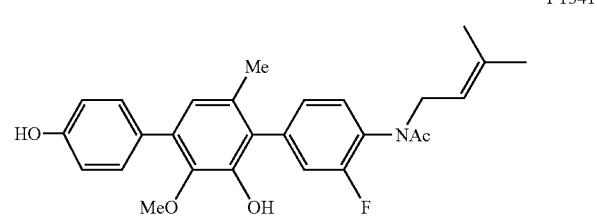
I-1342
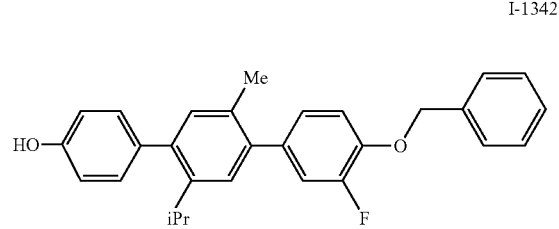
I-1343
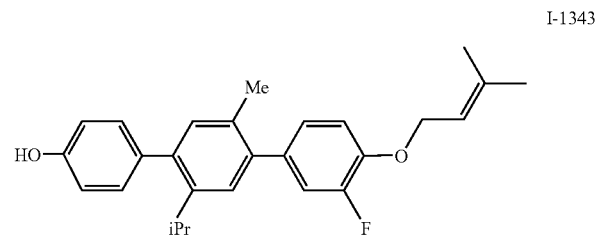
I-1344
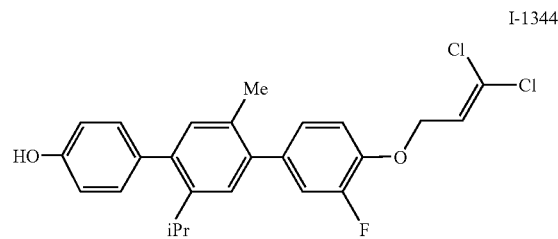

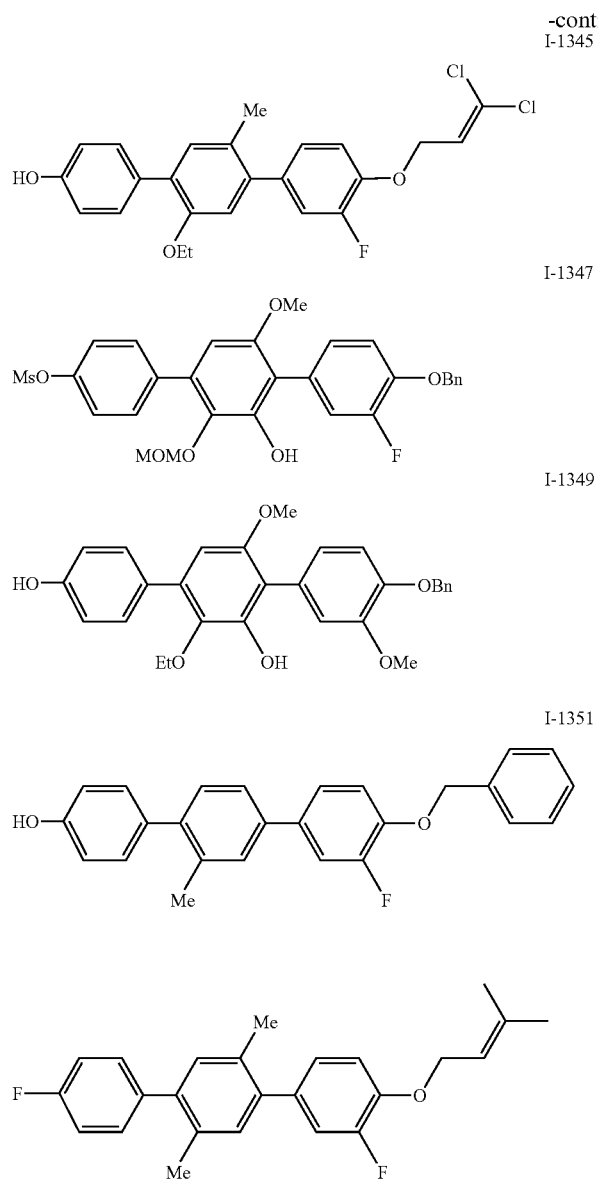
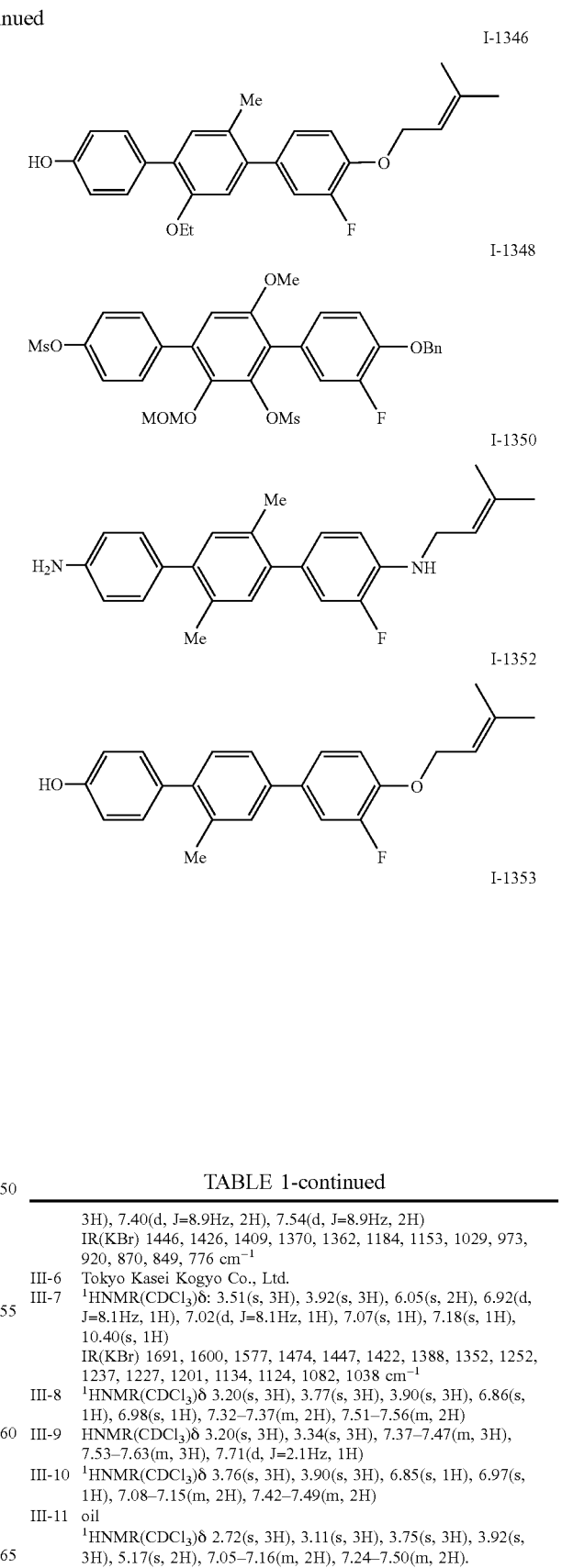

| TABLE 1 | |
|---|---|
| III-1 | m.p. 201–203° C.<br>$^1$HNMR(DMSO-$d_6$)δ 3.44(s, 3H), 3.48(s, 3H), 3.62(s, 3H), 3.92(s, 3H), 7.09(s, 1H), 7.40–7.53(m, 2H), 7.65–7.78(m, 2H) |
| III-2 | $^1$HNMR(CDCl$_3$)δ 3.47(s, 3H), 3.94(s, 3H),<br>7.13–7.24(m, 3H), 7.50–7.59(m, 2H), 10.41(s, 1H)<br>IR(KBr) 1700, 1562, 1479, 1438, 1393, 1226, 1199, 1180, 1161, 1076, 1047 cm$^{-1}$ |
| III-3 | m.p. 181–182° C.<br>$^1$HNMR(CDCl$_3$)δ 3.21(s, 3H), 3.40(s, 3H), 3.49(s, 3H), 3.90(s, 3H), 4.81(s, 2H), 4.85(s, 2H), 6.86(s, 1H), 7.32–7.40(m, 2H), 7.60–7.68(m, 2H)<br>IR(KBr) 1504, 1467, 1370, 1235, 1152, 1038, 1010, 870, 846, 785 cm$^{-1}$ |
| III-4 | $^1$HNMR(CDCl$_3$)δ 2.95(s, 3H), 3.18(s, 3H), 3.21(s, 3H), 3.41(s, 3H), 3.91(s, 3H), 6.84(s, 1H), 7.37(d, J=8.9Hz, 2H), 7.63(d, J=8.9Hz, 2H) |
| III-5 | m.p. 140–141° C.<br>$^1$HNMR(CDCl$_3$)δ 3.21(s, 3H), 3.45(s, 3H), 3.48(s, 3H), 3.96(s, 3H), 7.40(d, J=8.9Hz, 2H), 7.54(d, J=8.9Hz, 2H)<br>IR(KBr) 1446, 1426, 1409, 1370, 1362, 1184, 1153, 1029, 973, 920, 870, 849, 776 cm$^{-1}$ |
| III-6 | Tokyo Kasei Kogyo Co., Ltd. |
| III-7 | $^1$HNMR(CDCl$_3$)δ: 3.51(s, 3H), 3.92(s, 3H), 6.05(s, 2H), 6.92(d, J=8.1Hz, 1H), 7.02(d, J=8.1Hz, 1H), 7.07(s, 1H), 7.18(s, 1H), 10.40(s, 1H)<br>IR(KBr) 1691, 1600, 1577, 1474, 1447, 1422, 1388, 1352, 1252, 1237, 1227, 1201, 1134, 1124, 1082, 1038 cm$^{-1}$ |
| III-8 | $^1$HNMR(CDCl$_3$)δ 3.20(s, 3H), 3.77(s, 3H), 3.90(s, 3H), 6.86(s, 1H), 6.98(s, 1H), 7.32–7.37(m, 2H), 7.51–7.56(m, 2H) |
| III-9 | HNMR(CDCl$_3$)δ 3.20(s, 3H), 3.34(s, 3H), 7.37–7.47(m, 3H), 7.53–7.63(m, 3H), 7.71(d, J=2.1Hz, 1H) |
| III-10 | $^1$HNMR(CDCl$_3$)δ 3.76(s, 3H), 3.90(s, 3H), 6.85(s, 1H), 6.97(s, 1H), 7.08–7.15(m, 2H), 7.42–7.49(m, 2H) |
| III-11 | oil<br>$^1$HNMR(CDCl$_3$)δ 2.72(s, 3H), 3.11(s, 3H), 3.75(s, 3H), 3.92(s, 3H), 5.17(s, 2H), 7.05–7.16(m, 2H), 7.24–7.50(m, 2H). |

TABLE 2

III-12 oil
$^1$HNMR(CDCl$_3$)δ 3.51(s, 3H), 3.70(s, 3H), 3.86(s, 3H), 3.89(s, 3H), 5.28(s, 2H), 6.65(s, 1H), 6.97&7.47(ABq, J=8.6Hz, 4H)

III-13 m.p. 120–122° C.
$^1$HNMR(CDCl$_3$) 3.20(s, 3H), 3.53(s, 3H), 3.70(s, 3H), 3.89(s, 3H), 5.28(s, 2H), 6.63(s, 1H), 7.32–7.37(m, 2H), 7.56–7.61(m, 2H)
IR(KBr) 1505, 1468, 1427, 1375, 1237, 1175, 1153, 1100, 1072, 1003, 972 cm$^{-1}$

III-14 m.p. 146–147° C.
$^1$HNMR(CDCl$_3$) 3.85(s, 3H), 6.94–7.01(m, 2H), 7.38–7.56(m, 6H)
IR(KBr) 1603, 1522, 1481, 1288, 1255, 1036 cm$^{-1}$

III-15 $^1$HNMR(CDCl$_3$) 3.07(s, 6H), 3.49(s, 3H), 3.92(s, 3H), 6.95(brs, 2H), 7.20(s, 1H) 7.15(d, J=8.7Hz, 2H), 10.42(s, 1H)

III-16 $^1$HNMR(CDCl$_3$) 3.48(s, 3H), 3.50(s, 3H), 3.92(s, 3H), 6.81(s, 1H), 7.70(s, 4H)

III-17 $^1$HNMR(CDCl$_3$) 3.24(s, 3H), 3.49(s, 3H), 3.94(s, 3H), 7.21(s, 1H), 7.42(d, J=8.4Hz, 2H), 7.65(d, J=8.4Hz, 2H), 10.41(s, 1H)

III-18 m.p. 88–89° C.
$^1$HNMR(CDCl$_3$) 2.20(s, 3H), 2.38(s, 3H), 3.19(s, 3H), 7.06(s, 1H), 7.33(s, 4H), 7.45(s, 1H)
IR(KBr) 1479, 1366, 1195, 1173, 1151, 970, 865, 850, 796 cm$^{-1}$

III-19 m.p. 72–73° C.
$^1$HNMR(CDCl$_3$) 3.20(s, 3H), 7.20(dd, J=6.6, 8.4Hz, 1H), 7.35–7.44(m, 3H), 7.53–7.60(m, 2H)
IR(KBr) 1514, 1481, 1364, 1335, 1182, 1144, 979, 870, 798 cm$^{-1}$

III-20 m.p. 144–146° C.
$^1$HNMR(CDCl$_3$) 3.45(s, 3H), 3.89(s, 3H), 4.99(brs, 2H), 6.19(s, 1H), 6.42(s, 1H), 6.88–6.94(m, 2H), 7.44–7.49(m, 2H)
IR(KBr) 3471, 3392, 29863, 1612, 1596, 1461, 1410, 1223, 1175, 1099, 1079, 1011 cm$^{-1}$

TABLE 3

III-21 oil
$^1$HNMR(CDCl$_3$) 1.09(t, J=7.5Hz, 3H), 1.82–1.94(m, 2H), 3.58(s, 3H), 3.86(s, 3H), 4.06(t, J=6.6Hz, 2H), 6.63(s, 1H), 6.94–6.99(m, 2H), 7.44–7.49(m, 2H)
IR(film): 3100–2800(br), 1609, 1583, 1513, 1466, 1423, 1401, 1378, 1291, 1249, 1232, 1178, 1127, 1097, 1034, 1012 cm$^{-1}$ III-22 m.p. 83.5–84.5° C.
$^1$HNMR(CDCl$_3$) 3.20(br, 1H), 3.54(s, 3H), 3.85–3.90(m, 2H), 3.86(s, 3H), 3.90(s, 3H), 4.29–4.32(m, 2H), 6.66(s, 1H), 6.95–7.00(m, 2H), 7.45–7.50(m, 2H)
IR(KBr) 3600–2800(br), 1608, 1583, 1513, 1467, 1441, 1421, 1398, 1365, 1290, 1247, 1178, 1133, 1097, 1079, 1028, 1007 cm$^{-1}$ III-23 m.p. 99–101° C.
$^1$HNMR(CDCl$_3$) 3.20(s, 3H), 3.39(s, 3H), 3.91(s, 3H), 3.99(s, 3H), 6.89(s, 1H), 7.37(d, J=8.7Hz, 2H), 7.64(d, J=8.7Hz, 2H)
IR(KBr) 1747, 1466, 1367, 1348, 1153, 1059, 968, 859, 794 cm$^{-1}$ III-24 $^1$HNMR(CDCl$_3$) 3.22(s, 3H), 3.45(s, 3H), 3.94(s, 3H), 7.04(s, 1H), 7.32–7.43(m, 2H), 7.58–7.69(m, 2H), 10.42(s, 1H)

III-25 $^1$HNMR(CDCl$_3$) 2.46(broad, 1H), 3..21(s, 3H), 3.43(s, 3H), 3.90(s, 3H), 4.94(s, 2H), 6.83(s, 1H), 7.42–7.51(m, 2H), 7.57–7.68(m, 2H)

III-26 m.p. 109–110° C.
$^1$HNMR(CDCl$_3$) 1.97(br, 1H), 3.21(t, J=6.6Hz, 2H), 3.86(s, 3H), 3.89(s, 3H), 3.90(t, J=6.9Hz, 2H), 6.76(s, 1H), 6.95–7.00(m, 2H), 7.49–7.53(m, 2H)
IR(KBr) 3600–2800(br), 1609, 1581, 1511, 1462, 1441, 1426, 1385, 1289, 1250, 1237, 1179, 1116, 1078, 1046, 1031, 1005 cm$^{-1}$

III-27 foam
$^1$HNMR(CDCl$_3$) 1.52(s, 9H), 3.20(s, 3H), 3.41(s, 3H), 3.90(s, 3H), 6.16(s, 1H), 6.76(s, 1H), 7.35(d, J=8.7Hz, 2H), 7.61(d, J=8.7Hz, 2H)
IR(KBr) 3371, 1718, 1505, 1497, 1367, 1241, 1151, 872 cm$^{-1}$

TABLE 4

III-28 m.p. 167–170° C.
$^1$HNMR(CDCl$_3$) 2.73(s, 3H), 3.74(s, 3H), 3.92(s, 3H), 7.08–7.17 (m, 3H), 7.31–7.36(m, 2H)
IR(CHCl$_3$)2934, 1593, 1560, 1512, 1477, 1436, 1411, 1372, 1157, 1107, 1076, 997, 958, 892, 839, 815 cm$^{-1}$

III-29 m.p. 140–142° C.
$^1$HNMR(CDCl$_3$) 3.27(s, 3H), 3.79(s, 3H), 3.90(s, 3H), 6.86(s, 1H), 6.97(s, 1H), 7.29(ddd, J=8.4, 2.2, 0.9Hz, 1H), 7.39(dd, J=11.0, 2.2Hz, 1H), 7.43(t, J=8.4Hz, 1H)
IR(KBr) 1504, 1421, 1344, 1225, 1208, 916, 824 cm$^{-1}$ III-30 $^1$HNMR(CDCl$_3$) 3.77(s, 3H), 3.91(s, 3H), 3.95(s, 3H), 6.87(s, 1H), 7.01(s, 1H), 7.56(d, J=8.1Hz, 2H), 8.09(d, J=8.1Hz, 2H)

III-31 $^1$HNMR(CDCl$_3$) 3.78(s, 3H),3.91(s, 3H), 6.88(s, 1H), 6.97(s, 1H), 7.60(d, J=8.1Hz, 2H), 7.71(d, J=8.1Hz, 2H)

III-32 m.p. 147–148° C.
$^1$HNMR(CDCl$_3$) 3.79(s, 3H), 3.92(s, 3H), 6.89(s, 1H), 7.01(s, 1H), 7.64–7.69(m, 2H), 8.26–8.31(m, 2H)
IR(KBr) 3600–2800(br), 1595, 1511, 1490, 1422, 1354, 1249, 1215, 1145, 1106, 1032 cm$^{-1}$

III-33 $^1$HNMR(CDCl$_3$) 3.31(s, 3H), 3.53(s, 3H), 3.94(s, 3H), 7.19(s, 1H), 7.39(ddd, J=8.3, 2.3, 1.0Hz, 1H), 7.39(dd,J=10.3, 2.3Hz, 1H), 7.43(t, J=8.3Hz, 1H), 10.40(s, 1H)

III-34 $^1$HNMR(CDCl$_3$)δ0.13(s, 6H), 0.97(s, 9H), 2.51(s, 3H), 3.73(s, 3H), 3.93(s, 3H), 5.09(s, 2H), 6.84–6.99(m, 2H), 6.89(s, 1H), 7.05 (s, 1H), 7.29–7.48(m, 5H)

III-35 m.p. 124–128° C.
$^1$HNMR(CDCl$_3$) 2.62(s, 3H), 3.74(s, 3H), 3.91(s, 3H), 5.19(s, 2H), 7.00–7.18(m, 4H), 7.30–7.49(m, 5H)
IR(CHCl$_3$)2930, 1607, 1517, 1480, 1369, 1148, 1118, 1082, 1025, 969, 872 cm$^{-1}$

TABLE 5

III-36 oil
$^1$HNMR(CDCl$_3$)δ 0.13(s, 6H), 0.96(s, 3H), 3.01(s, 3H), 3.69(s, 3H), 3.86(s, 3H), 4.81(s, 2H), 5.08(s,2H),6.88–6.94(m, 3H), 7.30–7.47(m, 5H)
IR(KBr) 3023, 2932, 2858, 1579, 1512, 1471, 1381, 1264, 1120, 1083 cm$^{-1}$ III-37 oil
$^1$HNMR(CDC$_3$)δ0.78(t, J=7.5Hz, 3H), 1.03–1.25(m, 2H), 1.38–1.47(m, 2H), 3.68–3.72(m, 2H), 3.70(s, 3H), 3.86(s, 6H), 5.15(s, 2H), 5.63(s, 1H), 6.81 (dd, J=1.8, 8.4Hz, 1H), 6.86(s, 1H), 6.95–6.97(m, 2H), 7.36–7.46(m, 5H)
IR(CH$_3$Cl): 3543, 3200–2800(br), 1587, 1511, 1465, 1412, 1376, 1285, 1248, 1118, 1081, 1031 cm$^{-1}$ III-38 m.p. 104–105° C.
$^1$HNMR(CDCl$_3$) 3.11(s, 3H), 3.77(s, 3H), 3.90(s, 3H), 5.17(s, 2H), 6.84(s, 1H), 6.98(s, 1H), 7.11(d, J=8.7Hz, 1H), 7.37–7.48(m, 6H), 7.51(d, J=2.4Hz, 1H)
IR(KBr) 3600–2800(br), 1503, 1420, 1389, 1364, 1246, 1215, 1185, 1132, 1117, 1097, 1030 cm$^{-1}$ III-39 m.p. 134–136° C.
$^1$HNMR(CDCl$_3$) 3.78(s, 3H), 3.91(s, 3H), 5.29(s, 2H), 6.86(s, 1H), 6.97(s, 1H), 7.17(d, J=8.7Hz, 1H), 7.31–7.51(m,7H), 7.63 (dd, J=2.4, 8.7Hz, 1H), 8.01(d, J=2.4Hz, 1H)
IR(KBr) 3434, 1620, 1532, 1494, 1413, 1280, 1222, 1206, 1133, 1108, 1037 cm$^{-}$ III-40 m.p. 100–101° C.
$^1$HNMR(CDCl$_3$) 3.55(s, 3H), 3.77(s, 3H), 3.90(s, 3H), 5.26(s, 2H), 6.84(s, 1H), 6.97(s, 1H), 7.16–7.31(m, 3H)
IR(KBr) 3600–2800(br), 1524, 1503, 1449, 1401, 1380, 1268, 1246, 1222, 1200, 1156, 1126, 1098, 1078, 1030 cm$^{-1}$ III-41 m.p. 109–110° C.
$^1$HNMR(CDCl$_3$) 1.54(s, 9H), 3.76(s, 3H), 3.90(s, 3H), 6.75(br, 1H), 6.84(s, 1H), 6.97(s, 1H), 7.21–7.29(m, 2H), 8.13(t, J=8.7Hz, 1H)
IR(KBr) 3600–2800(br), 1720, 1593, 1531, 1509, 1427, 1393, 1245, 1223, 1214, 1201, 1162, 1137, 1105, 1029 cm$^{-1}$

TABLE 6

- III-42 foam
  $^1$HNMR(CDCl$_3$)δ 2.36(s, 3H), 3.74(s, 3H), 3.88(s, 3H), 6.69(dd, J=0.6, 3.6Hz, 1H), 6.85(s, 1H), 6.99(s, 1H), 7.24–7.27(m, 2H), 7.23(dd, J=1.8, 8.7Hz, 1H), 7.60(d, J=3.6Hz, 1H), 7.64(d, J=1.2Hz, 1H), 7.80–7.83(m, 2H), 8.02(d, J=8.4Hz, 1H)
  IR(KBr) 3600–2800(br), 1508, 1463, 1444, 1421, 1373, 1246, 1216, 1176, 1132, 1093, 1038 cm$^{-1}$
- III-43 foam
  $^1$HNMR(CDCl$_3$)δ 3.14(s, 3H), 3.51(s, 3H), 3.93(s, 3H), 520(s, 2H), 7.17(d, J=8.4Hz, 1H), 7.20(s, 1H), 7.38(m, 6H), 7.59(d, J=1.8Hz, 1H), 10.40(s, 1H)
  IR(CHCl$_3$)2941, 1703, 1613, 1603, 1580, 1513, 1475, 1426, 1372, 1295, 1264, 1169, 1137, 1112, 1088, 1044, 971, 954, 932, 838 cm$^{-1}$
- III-44 $^1$HNMR(CDCl$_3$)δ 0.20(s, 6H), 0.13(s, 6H), 0.77(s, 9H), 0.97(s, 9H), 3.73(s, 3H), 3.83(s, 3H)), 5.08(s, 2H), 6.06(s, 2H), 6.88–696(m, 3H), 7.01(s, 1H), 7.30–7.49(m, 5H)
- III-45 mp106–108° C.
  $^1$HNMR(CDCl$_3$)δ 3.21(s, 3H), 3.43(s, 3H), 3.94(s, 3H), 5.87(s, 1H), 7.39(d, J=9.0Hz, 2H), 7.55(d, J=9.0Hz, 2H)
  IR(KBr) 3410, 1460, 1422, 1362, 1146, 1037, 874, 915, 787 cm$^{-1}$
- III-46 mp123–124° C.
  $^1$HNMR(CDCl$_3$)δ 2.48(brs, 1H), 3.21(s, 3H), 3.43(s, 3H), 3.94(s, 3H), 4.93(brs, 2H), 6.83(s, 1H), 7.37(d, J=9.0Hz, 2H), 7.63(d, J=9.0Hz, 2H)
  IR(KBr) 3524, 1463, 1352, 1233, 1152, 1009, 979, 869 cm$^{-1}$
- III-47 mp107–109° C.
  $^1$HNMR(CDCl$_3$)δ 1.93(s, 6H), 2.45(s, 6H), 4.75(brs, 1H), 6.87–6.96(m, 4H)
  IR(KBr) 3367, 1612, 1509, 1433, 1214, 990, 824 cm$^{-1}$

TABLE 7

- III-48 oil
  $^1$HNMR(CDCl$_3$)δ 1.14(t, J=6.9Hz, 3H), 1.46(t, J=6.9Hz, 3H), 3.58(q, J=6.9Hz, 2H), 3.58(q, J=6.9Hz, 2H), 6.19(s, 1H), 6.41(s, 1H), 6.86–6.92(m, 2H), 7.43–7.49(m, 2H)
  IR(CHCl$_3$)3688, 3594, 3502, 2982, 1612, 1517, 1172, 1080, 1026, 925 cm$^{-1}$
- III-49 $^1$HNMR(CDCl$_3$)δ 0.02(s, 6H), 0.12(s, 6H), 0.90(s, 9H), 0.93(s, 9H), 4.54(s, 2H), 4.76(s, 2H), 6.84–6.89(m, 2H), 7.16–7.22(m, 2H), 7.37(s, 1H), 7.69(s, 1H)
- III-50 mp173–175° C.
  $^1$HNMR(CDCl$_3$)δ 3.21(s, 3H), 3.47(s, 3H), 3.89(s, 3H), 6.15(s, 1H), 6.42(s, 1H), 7.24–7.37(m, 2H), 7.61–7.66(m, 2H)
  IR(KBr) 3408, 2934, 1604, 1480, 1360, 1146, 1089, 1004, 865, 709, 547 cm$^{-1}$
- III-51 mp156–158° C.
  $^1$HNMR(CDCl$_3$)δ 3.21(s, 3H), 3.39(s, 3H), 3.90(s, 3H), 6.05(s, 1H), 7.36–7.44(m, 4H)
  IR(KBr) 3410, 2938, 1505, 1457, 1413, 1337, 1197, 1143, 1084, 1014, 876, 826, 542, 519 cm$^{-1}$
- III-52 mp181–183° C.
  $^1$HNMR(CDCl$_3$)δ 3.19(s, 3H), 3.88(s, 3H), 4.21–4.24(m, 2H), 4.39–4.42(m, 2H), 6.49(s, 1H), 7.45(ABq, J=8.7Hz, 4H)
  IR(KBr) 3435, 1598, 1505, 1474, 1425, 1366, 1178, 1147, 1113 cm$^{-1}$
- III-53 mp155–157° C.
  $^1$HNMR(CDCl$_3$)δ −0.11–0.02(m, 2H), 0.33–0.44(m, 2H), 0.91(m, 1H), 3.20(s, 3H), 3.41(d, J=7.0Hz, 2H), 3.50(s, 3H), 3.92(s, 3H), 6.88(s, 1H), 7.51(ABq, J=8.6Hz, 4H)
  IR(KBr) 3434, 1505, 1472, 1416, 1386, 1371, 1357, 1242, 1179, 1149, 1084 cm$^{-1}$
- III-54 mp105–107° C.
  $^1$HNMR(CDCl$_3$)δ 3.20(s, 3H), 3.39(s, 3H), 3.89(s, 3H), 4.77(s, 2H), 6.40(s, 1H), 7.33–7.55(m, 5H)
  IR(KBr) 3411, 1592, 1572, 1507, 1482, 1467, 1437, 1360, 1339, 1232, 1204, 1175, 1148, 1125, 1092 cm$^{-1}$

TABLE 8

- III-55 mp138–140° C.
  $^1$HNMR(CDCl$_3$)δ 1.14(t, J=7.0Hz, 3H), 3.59(q, J=7.0Hz, 2H), 3.88(s, 3H), 4.97(bs, 1H), 6.42(s, 1H), 6.86–6.94(m, 2H), 7.43–7.51(m, 2H)
  IR(KBr) 3384, 3291, 2978, 1614, 1593, 1576, 1519, 1484, 1469, 1455, 1436, 1417, 1366, 1306, 1285, 1257, 1203, 1171, 1127, 1094, 1029 cm$^{-1}$
- III-56 mp162–164° C.
  $^1$HNMR(CDCl$_3$)δ 2.77(s, 3H), 3.17(s, 3H), 3.75(s, 3H), 3.92(s, 3H), 7.10(s, 2H), 7.35–7.43(m, 4H)
  IR(CHCl$_3$)1594, 1561, 1507, 1478, 1464, 1374, 1331, 1178, 1149, 1109, 1080, 1000, 970, 894, 871, 844 cm$^{-1}$
- III-57 mp95–97° C.
  $^1$HNMR(CDCl$^3$)δ 2.35(s, 3H), 3.77(s, 3H), 6.84–6.87(m, 2H), 7.12(s, 1H), 7.13(s, 1H), 7.35–7.38(m, 2H)
  IR(CHCl$_3$)3596, 2959, 2939, 2840, 1611, 1563, 1517, 1489, 1464, 1438, 1384, 1367, 1329, 1295, 1258, 1173, 1102, 1049, 1035, 1001, 911, 891, 835 cm$^{-1}$
- III-58 mp173–175° C.
  $^1$HNMR(CDCl$_3$)δ 69.1–6.94(m, 2H), 7.31–7.34(m, 2H), 7.87(s, 1H), 8.09(s, 1H), 9.89(s, 1H), 10.28(s, 1H)
  IR(CHCl$_3$)3437, 1685, 1610, 1516, 1456, 1394, 1370, 1270, 1261, 1238, 1214, 1173, 1144, 1053, 1012, 939, 905, 829, 808, 557, 458 cm$^{-1}$
- III-59 mp173–175° C.
  $^1$HNMR(CDCl$_3$)δ 1.10(t, J=6.9Hz, 3H), 1.48(t, J=6.9Hz, 3H), 3.20(s, 3H), 3.47(s,3H), 366(q, J=6.9Hz, 2H), 4.11(q, J=6.9Hz, 2H), 6.79(s, 1H), 7.32–7.39(m, 2H), 7.60–7.66(m, 2H)
  IR(CHCl$_3$)1502, 1458, 1372, 1176, 1148, 1074, 1023, 967, 870 cm$^{-1}$
- III-60 $^1$HNMR(CDCl$_3$)δ 2.17(s, 3H), 2.39(s, 3H), 3.19(s, 3H), 5.80(s, 1H), 6.71(s, 1H), 7.33(s, 4H)

TABLE 9

- III-61 mp107–108° C.
  $^1$HNMR(CDCl$_3$)δ 3.21(s, 3H), 3.79(s, 3H), 4.04(s, 3H), 7.39(d, J=8.9Hz, 2H), 7.57(d, J=8.9Hz, 2H), 7.68(s, 1H), 10.17(s, 1H)
  IR(KBr) 1704, 1422, 1358, 1224, 1148, 1090, 1026, 974, 876 cm$^{-1}$
- III-62 mp121–122° C.
  $^1$HNMR(CDCl$_3$)δ 3.45(s, 3H), 3.47(s, 3H), 3.93(s, 3H), 4.68(s, 2H), 4.77(s, 2H), 7.22(s, 1H), 7.49(d, J=8.1Hz, 2H), 7.56(d, J=8.1Hz, 2H), 10.42 (s, 1H)
  IR(KBr) 1695, 1476, 1422, 1232, 1189, 1130, 1040, 860 cm$^{-1}$
- III-63 mp113–115° C.
  $^1$HNMR(CDCl$_3$)δ 2.18(s, 3H), 3.22(s, 3H), 3.89(s, 3H), 6.85(s, 1H), 7.11(s, 1H), 7.36(s, 4H)
  IR(KBr) 1497, 1413, 1354, 1230, 1146, 1097, 976, 864 cm$^{-1}$
- III-64 $^1$HNMR(CDCl$_3$) 5.65(s, 1H), 7.18(s, 1H), 7.30–7.35(m, 2H), 7.46–7.50(m, 3H)
- III-65 $^1$HNMR(CDCl$_3$)δ: 1.30(d, J=7.2Hz, 6H), 2.96(quintet, J=7.2Hz, 1H), 3.82(s, 3H), 3.89(s, 3H), 5.92(brs, 2H), 6.91(s, 1H), 7.30(d, J=8.1Hz, 2H), 7.44(s, 2H), 7.49(d, J=8.1Hz, 2H)
- III-66 mp118–122° C.
  $^1$HNMR(CDCl$_3$)δ 3.80(s, 3H), 3.91(s, 3H), 5.88(s, 2H), 6.84–6.92(m, 2H), 7.39–7.47(m, 3H)
  IR(KBr) 3600–2800(br), 1606, 1517, 1492, 1461, 1415, 1397, 1330, 1265, 1205, 1171, 1052 cm$^{-1}$
- III-67 mp227–230° C.
  $^1$HNMR(CDCl$_3$)δ 0.25(s, 6H), 1.02(s, 9H), 2.33(s, 3H), 2.82(s, 2H), 6.88–6.93(m, 2H), 7.16(s, 1H), 7.21–7.25(m, 3H), 8.11(s, 1H)
  IR(KBr) 3600–2800(br), 1608, 1514, 1393, 1346, 1267, 1167 cm$^{-1}$
- III-68 mp134–137 C.
  $^1$HNMR(CDCl$_3$)δ 3.00(s, 6H), 3.81(s, 3H), 3.91(s, 3H), 6.00(s, 2H), 6.77–6.82(m, 2H), 6.90(s, 1H), 7.41(s, 1H), 7.46–7.51(m, 3H)
  IR(KBr) 3600–2800(br), 1601, 1528, 1494, 1466, 1439, 1399, 1362, 1321, 1198, 1166, 1118, 1051 cm$^{-1}$

TABLE 10

III-69 mp144–148° C.
$^1$HNMR(CDCl$_3$)δ 2.38(s, 3H), 2.82(s, 3H), 3.01(s, 6H), 7.79–7.83 (m, 2H), 7.18(s, 2H), 7.27–7.31(m, 2H), 8.11(s, 1H)
IR(KBr) 3600–2800(br), 1612, 1523, 1443, 1389, 1328, 1271, 1160 cm$^{-1}$

III-70 mp122–126° C.
$^1$HNMR(CDCl$_3$)δ 0.10(s, 9H), 0.78(s, 6H), 2.96(s, 6H), 3.75(s, 3H), 3.84(s, 3H), 6.08(s, 2H), 6.72–6.78(m, 2H), 7.01(s, 1H), 7.22–7.29 (m, 2H)
IR(KBr) 3600–2800(br), 1613, 1528, 1463, 1416, 1402, 1360, 1345, 1251, 1218, 1195, 1136, 1092, 1062, 991 cm$^{-1}$

III-71 $^1$HNMR(CDCl$_3$)δ 2.21(s, 3H), 2.37(s, 3H), 3.89(s, 3H), 5.19(s, 2H), 6.75(d.d, J=8.4&2.1Hz, 1H), 6.81(d, J=2.1Hz, 1H), 6.92(d, J=8.4Hz, 1H), 7.08(s, 1H), 7.30–7.50(m, 6H)

III-72 oil
$^1$HNMR(CDCl$_3$)δ 2.51(s, 6H), 2.75(s, 6H), 5.15(s, 2H), 5.67(s, 1H), 6.94(s, 1H), 6.96(d, J=8.4Hz, 1H), 7.04(dd, J=2.1, 8.4Hz, 1H), 7.18(s, 1H), 7.20(d, J=2.1Hz, 1H), 7.37–7.47(m, 5H)
IR(CHCl$_3$)3032, 3428, 3000–2800(br), 1730, 1611, 1525, 1489, 1455, 1256, 1171, 1137, 1100, 1036 cm$^{-1}$ III-73 $^1$HNMR(CDCl$_3$)δ 2.21(s ,3H), 2.37(s, 3H), 5.15(s, 2H), 5.69(br, 1H), 6.73(dd, J=8.4, 1.8Hz, 1H), 6.89–6.99(m, 2H), 7.07(s, 1H), 7.26–7.46(m, 6H)

III-74 $^1$HNMR(CDCl$_3$)δ 1.09(t, J=7.2Hz, 3H), 1.22(t, J=7.5Hz, 3H), 2.55 (q, J=7.2Hz, 2H), 2.72(q, J=7.5Hz, 2H), 5.15(s, 2H), 5.70(s, 1H), 6.73(dd, J=8.4, 1.8Hz, 1H), 6.89(d, J=1.8Hz, 1H), 6.95(d, J=8.4Hz, 1H), 7.04(s, 1H), 7.38–7.47(m, 6H)
IR(CHCl$_3$)3542, 2970, 2933, 1586, 1508, 1480, 1384, 1324, 1290, 1160, 1127, 1064, 1011, 930, 898, 879, 857 cm$^{-1}$

III-75 $^1$HNMR(CDCl$_3$)δ 2.04(s, 3H), 3.70(s, 3H), 3.90(s, 3H), 5.19(s, 2H), 5.50(m, 1H), 6.73(dd, J=2.1Hz, 1H), 6.97–7.00(m, 2H), 7.29–7.48(m, 5H)

TABLE 11

III-76 $^1$HNMR(CDCl$_3$)δ 2.04(s, 3H), 3.90(s, 3H), 5.15(s, 2H), 5.49(s, 1H), 5.74(s, 1H), 6.71(dd, J=8.1, 2.1Hz, 1H), 6.85(d, J=2.1Hz, 1H), 6.99–7.03(m, 2H), 7.39–7.45(m, 5H)
IR(CHCl$_3$)3529, 2963, 2940, 1731, 1587, 1566, 1510, 1480, 1455, 1412, 1382, 1323, 1290, 1248, 1128, 1099, 1009, 935, 879 cm$^{-1}$

III-77 mp87–89° C.
$^1$HNMR(CDCl$_3$)δ 2.20(s, 3H), 2.37(s, 3H), 5.18(s, 2H), 6.90–7.10 (m, 4H), 730–7.51(m, 6H)
IR(CHCl$_3$)1510, 1482, 1381, 1298, 1267, 1233, 1127, 1008, 952, 875, 812 cm$^{-1}$

III-78 $^1$HNMR(CDCl$^3$)δ 1.25(d, J=6.9Hz, 6H), 2.24(s, 3H), 3.26(sept, J= 6.9Hz, 1H), 5.20(s, 2H), 6.95(ddd, J=8.3, 2.2, 1.2Hz, 1H), 7.06(t, J=8.3Hz, 1H), 7.06(dd, J=11.9, 2.2Hz, 1H), 7.10(s, 1H), 7.17(s, 1H), 7.32–7.51(m, 5H)
IR(KBr) 1492, 1420, 1228, 1203, 1140, 1012, 989, 841 cm$^{-1}$ III-79 $^1$HNMR(CDCl$_3$)δ 2.43(s, 3H), 5.19(s, 2H), 7.06(t, J=8.9Hz, 1H), 7.18–7.48(m, 10H)
IR(KBr) 1491, 1437, 1214, 1135, 890, 810, 748 cm$^{-1}$ III-80 mp77–79° C.
$^1$HNMR(CDCl$_3$)δ 3.921(s, 3H), 5.21(s, 2H), 6.90–6.99(m, 3H), 7.31–7.50(m, 7H)
IR(KBr) 3600–2800(br), 1518, 1477, 1418, 1237, 1212, 1167, 1140 cm$^{-1}$ III-81 mp103–105° C.
$^1$HNMR(CDCl$_3$)δ 2.16(s, 3H), 2.37(s, 3H), 2.42(s, 3H), 3.16(m, 3H), 5.21(s, 2H), 7.16–7.17(m, 3H), 7.24–7.27(m, 1H), 7.36–7.48 (m, 5H)
IR(CHCl$_3$)2940, 1613, 1514, 1478, 1455, 1423, 1366, 1331, 1292, 1264, 1176, 1140, 1126, 1096, 1045, 1009, 972, 955, 920, 843 cm$^{-1}$ III-82 $^1$HNMR(CDCl$_3$)δ 2.19(s, 3H), 3.88(s, 3H), 5.20(s, 2H), 6.84(s, 1H), 6.95(m, 1H), 7.03–7.05(m, 3H), 7.35–7.49(m, 5H)

III-83 mp83–85° C.
$^1$HNMR(CDCl$_3$)δ 2.19(s,3H), 3.88(s, 3H), 3.91(s, 3H), 5.21(s, 3H), 6.76(dd, J=8.4, 2.1Hz, 1H), 6.82(d, J=2.1Hz, 1H), 6.87(d, J=8.4Hz, 1H), 7.08(s, 1H), 7.32–7.50(m, 5H)
IR(CHCl$_3$)2962, 2937, 1613, 1579, 1499, 1464, 1455, 1443, 1421, 1319, 1249, 1170, 1140, 1103, 1029, 1008, 989, 901, 832 cm$^{-1}$

TABLE 12

III-84 oil
$^1$HNMR(CDCl$_3$)δ 1.44(d, J=6.9Hz, 3H), 2.19(s, 3H), 4.09(q, J= 6.9Hz, 2H), 5.20(s, 2H), 6.82(s, 1H), 6.94–7.08(m, 3H), 7.32–7.49 (m, 6H)
IR(CHCl$_3$)3597, 2928, 1731, 1609, 1523, 1494, 1476, 1387, 1298, 1261, 1173, 1127, 1048, 834 cm$^{-1}$ III-85 $^1$HNMR(CDCl$_3$)δ 2.26(s, 3H), 2.52(s, 3H), 3.90(s, 3H), 4.59(brs, 2H), 5.20(s, 2H),6.73–7.10(m, 4H), 7.27–7.52(m, 6H)

III-86 $^1$HNMR(CDCl$_3$)δ 2.33(s, 3H), 2.81(s, 3H), 4.60(brs, 2H), 5.20(s, 2H), 6.92–7.18(m, 4H), 7.30–7.52(m, 6H)

TABLE 13

I-1 m.p. 155.5–156° C.
$^1$HNMR(acetone–d$_6$)δ 1.77(brs, 3H), 1.79(brs, 3H), 3.37(s, 3H), 3.73 (s, 3H), 4.63(brd, J=6.6Hz, 2H), 5.52(m, 1H), 6.49(1H, s), 6.83(dd, J=2.2 and 8.2Hz, 1H), 6.92(d, J=2.2Hz, 1H), 6.94(m, 2H), 6.96(d, J= 8.2Hz, 1H), 7.54(m, 2H), 7.62(brs, 1H), 7.78(s, 1H), 8.64(brs, 1H)
IR(KBr) 3393, 2932, 1611, 1588, 1522, 1490, 1117, 1071, 1001 cI–3m$^{-1}$ I-2 $^1$HNMR(CDCl$_3$)δ 2.67(s, 3H), 3.13(s, 3H), 3.21(s, 3H), 3.56(s, 3H), 3.78(s, 3H), 5.19(s, 2H), 6.84(s, 1H), 7.15(d, J=8.6Hz, 1H), 7.30–7.50(m, 9H), 7.60–7.75(m, 2H)
IR(KBr) 1373, 1361, 1179, 1149, 1079, 874, 799 cm$^{-1}$ I-3 m.p. 155–157° C.
$^1$HNMR(CDCl$_3$)δ 1.76(s, 3H), 1.81(s, 3H), 2.71(s, 3H), 3.21(s, 3H), 3.23(s, 3H), 3.56(s, 3H), 3.78(s, 3H), 4.64(d, J=6.6Hz, 2H), 5.43–5.55(m, 1H), 6.84(s, 1H), 7.09(d, J=8.4Hz, 1H), 7.30–7.42 (m, 4H), 7.65–7.75(m, 2H)
IR(KBr) 1519, 1481, 1364, 1179, 1153, 1083, 970, 877, 796 cm$^{-1}$ I-4 $^1$HNMR(CDCl$_3$)δ 3.45(s, 3H), 3.75(s, 3H), 5.16(s, 2H), 6.44(s, 1H), 6.92–7.19(m, 5H), 7.34–7.44(m, 5H), 7.57–7.66(m, 2H)
IR(KBr) 3538, 3510, 3460, 3330, 1605, 1521, 1490, 1455, 1247, 1220, 1120, 1070, 1010 cm$^{-1}$ I-5 m.p. 136–138° C.
$^1$HNMR(CDCl$_3$)δ 2.68(s, 3H), 3.13(s, 3H), 3.55(s, 3H), 3.80(s, 3H), 5.19(s, 2H), 6.86(s, 1H), 7.16(d, J=8.7Hz, 1H), 7.33–7.49(m, 7H), 7.55–7.69(m, 2H), 7.82–7.87(m, 2H)
IR(KBr) 3433, 2937, 1609, 1519, 1474, 1463, 1364, 1322, 1295, 1274, 1235, 1183, 1167, 1120, 1095, 1077, 1016 cm$^{-1}$ I-6 foam
$^1$HNMR(CDCl$_3$)δ 1.77(s, 3H), 1.81(s, 3H), 2.72(s, 3H), 3.24(s, 3H), 3.49(s, 3H), 3.80(s, 3H), 4.64(d, J=6.9Hz, 2H), 5.50(m, 1H), 6.86(s, 1H), 7.10(d, J=8.7Hz, H), 7.35(dd, J=2.1, 8.7Hz, 1H), 7.39(d, J= 2.1Hz, 1H), 7.55–7.69(m, 2H), 7.82–7.87(m, 2H).
IR(CHCl$_3$)3030, 1608, 1518, 1480, 1369, 1322, 1269, 1230, 1179, 1131, 1120, 1097, 1081, 1015 cm$^{-1}$

TABLE 14

I-7 m.p. 92–94° C.
$^1$HNMR(CDCl$_3$)δ 1.76(s, 3H), 1.82(s, 3H), 3.46(s, 3H), 3.77(s, 3H), 4.62(d, J=6.9Hz, 2H), 5.31(m, 1H), 5.71(s, 1H), 5.85(s, 1H), 6.47(s, 1H), 6.93(dd, J=1.8, 8.7Hz, 1H), 6.97(d, J=8.7Hz, 1H), 7.05(m, 1H), 7.55–7.65(m, 2H), 7.83–7.91(m, 2H).
IR(KBr) 3466, 2939, 1609, 1587, 1518, 1498, 1486, 1464, 1437, 1406, 1361, 1324, 1245, 1216, 1155, 1125, 1073 cm$^{-1}$

I-8 $^1$HNMR(CDCl$_3$)δ 3.22(s, 3H), 3.45(s, 3H), 3.77(s, 3H), 4.74(s, 2H), 5.15(s, 2H), 6.93(s, 1H), 7.01(d, J=8.7Hz, 2H), 7.32–748(m, 9H), 7.73(d, J=9.0Hz, 2H)
IR(KBr) 3400, 1721, 1612, 1509, 1471, 1362, 1242, 1153, 1040, 1018 cm$^{-1}$

I-9 $^1$HNMR(CDCl$_3$)δ 1.03(t, J=7.2Hz, 3H), 2.16(dq, J=7.2, 6.0Hz, 2H), 3.46(s, 3H), 3.74(s, 3H), 4.68(d, J=5.4Hz, 2H), 5.70(m, 2H), 6.45(s, 1H), 6.91(d, J=8.7Hz, 2H), 6.96(brs, 2H), 7.07(brs, 1H), 7.53(d, J=8.7Hz, 2H)
IR(Nujol)3445, 3369, 1612, 1578, 1523, 1489, 1268, 1243, 1112, 1102, 1071, 1011, 998, 944, 824, 805, 781 cm$^{-1}$

TABLE 14-continued

I-10 m.p. 174–175° C.
$^1$HNMR(CDCl$_3$)δ 3.11(s, 3H), 3.21(s, 3H), 3.45(s, 3H), 3.73(s, 3H), 4.49(brs, 2H), 5.18(s, 2H), 6.85(s, 1H), 7.15(d, J=8.4Hz, 1H), 7.27(dd, J=8.4Hz, J=2.1Hz, 1H), 7.35–7.49(m, 8H), 7.70(m,2H)
IR(KBr) 1519, 1467, 1360, 1346, 1331, 1295, 1272, 1229, 1180, 1151, 1122, 1101, 1081, 1022, 980, 971, 954, 875, 849, 814, 798, 742, 525 cm$^{-1}$ I-11 $^1$HNMR(CDCl$_3$)δ 1.77(s, 3H), 1.82(s, 3H), 3.22(s, 6H), 3.45(s, 3H), 3.74(s, 3H), 4.49(brs, 2H), 4.53(d, J=7.2Hz, 2H), 5.45–5.55(m, 1H), 6.85(s, 1H), 7.08(d, J=8.7Hz, 1H), 7.26(dd, J=8.7 and 2.1 Hz, 1H), 7.33(d, J=2.1Hz, 1H), 7.36–7.41(m, 2H), 7.65–7.75(m, 2H)
IR(KBr) 3553, 3434, 1516, 1472, 1365, 1176, 1150, 973, 871 cm$^{-1}$ I-12 $^1$HNMR(DMSO-d$_6$)δ 1.72(s, 3H), 1.77(s, 3H), 3.35(s, 3H), 3.65(s, 3H), 4.20(brs, 2H), 4.47(brt, J=4.4Hz, 1H), 4.55(brd, J=6.6Hz, 2H), 5.40–5.57(m, 1H), 6.64(dd, J=8.2, 2.0Hz, 1H), 6.70(d, J=2.0 Hz, 1H), 6.75–7.00(m, 4H), 7.40–7.55(m, 2H)
IR(KBr) 3435, 1518, 1475, 1459, 1261, 1223, 988 cm$^{-1}$

TABLE 15

I-13 $^1$HNMR(CDCl$_3$)δ 2.71(s, 3H), 2.84(s, 3H), 3.20(s, 3H), 3.42(s, 3H), 3.76(s, 3H), 5.13(s, 2H), 5.67(s, 1H), 6.90 (s, LH), 6.89–6.96 (m, 2H), 7.00(m, J=1.8Hz, 1H), 7.32–7.50(m, 7H), 7.70(d, J=9.0 Hz, 2H)

I-14 m.p. 140–141° C.
$^1$HNMR(CDCl$_3$)δ 2.71(s, 3H), 2.83(s, 3H), 3.15(s, 3H), 3.21(s, 3H), 3.42(s, 3H), 3.77(s, 3H), 5.16(s, 2H), 6.90(s, 1H), 7.09(d, J=8.9Hz, 2H), 7.30–7.50(m, 9H), 7.70(d, J=8.9Hz, 2H)
IR(KBr) 1642, 1516, 1467, 1362, 1180, 1151, 1118, 1050, 867, 803, 708 cm$^{-1}$

I-15 m.p. 161–162° C
$^1$HNMR(CDCl$_3$)δ 1.76(s, 3H), 1.81(s, 3H), 2.72(s, 3H), 2.85(s, 3H), 3.21(s, 3H), 3.23(s, 3H), 3.42(s, 3H), 3.77(s, 3H), 4.61(d, J=6.6Hz, 2H), 5.49(t, J=6.6Hz, 1H), 6.90(S, 1H), 7.02(s, J=8.1Hz, 1H), 7.31–7.37(m, 2H), 7.38(d, J=8.9Hz,2H), 7.70(d, J=8.9Hz, 2H)
IR(KBr) 1643, 1516, 1467, 1362, 1277, 1236, 1180, 1150, 974, 882, 868, 847, 802, 710 cm$^{-1}$

I-16 m.p. 206–207° C.
$^1$HNMR(CDCl$_3$)δ 1.71(s, 3H), 1.76(s, 3H), 2.62(s, 3H), 2.69(s, 3H), 3.27(s, 3H), 3.71(s, 3H), 4.53(d, J=6.8Hz, 2H), 5.47(t, J=6.6 Hz, 1H), 6.61(dd, J=8.3 and 2.1Hz, 1H), 6.71(d, J=2.1Hz, 1H), 6.86(d, J=8.7Hz, 2H), 6.87(d, J=8.3Hz, 1H), 6.95(s, 1H), 7.47(d, J=8.7Hz, 2H), 8.83(brs, 1H), 9.59(brs, 1H)
IR(KBr) 3427, 3020, 1608, 1517, 1467, 1379, 1233, 1053, 1005, 839, 799, 759, 543 cm-1

I-17 m.p. 171–172° C.
$^1$HNMR(DMSO-d$_6$)δ 1.74(d, J=0.9Hz, 3H), 1.77(s, 3H), 2.97(s, 3H), 3.45(s, 3H), 3.51(s, 3H), 3.77(s, 3H), 4.65(d, J=6.6Hz, 2H), 5.48(m, 1H), 7.06–7.27(m,4H), 7.48 & 7.74(ABq, J=9.0Hz, 4H)
IR(KBr) 1523, 1483, 1394, 1366, 1271, 1175, 1151, 1087, 1071, 872, 861, 847, 796 cm$^{-1}$

I-18 $^1$HNMR(CDCl$_3$)δ 1.76(s, 3H), 1.80(s, 3H), 3.44(s, 3H), 3.76(s, 3H), 4.63(d, J=6.6Hz, 2H), 4.99(s, 1H), 5.48–5.62(m, 1H), 6.00(s, 1H), 6.45(s, 1H), 6.88–6.97(m, 2H), 7.04(dd, J=9.0, 9.0Hz, 1H), 7.15–7.29(m, 2H), 7.45–7.60(m, 2H)
IR(KBr) 3393, 1523, 1490, 1466, 1403, 1267, 1229, 1113, 1070 cm$^{-1}$

TABLE 16

I-19 $^1$HNMR(CDCl$_3$)δ 2.56(s, 3H), 3.21(s, 3H), 3.52(s, 3H), 3.69(s, 3H), 5.19(s, 2H), 5.76(s, 1H), 6.92(dd, J=8.4 and 2.0Hz, 1H), 7.04 (d, J=8.4Hz, 1H), 7.05(d, J=2.0Hz, 1H), 7.35–7.51(m, 7H), 7.60(d, J=8.6Hz, 2H)

I-20 $^1$HNMR(CDCl$_3$)δ 2.69(s, 3H), 3.14(s, 3H), 3.21(s, 3H), 3.53(s, 3H), 3.71(s, 3H), 5.20(s, 2H), 7.18(d, J=8.7Hz, 1H), 7.34–7.50(m, 9H), 7.59(d, J=8.7Hz, 2H)

TABLE 16-continued

I-21 m.p. 94–95° C.
$^1$HNMR(CDCl$_3$)δ 2.73(s, 3H), 3.21(s, 3H), 3.24(s, 3H), 3.53(s, 3H), 3.71(s, 3H), 4.65(d, J=6.9Hz, 2H), 5.50(t, J=6.9Hz, 1H), 7.12 (d, J=8.6Hz, 1H), 7.36(dd, J=8.6 and 2.1Hz, 1H), 7.41(d, J=2.1Hz, 2H), 7.41(d, J=8.8Hz, 2H), 7.59(d, J=8.8Hz, 2H)
IR(KBr) 1516, 1367, 1180, 1152, 1039, 975, 869, 799 cm$^{-1}$ I-22 m.p. 148–150° C.
$^1$HNMR(CDCl$_3$)δ 3.42(s, 3H), 3.65(s, 3H), 4.63(d, J=6.9Hz, 2H), 4.98(brs, 1H), 5.53(t, J=6.9Hz, 1H), 6.92–6.96(m, 4H), 7.07(s, 1H), 7.43(d, J=8.6Hz, 2H)
IR(KBr) 3398, 1612, 1587, 1523, 1462, 1410, 1261, 1211, 1099, 1036, 984, 952, 919, 838, 815 cm$^{-1}$ I-23 $^1$HNMR(CDCl$_3$)δ 2.28(t, J=6.3Hz, 1H), 2.60(s, 3H), 3.21(s, 3H), 3.55(s, 3H), 3.77(s, 3H), 4.78(d, J=6.3Hz, 2H), 5.18(s, 2H), 6.84 (s, 1H), 7.06(d, J=9.0Hz, 1H), 7.29–7.48(m, 9H), 7.69(d, J=8.7Hz, 2H)

I-24 $^1$HNMR(CDCl$_3$)δ 1.76(s, 3H), 1.81(s, 3H), 2.26(s, 3H), 2.50(s, 3H), 3.21(s, 3H), 3.56(s, 3H), 3.77(s, 3H), 4.57(d, J=6.2Hz, 2H), 5.51(t, J=6.2Hz, 1H), 6.83(s, 1H), 6.92(d, J=9.0Hz, 1H), 7.17–7.29(m, 2H), 7.36(d, J=8.7Hz, 2H), 7.70(d, J=8.7Hz, 2H)
IR(KBr) 3434, 1608, 1512, 1479, 1364, 1234, 1175, 1150, 1078, 1017 cm$^{-1}$

I-25 $^1$HNMR(CDCl$_3$)δ 1.75(s, 3H), 1.80(s, 3H), 2.27(s, 3H), 3.46(s, 3H), 3.74(s, 3H), 4.57(d, J=6.2Hz, 2H), 4.95(s, 1H), 5.53(t, J=6.2 Hz, 1H), 5.86(s, 1H), 6.45(s, 1H), 6.91(d, J=8.7Hz, 2H), 6.92(d, J=9.0Hz, 1H), 7.24(d, J=9.0Hz, 1H), 7.26(s, 1H), 7.53(d, J=8.7Hz, 2H)
IR(KBr) 3399, 1612, 1566, 158l, 1520, 1486, 1237, 1115, 1078, 1001 cm$^{-1}$

TABLE 17

I-26 m.p. 246–247° C.
$^1$HNMR(DMSO-d$_6$)δ 5.16(s, 3H), 6.84–6.87(m, 2H), 7.05(s, 2H), 7.14(s, 1H), 7.32–7.43(m, 3H), 7.49–7.64(m, 8H)
IR(KBr) 3600–3100(br), 1594, 1453, 1387, 1296, 1253, 1010 cm$^{-1}$

I-27 $^1$HNMR(DMSO-d$_6$)δ 3.38(s, 3H), 3.43(s, 3H), 5.28(s, 2H), 7.36–7.54(m, 8H), 7.69–7.86(m, 8H)
IR(KBr) 1488, 1354, 1286, 1178, 1151, 1116 cm$^{-1}$

I-28 m.p. 162–163° C.
$^1$HNMR(CDCl$_3$)δ 1.77(s, 3H), 1.82(s, 3H), 3.19(s, 3H), 3.23(s, 3H), 4.64(d, J=6.6Hz, 2H), 5.25–5.48(m, 1H), 7.09(d, J=9.0Hz, 1H), 7.36–7.40(m, 2H), 7.52(dd, J=2.4, 9.0Hz, 1H), 7.59(d, J=2.4 Hz, 1H), 7.62(s, 4H), 7.63–7.69(m, 2H)
IR(KBr) 1489, 1363, 1290, 1177, 1154, 1115, 971, 860, 809 cm$^{-1}$

I-29 m.p. 195° C.
$^1$HNMR(DMSO-d$_6$)δ 1.72(s, 3H), 1.75(s,3H), 4.57(d, J=6.3Hz, 2H), 5.45–5.50(m, 1H), 6.84–6.87(m, 2H), 6.98–7.11(m, 3H), 7.50–7.64(m, 6H)
IR(KBr) 3600–3200(br), 1609, 1594, 1497, 1257, 991 cm$^{-1}$

I-30 m.p. 145–148° C.
$^1$HNMR(CDCl$_3$)δ 1.60–2.20(m, 6H), 2.72(s, 3H), 3.21(s, 3H), 3.24(s, 3H), 3.56(s, 3H), 3.78(s, 3H), 4.92(m, 1H), 5.88(m, 1H), 6.02(m, 1H), 6.84(s, 1H), 7.12(d, J=8.6Hz, 1H), 7.34–7.40(m, 4H), 7.69(m, 2H)
IR(KBr) 1517, 1481, 1390, 1362, 1270, 1244, 1180, 1151, 1077, 1012, 973, 960, 873, 817, 799, 521 cm$^{-1}$

I-31 m.p. 108–110° C.
$^1$HNMR(CDCl$_3$)δ 1.60–2.20(m, 6H), 3.46(s, 3H), 3.75(s, 3H), 4.86(m, 1H), 5.02(bs, 1H), 5.75(s, 1H), 5.90(m, 1H),5.91(s, 1H), 6.00(m, 1H), 6.45(s, 1H), 6.90–7.07(m, 5H), 7.53(m, 2H)
IR(KBr) 3485, 1614, 1523, 1491, 1457, 1407, 1312, 1287, 1269, 1238, 1195, 1170, 1115, 1072, 1014 cm$^{-1}$

TABLE 18

I-32 m.p. 188–190° C.
$^1$HNMR(CDCl$_3$)δ 2.69(s, 3H), 3.21(s, 3H), 3.26(s, 3H), 3.56(s, 3H), 3.78(s, 3H), 4.84(m, 2H), 6.42(dt, J=15.6Hz, J=5.7Hz, 1H), 6.79(d, J=15.6Hz, 1H), 6.84(s, 1H), 7.15(d, J=8.4Hz, 1H), 7.28–

TABLE 18-continued 7.43(m, 9H), 7.68(m, 2H)
IR(KBr) 1519, 1479, 1447, 1391, 1360, 1301, 1273, 1241, 1228, 1201, 1175, 1152, 1120, 1079, 1014, 974, 959, 947, 868, 819, 795, 777, 743, 521 cm$^{-1}$ I-33 m.p. 157–159° C.
$^1$HNMR(CDCl$_3$)δ 3.46(s, 3H), 3.75(s, 3H), 4.81(m, 2H), 4.93(bs, 1H), 5.70(s, 1H), 5.91(s, 1H), 6.45(s, 1H), 6.46(d, J=15.9Hz, J=6.0Hz, 1H), 6.76(d, J=15.9Hz, 1H), 6.90–7.09(m, 5H), 7.26–7.46(m, 5H), 7.54(m, 2H)
IR(KBr) 3466, 1611, 1522, 1489, 1461, 284, 1248, 1192, 1165, 1114, 1073 cm$^{-1}$ I-34 m.p. 127–129° C.
$^1$HNMR(CDCl$_3$)δ 1.03 and 1.04(botht, bothJ=8.0Hz, total3H), 2.07–2.19(m, 2H), 2.71 and 2.72(boths, total3H), 3.21(s, 3H), 3.24(s, 3H), 3.56(s, 3H), 3.78(s, 3H), 4.00 and 4.71(bothm, total2H), 5.66–5.75 and 5.90–5.99(bothm, total2H), 6.84(s, 1H), 7.09(d, J=8.4Hz, 1H), 7.33–7.41(m, 5H), 7.68(m, 2H)
IR(KBr) 1519, 1482, 1390, 1362, 1232, 1180, 1150, 1077, 974, 873, 815, 799, 522 cm$^{-1}$ I-35 m.p. 166–168° C.
$^1$HNMR(CDCl$_3$)δ 1.04 and 1.05(botht, bothJ=7.5Hz, total3H), 2.09–2.19(m, 2H), 3.46(s, 3H), 3.74(s, 3H), 4.58 and 4.68(bothm, total2H), 5.01(bs, 1H), 5.69–5.78 and 5.87–5.95(bothm, total4H), 6.45(s, 1H), 6.90–7.06(m, 5H), 7.53(m, 2H)
IR(KBr) 3531, 3489, 3306, 1523, 1492, 1459, 1408, 1314, 1287, 1270, 1255, 1234, 1224, 1118, 1072, 1018, 1005, 822 cm$^{-1}$ I-36 m.p. 148–150° C.
$^1$HNMR(CDCl$_3$)δ 1.62(s, 3H), 1.69(s, 3H), 1.76(s, 3H), 2.08–2.20(m, 4H), 2.71(s, 3H), 3.21(s, 3H), 3.24(s, 3H), 3.56(s, 3H), 3.78(s, 3H), 4.66(d, J=6.3Hz, 2H), 5.09(m, 1H), 5.50(t, J=6.3Hz, 1H), 6.84(s, 1H), 7.10(d, J=8.4Hz, 1H), 7.33–7.41(m, 4H), 7.68(m, 2H)
IR(KBr) 1519, 1480, 1464, 1449, 1389, 1366, 1291, 1271, 1233, 1200, 1176, 1150, 1118, 1079, 1012, 973, 946, 876, 841, 816, 801, 523, 510 cm$^{-1}$

TABLE 19

I-37 $^1$HNMR(CDCl$_3$)δ 1.58(s, 3H), 1.63(s, 3H), 1.70(s, 3H), 2.05–2.20(m, 4H), 3.46(s, 3H), 3.75(s, 3H), 4.64(d, J=6.3Hz, 2H), 4.95(bs, 1H), 5.11(m, 1H), 5.53(m, 1H), 5.70(s, 1H), 5.90(s, 1H), 6.45(s, 1H), 6.91–7.08(m, 5H), 7.54(m, 2H)

I-38 m.p. 149–151° C.
$^1$HNMR(CDCl$_3$)δ 1.68(s, 3H), 1.74(s, 3H), 2.55(m, 2H), 2.73(s, 3H), 3.21(s, 3H), 3.22(s, 3H), 3.56(s, 3H), 3.77(s, 3H), 4.07(t, J=6.8Hz, 2H), 5.21(m, 1H), 6.84(s, 1H), 7.08(d, J=8.2Hz, 1H), 7.32–7.40(m, 4H), 7.68(m, 2H)
IR(KBr) 1520, 1483, 1389, 1363, 1296, 1180, 1151, 1079, 975, 872, 815, 799, 521 cm$^{-1}$

I-39 m.p. 105–107° C.
$^1$HNMR(CDCl$_3$)δ 1.68(s, 3H), 1.75(s, 3H), 2.53(m, 2H), 3.54(s, 3H), 3.74(s, 3H), 4.06(t, J=6.8Hz, 2H), 5.01(s, 1H), 5.22(m, 1H), 5.69(s, 1H), 5.90(s, 1H), 6.45(s, 1H), 6.90–7.06(m, 5H), 7.53(m, 2H)
IR(KBr) 3477, 3388, 1523, 1489, 1469, 1402, 1285, 1261, 1248, 1227, 1196, 1175, 1164, 1115, 1100, 1073, 1011 cm$^{-1}$

I-40 m.p. 155–157° C.
$^1$HNMR(CDCl$_3$)δ 1.89(t, J=2.4Hz, 3H), 3.45(s, 3H), 3.75(s, 3H), 4.74(q, J=2.4Hz, 2H), 5.00(bs, 1H), 5.66(s, 1H), 5.92(s, 1H), 6.45(s, 1H), 6.90–7.08(m, 5H), 7.54(m, 2H)
IR(KBr) 3446, 2224, 1523, 1488, 1402, 1266, 1238, 1203, 1187, 1166, 1102, 1068, 1009 cm$^{-1}$

I-41 $^1$HNMR(CDCl$_3$)δ 2.19(s, 3H), 3.45(s, 3H), 3.75(s, 3H), 4.62(m, 2H), 4.92(bs, 1H), 5.60(bs, 1H), 5.92(s, 1H), 5.99(m, 1H), 6.45(m, 1H), 6.91–7.08(m, 5H), 7.53(m, 2H)

I-42 oil
$^1$HNMR(CDCl$_3$)δ 1.76(s, 3H), 1.81(s, 3H), 2.87(s, 3H), 3.22(s, 6H), 3.55(s, 3H), 3.80(s, 3H), 4.66(d, J=7.5Hz, 2H), 5.61(m, 1H), 6.84(s, 1H), 7.37–7.41(m, 3H), 7.61(d, J=2.1Hz, 1H), 7.67(m, 2H)

TABLE 20

I-43 m.p. 132–136° C.
$^1$HNMR(CDCl$_3$)δ 1.74(s, 3H), 1.82(s, 3H), 3.44(s, 3H), 3.76(s, 3H), 4.62(m, 2H), 5.05(brs, 1H), 5.61(m, 1H), 5.79(s, 1H), 6.02(s, 1H), 6.44(s, 1H), 6.92(m, 2H), 7.04(d, J=2.1Hz, 1H), 7.20(d, J=2.1Hz, 1H), 7.53(m, 2H)
IR(KBr) 3495, 3422, 1611, 1520, 1473, 1400, 1355, 1315, 1280, 1227, 1194, 1173, 1111, 1077, 1023 cm$^{-1}$ I-44 m.p. 148–149° C.
$^1$HNMR(CDCl$_3$)δ 1.60(s, 3H), 1.70(s, 3H), 2.32–2.39(m, 2H), 2.65(s, 3H), 2.76–2.81(m, 2H), 3.21(s, 3H), 3.24(s, 3H), 3.56(s, 3H), 3.78(s, 3H), 5.16–5.21(m, 1H), 6.85(s, 1H), 7.30–7.40(m, 5H), 7.66–7.71(m, 2H)
IR(KBr) 1480, 1390, 1361, 1181, 1150, 1075 cm$^{-1}$ I-45 m.p. 73–75° C.
$^1$HNMR(CDCl$_3$)δ 1.63(s, 3H), 1.72(s, 3H), 2.32–2.39(m, 2H), 2.64–2.70(m, 2H), 3.46(s, 3H), 3.74(s, 3H), 4.83(s, 1H), 4.95(s, 1H), 5.27–5.31(m, 1H), 5.92(s, 1H), 6.45(s, 1H), 6.89–7.00(m, 4H), 7.21(d, J=10.5Hz, 1H), 7.52–7.55(m, 2H)
IR(KBr) 3600–3200(br), 3100–2800(br), 1612, 1579, 1523, 1487, 1452, 1400, 1360, 1226, 1174, 1111, 1072 cm$^{-1}$ I-46 $^1$HNMR(CDCl$_3$)δ 3.45(s, 3H), 3.75(s, 3H), 4.65(m, 2H), 4.85(s, 1H), 5.33(m, 1H), 5.44(m, 1H), 5.67(s, 1H), 5.91(s, 1H), 6.10(m, 1H), 6.45(s, 1H), 6.92(m, 2H), 6.95(m, 2H), 7.08(m, 1H), 7.54(m, 2H)

I-47 $^1$HNMR(acetone-d$_6$)δ 3.39(s, 3H), 3.72(s, 3H), 5.20(s, 2H), 6.48(s, 1H), 6.83(dd, J=2.0Hz, J=8.4Hz, 1H), 6.93(m, 2H), 6.96(d, J=2.0Hz, 1H), 7.04(d, J=8.4Hz, 1H), 7.34–7.45(m, 3H), 7.52(m, 2H), 7.52–7.58(m, 2H)
IR(CHCl$_3$)3522, 3348, 1699, 1612, 1589, 1521, 1489, 1458, 1402, 1288, 1114, 1071, 935 cm$^{-1}$ I-48 $^1$HNMR(acetone-d$_6$)δ 1.28(t, J=7.2Hz, 3H), 3.39(s, 3H), 3.72(s, 3H), 4.25(q, J=7.2Hz, 2H), 4.78(s, 2H), 6.49(s, 1H), 6.83(dd, J=1.8 and 8.4Hz, 1H), 6.93(m, 2H), 6.96(d, J=1.8Hz, 1H), 6.97(d, J=8.4Hz, 1H), 7.52(m, 2H), 7.63(s, 1H), 7.83(s, 1H), 8.50(s, 1H)

I-49 $^1$HNMR(acetone-d$_6$)δ 1.75(m, 3H), 3.39(s, 3H), 3.72(s, 3H), 4.56(m, 2H), 5.71–5.82(m, 1H), 5.84–5.96(m, 1H), 6.48(s, 1H), 6.82(dd, J=2.0 and 8.4Hz, 1H), 6.93(d, J=2.0Hz, 1H), 6.93(m, 2H), 6.95(d, J=8.4Hz, 1H), 7.52(m, 2H)

TABLE 21

I-50 $^1$HNMR(acetone-d$_6$) 1.75(m, 3H), 3.39(s, 3H), 3.72(s, 3H), 4.72(m, 2H), 5.73–5.75(m, 2H), 6.48(s, 1H), 6.83(dd, J=2.0 and 7.8Hz, 1H), 6.92–6.95(m, 3H), 6.97(d, J=7.8Hz, 1H), 7.52(m, 2H)

I-51 $^1$HNMR(acetone-d$_6$) 1.77(s, 3H), 1.79(s, 3H), 3.41(s, 3H), 3.72(s, 3H), 4.66(m, 2H), 5.53(m, 1H), 6.49(s, 1H), 6.85(m, 2H), 7.04(d, J=8.1Hz, 1H), 7.10(dd, J=2.1 and 8.1Hz, 1H), 7.19(d, J=2.1Hz, 1H), 7.25(m, 2H)

I-52 $^1$HNMR(CDCl$_3$)δ 2.58(t, J=2.2Hz, 1H), 2.73(s, 3H), 3.22(s, 3H), 3.26(s, 3H), 3.56(s, 3H), 3.78(s, 3H), 4.83(d, J=2.2Hz, 2H), 6.85(s, 1H), 7.21(d, J=8.4Hz, 1H), 7.35–7.46(m, 4H), 7.64–7.74(m, 2H)

I-53 $^1$HNMR(CDCl$_3$)δ 3.45(s, 3H), 3.76(s, 3H), 4.36(d, J=1.5Hz, 1H), 4.55(s, 2H), 4.76(dd, J=1.8 and 0.6Hz, 1H), 5.02(brs, 1H), 5.97(d, J=0.9Hz, 1H), 6.45(s, 1H), 6.90–6.96(m, 2H), 6.96–7.05(m, 2H), 7.10–7.12(m, 1H), 7.50–7.58(m, 2H)

I-54 $^1$HNMR(CDCl$_3$)δ 1.76(s, 3H), 1.82(s, 3H), 2.61(s, 3H), 3.53(s, 3H), 3.77(s, 3H), 4.61(d, J=6.9Hz, 2H), 5.17(brs, 1H), 5.45–5.50(m, 1H), 5.72(s, 1H), 6.84(s, 1H), 6.88–7.00(m, 4H), 7.02(d, J=1.8Hz, 1H), 7.50–7.57(m, 2H)

I-55 $^1$HNMR(CDCl$_3$)δ 0.99(d, J=6.5Hz, 6H), 1.74(q, J=6.5Hz, 2H), 1.85(m, 1H), 3.46(s, 3H), 3.75(s, 3H), 4.12(t, J=6.5Hz, 2H), 4.97(s, 1H), 5.65(s, 1H), 5.90(s, 1H), 6.45(s, 1H), 6.92(m, 2H), 6.95(m, 2H), 7.06(m, 1H), 7.54(m, 2H)

I-56 $^1$HNMR(CDCl$_3$)δ 1.34(s, 3H), 1.35(s, 3H), 3.15(dd, J=3.6 and 6.6Hz, 1H), 3.39(s, 3H), 3.72(s, 3H), 4.10(dd, J=6.6 and 11.1Hz, 1H), 4.34(dd, J=3.6 and 11.1Hz, 1H), 6.49(s, 1H), 6.83(dd, J=1.8 and 8.1Hz, 1H), 6.93(d, J=8.7Hz, 2H), 6.94(d, J=1.8Hz, 1H), 7.00(d, J=8.1Hz, 1H), 7.52(d, J=8.7Hz, 2H)

I-57 $^1$HNMR(CDCl$_3$)δ 2.68(s, 3H), 3.13(s, 3H), 3.53(s, 3H), 3.78(s, 3H), 5.19(s, 2H), 6.83(s, 1H), 7.10–7.19(m, 3H), 7.31–7.50(m, 7H), 7.57–7.64(m, 2H)
IR(KBr) 1607, 1520, 1481, 1373, 1231, 1176, 1119, 1078 cm$^{-1}$

TABLE 21-continued

I-58 $^1$HNMR(CDCl$_3$)δ 1.76(s, 3H), 1.82(s, 3H), 2.72(s, 3H), 3.23(s, 3H), 3.53(s, 3H), 3.78(s, 3H), 3.78(s, 3H), 4.64(d, J=6.6Hz, 2H), 6.84(t, J=6.6Hz, 1H), 5.83(s, 1H), 7.06–7.20(m, 3H), 7.31–7.40 (m, 2H), 7.56–7.65(m, 2H)
IR(KBr) 1603, 1521, 1483, 1376, 1366, 1176, 1085 cm$^{-1}$

TABLE 22

I-59 $^1$HNMR(CDCl$_3$)δ 1.76(s, 3H), 1.82(s, 3H), 3.45(s, 3H), 3.75(s, 3H), 4.62(d, J=6.9Hz, 2H), 5.52(t, J=6.9Hz, 1H), 5.71(brs, 1H), 5.89(s, 1H), 6.44(s, 1H), 6.90–7.19(m, 5H), 7.56–7.67(m, 2H)
IR(KBr) 3545, 3385, 1605, 1586, 1561, 1520, 1384, 1311, 1284, 1225, 1121, 1096 cm$^{-1}$ I-60 $^1$HNMR(CDCl$_3$)δ 3.49(s, 3H), 3.74(s, 3H), 5.15(s, 2H), 5.68(s, 1H), 5.91(s, 1H), 6.02(s, 2H), 6.43(s, 1H), 6.88–7.19(m, 6H), 7.31–7.48(m, 5H)
IR(CHCl$_3$)3535, 1615, 1588, 1519, 1500, 1482, 1410, 1290, 1241, 1204, 1092, 1041 cm$^{-1}$ I-61 $^1$HNMR(CDCl$_3$)δ 1.76(s, 3H), 1.81(s, 3H), 2.73(s, 3H), 3.23(s, 3H), 3.57(s, 3H), 3.77(s, 3H), 4.64(d, J=6.6Hz, 1H), 5.50(t, J=6.6Hz, 1H), 6.03(s, 2H), 6.83(s, 1H), 6.91(d, J=8.1Hz, 1H), 7.08 (d, J=8.1Hz, 1H), 7.09(d, J=8.1Hz, 1H), 7.14(s, 1H), 7.34(d, J=8.1Hz, 1H), 7.39(s, 1H)
IR(CHCl$_3$)1607, 1518, 1477, 1453, 1369, 1240, 1178, 1081 cm$^{-1}$ I-62 $^1$HNMR(CDCl$_3$)δ 1.76(s, 3H), 1.82(s, 3H), 3.49(s, 3H), 3.74(s, 3H), 4.61(d, J=6.9Hz, 2H), 5.53(t, J=6.9Hz, 1H), 5.68(s, 1H), 6.02 (s, 2H), 6.43(s, 1H), 6.88–6.96(m, 3H), 7.03–7.18(m, 3H)
IR(KBr) 3494, 1610, 1583, 1561, 1519, 1480, 1460, 1409, 1286, 1243, 1191, 1127, 1089, 1036 cm$^{-1}$ I-63 m.p. 201–202° C.
$^1$HNMR(CDCl$_3$)δ 3.78(s, 6H), 5.16(s, 4H), 5.69(s, 2H), 6.93(s, 2H), 6.99(d, J=8.4Hz, 2H), 7.08(dd, J=2.1 and 8.4Hz, 2H), 7.22(d, J=2.1Hz, 2H), 7.37–7.47(m, 10H),
IR(KBr) 3600–3100(br), 1584, 1523, 1454, 1272, 1245, 1210, 1130 cm$^{-1}$ I-64 m.p. 173–175° C.
$^1$HNMR(CDCl$_3$)δ 3.12(s, 6H), 3.80(s, 6H), 5.18(s, 4H), 6.92(s, 2H), 7.12(d, J=8.7Hz, 2H), 7.36–7.50(m, 12H), 7.60(d, J=2.1Hz, 2H)
IR(KBr) 1523, 1492, 1356, 1290, 1263, 1210, 1182, 1114 cm$^{-1}$

TABLE 23

I-65 $^1$HNMR(CDCl$_3$)δ 1.76(d, J=0.9Hz, 6H), 1.81(d, J=0.6Hz, 6H), 3.22(s, 6H), 3.80(s, 6H), 4.63(d, J=6.6Hz, 4H), 5.48–5.53(m, 2H), 6.92(s, 2H), 7.05(d, J=8.4Hz, 2H), 7.48(dd, J=2.1 and 8.4Hz, 2H), 7.57(d, J=2.1Hz, 2H)
IR(KBr) 1523, 1492, 1468, 1353, 1286, 1258, 1213, 1174, 1108 cm$^{-1}$ I-66 $^1$HNMR(CDCl$_3$)δ 1.76(s, 6H), 1.82(s, 6H), 3.78(s, 6H), 4.62(d, J=6.9Hz, 4H), 5.50–5.55(m, 2H), 5.71(s, 2H), 6.91–6.94(m, 4H), 7.08(dd, J=2.1 and 8.4Hz, 2H), 7.57(d, J=2.1Hz, 2H)
IR(KBr) 3600–3200(br), 1523, 1492, 1271, 1242, 1210, 1186, 1034 cm$^{-1}$ I-67 $^1$HNMR(CDCl$_3$)δ 1.77(s, 3H), 1.81(s, 3H), 3.22(s, 3H), 3.28(s, 3H), 3.79(s, 3H), 3.80(s, 3H), 4.63(d, J=6.6Hz, 2H), 5.48–5.53(m, 1H), 6.92(s, 1H), 6.93(s, 1H), 7.06(d, J=8.4Hz, 1H), 7.13(d, J=8.4Hz, 2H), 7.42–7.51(m, 3H), 7.57(d, J=2.1Hz, 1H)
IR(KBr) 3600–3200(br), 1525, 1493, 1362, 1293, 1210, 1172, 1107 cm$^{-1}$ I-68 m.p. 168–169° C.
$^1$HNMR(CDCl$_3$)δ 3.18(s, 3H), 3.78(s, 3H), 3.79(s, 3H), 5.17(s, 2H), 5.71(s, 1H), 6.92(s, 1H), 6.96(s, 1H), 6.99(d, J=8.7Hz, 1H), 7.08(dd, J=2.1 and 8.7Hz, 1H), 7.24(d, J=2.1Hz, 1H), 7.26–7.48 (m, 7H)
IR(KBr) 3600–3200(br), 1488, 1382, 1369, 1269, 1206, 1174, 1146 cm$^{-1}$ I-69 m.p. 155–157° C.
$^1$HNMR(CDCl$_3$)δ 3.12(s, 3H), 3.19(s, 3H), 3.80(s, 6H), 5.18(s, 2H), 6.92(s, 1H), 6.95(s, 1H), 7.12(d, J=8.7Hz, 1H), 7.32–7.51(m, 8H), 7.60–7.65(m, 3H)
IR(KBr) 1491, 1363, 1210, 1174, 1151, 1114 cm$^{-1}$ I-70 m.p. 109–110° C.
$^1$HNMR(CDCl$_3$)δ 1.77(s, 3H), 1.81(s, 3H), 3.19(s, 3H), 3.23(s, 3H), 3.80(s, 6H), 4.64(d, J=6.6Hz, 2H), 5.05–5.30(m, 1H), 6.92(s, 1H), 6.95(s, 1H), 7.06(d, J=8.7Hz, 1H), 7.33–7.37(m, 2H), 7.49 (dd, J=2.1 and 8.7Hz, 1H), 7.58(d, J=2.1Hz, 1H), 7.61–7.64(m, 2H)
IR(KBr) 1522, 1489, 1368, 1351, 1294, 1260, 1212, 1178, 1149, 1114, 975 cm$^{-1}$

TABLE 24

I-71 $^1$HNMR(CDCl$_3$)δ 1.72(s, 3H), 1.76(s, 3H), 3.72(s, 3H), 3.73(s, 3H), 4.56(d, J=6.6Hz, 2H), 5.46–5.49(brs, 1H), 6.79–6.82(m, 2H), 6.88–7.01(m, 5H), 7.34–7.39(m, 2H), 8.89(s, 1H), 9.45(s, 1H)
IR(KBr) 3600–3100(br), 1524, 1493, 1458, 1386, 1261, 1206, 1010 cm$^{-1}$ I-72 m.p. 123–124° C.
$^1$HNMR(CDCl$_3$)δ 1.77(s, 3H), 1.81(s, 3H), 3.19(s, 3H), 3.80(s, 6H), 4.64(d, J=6.9Hz, 2H), 5.52–5.57(m, 1H), 6.93(s, 1H), 6.94(s, 1H), 7.04(t, J=8.7Hz, 1H), 7.26–7.39(m, 3H), 7.60–7.65(m, 2H)
IR(KBr) 1524, 1494, 1463, 1379, 1265, 1211, 1174, 1154, 1130 cm$^{-1}$ I-73 m.p. 118–119° C.
$^1$HNMR(CDCl$_3$)δ 1.77(s, 3H), 1.81(s, 3H), 3.79(s, 3H), 3.80(s, 3H), 4.63(d, J=6.9Hz, 2H), 4.86(s, 1H), 5.52–5.57(m, 1H), 6.88–6.93(m, 4H), 7.03(t, J=8.7Hz, 1H), 7.26–7.29(m, 1H), 7.37(dd, J=2.4 and 12.9Hz, 1H), 7.40–7.50(m, 2H)
IR(KBr) 3600–3100(br), 1525, 1492, 1466, 1381, 1263, 1206 cm$^{-1}$ I-74 $^1$HNMR(CDCl$_3$)δ 2.63(s, 3H), 3.19(s, 3H), 5.18(s, 2H), 5.74(s, 1H), 7.03(d, J=8.4Hz, 1H), 7.07(dd, J=2.1 and 8.4Hz, 1H), 7.12(d, J=2.1Hz, 1H), 7.36–7.68(m, 12H)
IR(KBr) 3700–3200(br), 1486, 1367, 1353, 1197, 1179, 1147 cm$^{-1}$ I-75 $^1$HNMR(CDCl$_3$)δ 2.80(s, 3H), 3.14(s, 3H), 3.19(s, 3H), 5.20(s, 2H), 7.18(d, J=8.4Hz, 1H), 7.38–7.68(m, 14H)
IR(KBr) 1485, 1361, 1186, 1156, 1107 cm$^{-1}$ I-76 $^1$HNMR(CDCl$_3$)δ 1.78(s, 3H), 1.82(s, 3H), 2.81(s, 3H), 3.19(s, 3H), 3.26(s, 3H), 4.65(d, J=7.2Hz, 1H), 5.47–5.52(m, 1H), 7.11(d, J=8.7Hz, 1H), 7.37–7.67(m, 9H)
IR(KBr) 1486, 1365, 1186, 1154, 1106, 973, 926, 870, 810 cm$^{-1}$

TABLE 25

I-77 m.p. 174–176° C.
$^1$HNMR(CDCl$_3$)δ 1.72(s, 3H), 1.76(s, 3H), 4.55(d, J=6.0Hz, 2H), 5.45–5.49(m, 1H), 6.82–7.43(m, 10H), 8.84(s, 1H), 9.45(s, 1H), 9.53(s, 1H)
IR(KBr) 3600–3100(br), 1610, 1594, 1532, 1496, 1444, 1409, 1305, 1245, 1209 cm$^{-1}$

I-78 m.p. 134–135° C.
$^1$HNMR(CDCl$_3$)δ 3.78(s, 3H), 3.79(s, 3H), 5.17(s, 2H), 5.70(s, 1H), 6.91(s, 1H), 6.95(s, 1H), 6.99(d, J=8.4Hz, 1H), 7.07–7.14(m, 3H), 7.22(d, J=2.1Hz, 1H), 7.36–7.47(m, 5H), 7.52–7.57(m, 3H)
IR(KBr) 3600–3100(br), 1524, 1494, 1462, 1381, 1273, 1248, 1213 cm$^{-1}$

I-79 $^1$HNMR(CDCl$_3$)δ 3.12(s, 3H), 3.79(s, 3H), 3.80(s, 3H), 5.18(s, 2H), 6.92(s, 1H), 6.94(s, 1H), 7.09–7.15(m, 3H), 7.38–7.56(m, 8H), 7.60(d, J=2.1Hz, 1H)
IR(KBr) 1522, 1493, 1467, 1387, 1365, 1279, 1213, 1112 cm$^{-1}$

I-80 m.p. 110–111° C.
$^1$HNMR(CDCl$_3$)δ 1.77(s, 3H), 1.81(s, 3H), 3.22(s, 3H), 3.78(s, 3H), 3.80(s, 3H), 4.63(d, J=6.9Hz, 2H), 5.50–5.57(m, 1H), 6.91(s, 1H), 6.94(s, 1H), 7.04–7.14(m, 3H), 7.47–7.58(m, 4H)
IR(KBr) 1552, 1493, 1364, 1212, 1110, 970 cm$^{-1}$

I-81 $^1$HNMR(CDCl$_3$)δ 1.77(s, 3H), 1.82(s, 3H), 3.78(s, 3H), 3.79(s, 3H), 4.62(d, J=6.9Hz, 2H), 5.50–5.55(m, 1H), 5.72(s, 1H), 6.91–6.95(m, 3H), 7.06–7.14(m, 3H), 7.20(d, J=1.8Hz, 1H), 7.52–7.57 (m, 2H)
IR(KBr) 3536, 1520, 1493, 1386, 1271, 1241, 1210 cm$^{-1}$

TABLE 25-continued

I-82  $^1$HNMR(CDCl$_3$)δ 1.29(t, J=7.2Hz, 3H), 1.76(s, 3H), 1.79(s, 3H), 3.78(s, 6H), 3.78(q, 2H), 4.64(d, J=6.3Hz, 2H), 4.72(s, 2H), 5.53–5.78(m, 1H), 6.61(s, 1H), 6.94(s, 1H), 6.98(d, J=8.7Hz, 1H), 7.09–7.20(m, 4H), 7.52–7.57(m, 2H)
IR(KBr) 1758, 1524, 1496, 1461, 1387, 1263, 1209, 1147 cm$^{-1}$

TABLE 26

I-83  $^1$HNMR(CDCl$_3$)δ 2.76(s, 3H), 3.21(s, 3H), 3.55(s, 3H), 3.77(s, 3H), 5.26(s, 2H), 6.85(s, 1H), 7.17(d, J=8.7Hz, 1H), 7.31–7.50(m, 8H), 60–7.71(m, 3H), 7.92(s, 1H)
IR(KBr) 1684, 1606, 1512, 1478, 1177, 1150, 1080, 1016 cm$^{-1}$

I-84  $^1$HNMR(CDCl$_3$)δ 1.26(t, J=7.2Hz, 3H), 3.08(s, 3H), 3.22(s, 3H), 3.31(s, 3H), 3.74(s, 3H), 4.16(q, J=7.2Hz, 2H), 5.17(s, 2H), 6.44(d, J=16.5Hz, 1H), 6.89(s, 1H), 7.13(s, 2H), 7.27(d, J=8.4Hz, 1H), 7.35–7.50(m, 8H), 7.69(d, J=8.4Hz, 2H)
IR(KBr) 1708, 1633, 1513, 1465, 1367, 1271, 1230, 1176, 1151, 1120, 1017 cm$^{-1}$

I-85  $^1$HNMR(CDCl$_3$)δ 1.26(t, J=7.2Hz, 3H), 3.22(s, 3H), 3.31(s, 3H), 3.74(s, 3H), 4.16(q, J=7.2Hz, 2H), 5.15(s, 2H), 5.70(s, 1H), 6.53(d, J=16.5Hz, 1H), 6.69(dd, J=8.4 and 2.4Hz, 1H), 6.88(s, 2H), 7.00(d, J=8.4Hz, 1H), 7.33–7.50(m, 8H), 7.70(d, J=8.4Hz, 2H)
IR(KBr) 3398, 1675, 1627, 1581, 1512, 1465, 1370, 1284, 1256, 1221, 1148, 1074, 1017 cm$^{-1}$ I-86  $^1$HNMR(CDCl$_3$)δ 2.53(s, 3H), 3.21(s, 3H), 3.56(s, 3H), 3.77(s, 3H), 4.58(s, 2H), 5.24(s, 2H), 6.83(s, 1H), 6.96(d, J=8.4Hz, 1H), 7.28–7.57(m, 9H), 7.69(d, J=8.4Hz, 2H)
IR(KBr) 1605, 1512, 1479, 1366, 1233, 1175, 1149, 1080, 1015 cm$^{-1}$ I-87  $^1$HNMR(CDCl$_3$)δ 1.76(s, 3H), 1.81(s, 3H), 3.27(s, 3H), 3.78(s, 3H), 3.79(s, 3H), 4.63(d, J=6.6Hz, 2H), 5.40–5.50(m, 1H), 5.71(s, 1H), 6.07(s, 1H), 6.91–6.95(m, 3H), 7.05–7.20(m, 3H), 7.43–7.51 (m, 2H)
IR(KBr) 3600–3200(br), 1617, 1525, 1494, 1464, 1361, 1292, 1208, 1178, 1101, 1033 cm$^{-1}$ I-88  $^1$HNMR(CDCl$_3$)δ 2.57(s, 3H), 3.20(s, 3H), 3.56(s, 3H), 3.79(s, 3H), 5.18(s, 2H), 6.84(s, 1H), 7.06–7.15(m, 1H), 7.20–7.40(m, 9H), 7.47–7.57(m, 2H), 7.60–7.75(m, 3H), 8.20–8.25(m, 2H)

I-89  $^1$HNMR(CDCl$_3$)δ 3.44(s, 3H), 3.75(s, 3H), 5.01(s, 1H), 5.18(s, 2H), 6.01(s, 1H), 6.45(s, 1H), 6.88–6.97(m, 2H), 7.07(dd, J=8.4 and 8.4Hz, 1H), 7.15–7.21(m, 1H), 7.27(dd, J=12.3 and 2.1Hz, 1H), 7.29–7.43(m, 3H), 7.45–7.56(m, 4H)

TABLE 27

I-90  $^1$HNMR(CDCl$_3$)δ 1.68(s, 3H), 1.75(d, J=0.9Hz, 3H), 2.55(dt, J=6.9 and 6.9Hz, 2H), 2.70(s, 3H), 3.21(s, 3H), 3.55(s, 3H), 3.77(s, 3H), 4.04(t, J=6.9Hz, 2H), 5.17–5.28(m, 1H), 6.84(s, 1H), 7.04(dd, J=8.4 and 8.4Hz, 1H), 7.11–7.22(m, 2H), 7.34–7.42(m, 2H), 7.65–7.75(m, 2H)
IR(KBr) 1522, 1483, 1361, 1352, 1176, 1156, 1079, 963, 873, 801 cm$^{-1}$ I-91  $^1$HNMR(CDCl$_3$)δ 2.96(s, 3H), 3.52(s, 3H), 3.58(s, 6H), 3.73(s, 3H), 4.89(s, 2H), 5.19(s, 2H), 5.23(s, 2H), 5.25(s, 2H), 6.68(s, 1H), 6.98(d, J=8.4Hz, 1H), 7.04(dd, J=8.4 and 2.1Hz, 1H), 7.11 (m, 2H), 7.25(d, J=2.1Hz, 1H), 7.30–7.40(m, 5H), 7.51(m, 2H)
IR(KBr) 2952, 2935, 2896, 1609, 1521, 1477, 1463, 1438, 1383, 1269, 1249, 1228, 1183, 1153, 1130, 1116, 1078, 1066, 1020, 1008, 984, 944, 922, 903, 832, 801, 730 cm$^{-1}$ I-92  mp 122–124° C.
$^1$HNMR(CDCl$_3$)δ 2.70(brs, 3H), 3.55–3.60(br, 2H), 3.60(s, 3H), 3.75(s, 3H), 3.81–3.83(m, 2H), 3.87(s, 3H), 5.15(s, 2H), 5.68(s, 1H), 6.69(brs, 1H), 6.94(dd, J=2.1, 8.4Hz, 2H), 6.97–7.03(m, 3H), 7.07(d, J=1.8Hz, 1H), 7.38–7.48(m, 5H), 7.51–7.56(m, 2H)
IR(KBr) 3600–2800(br), 1607, 1597, 1550, 1518, 1477, 1462, 1452, 1392, 1289, 1248, 1228, 1175, 1122, 1096, 1084, 1015 cm$^{-1}$

TABLE 27-continued

I-93  $^1$HNMR(CDCl$_3$)δ 2.59(dt, J=6.6, 6.6Hz, 2H), 3.45(s, 3H), 3.74(s, 3H), 4.15(t, J=6.6Hz, 2H), 5.15(dm, J=10.2Hz, 1H), 5.21(dm, J=17.1Hz, 1H), 5.90(m, 1H), 6.45(s, 1H), 6.92(d, J=8.4Hz, 2H), 6.95(s, 2H), 7.06(brs, 1H), 7.53(d, J=8.4Hz, 2H)
IR(Nujol)3570, 3525, 3336, 3205, 1616, 1596, 1524, 1493, 1409, 1315, 1286, 1264, 1239, 1225, 1117, 1072, 821, 783 cm$^{-1}$ I-94  $^1$HNMR(CDCl$_3$)δ 0.36(m, 2H), 0.66(m, 2H), 1.31(m, 1H), 3.45(s, 3H), 3.74(s, 3H), 3.91(d, J=7.2Hz, 2H), 6.44(s, 1H), 6.91(d, J=8.7Hz, 2H), 6.93(m, 2H), 7.07(d, J=1.8Hz, 1H), 7.53(d, J=8.7Hz, 2H)
IR(Nujol)3570, 3491, 3364, 3178, 1617, 1598, 1583, 1524, 1494, 1408, 1313, 1285, 1266, 1240, 1224, 1115, 1072, 1011, 822, 786 cm$^{-1}$ I-95  $^1$HNMR(CDCl$_3$)δ 1.86(s, 3H), 3.45(s, 3H), 3.74(s, 3H), 4.54(s, 2H), 5.04(brs, 1H), 5.12(brs, 1H), 6.45(s, 1H), 6.91(d, J=8.7Hz, 2H), 6.95(m, 2H), 7.08(brs, 1H), 7.53(d, J=8.7Hz, 2H)
IR(Nujol)3536, 3364, 3179, 1614, 1586, 1524, 1493, 1407, 1309, 1284, 1265, 1238, 1226, 1115, 1073, 1011, 887, 821, 782 cm$^{-1}$

TABLE 28

I-96  $^1$HNMR(CDCl$_3$)δ 2.58(t, J=2.4Hz, 1H), 3.45(s, 3H), 3.74(s, 3H), 4.79(d, J=2.4Hz, 2H), 6.45(s, 1H), 6.92(d, J=8.7Hz, 2H), 6.98(dd, J=8.4, 2.1Hz, 1H), 7.07(d, J=8.4Hz, 1H), 7.09(d, J=2.1Hz, 1H), 7.53(d, J=8.7Hz, 2H)
IR(Nujol)3410, 3282, 1612, 1589, 1523, 1489, 1404, 1226, 1114, 1071, 1015, 826 cm$^{-1}$ I-97  $^1$HNMR(CDCl$_3$)δ 2.71(s, 3H), 3.21(s, 3H), 3.38(s, 3H), 3.56(s, 3H), 3.78(s, 3H), 5.47(s, 2H), 6.84(s, 1H), 7.00(d, J=8.6Hz, 1H), 7.34(dd, J=8.6, 2.0Hz, 1H), 7.38(d, J=8.8Hz, 2H), 7.46(d, J=2.0Hz, 1H), 7.55(m, 2H), 7.67(m, 1H), 7.68(d, J=8.8Hz, 2H), 7.99(m, 2H)

I-98  m.p. 200–203° C.
$^1$HNMR(CDCl$_3$)δ 2.38(s, 3H), 2.67(s, 3H), 3.12(s, 3H), 3.21(s, 3H), 3.56(s, 3H), 3.77(s, 3H), 5.14(s, 2H), 6.84(s, 1H), 7.15(d, J=8.7Hz, 1H), 7.21(d, J=8.1Hz, 2H), 7.34(d, J=8.1Hz, 2H), 7.34(dd, J=8.7, 2.4Hz, 1H), 7.38(d, J=8.7Hz, 2H), 7.40(d, J=2.4Hz, 1H), 7.68(d, J=8.7Hz, 2H)
IR(Nujol)1608, 1520, 1480, 1359, 1173, 1156, 1078, 1016, 976, 948, 872, 818, 791 cm$^{-1}$ I-99  $^1$HNMR(CDCl$_3$)δ 2.72(s, 3H), 3.13(s, 3H), 3.21(s, 3H), 3.55(s, 3H), 3.78(s, 3H), 5.15(s, 2H), 6.84(s, 1H), 7.09(d, J=8.7Hz, 1H), 7.12(dd, J=8.7, 7.2Hz, 1H), 7.35(dd, J=8.7, 2.1Hz, 1H), 7.38(d, J=8.7Hz, 2H), 7.40(d, J=2.1Hz, 1H), 7.45(dd, J=8.7, 5.1Hz, 1H), 7.68(d, J=8.7Hz, 2H)

I-100  $^1$HNMR(CDCl$_3$)δ 2.76(s, 3H), 3.19(s, 3H), 3.21(s, 3H), 3.55(s, 3H), 3.78(s, 3H), 5.25(s, 2H), 6.85(s, 1H), 7.13(d, J=8.4Hz, 1H), 7.32(dd, J=8.4, 1.8Hz, 1H), 7.36(dd, J=8.4, 1.8Hz, 1H), 7.38(d, J=8.7Hz, 2H), 7.42(d, J=1.8Hz, 1H), 7.45(d, J=1.8Hz, 1H), 7.59(d, J=8.4Hz, 1H), 7.68(d, J=8.7Hz, 2H)

I-101  m.p. 103–105° C.
$^1$HNMR(CDCl$_3$)δ 2.18(dd, J=1.5, 1.2Hz, 3H), 3.45(s, 3H), 3.74(s, 3H), 4.79(dd, J=5.7, 1.2Hz, 2H), 5.81(dt, J=5.7, 1.5Hz, 1H), 6.45 (s, 1H), 6.92(d, J=8.7Hz, 2H), 6.95(s, 1H), 6.96(s, 1H), 7.07(s, 1H), 7.52(d, J=8.7Hz, 2H)
IR(KBr) 3527, 3328, 2930, 1614, 1593, 1523, 1492, 1463, 1408, 1262, 1235, 1225, 1119, 1072, 1010, 828, 805 cm$^{-1}$

TABLE 29

I-102  m.p. 95–99° C.
$^1$HNMR(CDCl$_3$)δ 3.45(s, 3H), 3.74(s, 3H), 4.67(s, 2H), 5.47(m, 1H), 5.55(dd, J=2.7, 1.2Hz, 1H), 6.45(s, 1H), 6.92(d, J=8.7Hz, 2H), 7.01(m, 2H), 7.04(d, J=1.8Hz, 1H), 7.53(d, J=8.7Hz, 2H)

I-103  $^1$HNMR(CDCl$_3$)δ 3.45(s, 3H), 3.75(s, 3H), 4.59(d, J=4.2Hz, 2H), 6.45(s, 1H), 6.45(m, 1H), 6.55(d, J=12.9Hz, 1H), 6.92(d, J=8.7Hz, 2H), 6.96(m, 2H), 7.08(brs, 1H), 7.53(d, J=8.7Hz, 2H)

I-104  $^1$HNMR(CDCl$_3$)δ 3.45(s, 3H), 3.75(s, 3H), 4.64(dd, J=6.0 and 1.2Hz, 2H), 6.23(dt, J=13.2 and 6.0Hz, 1H), 6.42(dt, J=13.2 and 1.2Hz, 1H), 6.45(s, 1H), 6.91(d, J=8.7Hz, 2H), 6.96(brs, 2H), 7.08(brs, 1H), 7.58(d, J=8.7Hz, 2H)

TABLE 29-continued

I-105 ¹HNMR(CDCl₃)δ 3.46(s, 3H), 3.75(s, 3H), 3.98(d-like, J=7.2Hz, 1H), 4.64(d-like, J=3.9Hz, 1H), 6.04(dt, J=15.3, 4.8Hz, 1H), 6.06(1H, dt, J=15.3, 6.0Hz, 1H), 6.45(s, 1H), 6.92(d, J=8.7Hz, 2H), 6.95(s, 1H), 7.08(s, 2H), 7.53(d, J=8.7Hz, 2H)

I-106 foam
¹HNMR(CDCl₃)δ 1.76(s, 3H), 1.83(s, 3H), 2.08(s, 3H), 3.36(s, 3H), 3.71(s, 3H), 4.61(d, J=7.0Hz, 2H), 4.94(s, 1H), 5.54(t, J=7.0Hz, 1H), 5.70(s, 1H), 6.64(d, J=8.4, 2.0Hz, 1H), 6.74(s, 1H), 6.84(d, J=2.0Hz, 1H)
IR(KBr) 3410, 1520, 1476, 1390, 1243, 1225, 1101, 1084, 834, 812, 775 cm⁻¹

I-107 m.p. 112–114° C.
¹HNMR(CDCl₃)δ 3.03(s, 3H), 3.57(s, 3H), 3.74(s, 3H), 3.87(s, 3H), 4.90(S, 2H), 5.15(s, 2H), 5.63(brs, 1H), 6.68(s, 1H), 6.91–7.07(m, 5H), 7.38–7.51(m, 5H), 7.53(m, 2H)
IR(KBr) 3512, 2952, 2936, 1607, 1519, 1468, 1442, 1382, 1284, 1253, 1229, 1215, 1185, 1156, 1112, 1079, 1065, 1020, 983, 956, 914, 831 cm⁻¹

I-108 ¹HNMR(CDCl₃)δ 2.20(d, J=1.2Hz, 3H), 2.76(s, 3H), 3.22(s, 3H), 3.24(s, 3H), 3.56(s, 3H), 3.78(s, 3H), 4.65(m, 2H), 5.96(m, 1H), 7.07(d, J=8.4Hz, 1H), 7.34–7.41(m, 4H), 7.68(m, 2H)

TABLE 30

I-109 m.p. 153–154° C.
¹HNMR(CDCl₃)δ 2.20(d, J=1.5Hz, 3H), 2.75(s, 3H), 3.21(s, 3H), 3.23(s, 3H), 3.56(s, 3H), 3.78(s, 3H), 4.81(m, 2H), 5.80(m, 1H), 6.84(s, 1H), 7.10(d, J=8.1Hz, 1H), 7.34–7.41(m, 4H), 7.68(m, 2H)
IR(KBr) 1519, 1481, 1390, 1364, 1234, 1177, 1150, 1119, 1077, 1011, 969, 945, 876, 816, 799, 521 cm⁻¹

I-110 ¹HNMR(CDCl₃)δ 2.68(s, 3H), 3.11(s, 3H), 3.21(s, 3H), 3.56(s, 3H), 3.78(s, 3H), 3.83(s, 3H), 5.11(s, 2H), 6.84(s, 1H), 6.93(d, J=8.7Hz, 2H), 7.16(d, J=8.7Hz, 1H), 7.35(dd, J=8.7, 2.1Hz, 1H), 7.36–7.40(m, 5H), 7.68(d, J=8.7Hz, 2H)

I-111 ¹HNMR(CDCl₃)δ 2.78(s, 3H), 3.22(s, 6H), 3.55(s, 3H), 3.78(s, 3H), 5.23(s, 2H), 6.85(s, 1H), 7.08(d, J=8.7Hz, 1H), 7.34(dd, J=8.7, 2.1Hz, 1H), 7.39(d, J=8.7Hz, 2H), 7.42(d, J=2.1Hz, 1H), 7.44(brs, 2H), 7.68(d, J=8.7Hz, 2H), 8.70(brs, 2H)

I-112 ¹HNMR(CDCl₃)δ 2.70(s, 3H), 3.21(s, 3H), 3.24(s, 3H), 3.55(s, 3H), 3.78(s, 3H), 5.33(s, 2H), 6.84(s, 1H), 7.15(d, J=8.4Hz, 1H), 7.27(dd, J=7.5, 4.2Hz, 1H), 7.33(dd, J=8.4, 2.4Hz, 1H), 7.38(d, J=8.7Hz, 2H), 7.42(d, J=2.4Hz, 1H), 7.62(brd, J=7.5Hz, 1H), 7.68(d, J=8.7Hz, 2H), 7.76(ddd, J=7.5, 7.5, 1.8Hz, 1H), 8.61(d, J=4.2Hz, 1H)

I-113 ¹HNMR(CDCl₃)δ 2.76(s, 3H), 3.15(s, 3H), 3.21(s, 3H), 3.55(s, 3H), 3.78(s, 3H), 5.22(s, 2H), 6.85(s, 1H), 7.17(d, J=8.4Hz, 1H), 7.38(d, J=8.4, 2.1Hz, 1H), 7.38(m, 1H), 7.39(d, J=8.7Hz, 2H), 7.42(d, J=2.1Hz, 1H), 7.68(d, J=8.7Hz, 2H), 7.88(d, J=7.8Hz, 1H), 7.64(brs, 1H), 8.73(brs, 1H)

I-114 ¹HNMR(CDCl₃)δ 3.45(s, 3H), 3.74(s, 3H), 5.10(s, 2H), 6.45(s, 1H), 6.91(d, J=8.7Hz, 2H), 6.95(dd, J=8.4, 2.1Hz, 1H), 7.03(d, J=8.4Hz, 1H), 7.08(d, J=2.1Hz, 1H), 7.23(brd, J=7.8Hz, 2H), 7.34(brd, J=7.8Hz, 2H), 7.53(d, J=8.7Hz, 2H)
IR(Nujol)3464, 3344, 1611, 1581, 1523, 1490, 1266, 1113, 1073, 1011, 1000, 821, 782 cm⁻¹

I-115 ¹HNMR(CDCl₃)δ 3.45(s, 3H), 3.75(s, 3H), 5.11(s, 2H), 6.45(s, 1H), 6.92(d, J=8.7Hz, 2H), 6.96(dd, J=8.4, 2.1Hz, 1H), 7.01(d, J=8.4Hz, 1H), 7.09(d, J=2.1Hz, 1H), 7.11(dd, J=8.7, 8.7Hz, 2H), 7.42(dd, J=8.7, 5.4Hz, 2H), 7.54(d, J=8.7Hz, 2H)
IR(Nujol)3560, 3400, 1612, 1589, 1522, 1492, 1260, 1225, 1116, 1068, 1006, 992, 841, 826, 803, 786 cm⁻¹

TABLE 31

I-116 ¹HNMR(CDCl₃)δ 3.45(s, 3H), 3.75(s, 3H), 5.23(s, 2H), 6.45(s, 1H), 6.92(d, J=8.7Hz, 2H), 6.97(brs, 2H), 7.11(brs, 1H), 7.31(dd, J=8.4, 2.1Hz, 1H), 7.46(d, J=8.4Hz, 1H), 7.47(d, J=2.1Hz, 1H), 7.54(d, J=8.7Hz, 2H)
IR(Nujol)3460, 3359, 1610, 1594, 1522, 1490, 1264, 1164, 1110, 1072, 1008, 877, 824, 781 cm⁻¹

TABLE 31-continued

I-117 ¹HNMR(CDCl₃)δ 3.45(s, 3H), 3.75(s, 3H), 3.84(s, 3H), 5.07(s, 2H), 6.45(s, 1H), 6.92(d, J=8.7Hz, 2H), 6.95(d, J=9.0Hz, 2H), 6.96(dd, J =8.4, 1.8Hz, 1H), 7.04(d, J=8.4Hz, 1H), 7.08(d, J=1.8Hz, 1H), 7.37(d, J=8.7Hz, 2H), 7.53(d, J=9.0Hz, 2H)
IR(Nujol)3400, 1612, 1586, 1516, 1488, 1246, 1174, 1113, 1070, 1011, 823 cm⁻¹

I-118 ¹HNMR(DMSO-d₆)δ 3.29(s, 3H), 3.64(s, 3H), 5.20(s, 2H), 6.39(s, 1H), 6.64(dd, J=8.4, 2.1Hz, 1H), 6.79(d, J=2.1Hz, 1H), 6.84(d, J=8.7Hz, 2H), 6.92(d, J=8.4Hz, 1H), 7.43(d, J=8.7Hz, 2H), 7.52(d, J=6.0Hz, 2H), 8.59(d, J=6.0Hz, 2H)
IR(Nujol)3473, 3441, 1610, 1582, 1523, 1493, 1404, 1241, 1112, 1074, 1005, 816, 782 cm⁻¹

I-119 ¹HNMR(CDCl₃)δ 3.45(s, 3H), 3.74(s, 3H), 5.27(s, 2H), 6.45(s, 1H), 6.92(dd, J=8.4, 1.8Hz, 1H), 6.93(d, J=8.7Hz, 2H), 7.11(d, J=8.4Hz, 1H), 7.12(d, J=1.8Hz, 1H), 7.31(m, 1H), 7.36(brd, J=7.5Hz, 1H), 7.53(d, J=8.7Hz, 2H), 7.77(ddd, J=7.5, 7.5, 1.8Hz, 1H), 8.66(d, J=5.0Hz, 1H)
IR(Nujol)3555, 3467, 3342, 1608, 1597, 1586, 1522, 1466, 1210, 1117, 1080, 1016, 822, 761 cm⁻¹

I-120 ¹HNMR(CDCl₃)δ 3.45(s, 3H), 3.74(s, 3H), 5.21(s, 2H), 6.46(s, 1H), 6.91(d, J=8.7Hz, 2H), 6.99(brs, 2H), 7.11(brs, 1H), 7.40(dd, J=7.5, 5.0Hz, 1H), 7.53(d, J=8.7Hz, 2H), 7.83(d, J=7.5Hz, 1H), 8.64(brd, J=5.0Hz, 1H), 8.74(brs, 1H)
IR(Nujol)3342, 1609, 1586, 1522, 1489, 1253, 1118, 1074, 1010, 827, 782 cm⁻¹

I-121 m.p. 166–168° C.
¹HNMR(CDCl₃)δ 3.45(s, 3H), 3.75(s, 3H), 4.77(d, J=6.3Hz, 2H), 6.22(t, J=6.3Hz, 1H), 6.93(d, J=8.7Hz, 2H), 6.93(d, J=8.7Hz, 1H), 6.98(dd, J=8.7, 1.8Hz, 1H), 7.08(d, J=1.8Hz, 1H), 7.53(d, J=8.7Hz, 2H)
IR(KBr) 3474, 3411, 2957, 2930, 1615, 1589, 1569, 1523, 1492, 1407, 1286, 1263, 1230, 1113, 1070, 825 cm⁻¹

TABLE 32

I-122 m.p. 190–192° C.
¹HNMR(CDCl₃)δ 2.56(s, 3H), 3.22(s, 3H), 3.56(s, 3H), 3.79(s, 3H), 5.17(s, 2H), 5.73(s, 1H), 6.84(s, 1H), 6.93(dd, J=8.1 and 1.9Hz, 1H), 7.02(d, J=8.1Hz, 1H), 7.05(d, J=1.9Hz, 1H), 7.37–7.45(m, 1H), 7.71(d, J=8.6Hz, 2H)
IR(KBr) 3512, 1519, 1484, 1367, 1174, 1150, 1078, 957, 870, 798 cm⁻¹

I-123 foam
¹HNMR(CDCl₃)δ 3.08(s, 3H), 3.21(s, 3H), 3.44(s, 3H), 3.78(s, 3H), 5.15(s, 2H), 6.95(s, 1H), 7.11(d, J=8.7Hz, 1H), 7.33–7.47(m, 9H), 7.71(d, J=8.7Hz, 2H), 13.3–14.5(brs, 1H)
IR(KBr) : 3422, 1735, 1702, 1520, 1471, 1366, 1175, 1150, 1118, 971, 954, 863, 807 cm⁻¹

I-124 m.p. 258–259° C. (dec)
¹HNMR(DMSO-d₆)δ 3.32(s, 3H), 3.69(s, 3H), 5.10(2H, s), 6.65(dd, J=8.4, 2.1Hz, 1H), 6.79(d, J=2.1Hz, 1H), 6.86(d, J=8.4Hz, 2H), 6.90(s, 1H), 6.94(d, J=8.4Hz, 2H), 7.30–7.54(m, 7H), 8.98(s, 1H), 9.63(s, 1H)
IR(KBr) : 3437, 3157, 1702, 1610, 1590, 1521, 1474, 1464, 1379, 1260, 1245, 1224, 1081, 1014, 952, 834, 793, 748, 698 cm⁻¹

I-125 ¹HNMR(CDCl₃)δ 1.75(s, 3H), 1.81(s, 3H), 3.21(s, 3H), 3.41(s, 3H), 3.68(s, 3H), 3.77(s, 3H), 4.61(d, J=6.8Hz, 2H), 5.50(t, J=6.8Hz, 1H), 6.93(s, 1H), 7.02(d, J=8.5Hz, 1H), 7.27(d, J=8.5, 2.3Hz, 1H), 7.33(d, J=2.3Hz, 1H), 7.38(d, J=8.6Hz, 2H), 7.71(d, J=8.6Hz, 2H)

I-126 ¹HNMR(CDCl₃)δ 1.75(s, 3H), 1.81(s, 3H), 3.41(s, 3H), 3.65(s, 3H), 3.76(s, 3H), 4.59(d, J=6.0Hz, 2H), 5.06(s, 1H), 5.51(t, J=6.6Hz, 1H), 5.67(s, 1H), 6.83(dd, J=8.4, 2.1Hz, 1H), 6.87(s, 1H), 6.90–6.93(m, 3H), 6.98(d, J=2.1Hz, 1H), 7.54(d, J=9.0Hz, 2H)

I-127 m.p. 116–117° C.
¹HNMR(DMSO-d₆)δ 1.72(s, 3H), 1.76(s, 3H), 3.32(s, 3H), 3.70(s, 3H), 4.53(d, J=7.1Hz, 2H), 5.48(t, J=7.1Hz, 1H), 6.65(dd, J=8.4, 2.1Hz, 1H), 6.73(d, J=2.1Hz, 1H), 6.86(d, J=8.6Hz, 2H), 6.88(d, J=8.4Hz, 1H), 6.93(s, 1H), 7.47(d, J=8.6Hz, 2H), 8.84(s, 1H), 9.62(s, 1H), 11.9–13.4(brs, 1H)
IR(KBr) : 3446, 1703, 1611, 1593, 1520, 1471, 1380, 1260, 1225, 1081, 997, 952, 838 cm⁻¹

TABLE 33

I-128 oil
$^1$HNMR(CDCl$_3$)δ 1.65(s, 3H), 1.78(s, 3H), 2.96(s, 3H), 3.22(s, 3H), 3.25(s, 3H), 3.55(s, 3H), 3.79(s, 3H), 4.77(d, J=7.8Hz, 2H), 5.53(t, J=7.8Hz, 1H), 6.87(s, 1H), 7.39&7.67(ABq, J=8.7Hz, 4H), 7.70(d, J=2.1Hz, 1H), 7.86(d, J=2.1Hz, 1H), 10.36(s, 1H)
IR(CHCl$_3$)1691, 1473, 1374, 1230, 1226, 1209, 1178, 1152, 1086, 969, 874, 805 cm$^{-1}$ I-129 oil
$^1$HNMR(CDCl$_3$)δ 1.73(d, J=0.9Hz, 3H), 1.80(s, 3H), 2.89(s, 3H), 3.20(s, 3H), 3.22(s, 3H), 3.54(s, 3H), 3.79(s, 3H), 4.66(d, J=7.8Hz, 2H), 4.77(s, 2H), 5.55(m, 1H), 6.85(s, 1H), 7.39&7.68(ABq, J=9.0Hz, 4H), 7.39(d, J=2.1Hz, 1H), 7.44(d, J=2.1Hz, 1H)
IR(CHCl$_3$)1475, 1372, 1230, 1178, 1151, 1085, 969, 874 cm$^{-1}$ I-130 m.p. 189–190° C.
$^1$HNMR(CDCl$_3$)δ 1.36(s, 9H), 2.81(s, 3H), 3.22(s, 3H), 3.30(s, 3H), 3.56(s, 3H), 3.79(s, 3H), 6.86(s, 1H), 7.36–7.42(m, 3H), 7.54(d, J=1.8Hz, 1H), 7.67–7.72(m, 3H)
IR(KBr) 1472, 1363, 1331, 1179, 1153, 1082, 961, 950, 877, 846, 817, 791, 526 cm$^{-1}$ I-131 m.p. 147–148° C.
$^1$HNMR(CDCl$_3$)δ 2.95(s, 3H), 3.18(s, 3H), 3.22(s, 3H), 3.55(s, 3H), 3.79(s, 3H), 5.28(s, 2H), 6.86(s, 1H), 7.38–7.44(m, 7H), 7.67(m, 2H), 7.75(d, J=2.1Hz, 1H), 7.83(d, J=2.1Hz, 1H)
IR(KBr) 1687, 1512, 1472, 1365, 1352, 1234, 1201, 1180, 1151, 1082, 971, 947, 870, 846, 810, 794, 703, 523 cm$^{-1}$ I-132 m.p. 122–124° C.
$^1$HNMR(CDCl$_3$)δ 1.68(s, 3H), 1.74(s, 3H), 2.80(s, 3H), 3.22(s, 3H), 3.28(s, 3H), 3.56(s, 3H), 3.62(d, J=7.8Hz, 2H), 3.78(s, 3H), 5.31(m, 1H), 6.85(s, 1H), 7.34(dd, J=8.1Hz, J=1.8Hz, 1H), 7.39&7.68(ABq, J=8.7Hz, 4H), 7.43(d, J=8.1Hz, 1H), 7.46(d, J=1.8Hz, 1H)
IR(KBr) 1474, 1362, 1180, 1151, 1076, 1014, 968, 944, 870, 816, 799, 521 cm$^{-1}$ I-133 $^1$HNMR(CDCl$_3$)δ 1.73(d, J=0.9Hz, 3H), 1.82(s, 3H), 3.44(s, 3H), 3.75(s, 3H), 4.54(d, J=6.9Hz, 2H), 4.78(s, 2H), 5.30(s, 1H), 5.61(m, 1H), 5.67(s, 1H), 6.01(s, 1H), 6.45(s, 1H), 6.92&7.52(ABq, J=8.7Hz, 4H), 7.02(d, J=2.1Hz, 1H), 7.05(d, J=2.1Hz, 1H)
IR(KBr) 3428, 1612, 1522, 1483, 1458, 1403, 1362, 1334, 1304, 1266, 1226, 1174, 1116, 1083, 1024, 970, 938 cm$^{-1}$

TABLE 34

I-134 m.p. 167–168° C.
$^1$HNMR(CDCl$_3$)δ 1.39(d, J=1.2Hz, 3H), 1.70(s, 3H), 3.36(d, J=8.1Hz, 2H), 3.45(s, 3H), 3.74(s, 3H), 4.98(s, 1H), 5.29(m, 1H), 5.96(s, 1H), 6.45(s, 1H), 6.78(s, 1H), 6.93&7.54(ABq, J=8.7Hz, 4H), 6.96(dd, J=7.8Hz, J=1.8Hz, 1H), 7.09(d, J=1.8Hz, 1H), 7.49(d, J=7.8Hz, 1H)
IR(KBr) 3413, 3365, 2931, 1611, 1552, 1520, 1502, 1475, 1455, 1441, 1402, 1360, 1323, 1262, 1227, 1206, 1182, 1170, 1162, 1114, 1100, 1081, 1052, 1014, 941, 835, 816, 587, 542 cm$^{-1}$

I-135 m.p. 183–184° C.
$^1$HNMR(CDCl$_3$)δ 3.46(s, 3H), 3.74(s, 3H), 3.83(s, 3H), 4.78(m, 2H), 5.99(m, 1H), 6.44(m, 1H), 6.45(s, 1H), 6.92(d, J=8.7Hz, 2H), 6.94(dd, J=8.1, 1.8Hz, 1H), 7.00(d, J=8.1Hz, 1H), 7.10(d, J=1.8Hz, 1H), 7.53(d, J=8.7Hz, 2H)
IR(KBr) 3383, 2929, 1699, 1523, 1491, 1405, 1262, 1236, 1206, 1173, 1116, 1071, 1011, 822 cm$^{-1}$

I-136 $^1$HNMR(CD$_3$OD)δ 1.26(s, 3H), 1.29(s, 3H), 3.38(s, 3H), 3.68(s, 3H), 3.80(dd, J=8.4, 2.7Hz, 1H), 3.96(dd, J=9.6, 8.4Hz, 1H), 4.34(dd, J=9.6, 2.7Hz, 1H), 6.44(s, 1H), 6.80(dd, J=8.1, 1.8Hz, 1H), 6.85(d, J=8.7Hz, 2H), 6.86(d, J=1.8Hz, 1H), 7.96(d, J=8.1Hz, 1H), 7.46(d, J=8.7Hz, 2H)
IR(Nujol)3367, 1612, 1588, 1523, 1489, 1254, 1226, 1115, 1072, 1013, 940, 814 cm$^{-1}$ I-137 $^1$HNMR(CD$_3$OD)δ 3.38(s, 3H), 3.68(s, 3H), 4.02(dd, J=11.0, 3.6Hz, 1H), 4.12(dd, J=11.0, 1.8Hz, 1H), 5.48(dd, J=3.6, 1.8Hz, 1H), 6.43(s, 1H), 6.83–6.87(m, 3H), 6.85(d, J=8.7Hz, 2H), 7.46(d, J=8.7Hz, 2H)
IR(Nujol)3410, 1612, 1588, 1522, 1487, 1269, 1231, 1114, 1071, 1011, 947, 824 cm$^{-1}$ I-138 $^1$HNMR(CD$_3$OD)δ 3.38(s, 3H), 3.68(s, 3H), 4.70(d, J=5.4Hz, 2H), 6.43(s, 1H), 6.80(dd, J=8.1, 2.1Hz, 1H), 6.85(d, J=8.4Hz, 2H), 6.88(d, J=2.1Hz, 1H), 6.98(d, J=8.1Hz, 1H), 7.46(d, J=8.4Hz, 2H), 7.62(t, J=5.4Hz, 1H)
IR(Nujol)3368, 1612, 1589, 1523, 1489, 1253, 1226, 1114, 1072, 1011, 940, 825 cm$^{-1}$ I-139 $^1$HNMR(CDCl$_3$)δ 3.45(s, 3H), 3.74(s, 3H), 3.92(s, 3H), 4.75(d, J=5.1Hz, 2H), 6.45(s, 1H), 6.91(d, J=8.7Hz, 2H), 6.92(d, J=6.0Hz, 1H), 7.00(dd, J=6.0, 1.8Hz, 1H), 7.09(d, J=1.8Hz, 1H), 7.52(d, J=8.7Hz, 2H), 7.58(t, J=5.1Hz, 1H)
IR(Nujol)3399, 1612, 1589, 1523, 1489, 1252, 1226, 1115, 1072, 1043, 1014, 941, 825 cm$^{-1}$

TABLE 35

I-140 $^1$HNMR(CD$_3$OD)δ 3.38(s, 3H), 3.68(s, 3H), 4.51(s, 2H), 4.71(d, J=5.4Hz, 2H), 6.43(s, 1H), 6.80(dd, J=8.4, 2.1Hz, 1H), 6.85(d, J=8.4Hz, 2H), 6.87(d, J=2.1Hz, 1H), 6.98(d, J=8.4Hz, 1H), 7.46(d, J=8.4Hz, 2H), 7.75(t, J=5.4Hz, 1H)
IR(Nujol)3384, 1611, 1588, 1523, 1489, 1252, 1227, 1115, 1072, 1014, 824, 758 cm$^{-1}$ I-141 $^1$HNMR(CDCl$_3$)δ 3.45(s, 3H), 3.74(s, 3H), 4.76(d, J=5.1Hz, 2H), 5.15(s, 2H), 6.45(s, 1H), 6.86(d, J=8.4Hz, 1H), 6.92(d, J=8.7Hz, 2H), 6.94(dd, J=8.4, 2.1Hz, 1H), 7.08(d, J=2.1Hz, 1H), 7.31–7.40(m, 5H), 7.53(d, J=8.7Hz, 2H), 7.65(t, J=5.1Hz, 1H)
IR(Nujol)3399, 1011, 1588, 1523, 1489, 1251, 1225, 1115, 1072, 1013, 940, 825 cm$^{-1}$ I-142 $^1$HNMR(CDCl$_3$-CD$_3$OD1:1)δ 3.26(s, 3H), 2.64(m, 4H), 3.13(m, 4H), 3.44(s, 3H), 3.73(s, 3H), 4.78(d, J=4.5Hz, 2H), 6.45(s, 1H), 6.90(d, J=8.7Hz, 2H), 6.90(dd, J=8.4, 2.1Hz, 1H), 6.99(d, J=2.1Hz, 1H), 7.00(d, J=8.4Hz, 1H), 7.12(t, J=4.5Hz, 1H), 7.49(d, J=8.7Hz, 2H)
IR(Nujol)3492, 3297, 1607, 1561, 1523, 1486, 1247, 1224, 1113, 1011, 957, 828, 799 cm$^{-1}$ I-143 $^1$HNMR(CDCl$_3$)δ 3.09(m, 4H), 3.45(s, 3H), 3.74(s, 3H), 3.86(m, 4H), 4.82(d, J=4.2Hz, 2H), 6.44(s, 1H), 6.92(d, J=8.7Hz, 2H), 6.98(dd, J=8.4, 1.8Hz, 1H), 7.00(t, J=4.2Hz, 1H), 7.04(d, J=8.4Hz, 1H), 7.07(d, J=1.8Hz, 1H), 7.53(d, J=8.7Hz, 2H)
IR(Nujol)3366, 1611, 1586, 1523, 1488, 1268, 1227, 1114, 1070, 1011, 823 cm$^{-1}$ I-144 $^1$HNMR(CDCl$_3$)δ 1.29(t, J=6.9Hz, 3H), 2.65(dd, J=15.9, 6.6Hz, 1H), 2.81(dd, J=15.9, 6.6Hz, 1H), 3.44(s, 3H), 3.75(s, 3H), 4.03(dd, J=11.4, 6.9Hz, 1H), 4.20(q, J=6.9Hz, 2H), 4.35(dd, J=11.4, 2.4Hz, 1H), 4.66(ddt, J=6.9, 6.6, 2.4Hz, 1H), 6.44(s, 1H), 6.92(d, J=8.7Hz, 2H), 6.96–7.01(m, 3H), 7.53(d, J=8.7Hz, 2H)

I-145 oil
$^1$HNMR(CDCl$_3$)δ 1.68(s, 3H), 1.74(d, J=0.9Hz, 3H), 2.55(m, 2H), 3.44(s, 3H), 3.75(s, 3H), 4.04(t, J=7.2Hz, 2H), 4.97(bra, 1H), 5.23(m, 1H), 6.00(s, 1H), 6.45(s, 1H), 6.92&7.53(ABq, J=8.7Hz, 4H), 7.02(m, 1H), 7.17–7.22(m, 2H)
IR(KBr) 1613, 1525, 1490, 1475, 1463, 1454, 1402, 1304, 1269, 1231, 1112, 1072, 1019, 827 cm$^{-1}$

TABLE 36

I-146 m.p. 256–257° C.
$^1$HNMR(DMSO-d$_6$)δ 3.35(s, 3H), 3.44(s, 3H), 3.74(s, 3H), 5.22(s, 2H), 7.06(s, 1H), 7.28–7.56(m, 11H), 7.69(s, 1H), 7.76(d, J=8.6Hz, 2H)
IR(KBr): 3479, 3360, 1672, 1517, 1465, 1361, 1339, 1295, 1261, 1228, 1172, 1144, 1118, 1013, 957, 870, 852, 804, 751 cm$^{-1}$

I-147 m.p.. 163–164° C.
$^1$HNMR(CDCl$_3$)δ 1.74(s, 3H), 1.81(s, 3H), 3.43(s, 3H), 3.74(s, 3H), 4.58(d, J=6.8Hz, 2H), 5.50(t, J=6.8Hz, 1H), 5.80(s, 1H), 6.37(s, 1H), 6.86–6.95(m, 5H), 6.90(d, J=8.6Hz, 2H), 6.99(s, 1H), 7.49(d, J=8.6Hz, 2H)
IR(KBr): 3533, 3412, 3350, 1655, 1609, 1588, 1519, 1469, 1373, 1274, 1245, 1227, 1131, 1082, 1060, 999, 954, 838 cm$^{-1}$

I-148 $^1$HNMR(CDCl$_3$)δ 2.88(s, 3H), 3.22(s, 3H), 3.54(s, 3H), 3.77(s, 3H), 5.35(m, 2H), 6.85(s, 1H), 7.24(d, J=9.0Hz, 1H), 7.39(d, J=8.7Hz, 2H), 7.42–7.46(m, 5H), 7.65(d,d, J=9.0&2.1Hz, 1H), 7.68(d, J=8.7Hz, 2H), 8.26(d, J=2.1Hz, 1H)

TABLE 36-continued

I-149 ¹HNMR(CDCl₃)δ 1.80(s, 3H), 1.85(s, 3H), 3.43(s, 3H), 3.74(s, 3H), 4.80(d, J=6.9Hz, 2H), 5.76(t, J=6.9Hz, 1H), 6.46(s, 1H), 6.92 (d, J=8.4Hz, 2H), 7.14(d, J=8.7Hz, 1H), 7.49(d, J=8.4Hz, 2H)7.70 (d.d, J=8.7&2.1Hz, 1H), 8.28(d, J=2.1Hz, 1H)
IR(KBr) 3472, 1707, 1671, 1610, 1520, 1482, 1460, 1426, 1269, 1226, 1119, 1076, 1012 cm⁻¹

I-150 ¹HNMR(CDCl₃)δ 1.76(s, 3H), 1.81(s, 3H), 2.63(s, 3H), 3.21(s, 3H), 3.55(s, 3H), 3.77(s, 3H), 4.62(d, J=6.3Hz, 2H), 4.73(s, 2H), 5.50(t, J=6.3Hz, 1H), 6.84(s, 1H), 6.99(d, J=9.0Hz, 1H), 7.51–7.42(m, 9H), 7.70(d, J=9.0Hz, 2H)
IR(KBr) 3432, 1607, 1512, 1479, 1364, 1234, 1176, 1151, 1079, 1016 cm⁻¹

I-151 ¹HNMR(CDCl₃)δ 1.58(s, 3H), 1.81(s, 3H), 3.45(s, 3H), 3.73(s, 3H), 4.61(d, J=6.6Hz, 2H), 4.72(s, 2H), 5.52(t, J=6.6Hz, 1H), 6.45 (s, 1H), 6.91(d, J=8.7Hz, 2H), 6.98(d, J=8.4Hz, 1H), 7.36(d.d, J= 8.4&2.1Hz, 1H), 7.38(J=2.1Hz, 1H), 7.50(d, J=8.4Hz, 2H)
IR(KBr) 3580, 3411, 1611, 1521, 1485, 1464, 1397, 1233, 1113, 1077, 1024, 1001 cm⁻¹

I-152 ¹HNMR(CDCl₃)δ 3.50(s, 3H), 3.77(s, 3H), 5.15(s, 2H), 5.72(s, 1H), 6.03(s, 2H), 6.71(d.d, J=8.4&2.1Hz, 1H), 6.91(d, J=8.4Hz, 1H), 6.97(s, 1H), 6.98(d, J=8.4Hz, 1H), 7.07(d.d, J= 8.4&2.1Hz, 1H), 7.16(d, J=2.1Hz, 1H), 7.34–7.50(m, 5H), 989(s, 1H)
IR(KBr) 3446, 1697, 1587, 1511, 1470, 1383, 1285, 1240, 1127, 1036 cm⁻¹

TABLE 37

I-153 ¹HNMR(CDCl₃)δ 3.78(s, 3H), 3.79(s, 3H), 4.87(s, 1H), 5.16(s, 2H), 5.70(s, 1H), 6.88–6.91(m, 2H), 6.97(s, 1H), 7.00(s, 1H), 6.99 (d, J=8.4Hz, 1H), 7.08(dd, J=2.1, 8.4Hz, 1H), 7.23(d, J=2.1Hz, 1H), 7.34–7.49(m, 7H)

I-154 ¹HNMR(CDCl₃)δ 1.69(s, 3H), 1.74(s, 3H), 2.51–2.58(m, 2H), 3.19(s, 3H), 3.21(s, 3H), 3.79(s, 3H), 3.80(s, 3H), 4.07(t, J=6.9Hz, 2H), 5.18–5.27(m, 1H), 6.92(s, 1H), 6.95(s, 1H), 7.05(d, J=8.7Hz, 1H), 7.32–7.37(m, 2H), 7.49(dd, J=2.1, 8.7Hz, 1H), 7.58(d, J= 2.1Hz, 1H), 7.60–7.64(m, 2H)

I-155 ¹HNMR(CDCl₃)δ 1.69(s, 3H), 1.75(s, 3H), 2.53(q, J=6.9Hz, 2H), 3.77(s, 3H), 3.78(s, 3H), 4.07(t, J=6.9Hz, 2H), 4.97(s, 3H), 5.20–5.25(m, 1H), 5.71(s, 1H), 6.87–6.93(m, 3H), 7.07(dd, J=1.8, 8.4Hz, 1H), 7.20(d, J=1.8Hz, 1H), 7.45–7.50(m, 2H)

I-156 m.p. 163–175° C.
¹HNMR(CDCl₃)δ 2.76(s, 3H), 3.19(s, 3H), 3.22(s, 3H), 3.54(s, 3H), 3.79(s, 3H), 5.20(s, 2H), 5.68(s, 1H), 6.84(s, 1H), 6.97(d, J= 1.8Hz, 1H), 6.99(d, J=1.8Hz, 1H), 7.37–7.47(m, 7H), 7.68(m, 2H)
IR(KBr) 3436, 1480, 1415, 1391, 1363, 1233, 1178, 1151, 1079, 1024, 969, 953, 875, 801, 522 cm⁻¹

I-157 m.p. 176–178° C.
¹HNMR(CDCl₃)δ 2.08(s, 3H), 2.40, (s, 3H), 2.72(s, 3H), 3.21(s, 3H), 3.22(s, 3H), 3.55(s, 3H), 3.79(s, 3H), 5.13(s, 2H), 6.86(s, 1H), 7.39 and 7.68(ABq, J=8.7Hz, 4H), 7.47(d, J=2.1Hz, 1H), 7.49(d, J=2.1Hz, 1H)
IR(KBr) 1770, 1747, 1477, 1391, 1366, 1235, 1180, 1152, 1077, 873, 799, 522 cm⁻¹

I-158 m.p. 175–177° C.
¹HNMR(CDCl₃)δ 2.87(s, 3H), 3.13(s, 6H), 3.22(s, 3H), 3.55(s, 3H), 3.81(s, 3H), 5.22(s, 2H), 6.86(s, 1H), 7.38–7.45(m, 7H), 7.51–7.53(m, 2H), 7.67(m, 2H)
IR(KBr) 1479, 1367, 1180, 1151, 1080, 1019, 966, 876, 798, 525 cm⁻¹

TABLE 38

I-159 foam
¹HNMR(CDCl₃)δ 2.44(s, 3H), 3.21(s, 3H), 3.54(s, 3H), 3.76(s, 3H), 3.79(s, 3H), 4.77(s, 2H), 5.24(s, 2H), 6.83(s, 1H), 6.90–7.00 (m, 3H), 7.30–7.48(m, 5H), 7.37(d, J=8.8Hz, 2H), 7.69(d, J= 8.8Hz, 2H)
IR(KBr): 1758, 1519, 1481, 1365, 1236, 1176, 1150, 1079, 1013, 963, 872, 798 cm⁻¹

TABLE 38-continued

I-160 ¹HNMR(DMSO-d₆)δ 3.31(s, 3H), 3.65(s, 3H), 4.63(s, 2H), 5.15(s, 2H), 6.40(s, 1H), 6.83–6.90(m, 4H), 7.05(d, J=8.4Hz, 1H), 7.32–7.52(m, 7H), 8.57(s, 1H), 9.50(s, 1H), 12.0–13.9(brs, 1H)
IR(KBr): 3422, 1728, 1611, 1524, 1489, 1455, 1405, 1247, 1142, 1118, 1080, 1012, 818, 749, 742, 698 cm⁻¹

I-161 ¹HNMR(CDCl₃)δ 1.76(s, 3H), 1.79(s, 3H), 2.57(s, 3H), 3.21(s, 3H), 3.56(s, 3H), 3.77(s, 3H), 3.80(s, 3H), 4.64(d, J=6.5Hz, 2H), 4.74(s, 2H), 5.54(t, J=6.5Hz, 1H), 6.83(s, 1H), 6.88(d, J=1.5Hz, 1H), 7.02–7.03(m, 2H), 7.38(d, J=8.7Hz, 2H), 7.69(d, J=8.7Hz, 2H)

I-162 m.p. 147–149° C.
¹HNMR(DMSO-d₆)δ 1.73(s, 3H), 1.77(s, 3H), 3.30(s, 3H), 3.65(s, 3H), 4.57(d, J=6.6Hz, 2H), 4.60(s, 2H), 5.86(t, J=6.6Hz, 1H), 6.40 (s, 1H), 6.80(d, J=1.7Hz, 1H), 6.84(d, J=8.7Hz, 2H), 6.87(dd, J= 8.7Hz, 1H), 6.99(d, J=8.7Hz, 1H), 7.43(d, J=8.7Hz, 2H), 8.56(s, 1H), 9.51(s, 1H), 12.8(brs, 1H)
IR(KBr): 3483, 3376, 1737, 1612, 1523, 1489, 1460, 1397, 1271, 1231, 1175, 1120, 1072, 1012, 904, 820 cm⁻¹

I-163 m.p. 144–145° C.
¹HNMR(CDCl₃)δ 3.04(s, 3H), 3.20(s, 3H), 3.59(s, 3H), 3.75(s, 3H), 4.90(s, 2H), 5.16(s, 2H), 5.65(s, 1H), 6.67(s, 1H), 6.92(dd, J= 2.1, 8.4Hz, 1H), 7.00(d, J=8.4Hz, 1H), 7.06(d, J=2.1Hz, 1H), 7.26–7.47(m, 7H), 7.61–7.66(m, 2H)
IR(KBr) 3600–3200(br), 1517, 1477, 1449, 1382, 1361, 1277, 1235, 1199, 1150, 1112, 1079, 1064, 1010, 997 cm⁻¹

I-164 m.p. 80–83° C.
¹HNMR(CDCl₃)δ 2.99(s, 3H), 3.12(s, 3H), 3.20(s, 3H), 3.58(s, 3H), 3.75(s, 3H), 4.93(s, 2H), 5.18(s, 2H), 6.67(s, 1H), 7.12(d, J= 8.7Hz, 1H), 7.34–7.49(m, 9H), 7.60–7.65(m, 2H)

TABLE 39

I-165 m.p. 148–151° C.
¹HNMR(CDCl₃)δ 3.03(s, 3H), 3.57(s, 3H), 3.74(s, 3H), 4.89(s, 1H), 4.90(s, 2H), 5.15(s, 2H), 5.64(s, 1H), 6.67(s, 1H), 6.88–6.93 (m, 3H), 6.99(d, J=8.4 Hz, 1H), 7.06(d, J=1.8Hz, 1H), 7.20–7.49 (m, 7H)
IR(KBr) 3600–3200(br), 1609, 1590, 1519, 1477, 1459, 1381, 1253, 1216, 1156, 1111, 1077, 1066, 1012 cm⁻¹

I-166 m.p. 199° C.
¹HNMR(CDCl₃)δ 3.10(s, 3H), 3.21(s, 3H), 3.44(s, 3H), 3.76(s, 3H), 5.17(s, 2H), 6.03(s, 1H), 6.44(s, 1H), 7.14(d, J=8.4Hz, 1H), 7.36–7.49(m, 8H), 7.52(d, J=2.1Hz, 1H), 7.67–7.72(m, 2H)
IR(KBr) 3600–3200(br), 1520, 1486, 1362, 1183, 1152, 1110, 971 cm⁻¹

I-167 m.p. 113–115° C.
¹HNMR(CDCl₃)δ 0.76(t, J=7.2Hz, 3H), 1.46–1.55(m, 2H), 3.11(s, 3H), 3.20(s, 1H), 3.63(s, 1H), 3.71(t, J=6.6Hz, 2H), 5.18(s, 2H), 6.64(s, 1H), 7.11(d, J=8.7Hz, 1H), 7.33–7.50(m, 9H), 7.60–7.65 (m, 2H)
IR(KBr) 1517, 1475, 1365, 1345, 1293, 1233, 1177, 1149, 1109, 1079, 1017, 956 cm⁻¹

I-168 m.p. 56–58° C.
¹HNMR(CDCl₃)δ 0.76(t, J=7.5Hz, 3H), 1.44–1.56(m, 2H), 3.61(s, 3H), 3.71(t, J=6.6Hz, 2H), 3.74(s, 3H), 4.86(s, 1H), 5.15(s, 2H), 5.63(s, 1H), 6.65(s, 1H), 6.88–6.93(m, 3H), 6.98(d, J=8.4Hz, 1H), 7.04(d, J=1.8Hz, 1H), 7.37–7.50(m, 7H)
IR(KBr) 3600–3200(br), 1611, 1590, 1519, 1476, 1404, 1379, 1252, 1230, 1110, 1078, 1015 cm⁻¹

I-169 m.p. 101–103° C.
¹HNMR(CDCl₃)δ 0.77(t, J=7.5Hz, 3H), 1.44–1.55(m, 2H), 1.76(s, 3H), 1.81(s, 3H), 3.20(s, 3H), 3.21(s, 3H), 3.63(s, 3H), 3.71(t, J= 6.6Hz, 2H), 3.75(s, 3H), 4.63(d, J=6.6Hz, 2H), 5.48–5.53(m, 1H), 6.64(s, 1H), 7.04(d, J=8.4Hz, 1H), 7.32–7.38(m, 3H), 7.42(d, J= 2.1Hz, 1H), 7.60–7.65(m, 2H)
IR(KBr) 1514, 1473, 1370, 1359, 1290, 1233, 1174, 1149, 1107, 970 cm⁻¹

TABLE 40

I-170 m.p. 64–66° C.
$^1$HNMR(CDCl$_3$)δ 0.77(t, J=7.5Hz, 3H), 1.44–1.55(m, 2H), 1.76(s, 3H), 1.81(s, 3H), 3.20(s, 3H), 3.21(s, 3H), 3.63(s, 3H), 3.71(t, J=6.6Hz, 2H), 3.75(s, 3H), 4.63(d, J=6.6Hz, 2H), 5.48–5.53(m, 1H), 6.64(s, 1H), 7.04(d, J=8.4Hz, 1H), 7.32–7.38(m, 3H), 7.42(d, J=2.1Hz, 1H), 7.60–7.65(m, 2H)
IR(KBr) 3600–2800(br), 1612, 1590, 1520, 1475, 1462, 1405, 1381, 1285, 1244, 1226, 1110, 1079, 988 cm$^{-1}$

I-171 m.p. 148–150° C.
$^1$HNMR(CDCl$_3$)δ 1.74(d, J=0.9Hz, 3H), 1.80(s, 3H), 2.88(s, 3H), 3.22(s, 3H), 3.23(s, 6H), 3.55(s, 3H), 3.80(s, 3H), 4.72(d, J=7.5Hz, 2H), 5.55(m, 1H), 6.85(s, 1H), 7.39&7.67(ABq, J=8.7Hz, 4H), 7.40(s, 2H)
IR(KBr) 1514, 1479, 1411, 1366, 1179, 1152, 1079, 1022, 968, 875, 799, 525 cm$^{-1}$

I-172 $^1$HNMR(CDCl$_3$)δ 0.94(t, J=7.2Hz, 3H), 1.45(tq, J=7.2, 7.2Hz, 2H), 2.13(m, 2H), 3.46(s, 3H), 3.74(s, 3H), 4.68(d, J=5.4Hz, 2H), 5.72(m, 2H), 6.45(s, 1H), 6.92(d, J=8.7Hz, 2H), 6.96(brs, 2H), 7.07(brs, 1H), 7.53(d, J=8.7Hz, 2H)

I-173 $^1$HNMR(CDCl$_3$)δ 1.76(brd, J=6.3Hz, 3H), 3.46(s, 3H), 3.74(s, 3H), 4.70(d, J=5.4Hz, 2H), 5.77(m, 2H), 6.45(s, 1H), 6.91(d, J=8.7Hz, 2H), 6.96(brs, 2H), 7.07(brs, 1H), 7.53(d, J=8.7Hz, 2H)
IR(Nujol)3350, 1613, 1587, 1523, 1491, 1287, 1261, 1238, 1114, 1071, 1011, 936, 820, 783 cm$^{-1}$ I-174 $^1$HNMR(CDCl$_3$)δ 3.45(s, 3H), 3.76(s, 3H), 4.56(s, 2H), 5.55(s, 1H), 6.45(s, 1H), 6.93(d, J=8.7Hz, 2H), 7.01(d, J=8.4Hz, 1H), 7.08(dd, J=8.4, 2.1Hz, 1H), 7.27(d, J=2.1Hz, 1H), 7.54(d, J=8.7Hz, 2H)

I-175 $^1$HNMR(CDCl$_3$)δ 3.45(s, 3H), 3.74(s, 3H), 4.82(dd, J=6.6, 1.5Hz, 2H), 5.28(d, J=10.5Hz, 1H), 5.35(d, J=16.5Hz, 1H), 5.75(dt, J=10.8, 6.6Hz, 1H), 6.26(dd, J=10.5, 10.5Hz, 1H), 6.45(s, 1H), 6.66(ddd, J=16.5, 10.5, 10.5Hz, 1H), 6.92(d, J=8.7Hz, 2H), 6.96(m, 2H), 7.07(brs, 1H), 7.53(d, J=8.7Hz, 2H)
IR(Nujol)3399, 1611, 1591, 1523, 1489, 1248, 1226, 1113, 1071, 1009, 825 cm$^{-1}$

TABLE 41

I-176 $^1$HNMR(CDCl$_3$)δ 1.59(m, 6H), 2.17(m, 2H), 2.24, (m, 2H), 2.71(s, 3H), 3.21(s, 3H), 3.24(s, 3H), 3.50(s, 3H), 3.78(s, 3H), 4.65(d, J=7.2Hz, 2H), 5.43(t, J=7.2Hz, 1H), 6.84(s, 1H), 7.10(d, J=8.4Hz, 1H), 7.34(dd, J=8.4, 2.1Hz, 1H), 7.38(d, J=8.7Hz, 2H), 7.39(d, J=2.1Hz, 1H, 7.68(d, J=8.7Hz, 2H)

I-177 m.p. 177–178° C.
$^1$HNMR(CDCl$_3$)δ 2.31(t, J=5.7Hz, 2H), 2.39(t, J=5.7Hz, 2H), 2.76(s, 3H), 3.21(s, 3H), 3.24(s, 3H), 3.56(s, 3H), 3.70(t, J=5.7Hz, 2H), 3.73(t, J=5.7Hz, 2H), 3.78(s, 3H), 4.67(d, J=6.6Hz, 2H), 5.57(t, J=6.6Hz, 1H), 6.84(s, 1H), 7.09(d, J=8.4Hz, 1H), 7.35(dd, J=8.4, 2.1Hz, 1H), 7.38(d, J=8.7Hz, 2H), 7.39(d, J=2.1Hz, 1H), 7.67(d, J=8.7Hz, 2H)
IR(KBr) 2940, 1519, 1481, 1362, 1178, 1152, 1079, 818 cm$^{-1}$

I-178 $^1$HNMR(CDCl$_3$)δ 1.04(t, J=7.5Hz, 3H), 1.05(t, J=7.5Hz, 3H), 2.12(q, J=7.5Hz, 2H), 2.16(q, J=7.5Hz, 2H), 2.71(s, 3H), 3.21(s, 3H), 3.24(s, 3H), 3.56(s, 3H), 3.78(s, 3H), 4.67(d, J=6.6Hz, 2H), 5.45(t, J=6.6Hz, 1H), 6.84(s, 1H), 7.11(d, J=8.4Hz, 1H), 7.35(dd, J=8.4, 2.4Hz, 1H), 7.38(d, J=8.7Hz, 2H), 7.39(d, J=2.4Hz, 1H), 7.68(d, J=8.7Hz, 2H)

I-179 $^1$HNMR(CDCl$_3$)δ 1.05(t, J=7.5Hz, 3H), 1.76(s, 3H), 2.10(q, J=7.5Hz, 2H), 2.71(s, 3H), 3.21(s, 3H), 3.24(s, 3H), 3.56(s, 3H), 3.78(s, 3H), 4.66(d, J=6.9Hz, 2H), 5.48(t, J=6.9Hz, 1H), 6.84(s, 1H), 7.10(d, J=8.4Hz, 1H), 7.34(dd, J=8.4, 2.1Hz, 1H), 7.38(d, J=8.7Hz, 2H), 7.39(d, J=2.1Hz, 1H), 7.68(d, J=8.7Hz, 2H)

I-180 $^1$HNMR(CDCl$_3$)δ 1.76(s, 3H), 1.80(s, 6H), 2.72(s, 3H), 3.21(s, 3H), 3.21(s, 3H), 3.56(s, 3H), 3.78(s, 3H), 4.61(s, 2H), 6.84(s, 1H), 7.10(d, J=8.4Hz, 1H), 7.34(dd, J=8.4, 2.1Hz, 1H), 7.38(d, J=8.7Hz, 2H), 7.39(d, J=2.1Hz, 1H), 7.68(d, J=8.7Hz, 2H)

I-181 m.p. 157–158° C.
$^1$HNMR(CDCl$_3$)δ 1.55–1.65(m, 6H), 2.18(m, 2H), 2.23(m, 2H), 3.46(s, 3H), 3.74(s, 3H), 4.63d, J=7.2Hz, 2H), 5.47(t, J=72Hz 1H), 6.45(s, 1H), 6.91(d, J=8.4Hz, 2H), 6.96(br.s, 2H), 7.06(br.s, 1H), 7.52(d, J=8.4Hz, 2H)
IR(KBr) 3410, 2924, 2854, 1609, 1567, 1523, 1490, 1462, 1405, 1254, 1221, 1198, 1119, 1069, 824, 813 cm$^{-1}$

TABLE 42

I-182 m.p. 219–221° C.
$^1$HNMR(DMSO-d$_6$)δ 2.22(t, J=5.4Hz, 2H), 2.32(t, J=5.4Hz, 2H), 3.30(s, 3H), 3.56(t, J=5.4Hz, 2H), 3.61(t, J=5.4Hz, 2H), 3.64(s, 3H), 4.59(d, J=6.6Hz, 2H), 5.54(t, J=6.6Hz, 1H), 6.39(s, 1H), 6.64(dd, J=8.4, 2.1Hz, 1H), 6.73(d, J=2.1Hz, 1H), 6.84(d, J=8.7Hz, 2H), 6.89(d, J=8.4 Hz, 1H), 7.43(d, J=8.4Hz, 2H)
IR(KBr) 3392, 2948, 1609, 1586, 1522, 1492, 1271, 1239, 1219, 1118, 1076, 1007, 818 cm$^{-1}$

I-183 m.p. 149–150° C.
$^1$HNMR(CDCl$_3$)δ 1.03(t, J=7.5Hz, 3H), 1.07(t, J=7.5Hz, 3H), 2.13(q, J=7.5Hz, 2H), 2.15(q, J=7.5Hz, 2H), 3.46(s, 3H), 3.75(s, 3H), 4.64(d, J=6.6Hz, 2H), 5.48(t, J=6.6Hz, 1H), 6.45(s, 1H), 6.92(d, J=8.7Hz, 2H), 6.97(dd, J=7.8, 1.5Hz,, 1H), 6.97(d, J=7.8Hz, 1H), 7.06(d, J=1.5Hz, 1H), 7.52(d, J=8.7Hz, 2H)
IR(KBr) 3398, 2963, 2934, 1671, 1610, 1523, 1493, 1465, 1407, 1259, 1224, 1118, 1071, 813 cm$^{-1}$

I-184 m.p. 217–218° C.
$^1$HNMR(CDCl$_3$)δ 3.86(s, 3H), 5.16(s, 2H), 5.72(s, 1H), 6.97–7.01(m, 3H), 7.12(dd, J=2.4, 8.4Hz, 1H), 7.26(d, J=2.4Hz, 1H), 7.34–7.47(m, 5H), 7.54–7.58(m, 2H), 7.60(s, 4H)
IR(KBr) 3600–3200(br), 1605, 1590, 1493, 1298, 1282, 1253, 1206, 1183, 1022 c$^{-1}$

I-185 $^1$HNMR(CDCl$_3$)δ 1.21(t, J=6.9Hz, 3H), 1.77(s, 3H), 1.82(s, 3H), 2.38–2.46(m, 2H), 2.72–2.84(m, 2H), 3.18(s, 3H), 3.21(s, 3H), 3.35(s, 3H), 3.70(s, 3H), 4.06(q, J=6.9Hz, 2H), 4.63(d, J=6.6Hz, 2H), 5.52(t, J=6.6Hz, 1H), 6.75(s, 1H), 7.07(d, J=8.4Hz, 1H), 7.13(d.d, J=8.4&2.1Hz, 1H), 7.21(d, J=2.1Hz, 1H), 7.37(d, J=9.0Hz, 2H), 7.69(d, J=9.0Hz, 2H)
IR(KBr) 1727, 1517, 1469, 1364, 1291, 1234, 1179, 1152, 1118, 1080, 1003 cm$^{-1}$

I-186 $^1$HNMR(CDCl$_3$)δ 1.76(s, 3H), 1.82(s, 3H), 2.42–2.53(m, 2H), 2.72–2.86(m, 2H), 3.35(s, 3H), 3.69(s, 3H), 4.61(d, J=6.6Hz, 2H), 5.53(t, J=6.6Hz, 1H), 5.71(s, 1H), 6.68(d.d, J=8.4&2.1Hz, 1H), 6.76(s, 1H), 6.81(d, J=2.1Hz, 1H), 6.91(d, J=8.4Hz, 2H), 6.92(d, J=8.4Hz, 1H), 7.52(d, J=8.4 Hz, 2H)
IR(KBr) 3419, 1707, 1612, 1518, 1472, 1390, 1225, 1078 cm$^{-1}$

TABLE 43

I-187 $^1$HNMR(CDCl$_3$)δ 2.55(s, 3H), 3.54(s, 3H), 3.78(s, 3H), 5.18(s, 1H), 6.85(s, 1H), 6.91(d.d, J=8.4&2.1Hz, 1H), 7.03(d, J=8.4Hz, 1H), 7.04(d, J=2.1Hz, 1H), 7.33–7.48(m, 5H), 7.71(d, J=8.4Hz, 2H), 7.72(d, J=8.4Hz, 2H)
IR(KBr) 3442, 1617, 1517, 1485, 1485, 1394, 1357, 1331, 1171, 1124, 1077, 1067, 1016 cm$^{-1}$

I-188 $^1$HNMR(CDCl$_3$)δ 2.68(s, 3H), 3.13(s, 3H), 3.54(s, 3H), 3.79(s, 3H), 5.19(s, 2H), 6.86(s, 1H), 7.16(d, J=8.7Hz, 1H), 7.31–7.50(m, 7H), 7.72(d, J=8.7Hz, 2H), 7.76(d, J=8.7Hz, 2H)
IR(KBr) 1614, 1513, 1482, 1366, 1324, 1177, 1120, 1079, 1065, 1016 cm$^{-1}$

I-189 $^1$HNMR(CDCl$_3$)δ 2.68(s, 3H), 3.13(s, 3H), 3.54(s, 3H), 3.79(s, 3H), 5.19(s, 2H), 6.86(s, 1H), 7.16(d, J=8.7Hz, 1H), 7.31–7.50(m, 7H), 7.72(d, J=8.7Hz, 2H), 7.76(d, J=8.7Hz, 2H)
IR(KBr) 1614, 1513, 1482, 1366, 1324, 1177, 1120, 1079, 1065, 1016 cm$^{-1}$

I-190 $^1$HNMR(CDCl$_3$)δ 1.76(s, 3H), 1.82(s, 3H), 3.46(s, 3H), 3.76(s, 3H), 4.62(d, J=8.4Hz, 2H), 5.53(t, J=8.4Hz, 1H), 5.71(s, 1H), 5.85(s, 1H), 6.46(s, 1H), 6.94(d.d, J=8.1& 1.8Hz, 1H), 6.98(d, J=8.1Hz, 1H), 7.05(d, J=1.8Hz, 1H), 7.71(d, J=8.1Hz, 2H), 7.77(d, J=8.1Hz, 2H)
IR(KBr) 3552, 3505, 3466, 1613, 1509, 1487, 1397, 1324, 1288, 1245, 1163, 1110, 1065 cm$^{-1}$

I-191 $^1$HNMR(CDCl$_3$)δ 3.02(s, 6H), 3.48(s, 3H), 3.76(s, 3H), 5.15(s, 2H), 5.67(s, 1H), 5.95(s, 1H), 6.47(s, 1H), 6.81(d, J=8.7Hz, 2H), 6.96(d.d, J=8.4&2.1Hz, 1H), 7.04(d, J=8.4Hz, 1H), 7.10(d, J=2.1Hz, 1H), 7.31–7.49(m, 5H), 7.55(d, J=8.7Hz, 2H)
IR(KBr) 3543, 3500, 1605, 1526, 1486, 1459, 1245, 1198, 1110, 1070, 999 cm$^{-1}$

I-192 mp 122–124° C.
$^1$HNMR(CDCl$_3$)δ 2.70(brs, 3H), 3.55–3.60(br, 3H), 3.60(s, 3H), 3.75(s, 3H), 3.81–3.83(m, 2H), 3.87(s, 3H), 5.15(s, 2H), 5.68(s, 1H), 6.69(s, 1H), 6.94(d, J=2.1, 1H), 6.97–7.03(m, 3H), 7.07(d, J=1.8Hz, 1H), 7.38–7.48(m, 5H), 7.51–7.56(m, 2H)
IR(KBr) 3600–2800(br), 1607, 1597, 1550, 1518, 1477, 1462, 1452, 1392, 1289, 1248, 1228, 1175, 1122, 1096, 1084, 1015 cm$^{-1}$

TABLE 44

I-193 m.p. 160–163° C.
$^1$HNMR(CDCl$_3$)δ 3.60(s, 3H), 3.60–3.64(br, 2H), 3.76(s, 3H), 3.77–3.80(m, 2H), 5.15(s, 2H), 5.69(s, 1H), 5.88(s, 1H), 6.69(s, 1H), 6.90–6.94(m, 3H), 7.02(d, J=8.4Hz, 1 H), 7.08(d, J=2.1Hz, 1H), 7.38–7.51(m, 7H)
IR(KBr) 3600–3200(br), 1613, 1588, 1519, 1477, 1462, 1397, 1256, 1189, 1117, 1078, 1011 cm$^{-1}$

I-194 $^1$HNMR(CDCl$_3$) 3.02(s, 6H), 3.11(s, 3H), 3.50(s, 3H), 3.72(s, 3H), 4.43(brs, 1H), 4.58(brs, 1H), 5.18(s, 2H), 6.82(d, J=8.7Hz, 2H), 6.92(s, 1H), 7.16(d, J=9.3Hz, 1H), 7.31–7.51(m, 7H), 7.55(d, J=8.7Hz, 2H)
IR(KBr) 3432, 1611, 1526, 1476, 1356, 1291, 1232, 1186, 1117, 1079, 1012 cm$^{-1}$ I-195 m.p. 157–158° C.
$^1$HNMR(CDCl$_3$) 3.10(s, 3H), 3.21(s, 3H), 3.56(s, 3H), 3.69(s, 3H), 3.76(s, 3H), 4.47(s, 2H), 5.17(s, 2H), 6.68(s, 1H), 7.12(d, J=8.2Hz, 1H), 7.34–7.50(m, 9H), 7.63(d, J=8.6Hz, 2H)
IR(KBr): 1748, 1517, 1476, 1366, 1232, 1150, 1114, 968, 873, 812, 791, 750, 707 cm$^{-1}$ I-196 m.p. 189–191t(dec)
$^1$HNMR(DMSO-d$_6$) 3.45(s, 3H), 3.67(s, 3H), 4.25(s, 2H), 5.12(s, 2H), 6.66(dd, J=8.4, 2.0Hz, 1H), 6.69(s, 1H), 6.77(d, J=2.0Hz, 1H), 6.80(d, J=8.6Hz, 2H), 6.98(d, J=8.4Hz, 1H), 7.33–7.54(m, 7H), 9.01(s, 1H), 9.54(brs, 1H)
IR(KBr):3422, 3245, 1733, 1611, 1596, 1522, 1478, 1400, 1262, 1248, 1222, 1207, 1130, 1084, 1011, 836, 781, 744, 699 cm$^{-1}$ I-197 m.p. 151–152° C.
$^1$HNMR(CDCl$_3$) 1.76(s, 3H), 1.81(s, 3H), 3.20(s, 3H), 3.21(s, 3H), 3.56(s, 3H), 3.70(s, 3H), 3.75(s, 3H), 4.47(s, 2H), 4.63(d, J=6.9Hz, 2H), 5.51(t, J=6.9Hz, 1H), 6.68(s, 1H), 7.05(d, J=8.4Hz, 1H), 7.36(dd, J=8.4, 2.1Hz, 1H), 7.36(d, J=8.9Hz, 2H), 7.41(d, J=2.1Hz, 1H), 7.63(d, J=8.9Hz, 2H)
IR(KBr): 1751, 1517, 1475, 1366, 1234, 1150, 1113, 968, 872, 812, 707 cm$^{-1}$

TABLE 45

I-198 m.p. 155–156° C.
$^1$HNMR(DMSO-d$_6$) 1.72(s, 3H), 1.76(s, 3H), 3.42(s, 3H), 3.67(s, 3H), 4.25(s, 2H), 4.54(d, J=6.8Hz, 2H), 5.49(t, J=68Hz, 1H), 6.65 (dd, J=8.4, 1.9Hz, 1H), 6.69(s, 1H), 6.73(d, J=1.9Hz, 1H), 6.84(d, J=8.4Hz, 2H), 7.36(d, J=8.4Hz, 1H), 7.41(d, J=8.4Hz, 2H), 8.85(s, 1H), 9.55(s, 1H), 11.2–13.6(brs, 1H)
IR(KBr): 3411, 3243, 1733, 1611, 1594, 1522, 1477, 1398, 1247, 1207, 1126, 1083, 1015, 835, 788 cm$^{-1}$ I-199 $^1$HNMR(CDCl$_3$) 2.68(s, 3H), 3.13(s, 3H), 3.55(s, 3H), 3.80(s, 3H), 5.19(s, 2H), 6.88(s, 1H), 7.16(d, J=8.7Hz, 1H), 7.34(d, J=2.1Hz, 1H), 7.36–7.50(m, 6H), 7.81(d, J=8.4Hz, 2H), 7.98(d, J=8.4Hz, 2H)
IR(KBr) 1698, 1602, 1481, 1351, 1232, 1182, 1079 cm$^{-1}$ I-200 $^1$HNMR(CDCl$_3$) 2.42(s, 3H), 2.71(s, 3H), 3.03(s, 3H), 3.21(s, 3H), 3.56(s, 3H), 3.79(s, 3H), 5.17(s, 2H), 6.84(s, 1H), 7.19(d, J=8.4Hz, 1H), 7.22–7.30(m, 3H), 7.37(dd, J=8.4, 2.1Hz, 1H), 7.38(d, J=8.7Hz, 2H), 7.41(d, J=2.1Hz, 1H), 7.41–7.45(m, 1H), 7.68(d, J=8.7Hz, 2H)
IR(Nujol)1607, 1519, 1480, 1177, 1151, 1079, 970, 875, 798 cm$^{-1}$ I-201 $^1$HNMR(CDCl$_3$) 2.38(s, 3H), 2.67(s, 3H), 3.14(s, 3H), 3.21(s, 3H), 3.56(s, 3H), 3.78(s, 3H), 5.15(s, 2H), 6.84(s, 1H), 7.14(d, J=8.4Hz, 1H), 7.17(brd, J=7.5Hz, 1H), 7.23–7.30(m, 3H), 7.34(dd, J=8.4, 1.8Hz, 1H), 7.38(d, J=8.7Hz, 2H), 7.41(d, J=1.8Hz, 1H), 7.68(d, J=8.7Hz, 2H)
IR(Nujol)1606, 1519, 1482, 1180, 1150, 1078, 1011, 979, 876, 790 cm$^{-1}$ I-202 $^1$HNMR(CDCl$_3$) 2.30(s, 3H), 2.38(s, 6H), 2.74(s, 3H), 2.94(s, 3H), 3.21(s, 3H), 3.57(s, 3H), 3.79(s, 3H), 5.13(s, 2H), 6.85(s, 1H), 6.91(brs, 2H), 7.37(d, J=8.7Hz, 2H), 7.40(brs, 2H), 7.41(dd, J=8.4, 1.8Hz, 1H), 7.69(d, J=8.7Hz, 2H)
IR(CHCl$_3$)1610, 1518, 1477, 1370, 1177, 1149, 1082, 970, 873 cm$^{-1}$ I-203 $^1$HNMR(CDCl$_3$) 2.34(s, 6H), 2.66(s, 3H), 3.15(s, 3H), 3.21(s, 3H), 3.56(s, 3H), 3.78(s, 3H), 5.12(s, 2H), 6.84(s, 1H), 6.99(brs, 1H), 7.06(brs, 2H), 7.14(d, J=8.4Hz, 1H), 7.33(dd, J=8.4, 2.1Hz, 1H), 7.38(d, J=8.7Hz, 2H), 7.40(d, J=2.1Hz, 1H), 7.68(d, J=8.7Hz, 2H)
IR(Nujol)1607, 1519, 1480, 1178, 1152, 1097, 1014, 969, 876, 824, 797 cm$^{-1}$

TABLE 46

I-204 $^1$HNMR(CDCl$_3$) 2.72(s, 3H), 3.16(s, 3H), 3.21(s, 3H), 3.55(s, 3H), 3.78(s, 3H), 3.94(s, 3H), 5.25(s, 2H), 6.84(s, 1H), 7.11(d, J=8.4Hz, 1H), 7.34(dd, J=8.4, 2.1Hz, 1H), 7.38(d, J=8.7Hz, 2H), 7.47.42(d, J=2.1Hz, 1H), 7.55(d, J=8.4Hz, 2H), 7.68(d, J=8.7Hz, 2H), 8.09(d, J=8.4Hz, 2H)
IR(Nujol)1719, 1610, 1519, 1480, 1177, 1151, 1119, 1080, 1016, 969, 875, 798 cm$^{-1}$ I-205 m.p. 153–157° C.
$^1$HNMR(CDCl$_3$) 2.70(s, 3H), 3.16(s, 3H), 3.21(s, 3H), 3.56(s, 3H), 3.78(s, 3H), 5.13(s, 2H), 6.41(dd, J=3.3, 2.0Hz, 1H), 6.49(d, J=3.3Hz, 1H), 6.84(s, 1H), 7.20(d, J=8.7Hz, 1H), 7.37(dd, J=8.7, 2. 2.1Hz, 1H), .38(d, J=8.7Hz, 2H), 7.41(d, J=2.1Hz, 1H), 7.46(d, J=2.0Hz, 1H), 7.68(d, J=8.7Hz, 2H)
IR(Nujol)1605, 1518, 1482, 1375, 1361, 1180, 1150, 1079, 1013, 977, 876, 814, 800 cm$^{-1}$ I-206 $^1$HNMR(CDCl$_3$) 2.41(s, 3H), 3.46(s, 3H), 3.75(s, 3H), 5.13(s, 2H), 6.45(s, 1H), 6.92(d, J=8.7Hz, 2H), 6.99(dd, J=8.4, 2.1Hz, 1H), 7.07(d, J=8.4Hz, 1H), 7.09(d, J=2.1Hz, 1H), 7.22–7.34(m, 3H), 7.40(brd, J=7.8Hz, 1H), 7.53(d, J=8.7Hz, 2H)
IR(Nujol)3471, 3436, 3339, 1612, 1581, 1523, 1489, 1266, 1245, 1228, 1185, 1110, 1070, 1011, 998, 945, 823, 781 cm$^{-1}$ I-207 $^1$HNMR(CDCl$_3$) 2.40(s, 3H), 3.45(s, 3H), 3.75(s, 3H), 5.11(s, 2H), 6.45(s, 1H), 6.91(d, J=8.7Hz, 2H), 6.95(dd, J=8.4, 1.8Hz, 1H), 7.01(d, J=8.4Hz, 1H), 7.09(d, J=1.8Hz, 1H), 7.19(brd, J=7.5Hz, 1H), 7.22–7.34(m, 3H), 7.53(d, J=8.7Hz, 2H)
IR(Nujol)3410, 1611, 1589, 1523, 1489, 1246, 1225, 1114, 1071, 1011, 939, 824, 814, 778 cm$^{-1}$ I-208 m.p. 230–236° C.
$^1$HNMR(DMSO-d$_6$) 2.25(s, 3H), 2.35(s, 6H), 3.31(s, 3H), 3.65(s, 3H), 5.00(s, 2H), 6.39(s, 1H), 6.69(dd, J=8.4, 1.8Hz, 1H), 6.76(d, J=1.8Hz, 1H), 6.84(d, J=8.7Hz, 1H), 6.90(brs, 2H), 7.06(d, J=8.4Hz, 3H), 7.44(d, J=8.7Hz, 2H)
IR(Nujol)3475, 3361, 1609, 1579, 1521, 1260, 1244, 1110, 1071, 1012, 988, 822, 782 cm$^{-1}$ I-209 $^1$HNMR(CDCl$_3$) 2.35(s, 6H), 3.45(s, 3H), 3.75(s, 3H), 5.07(s, 2H), 6.45(s, 1H), 6.91(d, J=8.7Hz, 2H), 6.95(dd, J=8.4, 1.8Hz, 1H), 7.01(brs, 1H), 7.02(d, J=8.4Hz, 1H), 7.06(brs, 1H), 7.08(d, J=1.8Hz, 1H), 7.53(d, J=8.7Hz, 2H)
IR(Nujol)3410, 1610, 1588, 1523, 1489, 1248, 1225, 1114, 1071, 1011, 940, 825, 808, cm –1

TABLE 47

I-210 $^1$HNMR(CD$_3$OD)δ 3.37(s, 3H), 3.67(s, 3H), 5.25(s, 2H), 6.43(s, 1H), 6.77(dd, J=8.4, 2.1Hz, 1H), 6.84(d, J=8.7Hz, 2H), 6.89(d, J=2.1Hz, 1H), 6.94(d, J=8.4Hz, 1H), 7.45(d, J=8.7Hz, 2H), 7.60(d, J=8.4Hz, 2H), 8.04(d, J=8.4Hz, 2H)
IR(Nujol)3384, 1694, 1612, 1591, 1523, 1488, 1249, 1113, 1071, 1013, 940, 826, 812, 765 cm$^{-1}$ I-211 $^1$HNMR(CDCl$_3$) 3.45(s, 3H), 3.74(s, 3H), 5.09(s, 3H), 6.41(dd, J=3.3, 1.8Hz, 1H), 6.45(s, 1H), 6.47(d, J=3.3Hz, 1H), 6.92(d, J=8.7Hz, 2H), 6.97(dd, J=8.4, 2.1Hz, 1H), 7.07(d, J=2.1Hz, 1H), 7.08(d, J=8.4Hz, 1H), 7.48(dd, J=1.8, 1.0Hz, 1H), 7.54(d, J=8.7Hz, 2H)
IR(Nujol)3410, 1612, 1589, 1523, 1489, 1248, 1226, 1113, 1071, 1011, 939, 815, 747 cm$^{-1}$ I-212 m.p. 156–158° C.
$^1$HNMR(CDCl$_3$) 1.06(t, J=7.4Hz, 3H), 1.75(s, 3H), 2.10(q, J=7.4Hz, 2H), 3.46(s, 3H), 3.75(s, 3H), 4.64(d, J=7.0Hz, 2H), 5.52(t, J=7.0Hz, 1H), 6.45(s, 1H), 6.92(d, J=8.6Hz, 2H), 6.96(br.s, 2H), 7.06(br.s 1H), 7.53(d, J=8.6Hz, 2H)
IR(KBr) 3392, 2960, 2934, 1610, 1583, 1568, 1523, 1492, 1465, 1406, 1259, 1241, 1224, 1198, 1118, 1071, 824, 812 cm$^{-1}$

TABLE 47-continued

I-213  m.p. 175–177° C.
¹HNMR(CDCl₃)δ 1.77(s, 3H), 1.80(s, 6H), 3.46(s, 3H), 3.75(s, 3H), 4.59(s, 2H), 6.45(s, 1H), 6.92(d, J=8.7Hz, 2H), 6.96(br.s, 2H), 7.06(br.s, 1H), 7.53(d, J=8.7Hz, 2H)
IR(KBr) 3449, 2929, 1612, 1581, 1523, 1489, 1403, 1262, 1243, 1228, 1113, 1070, 823, 807 cm⁻¹

I-214  ¹HNMR(CDCl₃) 1.66(tt, J=6.6, 6.6Hz, 2H), 1.74(tt, J=6.6, 6.6Hz, 2H), 2.32(t, J=6.6Hz, 2H), 2.34(t, J=6.6Hz, 2H), 2.71(s, 3H), 3.21(s, 3H), 3.24(s, 3H), 3.56(s, 3H), 3.78(s, 3H), 4.62(d, J=6.9Hz, 2H), 5.60(m, 1H), 6.84(s, 1H), 7.09(d, J=8.7Hz, 1H), 7.34(dd, J=8.7, 2.1Hz, 1H), 7.37(d, J=8.7Hz, 2H), 7.38(d, J=2.1Hz, 1H), 7.67(d, J=8.7Hz, 2H)
IR(KBr) 2941, 1610, 1518, 1418, 1365, 1177, 1151, 1079, 847, 818 cm⁻¹

I-215  ¹HNMR(CDCl₃) 1.57–1.72(m, 4H), 2.05–2.13(m, 4H), 2.70(s, 3H), 3.21(s, 3H), 3.23(s, 3H), 3.56(s, 3H), 3.78(s, 3H), 4.48(s, 2H), 5.86(s, 1H), 6.84(s, 1H), 7.09(d, J=8.4Hz, 1H), 7.34(dd, J=8.4, 2.1Hz, 1H), 7.38(d, J=8.7Hz, 2H), 7.38(d, J=2.1Hz, 1H), 7.67(d, J=8.7Hz, 2H)
IR(KBr) 2936, 1610, 1518, 1481, 1365, 1177, 1151, 1079, 818 cm⁻¹

TABLE 48

I-216  ¹HNMR(CDCl₃)δ 1.74(d, J=6.6Hz, 3H), 2.54(d, J=2.1Hz, 1H), 2.70(s, 3H), 3.21(s, 3H), 3.24(s, 3H), 3.56(s, 3H), 3.78(s, 3H), 5.00(dd, J=6.6, 2.1Hz, 1H), 6.84(s, 1H), 7.28(d, J=8.7Hz, 1H), 7.36(dd, J=8.7, 2.1Hz, 1H), 7.38(d, J=8.7Hz, 2H), 7.41(d, J=2.1Hz, 1H), 7.68(d, J=8.7Hz, 2H)

TABLE 48-continued

IR(KBr) 3282, 3023, 2940, 1609, 1519, 1481, 1365, 1177, 1151, 1079, 970, 815 cm⁻¹

I-217  m.p. 80–85° C.
¹HNMR(CDCl₃) 1.62–1.77(m, 4H), 2.25–2.39(m, 4H), 3.46(s, 3H), 3.75(s, 3H), 4.60(d, J=7.0Hz, 2H), 5.63(m, 1H), 6.45(s, 1H), 6.92(d, J=8.6Hz, 1H), 6.95(br.s, 2H), 7.06(br.s, 1H), 7.68(d, J=8.6Hz, 2H)
IR(KBr) 3282, 3023, 2940, 1609, 1519, 1481, 1365, 1177, 1151, 1079, 970, 815 cm⁻¹

I-218  foam
¹HNMR(CDCl₃) 3.45(s, 3H), 3.77(s, 3H), 5.16(s, 2H), 5.69(brs, 1H), 5.86(s, 1H), 6.47(s, 1H), 6.95(dd, J=2.1, 8.4Hz, 1H), 7.04(d, J=8.4Hz, 1H), 7.08(d, J=2.1Hz, 1H), 7.34–7.65(m, 7H), 7.83–7.92(m, 2H)
IR(CHCl₃)3530, 3022, 1614, 1588, 1500, 1485, 1463, 1405, 1326, 1290, 1249, 1168, 1130, 1117, 1073, 1011 cm⁻¹

I-219  foam
¹HNMR(CDCl₃) 1.69(s, 3H), 1.74(s, 3H), 2.51–2.59(m, 2H), 2.74(s, 3H), 3.22(s, 3H), 3.55(s, 3H), 3.79(s, 3H), 4.07(t, J=6.6Hz, 2H), 5.21(m, 1H), 6.85(s, 1H), 7.08(d, J=8.7Hz, 1H), 7.35(dd, J=2.1, 8.7Hz, 1H), 7.39(d, J=2.1Hz, 1H), 7.55–7.69(m, 2H), 7.81–7.87(m, 2H)
IR(CHCl₃)3024, 1609, 1519, 1481, 1467, 1396, 1369, 1321, 1272, 1179, 1122, 1082, 1015 cm⁻¹

I-220  m.p. 124–126° C.
¹HNMR(CDCl₃) 1.69(s, 3H), 1.75(s, 3H), 2.50–2.57(m, 2H), 3.46(s, 3H), 3.76(s, 3H), 4.07(t, J=6.9Hz, 2H), 5.22(m, 1H), 5.69(brs, 1H), 5.84(s, 1H), 6.46(s, 1H), 6.93–7.05(m, 3H), 7.55–7.65(m, 2H), 7.82–7.91(m, 2H)
IR(KBr) 3406, 2935, 1587, 1519, 1501, 1488, 1459, 1359, 1323, 1304, 1291, 1274, 1223, 1170, 1126, 1113, 1075, 1018 cm⁻¹

TABLE 49

I-221  m.p. 187–189° C.
¹HNMR(CDCl₃) δ 2.33(s, 3H), 2.69(s, 3H), 3.21(s, 3H), 3.24(s, 3H), 3.55(s, 3H), 3.77(s, 3H), 4.17(s, 2H), 6.84(s, 1H), 7.12&7.25(ABq, J = 8.7 Hz, 1H), 7.31(dd, J = 8.1 Hz, J = 1.5 Hz, 1H), 7.38&7.67(ABq, J = 8.7 Hz, 4H), 7.42(d, J = 8.1 Hz, 1H), 7.46(d, J = 1.5 Hz, 1H)
IR(KBr)1512, 1474, 1417, 1391, 1356, 1343, 1177, 1149, 1082, 1054, 1013, 976, 961, 939, 867, 854, 844, 820, 812, 799, 523 cm⁻¹

I-222  m.p. 107–112° C.
¹HNMR(CDCl₃) δ 2.73(s, 3H), 3.22(s, 3H), 3.28(s, 3H), 3.55(s, 3H), 3.77(s, 3H), 4.34(s, 2H), 6.84(s, 1H), 7.19(m, 1H), 7.30(dd, J = 8.1 Hz, J = 1.8 Hz, 1H), 7.34–7.41(m, 3H), 7.46(d, J = 1.8 Hz, 1H), 7.49(d, J = 8.1 Hz, 1H), 7.62–7.69(m, 3H), 8.55(m, 1H)
IR(KBr)1474, 1389, 1364, 1179, 1151, 1081, 937, 873, 813, 797, 523 cm⁻¹

I-223  m.p. 212–214° C.
¹HNMR(CDCl³ + CD₃OD) δ 3.45(s, 3H), 3.74(s, 3H), 4.13(s, 2H), 6.45(s, 1H), 6.90–6.96(m, 3H), 7.12(d, J = 1.8 Hz, 1H), 7.18–7.26(m, 2H), 7.48–7.54(m, 3H), 7.68(m, 1H), 8.63(m, 1H)
IR(KBr)3504, 3272, 1612, 1596, 1574, 1521, 1492, 1463, 1436, 1405, 1362, 1310, 1265, 1222, 1172, 1116, 1083, 1052, 1017, 828 cm⁻¹

I-224  m.p. 199–200° C.
¹HNMR(CDCl₃) δ 1.46(d, J = 0.9 Hz, 3H), 1.77(s, 3H), 3.44(s, 3H), 3.74(s, 3H), 3.90(m, 2H), 5.25(m, 1H), 6.04(brs, 1H), 6.45(s, 1H), 6.93&7.53(ABq, J = 8.7 Hz, 4H), 7.00(m, 2H), 7.05(m, 1H)
IR(KBr)3404, 2999, 2932, 1612, 1595, 1522, 1483, 1454, 1432, 1401, 1376, 1357, 1271, 1223, 1119, 1080, 1055, 1015, 974, 938, 829, 817 cm⁻¹

I-225  m.p. 181–183° C.
¹HNMR(CDCl₃) δ 1.37(s, 9H), 3.45(s, 3H), 3.75(s, 3H), 4.93(brs, 1H), 6.00(s, 1H), 6.46(s, 1H), 6.93&7.54(ABq, J = 8.7 Hz, 4H), 6.99(s, 1H), 7.01(dd, J = 8.4 Hz, J = 1.5 Hz, 1H), 7.16(d, J = 1.5 Hz, 1H), 7.49(d, J = 8.4 Hz, 1H)
IR(KBr)3495, 3412, 2959, 2931, 1610, 1568, 1552, 1521, 1499, 1477, 1459, 1400, 1364, 1319, 1270, 1227, 1192, 1161, 1116, 1102, 1090, 1052, 1019, 942, 833, 817, 588 cm⁻¹

TABLE 50

I-226  m.p. 154–156° C.
¹HNMR(CDCl₃) δ 2.33(s, 3H), 3.45(s, 3H), 3.75(s, 3H), 3.90(s, 2H), 4.68(s, 1H), 5.97(s, 1H), 6.45(s, 1H), 6.60(s, 1H), 6.90–6.98(m, 3H), 7.10(s, 5H), 7.41(d, J = 8.1 Hz, 1H), 7.53(m, 2H)
IR(KBr)3462, 3368, 1611, 1550, 1521, 1499, 1472, 1455, 1437, 1401, 1362, 1321, 1293, 1267, 1229, 1187, 1174, 1164, 1118, 1077, 1050, 1011, 821 cm⁻¹

I-227  m.p. 172–174° C.
¹HNMR(CDCl₃) δ 1.38(d, J = 1.2 Hz, 3H), 1.76(s, 3H), 3.44(s, 3H), 3.75(s, 3H), 3.87(d, J = 7.8 Hz, 2H), 5.08(brs, 1H), 5.26(m, 1H), 6.08(s, 1H), 6.45(s, 1H), 6.94&7.53(ABq, J = 8.7 Hz, 4H), 7.11–7.14(m, 2H), 7.62(d, J = 8.7 Hz, 1H), 8.87(s, 1H)
IR(KBr)3412, 1613, 1520, 1478, 1458, 1443, 1404, 1360, 1346, 1290, 1270, 1224, 1200, 1171, 1119, 1078, 1054, 945 cm⁻¹

TABLE 50-continued

| | |
|---|---|
| I-228 | m.p. 173–175° C.<br>¹HNMR(CDCl₃) δ 1.69(s, 3H), 1.74(s, 3H), 2.10(s, 3H), 2.50–2.61(m, 2H), 3.20(s, 3H), 3.21(s, 3H), 3.37(s, 3H), 3.71(s, 3H), 4.08(t, J = 6.8 Hz, 2H), 5.21–5.25(m, 1H), 6.73(s, 1H), 7.03–7.18(m, 2H), 7.23–7.25(m, 2H), 7.37(d, J = 8.6 Hz, 2H), 7.69(d, J = 8.8 Hz, 2H)<br>IR(KBr)3600-3200(br), 3100-2800(br), 1610, 1527, 1523, 1477, 1432, 1365, 1240, 1172, 1160, 955, 923 cm⁻¹ |
| I-229 | m.p. 148–150° C.<br>¹HNMR(CDCl₃) δ 1.70(s, 3H), 1.77(s, 3H), 2.09(s, 3H), 2.48–2.62(m, 2H), 3.38(s, 3H), 3.73(s, 3H), 4.09(t, J = 7.0 Hz, 2H), 4.84(br, 1H), 5.19–5.22(m, 1H), 5.70(s, 1H), 6.71–6.96(m, 5H), 7.55(d, J = 8.2 Hz, 2H)<br>IR(KBr)3700-3200(br), 3100-2800(br), 1612, 1584, 1560, 1448, 1428, 1390, 1339, 1315, 1284, 1246, 1173, 1160, 1123, 1018, 999 cm⁻¹ |
| I-230 | m.p. 194–195° C.<br>¹HNMR(CDCl₃) δ 2.10(s, 3H), 2.39(s, 3H), 3.10(s, 3H), 3.21(s, 3H), 3.36(s, 3H), 3.71(s, 3H), 5.13(s, 2H), 6.73(s, 1H), 7.14–7.18(m, 8H), 7.69(d, J = 9.0 Hz, 2H)<br>IR(KBr)3600-3200(br), 3100-2800(br), 1516, 1475, 1360, 1332, 1292, 1266, 1228, 1199, 1174, 1151, 1119, 1098, 1084, 1005, 968 cm⁻¹ |

TABLE 51

| | |
|---|---|
| I-231 | m.p. 178–180° C.<br>¹HNMR(CDCl₃) δ 2.09(s, 3H), 2.40(s, 3H), 3.37(s, 3H), 3.72(s, 3H), 4.97(brs, 1H), 5.10(s, 2H), 5.67(br, 1H), 6.70–6.75(m, 2H), 6.86–7.03(m, 3H), 7.22–7.26(m, 2H), 7.32–7.34(m, 2H), 7.54(d, J = 8.2 Hz, 2H)<br>IR(KBr)3600-3200(br), 3100-2800(br), 1611, 1519, 1479, 1463, 1388, 1339, 1314, 1286, 1258, 1246, 1225, 1128, 1098, 1077, 1007 cm⁻¹ |
| I-232 | m.p. 177–179° C.<br>¹HNMR(CDCl₃) δ 2.54(s, 3H), 2.69(s, 3H), 3.13(s, 3H), 3.54(s, 3H), 3.77(s, 3H), 5.19(s, 2H), 6.85(s, 1H), 7.15(d, J = 8.4 Hz, 2H), 7.30–7.49(m, 9H), 7.53–7.59(m, 2H)<br>IR(CHCl₃)1516, 1476, 1368, 1266, 1176, 1118, 1077, 1080, 1013, 970, 876, 820 cm⁻¹ |
| I-233 | amorphouspowder<br>¹HNMR(CDCl₃) δ 2.54(s, 3H), 3.46(s, 3H), 3.75(s, 3H), 5.15(s, 2H), 5.67(brs, 1H), 5.90(s, 1H), 6.46(s, 1H), 6.95(d.d, J = 1.8&8.1 Hz, 1H), 7.02(d, J = 8.1 Hz, 1H), 7.09(d, J = 1.8 Hz, 1H), 7.31–7.49(m, 7H), 7.55–7.62(m, 2H)<br>IR(CHCl₃)3526, 1517, 1483, 1414, 1389, 1289, 1246, 1192, 1114., 1070, 1010, 937, 818 cm⁻¹ |
| I-234 | ¹HNMR(CDCl₃) δ 1.76(s, 3H), 1.81(s, 3H), 2.73(s, 3H), 3.24(s, 3H), 3.53(s, 3H), 3.79(s, 3H), 3.96(s, 3H), 4.64(d, J = 6.9 Hz, 2H), 5.49(t, J = 6.9 Hz, 1H), 6.87(s, 1H), 7.09(d, J = 8.4 Hz, 1H), 7.35(d.d, J = 8.4&2.1 Hz, 1H), 7.39(d, J = 2.1 Hz, 1H), 7.71(d, J = 8.4 Hz, 2H), 8.13(d, J = 8.4 Hz, 2H) |
| I-235 | ¹HNMR(CDCl₃) δ 2.69(s, 3H), 3.14(s, 3H), 3.55(s, 3H), 3.80(s, 3H), 5.20(s, 2H), 6.89(s, 1H), 7.16(d, J = 9.0 Hz, 1H), 7.34(d, J = 2.1 Hz, 1H), 7.36–7.51(m, 6H), 7.75(d, J = 8.4 Hz, 2H), 8.23(d, J = 8.4 Hz, 2H)<br>IR(KBr)3427, 1724, 1685, 1606, 1509, 1481, 1369, 1272, 1235, 1179, 1120, 1084, 1017 cm⁻¹ |
| I-236 | ¹HNMR(CDCl₃) δ 3.46(s, 3H), 3.77(s, 3H), 5.16(s, 3H), 6.50(s, 1H), 6.96(dd, J = 8..4&2.1 Hz, 1H), 7.03(d, J = 8.4 Hz, 1H), 7.09(d, J = 2.1 Hz, 1H), 7.34–7.50(m, 5H), 7.75(d, J = 8.1 Hz, 2H), 8.17(d, J = 8.1 Hz, 2H) |

TABLE 52

| | |
|---|---|
| I-237 | ¹HNMR(CDCl₃) δ 3.44(s, 3H), 3.76(s, 3H), 3.96(s, 3H), 5.16(s, 2H), 5.69(s, 1H), 5.89(s, 1H), 6.49(s, 1H), 6.96(d.d, J = 8..4&2.1 Hz, 1H), 7.03(d, J = 8.4 Hz, 1H), 7.09(d, J = 2.1 Hz, 1H), 7.32–7.50(m, 5H), 7.73(d, J = 8.4 Hz, 2H), 8.13(d, J = 8.4 Hz, 2H)<br>IR(KBr)3497, 3443, 1708, 1608, 1585, 1487, 1460, 1443, 1395, 1281, 1113, 1068, 1008 cm⁻¹ |
| I-238 | ¹HNMR(CDCl₃) δ 2.69(s, 3H), 3.13(s, 3H), 3.53(s, 3H), 3.79(s, 3H), 3.96(s, 3H), 5.19(s, 2H), 6.87(s, 1H), 7.15(d, J = 9.0 Hz, 1H), 7.31–7.50(m, 7H), 7.71(d, J = 8.4 Hz, 2H), 8.13(d, J = 8.4 Hz, 2H)<br>IR(KBr)1719, 1608, 1481, 1366, 1278, 1118, 1080, 1017 cm⁻¹ |
| I-239 | ¹HNMR(CDCl₃) δ 2.38(s, 3H), 2.68(s, 3H), 3.12(s, 3H), 3.53(s, 3H), 3.79(s, 3H), 3.96(s, 3H), 5.14(s, 2H), 6.87(s, 1H), 7.15(d, J = 8.7 Hz, 1H), 7.21(d, J = 8.4 Hz, 2H), 7.34(d, J = 8.4 Hz, 2H), 7.36(d, J = 8.7 Hz, 1H), 7.40(d, J = 2.1 Hz, 1H), 7.71(d, J = 8.7 Hz, 2H), 8.13(d, J = 8.4 Hz, 2H)<br>IR(KBr)1718, 1607, 1519, 1481, 1355, 1280, 1232, 1182, 1121, 1079, 1018 cm⁻¹ |
| I-240 | ¹HNMR(CDCl₃) δ 2.70(s, 3H), 3.03(s, 3H), 3.12(s, 3H), 3.55(s, 3H), 3.77(s, 3H), 5.18(s, 2H), 6.78–6.89(broad, 1H), 6.86(s, 1H), 7.14(d, J = 8.4 Hz, 1H), 7.31–7.49(m, 8H), 7.55(d, J = 8.4 Hz, 2H)<br>IR(KBr)1604, 1526, 1483, 1395, 1374, 1360, 1292, 1231, 1177, 1119, 1078, 1014 cm⁻¹ |
| I-241 | ¹HNMR(CDCl₃) δ 2.37(s, 3H), 2.69(s, 3H), 3.05(s, 3H), 3.12(s, 3H), 3.55(s, 3H), 3.77(s, 3H), 5.14(s, 2H), 6.85(s, 1H), 6.81–6.91(broad, 2H), 7.14(d, J = 8.4 Hz, 1H), 7.21(d, J = 8.1 Hz, 1H), 7.34(d, J = 8.1 Hz, 2H), 7.40(d, J = 2.1 Hz, 1H), 7.56(d, J = 8.4 Hz, 2H)<br>IR(KBr)1605, 1529, 1484, 1396, 1356, 1275, 1233, 1178, 1121, 1078, 1016 cm⁻¹ |
| I-242 | ¹HNMR(CDCl₃) δ 1.76(s, 3H), 1.81(s, 3H), 2.73(s, 3H), 3.03(s, 6H), 3.22(s, 3H), 3.55(s, 3H), 3.77(s, 3H), 4.63(d, J = 6.6 Hz, 2H), 5.49(t, J = 6.6 Hz, 1H), 6.75–6.91(broad, 2H), 6.86(s, 1H), 7.08(d, J = 8.7 Hz, 1H), 7.34(d.d, J = 8.7&2.1 Hz, 1H), 7.39(d, J = 2.1 Hz, 1H), 7.55(d, J = 8.7 Hz, 1H)<br>IR(KBr)1609, 1529, 1482, 1363, 1235, 1178, 1117, 1078, 1013 cm⁻¹ |
| I-243 | IR(KBr)3409, 1608, 1509, 1464, 1367, 1230, 1175, 1149, 1079, 1018 cm⁻¹ |

TABLE 53

| | |
|---|---|
| I-244 | ¹HNMR(CDCl₃) δ 1.72(s, 3H), 1.76(s, 3H), 2.55(m, 2H), 3.22(s, 3H), 3.45(s, 3H), 3.72(s, 3H), 4.07(d, J = 6.6 Hz, 2H), 4.46(d, J = 10.5 Hz, 1H), 4.51(d, J = 10.5 Hz, 1H), 4.66(d, J = 10.5 Hz, 1H), 4.75(d, J = 10.5 Hz, 1H), 5.24(brs, 1H), 6.84(s, 1H), 6.95(d, J = 8.7 Hz, 1H), 7.02(s, 1H), 7.21(d, J = 8.7 Hz, 1H), 7.39(d, J = 9.0 Hz, 2H), 7.71(d, J = 9.0 Hz, 2H)<br>IR(KBr)3307, 1609, 1509, 1465, 1364, 1235, 1180, 1152, 1082, 1021 cm⁻¹ |
| I-245 | m.p. 182–184° C.<br>¹HNMR(CDCl₃) δ 2.42(s, 3H), 2.70(s, 3H), 3.13(s, 3H), 3.53(s, 3H), 3.77(s, 3H), 5.19(s, 2H), 6.86(s, 1H), 7.13–7.53(m, 12H)<br>IR(KBr)3434, 3030, 2937, 1605, 1522, 1483, 1366, 1274, 1235, 1176, 1119, 1086, 1011 cm⁻¹ |
| I-246 | ¹HNMR(CDCl₃) δ 2.58(s, 3H), 3.21(s, 3H), 3.55(s, 3H), 3.77(s, 3H), 3.91(s, 3H), 5.26(m, 2H), 6.84(s, 1H), 7.12(d, J = 9.0 Hz, 1H), 7.27–7.54(m, 8H), 7.60(d, J = 8.7 Hz, 2H), 7.90(d, J = 2.1 Hz, 1H)<br>IR(KBr)1728, 1699, 1605, 1513, 1480, 1362, 1239, 1175, 1150, 1083, 1017 cm⁻¹ |
| I-247 | IR(KBr)1729, 1607, 1512, 1479, 1366, 1234, 1177, 1151, 1079, 1015 cm⁻¹ |
| I-248 | ¹HNMR(CDCl₃) δ 1.75(s, 3H), 1.79(s, 3H), 2.57(s, 3H), 3.21(s, 3H), 3.56(s, 3H), 3.78(s, 3H), 3.89(6, 3H), 4.63(d, J = 6.6 Hz, 2H), 5.49–5.58(m, 1H), 6.85(s, 1H), 6.93–7.00(m, 3H), 7.38(d, J = 8.7 Hz, 2H), 7.70(d, J = 8.7 Hz, 2H)<br>IR(KBr)1603, 1518, 1482, 1365, 1239, 1176, 1150, 1078 cm⁻¹ |
| I-249 | foam<br>¹HNMR(CDCl₃) δ 2.30(br, 1H), 2.76–2.82(m, 2H), 3.64–3.68(m, 2H), 3.87(s, 1H), 5.14(s, 2H), 5.70(s, 1H), 6.70(dd, J = 2.1, 8.4 Hz, 1H), 6.78(s, 1H), 6.84(d, J = 1.8 Hz, 1H), 6.97–7.0 1(m, 3H), 7.37–7.49(m, 5H), 7.56–7.61(m, 2H)<br>IR(KBr)3600-2800(br), 1608, 1583, 1517, 1464, 1387, 1287, 1247, 1225, 1178, 1082, 1015 cm⁻¹ |
| I-250 | m.p. 104–105° C.<br>¹HNMR(CDCl₃) δ 0.76(t, J = 7.5 Hz, 3H), 1.44–1.54(m, 2H), 3.61(s, 3H), 3.71(t, J = 6.6 Hz, 2H), 3.74(s, 3H), 3.87(s, 3H), 5.16(s, 2H), 5.63(s, 1H), 6.66(s, 1H), 6.90(dd, J = 2.1, 8.4 Hz, 1H), 6.96–7.01(m, 4H), 7.04(d, J = 1.8 Hz, 1H), 7.37–7.48(m, 5H), 7.51–7.56(m, 2H)<br>IR(KBr)3600-2800(br), 1608, 1593, 1518, 1474, 1462, 1379, 1294, 1251, 1226, 1183, 1109, 1078, 1040, 1008 cm⁻¹ |

TABLE 54

| | |
|---|---|
| I-251 | m.p. 103–105° C.<br>¹HNMR(CDCl³) δ 0.78(t, J = 7.2 Hz, 3H), 1.15–1.27(m, 2H), 1.43–1.51(m, 2H), 3.61(s, 3H), 3.73–3.77(m, 2H), 3.74(s, 3H), 3.87(s, 3H), 5.16(s, 2H), 5.63(s, 1H), 6.65(s, 1H), 6.90(dd, J = 2.1, 8.1 Hz, 1H), 6.96–7.01(m, 3H), 7.04(d, J = 2.1 Hz, 1H), 7.37–7.48(m, 5H), 7.51–7.56(m, 2H)<br>IR(KBr)3600-2800(br), 1607, 1518, 1467, 1375, 1288, 1251, 1179, 1113, 1084, 1020, 1008 cm⁻¹ |
| I-252 | m.p. 111.5–112.5° C.<br>¹HNMR(CDCl₃) δ 0.78(t, J = 7.5 Hz, 3H), 1.15–1.27(m, 2H), 1.41–1.50(m, 2H), 3.10(s, 3H), 3.61(s, 3H), 3.73–3.78(m, 2H), 3.74(s, 6H), 5.18(s, 2H), 6.66(s, 1H), 6.96–7.01(m, 2H), 7.10(d, J = 8.7 Hz, 1H), 7.26–7.55(m, 9H)<br>IR(KBr)3600-2800(br), 1609, 1518, 1464, 1440, 1375, 1355, 1289, 1269, 1249, 1181, 1170, 1107, 1080, 1019 cm⁻¹ |
| I-253 | ¹HNMR(CDCl₃) δ 1.76(s, 3H), 1.82(s, 3H), 3.45(s, 3H), 3.76(s, 3H), 4.62(d, J = 8.4 Hz, 2H), 5.54(t, J = 8.4 Hz, 1H), 6.49(s, 1H), 6.91–6.99(m, 2H), 7.05(d, J = 1.5 Hz), 7.74(d, J = 8.7 Hz, 2H), 8.15(d, J = 8.7 Hz, 2H)<br>IR(KBr)3474, 1687, 1607, 1509, 1417, 1397, 1316, 1287, 1240, 1109, 1071, 1006 cm⁻¹ |
| I-254 | ¹HNMR(CDCl₃) δ 2.39(s, 3H), 3.45(s, 3H), 3.76(s, 3H), 5.11(s, 2H), 6.49(s, 1H), 6.94(dd, J = 8.4&1.8 Hz, 1H), 7.04(d, J = 8.4 Hz, 1H), 7.06(d, J = 1.8 Hz, 1H), 7.19–7.38(m, 4H), 7.73(d, J = 8.4 Hz, 2H), 8.14(d, J = 8.4 Hz, 2H)<br>IR(KBr)3549, 3466, 1668, 1603, 1518, 1489, 1465, 1449, 1421, 1397, 1372, 1288, 1236, 1186, 1117, 1074, 1017 cm⁻¹ |
| I-255 | ¹HNMR(CDCl₃) δ 1.76(s, 3H), 1.82(s, 3H), 3.02(s, 6H), 3.48(s, 3H), 3.74(s, 3H), 4.61(d, J = 7.2 Hz, 2H), 5.53(t, J = 7.2 Hz, 1H), 5.66(s, 1H), 5.92(s, 1H), 6.47(s, 1H), 6.81(broad, 2H), 6.95(s, 2H), 7.06(s, 1H), 7.56(d, J = 8.7 Hz, 2H)<br>IR(KBr)3535, 3494, 3452, 1606, 1526, 1487, 1406, 1357, 1288, 1242, 1195, 1112 cm⁻¹ |
| I-256 | ¹HNMR(CDCl₃) δ 2.39(s, 3H), 3.02(s, 6H), 3.48(s, 3H), 3.74(s, 3H), 5.10(s, 2H), 5.66(s, 1H), 5.93(s, 1H), 6.47(s, 1H), 6.82(d, J = 8.4 Hz, 2H), 6.96(dd, J = 8.1& 1.8 Hz, 1H), 7.02(d, J = 8.1 Hz, 1H), 7.08(d, J = 1.8 Hz, 1H), 7.23(d, J = 7.8 Hz, 2H), 7.34(d, J = 7.8 Hz, 2H), 7.56 (d, J = 8.4 Hz, 2H)<br>IR(KBr)3536, 3379, 1610, 1586, 1528, 1489, 1460, 1443, 1361, 1288, 1250, 1225, 1195, 1117, 1072, 1008 cm⁻¹ |

TABLE 55

| | |
|---|---|
| I-257 | ¹HNMR(CDCl₃) δ 1.71(s, 3H), 1.76(s, 3H), 2.49–2.60(m, 2H), 3.44(s, 3H), 3.70(s, 3H), 4.06(t, J = 6.3 Hz, 2H), 4.48(d, J = 6.0 Hz, 2H), 4.71(d, J = 8.7 Hz, 2H), 5.23(t, J = 8.7 Hz, 1H), 5.37(broads, 1H), 6.84(s, 1H), 6.91–6.97(m, 1H), 6.92(d, J = 8.4 Hz, 2H), 7.18–7.23(m, 2H), 7.52(d, J = 8.7 Hz, 2H)<br>IR(KBr)3398, 1612, 1518, 1465, 1389, 1232, 1174, 1131, 1101, 1081, 1023 cm⁻¹ |
| I-258 | ¹HNMR(CDCl₃) δ :3.21(s, 3H), 3.41(s, 3H), 3.63(s, 3H), 3.77(s, 3H), 4.76(s, 2H), 5.15(s, 2H), 6.94(s, 1H), 6.99(d, J = 8.7 Hz, 1H), 7.23–7.49(m, 9H), 7.71(d, J = 8.7 Hz, 2H)<br>IR(KBr)3497, 1738, 1721, 1607, 1509, 1469, 1362, 1242, 1152, 1056, 1017 cm⁻¹ |
| I-259 | foam<br>¹HNMR(CDCl₃) δ 2.35(s, 6H), 2.73(s, 3H), 2.79(t, J = 5.7 Hz, 2H), 3.21(s, 3H), 3.31(s, 3H), 3.56(s, 3H), 3.78(s, 3H), 4.19(t, J = 5.7 Hz, 2H), 6.84(s, 1H), 7.09(d, J = 8.4 Hz, 1H), 7.34–7.41(m, 4H), 7.66–7.71(m, 2H)<br>IR(KBr)3600-2700(br), 1519, 1481, 1365, 1273, 1200, 1177, 1151, 1120, 1079, 1015 cm⁻¹ |
| I-260 | foam<br>¹HNMR(CDCl₃ + CD₃OD) δ 2.71(t, J = 5.1 Hz, 2H), 3.46(s, 6H), 3.73(s, 6H), 4.11(t, J = 5.1 Hz, 2H), 6.44(s, 1H), 6.87–6.99(m, 4H), 7.04 (d, J = 2.1 Hz, 1H), 7.49–7.53(m, 2H)<br>IR(KBr)3600-2200(br), 1607, 1583, 1519, 1475, 1407, 1390, 1275, 1252, 1226, 1114, 1062 cm⁻¹ |

TABLE 55-continued

| | |
|---|---|
| I-261 | m.p. 85–87° C.<br>¹HNMR(CDCl₃) δ 3.49(s, 3H), 3.75(s, 3H), 5.15(s, 2H), 5.23(brs, 1H), 5.68(brs, 1H), 5.89(s, 1H), 6.43(s, 1H), 6.95(dd, J = 8.3, 2.1 Hz, 1H), 7.03(d, J = 8.3 Hz, 1H), 7.08(d, J = 2.1 Hz, 1H), 7.08(t, J = 8.7 Hz, 1H), 7.33(ddd, J = 8.7, 2.1, 1.2 Hz, 1H), 7.37–7.47(m, 6H)<br>IR(KBr)3410, 1525, 1488, 1284, 1248, 1102, 1010, 759, 704 cm⁻¹ |

TABLE 56

| | |
|---|---|
| I-262 | m.p. 138–140° C.<br>¹HNMR(CDCl₃) δ 1.77(s, 3H), 1.82,(s, 3H), 3.21(s, 3H), 3.22(s, 3H), 3.48(s, 3H), 3.78(s, 3H), 4.64(d, J = 6.5 Hz, 2H), 5.51(t, J = 6.5 Hz, 1H), 7.05(d, J = 8.5 Hz, 1H), 7.08(s, 1H), 7.14(dd, J = 8.5, 2.2 Hz, 1H), 7.34(d, J = 2.2 Hz, 1H), 7.40(d, J = 8.7 Hz, 2H), 7.69(d, J = 8.7 Hz, 2H), 10.00(s, 1H)<br>IR(KBr)1693, 1514, 1470, 1361, 1348, 1275, 1239, 1175, 1151, 979, 969, 867, 845, 815 cm⁻¹ |
| I-263 | foam<br>¹HNMR(DMSO-d₆) δ 1.74(s, 3H), 1.78(s, 3H), 3.32(s, 3H), 3.44(s, 3H), 3.76(s, 3H), 4.66(d, J = 6.6 Hz, 2H), 5.49(t, J = 6.6 Hz, 1H), 7.11(s, 1H), 7.23–7.25(m, 3H), 7.48(d, J = 8.6 Hz, 2H), 7.77(d, J = 8.6 Hz, 2H), 13.1(brs, 1H)<br>IR(KBr)3431, 1737, 1518, 1471, 1177, 1151, 972, 864, 849 cm⁻¹ |
| I-264 | m.p. 153.5–155.5° C.<br>¹HNMR(CDCl₃) δ 2.58(s, 3H), 3.52(s, 3H), 3.77(s, 3H), 5.21(s, 2H), 6.83(s, 1H), 7.04–7.24(m, 5H), 7.30–7.49(m, 5H), 7.56–7.65(m, 2H)<br>IR(CHCl₃)1607, 1520, 1481, 1412, 1368, 1298, 1267, 1131, 1080, 1012, 960, 942, 907, 869, 836, 812 cm⁻¹ |
| I-265 | dp >116° C.<br>¹HNMR(CDCl₃ + CD₃OD) δ 2.69(s, 3H), 3.15(s, 3H), 3.16(s, 3H), 3.57(s, 3H), 3.80(s, 3H), 5.21(s, 2H), 6.88(s, 1H), 7.19(d, J = 8.4 Hz, 1H), 7.34–7.51(m, 7H), 7.83–7.90(m, 2H), 8.01–8.07(m, 5H)<br>IR(KBr)3434, 3028, 2934, 1596, 1519, 1460, 1365, 1308, 1276, 1173, 1148, 1119, 1108, 1012, 946, 841, 819 cm⁻¹ |
| I-266 | m.p. 136–138° C.<br>¹HNMR(CDCl₃) δ 3.43(s, 3H), 3.75(s, 3H), 5.19(s, 2H), 5.98(s, 1H), 6.44(s, 1H), 7.04–7.52(m, 10H), 7.57–7.65(m, 5H)<br>IR(CHCl₃)3496, 1612, 1521, 1488, 1454, 1412, 1391, 1313, 1267, 1157, 1113, 1069, 1010, 934, 825 cm⁻¹ |

TABLE 57

| | |
|---|---|
| I-267 | foam<br>¹HNMR(CDCl₃) δ 2.38(s, 3H), 3.10(s, 3H), 3.21(s, 3H), 3.41(s, 3H), 3.67(s, 3H), 3.77(s, 3H), 5.11(s, 2H), 6.93(s, 1H), 7.09(d, J = 8.6 Hz, 1H), 7.21(d, J = 8.2 Hz, 2H), 7.27(d, J = 2.1 Hz, 1H), 7.35(d, J = 8.2 Hz, 2H), 7.38(d, J = 8.9 Hz, 2H), 7.70(d, J = 8.9 Hz, 2H)<br>IR(KBr)1733, 1518, 1471, 1367, 1297, 1177,1151, 1118, 1059, 971, 862, 815 cm⁻¹ |
| I-268 | amorphous<br>¹HNMR(DMSO-d₆) δ 1.64(s, 3H), 1.70(s, 3H), 2.44(q, J = 7.2 Hz, 2H), 3.30(s, 3H), 3.70(s, 3H), 3.93(t, J = 7.2 Hz, 2H), 5.26(t, J = 7.2 Hz, 1H), 6.64(dd, J = 8.6, 2.1 Hz, 1H), 6.74(d, J = 2.1 Hz, 1H), 6.87(d, J = 8.9 Hz, 2H), 6.87(d, J = 8.6 Hz, 1H), 6.96(s, 1H), 7.48(d, J = 8.9 Hz, 2H), 8.84(s, 1H), 9.59(s, 1H), 12.8(brs, 1H)<br>IR(CHCl₃)3594, 3540, 1743, 1707, 1520, 1470, 1260, 1058 cm⁻¹ |
| I-269 | m.p. 206–208° C.(dec.)<br>¹HNMR(DMSO-d₆) δ 2.32(s, 3H), 3.32(s, 3H), 3.66(s, 3H), 5.05(s, 2H), 6.66(dd, J = 8.2, 2.1 Hz, 1H), 6.79(d, J = 2.1 Hz, 1H), 6.83(s, 1H), 6.84(d, J = 8.6 Hz, 2H), 6.89(d, J = 8.2 Hz, 1H), 7.20(d, J = 8.0 Hz, 2H), 7.38(d, J = 8.0 Hz, 2H), 7.45(d, J = 8.6 Hz, 2H), 8.91(s, 1H), 9.68(s, 1H), 12.7(brs, 1H)<br>IR(KBr)3413, 1710, 1612, 1591, 1520, 1471, 1377, 1227, 1083, 1059, 1013, 837, 809 cm⁻¹ |
| I-270 | foam<br>¹HNMR(CDCl₃) δ 2.42(s, 3H), 3.45(s, 3H), 3.75(s, 3H), 5.15(s, 2H), 5.68(s, 1H), 5.93(s, 1H), 6.47(s, 1H), 6.96(dd, J = 1.8, 8.1 Hz, 1H), 7.03(d, J = 1.8 Hz, 1H), 7.25–7.28(m, 2H), 7.35–7.48(m, 5H), 7.52–7.56(m, 2H)<br>IR(CHCl₃)3535, 3014, 1616, 1588, 1559, 1523, 1513, 1490, 1463, 1455, 1417, 1396, 1317, 1290, 1247, 1194, 1115, 1072, 1012 cm⁻¹ |
| I-271 | m.p. 143–145° C.<br>¹HNMR(CDCl₃) δ 2.70(s, 3H), 3.12(s, 3H), 3.54(s, 3H), 3.73(s, 3H), 3.84(s, 3H), 5.18(s, 2H), 6.83(s, 1H), 7.00–7.07(m, 2H), 7.14(d, J = 8.4 Hz, 1H), 7.33–7.49(m, 9H)<br>IR(KBr)3434, 2940, 1609, 1520, 1482, 1396, 1369, 1293, 1283, 1243, 1178, 1114, 1080, 1021, 1009 cm⁻¹ |

TABLE 58

| | |
|---|---|
| I-272 | foam<br>¹HNMR(CDCl₃) δ 3.45(s, 3H), 3.71(s, 3H), 3.86(s, 3H), 5.15(s, 2H), 5.67(s, 1H), 5.84(s, 1H), 6.42(s, 1H), 6.98(dd, J = 1.8, 8.4 Hz, 1H), 7.01–7.07(m, 2H), 7.11(d, J = 1.8 Hz, 1H), 7.35–7.45(m, 8H)<br>IR(CHCl₃)3534, 3024, 1617, 1587, 1517, 1503, 1483, 1462, 1409, 1290, 1247, 1226, 1215, 1122, 1104, 1072, 1013 cm⁻¹ |
| I-273 | m.p. 155–156° C.<br>¹HNMR(CDCl₃) δ 1.76(s, 3H), 1.81(s, 3H), 2.42(s, 3H), 2.73(s, 3H), 3.23(s, 3H), 3.53(s, 3H), 3.77(s, 3H), 4.63(d, J = 6.6 Hz, 2H), 5.49(m, 1H), 6.86(s, 1H), 7.09(d, J = 8.4 Hz, 1H), 7.25–7.53(m, 6H)<br>IR(KBr)3434, 2935, 1605, 1522, 1465, 1388, 1365, 1292, 1273, 1176, 1119, 1084, 1011 cm⁻¹ |

TABLE 58-continued

| | |
|---|---|
| I-274 | m.p. 138–140° C.<br>$^1$HNMR(CDCl$_3$) δ 1.76(s, 3H), 1.81(s, 3H), 2.73(s, 3H), 3.22(s, 3H), 3.54(s, 3H), 3.73(s, 3H), 3.84(s, 3H), 4.63(d, J = 6.9 Hz, 2H), 5.50(m, 1H), 6.83(s, 1H), 7.01–7.04(m, 2H), 7.08(d, J = 8.4 Hz, 1H), 7.26(d, J = 0.6 Hz, 1H), 7.34–7.43(m, 3H)<br>IR(KBr)3433, 2937, 1608, 1519, 1480, 1400, 1368, 1292, 1271, 1244, 1179, 1112, 1081, 1011 cm$^{-1}$ |
| I-275 | m.p. 95–97° C.<br>$^1$HNMR(CDCl$_3$) δ 1.76(s, 3H), 1.82(s, 3H), 2.42(s, 3H), 3.45(s, 3H), 3.74(s, 3H), 4.61(d, J = 6.6 Hz, 2H), 5.52(m, 1H), 5.69(s, 1H), 6.47(s, 1H), 6.95–7.07(m, 3H), 7.25–7.28(m, 2H), 7.52–7.55(m, 2H)<br>IR(KBr)3479, 2935, 1613, 1585, 1523, 1509, 1490, 1458, 1415, 1395, 1362, 1315, 1249, 1196, 1112, 1070, 1005 cm$^{-1}$ |
| I-276 | m.p. 155–158° C.<br>$^1$HNMR(CDCl$_3$) δ 1.76(d, J = 0.9 Hz, 3H), 1.82(d, J = 0.9 Hz, 3H), 3.45(s, 3H), 3.86(s, 3H), 4.61(d, J = 6.9 Hz, 2H), 5.35(m, 1H), 5.68(s, 1H), 5.82(s, 1H), 6.42(s, 1H), 6.96–7.09(m, 4H), 7.35–7.41(m, 2H)<br>IR(KBr)3428, 3005, 2952, 1613, 1583, 1517, 1505, 1487, 1464, 1451, 1411, 1387, 1359, 1317, 1289, 1245, 1140, 1101, 1070, 1013 cm$^{-1}$ |

TABLE 59

| | |
|---|---|
| I-277 | m.p. 173–175° C.<br>$^1$HNMR(CDCl$^3$) δ 1.68(s, 3H), 1.74(s, 3H), 2.42(s, 3H), 2.51–2.60(m, 2H), 2.75(s, 3H), 3.21(s, 3H), 3.53(s, 3H), 3.76(s, 3H), 4.07(t, J = 6.9 Hz, 2H), 5.21(m, 1H), 6.86(s, 1H), 7.06(d, J = 8.7 Hz, 1H), 7.25–7.28(m, 2H), 7.35(dd, J = 2.1, 8.7 Hz, 1H), 7.40(d, J = 2.1 Hz, 1H), 7.50–7.53(m, 2H)<br>IR(KBr)3434, 2934, 1606, 1523, 1482, 1388, 1369, 1277, 1236, 1177, 1118, 1085, 1012 cm$^{-1}$ |
| I-278 | m.p. 151–154° C.<br>$^1$HNMR(CDCl$_3$) δ 1.69(s, 3H), 1.74(d, J = 0.9 Hz, 3H), 2.51–2.59(m, 2H), 2.75(s, 3H), 3.21(s, 3H), 3.54(s, 3H), 3.73(s, 3H), 3.84(s, 3H), 4.07(t, J = 6.9 Hz, 2H), 5.21(m, 1H), 6.83(s, 1H), 7.00–7.08(m, 3H), 7.34–7.43(m, 4H)<br>IR(KBr)3434, 2935, 1610, 1581, 1522, 1479, 1399, 1362, 1283, 1246, 1180, 1125, 1114, 1082, 1046 cm$^{-1}$ |
| I-279 | m.p. 90–92° C.<br>$^1$HNMR(CDCl$_3$) δ 1.69(s, 3H), 1.75(s, 3H), 2.42(s, 3H), 2.49–2.56(m, 2H), 3.45(s, 3H), 3.74(s, 3H), 4.06(t, J = 6.6 Hz, 2H), 5.22(m, 1H), 5.67(s, 1H), 5.90(s, 1H), 6.46(s, 1H), 6.94–7.06(m, 3H), 7.25–7.28(m, 2H), 7.52–7.55(m, 2H)<br>IR(KBr)3529, 3381, 2927, 1616, 1586, 1522, 1490, 1465, 1418, 1398, 1360, 1315, 1289, 1251, 1225, 1192, 1114, 1070, 1011 cm$^{-1}$ |
| I-280 | m.p. 82–84° C.<br>$^1$HNMR(CDCl$_3$) δ 1.69(s, 3H), 1.75(s, 3H), 2.49–2.56(m, 2H), 3.45(s, 3H), 3.71(s, 3H), 3.85(s, 3H), 4.06(t, J = 6.6 Hz, 2H), 5.22(m, 1H), 5.67(s, 1H), 5.82(s, 1H), 6.42(s, 1H), 6.92–7.09(m, 5H), 7.35–7.43(m, 2H)<br>IR(KBr)3420, 3326, 2935, 1615, 1583, 1518, 1504, 1486, 1466, 1410, 1316, 1289, 1249, 1122, 1101, 1071, 1018 cm$^{-1}$ |
| I-281 | m.p. 166–168° C.<br>$^1$HNMR(CDCl$_3$) δ 2.38(s, 3H), 2.69(s, 3H), 3.11(s, 3H), 3.54(s, 3H), 3.73(s, 3H), 3.84(s, 3H), 5.14(s, 2H), 6.83(s, 1H), 7.00–7.44(m, 11H)<br>IR(KBr)3434, 2941, 1608, 1521, 1498, 1482, 1466, 1397, 1368, 1284, 1243, 1177, 1113, 1079, 1019 cm$^{-1}$ |

TABLE 60

| | |
|---|---|
| I-282 | m.p. 109–111° C.<br>$^1$HNMR(CDCl$_3$) δ 2.39(s, 3H), 3.45(s, 3H), 3.71(s, 3H), 3.85(s, 3H), 5.10(s, 2H), 5.67(s, 1H), 5.83(s, 1H), 6.42(s, 1H), 6.95–7.41(m, 11H)<br>IR(CHCl$_3$)3497, 2935, 1610, 1583, 1519, 1499, 1481, 1465, 1399, 1312, 1274, 1245, 1185, 1120, 1102, 1067, 1012 cm$^{-1}$ |
| I-283 | $^1$HNMR(CDCl$_3$) δ 2.38(s, 3H), 2.68(s, 3H), 3.12(s, 3H), 3.53(s, 1H), 3.77(s, 3H), 5.14(s, 2H), 6.83(s, 1H), 7.10–7.24(m, 5H),, 7.33(d, J = 8.4 Hz, 1H), 7.34(d, J = 8.4 Hz, 2H), 7.40(d, J = 2.1 Hz, 1H), 7.56–7.64(m, 2H)<br>IR(KBr)1603, 1520, 1482, 1367, 1297, 1277, 1251, 1232, 1176, 1120, 1084, 1012 cm$^{-1}$ |
| I-284 | $^1$HNMR(CDCl$_3$) δ 2.39(s, 3H), 3.45(s, 3H), 3.75(s, 3H), 5.10(s, 2H), 5.68(s, 1H), 5.88(s, 1H), 6.44(s, 1H), 6.95(dd, J = 8.4&2.1 Hz, 1H), 7.03(d, J = 8.4 Hz, 1H), 7.07(d, J = 2.1 Hz, 1H), 7.08–7.29(m, 4H), 7.34(d, J = 8.4 Hz, 2H), 7.56–7.65(m, 2H)s<br>IR(KBr)3504, 3330, 1604, 1596, 1490, 1461, 1455, 1424, 1360, 1318, 1242, 1223, 1121, 1071, 1009 cm$^{-1}$ |
| I-285 | $^1$HNMR(CDCl$_3$) δ 2.69(s, 3H), 3.13(s, 3H), 3.56(s, 3H), 3.78(s, 3H), 5.19(s, 2H), 6.85(s, 1H), 7.05–7.15(m, 1H), 7.15(d, J = 8.4 Hz, 1H), 7.30–7.49(m, 10H)<br>IR(KBr)1610, 1583, 1517, 1475, 1455, 1359, 1296, 1270, 1239, 1180, 1116, 1088, 1013 cm$^{-1}$ |
| I-286 | $^1$HNMR(CDCl$_3$) δ 3.47(s, 3H), 3.75(s, 3H), 5.15(s, 2H), 5.68(s, 1H), 5.89(s, 1H), 6.46(s, 1H), 6.95(dd, J = 8.4&2.1 Hz, 1H), 7.03(d, J = 8.4 Hz, 1H), 7.04–7.12(m, 2H), 7.35–7.51(m, 9H)<br>IR(KBr)3543, 3346, 1612, 1586, 1566, 1518, 1502, 1479, 1407, 1362, 1320, 1239, 1110, 1068, 1006 cm$^{-1}$ |
| I-287 | $^1$HNMR(CDCl$_3$) δ 2.68(s, 3H), 3.14(s, 3H), 3.58(s, 3H), 3.81(s, 3H), 5.20(s, 2H), 6.88(s, 1H), 7.16(d, J = 8.7 Hz, 1H), 7.32–7.49(m, 7H), 7.60–7.68(m, 1H), 7.98–8.04(m, 1H), 8.24–8.29(m, 1H), 8.44–8.47(m, 1H)<br>IR(KBr)1609, 1531, 1362, 1270, 1239, 1178, 1122, 1085, 1014 cm$^{-1}$ |
| I-288 | $^1$HNMR(CDCl$_3$) δ 3.49(s, 3H), 3.78(s, 3H), 5.17(s, 2H), 5.71(s, 1H), 5.83(s, 1H), 6.49(s, 1H))6.95(dd, J = 12.3&1.2 Hz, 1H), 7.02(d, J = 12.3 Hz, 1H), 7.08(d, J = 1.2 Hz, 1H), 7.33–7.50(m, 5H), 7.60–7.68(m, 1H), 7.97–8.06(m, 1H), 8.21–8.27(m, 1H), 8.52(s, 1H)<br>IR(KBr)3528, 3358, 1588, 1527, 1499, 1454, 1406, 1348, 1314, 1241, 1122, 1070, 1009 cm$^{-1}$ |

TABLE 61

| | |
|---|---|
| I-289 | ¹HNMR(CDCl₃) δ 2.68(s, 3H), 3.13(s, 3H), 3.55(s, 3H), 3.77(s, 3H), 5.19(s, 2H), 6.79–6.88(m, 1H), 6.86(s, 1H), 7.02–7.10(m, 2H), 7.15 (d, J = 8.4 Hz, 1H), 7.26–7.50(m, 8H)<br>IR(KBr)3479, 3388, 1623, 1603, 1518, 1478, 1396, 1358, 1176, 1118, 1081, 1013 cm⁻¹ |
| I-290 | ¹HNMR(CDCl₃) δ 3.11(s, 3H), 3.45(s, 3H), 3.77(s, 3H), 5.17(s, 2H), 6.05(s, 1H), 6.46(s, 1H))7.00–7.18(m, 1H), 7.14(d, J = 8.4 Hz, 1H), 7.33–7.50(m, 9H), 7.52(d, J = 2.1 Hz, 1H)<br>IR(KBr)3504, 1612, 1578, 1519, 1498, 1464, 1391, 1355, 1290, 1276, 1239, 1183, 1167, 1107, 1070, 1004 cm⁻¹ |
| I-291 | ¹HNMR(CDCl₃+ CD₃OD) δ 3.44(s, 3H), 3.75(s, 3H), 4.74(s, 2H), 5.13(s, 2H), 1H), 6.86–6.95(m, 3H), 6.99(d, J = 8.7 Hz, 1H), 7.30–7.48 (m, 7H), 7.52(d, J = 8.7 Hz, 2H)<br>IR(KBr)3433, 1707, 1611, 1518, 1473, 1463, 1379, 1250, 1174, 1132, 1089, 1058, 1016 cm⁻¹ |
| I-292 | ¹HNMR(CDCl₃ + CD₃OD) δ 3.41(s, 3H), 3.62(s, 3H), 3.75(s, 3H), 4.74(s, 2H), 5.15(s, 2H), 6.87–7.01(m, 4H), 7.30–7.55(m, 9H)<br>IR(KBr)3386, 1722, 1611, 1518, 1464, 1343, 1271, 1245, 1233, 1215, 1168, 1082, 1060, 1021 cm⁻¹ |
| I-293 | ¹HNMR(CDCl₃) δ 2.38(s, 3H), 2.69(s, 3H), 3.12(s, 3H), 3.56(s, 3H), 3.78(s, 3H), 5.14(s, 2H), 6.85(s, 1H), 7.05–7.45(m, 12H)<br>IR(KBr)1607, 1584, 1519, 1479, 1401, 1364, 1348, 1280, 1237, 1178, 1164, 1115, 1081, 1016 cm⁻¹ |
| I-294 | foam<br>¹HNMR(CDCl₃) δ 3.45(s, 3H), 3.75(s, 3H), 4.36(d, J = 2.1 Hz, 1H), 4.55(s, 2H), 4.76(d, J = 2.1 Hz, 1H), 6.45,(s, 1H), 6.92(d, J = 8.7 Hz, 2H), 6.99(d, J = 8.4 Hz, 1H), 7.20(dd, J = 1.5 and 8.4 Hz, 1H), 7.11(d, J = 1.5 Hz, 1H), 7.53(d, J = 8.7 Hz, 2H)<br>IR(Nujol)3425, 1612, 1588, 1523, 1487, 1295, 1268, 1228, 1113, 1069, 825 cm⁻¹ |
| I-295 | foam<br>¹HNMR(CDCl₃) δ 2.78(s, 3H), 3.21(s, 3H), 3.23(s, 3H), 3.55(s, 3H), 3.78(s, 3H), 4.79(d, J = 6.6 Hz, 2H), 6.21(t, J = 6.6 Hz, 1H), 6.85(s, 1H), 7.08(d, J = 8.7 Hz, 1H), 7.37(dd, J = 8.7, 2.1 Hz, 1H), 7.38(d, J = 8.7 Hz, 2H), 7.41(d, J = 2.1 Hz, 1H), 7.68(d, J = 8.7 Hz, 2H)<br>IR(Nujol)1632, 1607, 1519, 1482, 1180, 1150, 1079, 1011, 976, 876, 814, 798 cm⁻¹ |

TABLE 62

| | |
|---|---|
| I-296 | foam<br>¹HNMR(CD₃OD) δ 3.38(s, 3H), 3.68(s, 3H), 4.12(brs, 2H), 4.65(brs, 2H), 5.01(m, 2H), 6.43(s, 1H), 6.78(dd, J = 8.7, 1.8 Hz, 1H), 6.85(d, J = 8.7, 2H), 6.86(d, J = 1.8 Hz, 1H), 6.94(d, J = 8.4 Hz, 1H), 7.46(d, J = 8.7 Hz, 2H)<br>IR(Nujol)3411, 1612, 1591, 1520, 1485, 1461, 1253, 1223, 1115, 1008, 971, 944, 842, 810, 785 cm⁻¹ |
| I-297 | foam<br>¹HNMR(CD₃OD) δ 3.38(s, 3H), 3.68(s, 3H), 4.73(d, J = 5.1 Hz, 2H), 4.23(d, J = 5.1 Hz, 2H), 5.83(m, 2H), 6.43(s, 1H), 6.79(dd, J = 8.7, 1.8 Hz, 1H), 6.85(d, J = 8.7 Hz, 2H), 6.86(d, J = 1.8 Hz, 1H), 6.94(d, J = 8.7 Hz, 2H)<br>IR(Nujol)3393, 1611, 1588, 1523, 1489, 1460, 1248, 1114, 1071, 1013, 940, 824 cm⁻¹ |
| I-298 | foam<br>¹HNMR(CD₃OD) δ 1.77(s, 3H), 3.38(s, 3H), 3.68(s, 3H), 4.00(s, 2H), 5.72(d, J = 6.3 Hz, 2H), 5.81(t, J = 6.3 Hz, 1H), 6.43(s, 1H), 6.79(dd, J = 8.7, 1.8 Hz, 1H), 6.85(d, J = 8.7 Hz, 2H), 6.85(d, J = 1.8 Hz, 1H), 6.94(d, J = 8.4 Hz, 1H), 7.46(d, J = 8.7 Hz, 2H)<br>IR(Nujol)3384, 1608, 1585, 1523, 1494, 1457, 1262, 1242, 1227, 1116, 1078, 1008, 985, 822, 781 cm⁻¹ |
| I-299 | foam<br>¹HNMR(CD₃OD) δ 1.87(s, 3H), 3.83(s, 3H), 3.68(s, 3H), 4.17(s, 2H), 4.69(d, J = 6.6 Hz, 2H), 5.68(t, J = 6.3 Hz, 1H), 6.43(s, 1H), 6.79(dd, J = 8.7, 1.8 Hz, 1H), 6.85(d, J = 8.4 Hz, 2H), 6.85(d, J = 1.8 Hz, 1H), 6.94(d, J = 8.4 Hz, 1H), 7.46(d, J = 8.7 Hz, 2H)<br>IR(Nujol)3350, 3236, 1606, 1589, 1524, 1490, 1463, 1247, 1227, 1079, 1011, 992, 819, 790 cm⁻¹ |
| I-300 | foam<br>¹HNMR(CDCl₃) δ 1.87(s, 3H), 2.10(s, 3H), 3.45(s, 3H), 3.74(s, 3H), 4.68(s, 2H), 4.71(d, J = 6.0 Hz, 2H), 5.77(t, J = 6.0 Hz, 1H), 6.44(s, 1H), 6.92(d, J = 8.0 Hz, 2H), 6.95(m, 2H), 7.07(brs, 1H), 7.53(d, J = 6.0 Hz, 2H)<br>IR(Nujol)3409, 1724, 1612, 1587, 1523, 1489, 1460, 1239, 1114, 1071, 1012, 940, 825, 781 cm⁻¹ |

TABLE 63

| | |
|---|---|
| I-301 | foam<br>¹HNMR(CD₃OD) δ 2.93(d, J = 2.1 Hz, 1H), 3.38(s, 3H), 3.68(s, 3H), 4.06(dd, J = 9.9, 7.8 Hz, 1H), 4.20(dd, J = 9.9, 3.6 Hz, 1H), 4.74(ddd, J = 7.8, 3.6, 2.1 Hz, 1H), 6.44(s, 1H), 6.80(dd, J = 8.4, 1.8 Hz, 1H), 6.85(d, J = 8.7 Hz, 2H), 6.87(d, J = 1.8 Hz, 1H), 6.96(d, J = 8.4 Hz, 1H), 7.46(d, J = 8.7 Hz, 2H)<br>IR(Nujol)3282, 1655, 1612, 1588, 1523, 1489, 1460, 1254, 1226, 1072, 1013, 940, 825 cm⁻¹ |
| I-302 | foam<br>¹HNMR(CD₃OD) δ 3.30(s, 3H), 3.68(s, 3H), 4.75(d, J = 5.1 Hz, 2H), 6.44(s, 1H), 6.80(dd, J = 8.4, 1.8 Hz, 1H), 6.85(d, J = 8.4 Hz, 2H), 6.92(d, J = 1.8 Hz, 1H), 6.99(d, J = 8.7 Hz, 1H), 7.42(t, J = 5.1 Hz, 1H), 7.46(d, J = 8.4 Hz, 2H)<br>IR(Nujol)3474, 3316, 1678, 1611, 1584, 1523, 1487, 1458, 1268, 1231, 1115, 1171, 1011, 942, 824, 758 cm⁻¹ |
| I-303 | foam<br>¹HNMR(CD₃OD) δ 1.24(d, J = 7.2 Hz, 3H), 3.38(s, 3H), 3.68(s, 3H), 4.12(q, J = 7.2 Hz, 2H), 4.75(d, J = 4.8 Hz, 2H), 6.43(s, 1H), 6.80(dd, J = 8.4, 1.8 Hz, 1H), 6.85(d, J = 8.7 Hz, 2H), 6.91(d, J = 1.8 Hz, 1H), 6.99(d, J = 8.4 Hz, 1H), 7.46(d, J = 8.7 Hz, 2H), 7.52(t, J = 4.8 Hz, 1H)<br>IR(Nujol)3306, 1715, 1612, 1587, 1523, 1487, 1460, 1266, 1232, 1115, 1070, 824, 760 cm⁻¹ |
| I-304 | foam<br>¹HNMR(CDCl₃) δ 2.34(s, 3H), 2.38(s, 3H), 2.70(s, 3H), 3.07(s, 3H), 3.21(s, 3H), 3.56(s, 3H), 3.78(s, 3H), 5.13(s, 2H), 6.84(s, 1H), 7.03 (d, J = 7.8 Hz, 1H), 7.06(s, 1H), 7.18(d, J = 8.4 Hz, 1H), 7.28(d, J = 7.8 Hz, 1H), 7.36(dd, J = 2.1, 8.4 Hz, 1H), 7.38(d, J = 8.7 Hz, 2H), 7.40(d, J = 2.1 Hz, 1H), 7.68(d, J = 8.7 Hz, 2H)<br>IR(KBr)1611, 1518, 1480, 1365, 1177, 1151, 1080, 876, 816 cm⁻¹ |

TABLE 63-continued

I-305 foam
¹HNMR(CDCl₃) δ 1.25(d, J = 6.9 Hz, 6H), 2.67(s, 3H), 2.93(q, J = 6.9 Hz, 1H)3.13(s, 3H), 3.21(s, 3H), 3.56(s, 3H), 3.78(s, 3H), 5.15(s, 2H), 6.84(s, 1H), 7.16(d, J = 8.7 Hz, 1H), 7.26(d, J = 8.4 Hz, 2H), 7.34(dd, J = 2.4, 8.7 Hz, 1H), 7.38(d, J = 8.4 Hz, 4H), 7.40(d, J = 2.4 Hz, 1H), 7.68(d, J = 8.4 Hz, 2H)
IR(KBr)1609, 1519, 1481, 1365, 1177, 1151, 1080, 875, 819 cm⁻¹

TABLE 64

I-306 foam
¹HNMR(CDCl₃) δ 2.62(s, 3H), 3.15(s, 3H), 3.21(s, 3H), 3.55(s, 3H), 3.77(s, 3H), 5.36(s, 2H), 6.84(s, 1H), 7.18(d, J=8.7Hz, 1H), 7.26(s, 1H), 7.33(dd, J=2.1, 8.4Hz, 1H), 7.38(d, J=8.7Hz, 2H), 7.41(d, J=2.1Hz, 1H), 7.51(m, 2H), 7.57(dd, J=1.8, 8.4Hz, 1H), 7.68(d, J=8.7Hz, 2H), 7.84–7.93(m, 4H)
IR(KBr) 1608, 1519, 1480, 1364, 1177, 1151, 1079, 876, 819, 797 cm⁻¹

I-307 foam
¹HNMR(CDCl₃) δ 2.64(s, 3H), 3.21(s, 3H), 3.28(s, 3H), 3.55(s, 3H), 3.77(s, 3H), 5.51(s, 2H), 6.83(s, 1H), 7.18(d, J=8.4Hz, 1H), 7.31(dd, J=2.4, 8.4Hz, 1H), 7.37(d, J=8.7Hz, 2H), 7.42(d, J=2.4Hz, 1H), 7.58(dt, J=2.4, 7.2Hz, 1H), 7.67(d, J=8.7Hz, 2H), 7.74(d, J=8.4Hz, 1H), 7.76(dt, J=2.4, 7.2Hz, 1H), 7.85(d, J=7.2Hz, 1H), 8.06(d, J=7.2Hz, 1H), 8.23(d, J=7.2Hz, 1H)
IR(KBr) 1603, 1519, 1480, 1365, 1177, 1151, 1080, 876, 824, 797 cm⁻¹

I-308 foam
¹HNMR(CDCl₃) δ 2.76(s, 3H), 3.17(s, 3H), 3.21(s, 3H), 3.55(s, 3H), 3.78(s, 3H), 5.25(s, 2H), 6.85(s, 1H), 7.12(d, J=8.7Hz, 1H), 7.35(dd, J=2.1, 8.4Hz, 1H), 7.38(d, J=8.7Hz, 2H), 7.42(d, J=2.1Hz, 1H), 7.61(d, J=8.7Hz, 2H), 7.67(d, J=8.4Hz, 2H), 7.68(d, J=8.7Hz, 2H)
IR(KBr) 1610, 1522, 1489, 1402, 1245, 1181, 1164, 1110, 1071, 821, 805 cm⁻¹

I-309 m.p. 221–222° C.
¹HNMR(CDCl₃) δ 2.36(s, 3H), 2.38(s, 3H), 3.46(s, 3H), 3.75(s, 3H), 5.09(s, 2H), 6.45(s, 1H), 6.92(d, J=8.4Hz, 2H), 6.98(dd, J=2.1, 8.1Hz, 1H), 7.06(d, J=8.4Hz, 1H), 7.08(d, J=2.1Hz, 1H), 7.08(s, 1H), 7.28(d, J=8.4Hz, 1H), 7.53(d, J=8.4Hz, 2H)
IR(KBr) 3475, 1610, 1522, 1489, 1402, 1245, 1181, 1164, 1110, 1071, 821, 805 cm⁻¹

I-310 m.p. 153–155° C.
¹HNMR(CDCl₃) δ 1.27(d, J=6.9Hz, 6H), 2.95(q, J=6.9Hz, 1H), 3.45(s, 3H), 3.74(s, 3H), 5.11(s, 2H), 6.45(s, 1H), 6.91(d, J=8.4Hz, 2H), 6.96(dd, J=2.1, 8.1Hz, 1H), 7.03(d, J=8.1Hz, 1H), 7.08(d, J=2.1Hz, 1H), 7.28(d, J=8.1Hz, 2H), 7.38(d, J=8.1Hz, 2H), 7.53(d, J=8.4Hz, 2H)
IR(KBr) 3486, 1611, 1522, 1489, 1265, 1113, 1072, 1011, 823 cm⁻¹

TABLE 65

I-311 m.p. 176–177° C.
¹HNMR(CDCl₃) δ 3.45(s, 3H), 3.75(s, 3H), 5.32(s, 2H), 6.45(s, 1H), 6.91(d, J=8.4Hz, 2H), 6.97(dd, J=2.1, 8.4Hz, 1H), 7.06(d, J=8.4Hz, 1H), 7.10(d, J=2.1Hz, 1H), 7.53(d, J=8.4Hz, 2H), 7.50–7.57(m, 3H), 7.82–7.92(m, 4H)
IR(KBr) 3476, 1610, 1522, 1488, 1469, 1401, 1263, 1246, 1173, 1112, 1073, 1014, 1002, 819, 806 cm⁻¹

I-312 m.p. 235–237° C.
¹HNMR(CDCl₃) δ 3.44(s, 3H), 3.73(s, 3H), 5.49(s, 2H), 6.44(s, 1H), 6.92(d, J=8.4Hz, 2H), 6.93(dd, J=2.1, 8.4Hz, 1H), 7.14(d, J=2.1Hz, 1H), 7.18(d, J=8.4Hz, 1H), 7.38(d, J=8.4Hz, 1H), 7.52(d, J=8.4Hz, 2H), 7.58(dd, J=7.2, 7.2Hz, 1H), 7.77(dd, J=7.2, 7.2Hz, 1H), 7.85(d, J=7.2Hz, 1H), 8.21(d, J=7.2Hz, 1H), 8.22(d, J=7.2Hz, 1H)
IR(KBr) 3378, 1609, 1522, 1488, 1268, 1229, 1205, 1114, 1072, 1016, 825, 782 cm⁻¹

I-313 m.p. 159–161° C.
¹HNMR(CDCl₃) δ 3.45(s, 3H), 3.75(s, 3H), 5.22(s, 2H), 6.45(s, 1H), 6.92(d, J=8.4Hz, 2H), 6.96(br.s, 2H), 7.11(br.s, 1H), 7.53(d, J=8.4Hz, 2H), 7.57(d, J=8.4Hz, 2H), 7.68(d, J=8.4Hz, 2H),
IR(KBr) 3433, 1613, 1523, 1490, 1326, 1251, 1166, 1113, 1066, 1014, 825, cm⁻¹

I-314 m.p. 92–93° C.
¹HNMR(CDCl₃) δ 1.63(s, 3H), 1.74(s, 3H), 2.34–2.39(m, 1H), 2.67–2.72(m, 2H), 3.47(s, 3H), 3.74(s, 3H), 4.52–4.54(m, 2H), 5.30–5.33(m, 2H), 6.78–6.97(m, 4H), 7.20(d, J=7.2Hz, 1H), 7.56(d, J=8.0Hz, 2H)
IR(KBr) 3410, 2932, 1613, 1519, 1473, 1444, 1390, 1263, 1228, 1174 cm⁻¹

I-315 m.p. 85–86° C.
¹HNMR(CDCl₃) δ 1.76(s, 3H), 1.83(s, 3H), 2.17–2.40(m, 1H), 2.65–2.71(m, 2H), 3.24(s, 3H), 3.46(s, 3H), 3.80(s, 3H), 4.50–4.52(m, 2H), 6.70(s, 1H), 7.28–7.43(m, 5H), 7.73(d, J=8.6Hz, 2H)
IR(KBr) 3432, 2938, 1731, 1513, 1469, 1366, 1180, 1151, 970, 868 cm⁻¹

TABLE 66

I-316 m.p. 179–180° C.
¹HNMR(CDCl₃) δ 1.72(s, 3H), 1.76(s, 3H), 2.15–2.35(m, 1H), 2.61–2.70(m, 2H), 3.46(s, 3H), 3.76(s, 3H), 4.47–4.50(m, 2H), 6.68(s, 1H), 7.17–7.52(m, 5H), 7.69(d, J=8.4Hz, 2H)
IR(KBr) 3427, 2934, 1612, 1576, 1519, 1465, 1443, 1415, 1376, 1228, 1174, 846 cm⁻¹

I-317 m.p. 141–142° C.
¹HNMR(CDCl₃) δ 1.75(s, 3H), 1.80(s, 3H), 3.21(s, 3H), 3.39(s, 3H), 3.68(s, 3H), 3.77(s, 3H), 4.61(d, J=7.2Hz, 2H), 5.50(t, J=7.0Hz, 1H), 6.93(s, 1H), 6.99–7.33(m, 5H), 7.57–7.65(m, 2H)
IR(KBr) 3432, 2938, 1724, 1519, 1474, 1365, 1346, 1294, 1262, 1244, 1220, 1163, 1119, 1059, 953, 842, 805 cm⁻¹

I-318 m.p. 127–128° C.
¹HNMR(CDCl₃) δ 1.68(s, 3H), 1.74(s, 3H), 2.54(dt, J=4.2, 4.6Hz, 2H), 3.20(s, 3H), 3.39(s, 3H), 3.68(s, 3H), 3.76(s, 3H), 4.05(t, J=4.4Hz, 2H), 5.21(t, J=4.6Hz, 1H), 6.93(s, 1H), 7.00(d, J=5.6Hz, 1H), 7.11–7.18(m, 2H), 7.25–7.35(m, 3H), 7.61(dd, J=3.8, 5.8Hz)
IR(KBr) 3447, 2974, 2940, 1740, 1519, 1471, 1365, 1343, 1295, 1262, 1226, 1182, 1161, 1119, 1058, 952, 843, 814 cm⁻¹

I-319 m.p. 171–172° C.
¹HNMR(CDCl₃) δ 2.38(s, 3H), 3.10(s, 3H), 3.39(s, 3H), 3.66(s, 3H), 3.77(s, 3H), 5.11(s, 2H), 6.93(s, 1H), 7.07–7.36(m, 9H), 7.61(dd, J=3.4, 5.6Hz, 2H)
IR(KBr) 3431, 2937, 1724, 1519, 1474, 1440, 1346, 1296, 1259, 1243, 1222, 1165, 1121, 1060, 953, 843, 804 cm⁻¹

I-320 m.p. 155–156° C.
¹HNMR(CDCl₃) δ 3.40(s, 3H), 3.69(s, 3H), 3.77(s, 3H), 5.13(s, 2H), 5.70(brs, 1H), 6.82–7.42(m, 5H), 7.39–7.42(m, 5H), 7.62(dd, J=5.4, 8.6Hz)
IR(KBr) 3550, 3481, 2956, 1723, 1519, 1467, 1435, 1344, 1285, 1261, 1238, 1223, 1130, 1058, 1013, 840 cm⁻¹

TABLE 67

I-321 m.p. 159–160° C.
¹HNMR(CDCl₃) δ 3.11(s, 3H), 3.40(s, 3H), 3.66(s, 3H), 3.77(s, 3H), 5.16(s, 2H), 6.93(s, 1H), 7.07–7.49(m, 5H), 7.62(dd, J=3.0, 8.4Hz, 2H)

TABLE 67-continued

IR(KBr) 3441, 2952, 1732, 1519, 1469, 1445, 1381, 1356, 1342, 1291, 1273, 1243, 1226, 1162, 1119, 1081, 1057, 999, 950, 842, 805 cm$^{-1}$

I-322 m.p. 160–161° C.
$^1$HNMR(CDCl$_3$) δ 2.37(s, 3H), 2.93(s, 3H), 3.19(s, 3H), 3.22(s, 3H), 3.55(s, 3H), 3.79(s, 3H), 5.23(s, 2H), 6.86(s, 1H), 7.20(d, J=8.1Hz, 2H), 7.30(d, J=8.1Hz, 2H), 7.36–7.41(m, 2H), 7.64–7.70(m, 2H), 7.74(d, J=2.1Hz, 1H), 7.83(d, J=2.1Hz, 1H), 10.16(s, 1H)
IR(CHCl$_3$) 3027, 2940, 1692, 1473, 1373, 1227, 1152, 1085 cm$^{-1}$

I-323 powder
$^1$HNMR(CDCl$_3$) δ 2.37(s, 3H), 2.86(s, 3H), 3.13(s, 3H), 3.21(s, 3H), 3.54(s, 3H), 3.79(s, 3H), 4.64(s, 2H), 5.11(s, 2H), 6.85(s, 1H), 7.21(d, J=7.8Hz, 2H), 7.32–7.44(m, 6H), 7.65–7.70(m, 2H)
IR(CHCl$_3$) 3026, 2939, 1475, 1372, 1228, 1178, 1151, 1084 cm$^{-1}$ I-324 powder
$^1$HNMR(CDCl$_3$) δ 1.89–1.98(brs, 1H), 2.39(s, 3H), 3.45(s, 3H), 3.75(s, 3H), 4.77(s, 2H), 5.01(s, 3H), 5.46(s, 1H), 5.99(s, 1H), 6.45(s, 1H), 6.45–6.95(m, 2H), 7.05(s, 2H), 7.24(d, J=8.1Hz, 2H), 7.38(d, J=8.1Hz, 2H), 7.50–7.56(m, 2H)
IR(CHCl$_3$) 3514, 2937, 1731, 1613, 1522, 1484, 1403, 1228, 1173, 1082 cm$^{-1}$ I-325 powder
$^1$HNMR(CDCl$_3$) δ 2.31(s, 3H), 2.88(s, 3H), 3.07(s, 3H), 3.22(s, 3H), 3.51(s, 3H), 3.74(s, 3H), 5.23(s, 2H), 6.83(s, 1H), 7.11–7.18(m, 2H), 7.32–7.41(m, 4H), 7.62–7.68(m, 3H), 8.03(s, 1H)
IR(CHCl$_3$) 3026, 2939, 1742, 1472, 1374, 1227, 1179, 1129, 1085 cm$^{-1}$

TABLE 68

I-326 powder
$^1$HNMR(CD$_3$OD) δ 2.33(s, 3H), 3.38(s, 3H), 3.68(s, 3H), 5.11(s, 2H), 6.44(s, 1H), 6.82–6.88(m, 2H), 6.99(d, J=1.8Hz, 1H), 7.13–7.19(m, 3H), 7.42–7.50(m, 4H)
IR(KBr) 3411, 2935, 1680, 1611, 1520, 1457, 1404, 1281, 1230, 1114 cm$^{-1}$ I-327 powder
$^1$HNMR(CDCl$_3$) δ 1.72(s, 3H), 1.79(s, 3H), 3.12(s, 3H), 3.21(s, 3H), 3.27(s, 3H), 3.52(s, 3H), 3.53(s, 3H), 4.81(d, J=7.5Hz, 2H), 5.51(m, 1H), 7.38–7.43(m, 2H), 7.45–7.50(m, 2H), 7.80(d, J=2.1Hz, 1H), 7.97(d, J=2.1Hz, 1H)
IR(CHCl$_3$) 3032, 2941, 1543, 1377, 1209 cm$^{-1}$ I-328 m.p. 205–206° C.
$^1$HNMR(CDCl$_3$) δ 1.75(s, 3H), 1.80(s, 3H), 3.41(s, 3H), 3.47(s, 3H), 4.66(d, J=6.6Hz, 2H), 5.06(s, 1H), 5.53(m, 1H), 6.33(s, 1H), 6.89–6.95(m, 2H), 7.28–7.34(m, 2H), 7.38–7.40(m, 1H), 7.99(d, J=2.1Hz, 1H), 10.83(d, J=0.6Hz, 1H)
IR(KBr) 3476, 2940, 1614, 1532, 1371, 1238, 1094, 1035 cm$^{-1}$ I-329 m.p. 144–145° C.
$^1$HNMR(CDCl$_3$) δ 2.83(s, 3H) 3.22(s, 3H), 3.28(s, 3H), 3.55(s, 3H), 3.79(s, 3H), 6.86(s, 1H), 7.37–7.45(m, 3H), 7.47–7.53(m, 3H), 7.65–7.70(m, 2H)
IR(KBr) 3434, 3019, 2939, 1515, 1480, 1370, 1176, 1150, 1081 cm$^{-1}$ I-330 amorphous
$^1$HNMR(CDCl$_3$) δ 1.68(s, 3H), 1.74(s, 3H), 2.54(q, J=7.2Hz, 2H), 3.21(s, 3H), 3.41(s, 3H), 3.65(s, 3H), 3.77(s, 3H), 4.03(t, J=7.2Hz, 2H), 5.23(t, J=7.2Hz, 1H), 6.94(s, 1H), 6.98(t, J=8.6Hz, 1H), 7.05(ddd, J=8.6, 2.1, 0.9Hz, 1H), 7.14(dd, J=12.0, 2.1Hz, 1H), 7.38(d, J=8.7Hz, 2H), 7.71(d, J=8.7Hz, 2H)
IR(CHCl$_3$) 1732, 1521, 1471, 1375, 1262, 1230, 1150, 1061, 874 cm$^{-1}$

TABLE 69

I-331 m.p. 146–148° C.
$^1$HNMR(CDCl$_3$) δ 1.56(s, 3H), 1.80(s, 3H), 3.21(s, 3H), 3.41(s, 3H), 3.65(s, 3H), 3.77(s, 3H), 4.61(d, J=6.9Hz, 2H), 5.54(t, J=6.9Hz, 1H), 6.94(s, 1H), 6.98(t, J=8.4Hz, 1H), 7.05(ddd, J=8.4,

TABLE 69-continued 2.4, 0.9Hz, 1H), 7.14(dd, J=12.0, 2.4Hz, 1H), 7.38(d, J=8.7Hz, 2H), 7.71(d, J=8.7Hz, 2H)
IR(KBr) 1736, 1519, 1471, 1357, 1257, 1150, 1061, 984, 872 cm$^{-1}$ I-332 m.p. 170–171° C.
$^1$HNMR(DMSO-d$_6$) δ 1.73(s, 3H), 1.77(s, 3H), 3.31(s, 3H), 3.73(s, 3H), 4.62(d, J=7.0Hz, 2H), 5.48(t, J=7.0Hz, 1H), 6.87(d, J=8.9Hz, 2H), 7.00(s, 1H), 7.03(ddd, J=8.7, 2.3, 0.9Hz, 1H), 7.10(dd, J=12.3, 2.3Hz, 1H), 7.18(t, J=8.7Hz, 1H), 7.48(d, J=8.9Hz, 2H), 9.60(s, 1H), 12.9(brs, 1H)
IR(KBr) 3258, 1687, 1615, 1523, 1465, 1373, 1260, 1233, 1057, 994, 835, 823 cm$^{-1}$ I-333 m.p. 172–174° C.
$^1$HNMR(CDCl$_3$) δ 3.21(s, 3H), 3.41(s, 3H), 3.61(s, 3H), 3.77(s, 3H), 5.17(s, 2H), 6.94(s, 1H), 7.01–7.04(m, 2H), 7.13–7.18(m, 1H), 7.33–7.49(m, 7H), 7.70(d, J=9.0Hz, 2H)
IR(KBr) 1725, 1522, 1463, 1346, 1261, 1230, 1147, 1058, 878, 756 cm$^{-1}$ I-334 m.p. 149–151° C.
$^1$HNMR(CDCl$_3$) δ 2.36(s, 3H), 3.21(s, 3H), 3.41(s, 3H), 3.61(s, 3H), 3.77(s, 3H), 5.13(s, 2H), 6.93(s, 1H), 7.00–7.03(m, 2H), 7.12–7.17(m, 1H), 7.20(d, J=8.4Hz, 2H), 7.35(d, J=8.4Hz, 2H), 7.38(d, J=8.7Hz, 2H), 7.70(d, J=8.7Hz, 2H)
IR(KBr) 1731, 1519, 1472, 1370, 1298, 1152, 1058, 874, 791 cm$^{-1}$

TABLE 70

I-335 m.p. 173–174° C.
$^1$HNMR(DMSO-d$_6$) δ 1.64(s, 3H), 1.70(s, 3H), 2.45(q, J=6.9Hz, 2H), 3.31(s, 3H), 3.73(s, 3H), 4.04(t, J=6.9Hz, 2H), 5.22(t, J=6.9Hz, 1H), 6.87(d, J=8.7Hz, 2H), 6.99(s, 1H), 7.03(ddd, J=8.7, 2.1, 0.9Hz, 1H), 7.10(dd, J=12.3, 2.1Hz, 1H), 7.16(t, J=8.7Hz, 1H), 7.48(d, J=8.7Hz, 2H), 9.61(s, 1H), 12.9(brs, 1H)
IR(KBr) 3303, 1696, 1523, 1473, 1371, 1261, 1241, 1061, 1009, 839 cm$^{-1}$ I-336 m.p. 222–224° C.
$^1$HNMR(DMSO-d$_6$) δ 3.31(s, 3H), 3.73(s, 3H), 5.20(s, 2H), 6.87(d, J=8.7Hz, 2H), 7.00(s, 1H), 7.03–7.07(m, 1H), 7.13(dd, J=12.3, 2.1Hz, 1H), 7.26(t, J=8.7Hz, 1H), 7.36–7.52(m, 7H), 9.61(s, 1H), 12.9(brs, 1H)
IR(KBr) 3268, 1689, 1523, 1465, 1374, 1261, 1055, 836 cm$^{-1}$ I-337 m.p. 205–206° C.
$^1$HNMR(DMSO-d$_6$) δ 2.32(s, 3H), 3.31(s, 3H), 3.72(s, 3H), 5.15(s, 2H), 6.87(d, J=8.7Hz, 2H), 6.99(s, 1H), 7.04(ddd, J=9.0, 1.9, 0.9Hz, 1H), 7.12(dd, J=12.3, 1.9Hz, 1H), 7.23(d, J=8.0Hz, 2H), 7.24(t, J=9.0Hz, 1H), 7.38(d, J=8.0Hz, 2H), 7.48(d, J=8.7Hz, 2H), 9.60(s, 1H), 12.9(brs, 1H)
IR(KBr) 3303, 1696, 1523, 1464, 1261, 1241, 1056, 993, 838, 811, 791 cm$^{-1}$ I-338 m.p. 120–121° C.
$^1$HNMR(CDCl$_3$) δ 3.13(s, 3H), 3.50(s, 3H), 3.78(s, 3H), 5.08(s, 1H), 5.20(s, 2H), 6.90(m, 2H), 7.09(s, 1H), 7.15–7.19(m, 3H), 7.37–7.50(m, 5H), 7.56(dd, J=10.8, 2.1Hz, 1H), 7.64(d, J=2.4Hz, 1H), 9.90(s, 1H)
IR(KBr) 3460, 2934, 1694, 1609, 1585, 1518, 1467, 1442, 1348, 1295, 1273, 1255, 1238, 1171, 1123, 1075, 1003, 960, 828, 807, 755, 700, 653, 582, 522 cm$^{-1}$ I-339 m.p. 256–258° C.
$^1$HNMR(DMSO-d$_6$) δ 3.34(s, 3H), 3.35(s, 3H), 3.72(s, 3H), 5.28(s, 2H), 6.75(d, J=8.1Hz, 1H), 7.05–7.11(m, 3H), 7.36–7.45(m, 4H), 7.53(d, J=8.1Hz, 2H), 7.60–7.66(m, 2H), 9.44(s, 1H), 12.84(s, 1H)
IR(KBr) 3459, 2940, 2563, 1706, 1612, 1522, 1469, 1349, 1294, 1258, 1185, 1114, 1082, 1063, 1000, 961, 919, 827, 756, 699, 524 cm$^{-1}$

TABLE 71

I-340 m.p. 165–166° C.
$^1$HNMR(CDCl$_3$) δ 3.14(s, 3H), 3.19(s, 3H), 3.51(s, 3H),

TABLE 71-continued 3.76(s, 3H), 5.21(s, 2H), 7.11(s, 1H), 7.17(d, J=8.4Hz, 1H), 7.29–7.50(m, 9H), 7.57(dd, J=8.1, 2.1Hz, 1H), 7.65(d, J=2.1Hz, 1H), 10.02(s, 1H)
IR(CHCl$_3$) 2938, 2844, 1698, 1613, 1590, 1515, 1469, 1372, 1331, 1293, 1255, 1174, 1150, 1122, 1092, 1005, 969, 873, 816 cm$^{-1}$ I-341 m.p. 195–197° C.
$^1$HNMR(CDCl$_3$) δ 3.13(s, 3H), 3.18(s, 3H), 3.47(s, 3H), 3.77(s, 3H), 5.20(s, 2H), 6.97(s, 1H), 7.17(d, J=8.7Hz, 1H), 7.30–7.50(m, 9H), 7.58(dd, J=8.7, 1.8Hz, 1H), 7.67(d, J=1.8Hz, 1H)
IR(CHCl$_3$) 2938, 1740, 1707, 1601, 1516, 1472, 1371, 1293, 1260, 1174, 1149, 1117, 1082, 1060, 1002, 971, 875 cm$^{-1}$ I-342 m.p. 207–209° C.
$^1$HNMR(CD$_3$OD) δ 3.40(s, 3H), 3.72(s, 3H), 5.21(s, 2H), 6.76–6.78(m, 2H), 6.97(s, 1H), 7.01–7.17(m, 4H), 7.31–7.52(m, 6H)
IR(KBr) 3366, 1705, 1612, 1591, 1522, 1473, 1434, 1375, 1253, 1234, 1130, 1084, 1061, 998, 918, 864, 835, 813, 792, 743, 697, 648, 526 cm$^{-1}$ I-343 m.p. 206–208° C.
$^1$HNMR(CDCl$_3$) δ 3.14(s, 3H), 3.48(s, 3H), 3.72(s, 3H), 5.20(s, 2H), 5.48(br, 1H), 6.85–6.89(m, 3H), 7.15–7.19(m, 3H), 7.37–7.51(m, 8H), 7.56(dd, J=8.4, 2.4Hz, 1H), 7.68(d, J=2.4Hz, 1H)
IR(CHCl$_3$) 3320, 2938, 1612, 1520, 1474, 1371, 1292, 1257, 1172, 1120, 1090, 1005, 972, 857, 837, 818 cm$^{-1}$ I-344 m.p. 187–190° C.
$^1$HNMR(CDCl$_3$) δ 2.33(s, 3H), 3.13(s, 3H), 3.50(s, 3H), 3.76(s, 3H), 5.20(s, 2H), 7.10(s, 1H), 7.15–7.19(m, 3H), 7.28–7.50(m, 7H), 7.56(dd, J=8.7, 2.4Hz, 1H), 7.64(d, J=2.4Hz, 1H), 9.93(s, 1H)
IR(CHCl$_3$) 2930, 2836, 1750, 1695, 1588, 1513, 1465, 1369, 1329, 1220, 1166, 1122, 1091, 1003, 962, 912, 848, 813 cm$^{-1}$

TABLE 72

I-345 m.p. 218–220° C.
$^1$HNMR(DMSO-d$_6$) δ 2.29(s, 3H), 3.36(s, 3H), 3.37(s, 3H), 3.76(s, 3H), 5.29(s, 2H), 7.11–7.16(m, 3H), 7.31–7.46(m, 6H), 7.52–7.55(m, 2H), 7.62–7.68(m, 2H), 13.00(br, 1H)
IR(KBr) 3433, 2940, 2600, 1757, 1713, 1652, 1611, 1518, 1471, 1365, 1295, 1260, 1216, 1200, 1171, 1117, 1082, 1061, 1022, 998, 975, 916, 897, 829, 804, 735, 697, 525 cm$^{-1}$

I-346 m.p. 206–208° C.
$^1$HNMR(CDCl$_3$) δ 2.31(s, 3H), 3.13(s, 3H), 3.45(s, 3H), 3.58(s, 3H), 3.76(s, 3H), 5.19(s, 2H), 6.95(s, 1H), 7.08–7.16(m, 3H), 7.34–7.50(m, 7H), 7.57(dd, J=8.7, 2.4Hz, 1H), 7.67(d, J=2.4Hz, 1H)
IR(CHCl$_3$) 2939, 1732, 1613, 1599, 1518, 1468, 1371, 1290, 1169, 1117, 1081, 1064, 1004, 972, 961, 905, 847, 828 cm$^{-1}$

I-347 m.p. 201–203° C.
$^1$HNMR(DMSO-d$_6$) δ 1.72(s, 3H), 1.76(s, 3H), 3.34(s, 3H), 3.63(s, 3H), 4.51(d, J=4.2Hz, 2H), 5.49(t, J=4.6Hz, 1H), 6.66(s, 1H), 6.76(s, 2H), 6.86(s, 1H), 7.23–7.29(m, 2H), 7.62–7.66(m, 2H)
IR(KBr) 3431, 2935, 1575, 1516, 1462, 1444, 1421, 1397, 1375, 1224, 1159, 1063, 837 cm$^{-1}$

I-348 m.p. 265–266° C.
$^1$HNMR(DMSO-d$_6$) δ 2.31(s, 3H), 3.33(s, 3H), 3.62(s, 3H), 5.03(s, 2H), 6.66(s, 1H), 6.72–6.90(m, 4H), 7.18–7.28(m, 3H), 7.38(d, J=5.2Hz, 2H), 7.64(dd, J=4.0, 5.4Hz, 2H)
IR(KBr) 3428, 2925, 1575, 1516, 1463, 1442, 1396, 1374, 1248, 1221, 1129, 1087, 1068 cm$^{-1}$

I-349 m.p. 262–263° C.
$^1$HNMR(DMSO-d$_6$) δ 1.64(s, 3H), 1.70(s, 3H), 2.43(dt, J=4.6, 5.0Hz, 2H), 3.34(s, 3H), 3.62(s, 3H), 3.91(t, J=4.8Hz, 2H), 5.25(t, J=4.6Hz, 1H), 6.70(s, 1H), 6.75(s, 2H), 6.87(s, 1H), 7.23–7.29(m, 2H), 7.64(dd, J=2.0, 5.8Hz, 2H)
IR(KBr) 3430, 2934, 1575, 1516, 1464, 1443, 1422, 1398, 1375, 14246, 1225, 1065, 1015 cm$^{-1}$

TABLE 73

I-350 $^1$HNMR(CDCl$_3$) δ 1.76(s, 3H), 1.81(d, J=0.6Hz, 3H), 2.54(s, 3H), 2.73(s, 3H), 3.23(s, 3H), 3.54(s, 3H), 3.77(s, 3H), 4.63(d, J=6.6Hz, 2H), 5.49(m, 1H), 6.85(s, 1H), 7.09(d, J=8.4Hz, 1H), 7.30–7.40(m, 4H), 7.53–7.59(m, 2H)
IR(CHCl$_3$) 2936, 1606, 1515, 1475, 1366, 1116, 1078, 970, 875, 820 cm$^{-1}$

I-351 $^1$HNMR(CDCl$_3$) δ 1.68(s, 3H), 1.74(d, J=0.9Hz, 3H), 2.48–2.60(m, 5H), 2.75(s, 3H), 3.21(s, 3H), 3.54(s, 3H), 3.77(s, 3H), 4.07(t, J=6.91Hz, 2H), 5.21(m, 1H), 6.85(s, 1H), 7.07(d, J=8.7Hz, 1H), 7.30–7.42(m, 4H), 7.53–7.59(m, 2H)
IR(CHCl$_3$) 2928, 1607, 1517, 1476, 1367, 1267, 1118, 1080, 1014, 971, 892, 822 cm$^{-1}$

I-352 m.p. 201–203° C.
$^1$HNMR(CDCl$_3$) δ 3.35(s, 3H), 3.75(s, 3H), 3.76(s, 3H), 5.26(s, 2H), 6.79–6.83(m, 2H), 6.97(s, 1H), 7.01(s, 1H), 7.31–7.54(m, 10H), 9.45(s, 1H)
IR(KBr) 3600–2800(br), 1610, 1525, 1492, 1462, 1377, 1337, 1298, 1208, 1171, 1114, 1054, 1031 cm$^{-1}$

I-353 m.p. 141–143° C.
$^1$HNMR(CDCl$_3$) δ 3.56(s, 3H), 3.78(s, 3H), 3.80(s, 3H), 4.86(s, 1H), 5.26(s, 2H), 6.88–6.92(m, 2H), 6.92(s, 1H), 6.93(s, 1H), 7.24–7.29(m, 2H), 7.36–7.41(m, 1H), 7.45–7.50(m, 2H)
IR(KBr) 3600–2800(br), 1612, 1524, 1491, 1463, 1448, 1378, 1263, 1205, 1177, 1153, 1071, 1053, 1026 cm$^{-1}$

I-354 m.p. 115–115.5° C.
$^1$HNMR(CDCl$_3$) δ 3.19(s, 3H), 3.56(s, 3H), 3.79(s, 3H), 3.80(s, 3H), 5.27(s, 2H), 6.93(s, 1H), 6.94(s, 1H), 7.25–7.27(m, 2H), 7.32–7.40(m, 3H), 7.60–7.64(m, 2H)
IR(KBr) 3600–2800(br), 1524, 1492, 1463, 1379, 1266, 1210, 1174, 1154, 1126, 1082, 1053, 1029 cm$^{-1}$

I-355 m.p. 139–140° C.
$^1$HNMR(CDCl$_3$) δ 1.77(d, J=0.6Hz, 3H), 1.81(d, J=0.9Hz, 3H), 3.82(s, 6H), 4.64(d, J=6.9Hz, 2H), 5.52–5.57(m, 1H), 6.95(s, 1H), 6.97(s, 1H), 7.04(t, J=8.4Hz, 1H), 7.26–7.31(m, 1H), 7.37(dd, J=2.1, 12.6Hz, 1H), 7.73–7.77(m, 2H), 8.26–8.31(m, 1H)
IR(KBr) 3600–2800(br), 1593, 1524, 1508, 1486, 1464, 1380, 1355, 1278, 1264, 1211, 1054, 1029 cm$^{-1}$

TABLE 74

I-356 foam
$^1$HNMR(CDCl$_3$) δ 2.68(s, 3H), 3.13(s, 3H), 3.53(s, 3H), 3.78(s, 3H), 5.19(s, 2H), 6.83(s, 1H), 7.10–7.19(m, 3H), 7.30–7.50(m, 7H), 7.56–7.64(m, 2H)
IR(KBr) 1607, 1520, 1482, 1365, 1232, 1177, 1119, 1082, 1013 cm$^{-1}$ I-357 $^1$HNMR(CDCl$_3$) δ 2.39(s, 3H), 3.48(s, 3H), 3.75(s, 3H), 5.11(s, 2H), 5.67(s, 1H), 5.88(s, 1H), 6.46(s, 1H), 6.95(d.d, J=8.7&1.8Hz, 1H), 7.02–7.11(m, 1H), 7.03(d, J=8.7Hz, 1H), 7.07(d, J=1.8Hz, 1H), 7.22(d, J=8.7Hz, 2H), 7.34(d, J=8.7Hz, 2H), 7.36–7.47(m, 3H)
IR(KBr) 3546, 3511, 1611, 1586, 1517, 1478, 1405, 1360, 1318, 1240, 1109, 1068, 1007 cm$^{-1}$ I-358 $^1$HNMR(CDCl$_3$) δ 3.03(s, 6H), 3.48(s, 3H), 3.77(s, 3H), 5.15(s, 2H), 5.71(s, 1H), 6.73(dd, J=8.7&1.8Hz, 1H), 6.82(d, J=8.4Hz, 2H), 6.97(d, J=1.8Hz, 1H), 6.98(d, J=8.7Hz, 1H), 7.11(s, 1H), 7.33–7.48(m, 3H), 7.56(d, J=8.7Hz, 2H), 9.92(s, 1H)
IR(KBr) 3524, 3447, 1697, 1612, 1586, 1525, 1468, 1364, 1283, 1257, 1230, 1201, 1127, 1103, 1073, 1020 cm$^{-1}$ I-359 $^1$HNMR(CDCl$_3$) δ 3.04(s, 6H), 3.14(s, 3H), 3.48(s, 3H), 3.76(s, 3H), 5.17(s, 2H), 6.84(d, J=8.7Hz, 2H), 7.06–7.17(m, 3H), 7.34(d, J=1.8Hz, 1H), 7.35–7.50(m, 6H), 7.55(d, J=8.7Hz, 2H), 10.08(s, 1H)
IR(KBr) 1698, 1610, 1527, 1470, 1357, 1290, 1232, 1183, 1115, 1083, 1018 cm$^{-1}$ I-360 $^1$HNMR(CDCl$_3$) δ 2.56(s, 3H), 3.02(s, 6H), 3.54(s, 3H), 3.76(s, 3H), 5.16(s, 2H), 5.67(s, 1H), 6.80(d, J=8.4Hz, 2H), 6.85(s, 1H), 6.91(d.d, J=8.4&2.1Hz, 1H), 7.01(d, J=8.4Hz, 1H), 7.05(d, J=2.1Hz, 1H), 7.30–7.47(m, 5H), 7.55(d, J=8.7Hz, 2H)
IR(KBr) 3542, 3436, 1605, 1530, 1483, 1391, 1360, 1287, 1253, 1234, 1169, 1074, 1016 cm$^{-1}$ I-361 $^1$HNMR(CDCl$_3$) δ 1.31(d, J=6.9Hz, 6H), 2.57(s, 3H), 2.97(quint, J=6.9Hz, 1H), 3.54(s, 3H), 3.76(s, 3H), 5.17(s, 2H), 5.68(s, 1H), 6.86(s, 1H), 6.92(dd, J=8.4&2.1Hz, 1H), 7.02(d, J=8.4Hz, 1H),

TABLE 74-continued 7.05(d, J=2.1Hz, 1H), 7.31(d, J=8.1Hz, 2H), 7.34–7.46(m, 5H), 7.55(d, J=8.1Hz, 2H)
IR(KBr) 3446, 1606, 1585, 1522, 1484, 1457, 1394, 1356, 1289, 1257, 1228, 1172, 1076, 1018, 1007 cm$^{-1}$

TABLE 75

I-362 $^1$HNMR(CDCl$_3$) δ 1.31(d, J=6.9Hz, 6H), 2.98(quint, J=6.9Hz, 1H), 3.46(s, 3H), 3.74(s, 3H), 5.15(s, 2H), 5.67(s, 1H), 5.92(s, 1H), 6.48(s, 1H), 6.97(dd, J=8.4&1.8Hz, 1H), 7.03(d, J=8.4Hz, 1H), 7.10(d, J=1.8Hz, 1H), 7.25(s, 1H), 7.31(d, J=7.8Hz, 2H), 7.34–7.49(m, 5H), 7.57(d, J=7.8Hz, 2H)
IR(KBr) 3538, 3505, 3465, 1610, 1586, 1552, 1518, 1584, 1458, 1398, 1281, 1288, 1245, 1198, 1112, 1071, 1002 cm$^{-1}$ I-363 $^1$HNMR(CDCl$_3$) δ 2.66(s, 3H), 3.06(s, 3H), 3.13(s, 3H), 3.57(s, 3H), 3.67(s, 3H), 3.78(s, 3H), 5.19(s, 2H), 6.44(s, 1H), 6.85(s, 1H), 7.15(d, J=8.7Hz, 1H), 7.28–7.51(m, 10H)
IR(KBr) 3443, 1604, 1518, 1479, 1364, 1237, 1177, 1153, 1118, 1078, 1014 cm$^{-1}$ I-364 $^1$HNMR(CDCl$_3$) δ 1.77(s, 3H), 1.81(s, 3H), 2.70(s, 3H), 3.06(s, 3H), 3.24(s, 3H), 3.58(s, 3H), 3.78(s, 3H), 4.64(d, J=6.6Hz, 2H), 5.49(t, J=6.6Hz, 1H), 6.42(s, 1H), 6.85(s, 1H), 7.09(d, J=8.4Hz, 1H), 7.28–7.49(m, 5H)
IR(KBr) 3432, 3285, 1604, 1518, 1479, 1364, 1328, 1291, 1269, 1237, 1177, 1154, 1117, 1078 cm$^{-1}$ I-365 $^1$HNMR(CDCl$_3$) δ 1.57(s, 3H), 1.67(s, 3H), 1.77(s, 3H), 1.81(s, 3H), 2.70(s, 3H), 2.96(s, 3H), 3.24(s, 3H), 3.53(s, 3H), 3.78(s, 3H), 4.32(d, J=7.2Hz, 2H), 4.64(d, J=6.9Hz, 2H), 5.25(t, J=6.9Hz, 1H), 5.49(t, J=7.2Hz, 1H), 6.85(s, 1H), 7.09(d, J=8.7Hz, 1H), 7.31–7.41(m, 3H), 7.44–7.64(m, 3H)
IR(KBr) 3433, 1600, 1517, 1474, 1365, 1339, 1237, 1178, 1153, 1118, 1078, 1014 cm$^{-1}$ I-366 $^1$HNMR(CDCl$_3$) δ 1.76(s, 3H), 1.82(s, 3H), 3.08(s, 3H), 3.48(s, 3H), 3.75(s, 3H), 4.62(d, J=7.2Hz, 2H), 5.54(t, J=7.2Hz, 1H), 5.70(s, 1H), 5.85(s, 1H), 6.40(s, 1H), 6.46(s, 1H), 6.89–7.00(m, 2H), 7.05(d, J=1.5Hz, 1H), 7.43–7.51(m, 3H)
IR(KBr) 3437, 1605, 1585, 1518, 1482, 1386, 1323, 1243, 1152, 1114, 1071, 1002 cm$^{-1}$ I-367 $^1$HNMR(CDCl$_3$) δ 2.37(s, 3H), 3.21(s, 3H), 3.47(s, 3H), 3.64(s, 3H), 3.77(s, 3H), 3.84(s, 3H), 5.17(s, 2H), 6.63(s, 1H), 6.78(s, 1H), 7.10(s, 1H), 7.20(d, J=8.1Hz, 2H), 7.40(d, J=8.1Hz, 2H), 7.41(d, J=9.3Hz, 2H), 7.70(d, J=9.3Hz, 2H)
IR(KBr) 1702, 1607, 1589, 1518, 1468, 1356, 1216, 1151, 1067, 1039, 1018 cm$^{-1}$

TABLE 76

I-368 $^1$HNMR(CDCl$_3$) δ 2.37(s, 3H), 3.21(s, 3H), 3.48(s, 6H), 3.65(s, 3H), 3.73(s, 3H), 3.83(s, 3H), 4.32(d, J=11.4Hz, 1H), 4.51(d, J=11.4Hz, 1H), 5.17(s, 2H), 6.93(s, 1H), 6.71(s, 1H), 6.88(s, 1H), 7.21(d, J=8.4Hz, 2H), 7.32–7.41(m, 4H), 7.73(d, J=8.4Hz, 2H)
IR(KBr) 3514, 1608, 1516, 1465, 1355, 1215, 1149, 1076, 1039, 1017 cm$^{-1}$

I-369 m.p. 125–127° C.
$^1$HNMR(CDCl$_3$) δ 2.60(s, 3H), 3.52(s, 3H), 3.73(s, 3H), 3.84(s, 3H), 5.20(s, 2H), 6.83(s, 1H), 7.00–7.48(m, 12H)
IR(KBr) 3434, 2943, 1611, 1580, 1520, 1498, 1480, 1398, 1297, 1268, 1245, 1179, 1129, 1079, 1009 cm$^{-1}$

I-370 m.p. 137–139° C.
$^1$HNMR(CDCl$_3$) δ 3.43(s, 3H), 3.71(s, 3H), 3.85(s, 3H), 5.19(s, 2H), 5.92(s, 1H), 6.43(s, 1H), 7.01–7.51(m, 12H)
IR(KBr) 3391, 2937, 1615, 1583, 1520, 1503, 1482, 1464, 1405, 1359, 1314, 1292, 1273, 1239, 1121, 1108, 1069, 1005 cm$^{-1}$

I-371 m.p. 92–94° C.
$^1$HNMR(CDCl$_3$) δ 1.76(s, 3H), 1.81(s, 3H), 2.70(s, 3H), 3.53(s, 3H), 3.73(s, 3H), 3.84(s, 3H), 4.63(d, J=6.9Hz, 2H), 5.53(m, 1H), 6.84(s, 1H), 7.00–7.45(m, 7H)
IR(KBr) 3433, 2938, 1609, 1581, 1523, 1499, 1480, 1401, 1368, 1297, 1268, 1240, 1178, 1118, 1079, 1021 cm$^{-1}$

TABLE 76-continued

I-372 foam
$^1$HNMR(CDCl$_3$) δ 1.68(s, 3H), 1.74(d, J=0.6Hz, 3H), 2.50–2.59(m, 2H), 2.71(s, 3H), 3.53(s, 3H), 3.73(s, 3H), 3.84(s, 3H), 4.04(t, J=7.2Hz, 2H), 5.23(m, 1H), 6.83(s, 1H), 7.00–7.42(m, 7H)
IR(CHCl$_3$) 3011, 2938, 1612, 1581, 1522, 1500, 1480, 1465, 1398, 1370, 1301, 1268, 1238, 1209, 1176, 1119, 1081, 1017 cm$^{-1}$ I-373 m.p. 95–98° C.
$^1$HNMR(CDCl$_3$) δ 1.76(s, 3H), 1.80(s, 3H), 3.43(s, 3H), 3.72(s, 3H), 3.85(s, 3H), 4.63(d, J=6.6Hz, 2H), 5.56(m, 1H), 5.92(s, 1H), 6.43(s, 1H), 7.01–7.42(m, 7H)
IR(KBr) 3318, 2937, 1612, 1598, 1500, 1485, 1464, 1450, 1361, 1298, 1275, 1240, 1104, 1072, 1011 cm$^{-1}$

TABLE 77

I-374 m.p. 69–71° C.
$^1$HNMR(CDCl$_3$) δ 1.68(s, 3H), 1.74(d, J=0.6Hz, 3H), 2.50–2.60(m, 2H), 3.43(s, 3H), 3.71(s, 3H), 3.85(s, 3H), 4.04(t, J=7.2Hz, 2H), 5.23(m, 1H), 5.91(s, 1H), 6.43(s, 1H), 7.00–7.42(m, 7H)
IR(KBr) 3385, 2933, 1611, 1583, 1521, 1503, 1485, 1466, 1403, 1358, 1299, 1276, 1241, 1122, 1104, 1071, 1011 cm$^{-1}$

I-375 m.p. 105–107° C.
$^1$HNMR(CDCl$_3$) δ 2.36(s, 3H), 2.59(s, 3H), 3.52(s, 3H), 3.73(s, 3H), 3.84(s, 3H), 5.16(s, 2H), 6.83(s, 1H), 7.00–7.42(m, 11H)
IR(KBr) 3433, 2940, 1609, 1581, 1522, 1499, 1481, 1461, 1401, 1366, 1296, 1269, 1240, 1178, 1117, 1079, 1021, 1011 cm$^{-1}$

I-376 m.p. 142–144° C.
$^1$HNMR(CDCl$_3$) δ 2.37(s, 3H), 3.42(s, 3H), 3.71(s, 3H), 3.85(s, 3H), 5.14(s, 2H), 5.91(s, 1H), 6.43(s, 1H), 7.01–7.42(m, 11H)
IR(KBr) 3367, 2936, 1615, 1583, 1520, 1502, 1482, 1464, 1447, 1405, 1359, 1317, 1291, 1274, 1239, 1121, 1109, 1070, 1009 cm$^{-1}$

I-377 m.p. 174–176° C.
$^1$HNMR(CDCl$_3$) δ 3.21(s, 3H), 3.41(s, 3H), 3.63(s, 3H), 3.77(s, 3H), 5.30(s, 2H), 6.94(s, 1H), 7.03–7.05(m, 2H), 7.15–7.20(m, 1H), 7.25(m, 1H), 7.38(d, J=8.9Hz, 2H), 7.62(d, J=7.8Hz, 1H), 7.71(d, J=8.9Hz, 2H), 7.76(dt, J=7.8, 1.5Hz, 1H), 8.60(m, 1H)
IR(KBr) 1732, 1523, 1474, 1368, 1148, 1061, 863, 845, 790 cm$^{-1}$

I-378 m.p. >260° C.
$^1$HNMR(DMSO-d$_6$) δ 3.32(s, 3H), 3.73(s, 3H), 5.28(s, 2H), 6.87(d, J=8.7Hz, 2H), 7.00(s, 1H), 7.04(dd, J=8.9, 1.8Hz, 1H), 7.16(dd, J=12.3, 1.8Hz, 1H), 7.26(t, J=8.9Hz, 1H), 7.39(m, 1H), 7.57(d, J=8.7Hz, 2H), 7.58(d, J=7.8Hz, 1H), 7.89(dt, J=7.8, 1.5Hz, 1H), 8.61(m, 1H), 9.61(s, 1H), 12.9(brs, 1H)
IR(KBr) 3383, 1735, 1705, 1610, 1522, 1471, 1272, 1226, 1059, 1014, 838, 762 cm$^{-1}$ I-379 m.p. 137–138° C.
$^1$HNMR(CDCl$_3$) δ 1.77(s, 3H), 1.82(s, 3H), 3.46(s, 3H), 3.79(s, 3H), 4.64(d, J=4.6Hz, 1H), 5.56(t, J=4.6Hz, 1H), 6.92–7.20(m, 6H), 7.61(dd, J=3.6, 5.8Hz, 2H), 9.96(Brs, 1H)
IR(KBr) 3434, 2966, 2935, 2839, 1702, 1695, 1521, 1466, 1378, 1299, 1287, 1272, 1240, 1012, 840 cm$^{-1}$

TABLE 78

I-380 m.p. 98–99° C.
$^1$HNMR(CDCl$_3$) δ 2.37(s, 3H), 3.45(s, 3H), 3.78(s, 3H), 5.15(s, 2H), 6.93–7.26(m, 4H), 7.36(d, J=7.8Hz, 2H), 7.62(dd, J=4.0, 8.8Hz, 2H), 9.94(s, 1H)
IR(KBr) 3446, 2933, 2845, 1699, 1521, 1473, 1463, 1381, 1293, 1261, 1238, 1221, 1131, 803 cm$^{-1}$

I-381 m.p. 118–119° C.
$^1$HNMR(CDCl$_3$) δ 1.69(s, 3H), 1.74(s, 3H), 2.54(dt, J=5.0, 7.8Hz, 2H), 3.45(s, 3H), 3.78(s, 3H), 4.05(t, J=7.2Hz, 2H), 5.24(t, J=4.4Hz, 1H), 6.95–7.16(m, 6H), 7.61(dd, J=3.4, 8.8Hz, 2H), 9.95(brs, 1H)
IR(KBr) 3433, 2959, 2930, 2842, 1701, 1602, 1522, 1464, 1379, 1303, 1263, 1222, 1132, 1018 cm$^{-1}$

TABLE 78-continued

I-382 m.p. 93–94° C.
¹HNMR(DMSO-d₆) δ 1.74(s, 3H), 1.78(s, 3H), 3.32(s, 3H), 3.71(s, 3H), 4.62(d, J=7.0Hz, 2H), 5.48(t, J=5.8Hz, 1H), 6.91(s, 1H), 7.09–7.35(m, 2H), 7.64–7.71(m, 2H)
IR(KBr) 3433, 2976, 2937, 1707, 1604, 1520, 1472, 1376, 1300, 1265, 1226, 1160, 1131, 1060, 839 cm⁻¹

I-383 m.p. 98–99° C.
¹HNMR(DMSO-d₆) δ 2.32(s, 3H), 3.31(s, 3H), 3.70(s, 3H), 5.13(s, 2H), 6.88(s, 1H), 7.14–7.39(m, 5H), 7.63–7.70(m, 2H)
IR(KBr) 3433, 2981, 2937, 1704, 1603, 1520, 1470, 1375, 1301, 1266, 1226, 1159, 1061, 839 cm⁻¹

I-384 oil
¹HNMR(DMSO-d₆) δ 1.68(s, 3H), 1.74(s, 3H), 2.48–2.56(m, 2H), 3.57(s, 3H), 3.77(s, 3H), 3.98(t, J=4.8Hz, 2H), 5.26(t, J=4.2Hz, 1H), 6.84(s, 1H), 7.05–7.36(m, 5H), 7.63–7.70(m, 2H)
IR(KBr) 3433, 2979, 2938, 1726, 1603, 1522, 1470, 1376, 1301, 1264, 1226, 1160, 1132, 1080, 1058, 840 cm⁻¹

I-385 m.p. 137–138° C.
¹HNMR(CDCl₃) δ 1.77(s, 3H), 1.82(s, 3H), 2.55(s, 3H), 3.21(s, 3H), 3.57(s, 3H), 3.78(s, 3H), 4.56(d, J=7.0Hz, 2H), 5.52(t, J=7.4Hz, 1H), 6.84(s, 1H), 7.02(d, J=8.8Hz, 2H), 7.34–7.40(m, 4H), 7.70(d, J=8.8Hz, 2H)
IR(KBr) 3434, 2938, 1607, 1519, 1366, 1244, 1174, 1151, 1072, 871, 796 cm⁻¹

TABLE 79

I-386 m.p. 169–170° C.
¹HNMR(CDCl₃) δ 2.48(s, 3H), 3.21(s, 3H), 3.56(s, 3H), 3.77(s, 3H), 5.08(s, 2H), 6.84(s, 1H), 7.07(d, J=5.8Hz, 2H), 7.19–7.39(m, 4H), 7.70(d, J=6.0Hz, 2H)
IR(KBr) 3432, 3016, 2935, 1605, 1519, 1479, 1368, 1357, 1233, 1176, 1151, 1076, 876, 843, 798 cm⁻¹

I-387 m.p. 140–141° C.
¹HNMR(CDCl₃) δ 1.68(s, 3H), 1.75(s, 3H), 2.51(dt, J=4.4, 4.6Hz, 2H), 2.55(s, 3H), 3.21(s, 3H), 3.56(s, 3H), 3.77(s, 3H), 3.97(t, J=4.8Hz, 2H), 5.26(t, J=4.0Hz, 1H), 6.84(s, 1H), 6.99(d, J=5.8Hz, 2H), 7.34–7.39(m, 4H), 7.70(d, J=5.8Hz, 2H)
IR(KBr) 3445, 2937, 1608, 1519, 1480, 1391, 1361, 1351, 1237, 1177, 1154, 1077, 962, 871, 862, 800 cm⁻¹

I-388 m.p. 124–125° C.
¹HNMR(DMSO-d₆) δ 1.73(s, 3H), 1.75(s, 3H), 3.30(s, 3H), 3.65(s, 3H), 4.54(d, J=6.6Hz, 2H), 5.47(t, J=6.4Hz, 1H), 6.40(s, 1H), 6.82–6.94(m, 4H), 7.20(d, J=8.6Hz, 2H), 7.44(d, J=8.2Hz, 2H)
IR(KBr) 3411, 2934, 1608, 1523, 1487, 1396, 1231, 1175, 1105, 1072, 996, 898 cm⁻¹

I-389 m.p. 93–94° C.
¹HNMR(DMSO-d₆) δ 2.32(s, 3H), 3.32(s, 3H), 3.64(s, 3H), 5.08(s, 2H), 6.40(s, 1H), 6.84(d, J=8.6Hz, 2H), 6.98(d, J=8.6Hz, 2H), 7.19–7.23(m, 4H), 7.34–7.46(m, 4H)
IR(KBr) 3398, 2933., 1609, 1523, 1486, 1461, 1398, 1235, 1174, 1119, 1071, 997, 829 cm⁻¹

I-390 oil
¹HNMR(DMSO-d₆) δ 1.72(s, 3H), 1.74(s, 3H), 2.52(dt, J=4.8, 5.0Hz, 2H), 3.24(s, 3H), 3.58(s, 3H), 4.06(t, J=7.2Hz, 2H), 5.24(t, J=4.4Hz, 1H), 6.80–6.95(m, 4H), 7.22(d, J=8.4Hz, 2H), 7.46(d, J=8.2Hz, 2H)
IR(KBr) 3340, 2934, 1608, 1522, 1486, 1396, 1285, 1230, 1175, 1106, 1072, 996, 828 cm⁻¹

I-391 ¹HNMR(CDCl₃+CD₃OD) δ 3.05(s, 3H), 3.48(s, 3H), 3.75(s, 3H), 5.16(s, 2H), 5.97(s, 1H), 6.02(s, 1H), 6.47(s, 1H), 6.94(d.d, J=8.4&1.8Hz, 1H), 7.04(d, J=8.4Hz, 1H), 7.07(d, J=1.8Hz, 1H), 7.22–7.52(m, 9H)
IR(KBr) 3548, 3357, 1603, 1589, 1520, 1487, 1460, 1445, 1410, 1329, 1286, 1247, 1153, 1115, 1077, 1010 cm⁻¹

TABLE 80

I-392 ¹HNMR(CDCl₃) δ 2.37(s, 3H), 2.77–2.88(broad, 1H), 3.47(s, 3H), 3.64(s, 3H), 3.72(s, 3H), 3.82(s, 3H), 4.32(d.d, J=11.1&0.6Hz, 1H), 4.45–4.56(broad, 1H), 4.92(s, 1H), 5.16(s, 2H), 6.70(d, J=9.3Hz, 2H), 6.88(s, 1H), 6.92(d, J=9.0Hz, 2H), 7.22(d, J=8.4Hz,

TABLE 80-continued

2H), 7.38(d, J=8.4Hz, 2H), 7.56(d, J=9.0Hz, 2H)
IR(KBr) 3476, 1610, 1519, 1476, 1463, 1386, 1265, 1215, 1074, 1041, 1010 cm⁻¹

I-393 foam
¹HNMR(CD₃OD) δ 2.34(s, 3H), 3.38(s, 3H), 3.68(s, 3H), 4.00(dd, J=9.9, 8.7Hz, 1H), 4.17(dd, J=9.9, 3.0Hz, 1H), 5.06(dd, J=8.7, 3.0Hz, 1H), 6.43(s, 1H), 6.78(dd, J=8.7, 1.8, 1H), 6.85(d, J=8.7Hz, 2H), 6.88(d, J=1.8Hz, 1H), 6.91(d, J=8.4Hz, 1H), 7.20(d, J=8.1Hz, 2H), 7.36(d, J=8.1Hz, 2H), 7.46(d, J=8.7Hz, 2H)
IR(Nujol) 3367, 1655, 1612, 1586, 1523, 1489, 1459, 1254, 1225, 1115, 1072, 1015, 941, 817 cm⁻¹

I-394 foam
¹HNMR(CD₃OD) δ 3.38(s, 3H), 3.67(s, 3H), 4.02(dd, J=10.2, 9.0Hz, 1H), 4.20(dd, J=10.2, 3.3Hz, 1H), 5.11(dd, J=9.0, 3.3Hz, 1H), 6.43(s, 1H), 6.78(dd, J=8.4, 2.1, 1H), 6.85(d, J=8.7Hz, 2H), 6.88(d, J=2.1Hz, 1H), 6.91(d, J=8.4Hz, 1H), 7.46(d, J=8.7Hz, 2H), 7.30~7.50(m, 5H)
IR(Nujol) 3368, 1655, 1612, 1587, 1523, 1489, 1456, 1254, 1225, 1114, 1072, 1014, 941, 825, 764 cm⁻¹

I-395 foam
¹HNMR(CDCl₃) δ 2.48(s, 3H), 2.82(s, 3H), 3.16(s, 3H), 3.22(s, 3H), 3.54(s, 3H), 3.77(s, 3H), 6.85(s, 3H), 7.34~7.38(m, 2H), 7.38(d, J=8.1Hz, 2H), 7.39(d, J=8.7Hz, 2H), 7.46(d, J=1.8Hz, 1H), 7.46(d, J=8.7Hz, 2H), 7.82(d, J=8.1Hz, 2H)
IR(Nujol) 1597, 1514, 1479, 1464, 1177, 1152, 1085, 969, 883, 846, 797, 729 cm⁻¹

I-396 foam
¹HNMR(CDCl₃) δ 2.85(s, 3H), 3.14(s, 3H), 3.22(s, 3H), 3.54(s, 3H), 3.77(s, 3H), 6.85(s, 1H), 7.36(m, 2H), 7.39(d, J=8.7Hz, 2H), 7.45, (m, 1H), 7.60(m, 2H), 7.66(d, J=8.7Hz, 2H), 7.74(m, 1H), 7.94(m, 2H)
IR(Nujol) 1612, 1584, 1514, 1479, 1451, 1179, 1152, 1085, 969, 949, 846, 797, 737 cm⁻¹

TABLE 81

I-397 foam
¹HNMR(CDCl₃) δ 2.73(s, 3H), 3.21(s, 6H), 3.55(s, 3H), 3.77(s, 3H), 5.20(s, 2H), 6.84(s, 1H), 7.16(brs, 1H), 7.22(d, J=8.1Hz, 1H), 7.33, (d, J=2.4Hz, 1H), 7.37(brs, 2H), 7.38(d, J=8.7Hz, 2H), 7.65(brs, 1H), 7.67(d, J=8.7Hz, 2H)
IR(Nujol) 1608, 1519, 1480, 1464, 1176, 1151, 1080, 972, 876, 846, 798 cm⁻¹

I-398 foam
¹HNMR(CDCl₃) δ 2.91(s, 3H), 3.19(s, 3H), 3.22(s, 3H), 3.54(s, 3H), 3.78(s, 3H), 5.26(s, 2H), 5.34(s, 2H), 7.04(brs, 1H), 7.05(s, 2H), 7.12(brs, 1H), 7.39(d, J=8.7Hz, 2H), 7.36~7.43(m, 3H), 7.67(d, J=8.7Hz, 2H)
IR(Nujol) 1608, 1519, 1480, 1463, 1176, 1151, 1079, 972, 876, 799 cm⁻¹

I-399 m.p. 203–205° C.
¹HNMR(DMSO-d₆) δ 2.87(s, 3H), 3.35(s, 3H), 3.45(s, 3H), 3.52(s, 3H), 3.78(s, 3H), 5.39(s, 2H), 7.07(s, 1H), 7.08(d, J=3.9Hz, 1H), 7.16(d, J=3.9Hz, 1H), 7.31(dd, J=9.0, 1.8Hz, 1H), 7.33(s, 1H), 7.42(d, J=9.0Hz, 1H), 7.49(d, J=8.7Hz, 2H), 7.74(d, J=8.7Hz, 2H)
IR(Nujol) 1609, 1520, 1481, 1455, 1231, 1080, 1013, 984, 947, 878, 832, 798 cm⁻¹

I-400 foam
¹HNMR(CDCl₃) δ 2.72(s, 3H), 3.14(s, 3H), 3.21(s, 3H), 3.55(s, 3H), 3.77(s, 3H), 5.14(s, 2H), 6.84(s, 1H), 7.11(d, J=8.7Hz, 1H), 7.34(dd, J=2.1, 8.7Hz, 1H), 7.34(d, J=8.4Hz, 2H), 7.37(d, J=8.4Hz, 2H), 7.41(d, J=2.1Hz, 1H), 7.54(d, J=8.4Hz, 2H), 7.68(d, J=8.4Hz, 2H)

I-401 foam
¹HNMR(CDCl₃) δ 2.83(s, 3H), 3.14(s, 3H), 3.22(s, 3H), 3.55(s, 3H), 3.78(s, 3H), 5.26(s, 2H), 6.85(s, 1H), 7.24(d, J=8.4Hz, 1H), 7.38(d, J=8.4Hz, 1H), 7.41(dd, J=2.1, 8.4Hz, 1H), 7.44(d, J=2.1Hz, 1H), 7.67(d, J=8.4Hz, 2H)
IR(KBr) 1609, 1523, 1509, 1481, 1367, 1402, 1178, 1152, 1080, 973, 943, 876, 798 cm⁻¹

TABLE 82

I-402 foam
$^1$HNMR(CDCl$_3$)δ 2.68(s, 3H), 3.14(s, 3H), 3.21(s, 3H), 3.55(s, 3H), 3.66(s, 2H), 3.71(s, 3H), 3.78(s, 3H), 5.18(s, 2H), 6.84(s, 1H), 7.14(d, J=8.4Hz, 1H), 7.32(d, J=8.7Hz, 1H), 7.35(dd, J=2.1, 8.7Hz, 1H), 7.37(d, J=8.4Hz, 2H), 7.39(d, J=2.1Hz, 1H), 7.42(d, J=8.4Hz, 2H), 7.67(d, J=8.4Hz, 2H)
IR(KBr) 1736, 1610, 1519, 1481, 1365, 1177, 1151, 1079, 876, 817, 798 cm$^{-1}$ I-403 foam
$^1$HNMR(CDCl$_3$)δ 2.70(s, 3H), 3.16(s, 3H), 3.21(s, 3H), 3.56(s, 3H), 3.78(s, 3H), 5.24(s, 2H), 6.84(s, 1H), 7.18(d, J=8.4Hz, 1H), 7.36(dd, J=1.5, 8.4Hz, 1H), 7.38(d, J=8.4Hz, 2H), 7.41(d, J=1.5Hz, 1H), 7.46(m, 2H), 7.54(d, J=8.1Hz, 2H), 7.62(m, 3H), 7.64(d, J=8.1Hz, 2H), 7.68(d, J=8.4Hz, 2H)
IR(KBr) 1609, 1519, 1481, 1365, 1177, 1151, 1079, 1014, 876, 818, 797 cm-1

I-404 m.p. 128–130° C.
$^1$HNMR(CDCl$_3$)δ 2.75(s, 3H), 2.92(s, 3H), 3.18(t, J=6.9Hz, 2H), 3.21(s, 3H), 3.55(s, 3H), 3.77(s, 3H), 4.34(t, J=6.9Hz, 2H), 6.81(s, 1H), 7.08(d, J=8.4Hz, 1H), 7.29(m, 2H), 7.32(br.s, 3H), 7.35(dd, J=2.1, 8.4Hz, 1H), 7.38(d, J=8.4Hz, 2H), 7.39(d, J=2.1Hz, 1H), 7.67(d, J=8.4Hz, 2H)
IR(KBr) 1609, 1520, 1481, 1364, 1177, 1151, 1080, 872, 815, 797 cm$^{-1}$

I-405 foam
$^1$HNMR(CDCl$_3$)δ 1.71(d, J=6.3Hz, 3H), 2.45(br.s, 3H), 3.20(s, 3H), 3.28(s, 3H), 3.53(s, 3H), 3.75(s, 3H), 5.43(q, J=6.3Hz, 1H), 6.81(s, 1H), 6.90(d, J=8.4Hz, 1H), 7.16(dd, J=2.1, 8.4Hz, 1H), 7.30(m, 1H), 7.36(d, J=2.1Hz, 1H), 7.37(d, J=8.4Hz, 2H), 7.35–7.41(m, 4H), 7.66(d, J=8.4Hz, 2H)
IR(KBr) 1609, 1518, 1480, 1365, 1177, 1151, 1078, 874, 818, 798 cm$^{-1}$

TABLE 83

I-406 foam
$^1$HNMR(CDCl$_3$)δ 1.02(t, J=9.0Hz, 3H), 2.04(dq, J=6.3, 9.0Hz, 2H), 2.39(br.s, 3H), 3.20(s, 3H), 3.30(s, 3H), 3.53(s, 3H), 3.75(s, 3H), 5.18(t, J=6.3Hz, 1H), 6.80(s, 1H), 6.88(d, J=8.4Hz, 1H), 6.92(m, 1H), 7.14(dd, J=2.4, 8.4Hz, 1H), 7.25–7.40(m, 7H), 7.66(d, J=8.4Hz, 2H)
IR(KBr) 1609, 1518, 1480, 1365, 1177, 1151, 1079, 874, 819, 797 cm$^{-1}$ I-407 foam
$^1$HNMR(CDCl$_3$)δ 2.46(s, 3H), 3.07(s, 3H), 3.20(s, 3H), 3.54(s, 3H), 3.76(s, 3H), 6.33(s, 1H), 6.82(s, 1H), 6.99(d, J=9.0Hz, 1H), 7.19(dd, J=2.1, 9.0Hz, 1H), 7.26–7.40(m, 9H), 7.43–7.47(m, 4H), 7.66(d, J=8.4Hz, 2H)
IR(KBr) 1607, 1518, 1481, 1364, 1177, 1151, 1081, 873, 822, 798 cm$^{-1}$ I-408 m.p. 179–180° C.
$^1$HNMR(CDCl$_3$)δ 1.69(d, J=6.3Hz, 3H), 2..34(br.s, 3H), 2.45(s, 3H), 3.20(s, 3H), 3.27(s, 3H), 3.54(s, 3H), 3.75(s, 3H), 5.40(q, J=6.3Hz, 1H), 6.81(s, 1H), 6.92(d, J=8.7Hz, 1H), 7.15(d, J=8.7Hz, 2H), 7.16(dd, J=2.1, 8.4Hz, 1H), 7.27(d, J=8.7Hz, 1H), 7.35(d, J=2.1Hz, 1H), 7.37(d, J=8.4Hz, 2H), 7.66(d, J=8.4Hz, 2H)
IR(KBr) 1609, 1518, 1480, 1365, 1177, 1151, 1078, 874, 819, 797 cm$^{-1}$ I-409 m.p. 243–244° C.
$^1$HNMR(DMSO-d$_6$)δ 3.30(s, 3H), 3.64(s, 3H), 5.19(s, 2H), 6.39 (s, 1H), 6.64(dd, J=1.8, 8.4Hz, 1H), 6.77(d, J=1.8Hz, 1H), 6.83(d, J=8.4Hz, 2H), 6.97(d, J=8.4Hz, 2H), 7.37(d, J=7.5Hz, 1H), 7.44(d, J=8.4Hz, 2H), 7.48(t, J=8.4Hz, 2H), 7.60(d, J=8.4Hz, 2H), 7.67–7.73(m, 5H)
IR(KBr) 3421, 1610, 1523, 1488, 1463, 1403, 1176, 1115, 1072, 821 cm$^{-1}$ I-410 foam
$^1$HNMR(CDCl$_3$)δ 3.18(t, J=6.9Hz, 2H), 3.45(s, 3H), 3.73(s, 3H), 4.31(t, J=6.9Hz, 2H), 6.44(s, 1H), 6.91(d, J=8.4Hz, 2H), 6.94(br.s, 2H), 7.03(br.s, 1H), 7.23–7.37(m, 5H), 7.53(d, J=8.4Hz, 2H)
IR(KBr) 3434, 1612, 1587, 1523, 1489, 1455, 1403, 1250, 1113, 1070, 1011, 825, 815 cm$^{-1}$

TABLE 84

I-411 foam
$^1$HNMR(CDCl$_3$)δ 1.70(d, J=6.0Hz, 3H), 3.44(s, 3H), 3.72(s, 3H), 5.36(q, J=6.0Hz, 1H), 6.42(s, 1H), 6.78(d, J=8.1Hz, 1H), 6.81(dd, J=1.5, 8.7Hz, 1H), 6.91(d, J=8.4Hz, 2H), 7.06(d, J=1.5Hz, 1H), 7.26–7.42(m, 4H), 7.51(d, J=8.4Hz, 2H)
IR(KBr) 3472, 1612, 1587, 1523, 1488, 1454, 1403, 1248, 1113, 1070, 1011, 825, cm$^{-1}$ I-412 foam
$^1$HNMR(CDCl$_3$)δ 1.03(t, J=7.2Hz, 3H), 1.94(m, 1H), 2.06(m, 1H), 3.43(s, 3H), 3.72(s, 3H), 5.08(dd, J=7.2, 5.4Hz, 1H), 6.43(s, 1H), 6.73(d, J=8.4Hz, 1H), 6.78(dd, J=1.8, 8.4Hz, 1H), 6.90(d, J=8.4Hz, 2H), 7.05(d, J=1.8Hz, 1H), 7.25–7.38(m, 5H), 7.51(d, J=8.4Hz, 2H)
IR(KBr) 3434, 1612, 1522, 1488, 1454, 1403, 1247, 1113, 1070, 1011, 826, 811 cm$^{-1}$ I-413 foam
$^1$HNMR(CDCl$_3$)δ 3.44(s, 3H), 3.73(s, 3H), 6.25(s, 1H), 6.43(s, 1H), 7.26(m, 2H), 6.90(d, J=8.4Hz, 2H), 7.08(d, J=2.1Hz, 1H), 7.29–7.43(m, 10H), 7.51(d, J=8.4Hz, 2H)
IR(KBr) 3432, 1611, 1523, 1489, 1454, 1402, 1226, 1110, 1069, 1011, 825 cm$^{-1}$ I-414 foam
$^1$HNMR(CDCl$_3$)δ 1.69(d, J=6.3Hz, 3H), 2..35(s, 3H), 3.44(s, 3H), 3.72(s, 3H), 5.33(q, J=6.3Hz, 1H), 6.42(s, 1H), 6.80(br.s, 1H), 6.90(d, J=8.4Hz, 2H), 7.05(br.s, 1H), 7.18(d, J=7.8Hz, 2H), 7.29(d, J=7.8Hz, 2H), 7.51(d, J=8.4Hz, 2H)
IR(KBr) 3433, 1612, 1522, 1488, 1459, 1403, 1248, 1113, 1069, 1011, 817 cm$^{-1}$ I-415 m.p. 164–167° C.
$^1$HNMR(CDCl$_3$)δ 3.79(s, 3H), 3.80(s, 3H), 4.81(brs, 1H), 5.29(s, 2H), 6.88–6.94(m, 4H), 7.16(d, J=8.7Hz, 1H), 7.32–7.52(m, 7H), 7.73(dd, J=2.1, 8.7Hz, 1H), 8.10(d, J=2.1Hz, 1H)
IR(KBr) 3513, 2930, 1618, 1529, 1497, 1448, 1387, 1354, 1296, 1257, 1211, 1168, 1091, 1064, 1024 cm$^{-1}$

TABLE 85

I-416 m.p. 155–159° C.
$^1$HNMR(CDCl$_3$)δ 3.20(s, 3H), 3.39(s, 3H), 3.82(s, 3H), 3.83(s, 3H), 6.95(s, 1H), 6.96(s, 1H), 7.34–7.38(m, 2H), 7.58–7.64(m, 3H), 7.87(dd, J=2.1, 8.4Hz, 1H), 8.26(d, J=2.1Hz, 1H)
IR(KBr) 3433, 2944, 1539, 1519, 1487, 1358, 1216, 1176, 1150, 1086, 1057, 1031 cm$^{-1}$

I-417 m.p. 124–126° C.
$^1$HNMR(CDCl$_3$)δ 3.19(s, 3H), 3.80(s, 6H), 5.30(s, 2H), 6.93(s, 1H), 6.94(s, 1H), 7.18(d, J=9.0Hz, 1H), 7.32–7.52(m, 7H), 7.59–7.64(m, 2H), 7.73(dd, J=2.1, 9.0Hz, 1H), 8.10(d, J=2.1Hz, 1H)
IR(KBr) 3433, 2937, 1619, 1531, 1491, 1465, 1450, 1358, 1290, 1256, 1211, 1176, 1150, 1088, 1062, 1033 cm$^{-1}$

I-418 m.p. 151–153° C.
$^1$HNMR(CDCl$_3$)δ 3.18(s, 3H), 3.781(s, 3H), 3.784(s, 3H), 5.14 (s, 2H), 6.90-7.00(m, 5H), 7.31-7.50(m, 7H), 7.60-7.65(m, 2H)
IR(KBr) 3480, 3383, 2930, 1610, 1523, 1489, 1467, 1383, 1358, 1330, 1211, 1175, 1147, 1024 cm$^{-1}$

I-419 m.p. 198–200° C.
$^1$HNMR(CDCl$_3$)δ 3.77(s, 6H), 5.13(s, 2H), 6.86–7.00(m, 7H), 7.34–7.50(m, 7H)
IR(KBr) 3403, 3327, 1611, 1592, 1525, 1492, 1462, 1444, 1384, 1318, 1273, 1243, 1209, 1178, 1149, 1110, 1058, 1037, 1006 cm$^{-1}$

I-420 m.p. 168–171° C.
$^1$HNMR(CDCl$_3$)δ 2.99(s, 3H), 3.19(s, 3H), 3.80(s, 3H), 3.81(s, 3H), 5.16(s, 2H), 6.83(brs, 1H), 6.92(s, 1H), 6.96(s, 1H), 7.06(d, J=8.7Hz, 1H), 7.32–7.46(m, 8H), 7.60–7.64(m, 2H), 7.81(d, J=2.1Hz, 1H)
IR(KBr) 3403, 3327, 1611, 1592, 1525, 1492, 1462, 1444, 1384, 1318, 1273, 1243, 1209, 1178, 1149, 1110, 1058, 1037, 1006 cm$^{-1}$ I-421 m.p. 168–171° C.
$^1$HNMR(CDCl$_3$)δ 3.19(s, 3H), 3.80(s, 3H), 3.81(s, 3H), 5.23(s, 2H), 6.93(s, 1H), 6.97(s, 1H), 7.07(d, J=8.7Hz, 1H), 7.33–7.45(m, 8H), 7.61–7.65(m, 2H), 8.58(d, J=2.4Hz, 1H),

TABLE 85-continued 8.66(brs, 1H)
IR(KBr) 3401, 1723, 1613, 1595, 1549, 1518, 1486, 1385, 1365, 1330, 1299, 1256, 1212, 1151, 1119, 1060, 1037, 1017 cm$^{-1}$

TABLE 86

I-422　m.p. 159–160° C.
　　　$^1$HNMR(CDCl$_3$)δ 1.69(s, 3H), 1.74, (s, 3H), 2.55(q, J=7.2Hz, 2H), 2.73(s, 3H), 3.22(s, 3H), 3.55(s, 3H), 3.77(s, 3H), 4.06(t, J=7.2Hz, 2H), 5.24(t, J=7.2Hz, 1H), 6.85(s, 1H), 7.07(d, J=8.6Hz, 1H), 7.39(d, J=8.7Hz, 2H), 7.55(dd, J=8.6, 2.1Hz, 1H), 7.63(d, J=2.1Hz, 1H), 7.68(d, J=8.7Hz, 2H)
　　　IR(KBr) 1515, 1481, 1359, 1325, 1175, 1140, 1079, 870, 799 cm$^{-1}$
I-423　m.p. 180–182° C.
　　　$^1$HNMR(CDCl$_3$)δ 1.76(s, 3H), 1.81, (s, 3H), 2.71(s, 3H), 3.22(s, 3H), 3.55(s, 3H), 3.78(s, 3H), 4.06(d, J=6.3Hz, 2H), 5.50(t, J=6.3Hz, 1H), 6.85(s, 1H), 7.09(d, J=8.7Hz, 2H), 7.39(d, J=8.7Hz, 2H), 7.55(dd, J=8.7, 2.0Hz, 1H), 7.64(d, J=2.0Hz, 1H), 7.68(d, J=8.7Hz, 2H)
　　　IR(KBr) 1514, 1479, 1360, 1241, 1174, 1132, 1078, 866, 800 cm$^{-1}$
I-424　m.p. 176–178° C.
　　　$^1$HNMR(CDCl$_3$)δ 2.64(s, 3H), 3.22(s, 3H), 3.55(s, 3H), 3.78(s, 3H), 5.26(s, 2H), 6.85(s, 1H), 7.14(d, J=8.6Hz, 1H), 7.33–7.48(m, 7H), 7.54(dd, J=8.6, 2.1Hz, 1H), 7.66–7.70(m, 3H)
　　　IR(KBr) 1517, 1482, 1367, 1327, 1178, 1150, 1135, 1081, 878, 797 cm$^{-1}$
I-425　m.p. 199–200° C.
　　　$^1$HNMR(CDCl$_3$)δ 2.37(s, 3H), 2.63(s, 3H), 3.21(s, 3H), 3.55(s, 3H), 3.78(s, 3H), 5.21(s, 2H), 6.84(s, 1H), 7.13(d, J=8.7Hz, 1H), 7.20(d, J=8.0Hz, 2H), 7.34(d, J=8.0Hz, 2H), 7.38(d, J=9.0Hz, 2H), 7.53(dd, J=8.7, 1.8Hz, 1H), 7.66(d, J=1.8Hz, 1H), 7.68(d, J=9.0Hz, 2H)
　　　IR(KBr) 1517, 1481, 1366, 1326, 1255, 1177, 1151, 1082, 871, 798 cm$^{-1}$
I-426　amorphous
　　　$^1$HNMR(CDCl$_3$)δ 1.68(s, 3H), 1.73(s, 3H), 2.54(q, J=7.2Hz, 2H), 3.44(s, 3H), 3.75(s, 3H), 4.05(t, J=7.2Hz, 2H), .5.07(s, 2H), 5.24(t, J=7.2Hz, 1H), 6.02(s, 1H), 6.45(s, 1H), 6.92(d, J=8.6Hz, 2H), 7.41(d, J=8.6Hz, 2H), 7.53(d, J=8.6Hz, 2H), 7.59(dd, J=8.6, 2.0Hz, 1H), 7.63(d, J=2.0Hz, 1H)
　　　IR(CHCl$_3$)3595, 3506, 1614, 1523, 1489, 1326, 1281, 1258, 1122, 1079, 1057 cm$^{-1}$

TABLE 87

I-427　m.p. 180–182° C.
　　　$^1$HNMR(CDCl$_3$)δ 1.75(s, 3H), 1.80(s, 3H), 3.44(s, 3H), 3.76(s, 3H), 4.66(d, J=6.6Hz, 2H), 4.87(s, 1H), 5.52(t, J=6.6Hz, 1H), 6.02(s, 1H), 6.46(s, 1H), 6.93(d, J=8.9Hz, 2H), 7.06(d, J=8.4Hz, 1H), 7.53(d, J=8.9Hz, 2H), 7.59(dd, J=8.4, 2.1Hz, 1H), 7.71(d, J=2.1Hz, 1H),
　　　IR(KBr) 3406, 1615, 1522, 1488, 1399, 1324, 1280, 1256, 1138, 1116, 1076, 1054, 996, 835, 826 cm$^{-1}$
I-428　m.p. 133–135° C.
　　　$^1$HNMR(CDCl$_3$)δ 3.44(s, 3H), 3.75(s, 3H), 4.87(s, 1H), 5.23(s, 2H), 6.03(s, 1H), 6.46(s, 1H), 6.93(d, J=8.6Hz, 2H), 7.11(d, J=8.4Hz, 1H), 7.32–7.49(m, 5H), 7.53(d, J=8.6Hz, 2H), 7.60(dd, J=8.4, 2.1Hz, 1H), 7.75(d, J=2.1Hz, 1H),
　　　IR(KBr) 3397, 1612, 1523, 1489, 1400, 1321, 1257, 1132, 1084, 1056, 1002, 832 cm$^{-1}$
I-429　m.p. 174–176° C.
　　　$^1$HNMR(CDCl$_3$)δ 2.37(s, 3H), 3.44(s, 3H), 3.75(s, 3H), 4.88(s, 1H), 5.18(s, 2H), 6.02(s, 1H), 6.45(s, 1H), 6.93(d, J=8.6Hz, 2H), 7.11(d, J=8.4Hz, 1H), 7.21(d, J=8.1Hz, 2H), 7.36(d, J=8.1Hz, 2H), 7.53(d, J=8.6Hz, 2H), 7.59(dd, J=8.4, 2.1Hz, 1H), 7.74(d, J=2.1Hz, 1H),
　　　IR(KBr) 3481, 3376, 1616, 1520, 1491, 1327, 1260, 1119, 1081, 1004, 827 cm$^{-1}$

TABLE 87-continued

I-430　$^1$HNMR(CDCl$_3$)δ 2.37(s, 3H), 2.54(s, 3H), 2.68(s, 3H), 3.12(s, 3H), 3.54(s, 3H), 3.77(s, 3H), 5.14(s, 2H), 6.85(s, 1H), 7.12–7.24(m, 3H), 7.30–7.44(m, 6H), 7.53–7.59(m, 2H)
　　　IR(CHCl$_3$)1608, 1517, 1476, 1367, 1117, 1080, 1013, 970, 876 cm$^{-1}$
I-431　m.p. 164–168° C.
　　　$^1$HNMR(CDCl$_3$)δ 1.76(s, 3H), 1.82(s, 3H), 2.54(s, 3H), 3.47(s, 3H), 3.75(s, 3H), 4.62(d, J=6.9Hz, 2H), 5.53(m, 1H), 5.69(s, 1H), 5.89(s, 1H), 6.46(s, 1H), 6.92–7.08(m, 3H), 7.30–7.38(m, 2H), 7.55–7.62(m, 2H)
　　　IR(CHCl$_3$)3518, 2968, 1584, 1516, 1483, 1460, 1414, 1388, 1310, 1289, 1243, 1114, 1069, 1011, 936, 818 cm$^{-1}$
I-432　m.p. 179–181° C.
　　　$^1$HNMR(CDCl$_3$)δ 2.39(s, 3H), 2.54(s, 3H), 3.46(s, 3H), 3.74(s, 3H), 5.10(s, 2H), 5.67(s, 1H), 5.89(s, 1H), 6.46(s, 1H), 6.81(dd, J=2.1, 8.4Hz, 1H), 7.03(d, J=8.4Hz, 1H), 7.08(d, J=2.1Hz, 1H), 7.20–7.26(m, 2H), 7.31-7.37(m, 4H), 7.55–7.61(m, 2H)
　　　IR(CHCl$_3$)3524, 2930, 1585, 1517, 1483, 1460, 1414, 1389, 1310, 1289, 1245, 1114, 1090, 1070, 1009, 937, 818 cm$^{-1}$

TABLE 88

I-433　m.p. 111–112° C.
　　　$^1$HNMR(CDCl$_3$)δ 1.76(d, J=0.6Hz, 3H), 1.81(d, J=0.9Hz, 3H), 2.69(s, 3H), 3.52(s, 3H), 3.78(s, 3H), 4.63(t, J=6.6Hz, 2H), 5.53(m, 1H), 6.84(s, 1H), 7.02–7.25(m, 5H), 7.56–7.65(m, 2H)
　　　IR(CHCl$_3$)2932, 1607, 1520, 1481, 1368, 1266, 1080, 1012, 961, 907, 836, 812 cm$^{-1}$
I-434　m.p. 97–101° C.
　　　$^1$HNMR(CDCl$_3$)δ 1.69(s, 3H), 1.75(d, J=0.9Hz, 3H), 2.48–2.58(m, 5H), 3.46(s, 3H), 3.47(s, 3H), 4.06(t, J=6.9Hz, 2H), 5.22(m, 1H), 5.67(s, 1H), 5.88(s, 1H), 6.46(s, 1H), 6.92–6.97(m, 2H), 7.05(m, 1H), 7.30–7.38(m, 2H), 7.55–7.62(m, 2H)
　　　IR(CHCl$_3$)3518, 2928, 1584, 1517, 1483, 1414, 1388, 1290, 1246, 1114, 1090, 1070, 1011, 937, 907, 818 cm$^{-1}$
I-435　m.p. 127–129° C.
　　　$^1$HNMR(CDCl$_3$)δ 1.68(s, 3H), 1.74(d, J=1.2Hz, 3H), 2.50–2.60(m, 2H), 2.71(s, 3H), 3.52(s, 3H), 3.77(s, 3H), 4.04(t, J=7.2Hz, 2H), 5.23(m, 1H), 6.83(s, 1H), 7.00–7.21(m, 5H), 7.57–7.64(m, 2H)
　　　IR(CHCl$_3$)2930, 1520, 1481, 1368, 1266, 1080, 1012, 960, 836, 812 cm$^{-1}$
I-436　m.p. 159–161° C.
　　　$^1$HNMR(CDCl$_3$)δ 2.36(s, 3H), 2.57(s, 3H), 3.52(s, 3H), 3.77(s, 3H), 5.16(s, 2H), 6.83(s, 1H), 7.05–7.24(m, 7H), 7.31–7.37(m, 2H), 7.56–7.65(m, 2H)
　　　IR(CHCl$_3$)1520, 1481, 1368, 1267, 1131, 1080, 1012, 960, 836 cm$^{-1}$
I-437　m.p. 120–124° C.
　　　$^1$HNMR(CDCl$_3$)δ 1.76(d, J=0.6Hz, 3H), 1.81(d, J=0.6Hz, 3H), 3.43(s, 3H), 3.67(s, 3H), 4.63(d, J=6.6Hz, 2H), 5.56(m, 1H), 5.96(s, 1H), 6.44(s, 1H), 7.00–7.24(m, 5H), 7.57–7.66(m, 2H)
　　　IR(CHCl$_3$)3522, 2930, 1586, 1518, 1484, 1415, 1390, 1311, 1290, 1248, 1115, 1090, 1071, 1012, 938, 818 cm$^{-1}$

TABLE 89

I-438　m.p. 140.5–141.5° C.
　　　$^1$HNMR(CDCl$_3$)δ 2.37(s, 3H), 3.43(s, 3H), 3.75(s, 3H), 5.14(s, 2H), 5.97(s, 1H), 6.44(s, 1H), 7.04–7.28(m, 7H), 7.36(d, J=8.1Hz, 1H), 7.57–7.65(m, 2H)
　　　IR(CHCl$_3$)3496, 2932, 1613, 1520, 1488, 1460, 1391, 1313, 1267, 1113, 1069, 1010, 934, 825 cm$^{-1}$
I-439　m.p. 76.5–77.5° C.
　　　$^1$HNMR(CDCl$_3$)δ 1.68(s, 3H), 1.74(d, J=0.9Hz, 3H), 2.49–2.60(m, 2H), 3.43(s, 3H), 3.75(s, 3H), 4.05(t, J=7.2Hz, 2H), 5.23(m, 1H), 5.96(s, 1H), 6.44(s, 1H), 6.99–7.28(m, 5H),

TABLE 89-continued 7.57–7.66(m, 2H)
IR(CHCl$_3$)3498, 2930, 1613, 1521, 1489, 1391, 1310, 1267, 1113, 1070, 1011, 934, 825 cm$^{-1}$ I-440 m.p. 174–176° C.
$^1$HNMR(CDCl$_3$)δ 2.80(s, 3H), 3.46(s, 3H), 3.76(s, 3H), 5.16(s, 2H), 5.71(s, 1H), 5.88(s, 1H), 6.47(s, 1H), 6.95(dd, J=1.8, 8.4Hz, 1H), 7.04(d, J=8.4Hz, 1H), 7.08(d, J=1.8Hz, 1H), 7.34–7.49(m, 5H), 7.72–7.85(m, 4H)
IR(CHCl$_3$)3518, 1587, 1516, 1483, 1459, 1415, 1387, 1290, 1114, 1070, 1041, 1011, 936, 821 cm$^{-1}$ I-441 m.p. 199–202° C.
$^1$HNMR(d6-DMSO)δ 3.28(s, 3H), 3.34(s, 3H), 3.67(s, 3H), 5.14(s, 2H), 6.52(s, 1H), 6.66(dd, J=2.1, 8.4Hz, 1H), 6.79(d, J=2.1Hz, 1H), 6.97(d, J=8.4Hz, 1H), 7.30–7.56(m, 5H), 7.86–7.93(m, 2H), 7.98–8.04(m, 2H), 8.65–9.02(brs, 2H)
IR(KBr) 3487, 3413, 3004, 1597, 1518, 1500, 1482, 1456, 1360, 1310, 1281, 1231, 1146, 1118, 1090, 1068, 1016, 1004, 961 cm$^{-1}$ I-442 m.p. 80–84° C.
$^1$HNMR(CDCl$_3$)δ 1.15(t, J=7.2Hz, 3H), 3.60(q, J=7.2Hz, 2H), 3.75(s, 3H), 5.03(s, 1H), 5.15(s, 2H), 5.69(s, 1H), 5.98(s, 1H), 6.45(s, 1H), 6.88–6.94(m, 2H), 6.96(dd, J=2.1, 8.1Hz, 1H), 7.02(d, J=8.1Hz, 1H), 7.10(d, J=2.1Hz, 1H), 7.34–7.49(m, 5H), 7.51–7.59(m, 2H)
IR(CHCl$_3$)3528, 1612, 1521, 1488, 1454, 1412, 1383, 1286, 1246, 1113, 1069, 1023, 886, 825 cm$^{-1}$

TABLE 90

I-443 m.p. 168–169° C.
$^1$HNMR(CDCl$_3$)δ 1.14(t, J=6.9Hz, 3H), 2.66(s, 3H), 3.13(s, 3H), 3.20(s, 3H), 3.72(q, J=6.9Hz, 2H), 3.78(s, 3H), 5.19(s, 2H), 6.84(s, 1H), 7.15(d, J=8.4Hz, 1H), 7.31–7.49(m, 9H), 7.66–7.73(m, 5H)
IR(CHCl$_3$)1517, 1479, 1369, 1148, 1117, 1082, 969, 873 cm$^{-1}$

I-444 m.p. 192–194° C.
$^1$HNMR(CDCl$_3$)δ 3.13(s, 3H), 3.44(s, 3H), 3.63(s, 3H), 3.76(s, 3H), 5.14(br, 1H), 5.19(s, 2H), 6.81–6.84(m, 2H), 6.94(s, 1H), 7.14(d, J=8.4Hz, 1H), 7.22–7.25(m, 2H), 7.37–7.50(m, 5H), 7.57(dd, J=8.7, 2.1Hz, 1H), 7.67(d, J=2.1Hz, 1H)
IR(CHCl$_3$)3595, 3441, 1730, 1613, 1522, 1472, 1371, 1291, 1258, 1172, 1164, 1003, 972, 961, 904, 838 cm$^{-1}$

I-445 m.p. 179–180° C.
$^1$HNMR(CDCl$_3$)δ 1.77(s, 3H), 1.82(s, 3H), 2.31(s, 3H), 3.24(s, 3H), 3.45(s, 3H), 3.58(s, 3H), 3.76(s, 3H), 4.64(d, J=6.9Hz, 2H), 6.95(s, 1H), 7.06–7.13(m, 3H), 7.35–7.38(m, 2H), 7.57(dd, J=8.4, 2.4Hz, 1H), 7.64(d, J=2.4Hz, 1H)
IR(CHCl$_3$)2938, 1732, 1614, 1599, 1518, 1470, 1445, 1370, 1345, 1290, 1228, 1200, 1169, 1116, 1081, 1003, 973, 905, 846, 829 cm$^{-1}$

I-446 m.p. 137–138° C.
$^1$HNMR(CDCl$_3$)δ 3.13(s, 3H), 3.45(s, 3H), 3.59(s, 3H), 3.77(s, 3H), 3.88(s, 3H), 4.23(s, 2H), 5.19(s, 2H), 6.96(s, 1H), 7.15(d, J=8.7Hz, 1H), 7.35–7.50(m, 9H), 7.60(dd, J=8.7, 2.4Hz, 1H), 7.67(d, J=2.4Hz, 1H)
IR(CHCl$_3$)2954, 1750, 1734, 1614, 1516, 1471, 1387, 1372, 1345, 1291, 1258, 1173, 1147, 1118, 1081, 1064, 1004, 877 cm$^{-1}$

I-447 m.p. 184–185° C.
$^1$HNMR(CDCl$_3$)δ 3.44(s, 3H), 3.60(s, 3H), 3.74(s, 3H), 4.70(br, 2H), 5.17(s, 2H), 6.95–7.02(m, 4H), 7.17(dd, J=8.4, 2.1Hz, 1H), 7.25(s, 1H), 7.31–7.34(d, J=8.7Hz, 2H), 7.38–7.47(m, 5H)
IR(CHCl$_3$)3541, 2937, 1776, 1733, 1608, 1519, 1474, 1442, 1344, 1291, 1157, 1130, 1085, 1063, 1002, 900, 862, 835 cm$^{-1}$

TABLE 91

I-448 m.p. 176–178° C.
$^1$HNMR(CDCl$_3$)δ 3.12(s, 3H), 3.44(s, 3H), 3.60(s, 3H), 3.76(s, 3H), 3.83(s, 3H), 4.66(s, 2H), 5.19(s, 2H),

TABLE 91-continued 6.91–6.96(m, 3H), 7.14(d, J=8.4Hz, 1H), 7.28–7.49(m, 7H), 7.57(dd, J=8.7, 2.4Hz, 1H), 7.67(d, J=2.4Hz, 1H)
IR(CHCl$_3$)2953, 2939, 1758, 1732, 1610, 1519, 1471, 1444, 1371, 1345, 1291, 1177, 1117, 1085, 1064, 1002, 973, 961, 904, 837 cm$^{-1}$ I-449 m.p. 124–126° C.
$^1$HNMR(CDCl$_3$)δ 1.69(s, 3H), 1.74(d, J=0.9Hz, 3H), 2.31(s, 3H), 2.53–2.60(m, 2H), 3.23(s, 3H), 3.44(s, 3H), 3.58(s, 3H), 3.76(s, 3H), 4.09(t, J=6.6Hz, 2H), 5.22(s, 1H), 6.95(s, 1H), 7.07(d, J=8.4Hz, 1H), 7.10–7.13(m, 2H), 7.34–7.37(m, 2H), 7.57(dd, J=9.0, 2.4Hz, 1H), 7.64(d, J=2.4Hz, 1H)
IR(CHCl$_3$)2938, 1732, 1614, 1518, 1469, 1445, 1370, 1291, 1257, 1170, 1167, 1081, 1004, 973, 961, 906, 846 cm$^{-1}$ I-450 m.p. 160–161° C.
$^1$HNMR(CDCl$_3$)δ 1.69(s, 3H), 1.74(d, J=0.9, 3H), 2.53–2.60(m, 2H), 3.23(s, 3H), 3.45(s, 3H), 3.62(s, 3H), 3.76(s, 3H), 4.08(t, J=6.6Hz, 2H), 4.91(br, 1H), 5.20–5.25(m, 1H), 6.83–6.86(m, 2H), 6.94(s, 1H), 7.06(d, J=8.7Hz, 2H), 7.23–7.26(m, 2H), 7.57(dd, J=8.7, 2.4Hz, 1H), 7.64(d, J=2.4Hz, 1H)
IR(CHCl$_3$)3595, 3448, 2937, 1730, 1613, 1522, 1469, 1445, 1370, 1345, 1292, 1260, 1172, 1117, 1081, 1064, 1003, 973, 864, 837 cm$^{-1}$ I-451 m.p. 182–184° C.
$^1$HNMR(CDCl$_3$)δ 1.70(d, J=0.6Hz, 3H), 1.81(d, J=0.9Hz, 3H), 3.24(s, 3H), 3.45(s, 3H), 3.63(s, 3H), 3.75(s, 3H), 4.64(d, J=6.6Hz, 2H), 5.48–5.54(m, 1H), 5.76(br, 1H), 6.78–6.82(m, 2H), 6.95(s, 1H), 7.08(d, J=8.7Hz, 1H), 7.19–7.24(m, 2H), 7.56(dd, J=8.7, 2.4Hz, 1H), 7.64(d, J=2.4Hz, 1H)
IR(CHCl$_3$)3595, 3445, 2939, 1730, 1613, 1522, 1471, 1445, 1369, 1345, 1291, 1257, 1172, 1116, 1081, 1064, 1002, 973, 904, 838 cm$^{-1}$ I-452 m.p. 250–253° C. (dec.)
$^1$HNMR(CD$_3$OD)δ 3.41(s, 3H), 3.71(s, 3H), 4.58(s, 2H), 5.21(s, 2H), 6.29–6.95(m, 3H), 7.02–7.03(m, 2H), 7.17(s, 1H), 7.26–7.41(m, 5H), 7.49–7.52(m, 2H)
IR(KBr) 3424, 2933, 2553, 1709, 1608, 1519, 1467, 1383, 1333, 1291, 1229, 1129, 1084, 1060, 1001, 915, 861, 841, 727, 697 cm$^{-1}$

TABLE 92

I-453 foam
$^1$HNMR(CDCl$_3$)δ 1.69(s, 3H), 1.75(d, J=1.2Hz, 3H), 2.51–2.58(m, 2H), 3.43(s, 3H), 3.62(s, 3H), 3.75(s, 3H), 4.08(t, J=6.9Hz, 2H), 4.85(br, 1H), 5.23(m, 1H), 5.71(br, 1H), 6.82–6.85(m, 2H), 6.90–6.94(m, 2H), 7.16(dd, J=8.4, 2.1Hz, 1H), 7.23–7.26(m, 3H)
IR(CHCl$_3$)3596, 3541, 2936, 1730, 1612, 1590, 1522, 1470, 1395, 1345, 1290, 1258, 1173, 1130, 1081, 1063, 1004, 861, 836 cm$^{-1}$ I-454 m.p. 166–167° C.
$^1$HNMR(CDCl$_3$)δ 1.77(s, 3H), 1.82(s, 3H), 3.48(s, 3H), 3.75(s, 3H), 4.64(d, J=6.6Hz, 2H), 5.51–5.55(m, 1H), 5.75(br, 1H), 6.77–6.80(m, 2H), 6.93–6.96(m, 2H), 7.17(dd, J=8.1, 2.1Hz, 1H), 7.23–7.28(m, 3H)
IR(KBr) 3447, 2937, 1590, 1559, 1522, 1473, 1382, 1338, 1295, 1259, 1131, 1080, 1059, 999, 918, 862, 837, 815, 791, 754 cm$^{-1}$ I-455 m.p. 168–170° C.
$^1$HNMR(CD$_3$OD)δ 1.68(s, 3H), 1.74(s, 3H), 2.50–2.58(m, 2H), 3.41(s, 3H), 3.73(s, 3H), 4.05(t, J=6.9Hz, 2H), 5.29(m, 1H), 6.76–6.79(m, 2H), 6.98–7.17(m, 6H)
IR(KBr) 3411, 2964, 2936, 1685, 1613, 1590, 1523, 1472, 1379, 1293, 1259, 1229, 1131, 1082, 1061, 1000, 962, 861, 838, 814, 791, 754, 529 cm$^{-1}$ I-456 m.p. 153–155° C.
$^1$HNMR(CDCl$_3$)δ 3.14(s, 3H), 3.50(s, 3H), 3.77(s, 3H), 5.20(s, 2H), 7.10–7.28(m, 6H), 7.38–7.50(m, 5H), 7.56(dd, J=8.4, 2.1Hz, 1H), 7.65(d, J=2.1Hz, 1H), 9.98(s, 1H)
IR(CHCl$_3$)2938, 2843, 1697, 1604, 1590, 1517, 1469, 1372, 1331, 1293, 1254, 1172, 1159, 1123, 1093, 1005, 963, 818 cm$^{-1}$ I-457 m.p. 143–145° C.
$^1$HNMR(CDCl$_3$)δ 1.77(s, 3H), 1.83(s, 3H), 3.44(s, 3H), 3.63(s, 3H), 3.75(s, 3H), 4.63(d, J=6.6Hz, 2H), 5.53(m, 1H), 5.72(br, 1H), 6.82–6.85(m, 2H), 6.92–6.95(m, 2H), 7.16(dd, J=8.4, 2.4Hz, 1H), 7.23–7.26(m, 3H)

TABLE 92-continued

IR(CHCl₃)3595, 3537, 2938, 1729, 1612, 1591, 1522, 1473, 1395, 1344, 1290, 1258, 1173, 1129, 1081, 1063, 1003, 900, 862, 836 cm⁻¹

TABLE 93

I-458 powder
¹HNMR(CDCl₃) δ 2.37(s, 3H), 3.08(s, 3H), 3.11(s, 3H), 3.21(s, 3H), 3.51(s, 3H), 3.52(s, 3H), 5.26(s, 2H), 7.19–7.23(m, 2H), 7.36–7.43(m, 4H), 7.45–7.50(m, 2H), 7.82(d, J=2.1Hz, 1H), 7.98(d, J=2.1Hz, 1H)
IR(CHCl₃)3033, 2942, 1543, 1377, 1220, 1181, 1153, 1034 cm⁻¹

I-459 m.p. 182–187° C. (dec.)
¹HNMR(CDCl₃) δ 2.36(s, 3H), 2.73(s, 3H), 3.16(s, 3H), 3.22(s, 3H), 3.43(s, 3H), 3.47(s, 3H), 5.08(s, 2H), 6.85(brs, 1H), 6.92(brs, 1H), 7.17–7.21(m, 2H), 7.32–7.38(m, 2H), 7.39–7.44(m, 2H), 7.50–7.55(m, 2H)
IR(CHCl₃)3030, 2939, 1618, 1599, 1513, 1468, 1416, 1372, 1178, 1150, 1031 cm⁻¹

I-460 powder
¹HNMR(CDCl₃) δ 2.38(s, 3H), 2.83(s, 3H), 3.05(s, 3H), 3.22(s, 3H), 3.56(s, 3H), 3.80(s, 3H), 3.91(s, 3H), 5.13(s, 2H), 6.86(s, 1H), 7.20–7.24(m, 2H), 7.37–7.46(m, 4H), 7.65–7.70(m, 3H), 7.89(d, J=2.1Hz, 1H)
IR(CHCl₃)3032, 2940, 1728, 1473, 1373, 1232, 1179, 1150, 1085 cm⁻¹

I-461 amorphous
¹HNMR(CDCl₃) δ 3.78(s, 6H), 5.16(s, 2H), 5.31(s, J=3.6Hz, 1H), 5.72(s, 1H), 6.91(s, 1H), 6.94(s, 1H), 6.99(d, J=8.2Hz, 1H), 7.04(t, J=8.6Hz, 1H), 7.08(dd, J=8.2, 2.1Hz, 1H), 7.22(d, J=2.1Hz, 1H), 7.25(ddd, J=8.6, 1.8, 0.9Hz, 1H), 7.34–7.46(m, 6H)
IR(CHCl₃)3577, 3548, 1526, 1495, 1280, 1635 cm⁻¹

I-462 m.p. 153–155° C.
¹HNMR(CDCl₃) δ 3.12(s, 3H), 3.26(s, 3H), 3.80(s, 3H), 3.81(s, 3H), 5.18(s, 2H), 6.91(s, 1H), 6.94(s, 1H), 7.12(d, J=8.4Hz, 1H), 7.36–7.50(m, 8H), 7.59(d, J=1.8Hz, 1H)
IR(CHCl₃)1494, 1367, 1212, 1180, 1116, 872, 808 cm⁻¹

TABLE 94

I-463 m.p. 125–127° C.
¹HNMR(CDCl₃) δ 1.77(s, 3H), 1.82(s, 3H), 3.23(s, 3H), 3.27(s, 3H), 3.80(s, 3H), 3.82(s, 3H), 4.64(d, J=6.7Hz, 2H), 5.51(t, J=6.7Hz, 1H), 6.91(s, 1H), 6.95(s, 1H), 7.06(d, J=8.7Hz, 1H), 7.37(dd, J=8.7, 1.9Hz, 1H), 7.40–7.47(m, 2H), 7.50(d, J=2.4Hz, 1H), 7.57(d, J=1.9Hz, 1H)
IR(KBr) 1523, 1496, 1370, 1213, 1175, 1116, 1035, 977, 832, 807 cm⁻¹

I-464 m.p. 149–151° C.
¹HNMR(CDCl₃) δ 1.69(s, 3H), 1.74(s, 3H), 2.55(q, J=7.0Hz, 2H), 3.21(s, 3H), 3.26(s, 3H), 3.80(s, 3H), 3.81(s, 3H), 4.07(t, J=7.0Hz, 2H), 5.21(t, J=7.0Hz, 1H), 6.91(s, 1H), 6.94(s, 1H), 7.05(d, J=8.4Hz, 1H), 7.37(dd, J=8.4, 2.1Hz, 1H), 7.40–7.47(m, 2H), 7.50(d, J=2.1Hz, 1H), 7.57(d, J=2.1Hz, 1H)
IR(KBr) 1523, 1495, 1368, 1212, 1176, 1116, 1035, 976, 832, 806 cm⁻¹

I-465 m.p. 148–150° C.
¹HNMR(CDCl₃) δ 2.38(s, 3H), 3.11(s, 3H), 3.26(s, 3H), 3.80(s, 3H), 3.81(s, 3H), 5.13(s, 2H), 6.91(s, 1H), 6.94(s, 1H), 7.12(d, J=8.4Hz, 1H), 7.22(d, J=7.8Hz, 2H), 7.35(d, J=7.8Hz, 2H), 7.37(dd, J=8.4, 1.8Hz, 1H), 7.40–7.50(m, 3H), 7.59(d, J=1.8Hz, 1H)
IR(KBr) 1523, 1490, 1370, 1181, 1115, 971, 868, 806 cm⁻¹

I-466 m.p. 109–112° C.
¹HNMR(CDCl₃) δ 1.76(s, 3H), 1.82(s, 3H), 3.79(s, 6H), 4.62(d, J=6.9Hz, 2H), 5.26(d, J=3.9Hz, 1H), 5.52(t, J=6.9Hz, 1H), 5.72(s, 1H), 6.91(s, 1H), 6.93(d, J=8.6Hz, 1H), 6.94(s, 1H), 7.04(t, J=8.7Hz, 1H), 7.07(dd, J=8.6, 2.1Hz, 1H), 7.19(d, J=2.1Hz, 1H), 7.25(ddd, J=8.7, 1.8, 0.9Hz, 1H), 7.37(d, J=12.0, 1.8Hz, 1H)
IR(CHCl₃) 3578, 3542, 1526, 1495, 1280, 1055, 1035 cm⁻¹

TABLE 95

I-467 amorphous
¹HNMR(CDCl₃) δ 2.39(s, 3H), 3.79(s, 6H), 5.11(s, 2H), 5.40(brs, 1H), 5.73(s, 1H), 6.91(s, 1H), 6.94(s, 1H), 6.99(d, J=8.4Hz, 1H), 7.04(t, J=8.7Hz, 1H), 7.08(dd, J=8.4, 2.1Hz, 1H), 7.21(d, J=2.1Hz, 1H), 7.23(d, J=7.7Hz, 2H), 7.25(ddd, J=8.7, 2.1, 1.2Hz, 1H), 7.34(d, J=7.7Hz, 2H), 7.37(dd, J=11.7, 2.1Hz, 1H)
IR(CHCl₃) 3577, 3545, 1526, 1495, 1280, 1055, 1035, 868 cm⁻¹

I-468 amorphous
¹HNMR(CDCl₃) δ 1.69(s, 3H), 1.75(s, 3H), 2.53(q, J=7.0Hz, 2H), 3.78(s, 3H), 3.79(s, 3H), 4.07(t, J=7.2Hz, 2H), 522(t, J=7.0Hz, 1H), 5.27(d, J=3.9Hz, 1H), 5.71(s, 1H), 6.91(s, 1H), 6.91(s, 1H), 6.91(d, J=8.6Hz, 1H), 6.94(s, 1H), 7.04(t, J=8.4Hz, 1H), 7.06(dd, J=8.6, 2.1Hz, 1H), 7.19 (d, J=2.1Hz, 1H), 7.25(ddd, J=8.4, 1.9, 1.1Hz, 1H), 7.37(dd, J=12.0, 1.9Hz, 1H)
IR(CHCl₃) 3578, 1526, 1495, 1280, 1055, 1035 cm⁻¹

I-469 m.p. 190–191° C.
¹HNMR(CDCl₃) δ 2.38(s, 3H), 3.11(s, 3H), 3.19(s, 3H), 3.80(s, 6H), 5.13(s, 2H), 6.92(s, 1H), 6.94(s, 1H), 7.12(d, J=8.7Hz, 1H), 7.22(d, J=7.8Hz, 1H), 7.32–7.37(m, 4H), 7.49(dd, J=2.1, 8.4Hz, 1H), 7.59(d, J=1.8Hz, 1H), 7.60–7.65(m, 2H)
IR(KBr) 3600–2800(br), 1521, 1492, 1468, 1386, 1366, 1336, 1292, 1272, 1259, 1202, 1174, 1150, 1113 cm⁻¹

I-470 m.p. 147–148° C.
¹HNMR(CDCl₃) δ 2.37(s, 3H), 3.19(s, 3H), 3.79(s, 3H), 3.80(s, 3H), 5.16(s, 2H), 6.92(s, 1H), 6.93(s, 1H), 7.06(t, J=8.7Hz, 1H), 7.20–7.27(m, 3H), 7.32–7.41(m, 5H), 7.60–7.64(m, 2H)
IR(KBr) 3600–2800(br), 1523, 1492, 1462, 1454, 1379, 1359, 1299, 1278, 1264, 1210, 1175, 1151, 1129, 1054, 1031, 1009 cm⁻¹

I-471 m.p. 170–172° C.
¹HNMR(CDCl₃) δ 3.19(s, 3H), 3.24(s, 3H), 3.79(s, 3H), 3.80(s, 3H), 5.12(s, 2H), 6.92(s, 1H), 6.94(s, 1H), 7.11(d, J=8.7Hz, 1H), 7.26–7.30(m, 2H), 7.32–7.37(m, 2H), 7.47(dd, J=2.4, 8.4Hz, 1H), 7.61–7.64(m, 3H), 7.74–7.80(m, 1H), 8.61–8.63(m, 1H)
IR(KBr) 3600–2800(br), 1522, 1491, 1462, 1361, 1296, 1264, 1212, 1177, 1149, 1115, 1030 cm⁻¹

TABLE 96

I-472 m.p. 174–175° C.
¹HNMR(CDCl₃) δ 3.19(s, 3H), 3.79(s, 3H), 3.80(s, 3H), 5.33(s, 2H), 692(s, 1H), 6.93(s, 1H), 7.07(d, J=8.7Hz, 1H), 7.23–7.28(m, 2H), 7.32–7.37(m, 2H), 7.41(dd, J=1.8, 12.6Hz, 1H), 7.60–7.64(m, 3H), 7.73–7.79(m, 1H), 8.60–8.63(m, 1H)
IR(KBr) 3600–2800(br), 1524, 1491, 1464, 1380, 1361, 1302, 1267, 1209, 1172, 1149, 1130, 1034, 1024 1008 cm⁻¹

I-473 m.p. 118.5–119.5° C.
¹HNMR(CDCl₃) δ 1.77(s, 3H), 1.80(d, J=0.9Hz, 3H), 3.78(s, 3H), 3.79(s, 3H), 4.63(d, J=6.9Hz, 2H), 5.52–5.57(m, 1H), 6.73–6.78(m, 2H), 6.91(s, 1H), 6.93(s, 1H), 7.02(t, J=8.7Hz, 1H), 7.25–7.30(m, 1H), 7.35–7.43(m, 3H)
IR(KBr) 3600–2800(br), 1625, 1527, 1491, 1461, 1449, 1378, 1298, 1279, 1259, 1207, 1184, 1125, 1055, 1031 cm⁻¹

I-474 m.p. 156–158° C.
¹HNMR(CDCl₃) δ 1.77(s, 3H), 1.81(s, 3H), 3.08(s, 3H), 3.80(s, 3H), 3.81(s, 3H), 4.64(d, J=6.6Hz, 2H), 5.52–5.58(m, 1H), 6.43(brs, 1H), 6.93(s, 1H), 6.94(s, 1H), 7.03(t, J=8.4Hz, 1H), 7.26–7.30(m, 3H), 7.37(dd, J=1.8, 12.6Hz, 1H), 7.57–7.61(m, 2H)
IR(KBr) 3600–2800(br), 1526, 1495, 1463, 1382, 1325, 1300, 1267, 1210, 1156, 1139, 1129, 1054, 1032 cm⁻¹

I-475 m.p. 158–160° C.
¹HNMR(CDCl₃) δ 1.77(s, 3H), 1.81(s, 3H), 3.80(s, 6H), 4.64(d, J=6.6Hz, 2H), 4.73(brs, 2H), 5.53–5.57(m, 1H), 6.51(brs, 1H), 6.93(s, 1H), 6.94(s, 1H), 7.03(t, J=8.7Hz, 1H), 7.26–7.31(m, 3H), 7.37(dd, J=2.1, 12.6Hz, 1H), 7.57–7.61(m, 2H)
IR(KBr) 3600–2800(br), 1527, 1495, 1462, 1395, 1326, 1299, 1264, 1208, 1170, 1130, 1054, 1031 cm⁻¹

I-476 m.p. 138–140° C.
¹HNMR(CDCl₃) δ 1.77(s, 3H), 1.81(s, 3H), 2.21(s, 3H), 3.78(s, 3H), 3.80(s, 3H), 4.63(d, J=6.9Hz, 2H), 5.53–5.57(m, 1H), 6.93(s, 1H), 6.94(s, 1H), 7.03(t, J=8.4Hz, 1H), 7.20(brs, 1H), 7.26–7.30(m, 1H), 7.37(dd, J=2.1, 12.6Hz, 1H), 7.56(m, 4H)
IR(KBr) 3600–2800(br), 1666, 1604, 1527, 1494, 1463, 1448, 1379, 1317, 1299, 1264, 1209, 1130, 1055, 1032 cm⁻¹

TABLE 97

I-477 m.p. 200–202° C.
¹HNMR(CDCl₃ + CD₃OD) δ 1.77(s, 3H), 1.81(s, 3H), 3.79(s, 3H), 3.80(s, 3H), 4.64(d, J=6.6Hz, 2H), 5.52–5.57(m, 1H), 6.93(s, 1H), 6.94(s, 1H), 7.03(t, J=9.0Hz, 1H), 7.27–7.30(m, 1H), 7.34–7.41(m, 3H), 7.52–7.55(m, 2H)
IR(KBr) 3600–2800(br), 2404, 1684, 1660, 1584, 1528, 1493, 1462, 1386, 1301, 1274, 1263, 1209, 1132, 1053, 1029 cm⁻¹

I-478 m.p. 195–196.5° C.
¹HNMR(CDCl₃) δ 1.55(s, 9H), 3.78(s, 3H), 3.79(s, 3H), 4.85(s, 1H), 6.75(brs, 1H), 6.88–6.92(m, 2H), 6.92(s, 1H), 6.93(s, 1H), 7.31–7.39(m, 3H), 7.45–7.49(m, 2H), 8.12(t, J=7.5Hz, 1H)
IR(KBr) 3600–2800(br), 1729, 1590, 1531, 1500, 1464, 1394, 1261, 1240, 1199, 1156, 1055, 1033, 1023 cm⁻¹

I-479 m.p. 172–174° C.
¹HNMR(CDCl₃) δ 1.55(s, 9H), 3.19(s, 3H), 3.79(s, 3H), 3.80(s, 3H), 6.75(d, J=2.1Hz, 1H), 6.92(s, 1H), 6.94(s, 1H), 7.26–7.39(m, 5H), 7.60–7.65(m, 2H)
IR(KBr) 3600–2800(br), 1728, 1590, 1531, 1513, 1494, 1464, 1391, 1367, 1352, 1240, 1206, 1179, 1145, 1056, 1033, 1024 cm⁻¹

I-480 m.p. 152–153° C.
¹HNMR(CDCl₃) δ 1.74(s, 3H), 1.77(s, 3H), 3.18(s, 3H), 3.78(d, J=9.9Hz, 2H), 3.79(s, 6H), 3.93(brs, 1H), 5.35–5.40(m, 1H), 6.75(t, J=8.4Hz, 1H), 6.91(s, 1H), 6.95(s, 1H), 7.24–7.36(m, 4H), 7.60–7.65(m, 2H)
IR(KBr) 3600–2800(br), 1630, 1530, 1488, 1466, 1380, 1366, 1346, 1259, 1213, 1176, 1149, 1124, 1054, 1027 cm⁻¹

I-481 foam
¹HNMR(CDCl₃) δ 2.40(s, 3H), 3.19(s, 3H), 3.77(s, 3H), 3.78(s, 3H), 6.80(t, d = 2.4Hz, 1H), 6.90(s, 1H), 6.91(s, 1H), 7.25–7.36(m, 6H), 7.58–7.65(m, 3H), 7.72–7.76(m, 2H)
IR(KBr) 3600–2800(br), 1522, 1490, 1366, 1342, 1211, 1164, 1151, 1091, 1053, 1030 cm⁻¹

TABLE 98

I-482 m.p. 201–203° C.
¹HNMR(CDCl₃) δ 2.45(s, 3H), 3.20(s, 3H), 3.82(s, 6H), 6.95(s, 1H), 6.98(s, 1H), 7.32–7.48(m, 6H), 7.61–7.66(m, 2H), 7.80–7.84(m, 2H), 8.10(d, J=3.3Hz, 1H), 8.55(d, J=8.4Hz, 1H)
IR(KBr) 3600–2800(br), 1671, 1592, 1524, 1494, 1388, 1366, 1328, 1265, 1207, 1172, 1150, 1052, 1024 cm⁻¹

I-483 m.p. 132–134° C.
¹HNMR(CDCl₃) δ 1.55(s, 9H), 3.00(s, 6H), 3.79(s, 6H), 6.73(d, J=2.4Hz, 1H), 6.81(m, 2H), 6.92(s, 1H), 6.96(s, 1H), 7.32–7.39(m, 2H), 7.48–7.52(m, 2H), 8.11(t, J=8.1Hz, 1H)
IR(KBr) 3600–2800(br), 1728, 1610, 1591, 1533, 1499, 1459, 1446, 1381, 1365, 1238, 1206, 1159, 1055, 1030 cm⁻¹

I-484 foam
¹HNMR(CDCl₃) δ 1.74(s, 3H), 1.77(s, 3H), 3.00(s, 6H), 3.78(d, J=9.6Hz, 1H), 3.78(s, 3H), 3.79(s, 3H), 5.34–5.38(m, 1H), 6.75(t, J=8.4Hz, 1H), 6.92(s, 1H), 6.94(s, 1H), 6.93–6.95(m, 1H), 7.23–7.32(m, 3H), 7.48–7.52(m, 2H)
IR(KBr) 3600–2800(br), 1625, 1611, 1531, 1494, 1446, 1380, 1340, 1257, 1207, 1123, 1055, 1032 cm⁻¹

I-485 foam
¹HNMR(CDCl₃) δ 2.40(s, 3H), 3.00(s, 6H), 3.76(s, 3H), 3.77(s, 3H), 6.70(t, J=2.4Hz, 1H), 6.80(t, J=8.7Hz, 2H), 6.87(s, 1H), 6.94(s, 1H), 7.24–7.33(m, 4H), 7.46–7.50(m, 2H), 7.60(t, J=9.0Hz, 1H), 7.71–7.75(m, 2H)
IR(KBr) 3600–2800(br), 1609, 1529, 1493, 1446, 1381, 1340, 1208, 1164, 1090, 1054, 1031 cm⁻¹

I-486 m.p. 184–186° C.
¹HNMR(CDCl₃) δ 2.45(s, 3H), 3.01(s, 6H), 3.80(s, 3H), 3.81(s, 3H), 6.82(d, J=7.5Hz, 2H), 6.95(s, 1H), 6.98(s, 1H), 7.32(d, J=8.1Hz, 2H), 7.40–7.52(m, 4H), 7.80–7.84(m, 2H), 8.08(d, J=2.7Hz, 1H), 8.52(t, J=8.4Hz, 1H)
IR(KBr) 3600–2800(br), 1647, 1608, 1530, 1497, 1379, 1365, 1284, 1267, 1206, 1051, 1030 cm⁻¹

TABLE 99

I-487 foam
¹HNMR(CDCl₃) δ 2.36(s, 3H), 3.77(s, 6H), 4.81(brs, 1H), 6.69(dd, J=0.9, 3.6Hz, 1H), 6.88–6.92(m, 2H), 6.94(s, 1H), 6.95(s, 1H), 7.23–7.26(m, 2H), 7.46–7.51(m, 2H), 7.53(dd, J=1.5, 8.4Hz, 1H), 7.59(d, J=3.6Hz, 1H), 7.73(d, J=0.9Hz, 1H), 7.80–7.84(m, 2H), 8.02(d, J=8.4Hz, 1H)
IR(KBr) 3600–2800(br), 1611, 1594, 1520, 1498, 1459, 1444, 1369, 1259, 1208, 1170, 1129, 1092, 1051, 1028 cm⁻¹

I-488 m.p. 219–220° C.
¹HNMR(CDCl₃) δ 2.37(s, 3H), 3.19(s, 3H), 3.78(s, 3H), 3.79(s, 3H), 6.70(dd, J=0.9, 3.6Hz, 1H), 6.94(s, 1H), 6.97(s, 1H), 7.24–7.27(m, 2H), 7.32–7.37(m, 2H), 7.53(dd, J=1.8, 8.7Hz, 1H), 7.60(d, J=3.6Hz, 1H), 7.61–7.66(m, 2H), 7.73(d, J=0.9Hz, 1H), 7.80–7.84(m, 2H), 8.03(d, J=8.7Hz, 1H)
IR(KBr) 3600–2800(br), 1513, 1494, 1464, 1444, 1373, 1209, 1173, 1155, 1122, 1049 cm⁻¹

I-489 ¹HNMR(CDCl₃) δ 3.79(s, 3H), 3.80(s, 3H), 3.94(s, 3H), 5.17(s, 2H), 5.71(s, 1H), 6.96(s, 1H), 6.97(s, 1H), 6.99(d, J=8.7Hz, 1H), 7.09(d.d, J=8.7&2.4Hz, 1H), 7.22(d, J=2.4Hz), 7.26(s, 1H), 7.32–7.49(m, 5H), 7.66(d, J=8.7Hz, 2H), 8.09(d, J=8.7Hz, 2H)
IR(KBr) 3383, 1702, 1606, 1489, 1381, 1291, 1206, 1111, 1032, 1002 cm⁻¹

I-490 ¹HNMR(CDCl₃) δ 3.12(s, 3H), 3.79(s, 3H), 3.81(s, 3H), 3.95(s, 3H), 5.18(s, 2H), 6.96(s, 2H), 7.12(d, J=8.4Hz, 1H), 7.31–7.53(m, 6H), 7.60(d, J=2.1Hz, 1H), 7.65(d, J=8.7Hz, 2H), 8.10(d, J=8.7Hz, 2H)
IR(KBr) 1720, 1607, 1492, 1362, 1275, 1211, 1112, 1057, 1032 cm⁻¹

I-491 ¹HNMR(CDCl₃) δ 3.12(s, 3H), 3.80(s, 3H), 3.81(s, 3H), 5.18(s, 2H), 6.92(s, 1H), 6.96(s, 1H), 7.13(d, J=8.4Hz, 1H), 7.31–7.52(m, 6H), 7.70(d, J=2.1Hz, 1H), 7.66–7.77(m, 4H)
IR(KBr) 3433, 1685, 1606, 1509, 1492, 1372, 1318, 1264, 1211, 1183, 1111, 1055, 1031 cm⁻¹

I-492 ¹HNMR(CDCl₃) δ 3.79(s, 3H), 3.80(s, 3H), 5.17(s, 2H), 5.71(s, 2H), 6.91(s, 1H), 6.97(s, 1H), 7.00(d, J=8.4Hz, 1H), 7.08(dd, J=8.4&2.4Hz, 1H), 7.22(d, J=2.4Hz, 1H), 7.32–7.49(m, 5H), 7.70(s, 4H)
IR(KBr) 3291, 2242, 1607, 1579, 1488, 1384, 1324, 1272, 1209, 1130, 1054, 1034, 1001 cm⁻¹

TABLE 100

I-493 ¹HNMR(CDCl₃) δ 3.12(s, 3H), 3.80(s, 3H), 3.81(s, 3H), 5.18(s, 2H), 6.92(s, 1H), 6.96(s, 1H), 7.12(d, J=8.4Hz, 1H), 7.31–7.72(m, 6H), 7.60(d, J=1.8Hz, 1H), 7.65–7.74(m, 4H)
IR(KBr) 2223, 1604, 1490, 1363, 1296, 1264, 1213, 1172, 1117, 1055, 1036, 1026 cm⁻¹

I-494 ¹HNMR(CDCl₃) δ 1.77(s, 3H), 1.81(s, 3H), 3.23(s, 3H), 3.80(s, 3H), 3.81(s, 3H), 3.95(s, 3H), 4.64(d, J=6.6Hz, 2H), 5.51(t, J=6.6Hz, 1H), 6.96(s, 2H), 7.06(d, J=8.7Hz, 1H), 7.50(d.d, J=8.7&2.1Hz, 1H), 7.59(d, J=2.1Hz, 1H), 7.65(d, J=8.7Hz, 2H), 8.10(d, J=8.7Hz, 2H)
IR(KBr) 1720, 1608, 1508, 1492, 1384, 1357, 1273, 1179, 1110, 1026, 1019 cm⁻¹

I-495 ¹HNMR(CDCl₃) δ 2.38(s, 3H), 3.12(s, 3H), 3.80(s, 6H), 3.81(s, 3H), 3.95(s, 3H), 5.14(s, 2H), 6.96(s, 2H), 7.13(d, J=8.4Hz, 1H), 7.21(d, J=7.8Hz, 2H), 7.35(d, J=7.8Hz, 2H), 7.49(d.d, J=8.4&1.8Hz, 1H), 7.60(d, J=1.8Hz, 1H), 7.65(d, J=8.7Hz, 2H), 8.10(d, J=8.7Hz, 2H)
IR(KBr) 1697, 1607, 1492, 1364, 1286, 1263, 1213, 1178, 1115, 1057, 1030 cm⁻¹

I-496 IR(KBr) 1730, 1701, 1610, 1515, 1465, 1359, 1238, 1186, 1116, 1082, 1064, 1016 cm⁻¹

I-497 ¹HNMR(CDCl₃) δ 1.75(s, 3H), 1.80(s, 3H), 2.89(s, 6H), 3.21(s, 3H), 3.44(s, 3H), 3.68(s, 3H), 3.77(s, 1H), 4.61(d, J=8.4Hz, 2H), 5.49(t, J=8.4Hz, 1H), 6.92(s, 1H), 7.01(d, J=8.4Hz, 1H), 7.25–7.28(m, 3H), 7.33(d, J=2.1Hz, 1H), 7.52(dd, J=8.4&1.8Hz, 1H), 7.66(d, J=2.4Hz, 1H)
IR(KBr) 1727, 1598, 1515, 1467, 1360, 1295, 1258, 1241, 1116, 1084 cm⁻¹

I-498 ¹HNMR(CDCl₃) δ 2.38(s, 3H), 2.89(s, 6H), 3.10(s, 3H), 3.44(s, 3H), 3.66(s, 3H), 3.77(s, 3H), 5.11(s, 3H), 6.93(s, 1H), 7.06–7.15(m, 2H), 7.17–7.29(m, 4H), 7.31–7.37(m, 3H), 7.53(d.d, J=8.7&1.8Hz, 1H), 7.66(d, J=1.8Hz, 1H)

TABLE 100-continued

IR(KBr) 1732, 1701, 1598, 1518, 1466, 1352, 1294, 1121, 1085, 1060, 1015 cm$^{-1}$

I-499  $^1$HNMR(CDCl$_3$) δ 2.88(s, 6H), 3.44(s, 3H), 3.64(s, 3H), 3.77(s, 3H), 5.17(s, 2H), 5.65(s, 1H), 6.84(dd, J=8.1&2.1Hz, 1H), 6.92(s, 1H), 6.95(d, J=8.1Hz, 1H), 7.01(d, J=2.1Hz, 1H), 7.12(d, J=8.4Hz, 1H), 7.31–7.46(m, 6H), 7.53(d.d, J=8.4&1.8Hz, 1H), 7.66(d, J=1.8Hz, 1H)
IR(KBr) 3526, 3434, 1732, 1598, 1515, 1460, 1344, 1260, 1240, 1222, 1061, 1013 cm$^{-1}$

TABLE 101

I-500  $^1$HNMR(CDCl$_3$) δ 2.60(s, 3H), 3.43(s, 3H), 3.72(s, 3H), 3.75(s, 3H), 5.17(s, 2H), 5.67(s, 1H), 6.77(s, 1H), 6.94(dd, J=8.4&1.8Hz, 1H), 7.02(d, J=8.4 Hz, 1H), 7.06(d, J=1.8Hz, 1H), 7.32–7.50(m, 7H), 7.53–7.62(m, 1H), 7.94(d, J=7.8Hz, 1H)
IR(KBr) 1732, 1719, 1585, 1521, 1481, 1403, 1352, 1289, 1253, 1225, 1172, 1073, 1012 cm$^{-1}$

I-501  $^1$HNMR(CDCl$_3$) δ 2.73(s, 3H), 3.12(s, 3H), 3.43(s, 3H), 3.72(s, 3H), 3.76(s, 3H), 5.19(s, 2H), 6.78(s, 1H), 7.15(d, J=8.4Hz, 1H), 7.31–7.63(m, 10H), 9.96(d, J=6.6Hz, 1H)
IR(KBr) 1726, 1609, 1520, 1480, 1400, 1371, 1294, 1262, 1179, 1075, 1009 cm$^{-1}$

I-502  $^1$HNMR(CDCl$_3$) δ 1.78(s, 3H), 1.81(s, 3H), 3.22(s, 3H), 3.48(s, 3H), 3.71(s, 3H), 3.77(s, 3H)), 3.82(s, 3H), 4.66(d, J=6.9Hz, 2H), 5,56(t, J=6.9Hz, 1H), 6.62(s, 1H), 6.70(s, 1H), 7.11(s, 1H), 7.38(d, J=8.7Hz, 1H), 7.69(d, J=8.7Hz, 1H)
IR(KBr) 1699, 1607, 1587, 1516, 1468, 1354, 1216, 1152, 1067, 1044, 1004 cm$^{-1}$

I-503  $^1$HNMR(CDCl$_3$) δ 1.78(s, 3H), 1.81(s, 3H), 3.21(s, 3H), 3.48(s, 3H), 3.72(s, 3H), 3.74(s, 3H), 3.82(s, 3H), 4.33(d, J=11.7Hz, 1H), 4.54(d, J=11.7Hz, 1H), 4.65(d, J=8.4Hz, 1H), 5.57(t, J=8.4Hz, 1H), 6.68(s, 1H), 6.69(s, 1H), 6.89(s, 1H), 7.38(d, J=8.7Hz, 2H), 7.73(d, J=8.7Hz, 2H)
IR(KBr) 3530, 1609, 1515, 1467, 1356, 1214, 1174, 1151, 1075, 1039, 1004 cm$^{-1}$

I-504  $^1$HNMR(CDCl$_3$) δ 1.77(s, 3H), 1.80(s, 3H), 3.22(s, 3H), 3.45(s, 3H), 3.75(s, 3H), 3.77(s, 3H), 3.81(s, 3H), 4.62(d, J=6.9Hz, 2H), 5.55(t, J=6.9Hz, 1H), 6.64(s, 1H), 6.77(s, 1H), 6.97(s, 1H), 7.39(d, J=8.7Hz, 2H), 7.72(d, J=8.7Hz, 2H)
IR(KBr) 3431, 1735, 1706, 1609, 1514, 1474, 1367, 1206, 1176, 1150, 1055, 1039 cm$^{-1}$

I-505  $^1$HNMR(CDCl$_3$) δ 1.77(s, 3H), 1.80(s, 3H), 2.94(broad, 1H), 3.47(s, 3H), 3.72(s, 3H), 3.73(s, 3H), 3.81(s, 3H), 4.32(s, 1H), 4.36(s, 1H), 4.65(d, J=6.6Hz, 2H), 5.34(s, 1H), 5.57(t, J=6.6Hz, 1H), 6.69(s, 1H), 6.70(s, 1H), 6.89(s, 1H), 6.91(s, 1H), 7.55(d, J=8.1Hz, 2H)
IR(KBr) 3466, 1610, 1517, 1475, 1463, 1386, 1265, 1215, 1170, 1147, 1075 1042, 1007 cm$^{-1}$ I-506  $^1$HNMR(CDCl$_3$) δ 1.76(s, 3H), 1.79(s, 3H), 3.44(s, 3H), 3.74(s, 3H), 3.76(s, 3H), 3.80(s, 3H), 4.63(d, J=7.2Hz, 2H), 5.30(s, 1H), 5.49–5.60(m, 1H), 6.63(s, 1H), 6.78(s, 1H), 6.94(d, J=8.7Hz, 1H), 6.97(s, 1H), 7.54(.d, J=8.7Hz, 2H)
IR(KBr) 3382, 1726, 1699, 1611, 1519, 1470, 1206, 1174, 1143, 1074, 1056, 997 cm$^{-1}$

TABLE 102

I-507  $^1$HNMR(CDCl$_3$) δ 1.77(s, 3H), 1.79(s, 3H), 3.41(s, 3H), 3.60(s, 3H), 3.74(s, 3H), 3.77(s, 3H), 3.81(s, 3H), 4.63(d, J=6.9Hz, 2H), 4.74–5.02(broad, 1H), 5.52–5.60(m, 1H), 6.63(s, 1H), 6.75(s, 1H), 6.91(d, J=8.7Hz, 2H), 6.94(s, 1H), 7.54(d, J=8.7Hz, 2H)
IR(KBr) 3423, 1734, 1612, 1520, 1475, 1441, 1395, 1337, 1267, 1215, 1173, 1140, 1017 cm$^{-1}$ I-508  $^1$HNMR(CDCl$_3$) δ 3.21(s, 3H), 3.45(s, 3H), 3.73(s, 3H), 4.41–4.62(m, 2H), 5.16(s, 2H), 5.71(s, 1H), 6.79(d.d, J=8.1& 2.1Hz, 1H), 6.84(s, 1H), 6.92(d, J=2.1Hz, 1H), 7.01(d, J=8.1Hz, 1H), 7.32–7.50(m, 7H), 7.71(d, J=8.4Hz, 2H)
IR(KBr) 3496, 3255, 1607, 1590, 1528, 1473, 1464, 1358, 1247, 1147, 1071, 1017 cm$^{-1}$

TABLE 102-continued

I-509  $^1$HNMR(CDCl$_3$) δ 3.21(s, 3H), 3.45(s, 3H), 3.73(s, 3H), 3.89(s, 3H), 4.51(d, J=6.3Hz, 2H), 5.20(s, 2H), 6.80(d.d, J=8.1&2.1Hz, 1H), 6.85(s, 1H), 6.89(d, J=2.1Hz, 1H), 6.97(d, J=8.1Hz, 1H), 7.29–7.51(m, 7H), 7.71(d, J=8.7Hz, 2H)
IR(KBr) 3412, 1603, 1586, 1515, 1464, 1364, 1242, 1175, 1151, 1081, 1020, 1006 cm$^{-1}$

I-510  $^1$HNMR(CDCl$_3$) δ 1.76(s, 3H), 1.80(s, 3H), 3.22(s, 3H), 3.45(s, 3H), 3.73(s, 3H), 3.87(s, 3H), 4.52(s, 2H), 4.64(d, J=6.6Hz, 2H), 5.57(t, J=6.6Hz, 1H), 6.83(dd, J=7.5& 1.2Hz, 1H), 6.86(d, J=1.2Hz, 1H), 6.96(d, J=7.5Hz, 1H)
IR(KBr) 3433, 1598, 1579, 1517, 1469, 1372, 1244, 1221, 1174, 1149, 1072, 1017 cm$^{-1}$

I-511  $^1$HNMR(CDCl$_3$) δ 2.36(s, 3H), 3.21(s, 3H), 3.45(s, 3H), 3.72(s, 3H), 3.88(s, 3H), 4.50(s, 2H), 5.16(s, 2H), 6.80(dd, J=8.1&2.1Hz, 1H), 6.85(s, 1H), 6.88(d, J=2.1Hz, 1H), 6.97(d, J=8.1Hz, 1H), 7.20(d, J=8.4Hz, 2H), 7.33–7.42(m, 4H), 7.71(d, J=8.4Hz, 2H)
IR(KBr) 3502, 1604, 1510, 1465, 1383, 1360, 1266, 1239, 1227, 1147, 1071, 1008 cm$^{-1}$

I-512  $^1$HNMR(CDCl$_3$) δ 3.45(s, 3H), 3.72(s, 3H), 3.89(s, 3H), 4.48(s, 2H), 5.20(s, 2H), 6.81(d, J=8.1&2.1Hz, 1H), 6.86(s, 1H), 6.88–6.99(m, 4H), 7.27–7.43(m, 3H), 7.46–7.54(m, 4H)
IR(KBr) 3528, 1610, 1591, 1517, 1474, 1461, 1438, 1388, 1263, 1239, 1173, 1140, 1017 cm$^{-1}$

I-513  $^1$HNMR(CDCl$_3$) δ 1.75(s, 3H), 1.79(s, 3H), 2.47(broads, 1H), 3.45(s, 3H), 3.73(s, 3H), 3.86(s, 3H), 4.52(s, 2H), 4.63(d, J=6.6Hz, 2H), 5.16(s, 1H), 5.56(d, J=6.6Hz, 1H), 6.82–6.97(m, 6H), 7.53(d, J=9.0Hz, 2H)
IR(KBr) 3477, 3246, 1609, 1586, 1518, 1464, 1439, 1387, 1266, 1240, 1221, 1173, 1141, 1079, 1011, 1002 cm$^{-1}$

TABLE 103

I-514  $^1$HNMR(CDCl$_3$) δ 2.36(s, 3H), 2.48(broad, 1H), 3.44(s, 3H), 3.72(s, 3H), 3.88(s, 3H), 4.50(s, 2H), 5.16(s, 3H), 6.76–6.98(m, 6H), 7.19(d, J=7.8Hz, 2H), 7.36(d, J=7.8Hz, 2H), 7.52(d, J=8.7Hz, 2H)
IR(KBr) 3544, 3239, 1614, 1593, 1519, 1463, 1386, 1266, 1240, 1218, 1173, 1139, 1074, 1010 cm$^{-1}$ I-515  m.p. 159–160° C.
$^1$HNMR(CDCl$_3$) δ 3.19(s, 3H), 3.34(s, 3H), 3.79(s, 3H), 3.80(s, 3H), 5.18(ABq, J=12.3Hz, 2H), 6.92(s, 1H), 6.93(s, 1H), 7.08(d, J=8.7Hz, 1H), 7.33–7.64(m, 11H)
IR(KBr) 3433, 2937, 1694, 1520, 1492, 1369, 1288, 1243, 1211, 1176, 1150, 1100 cm$^{-1}$ I-516  $^1$HNMR(CDCl$_3$) δ 2.91(s, 3H), 3.777(s, 3H), 3.783(s, 3H), 4.85(brs, 1H), 5.12(s, 2H), 6.87–7.00(m, 7H), 7.32–7.50(m, 7H)
IR(KBr) 3432, 2938, 1609, 1590, 1525, 1494, 1380, 1254, 1207, 1174, 1152, 1058, 1031 cm$^{-1}$ I-517  m.p. 213–215° C.
$^1$HNMR(CDCl$_3$) δ 2.99(s, 3H), 3.779(s, 3H), 3.804(s, 3H), 4.86(brs, 1H), 5.16(s, 2H), 6.83(brs, 1H), 6.93(s, 1H), 6.94(s, 1H), 7.06(d, J=8.7Hz, 1H), 7.35(dd, J=2.1, 8.7Hz, 1H), 7.41–7.49(m, 7H), 7.81(d, J=2.1Hz, .1H)
IR(KBr) 3409, 3374, 1610, 1525, 1491, 1371, 1321, 1251, 1208, 1145, 1120, 1037 cm$^{-1}$ I-518  powder
$^1$HNMR(CDCl$_3$) δ 1.75(s, 3H), 1.81(s, 3H), 2.84(s, 3H), 3.21(s, 3H), 3.22(s, 3H), 3.55(s, 3H), 3.79(s, 3H), 3.93(s, 3H), 4.67(d, J=7.2Hz, 2H), 5.59(m, 1H), 6.85(s, 1H), 7.36–7.42(m, 2H), 7.62(d, J=2.1Hz, 1H), 7.65–7.70(m, 2H), 7.86(d, J=2.1Hz, 1H)
IR(CHCl$_3$)3026, 2940, 1728, 1510, 1473, 1373, 1179, 1150, 1086 cm$^{-1}$ I-519  powder
$^1$HNMR(CDCl$_3$) δ 1.69(s, 3H), 1.74(s, 3H), 2.52–2.61(m, 2H), 2.86(s, 3H), 3.20(s, 3H), 3.21(s, 3H), 3.55(s, 3H), 3.79(s, 3H), 3.93(s, 3H), 4.21(t, J=6.9Hz, 2H), 5.26(m, 1H), 6.86(s, 1H), 7.36–7.42(m, 2H), 7.62(d, J=2.1Hz, 1H), 7.65–7.70(m, 2H), 7.86(d, J=2.1Hz, 1H)
IR(CHCl$_3$)3024, 2939, 1729, 1511, 1475, 1447, 1373, 1179, 1150, 1085 cm$^{-1}$

TABLE 104

I-520 powder
$^1$HNMR(CDCl$_3$) δ 2.84(s, 3H), 3.21(s, 3H), 3.22(s, 3H), 3.56(s, 3H), 3.81(s, 3H), 3.88(s, 3H), 5.30(s, 2H), 6.86(s, 1H), 7.26–7.32(m, 1H), 7.37–7.42(m, 2H), 7.65–7.72(m, 4H), 7.76–7.83(m, 1H), 7.92(d, J=2.1Hz, 1H), 8.60–8.63(m, 1H)
IR(KBr) 3434, 3019, 2940, 1730, 1511, 1474, 1367, 1178, 1151, 1082 cm$^{-1}$ I-521 powder
$^1$HNMR(CDCl$_3$+ CD$_3$OD) δ 1.69(s, 3H), 1.77(s, 3H), 2.51–2.58(m, 2H), 3.43(s, 3H), 3.73(s, 3H), 4.23(t, J=6.6Hz, 2H), 6.44(s, 1H), 6.89–6.95(m, 2H), 7.24(d, J=1.8Hz, 1H), 7.46–7.52(m, 2H), 7.65–7.67(m, 1H)
IR(KBr) 3434, 2934, 1716, 1611, 1402, 1226, 1116, 1082, 1027 cm$^{-1}$ I-522 m.p. 240–243° C.
$^1$HNMR(CDCl$_3$+ CD$_3$OD) δ 3.44(s, 3H), 3.75(s, 3H), 5.31(s, 2H), 6.46(s, 1H), 6.89–6.95(m, 2H), 7.30–7.31(m, 1H), 7.35–7.42(m, 2H), 7.47–7.53(m, 2H), 7.56(d, J=2.4Hz, 1H), 7.79–7.86(m, 1H), 8.65–8.68(m, 1H)
IR(KBr) 3411, 2937, 1683, 1611, 1521, 1406, 1230, 1115, 1082, 1026 cm$^{-1}$ I-523 m.p. 136–137° C.
$^1$HNMR(CDCl$_3$) δ 2.25(s, 3H), 2.29(s, 3H), 3.12(s, 3H), 3.20(s, 3H), 5.18(s, 2H), 7.11(s, 1H), 7.14(s, 1H), 7.23–7.51(m, 12H)
IR(KBr) 1518, 1488, 1357, 1263, 1170, 1150, 1110, 970, 873, 848, 809 cm$^{-1}$ I-524 m.p. 121–122° C.
$^1$HNMR(CDCl$_3$) δ 1.77(s, 3H), 1.82(s, 3H), 2.25(s, 3H), 2.29(s, 3H), 3.20(s, 3H), 3.23(s, 3H), 4.64(d, J=6.6Hz, 2H), 5.52(t, J=6.6Hz, 1H), 7.06(d, J=8.4Hz, 1H), 7.11(s, 1H), 7.14(s, 1H), 7.24(d, J=2.1Hz, 1H), 7.31–7.45(m, 5H)
IR(KBr) 1518, 1487, 1363, 1170, 1150, 1108, 970, 869, 848, 808 cm$^{-1}$ I-525 m.p. 149–151° C.
$^1$HNMR(CDCl$_3$) δ 1.77(s, 3H), 1.83(d, J=0.6Hz, 3H), 2.26(s, 3H), 2.28(s, 3H), 4.62(d, J=6.9Hz, 2H), 4.80(s, 1H), 5.53(m, 1H), 5.72(s, 1H), 6.82(dd, J=2.1, 8.4Hz, 1H), 6.85–6.94(m, 3H), 6.96(d, J=2.1Hz, 1H), 7.10(s, 1H), 7.12(s, 1H), 7.21–7.28(m, 2H)
IR(KBr) 3521, 3395, 1612, 1584, 1522, 1490, 1457, 1285, 1263, 1242, 1200, 1170, 1125, 1014, 834 cm$^{-1}$

TABLE 105

I-526 foam
$^1$HNMR(CDCl$_3$) δ 2.43(s, 3H), 2.76(s, 3H), 2.90(s, 3H), 3.22(s, 3H), 3.56(s, 3H), 3.80(s, 3H), 5.30(s, 2H), 6.28(t, J=3.3Hz, 1H), 6.42(dd, J=3.3, 1.6Hz, 1H), 6.85(s, 1H), 7.12,(d, J=8.4Hz, 1H), 7.32(d, J=8.7Hz, 2H), 7.34–7.37(m, 2H), 7.39(d, J=8.7Hz, 2H), 7.40(d, J=1.8Hz, 1H), 7.69(d, J=8.7Hz, 2H), 7.78(d, J=8.7Hz, 2H)
IR(Nujol) 1608, 1597, 1519, 1480, 1464, 1176, 1152, 1087, 972, 875, 817, 798 cm$^{-1}$ I-527 foam
$^1$HNMR(CDCl$_3$) δ 2.96(s, 3H), 3.21(s, 3H), 3.37(s, 3H), 3.52(s, 3H), 3.77(s, 3H), 5.58(s, 2H), 6.84(s, 1H), 7.19(d, J=8.4Hz, 1H), 7.24~7.28(m, 4H), 7.31,(dd, J=8.4, 1.8Hz, 1H), 7.33(d, J=1.8Hz, 1H), 7.38(d, J=8.7Hz, 2H), 7.67(d, J=87Hz, 2H)
IR(Nujol) 1664, 1609, 1519, 1480, 1457, 1176, 1151, 1079, 970, 947, 876, 798, 748 cm$^{-1}$ I-528 foam
$^1$HNMR(CDCl$_3$) δ 2.73(s, 3H), 2.94(s, 3H), 3.21(s, 3H), 3.33(t, J=6.3Hz, 2H), 3.55(s, 3H), 3.77(s, 3H), 4.55(t, J=6.3Hz, 2H), 6.83(s, 1H), 7.14(d, J=8.1Hz, 1H), 7.18(brdd, J=7.8, 5.1Hz, 1H), 7.33(brd, J=7.8Hz, 1H), 7.35(dd, J=8.1, 1.8Hz, 1H), 7.37(d, J=1.8Hz, 1H), 7.38(d, J=8.7Hz, 2H), 7.65(m, 1H), 7.67(d, J=8.7Hz, 2H), 8.56(brd, J=5.1Hz, 1H)
IR(Nujol) 1608, 1593, 1520, 1479, 1466, 1177, 1151, 1079, 970, 872, 816, 798 cm$^{-1}$ I-529 m.p. 203–205° C.
HNMR(DMSO-d$_6$) δ 2.42(s, 3H), 2.80(s, 3H), 3.45(s, 3H), 3.51(s, 3H), 3.56(s, 3H), 3.78(s, 3H), 5.36(s, 2H), 7.07(s, 1H), 7.23(s, 1H), 7.26~7.28(m, 3H), 7.48,(d, J=8.7Hz, 2H), 7.74(d, J=8.7Hz, 2H)
IR(Nujol) 1599, 1518, 1480, 1466, 1176, 1081, 1013, 976, 570, 830, 797, 755 cm$^{-1}$

TABLE 105-continued

I-530 foam
$^1$HNMR(CD$_3$OD) δ 3.38(s, 3H), 3.68(s, 3H), 5.41(s, 2H), 6.44(s, 61H), 6.82(dd, J=8.4, 2.1Hz, 1H), 6.85(d, J=8.7Hz, 2H), 6.93(d, J=2.1Hz, 1H), 7.06(d, J=8.4Hz, 1H), 7.27(m, 2H), 7.46(d, J=8.7Hz, 2H), 7.60(m, 2H)
IR(Nujol) 3304, 161, 1590, 1522, 1488, 1458, 1254, 1115, 1074, 1046, 1014, 942, 825, 745 cm$^{-1}$

TABLE 106

I-531 m.p. 159–162° C.
$^1$HNMR(DMSO-d$_6$) δ 2.92(s, 3H), 3.41(s, 3H), 3.45(s, 3H), 3.52(s, 3H), 3.79(s, 3H), 5.33(s, 2H), 7.09(s, 1H), 6.82~7.45(m, 3H), 7.49(d, J=9.0Hz, 2H), 7.75(d, J=9.0Hz, 2H)
IR(Nujol) 1604, 1519, 1481, 1469, 1235, 1171, 1154, 1085, 1012, 967, 874, 849, 798 cm$^{-1}$ I-532 m.p. 214–216° C.
$^1$HNMR(DMSO-d$_6$) δ 2.54(s, 3H), 3.42(s, 3H), 3.45(s, 3H), 3.52(s, 3H), 3.73(s, 3H), 3.79(s, 3H), 4.99(s, 2H), 7.08(s, 1H), 7.24(d, J=9.3Hz, 1H), 7.29(dd, J=9.3, 1.8Hz, 1H), 7.30(d, J=1.8Hz, 1H), 7.48(d, J=8.7Hz, 2H), 7.74(d, J=5.7Hz, 2H)
IR(Nujol) 1767, 1606, 1521, 1481, 1463, 1216, 1175, 1151, 1080, 1013, 977, 946, 878, 821, 798 cm$^{-1}$ I-533 m.p. 225–227° C.
$^1$HNMR(DMSO-d$_6$) δ 2.86(s, 3H), 3.45(s, 3H), 3.46(s, 3H), 3.52(s, 3H), 3.78(s, 3H), 4.46(s, 2H), 7.08(s, 1H), 7.20(d, J=8.4Hz, 1H), 7.28–7.32(m, 2H), 7.48(d, J=8.7Hz, 2H), 7.74(d, J=8.7Hz, 2H)
IR(Nujol) 3340, 1677, 1619, 1519, 1477, 1463, 1443, 1176, 1150, 1088, 971, 871, 829, 794 cm$^{-1}$ I-534 foam
$^1$HNMR(DMSO-d$_6$) δ 2.96(s, 3H), 3.45(s, 3H), 3.47(s, 3H), 3.52(s, 3H), 3.79(s, 3H), 4.64(s, 2H), 7.08(s, 1H), 7.18(d, J=8.4Hz, 1H), 7.31(dd, J=8.4, 1.8Hz, 1H), 7.34(d, J=1.8Hz, 1H), 7.48(d, J=8.7Hz, 2H), 7.74(d, J=8.7Hz, 2H)
IR(Nujol) 3464, 3362, 1693, 1606, 1520, 1481, 1176, 1151, 1080, 876, 822, 799 cm$^{-1}$ I-535 m.p. 163–165° C.
$^1$HNMR(CDCl$_3$) δ 2.73(s, 3H), 3.16(s, 3H), 3.21(s, 3H), 3.55(s, 3H), 3.78(s, 3H), 4.85(ddd, J=1.5, 1.5, 5.4Hz, 2H), 5.25(s, 2H), 5.31(ddd, J=1.5, 3.0, 10.5, Hz, 1H), 5.43(ddd, J=1.5, 3.0, 17.1Hz, 1H), 6.05(ddd, J=5.4, 10.5, 17.1Hz, 1H), 6.84(s, 1H), 7.11(d, J=8.7Hz, 1H), 7.34(dd, J=2.1, 8.7Hz, 1H), 7.38(d, J=8.4Hz, 2H), 7.41(d, J=2.1Hz, 1H), 7.56(d, J=8.4Hz, 2H), 7.67(d, J=8.4Hz, 2H), 8.11(d, J=8.4Hz, 2H)
IR(KBr) 1718, 1612, 1519, 1481, 1365, 1273, 1177, 1151, 1119, 1080, 1015, 969, 876 cm$^{-1}$

TABLE 107

I-536 m.p. 115–117° C.
$^1$HNMR(CDCl$_3$) δ 2.68(s, 3H), 3.13(s, 3H), 3.21(s, 3H), 3.55(s, 3H), 3.68(s, 2H), 3.78(s, 3H), 4.61(ddd, J=1.5, 1.5, 5.7Hz, 2H), 5.17(s, 2H), 5.23,(ddd, J=1.5, 3.0, 10.5,Hz, 1H), 5.28(ddd, J=1.5, 3.0, 16.8Hz, 1H), 5.91(ddd, J=5.7, 10.5, 16.8Hz, 1H), 6.84(s, 1H), 7.13(d, J=8.4Hz, 1H), 7.33(d, J=8.1Hz, 2H), 7.34(dd, J=2.1, 8.4Hz, 1H), 7.38(d, J=8.4Hz, 2H), 7.40(d, J=2.1Hz, 1H), 7.42(d, J=8.1Hz, 2H), 7.68(d, J=8.4Hz, 2H)
IR(KBr) 1734, 1609, 1520, 1481, 1365, 1236, 1177, 1151, 1119, 1079, 970, 876, 797 cm$^{-1}$ I-537 m.p. 227–229° C.
$^1$HNMR(CDCl$_3$) δ 2.73(s, 3H), 3.16(s, 3H), 3.21(s, 3H), 3.54(s, 3H), 3.77(s, 3H), 5.26(s, 2H), 6.83(s, 1H), 7.11(d, J=12.3Hz, 2H), 7.32(d, J=12.3Hz, 2H), 7.41(s, 1H), 7.57(d, J=12.3Hz, 1H), 7.66(d, J=12.3Hz, 2H), 8.13(d, J=12.3Hz, 2H)
IR(KBr) 3430, 1694, 1612, 1519, 1481, 1365, 1177, 1151, 1079, 875, 798 cm$^{-1}$

TABLE 107-continued

I-538 m.p. 149–151° C.
¹HNMR(CDCl₃) δ 2.66(s, 3H), 3.13(s, 3H), 3.21(s, 3H), 3.55(s, 3H), 3.68(s, 2H), 3.77(s, 3H), 5.17(s, 2H), 6.84(s, 1H), 7.13(d, J=8.4Hz, 1H), 7.30–7.55(m, 4H), 7.38(d, J=8.4Hz, 2H), 7.67(d, J=84Hz, 2H), 7.67(m, 2H)
IR(KBr) 3423, 1716, 1610, 1519, 1481, 1365, 1235, 1177, 1151, 1119, 1080, 876, 798 cm⁻¹

I-539 m.p. 144–146° C.
¹HNMR(CDCl₃) δ 2.32(s, 3H), 2.69(s, 3H), 3.14(s, 3H), 3.21(s, 3H), 3.56(s, 3H), 3.78(s, 3H), 5.18(s, 2H), 6.84(s, 1H), 7.14(s, 3H), 7.15(d, J=8.4Hz, 1H), 7.34(dd, J=2.1, 8.4Hz, 1H), 7.38(d, J=8.4Hz, 2H), 7.40(d, J=2.1Hz, 1H), 7.48(d, J=8.7Hz, 2H), 7.67(d, J=8.4Hz, 2H)
IR(KBr) 1760, 1519, 1481, 1365, 1177, 1151, 1119, 1079, 876, 797 cm⁻¹

I-540 m.p. 228–231° C.
¹HNMR(CDCl₃) δ 2.81(s, 3H), 3.20(s, 3H), 3.21(s, 3H), 3.55(s, 3H), 3.78(s, 3H), 5.30(s, 2H), 6.85(s, 1H), 7.11(d, J=8.4Hz, 1H), 7.35(dd, J=2.1, 8.4Hz, 1H), 7.39(d, J=8.4Hz, 2H), 7.41(d, J=2.1Hz, 1H), 7.67(d, J=8.4Hz, 2H), 7.69(d, J=8.7Hz, 2H), 8.28(d, J=8.7Hz, 2H)
IR(KBr) 1608, 1521, 1481, 1361, 1179, 1148, 1080, 880, 799 cm⁻¹

TABLE 108

I-541 m.p. 153–156° C.
¹HNMR(CDCl₃) δ 1.53(s, 9H), 2.69(s, 3H), 3.15(s, 3H), 3.21(s, 3H), 3.55(s, 3H), 3.78(s, 3H), 5.19(s, 2H), 6.84(s, 1H), 7.10(dd, J=7.5, 7.5Hz, 1H), 7.17(d, J=7.5Hz, 1H), 7.23(d, J=8.4Hz, 1H), 7.26(dd, J=7.5, 7.5,Hz, 1H), 7.33(d, J=7.5Hz, 1H), 7.37(dd, J=2.1, 8.4Hz, 1H), 7.38(d, J=8.4Hz, 2H), 7.40(d, J=2.1Hz, 1H), 7.67(d, J=8.4Hz, 2H)
IR(KBr) 3405, 1724, 1519, 1480, 1366, 1236, 1177, 1153, 1080, 970, 875, 798 cm⁻¹

I-542 m.p. 178–182° C.
¹HNMR(CDCl₃) δ 2.70(s, 3H), 3.15(s, 3H), 3.21(s, 3H), 3.55(s, 3H), 3.78(s, 3H), 5.14(s, 2H), 6.76(m, 2H), 6.84(s, 1H), 7.19(m, 2H), 7.26(d, J=8.7Hz, 1H), 7.37(d, J=2.7Hz, 1H), 7.36(dd, J=2.7, 8.7Hz, 1H), 7.38(d, J=8.7Hz, 2H), 7.68(d, J=8.7Hz, 2H)
IR(KBr) 3448, 1627, 1608, 1519, 1497, 1364, 1177, 1151, 1079, 971, 876, 798 cm⁻¹

I-543 m.p. 187–189° C.
¹HNMR(CDCl₃) δ 2.38(s, 3H), 3.39(s, 3H), 3.45(s, 3H), 5.11–5.14(m, 3H), 5.89(s, 1H), 6.33(s, 1H), 6.88–6.94(m, 2H), 7.20–7.36(m, 6H), 7.43(d, J=2.1Hz, 1H), 7.76(d, J=0.6Hz, 1H)
IR(KBr) 3414, 2942, 1613, 1534, 1469, 1355, 1266, 1172, 1092, 1030 cm⁻¹

I-544 m.p. 207–215° C. (dec.)
¹HNMR(d₆-DMSO) δ 2.37(s, 3H), 3.67(brs, 2H), 4.56(brs, 2H), 4.90(s, 2H), 6.14–6.20(m, 2H), 6.86(d, J=8.7Hz, 2H), 7.11–7.22(m, 4H), 7.42(d, J=8.7Hz, 2H), 7.52(s, 1H), 8.94(s, 1H), 9.47(s, 1H)
IR(KBr) 3388, 3301, 2932, 1612, 1591, 1521, 1458, 1413, 1288, 1030 cm⁻¹

I-545 m.p. 108–110° C.
¹HNMR(CDCl₃) δ 1.69(s, 3H), 1.74(s, 3H), 2.49–2.59(m, 2H), 3.03(s, 3H), 3.20(s, 3H), 3.56(s, 3H), 3.75(s, 3H), 4.06(t, J=6.6Hz, 2H), 4.93(s, 2H), 5.22(m, 1H), 6.66(s, 1H), 7.04(d, J=8.7Hz, 1H), 7.09–7.17(m, 2H), 7.37(dd, J=2.1, 8.7Hz, 1H), 7.44(d, J=2.1Hz, 1H), 7.51–7.58(m, 2H)
IR(KBr) 3434, 2933, 1604, 1521, 1473, 1383, 1360, 1278, 1160, 1121, 1054, 1017 cm⁻¹

TABLE 109

I-546 m.p. 109–110° C.
¹HNMR(CDCl₃) δ 1.69(s, 3H), 1.75(s, 3H), 248–2.58(m, 2H), 4.07(t, J=6.6Hz, 2H), 5.22(m, 1H), 5.69(s, 1H), 5.87(s, 1H), 6.44(s, 1H), 6.93–6.95(m, 2H), 7.04–7.06(m, 1H), 7.10–7.18(m, 2H),

TABLE 109-continued 7.58–7.64(m, 2H)
IR(KBr)3411, 2932, 1608, 1587, 1522, 1491, 1226, 1111, 1074, 1017 cm⁻¹

I-547 m.p. 141–142° C.
¹HNMR(CDCl₃) δ 3.03(s, 3H), 3.57(s, 3H), 3.75(s, 3H), 4.90(s, 2H), 5.16(s, 2H), 5.65(brs, 1H), 6.66(s, 1H), 6.92(dd, J=1.8, 8.4Hz, 1H), 6.99(d, J=8.4Hz, 1H), 7.06(d, J=1.8Hz, 1H), 7.10–7.17(m, 2H), 7.35–7.47(m, 5H), 7.52–7.59(m, 2H)
IR(KBr)3529, 3439, 2932, 1601, 1518, 1477, 1461, 1380, 1251, 1224, 1157, 1113, 1094, 1076 cm⁻¹

I-548 m.p. 133–136° C.
¹HNMR(CDCl₃) δ 2.98(s, 3H), 3.12(s, 3H), 3.56(s, 3H), 3.75(s, 3H), 4.94(s, 2H), 5.18(s, 2H), 6.67(s, 1H), 7.09–7.17(m, 3H), 7.34–7.49(m, 7H), 7.51–7.58(m, 2H)
IR(KBr)3434, 2941, 1598, 1519, 1481, 1383, 1365, 1279, 1231, 1164, 1099, 1081 cm⁻¹

I-549 m.p. 161–162° C.
¹HNMR(CDCl₃) δ 3.10(s, 3H), 3.42(s, 3H), 3.76(s, 3H), 5.17(s, 2H), 6.05(s, 1H), 6.44(s, 1H), 7.11–7.20(m, 3H), 7.33–7.50(m, 7H), 7.52(d, J=2.1Hz, 1H), 7.57–7.65(m, 2H)
IR(KBr)3488, 2938, 1613, 1523, 1486, 1290, 1223, 1107, 1071, 1012 cm⁻¹

I-550 m.p. 113–115° C.
¹HNMR(CDCl₃) δ 2.37(s, 3H), 2.98(s, 3H), 3.11(s, 3H), 3.56(s, 3H), 3.75(s, 3H), 4.93(s, 2H), 5.13(s, 2H), 6.66(s, 1H), 7.09–7.17(m, 3H), 7.18–7.23(m, 2H), 7.32–7.39(m, 3H), 7.45(d, J=1.8Hz, 1H), 7.51–7.58(m, 2H)
IR(KBr)3434, 2934, 1738, 1601, 1520, 1478, 1466, 1376, 1356, 1236, 1159, 1109, 1070, 1014 cm⁻¹

TABLE 110

I-551 m.p. 138–140° C.
¹HNMR(CDCl₃) δ 2.38(s, 3H), 3.04(s, 3H), 3.57(s, 3H), 3.74(s, 3H), 4.90(s, 2H), 5.11(s, 2H), 5.63(s, 1H), 6.66(s, 1H), 6.91(dd, J=2.1, 8.4Hz, 1H), 6.99(d, J=8.4Hz, 1H), 7.05(d, J=1.8Hz, 1H), 7.08–7.17(m, 2H), 7.22(d, J=7.8Hz, 2H), 7.33(d, J=7.8Hz, 2H), 7.52–7.59(m, 2H)
IR(KBr)3446, 2934, 1601, 1518, 1476, 1461, 1379, 1252, 1224, 1158, 1092, 1011 cm⁻¹

I-552 m.p. 188–190° C.
¹HNMR(CDCl₃) δ 2.38(s, 3H), 3.10(s, 3H), 3.42(s, 3H), 3.75(s, 3H), 5.12(s, 2H), 6.04(s, 1H), 6.43(s, 1H), 7.11–7.25(m, 5H), 7.35(d, J=7.8Hz, 2H), 7.42(dd, J=2.4, 8.7Hz, 1H), 7.51(d, J=2.4Hz, 1H), 7.57–7.65(m, 2H)
IR(KBr)3433, 2963, 1611, 1523, 1485, 1355, 1282, 1226, 1163, 1106, 1071 cm⁻¹

I-553 m.p. 149–150° C.
¹HNMR(CDCl₃) δ 3.13(s, 3H), 3.21(s, 3H), 5.20(s, 2H), 7.17(d, J=8.4Hz, 1H), 7.24(m, 1H), 7.36–7.54(m, 9H), 7.58(dd, J=1.2, 2.4Hz, 1H), 7.60–7.67(m, 2H)
IR(KBr)1524, 1485, 1354, 1292, 1263, 1181, 1150, 1114, 977, 869, 858, 850, 812, 796 cm⁻¹

I-554 m.p. 92–93° C.
¹HNMR(CDCl₃) δ 1.69(s, 3H), 1.74(d, J=1.2Hz, 3H), 2.25(s, 3H), 2.28(s, 3H), 2.56(dt, J=6.6, 7.2Hz, 2H), 3.20(s, 3H), 3.21(s, 3H), 4.07(t, J=7.2Hz, 2H), 5.22(m 1H), 7.05(d, J=8.4Hz, 1H), 7.11(s, 1H), 7.13(s, 1H), 7.25(dd, J=2.1, 8.4Hz, 1H), 7.31–7.43(m, 5H)
IR(KBr)1518, 1488, 1355, 1293, 1264, 1169, 1151, 1109, 970, 872, 818 cm⁻¹

I-555 m.p. 126–127° C.
¹HNMR(CDCl₃) δ 1.77(s, 3H), 1.82(s, 3H), 3.20(s, 3H), 3.23(s, 3H), 4.65(d, J=6.6Hz, 2H), 5.50(m 1H), 7.10(d, J=8.7Hz, 1H), 7.18–7.27(m, 2H), 7.36–7.43(m, 2H), 7.50(dd, J=1.5, 8.7Hz, 1H), 7.55(d, J=1.5Hz, 1H), 7.60–7.66(m, 2H)
IR(KBr)1527, 1489, 1359, 1295, 1266, 1177, 1153, 1118, 974, 894, 874 cm⁻¹

TABLE 111

I-556 m.p. 154–155° C.
$^1$HNMR(CDCl$_3$) δ 2.25(s, 3H), 2.28(s, 3H), 2.38(s, 3H), 3.11(s, 3H), 3.20(s, 3H), 5.13(s, 2H), 7.11(s, 1H), 7.14(s, 1H), 7.19–7.28(m, 4H), 7.31–7.43(m, 7H)
IR(KBr) 1520, 1487, 1365, 1284, 1260, 1192, 1172, 1152, 1108, 967, 867, 809, 795 cm$^{-1}$

I-557 m.p. 112–113° C.
$^1$HNMR(CDCl$_3$) δ 1.69(s, 3H), 1.76(s, 3H), 2.26(s, 3H), 2.27(s, 3H), 2.54(dt, J=7.2, 6.9Hz, 2H), 4.07(t, J=6.9Hz, 2H), 4.86(s, 1H), 5.23(m, 1H), 5.71(s, 1H), 6.82(dd, J=2.1, 8.4Hz, 1H), 6.85–6.93 (m, 3H), 6.96(d, J=2.1Hz, 1H), 7.10(s, 1H), 7.12(s, 1H), 7.22–7.27(m, 2H)
IR(KBr)3380, 1613, 1586, 1523, 1490, 1471, 1431, 1391, 1293, 1261, 1246, 1205, 1171, 1130, 836 cm$^{-1}$

I-558 m.p. 141–142° C.
$^1$HNMR(CDCl$_3$) δ 1.77(s, 3H), 1.82(s, 3H), 4.63(d, J=6.9Hz, 2H), 5.06(s, 1H), 5.52(m, 1H), 5.75(s, 1H), 6.89–6.97(m, 3H), 7.07(dt, J=8.4, 1.8Hz, 1H), 7.14–7.23(m, 3H), 7.44–7.51(m, 2H)
IR(KBr)3429, 1612, 1594, 1531, 1489, 1467, 1449, 1401, 1259, 1213, 1169, 1132, 835, 781 cm$^{-1}$

I-559 m.p. 179–180° C.
$^1$HNMR(CDCl$_3$) δ 2.26(s, 3H), 2.28(s, 3H), 2.39(s, 3H), 4.81(s, 1H), 5.11(s, 2H), 5.70(s, 1H), 6.83(dd, J=2.1, 8.4Hz, 1H), 6.86–6.91(m, 2H), 6.98(d, J=8.4Hz, 1H), 6.98(d, J=2.1Hz, 1H), 7.10(s, 1H), 7.12(s, 1H), 7.21–7.28(m, 4H), 7.32–7.38(m, 2H)
IR(KBr)3317, 1609, 1520, 1489, 1426, 1378, 1247, 1206, 1175, 1124, 1006, 792 cm$^{-1}$

I-560 foam
$^1$HNMR(DMSO-d$_6$) δ 3.74(s, 3H), 3.75(s, 3H), 4.62(d, J=5.0Hz, 2H), 5.02(t, J=5.0Hz, 1H), 5.19(s, 2H), 6.94(s, 1H), 6.99(s, 1H), 7.06(d, J=8.0Hz, 1H), 7.22(ddd, J=8.6, 2.0, 0.8Hz, 1H), 7.32–7.52(m, 8H), 7.57(d, J=2.4Hz, 1H), 9.91(brs, 1H)
IR(KBr)3257, 1525, 1491, 1464, 1453, 1382, 1207, 1035, 764, 737 cm$^{-1}$

TABLE 112

I-561 m.p. 147–148° C.
$^1$HNMR(CDCl$_3$) δ 3.27(s, 3H), 3.79(s, 3H), 3.82(s, 3H), 5.26(s, 2H), 6.92(s 1H), 6.95(s, 1H), 7.13(d, J=8.7Hz, 1H), 7.35–7.50(m, 8H), 7.80(dd, J=8.7, 2.7Hz, 1H), 8.05(d, J=2.7Hz, 1H), 10.62(s, 1H)
IR(KBr)1682, 1606, 1489, 1377, 1345, 1261, 1209, 1168, 1119, 1038, 871, 832 cm$^{-1}$

I-562 m.p. 189–191° C.
$^1$HNMR(DMSO-d$_6$) δ 3.53(s, 3H), 3.80(s, 3H), 3.80(s, 3H), 5.27 (s, 2H), 7.05(s, 1H), 7.10(s, 1H), 7.25(d, J=8.7Hz, 1H), 7.30–7.59(m, 7H), 7.66(dd, J=11.7, 2.1Hz, 1H), 7.67(dd, J=8.7, 2.3Hz, 1H), 7.84(d, J=2.3Hz, 1H), 12.7(brs, 1H)
IR(KBr)3433, 1705, 1492, 1371, 1250, 1207, 1168, 1033, 868 cm$^{-1}$ I-563 m.p. 204–207° C.
$^1$HNMR(CDCl$_3$) δ 1.36(s, 9H), 3.20(s, 3H), 3.41(s, 3H), 3.74(s, 3H), 5.15(s, 2H), 5.65(s, 1H), 5.77(s, 1H), 6.80(s, 1H), 6.83(dd, J=8.4, 2.0Hz, 1H), 6.96(d, J=2.0Hz, 1H), 6.98(d, J=8.4Hz, 1H), 7.34–7.45(m, 7H), 7.68(d, J=8.7Hz, 2H)
IR(KBr)3408, 3337, 1692, 1498, 1474, 1466, 1347, 1251, 1150, 870, 855 cm$^{-1}$ I-564 m.p. 179–182° C.
$^1$HNMR(DMSO-d$_6$) δ 3.76(s, 3H), 3.76(s, 3H), 5.26(s, 2H), 6.99 (s, 1H), 7.00(t, J=8.7Hz, 1H), 7.01(s, 1H), 7.22(ddd, J=8.7, 2.4Hz, 1H), 7.24(d, J=8.9Hz, 1H), 7.32–7.54(m, 6H), 7.65(dd, J=8.9, 2.4Hz, 1H), 7.82(d, J=2.4Hz, 1H), 9.91(s, 1H), 12.6(brs, 1H)
IR(KBr)3422, 3277, 1726, 1526, 1491, 1416, 1396, 1284, 1210, 1031 cm$^{-1}$ I-565 m.p. 178–180° C.
$^1$HNMR(DMSO-d$_6$) δ 3.30(s, 3H), 3.43(s, 3H), 3.61(s, 3H), 4.31 (s, 2H), 5.14(s, 2H), 6.25(s, 1H), 6.61(dd, J=8.4, 1.9Hz, 1H), 7.05 (d, J=8.4Hz, 1H), 7.33–7.44(m, 6H), 7.50–7.54(m, 2H), 7.70(d, J=8.7Hz, 2H), 9.08(s, 1H)
IR(KBr)3435, 3378, 1593, 1518, 1481, 1360, 1245, 1147, 1119, 1010, 871 cm$^{-1}$

TABLE 113

I-566 foam
$^1$HNMR(DMSO-d$_6$) δ 3.27(s, 3H), 3.59(s, 3H), 4.21(s, 2H), 5.13 (s, 2H), 6.17(s, 1H), 6.60(dd, J=8.3, 1.4Hz, 1H), 6.70(d, J=1.4Hz, 1H), 6.82(d, J=8.4Hz, 2H), 7.03(d, J=8.3Hz, 1H), 7.33–7.53(m, 7H), 9.07(brs, 1H), 9.45(brs, 1H)
IR(KBr)3390, 1609, 1592, 1522, 1484, 1247, 1227, 1119, 1011, 812 cm$^{-1}$ I-567 m.p. 146–148° C.
$^1$HNMR(DMSO-d$_6$) δ 1.64(s, 3H), 1.70(s, 3H), 2.44(q, J=6.9Hz, 2H), 3.53(s, 3H), 3.78(s, 3H), 3.80(s, 3H), 4.05(t, J=6.9Hz, 2H), 5.26(t, J=6.9Hz, 2H), 7.05(s, 1H), 7.10(s, 1H), 7.19(d, J=8.4Hz, 1H), 7.50(dd, J=8.4, 2.0Hz, 1H), 7.57(t, J=8.3Hz, 1H), 7.65(dd, J=8.3, 1.9, 0.9Hz, 1H), 7.66(dd, J=11.9, 1.9Hz, 1H), 7.79(d, J=2.0Hz, 1H), 12.5(brs, 1H)
IR(KBr)3434, 3299, 1727, 1489, 1375, 1341, 1209, 1172, 1033, 851, 824 cm$^{-1}$ I-568 m.p. 179–181° C.
$^1$HNMR(CDCl$_3$) δ 1.31(s, 9H), 3.11(s, 3H), 3.20(s, 3H), 3.39(s, 3H), 3.74(s, 3H), 5.16(s, 2H), 5.98(s, 1H), 6.79(s, 1H), 7.09(d, J=8.5Hz, 1H), 7.29(dd, J=8.5, 1.9Hz, 1H), 7.35–7.49(m, 8H), 7.66(d, J=8.7Hz, 2H)
IR(KBr)3404, 3341, 1690, 1517, 1465, 1369, 1348, 1174, 1151, 869, 814 cm$^{-1}$ I-569 m.p. 189–191° C.
$^1$HNMR(DMSO-d$_6$) δ 3.31(s, 3H), 3.33(s, 3H), 3.43(s, 3H), 3.64 (s, 3H), 4.48(s, 2H), 5.25(s, 2H), 6.28(s 1H), 7.24(d, J=9.0, 2.0Hz, 1H), 7.24(d, J=2.0Hz, 1H), 7.34–7.46(m, 6H), 7.52–7.55 (m, 2H), 7.70(d, J=9.0Hz, 2H)
IR(KBr)3490, 3392, 1596, 1518, 1483, 1364, 1150, 872, 813 cm$^{-1}$ I-570 m.p. 194–196° C.
$^1$HNMR(CDCl$_3$) δ 3.07(s, 3H), 3.22(s, 3H), 3.36(s, 3H), 3.77(s, 3H), 5.16(s, 2H), 6.92(s, 1H), 7.13(d, J=8.6Hz, 1H), 7.25(dd, J= 8.6, 2.1Hz, 1H), 7.29(d, J=2.1Hz, 1H), 7.36–7.47(m, 7H), 7.63 (brs, 1H), 7.67(d, J=8.4Hz, 2H)
IR(KBr)3433, 3329, 1737, 1518, 1476, 1369, 1168, 1148, 878 cm$^{-1}$

TABLE 114

I-571 m.p. 184–186° C.
$^1$HNMR(CDCl$_3$) δ 2.31(s, 3H), 2.38(s, 3H), 3.12(s, 3H), 3.45(s, 3H), 3.58(s, 3H), 3.76(s, 3H), 5.14(s, 2H), 6.95(s, 1H), 7.11–7.23 (m, 5H), 7.34–7.37(m, 4H), 7.57(dd, J=8.7, 2.4Hz, 1H), 7.66(d, J=2.4Hz, 1H)
IR(CHCl$_3$)2952, 1732, 1614, 1599, 1518, 1467, 1445, 1370, 1290, 1256, 1169, 1117, 1081, 1064, 1003, 973, 905, 827 cm$^{-1}$

I-572 m.p. 218–220° C.
$^1$HNMR(CDCl$_3$) δ 2.38(s, 3H), 3.12(s, 3H), 3.44(s, 3H), 3.63(s, 3H), 3.76(s, 3H), 5.14(s, 2H), 6.80–6.83(m, 2H), 6.94(s, 1H), 7.14 (d, J=8.7Hz, 1H), 7.21–7.23(m, 4H), 7.35–7.37(m, 2H), 7.56(dd, J=8.7, 2.4Hz, 1H), 7.66(d, J=2.4Hz, 1H)
IR(CHCl$_3$)3596, 2939, 1720, 1613, 1522, 1466, 1445, 1370, 1346, 1291, 1258, 1183, 1172, 1116, 1081, 1064, 1003, 973, 904, 866, 837 cm$^{-1}$

I-573 m.p. 197–199° C.
$^1$HNMR(CD$_3$OD) δ 3.19(s, 3H), 3.43(s, 3H), 3.76(s, 3H), 5.25(s, 2H), 7.06–7.12(m, 3H), 7.32–7.43(m, 6H), 7.52–7.54(m, 2H), 7.60(dd, J=8.4, 2.4Hz, 1H), 7.66(d, J=2.4Hz, 1H)
IR(KBr)3421, 2941, 1738, 1708, 1643, 1519, 1472, 1354, 1297, 1259, 1228, 1171, 1119, 1081, 1063, 1001, 958, 920, 871, 826, 755, 697, 524 cm$^{-1}$

I-574 m.p. 151–153° C.
$^1$HNMR(CDCl$_3$) δ 2.39(s, 3H), 3.44(s, 3H), 3.64(s, 3H), 3.74(s, 3H), 5.12(s, 2H), 5.78(br, 2H), 6.78–6.81(m, 2H), 6.94(s, 1H), 6.99(d, J=8.4Hz, 1H), 7.15–7.25(m, 6H), 7.33–7.36(m, 2H)
IR(CHCl$_3$)3595, 3541, 2952, 1730, 1612, 1591, 1521, 1474, 1395, 1345, 1323, 1290, 1258, 1173, 1129, 1081, 1063, 1004, 901, 863, 836 cm$^{-1}$

I-575 m.p. 195–196° C.
$^1$HNMR(CD$_3$OD) δ 2.34(s, 3H), 3.40(s, 3H), 3.72(s, 3H), 5.16(s, 2H), 6.75–6.78(m, 2H), 6.96(s, 1H), 7.02(s, 1H), 7.14–7.21(m, 6H), 7.36–7.39(m, 2H)
IR(KBr)3530, 3398, 2942, 1708, 1610, 1593, 1520, 1465, 1373, 1334, 1256, 1233, 1127, 1078, 1056, 996, 960, 864, 834, 791, 755, 690, 651, 605, 534 cm$^{-1}$

TABLE 115

I-576 m.p. 82–84° C.
$^1$HNMR(CDCl$_3$) δ 1.70(s, 3H), 1.75(s, 3H), 2.54–2.59(m, 2H), 3.24(s, 3H), 3.50(s, 3H), 3.77(s, 3H), 4.10(t, J=6.9Hz, 2H), 5.23 (m, 1H), 7.07–7.12(m, 4H), 7.23–7.28(m, 2H), 7.57(dd, J=8.7, 2.4Hz, 1H), 7.63(d, J=2.4Hz, 1H), 9.99(s, 1H)
IR(CHCl$_3$)2936, 1697, 1604, 1591, 1518, 1469, 1445, 1371, 1331, 1294, 1232, 1172, 1159, 1123, 1093, 1005, 964 cm$^{-1}$

I-577 m.p. 126–128° C.
$^1$HNMR(CD$_3$OD) δ 1.70(s, 3H), 1.74(d, J=0.9Hz, 3H), 2.53–2.61(m, 2H), 3.25(s, 3H), 3.44(s, 3H), 3.75(s, 3H), 4.13(t, J=6.3Hz, 2H), 5.29(m, 1H), 7.04–7.11(m, 3H), 7.24(d, J=8.7Hz, 1H), 7.33–7.38(m, 2H), 7.58–7.65(m, 2H)
IR(KBr)3432, 2940, 2566, 1735, 1711, 1646, 1613, 1519, 1470, 1447, 1366, 1297, 1264, 1228, 1172, 1118, 1081, 1063, 1001, 962, 920, 898, 871, 828, 796, 695, 524 cm$^{-1}$

I-578 m.p. 202–204° C.
$^1$HNMR(CDCl$_3$) δ 3.13(s, 3H), 3.45(s, 3H), 3.61(s, 3H), 3.76(s, 3H), 5.19(s, 2H), 6.95(s, 1H), 7.05–7.11(m, 2H), 7.14(d, J=8.7Hz, 1H), 7.30–7.49(m, 7H), 7.57(dd, J=8.7, 2.4Hz, 1H), 7.67(d, J=2.4Hz, 1H)
IR(CHCl$_3$)2952, 1731, 1603, 1519, 1472, 1445, 1371, 1345, 1291, 1172, 1159, 1117, 1081, 1064, 1004, 972, 960, 904 cm$^{-1}$

I-579 m.p. 197–199° C.
$^1$HNMR(CDCl$_3$) δ 2.71(s, 3H), 3.56, (s, 3H), 3.75(s, 3H), 5.18(s, 2H), 5.72, (s, 1H), 6.86(s, 1H), 7.00(d, J=8.4Hz, 1H), 7.12–7.18(m, 3H), 7.24(d, J=2.1Hz, 1H), 7.38–7.46(m, 7H)
IR(CHCl$_3$)3543, 2939, 1602, 1521, 1482, 1465, 1394, 1370, 1328, 1254, 1178, 1159, 1130, 1081, 1005, 964, 840, 816 cm$^{-1}$

I-580 m.p. 199–201° C.
$^1$HNMR(CD$_3$OD) δ 3.40(s, 3H), 3.73(s, 6H), 5.22(s, 2H), 7.00(s, 1H), 7.03–7.11(m, 4H), 7.17(m, 1H), 7.31–7.41(m, 5H), 7.49–7.52(m, 2H)
IR(KBr)3527, 3434, 2940, 1701, 1591, 1518, 1465, 1380, 1335, 1320, 1291, 1270, 1222, 1161, 1130, 1078, 1056, 1002, 916, 868, 837, 747, 698, 633, 599, 526, 480 cm$^{-1}$

TABLE 116

I-581 m.p. 122–123° C.
$^1$HNMR(CDCl$_3$) δ 1.78(s, 3H), 1.82(s, 3H), 3.25(s, 3H), 3.50(s, 3H), 3.76(s, 3H), 4.66(d, J=6.9Hz, 2H), 5.52(m, 1H), 7.09–7.14 (m, 4H), 7.23–7.27(m, 2H), 7.56(dd, J=8.7, 2.1Hz, 1H), 7.63(d, J=2.1Hz, 1H), 9.99(s, 1H)
IR(CHCl$_3$)2938, 1679, 1604, 1591, 1517, 1469, 1445, 1371, 1331, 1292, 1172, 1159, 1122, 1092, 1004, 973 cm$^{-1}$

I-582 m.p. 158–159° C.
$^1$HNMR(CDCl$_3$) δ 2.69(s, 3H), 3.13(s, 3H), 3.57(s, 3H), 3.76(s, 3H), 5.19(s, 2H), 6.85(s, 1H), 7.13–7.18(m, 3H), 7.37–7.49(m, 7H), 7.56(dd, J=9.0, 2.1Hz, 1H), 7.62(d, J=2.1Hz, 1H)
IR(CHCl$_3$)2939, 1603, 1521, 1482, 1464, 1294, 1253, 1177, 1119, 1082, 1003, 963, 876, 842 cm$^{-1}$

I-583 m.p. 145–147° C.
$^1$HNMR(CDCl$_3$) δ 2.68(s, 3H), 3.54(s, 3H), 3.56(s, 3H), 3.75(s, 3H), 5.21(s, 2H), 5.27(s, 2H), 6.85 (s 1H), 7.00(d, J=8.7Hz, 1H), 7.13–7.23(m, 3H), 7.33–7.49(m, 8H)
IR(CHCl$_3$)2938, 1731, 1603, 1520, 1482, 1370, 1249, 1178, 1158, 1134, 1081, 1004, 961, 840, 815 cm$^{-1}$

I-584 m.p. 160–162° C.
$^1$HNMR(CDCl$_3$) δ 3.47(s, 3H), 3.74(s, 3H), 5.18(s, 2H), 5.72(s, 1H), 6.00(s, 1H), 6.46(s, 1H), 7.01(d, J=8.4Hz, 1H), 7.10–7.19(m, 3H), 7.27(d, J=2.1Hz, 1H), 7.36–7.48(m, 7H)
IR(CHCl$_3$)3540, 2938, 1603, 1568, 1522, 1490, 1464, 1416, 1396, 1325, 1263, 1158, 1111, 1072, 1002, 838 cm$^{-1}$

I-585 m.p. 133–134° C.
$^1$HNMR(CD$_3$OD) δ 1.80(d, J=0.9Hz, 3H), 1.82(d, J=0.9Hz, 3H), 3.26(s, 3H), 3.44(s, 3H), 3.76(s, 3H), 4.71(d, J=6.9Hz, 2H), 5.55 (m, 1H), 7.06–7.12(m, 3H), 7.26(d, J=8.7Hz, 1H), 7.34–7.36(m, 2H), 7.58–7.63(m, 2H)
IR(KBr)3422, 2939, 1736, 1702, 1603, 1519, 1472, 1368, 1293, 1228, 1187, 1173, 1117, 1081, 1061, 1003, 975, 961, 920, 827, 759, 701, 523 cm$^{-1}$

TABLE 117

I-586 m.p. 152–153° C.
$^1$HNMR(CDCl$_3$) δ 1.69(s, 3H), 1.74(d, J=0.9Hz, 3H), 2.55–2.57 (m, 2H), 3.23(s, 3H), 3.44(s, 3H), 3.60(s, 3H), 3.77(s, 3H), 4.09(t, J=6.6Hz, 2H), 5.22(m, 1H), 6.95(s, 1H), 7.05–7.11(m, 3H), 7.30–7.35(m, 2H), 7.57(dd, J=8.7, 2.4Hz, 1H), 7.64(d, J=2.4Hz, 1H)
IR(CHCl$_3$)2938, 1731, 1601, 1519, 1469, 1445, 1370, 1345, 1291, 1172, 1159, 1117, 1081, 1064, 1004, 973, 904, 864, 840 cm$^{-1}$

I-587 m.p. 132–133° C.
$^1$HNMR(CDCl$_3$) δ 3.44(s, 3H), 3.61(s, 3H), 3.75(s, 3H), 5.18(s, 2H), 5.71(s, 1H), 6.95(s, 1H), 6.99–7.10(m, 3H), 7.17(dd, J=8.4, 2.1Hz, 1H), 7.25–7.47(m, 8H)
IR(CHCl$_3$)3542, 2952, 2938, 1731, 1597, 1519, 1474, 1392, 1345, 1321, 1290, 1266, 1159, 1130, 1080, 1063, 1000, 900, 862, 839 cm$^{-1}$

I-588 m.p. 92–94° C.
$^1$HNMR(CDCl$_3$) δ 1.69(d, J=0.6Hz, 3H), 1.76(d, J=1.2Hz, 3H), 2.51–2.58(m, 2H), 3.45(s, 3H), 3.75(s, 3H), 4.09(t, J=6.9Hz, 2H), 5.23(m, 1H), 5.70(br, 1H), 6.92(d, J=8.4Hz, 1H), 6.97(s, 1H), 7.05–7.10(m, 2H), 7.16(dd, J=8.4, 2.1Hz, 1H), 7.23(d, J=2.1Hz, 1H), 7.33–7.38(m, 2H)
IR(KBr)3534, 3432, 2936, 1713, 1597, 1519, 1473, 1377, 1322, 1260, 1231, 1158, 1130, 1081, 1063, 1004, 961, 919, 837, 808, 791, 754, 705, 521 cm$^{-1}$

I-589 m.p. 120–122° C.
$^1$HNMR(CDCl$_3$) δ 1.69(s, 3H), 1.76(s, 3H), 2.51–2.58(m, 2H), 3.44(s, 3H), 3.61(s, 3H), 3.75(s, 3H), 4.09(t, J=6.6Hz, 2H), 5.23 (m, 1H), 5.73(s, 1H), 6.92(d, J=8.4Hz, 1H), 6.96(s, 1H), 7.04–7.10(m, 2H), 7.16(dd, J=8.1, 1.8Hz, 1H), 7.23(d, J=1.8Hz, 1H), 7.31–7.36(m, 2H)
IR(CHCl$_3$)3541, 2937, 1731, 1598, 1519, 1471, 1391, 1345, 1323, 1290, 1265, 1159, 1130, 1080, 1063, 1005, 839 cm$^{-1}$

I-590 m.p. 154–156° C.
$^1$HNMR(CDCl$_3$) δ 1.77(s, 3H), 1.82(s, 3H), 3.24(s, 3H), 3.45(s, 3H), 3.61(s, 3H), 3.76(s, 3H), 4.64(d, J=7.2Hz, 2H), 5.51(m, 1H), 6.95(s, 1H), 7.05–7.11(m, 3H), 7.31–7.35(m, 2H), 7.57(dd, J=8.7, 2.4Hz, 1H), 7.64(d, J=2.4Hz, 1H)
IR(CHCl$_3$)2938, 1731, 1602, 1519, 1472, 1445, 1370, 1345, 1290, 1186, 1116, 1080, 1064, 1003, 973, 904, 840 cm$^{-1}$

TABLE 118

I-591 m.p. 181–182° C.
$^1$HNMR(CD$_3$OD) δ 1.77(s, 3H), 1.80(d, J=0.9Hz, 3H), 3.42(s, 3H), 3.74(s, 3H), 4.65(d, J=6.9Hz, 2H), 5.55(m, 1H), 6.99–7.11 (m, 5H), 7.15(d, J=2.1Hz, 1H), 7.32–7.36(m, 2H)
IR(KBr)3529, 3424, 2937, 1714, 1598, 1519, 1473, 1417, 1372, 1336, 1321, 1258, 1235, 1157, 1129, 1080, 1062, 1004, 989, 917, 854, 839, 807, 791, 752, 703 cm$^{-1}$

I-592 m.p. 109–110° C.
$^1$HNMR(CDCl$_3$) δ 1.78(s, 3H), 1.83(s, 3H), 3.44(s, 3H), 3.61(s, 3H), 3.75(s, 3H), 4.63(d, J=6.6Hz, 2H), 5.53(m, 1H), 5.72(s, 1H), 6.94(d, J=8.1Hz, 1H), 6.96(s, 1H), 7.04–7.10(m, 2H), 7.16(dd, J=8.4, 2.1Hz, 1H), 7.23(d, J=2.1Hz, 1H), 7.31–7.36(m, 2H)
IR(CHCl$_3$)3538, 2938, 1731, 1598, 1519, 1473, 1391, 1345, 1290, 1264, 1159, 1129, 1080, 1063, 1004, 900, 862, 839 cm$^{-1}$

I-593 m.p. 185–187° C.
$^1$HNMR(CDCl$_3$) δ 3.78(s, 3H), 3.80(s, 3H), 4.82(s, 1H), 6.61(m, 1H), 6.88–6.93(m, 2H), 6.96(s, 1H), 7.04(s, 1H), 7.23–7.25(m, 1H), 7.45(d, J=0.9Hz, 1H), 7.48–7.53(m, 2H), 7.83(d, J=0.9Hz, 1H), 8.18(brs, 1H)
IR(KBr)3600–3200(br), 1611, 1523, 1496, 1464, 1447, 1388, 1268, 1239, 1202, 1046, 1025 cm$^{-1}$ I-594 m.p. 188–189° C.
$^1$HNMR(CDCl$_3$) δ 3.19(s, 3H), 3.79(s, 3H), 3.81(s, 3H), 6.61–6.62(m, 1H), 6.96(s, 1H), 7.06(s, 1H), 7.24–7.26(m, 1H), 7.33–7.37(m, 2H), 7.45(brs, 2H), 7.64–7.68(m, 2H), 7.84(d, J=0.9Hz, 1H), 8.21(brs, 1H)
IR(KBr)3600–3200(br), 1518, 1494, 1465, 1419, 1389, 1351, 1331, 1314, 1213, 1177, 1145, 1051, 1027 cm$^{-1}$ I-595 m.p. 98–101° C.
$^1$HNMR(CDCl$_3$) δ 1.77(s, 3H), 1.78(s, 3H), 1.82(s, 3H), 1.85(s, 3H), 3.78(s, 3H), 3.79(s, 3H), 4.56(d, J=6.9Hz, 2H), 4.72(d, J=6.9Hz, 2H), 5.39–5.44(m, 1H), 5.52–5.57(m, 1H), 6.53(d, J=3.0Hz, 1H), 6.97–7.03(m, 4H), 7.12(d, J=3.3Hz, 1H), 7.38(d, J=

TABLE 118-continued 8.4Hz, 1H), 7.45(dd, J=1.8, 8.7Hz, 1H), 7.52–7.57(m, 2H), 7.81(d, J=1.5Hz, 1H)
IR(KBr)3600–2800(br), 1606, 1498, 1476, 1463, 1382, 1262, 1241, 1206, 1177, 1052, 1030 cm$^{-1}$

TABLE 119

I-596 m.p. 207–210° C.
$^1$HNMR(CDCl$_3$) δ 3.19(s, 3H), 3.80(s, 3H), 3.81(s, 3H), 5.50(s, 2H), 6.65(d, J=3.0Hz, 1H), 6.81(d, J=7.8Hz, 1H), 6.96(s, 1H), 7.05(s, 1H), 7.19–7.22(m, 1H), 7.25–7.45(m, 6H), 7.54–7.60(m, 1H), 7.64–7.69(m, 2H), 7.86(brs, 1H), 8.61–8.64(m, 1H)
IR(KBr)3600–3200(br), 1496, 1478, 1364, 1347, 1210, 1176, 1155, 1052, 1028 cm$^{-1}$ I-597 m.p. 222–224° C.
$^1$HNMR(CDCl$_3$) δ 2.36(s, 3H), 2.53(s, 3H), 3.77(s, 3H), 3.78(s, 3H), 6.69(dd, J=0.9, 4.2Hz, 1H), 6.95(s, 1H), 6.96(s, 1H), 7.23–7.28(m, 2H), 7.31–7.35(m, 2H), 7.51–7.54(m, 3H), 7.59(d, J=3.3Hz, 1H), 7.73(d, J=1.2Hz, 1H), 7.80–7.84(m, 1H), 8.03(d, J=1.2Hz, 1H)
IR(KBr)3600–3200(br), 1509, 1487, 1464, 1444, 1366, 1208, 1172, 1129, 1092, 1049, 1028 cm$^{-1}$ I-598 m.p. 126–127° C.
$^1$HNMR(CDCl$_3$) δ 1.69(s, 3H), 1.71(d, J=0.9Hz, 3H), 2.56(dt, J=6.6, 6.9Hz, 2H), 3.20(s, 3H), 3.22(s, 3H), 4.08(t, J=6.9Hz, 2H), 5.21(m, 1H), 7.08(d, J=8.4Hz, 1H), 7.18–7.27(m, 2H), 7.36–7.43(m, 2H), 7.50(dd, J=1.8, 8.4Hz, 1H), 7.56(d, J=1.8Hz, 1H), 7.59–7.66(m, 2H)
IR(KBr)1528, 1488, 1469, 1395, 1362, 1342, 1297, 1265, 1201, 1176, 1152, 1116, 968, 890, 872, 818 cm$^{-1}$ I-599 m.p. 169–170° C.
$^1$HNMR(DMSO-d$_6$) δ 2.32(s, 3H), 3.37(s, 3H), 3.45(s, 3H), 5.23(s, 2H), 7.23(d, J=7.8Hz, 2H), 7.37–7.44(m, 3H), 7.47–7.53(m, 2H), 7.56–7.66(m, 4H), 7.75(d, J=7.5Hz, 2H)
IR(KBr)1525, 1485, 1366, 1355, 1291, 1262, 1181, 1150, 1116, 969, 869, 811 cm$^{-1}$ I-600 m.p. 123–124° C.
$^1$HNMR(CDCl$_3$) δ 1.68(s, 3H), 1.75(d, J=0.9Hz, 3H), 2.53(dt, J=7.2, 6.9Hz, 2H), 4.07(t, J=6.9Hz, 2H), 4.91(s, 2H), 5.22(m, 1H), 5.72(s, 1H), 6.89–6.95(m, 2H), 7.07(m, 1H), 7.14–7.22(m, 4H), 7.44–7.51(m, 2H)
IR(KBr)3448, 1612, 1593, 1530, 1489, 1475, 1401, 1262, 1212, 1181, 1169, 1132, 839, 779 cm$^{-1}$

TABLE 120

I-601 m.p. 184–185° C.
$^1$HNMR(DMSO-d$_6$) δ 2.31(s, 3H), 5.13(s, 2H), 6.85–6.91(m, 2H), 6.97(m, 1H), 7.07(d, J=8.4Hz, 1H), 7.07(d, J=1.8Hz, 1H), 7.20(d, J=8.1Hz, 2H), 7.32–7.48(m, 6H)
IR(KBr)3290, 1614, 1529, 1491, 1459, 1449, 1405, 1380, 1267, 1254, 1167, 1132, 783 cm$^{-1}$

I-602 m.p. 141–142° C.
$^1$HNMR(CDCl$_3$) δ 1.77(s, 3H), 1.82(s, 3H), 3.46(s, 3H), 3.78(s, 3H), 4.56(d, J=6.8Hz, 2H), 5.54(t, J=6.6Hz, 1H), 6.96–7.26(m, 7H), 7.61(dd, J=5.2, 8.6Hz, 2H), 9.88(s 1H)
IR(KBr)3433, 2955, 2922, 2865, 2833, 1687, 1604, 1515, 1462, 1288, 1258, 1232, 1180, 1160, 1070, 998, 845 cm$^{-1}$

I-603 m.p. 169–170° C.
$^1$HNMR(CDCl$_3$) δ 2.38(s, 3H), 3.46(s, 3H), 3.77(s, 3H), 5.07(s, 2H), 7.02–7.38(m, 7H), 7.61(dd, J=5.4, 8.8Hz, 2H), 9.89(brs, 1H)
IR(KBr)3433, 2936, 2840, 1698, 1517, 1462, 1251, 1233, 1067, 999, 837 cm$^{-1}$ I-604 m.p. 120–121° C.
$^1$HNMR(CDCl$_3$) δ 1.68(s, 3H), 1.74(s, 3H), 2.50–2.57(m, 2H), 3.46(s, 3H), 3.77(s, 3H), 3.98(t, J=7.0Hz, 2H), 5.24(t, J=7.0Hz, 1H), 6.94–7.26(m, 7H), 7.61(dd, J=5.4, 8.8Hz, 2H), 9.88(brs, 1H)
IR(KBr)3435, 2960, 2937, 2876, 1698, 1605, 1516, 1464, 1441, 1379, 1296, 1272, 1233, 1221, 1161, 1073, 1024, 845, 807 cm$^{-1}$

TABLE 120-continued

I-605 m.p. 151–152° C.
$^1$HNMR(DMSO-d$_6$) δ 1.34(s, 6H), 3.07–3.15(m, 1H), 3.32(s, 3H), 3.67(s, 3H), 3.97–4.08(m, 1H), 4.28–4.34(m, 1H), 6.48(s, 1H), 7.00(d, J=7.8Hz, 2H), 7.22–7.35(m, 4H), 7.66(dd, J=3.2, 6.0Hz, 2H), 8.72(brs, 1H)
IR(KBr)3460, 2960, 2935, 1607, 1521, 1488, 1456, 1392, 1244, 1226, 1160, 1122, 1073, 818 cm$^{-1}$ I-606 m.p. 164–165° C.
$^1$HNMR(DMSO-d$_6$) δ 2.32(s, 3H), 3.31(s, 3H), 3.66(s, 3H), 5.08(s, 2H), 6.46(s, 1H), 6.99(d, J=5.8Hz, 2H), 7.20–7.38(m, 4H), 7.65(dd, J=3.6, 6.2Hz, 2H), 8.69(brs, 1H)
IR(KBr)3367, 2940, 1605, 1519, 1484, 1466, 1449, 1390, 1229, 1181, 1158, 1059, 1006, 987, 831, 817 cm$^{-1}$

TABLE 121

I-607 m.p. 103–104° C.
$^1$HNMR(DMSO-d$_6$) δ 1.37(s, 6H), 2.47–2.59(m, 2H), 3.31(s, 3H), 3.66(s, 3H), 3.94–4.05(m, 1H), 4.26–4.34(m, 1H), 6.44(s, 1H), 7.02(d, J=7.6Hz, 2H), 7.18–7.35(m, 4H), 7.64(dd, J=3.4, 6.6Hz, 2H), 8.77(brs, 1H)
IR(KBr)3400, 2993, 2961, 2930, 1607, 1522, 1486, 1471, 1454, 1393, 1226, 1123, 1072, 835, 819 cm$^{-1}$ I-608 m.p. 157–158° C.
$^1$HNMR(DMSO-d$_6$) δ 1.73(s, 3H), 1.77(s, 3H), 3.31(s, 3H), 3.72(s, 3H), 4.54(d, J=6.9Hz, 2H), 5.47(t, J=7.2Hz, 1H), 6.93(d, J=8.7Hz, 2H), 7.05(s, 1H), 7.19(d, J=9.0Hz, 2H), 7.30–7.36(m, 2H), 7.70(dd, J=5.4, 8.7Hz, 2H)
IR(KBr)3406, 2936, 1712, 1608, 1519, 1472, 1444, 1375, 1235, 839 cm$^{-1}$ I-609 m.p. 215–216° C.
$^1$HNMR(DMSO-d$_6$) δ 2.34(s, 3H), 3.33(s, 3H), 3.74(s, 3H), 5.09(s, 2H), 7.00–7.07(m, 3H), 7.22–7.39(m, 8H), 7.73(dd, J=5.6, 8.0Hz, 2H)
IR(KBr)3494, 3289, 2938, 1745, 1698, 1520, 1471, 1461, 1378, 1296, 1239, 1183, 1159, 829 cm$^{-1}$ I-610 m.p. 169–170° C.
$^1$HNMR(DMSO-d$_6$) δ 1.64(s, 3H), 1.71(s, 3H), 2.41–2.46(m, 2H), 3.32(s, 3H), 3.73(s, 3H), 3.97(t, J=6.6Hz, 2H), 5.23(t, J=7.2Hz, 1H), 6.93(d, J=8.1Hz, 2H), 7.05(s, 1H), 7.20(d, J=7.2Hz, 2H), 7.30–7.36(m, 2H), 7.70(dd, J=4.5, 7.5Hz, 2H)
IR(KBr)3424, 2933, 1701, 1609, 1519, 1471, 1379, 1294, 1248, 1061, 839 cm$^{-1}$ I-611 m.p. 167–168° C.
$^1$HNMR(CDCl$_3$) δ 1.75(s, 3H), 1.82(s, 3H), 2.35(s, 6H), 2.45(s, 3H), 3.21(s, 3H), 3.56(s, 3H), 3.70(s, 3H), 4.35(d, J=6.9Hz, 2H), 5.60(t, J=7.2Hz, 1H), 6.84(s, 1H), 7.08(s, 2H), 7.38(d, J=8.7Hz, 2H), 7.70(d, J=9.0Hz, 2H)
IR(KBr)3433, 2932, 1509, 1475, 1376, 1359, 1232, 1177, 1152, 1085, 966, 874, 797 cm$^{-1}$

TABLE 122

I-612 m.p. 175–176° C.
$^1$HNMR(CDCl$_3$) δ 2.35(s, 6H), 2.39(s, 3H), 2.49(s, 3H), 3.21(s, 3H), 3.56(s, 3h), 3.79(s, 3H), 4.83(s, 2H), 6.84(s, 1H), 7.10(s, 2H), 7.22(d, J=7.5Hz, 2H), 7.38(d, J=8.4Hz, 4H), 7.70(d, J=9.0Hz, 2H)
IR(KBr)3434, 2936, 1510, 1475, 1363, 1229, 1176, 1152, 1083, 964, 871, 803 cm$^{-1}$

I-613 m.p. 138–139° C.
$^1$HNMR(CDCl$_3$) δ 1.69(s, 3H), 1.75(s, 3H), 2.33(s, 6H), 2.52–2.55(m, 2H), 3.21(s, 3H), 3.56(s, 3H), 3.78(s, 3H), 3.79(t, J=6.9Hz, 2H), 5.27(t, J=6.6Hz, 1H), 6.83(s, 3H), 7.08(s, 6H), 7.38(d, J=5.7Hz, 2H), 7.70(d, J=9.0Hz, 2H)
IR(KBr)3432, 2939, 1509, 1476, 1448, 1362, 1237, 1172, 1155, 1103, 1081, 963, 873, 800 cm$^{-1}$

I-614 m.p. 89–90° C.
$^1$HNMR(DMSO-d$_6$) δ 1.74(s, 3H), 1.77(s, 3h), 3.36(s, 3H), 3.67(s, 3H), 4.22(d, J=3.0Hz, 2H), 4.56(d, J=6.3Hz, 2H), 5.48(t, J=5.7Hz,

TABLE 122-continued

1H), 6.93–6.96(m, 3H), 7.11(d, J=8.7Hz, 2H), 7.28–7.34(m, 2H), 7.68(dd, J=6.0, 8.7Hz, 2H)
IR(KBr)3528, 3418, 2935, 1608, 1518, 1472, 1233, 1004, 836 cm$^{-1}$

I-615 m.p. 89–90° C.
$^1$HNMR(DMSO-d$_6$) δ 2.33(s, 3H), 3.36(s, 3H), 3.67(s, 3H), 4.22(d, J=3.9Hz, 2H), 4.59(t, J=4.2Hz, 1H), 5.09(s, 2H), 6.94(s, 1H), 7.02(d, J=8.4Hz, 2H), 7.22(d, J=8.4Hz, 4H), 7.28–7.39(m, 4H), 7.68(dd, J=5.7, 8.4Hz, 2H)
IR(KBr)3485, 2931, 1517, 1473, 1460, 1383, 1243, 1225, 1079, 1014, 1001, 834, 798 cm$^{-1}$

I-616 oil
$^1$HNMR(DMSO-d$_6$) δ 1.75(s, 3H), 1.78(s, 3H), 2.47–2.52(m, 2H), 3.39(s, 3H), 3.71(s, 3H), 4.25(d, J=3.3Hz, 2H), 4.49(d, J=6.3Hz, 2H), 5.46(t, J=5.7Hz, 1H), 6.91–6.95(m, 3H), 7.13(d, J=8.4Hz, 2H), 7.24–7.32(m, 2H), 7.67(dd, J=5.7, 8.4Hz, 2H)
IR(KBr)3528, 3419, 2935, 1608, 1518, 1472, 1383, 1232, 1004, 837 cm$^{-1}$

TABLE 123

I-617 m.p. 138–139° C.
$^1$HNMR(DMSO-d$_6$) δ 1.70(s, 3H), 1.77(s, 3H), 2.24(s, 6H), 3.30(s, 3H), 3.64(s, 3H), 4.31(d, J=6.9Hz, 2H), 5.56(t, J=6.6Hz, 1H), 6.39(s, 1H), 6.84(d, J=8.4Hz, 2H), 6.91(s, 2H), 7.44(d, J=8.4Hz, 2H), 8.50(s, 1H), 9.50(s, 1H)
IR(KBr)3400, 2966, 2934, 1609, 1519, 1465, 1444, 1389, 1362, 1269, 1228, 1211, 1194, 1171, 1118, 1089, 1027, 953 cm$^{-1}$

I-618 m.p. 122–123° C.
$^1$HNMR(DMSO-d$_6$) δ 2.29(s, 6H), 2.37(s, 3H), 3.30(s, 3H), 3.67(s, 3H), 4.81(s, 2H), 6.43(s, 1H), 6.86(d, J=7.5Hz, 2H), 6.97(s, 2H), 7.27 (d, J=6.9Hz, 2H), 7.42–7.48(m, 2H), 8.54(s, 1H), 9.52(s, 1H)
IR(KBr)3483, 3423, 2931, 1735, 1709, 1612, 1520, 1477, 1454, 1411, 1395, 1362, 1224, 1176, 1117, 1089, 1028 cm$^{-1}$

I-619 m.p. 81–82° C.
$^1$HNMR(DMSO-d$_6$) δ 1.70(s, 3H), 1.76(s, 3H), 2.18–2.30(m, 2H), 2.27(s, 3H), 3.34(s, 3H), 3.68(s, 3H), 3.80(t, J=4.5Hz, 2H), 5.34(t, J=5.1Hz, 1H), 6.43(s, 1H), 6.88(d, J=7.5Hz, 2H), 6.94(s, 6H), 7.46–7.50(m, 2H), 8.53(s, 1H), 9.54(s, 1H)
IR(KBr)3410, 2930, 1612, 1521, 1479, 1454, 1395, 1361, 1265, 1227, 1174, 1117, 1090, 1028, 825 cm$^{-1}$

I-620 m.p. 161–162° C.
$^1$HNMR(CDCl$_3$) δ 1.32(s, 9H), 2.38(s, 3H), 3.10(s, 3H), 3.20(s, 3H), 3.39(s, 3H), 3.74(s, 3H), 5.12(s, 2H), 5.96(s, 1H), 6.79(s, 1H), 7.09(d, J=8.4Hz, 1H), 7.21(d, J=7.8Hz, 2H), 7.28(dd, J=8.4, 1.8Hz, 1H), 7.33–7.38(m, 5H), 7.67(d, J=8.4Hz, 2H)
IR(KBr)3398, 1718, 1518, 1472, 1366, 1173, 1151, 877, 867, 813 cm$^{-1}$

I-621 m.p. 139–141° C.
$^1$HNMR(CDCl$_3$) δ 1.33(s, 9H), 1.68(s, 3H), 1.74(s, 3H), 2.54(q, J=6.9Hz, 2H), 3.19(s, 3H), 3.20(s, 3H), 3.39(s, 3H), 3.73(s, 3H), 4.05(t, J=6.9Hz, 2H), 5.21(t, J=6.9Hz, 1H), 5.95(s, 1H), 6.79(s, 1H), 7.02(d, J=8.4Hz, 1H), 7.29(dd, J=8.4, 1.9Hz, 1H), 7.33(d, J=1.9Hz, 1H), 7.36(d, J=8.7Hz, 2H), 7.66(d, J=8.7Hz, 2H)
IR(KBr)3416, 1720, 1519, 1469, 1365, 1237, 1152, 1117, 975, 872, 815 cm$^{-1}$

TABLE 124

I-622 m.p. 197–199° C.
$^1$HNMR(DMSO-d$_6$) δ 2.33(s, 3H), 3.31(s, 6H), 3.43(s, 3H), 3.64(s, 3H), 3.74(s, 3H), 4.47(s, 2H), 5.19(s, 2H), 6.28(s, 1H), 7.21–7.25(m, 4H), 7.35(d, J=8.7Hz, 1H), 7.40–7.44(m, 4H), 7.70(d, J=9.0Hz, 2H)
IR(KBr) 3482, 3385, 1597, 1519, 1484, 1368, 1353, 1150, 872, 813 cm$^{-1}$

I-623 m.p. 99–101° C.
$^1$HNMR(DMSO-d$_6$) δ 2.32(s, 3H), 3.27(s, 3H), 3.59(s, 3H), 4.21(s, 2H), 5.08(s, 2H), 6.17(s, 1H), 6.58(dd, J=8.0, 1.8Hz, 1H), 6.69(d, J=1.8Hz, 1H), 6.82(d, J=8.7Hz, 2H), 7.01(d, J=8.0Hz, 1H), 7.21(d, J=7.8Hz, 2H), 7.39(d, J=7.8Hz, 2H), 7.41(d, J=8.7Hz, 2H), 9.02(brs, 1H), 9.45(brs, 1H), 9.45(brs, 1H)
IR(KBr) 3390, 1609, 1592, 1521, 1484, 1246, 1227, 1117, 1011, 810 cm$^{-1}$ I-624 m.p. 215–217° C.
$^1$HNMR(CDCl$_3$+CD$_3$OD)d3.78(s, 3H), 3.79(s, 3H), 5.49(s, 2H), 6.64(dd, J=0.66, 2.7Hz, 1H), 6.79(d, J=8.1Hz, 1H), 6.90(d, J=8.7Hz, 2H), 6.96(s, 1H), 7.02(s, 1H), 7.19–7.32(m, 3H), 7.40–7.50(m, 3H), 7.56–7.60(m, 1H), 7.85(d, J=0.9Hz, 1H), 8.58–8.60(m, 1H)
IR(KBr) 3600–2600(br), 1611, 1599, 1500, 1477, 1445, 1395, 1264, 1238, 1210, 1052, 1029, 1008 cm$^{-1}$ I-625 m.p. 213–214° C.
$^1$HNMR(CDCl$_3$) δ 2.36(s, 3H), 3.77(s, 6H), 6.70(dd, J=0.6, 3.6Hz, 1H), 6.93(s, 1H), 6.96(s, 1H), 7.08–7.16(m, 2H), 7.24–7.28(m, 2H), 7.51–7.60(m, 4H), 7.73(d, J=1.5Hz, 1H), 7.80–7.84(m, 2H), 8.03(d, J=9.0Hz, 1H)
IR(KBr) 3600–2800(br), 1597, 1517, 1496, 1464, 1444, 1372, 1209, 1189, 1172, 1157, 1121, 1092, 1050, 1028 cm$^{-1}$ I-626 $^1$HNMR(CDCl$_3$+CD$_3$OD) δ 3.13(s, 3H), 3.81(s, 3H), 3.82(s, 3H), 5.19(s, 2H), 6.97(s, 1H), 6.99(s, 1H), 7.14(d, J=8.7Hz, 1H), 7.34–7.52(m, 6H), 7.61(d, J=2.1Hz, 1H), 7.73(d, J=8.4Hz, 2H), 8.12(d, J=8.4Hz, 2H)
IR(KBr) 3432, 1616, 1520, 1494, 1452, 1388, 1352, 1282, 1261, 1211, 1186, 1175, 1113, 1058, 1033 cm$^{-1}$ I-627 $^1$HNMR(CDCl$_3$) δ 3.81(s, 6H), 5.17(s, 2H), 6.99(s, 1H), 7.00(d, J=8.4Hz, 1H), 7.09(dd, J=8.4& 1.8Hz, 1H), 7.23(d, J=1.8Hz, 1H), 7.33–7.50 (m, 5H), 7.76(d, J=8.4Hz, 2H), 8.10(d, J=8.4Hz, 2H)
IR(KBr) 3551, 3520, 3399, 1615, 1587, 1576, 1521, 1488, 1455, 1383, 1268, 1245, 1208, 1126, 1055, 1034, 1003 cm$^{-1}$

TABLE 125

I-628 $^1$HNMR(CDCl$_3$) δ 3.05(s, 3H), 3.47(s, 3H), 3.75(s, 3H), 5.15(s, 2H), 6.45(s, 1H), 6.94(dd, J=8.4&1.8Hz, 1H), 7.03(d, J=8.4Hz, 1H), 7.06(d, J=1.8Hz, 1H), 7.30(d, J=8.1Hz, 2H, 7.36–7.51(m, 5H), 7.63(d, J=8.1Hz, 2H)
IR(KBr) 3525, 3472, 1609, 1588, 1522, 1487, 1455, 1407, 1321, 1286, 1242, 1148, 1115, 1071, 1013 cm$^{-1}$

I-629 $^1$HNMR(CDCl$_3$) δ 2.68(s, 3H), 3.07(s, 3H), 3.14(s, 3H), 3.55(s, 3H), 3.78(s, 3H), 5.19(s, 2H), 6.85(s, 1H), 7.16(d, J=8.7Hz, 1H), 7.27–7.50(m, 9H), 7.62(d, J=9.0Hz, 2H)
IR(KBr) 3432, 1611, 1522, 1482, 1462, 1392, 1358, 1295, 1233, 1178, 1154, 1119, 1082, 1012 cm$^{-1}$

I-630 $^1$HNMR(CDCl$_3$) δ 2.88(s, 3H), 3.08(s, 3H), 3.28(s, 3H), 3.30(s, 3H), 3.54(s, 3H), 3.79(s, 3H), 6.87(s, 1H), 7.32(d, J=8.4Hz, 2H), 7.43 (d.d, J=8.4&2.1Hz, 1H), 7.54–7.65(m, 4H)
IR(KBr) 3432, 1612, 1519, 1481, 1367, 1332, 1232, 1177, 1154, 1077, 1011 cm$^{-1}$

I-631 $^1$HNMR(CDCl$_3$) δ 1.57(s, 3H), 169(s, 3H), 2.66(s, 3H), 2.97(s, 3H), 3.13(s, 3H), 3.54(s, 3H), 3.77(s, 3H), 4.31(d, J=7.2Hz, 2H), 5.19(s, 2H), 5.21–5.32 (m, 1H), 6.86(s, 1H), 7.15(.d, J=8.7Hz, 1H), 7.30–7.52(m, 9H), 7.63(d, J=8.4Hz, 2H)
IR(KBr) 1609, 1520, 1481, 1365, 1338, 1294, 1270, 1233, 1178, 1153, 1118, 1078, 1015, 947 cm$^{-1}$

I-632 $^1$HNMR(CDCl$_3$) δ 1.45(s, 3H), 1.59(s, 3H), 1.66(s, 3H), 1.70(s, 3H), 2.97(s, 3H), 3.11(s, 3H), 3.64(s, 3H), 3.75(s, 3H), 4.28(d, J=8.4Hz, 2H), 4.32(d, J=8.4Hz, 2H), 5.18(s, 2H), 5.23(t, J=8.4Hz, 1H)), 5.29(t, J=8.4Hz, 1H), 6.70(s, 1H), 7.10(d, J=8.4Hz, 1H), 7.30–7.51(m, 9H), 7.58 d, J=8.4Hz, 2H

I-633 $^1$HNMR(CDCl$_3$) δ 1.58(s, 3H), 1.69(s, 3H), 2.97(s, 3H), 3.45(s, 3H), 3.75(s, 3H), 4.33(d, J=75Hz, 2H), 5.16(s, 2H), 5.24–5.33(m, 1H), 5.69 (s, 1H), 5.87(s, 1H), 6.47(s, 1H), 6.95(d, d, J=8.4& 2.1Hz, 1H), 7.03(d, J=8.4Hz, 1H), 7.09(.d, J=2.1Hz, 1H), 7.31–7.50(m, 7H), 7.65 (d, J=8.4Hz, 2H)
IR(KBr) 3450, 1609, 1590, 1558, 1524, 1487, 1448, 1421, 1320, 1233, 1143, 1117, 1073, 1019 cm$^{-1}$

I-634 $^1$HNMR(CDCl$_3$) δ 1.57(s, 3H), 1.68(s, 3H), 2.66(s, 3H), 2.70(s, 3H), 3.13(s, 3H), 3.54(s, 3H), 3.78(s, 3H), 4.33(d, J=8.4Hz, 2H), 5.19(s, 2H), 5.26(t, J=8.4Hz, 1H), 6.86(s, 1H), 7.15(d, J=8.7Hz, 1H), 7.30–7.49(m, 9H), 7.63(d, J=8.4Hz, 2H)
IR(KBr) 1645, 1517, 1480, 1372, 1337, 1233, 1213, 1178, 1154, 1076, 1014 cm$^{-1}$

TABLE 126

I-635 ¹HNMR(CDCl₃) δ 1.58(s, 3H), 1.69(s, 3H), 2.82(s, 3H), 2.97(s, 3H), 3.29(s, 3H), 3.53(s, 3H), 3.77(s, 3H), 4.33(d, J=7.2Hz, 2H), 5.27(t, J=7.2Hz, 1H), 6.25(s, 1H), 6.86(s, 1H), 7.17(d, J=9.0Hz, 1H)), 7.23–7.32(m, 2H), 7.41(d, J=8.7Hz, 2H), 7.63(d, J=8.7Hz, 2H)
IR(KBr) 3431, 1611, 1522, 1482, 1364, 1337, 1294, 1231, 1178, 1153, 1077, 1014 cm⁻¹

I-636 ¹HNMR(CDCl₃) δ 1.76(s, 3H), 1.82(s, 3H), 3.09(s, 3H), 3.47(s, 3H), 3.75(s, 3H), 4.62(d, J=6.9Hz, 2H), 5.47–5.58(m, 1H), 5.71(s, 1H), 5.87 (s, 1H), 6.45(s, 1H), 6.60(s, 1H), 6.89–7.01(m, 2H), 7.05(d, J=0.6Hz, 1H), 7.30(.d, J=8.7Hz, 2H), 7.65(d, J=8.7Hz, 2H)
IR(KBr) 3448, 3265, 1612, 1585, 1521, 1487, 1330, 1287, 1243, 1225, 1152, 1112, 1069, 971 cm⁻¹

I-637 ¹HNM²R(CDCl₃) δ 1.57(s, 3H), 1.69(s, 3H), 1.77(s, 3H), 1.81(s, 3H), 2.70(s, 3H), 2.97(s, 3H), 3.24(s, 3H), 3.54(s, 3H), 3.78(s, 3H), 4.32(d, J=6.9Hz, 2H), 4.64(d, J=6.6Hz, 2H), 5.27(t, J=6.9Hz, 1H), 5.49(t, J=6.6Hz, 1H), 6.86(s, 1H), 7.09(d, J=8.4Hz, 1H), 7.32–7.44(m, 4H), 7.63(d, J=8.4Hz, 2H)
IR(KBr) 1609, 1520, 1481, 1365, 1339, 1292, 1270, 1236, 1178, 1153, 1118, 1078, 1015 cm⁻¹

I-638 ¹HNMR(CDCl₃) δ 1.58(s, 3H), 1.69(s, 3H), 1.76(s, 3H), 1.82(s, 3H), 2.97(s, 3H), 3.45(s, 3H), 3.75(s, 3H), 4.32(d, J=7.8Hz, 2H), 4.63.(d, J=7.8Hz, 2H), 5.23–5.33(m, 1H), 5.48–5.57(m, 1H), 5.69(s, 1H), 5.85(s, 1H), 6.46(s, 1H), 6.89–7.02(m, 2H), 7.05 (d, J=1.8Hz, 1H), 7.40 (d, J=8.7Hz, 2H), 7.65(d, J=8.7Hz, 2H)
IR(KBr) 3450, 1609, 1588, 1557, 1525, 1487, 1445, 1327, 1248, 1148, 1114, 1072, 1015 cm⁻¹

I-639 ¹HNMR(CDCl₃) δ 2.55(s, 3H), 2.67(s, 3H), 3.58(s, 3H), 3.79(s, 3H), 5.18(s, 2H), 5.71(s, 1H), 6.85(s, 1H), 6.91 (d.d, J=8.4& 2.1Hz, 1H), 7.03(d, J=8.4Hz, 1H), 7.04(d, J=2.1Hz, 1H), 7.32–7.48 (m, 6H), .7.85.(d.d, J=7.8& 1.5Hz, 1H), 8.22(d, J=1.5Hz, 1H)
IR(KBr) 3457, 1739, 1529, 1481, 1407, 1376, 1346, 1279, 1243, 1177, 1128, 1071, 1012 cm⁻¹

I-640 ¹HNMR(CDCl₃) δ 2.67(s, 3H), 2.68(s, 3H), 3.13(s, 3H), 3.58(s, 3H), 3.80(s, 3H), 5.19(s, 2H), 6.86(s, 1H), 7.15(d, J=8.7Hz, 1H), 7.31–7.49 (m, 8H), 7.83 (d.d, J=8.1&1.8Hz, 1H), 8.21(d, J=1.8Hz, 1H)
IR(KBr) 3433, 1609, 1530, 1481, 1372, 1290, 1268, 1238, 1177, 1118, 1075, 1012 cm⁻¹

TABLE 127

I-641 ¹HNMR(CDCl₃) δ 2.67(s, 3H), 3.50(s, 3H), 3.77(s, 3H), 5.16(s, 2H), 5.70(s, 1H), 5.83(s, 1H), 6.47(s, 1H), 6.94 (d.d, J=8.7& 1.8Hz, 1 H), 7.04 (.d, J=8.7Hz, 1H), 7.07(d, J=1.8Hz, 1H), 7.34–7.48(m, 5H), 7.82(d.d, J=8.1&1.8Hz, 1H), 8.26(d, J=1.8Hz, 1H)
IR(KBr) 3555, 3377, 1590, 1529, 1503, 1451, 1414, 1341, 1324, 1242, 1225, 1121 cm⁻¹

I-642 ¹HNMR(CDCl₃) δ 2.29(s, 3H), 2.68(s, 3H), 3.12(s, 3H), 3.56(s, 3H), 3.76(s, 3H), 5.18(s, 2H), 6.85(s, 1H), 7.00–7.20(m, 4H), 7.31–7.49(m, 7H)
IR(KBr) 3407, 1624, 1518, 1480, 1361, 1287, 1270, 1234, 1175, 1117, 1084 1009 cm⁻¹

I-643 ¹HNMR(CDCl₃) δ 2.40(s, 3H), 2.67(s, 3H), 3.09(s, 3H), 3.13(s, 3H), 3.59(s, 3H), 3.78(s, 3H), 5.19(s, 1H), 6.17(s, 1H), 6.85(s, 1H), 7.15(d, J=8.4 Hz, 1H), 7.30–7.49(m, 9H), 7.69(d, J=1.8Hz, 1H)
IR(KBr) 3433, 3304, 1608, 1519, 1481, 1365, 1326, 1294, 1269, 1237, 1177, 1156, 1114, 1079, 1015 cm⁻¹

I-644 ¹HNMR(CDCl₃) δ 2.09(s, 3H), 2.39(s, 3H), 2.68(s, 3H), 3.13(s, 3H), 3.49(s, 3H), 3.76(s, 3H), 5.19(s, 2H), 6.30(s, 1H), 6.77(s, 1H), 7.12–7.24(m, 3H), 7.31–7.49(m, 9H), 7.54(d, J=1.8Hz, 1H), 7.67(d, J=8.4Hz, 2H)
IR(KBr) 3434, 1608, 1519, 1481, 1366, 1293, 1269, 1237, 1164, 1114, 1081, 1016 cm⁻¹

I-645 ¹HNMR(CDCl₃) δ 2.09(s, 3H), 2.39(s, 3H), 3.43(s, 3H), 3.73(s, 3H), 5.16(s, 2H), 5.30(s, 1H), 5.68(s, 1H), 5.89(s, 1H), 6.32(s, 1H), 6.36 (s, 1H), 6.95.(d.d, J=8.7&2.1Hz, 1H), 7.03 (d, J=8.7Hz, 1H), 7.08(d, J=2.1Hz, 1H), 7.14–7.28(m, 3H), 7.34–7.50(m, 5H), 7.61 (.d, J=1.5Hz, 1H), 7.68 (d, J=8.4Hz, 2H)
IR(KBr) 3465, 3270, 1612, 1587, 1558, 1519, 1487, 1454, 1384, 1244, 1160, 1123, 1105, 1091, 1070, 1009 cm⁻¹

I-646 ¹HNMR(CDCl₃) δ 2.48(s, 3H), 2.63(s, 3H), 3.02(s, 3H), 3.13(s, 3H), 3.28(s, 2H), 3.54(s, 3H), 3.78(s, 3H), 5.19(s, 2H), 6.85(s, 1H), 7.15(d, J=8.4Hz, 1H), 7.30–7.49(m, 9H), 7.59(s, 1H)
IR(KBr) 3433, 1606, 1519, 1481, 1364, 1341, 1292, 1272, 1233, 1178, 1148, 1118, 1082 cm⁻¹

TABLE 127-continued

I-647 ¹HNMR(CDCl₃) δ 2.48(s, 3H), 3.02(s, 3H), 3.28(s, 3H), 3.46(s, 3H), 3.75(s, 3H), 5.16(s, 2H), 5.70(s, 1H), 5.84(s, 1H), 6.47(s, 1H), 6.94 (d.d, J=8.4&2.1Hz, 1H), 7.03(.d, J=8.4Hz, 1H), 7.07(d, J=2.1Hz, 1H), 7.33–7.53(m, 7H), 7.62(d, J=1.8Hz, 1H)
IR(KBr) 3528, 3429, 1609, 1584, 1558, 1517, 1487, 1454, 1331, 1317, 1137, 1115, 1068, 1002 cm⁻¹

TABLE 128

I-648 ¹HNMR(CDCl₃) δ 1.55(s, 3H), 2.45(s, 3H), 2.79(s, 3H), 3.02(s, 3H), 3.29(s, 3H), 3.52(s, 3H), 3.77(s, 3H), 4.12–4.31(m, 2H), 5.22–5.31(m, 1H), 6.30(s, 1H), 6.84(s, 1H), 7.17(d, J=8.7Hz, 1H), 7.25–7.32(m, 2H), 7.39(d, J=8.4Hz, 1H), 7.45(d.d, J=8.4&1.8Hz, 1H), 7.53(d, J=1.8Hz, 1H)
IR(KBr) 3431, 1609, 1522, 1481, 1365, 1334, 1294, 1235, 1178, 1150, 1077, 1013 cm⁻¹

I-649 ¹HNMR(CDCl₃) δ 1.54(s, 3H), 1.68(s, 3H), 1.76(s, 3H), 1.81(s, 3H), 2.45(s, 3H), 2.68(s, 3H), 3.02(s, 3H), 3.24(s, 3H), 3.52(s, 3H), 3.78(s, 3H), 4.10–4.34(m, 2H), 4.64(d, J=7.2Hz, 2H), 5.21–5.30(m, 1H), 5.45–5.53(m, 1H), 6.84(s, 1H), 7.08(d, J=8.4Hz, 1H), 7.31–7.48(m, 4H), 7.53(d, J=1.5Hz, 1H)
IR(KBr) 3432, 1606, 1518, 1481, 1362, 1340, 1292, 1276, 1236, 1177, 1153, 1116, 1076, 1010 cm⁻¹

I-650 ¹HNMR(CDCl₃) δ 1.56(s, 3H), 1.68(s, 3H), 1.76(s, 3H), 1.82(s, 3H), 2.44(s, 3H), 3.02(s, 3H), 3.45(s, 3H), 3.75(s, 3H), 4.10–4.32 (m, 2H), 4.62 (d, J=7.2Hz, 2H), 5.22–5.32(m, 1H), 5.48–5.57(m, 1H), 5.60–5.80(brroad, 1H), 5.82(s, 1H), 6.46(s, 1H), 6.92 (d.d, J=8.1&1.8Hz, 1H), 6.97(d, J=8.1Hz, 1H), 7.04(d, J=1.8Hz, 1H), 7.38(d, J=8.1Hz, 1H), 7.47(d.d, J=8.1&1.8Hz, 1H), 7.57 (d, J=1.8Hz, 1H)
IR(KBr) 3433, 1610, 1586, 1557, 1518, 1486, 1336, 1240, 1149, 1110, 1069 cm⁻¹

I-651 ¹HNMR(CD₃OD) δ 3.33(s, 3H), 3.66(s, 3H), 5.18(s, 2H), 6.42(s, 1H), 1H), 6.75(dd, J=8.4&2.1Hz, 1H), 6.87(d, J=2.1Hz, 1H), 6.95 (d, J=8.4Hz, 1H), 7.26–7.58(m, 8H), 7.81(d.d, J=7.8&1.2Hz, 1H)
IR(KBr) 3446, 1698, 1586, 1517, 1498, 1481, 1454, 1408, 1287, 1247, 1117, 1069, 1010 cm⁻¹

I-652 ¹HNMR(CDCl₃) δ 1.76(s, 3H), 1.81(s, 3H), 2.76(s, 3H), 3.23(s, 3H), 3.43(s, 3H), 3.72(s, 3H), 3.76(s, 3H), 4.64(d, J=6.6Hz, 2H), 5.50(t, J=6.6Hz, 1H), 6.78(s, 1H), 7.08(d, J=8.7Hz, 1H), 7.33–7.51(m, 4H), 7.56–7.63(m, 1H), 7.96(d.d, J=7.5&1.2Hz, 1H)
IR(KBr) 1725, 1609, 1520, 1480, 1400, 1366, 1295, 1260, 1178, 1119, 1073, 1010 cm⁻¹

I-653 ¹HNMR(CDCl₃) δ 2.38(s, 3H), 2.72(s, 3H), 3.12(s, 3H), 3.43(s, 3H), 3.73(s, 3H), 3.76(s, 3H), 5.14(s, 2H), 6.79(s, 1H), 7.13–7.24 (m, 3H), 7.30–7.38(m, 3H), 7.41–7.51(m, 3H), 7.56–7.63(m, 1H), 795(d.d, J=7.5&1.2Hz, 1H)
IR(KBr) 1725, 1610, 1520, 1481, 1401, 1370, 1293, 1262, 1179, 1119, 1076, 1011 cm⁻¹

TABLE 129

I-654 ¹HNMR(CDCl₃) δ 1.75(s, 3H), 1.81(s, 3H), 3.56(s, 3H), 3.72(s, 3H), 4.60(d, J=6.6Hz, 2H), 5.29(s, 1H), 5.46–5.56(m, 1H), 5.56–6.00(broad, 1H), 6.42(s, 1H), 6.94(s, 2H), 7.05(s, 1H), 7.43–7.52 (m, 2H), 7.56–7.65(m, 1H), 7.99(.d, J=8.7Hz, 1H)
IR(KBr) 3433, 1697, 1585, 1517, 1481, 1454, 1410, 1287, 1244, 1117, 1068 cm⁻¹

I-655 ¹HNMR(CDCl₃) δ 2.39(s, 3H), 3.37(s, 3H), 3.72(s, 3H), 5.10(s, 2H), 6.41(s, 1H), 6.94(dd, J=8.1&2.1Hz, 1H), 7.02(d, J=8.1Hz, 1H), 7.06(d, J=2.1Hz, 1H), 7.23(d, J=7.8Hz, 2H), 7.35(.d, J=7.8Hz, 2H), 7.42–7.63(m, 3H), 7.96(d, J=7.8Hz, 1H)
IR(KBr) 3538, 3443, 1685, 1518, 1458, 1413, 1253, 1116, 1069, 1010 cm⁻¹

I-656 m.p. 110–112° C.
¹HNMR(CDCl₃) δ 1.69(s, 3H), 1.74(s, 3H), 2.55(q, J=7.1 Hz, 2H), 3.20(s, 3H), 3.21(s, 3H), 3.39(s, 3H), 3.70(s, 3H), 4.07(t, J=

TABLE 129-continued 7.1Hz, 2H), 5.22(t, J=7.1Hz, 1H), 6.28(s, 1H), 7.09(d, J=8.4Hz, 1H), 7.32(dd, J=8.4, 2.0Hz, 1H), 7.36(d, J=8.9Hz, 2H), 7.37(d, J=2.0Hz, 1H), 7.69(d, J=8.9Hz, 2H)
IR(KBr) 3477, 3402, 1607, 1518, 1481, 1365, 1151, 1111, 872, 813 cm$^{-1}$ I-657 m.p. 159–162° C.
$^1$HNMR(DMSO-d$_6$) δ 1.64(s, 3H), 1.71(s, 3H), 2.45(q, J=6.7Hz, 2H), 3.27(s, 3H), 3.59(s, 3H), 3.96(t, J=6.7Hz, 2H), 4.22(s, 2H), 5.26(t, J=6.7Hz, 1H), 6.17(s, 1H), 6.60(dd, J=8.1,2.0Hz, 1H), 6.67(d, J=2.0Hz, 1H), 6.83(d, J=8.7Hz, 2H), 6.95(d, J=8.1Hz, 1H), 7.42(d, J=8.7Hz, 2H), 8.89(s, 1H), 9.46(s, 1H)
IR(KBr) 3447, 3401, 3361, 1611, 1522, 1486, 1260, 1228, 1122, 1001, 814 cm$^{-1}$ I-658 m.p. 146–147° C.
$^1$HNMR(CDCl$_3$) δ 1.14(t, J=7.2Hz, 3H), 1.76(d, J=0.9Hz, 3H), 1.81(d, J=0.3Hz, 3H), 2.70(s, 3H), 3.20(s, 3H), 3.23(s, 3H), 3.72(q, J=7.2Hz, 2H), 3.78(s, 3H), 4.64(d, J=6.6Hz, 2H), 5.49(m, 1H), 6.84(s, 1H), 7.09(d, J=8.4Hz, 1H), 7.31–7.41(m, 4H), 7.66–7.74(m, 2H)
IR(CHCl$_3$)2930, 1608, 1517, 1479, 1369, 1148, 1116, 1082, 969, 872 cm$^{-1}$ I-659 m.p.174–175° C.
$^1$HNMR(CDCl$_3$) δ 1.14(t, J=6.9Hz, 3H), 2.37(s, 3H), 2.65(s, 3H), 3.12(s, 3H), 3.20(s, 3H), 3.72(q, J=6.9Hz, 2H), 3.77(s, 3H), 5.14(s, 2H), 6.84(s, 1H), 7.15(d, J=8.4Hz, 1H), 7.18–7.42(m, 6H), 7.66–7.73(m, 2H)
IR(CHCl$_3$)1517, 1479, 1369, 1268, 1148, 1117, 1082, 969, 872 cm$^{-1}$

TABLE 130

I-660 m.p. 147.5–148° C.
$^1$HNMR(CDCl$_3$) δ 1.14(t, J=7.2Hz, 3H), 1.68(s, 3H), 1.74(d, J=0.9Hz, 3H), 2.50–2.59(m, 2H), 2.72(s, 3H), 3.20(s, 3H), 3.22(s, 3H), 3.72(q, J=7.2Hz, 2H), 3.77(s, 3H), 4.07(d, J=6.9Hz, 2H), 5.21(m, 1H), 6.84(s, 1H), 7.07(d, J=8.7Hz, 1H), 7.31–7.42(m, 4H), 7.66–7.74(m, 2H)
IR(CHCl$_3$)2930, 1607, 1517, 1480, 1369, 1148, 1118, 1082, 1025, 969, 872 cm$^{-1}$

I-661 m.p. 154–157° C.
$^1$HNMR(CDCl$_3$) δ 1.15(t, J=7.2Hz, 3H), 1.76(s, 3H), 1.82(s, 3H), 3.60(q, J=7.2Hz, 2H), 3.75(s, 3H), 4.61(d, J=6.9HZ, 2H), 4.93(s, 1H), 5.53(m, 1H), 5.69(s, 1H), 5.96(s, 1H), 6.45(s, 1H), 6.80–6.98(m, 4H), 7.07(m, 1H), 7.51–7.58(m, 2H)
IR(CHCl$_3$)3592, 3528, 2976, 2934, 1611, 1521, 1488, 1460, 1384, 1286, 1243, 1169, 1112, 1068, 994, 885, 824 cm$^{-1}$

I-662 m.p. 130.5–133° C.
$^1$HNMR(CDCl$_3$) δ 1.15(t, J=7.2Hz, 3H), 2.39(s, 3H), 3.59(q, J=7.2Hz, 2H), 3.74(s, 3H), 4.83(S, 1H), 5.10(s, 2H), 5.66(s, 1H), 5.97(s, 1H), 6.44(s, 1H), 6.87–6.94(m, 2H), 6.96(dd, J=1.8, 8.4Hz, 1H), 7.02(d, J=8.4Hz, 1H), 7.09(d, J=1.8Hz, 1H), 7.19–7.26(m, 2H), 7.30–7.38(m, 2H), 7.51–7.58(m, 2H)
IR(CHCl$_3$)3524, 1612, 1521, 1488, 1460, 1383, 1286, 1246, 1113, 1069, 1027, 907, 873 cm$^{-1}$

I-663 amorphous powder
$^1$HNMR(CDCl$_3$) δ 1.15(t, J=7.2Hz, 3H), 1.68(d, J=0.6Hz, 3H), 1.74(d, J=0.9Hz, 3H), 2.48–2.56(m, 2H), 3.60(q, J=7.2Hz, 2H), 3.74(s, 3H), 4.06(d, J=6.9Hz, 2H), 4.95(s, 1H), 5.22(m, 1H), 5.68(s, 1H), 5.96(s, 1H), 6.44(s, 1H), 6.88–6.99(m, 4H), 7.06(d, J=1.2Hz, 1H), 7.51–7.58(m, 2H)
IR(CHCl$_3$)3528, 2972, 1611, 1521, 1488, 1384, 1286, 1246, 1112, 1068, 1024, 883, 824 cm$^{-1}$ I-664 m.p. 113–116° C.
$^1$HNMR(CDCl$_3$) δ 2.55(s, 6H), 3.45(s, 3H), 3.74(s, 3H), 5.31(s, 2H), 6.44(s, 1H), 6.92(d, J=8.7Hz, 2H), 6.94(dd, J=8.4, 2.1Hz, 1H), 7.10(s, 1H), 7.10(d, J=2.1Hz, 1H), 7.20(d, J=8.7Hz, 1H), 7.52(d, J=8.7Hz, 2H)
IR(Nujol)3491, 3443, 3304, 3155, 1662, 1608, 1523, 1492, 1464, 1251, 1215, 1111, 1067, 811, 782 cm$^{-1}$

TABLE 131

I-665 m.p. >260° C.
$^1$HNMR(CD$_3$OD) δ 3.39(s, 3H), 3.68(s, 3H), 5.40(s, 2H), 6.44(s, 1H), 6.83(dd, J=8.4, 2.1Hz, 1H), 6.85(d, J=8.7, 2H), 6.90(d, J=2.1Hz, 1H), 7.11(d, J=8.4Hz, 1H), 7.46(d, J=8.7Hz, 2H)
IR(Nujol)3350, 2668, 1611, 1595, 1530, 1488, 1458, 1402, 1253, 1213, 1116, 1073, 1016, 837, 817, 781 cm$^{-1}$ I-666 foam
$^1$HNMR(CDCl$_3$) δ 2.34(s, 3H), 2.44(s, 3H), 2.83(s, 3H), 3.12(s, 3H), 3.22(s, 3H), 3.55(s, 3H), 3.78(s, 3H), 4.92(s, 2H), 6.85(s, 1H), 7.17(d, J=8.4Hz, 1H), 7.37~7.42(m, 2H), 7.39(d, J=8.7Hz, 2H), 7.68(d, J=8.7Hz, 2H)
IR(Nujol)1638, 1608, 1519, 1480, 1459, 1177, 1151, 1079, 971, 876, 844, 798 cm$^{-1}$ I-667 foam
$^1$HNMR(CDCl$_3$) δ 2.07(s, 3H), 2.53(s, 3H), 2.96(s, 3H), 3.23(s, 3H), 3.27(s, 3H), 3.54(s, 3H), 3.78(s, 3H), 4.86(s, 2H), 6.86(s, 1H), 7.11(d, J=9.0Hz, 1H), 7.33~7.41(m, 2H), 7.39(d, J=8.7Hz, 2H), 7.67(d, J=8.7Hz, 2H)
IR(Nujol)1724, 1688, 1610, 1520, 1481, 1464, 1234, 1177, 1151, 1123, 1081, 876, 798 cm$^{-1}$ I-668 m.p. 221–223° C.
$^1$HNMR(DMSO-d$_6$) δ 3.30(s, 3H), 3.64(s, 3H), 5.16(s, 2H), 6.39(s, 1H), 6.66(dd, J=8.4, 2.1Hz, 1H), 6.77(d, J=2.1Hz, 1H), 6.84(d, J=8.7Hz, 2H), 7.00(d, J=8.4Hz, 1H), 7.34(s, 1H), 7.44(d, J=8.7Hz, 2H), 8.43(s, 1H)
IR(Nujol)3535, 3411, 1611, 1582, 1521, 1488, 1463, 1244, 1194, 1135, 1119, 1074, 1014, 930, 826, 809 cm$^{-1}$ I-669 foam
$^1$HNMR(CDCl$_3$) δ 2.79(s, 3H), 3.17(s, 3H), 3.22(s, 3H), 3.55(s, 3H), 3.78(s, 3H), 5.21(s, 2H), 6.85(s, 1H), 7.19(d, J=8.4Hz, 1H), 7.23(s,1H), 7.38(dd, J=8.7, 2.1Hz, 1H), 7.39(d, J=8.7Hz, 2H), 7.42(d, J=2.1Hz, 1H), 7.68(d, J=8.7Hz, 2H), 7.94(8, 1H)
IR(Nujol)1608, 1519, 1480, 1463, 1177, 1151, 1119, 1079, 971, 876, 798 cm$^{-1}$

TABLE 132

I-670 m.p. 198–201° C.
$^1$HNMR(DMSO-d$_6$) δ 2.88(s, 3H), 3.39(s, 3H), 3.45(s, 3H), 3.52(s, 3H), 3.78(s, 3H), 4.58(s, 2H), 5.60(s, 1H), 7.07(s, 1H), 7.29(dd, J=9.0, 1.8Hz, 1H), 7.30(d, J=1.8, Hz, 1H), 7.37(d, J=9.0Hz, 1H), 7.48(d, J=8.7Hz, 2H), 7.74(d, J=8.7Hz, 2H), 9.39(s, 1H)
IR(Nujol)3576, 3500, 3405, 3391, 1668, 1607, 1590, 1520, 1480, 1462, 1175, 1156, 1081, 1014, 880, 836, 826, 801 cm$^{-1}$ I-671 foam
$^1$HNMR(CDCl$_3$) δ 2.61(s, 3H), 2.73(s, 3H), 3.21(s, 3H), 3.23(s, 3H), 3.55(s, 3H), 3.78(s, 3H), 5.32(s, 2H), 6.84(s, 1H), 7.17(d, J=8.4Hz, 1H), 7.36(dd, J=8.4, 2.1Hz, 1H), 7.38(d, J=8.7, Hz, 2H), 7.43(d, J=2.1Hz, 1H), 7.68(d, J=8.7Hz, 2H), 8.46(s, 1H), 8.75(s, 1H)
IR(Nujol)1608, 1519, 1481, 1463, 1177, 1151, 1080, 971, 876, 798 cm$^{-1}$ I-672 foam
$^1$HNMR(CDCl$_3$) δ 2.75(s, 3H), 3.21(s, 3H), 3.25(s, 3H), 3.55(s, 3H), 3.78(s, 3H), 5.37(s, 2H), 6.84(s, 1H), 7.17(d, J=8.4Hz, 1H), 7.36(dd, J=8.4, 2.1Hz, 1H), 7.38(d, J=8.7, Hz, 2H), 7.43(d, J=2.1Hz, 1H), 7.68(d, J=8.7Hz, 2H), 8.59(s, 1H), 8.92(s, 1H)
IR(Nujol)1608, 1519, 1480, 1463, 1177, 1151, 1080, 971, 876, 798 cm$^{-1}$ I-673 foam
$^1$HNMR(CDCl$_3$) δ 2.70(s, 3H), 3.15(s, 3H), 3.21(s, 3H), 3.55(s, 3H), 3.78(s, 3H), 5.14(s, 2H), 6.77(m, 2H), 6.84(s, 1H), 7.19(m, 2H), 7.26(d, J=8.4Hz, 1H), 7.37(d, J=2.1Hz, 1H), 7.38(dd, J=2.1, 8.4Hz, 1H), 7.68(d, J=8.4Hz, 2H)

I-674 m.p.153–156° C.
$^1$HNMR(CDCl$_3$) δ 2.18(s, 3H), 2.81(s, 3H), 3.18(s, 3H), 3.22(s, 3H), 3.55(s, 3H), 3.79(s, 3H), 5.14(s, 2H), 6.86(s, 1H), 7.18(dd, J=8.1, 8.1Hz, 1H), 7.24(d, J=8.1Hz, 1H), 7.26(d, J=8.4Hz, 1H), 7.36(d, J=1.8Hz, 1H), 7.38(d, J=8.4Hz, 2H), 7.39(dd, J=1.8, 8.4Hz, 1H), 7.43(d, J=8.1, 8.1Hz, 1H), 7.67(d, J=8.4Hz, 2H), 7.90(d, J=8.1Hz, 1H)
IR(KBr) 3384, 1689, 1519, 1481, 1364, 1177, 1151, 1079, 970, 874, 798 cm$^{-1}$

TABLE 133

I-675 foam
$^1$HNMR(CDCl$_3$) δ 2.76(s, 3H), 3.16(s, 3H), 3.22(s, 3H), 3.23(s, 3H), 3.55(s, 3H), 3.78(s, 3H), 5.23(s, 2H), 6.85(S, 1H), 7.23(dd, J =7.5, 7.5Hz, 1H), 7.37(s, 2H), 7.38(d, J=8.4Hz, 2H), 7.43(m, 3H), 7.54(d, J=7.5HZ, 1H), 7.68(d, J=8.4Hz, 2H)
IR(KBr) 3435, 1609, 1519, 1481, 1364, 1177, 1152, 1079, 972, 876, 798 cm$^{-1}$ I-676 m.p. 163–165° C.
$^1$HNMR(CDCl$_3$ ) δ 2.78(s, 3H), 3.03(s, 3H), 3.21(s, 3H), 3.45(s, 6H), 3.55(s, 3H), 3.79(s, 3H), 5.31(s, 2H), 6.84(s, 1H), 7.22(d, J= 8.4Hz, 1H), 7.37(dd, J=2.4, 8.4Hz, 1H), 7.38(d, J=8.4Hz, 2H), 7.42(m, 2H), 7.53(m, 2H), 7.67(d, J=8.4HZ, 2H), 7.68(m, 1H)
IR(KBr) 1609, 1519, 1481, 1365, 1176, 1161, 1080, 973, 875, 799 cm$^{-1}$ I-677 m.p. 153–156° C.
$^1$HNMR(CDCl$_3$ a) δ 2.69(s, 3H), 2.98(s, 3H), 3.17(s, 3H), 3.21(s, 3H), 3.33(s, 3H), 3.56(s, 3H), 3.78(s, 3H), 5.44(s, 2H), 6.84(s, 1H), 7.21(d, J=8.7Hz, 1H), 7.31–7.46(m, 5H), 7.38(d, J=8.4Hz, 2H), 7.68(d, J=8.4Hz, 2H), 7.72(m, 1H)
IR(KBr) 1610, 1519, 1481, 1365, 1177, 1149, 1079, 963, 876, 799 cm$^{-1}$ I-678 foam
$^1$HNMR(CDCl$_3$ ) δ 2.60(s, 3H), 2.75(s, 6H), 3.17(s, 3H), 3.21(s, 3H), 3.55(s, 3H), 3.78(s, 3H), 5.31(s, 2H), 6.83(s, 1H), 7.08(dd, J= 7.5, 7.5Hz, 1H), 7.16(d, J=8.4Hz, 1H), 7.17(d, J=7.5Hz, 1H), 7.30 (dd, J=2.1, 8.4HZ, 1H), 7.32(dd, J=7.5, 7.5Hz, 1H), 7.37(d, J= 8.4Hz, 2H), 7.38(d, J=2.1Hz, 1H), 7.52(d, J=7.5Hz, 1H), 7.68(d, J=8.4Hz, 2H)
IR(KBr) 1609, 1519, 1480, 1365, 1235, 1177, 1151, 1079, 970, 874, 797 cm$^{-1}$ I-679 m.p.95–97° C.
$^1$HNMR(CDCl$_3$ 3) δ 1.76(s, 3H), 1.80(s, 3H), 3.03(s, 3H), 3.21(s, 3H), 3.56(s, 3H), 3.75(m, 3H), 4.63(d, J=6.9Hz, 2H), 4.93(8, 2H), 5.51(m, 1H), 6.66(s, 1H), 7.05(d, J=8.4Hz, 1H), 7.09–7.17(m, 2H), 7.37(dd, J=2.4, 8.4Hz, 1H), 7.44(d, J=2.4Hz, 1H), 7.51–7.58 (m, 2H)
IR(KBr) 3435, 2936, 1605, 1519, 1475, 1382, 1365, 1232, 1161, 1109, 1080 cm$^{-1}$

TABLE 134

I-680 m.p. 142–144° C.
$^1$HNMR(CDCl$_3$) δ 1.76(s, 3H), 1.81(s, 3H), 3.07(s, 3H), 3.57(s, 3H), 3.74(s, 3H), 4.61(d, J=6.6HZ, 2H), 4.90(s, 2H), 5.51(m, 1H), 5.65(s, 1H), 6.66(s, 1H), 6.92(m, 2H), 7.03(m, 1H), 7.09–7.17(m, 2H), 7.52–7.58(m, 2H)
IR(KBr) 3455, 2964, 2932, 1606, 1583, 1519, 1479, 1387, 1283, 1227, 1153, 1115, 1080, 1094, 1004 cm$^{-1}$

I-681 m.p. 158–160° C.
$^1$HNMR(CDCl$_3$) δ 1.76(s, 3H), 1.81(s, 3H), 3.20(s, 3H), 3.42(s, 3H), 3.76(s, 3H), 4.63(d, J=6.6Hz, 2H), 5.51(m, 1H), 6.04(s, 1H), 6.43(s, 1H), 7.07(d, J=8.4Hz, 1H), 7.11–7.19(m, 2H), 7.42(dd, J= 2.1, 8.4Hz, 1H), 7.50(d, J=2.1Hz, 1H), 7.58–7.65(m, 2H)
IR(KBr) 3505, 3440, 1613, 1522, 1489, 1386, 1352, 1292, 1227, 1109, 1013 cm$^{-1}$

I-682 m.p. 175–178° C.
$^1$HNMR(CDCl$_3$) δ 1.63(s, 3H), 1.92–2.13(m, 4H), 3.22(s, 3H), 3.42(s, 3H), 3.76(s, 3H), 4.13(t, J=6.3Hz, 2H), 6.04(s, 1H), 6.44(s, 1H), 7.06(d, J=8.4Hz, 1H), 7.11–7.19(m, 2H), 7.43(dd, J=2.1, 8.4Hz, 1H), 7.49(d, J=2.1Hz, 1H), 7.57–7.65(m, 2H)
IR(KBr) 3467, 2973, 2943, 1613, 1523, 1489, 1359, 1232, 1113, 1072 cm$^{-1}$

I-683 powder
$^1$HNMR(CDCl$_3$ ) δ 1.69(s, 3H), 1.75(s, 3H), 2.48–2.57(m, 2H), 3.08(s, 3H), 3.57(s, 3H), 3.74(s, 3H), 4.06(t, J=6.9Hz, 2H), 490(s, 2H), 5.22(m, 1H), 5.64(s, 1H), 6.66(s, 1H), 6.91(m, 2H), 7.03(m, 1H), 7.08–7.17(m, 2H), 7.52–7.59(m, 2H)
IR(KBr) 3432, 2930, 1604, 1583, 1518, 1475, 1382, 1280, 1249, 1222, 1160, 1111, 1082 cm$^{-1}$ I-684 m.p. 151–153° C.
$^1$HNMR(CDCl$_3$ ) δ 1.69(s, 3H), 1.73(s, 3H), 2.50–2.59(m, 2H), 3.19(s, 3H), 3.42(s, 3H), 3.76(s, 3H), 4.06(t, J=6.9Hz, 2H), 5.21 (m, 1H), 6.02(s, 1H), 6.43(s, 1H), 7.05(d, J=8.4Hz, 1H), 7.11–7.19 (m, 2H), 7.42(dd, J=2.4, 8.4Hz, 1H), 7.50(d, J=2.4Hz, 1H), 7.57–7.65(m, 2H)
IR(KBr) 3457, 2937, 1613, 1523, 1489, 1465, 1390, 1361, 1295, 1234, 1185, 1110, 1072, 1013 cm$^{-1}$

TABLE 135

I-685 m.p.156–158° C.
$^1$HNMR(CDCl$_3$) δ 1.76(s, 3H), 1.81(s, 3H), 3.21(s, 3H), 3.42(s, 3H), 3.76(s, 3H), 4.54(d, J=6, 9Hz, 2H), 5.52(t, J=.9Hz, 1H), 6.94 (s, 1H), 6.94(d, J=8.7Hz, 2H), 7.29(d, J=8.7Hz, 2H), 7.37(d, J= 8.7Hz, 2H), 7.71(d, J=8.7Hz, 2H)
IR(KBr) 1734, 1517, 1464, 1360, 1237, 1150, 1061, 988, 862 cm$^{-1}$

I-686 m.p. 189–191° C.
$^1$HNMR(CDCl$_3$) δ 3.21(s, 3H), 3.21(s, 3H), 3.42(s, 3H), 3.61(s, 3H), 3.76(s, 3H), 5.09(s, 2H), 6.94(s, 1H), 7. 10(d, J=8.4Hz, 2H), 7.28–7.48(m, 9H), 7.71(d, J=8.4Hz, 2H)
IR(KBr) 1727, 1518, 1469, 1365, 1239, 1152, 1061, 865 cm$^{-1}$

I-687 m.p. 112–113° C.
$^1$HNMR(CDCl$_3$) δ 1.68(s, 3H), 1.74(s, 3H), 2.50(q, J=7.2Hz, 2H), 3.21(s, 3H), 3.42(s, 3H), 3.62(s, 3H), 3.76(s, 3H), 3.96(t, J=7.2Hz, 2H), 5.23(t, J=7.2Hz, 1H), 6.92(d, J=8.8Hz, 2H), 6.93(s, 1H), 7.28 (d, J=8.8Hz, 2H), 7.37(d, J=8.8Hz, 2H), 7.71(d, J=8.8Hz, 2H)
IR(KBr) 1735, 1519, 1469, 1361, 1246, 1153, 1059, 877, 861, 847, 791 cm$^{-1}$

I-688 m.p. 191–193° C.
$^1$HNMR(DMSO-d$_6$) δ 1.73(s, 3H), 1.76(s, 3H), 3.31(s, 3H), 3.71 (s, 3H), 4.54(d, J=6, 9Hz, 2H), 5.46(t, J=6.9Hz, 1H), (s, 1H), 6.87 (d, J=8.7Hz, 2H), 6.91(s, 1H), 6.92(d, J=8.7Hz, 2H), 7.19(d, J= 8.7Hz, 2H), 7.48(d, J=8.7Hz, 2H), 9.59(s, 1H), 12.8(brs, 1H)
IR(KBr) 3462, 1695, 1609, 1520, 1472, 1231, 1177, 1062, 1001, 837 cm$^{-1}$ I-689 m.p. 229–232° C.
$^1$HNMR(DMSO-d$_6$) δ 3.31(s, 3H), 3.71(s, 3H), 5.12(s, 2H), 6.87 (d, J=8.8Hz, 2H), 6.98(s, 1H), 7.01(d, J=8.8Hz, 2H), 7.21(d, J= 8.8Hz, 2H), 7.34–7.50(m, 7H), 9.58(s, 1H), 12.8(brs, 1H)
IR(KBr) 3424, 3238, 1685, 1610, 1521, 1464, 1379, 1235, 1180, 1057, 1001, 826 cm$^{-1}$

TABLE 136

I-690 m.p. 171–172° C.
$^1$HNMR(DMSO-d$_6$) δ 1.64(s, 3H), 1.70(s, 3H), 2.43(q, J=6.9Hz, 2H), 3.31(s, 3H), 3.70(s, 3H), 3.96(t, J=6.9Hz, 2H), 5.23(t, J= 6.9Hz, 1H), 6.87(d, J=8.8Hz, 2H), 6.91(d, J=8.8Hz, 2H), 6.98(s, 1H), 7.19(d, J=8.8Hz, 2H), 7.48(d, J=8.8Hz, 2H), 9.58(s, 1H), 12.8(brs, 1H)
IR(KBr) 3402, 3266, 1689, 1612, 1521, 1470, 1376, 1241, 1181, 1063, 1001, 829 cm$^{-1}$ I-691 m.p. 191–193° C.
$^1$HNMR(CDCl$_3$) δ 2.55(s, 3H), 3.52(s, 3H), 3.77(s, 3H), 5.17(s, 2H), 5.70(s, 1H), 6.83(s, 1H), 6.91(dd, J=1.8, 8.1Hz, 1H), 7.00–7.05(m, 2H), 7.10–7.19 (m, 2H), 7.34–7.45(m, 5H), 7.57–7.65(m, 2H)
IR(KBr) 3030, 2934, 1606, 1523, 1487, 1391, 1358, 1290, 1228, 1077, 1019, 947, 831, 815, 803 cm$^{-1}$ I-692 m.p. 172–173° C.
$^1$HNMR(CDCl$_3$ ) δ 2.47(s, 3H), 3.52(s, 3H), 3.53(s, 3H), 3.77(s, 3H), 5.21(s, 2H), 5.25(s, 2H), 6.82(s, 1H), 7.01–7.03(m, 2H), 7.11–7.18(m, 2H), 7.22–7.41 (m, 6H), 7.57–7.63(m, 2H)
IR(KBr) 3010, 2931, 1602, 1519, 1484, 1385, 1369, 1232, 1174, 1085, 847, 806, 729, 527 cm$^{-1}$ I-693 m.p. 129–132° C.
$^1$HNMR(CDCl$_3$ ) δ 3.44(s, 3H), 3.53(s, 3H), 3.75(s, 3H), 5.20(s, 2H), 5.26(s, 2H), 5.91(s, 1H), 6.44(s, 1H), 7.01(d, J=8.1Hz, 1H), 7.08 (dd, J=1.8Hz, 8.1Hz, 1H), 7.11–7.18(m, 2H), 7.28–7.50(m, 6H), 7.57–7.64(m, 2H)
IR(KBr) 2996, 2952, 2932, 2895, 1609, 1522, 1488, 1229, 1120, 1075, 999, 911, 815, 724, 582 cm$^{-1}$ I-694 m.p. 124–126° C.
$^1$HNMR(CDCl$_3$) δ 1.76(d, J=0.6Hz, 3H), 1.80(d, J=0.9Hz, 3H),

TABLE 136-continued 2.69(2H, s), 3.54(s, 3H), 3.57(s, 3H), 3.76(s, 3H), 4.64(d, J=6.6Hz, 2H), 5.26(s, 3H), 5.54(m, 1H), 6.86(s, 1H), 6.98(d, J=8.7Hz, 1H), 7.13–7.25(m, 3H), 7.38–7.43(m, 3H)
IR(CHCl$_3$)2935, 2855, 1675, 1603, 1520, 1481, 1387, 1370, 1247, 1178, 1158, 1134, 1081, 1003, 961, 839, 814 cm$^{-1}$

TABLE 137

I-695 m.p. 141–142° C.
$^1$HNMR(CDCl$_3$) δ 2.34(s, 3H), 2.48(s, 3H), 5.16(s, 2H), 5.70(s, 1H), 6.82(dd, J=8.4, 2.1Hz, 1H), 6.97–7.00(m, 2H), 7.07–7.13(m, 4H), 7.32–7.46(m, 7H)
IR(CHCl$_3$)3543, 3023, 2871, 1604, 1587, 1520, 1489, 1469, 1383, 1267, 1243, 1158, 1126, 1014, 957, 877, 839 cm$^{-1}$

I-696 mp 178–180° C.
$^1$HNMR(CDCl$_3$) δ 2.75(s, 3H), 3. 18(s, 3H), 3.55(s, 3H), 3.76(s, 3H), 5. 18(s, 2H), 5.72(s, 1H), 6.87(s, 1H), 7.00(d, J=8.7Hz, 1H), 7.15 (dd, J=8.7, 2.1Hz, 1H), 7.24–7.28(m, 2H), 7.36–7.50(m, 8H)
IR(CHCl$_3$)3543, 3027, 2939, 1519, 1481, 1371, 1330, 1254, 1204, 1177, 1150, 1082 1005, 969, 873 cm$^{-1}$

I-697 mp 129–130° C.
$^1$HNMR(CDCl$_3$) δ 2.24(s, 3H), 2.29(s, 3H), 3.12(s, 3H), 5.18(s, 2H), 7.08–7.14(m, 5H), 7.25–7.50(m, 9H)
IR(CHCl$_3$)2925, 2871, 1604, 1520, 1490, 1455, 1369, 1291, 1262, 1169, 1111, 1007, 972, 957, 882, 840, 816 cm$^{-1}$

I-698 mp 124–125° C.
$^1$HNMR(CDCl$_3$) δ 1.77(s, 3H), 1.81–1.82(d, J=0.9Hz, 3H), 2.24(s, 3H), 2.28(s, 3H), 3.22(s, 3H), 4.63(d, J=6.6Hz, 2H), 5.52(m, 1H), 7.04–7.14(m, 5H), 7.24–7.34(m, 4H)
IR(KBr) 2978, 2924, 2868, 1893, 1771, 1604, 1520, 1489, 1368, 1290, 1261, 1169, 1109, 1046, 973, 957, 882, 740, 816 cm$^{-1}$

I-699 oil
$^1$HNMR(CDCl$_3$) δ 1.69(s, 3H), 1.74–1.75(d, J=0.9Hz, 3H), 2.24 (s, 3H), 2.28(s, 3H), 2.55(m, 2H), 3.21(s, 3H), 4.05–4.10(t, J=6.9Hz, 2H), 5.22(m, 1H), 7.03–7.14(m, 5H), 7.24–7.34(m, 4H)
IR(CHCl$_3$)2970, 2926, 2875, 1605, 1520, 1490, 1470, 1368, 1292, 1277, 1169, 1110, 1016, 973, 958, 878, 840, 819 cm$^{-1}$ I-700 mp 121–123° C.
$^1$HNMR(CDCl$_3$ 3) δ 2.24(s, 3H), 2.83(s, 3H), 2.98(s, 3H), 3.11(s, 3H), 5.13(s, 2H), 7.08–7.14(m, 4H), 7.21–7.37(m, 9H)
IR(CHCl$_3$)2925, 1605, 1520, 1489, 1369, 1262, 1169, 1014, 1003, 972, 957, 882, 840, 816 cm$^{-1}$

TABLE 138

I-701 mp 215–217° C.
$^1$HNMR (CDCl$_3$) δ 2.73(s, 3H), 3.13(s, 3H), 3.18(s, 3H), 3.57(s, 3H), 3.78(s, 3H), 5.20(s, 2H), 6.86(s, 1H), 7.16(d, J=8.7Hz, 1H), 7.35–7.50(m, 9H), 7.56(dd, J=8.4, 2.4Hz, 1H), 7.62(d, J=2.4Hz, 1H)
IR (CHCl$_3$)2939, 1613, 1519, 1480, 1371, 1294, 1254, 1176, 1150, 1119, 1083, 1003, 970, 871, 849, 816 cm$^{-1}$

I-702 mp 71–73° C.
$^1$HNMR (CDCl$_3$) δ 1.77(s, 3H), 1.83(s, 3H), 2.24(s, 3H), 2.29(s, 3H), 4.61–4.64(d, J=6.9Hz, 2H), 5.54(m, 1H), 5.71(s, 1H), 6.80–6.84(dd, J=8.4, 2.1Hz, 1H), 6.92(d, J=8.4Hz, 1H), 7.07–7.13(m, 4H), 7.30–7.37(m, 4H)
IR (KBr) 3537, 2977, 2924, 2868, 1604, 1585, 1520, 1489, 1450, 1386, 1292, 1267, 1242, 1158, 1125, 996, 957, 839 cm$^{-1}$

I-703 oil
$^1$HNMR (CDCl$_3$) δ 1.69(s, 3H), 1.75–1.76(d, J=0.9Hz, 3H), 2.24 (s, 3H), 2.28(s, 3H), 2.50–2.57(td, J=6.9, 6.3 Hz, 2H), 4.05–4.10(t, J=6.3Hz, 2H), 5.24(m, 1H), 5.70(s, 1H), 6.81(dd, J=8.4, 1.8Hz, 1H), 6.90(d, J=8.4 Hz, 1H), 6.96 (d, J=1.8Hz, 1H), 7.06–7.13(m, 4H), 7.26–7.34(m, 2H)
IR (CHCl$_3$)3540, 2972, 2925, 2877, 1604, 1585, 1520, 1490, 1387, 1293, 1267, 1245, 1158, 1127, 1016, 957, 839 cm$^{-1}$ I-704 mp 113–115° C.
$^1$HNMR (CDCl$_3$) δ 2.24(s, 3H), 2.28(s, 3H), 2.39(s, 3H), 5.11(s, 211), 5.69(s, 1H), 6.82(dd, J=8.4, 2.4Hz, 1H), 6.97–7.00(m, 2H),
7.07–7.13(m, 3H), 7.22–7.36(m, 7H)
IR (CHCl$_3$)3541, 2925, 2871, 1604, 1586, 1520, 1490, 1469, 1380, 1324, 1308, 1292, 1267, 1243, 1201, 1158, 1126, 1013, 957, 876, 839 cm$^{-1}$

TABLE 139

I-705 foam
$^1$H NMR (CDCl$_3$) δ 3.20(s, 3H), 3.27(s, 3H), 3.43(s, 3H), 3.73(s, 3H), 4.37(br d, J=5.7Hz, 2H), 4.58(s, 2H), 5.16(s, 2H), 5.68(s, 1H), 6.82(dd, J=8.2, 1.7Hz, 1H), 6.88(s, 1H), 6.97(d, J=1.7Hz, 1H), 6.98(d, J=8.2Hz, 1H), 7.35–7.47(m, 7H), 7.71(d, J=8.7Hz, 2H)
IR(KBr) 3464, 1515, 1474, 1369, 1230, 1199, 1176, 1149, 1039, 873 cm$^{-1}$ I-706 foam
$^1$H NMR(CDCl$_3$) δ 2.42(br s, 1H), 3.12(s, 3H), 3.22(s, 3H), 3.45(s, 3H), 3.74(s, 3H), 4.49(br s, 1H), 5.18(s, 2H), 6.85(s, 1H), 7.15(d, J=8.6Hz, 1H), 7.27(dd, J=8.6, 2.0Hz, 1H), 7.35–7.50(m, 8H), 7.71(d, J=8.6Hz, 2H)
IR(KBr) 3583, 3435, 1519, 1467, 1412, 1229, 1180, 1150, 1022, 875, 849, 798, 742, 706 cm$^{-1}$ I-707 mp 120–121° C.
$^1$H NMR(CDCl$_3$) δ 3.45(s, 3H), 3.45(s, 3H), 3.75(s, 3H), 4.66(s, 2H), 4.77(s, 2H), 5.15(s, 2H), 5.67(s, 1H), 5.91(s, 1H), 6.47(s, 1H), 6.96(dd, J=8.4, 1.9Hz, 1H), 7.03(d, J=8.4Hz, 1H), 7.09(d, J=1.9Hz, 1H), 7.37–7.47(m, 7H), 7.64(d, J=8.4Hz, 2H)
IR(KBr) 3504, 3461, 1522, 1485, 1466, 1384, 1466, 1384, 1283, 1245, 1197, 1110, 1042, 925, 812, 749 cm$^{-1}$ I-708 mp 156–158° C.
$^1$H NMR(CDCl$_3$) δ 3.11(s, 3H), 3.21(s, 3H), 3.28(s, 3H), 3.42(s, 3H), 3.73(s, 3H), 4.38(s, 2H), 4.58(s, 2H), 5.18(s, 2H), 6.88(s, 1H), 7.12(d, J=8.7Hz, 1H), 7.27(dd, J=8.7, 2.1Hz, 1H), 7.35–7.50 (m, 8H), 7.70(d, J=8.7Hz, 2H)
IR(KBr) 1514, 1469, 1360, 1177, 1149, 1099, 1042, 870 cm$^{-1}$ I-709 mp 188–190° C.
$^1$H NMR(CDCl$_3$) δ 1.70(t, J=5.7Hz, 1H), 3.45(s, 3H), 3.75(s, 3H), 4.77(d, J=5.7Hz, 2H), 5.16(s, 2H), 5.68(s, 1H), 5.91(s, 1H), 6.47 (s, 1H), 6.96(dd, J=8.5, 1.7Hz, 1H), 7.03(d, J=8.5Hz, 1H), 7.09(d, J=1.7Hz, 1H), 7.37–7.48(m, 7H), 7.65 (d, J=8.4Hz, 2H)
IR(KBr) 3547, 3492, 3451, 1521, 1487, 1385, 1288, 1249, 1209, 1108, 1011, 746, 702 cm$^{-1}$

TABLE 140

I-710 mp 178–180° C.
$^1$H NMR(CDCl$_3$) δ 2.43(br s, 1H), 3.44(s, 3H), 3.72(s, 3H), 4.52(m, 2H), 4.93(s, 1H), 5.15(s, 2H), 5.70(s, 1H), 6.79(dd, J=8.1, 2.1Hz, 1H), 6.84(s, 1H), 6.92(d, J=8.7Hz, 1H), 6.93(d, J=2.1Hz, 1H), 7.00(d, J=8.7Hz, 1H), 7.38–7.48(m, 5H), 7.54(d, J=9.0Hz, 2H)
IR(KBr) 3447, 3214, 1609, 1518, 1477, 1459, 1391, 1260, 1221, 1008, 984, 833, 799, 751 cm$^{-1}$

I-711 foam
$^1$H NMR(CDCl$_3$) δ 2.85(s, 3H), 3.22(s, 3H), 3.30(s, 3H), 3.54(s, 3H), 3.78(s, 3H), 5.02(s, 2H), 6.85(s, 1H), 7.08(d, J=8.4Hz, 1H), 7.32(d, J=2.1Hz, 1H), 7.37(dd, J=8.4, 2.1Hz, 1H), 7.39(s, J=8.7Hz, 2H), 7.67(d, J=8.7Hz, 2H)
IR(Nujol) 3423, 3320, 3215, 1610, 1519, 1480, 1454, 1176, 1151, 1080, 969, 876, 798 cm$^{-1}$ I-712 foam
$^1$H NMR(CDCl$_3$) δ 2.62(s, 3H), 3.45(s, 3H), 3.74(s, 3H), 5.28(s, 2H), 6.45(s, 1H), 6.92(d, J=8.7Hz, 2H), 6.95(dd, J=8.4, 2.1Hz, 1H), 7.10(d, J=8.4Hz, 1H), 7.11(d, J=2.1Hz, 1H), 7.53(d, J=8.7Hz, 2H), 8.50(brs, 1H), 8.60(brs, 1H)
IR(Nujol) 3207, 1611, 1589, 1523, 1489, 1460, 1227, 1116, 1072, 1014, 943, 822, 759 cm$^{-1}$ I-713 mp 231–233° C.
$^1$H NMR(CDCl$_3$) δ 3.30(s, 3H), 3.64(s, 3H), 5.28(s, 2H), 6.39(s, 1H), 6.67(dd, J=8.4, 2.1Hz, 1H), 6.80(d, J=2.1Hz, 1H), 6.84(d, J=

TABLE 140-continued 8.7Hz, 2H), 7.01(d, J=8.4Hz, 1H), 7.44(d, J=8.7Hz, 2H), 8.64(d, J=2.4Hz, 1H), 8.67(dd, J=2.4, 1.2Hz, 1H), 8.94(d, J=1.2Hz, 1H)
IR(Nujol) 3369, 3164, 1612, 1600, 1585, 1522, 1493, 1385, 1255, 1118, 1073, 1013, 934, 824, 798, 778 cm$^{-1}$ I-714 foam
$^1$H NMR(CDCl$_3$) δ 2.83(s, 3H), 3.22(s, 3H), 3.27(s, 3H), 3.55(s, 3H), 3.78(s, 3H), 5.18(s, 2H), 6.85(s, 1H),7.20(d, J=8.4Hz, 1H), 7.39(d, J=8.7Hz, 2H), 7.40(dd, J=8.4, 2.1Hz, 1H), 7.45(d, J=2.1Hz, 1H), 7.67(d, J=8.7Hz, 2H)
IR(Nujol) 3264, 1650, 1607, 1517, 1480, 1175, 1150, 1078, 946, 876, 798 cm$^{-1}$

TABLE 141

I-715 foam
$^1$H NMR(CDCl$_3$) δ 2.76(s, 3H), 2.77(s, 3H), 3.21(s, 3H), 3.24(s, 3H), 3.55(s, 3H), 3.78(s, 3H), 5.35(s, 2H), 6.84(s, 1H), 7.25(d, J=8.4Hz, 1H), 7.38(d, J=8.7Hz, 2H), 7.38(dd, J=8.4, 2.1Hz, 1H), 7.44(d, J=2.1Hz, 1H), 7.68(d, J=8.7Hz, 2H)
IR(Nujol) 1607, 1578, 1519, 1465, 1176, 1151, 1079, 971, 947, 876, 846, 797 cm$^{-1}$ I-716 mp 227–229° C.
$^1$H NMR(DMSO-d$_6$) δ 2.87(s, 3H), 3.39(s, 3H), 3.45(s, 3H), 3.52(s, 3H), 3.79(s, 3H), 5.23(s, 2H), 7.08(s, 1H), 7.33(d, J=2.1Hz, 1H), 7.35(dd, J=8.4, 2.1Hz, 1H), 7.44(d, J=8.4Hz, 1H), 7.49(d, J=8.7Hz, 2H), 7.74(d, J=8.7Hz, 2H)
IR(Nujol) 3276, 1651, 1605, 1520, 1480, 1463, 1174, 1150, 1079, 947, 879, 798 cm$^{-1}$ I-717 m.p 180–181° C.
$^1$H NMR(CDCl$_3$) δ 3.07(s, 3H), 3.45(s, 3H), 3.75(s, 3H), 5.18(s, 2H), 6.45(s, 1H),6.92(d, J=8.7Hz, 2H), 6.99(dd, J=1.8, 8.4Hz, 1H), 7.08(d, J=1.8Hz, 1H), 7.10(d, J=8.4Hz, 1H), 7.25(t, J=7.2Hz, 1H), 7.44(m, 2H), 7.53(d, J=8.7Hz, 2H), 7.61(d, J=8.1Hz, 1H)

I-718 foam
$^1$H NMR(CDCl$_3$) δ 3.06(s, 3H), 3.45(s, 3H), 3.74(s, 3H), 5.17(s, 2H), 6.45(s, 1H), 6.93(d, J=8.7Hz, 2H), 6.98(dd, J=8.7Hz, 1H), 7.08(d, J=2.1Hz, 1H), 7.10.(d, J=8.4Hz, 1H), 7.24(m, 1H), 7.43(m, 2H), 7.51(d, J=8.7Hz, 2H), 7.61(m, 1H)
IR(KBr) 3430, 1611, 1590, 1523, 1490, 1402, 1323, 1242, 1149, 1112, 1070, 1010, 971, 826 cm$^{-1}$ I-719 foam
$^1$H NMR(CDCl$_3$) δ 2.80(s, 6H), 3.47(s, 3H), 3.76(s, 3H), 5.08(s, 2H), 6.46(s, 1H), 6.92(d, J=8.7Hz, 2H), 7.10(d, J=2.1Hz, 1H), 7.15(d, J=8.7Hz, 1H), 7.20(d, J=7.2Hz, 1H), 7.34–7.45(m, 3H), 7.55(d, J=8.7Hz, 2H)
IR(KBr) 3427, 1611, 1585, 1522, 1488, 1404, 1224, 1113, 1069, 1011, 940, 824, 767 cm$^{-1}$

TABLE 142

I-720 foam
$^1$H NMR(CDCl$_3$) δ 1.52(s, 9H), 2.67(s, 3H), 3.19(s, 3H), 3.21(s, 3H), 3.56(s, 3H), 3.78(s, 3H), 5.17(s, 2H), 6.54(br.s, 1H), 7.11(m, 1H), 7.12(d, J=9.0Hz, 1H), 7.25(m, 1H), 7.30(d, J=7.5Hz, 1H), 7.32(dd, J=1.8, 9.0Hz, 1H), 7.36(d, J=8.7Hz, 2H), 7.41(d, J=1.8Hz, 1H), 7.60(s, 1H), 7.67(d, J=8.7Hz, 2H)
IR(KBr) 1724, 1610, 1520, 1481, 1366, 1234, 1177, 1153, 1079, 969, 875, 797 cm$^{-1}$ I-721 m.p 187–191° C.
$^1$H NMR(CDCl$_3$) δ 2.66(s, 3H), 3.17(s, 3H), 3.21(s, 3H), 3.55(s, 3H), 3.78(s, brs), 5.11(s, 2H), 6.65(d, J=8.4Hz, 1H), 6.81(m, 1H), 6.84(s, 1H), 7.12(d, J=8.7Hz, 1H), 7.17(t, J=8.7Hz, 1H), 7.32(dd, J=2.1, 8.7Hz, 1H), 7.37(d, J=8.7Hz, 2H), 7.40(d, J=2.1Hz, 1H), 7.67(d, J=8.7Hz, 2H)
IR(KBr) 1624, 1606, 1519, 1481, 1361, 1176, 1148, 1081, 980, 876, 780 cm$^{-1}$ I-722 m.p 143–146° C.
$^1$H NMR(CDCl$_3$) δ 2.18(s, 3H), 2.71(s, 3H), 3.18(s, 3H), 3.21(s, 3H), 3.55(s, 3H), 3.78(s, 3H), 5.18(s, 2H), 6.84(8, 1H), 7.12(d, J=8.7Hz, 1H), 7.17(d, J=7.2Hz, 1H), 7.33(m, 2H), 7.37(d,

TABLE 142-continued

J=8.7Hz, 2H), 7.41(d, J=2.1Hz, 1H), 7.45(d, J=7.2Hz, 1H), 7.67(d, J=8.7Hz, 2H), 7.67(m, 1H)
IR(KBr) 1693, 1609, 1519, 1481, 1364, 1364, 1173, 1149, 1079, 874, 802 cm$^{-1}$

I-723 foam
$^1$H NMR(CDCl$_3$) δ 2.86(s, 3H), 3.00(s, 3H), 3.22(s, 3H), 3.55(s, 3H), 3.78(s, 3H), 5.22(8, 2H), 6.59(s, 1H), 6.85(s, 1H), 7.10(d, J=8.4Hz, 1H), 7.25(m, 3H), 7.32(d, J=2.1, 8.7Hz, 1H), 7.37(m, 1H), 7.38(d, J=2.1Hz, 1H), 7.38(d, J=8.7Hz, 1H), 7.67(d, J=8.7Hz, 2H)
IR(KBr) 1610, 1519, 1480, 1364, 1176, 1150, 1079, 971, 876, 797 cm$^{-1}$

TABLE 143

I-724 foam
$^1$H NMR(CDCl$_3$) δ 2.74(s, 3H), 3.18(s, 3H), 3.21(s, 3H), 3.43(s, 6H), 3.55(s, 3H), 3.78(s, 3H), 5.24(s, 2H), 6.84(s, 1H), 7.13(d, J=8.4Hz, 1H), 7.36(dt, J=2.1, 8.4Hz, 1H), 7.37(m, 1H), 7.39(d, J=8.7Hz, 2H), 7.40(d, J=2.1Hz, 1H), 7.51(m, 2H), 7.61(s, 1H), 7.67(d, J=8.7Hz, 2H)
IR(KBr) 1609, 1523, 1481, 1353, 1176, 1161, 1080, 890, 799 cm$^{-1}$ I-725 m.p 147–150° C.
$^1$H NMR(CDCl$_3$) δ 2.79(s, 3H), 2.83(s, 3H), 3.20(s, 3H), 3.21(s, 3H), 3.35(s, 3H), 3.55(s, 3H), 3.78(s, 3H), 5.22(s, 2H), 6.85(s, 1H), 7.11(d, J=8.7Hz, 1H), 7.32–7.46(m, 7H), 7.62(s, 1H), 7.67(d, J=8.4Hz, 2H)
IR(KBr) 1608, 1518, 1480, 1364, 1178, 1153, 1077, 968, 795 cm$^{-1}$ I-726 m.p 224–226° C.
$^1$H NMR(CDCl$_3$) δ 2.85(s, 3H), 2.91(s, 6H), 3.36(s, 3H), 3.45(s, 3H), 3.51(s, 3H), 3.78(s, 3H), 5.19(s, 2H), 6.69(d, J=8.1Hz, 1H), 6.76(d, J=8.1Hz, 1H), 6.89(s, 1H), 7.07(s, 1H), 7.20(t, J=8.1Hz, 1H), 7.30(m, 3H), 7.48(d, J=8.7Hz, 2H), 7.74(d, J=8.7Hz, 2H)
IR(KBr) 1608, 1519, 1480, 1360, 1178, 1146, 1081, 879, 826 cm$^{-1}$ I-727 foam
$^1$H NMR(CDCl$_3$) δ 2.82(s, 3H), 3.18(s, 6H), 3.21(s, 3H), 3.53(s, 3H), 3.76(s, 3H), 5.17(s, 2H), 6.84(s, 1H), 7.11(d, J=8.4Hz, 1H), 7.20(d, J=4.8Hz, 1H), 7.30–7.47(m, 8H), 7.76(d, J=8.7Hz, 2H)
IR(KBr) 3430, 1677, 1609, 1519, 1481, 1364, 1202, 1177, 1150, 1079, 876, 799 cm$^{-1}$ I-728 foam
$^1$H NMR(CDCl$_3$) δ 3.45(s, 3H), 3.75(s, 3H), 5.06(s, 2H), 6.45(s, 1H), 6.68(d, J=7.5Hz, 1H), 6.77(s, 1H), 6.82(d, J=7.5Hz, 1H), 6.91(d, J=8.7Hz, 2H), 6.93(dd, J=1.8, 8.4Hz, 1H), 6.99(d, J=8.4Hz, 1H), 7.07(d, J=1.8Hz, 1H), 7.19(t, J=7.5Hz, 1H), 7.54(d, J=8.7Hz, 2H)
IR(KBr) 3413, 1611, 1522, 1488, 1461, 1405, 1251, 1119, 1076, 1007, 813, 784 cm$^{-1}$

TABLE 144

I-729 m.p 90–93° C.
$^1$H NMR(CDCl$_3$) δ 3.01(s, 3H), 3.45(s, 3H), 3.75(s, 3H), 5.16(s, 2H), 6.45(s, 1H), 6.81(s, 1H), 6.92(d, J=8.7Hz, 2H), 6.95(d, J=1.8Hz, 1H), 6.96(m, 2H), 7.24(m, 2H), 7.40(t, J=7.2Hz, 1H), 7.52(d, J=8.7Hz, 2H)
IR(KBr) 3434, 1612, 1592, 1523, 1489, 1325, 1248, 1224, 1147, 1113, 1070, 1010, 972 cm$^{-1}$

I-730 mp 79–81° C.
$^1$H NMR(CDCl$_3$) δ 2.34(s, 6H), 3.48(s, 3H), 3.76(s, 3H), 4.72(brs, 1H), 5.16(s, 2H), 5.68(brs, 1H), 5.93(brs, 1H), 6.44(s, 1H), 6.99–7.10(m, 3H), 7.26–7.49(m, 7H)
IR(KBr) 3467, 2933, 1613, 1701, 1517, 1482, 1454, 1424, 1389, 1321, 1196, 1148, 1113, 1073 cm$^{-1}$ I-731 mp 189–191° C.
$^1$H NMR(CDCl$_3$) δ 3.20(s, 3H), 3.81(s, 6H), 5.14(s, 2H), 5.65(brs, 1H), 6.79(s, 2H), 6.79–7.02(m, 5H), 7.36–7.46(m, 6H), 7.66(d, J=8.6Hz, 2H)
IR(KBr) 3439, 2937, 1594, 1567, 1523, 1487, 1351, 1240, 1202, 1146, 1126, 874 cm$^{-1}$

TABLE 144-continued

I-732 mp 196–197° C.
$^1$H NMR(DMSO-d$_6$) δ 3.32(s, 3H), 3.43(s, 6H), 3.79(s, 6H), 5.24(s, 2H), 7.00(s, 2H), 7.23–7.30(m, 3H), 7.35–7.55(m, 7H), 7.88(d, J=8.4Hz, 2H)
IR(KBr) 3434, 1602, 1561, 1523, 1485, 1362, 1288, 1238, 1201, 1181, 1148, 1126, 1115, 966, 914, 813 cm$^{-1}$

I-733 mp 202–203° C.
$^1$H NMR(DMSO-d$_6$) δ 2.40(s, 6H), 3.31(s, 3H), 3.34(s, 3H), 3.51(s, 3H), 3.58(s, 3H), 3.77(s, 3H), 5.27(s, 2H), 7.03(s, 1H), 7.32–7.530(m, 10H)
IR(KBr) 3434, 3028, 2944, 1515, 1475, 1463, 1361, 1290, 1272, 1247, 1179, 1085, 967, 815, 804 cm$^{-1}$

TABLE 145

I-734 mp 140–141° C.
$^1$H NMR(CDCl$_3$) δ 1.77(s, 3H), 1.82(s, 3H), 3.21(s, 3H), 3.83(s, 6H), 4.63(d, J=4.6Hz, 2H), 5.52–5.53(m, 1H), 6.79(s, 1H), 7.05(d, J=8.8Hz, 1H), 7.29–7.42(m, 4H), 7.67(d, J=8.6Hz, 2H)
IR(KBr) 3434, 2936, 1602, 1565, 1487, 1365, 1242, 1182, 1152, 1123, 1113, 974, 874, 811 cm$^{-1}$

I-735 mp 168–169° C.
$^1$H NMR(CDCl$_3$) δ 2.38(s, 3H), 3.09(s, 3H), 3.20(s, 3H), 3.81(s, 6H), 5.11(s, 2H), 6.78(s, 2H), 713–7.42(m, 9H), 7.66(d, J=8.8Hz, 2H)
IR(KBr) 3433, 1601, 1566, 1486, 1367, 1246, 1182, 1153, 1114, 973, 869, 824 cm$^{-1}$

I-736 mp 192–194° C.
$^1$H NMR(CDCl$_3$) δ 1.77(s, 3H), 1.82(s, 3H), 2.47(s, 6H), 2.72(s, 3H), 3.24(s, 3H), 3.36(s, 3H), 3.57(s, 3H), 3.79(s, 3H), 4.64 (d, J=6.6Hz, 2H), 5.47–5.55(m, 1H), 6.83(s, 1H), 7.09(d, J=9.0Hz, 1H), 7.33–7.40(m, 4H)
IR(KBr) 3435, 1942, 1516, 1474, 1382, 1357, 1288, 1178, 1096, 966, 862, 805 cm$^{-1}$

I-737 mp 224–225° C.
$^1$H NMR(CDCl$_3$) δ 2.38(s, 3H), 2.46(s, 6H), 2.66(s, 3H), 3.12(s, 3H), 3.35(s, 3H), 3.55(s, 3H), 3.77(8, 3H), 5.14(s, 2H), 6.82 (s, 1H), 712–7.40(m, 9H)
IR(KBr) 3435, 2941, 1518, 1474, 1360, 1274, 1179, 1095, 1085, 967, 862, 815, 805 cm$^{-1}$

I-738 mp 203–204° C.
$^1$H NMR(CDCl$_3$) δ 1.76(s, 3H), 1.82(s, 3H), 2.46(s, 6H), 2.45–2.58(m, 2H), 2.73(s, 3H), 3.22(s, 3H), 3.35(s, 3H), 3.55(s, 3H), 3.77(s, 3H), 4.07(d, J=6.6Hz, 2H), 5.18–5.25(m, 1H), 6.82(s, 1H), 7.07(s, J=8.2Hz, 1H), 7.32–7.39(m, 4H)
IR(KBr) 3434, 2941, 1519, 1473, 1359, 1276, 1178, 1114, 1085, 967, 860, 811 cm$^{-1}$

TABLE 146

I-739 mp 158–159° C.
$^1$H NMR (DMSO-do) δ 1.72(s, 3H), 1.76(s, 3H), 3.72(s, 6H), 4.54(d, J=6.0Hz, 2H), 5.45–5.52(m, 1H), 6.55–6.59(m, 2H), 6.84–6.90(m, 5H), 7.57(d, J=8.2Hz, 2H), 8.70(brs, 1H), 9.53(brs, 1H)
IR(KBr) 3465, 2932, 1610, 1523, 1487, 1460, 1283, 1281, 1123, 1010, 819 cm$^{-1}$ I-740 mp 180–181° C.
$^1$H NMR(CDCl$_3$) δ 2.32(s, 3H), 3.72(s, 6H), 5.08(s, 2H), 6.54–6.58(m, 1H), 6.68(s, 1H), 6.85–6.95(m, 5H), 7.21(d, J=7.6Hz, 2H), 7.39(d, J=7.8Hz, 2H), 7.57(d, J=8.4Hz, 2H), 8.83(brs, 1H), 9.54(brs, 1H)
IR(KBr) 3519, 2937, 1607, 1562, 1523, 1461, 1400, 1246, 1176, 1125, 1003, 821 cm$^{-1}$ I-741 mp 105–106° C.
$^1$H NMR(CDCl$_3$) δ 2.13(s, 6H), 3.17(s, 3H), 5.16(s, 2H), 5.85(brs, 1H), 6.61–6.66(m, 1H), 6.77(s, 1H), 7.01(d, J=8.2Hz, 1H), 7.25–7.46(m, 9H), 7.65(d, J=8.8Hz, 2H)
IR(KBr) 3466, 3031, 2934, 1585, 1513, 1476, 1366, 1285, 1198, 1175, 1148, 1127, 1014, 968, 868, 840 cm$^{-1}$

TABLE 146-continued

I-742 mp 92–93° C.
$^1$H NMR(DMSO-d$_6$) δ 1.74(s, 3H), 1.78(s, 3H), 2.24(s, 6H), 3.31(s, 3H), 3.65(s, 3H), 4.56(d, J=6.8Hz, 2H), 5.52(t, J=6.0Hz, 1H), 6.37(s, 1H), 6.64–6.76(m, 2H), 6.88–6.93(m, 1H), 7.16–7.20(m, 2H), 8.31(brs, 1H), 8.45(brs, 1H), 8.73(brs, 1H)
IR(KBr) 3443, 2932, 1707, 1613, 1516, 1484, 1462, 1387, 1280, 1243, 1196, 1114, 1074, 979 cm$^{-1}$ I-743 mp 180–181° C.
$^1$H NMR(DMSO-d$_6$) δ 2.22(s, 6H), 2.32(s, 3H), 3.29(s, 3H), 3.63(s, 3H), 5.08(s, 2H), 6.61–6.65(m, 1H), 6.75(s, 1H), 6.93(d, J=8.2Hz, 1H), 7.13–7.22(m, 4H), 7.39(d, J=7.4Hz, 2H), 8.30(brs, 1H), 8.44(brs, 1H), 8.84(brs, 1H)
IR(KBr) 3443, 2930, 1686, 1614, 1587, 1518, 14863, 1462, 1385, 1281, 1246, 1197, 1113, 1073, 1009, 806 cm$^{-1}$

TABLE 147

I-744 mp 123–124° C.
$^1$H NMR (DMSO-d$_6$) δ 1.65(s, 3H), 1.71(s, 3H), 2.23(s, 6H), 2.36–2.51(m, 2H), 3.31(s, 3H), 3.64(s, 3H), 3.91–3.98(m, 2H), 5.22–5.28(m, 1H), 6.36(s, 1H), 6.65–6.88(m, 3H), 7.16(s, 1H), 8.30(brs, 1H), 8.44(brs, 1H), 8.70(brs, 1H)
IR(KBr) 3444, 2930, 1686, 1613, 1518, 1483, 1390, 1283, 1248, 1198, 1113, 1074, 1013 cm$^{-1}$ I-745 mp 174–177° C.
$^1$H NMR(CDCl$_3$) δ 1.77–1.78(d, J=0.9Hz, 3H), 1.82–1.83(d, J=0.9Hz, 3H), 2.74(s, 3H), 3.18(s, 3H), 3.25(s, 3H), 3.57(s, 3H), 3.78(s, 3H), 4.64–4.67(d, J=6.9Hz, 2H), 5.51(m, 1H), 6.86(s, 1H), 7.09(d, J=8.4Hz, 1H), 7.35–7.40(m, 2H), 7.45–7.49(m, 2H), 7.55–7.60(m, 2H)
IR(CHCl$_3$) 2939, 1613, 1519, 1480, 1371, 1331, 1292, 1251, 1176, 1150, 1118, 1082, 971, 871, 849 cm$^{-1}$ I-746 mp 134–136° C.
$^1$H NMR(CDCl$_3$) δ 1.69(s, 3H), 1.75(s, 3H), 2.53–2.60(dt, J=6.6, 5.7Hz, 2H), 2.73(s, 3H), 3.18(s, 3H), 3.23(s, 3H), 3.56(s, 3H), 3.78(s, 3H), 4.07–4.11(t, J=5.7Hz, 2H), 5.22(m, 1H), 6.86(s, 1H), 7.07(d, J=9.0Hz, 1H), 7.35–7.40(m, 2H), 7.45–7.49(m, 2H), 7.55–7.60(m, 2H)
IR(CHCl$_3$) 2938, 1614, 1519, 1480, 1448, 1371, 1331, 1294, 1228, 1176, 1150, 1119, 1083, 1004, 970, 870, 849, 819 cm$^{-1}$ I-747 mp 182–183° C.
$^1$H NMR(CDCl$_3$) δ 2.26(s, 3H), 2.28(s, 3H), 4.74(s, 1H), 5.16(s, 2H), 5.69(s, 1H), 6.81–6.89(m, 3H), 6.96–6.99(m, 2H), 7.10–7.12(d, J=4.8Hz, 2H), 7.23–7.26(m, 2H), 7.39–7.45(m, 5H)
IR(CHCl$_3$) 3597, 3543, 2924, 2871, 1611, 1587, 1522, 1490, 1455, 1382, 1171, 1126, 1012, 836 cm$^{-1}$ I-748 mp 158–161° C.
$^1$H NMR(CDCl$_3$) δ 2.38(s, 3H), 2.74(s, 3H), 3.12(s, 3H), 3.18(s, 3H), 3.57(s, 3H), 3.78(s, 3H), 5.15(s, 2H), 6.86(s, 1H), 7.16(d, J=8.7Hz, 1H), 7.21–7.24(d, J=7.8Hz, 1H), 7.35–7.40(m, 5H), 7.45–7.49(m, 2H), 7.52–7.62(m, 2H)
IR(CHCl$_3$) 2939, 1732, 1614, 1519, 1480, 1331, 1294, 1253, 1176, 1150, 1119, 1082, 1003, 970, 869, 816 cm$^{-1}$

TABLE 148

I-749 mp 174–176° C.
$^1$H NMR(CDCl$_3$) δ 1.75(s, 3H), 1.79(s, 3H), 2.58(s, 3H), 3.52(s, 3H), 3.53(s, 3H), 3.78(s, 3H), 4.62(d, J=6.9Hz, 2H), 5.48–5.55(m, 1H), 6.83(s, 1H), 6.99(d, J=8.7Hz, 1H), 7.09(dd, J=1.8, 8.1Hz, 1H), 7.11–7.19(m, 2H), 7.22(d, J=1.8Hz, 1H), 7.57–7.65(m, 2H)
IR(KBr) 2932, 1602, 1519, 1485, 1385, 1368, 1174, 1086, 1015, 986, 848, 804, 527 cm$^{-1}$

I-750 mp 129–131° C.
$^1$H NMR(CDCl$_3$) δ 1.75(s, 3H), 1.79(s, 3H), 3.45(s, 3H), 3.53(s, 3H), 3.75(s, 3H), 4.62(d, J=6.6Hz, 2H), 5.24(s, 2H), 5.50–5.58(m, 1H), 5.90(s, 1H), 6.44(s, 1H), 6.99(d, J=8.7Hz, 1H), 7.08–7.18(m, 3H), 7.29(d, J=1.8Hz, 1H), 7.58–7.64(m, 2H)
IR(KBr) 3361, 2953, 2934, 1522, 1488, 1460, 1391, 1230, 1154, 1121, 1071, 993, 912, 817, 587 cm$^{-1}$

TABLE 148-continued

I-751  mp 148–150° C.
$^1$H NMR(CDCl$_3$) δ 1.68(s, 3H), 1.74(s, 3H), 2.51–2.60(m, 5H), 3.53(s, 6H), 3.77(s, 3H), 4.02(t, J=7.2Hz, 2H), 5.19–5.25(m, 3H), 6.83(s, 1H), 6.98(d, J=8.4Hz, 1H), 7.08(dd, J=2.1, 8.4Hz, 1H), 7.11–7.18(m, 2H), 7.21(d, J=2.1Hz, 1H), 7.57–7.64(m, 2H)
IR(KBr) 2931, 1603, 1519, 1484, 1386, 1370, 1231, 1175, 1086, 1015, 983, 961, 847, 728, 526 cm$^{-1}$

I-752  mp 99–101° C.
$^1$H NMR(CDCl$_3$) δ 1.68(s, 3H), 1.73(s, 3H), 2.55(q, J=7.2Hz, 2H), 3.44(s, 3H), 3.54(s, 3H), 3.75(s, 3H), 4.04(t, J=7.2Hz, 2H), 5.20–5.25(m, 3H), 5.89(s, 1H), 6.44(s, 1H), 6.98(d, J=8.1Hz, 1H), 7.09–7.18(m, 3H), 7.26–7.27(m, 1H), 7.58–7.63(m, 2H)
IR(KBr) 3349, 2930, 1609, 1523, 1489, 1231, 1152, 1121, 1072, 994, 912, 813, 588 cm$^{-1}$

TABLE 149

I-753  mp 115–117° C.
$^1$H NMR(CDCl$_3$) δ 1.69(s, 3H), 1.75(s, 3H), 2.53(q, J=6.9Hz, 2H), 2.62(s, 3H), 3.53(s, 3H), 3.77(s, 3H), 4.06(t, J=6.9Hz, 2H), 5.18–5.25(m, 1H), 5.70(s, 1H), 6.83(s, 1H), 6.89–6.95(m, 2H), 7.02(d, J=1.2Hz, 1H), 7.10–7.18(m, 2H), 7.57–7.65(m, 2H)
IR(KBr) 3545, 2931, 1604, 1520, 1485, 1370, 1249, 1232, 1175, 1084, 1012, 813, 526 cm$^{-1}$

I-754  $^1$H NMR(CDCl$_3$) δ 1.14(t, J=6.9Hz, 3H), 1.29(t, J=6.9Hz, 3H), 2.50(s, 3H), 3.19(s, 3H), 3.71(q, J=6.9Hz, 2H), 4.00(q, J=6.9Hz, 2H), 5.18(s, 2H), 5.68(s, 1H), 6.83(s, 1H), 6.91(dd, J=1.8, 8.4Hz, 1H), 7.00(d, J=8.4Hz, 1H), 7.04(d, J=1.8Hz, 1H), 7.32–7.48(m, 7H), 7.66–7.74(m, 2H)
IR(CHCl$_3$) 3532, 2976, 1586, 1516, 1468, 1369, 1282, 1174, 1148, 1068, 1016, 967, 907, 871 cm$^{-1}$

I-755  amorphous powder
$^1$H NMR(CDCl$_3$) δ 1.15(t, J=6.9Hz, 3H), 1.28(t, J=6.9Hz, 3H), 3.59(q, J=6.9Hz, 2H), 3.97(q, J=6.9Hz, 2H), 4.89(s, 1H), 5.15(s, 2H), 5.64(s, 1H), 5.98(s, 1H), 6.45(s, 1H), 6.86–6.94(m, 2H), 6.96–7.04(m, 2H), 7.12(d, J=2.4Hz, 1H), 7.35–7.56(m, 7H),
IR(CHCl$_3$) 3534, 1610, 1521, 1488, 1383, 1169, 1116, 1064, 1018, 832 cm$^{-1}$ I-756  mp 126–129° C.
$^1$H NMR(CDCl$_3$) δ 1.14(t, J=6.9Hz, 3H), 1.30(t, J=6.9Hz, 3H), 1.76(s, 3H), 1.81(s, 3H), 2.69(s, 3H), 3.20(s, 3H), 3.23(s, 3H), 3.72(q, J=6.9Hz, 2H), 4.00(q, J=6.9Hz, 2H), 4.64(s, J=6.6Hz, 2H), 5.49(m, 1H), 6.84(s, 1H), 7.08(d, J=8.7Hz, 1H), 7.32–7.42(m, 4H), 7.56–7.72(m, 2H)
IR(CHCl$_3$) 1609, 1516, 1467, 1369, 1267, 1229, 1175, 1148, 1115, 1069, 968, 907, 871 cm$^{-1}$

TABLE 150

I-757  mp 123–135° C. (dec.)
$^1$H NMR(CDCl$_3$) δ 1.14(t, J=6.9Hz, 3H), 1.29(t, J=6.9Hz, 3H), 2.37(s, 3H), 2.64(s, 3H), 3.12(s, 3H), 3.20(s, 3H), 3.71(q, J=6.9Hz, 2H), 4.00(q, J=6.9Hz, 2H), 5.14(s, 2H), 6.83(s, 1H), 7.14(d, J=8.7Hz, 1H), 7.18–7.24(m, 2H), 7.31–7.40(m, 5H), 7.41(d, J=2.1Hz, 1H), 7.65–7.72(m, 2H)
IR(CHCl$_3$) 1607, 1517, 1467, 1369, 1330, 1268, 1175, 1148, 1116, 1069, 1026, 967, 907, 871 cm$^{-1}$ I-758  amorphous powder
$^1$H NMR(CDCl$_3$) δ 1.15(t, J=6.9Hz, 3H), 1.28(t, J=6.9Hz, 3H), 1.76(s, 3H), 1.82(d, J=0.6Hz, 3H), 3.59(q, J=6.9Hz, 2H), 3.97(q, J=6.9Hz, 2H), 4.61(q, J=6.9Hz, 2H), 4.87(s, 1H), 5.53(m, 1H), 5.66(s, 1H), 5.97(s, 1H), 6.45(s, 1H), 6.86–7.00(m, 4H), 7.09(d, J=1.8Hz, 1H), 7.50–7.57(m, 2H)
IR(CHCl$_3$) 3528, 2978, 1611, 1521, 1487, 1412, 1383, 1168, 1115, 1064, 905, 831 cm$^{-1}$ I-759  amorphous powder
$^1$H NMR(CDCl$_3$) δ 1.15(t, J=6.9Hz, 3H), 1.27(t, J=6.9Hz, 3H), 2.39(s, 3H), 3.59(q, J=6.9Hz, 2H), 3.97(q, J=6.9Hz, 2H), 4.88(s, 1H), 5.10(s, 2H), 5.64(s, 1H), 5.97(s, 1H), 6.45(s, 1H), 6.97–7.01(m, 2H), 7.11(d, J=1.5Hz, 1H), 7.20–7.26(m, 2H),

TABLE 150-continued 7.32–7.37(m, 2H), 7.50–7.56(m, 2H)
IR(CHCl$_3$) 3526, 2974, 1612, 1520, 1488, 1412, 1383, 1285, 1246, 1116, 1065, 1027, 870 cm$^{-1}$ I-760  mp 169–171° C.
$^1$H NMR(CDCl$_3$) δ 2.71(s, 3H), 3.01(s, 3H), 3.10(s, 3H), 3.21(s, 3H), 3.36(s, 3H), 3.56(s, 3H), 3.77(s, 3H), 4.83(s, 2H), 6.84(s, 1H), 7.05(d, J=8.4Hz, 1H), 7.32(dd, J=2.1, 8.4Hz, 1H), 7.36–7.42(m, 2H), 7.42(d, J=2.1Hz, 1H), 7.65–7.72(m, 2H)
IR(CHCl$_3$) 1666, 1517, 1479, 1368, 1175, 1148, 1119, 1083, 1014, 968, 871 cm$^{-1}$

TABLE 151

I-761  mp 175–177° C.
$^1$H NMR(DMSO-d$_6$) δ 1.70(s, 6H), 3.67–3.73(m, 2H), 3.71(s, 3H), 3.72(s, 3H), 4.59(br, 1H), 5.27–5.31(m, 1H), 6.50(d, J=8.1Hz, 1H), 6.77–6.95(m, 6H), 7.34–7.40(m, 2H), 9.23(br s, 1H), 9.42(br s, 1H)
IR(KBr) 3600–2400(br), 1609, 1522, 1492, 1463, 1384, 1263, 1208, 1174, 1129, 1055, 1033 cm

I-762  mp 151–153° C.
$^1$H NMR(CDCl$_3$) δ 1.78(s, 3H), 1.85(s, 3H), 3.78(s, 3H), 3.80(s, 3H), 4.72(d, J=6.9Hz, 2H), 5.39–5.44(m, 1H), 6.53(d, J=3.0Hz, 1H), 6.95(s, 1H), 7.05(d, J=8.4Hz, 1H), 7.09–7.16(m, 3H), 7.38(d, J=8.7Hz, 1H), 7.45(dd, J=1.8, 8.7Hz, 1H), 7.54–7.60(m, 3H), 7.80(d, J=1.8Hz, 1H),
IR(KBr) 3600–2800(br), 1509, 1496, 1481, 1462, 1447, 1383, 1207, 1158, 1051 cm$^{-1}$

I-763  mp 138–139° C.
$^1$H NMR(CDCl$_3$) δ 3.78(s, 3H), 3.79(s, 3H), 6.64(dd, J=0.9, 2.7Hz, 1H), 6.80(d, J=7.8Hz, 1H), 6.94(s, 1H), 7.04(s, 1H), 7.09–7.21(m, 3H), 7.25–7.27(m, 1H), 7.32(d, J=8.7Hz, 1H), 7.42(dd, J=1.8, 8.4Hz, 1H), 7.53–7.59(m, 3H), 8.60–8.63(m, 1H)
IR(KBr) 3600–2800(br), 1590, 1510, 1497, 1478, 1430, 1384, 1209, 1158, 1053, 1026 cm$^{-1}$

I-764  mp 172–174° C.
$^1$H NMR(CDCl$_3$) δ 2.32(s, 3H), 3.78(s, 3H), 3.79(s, 3H), 5.30(s, 2H), 6.59(d, J=3.3Hz, 1H), 6.94(s, 1H), 7.04(s, 1H), 7.04–7.15(m, 7H), 7.34(d, J=8.4Hz, 1H), 7.41(dd, J=1.8, 8.7Hz, 1H), 7.55–7.59(m, 2H), 7.82–7.83(m, 1H)
IR(KBr) 3600–2800(br), 1516, 1497, 1482, 1466, 1382, 1306, 1219, 1209, 1159, 1051, 1026 cm$^{-1}$

I-765  mp 134–136° C.
$^1$H NMR(DMSO-d$_6$) δ 1.70(s, 3H), 1.71(s, 3H), 3.72–3.74(m, 2H), 373(s, 3H), 3.74(s, 3H), 5.25(br s, 1H), 5.50–5.58(m, 1H), 6.66–6.72(m, 1H), 6.78–6.83(m, 1H), 6.92(s, 3H), 6.95(s, 1H), 7.19–7.29(m, 2H), 7.30–7.39(m, 2H), 9.45(br s, 3H),
IR(KBr) 3600–2800(br), 1624, 1610, 1526, 1494, 1461, 1382, 1255, 1208, 1175, 1120, 1054, 1031 cm$^{-1}$

TABLE 152

I-766  mp 166–168° C.
$^1$H NMR(CDCl$_3$) δ 2.40(s, 3H), 3.77(s, 6H), 4.82(s, 1H), 6.71(d, J=2.4Hz, 1H), 6.86–6.93(m, 4H), 7.22–7.32(m, 4H), 7.43–7.48(m, 2H), 7.58–7.64(m, 1H), 7.71–7.75(m, 2H)
IR(KBr) 3600–2800(br), 1611, 1524, 1492, 1382, 1336, 1265, 1209, 1162, 1090, 1053, 1030 cm$^{-1}$

I-767  mp 139–140° C.
$^1$H NMR(CDCl$_3$) δ 3.78(s, 3H), 3.80(s, 3H), 6.60–6.62(m, 1H), 6.95(s, 1H), 7.05(s, 1H), m), 7.08–7.16(m, 2H), 7.23–7.26(m, 1H), 7.45(d, J=1.2Hz, 2H), 7.54–7.61(m, 2H), 7.83(s, J=0.6Hz, 1H), 8.18(br s, 1H)
IR(KBr) 3600–2800(br), 1520, 1497, 1465, 1448, 1414, 1383, 1313, 1218, 1205, 1159, 1048, 1024 cm$^{-1}$

I-768  $^1$H NMR(CDCl$_3$) δ 2.26(s, 3H), 3.48(s, 3H), 3.75(s, 3H), 5.16(s, 2H), 5.69(s, 1H), 5.89(s, 1H), 6.45(s, 1H), 6.94(d.d, J=8.4 & 2.1Hz, 1H), 7.02(d, J=8.4Hz, 1H), 7.08(d, J=2.1Hz, 1H), 7.35–7.50(m, 8H), 8.36 –8.44(m, 1H)
IR(KBr) 3384, 1592, 1525, 1487, 1455, 1397, 1312, 1250, 1122, 1102, 1069, 1011 cm$^{-1}$

TABLE 152-continued

I-769    $^1$H NMR(CDCl$_3$) δ 2.26(s, 3H), 2.68(s, 3H), 3.13(s, 3H), 3.56(s, 3H), 3.78(s, 3H), 5.19(s, 2H), 6.84(s, 1H), 7.15(d, J=8.4Hz, 1H), 7.30–7.51(m, 10H), 8.37–8.47(m, 1H)
IR(KBr)3384, 1704, 1590, 1524, 1481, 1389, 1357, 1272, 1240, 1174, 1114, 1082, 1017 cm$^{-1}$

I-770    $^1$H NMR(CDCl$_3$) δ 2.67(s, 3H), 2.84(s, 3H), 3.28(s, 3H), 3.56(s, 3H), 3.78(s, 3H), 6.26(s, 1H), 6.85(6, 1H), 7.17(d, J=9.0Hz, 1H), 7.24–7.33(m, 2H), 7.35–7.50(m, 3H), 8.37–8.50(m, 1H)
IR(KBr)3383, 1674, 1595, 1526, 1482, 1363, 1177, 1078, 1012 cm$^{-1}$

I-771    $^1$H NMR(CDCl$_3$) δ 1.76(s, 3H), 1.81(s, 3H), 2.26(s, 3H), 2.72(s, 3H), 3.23(s, 3H), 3.56(s, 3H), 3.78(s, 3H), 4.64(d, J=7.2Hz, 2H), 5.44–5.53(m, 1H), 6.84(s, 1H), 7.09(.d, J=8.4Hz, 1H), 7.30–7.53(m, 5H), 8.38–8.47(m, 1H)
IR(KBr) 3376, 1697, 1594, 1524, 1481, 1365, 1270, 1239, 1177, 1112, 1079, 1013 cm$^{-1}$

TABLE 153

I-772    $^1$H NMR(CDCl$_3$) δ 2.26(s, 3H), 2.38(s, 3H), 2.68(s, 3H), 3.12(s, 3H), 3.56(s, 3H), 3.78(s, 3H), 5.14(s, 2H), 6.84(s, 1H), 7.12–7.50(m, 9H), 8.35–8.44(m, 1H)
IR(KBr)3365, 1693, 1622, 1591, 1526, 1477, 1374, 1314, 1291, 1180, 1165, 1111, 1078 cm$^{-1}$

I-773    $^1$H NMR(CDCl$_3$) δ 1.76(s, 3H), 1.82(s, 3H), 2.26(s, 3H), 3.48(s, 3H), 3.75(s, 3H), 4.62(d, J=6.9Hz, 2H), 5.46–5.58(m, 1H), 5.71(s, 1H), 5.86(s, 1H), 6.44(s, 1H), 6.87–7.00(m, 3H), 7.05(.d, J=1.8Hz, 1H), 7.33–7.52(m, 3H), 8.36–8.47(m, 1H)
IR(KBr) 1737, 1604, 1519, 1482, 1392, 1366, 1267, 1173, 1131, 1084, 1062, 1009 cm$^{-1}$

I-774    $^1$H NMR(CDCl$_3$) δ :2.25(s, 3H), 2.38(s, 3H), 3.48(s, 3H), 3.75(s, 3H), 5.10(s, 2H), 5.12(brs, 1H), 5.90(s, 1H), 6.44(s, 1H), 6.94(.d.d, J=8.4 &1.8Hz, 1H), 7.02(.d, J=8.4Hz, 1H), 7.06(.d, J=1.8Hz, 1H), 7.18–7.52(m, 6H), 8.35–8.44(m, 1H)
IR(KBr) 1686, 1590, 1524, 1488, 1398, 1314, 1257, 1102, 1068, 1008 cm$^{-1}$ I-775    $^1$H NMR(CDCl$_3$) δ 3.47(s, 3H), 3.76(s, 3H), 5.16(s, 2H), 5.71(s, 1H), 5.82(s, 1H), 6.45(s, 1H), 6.97(d.d, J=8.4 & 2.1Hz, 1H), 7.04(d, J=8.4Hz, 1H), 7.07(d, J=2.1Hz, 1H), 7.22–7.30(m, 1H), 7.33–7.49(m, 5H), 7.92–7.98(m, 1H), 8.09–8.14(m, 1H), 10.44(s, 1H)
IR(KBr) 3492, 3459, 1692, 1605, 1518, 1486, 1388, 1294, 1238, 1200, 1115, 1100, 1070, 1008 cm$^{-1}$ I-776    $^1$H NMR(CDCl$_3$) δ 2.35(d, J=1.8Hz, 3H), 2.68(s, 3H), 3.13(s, 3H), 3.23(s, 3H), 3.78(s, 3H), 5.19(s, 2H), 6.82(s, 1H), 7.04–7.17(m, 2H), 7.30–7.49(m, 9H)
IR(KBr) 1606, 1518, 1478, 1364, 1295, 1271, 1240, 1182, 1118, 1087, 1077, 1017 cm$^{-1}$ I-777    $^1$H NMR(CDCl$_3$) δ 1.76(s, 3H), 1.81(s, 3H), 2.35(s, 3H), 2.72(s, 3H), 3.23(s, 3H), 3.53(s, 3H), 3.78(s, 3H), 4.64(d, J=6.6Hz, 2H), 5.45–5.53(m, 1H), 6.82(s, 1H), 7.03–7.14(m, 2H), 7.32–7.47(m, 4H)
IR(KBr) 1607, 1520, 1482, 1374, 1363, 1240, 1179, 1115, 1079 cm$^{-1}$

TABLE 154

I-778    $^1$H NMR(CDCl$_3$) δ 2.35(d, J=1.2Hz, 3H), 3.45(s, 3H), 3.75(s, 3H), 5.15(s, 2H), 5.68(s, 1H), 5.90(s, 1H), 6.43(s, 1H), 6.92–7.12(m, 4H), 7.31–7.50(m, 7H)
IR(KBr) 3536, 3398, 1609, 1587, 1518, 1487, 1244, 1192, 1110, 1071, 1010 cm$^{-1}$

I-779    $^1$H NMR(CDCl$_3$) δ 1.76(s, 3H), 1.82(s, 3H), 2.35(s, 3H), 3.45 (s, 3H), 3.74(s, 3H), 4.61(d, J=6.9Hz, 2H), 5.43–5.60(m, 1H), 6.43(s, 1H), 6.87–7.15(m, 3H), 7.36–7.51(m, 2H)
IR(KBr) 3512, 3444, 1611, 1585, 1518, 1488, 1462, 1447, 1416, 1305, 1288, 1243, 1207, 1112, 1103, 1070, 1012 cm$^{-1}$

I-780    $^1$H NMR(CDCl$_3$) δ 3.45(s, 3H), 3.75(s, 3H), 4.84(s, 2H), 5.15 (s, 2H), 5.70(s, 1H), 5.88(s, 1H), 6.44(s, 1H), 6.91–7.20(m, 4H), 7.32–7.48(m, 5H), 7.52–7.61(m, 1H), 7.64–7.74(m, 1H)

TABLE 154-continued

IR(KBr) 3523, 3428, 1610, 1587, 1516, 1482, 1463, 1400, 1321, 1285, 1238, 1187, 1106 cm$^{-1}$

I-781    $^1$H NMR(CDCl$_3$) δ 2.68(s, 3H), 3.13(s, 3H), 3.54(s, 3H), 3.78 (s, 3H), 5.19(s, 2H), 5.44(d.d, J=18&0.6Hz, 1H), 5.90(d.d, J=18&0.9Hz, 1H), 6.84(s, 1H), 6.86–6.98(m, 1H), 7.09–7.18 (m, 2H), 7.31–7.52(m, 8H), 7.71(d.d, J=7.2&2.4Hz, 1H)
IR(KBr) 1608, 1518, 1479, 1365, 1235, 1177, 1118, 1079, 1013 cm$^{-1}$

I-782    $^1$H NMR(CDCl$_3$) δ 1.59(d, J=6.3Hz, 3H), 2.68(s, 3H), 3.13 (s, 3H), 3.55(s, 3H), 3.78(s, 3H), 5.19(s, 2H), 5.21–5.30(m, 1H), 6.84(s, 1H), 7.08–7.17(m, 3H), 7.32–7.56(m, 7H), 7.69–7.75(m, 1H)
IR(KBr) 3543, 3433, 1609, 1518, 1480, 1364, 1235, 1178, 1117, 1078, 1014 cm$^{-1}$

I-783    $^1$H NMR(CDCl$_3$) δ 1.59(d, J=6.0Hz, 3H), 2.01(brs, 1H), 3.47 (s, 3H), 3.76(s, 3H), 5.16(s, 2H), 5.15–5.30(m, 1H), 5.72(s, 1H), 5.91(s, 1H), 6.46(s, 1H), 6.89–7.16(m, 4H), 7.30–7.60(m, 6H), 7.68–7.85(m, 1H)
IR(KBr) 3467, 1613, 1586, 1517, 1484, 1455, 1421, 1395, 1287, 1238, 1111,1070, 1010 cm$^{-1}$

TABLE 155

I-784    $^1$H NMR(CDCl$_3$) δ 1.77(s, 3H), 1.81(s, 3H), 3.23(s, 3H), 3.81 (s, 6H), 4.64(d, J=6.6Hz, 2H), 5.47–5.54(m, 1H), 6.91(s, 1H), 6.96(s, 1H), 7.06(.d, J=8.4Hz, 1H), 7.49(d.d, J=8.4&2.1 Hz, 1H), 7.58(d, J=2.1Hz, 1H), 7.60–7.74(m, 4H)
IR(KBr) 2228, 1610, 1490, 1348, 1295, 1266, 1209, 1174, 1112, 1056, 1038, 1000 cm$^{-1}$

I-785    mp 169–170° C.
$^1$H NMR(CDCl$_3$) δ 2.07(s, 6H), 3.20(s, 3H), 5.16(s, 2H), 5.71 (brs, 1H), 6.97–7.45(m, 14H)
IR(KBr) 3357, 3023, 2933, 1698, 1516, 1478, 1362, 1260, 1227, 1152, 1132, 962, 869 cm$^{-1}$ I-786    mp 169–170° C.
$^1$H NMR(CDCl$_3$) δ 2.13(s, 6H), 3.11(s, 3H), 3.18(s, 3H), 5.18 (s, 2H), 7.09–7.47(m, 12H), 7.64(d, J=9.0Hz, 2H)
IR(KBr) 3434, 3035, 2938, 1516, 1474, 1362, 1290, 1197, 1182, 1174, 1149, 1114, 973, 857, 842 cm$^{-1}$ I-787    $^1$H NMR(CDCl$_3$) δ 2.08(s, 6H), 3.12(s, 3H), 3.21(s, 3H), 5.18 (s, 2H), 7.12–7.58(m, 14H)
IR(KBr) 3494, 3292, 3033, 2934, 1753, 1712, 1517, 1478, 1358, 1294, 1261, 1173, 1151, 967, 870 cm$^{-1}$ I-788    mp 105–106° C.
$^1$H NMR(CDCl$_3$) δ 1.75(s, 3H), 1.85(s, 3H), 2.12(s, 6H), 3.18 (s, 3H), 3.22(s, 3H), 4.64(d, J=7.0Hz, 2H), 5.52(t, J=6.8 Hz, 1H), 7.08(s, 1H), 7.16–7.38(m, 6H), 7.64(d, J=8.8Hz, 2H)
IR(KBr) 3434, 2934, 1514, 1474 1362, 1285, 1152, 1113, 971, 916, 861, 845 cm$^{-1}$ I-789    mp 148–149° C.
$^1$H NMR(CDCl$_3$) δ 2.12(s, 6H), 2.39(s, 3H), 3.10(s, 3H), 3.18 (s, 3H), 5.13(s, 2H), 7.10–7.38(m, 11H), 7.64(d, J=8.6Hz, 2H)
IR(KBr) 3435, 3027, 2931, 1678, 1516, 1475, 1362, 1288, 1182, 1151, 1113, 969, 916, 861 cm$^{-1}$

TABLE 156

I-790    mp 139–140° C.
$^1$H NMR(CDCl$_3$) δ 1.76(s, 3H), 1.82(s, 3H), 2.14(s, 6H), 2.46–2.58(m, 2H), 3.14(s, 3H), 3.19(s, 3H), 4.07(d, J=7.0Hz, 2H), 5.16–5.23(m, 1H), 7.05(s, 1H), 7.14–7.41(m, 6H), 7.66 (d, J=8.4Hz, 2H)
IR(KBr) 3433, 2946, 1514, 1467, 1360, 1282, 1180, 1152, 1115, 868 cm$^{-1}$

I-791    mp 123–124° C.
$^1$H NMR(DMSO-d$_6$) δ 1.72(s, 3H), 1.77(s, 3H), 2.03(s, 6H), 4.56(d, J=6.6Hz, 2H), 5.50(t, J=6.0Hz, 1H), 6.49(d, J=9.6 Hz, 1H), 6.55(s, 1H), 6.83(d, J=8.4Hz, 2H), 6.98(d, J=8.1 Hz, 1H), 7.27(s, 2H), 7.48(d, J=5.6Hz, 2H), 8.92(brs, 1H),

TABLE 156-continued

| | |
|---|---|
| | 9.48(brs, 1H)<br>IR(KBr) 3337, 2930, 1612, 1518, 1471, 1285, 1258, 1207, 1123, 999, 834 cm$^{-1}$ |
| I-792 | mp 230–231° C.<br>$^1$H NMR(DMSO-d$_6$) δ 2.04(s, 6H), 2.33(s, 3H), 5.09(s, 2H), 6.50(d, J=8.4Hz, 1H), 6.59(s, 1H), 6.85(d, J=8.1Hz, 2H), 7.04(d, J=5.4Hz, 1H), 7.23(d, J=7.5Hz, 2H), 7.29(s, 1H), 7.41(d, J=7.8Hz, 2H), 7.49(d, J=8.7Hz, 2H), 9.05(brs, 1H), 9.50(brs, 1H)<br>IR(KBr) 3287, 1609, 1519, 1475, 1298, 1245, 1126, 1006, 841 cm$^{-1}$ |
| I-793 | mp 118–119° C.<br>$^1$H NMR(DMSO-d$_6$) δ 1.64(s, 3H), 1.70(s, 3H), 2.03(s, 6H), 2.42–2.50(m, 2H), 3.96(t, J=6.9Hz, 2H), 5.27(t, J=7.2Hz, 2H), 6.49(d, J=8.1Hz, 1H), 6.55(s, 1H), 6.84(d, J=8.4Hz, 2H), 6.96(d, J=8.1Hz, 1H), 7.27(s, 2H), 7.48(d, J=8.7Hz, 2H), 8.89(brs, 1H), 9.48(brs, 1H)<br>IR(KBr) 3392, 2928, 1610, 1519, 1466, 1250, 1230, 1205, 1178, 1128, 1031, 834, 808 cm$^{-1}$ |
| I-794 | mp 139–140° C.<br>$^1$H NMR(DMSO-d$_6$) δ 1.75(s, 3H), 1.77(s, 3H), 2.50(s, 6H), 3.39(s, 3H), 3.44(s, 3H), 4.69(d, J=6.2Hz, 2H), 5.50(t, J=6.6Hz, 1H), 7.29–7.33(m, 3H), 7.41–7.47(m, 4H), 7.59–7.68(m, 2H)<br>IR(KBr) 3433, 2933, 1675, 1516, 1473, 1366, 1358, 1292, 1259, 1182, 1172, 1151, 969, 873 cm$^{-1}$ |

TABLE 157

| | |
|---|---|
| I-795 | mp 151–152° C.<br>$^1$H NMR(DMSO-d$_6$) δ 2.05(s, 6H), 2.18(s, 3H), 3.36(s, 3h), 3.44(s, 3H), 5.22(s, 2H), 7.08–7.63(m, 13H)<br>IR(KBr) 3434, 3023, 2928, 1517, 1477, 1368, 1293, 1261, 1183, 1152, 966, 870 cm$^{-1}$ |
| I-796 | mp 159–160° C.<br>$^1$H NMR(DMSO-d$_6$) δ 1.65(s, 3H), 1.70(s, 3H), 2.05(s, 6H), 2.48–2.53(m, 2H), 3.38(s, 3H), 3.44(s, 3H), 4.10(t, J=7.4Hz, 2H), 5.21–5.27(m, 1H), 7.28–7.34(m, 3H), 7.41–7.47(m, 4H), 7.59–7.64(m, 2H)<br>IR(KBr) 3434, 2938, 1519, 1478, 1439, 1362, 1295, 1269, 1173, 1152, 1125, 960, 870, 839 cm$^{-1}$ |
| I-797 | mp 130–131° C.<br>$^1$H NMR(DMSO-d$_6$) δ 1.72(s, 3H), 1.75(s, 3H), 2.02(s, 6H), 4.59(d, J=6.4Hz, 2H), 5.48(t, J=7.2Hz, 1H), 6.81–7.07(m, 7H), 7.25(s, 2H), 8.96(brs, 1H), 9.41(brs, 1H)<br>IR(KBr) 3392, 1608, 1589, 1518, 1475, 1322, 1258, 1170, 1127, 974, 836, 808 cm$^{-1}$ |
| I-798 | mp 143–144° C.<br>$^1$H NMR(DMSO-d$_6$) δ 2.03(s, 6H), 2.32(s, 3H), 5.12(s, 2H), 6.82–7.41(m, 13H), 9.10(brs, 1H), 9.41(brs, 1H)<br>IR(KBr) 3344, 1609, 1521, 1427, 1255, 1236, 1205, 1129, 998, 832, 806, 792 cm$^{-1}$ |
| I-799 | mp 163–164° C.<br>$^1$H NMR(DMSO-d$_6$) δ 1.87(s, 3H), 1.90(s, 3H), 3.42(s, 3H), 5.15(s, 2H), 6.88–7.03(m, 4H), 7.24–7.58(m, 9H), 7.97(brs, 1H), 9.02(brs, 1H)<br>IR(KBr) 3563, 3476, 3001, 2922, 1698, 1527, 1512, 1476, 1359, 1303, 1261, 1237, 1210, 1195, 1167, 1146, 871 cm$^{-1}$ |
| I-800 | $^1$H NMR(CDCl$_3$) δ 1.30(d, J=6.6Hz, 6H), 2.58(s, 3H), 2.97 (quintet, J=6.6Hz, 1H), 3.21(s, 3H), 3.54(s, 3H), 3.77(s, 3H), 5.17(s, 2H), 6.87(s, 1H), 7.11(d, J=9.0Hz, 1H), 7.22–7.35(m, 8H), 7.47–7.68(m, 6H), 8.19–8.25(m, 2H)<br>IR(KBr) 1737, 1604, 1519, 1482, 1392, 1366, 1267, 1173, 1131, 1084, 1062, 1009 cm$^{-1}$ |

TABLE 158

| | |
|---|---|
| I-801 | $^1$H NMR(CDCl$_3$) δ 2.56(s, 3H), 3.55(s, 3H), 3.78(s, 3H), 5.17 (s, 2H), 5.69(s, 1H), 6.84(s, 1H), 6.91(d.d, J=8.4&1.8Hz, 1H), 7.02(d, J=8.4Hz, 1H), 7.04(d, J=1.8Hz, 1H), 7.04–7.14 |

TABLE 158-continued

| | |
|---|---|
| | (m, 1H), 7.33–7.47(m, 8H)<br>IR(KBr) 3446, 1613, 1585, 1522, 1477, 1396, 1357, 1291, 1243, 1204, 1174, 1076,1017, 1006 cm$^{-1}$ |
| I-802 | foam<br>$^1$H NMR(CDCl$_3$) δ 2.82(s, 3H), 3.22(s, 3H), 3.25(s, 3H), 3.26 (s, 3H), 3.55(s, 3H), 3.78(s, 3H), 5.48(s, 2H), 6.85(s, 1H), 7.27 (d, J=8.4Hz, 1H), 7.39(d, J=8.7Hz, 2H), 7.40(dd, J=8.4, 2.1Hz, 1H), 7.43(d, J=2.1Hz, 1H), 7.67(d, J=8.7Hz, 2H)<br>IR(Nujol) 1608, 1519, 1480, 1462, 1365, 1176, 1151, 1079, 970, 876, 798 cm$^{-1}$ |
| I-803 | foam<br>$^1$H NMR(CD3OD) δ 3.28(s, 3H), 3.68(s, 3H), 5.17(s, 2H), 6.43 (s, 1H), 6.81(dd, J=8.4, 2.1Hz, 1H), 6.85(d, J=8.7Hz, 2H), 6.89(d, J=2.1Hz, 1H), 7.03(d, J=8.4Hz, 1H), 7.46(d, J=8.7Hz, 2H)<br>IR(Nujol) 3342, 1611, 1592, 1523, 1488, 1460, 1251, 1225, 1114, 1072, 1012, 941, 826, 756 cm$^{-1}$ |
| I-804 | mp 150–152° C.<br>$^1$H NMR(DMSO-d$_6$) δ 3.31(s, 3H), 3.64(s, 3H), 5.00(s, 2H), 6.39(s, 1H), 6.66(dd, J=8.4, 2.1Hz, 1H), 6.79(d, J=2.1Hz, 1H), 6.84(d, J=8.7Hz, 2H), 6.98(d, J=8.4Hz, 1H), 7.44(d, J=8.7Hz, 2H)<br>IR(Nujol) 3459, 3291, 1612, 1594, 1522, 1489, 1458, 1257, 1226, 1101, 1073, 1011, 960, 823 cm$^{-1}$ |
| I-805 | mp 190–192° C.<br>$^1$H NMR(DMSO-d$_6$) δ 2.88(s, 3H), 3.41(s, 3H), 3.45(s, 3H), 3.52(s, 3H), 3.79(s, 3H), 5.43(s, 2H), 7.08(s, 1H), 7.16(s, 1H), 7.32~7.36(m, 2H), 7.46(d, J=8.4Hz, 1H), 7.49(d, J=8.7Hz, 2H), 7.53~7.64(m, 3H), 7.74(d, J=8.7Hz, 2H), 7.88~7.91(m, 2H)<br>IR(Nujol) 1604, 1519, 1481, 1462, 1367, 1175, 1081, 1009, 878, 841, 816, 801 cm$^{-1}$ |

TABLE 159

| | |
|---|---|
| I-806 | foam<br>$^1$H NMR(CDCl$_3$) δ 3.45(s, 3H), 3.74(s, 3H), 5.31(s, 2H), 6.94 (s, 1H), 6.45(s, 1H), 6.64(s, 1H), 6.93(d, J=8.7Hz, 2H), 6.98 (dd, J=8.4, 2.1Hz, 1H),7.09(d, J=8.4Hz, 1H), 7.11(d, J=2.1Hz, 1H), 7.46~7.50(m, 3H), 7.53(d, J=8.7Hz, 2H), 7.78~7.82(m, 2H)<br>IR(Nujol) 3367, 1612, 1592, 1523, 1489, 1455, 1253, 1226, 1115, 1073, 1013, 942, 816, 767 cm$^{-1}$ |
| I-807 | foam<br>$^1$H NMR(CDCl$_3$) δ 2.76(s, 3H), 3.21(s, 3H), 3.30(s, 3H), 3.56 (s, 3H), 3.78(s, 3H), 5.38(s, 2H), 6.84(s, 1H), 7.21(d, J=8.4 Hz, 1H), 7.38(d, J=8.7Hz, 2H), 7.38(dd, J=8.4, 2.1Hz, 1H), 7.45(d, J=2.1Hz, 1H), 7.67(d, J=8.7Hz, 2H), 8.80(s, 1H)<br>IR(Nujol) 1608, 1519, 1480, 1463, 1365, 1177, 1151, 1079, 971, 876, 798 cm$^{-1}$ |
| I-808 | mp 193–195° C.<br>$^1$H NMR(CDCl$_3$) δ 2.64(s, 3H), 2.74(s, 3H), 3.21(s, 3H), 3.30 (s, 3H), 3.56(s, 3H), 3.78(s, 3H), 5.28(s, 2H), 6.84(s, 1H), 7.21 (d, J=8.4Hz, 1H), 7.38(d, J=8.7Hz, 2H), 7.38(dd, J=8.4, 2.1Hz, 1H), 7.44(d, J=2.1Hz, 1H), 7.68(d, J=8.7Hz, 2H)<br>IR(Nujol) 1606, 1591, 1522, 1480, 1463, 1359, 1174, 1152, 1079, 1012, 946, 877, 834, 796 cm$^{-1}$ |
| I-809 | foam<br>$^1$H NMR(CDCl$_3$) δ 1.42(t, J=7.5Hz, 3H), 2.73(s, 3H), 2.96 (q, J=7.5Hz, 2H), 3.21(s, 3H), 3.31(s, 3H), 3.56(s, 3H), 3.78 (s, 3H), 5.28(s, 2H), 6.84(s, 1H), 7.21(d, J=8.4Hz, 1H), 7.38 (d, J=8.7Hz, 2H), 7.38(dd, J=8.4, 2.1Hz, 1H), 7.44(d, J=2.1Hz, 1H), 7.68(d, J=8.7Hz, 2H)<br>IR(KBr) 3434, 1609, 1579, 1519, 1481, 1365, 1177, 1151, 1080, 970, 876, 797 cm$^{-1}$ |

TABLE 160

| | |
|---|---|
| I-810 | foam<br>$^1$H NMR(CDCl$_3$) δ 2.71(s, 3H), 3.21(s, 3H), 3.35(s, 3H), 3.56 |

TABLE 160-continued

| | |
|---|---|
| | (s, 3H), 3.78(s, 3H), 5.38(s, 2H), 6.84(s, 1H), 7.25(d, J=8.4 Hz, 1H), 7.38(d, J=8.7Hz, 2H), 7.40(dd, J=8.4, 2.1Hz, 1H), 7.46(d, J=2.1Hz, 1H), 7.54~7.64(m, 3H), 7.68(d, J=8.7Hz, 2H), 8.12~8.16(m, 2H)<br>IR(KBr) 3433, 1609, 1561, 1519, 1480, 1365, 1177, 1151, 1081, 971, 876, 798 cm$^{-1}$ |
| I-811 | foam<br>$^1$H NMR(CDCl$_3$) δ 2.51(s, 3H), 2.54(s, 3H), 2.63(s, 3H), 2.72 (s, 3H), 3.16(s, 3H), 3.21(s, 3H), 3.56(s, 3H), 3.78(s, 3H), 5.27 (s, 2H), 6.84(s, 1H), 7.27(d, J=8.4Hz, 1H), 7.36(dd, J=8.4, 2.1Hz, 1H), 7.38(d, J=8.7Hz, 2H), 7.41(d, J=2.1Hz, 1H), 7.68(d, J=8.7Hz, 2H)<br>IR(KBr) 3435, 1614, 1519, 1480, 1364, 1177, 1151, 1080, 972, 876, 798 cm$^{-1}$ |
| I-812 | foam<br>$^1$H NMR(CDCl$_3$) δ 2.74(s, 6H), 3.17(s, 3H), 3.21(s, 3H), 3.55 (s, 3H), 3.78(s, 3H), 5.35(s, 2H), 6.84(s, 1H), 7.28(d, J=8.4 Hz, 1H), 7.36(dd, J=8.4, 2.1Hz, 1H), 7.38(d, J=8.7Hz, 2H), 7.41(d, J=2.1Hz, 1H), 7.68(d, J=8.7Hz, 2H), 8.41(d, J=2.4Hz, 1H), 8.50(d, J=2.4Hz, 1H)<br>IR(KBr) 3433, 1609, 1519, 1481, 1364, 1177, 1151, 1080, 971, 876, 798 cm$^{-1}$ |
| I-813 | foam<br>$^1$H NMR(DMSO-d$_6$) δ 2.47(s, 6H), 2.55(s, 3H), 3.30(s, 3H), 3.64(s, 3H), 5.16(s, 2H), 6.39(s, 1H), 6.66(dd, J=8.4, 2.1Hz, 1H), 6.76(d, J=2.1Hz, 1H), 6.84(d, J=8.7Hz, 2H), 7.03(d, J=8.4Hz, 1H), 7.44(d, J=8.7Hz, 2H),<br>IR(KBr) 3399, 3165, 1611, 1521, 1488, 1406, 1362, 1213, 1114, 1069, 1014, 818, 759 cm$^{-1}$ |

TABLE 161

| | |
|---|---|
| I-814 | mp 240–241° C.<br>$^1$H NMR(DMSO-d$_6$) δ 2.66(s, 3H), 3.30(s, 3H), 3.64(s, 3H), 5.26(s, 2H), 6.39(s, 1H), 6.66(dd, J=8.4, 2.1Hz, 1H), 6.77(d, J=2.1Hz, 1H), 6.84(d, J=8.7Hz, 2H), 7.02(d, J=8.4Hz, 1H), 7.44(d, J=8.7Hz, 2H), 8.48(d, J=2.7Hz, 1H), 8.53(d, J=2.7Hz, 1H)<br>IR(Nujol) 3513, 3491, 3070, 1610, 1581, 1523, 1488, 1459, 1408, 1275, 1236, 1216, 1111, 1065, 1040, 821, 785 cm$^{-1}$ |
| I-815 | mp 288–290° C.(decomp.)<br>$^1$H NMR(DMSO-d$_6$) δ 2.89(s, 3H), 3.41(s, 3H), 3.45(s, 3H), 3.52(s, 3H), 3.79(s, 3H), 4.95(s, 2H), 5.65(s, 1H), 7.08(s, 1H), 7.26(d, J=8.4Hz, 1H), 7.33(dd, J=8.4, 2.1Hz, 1H), 7.38(d, J=2.1Hz, 1H), 7.49(d, J=8.7Hz, 2H), 7.74(d, J=8.7Hz, 2H),<br>IR(Nujol) 3120, 1712, 1671, 1604, 1516, 1480, 1462, 1364, 1172, 1078, 1015, 970, 874, 841, 796 cm$^{-1}$ |
| I-816 | mp 204–206° C.<br>$^1$H NMR(DMSO-d$_6$) δ 2.87(s, 3H), 3.45(s, 3H), 3.46(s, 3H), 3.52(s, 3H), 3.78(s, 3H), 5.40(s, 2H), 7.08(s, 1H), 7.32(dd, J=8.4, 2.1Hz, 1H), 7.33(d, J=8.4Hz, 1H), 7.39(d, J=2.1Hz, 1H), 7.48(d, J=8.7Hz, 2H), 7.71(dd, J=5.1, 1.2Hz, 1H), 7.74(d, J=8.7Hz, 2H), 8.88(d, J=5.1Hz, 1H), 9.21(d, J=1.2Hz, 1H)<br>IR(Nujol) 1608, 1586, 1557, 1521, 1480, 1464, 1360, 1352, 1176, 1156, 1078, 884, 835, 818, 799 cm$^{-1}$ |
| I-817 | foam<br>$^1$H NMR(CDCl$_3$) δ 2.20(s, 3H), 3.45(s, 3H), 3.75(s, 3H), 5.15(s, 2H), 6.45(s, 1H), 6.92(d, J=8.7Hz, 2H), 6.94(dd, J=1.8, 8.4Hz, 1H), 6.98(d, J=8.4Hz, 1H), 7.09(d, J=1.8Hz, 1H), 7.18(m, 1H), 7.37(t, J=7.2Hz, 1H), 7.53(d, J=8.7Hz, 2H), 7.55(m, 2H) |

TABLE 162

| | |
|---|---|
| I-818 | m.p 163–166° C.<br>$^1$H NMR(CDCl$_3$) δ 1.53(s, 9H), 2.67(s, 3H), 3.11(s, 3H), 3.21 (s, 3H), 3.56(s, 3H), 3.77(s, 3H), 5.12(s, 2H), 6.52(s, 1H), 6.84(s, 1H), 7.13(d, J=8.4Hz, 1H), 7.33(dd, J=2.1, 8.4Hz, |

TABLE 162-continued

| | |
|---|---|
| | 1H), 7.38(d, J=8.7Hz, 2H), 7.39(m, 5H), 7.74(d, J=8.7Hz, 2H)<br>IR(KBr) 1692, 1614, 1520, 1480, 1390, 1367, 1231, 1175, 1152, 1078, 876, 799 cm$^{-1}$ |
| I-819 | m.p 172° C.<br>$^1$H NMR(CDCl$_3$) δ 2.77(s, 3H), 3.05(s, 3H), 3.16(s, 3H), 3.22 (s, 3H), 3.36(s, 3H), 3.78(s, 3H), 5.16(s, 2H), 6.46(s, 1H), 6.85 (s, 1H), 7.14(d, J=8.4Hz, 1H), 7.25(d, J=8.7Hz, 2H), 7.35 (dd, J=2.1, 8.4Hz, 1H), 7.39(d, J=8.7Hz, 2H), 7.40(d, J= 2.1, 1H), 7.47(d, J=8.4Hz, 2H), 7.67(d, J=8.7Hz, 2H)<br>IR(KBr) 1608, 1519, 1480, 1361, 1175, 1154, 1079, 972, 876, 801 cm$^{-1}$ |
| I-820 | mp 180–182° C.<br>$^1$H NMR(CDCl$_3$) δ 2.69(s, 3H), 3.14(s, 3H), 3.21(s, 3H), 3.53 (s, 3H), 3.71(d, J=0.9Hz, 3H), 5.20(s, 2H), 6.93(d, J=8.4 Hz, 1H), 7.34–7.49(m, 9H), 7.59(dd, J=9.0, 1.2Hz, 2H)<br>IR(KBr) 1518, 1469, 1357, 1179, 1151, 1038, 871, 821 cm$^{-1}$ |
| I-821 | mp 183–185° C.<br>$^1$H NMR(CDCl$_3$) δ 3.41(s, 3H), 3.66(d, J=0.9Hz, 3H), 4.91 (s, 1H), 5.17(s, 2H), 5.62(s, 1H), 5.70(s, 1H), 6.92–6.96(m, 2H), 6.97(dd, J=8.4, 2.0Hz, 1H), 7.04(d, J=8.4Hz, 1H), 7.10(d, J=2.0Hz, 1H), 7.36–7.48(m, 7H)<br>IR(KBr) 3541, 3398, 1588, 1523, 1461, 1410, 1320, 1261, 1217, 1037, 836, 747 cm$^{-1}$ |
| I-822 | mp 108–110° C.<br>$^1$H NMR(CDCl$_3$) δ 2.69(s, 3H), 3.13(s, 3H), 3.45(s, 3H), 3.53 (s, 3H), 3.77(s, 3H), 4.66(s, 2H), 4.76(s, 2H), 5.19(s, 2H), 6.86 (s, 1H), 7.71(d, J=8.4Hz, 1H), 7.33–7.48(m, 9H), 7.62(d, J= 8.4Hz, 2H)<br>IR(KBr) 1482, 1390, 1307, 1276, 1177, 1083, 1053, 1013, 807 cm$^{-1}$ |

TABLE 163

| | |
|---|---|
| I-823 | mp 192–194° C.<br>$^1$H NMR(CDCl$_3$) δ 1.70(br s, 1H), 2.69(s, 3H), 3.13(s, 3H), 3.53(s, 3H), 3.77(s, 3H), 4.78(s, 2H), 5.19(s, 2H), 6.87(s, 1H), 7.15(d, J=8.4Hz, 1H), 7.35(dd, J=8.4, 2.3Hz, 1H), 7.37–7.49 (m, 8H), 7.63(d, J=7.8Hz, 2H)<br>IR(KBr) 3554, 3434, 1522, 1481, 1389, 1364, 1277, 1234, 1174, 1085, 1012, 807 cm$^{-1}$ |
| I-824 | mp 135–137° C.<br>$^1$H NMR(CDCl$_3$) δ 3.19(s, 3H), 3.60(s, 3H), 3.71(s, 3H), 4.96 (s, 1H), 5.18(s, 2H), 5.78(s, 1H), 6.73(s, 1H), 6.88(dd, J=8.3, 2.1Hz, 1H), 7.02(d, J=2.1Hz, 1H), 7.08(d, J=8.3Hz, 1H), 7.34(d, J=8.6Hz, 2H), 7.41–7.47(m, 5H), 7.63(d, J=8.6Hz, 2H)<br>IR(KBr) 3479, 1473, 1347, 1149, 1010, 869, 803, 784, 747 cm$^{-1}$ |
| I-825 | mp 149–151° C.<br>$^1$H NMR(CDCl$_3$) δ 2.68(s, 3H), 3.13(s, 3H), 3.20(s, 3H), 3.69 (s, 3H), 3.71(s, 3H), 5.20(s, 2H), 7.18(d, J=8.7Hz, 1H), 7.21 (s, 1H), 7.35–7.50(m, 9H), 7.63(d, J=8.1Hz, 2H)<br>IR(KBr) 1519, 1469, 1353, 1173, 1149, 1050, 966, 873, 849, 810 cm$^{-1}$ |
| I-826 | mp 82–85° C.<br>$^1$H NMR(CDCl$_3$) δ 1.78(s, 3H), 1.82(s, 3H), 2.70(s, 3H), 3.20 (s, 3H), 3.25(s, 3H), 3.69(s, 3H), 3.70(s, 3H), 4.65(d, J=6.9 Hz, 2H), 5.51(t, J=6.9Hz, 1H), 7.11(d, J=8.8Hz, 1H), 7.21 (s, 1H), 7.37(d, J=8.9Hz, 2H), 7.38(dd, J=8.8, 2.2Hz, 1H), 7.42(d, J=2.2Hz, 1H), 7.63(d, J=8.9Hz, 2H)<br>IR(KBr) 1516, 1468, 1363, 1180, 1151, 1045, 967, 846, 788 cm$^{-1}$ |
| I-827 | amorphous<br>$^1$H NMR(CDCl$_3$) δ 1.77(s, 3H), 1.83(s, 3H), 3.58(s, 3H), 3.70 (s, 3H), 4.64(d, J=6.7Hz, 2H), 4.97(s, 1H), 5.04(s, 1H), 5.53 (t, J=6.7Hz, 1H), 5.81(s, 1H), 6.73(s, 1H), 6.87(dd, J=8.1, 2.0Hz, 1H), 6.88(d, J=8.7Hz, 2H), 6.99(d, J=2.0Hz, 1H), 7.00(d, J=8.1Hz, 1H), 7.47(d, J=8.7Hz, 2H)<br>IR(CHCl$_3$) 3595, 3536, 1613, 1584, 1521, 1474, 1406, 1356, 1266, 1094, 1062, 1014, 973, 835 cm$^{-1}$ |

TABLE 164

I-828  mp 161–162° C.
$^1$H NMR(CDCl$_3$) δ 3.58(s, 3H), 3.71(s, 3H), 4.85(s, 1H), 4.93 (s, 1H), 5.18(s, 2H), 5.78(s, 1H), 6.73(s, 1H), 6.87–6.92(m, 3H), 7.02(d, J=1.8Hz, 1H), 7.07(d, J=8.1Hz, 1H), 7.37–7.51 (m, 7H)
IR(KBr) 3510, 3442, 3326, 1523, 1485, 1453, 1395, 1239, 1061, 1003, 972, 836, 753 cm$^{-1}$

I-829  mp 85–87° C.
$^1$H NMR(CDCl$_3$) δ 1.69(s, 3H), 1.75(s, 3H), 2.57(q, J=6.9 Hz, 2H), 2.70(s, 3H), 3.20(s, 3H), 3.24(s, 3H), 3.69(s, 3H), 4.09(t, J=6.9Hz, 2H), 5.22(t, J=6.9Hz, 1H), 7.10 (d, J=8.4Hz, 1H), 7.21(s, 1H), 7.37–7.44(m, 9H), 7.63(d, J= 8.4Hz, 2H)
IR(KBr) 1519, 1468, 1362, 1179, 1150, 1046, 967, 865, 847 cm$^{-1}$

I-830  mp 160–162° C.
$^1$H NMR(CDCl$_3$) δ 2.38(s, 3H), 2.68(s, 3H), 3.12(s, 3H), 3.20 (s, 3H), 3.69(s, 3H), 3.70(s, 3H), 5.15(s, 2H), 7.16–7.25(m, 4H), 7.34–7.44(m, 6H), 7.63(d, J=8.1Hz, 2H)
IR(KBr) 1519, 1469, 1365, 1173, 1149, 1049, 965, 873, 849, 808 cm$^{-1}$

I-831  amorphous
$^1$H NMR(CDCl$_3$) δ 1.69(s, 3H), 1.76(s, 3H), 2.55(q, J=6.9 Hz, 1H), 3.58(s, 3H), 3.69(s, 3H), 4.08(t, J=6.9Hz, 2H), 4.98 (s, 1H), 5.18(s, 1H), 5.23(t, J=6.9Hz, 1H), 5.80(s, 1H), 6.72 (s, 1H), 6.86–6.89(m, 3H), 6.97–7.00(m, 3H), 7.47(d, J=8.4 Hz, 2H)
IR(KBr) 3595, 3538, 1521, 1471, 1265, 1173, 1095, 1063, 1015, 835 cm$^{-1}$ I-832  mp 200–201° C.
$^1$H NMR(CDCl$_3$) δ 2.40(s, 3H), 3.58(s, 3H), 3.70(s, 3H), 4.80 (s, 1H), 4.92(s, 1H), 5.13(s, 2H), 5.77(s, 1H), 6.73(s, 1H), 6.88 (dd, J=8.1, 2.0Hz, 1H), 6.89(d, J=8.4Hz, 2H), 7.01(d, J= 1.8Hz, 1H), 7.07(d, J=8.4Hz, 1H), 7.24(d, J=7.8Hz, 2H), 7.35(d, J=7.8Hz, 2H), 7.48(d, J=8.4Hz, 2H),
IR(KBr) 3419, 1610, 1523, 1485, 1393, 1243, 1065, 1004, 972, 833, 795 cm$^{-1}$

TABLE 165

I-833  mp 141–142° C.
$^1$H NMR(CDCl$_3$) δ 2.03(s, 3H), 2.11(s, 3H), 2.54(s, 3H), 3.15 (s, 3H), 3.21(s, 3H), 5.20(s, 2H), 7.12–7.26(m, 5H), 7.38–7.50 (m, 8H)
IR(KBr) 3435, 3033, 2938, 1518, 1470, 1364, 1178, 1149, 1109, 970, 871, 839 cm$^{-1}$

I-834  mp 188–189° C.
$^1$H NMR(CDCl$_3$) δ 3.49(s, 3H), 3.72(s, 3H), 5.15(s, 2H), 5.68 (brs, 1H), 5.84(brs, 1H), 6.42–6.56(m, 3H), 6.98–7.08(m, 3H), 7.23–7.31(m, 3H), 7.23–7.31(m, 2H), 7.38–7.45(m, 4H)
IR(KBr) 3420, 3328, 1627, 1584, 1523, 1489, 1460, 1412, 1316, 1288, 1249, 1172, 1128, 1115, 1068, 1000, 849, 812, 746 cm$^{-1}$ I-835  mp 180–181° C.
$^1$H NMR(CDCl$_3$) δ 3.51(s, 3H), 3.75(s, 3H), 5.17(s, 2H), 5.70 (brs, 1H), 5.77(brs, 1H), 6.45(s, 1H), 6.95–7.10(m, 4H), 7.27–7.46(m, 8H), 7.96(brs, 1H)
IR(KBr) 3422, 3358, 1706, 1602, 1489, 1454, 1410, 1289, 1253, 1203, 1180, 1125, 1101, 1071, 1015 cm$^{-1}$ I-836  mp 148–149° C.
$^1$H NMR(DMSO-d$_6$) δ 1.77(s, 3H), 1.80(s, 3H), 2.54(s, 6H), 3.35(s, 3H), 3.42(s, 3H), 3.48(s, 3H), 4.73(d, J=4.5Hz, 2H), 5.50–5.53(m, 1H), 7.30–7.54(m, 8H)
IR(KBr) 3495, 3293, 1754, 1712, 1516, 1359, 1359, 1243, 1175, 1147, 971, 866, 845 cm$^{-1}$ I-837  mp 136–138° C.
$^1$H NMR(DMSO-d$_6$) δ 2.32(s, 3H), 2.50(s, 6H), 3.31(s, 3H), 3.35(s, 3H), 3.44(s, 3H), 5.23(s, 2H), 7.21–7.47(m, 12H)
IR(KBr) 3495, 3292, 3028, 2934, 1754, 1710, 1516, 1357, 1176, 1147, 972, 868, 842 cm$^{-1}$

TABLE 166

I-838  mp 195–196° C.
$^1$H NMR(CDCl$_3$) δ 1.44(t, J=7.2Hz, 3H), 3.46(s, 3H), 3.69 (s, 3H), 3.86(s, 6H), 4.44(q, J=7.0Hz, 2H), 5.15(s, 2H), 5.66 (brs, 1H), 5.72(brs, 1H), 6.27(s, 1H), 7.01(s, 2H), 7.13(s, 1H), 7.38–7.46(m, 7H)
IR(KBr) 3485, 2937, 1713, 1580, 1464, 1455, 1407, 1324, 1243, 1123, 1102, 1069, 1014, 763 cm$^{-1}$ I-839  mp 150–151° C.
$^1$H NMR(DMSO-d$_6$) δ 1.72(s, 3H), 1.76(s, 3H), 1.88(s, 3H), 1.90(s, 3H), 4.55(d, J=5.8Hz, 2H), 5.44–5.50(m, 1H), 6.80–6.97(m, 8H), 7.81(brs, 1H), 8.85(brs, 1H), 9.38(brs, 1H)
IR(KBr) 3495, 3293, 1753, 1711, 1429, 1390, 1360, 1242, 1217, 1178, 1143, 781 cm$^{-1}$ I-840  mp 149–150° C.
$^1$H NMR(DMSO-d$_6$) δ 1.71(s, 3H), 1.75(s, 3H), 2.00(s, 6H), 2.59(s, 3H), 4.57(d, J=6.4Hz, 2H), 5.42–5.47(m, 1H), 6.84–7.13(m, 8H), 9.13(brs, 1H), 9.50(brs, 1H)
IR(KBr) 3451, 2933, 1612, 1587, 1518, 1472, 1348, 1259, 1211, 1171, 1121, 1087, 969, 872, 835, 813 cm$^{-1}$ I-841  mp 203–204° C.
$^1$H NMR(DMSO-d$_6$) δ 1.87(s, 3H), 1.89(s, 3H), 2.31(s, 3H), 5.09(s, 2H), 6.80–7.00(m, 8H), 7.20(d, J=7.8Hz, 2H), 7.39 (d, J=7.8Hz, 2H), 7.81(brs, 1H), 8.97(brs, 1H), 9.38(brs, 1H)
IR(KBr) 3491, 3398, 2921, 1611, 1516, 1476, 1259, 1183, 1155, 996, 794 cm$^{-1}$ I-842  mp 128–129° C.
$^1$H NMR(DMSO-d$_6$) δ 2.01(s, 6H), 2.34(s, 3H), 2.63(s, 3H), 5.12(s, 2H), 6.85–7.13(m, 8H), 7.18(d, J=7.6Hz, 2H), 7.36 (d, J=7.6Hz, 2H), 9.15(brs, 1H), 9.55(brs, 1H)
IR(KBr) 3432, 3305, 1735, 1607, 1523, 1482, 1398, 1360, 1294, 1284, 1179, 1080, 816 cm$^{-1}$

TABLE 167

I-843  mp 203–204° C.
$^1$H NMR(CDCl$_3$) δ 2.66(s, 3H), 3.13(s, 3H), 3.59(s, 3H), 3.76 (s, 3H), 5.19(s, 2H), 6.85(s, 1H), 7.13–7.69(m, 11H), 8.07(brs, 1H)
IR(KBr) 3432, 3305, 1735, 1607, 1523, 1482, 1398, 1360, 1294, 1284, 1179, 1080, 816 cm$^{-1}$ I-844  mp 109–110° C.
$^1$H NMR(DMSO-d$_6$) δ 1.36(t, J=7.2Hz, 3H), 2.82(s, 3H), 3.24 (s, 3H), 3.47(s, 3H), 3.66(s, 3H), 3.79(s, 6H), 4.38(q, J=7.0 Hz, 2H), 5.26(s, 2H), 6.78(s, 1H), 7.32–7.52(m, 10H)
IR(KBr) 3432, 2940, 1716, 1579, 1465, 1407, 1366, 1322, 1240, 1179, 1123, 1078, 815, 796 cm$^{-1}$ I-845  mp 113–115° C.
$^1$H NMR(CDCl$_3$) δ 2.25(s, 3H), 2.27(s, 3H), 3.20(s, 3H), 5.20 (s, 2H), 7.03–7.15(m, 5H), 7.33–7.51(m, 9H))
IR(CHCl$_3$) 2925, 1618, 1580, 1521, 1455, 1373, 1314, 1299, 1268, 1174, 1149, 1126, 1018, 970, 874 cm$^{-1}$ I-846  mp 155–157° C.
$^1$H NMR(CDCl$_3$) δ 2.26(s, 6H), 4.69(s, 1H), 5.19(s, 2H), 6.87–6.90(m, 2H), 7.03–7.15(m, 5H), 7.22–7.50(m, 7H)
IR(CHCl$_3$) 3596, 2952, 2924, 1612, 1582, 1523, 1490, 1455, 1425, 1383, 1259, 1171, 1125, 1012, 956, 877 cm$^{-1}$ I-847  mp 81–84° C.
$^1$H NMR(CDCl$_3$) δ 1.07–1.14(m, 6H), 2.55–2.66(m, 4H), 4.73 (s, 1H), 5.16(s, 2H), 5.70(s, 1H), 6.82–6.91(m, 3H), 6.92–6.99 (m, 2H), 7.10–7.12(d, J=4.2Hz, 2H), 7.22–7.25(m, 2H), 7.38–7.49(m, 5H)
IR(CHCl$_3$) 3596, 3542, 2968, 2932, 2872, 1731, 1611, 1588, 1520, 1489, 1455, 1380, 1327, 1289, 1256, 1171, 1126, 1011, 903, 878, 836 cm$^{-1}$ I-848  mp 125–127° C.
$^1$H NMR(CDCl$_3$) δ 1.77(s, 3H), 1.82(s, 3H), 2.26(s, 3H), 2.28 (s, 3H), 3.20(s, 3H), 4.63–4.65(d, J=6.9Hz, 2H), 5.56(m, 1H), 7.02–7.13(m, 5H), 7.31–7.43(m, 4H)
IR(CHCl$_3$) 2924, 1619, 1578, 1488, 1373, 1298, 1266, 1174, 1149, 1125, 970, 874 cm$^{-1}$

TABLE 168

I-849 mp 141–143° C.
¹H NMR(CDCl₃) δ 1.07–1.14(m, 6H), 2.53–2.65(m, 4H), 3.12 (s, 3H), 3.20(s, 3H), 5.18(s, 2H), 7.10–7.14(m, 3H), 7.24–7.27 (m, 2H), 7.33–7.50(m, 9H)
IR(CHCl₃) 2969, 2934, 1614, 1517, 1487, 1371, 1331, 1289, 1263, 1173, 1149, 1111, 970, 938, 872 cm⁻¹

I-850 mp 90–91° C.
¹H NMR(CDCl₃) δ 2.13(s, 3H), 2.29(s, 3H), 2.35(s, 3H), 3.16 (s, 3H), 5.21(s, 2H), 6.87–6.90(m, 2H), 7.09–7.49(m, 11H)
IR(CHCl₃) 3596, 1731, 1613, 1520, 1478, 1362, 1261, 1173, 1119, 1086, 1025, 972, 953, 874 cm⁻¹

I-851 mp 94–96° C.
¹H NMR(CDCl₃) δ 1.76–1.77(d, J=0.3Hz, 3H), 1.81–1.82(d, J=0.9Hz, 3H), 2.26(s, 3H), 2.27(s, 3H), 4.62–4.64(d, J=6.9 Hz, 2H), 4.71(s, 1H), 5.56(m, 1H), 6.87–6.91(m, 2H), 7.00–7.13 (m, 5H), 7.23–7.27(m, 2H)
IR(CHCl₃) 3596, 2923, 1675, 1613, 1579, 1523, 1490, 1386, 1297, 1171, 1124, 990, 956, 877, 836 cm⁻¹

I-852 mp 106–108° C.
¹H NMR(CDCl₃) δ 2.63(s, 3H), 3.52(s, 3H), 3.77(s, 3H), 5.24 (s, 2H), 6.84(s, 1H), 6.84(s, 1H), 7.12–7.20(m, 3H), 7.35–7.50 (m, 7H), 7.56–7.64(m, 2H)
IR(KBr) 2935, 1604, 1523, 1483, 1373, 1232, 1086, 1011, 945, 847, 728, 605, 523, 506 cm⁻¹

I-853 mp 136–138° C.
¹H NMR(CDCl₃) δ 1.77(s, 3H), 1.81(s, 3H), 2.67(s, 3H), 3.53 (s, 3H), 3.78(s, 3H), 4.67(d, J=6.9Hz, 2H), 5.47–5.53(m, 1H), 6.84(s, 1H), 7.10–7.19(m, 3H), 7.31(d, J=2.1Hz, 1H), 7.38 (dd, J=2.1, 8.1Hz, 1H), 7.57–7.64(m, 2H)
IR(KBr) 2936, 1604, 1523, 1484, 1435, 1373, 1225, 1086, 1011, 943, 848, 783, 606, 508 cm⁻¹

TABLE 169

I-854 mp 128–130° C.
¹H NMR (CDCl₃) δ 1.74 (s, 3H), 1.81 (s, 3H), 2.62 (s, 3H), 3.52 (s, 3H), 3.79 (s, 3H), 4.63–4.67 (m, 2H), 5.45–5.53 (m, 1H), 6.86 (s, 1H), 7.01 (dd, J = 2.1 Hz, 8.4 Hz, 1H), 7.10 (d, J = 1.8 Hz, 1H), 7.13–7.20 (m, 2H), 7.29 (d, J = 8.4 Hz, 1H), 7.59–7.64 (m, 2H)
IR (KBr) 2940, 1600, 1518, 1484, 1418, 1366, 1232, 1080, 984, 893, 838, 812, 621, 524 cm⁻¹

I-855 mp 141–143° C.
¹H NMR (CDCl₃) δ 1.76 (s, 3H), 1.82 (s, 3H), 2.61 (s, 3H), 3.53 (s, 3H), 3.77 (s, 3H), 4.62 (d, J = 6.9 Hz, 2H), 5.47–5.53 (m, 1H), 5.70 (s, 1H), 6.83 (s, 1H), 6.91 (dd, J = 2.1, 8.1 Hz, 1H), 6.96 (d, J = 8.1 Hz, 1H), 7.02 (d, J = 2.1 Hz, 1H), 7.10–7.19 (m, 2H), 7.59–7.64 (m, 2H)
IR (KBr) 3531, 2931, 1604, 1520, 1484, 1372, 1233, 1175, 1083, 1011, 814, 800, 781, 727, 526 cm⁻¹

I-856 mp 217–220° C.
¹H NMR (CDCl₃) δ 2.75 (s, 3H), 3.51 (s, 3H), 3.78 (s, 3H), 5.78 (s, 1H), 6.85 (s, 1H), 7.03 (dd, J = 1.8, 8.4 Hz, 1H), 7.11–7.20 (m, 3H), 7.32 (d, J = 8.4 Hz, 1H), 7.58–7.63 (m, 2H)
IR (KBr) 3434, 2941, 1611, 1487, 1423, 1363, 1209, 1076, 891, 818, 621, 573, 513 cm⁻¹

I-857 mp 183–185° C.
¹H NMR (CDCl₃) δ 1.92 (s, 3H), 3.20 (s, 3H), 3.53 (s, 3H), 3.78 (s, 3H), 3.93 (s, 3H), 4.31 (s, 4H), 6.79–6.83 (m, 2H), 6.90–6.94 (m, 2H), 7.16–7.41 (m, 12H), 7.66–7.71 (m, 2H),
IR (KBr) 3030, 2936, 1604, 1517, 1482, 1362, 1232, 1232, 1180, 1120, 1082, 877, 799, 701, 526 cm⁻¹

I-858 mp 192–194° C.
¹H NMR (CDCl₃) δ 2.57 (s, 3H), 3.21 (s, 3H), 3.56 (s, 3H), 3.77 (s, 3H), 3.87 (s, 3H), 6.77–6.89 (m, 4H), 7.34–7.40 (m, 2H), 7.67–7.72 (m, 2H)
IR (KBr) 3451, 3368, 2937, 1622, 1524, 1481, 1359, 1174, 1149, 1086, 962, 869, 802, 525 cm⁻¹

TABLE 170

I-859 mp 210–212° C.
¹H NMR (CDCl₃) δ 1.92 (s, 3H), 2.23 (s, 3H), 3.46 (s, 3H), 3.74 (s, 3H), 3.89 (s, 3H), 5.24 (s, 1H), 5.80 (s, 1H), 5.94 (s, 1H), 6.46 (s, 1H), 6.90–6.96 (m, 1H), 7.01 (d, J = 1.8 Hz, 1H), 7.08 (dd, J = 1.8, 8.1 Hz, 1H), 7.50–7.55 (m, 2H), 7.76 (s, 1H), 8.52 (d, J = 8.1 Hz, 1H),
IR (KBr) 3420, 2938, 1636, 1610, 1526, 1496, 1398, 1225, 1164, 1073, 1026, 831 cm⁻¹

I-860 mp 183–185° C.
¹H NMR (DMSO-d₆) δ 2.43 (s, 6H), 2.45 (s, 6H), 5.13 (s, 2H), 6.76–6.82 (m, 4H), 6.91 (dd, J = 2.1, 8.4 Hz, 1H), 7.01 (d, J = 8.4 Hz, 1H), 7.09 (d, J = 2.1 Hz, 1H), 7.31–7.43 (m, 5H), 7.48–7.53 (m, 2H), 9.02 (br s, 1H), 9.32 (br s, 1H)
IR (KBr) 3600–2800(br), 1609, 1581, 1521, 1493, 1455, 1437, 1384, 1321, 1275, 1215, 1193, 1142, 1007 cm⁻¹

I-861 mp 172–174° C.
¹H NMR (CDCl₃) δ 2.50 (s, 6H), 2.53 (s, 6H), 3.11 (s, 3H), 3.19 (s, 3H), 5.18 (s, 2H), 6.89 (s, 1H), 6.93 (s, 1H), 7.12 (d, J = 8.4 Hz, 1H), 7.30–7.54 (m, 8H), 7.66–7.71 (m, 2H), 7.73 (d, J = 2.1 Hz, 1H)
IR (KBr) 3600–2800(br), 1613, 1518, 1491, 1455, 1361, 1348, 1276, 1178, 1159, 1109, 970 cm⁻¹

I-862 mp 173–175° C.
¹H NMR (CDCl₃) δ 1.77 (s, 3H), 1.82 (s, 3H), 2.51 (s, 6H), 2.53 (s, 6H), 3.19 (s, 3H), 3.22 (s, 3H), 4.63 (d, J = 7.2 Hz, 2H), 5.49–5.53 (m, 1H), 6.89 (s, 1H), 6.93 (s, 1H), 7.05 (d, J = 9.0 Hz, 1H), 7.26–7.35 (m, 2H), 7.51 (dd, J = 1.8, 8.1 Hz, 1H), 7.67–7.70 (m, 3H)
IR (KBr) 3600–2800(br), 1519, 1491, 1363, 1331, 1291, 1257, 1175, 1147, 1105, 1013, 980, 966 cm⁻¹

I-863 mp 150–152° C.
¹H NMR (DMSO-d₆) δ 1.72 (s, 3H), 1.76 (s, 3H), 2.43 (s, 6H), 2.45 (s, 6H), 4.55 (d, J = 6.6 Hz, 2H), 5.47–5.51 (m, 1H), 6.78–6.83 (m, 4H), 6.90–7.06 (m, 3H), 7.38–7.42 (m, 2H), 8.87 (br s, 1H), 9.39 (br s, 1H)
IR (KBr) 3600–2800(br), 1610, 1585, 1522, 1495, 1476, 1448, 1385, 1292, 1275, 1199, 1171, 1136, 985, 948 cm⁻¹

TABLE 171

I-864 mp 175–177° C.
¹H NMR (DMSO-d₆) δ 2.44 (s, 12H), 5.13 (s, 4H), 6.77 (s, 2H), 6.90–7.09 (m, 8H), 7.33–7.52 (m, 8H), 9.01 (s, 2H)
IR (KBr) 3600–2800(br), 1582, 1518, 1491, 1454, 1384, 1328, 1270, 1242, 1191, 1141, 1123, 1046, 1006 cm⁻¹

I-865 mp 175–177° C.
¹H NMR (CDCl₃) δ 2.52 (s, 12H), 3.11 (s, 6H), 5.17 (s, 4H), 6.91 (s, 2H), 7.11 (d, J = 8.4 Hz, 2H), 7.36–7.52 (m, 12H), 7.72 (d, J = 2.1 Hz, 2H)
IR (KBr) 3600–2800(br), 1612, 1520, 1496, 1455, 1364, 1348, 1265, 1184, 1164, 1117, 1005, 971 cm⁻¹

I-866 mp 180–182° C.
¹H NMR (CDCl₃) δ 1.77 (s, 6H), 1.81 (s, 6H), 2.52 (s, 12H), 3.22 (s, 6H), 4.63 (d, J = 6.9 Hz, 2H), 5.49–5.54 (m, 2H), 6.90 (s, 2H), 7.04 (d, J = 8.4 Hz, 2H), 7.50 (dd, J = 2.1, 8.4 Hz, 2H), 7.04 (d, J = 2.1 Hz, 2H)
IR (KBr) 3600–2800(br), 1520, 1494, 1365, 1274, 1186, 1161, 1113, 996, 973 cm⁻¹

I-867 mp 165–168° C.
¹H NMR (DMSO-d₆) δ 1.72 (s, 6H), 1.76 (s, 6H), 2.45 (s, 12H), 4.55 (d, J = 6.0 Hz, 4H), 5.45–5.55 (m, 2H), 6.77 (s, 2H), 6.89–6.98 (m, 4H), 7.03–7.07 (m, 2H), 8.86 (br s, 2H)
IR (KBr) 3600–2800(br), 1579, 1519, 1497, 1476, 1456, 1384, 1277, 1238, 1195, 1142, 1126, 1050, 994 cm⁻¹

I-868 mp 76–78° C.
¹H NMR (CDCl₃) δ 3.47 (s, 3H), 3.75 (s, 3H), 3.94 (s, 3H), 5.15 (s, 2H), 5.68 (s, 1H), 5.69 (s, 1H), 5.92 (s, 1H), 6.46 (s, 1H), 6.93–7.15 (m, 5H), 7.22 (d, J = 1.5 Hz, 1H), 7.34–7.49 (m, 5H)
IR (CHCl₃) 3528, 1586, 1520, 1489, 1461, 1399, 1287, 1260, 1110, 1070, 1010, 907, 819 cm⁻¹

I-869 mp 140–142° C.
¹H NMR (CDCl₃) δ 2.65 (s, 3H), 3.13 (s, 3H), 3.25 (s, 3H), 3.57 (s, 3H), 3.78 (s, 3H), 3.94 (s, 3H), 5.19 (s, 2H), 6.85 (s, 1H), 7.13–7.19 (m, 2H), 7.30–7.50 (m, 9H)

TABLE 171-continued

IR (CHCl$_3$) 1598, 1516, 1480, 1367, 1266, 1176, 1115, 1081, 1012, 969, 918, 867, 808 cm$^{-1}$

TABLE 172

I-870 mp 189–190° C.
$^1$H NMR (CDCl$_3$) δ 1.76 (d, J = 0.9 Hz, 3H), 1.81 (s, 3H), 2.69 (s, 3H), 3.24 (s, 3H), 3.25 (s, 3H), 3.58 (s, 3H), 3.78 (s, 3H), 3.94 (s, 3H), 4.64 (d, J = 6.6 Hz, 2H), 5.49 (m, 1H), 6.85 (s, 1H), 7.10 (d, J = 8.4 Hz, 1H), 7.17 (d.d, J = 2.1, 8.4 Hz, 1H), 7.30–7.42 (m, 4H)
IR (CHCl$_3$) 2932, 1599, 1516, 1480, 1367, 1329, 1266, 1177, 1115, 1082, 1032, 1013, 970, 907, 868, 807 cm$^{-1}$
I-871 mp 187–190° C.
$^1$H NMR (CDCl$_3$) δ 2.38 (s, 3H), 2.64 (s, 3H), 3.13 (s, 3H), 3.25 (s, 3H), 3.58 (s, 3H), 3.78 (s, 3H), 3.94 (s, 3H), 5.14 (s, 2H), 6.84 (s, 1H), 7.13–7.24 (m, 4H), 7.30–7.42 (m, 6H)
IR (CHCl$_3$) 2966, 1598, 1517, 1480, 1462, 1368, 1329, 1267, 1177, 1116, 1082, 1032, 970, 907, 868, 808 cm$^{-1}$
I-872 mp 192–194° C.
$^1$H NMR (CDCl$_3$) δ 1.15 (t, J = 6.9 Hz, 3H), 1.76 (s, 3H), 1.82 (s, 3H), 2.59 (s, 3H), 3.69 (q, J = 6.9 Hz, 2H), 3.77 (s, 3H), 4.61 (d, J = 6.9 Hz, 2H), 4.99 (s, 1H), 5.50 (m, 1H), 5.70 (s, 1H), 6.84 (s, 1H), 6.88–6.97 (m, 3H), 7.02 (d, J = 1.8 Hz, 1H), 7.52–7.58 (m, 2H)
IR (CHCl$_3$) 3536, 2934, 1609, 1520, 1482, 1410, 1365, 1279, 1243, 1172, 1128, 1080, 1029, 972, 952, 872, 833, 812 cm$^{-1}$
I-873 $^1$H NMR (CDCl$_3$) δ 3.46 (s, 3H), 3.70 (s, 2H), 3.74 (s, 3H), 3.75 (s, 3H), 5.15 (s, 2H), 5.67 (s, 1H), 5.90 (s, 1H), 6.47 (s, 1H), 6.96 (d.d, J = 8.4 & 1.8 Hz, 1H), 7.03 (d, J = 8.4 Hz, 1H), 7.09 (d, J = 1.8 Hz, 1H), 7.33–7.44 (m, 7H), 7.61 (.d, J = 8.4 Hz, 1H)
IR (KBr) 3536,3389, 1732, 1587, 1519, 1487, 1438, 1393, 1249, 1217, 1166, 1110, 1069,1001 cm$^{-1}$
I-874 $^1$H NMR (CDCl$_3$) δ 3.46 (s, 3H), 3.74 (s, 5H), 5.15 (s, 2H), 5.68 (s, 1H), 5.91 (s, 1H), 6.47 (s, 1H), 6.96 (d.d, J = 8.4 & 1.8 Hz, 1H), 7.03 (.d, J = 8.4 Hz, 1H), 7.09 (.d, J = 8.4 Hz, 1H), 7.32–7.49 (m, 7H), 7.62 (d, J = 8.1 Hz, 2H)
IR (KBr) 3381, 1715, 1698, 1608, 1581, 1523, 1485, 1455, 1396, 1294, 1235, 1112, 1072,1017 cm$^{-1}$
I-875 $^1$H NMR (CDCl$_3$) δ 2.69 (s, 3H), 3.13 (s, 3H), 3.54 (s, 3H), 3.70 (s, 2H), 3.74 (s, 3H), 3.77 (s, 3H), 5.19 (s, 2H), 6.86 (s, 1H), 7.15 (d, J = 8.7 Hz, 1H), 7.30–7.40 (m, 9H), 7.59 (.d, J = 8.1 Hz, 2H)
IR (KBr) 1734, 1721, 1606, 1481, 1398, 1361, 1244, 1175, 1120, 1078, 1010 cm$^{-1}$

TABLE 173

I-876 $^1$H NMR (CDCl$_3$) δ 1.76 (s, 3H), 1.81 (s, 3H), 2.73 (s, 3H), 3.23 (s, 3H), 3.54 (s, 3H), 3.70 (s, 2H), 3.74 (s, 3H), 3.77 (s, 3H), 4.64 (d, J = 6.9 Hz, 2H), 5.46–5.55 (m, 1H), 6.86 (s, 1H), 7.09 (d, J = 8.4 Hz, 1H), 7.35 (d.d, J = 8.4 & 2.1 Hz, 1H), 7.37 (d, J = 8.1 Hz, 2H), 7.39 (d, J = 2.1 Hz, 1H), 7.59 (d, J = 8.1 Hz, 2H)
$^1$H NMR (CDCl$_3$) δ
IR (KBr) 3447, 1735, 1608, 1522, 1482, 1365, 1177, 1117, 1078, 1013 cm$^{-1}$
I-877 $^1$H NMR (CDCl$_3$) δ 1.76 (s, 3H), 1.82 (s, 3H), 3.46 (s, 3H), 3.74 (s, 5H), 3H), 4.62 (d, J = 6.9 Hz, 2H), 5.46–5.58 (m, 1H), 5.69 (s, 1H), 5.89 (s, 1H), 6.47 (s, 1H), 6.96 (s, 2H), 7.06 (s, 1H), 7.38 (d, J = 8.4 Hz, 2H), 7.62 (d, J = 8.4 Hz, 2H)
I-878 $^1$H NMR (CDCl$_3$) δ 1.76 (s, 3H), 1.82 (s, 3H), 3.46 (s, 3H), 3.70 (s, 2H), 3.74 (s, 6H), 4.62 (d, J = 6.9 Hz, 2H), 5.46–5.58 (m, 1H), 5.68 (s, 1H), 5.88 (s, 1H), 6.47 (s, 1H), 6.96 (s, 2H), 7.06 (s, 1H), 7.37 (d, J = 8.4 Hz, 2H), 7.61 (d, J = 8.4 Hz, 2H)
IR (KBr) 3527,3386, 1734, 1609, 1586, 1520, 1487, 1439, 1396, 1219, 1167, 1111, 1068,1010 cm$^{-1}$
I-879 mp 136–139° C.
$^1$H NMR (CDCl$_3$) δ 1.7 (br s, 1H), 1.76 (s, 3H), 1.81 (s, 3H), 2.73 (s, 3H), 3.23 (s, 3H), 3.53 (s, 3H), 3.78 (s, 3H), 4.64 (d, J = 6.7 Hz, 2H), 4.78 (s, 2H), 5.49 (t, J = 6.8 Hz, 1H), 6.87 (s, 1H), 7.09 (d, J = 8.6 Hz, 1H), 7.35 (dd, J = 8.6, 2.1 Hz, 1H), 7.40 (d, J =

TABLE 173-continued 2.1 Hz, 1H), 7.47 (d, J = 8.1 Hz, 2H), 7.64 (d, J = 8.1 Hz, 2H)
IR (KBr) 3553, 3434, 1481, 1389, 1363, 1235, 1175, 1084, 1011, 972, 806 cm$^{-1}$
I-880 mp 180–181° C.
$^1$H NMR (CDCl$_3$) δ 1.70 (br s, 1H), 1.76 (s, 3H), 1.82 (s, 3H), 3.46 (s, 3H), 3.75 (s, 3H), 4.62 (d, J = 6.9 Hz, 2H), 4.77 (s, 2H), 5.53 (t, J = 6.9 Hz, 1H), 5.69 (s, 1H), 5.89 (s, 1H), 6.47 (s, 1H), 6.94–6.96 (m, 2H), 7.05–7.07 (m, 1H), 7.46 (d, J = 8.1 Hz, 2H), 7.65 (d, J = 8.4 Hz, 2H)
IR (KBr) 3509, 3367, 1522, 1487, 1461, 1396, 1289, 1249, 1213, 1116, 1071, 1009, 992, 942, 797, 782 cm$^{-1}$

TABLE 174

I-881 mp 122–123° C.
$^1$H NMR (CDCl$_3$) δ 1.77 (s, 3H), 1.82 (s, 3H), 2.34 (t, J = 6.5 Hz, 1H), 3.22 (s, 3H), 3.45 (s, 3H), 3.73 (s, 3H), 4.5 (m, 2H), 4.64 (d, J = 6.6 Hz, 2H), 5.56 (t, J = 6.6 Hz, 1H), 6.84 (s, 1H), 6.99–7.10 (m, 3H), 7.39 (d, J = 8.7 Hz, 2H), 7.71 (d, J = 8.7 Hz, 2H)
IR (KBr) 3579, 1518, 1471, 1360, 1261, 1230, 1148, 1019, 966, 881, 843 cm$^{-1}$
I-882 mp 156–158° C.
$^1$H NMR (CDCl$_3$) δ 1.76 (s, 3H), 1.81 (s, 3H), 2.49 (t, J = 6.6 Hz, 1H), 3.44 (s, 3H), 3.72 (s, 3H), 4.49 (br s, 2H), 4.63 (d, J = 6.7 Hz, 2H), 5.04 (s, 1H), 5.55 (t, J = 6.7 Hz, 1H), 6.85 (s, 1H), 6.92 (d, J = 8.9 Hz, 2H), 6.98–7.10 (m, 3H), 7.53 (d, J = 8.9 Hz, 2H)
IR (KBr) 3433, 3234, 1609, 1520, 1472, 1266, 1227, 994, 836 cm$^{-1}$
I-883 mp 168–170° C.
$^1$H NMR (CDCl$_3$) δ 2.50 (t, J = 6.5 Hz, 1H), 3.44 (s, 3H), 3.73 (s, 3H), 4.49 (br s, 2H), 4.78 (s, 2H), 5.06 (s, 1H), 6.24 (t, J = 6.1 Hz, 1H), 6.85 (s, 1H), 6.93 (d, J = 8.6 Hz, 2H), 6.97–7.13 (m, 3H), 7.53 (d, J = 8.6 Hz, 2H)
IR (KBr) 3544, 3412, 3267, 1613, 1521, 1475, 1263, 1229, 1011, 884, 816 cm$^{-1}$
I-884 mp153–154° C.
$^1$H NMR (CDCl$_3$) δ 3.49 (s, 3H), 3.77 (s, 3H), 5.17 (s, 2H), 5.76 (brs, 2H), 6.45 (s, 1H), 6.91–7.07 (m, 3H), 7.26–7.45 (m, 5H), 7.93 (d, J = 8.2 Hz, 2H), 8.00 (brs, 1H), 8.27 (d, J = 8.4 Hz, 2H)
IR(KBr) 3448, 2962, 2938, 1738, 1627, 1604, 1589, 1519, 1486, 1319, 1250, 1153, 1115, 1071, 1011 cm$^{-1}$
I-885 mp81–82° C.
$^1$H NMR (CDCl$_3$) δ 1.51 (s, 3H), 1.54 (s, 3H), 1.74 (s, 3H), 1.77 (s, 3H), 2.70 (s, 3H), 3.24 (s, 3H), 3.60 (s, 3H), 3.78 (s, 3H), 4.38 (d, J = 7.5 Hz, 2H), 4.65 (d, J = 6.6 Hz, 2H), 6.86 (s, 1H), 7.06–7.11 (m, 3H), 7.35–7.41 (m, 2H), 7.52–7.57 (m, 1H)
IR(KBr) 3433, 2938, 1699, 1618, 1521, 1481, 1367, 1209, 1178, 1115, 1081, 972, 950, 813, 793 cm$^{-1}$

TABLE 175

I-886 mp208–209° C.
$^1$H NMR (CDCl$_3$) δ 1.77 (s, 3H), 1.81 (s, 3H), 2.71 (s, 3H), 3.23 (s, 3H), 3.60 (s, 3H), 3.76 (s, 3H), 4.64 (d, J = 7.2 Hz, 2H), 5.49 (t, J = 8.7 Hz, 1H), 6.85 (s, 1H), 7.09 (d, J = 8.7 Hz, 1H), 7.26–7.40 (m, 3H), 7.52–7.58 (m, 1H), 7.69–7.73 (m, 1H), 8.02 (brs, 1H)
IR(KBr) 3357, 2939, 1736, 1606, 1523, 1483, 1398, 1370, 1294, 1243, 1179, 1111, 1079, 965, 827, 814, 795 cm$^{-1}$
I-887 mp89–90° C.
$^1$H NMR (CDCl$_3$) δ 2.34 (s, 3H), 2.38 (s, 3H), 2.64 (s, 3H), 3.12 (s, 3H), 3.53 (s, 3H), 3.77 (s, 3H), 4.92 (s, 2H), 5.14 (s, 2H), 6.83 (s, 1H), 6.89 (d, J = 8.7 Hz, 2H), 7.11–7.46 (m, 12H)
IR(KBr) 3434, 2939, 1699, 1617, 1520, 1481, 1367, 1211, 1178, 1114, 1081, 952, 813, 794 cm$^{-1}$
I-888 mp181–182° C.
$^1$H NMR (CDCl$_3$) δ 2.38 (s, 3H), 2.66 (s, 3H), 3.12 (s, 3H), 3.59 (s, 3H), 3.76 (s, 3H), 5.14 (s, 2H), 6.85 (s, 1H), 7.14–7.41 (m, 8H), 7.52–7.58 (m, 1H), 7.69–7.73 (m, 1H), 8.02 (brs, 1H)
IR(KBr) 3348, 3030, 2940, 1733, 1607, 1523, 1482, 1397, 1366,

TABLE 175-continued 1281, 1242, 1212, 1179, 1128, 1112, 1080, 971, 944, 815, 799 cm$^{-1}$ I-889 mp155–157° C.
$^1$H NMR (CDCl$_3$) δ 1.46 (t, J = 7.0 Hz, 3H), 1.76 (s, 3H), 1.82 (s, 3H), 2.73 (s, 3H), 3.23 (s, 3H), 3.56 (s, 3H), 3.74 (s, 3H), 4.46 (q, J = 7.4 Hz, 2H), 4.65 (d, J = 7.2 Hz, 2H), 5.48–5.54 (m, 1H), 6.69 (s, 1H), 7.09 (d, J = 8.4 Hz, 2H), 7.28–7.47 (m, 4H)
IR(KBr) 3434, 2938, 1716, 1579, 1477, 1464, 1409, 1366, 1241, 1178, 1124, 1078, 955, 815, 796 cm$^{-1}$ I-890 mp82–83° C.
$^1$H NMR (CDCl$_3$) δ 2.67 (s, 3H), 3.13 (s, 3H), 3.58 (s, 3H), 3.80 (s, 3H), 5.19 (s, 2H), 6.84 (s, 1H), 7.13–7.49 (m, 8H), 7.89–7.96 (m, 2H), 8.27 (brs, 1H), 8.27–8.31 (m, 1H)
IR(KBr) 3447, 3033, 2940, 1743, 1521, 1482, 1367, 1312, 1272, 1249, 1178, 1119, 1080, 957, 817, 799 cm$^{-1}$

TABLE 176

I-891 mp86–87° C.
$^1$H NMR (CDCl$_3$) δ 2.68 (s, 3H), 3.10 (s, 3H), 3.15 (s, 3H), 3.62 (s, 3H), 3.81 (s, 3H), 5.22 (s, 2H), 6.85 (s, 1H), 7.16–7.50 (m, 9H), 7.88–7.94 (m, 2H)
IR(KBr) 3413, 2938, 1519, 1483, 1366, 1313, 1162, 1119, 1090, 1079, 957, 812 cm$^{-1}$

I-892 mp97–98° C.
$^1$H NMR (CDCl$_3$) δ 1.53 (s, 3H), 1.55 (s, 3H), 1.76 (s, 3H), 1.78 (s, 3H), 3.63 (s, 3H), 3.75 (s, 3H), 4.26 (d, J = 7.4 Hz, 2H), 4.62 (d, J = 6.8 Hz, 2H), 5.65 (brs, 1H), 5.72 (brs, 1H), 6.84 (s, 1H), 7.04–7.13 (m, 3H), 7.35–7.43 (m, 2H), 7.51–7.58 (m, 1H)
IR(KBr) 3453, 3379, 2973, 2931, 1719, 1629, 1529, 1490, 1406, 1313, 1288, 1247, 1193, 1101, 1072, 1015, 993, 816, 786 cm$^{-1}$ I-893 mp89–90° C.
$^1$H NMR (DMSO-d$_6$) δ 1.75 (s, 3H), 1.78 (s, 3H), 3.31 (s, 3H), 3.62 (s, 3H), 4.56 (d, J = 6.9 Hz, 2H), 5.52 (t, J = 6.0 Hz, 1H), 6.33 (s, 1H), 6.34–6.47 (m, 2H), 6.74 (brs, 2H), 6.74–6.75 (m, 1H), 6.87–6.91 (m, 1H), 7.11–7.12 (m, 1H), 7.32–7.34 (m, 1H), 8.52 (brs, 1H), 8.75 (brs, 1H)
IR(KBr) 3424, 2933, 2614, 1719, 1625, 1585, 1523, 1488, 1408, 1287, 1247, 1125, 1070, 819, 788 cm$^{-1}$ I-894 mp167–168° C.
$^1$H NMR (CDCl$_3$) δ 2.31 (s, 3H), 2.38 (s, 3H), 3.52 (s, 3H), 3.76 (s, 3H), 4.91 (s, 2H), 5.13 (s, 2H), 5.65 (brs, 1H), 5.77 (brs, 1H), 6.85 (s, 1H), 6.84–6.93 (m, 2H), 7.10–7.44 (m, 12H)
IR(KBr) 3425, 2933, 2614, 1719, 1625, 1585, 1522, 1488, 1408, 1287, 1247, 1125 cm$^{-1}$ I-895 mp93–94° C.
$^1$H NMR (DMSO-d$_6$) δ 2.11 (s, 3H), 3.34 (s, 3H), 3.62 (s, 3H), 5.10 (s, 2H), 6.32 (s, 2H), 6.41–6.49 (m, 2H), 6.65 (d, J = 9.3 Hz, 1H), 6.78 (s, 1H), 6.95 (d, J = 8.7 Hz, 1H), 7.09–7.14 (m, 1H), 7.22 (d, J = 8.4 Hz, 2H), 7.41 (d, J = 8.1 Hz, 2H), 8.49 (brs, 1H), 8.87 (brs, 1H)
IR(KBr) 3424, 2932, 1717, 1626, 1585, 1523, 1488, 1409, 1248, 1125, 1106, 1070, 811, 793 cm$^{-1}$

TABLE 177

I-896 mp149–150° C.
$^1$H NMR (DMSO-d$_6$) δ 1.72 (s, 3H), 1.77 (s, 3H), 3.32 (s, 3H), 3.55 (s, 3H), 3.76 (s, 6H), 4.55 (d, J = 6.3 Hz, 2H), 5.50 (t, J = 6.6 Hz, 1H), 6.15 (s, 1H), 6.68 (d, J = 2.1 Hz, 1H), 6.91 (d, J = 8.7 Hz, 1H), 7.30 (s, 2H), 8.41 (brs, 1H), 8.74 (brs, 1H)
IR(KBr) 3423, 2936, 1694, 1578, 1459, 1410, 1319, 1229, 1126, 1067 cm$^{-1}$ I-897 mp107–108° C.
$^1$H NMR (CDCl$_3$) δ 2.70 (s, 3H), 3.12 (s, 3H), 3.55 (s, 3H), 3.72 (s, 3H), 3.78 (s, 6H), 5.18 (s, 2H), 6.65 (s, 1H), 6.70 (d, J = 4.2 Hz, 1H), 7.14 (d, J = 8.4 Hz, 1H), 7.26–7.48 (m, 9H)
IR(KBr) 3434, 2941, 1517, 1488, 1366, 1353, 1261, 1177, 1102, 1074, 844, 818, 796 cm$^{-1}$

TABLE 177-continued

I-898 powder
$^1$H NMR (CDCl$_3$) δ 1.63 (s, 3H), 1.70 (s, 3H), 3.48 (s, 3H), 3.73–3.76 (m, 7H), 3.87 (s, 3H), 4.98 (s, 1H), 5.24–5.32 (m, 2H), 5.90 (s, 1H), 6.47 (s, 1H), 6.89–7.02 (m, 5H), 7.51–7.57 (m, 2H)
IR (KBr) 3447, 2930, 1612, 1523, 1488, 1455, 1398, 1230, 1120, 1080, 1037, 818, 592 cm$^{-1}$ I-899 mp 171–173° C.
$^1$H NMR (CDCl$_3$) δ 1.73 (s, 3H), 1.76 (s, 3H), 3.48 (s, 3H), 3.73–3.76 (m, 5H), 4.23 (s, 1H), 4.92 (s, 1H), 5.37–5.43 (m, 1H), 5.84 (s, 1H), 6.46 (s, 1H), 6.70 (d, J = 8.1 Hz, 1H), 6.86–7.01 (m, 5H), 7.51–7.56 (m, 2H)
IR (KBr) 3392, 2934, 1612, 1526, 1489, 1398, 1222, 1116, 1075, 829, 590 cm$^{-1}$ I-900 mp 78–79° C.
$^1$H NMR (CDCl$_3$) δ 2.14 (s, 3H), 2.29 (s, 3H), 2.36 (s, 3H), 3.16 (s, 3H), 3.20 (s, 3H), 5.22 (s, 2H), 7.10 (s, 1H), 7.16 (d, J = 8.7 Hz, 1H), 7.22–7.49 (m, 11H)
IR (CHCl$_3$) 2939, 1612, 1516, 1476, 1415, 1370, 1291, 1269, 1174, 1150, 1119, 1087, 1018, 971, 954, 873 cm$^{-1}$

TABLE 178

I-901 mp 114–116° C.
$^1$H NMR (CDCl$_3$) δ 1.08–1.14 (m, 6H), 1.77 (s, 3H), 1.81–1.82 (d, J = 0.6 Hz, 3H), 2.53–2.65 (m, 4H), 3.21 (s, 3H), 3.23 (s, 3H), 4.62–4.65 (d, J = 6.6 Hz, 2H), 5.52 (m, 1H), 7.04–7.13 (m, 2H), 7.23–7.26 (m, 2H), 7.32–7.42 (m, 5H)
IR (CHCl$_3$) 2970, 2934, 2874, 1674, 1614, 1572, 1517, 1487, 1415, 1370, 1331, 1288, 1262, 1172, 1149, 1109, 971, 937, 872, 849 cm$^{-1}$

I-902 mp 97–99° C.
$^1$H NMR (CDCl$_3$) δ 1.07–1.14 (m, 6H), 1.77 (s, 3H), 1.83 (s, 3H), 2.55–2.66 (m, 4H), 4.61–4.64 (d, J = 6.6 Hz, 2H), 5.06 (s, 1H), 5.54 (m, 1H), 5.77 (s, 1H), 7.24–7.64 (m, 4H), 6.97 (d, J = 2.1 Hz, 1H), 7.10–7.12 (d, J = 5.7 Hz, 2H), 7.23–7.26 (m, 2H)
IR (CHCl$_3$) 3596, 3537, 2969, 2933, 27873, 1675, 1612, 1586, 1520, 1489, 1385, 1327, 1290, 1257, 1171, 1125, 996, 903, 877, 836 cm$^{-1}$

I-903 mp 69–71° C.
$^1$H NMR (CDCl$_3$) δ 1.78 (s, 3H), 1.82 (s, 3H), 2.15 (s, 3H), 2.30 (s, 3H), 2.43 (s, 3H), 2.43 (s, 3H), 3.21 (s, 3H), 3.27 (s, 3H), 4.64–4.67 (d, J = 6.9 Hz, 2H), 5.50 (s, 2H), 7.10–7.13 (d, J = 9.9 Hz, 2H), 7.23–7.26 (m, 2H), 7.34–7.42 (m, 5H)
IR (CHCl$_3$) 2939, 1612, 1516, 1476, 1415, 1370, 1331, 1290, 1268, 1174, 1150, 1119, 1086, 971, 954, 873 cm$^{-1}$

I-904 mp 125–127° C.
$^1$H NMR (CDCl$_3$) δ 2.27 (s, 6H), 3.91 (s, 3H), 4.88 (br, 1H), 5.20 (s, 2H), 6.83–6.96 (m, 5H), 7.12–7.13 (d, J = 4.5 Hz, 2H), 7.22–7.50 (m, 7H)
IR (CHCl$_3$) 3596, 2957, 2936, 1611, 1586, 1522, 1490, 1464, 1454, 1326, 1257, 1172, 1138, 1033, 835 cm$^{-1}$

I-905 mp 145–146° C.
$^1$H NMR (CDCl$_3$) δ 2.26 (s, 3H), 2.28 (s, 3H), 3.20 (s, 3H), 3.91 (s, 3H), 5.21 (s, 2H), 6.83 (dd, J = 8.1, 2.1 Hz, 1H), 6.91–6.96 (m, 2H), 7.11 (s, 1H), 7.15 (s, 1H), 7.32–7.50 (m, 9H)
IR (CHCl$_3$) 2938, 1604, 1584, 1519, 1488, 1464, 1454, 1373, 1330, 1260, 1175, 1149, 1033, 1018, 970, 873, 847 cm$^{-1}$

TABLE 179

I-906 mp 132–134° C.
$^1$H NMR (CDCl$_3$) δ 2.27 (s, 3H), 2.87, (s, 3H), 3.91 (s, 3H), 5.16 (s, 2H), 5.21 (s, 2H), 5.70 (s, 1H), 6.82–6.86 (m, 2H), 6.92–7.00 (m, 4H), 7.13 (s, 2H), 7.32–7.50 (m, 10H)
IR (CHCl$_3$) 3542, 2936, 2871, 1585, 1519, 1491, 1454, 1382, 1322, 1273, 1175, 1137, 1014, 897, 877, 857 cm$^{-1}$

I-907 mp 181–182° C.
$^1$H NMR (CDCl$_3$) δ 1.77 (s, 3H), 1.82 (s, 3H), 2.13 (s, 3H), 2.30 (s, 3H), 2.35 (s, 3H), 4.61–4.64 (d, J = 6.9 Hz, 2H), 5.37 (s, 1H), 5.51 (m, 1H), 5.78 (s, 1H), 6.81 (dd, J = 8.1, 2.1 Hz, 1H), 6.86–

TABLE 179-continued 6.97 (m, 3H), 7.08 (s, 1H), 7.19–7.22 (m, 2H), 7.26 (s, 1H)
IR (CHCl$_3$) 3595, 3536, 2936, 1613, 1587, 1519, 1479, 1453, 1359, 1330, 1279, 1246, 1173, 1127, 1085, 1024, 974, 950, 881, 867 cm$^{-1}$ I-908 mp 167–168° C.
$^1$H NMR (CDCl$_3$) δ 1.77–1.78 (d, J = 0.9 Hz, 3H), 1.84 (s, 3H), 2.08 (s, 3H), 2.15 (s, 3H), 4.63–4.65 (d, J = 6.9 Hz, 2H), 4.82 (s, 1H), 5.05 (s, 1H), 5.55 (m, 1H), 5.80 (m, 1H), 6.74 (s, 1H), 6.78 (dd, J = 8.4, 2.1 Hz, 1H), 6.87–6.95 (m, 3H), 7.00 (d, J = 8.4 Hz, 1H), 7.23–7.26 (m, 2H)
IR (CHCl$_3$) 3594, 3534, 2923, 2869, 1675, 1613, 1584, 1520, 1488, 1455, 1399, 1289, 1247, 1166, 1127, 1091, 994, 948, 835 cm$^{-1}$ I-909 mp 170–172° C.
$^1$H NMR (DMSO-d$_6$) δ 1.72 (s, 3H), 1.76 (s, 3H), 3.31 (s, 3H), 3.63 (s, 3H), 4.54 (d, J = 6.5 Hz, 2H), 5.17 (s, 2H), 5.49 (t, J = 6.5 Hz, 1H), 6.36 (s, 1H), 6.63 (d, J = 8.4 Hz, 2H), 6.63 (dd, J = 8.4, 2.1 Hz, 1H), 6.72 (d, J = 2.1 Hz, 1H), 6.88 (d, J = 8.4 Hz, 1H), 7.31 (d, J = 8.4 Hz, 2H), 8.40 (s, 1H), 8.70 (s, 1H)
IR (KBr) 3416, 3329, 1614, 1523, 1489, 1408, 1242, 1219, 1115, 1070, 997, 817, 787 cm$^{-1}$

TABLE 180

I-910 mp 207–209° C.
$^1$H NMR (CDCl$_3$) δ 1.54 (s, 9H), 2.69 (s, 3H), 3.12 (s, 3H), 3.52 (s, 3H), 3.77 (s, 3H), 5.18 (s, 2H), 6.56 (s, 1H), 6.85 (s, 1H), 7.14 (d, J = 8.7 Hz, 1H), 7.32–7.48 (m, 9H), 7.57 (d, J = 8.7 Hz, 2H)
IR (KBr) 3373, 1734, 1525, 1369, 1227, 1177, 1158, 1080, 816, 793 cm$^{-1}$

I-911 mp 214–216° C.
$^1$H NMR (DMSO-d$_6$) δ 2.84 (s, 3H), 3.33 (s, 3H), 3.46 (s, 3H), 3.75 (s, 3H), 5.26 (s, 2H), 5.30 (s, 2H), 6.66 (d, J = 8.7 Hz, 2H), 6.93 (s, 1H), 7.24–7.45 (m, 8H), 7.52 (m, 2H)
IR (KBr) 3468, 3386, 1604, 1523, 1482, 1392, 1361, 1175, 1085, 815 cm$^{-1}$

I-912 mp 215–218° C.
$^1$H NMR (CDCl$_3$) δ 2.67 (s, 3H), 3.13 (s, 3H), 3.53 (s, 3H), 3.78 (s, 3H), 5.19 (s, 2H), 6.86 (s, 1H), 7.15 (d, J = 8.4 Hz, 1H), 7.32–7.48 (m, 7H), 7.69 (s, 4H), 8.02 (br s, 1H)
IR (KBr) 3307, 1733, 1482, 1393, 1361, 1284, 1177, 1084, 1012, 967, 945, 816 cm$^{-1}$

I-913 mp 203–205° C.
$^1$H NMR (CDCl$_3$) δ 1.77 (s, 3H), 1.81 (s, 3H), 2.71 (s, 3H), 3.24 (s, 3H), 3.54 (s, 3H), 3.79 (s, 3H), 4.64 (d, J = 6.8 Hz, 2H), 5.50 (t, J = 6.8 Hz, 1H), 6.86 (s, 1H), 7.09 (d, J = 8.4 Hz, 1H), 7.35 (dd, J = 8.4, 2.0 Hz, 1H), 7.39 (d, J = 2.0 Hz, 1H), 7.69 (s, 4H), 8.01 (br s, 1H)
IR (KBr) 3311, 1735, 1482, 1393, 1362, 1177, 1083, 976, 945, 818 cm$^{-1}$

I-914 mp 105–107° C.
$^1$H NMR (CDCl$_3$) δ 1.76 (s, 3H), 1.80, (s, 3H), 2.27 (s, 3H), 2.29 (s, 3H), 3.20 (s, 3H), 3.89 (s, 3H), 4.63–4.65 (d, J = 6.6 Hz, 2H), 5.57 (m, 1H), 6.87–6.96 (m, 3H), 7.12 (s, 1H), 7.17 (s, 1H), 7.33–7.43 (m, 4H)
IR (CHCl$_3$) 2937, 2866, 1604, 1583, 1519, 1488, 1464, 1373, 1331, 1259, 1175, 1149, 1035, 970, 873 cm$^{-1}$

TABLE 181

I-915 mp 164–165° C.
$^1$H NMR (CDCl$_3$) δ 1.75–1.76 (d, J = 0.6 Hz, 3H), 1.79–1.80 (d, J = 0.9 Hz, 3H), 2.27 (s, 3H), 2.28 (s, 3H), 3.89 (s, 3H), 4.62–4.65 (d, J = 6.6 Hz, 2H), 4.78 (br, 1H), 5.57 (m, 1H), 6.86–6.96 (m, 4H), 7.12 (s, 1H), 7.15 (s, 1H), 7.22–7.27 (m, 3H)
IR (CHCl$_3$) 3596, 2936, 2865, 1676, 1611, 1584, 1522, 1490, 1464, 1385, 1327, 1257, 1172, 1138, 1100, 1035, 996, 952, 896, 835 cm$^{-1}$

TABLE 181-continued

I-916 mp 172–173° C.
$^1$H NMR (CDCl$_3$) δ 1.72 (s, 3H), 1.77 (s, 6H), 1.81 (s, 3H), 2.70 (s, 3H), 3.11 (s, 3H), 3.24 (s, 3H), 3.57 (s, 3H), 3.80 (s, 3H), 4.06–4.27 (m, 2H), 4.64 (d, J = 7.2 Hz, 2H), 5.37–5.50 (m, 2H), 6.85 (s, 1H), 7.10 (d, J = 8.6 Hz, 1H), 7.32–7.39 (m, 2H), 7.52 (d, J = 8.4 Hz, 1H), 7.84 (d, J = 9.6 Hz, 1H), 7.94 (s, 1H)
IR(KBr) 3434, 1519, 1482, 1366, 1346, 1308, 1178, 1157, 1120, 1090, 1078, 957, 805 cm$^{-1}$

I-917 mp 78–80° C.
$^1$H NMR (CDCl$_3$) δ 3.47 (s, 3H), 3.69 (s, 6H), 3.80 (s, 6H), 5.14 (s, 2H), 5.66 (brs, 1H), 5.76 (brs, 1H), 6.30 (s, 1H), 6.69 (d, J = 8.2 Hz, 2H), 7.02 (s, 2H), 7.14 (s, 1H), 7.34–7.46 (m, 6H)
IR(KBr) 3443, 2935, 1614, 1587, 1517, 1470, 1250, 1110, 744 cm$^{-1}$ I-918 mp 83–84° C.
$^1$H NMR (DMSO-d$_6$) δ 3.34 (s, 3H), 3.72 (s, 3H), 5.13 (s, 2H), 5.72 (brs, 2H), 6.41 (s, 1H), 6.62–6.93 (m, 4H), 7.32–7.61 (m, 7H), 8.54 (brs, 1H), 8.88 (brs, 1H)
IR(KBr) 3398, 2936, 1731, 1633, 1586, 1521, 1489, 1455, 1432, 1402, 1291, 1216, 1112, 1071 cm$^{-1}$ I-919 mp 74–75° C.
$^1$H NMR (CDCl$_3$) δ 2.02 (s, 6H), 3.11 (s, 3H), 3.21 (s, 3H), 5.02 (brs, 1H), 5.18 (s, 2H), 6.96 (s, 1H), 7.04–7.18 (m, 3H), 7.37–7.59 (m, 9H)
IR(KBr) 3503, 3032, 2937, 1513, 1474, 1365, 1289, 1197, 1175, 1149, 1114, 970, 867, 811 cm$^{-1}$

TABLE 182

I-920 mp 78–79° C.
$^1$H NMR (CDCl$_3$) δ 1.73 (s, 3H), 1.78 (s, 6H), 1.83 (s, 3H), 3.11 (s, 3H), 3.48 (s, 3H), 3.77 (s, 3H), 4.07–4.29 (m, 2H), 4.64 (d, J = 6.8 Hz, 2H), 5.41–5.55 (m, 2H), 5.73 (s, 1H), 5.82 (s, 1H), 6.47 (s, 1H), 6.94–7.05 (m, 3H), 7.53 (d, J = 8.0 Hz, 1H), 7.86 (d, J = 8.6 Hz, 1H), 8.00 (s, 1H)
IR(KBr) 3449, 2971, 2935, 1519, 1489, 1424, 1338, 1310, 1226, 1152, 1117, 1070, 1059, 773 cm$^{-1}$

I-921 mp 176–177° C.
$^1$H NMR (CDCl$_3$) δ 2.10 (s, 3H), 2.18 (s, 3H), 2.47 (s, 3H), 3.12 (s, 3H), 3.23 (s, 3H), 5.20 (s, 2H), 7.09–7.21 (m, 3H), 7.39–7.51 (m, 8H), 7.60 (d, J = 8.4 Hz, 2H)
IR(KBr) 3433, 3033, 2937, 1516, 1470, 1360, 1291, 1267, 1176, 1150, 1119, 976, 857 cm$^{-1}$

I-922 mp 170–172° C.
$^1$H NMR (DMSO-d$_6$) δ 3.36 (s, 3H), 3.66 (s, 3H), 4.22 (br d, J = 2.5 Hz, 2H), 4.50 (t, J = 4.5 Hz, 1H), 4.57 (d, J = 5.7 Hz, 2H), 4.60 (d, J = 5.7 Hz, 2H), 4.97 (t, J = 5.7 Hz, 1H), 5.17 (s, 2H), 5.23 (t, J = 5.7 Hz, 1H), 6.93 (s, 1H), 7.04 (d, J = 8.4 Hz, 1H), 7.14 (dd, J = 8.4, 2.3 Hz, 1H), 7.28–7.37 (m, 2H), 7.40–7.45 (m, 4H), 7.49–7.53 (m, 2H), 7.61 (d, J = 8.1 Hz, 2H)
IR (KBr) 3322, 1462, 1385, 1228, 1037, 1006, 750, 700 cm$^{-1}$

I-923 mp 130–132° C.
$^1$H NMR (CDCl$_3$) δ 1.55 (s, 9H), 1.62 (s, 3H), 2.30 (s, 12H), 3.00 (s, 6H), 6.73 (br s, 1H), 6.78–6.82 (m, 2H), 7.07–7.14 (m, 4H), 7.24–7.27(m, 2H), 8.07–8.13 (m, 2H)
IR (KBr) 3600–2800(br), 1732, 1624, 1610, 1583, 1530, 1493, 1366, 1347, 1320, 1236, 1154 cm$^{-1}$

I-924 mp 104–106° C.
$^1$H NMR (CDCl$_3$) δ 2.27 (s, 3H), 2.30 (s, 3H), 3.00 (s, 6H), 3.74 (br s, 2H), 6.77–6.85 (m, 3H), 6.96 (dd, J = 1.8, 8.1 Hz, 1H), 7.03 (dd, J = 2.1, 12.0 Hz, 1H), 7.09 (s, 1H), 7.13 (s, 1H), 7.24–7.29 (m, 2H)
IR (KBr) 3600–2800(br), 1631, 1608, 1580, 1530, 1487, 1436, 1363, 1233, 1195 cm$^{-1}$

TABLE 183

I-925 mp 100–102° C.
$^1$H NMR (CDCl$_3$) δ 1.75 (d, J = 0.6 Hz, 3H), 1.78 (d, J = 0.6 Hz, 3H), 2.29 (s, 3H), 2.30 (s, 3H), 3.00 (s, 6H), 3.77 (d, J = 6.6 Hz,

TABLE 183-continued

2H), 3.87 (br s, 2H), 5.37–5.40 (m, 1H), 6.71–6.83 (m, 3H), 7.00–7.03 (m, 2H), 7.11 (s, 1H), 7.13 (s, 1H), 7.25–7.29 (m, 2H)
IR (KBr) 3600–2800(br), 1623, 1610, 1529, 1490, 1441, 1348, 1328, 1253, 1229, 1120, 1065 cm$^{-1}$

I-926 mp 178–180° C.
$^1$H NMR (CDCl$_3$) δ 2.27 (s, 3H), 2.32 (s, 3H), 3.01 (s, 6H), 6.78–6.83 (m, 2H), 7.10 (s, 1H), 7.16 (s, 1H), 7.18–7.28 (m, 4H), 8.12 (br s, 1H), 8.27–8.33 (m, 1H)
IR (KBr) 3600–2800(br), 1709, 1613, 1532, 1490, 1356, 1283, 1229, 1188, 1167 cm$^{-1}$

I-927 mp 154–156° C.
$^1$H NMR (CDCl$_3$) δ 1.94 (d, J = 1.2 Hz, 3H), 2.26 (d, J = 1.2 Hz, 3H), 2.27 (s, 3H), 2.31 (s, 3H), 3.00 (s, 6H), 5.79–5.80 (m, 1H), 6.78–6.82 (m, 3H), 7.09–7.16 (m, 4H), 7.16–7.24 (m, 2H), 8.38–8.44 (m, 1H)
IR (KBr) 3600–2800(br), 1681, 1665, 1643, 1610, 1528, 1506, 1487, 1442, 1359, 1317, 1237, 1198, 1159 cm$^{-1}$

I-928 mp 183–185° C.
$^1$H NMR (CDCl$_3$) δ 1.44 (t, J = 7.5 Hz, 3H), 2.27 (s, 3H), 2.31 (s, 3H), 3.16–3.23 (m, 2H), 6.53 (d, J = 2.4 Hz, 1H), 6.78–6.82 (m, 2H), 7.09 (s, 1H), 7.14–7.18 (m, 3H), 7.24–7.27 (m, 3H), 7.59–7.65 (m, 1H)
IR (KBr) 3600–2800(br), 1607, 1527, 1491, 1451, 1436, 1359, 1336, 1271, 1222, 1153, 1110 cm$^{-1}$

I-929 mp 184–186° C.
$^1$H NMR (CDCl$_3$) δ 2.26 (s, 3H), 2.32 (s, 3H), 3.01 (s, 6H), 6.78–6.83 (m, 2H), 7.10 (s, 1H), 7.18 (s, 1H), 7.23–7.27 (m, 1H), 7.65 (dd, J = 1.8, 8.1 Hz, 1H), 7.70 (d, J = 2.1 Hz, 1H), 8.19–8.24 (m, 1H)
IR (KBr) 3600–2800(br), 1721, 1612, 1536, 1490, 1325, 1282, 1242, 1197, 1169, 1123, 1054 cm$^{-1}$

TABLE 184

I-930 mp 212–215° C.
$^1$H NMR (DMSO-d$_6$) δ 2.83 (s, 3H), 3.43 (s, 3H), 3.45 (s, 3H), 3.52 (s, 3H), 3.79 (s, 3H), 4.87 (s, 2H), 7.08 (s, 1H), 7.21 (d, J = 8.4 Hz, 1H), 7.27~7.32 (m, 2H), 7.48 (d, J = 8.7 Hz, 2H), 7.74 (d, J = 8.7 Hz, 2H)
IR (Nujol) 1731, 1604, 1519, 1480, 1237, 1174, 1081, 1013, 876, 839, 822, 804 cm$^{-1}$ I-931 mp 166–168° C.
$^1$H NMR (CDCl$_3$) δ 3.45 (s, 3H), 3.75 (s, 3H), 4.67 (d, J = 9.0 Hz, 2H), 6.45 (s, 1H), 6.78 (t, J = 9.0 Hz, 1H), 6.92 (d, J = 8.7 Hz, 2H), 6.92 (d, J = 8.4 Hz, 1H), 6.98 (dd, J = 8.4, 2.1 Hz, 1H), 7.09 (d, J = 2.1 Hz, 1H), 7.53 (d, J = 8.7 Hz, 2H)
IR (Nujol) 3399, 1611, 1588, 1523, 1488, 1460, 1224, 1113, 1070, 1012, 939, 825, 813, 795 cm$^{-1}$ I-932 foam
$^1$H NMR (CDCl$_3$) δ 3.45 (s, 3H), 3.75 (s, 3H), 4.64~4.74 (m, 3H), 6.45 (s, 1H), 6.92 (d, J = 8.7 Hz, 2H), 6.93 (d, J = 8.4, Hz, 1H), 6.97 (dd, J = 8.4, 2.1 Hz, 1H), 7.08 (d, J = 2.1 Hz, 1H), 7.53 (d, J = 8.7 Hz, 2H)
IR (Nujol) 3570, 3461, 3357, 3180, 1753, 1616, 1596, 1524, 1495, 1408, 1313, 1287, 1264, 1240, 1200, 1114, 1073, 1011, 906, 825 cm$^{-1}$ I-933 mp 120–123° C.
$^1$H NMR (CDCl$_3$) δ 1.69 (s, 3H), 1.74 (s, 6H), 1.80 (s, 3H), 3.49 (s, 3H), 6.68–3.75 (m, 5H), 4.58 (d, J = 6.6 Hz, 2H), 5.31–5.41 (m, 1H), 5.50–5.56 (m, 1H), 5.81 (s, 1H), 6.46 (s, 1H), 6.68–6.74 (m, 2H), 6.85–6.93 (m, 3H), 7.50–7.56 (m, 2H)
IR (KBr) 3460, 2969, 2929, 1609, 1523, 1490, 1398, 1247, 1117, 1078, 1013, 824, 778, 708, 589 cm$^{-1}$ I-934 mp 171–173° C.
$^1$H NMR (CDCl$_3$) δ 1.75 (s, 3H), 1.80 (s, 3H), 3.47 (s, 3H), 3.73 (s, 3H), 3.81 (s, 2H), 4.58 (d, J = 6.9 Hz, 2H), 5.50–5.57 (m, 1H), 5.82 (s, 1H), 6.44 (s, 1H), 6.77–6.94 (m, 5H), 7.50–7.55 (m, 2H)
IR (KBr) 3382, 3320, 2929, 1613, 1523, 1490, 1405, 1262, 1221, 1120, 1067, 1011, 844, 818, 598 cm$^{-1}$

TABLE 185

I-935 mp 220–221° C.
$^1$H NMR (DMSO-d$_6$) δ 1.74 (s, 3H), 1.77 (s, 3H), 2.08 (s, 3H), 3.30 (s, 3H), 3.64 (s, 3H), 4.64 (d, J = 7.2 Hz, 2H), 5.48–5.54 (m, 1H), 6.40 (s, 1H), 6.80–6.87 (m, 3H), 6.93–7.03 (m, 2H), 7.42–7.46 (m, 2H), 7.85 (s, 1H), 8.58 (s, 1H), 8.96 (s, 1H), 9.56 (s, 1H)
IR (KBr) 3476, 3400, 3322, 2935, 1658, 1610, 1542, 1520, 1487, 1270, 1258, 1225, 1115, 1010, 825, 596 cm$^{-1}$

I-936 mp 149–150° C.
$^1$H NMR (CDCl$_3$) δ 1.48 (s, 3H), 1.67 (s, 3H), 1.76 (s, 3H), 1.80 (s, 3H), 3.63 (s, 3H), 3.74 (s, 3H), 4.27 (d, J = 7.5 Hz, 2H), 4.63 (d, J = 6.6 Hz, 2H), 5.01 (s, 1H), 5.20–5.28 (m, 1H), 5.52–5.60 (m, 1H), 6.66 (s, 1H), 6.91 (d, J = 8.7 Hz, 2H), 7.01 (t, J = 8.7 Hz, 1H), 7.10–7.22 (m, 2H), 7.48 (d, J = 8.7 Hz, 2H)
IR (KBr) 3335, 2936, 1671, 1614, 1596, 1522, 1441, 1403, 1369, 1265, 1233, 1111, 1077, 1008, 945, 832 cm$^{-1}$

I-937 mp 122–123° C.
$^1$H NMR (CDCl$_3$) δ 3.44 (s, 3H), 3.76 (s, 3H), 4.77 (d, J = 6.3 Hz, 2H), 5.05 (s, 1H), 6.04 (s, 1H), 6.24 (t, J = 6.3 Hz, 1H), 6.45 (s, 1H), 6.92 (d, J = 8.7 Hz, 2H) 7.01 (t, J = 8.7 Hz, 1H), 7.19–7.30 (m, 2H), 7.53 (d, J = 8.7 Hz, 2H)
IR (KBr) 3582, 3502, 3237, 2950, 1614, 1524, 1490, 1453, 1403, 1301, 13267, 1231, 1112, 1073, 1019, 881, 827 cm$^{-1}$

I-938 mp143–144° C.
$^1$H NMR (CDCl$_3$) δ 1.79 (s, 3H), 1.84 (s, 3H), 2.10 (s, 3H), 2.17 (s, 3H), 2.47 (s, 3H), 3.23 (s, 3H), 3.24 (s, 3H), 4.66 (d, J = 6.6 Hz, 2H), 5.20–5.55 (m, 1H), 7.09–7.16 (m, 4H), 7.40 (d, J = 8.7 Hz, 2H), 7.60 (d, J = 8.1 Hz, 2H)
IR(KBr) 3433, 2935, 1513, 1472, 1366, 1188, 1178, 1152, 1117, 974, 857 cm$^{-1}$

I-939 mp80–81° C.
$^1$H NMR (CDCl$_3$) δ 3.47 (s, 3H), 3.48 (s, 3H), 3.68 (s, 3H), 3.81 (s, 6H), 4.79 (s, 2H), 5.13 (s, 2H), 5.14 (s, 2H), 5.65 (s, 1H), 5.75 (s, 1H), 6.28 (s, 1H), 6.69 (s, 2H), 7.01 (s, 2H), 7.14 (s, 1H), 7.40–7.45 (m, 5H)
IR(KBr) 3433, 2937, 1720, 1582, 1508, 1455, 1407, 1285, 1239, 1125, 1069, 1051, 1011 cm$^{-1}$

TABLE 186

I-940 mp71–72° C.
$^1$H NMR (CDCl$_3$) δ 1.76 (s, 3H), 1.81 (s, 3H), 2.73 (s, 3H), 3.21 (s, 3H), 3.55 (s, 3H), 3.72 (s, 3H), 3.78 (s, 6H), 4.63 (d, J = 6.8 Hz, 2H), 5.46–5.52 (m, 1H), 6.65 (s, 1H), 6.70 (d, J = 3.8 Hz, 2H), 7.07 (d, J = 8.4 Hz, 1H), 7.34–7.46 (m, 3H)
IR(KBr) 3433, 2938, 1674, 1609, 1587, 1518, 14732, 1365, 1252, 1178, 1109, 1077, 971, 945, 815, 796 cm$^{-1}$

I-941 mp98–99° C.
$^1$H NMR (CDCl$_3$) δ 1.74 (s, 3H), 1.78 (s, 3H), 3.50 (s, 3H), 3.71 (s, 3H), 3.72 (d, J = 8.1 Hz, 2H), 5.35 (t, J = 7.2 Hz, 1H), 5.64 (s, 1H), 5.77 (s, 1H), 6.43 (s, 1H), 7.02–7.15 (m, 3H), 7.32–7.41 (m, 2H), 7.49–7.56 (m, 1H)
IR(KBr) 3408, 2934, 1627, 1529, 1491, 1444, 1405, 1246, 1175, 1102, 1069, 822, 783 cm$^{-1}$

I-942 $^1$H NMR (CDCl$_3$) δ 1.77 (s, 3H), 1.82 (s, 3H), 2.68 (s, 3H), 2.73 (s, 3H), 3.25 (s, 3H), 3.60 (s, 3H), 3.81 (s, 3H), 4.65 (d, J = 6.3 Hz, 2H), 5.44–5.53 (m, 1H), 6.87 (s, 1H), 7.10 (.d, J = 8.7 Hz, 1H), 7.30–7.47 (m, 3H), 7.84 (d,d, J = 7.8 & 2.1 Hz, 1H), 8.22 (d, J = 2.1 Hz, 1H)
IR (KBr) 1530, 1480, 1362, 1272, 1237, 1179, 1077 cm$^{-1}$

I-943 $^1$H NMR (CDCl$_3$) δ 2.69 (s, 3H), 3.12 (s, 3H), 3.56 (s, 3H), 3.77 (s, 3H), 3.84 (s, 2H), 5.18 (s, 2H), 6.82 (s, 1H), 6.84 (d, J = 8.1 Hz, 1H), 7.14 (.d, J = 8.4 Hz, 1H), 7.21–7.50 (m, 9H)
IR (KBr) 3466,3377, 1634, 1583, 1525, 1488, 1461, 1400, 1288, 1245, 1196, 1105, 1069 cm$^{-1}$

I-944 $^1$H NMR (CDCl$_3$) δ 1.76 (s, 3H), 1.82 (s, 3H), 3.49 (s, 3H), 3.75 (s, 3H), 4.61 (d, J = 6.6 Hz, 2H), 5.48–5.57 (m, 1H), 5.59–5.75 (m, 1H), 5.88 (s, 1H), 6.43 (s, 1H), 6.83–7.07 (m, 4H), 7.21–7.30 (m, 1H), 7.35 (d,d, J = 12.3 & 1.8 Hz, 2H)
IR (KBr) 3465,3377, 1634, 1525, 1488, 1460, 1400, 1287, 1245, 1195, 1105, 1068 cm$^{-1}$

I-945 $^1$H NMR (CDCl$_3$) δ 2.02 (s, 6H), 2.15 (s, 3H), 3.20 (s, 3H), 5.20 (s, 3H), 6.81–6.86(m, 1H),6.93 (d,d, J = 10.7 & 2.1 Hz, 1H), 6.97 (s, 1H), 7.04–7.12 (m, 1H), 7.31–7.52 (m, 9H)
IR (KBr) 1513, 1468, 1362, 1295, 1264, 1227, 1193, 1171, 1151, 1003,965 cm$^{-1}$

TABLE 187

- I-946 ¹H NMR (CDCl₃) δ 2.02 (s, 6H), 2.15 (s, 3H), 3.20 (s, 3H), 5.14 (d, J = 3.9 Hz, 1H), 6.81–6.86 (m, 1H), 6.91 (d,d, J = 10.1 & 2.1 Hz, 1H), 6.97 (s, 1H), 7.04–7.12 (m, 1H), 7.30–7.42 (m, 4H)
  IR (KBr) 3414, 1624, 1595, 1518, 1473, 1360, 1294, 1170, 1144, 1120, 1104, 1016 cm⁻¹
- I-947 ¹H NMR (CDCl₃) δ 1.77 (s, 3H), 1.82 (s, 3H), 2.02 (s, 6H), 2.16 (s, 3H), 3.20 (s, 3H), 4.64 (d, J = 6.6 Hz, 2H), 5.53–5.61 (m, 1H), 6.82–7.09 (m, 4H), 7.33 (d, J = 9.0 Hz, 2H), 7.39 (d, J = 9.0 Hz, 2H)
  IR (KBr) 1514, 1468, 1376, 1294, 1262, 1175, 1152,992,968 cm⁻¹
- I-948 ¹H NMR (CDCl₃) δ 1.77 (s, 3H), 1.82 (s, 3H), 2.02 (s, 6H), 2.17 (s, 3H), 4.64 (d, J = 6.6 Hz, 2H), 4.81 (s, 1H), 5.52–5.60 (m, 1H), 6.82–7.08 (m, 6H), 7.22 (.d, J = 8.7 Hz, 2H)
  IR (KBr) 3568,3417, 1613, 1517, 1471, 1287, 1261, 1230, 1192, 1132, 1102, 1001 cm⁻¹
- I-949 ¹H NMR (CDCl₃) δ 3.02 (s, 6H), 3.46 (s, 3H), 3.75 (s, 3H), 5.18 (s, 2H), 6.03 (s, 1H), 6.47 (s, 1H), 6.82 (d, J = 8.7 Hz, 2H), 7.03–7.51 (m, 8H), 7.55 (.d, J = 8.7 Hz, 2H)
  IR (KBr) 3502, 1604, 1527, 1488, 1359, 1267, 1233, 1198, 1110, 1070 cm⁻¹
- I-950 ¹H NMR (CDCl₃) δ 2.60 (s, 3H), 3.03 (s, 6H), 3.54 (s, 3H), 3.76 (s, 3H), 5.21 (s, 2H), 6.80 (d, J = 8.7 Hz, 2H), 6.86 (s, 1H),7.03–7.49 (m, 8H), 7.54 (.d, J = 8.7 Hz, 2H)
  IR (KBr) 1602, 1530, 1483, 1444, 1395, 1366, 1233, 1179, 1078, 1015 cm⁻¹
- I-951 ¹H NMR (CDCl₃) δ 2.76 (s, 3H), 3.02 (s, 6H), 3.54 (s, 3H), 3.76 (s, 3H), 5.28 (s, 1H), 6.81 (d, J = 9.0 Hz, 2H), 6.86 (s, 1H), 7.04–7.23 (m, 3H), 7.54 (d, J = 9.0 Hz, 2H)
  IR (KBr) 3375, 1607, 1530, 1483, 1395, 1346, 1292, 1228, 1163, 1077, 1009 cm⁻¹
- I-952 ¹H NMR (CDCl₃) δ 1.76 (s, 3H), 1.80 (s, 3H), 2.71 (s, 3H), 3.02 (s, 6H), 3.55 (s, 3H), 3.76 (s, 3H), 4.63 (d, J = 6.9 Hz, 2H), 5.49–5.57 (m, 1H), 6.82 (.d, J = 8.7 Hz, 2H), 6.86 (s, 1H), 7.01–7.23 (m, 3H), 7.54 (d, J = 8.7 Hz, 2H)
  IR (KBr) 1602, 1531, 1484, 1389, 1369, 1258, 1235, 1197, 1176, 1084 cm⁻¹

TABLE 188

- I-953 ¹H NMR (CDCl₃) δ 1.76 (s, 3H), 1.80 (s, 3H), 3.02 (s, 6H), 3.47 (s, 3H), 3.75 (s, 3H), 4.63 (d, J = 6.9 Hz, 2H), 5.51–5.60 (m, 1H), 6.03 (s, 1H), 6.47 (s, 1H), 6.82 (.d, J = 8.7 Hz, 2H), 6.99–7.08 (m, 1H), 7.16–7.29 (m, 2H), 7.55 (d, J = 8.7 Hz, 2H)
  IR (KBr) 3498, 1604, 1528, 1488, 1360, 1266, 1234, 1198, 1110, 1067 cm⁻¹
- I-954 ¹H NMR (CDCl₃) δ 3.02 (s, 6H), 3.47 (s, 3H), 3.75 (s, 3H), 5.14 (s, 1H), 6.03 (s, 1H), 6.47 (s, 1H), 6.82 (d, J = 9.0 Hz, 2H), 7.02–7.09 (m, 1H), 7.15–7.29 (m, 2H), 7.55 (d, J = 9.0 Hz, 2H)
  IR (KBr) 3492,3383, 1607, 1529, 1488, 1397, 1223, 1103, 1065, 1006 cm⁻¹
- I-955 ¹H NMR (CDCl₃) δ 2.01 (s, 6H), 2.17 (s, 3H), 4.75 (s, 1H), 5.19 (s, 2H), 6.83–7.15(m, 7H), 7.30–7.53 (m, 6H)
  IR (KBr) 3542, 1607, 1579, 1513, 1469, 1263, 1126, 1107, 1015 cm⁻¹
- I-956 ¹H NMR (CDCl₃) δ 1.76 (s, 3H), 1.82 (s, 3H), 2.66 (s, 3H), 3.50 (s, 3H), 3.77 (s, 3H), 4.62 (d, J = 6.4 Hz, 2H), 5.48–5.56 (m, 1H), 5.71 (s, 1H), 5.81 (s, 1H), 5.47 (s, 1H), 6.90–7.00 (m, 2H), 7.04 (d, J = 1.8 Hz, 1H), 7.42 (.d, J = 7.8 Hz, 2H), 7.82 (d,d, J = 7.8 & 1.8 Hz, 1H), 8.26(.d, J = 1.5 Hz, 1H)
  IR (KBr) 3520,3419, 1585, 1529, 1506, 1344, 1313, 1290, 1251, 1226, 1118, 1079 cm⁻¹
- I-957 mp 123–126° C.
  ¹H NMR (CDCl₃) δ 1.75 (s, 3H), 1.78 (d, J = 0.9 Hz, 3H), 3.47 (s, 3H), 3.75 (s, 3H), 3.87 (s, 3H), 3.88 (s, 3H), 4.63 (d, J = 6.6 Hz, 2H), 5.57 (m, 1H), 5.92 (s, 1H), 6.47 (s, 1H), 6.95–7.40 (m, 5H), 7.56–7.62 (m, 2H)
  IR (CHCl₃) 3510, 2934, 1608, 1519, 1489, 1461, 1394, 1285, 1243, 1175, 1115, 1075, 1034, 1008, 926, 823 cm⁻¹
- I-958 mp 163–164° C.
  ¹H NMR (CDCl₃) δ 1.75 (s, 3H), 1.78 (s, 3H), 3.61 (s, 3H), 3.65 (s, 3H), 3.75 (s, 3H), 3.88 (s, 3H), 4.64 (d, J = 6.6 Hz, 2H), 4.99 (s, 1H), 5.58 (m, 1H), 6.68 (s, 1H), 6.88–6.98 (m, 5H), 7.46–7.52 (m, 2H)
  IR (CHCl₃) 3592, 2934, 1610, 1517, 1461, 1387, 1237, 1171, 1136, 1111, 1084, 1036, 1012, 830 cm⁻¹

TABLE 189

- I-959 mp 142–146° C.
  ¹H NMR (CDCl₃) δ 1.76 (s, 3H), 1.82 (s, 3H), 3.47 (s, 3H), 3.75 (s, 3H), 3.94 (s, 3H), 4.61 (d, J = 6.6 Hz, 2H), 5.53 (m, 1H), 5.69 (s, 1H), 5.70 (s, 1H), 5.91 (s, 1H), 6.46 (s, 1H), 6.94–7.26 (m, 6H)
  IR (CHCl₃) 3526, 2930, 1585, 1520, 1489, 1460, 1399, 1287, 1260, 1110, 1070, 1010, 819 cm⁻¹
- I-960 mp 141–145° C.
  ¹H NMR (CDCl₃) δ 2.39 (s, 3H), 3.47 (s, 3H), 3.94 (s, 3H), 5.10 (s, 2H), 5.68 (s, 1H), 5.69 (s, 1H), 5.92 (s, 1H), 6.46 (s, 1H), 6.93–7.38 (m, 6H)
  IR (CHCl₃) 3528, 1585, 1519, 1489, 1460, 1399, 1260, 1110, 1070, 1009, 863 cm⁻¹
- I-961 mp 152–154° C.
  ¹H NMR (CDCl₃) δ 2.26 (s, 3H), 4.79 (br, 1H), 5.19 (s, 2H), 6.87–6.90 (m, 2H), 7.03–7.15 (m, 4H), 7.22–7.26 (m, 2H), 7.34–7.50 (m, 6H)
  IR (CHCl₃) 3596, 2925, 2869, 1612, 1581, 1523, 1490, 1455, 1383, 1313, 1298, 1259, 1171, 1125, 1100, 1012, 956, 877, 836 cm⁻¹
- I-962 mp 150–151° C.
  ¹H NMR (CDCl₃) δ 2.28 (s, 3H), 3.90 (s, 3H), 4.77–4.79 (d, J = 6.0 Hz, 2H), 6.26 (d, J = 6.0 Hz, 1H), 6.88–6.91 (m, 5H), 7.13–7.14 (d, J = 2.7 Hz, 2H), 7.24–7.27 (m, 2H)
  IR (CHCl₃) 3596, 2958, 1732, 1612, 1587, 1522, 1490, 1464, 1325, 1257, 1172, 1139, 1100, 1032, 886, 835 cm⁻¹
- I-963 mp 93–94° C.
  ¹H NMR (CDCl₃) δ 2.27 (s, 3H), 4.76–4.79 (d, J = 6.0 Hz, 2H), 5.12 (br, 1H), 6.24 (t, J = 6.0 Hz, 1H), 6.88–7.15 (m, 7H), 7.22–7.26 (m, 2H)
  IR (CHCl₃) 3596, 2925, 2867, 1613, 1583, 1523, 1490, 1458, 1424, 1388, 1258, 1171, 1126, 1100, 1022, 956, 886, 836 cm⁻¹

TABLE 190

- I-964 foam
  ¹H NMR (CDCl₃) δ 3.47 (s, 3H), 3.74 (s, 3H), 5.06 (s, 1H), 5.15 (s, 2H), 5.70 (s, 1H), 5.94 (s, 1H), 6.46 (s, 1H), 6.81–7.50 (m, 12H)
  IR (CHCl₃) 3534, 1609, 1587, 1518, 1504, 1482, 1463, 1455, 1407, 1322, 1290, 1249, 1200, 1112, 1072, 1011 cm⁻¹
- I-965 foam
  ¹H NMR (CDCl₃) δ 3.61 (s, 3H), 3.75 (s, 3H), 5.16 (s, 2H), 5.72 (s, 2H), 6.46 (s, 1H), 6.83 (s, 1H), 6.94 (dd, J = 2.0, 8.4 Hz, 1H), 7.00–7.12 (m, 4H), 7.29–7.50 (m, 7H)
  IR (CHCl₃) 3531, 1587, 1516, 1498, 1482, 1462, 1455, 1410, 1362, 1308, 1288, 1248, 1202, 1121, 1092, 1070, 1006 cm⁻¹
- I-966 mp 174–175° C.
  ¹H NMR (CDCl₃) δ 2.28 (s, 3H), 3.38 (s, 3H), 3.71 (s, 3H), 5.16 (s, 2H), 5.68 (s, 1H), 5.88 (s, 1H), 6.30 (s, 1H), 6.98 (dd, J = 1.8, 8.4 Hz, 1H), 7.04 (d, J = 8.4 Hz, 1H), 7.11 (d, J = 1.8 Hz, 1H), 7.22–7.49 (m, 9H)
  IR (KBr) 3516, 3398, 1587, 1516, 1500, 1484, 1453, 1412, 1306, 1285, 1247, 1231, 1202, 1126, 1101, 1072, 1019, 769, 737 cm⁻¹
- I-967 mp 103–104° C.
  ¹H NMR (CDCl₃) δ 2.26 (s, 6H), 4.61–4.78 (m, 3H), 4.84 (s, 1H), 6.84–6.92 (m, 2H), 6.97–7.16 (m, 5H), 7.21–7.27 (m, 2H)
  IR (KBr) 3409, 1742, 1523, 1489, 1315, 1295, 1259, 1231, 1206, 1193, 1124, 1001, 834, 815 cm⁻¹
- I-968 mp 90–91° C.
  ¹H NMR (CDCl₃) δ 1.77 (s, 6H), 1.82 (d, J = 0.9 Hz, 6H), 2.27 (s, 6H), 4.56 (d, J = 6.6 Hz, 2H), 5.13 (d, J = 6.6 Hz, 2H), 5.49–5.60 (m, 2H), 6.94–7.00 (m, 2H), 7.01–7.14 (m, 5H), 7.25–7.31 (m, 2H)
  IR (KBr) 1608, 1522, 1488, 1378, 1299, 1288, 1273, 1259, 1242, 1196, 1176, 1014, 831, 811, 776 cm⁻¹

TABLE 191

- I-969 mp 200–203° C.
  ¹H NMR (CDCl₃) δ 2.00 (s, 3H), 2.25 (s, 3H), 3.46 (s, 3H), 3.73 (s, 3H), 3.83 (s, 3H), 5.25 (s, 1H), 6.01–6.03 (m, 1H), 6.06 (s,

TABLE 191-continued

I-970 (cont.) 1H), 6.45 (s, 1H), 6.86–6.90 (m, 2H), 7.04–7.14 (m, 3H), 7.47–7.52 (m, 2H)
IR (KBr) 3433, 2937, 1721, 1651, 1523, 1489, 1398, 1264, 1225, 1136, 1071, 1035, 927, 823, 530 cm$^{-1}$ I-970 mp 157–160° C.
$^1$H NMR (CDCl$_3$) δ 1.74 (s, 3H), 1.80 (s, 3H), 2.86 (s, 3H), 3.49 (s, 3H), 3.75 (s, 3H), 4.57 (d, J = 6.6 Hz, 2H), 5.08 (s, 1H), 5.50–5.57 (m, 1H), 5.82 (s, 1H), 6.46 (s, 1H), 6.66 (d, J = 2.1 Hz, 1H), 6.73 (dd, J = 2.1, 8.1 Hz, 1H), 6.86–6.94 (m, 3H), 7.50–7.56 (m, 2H)
IR (KBr) 3392, 2934, 1611, 1523, 1490, 1397, 1242, 1216, 1112, 1074, 1002, 592 cm$^{-1}$ I-971 mp 153–155° C.
$^1$H NMR (CDCl$_3$) δ 1.77 (s, 3H), 1.82 (s, 3H), 2.10 (s, 3H), 3.20 (s, 3H), 3.21 (s, 3H), 3.36 (s, 3H), 3.71 (s, 3H), 4.63 (d, J = 6.9 Hz, 2H), 5.52 (t, J = 6.9 Hz, 1H), 7.06 (d, J = 8.4 Hz, 1H), 7.14 (dd, J = 8.4, 2.1 Hz, 1H), 7.23 (d, J = 2.1 Hz, 1H), 7.36 (d, J = 8.9 Hz, 2H), 7.69 (d, J = 8.9 Hz, 2H)
IR (KBr) 1515, 1474, 1365, 1229, 1175, 1151, 1096, 973, 870, 810 cm$^{-1}$ I-972 amorphous
$^1$H NMR (CDCl$_3$) δ 1.77 (s, 3H), 1.82 (s, 3H), 2.43 (s, 3H), 3.44 (s, 3H), 3.71 (s, 3H), 4.49 (d, J = 9.9 Hz, 2H), 4.62 (d, J = 6.6 Hz, 2H), 4.72 (d, J = 7.2 Hz, 2H), 5.53 (t, J = 6.6 Hz, 1H), 6.86 (s, 1H), 6.96 (d, J = 8.7 Hz, 1H), 7.21–7.30 (m, 4H), 7.54 (d, J = 8.1 Hz, 2H)
IR (KBr) 3599, 1463, 1386, 1081, 1007 cm$^{-1}$

TABLE 192

I-973 mp 83–86° C.
$^1$H NMR (DMSO-d$_6$) δ 1.74 (s, 3H), 1.77 (s, 3H), 3.36 (s, 3H), 3.65 (s, 3H), 4.23 (d, J = 23.1 Hz, 2H), 4.48 (t, J = 4.4 Hz, 1H), 4.52 (d, J = 5.4 Hz, 2H), 4.52–4.60 (m, 4H), 4.89 (t, J = 5.6 Hz, 1H), 5.22 (t, J = 5.9 Hz, 1H), 5.48 (t, J = 6.6 Hz, 1H), 6.92 (s, 1H), 6.96 (d, J = 8.6 Hz, 1H), 7.12 (dd, J = 8.6, 1.5 Hz, 1H), 7.26 (d, J = 1.5 Hz, 1H), 7.42 (d, J = 8.0 Hz, 2H), 7.61 (d, J = 8.0 Hz, 2H)
IR (KBr) 3399, 1464, 1386, 1230, 1005 cm$^{-1}$

I-974 mp 177–179° C.
$^1$H NMR (CDCl$_3$) δ 1.31 (d, J = 6.9 Hz, 6H), 2.70 (s, 3H), 2.98 (sept, J = 6.9 Hz, 1H), 3.12 (s, 3H), 3.54 (s, 3H), 3.76 (s, 3H), 5.19 (s, 2H), 6.87 (s, 1H), 7.15 (d, J = 8.4 Hz, 1H), 7.30–7.49 (m, 9H), 7.54 (d, J = 7.8 Hz, 2H)
IR (KBr) 1512, 1480, 1369, 1176, 1084, 1014, 813, 798 cm$^{-1}$ I-975 mp 180–182° C.
$^1$H NMR (CDCl$_3$) δ 1.31 (d, J = 6.6 Hz, 6H), 1.76 (s, 3H), 1.81 (s, 3H), 2.74 (s, 3H), 2.98 (sept, J = 6.6 Hz, 1H), 3.22 (s, 3H), 3.54 (s, 3H), 3.77 (s, 3H), 4.63 (d, J = 6.7 Hz, 2H), 5.49 (t, J = 6.7 Hz, 1H), 6.87 (s, 1H), 7.08 (d, J = 8.4 Hz, 1H), 7.31 (d, J = 8.1 Hz, 2H), 7.35 (dd, J = 8.4, 2.1 Hz, 1H), 7.40 (d, J = 2.1 Hz, 1H), 7.54 (d, J = 8.1 Hz, 2H)
IR(KBr) 1520, 1481, 1366, 1177, 1083, 1012, 975, 944, 815, 797 cm$^{-1}$ I-976 mp 125–126° C.
$^1$H NMR (CDCl$_3$) δ 1.31 (d, J = 6.9 Hz, 6H), 1.76 (s, 3H), 1.82 (s, 3H), 2.97 (sept, J = 6.9 Hz, 1H), 3.46 (s, 3H), 3.74 (s, 3H), 4.61 (d, J = 7.1 Hz, 2H), 5.53 (t, J = 7.1 Hz, 1H), 5.68 (s, 1H), 5.91 (s, 1H), 6.48 (s, 1H), 6.95–6.96 (m, 2H), 7.06–7.07 (m, 1H), 7.31 (d, J = 8.0 Hz, 2H), 7.57 (d, J = 8.0 Hz, 2H)
IR (KBr) cm$^{-1}$

TABLE 193

I-977 foam
$^1$H NMR (CDCl$_3$) δ 2.68 (s, 3H), 3.13 (s, 3H), 3.20 (s, 3H), 3.57 (s, 3H), 3.79 (s, 3H), 5.19 (s, 2H), 6.86 (s, 1H), 7.15 (d, J = 8.7 Hz, 1H), 7.31–7.62 (m, 11H)
IR (CHCl$_3$) 1517, 1475, 1371, 1227, 1219, 1176, 1117, 1081, 968, 925, 856, 821 cm$^{-1}$

TABLE 193-continued

I-978 foam
$^1$H NMR (CDCl$_3$) δ 2.65 (s, 3H), 2.94 (s, 3H), 3.14 (s, 3H), 3.59 (s, 3H), 3.76 (s, 3H), 5.19 (s, 2H), 6.86 (s, 1H), 7.16 (d, J = 8.7 Hz, 1H), 7.33–7.57 (m, 11H)
IR (CDCl$_3$) 1517, 1477, 1398, 1370, 1268, 1233, 1216, 1177, 1159, 1079, 972, 894, 856, 818 cm$^{-1}$ I-979 foam
$^1$H NMR (CDCl$_3$) δ 1.77 (s, 3H), 1.81 (s, 3H), 2.69 (s, 3H), 2.94 (s, 3H), 3.25 (s, 3H), 3.60 (s, 3H), 3.76 (s, 3H), 4.64 (d, J = 6.9 Hz, 2H), 5.50 (m, 1H), 6.86 (s, 1H), 7.10 (d, J = 8.4 Hz, 1H), 7.34–7.57 (m, 11H)
IR (CHCl$_3$) 1517, 1476, 1398, 1369, 1234, 1178, 1159, 1105, 1079, 972, 895, 854, 814, 801 cm$^{-1}$ I-980 foam
$^1$H NMR (CDCl$_3$) δ 1.76 (d, J = 0.9 Hz, 3H), 1.81 (d, J = 0.9 Hz, 3H), 2.71 (s, 3H), 3.20 (s, 3H), 3.24 (s, 3H), 3.57 (s, 3H), 3.79 (s, 3H), 4.64 (d, J = 6.6 Hz, 2H), 5.49 (m, 1H), 6.86 (s, 1H), 7.09 (d, J = 8.7 Hz, 1H), 7.31–7.40 (m, 3H), 7.48–7.55 (m, 3H)
IR (CHCl$_3$) 1517, 1474, 1365, 1269, 1236, 1177, 1140, 1116, 1078, 964, 923, 854, 814 cm$^{-1}$ I-981 mp 122–123° C.
$^1$H NMR (CDCl$_3$) δ 1.77 (s, 3H), 1.82 (d, J = 0.4 Hz, 3H), 3.62 (s, 3H), 3.75 (s, 3H), 4.63 (d, J = 6.6 Hz, 2H), 5.53 (m, 1H), 5.70 (s, 1H), 5.73 (s, 1H), 6.46 (s, 1H), 6.86 (s, 1H), 6.89–7.13 (m, 4H), 7.29–7.46 (m, 3H)
IR (KBr) 3366, 1587, 1496, 1482, 1462, 1449, 1408, 1371, 1313, 1290, 1245, 1210, 1126, 1093, 1073, 1001, 783, 770 cm$^{-1}$

TABLE 194

I-982 mp 171–172° C.
$^1$H NMR (CDCl$_3$) δ 1.76 (s, 3H), 1.82 (s, 3H), 3.48 (s, 3H), 3.74 (s, 3H), 4.61 (d, J = 6.9 Hz, 2H), 4.91 (s, 1H), 5.53 (m, 1H), 5.70 (s, 1H), 5.91 (s, 1H), 6.46 (s, 1H), 6.86 (m, 1H), 6.91–7.02 (m, 2H), 7.06 (m, 1H), 7.13 (m, 1H), 7.21 (m, 1H), 7.32 (m, 1H)
IR (KBr) 3368, 1585, 1519, 1507, 1484, 1460, 1450, 1403, 1294, 1255, 1237, 1206, 1110, 1072, 1006, 789, 766 cm$^{-1}$

I-983 mp 92.5–93° C.
$^1$H NMR (CDCl$_3$) δ 1.77 (s, 3H), 1.83 (d, J = 0.9 Hz, 3H), 2.26 (s, 3H), 2.27 (s, 3H), 4.63 (d, J = 6.9 Hz, 2H), 5.13 (d, J = 3.9 Hz, 1H), 5.55 (m, 1H), 6.98–7.14 (m, 8H)
IR (CHCl) 3578, 2922, 1618, 1522, 1490, 1383, 1282, 1120, 979, 873, 824 cm$^{-1}$

I-984 mp 89–95° C.
$^1$H NMR (CDCl$_3$) δ 1.77 (d, J = 6H), 1.81 (d, J = 0.9 Hz, 6H), 2.27 (s, 6H), 4.63 (d, J = 6.6 Hz, 4H), 5.55 (m, 2H), 6.98–7.14 (m, 8H)
IR (CHCl$_3$) 2930, 1576, 1520, 1490, 1382, 1296, 1270, 1127, 987, 874 cm$^{-1}$

I-985 mp 74–75° C.
$^1$H NMR (CDCl$_3$) δ 2.16 (s, 3H), 2.69 (s, 3H), 3.14 (s, 3H), 3.20 (s, 3H), 3.56 (s, 3H), 5.20 (s, 2H), 7.16–7.49 (m, 11H), 7.65–7.68 (m, 2H)
IR (CHCl$_3$) 2939, 1732, 1613, 1518, 1478, 1454, 1415, 1371, 1331, 1292, 1268, 1176, 1150, 1118, 1088, 1010, 969, 950, 872 cm$^{-1}$

I-986 mp 50–52° C.
$^1$H NMR (CDCl$_3$) δ 1.77 (s, 3H), 1.82 (s, 3H), 2.16 (s, 3H), 2.74 (s, 3H), 3.20 (s, 3H), 3.24 (s, 3H), 3.57 (s, 3H), 4.64–4.66 (d, J = 6.3 Hz, 2H), 5.50 (m, 1H), 7.10–7.39 (m, 6H), 7.66–7.68 (m, 2H)
IR (CHCl$_3$) 2938, 1613, 1518, 1477, 1370, 1331, 1290, 1267, 1176, 1150, 1117, 1088, 970, 949, 871 cm$^{-1}$

TABLE 195

I-987 $^1$H NMR (CDCl$_3$) δ 1.59–1.60 (d, J = 0.6 Hz, 3H), 1.70–1.71 (d, J = 0.9 Hz, 3H), 2.26 (s, 3H), 2.28 (s, 3H), 2.36 (m, 1H), 2.77 (m, 1H), 3.20 (s, 3H), 3.23 (s, 3H), 5.24 (m, 1H), 7.12 (s, 1H), 7.15 (s, 1H), 7.23–7.25 (m, 1H), 7.33–7.42 (m, 6H)

I-988 mp 159–161° C.
$^1$H NMR (CDCl$_3$) δ 1.76 (s, 3H), 1.82 (s, 3H), 2.12 (s, 3H), 3.48

TABLE 195-continued (s, 3H), 4.61–4.64 (d, J = 6.6 Hz, 2H), 4.75 (br, 1H), 5.54 (m, 1H), 5.69 (s, 1H), 5.73 (s, 1H), 6.77–6.98 (m, 6H), 7.51–7.54 (m, 2H)
IR (CHCl$_3$) 3595, 3529, 2937, 1613, 15787, 1522, 1489, 1455, 1401, 1310, 1289, 1173, 1127, 1095, 1009, 939, 835 cm$^{-1}$ I-989 mp 126–128° C.
$^1$H NMR (CDCl$_3$) δ 2.25 (s, 3H), 3.78 (s, 3H), 5.16 (s, 2H), 5.75 (br, 1H), 6.83–6.89 (m, 4H), 6.98–7.00 (m, 2H), 7.17 (s, 1H), 7.40–7.47 (m, 7H)
IR (CHCl$_3$) 3596, 3543, 2937, 1610, 1588, 1523, 1493, 1465, 1455, 1388, 1328, 1315, 1262, 1173, 1126, 1038, 1012, 835 cm$^{-1}$ I-990 mp 87–90° C.
$^1$H NMR (CDCl$_3$) δ 1.59–1.60 (d, J = 0.6 Hz, 3H), 1.72–1.73 (d, J = 0.9 Hz, 3H), 2.26 (s, 3H), 2.28 (s, 3H), 2.34–2.37 (m, 2H), 2.66–2.71 (m, 2H), 4.84–4.86 (br, 2H), 5.28 (m, 1H), 6.79 (d, J = 1.5 Hz, 1H), 6.86–6.89 (m, 3H), 7.11–7.17 (m, 3H), 7.23–7.26 (m, 2H)
IR (CHCl$_3$) 3598, 2925, 2859, 1612, 1569, 1521, 1488, 1450, 1425, 1414, 1328, 1257, 1171, 1101, 958, 836 cm$^{-1}$ I-991 mp 174–176° C.
$^1$H NMR (CDCl$_3$) δ 2.26 (s, 3H), 3.13 (s, 3H), 3.18 (s, 3H), 3.80 (s, 3H), 5.19 (s, 2H), 6.84 (s, 1H), 7.13 (d, J = 8.4 Hz, 1H), 7.18 (s, 1H), 7.28–7.50 (m, 9H), 7.59–7.62 (m, 2H)
IR (CHCl$_3$) 2940, 1732, 1613, 1520, 1490, 1465, 1455, 1415, 1371, 1331, 1291, 1260, 1173, 1149, 1111, 1038, 1018, 1003, 971, 872, 813 cm$^{-1}$

TABLE 196

I-992 mp 135–137° C.
$^1$H NMR (CDCl$_3$) δ 1.77–1.78 (d, J = 0.9 Hz, 3H), 1.82–1.83 (d, J = 0.6 Hz, 3H), 2.26 (s, 3H), 3.18 (s, 3H), 3.24 (s, 3H), 3.80 (s, 3H), 4.64 (d, J = 6.6 Hz, 2H), 5.52 (m, 1H), 6.84 (s, 1H), 7.07 (d, J = 8.7 Hz, 1H), 7.18 (s, 1H), 7.25–7.35 (m, 4H), 7.59–7.62 (m, 2H)
IR (CHCl$_3$) 3596, 3539, 2937, 1610, 1587, 1523, 1492, 1464, 1454, 1388, 1328, 1315, 1292, 1261, 1173, 1126, 1038, 996, 834 cm$^{-1}$

I-993 mp 131–133° C.
$^1$H NMR (CDCl$_3$) δ 1.77 (s, 3H), 1.83 (s, 3H), 2.26 (s, 3H), 3.78 (s, 3H), 4.61–4.64 (d, J = 6.9 Hz, 2H), 5.17 (br, 1H), 5.35 (m, 1H), 5.78 (br, 1H), 6.83–6.99 (m, 6H), 7.17 (s, 1H), 7.44–7.47 (m, 2H)
IR (CHCl$_3$) 3596, 3539, 2937, 1610, 1587, 1523, 1492, 1464, 1454, 1388, 1328, 131, 1292, 1261, 1173, 1126, 1038, 996, 834 cm$^{-1}$

I-994 mp 127–130° C.
$^1$H NMR (CDCl$_3$) δ 1.73 (d, J = 0.9 Hz, 3H), 1.76 (d, J = 0.9 Hz, 3H), 2.99 (s, 6H), 3.73–3.76 (m, 2H), 3.78 (s, 3H), 5.37–5.40 (m, 1H), 5.83 (m, 1H), 6.78–6.84 (m, 2H), 6.95 (s, 1H), 6.96 (s, 1H), 7.06–7.12 (m, 2H), 7.48–7.53 (m, 2H)

I-995 mp91–93° C.
$^1$H NMR (CDCl$_3$) δ 1.78 (s, 3H), 1.84 (s, 3H), 2.02 (s, 6H), 4.63 (d, J = 6.4 Hz, 2H), 5.07 (s, 1H), 5.15 (s, 1H), 5.55 (t, J = 7.0 Hz, 1H), 6.63 (dd, J = 2.0, 8.2 Hz, 1H), 6.77 (d, J = 2.0 Hz, 1H), 6.93–6.99 (m, 4H), 7.39 (d, J = 8.6 Hz, 2H)
IR(KBr) 3423, 2921, 1611, 1518, 1474, 1282, 1244, 1205, 1125, 1089, 995, 837, 815, 785 cm$^{-1}$

I-996 mp185–186° C.
$^1$H NMR (CDCl$_3$) δ 1.32 (t, J = 7.5 Hz, 3H), 2.71 (q, J = 7.5 Hz, 2H), 3.46 (s, 3H), 3.76 (s, 3H), 5.15 (s, 2H), 5.69 (s, 1H), 5.89 (s, 1H), 6.94–7.08 (m, 3H), 7.37–7.46 (m, 5H), 7.54–7.59 (m, 2H), 7.82 (brs, 1H), 7.93 (d, J = 8.1 Hz, 1H)
IR(KBr) 3504, 3269, 2968, 2936, 1708, 1532, 1518, 1487, 1311, 1286, 1193, 1121, 1071, 1014 cm$^{-1}$

TABLE 197

I-997 mp77–78° C.
$^1$H NMR (CDCl$_3$) δ 1.73 (s, 3H), 1.77 (s, 3H), 1.82 (s, 3H), 2.70 (s, 3H), 3.25 (s, 3H), 3.55 (s, 3H), 3.82 (s, 3H), 4.65 (d, J = 6.9 Hz, 2H), 4.94 (d, J = 7.5 Hz, 2H), 5.31 (t, J = 8.7 Hz, 1H), 5.50 (t, J = 6.6 Hz, 1H), 6.87 (s, 1H), 7.10 (d, J = 8.4 Hz, 1H), 7.28–7.39 (m, 3H), 7.87 (d, J = 8.1 Hz, 1H), 7.99 (s, 1H)
IR(KBr) 3431, 2939, 1702, 1518, 1483, 1368, 1308, 1204, 1177, 1121, 1092, 1079, 957, 804 cm$^{-1}$

I-998 mp144–145° C.
$^1$H NMR (CDCl$_3$) δ 1.76 (s, 3H), 1.82 (s, 3H), 3.48 (s, 3H), 3.69 (s, 3H), 3.80 (s, 6H), 4.61 (d, J = 6.9 Hz, 2H), 5.51 (t, J = 4.8 Hz, 1H), 5.66 (brs, 1H), 5.76 (brs, 1H), 6.30 (s, 1H), 6.69 (d, J = 8.1 Hz, 2H), 6.93–7.01 (m, 2H), 7.11 (d, J = 2.1 Hz, 1H), 7.31–7.37 (m, 1H)
IR(KBr) 3476, 2936, 1589, 1517, 1500, 1472, 1408, 1288, 1249, 1111 cm$^{-1}$ I-999 mp82–83° C.
$^1$H NMR (CDCl$_3$) δ 2.71 (s, 3H), 3.15 (s, 3H), 3.48 (s, 3H), 3.56 (s, 3H), 3.72 (s, 3H), 3.80 (s, 6H), 4.66 (s, 2H), 4.79 (s, 2H), 5.19 (s, 2H), 6.69 (s, 1H), 7.14–7.17 (m, 1H), 7.36–7.49 (m, 8H)
IR(KBr) 3434, 2939, 1719, 1613, 1581, 1508, 1463, 1396, 1365, 1294, 1272, 1238, 1177, 1122, 1078, 814 cm$^{-1}$ I-1000 mp85–86° C.
$^1$H NMR (CDCl$_3$) δ 1.31 (t, J = 7.5 Hz, 3H), 2.66 (s, 3H), 2.71 (q, J = 7.6 Hz, 2H), 3.13 (s, 3H), 3.55 (s, 3H), 3.78 (s, 3H), 5.19 (s, 2H), 6.85 (s, 1H), 7.15 (d, J = 8.8 Hz, 1H), 7.33–7.59 (m, 4H), 7.85 (brs, 1H), 7.94 (d, J = 8.4 Hz, 1H)
IR(KBr) 3432, 2939, 1727, 1519, 1480, 1365, 1237, 1165, 1079, 959, 803 cm$^{-1}$ I-1001 mp105–106° C.
$^1$H NMR (CDCl$_3$) δ 1.76 (s, 6H), 1.79 (s, 3H), 1.82 (s, 3H), 3.49 (s, 3H), 3.75 (s, 3H), 3.81 (d, J = 6.6 Hz, 2H), 4.62 (d, J = 7.2 Hz, 2H), 5.37 (t, J = 6.3 Hz, 1H), 5.53 (t, J = 6.9 Hz, 1H), 5.68 (brs, 1H), 5.87 (brs, 1H), 6.82 (d, J = 8.4 Hz, 1H), 6.95 (s, 2H), 7.05 (s, 1H), 7.26 (s, 1H), 7.69 (dd, J = 2.1, 8.4 Hz, 1H), 7.75 (brs, 1H)
IR(KBr) 3459, 2934, 1622, 1582, 1525, 1493, 1467, 1327, 1240, 1139, 1113, 1070, 817 cm$^{-1}$

TABLE 198

I-1002 mp89–91° C.
$^1$H NMR (CDCl$_3$) δ 2.70 (s, 3H), 3.12 (s, 3H), 3.55 (s, 3H), 3.71 (s, 3H), 3.79 (s, 6H), 4.77 (s, 2H), 5.18 (s, 2H), 6.69 (s, 2H), 7.14 (d, J = 8.8 Hz, 1H), 7.38–7.52 (m, 8H)
IR(KBr) 3440, 2939, 1721, 1612, 1581, 1508, 1463, 1395, 1364, 1238, 1178, 1120, 1078, 962, 814, 523 cm$^{-1}$

I-1003 mp196–197° C.
$^1$H NMR (CDCl$_3$) δ 2.26 (s, 3H), 3.48 (s, 3H), 3.76 (s, 3H), 5.16 (s, 2H), 5.69 (brs, 1H), 5.83 (brs, 1H), 6.44 (s, 1H), 6.93–7.05 (m, 4H), 7.26–7.45 (m, 6H), 7.84 (d, J = 8.1 Hz, 1H), 7.92 (s, 1H), 8.29 (brs, 1H)
IR(KBr) 3407, 2934, 1672, 1589, 1524, 1459, 1425, 1400, 1316, 1288, 1213, 1119, 1057, 1006, 745 cm$^{-1}$ I-1004 mp80–81° C.
$^1$H NMR (CDCl$_3$) δ 1.29 (t, J = 7.5 Hz, 3H), 1.72 (s, 3H), 1.76 (s, 6H), 1.81 (s, 3H), 2.70 (s, 3H), 2.71 (q, J = 7.5 Hz, 2H), 3.24 (s, 3H), 3.50 (s, 3H), 3.81 (s, 3H), 4.64 (d, J = 6.3 Hz, 2H), 4.72–4.76 (m, 2H), 5.31 (t, J = 6.9 Hz, 1H), 5.50 (t, J = 6.3 Hz, 1H), 6.87 (s, 1H), 7.08–7.12 (m, 2H), 7.34–7.41 (m, 3H), 7.61 (s, 1H)
IR(KBr) 3434, 2974, 2938, 1694, 1517, 1480, 1366, 1237, 1202, 1177, 1080, 972, 807, 523 cm$^{-1}$ I-1005 mp157–158° C.
$^1$H NMR (CDCl$_3$) δ 1.31 (t, J = 7.8 Hz, 3H), 1.77 (s, 3H), 1.81 (s, 3H), 2.71 (s, 3H), 2.71 (q, J = 7.8 Hz, 2H), 3.24 (s, 3H), 3.55 (s, 3H), 3.78 (s, 3H), 4.64 (d, J = 6.6 Hz, 2H), 5.50 (t, J = 8.1 Hz, 2H), 6.85 (s, 1H), 7.09 (d, J = 8.4 Hz, 1H), 7.33–7.38 (m, 2H), 7.52 (d, J = 8.1 Hz, 1H), 7.58 (s, 1H), 7.84 (brs, 1H), 7.94 (d, J = 8.1 Hz, 1H)
IR(KBr) 3434, 3350, 2938, 1727, 1523, 1480, 1368, 1248, 1178, 1165, 1080, 972, 816, 802, 522 cm$^{-1}$ I-1006 mp91–93° C.
$^1$H NMR (CDCl$_3$) δ 1.30 (t, J = 7.5 Hz, 3H), 1.75 (s, 6H), 1.79 (s, 3H), 1.81 (s, 3H), 2.55 (q, J = 7.5 Hz, 2H), 3.48 (s, 3H), 3.74 (s, 3H), 3.79 (d, J = 6.3 Hz, 2H), 4.61 (d, J = 6.6 Hz, TABLE 198-continued 2H), 5.41 (t, J = 6.0 Hz, 1H), 5.53 (t, J = 6.9 Hz, 1H), 5.67 (brs, 1H), 5.94 (brs, 1H), 6.48 (s, 1H), 6.72 (d, J = 8.4 Hz, 1H), 6.95 (s, 2H), 7.07 (s, 1H), 7.37–7.45 (m, 2H), 7.64 (d, J = 7.5 Hz, 1H),
IR(KBr) 3433, 2932, 1609, 1521, 1489, 1461, 13958, 1308, 1286, 1245, 1192, 1114, 1072, 1011, 811 cm$^{-1}$

TABLE 199

I-1007 mp 71–72° C.
$^1$H NMR(CDCl$_3$) δ 1.31(t, J=7.5Hz, 3H), 1.76(s, 3H), 1.82 (s, 3H), 2.60(q, J=7.2Hz, 2H), 3.47(s, 3H), 3.75(s, 3H), 4.61(d, J=6.6Hz, 2H), 5.53(t, J=6.9Hz, 2H), 5.69(brs, 1H), 5.93(brs, 1H), 6.47(s, 1H), 6.78(d, J=8.1Hz, 1H), 6.95 (s, 2H), 7.06(s, 1H), 7.26(s, 1H), 7.39(s, 1H)
IR(KBr) 3436, 2932, 1620, 1584, 1519, 1487, 1459, 1397, 1285, 1242, 1112, 1072, 819 cm$^{-1}$ I-1008 mp 171–173° C.
$^1$H NMR(CDCl$_3$) δ 3.46(s, 3H), 3.75(s, 3H), 5.15(s, 2H), 5.68(s, 1H), 5.88(s, 1H), 6.44(s, 1H), 6.95(dd, J=8.4, 1.9 Hz, 1H), 7.03(d, J=8.4Hz, 1H), 7.08(d, J=1.9Hz, 1H), 7.37–7.48(m, 7H), 7.59(d, J=8.4Hz, 2H)
IR(KBr) 3544, 3514, 3462, 1517, 1482, 1388, 1284, 1247, 1089, 1107, 1069, 1006, 938, 822 cm$^{-1}$ I-1009 mp 180–182° C.
$^1$H NMR(CDCl$_3$) δ 2.68(s, 3H), 3.13(s, 3H), 3.53(s, 3H), 3.77(s, 3H), 5.19(s, 2H), 6.83(s, 1H), 7.15(d, J=8.4Hz, 1H), 7.32–7.49(m, 9H), 7.57(d, J=8.7Hz, 2H)
IR(KBr) 1518, 1478, 1370, 1177, 1085, 1012, 813, 797 cm$^{-1}$ I-1010 mp 128–130° C.
$^1$H NMR(CDCl$_3$) δ 1.76(s, 3H), 1.82(s, 3H), 3.46(s, 3H), 3.75(s, 3H), 4.62(d, J=7.0Hz, 2H), 5.53(t, J=7.0Hz, 1H), 5.69(s, 1H), 5.85(s, 1H), 6.44(s, 1H), 6.93(dd, J=8.4, 1.6 Hz, 1H), 6.97(d, J=8.4Hz, 1H), 7.05(d, J=1.6Hz, 1H), 7.42 (d, J=8.4Hz, 2H), 7.59(d, J=8.4Hz, 2H)
IR(KBr) 1517, 1482, 1287, 1244, 1106, 1070, 1013, 822, 783 cm$^{-1}$ I-1011 mp 138–140° C.
$^1$H NMR(CDCl$_3$) δ 1.76(s, 3H), 1.81(s, 3H), 2.72(s, 3H), 3.23(s, 3H), 3.54(s, 3H), 3.78(s, 3H), 4.64(d, J=6.5Hz, 2H), 5.49(t, J=6.5Hz, 1H), 6.83(s, 1H), 7.09(d, J=8.3Hz, 1H), 7.34(dd, J=8.3, 2.0Hz, 1H), 7.39(d, J=2.0Hz, 1H), 7.43(d, J=8.6Hz, 2H), 7.57(d, J=8.6Hz, 2H)
IR(KBr) 1518, 1478, 1369, 1177, 1083, 972, 814, 795 cm$^{-1}$

TABLE 200

I-1012 mp 135–138° C.
$^1$H NMR(CDCl$_3$) δ 1.55–1.63(m, 2H), 1.77(s, 6H), 1.83(s, 6H), 4.56(d, J=6.6Hz, 4H), 4.66(d, J=4.5Hz, 4H), 5.50–5.58(m, 2H), 6.96–7.01(m, 4H), 7.32–7.38(m, 4H), 7.45(s, 2H)
IR(KBr) 3339, 2914, 1609, 1520, 1488, 1385, 1289, 1238, 1177, 1000, 834, 651 cm$^{-1}$

I-1013 mp 202–205° C.
$^1$H NMR(CDCl$_3$ + CD3OD) δ 1.78(s, 3H), 1.82(s, 3H), 4.57 (d, J=6.6Hz, 2H), 4.62(s, 4H), 5.50–5.56(m, 1H), 6.86–7.00 (m, 4H), 7.24–7.37(m, 4H), 7.44(s, 2H)
IR(KBr) 3399, 2974, 2930, 1610, 1522, 1489, 1438, 1383, 1238, 1176, 999, 903, 838, 538 cm$^{-1}$

I-1014 mp 219–221° C.
$^1$H NMR(CDCl$_3$) δ 2.22(s, 3H), 2.69(s, 3H), 3.13(s, 3H), 3.53(s, 3H), 3.77(s, 3H), 5.19(s, 2H), 6.85(s, 1H), 7.15(d, J=8.4Hz, 1H), 7.32–7.49(m, 7H), 7.60(s, 4H)
IR(KBr) 3384, 1701, 1604, 1524, 1482, 1355, 1294, 1176, 1084, 1011, 945, 818 cm$^{-1}$

I-1015 mp 173–175° C.
$^1$H NMR(DMSO-d$_6$) δ 1.74(s, 3H), 1.77(s, 3H), 2.08(s, 3H), 2.87(s, 3H), 3.35(s, 3H), 3.47(s, 3H), 3.77(s, 3H), 4.68(d, J=6.4Hz, 2H), 5.48(t, J=6.4Hz, 1H), 7.02(s, 1H), 7.26–7.29(m, 3H), 7.57(d, J=8.7Hz, 2H), 7.70(d, J=8.7Hz, 2H), 10.07(s, 1H)

TABLE 200-continued

IR(KBr) 3383, 1704, 1235, 1524, 1481, 1360, 1177, 1083, 976, 816 cm$^{-1}$

I-1016 mp 144–145° C.
$^1$H NMR(CDCl$_3$) δ 1.77(s, 3H), 1.81(s, 3H), 2.70(s, 3H), 3.21(s, 3H), 3.52(s, 3H), 3.69(d, J=1.6Hz, 3H), 4.65(d, J=6.8Hz, 2H), 5.53(t, J=6.8Hz, 1H), 7.08(t, J=8.4Hz, 1H), 7.16(dd, J=8.4, 1.8Hz, 1H), 7.20(dd, J=11.7, 1.8Hz, 1H), 7.41(d, J=8.8Hz, 2H), 7.59(dd, J=8.8, 1.4Hz, 2H)
IR(KBr) 1521, 1470, 1368, 1265, 1177, 1151, 1038, 971, 875 cm$^{-1}$

TABLE 201

I-1017 mp 196–198° C.
$^1$H NMR(DMSO-d$_6$) δ 1.72(s, 3H), 1.76(s, 3H), 2.07(s, 3H), 3.31(s, 3H), 3.65(s, 3H), 4.55(d, J=6.6Hz, 2H), 5.49(t, J= 6.6Hz, 1H), 6.43(s, 1H), 6.65(dd, J=8.4, 1.9Hz, 1H), 6.73 (d, J=1.9Hz, 1H), 6.90(d, J=8.4Hz, 1H), 7.55(d, J=8.6 Hz, 2H), 7.66(d, J=8.6Hz, 2H), 8.58(br s, 1H), 8.70(br s, 1H), 10.02(s, 1H)
IR(KBr) 3358, 1661, 1596, 1523, 1489, 1396, 1308, 1254, 1227, 1114, 1074 cm$^{-1}$

I-1018 mp 141–143° C.
$^1$H NMR(CDCl$_3$) δ 1.76(s, 3H), 1.81(s, 3H), 3.40(s, 3H), 3.64(d, J=0.9Hz, 3H), 4.64(d, J=6.9Hz, 2H), 4.89(s, 1H), 5.56(t, J=6.9Hz, 1H), 5.70(s, 1H), 6.94(d, J=8.7Hz, 2H), 7.06(t, J=8.7Hz, 1H), 7.21(ddd, J=8.4, 2.1, 1.1Hz, 1H), 7.27(dd, J=12.3, 2.1Hz, 1H), 7.44(dd, J=8.7, 1.5Hz, 2H)
IR(KBr) 3485, 1523, 1466, 1402, 1266, 1173, 1036, 961, 918, 837, 814 cm$^{-1}$ I-1019 mp 81–82° C.
$^1$H NMR(CDCl$_3$) δ 1.77(s, 3H), 1.81(s, 3H), 2.26(s, 3H), 2.72(s, 3H), 3.23(s, 3H), 3.57(s, 3H), 3.79(s, 3H), 4.64(d, J=6.3Hz, 2H), 5.49(t, J=6.3Hz, 1H), 6.83(s, 1H), 7.09(d, J=8.4Hz, 1H), 7.33–7.39(m, 2H), 7.48(s, 1H), 7.82(d, J= 6.0Hz, 1H), 7.88(s, 1H), 8.32(brs, 1H)
IR(KBr) 3382, 2939, 1736, 1520, 1483, 1365, 1293, 1178, 1119, 1078, 958, 802, 521 cm$^{-1}$ I-1020 mp 93–94° C.
$^1$H NMR(CDCl$_3$) δ 2.62(s, 3H), 2.99(s, 3H), 3.15(s, 3H), 3.20(s, 3H), 3.83(s, 3H), 5.21(s, 2H), 6.91(s, 2H), 7.17(d, J=8.2Hz, 1H), 7.35–7.48(m, 8H), 7.63(d, J=8.4Hz, 2H)
IR(KBr) 3434, 3033, 2938, 1611, 1520, 1479, 1366, 1179, 1151, 1085, 969, 850, 793, 519 cm$^{-1}$

TABLE 202

I-1021 mp 74–75° C.
$^1$H NMR(CDCl$_3$) δ 1.76(s, 3H), 1.82(s, 3H), 3.48(s, 3H), 3.75(s, 3H), 4.61(d, J=6.3Hz, 2H), 5.53(t, J=5.4Hz, 1H), 5.69(brs, 1H), 5.86(brs, 1H), 6.42(s, 1H), 6.83(d, J=8.7Hz, 1H), 6.91–6.98(m, 2H), 7.04(s, 1H), 7.62(d, J=8.7Hz, 1H), 7.73(s, 1H)
IR(KBr) 3495, 3398, 2935, 1633, 1522, 1487, 1291, 1246, 1112, 1072, 821, 788 cm$^{-1}$ I-1022 mp 76–77° C.
$^1$H NMR(CDCl$_3$) δ 1.77(s, 3H), 1.82(s, 3H), 1.84(s, 3H), 3.52(s, 3H), 3.78(s, 3H), 4.63(d, J=6.9Hz, 2H), 5.53(t, J= 6.6Hz, 1H), 5.74(brs, 1H), 5.80(brs, 1H), 6.47(s, 1H), 6.92–7.00(m, 2H), 7.04(s, 1H), 7.38(d, J=8.1Hz, 1H), 7.93(d, J= 8.1Hz, 1H), 8.04(s, 1H)
IR(KBr) 3411, 2934, 1662, 1519, 1488, 1425, 1309, 1245, 1175, 1128, 1071, 1050 cm$^{-1}$ I-1023 mp 81–82° C.
$^1$H NMR(CDCl$_3$) δ 1.77(s, 3H), 1.81(s, 3H), 2.66(s, 3H), 2.99(s, 3H), 3.18(s, 3H), 3.25(s, 3H), 3.82(s, 3H), 4.64(d, J=6.6Hz, 2H), 5.49(t, J=6.0Hz, 1H), 6.90(s, 1H), 7.10(d, J=8.4Hz, 1H), 7.38–7.43(m, 3H), 7.62(d, J=8.8Hz, 1H), 8.02(s, 1H)

TABLE 202-continued

I-1024
IR(KBr) 3434, 3027, 2938, 1672, 1611, 1520, 1479, 1365, 1179, 1117, 1074, 970, 847, 793, 519 cm$^{-1}$
mp 77–79° C.
$^1$H NMR(CDCl$_3$) δ 1.78(s, 3H), 1.83(s, 3H), 3.77(s, 3H), 4.63(d, J=6.6Hz, 2H), 5.53(t, J=6.2Hz, 1H), 5.76(brs, 2H), 6.52(s, 1H), 6.91–7.02(m, 6H), 7.46(d, J=8.4Hz, 2H)
IR(KBr) 3465, 2935, 1613, 1586, 1524, 1487, 1359, 1282, 1245, 1222, 1173, 1157, 1112, 1065, 974, 857, 521 cm$^{-1}$ I-1025 mp 78–79° C.
$^1$H NMR(CDCl$_3$) δ 2.73(s, 3H), 2.78(s, 3H), 3.15(s, 3H), 3.21(s, 3H), 3.62(s, 3H), 5.22(s, 2H), 7.20(d, J=8.4Hz, 1H), 7.37–7.44(m, 10H), 7.68(d, J=8.8Hz, 2H)
IR(KBr) 3433, 3032, 2939, 1519, 1473, 1366, 1178, 1151, 1004, 966, 870, 847, 795, 524 cm$^{-1}$

TABLE 203

I-1026 mp 158–159° C.
$^1$H NMR(CDCl$_3$) δ 1.47(t, J=6.9Hz, 3H), 2.41(s, 3H), 3.21(s, 3H), 3.55(s, 3H), 3.77(s, 3H), 4.14(q, J=6.9Hz, 2H), 5.22(s, 2H), 6.83(s, 1H), 6.91(dd, J=2.1, 8.1Hz, 1H), 6.96–7.01(m, 2H), 7.28–7.48(m, 7H), 7.66–7.72(m, 2H)
IR(KBr) 1517, 1482, 1392, 1362, 1240, 1194, 1175, 1146, 1084, 963, 878, 797 cm$^{-1}$

I-1027 mp 106–107° C.
$^1$H NMR(CDCl$_3$) δ 2.27(s, 6H), 3.87(s, 3H), 5.20(s, 2H), 6.93–7.00(m, 2H), 7.01–7.17(m, 5H), 7.23–7.52(m, 7H)
IR(KBr) 1607, 1522, 1490, 1467, 1455, 1383, 1294, 1267, 1246, 1178, 1125, 1028, 1011, 836, 813, 744 cm$^{-1}$

I-108 mp 162–163° C.
$^1$H NMR(CDCl$_3$) δ 1.45(t, J=6.9Hz, 3H), 3.46(s, 3H), 3.74(s, 3H), 4.15(q, J=6.9Hz, 2H), 4.98(s, 1H), 5.19(s, 2H), 5.91(s, 1H), 6.45(s, 1H), 6.88–6.94(m, 2H), 6.95–7.03(m, 2H), 7.05(d, J=1.2Hz, 1H), 7.27–7.41(m, 3H), 7.45–7.56(m, 4H)
IR(KBr) 3424, 3343, 1611, 1521, 1488, 1462, 1454, 1400, 1379, 1358, 1317, 1290, 1278, 1262, 1240, 1225, 1201, 1185, 1127, 1110, 1068, 1026, 1007, 828, 731 cm$^{-1}$

I-1029 mp 73–74° C.
$^1$H NMR(CDCl$_3$) δ 1.77(s, 3H), 1.82(s, 3H), 2.27(s, 6H), 3.86(s, 3H), 4.63(d, J=7.2Hz, 2H), 5.56(m, 1H), 6.92–7.00(m, 2H), 7.00–7.16(m, 5H), 7.26–7.34(m, 2H)
IR(KBr) 1610, 1521, 1489, 1461, 1438, 1297, 1276, 1249, 1231, 1181, 1122, 1028, 985, 835 cm$^{-1}$

I-1030 mp 86–87° C.
$^1$H NMR(CDCl$_3$) δ 1.46(t, J=6.9Hz, 3H), 1.75(s, 3H), 1.79(d, J=0.9Hz, 3H), 2.54(s, 3H), 3.21(s, 3H), 3.56(s, 3H), 3.78(s, 3H), 4.12(q, J=6.9Hz, 2H), 4.63(d, J=6.3Hz, 2H), 5.53(m, 1H), 6.84(s, 1H), 6.93–7.01(m, 3H), 7.35–7.41(m, 2H), 7.67–7.73(m, 2H)
IR(KBr) 1518, 1480, 1449, 1413, 1389, 1366, 1239, 1199, 1180, 1150, 1082, 970, 872, 798 cm$^{-1}$

TABLE 204

I-1031 mp 145–146° C.
$^1$H NMR(CDCl$_3$) δ 1.44(t, J=6.9Hz, 3H), 1.74(s, 3H), 1.77(d, J=0.9Hz, 3H), 3.47(s, 3H), 3.75(s, 3H), 4.13(q, J=6.9 Hz, 2H), 4.63(d, J=6.6Hz, 2H), 5.10(s, 1H), 5.56(m, 1H), 5.91(s, 1H), 6.46(s, 1H), 6.89–6.94(m, 2H), 6.95–7.03(m, 3H), 7.50–7.56(m, 2H)
IR(KBr) 3404, 1611, 1520, 1487, 1464, 1442, 1391, 1358, 1293, 1264, 1237, 1224, 1192, 1112, 1071, 1030, 1002, 831 cm$^{-1}$

I-1032 mp 142–145° C.
$^1$H NMR(CDCl$_3$) δ 3.13(s, 3H), 3.21(s, 3H), 4.63(s, 2H), 4.65(s, 2H), 5.19(s, 2H), 7.15(d, J=8.4Hz, 1H), 7.33–7.52(m, 13H)
IR(KBr) 3519, 3422, 3380, 3032, 2933, 1611, 1519, 1487, 1364, 1171, 1148, 1109, 969, 871, 817, 527 cm$^{-1}$

TABLE 204-continued

I-1033 mp 103–106° C.
$^1$H NMR(CDCl$_3$ + CD3OD) δ 1.78(s, 3H), 1.82(s, 3H), 3.22(s, 3H), 3.24(s, 3H), 4.58–4.67(m, 6H), 5.46–5.54(m, 1H), 7.09(d, J=8.4Hz, 1H), 7.33–7.53(m, 8H)
IR(KBr) 3512, 3414, 3012, 2941, 1612, 1519, 1488, 1362, 1335, 1146, 997, 972, 876, 524 cm$^{-1}$

I-1034 mp 184–187° C.
$^1$H NMR(CDCl$_3$ + CD3OD) δ 1.78(s, 3H), 1.82(s, 3H), 4.59–4.65(m, 6H), 5.52–5.59(m, 1H), 6.84–6.98(m, 5H), 7.23–7.28(m, 2H), 7.44(s, 1H), 7.45(s, 1H)
IR(KBr) 3400, 2931, 1611, 1521, 1491, 1247, 1203, 1009, 987, 834 cm$^{-1}$

I-1035 mp 95–96° C.
$^1$H NMR(CDCl$_3$) δ 2.27(s, 6H), 2.41(s, 3H), 5.19(s, 2H), 7.02–7.18(m, 5H), 7.22–7.54(m, 9H)
IR(KBr) 1522, 1512, 1454, 1377, 1309, 1297, 1274, 1267, 1236, 1125, 1008, 877, 822, 742, 696 cm$^{-1}$

I-1036 mp 95–96° C.
$^1$H NMR(CDCl$_3$) δ 2.24(s, 3H), 2.27(s, 3H), 5.19(s, 2H), 6.99–7.15(m, 5H), 7.26–7.52(m, 9H)
IR(KBr) 1518, 1499, 1482, 1454, 1380, 1300, 1278, 1262, 1227, 1125, 1090, 1021, 1015, 875, 834, 817, 739 cm$^{-1}$

TABLE 205

I-1037 mp 58–59° C.
$^1$H NMR(CDCl$_3$) δ 1.77(d, J=0.6Hz, 3H), 1.81(d, J=0.9 Hz, 3H), 2.27(s, 6H), 2.41(s, 3H), 4.63(d, J=6.6Hz, 2H), 5.56(m, 1H), 6.98–7.14(m, 5H), 7.21–7.29(m, 4H)
IR(KBr) 1520, 1490, 1460, 1444, 1385, 1294, 1271, 1262, 1232, 1125, 1001, 828, 818 cm$^{-1}$

I-1038 mp 67–68° C.
$^1$H NMR(CDCl$_3$) δ 1.77(s, 3H), 1.81(d, J=0.9Hz, 3H), 2.25(s, 3H), 2.27(s, 3H), 4.64(d, J=6.6Hz, 2H), 5.55(m, 1H), 6.90–7.14(m, 5H), 7.26–7.32(m, 2H), 7.36–7.42(m, 2H)
IR(KBr) 1518, 1500, 1482, 1466, 1309, 1299, 1267, 1229, 1124, 1090, 995, 834 cm$^{-1}$

I-1039 mp 153–155° C.
$^1$H NMR(CDCl$_3$) δ 3.45(s, 3H), 3.75(s, 3H), 4.84(d, J=4.2 Hz, 2H), 6.43~6.51(m, 2H), 6.45(s, 1H), 6.92(d, J=8.7Hz, 2H), 6.94~7.00(m, 2H), 7.08(brs, 1H), 7.53(d, J=8.7Hz, 2H)
IR(KBr) 3411, 1612, 1588, 1523, 1489, 1288, 1245, 1224, 1113, 1070, 1011, 938, 824 cm$^{-1}$ I-1040 foam
$^1$H NMR(CDCl$_3$) δ 3.28(d, J=2.4Hz, 1H), 3.45(s, 3H), 3.75(s, 3H), 4.94(dd, J=6.0, 1.8Hz, 2H), 5.74(ddt, J=11.1, 2.4, 1.8Hz, 1H), 6.27(dt, J=11.1, 6.0Hz, 1H), 6.45(s, 1H), 6.92(d, J=8.7Hz, 2H), 6.94–7.00(m, 2H), 7.07(d, J=2.1Hz, 1H), 7.53(d, J=8.7Hz, 2H)
IR(KBr) 3433, 3279, 1612, 1588, 1523, 1489, 1286, 1248, 1223, 1113, 1070, 1011, 938, 825 cm$^{-1}$ I-1041 foam
$^1$H NMR(CDCl$_3$) δ 3.45(s, 3H), 3.75(s, 3H), 4.90(d, J=1.8 Hz, 2H), 5.55(dd, J=10.8, 2.4Hz, 1H), 5.71(dd, J=17.7, 2.4 Hz, 1H), 5.85(ddt, J=17.7, 10.8, 1.8Hz, 1H), 6.45(s, 1H), 6.92(d, J=8.7Hz, 2H), 6.97(dd, J=8.4, 2.1Hz, 1H), 7.07 (d, J=8.4Hz, 1H), 7.08(d, J=2.1Hz, 1H), 7.53(d, J=8.7 Hz, 2H)
IR(KBr) 3433, 1612, 1589, 1523, 1489, 1286, 1224, 1192, 1112, 1070, 1002, 937, 825, 815 cm$^{-1}$

TABLE 206

I-1042 mp 185–187° C.
$^1$H NMR(CDCl$_3$) δ 1.76(s, 3H), 1.81(s, 3H), 2.76(s, 3H), 3.23(s, 3H), 3.50(s, 3H), 3.78(s, 3H), 4.64(d, J=6.6Hz, 2H), 5.50(t, J=6.6Hz, 1H), 6.63(t, J=2.4Hz, 1H), 6.95(s, 1H), 7.09(d, J=8.5Hz, 1H), 7.26–7.29(m, 1H), 7.37(dd, J=

TABLE 206-continued

| | |
|---|---|
| | 8.5, 2.1Hz, 1H), 7.42(d, J=2.1Hz, 1H), 7.45–7.51(m, 2H), 7.89(s, 1H), 8.26(br s, 1H)<br>IR(KBr) 3418, 1473, 1362, 1177, 1079, 961, 817, 796 cm$^{-1}$ |
| I-1043 | mp 152–154° C.<br>$^{1}$H NMR(CDCl$_3$) δ 1.76(s, 3H), 1.82(s, 3H), 3.43(s, 3H), 3.76(s, 3H), 4.61(d, J=6.9Hz, 2H), 5.53(t, J=6.9Hz, 1H), 5.69(s, 1H), 5.98(s, 1H), 6.55(s, 1H), 6.63(t, J=2.1Hz, 1H), 6.94–7.01(m, 2H), 7.10(d, J=0.9Hz, 1H), 7.25–7.27(m, 1H), 7.46(d, J=8.4Hz, 1H), 7.51(dd, J=8.5, 1.5Hz, 1H), 7.89 (s, 1H), 8.24(br s, 1H)<br>IR(CHCl$_3$) 3529, 3480, 1515, 1495, 1407, 1291, 1246, 1107, 1070 cm$^{-1}$ |
| I-104 | mp 127–128° C.<br>$^{1}$H NMR(CDCl$_3$) δ 2.45(s, 3H), 3.52(s, 3H), 3.77(s, 3H), 3.91(s, 3H), 5.22(s, 2H), 6.84(s, 1H), 6.91(dd, J=8.4, 2.1 Hz, 1H), 6.79–7.00(m, 2H), 7.12–7.18(m, 2H), 7.30–7.47(m, 5H), 7.59–7.63(m, 2H)<br>IR(CHCl$_3$) 2938, 2843, 1606, 1585, 1520, 1483, 1464, 1443, 1390, 1368, 1174, 1141, 1083, 1013, 962, 936, 865, 838 cm$^{-1}$ |
| I-1045 | mp 124–127° C.<br>$^{1}$H NMR(CDCl$_3$) δ 2.46(s, 3H), 3.55(s, 3H), 3.77(s, 3H), 3.91(s, 3H), 5.21(s, 2H), 5.42(br, 1H), 6.82(s, 1H), 6.90(dd, J=8.4, 1.8Hz, 1H), 6.97–7.10(m, 3H), 7.29–7.47(m, 7H)<br>IR(CHCl$_3$) 3579, 2938, 1600, 1523, 1484, 1464, 1393, 1368, 1327, 1282, 1174, 1141, 1081, 1036, 1012, 962, 908 cm$^{-1}$ |
| I-1046 | mp 178–180° C.<br>$^{1}$H NMR(CDCl$_3$) δ 2.44(s, 3H), 3.29(s, 3H), 3.58(s, 3H), 3.78(s, 3H), 3.91(s, 3H), 5.22(s, 2H), 6.83(s, 1H), 6.99(dd, J=8.1, 2.1Hz, 1H), 6.97–7.25(m, 2H), 7.31–7.58(m, 8H)<br>IR(CHCl$_3$) 2939, 2840, 1591, 1519, 1483, 1464, 1374, 1331, 1173, 1141, 1116, 1082, 1012, 964, 863 cm$^{-1}$ |

TABLE 207

| | |
|---|---|
| I-107 | mp 98–99° C.<br>$^{1}$H NMR(CDCl$_3$) δ 2.35(s, 3H), 5.22(s, 2H), 6.59(t, J F–H = 54.6Hz, 2H), 7.09–7.50(m, 12H), 7.74–7.75(d, J=4.5Hz, 2H)<br>IR(CHCl$_3$) 1752, 1523, 1493, 1384, 1273, 1169, 1133, 1070, 1037, 916, 851 cm$^{-1}$ |
| I-1048 | mp 112–114° C.<br>$^{1}$H NMR(CDCl$_3$) δ 1.75–1.76(d, J=0.6Hz, 3H), 1.78–1.79 (d, J=0.9Hz, 3H), 2.57(s, 3H), 3.53(s, 3H), 3.78(s, 3H), 3.89(s, 3H), 4.62–4.64(d, J=7.5Hz, 2H), 5.54(m, 1H), 6.84 (s, 1H), 6.96–6.97(m, 3H), 7.12–7.18(m, 2H), 7.59–7.64(m, 2H)<br>IR(CHCl$_3$) 2938, 1606, 1583, 1519, 1483, 1464, 1443, 1416, 1389, 1368, 1175, 1141, 1083, 1038, 1013, 962, 936, 865, 838 cm$^{-1}$ |
| I-1049 | mp 203–204° C.<br>$^{1}$H NMR(CD3OD) δ 4.53(s, 2H),4.55(s, 2H), 5.21(s, 2H), 6.84–6.88(m, 2H), 7.12–7.50(m, 12H)<br>IR(KBr) 3380, 1611, 1586, 1523, 1490, 1462, 1434, 1380, 1317, 1300, 1258, 1194, 1173, 1128, 1033, 1007, 906, 871, 836, 817, 787, 730, 693, 646 cm$^{-1}$ |
| I-1050 | mp 99–100° C.<br>$^{1}$H NMR(CDCl$_3$) δ 1.75(s, 3H), 1.78–1.79(d, J=0.9Hz, 3H), 3.46(s, 3H), 3.75(s, 3H), 3.88(s, 3H), 4.62–4.64(d, J= 6.6Hz, 2H), 5.57(m, 1H), 5.89(s, 1H), 6.46(s, 1H), 6.96–7.02 (m, 3H), 7.12–7.18(m, 2H), 7.59–7.64(m, 2H)<br>IR(CHCl$_3$) 3513, 2938, 1605, 1583, 1490, 1423, 1407, 1392, 1362, 1318, 1269, 1177, 1158, 1140, 1118, 1078, 1038, 1012, 930, 846, 826 cm$^{-1}$ |
| I-1051 | mp 153–154° C.<br>$^{1}$H NMR(CDCl$_3$) δ 1.76(s, 3H), 1.79–1.80(d, J=0.9Hz, 3H), 2.57(s, 3H), 3.29(s, 3H), 3.60(s, 3H), 3.79(s, 3H), 3.89(s, 3H), 4.62–4.64(d, J=6.6Hz, 2H), 5.54(m, 1H), 6.84(s, 1H), 6.96–6.97(m, 4H), 7.46–7.59(m, 3H)<br>IR(CHCl$_3$) 2938, 1592, 1519, 1483, 1464, 1374, 1332, 1239, 1173, 1141, 1116, 1082, 1038, 1011, 965, 864 cm$^{-1}$ |

TABLE 208

| | |
|---|---|
| I-1052 | amorphous<br>$^{1}$H NMR(CDCl$_3$) δ 2.12(s, 3H), 3.47(s, 3H), 5.15(s, 2H), 5.82–6.08(m, 3H), 6.70–6.95(m, 5H), 7.02(d, J=8.1Hz, 1H), 7.39–7.52(m, 7H)<br>IR(CHCl$_3$) 3597, 3535, 2937, 1731, 1612, 1589, 1522, 1489, 1455, 1401, 1382, 1328, 1309, 1288, 1173, 1128, 1096, 1011, 939, 835 cm$^{-1}$ |
| I-1053 | mp 141–142° C.<br>$^{1}$H NMR(CDCl$_3$) δ 1.75(s, 3H), 1.78–1.79(d, J=0.9Hz, 3H), 3.49(s, 3H), 3.76(s, 3H), 3.89(s, 3H), 4.62–4.64(d, J=6.6 Hz, 2H), 5.30(d, J F–H=3.3Hz, 1H), 5.57(m, 1H), 5.88(s, 1H), 6.45(s, 1H), 6.99–7.11(m, 4H), 7.33(m, 1H), 7.43(dd, J=11.7, 2.1Hz, 1H)<br>IR(CHCl$_3$) 3578, 3514, 1621, 1600, 1583, 1523, 1492, 1464, 1397, 1320, 1279, 1175, 1140, 1116, 1100, 1076, 1038, 1011, 902 cm$^{-1}$ |
| I-1054 | mp 138–140° C.<br>$^{1}$H NMR(CDCl$_3$) δ 5.17(s, 2H), 5.60(s, 1H), 5.72(s, 1H), 6.98–7.02(m, 2H), 7.10–7.14(m, 3H), 7.18(s, 1H), 7.35(s, 1H), 7.37–7.47(m, 5H), 7.59–7.61(m, 2H)<br>IR(KBr) 3600–2800(br), 1590, 1528, 1503, 1483, 1454, 1386, 1294, 1254, 1223, 1187, 1132, 1086, 1009 cm$^{-1}$ |
| I-1055 | mp 176–178° C.<br>$^{1}$H NMR(CDCl$_3$) δ 3.13(s, 3H), 3.32(s, 3H), 5.19(s, 2H), 7.16(d, J=8.7Hz, 1H), 7.37–7.55(m, 9H), 7.61–7.64(m, 4H)<br>IR(KBr) 3600–2800(br), 1611, 1525, 1503, 1469, 1359, 1290, 1244, 1170, 1088, 979 cm$^{-1}$ |
| I-1056 | mp 134–136° C.<br>$^{1}$H NMR(CDCl$_3$) δ 1.77(s, 3H), 1.81(s, 3H), 3.23(s, 3H), 3.32(s, 3H), 4.64(d, J=6.9Hz, 1H), 5.48–5.54(m, 1H), 7.10 (d, J=8.4Hz, 1H), 7.44–7.55(m, 4H), 7.58–7.65(m, 4H)<br>IR(KBr) 3600–2800(br), 1609, 1527, 1504, 1469, 1351, 1289, 1277, 1186, 1171, 1115, 1089, 973 cm$^{-1}$ |

TABLE 209

| | |
|---|---|
| I-1057 | mp 97–100° C.<br>$^{1}$H NMR(CDCl$_3$) δ 1.77(d, J=0.9Hz, 3H), 1.82(d, J=0.9 Hz, 3H), 4.63(d, J=7.2Hz, 2H), 5.50–5.54(m, 1H), 5.62(br s, 1H), 5.74(br s, 1H), 6.95(d, J=8.7Hz, 1H), 7.12(dd, J= 2.4, 8.7Hz, 1H), 7.18(s 1H), 7.24(d, J=2.4Hz, 1H), 7.36 (s, 1H), 7.42–7.46(m, 2H), 7.58–7.62(m, 2H)<br>IR(KBr) 3600–2800(br), 1599, 1588, 1528, 1482, 1385, 1326, 1289, 1252, 1212, 1193, 1132, 1112, 1084, 1056, 1001 cm$^{-1}$ |
| I-1058 | mp 216–218° C.<br>$^{1}$H NMR(DMSO-d$_6$) δ 2.93(s, 12H), 3.73(s, 6H), 6.74–6.79 (m, 4H), 6.92(s, 2H), 7.38–7.43(m, 4H)<br>IR(KBr) 3600–2800(br), 1616, 1533, 1496, 1458, 1442, 1387, 1360, 1230, 1202, 1169, 1059, 1035 cm$^{-1}$ |
| I-1059 | mp 122–123° C.<br>$^{1}$H NMR(CDCl$_3$) δ 1.74(d, J=0.6Hz, 3H), 1.78(d, J=0.6 Hz, 3H), 2.26(s, 3H), 2.29(s, 3H), 3.77(d, J=6.9Hz, 2H), 4.83(br, 1H), 5.36–5.41(m, 1H), 6.61–6.77(m, 2H), 6.86–6.91 (m, 2H), 6.99–7.04(m, 2H), 7.10(s, 1H), 7.11(s 1H), 7.21–7.26(m, 2H)<br>IR(KBr) 3600–2800(br), 1626, 1608, 1526, 1489, 1428, 1336, 1300, 1252, 1209, 1187 cm$^{-1}$ |
| I-1060 | mp foam<br>$^{1}$H NMR(CDCl$_3$) δ 1.74(s, 3H), 1.77(s, 3H), 2.27(s, 3H), 2.31(s, 3H), 3.76(d, J=6.6Hz, 2H), 3.86(s, 3H), 5.38–5.43 (m, 1H), 6.66(d, J=8.1Hz, 1H), 6.80(d, J=1.8Hz, 1H), 6.86–6.90(m, 3H), 7.11(s, 1H), 7.16(s 1H), 7.23–7.26(m, 2H)<br>IR(CHCl$_3$) 3600–2800(br), 1730, 1611, 1525, 1489, 1455, 1256, 1171, 1137, 1100, 1036 cm$^{-1}$ |
| I-1061 | mp 191–193° C.<br>$^{1}$H NMR(CDCl$_3$) δ 3.01(s, 6H), 3.79(s, 3H), 3.80(s, 3H), 6.79–6.83(m, 2H), 6.92(s, 1H), 6.98(s 1H), 7.41–7.51(m, 4H), 8.12(br s, 1H), 8.26–8.32(m, 1H)<br>IR(KBr) 3600–2800(br), 1712, 1617, 1600, 1536, 1494, 1460, 1446, 1385, 1364, 1290, 1212, 1162, 1057, 1035 cm$^{-1}$ |

TABLE 210

I-1062 mp 240–245° C.
$^1$H NMR(CDCl$_3$) δ 3.82(s, 6H), 6.95(s, 2H), 7.41–7.49(m, 4H), 8.13(br s, 2H), 8.29–8.35(m, 1H)
IR(KBr) 3600–2800(br), 1725, 1598, 1544, 1492, 1381, 1294, 1215, 1197, 1165, 1109, 1055, 1033 cm$^{-1}$

I-1063 $^1$H NMR(CDCl$_3$) δ 1.99(s, 6H), 2.17(s, 3H), 3.21(s, 3H), 5.20(s, 2H), 6.95–7.11(m, 4H), 7.23(d, J=8.7Hz, 2H), 7.33–7.52(m, 7H)
IR(KBr) 1617, 1577, 1513, 1366, 1295, 1267, 1198, 1173, 1149, 1127, 1106 cm$^{-1}$

I-1064 $^1$H NMR(CDCl$_3$) δ 1.99(s, 6H), 2.17(s, 3H), 3.21(s, 3H), 5.18(d, J=3.9Hz, 1H), 6.97–7.10(m, 4H), 7.23(d, J=8.7 Hz, 2H), 7.37(d, J=8.7Hz, 2H)
IR(KBr) 3442, 1620, 1597, 1519, 1472, 1356, 1279, 1232, 1174, 1147, 1103 cm$^{-1}$

I-1065 $^1$H NMR(CDCl$_3$) δ 1.78(s, 3H), 1.83(s, 3H), 2.00(s, 6H), 2.19(s, 3H), 3.22(s, 3H), 4.65(d, J=6.3Hz, 2H), 5.52–5.62(m, 1H), 6.96–7.13(m, 4H), 7.24(d, J=8.7Hz, 2H), 7.38(d, J=8.7Hz, 2H)
IR(KBr) 1617, 1576, 1514, 1466, 1359, 1297, 1268, 1204, 1151, 1002 cm$^{-1}$

I-1066 $^1$H NMR(CDCl$_3$) δ 1.77(s, 3H), 1.81(s, 3H), 2.01(s, 6H), 2.18(s, 3H), 4.63(d, J=6.9Hz, 2H), 4.75(s, 1H), 5.52–5.60(m, 1H), 6.82–7.11(m, 8H)
IR(KBr) 3433, 1606, 1517, 1466, 1297, 1269, 1221, 1128, 1107, 1004 cm$^{-1}$

I-1067 $^1$H NMR(CDCl$_3$) δ:2.25(s, 3H), 2.27(s, 3H), 2.31(s, 3H), 3.20(s, 3H), 4.75(s, 1H), 6.83(d, J=8.4Hz, 1H), 7.05–7.14(m, 4H), 7.34(d, J=8.4Hz, 2H), 7.42(d, J=8.4Hz, 2H)
IR(KBr) 3494,3435, 1604, 1517, 1488, 1375, 1327, 1199, 1171, 1148, 1118 cm$^{-1}$

I-1068 $^1$H NMR(CDCl$_3$) δ 1.77(s, 3H), 1.82(s, 3H), 2.25(s, 3H), 2.28(s, 6H), 3.20(s, 3H), 4.58(d, J=6.6Hz, 2H), 5.50–5.58(m, 1H), 6.88(d, J=9.0Hz, 1H), 7.08–7.16(m, 4H), 7.34(.d, J=8.7Hz, 2H), 742(d, J 8.7Hz, 2H)
IR(KBr) 1604, 1513, 1486, 1367, 1238, 1176, 1153, 1131, 1002 cm$^{-1}$

TABLE 211

I-1069 $^1$H NMR(CDCl$_3$) δ 1.76(s, 3H), 1.81(s, 3H), 2.26(s, 3H), 2.28(s, 6H), 4.57(d, J=6.6Hz, 2H), 4.80(s, 1H), 5.50–5.58(m, 1H), 6.85–6.91(m, 3H), 7.09–7.17(m, 3H), 7.21–7.28(m, 3H)
IR(KBr) 3436, 1608, 1518, 1488, 1238, 1130, 1008 cm$^{-1}$

I-1070 $^1$H NMR(CDCl$_3$) δ:2.26(s, 3H), 2.30(s, 3H), 3.00(s, 6H), 5.19(s, 2H), 6.80(.d, J=8.7Hz, 2H), 7.02–7.16(m, 5H), 7.26(d, J=8.7Hz, 2H), 7.33–7.51(m, 5H)
IR(KBr) 1608, 1527, 1490, 1355, 1297, 1270, 1262, 1231, 1121, 1022 cm$^{-1}$

I-1071 $^1$H NMR(CDCl$_3$) δ 2.26(s, 3H), 2.30(s, 3H), 3.01(s, 6H), 5.09(s, 1H), 6.80(.d, J=8.4Hz, 2H), 7.01–7.15(m, 5H), 7.27(.d, J=8.4Hz, 2H)
IR(KBr) 3432, 1613, 1590, 1526, 1489, 1307, 1283, 1241, 1138, 1111 cm$^{-1}$

I-1072 $^1$H NMR(CDCl$_3$) δ:1.77(s, 3H), 1.81(s, 3H), 2.27(s, 3H), 2.30(s, 3H), 3.00(s, 6H), 4.63(d, J=6.6Hz, 2H), 5.51–5.59(m, 1H), 6.80(d, J=8.4Hz, 2H), 6.97–7.16(m, 5H), 7.27(d, J=8.14Hz, 2H)
IR(KBr) 1611, 1528, 1489, 1353, 1297, 1266, 1228, 1122, 1011 cm$^{-1}$

I-1073 mp 182–184° C.
$^1$H NMR(CDCl$_3$) δ 1.48(s, 3H), 1.67(s, 3H), 1.91(s, 3H), 3.46(s, 3H), 3.76(s, 3H), 3.84(s, 3H), 3.94–4.03(m, 1H), 4.05–4.59(m, 1H), 5.23–5.32(m, 1H), 5.74(br s, 1H), 6.05(s, 1H), 6.48(s, 1H), 6.93–6.99(m, 3H), 7.04–7.10(m, 3H), 7.51–7.56(m, 3H)
IR(KBr) 3400, 2934, 1625, 1523, 1396, 1227, 1119, 1077, 1036, 826, 589 cm$^{-1}$

I-1074 mp 153–154° C.
$^1$H NMR(CDCl$_3$) δ 1.74(s, 3H), 1.78(s, 3H), 2.30(s, 3H), 2.31(s, 3H), 3.75(d, J=6.6Hz, 2H), 3.86(s, 3H), 3.87(s, 3H), 5.37–5.45(m, 1H), 6.66(d, J=8.4Hz, 1H), 6.74–6.83(m,

TABLE 211-continued

5H), 6.89(dd, J=1.8, 8.1Hz, 1H), 7.14(s, 1H), 7.16(s, 1H)
IR(KBr) 3408, 3389, 3294, 3210, 2919, 2835, 1528, 1495, 1275, 1208, 1032, 856, 826 cm$^{-1}$

TABLE 212

I-1075 mp 168–171° C.
$^1$H NMR(CDCl$_3$) δ 1.74(s, 6H), 1.77(s, 6H), 2.31(s, 6H), 3.75(d, J=6.9Hz, 4H), 3.86(s, 6H), 5.37–5.45(m, 2H), 6.66(d, J=8.1Hz, 2H), 6.80(d, J=1.8Hz, 2H), 6.89(dd, J=1.8, 8.1Hz, 2H), 7.16(s, 1H)
IR(KBr) 3423, 2968, 2927, 2912, 2849, 1609, 1526, 1498, 1454, 1261, 1209, 1135, 1030, 855, 803 cm$^{-1}$

I-1076 mp 79–80° C.
$^1$H NMR(CDCl$_3$) δ 2.54(s, 3H), 3.19(s, 3H), 3.85(s, 3H), 5.17(s, 2H), 5.71(brs, 1H), 6.93(d, J=8.1Hz, 1H), 7.01–7.07(m, 3H), 7.24–7.26(m, 2H), 7.37–7.43(m, 7H), 7.66(d, J=8.7 Hz, 2H)
IR(KBr) 3466, 3029, 2939, 2937, 1610, 1520, 1482, 1365, 1246, 1201, 1175, 1150, 1073, 969, 872, 839, 804 cm$^{-1}$ I-1077 mp 151–152° C.
$^1$H NMR(CDCl$_3$) δ 4.00(s, 3H), 4.91(brs, 1H), 5.24(s, 2H), 6.89(d, J=8.2Hz, 2H), 7.00(d, J=8.0Hz, 1H), 7.12–7.47(m, 10H), 7.71(d, J=7.4Hz, 1H), 7.89(s, 1H)
IR(KBr) 3422, 1612, 1526, 1491, 1454, 1329, 1287, 1269, 1248, 1171, 1136, 1103, 1019, 827 cm$^{-1}$ I-1078 mp 173–174° C.
$^1$H NMR(CDCl$_3$) δ 3.13(s, 3H), 4.92(brs, 1H), 5.19(s, 2H), 6.88(d, J=8.6Hz, 2H), 7.15–7.26(m, 4H), 7.35–7.59(m, 7H), 7.69(d, J=9.4Hz, 1H), 7.86(s, 1H)
IR(KBr) 3426, 1613, 1527, 1489, 1435, 1361, 1330, 1294, 1243, 1164, 1118, 1070, 978, 821 cm$^{-1}$ I-1079 mp 168–169° C.
$^1$H NMR(CDCl$_3$) δ 3.20(s, 3H), 3.99(s, 3H), 5.22(s, 2H), 6.89(d, J=8.8Hz, 1H), 7.11–7.15(m, 2H), 7.31–7.49(m, 10H), 7.73(d, J=7.4Hz, 1H), 7.90(s, 1H)
IR(KBr) 3434, 1603, 1524, 1488, 1369, 1335, 1244, 1178, 1143, 1119, 1006, 871 cm$^{-1}$

TABLE 213

I-1080 mp 68–69° C.
$^1$H NMR(CDCl$_3$) δ 3.13(s, 3H), 3.19(s, 3H), 5.19(s, 2H), 7.18(d, J=8.6Hz, 2H), 7.26–7.59(m, 11H), 7.73(d, J=9.2 Hz, 1H), 7.89(s, 1H)
IR(KBr) 3431, 3034, 2938, 1613, 1524, 1487, 1367, 1330, 1293, 1242, 1175, 1151, 1118, 970, 872, 828 cm$^{-1}$

I-1081 $^1$H NMR(CDCl$_3$) δ 1.78(s, 3H), 1.84(s, 3H), 3.51(s, 3H), 4.64(d, J=5.6Hz, 2H), 5.08(brs, 2H), 5.49–5.54(m, 1H), 5.75(brs, 1H), 5.85(brs, 1H), 6.14(s, 1H), 6.89–7.12(m, 5H), 7.53(d, J=8.4Hz, 2H)
IR(KBr) 3444, 2934, 1612, 1523, 1485, 1403, 1360, 1251, 1172, 1006, 971, 837, 527 cm$^{-1}$ I-1082 mp 71–72° C.
$^1$H NMR(CDCl$_3$) δ 2.46(s, 3H), 3.20(s, 3H), 3.86(s, 3H), 3.91(s, 3H), 5.21(s, 2H), 6.87–7.03(m, 3H), 7.11(s, 1H), 7.24–7.41(m, 8H), 7.67(d, J=8.8Hz, 2H)
IR(KBr) 3434, 3028, 2936, 1609, 1521, 1482, 1365, 1239, 1176, 1074, 969, 869, 804 cm$^{-1}$ I-1083 mp 73–74° C.
$^1$H NMR(CDCl$_3$) δ 2.66(s, 3H), 3.13(s, 3H), 3.20(s, 3H), 3.86(s, 3H), 5.19(s, 2H), 7.08(d, J=1.6Hz, 1H), 7.16(d, J=8.4Hz, 1H), 7.21–7.28(m, 2H), 7.37–7.42(m, 8H), 7.66(d, J=8.4Hz, 2H)
IR(KBr) 3432, 3031, 2938, 1610, 1523, 1480, 1365, 1176, 1151, 1074, 970, 875, 807, 524 cm$^{-1}$ I-1084 mp 110–111° C.
$^1$H NMR(CDCl$_3$) δ 1.78(s, 3H), 1.81(s, 3H), 3.21(s, 3H), 3.98(s, 3H), 4.67(d, J=6.6Hz, 2H), 5.57(t, J=6.8Hz, 1H),

TABLE 213-continued 7.01(d, J=8.0Hz, 1H), 7.15–7.21(m, 2H), 7.28–7.45(m, 4H), 7.76(d, J=7.6Hz, 1H), 7.93(s, 1H), 8.03(s, 1H)
IR(KBr) 3434, 3010, 2931, 1524, 1488, 1368, 1336, 1247, 1173, 1149, 1121, 1007, 871, 562 cm$^{-1}$

TABLE 214

I-1085 mp 147–148° C.
$^1$H NMR(CDCl$_3$) δ 1.76(s, 3H), 1.79(s, 3H), 3.96(s, 3H), 4.65(d, J=6.3Hz, 2H), 4.91(brs, 1H), 5.55(t, J=5.7Hz, 1H), 6.88(d, J=8.1Hz, 2H), 6.99(d, J=8.4Hz, 1H), 7.12–7.26(m, 4H), 7.36(d, J=8.1Hz, 1H), 7.89(s, 1H)
IR(KBr) 3450, 2938, 1612, 1524, 1490, 1436, 1340, 1264, 1230, 1212, 1139, 1123, 984, 835 cm$^{-1}$ I-1086 mp 134–135° C.
$^1$H NMR(CDCl$_3$) δ 1.77(s, 3H), 1.82(s, 3H), 4.64(d, J=6.6Hz, 2H), 4.84(brs, 1H), 5.52(t, J=7.2Hz, 1H), 5.77(s, 1H), 6.87(d, J=8.7Hz, 1H), 6.96(d, J=8.4Hz, 1H), 7.12(dd, J=2.4, 8.7Hz, 1H), 7.35(d, J=8.1Hz, 1H), 7.70(d, J=8.4Hz, 1H), 7.89(s, 1H)
IR(KBr) 3367, 1610, 1489, 1442, 1333, 1265, 1193, 1165, 1124, 834, 805 cm$^{-1}$ I-1087 mp 156–157° C.
$^1$H NMR(CDCl$_3$) δ 1.78(s, 3H), 1.81(s, 3H), 3.82(s, 3H), 3.89(s, 3H), 4.65(d, J=6.2Hz, 2H), 4.95(brs, 1H), 5.22(brs, 1H), 5.58(t, J=6.0Hz, 1H), 6.73(s, 1H), 6.87–7.00(m, 6H), 7.53(d, J=8.4Hz, 2H)
IR(KBr) 3394, 2934, 1610, 1526, 1499, 1455, 1402, 1240, 1221, 1139, 1099, 894, 815 cm$^{-1}$ I-1088 mp 69–70° C.
$^1$H NMR(CDCl$_3$) δ 1.77(s, 3H), 1.83(s, 3H), 3.80(s, 3H), 4.63(d, J=7.0Hz, 2H), 4.93(brs, 1H), 5.22(brs, 1H), 5.52(t, J=7.0Hz, 1H), 5.78(brs, 1H), 6.70(d, J=1.6Hz, 1H), 6.83–7.01(m, 6H), 7.51(d, J=8.8Hz, 2H)
IR(KBr) 3411, 2933, 1611, 1526, 1492, 1453, 1263, 1242, 1220, 1190, 1172, 1096, 907, 822 cm$^{-1}$ I-1089 mp 160–161° C.
$^1$H NMR(CDCl$_3$) δ 1.39(d, J=6.0Hz, 6H), 2.40(s, 3H), 3.21(s, 3H), 3.55(s, 3H), 3.77(s, 3H), 4.55(m, 1H), 5.20(s, 2H), 6.83(s, 1H), 6.93(dd, J=1.8, 8.1Hz, 1H), 7.01(d, J=8.1Hz, 1H), 7.01(d, J=1.8Hz, 1H), 7.28–7.48(m, 7H), 7.66–7.72(m, 2H)
IR(KBr) 1515, 1480, 1463, 1391, 1363, 1239, 1192, 1176, 1149, 1082, 1018, 962, 873, 800 cm$^{-1}$

TABLE 215

I-1090 mp 154–155° C.
$^1$H NMR(CDCl$_3$) δ 2.59(s, 3H), 3.21(s, 3H), 3.54(s, 3H), 3.77(s, 3H), 5.23(s, 2H), 6.84(s, 1H), 7.06(d, J=8.4Hz, 1H), 7.24–7.50(m, 9H), 7.65–7.71(m, 2H)
IR(KBr) 1513, 1479, 1365, 1267, 1232, 1178, 1150, 1079, 971, 959, 875, 797 cm$^{-1}$

I-1091 mp 137–138° C.
$^1$H NMR(CDCl$_3$) δ 1.38(d, J=6.3Hz, 6H), 3.46(s, 3H), 3.74(s, 3H), 4.54(m, 1H), 4.96(s, 1H), 5.17(s, 2H), 5.92(s, 1H), 6.45(s, 1H), 6.89–6.94(m, 3H), 7.00–7.11(m, 3H), 7.27–7.41(m, 3H), 7.45–7.56(m, 4H)
IR(KBr) 3443, 3356, 1611, 1521, 1488, 1458, 1393, 1269, 1236, 1138, 1112, 1074, 1013, 830, 743 cm$^{-1}$

I-1092 mp 75–76° C.
$^1$H NMR(CDCl$_3$) δ 1.37(d, J=5.8Hz, 6H), 1.75(s, 3H), 1.79(s, 3H), 2.53(s, 3H), 3.21(s, 3H), 3.56(s, 3H), 3.78(s, 3H), 4.51(m, 1H), 4.61(d, J=6.6Hz, 2H), 5.52(m, 1H), 6.84(s, 1H), 6.96–7.02(m, 3H), 7.34–7.42(m, 2H), 7.65–7.74(m, 2H)
IR(KBr) 1516, 1480, 1449, 1360, 1332, 1240, 1199, 1177, 1152, 1083, 964, 873, 797 cm$^{-1}$

I-1093 mp 119–120° C.
$^1$H NMR(CDCl$_3$) δ 1.37(d, J=6.3Hz, 6H), 1.73(s, 3H), 1.77(d, J=0.9Hz, 3H), 3.46(s, 3H), 3.75(s, 3H), 4.51(m, 1H), 4.61(d, J=6.6Hz, 2H), 5.14(s, 1H), 5.54(m, 1H), 5.93(s, 1H), 6.46(s, 1H), 6.89–6.95(m, 2H), 6.98(d, J=8.1Hz, 1H), 7.01–7.07(m, 2H), 7.50–7.56(m, 2H)
IR(KBr) 3426, 1610, 1522, 1488, 1455, 1402, 1267, 1237, 1174, 1135, 1112, 1079, 1020 cm$^{-1}$

I-1094 mp 150–151° C.
$^1$H NMR(CDCl$_3$) δ 3.44(s, 3H), 3.75(s, 3H), 4.90(s, 1H), 5.20(s, 2H), 5.99(s, 1H), 6.44(s, 1H), 6.88–6.95(m, 2H), 7.04(d, J=8.4Hz, 1H), 7.29–7.44(m, 4H), 7.47–7.56(m, 5H)
IR(KBr) 3410, 1610, 1519, 1484, 1463, 1455, 1410, 1382, 1359, 1285, 1264, 1229, 1118, 1074, 1060, 1014, 995 cm$^{-1}$

I-1095 $^1$H NMR(CDCl$_3$) δ 0.96(s, 3H), 0.98(s, 3H), 1.53–1.82(m, 3H), 2.99(s, 6H), 3.20(t, J=7.2Hz, 2H), 3.78(s, 3H), 3.79(s, 3H), 3.87(br, 1H), 6.71–6.83(m, 3H), 6.92(s, 1H), 6.94(s 1H), 7.23–7.31(m, 2H), 7.47–7.52(m, 2H)

TABLE 216

I-1096 mp 87–89° C.
$^1$H NMR(CDCl$_3$) δ 1.70(s, 3H), 1.75(s, 3H), 2.82(s, 3H), 3.00(s, 3H), 3.74–3.80(m, 2H), 3.78(s, 3H), 3.80(s, 3H), 5.29–5.34(m, 1H), 6.79–6.83(m, 2H), 6.92–6.97(m, 3H), 7.25–7.34(m, 2H), 7.47–7.52(m, 2H)
IR(KBr) 3600–2800(br), 1613, 1531, 1495, 1460, 1448, 1380, 1359, 1253, 1210, 1057, 1036 cm$^{-1}$

I-1097 mp 167–169° C.
$^1$H NMR(CDCl$_3$) δ 2.92(s, 3H), 3.00(s, 6H), 3.78(s, 3H), 3.79(s, 3H), 4.02(br, 1H), 6.71–6.83(m, 3H), 6.92(s, 1H), 6.95(s, 1H), 7.25–7.32(m, 2H), 7.47–7.52(m, 2H)
IR(KBr) 3600–2800(br), 1625, 1613, 1533, 1497, 1462, 1445, 1381, 1358, 1328, 1262, 1205, 1163, 1051, 1031 cm$^{-1}$

I-1098 mp 114–115° C.
$^1$H NMR(CDCl$_3$) δ 2.27(s, 6H), 2.54(s, 3H), 5.19(s, 2H), 7.00–7.16(m, 5H), 7.26–7.51(m, 9H)
IR(KBr) 1519, 1501, 1483, 1454, 1310, 1295, 1263, 1232, 1123, 998, 744 cm$^{-1}$

I-1099 mp 68–69° C.
$^1$H NMR(CDCl$_3$) δ 1.62(br s, 1H), 1.77(s, 3H), 1.82(s, 3H), 2.27(s, 3H), 2.28(s, 3H), 4.64(d, J=6.8Hz, 2H), 4.76(s, 2H), 5.56(m, 1H), 7.00–7.16(m, 5H), 7.33–7.48(m, 4H)
IR(KBr) 3433, 1522, 1490, 1384, 1311, 1296, 1266, 1232, 1194, 1122, 1025, 1013, 992, 841, 818 cm$^{-1}$

I-1100 mp 68–69° C.
$^1$H NMR(CDCl$_3$) δ 1.62(br s, 1H), 1.77(s, 3H), 1.82(s, 3H), 2.27(s, 3H), 2.28(s, 3H), 4.64(d, J=6.8Hz, 2H), 4.76(s, 2H), 5.56(m, 1H), 7.00–7.16(m, 5H), 7.33–7.48(m, 4H)
IR(KBr) 3433, 1522, 1490, 1384, 1311, 1296, 1266, 1232, 1194, 1122, 1025, 1013, 992, 841, 818 cm$^{-1}$

TABLE 217

I-1101 mp 171° C.
$^1$H NMR(CDCl$_3$) δ 1.77(s, 3H), 1.81(d, J=0.9Hz, 3H), 2.68(s, 3H), 3.21(s, 3H), 3.55(s, 3H), 3.78(s, 3H), 4.65(d, J=6.6Hz, 2H), 5.53(m, 1H), 6.84(s, 1H), 7.03(d, J=8.7Hz, 1H), 7.29(dd, J=2.1, 8.7Hz, 1H), 7.36–7.41(m, 2H), 7.46(d, J=2.1Hz, 1H), 7.66–7.72(m, 2H)
IR(KBr) 1510, 1477, 1376, 1358, 1349, 1294, 1237, 1196, 1173, 1145, 1077, 1004, 958, 861, 801 cm$^{-1}$

I-1102 mp 168–169° C.
$^1$H NMR(CDCl$_3$) δ 1.76(d, J=0.3Hz, 3H), 1.80(d, J=0.9Hz, 3H), 3.44(s, 3H), 3.75(s, 3H), 4.64(d, J=6.6Hz, 2H), 4.97(s, 1H), 5.55(m, 1H), 6.00(s, 1H), 6.45(s, 1H), 6.89–6.95(m, 2H), 7.01(d, J=8.4Hz, 1H), 7.33(dd, J=2.1, 8.4Hz, 1H), 7.51(d, J=2.1Hz, 1H), 7.51–7.56(m, 2H)
IR(KBr) 3396, 1613, 1521, 1485, 1467, 1440, 1408, 1384, 1357, 1286, 1264, 1229, 1116, 1076, 1056, 993, 834 cm$^{-1}$

TABLE 217-continued

I-1103 mp 176–177° C.
$^1$H NMR(CDCl$_3$) δ 1.77(s, 3H), 1.80(s, 3H), 2.09(s, 3H), 2.16(s, 3H), 3.87(s, 3H), 4.65(d, J=7.2Hz, 2H), 4.78 (br s, 1H), 5.06(s, 1H), 5.40–5.60(m.1H), 6.76(s, 1H), 6.82–6.91(m, 4H), 7.02(d, J=7.8Hz, 1H), 7.22–7.27 (m, 2H)
IR(CHCl$_3$) 3597, 3533, 3026, 3010, 2921, 1731, 1612, 1520, 1488, 1240, 1172 cm$^{-1}$

I-1104 mp 185–186° C.
$^1$H NMR(CDCl$_3$) δ 1.78(s, 3H), 1.82(s, 3H), 2.06(s, 3H), 2.15(s, 3H), 4.66(d, J=6.9Hz, 2H), 4.71(s, 1H), 4.89 (s, 1H), 5.53–5.58(m, 1H), 6.75(s, 1H), 6.86–6.91(m, 2H), 6.90–7.00(m, 3H), 7.21–7.26(m, 2H)
IR(CHCl$_3$) 3691, 3598, 3546, 3068, 2922, 1674, 1613, 1520, 1488, 1298, 1262, 1165 cm$^{-1}$

I-1105 mp 143–144° C.
$^1$H NMR(CDCl$_3$) δ 2.48(s, 3H), 3.21(s, 3H), 3.52(s, 3H), 3.67(d, J=1.2Hz, 3H), 3.92(s, 3H), 5.23(s, 2H), 6.92–7.02(m, 3H), 7.31–7.48(m, 7H), 7.60(dd, J=8.7, 1.5Hz, 2H)
IR(KBr) 1519, 1470, 1370, 1256, 1173, 1152, 1029, 872 cm$^{-1}$

TABLE 218

I-1106 mp 128–130° C.
$^1$H NMR(CDCl$_3$) δ 1.76(s, 3H), 1.80(s, 3H), 2.59(s, 3H), 3.21(s, 3H), 3.53(s, 3H), 3.67(d, J=0.9Hz, 3H), 3.90(s, 3H), 4.64(d, J=6.9Hz, 2H), 5.55(t, J=6.9Hz, 1H), 6.97–7.00(m, 3H), 7.41(d, J=8.8Hz, 2H), 7.60(dd, J=8.8, 1.1 Hz, 2H)
IR(KBr) 1519, 1361, 1258, 1175, 1148, 1041, 978, 874 cm$^{-1}$

I-117 mp 168–170° C.
$^1$H NMR(CDCl$_3$) δ 1.76(s, 3H), 1.79(s, 3H), 3.43(s, 3H), 3.63(d, J=0.9Hz, 3H), 3.89(s, 3H), 4.65(d, J=6.8Hz, 2H), 5.01(s, 1H), 5.57(t, J=6.8Hz, 1H), 5.65(s, 1H), 6.90–7.06(m, 5H), 7.43(dd, J=8.7, 1.5Hz, 2H)
IR(KBr) 3433, 1523, 1464, 1397, 1253, 1216, 1038, 977, 838, 814 cm$^{-1}$

I-1108 mp 127–128° C.
$^1$H NMR(CDCl$_3$) δ 2.25(s, 3H), 2.27(s, 3H), 3.20(s, 3H), 5.22(s, 2H), 7.02(d, J=8.4Hz, 1H), 7.10(s, 1H), 7.11 (s, 1H), 7.18(dd, J=2.1, 8.4Hz, 1H), 7.31–7.54(m, 10H)
IR(KBr) 1513, 1484, 1369, 1284, 1243, 1175, 1150, 1061, 984, 968, 868, 847, 791, 718 cm$^{-1}$

I-1109 mp 161–162° C.
$^1$H NMR(CDCl$_3$) δ 2.26(s, 3H), 2.28(s, 3H), 5.16(s, 2H), 5.19(s, 2H), 5.70(br s, 1H), 6.82(dd, J=2.1, 8.4Hz, 1H), 6.96–7.16(m, 7H), 7.31–7.51(m, 10H)
IR(KBr) 3449, 1521, 1492, 1470, 1455, 1394, 1294, 1279, 1247, 1232, 1199, 1185, 1129, 1013, 740, 695 cm$^{-1}$

I-110 mp 133–134° C.
$^1$H NMR(CDCl$_3$) δ 2.26(s, 6H), 4.80(br s, 1H), 5.21(s, 2H), 6.85–6.93(m, 2H), 7.02(d, J=8.4Hz, 1H), 7.09(s, 1H), 7.17(s, 1H), 7.15–7.52(m, 9H)
IR(KBr) 3350, 1601, 1519, 1485, 1453, 1387, 1289, 1255, 1169, 1060, 839, 813, 731 cm$^{-1}$

TABLE 219

I-1111 mp 83–84° C.
$^1$H NMR(CDCl$_3$) δ 1.78(d, J=0.3Hz, 3H), 1.82(d, J=0.9 Hz, 3H), 2.26(s, 3H), 2.27(s, 3H), 3.20(s, 3H), 4.65(d, J=6.6Hz, 2H), 5.55(m, 1H), 6.99(d, J=8.4Hz, 1H), 7.11 (s, 1H), 7.12(s, 1H), 7.19(dd, J=2.1, 8.4Hz, 1H), 7.38(d, J=2.1Hz, 1H), 7.32–7.43(m, 4H)
IR(KBr) 1514, 1485, 1364, 1286, 1253, 1197, 1178, 1156, 1057, 976, 882, 851 cm$^{-1}$

I-1112 mp 86–87° C.
$^1$H NMR(CDCl$_3$) δ 1.77(d, J=0.6Hz, 3H), 1.82(d, J=0.9 Hz, 3H), 2.27(s, 6H), 4.65(d, J=6.6Hz, 2H), 5.00(s, 1H), 5.55(m, 1H), 6.86–6.92(m, 2H), 6.98(d, J=8.4Hz, 1H), 7.10(s, 1H), 7.11(s, 1H), 7.20(dd, J=2.1, 8.4Hz, 1H), 7.22–7.26(m, 2H), 7.38(d, J=2.1Hz, 1H)
IR(KBr) 3339, 1608, 1530, 1492, 1429, 1362, 1288, 1258, 1232, 1213, 1189, 1112, 889, 783 cm$^{-1}$

I-1113 amorphous
$^1$H NMR(CDCl$_3$) δ 1.76(s, 3H), 3.32(s, 6H), 3.44(s, 3H), 3.74(s, 3H), 5.23(s, 2H), 7.02(s, 1H), 7.14–7.20(m, 2H), 7.28(d, J=8.7Hz, 1H), 7.32–7.55(m, 7H), 7.72(d, J=8.4 Hz, 2H), 9.22(s, 1H),
IR(KBr) 3382, 1684, 1518, 1469, 1365, 1237, 1150, 1017, 972, 872, 815 cm$^{-1}$ I-1114 mp 173–175° C.
$^1$H NMR(CDCl$_3$) δ 1.76(s, 3H), 1.81(s, 3H), 1.97(s, 3H), 3.19(s, 6H), 3.21(s, 3H), 3.37(s, 3H), 3.75(s, 3H), 4.62(d, J=6.9Hz, 2H), 5.50(t, J=6.9Hz, 1H), 6.85(m, 2H), 7.06 (d, J=8.4Hz, 1H), 7.25(m, 1H), 7.37(br s, 1H), 7.66(d, J=8.7Hz, 2H)
IR(KBr) 3421, 1518, 1470, 1366, 115, 1107, 970, 814 cm$^{-1}$

TABLE 220

I-1115 mp 96–98° C.
$^1$H NMR(DMSO-d$_6$) δ 1.72(s, 3H), 1.77(s, 3H), 3.27(s, 3H), 3.59(s, 3H), 4.21(s, 2H), 4.55(d, J=6.3Hz, 2H), 5.50 (t, J=6.3Hz, 1H), 6.17(s, 1H), 6.59(dd, J=8.1, 1.8Hz, 1H), 6.66(d, J=1.8Hz, 1H), 6.82(d, J=8.7Hz, 2H), 6.97 (d, J=8.1Hz, 1H), 7.42(d, J=8.7Hz, 2H), 8.89(br s, 1H), 9.45(br s, 1H)
IR(KBr) 3431, 3396, 3319, 1611, 1521, 1486, 1264, 1172, 1111, 987, 826 cm$^{-1}$

I-1116 mp 186–188° C.
$^1$H NMR(DMSO-d$_6$) δ 1.72(s, 3H), 1.76(s, 6H), 3.28(s, 3H), 3.68(s, 3H), 4.54(d, J=6.6Hz, 2H), 5.48(t, J=6.6 Hz, 1H), 6.53–6.58(m, 1H), 6.65(d, J=1.8Hz, 1H), 6.83–6.89(m, 4H), 7.43(d, J=8.4Hz, 2H), 8.73(br s, 1H), 8.96 (br s, 1H), 9.53(br s, 1H)
IR(KBr) 3429, 1652, 1611, 1519, 1474, 1250, 1080, 1018, 981, 836 cm$^{-1}$

I-1117 mp 210–213° C.
$^1$H NMR(CDCl$_3$) δ 3.48(s, 3H), 3.77(s, 3H), 5.16(s, 2H), 5.71(s, 1H), 5.85(s, 1H), 6.48(s, 1H), 6.95(dd, J=8.4, 2.1 Hz, 1H), 7.04(d, J=8.4Hz, 1H), 7.07(d, J=2.1Hz, 1H), 7.40–7.48(m, 5H), 7.83(d, J=9.0Hz, 2H), 8.32(d, J=9.0 Hz, 2H)
IR(KBr) 3499, 1511, 1343, 1284, 1247, 1195, 1109, 1070, 1013 cm$^{-1}$

I-1118 mp 156–158° C.
$^1$H NMR(CDCl$_3$) δ 2.67(s, 3H), 3.14(s, 3H), 3.56(s, 3H), 3.80(s, 3H), 5.20(s, 2H), 6.87(s, 1H), 7.16(d, J=8.7Hz, 1H), 7.32–7.48(m, 7H), 7.82(d, J=9.2Hz, 2H), 8.32(d, J=9.2Hz, 2H)
IR(KBr) 1518, 1479, 1350, 1177, 1119, 1079, 947, 816 cm$^{-1}$

I-1119 mp 173–175° C.
$^1$H NMR(CDCl$_3$) δ 1.77(s, 3H), 1.81(s, 3H), 2.71(s, 3H), 3.24(s, 3H), 3.57(s, 3H), 3.80(s, 3H), 4.64(d, J=6.7Hz, 2H), 5.50(t, J=6.7Hz, 1H), 6.87(s, 1H), 7.10(d, J=8.4 Hz, 1H), 7.35(d, J=8.4, 2.1Hz, 1H), 7.39(d, J=2.0Hz, 1H), 7.82(d, J=9.0Hz, 2H), 8.32(d, J=9.0Hz, 2H)
IR(KBr) 1519, 1479, 1360, 1178, 1075, 946, 850, 799 cm$^{-1}$

TABLE 221

I-1120 mp 191–193° C.
$^1$H NMR(CDCl$_3$) δ 1.77(s, 3H), 1.82(s, 3H), 3.48(s, 3H), 3.77(s, 3H), 4.63(d, J=6.6Hz, 2H), 5.53(t, J=6.6Hz, 1H), 5.72(s, 1H), 5.83(s, 1H), 6.48(s, 1H), 6.93(dd, J=8.1, 1.8Hz, 1H), 6.98(d, J=8.1Hz, 1H), 7.04(d, J=1.8 Hz, 1H), 7.83(d, J=9.0Hz, 2H), 8.32(d, J=9.0Hz, 2H)
IR(KBr) 3492, 1588, 1511, 1482, 1345, 1283, 1244, 1116, 1069, 1010 cm$^{-1}$

TABLE 221-continued

I-1121 mp 135–138° C.
$^1$H NMR(CDCl$_3$) δ 1.76(s, 3H), 1.82(s, 3H), 3.61(s, 3H), 3.67(s, 3H), 3.73(s, 3H), 4.62(d, J=6.9Hz, 2H), 5.00(br. s, 1H), 5.50–5.57(m, 1H), 5.69(br. s, 1H), 6.65(s, 1H), 6.86–6.96(m, 4H), 7.00(d, J=1.8Hz, 1H), 7.48(d, J=8.4 Hz, 2H)
IR(KBr) 3428, 2938, 1680, 1613, 1594, 1520, 1479, 1460, 1393, 1260, 1226, 1104, 1081, 993, 834 cm$^{-1}$

I-1122 mp 140–142° C.
$^1$H NMR(CDCl$_3$) δ 1.78(s, 3H), 1.82(s, 3H), 2.34(s, 3H), 4.65–4.67(d, J=6.9Hz, 2H), 5.55(m, 1H), 6.41–6.78(dt, J F–H=54.6, 3.3Hz, 2H), 7.05–7.25(m, 5H), 7.26–7.45(m, 2H), 7.75(m, 2H)
IR(CHCl$_3$) 1752, 1523, 1493, 1435, 1385, 1301, 1272, 1169, 1132, 1070, 1037, 916, 889 cm$^{-1}$

I-1123 mp 178–180° C.
$^1$H NMR(CDCl$_3$) δ 1.75(s, 3H), 1.78–1.79(d, J=0.6Hz, 3H), 2.13(s, 3H), 3.50(s, 3H), 3.87(s, 3H), 4.63–4.65(d, J=6.6Hz, 2H), 5.00(br, 1H), 5.57(m, 1H), 5.75(s, 1H), 6.79(s, 1H), 6.84–7.00(m, 5H), 7.50–7.53(m, 2H)
IR(CHCl$_3$) 3596, 3528, 2937, 1612, 1584, 1522, 1489, 1454, 1400, 1259, 1173, 1139, 1102, 1009, 930, 865, 835 cm$^{-1}$

I-1124 mp 173–174° C.
$^1$H NMR(CDCl$_3$) δ 3.03(s, 6H), 3.54(s, 3H), 3.76(s, 3H), 3.91(s, 3H), 5.22(s, 2H), 6.80–6.99(m, 6H), 7.28–7.58(m, 7H)
IR(CHCl$_3$) 2938, 1731, 1609, 1527, 1485, 1442, 1394, 1365, 1174, 1141, 1082, 1037, 1013, 961, 936, 863 cm$^{-1}$

TABLE 222

I-1125 mp 103–106° C.
$^1$H NMR(CDCl$_3$) δ 1.78(s, 3H), 1.82–1.83(d, J=0.9Hz, 3H), 4.65–4.67(d, J=6.9Hz, 2H), 5.55(m, 1H), 6.41–6.78(td, J F–H=54.9, 2.7Hz, 2H), 6.94–7.31(m, 7H), 7.73(m, 2H)
IR(CHCl$_3$) 3592, 1612, 1525, 1495, 1385, 1301, 1263, 1187, 1173, 1132, 1069, 1036, 917, 889, 838 cm$^{-1}$

I-1126 mp 153–155° C.
$^1$H NMR(CDCl$_3$) δ 1.75(s, 3H), 1.78–1.79(d, J=0.9Hz, 3H), 2.58(s, 3H), 3.03(s, 6H), 3.55(s, 3H), 3.77(s, 3H), 3.88(s, 3H), 4.61–4.64(d, J=6.9Hz, 2H), 5.54(m, 1H), 6.80–6.97(m, 6H), 7.54–7.57(d, J=8.7Hz, 2H)
IR(CHCl$_3$) 2938, 1609, 1527, 1485, 1464, 1442, 1392, 1365, 1174, 1140, 1082, 1038, 1012, 961, 935 cm$^{-1}$

I-1127 mp 160–161° C.
$^1$H NMR(CDCl$_3$) δ 2.12(s, 3H), 3.49(s, 3H), 3.89(s, 3H), 4.89(br, 1H), 5.21(s, 2H), 5.76(s, 1H), 6.79–6.92(m, 5H), 7.00(d, J=8.4Hz, 1H), 7.31–7.53(m, 7H)
IR(CHCl$_3$) 3594, 3517, 2937, 1731, 1612, 1589, 1522, 1489, 1455, 1400, 1327, 1259, 1240, 1173, 1139, 1102, 1011, 930, 865, 835 cm$^{-1}$

I-1128 mp 149–150° C.
$^1$H NMR(CDCl$_3$) δ 1.74–1.75(d, J=0.9Hz, 3H), 1.78–1.79(d, J=0.9Hz, 3H), 3.03(s, 6H), 3.49(s, 3H), 3.75(s, 3H), 3.88 s, 3H), 4.62–4.64(d, J=6.6Hz, 2H), 5.57(m, 1H), 5.95(s, 1H), 6.49(s, 1H), 6.81–6.84(m, 2H), 6.95–7.03(m, 3H), 7.55–7.58(m, 2H)
IR(CHCl$_3$) 3509, 2937, 1675, 1610, 1584, 1528, 1492, 1464, 1397, 1362, 1323, 1197, 1175, 1140, 1117, 1078, 1038, 1011, 929, 835 cm$^{-1}$

I-1129 mp 163–165° C.
$^1$H NMR(CDCl$_3$) δ 2.15(s, 3H), 2.47(s, 3H), 3.20(s, 3H), 3.55(s, 3H), 3.90(s, 3H), 5.22(s, 2H), 6.80(dd, J=8.4, 2.1 Hz, 1H), 6.88(d, J=2.1Hz, 1H), 7.00(d, J=8.4Hz, 1H), 7.17(s, 1H), 7.35–7.47(m, 7H), 7.66–7.69(m, 2H)
IR(CHCl$_3$) 2938, 1604, 1584, 1518, 1478, 1370, 1331, 1241, 1176, 1150, 1010, 987, 937, 872, 846 cm$^{-1}$

TABLE 223

I-1130 mp 142–144° C.
$^1$H NMR(CDCl$_3$) δ 1.76–1.77(d, J=0.9Hz, 3H), 1.79–1.80(d, J=0.9Hz, 3H), 2.16(s, 3H), 2.60(s, 3H), 3.20(s, 3H), 3.57(s, 3H), 3.88(s, 3H), 4.62–4.65(d, J=6.6Hz, 2H), 5.55(m, 1H), 6.83–6.87(m, 2H), 7.00(d, J=8.4Hz, 1H), 7.18(s, 1H), 7.35–7.38(m, 2H), 7.67–7.70(m, 2H)
IR(CHCl$_3$) 1604, 1582, 1517, 1478, 1416, 1370, 1332, 1240, 1176, 1150, 1093, 1008, 987, 936, 872 cm$^{-1}$

I-1131 mp 121–123° C.
$^1$H NMR(DMSO-d$_6$) δ 1.70(s, 3H), 1.71(s, 3H), 3.71–3.75(m, 4H), 3.75(s, 6H), 5.21–5.27(m, 2H), 5.54–5.59(m, 2H), 6.65–6.71(m, 2H), 6.95(s, 2H), 7.19–7.29(m, 4H)
IR(KBr) 3600–2800(br), 1627, 1536, 1497, 1470, 1454, 1375, 1341, 1257, 1208, 1125, 1053, 1035 cm$^{-1}$

I-1132 mp 169–170° C.
$^1$H NMR(CDCl$_3$) δ 1.77(d, J=0.6Hz, 3H), 1.81(d, J=0.9 Hz, 3H), 2.26(s, 6H), 4.63(d, J=6.6Hz, 2H), 5.31(s, 1H), 5.34(s, 1H), 5.55(m, 1H), 6.80(dd, J=2.1, 8.1Hz, 1H), 6.89(d, J=2.1Hz, 1H), 6.92(d, J=8.1Hz, 1H), 6.98–7.13(m, 5H)
IR(KBr) 3338, 1619, 1595, 1523, 1492, 1475, 1451, 1427, 1385, 1357, 1309, 1298, 1270, 1223, 1193, 1172, 1122, 1113, 999, 983, 871, 819, 785 cm$^{-1}$

I-1133 mp 135–136° C.
$^1$H NMR(CDCl$_3$) δ 1.14(t, J=6.9Hz, 3H), 2.42(s, 3H), 3.20(s, 3H), 3.73(q, J=6.9Hz, 2H), 3.77(s, 3H), 3.91(s, 3H), 5.22(s, 2H), 6.84(s, 1H), 6.91(dd, J=1.8, 8.4Hz, 1H), 6.98(d, J=8.4Hz, 1H), 7.00(d, J=1.8Hz, 1H), 7.28–7.47(m, 7H), 7.68–7.73(m, 2H)
IR(KBr) 1516, 1481, 1381, 1363, 1332, 1238, 1228, 1175, 1147, 1080, 1036, 865, 843, 800 cm$^{-1}$

TABLE 224

I-1134 mp 154–155° C.
$^1$H NMR(CDCl$_3$) δ 1.15(t, J=7.2Hz, 3H), 1.75(d, J=0.9 Hz, 3H), 1.79(d, J=0.9Hz, 3H), 2.54(s, 3H), 3.21(s, 3H), 3.72(q, J=7.2Hz, 2H), 3.78(s, 3H), 3.88(s, 3H), 4.63(d, J=6.9Hz, 2H), 5.54(m, 1H), 6.85(s, 1H), 6.95–6.98(m, 3H), 7.34–7.40(m, 2H), 7.68–7.74(m, 2H)
IR(KBr) 1519, 1481, 1467, 1365, 1335, 1245, 1231, 1184, 1157, 1081, 1038, 972, 889, 872, 840, 800 cm$^{-1}$

I-1135 mp 136–137° C.
$^1$H NMR(CDCl$_3$) δ 1.16(t, J=6.9Hz, 3H), 1.74(s, 3H), 1.78(s, 3H), 3.61(q, J=6.9Hz, 2H), 3.75(s, 3H), 3.88(s, 3H), 4.63(d, J=6.9Hz, 2H), 5.03(s, 1H), 5.57(m, 1H), 5.99(s, 1H), 6.46(s, 1H), 6.89–6.94(m, 2H), 6.97(d, J=8.7Hz, 1H), 7.01(d, J=1.8Hz, 1H), 7.02(dd, J=1.8, 8.7Hz, 1H), 7.51–7.57(m, 2H)
IR(KBr) 3433, 1613, 1522, 1489, 1464, 1443, 1402, 1383, 1364, 1270, 1235, 1214, 1174, 1140, 1113, 1072, 1036, 983, 825 cm$^{-1}$

I-1136 mp 155–157° C.
$^1$H NMR(CDCl$_3$) δ 2.05(t, J=2.7Hz, 1H), 2.76(dt, J=6.3, 2.7Hz, 2H), 2.77(s, 3H), 3.21(s, 3H), 3.28(s, 3H), 3.56(s, 3H), 3.78(s, 3H), 4.23(t, J=6.3Hz, 2H), 6.84(s, 1H), 7.09(d, J=8.4Hz, 1H), 7.36(dd, J=8.4, 2.1Hz, 1H), 7.38(d, J=8.7Hz, 2H), 7.41(d, J=2.1Hz, 1H), 7.68(d, J=8.7Hz, 2H)
IR(Nujol) 3285, 1608, 1519, 1176, 1151, 1119, 1079, 970, 870, 815, 797 cm$^{-1}$ I-1137 foam
$^1$H NMR(CDCl$_3$) δ 1.83(s, 3H), 2.58(t, J=6.6Hz, 2H), 2.74(s, 3H), 3.21(s, 3H), 3.22(s, 3H), 3.56(s, 3H), 3.78(s, 3H), 4.22(t, J=6.6Hz, 2H), 4.84(brs, 1H), 4.89(brs, 1H), 6.84(s, 1H), 7.10(d, J=8.4Hz, 1H), 7.32~7.43(m, 4H), 7.68(d, J=8.7Hz, 2H),
IR(Nujol) 1608, 1519, 1176, 1150, 1119, 1078, 968, 869, 816 cm$^{-1}$

TABLE 225

I-1138 foam
$^1$H NMR(CDCl$_3$) δ 1.81(s, 3H), 2.55(t, J=6.6Hz, 2H), 3.45 (s, 3H), 3.74(s, 3H), 4.20(t, J=6.6Hz, 2H), 4.85(brs, 1H), 4.89(brs, 1H), 6.45(s, 1H), 6.86~7.07(m, 5H), 7.53(d, J=8.7Hz, 2H),
IR(Nujol) 3531, 3328, 1612, 1587, 1523, 1489, 1287, 1226, 1115, 1072, 1011 cm$^{-1}$ I-1139 foam
$^1$H NMR(CDCl$_3$) δ 2.07(t, J=2.7Hz, 1H), 2.72(dt, J=6.6, 2.7Hz, 2H), 3.45(s, 3H), 3.75(s, 3H), 4.21(t, J=6.6Hz, 2H), 6.45(s, 1H), 6.87~7.10(m, 5H), 7.53(d, J=8.7Hz, 2H)
IR(Nujol) 3482, 3305, 1609, 1597, 1527, 1494, 1253, 1240, 1227, 1127, 1118, 1079, 1010 cm$^{-1}$ I-1140 m.p 194–197° C.
$^1$H NMR(DMSO) δ 3.29(s, 3H), 3.64(s, 3H), 5.42(s, 2H), 6.38(s, 1H), 6.61(dd, J=2.0, 8.2Hz, 1H), 6.74(d, J=2.0 Hz, 1H), 6.84(d, J=8.6Hz, 2H), 6.96(d, J=8.2Hz, 1H), 7.19 (d, J=7.8Hz, 1H), 7.41(d, J=7.8Hz, 1H), 7.43(d, J=8.4 Hz, 2H)
IR(KBr) 3432, 1611, 1566, 1523, 1488, 1430, 1400, 1380, 1241, 1113, 1071, 814 cm$^{-1}$ I-1141 foam
$^1$H NMR(CDCl$_3$) δ 3.45(s, 3H), d 3.75(s, 3H), 3.92(s, 3H), 5.53(s, 2H), 6.45(s, 1H), 6.92(d, J=8.7Hz, 2H), 6.94(dd, J=2.1, 8.7Hz, 1H), 7.01(d, J=8.7Hz, 1H), 7.10(d, J=2.1 Hz, 1H), 7.28(d, J=4.8Hz, 1H), 7.52(d, J=4.8Hz, 1H), 7.53 (d, J=8.4Hz, 2H)
IR(KBr) 3423, 1702, 1684, 1611, 1523, 1489, 1439, 1402, 1282, 1112, 1073, 1010, 814 cm$^{-1}$ I-1142 foam
$^1$H NMR(CDCl$_3$) δ 2.74(s, 3H), 3.21(s, 3H), 3.22(s, 3H), 3.55(s, 3H), d 3.78(s, 3H), 3.91(s, 3H), 5.19(s, 2H), 6.60(d, J=3.6Hz, 1H), 6.84(s, 1H), 7.15(d, J=8.4Hz, 1H), 7.17 (d, J=3.6Hz, 1H), 7.36(dd, J=2.1, 8.4Hz, 1H), 7.38(d, J= 8.7Hz, 2H), 7.41(d, J=2.1Hz, 1H), 7.67(d, J=8.7Hz, 2H)
IR(KBr) 1728, 1519, 1481, 1365, 1177, 1150, 1079, 969, 876, 797 cm$^{-1}$

TABLE 226

I-1143 foam
$^1$H NMR(CDCl$_3$) δ 2.77(s, 3H), 3.21(s, 3H), 3.23(s, 3H), 3.56(s, 3H), d 3.78(s, 3H), 4.18(m, 2H), 4.78(m, 2H), 5.94 (m, 2H), 6.84(s, 1H), 7.11(d, J=8.4Hz, 1H), 7.36(dd, J= 2.1, 8.4Hz, 1H), 7.38(d, J=8.7Hz, 2H), 7.40(d, J=2.1Hz, 1H), 7.67(d, J=8.7Hz, 2H)
IR(KBr) 1609, 1519, 1481, 1367, 1177, 1150, 1079, 970, 876, 797 cm$^{-1}$ I-1144 foam
$^1$H NMR(CDCl$_3$) δ 2.75(s, 3H), 3.21(s, 3H), 3.24(s, 3H), 3.55(s, 3H), d 3.78(s, 3H), 4.11(m, 2H), 4.64(m, 2H), 6.05 (t, J=4.5Hz, 1H), 6.06(t, J=5.1Hz, 1H), 6.84(s, 1H), 7.07 (d, J=8.7Hz, 1H), 7.35(dd, J=2.1, 8.7Hz, 1H), 7.38(d, J= 8.7Hz, 2H), 7.40(d, J=2.1Hz, 1H), 7.67(d, J=8.7Hz, 2H)
IR(KBr) 1609, 1519, 1481, 1364, 1177, 1151, 1079, 969, 874, 797 cm$^{-1}$ I-1145 m.p 203–205° C.
$^1$H NMR(CDCl$_3$) δ 2.83(s, 3H), 3.22(s, 3H), 3.25(s, 3H), 3.55(s, 3H), d 3.79(s, 3H), 4.30(t, J=1.8Hz, 2H), 4.88(t, J=1.8Hz, 2H), 6.84(s, 1H), 7.20(d, J=8.7Hz, 1H), 7.37 (dd, J=2.1, 8.7Hz, 1H), 7.39(d, J=8.7Hz, 2H), 7.42(d, J= 2.1Hz, 1H), 7.67(d, J=8.7Hz, 2H)
IR(KBr) 3443, 1606, 1519, 1481, 1360, 1179, 1150, 1079, 877, 798 cm$^{-1}$ I-1146 m.p 173–174° C.
$^1$H NMR(CD3OD) δ 3.38(s, 3H), 3.68(s, 3H), 4.23(t, J=1.8 Hz, 2H), 4.83(t, J=1.8Hz, 2H), 6.43(s, 1H), 6.79(dd, J= 2.1, 8.1Hz, 1H), 6.85(d, J=8.7Hz, 2H), 6.86(d, J=2.1Hz, 1H), 7.04(d, J=8.1Hz, 1H), 7.45(d, J=8.7Hz, 2H)
IR(KBr) 3399, 1612, 1586, 1523, 1487, 1401, 1217, 1114, 1067, 1013, 996, 828 cm$^{-1}$

TABLE 227

I-1147 foam
$^1$H NMR(CDCl$_3$) δ 3.39(s, 3H), 3.45(s, 3H), 3.74(s, 3H), 4.17(t, J=1.8Hz, 2H), 4.83(t, J=1.8Hz, 2H), 6.45(s, 1H), 6.91(d, J=8.7Hz, 2H), 6.97(dd, J=2.1, 8.1Hz, 1H), 7.05 (d, J=8.1Hz, 1H), 7.08(d, J=2.1Hz, 1H), 7.52(d, J=8.7 Hz, 2H)
IR(KBr) 3411, 1612, 1589, 1523, 1489, 1404, 1224, 1114, 1071, 1010, 939, 816 cm$^{-1}$ I-1148 foam
$^1$H NMR(CDCl$_3$) δ 1.14(t, J=7.5Hz, 3H), 2.23(q, J=7.5 Hz, 2H), 2.71(s, 3H), 3.21(s, 3H), 3.27(s, 3H), 3.60(s, 3H), 3.78(s, 3H), 4.80(s, 2H), 6.84(s, 1H), 7.20(d, J=9.0Hz, 1H), 7.37(dd, J=2.1, 9.0Hz, 1H), 7.38(d, J=8.7Hz, 2H), 7.42(d, J=2.1Hz, 1H), 7.68(d, J=8.7Hz, 2H)
IR(KBr) 2232, 1609, 1519, 1481, 1365, 1177, 1151, 1079, 970, 876, 797 cm$^{-1}$ I-1149 mp >280° C.(decomp.)
$^1$H NMR(DMSO-d$_6$) δ 3.30(s, 3H), 3.64(s, 3H), 4.85(s, 2H), 6.39(s, 1H), 6.69(dd, J=8.4, 2.1Hz, 1H), 6.79(d, J=2.1Hz, 1H), 6.84(d, J=8.7Hz, 2H), 6.94(d, J=8.4Hz, 1H), 7.44(d, J=8.7Hz, 2H), 8.54(s, 1H)
IR(Nujol) 3166, 1707, 1671, 1611, 1586, 1523, 1489, 1288, 1259, 1211, 1115, 1075, 1012, 814 cm$^{-1}$ I-1150 foam
$^1$H NMR(CDCl$_3$) δ 1.91(s, 3H), 3.45(s, 3H), 3.75(s, 3H), 4.89(s, 2H), 5.29(brs, 1H), 5.36(brs, 1H), 6.45(s, 1H), 6.92 (d, J=8.7Hz, 2H), 6.97(dd, J=8.4, 2.1Hz, 1H), 7.07(d, J= 8.4Hz, 1H), 7.08(d, J=2.1Hz, 1H), 7.54(d, J=8.7Hz, 2H)
IR(KBr) 3432, 1612, 1588, 1523, 1489, 1288, 1224, 1192, 1113, 1070, 1010, 938, 825, 813 cm$^{-1}$ I-1151 foam
$^1$H NMR(CDCl$_3$) δ 3.45(s, 3H), 3.75(s, 3H), 4.98(d, J=1.8 Hz, 2H), 5.92(dt, J=7.5, 1.8Hz, 1H), 6.45(s, 1H), 6.46(d, J=7.5Hz, 1H), 6.92(d, J=8.7Hz, 2H), 6.98(dd, J=8.4, 2.1 Hz, 1H), 7.09(d, J=2.1Hz, 1H), 7.11(d, J=8.4Hz, 1H), 7.53 (d, J=8.7Hz, 2H)
IR(KBr) 3410, 1612, 1589, 1523, 1489, 1403, 1224, 1112, 1070, 1011, 938, 826 cm$^{-1}$

TABLE 228

I-1152 foam
$^1$H NMR(CDCl$_3$) δ 3.45(s, 3H), 3.75(s, 3H), 4.89(d, J=2.1 Hz, 2H), 5.97(dt, J=13.8, 2.1Hz, 1H), 6.45(s, 1H), 6.61(d, J=13.8Hz, 1H), 6.92(d, J=8.7Hz, 2H), 6.97(dd, J=8.4, 2.1Hz, 1H), 7.04(d, J=8.4Hz, 1H), 7.09(d, J=2.1Hz, 1H), 7.54(d, J=8.7Hz, 2H)
IR(KBr) 3427, 1612, 1588, 1523, 1489, 1403, 1226, 1192, 1175, 1113, 1070, 1011, 938, 918, 826 cm$^{-1}$ I-1153 mp 188–189° C.
$^1$H NMR(CDCl$_3$) δ 2.84(s, 3H), 3.33(s, 3H), 3.74(s, 3H), 3.98(s, 3H), 4.18(s, 3H), 5.38(s, 2H), 7.05(s, 1H), 7.36–7.64 (m, 10H), 8.61(d, J=8.7Hz, 1H), 8.82(brs, 1H)
IR(KBr) 3381, 2942, 1724, 1538, 1481, 1369, 1296, 1177, 1163, 1082, 963, 821 cm$^{-1}$ I-1154 mp 78–80° C.
$^1$H NMR(CDCl$_3$) δ 2.17(s, 3H), 2.67(s, 3H), 3.13(s, 3H), 3.57(s, 3H), 3.79(s, 3H), 5.19(s, 2H), 6.83(s, 1H), 7.15(d, J=8.6Hz, 1H), 7.31–7.45(m, 7H), 7.62(d, J=8.2Hz, 1H), 7.79(s, 1H), 8.44(d, J=8.6Hz, 1H), 8.51(brs, 1H)
IR(KBr) 3398, 2939, 1739, 1529, 1477, 1368, 1287, 1240, 1177, 1119, 1078, 957, 815, 796, 522 cm$^{-1}$ I-1155 mp 74–75° C.
$^1$H NMR(CDCl$_3$) δ 1.68(s, 3H), 1.76(s, 6H), 1.81(s, 3H), 2.69(s, 3H), 3.24(s, 3H), 3.52(s, 3H), 3.80(s, 3H), 3.88(s, 3H), 3.88–4.02(m, 2H), 4.64(d, J=7.2Hz, 2H), 5.25(d, J= 7.8Hz, 1H), 5.50(t, J=5.7Hz, 1H), 6.88(s, 1H), 7.08–7.38 (m, 6H)
IR(KBr) 3412, 2939, 1697, 1519, 1483, 1366, 1268, 1207, 1178, 1080, 964, 808, 523 cm$^{-1}$ I-1156 mp 72–74° C.
$^1$H NMR(CDCl$_3$) δ 1.95(s, 3H), 1.99(s, 3H), 2.87(s, 3H), 3.42(s, 3H), 3.74(s, 3H), 3.97(s, 3H), 4.16(s, 3H), 4.82(d, J=6.6Hz, 2H), 5.68(t, J=5.7Hz, 1H), 7.04(s, 1H), 7.27(d,

TABLE 228-continued

J=8.1Hz, 1H), 7.39–7.56(m, 4H), 8.60(d, J=8.4Hz, 1H), 8.81(brs, 1H)
IR(KBr) 3407, 2940, 1731, 1601, 1538, 1481, 1366, 1294, 1178, 1165, 1079, 805, 562 cm$^{-1}$

TABLE 229

I-1157 mp 68–69° C.
$^1$H NMR(CDCl$_3$) δ 1.70(s, 3H), 1.77(s, 3H), 1.81(s, 3H), 2.70(s, 3H), 3.25(s, 3H), 3.55(s, 3H), 3.81(s, 3H), 4.64(d, J=6.6Hz, 2H), 5.27(t, J=7.5Hz, 1H), 5.50(t, J=6.9Hz, 1H), 6.86(s, 1H), 7.10(d, J=8.4Hz, 1H), 7.25–7.40(m, 3H), 7.57(d, J=8.1Hz, 1H), 7.76(s, 1H)
IR(KBr) 3422, 2939, 1701, 1519, 1480, 1368, 1203, 1177, 1078, 957, 801, 522 cm$^{-1}$

I-1158 mp 64–66° C.
$^1$H NMR(CDCl$_3$) δ 3.47(s, 3H), 3.74(s, 3H), 5.19(s, 2H), 5.86(brs, 1H), 6.44(s, 1H), 7.08–7.69(m, 11H), 8.06(brs, 1H)
IR(KBr) 3399, 2938, 1726, 1624, 1604, 15263, 1487, 1403, 1302, 1208, 1178, 1068, 695, 520 cm$^{-1}$ I-119 mp 68–70° C.
$^1$H NMR(CDCl$_3$) δ 2.57(s, 3H), 3.57(s, 3H), 3.76(s, 3H), 5.21(s, 2H), 6.84(s, 1H), 7.11–7.73(m, 11H), 8.29(brs, 1H)
IR(KBr) 3422, 2939, 1728, 1605, 1523, 1482, 1397, 1367, 1233, 1209, 1178, 1078, 795, 725, 542 cm$^{-1}$ I-1160 mp 72–73° C.
$^1$H NMR(CDCl$_3$) δ 1.75(s, 6H), 1.78(s, 3H), 1.82(s, 3H), 3.48(s, 3H), 3.75(s, 3H), 3.76(d, J=7.2Hz, 2H), 3.89(s, 3H), 4.38(brs, 1H), 4.61(d, J=6.9Hz, 2H), 5.41(t, J=6.3 Hz, 1H), 5.53(t, J=6.9Hz, 1H), 5.68(brs, 1H), 5.94(brs, 1H), 6.49(s, 3H), 6.69(d, J=8.4Hz, 1H), 6.95(s, 1H), 7.06(s, 1H), 7.13–7.15(m, 2H), 7.26(s, 1H)
IR(KBr) 3423, 2932, 1608, 1528, 1490, 1459, 1250, 1113, 1071, 805, 757 cm$^{-1}$ I-1161 mp 68–69° C.
$^1$H NMR(CDCl$_3$) δ 1.76(s, 3H), 1.81(s, 3H), 3.48(s, 3H), 3.75(s, 3H), 3.91(s, 3H), 4.61(d, J=7.2Hz, 2H), 5.53(t, J=6.0Hz, 1H), 5.91(brs, 2H), 6.47(s, 1H), 6.83(d, J=8.1Hz, 2H), 6.95(s, 1H), 7.06–7.09(m, 2H), 7.16(s, 1H), 7.26(s, 1H)
IR(KBr) 3406, 2933, 1524, 1490, 1397, 1270, 1241, 1116, 1075, 1069, 811, 773 cm$^{-1}$

TABLE 230

I-1162 mp 81–83° C.
$^1$H NMR(CDCl$_3$) δ 1.76(s, 6H), 1.79(s, 3H), 1.81(s, 3H), 3.50(s, 3H), 3.75(s, 3H), 3.80(d, J=6.6Hz, 2H), 4.36(brs, 1H), 4.61(d, J=6.9Hz, 2H), 5.39(t, J=6.3Hz, 1H), 5.53(t, J=6.6Hz, 1H), 5.68(brs, 1H), 5.90(brs, 1H), 6.43(s, 1H), 6.73(d, J=8.4Hz, 1H), 6.95(s, 1H), 7.05(s, 1H), 7.26(d, J=0.9Hz, 1H), 7.47(dd, J=2.1, 8.4Hz, 1H), 7.59(d, J=2.1Hz, 1H)
IR(KBr) 3484, 2931, 1607, 1525, 1488, 1310, 1243, 1114, 1070, 1009, 808 cm$^{-1}$ I-1163 mp 87–89° C.
$^1$H NMR(CDCl$_3$) δ 2.81(s, 3H), 3.60(s, 3H), 3.77(s, 3H), 3.98(d, J=6.3Hz, 2H), 4.80(d, J=6.3Hz, 2H), 6.07(t, J=6.0Hz, 1H), 6.25(t, J=6.3Hz, 1H), 6.46–6.53(m, 2H), 6.86(s, 1H), 7.05–7.38(m, 4H)
IR(KBr) 3411, 2937, 1628, 1527, 1482, 1364, 1233, 1176, 1077, 960, 879, 792, 524 cm$^{-1}$ I-1164 amorphous
$^1$H NMR(CDCl$_3$) δ 2.68(s, 3H), 3.13(s, 3H), 3.43(s, 3H), 3.54(s, 3H), 3.80(s, 3H), 5.19(s, 2H), 6.87(s, 1H), 7.16(d, J=8.7Hz, 2H), 7.32–7.49(m, 9H), 7.69(d, J=8.4Hz, 2H)
IR(KBr) 1698, 1522, 1482, 1367, 1080, 1014, 947, 815, 795 cm$^{-1}$ I-1165 foam
$^1$H NMR(CDCl$_3$) δ 1.47(s, 3H), 1.72(s, 3H), 1.77(s, 3H), 1.81(s, 3H), 2.71(s, 3H), 3.24(s, 3H), 3.51(s, 3H), 3.80(s, 3H), 4.37(d, J=7.8Hz, 2H), 4.64(d, J=6.6Hz, 2H), 5.29(t, J=7.8Hz, 1H), 5.50(t, J=6.6Hz, 1H), 6.88(s, 1H), 7.09(d, J=8.4Hz, 1H), 7.27(d, J=8.7Hz, 2H), 7.35(dd, J=8.4, 2.3 Hz, 1H), 7.39(d, J=2.3Hz, 1H), 7.66(d, J=8.7Hz, 2H)
IR(KBr) 1696, 1521, 1482, 1366, 1177, 1080, 972, 946, 814, 795 cm$^{-1}$ I-1166 mp 135–136° C.
$^1$H NMR(CDCl$_3$) δ 1.77(s, 3H), 1.81(s, 3H), 2.71(s, 3H), 3.24(s, 3H), 3.54(s, 3H), 3.80(s, 3H), 4.64(d, J=6.7Hz, 2H), 5.50(t, J=6.7Hz, 1H), 6.87(s, 1H), 7.10(d, J=8.4Hz, 1H), 7.34(d, J=8.1Hz, 2H), 7.35(dd, J=8.4, 2.2Hz, 1H), 7.39(d, J=2.2Hz, 1H), 7.69(d, J=8.1Hz, 2H)
IR(KBr) 1702, 1522, 1481, 1362, 1275, 1150, 1081, 1014, 978, 817, 793 cm$^{-1}$

TABLE 231

I-1167 mp 169–171° C.
$^1$H NMR(DMSO-d$_6$) δ 1.71(s, 3H), 1.72(s, 6H), 1.76(s, 3H), 3.31(s, 3H), 3.63(s, 3H), 3.64(m, 2H), 4.54(d, J=6.8Hz, 2H), 5.29(t, J=7.5Hz, 1H), 5.49(t, J=6.8Hz, 1H), 5.75(t, J=8.1Hz, 1H), 6.37(s, 1H), 6.63(d, J=8.4Hz, 2H), 6.64 (dd, J=8.1, 2.0Hz, 1H), 6.73(d, J=2.0Hz, 1H), 6.88(d, J=8.4Hz, 2H), 7.37(d, J=8.4Hz, 2H), 8.41(s, 1H), 8.70(s, 1H)
IR(KBr) 3473, 3276, 1608, 1523, 1491, 1310, 1252, 1190, 1112, 1072, 934, 824, 776 cm$^{-1}$

I-1168 mp 159–160° C.
$^1$H NMR(DMSO-d$_6$) δ 1.72(s, 3H), 1.76(s, 3H), 3.31(s, 3H), 3.64(s, 3H), 4.54(d, J=6.8Hz, 2H), 5.49(t, J=6.8Hz, 1H), 5.76(br s, 1H), 6.37(s, 1H), 6.61(d, J=8.4Hz, 2H), 6.64(dd, J=8.1, 2.0Hz, 1H), 6.73(d, J=2.0Hz, 1H), 6.88(d, J=8.1 Hz, 1H), 7.39(d, J=8.4Hz, 2H), 7.37(d, J=8.4Hz, 2H), 8.42 (br s, 1H), 8.70(br s, 1H)
IR(KBr) 3458, 3332, 1609, 1524, 1492, 1411, 1393, 1295, 1234, 1107, 1071, 1012, 994, 781 cm$^{-1}$

I-1169 mp 183–184° C.
$^1$H NMR(CDCl$_3$) δ 1.76(d, J=0.6Hz, 3H), 1.82(s, 3H), 3.13 (s, 3H), 3.48(s, 3H), 3.76(s, 3H), 4.63(d, J=6.9Hz, 2H), 5.53(m, 1H), 5.72(s, 1H), 5.83(s, 1H), 6.46(s, 1H), 6.93(dd, J=1.8, 8.4Hz, 1H), 6.98(d, J=8.4Hz, 1H), 7.04(d, J=1.8 Hz, 1H), 7.82–7.89(m, 2H), 8.00–8.06(m, 2H)
IR(KBr) 3445, 1593, 1499, 1482, 1461, 1387, 1311, 1278, 1245, 1189, 1146, 1111, 1086, 1068, 1010, 997, 942, 766 cm$^{-1}$

I-1170 mp 178–179° C.
$^1$H NMR(CDCl$_3$) δ 1.76(s, 3H), 1.82(s, 3H), 2.80(s, 3H), 3.47(s, 3H), 3.76(s, 3H), 4.62(d, J=7.2Hz, 2H), 5.53(m, 1H), 5.72(s, 1H), 5.86(s, 1H), 6.47(s, 1H), 6.94(dd, J=1.8, 8.1Hz, 1H), 6.98(d, J=8.1Hz, 1H), 7.05(d, J=1.8Hz, 1H), 7.72–7.77(m, 2H), 7.79–7.85(m, 2H)
IR(KBr) 3420, 1587, 1527, 1482, 1449, 1430, 1416, 1390, 1357, 1290, 1240, 1214, 1198, 1135, 1115, 1073, 1019, 998, 975, 962, 937, 831 cm$^{-1}$

TABLE 232

I-1171 mp 136–139° C.
$^1$H NMR(CDCl$_3$) δ 1.73(s, 3H), 1.77(s, 3H), 2.99(s, 6H), 3.71(d, J=6.6Hz, 2H), 3.76(s, 3H), 3.78(s, 3H), 5.32–5.37 (m, 1H), 6.36–6.46(m, 2H), 6.79–6.84(m, 2H), 6.89(s, 1H), 6.95(s, 1H), 7.18–7.24(m, 1H), 7.47–7.52(m, 2H)
IR(KBr) 3600–2800(br), 1626, 1609, 1531, 1493, 1460, 1444, 1388, 1345, 1232, 1207, 1173, 1124, 1050, 1028 cm$^{-1}$

I-1172 mp 113–114° C.
$^1$H NMR(CDCl$_3$) δ 3.00(s, 6H), 3.77(s, 3H), 3.78(s, 3H), 6.78–6.84(m, 3H), 6.88(s, 1H), 6.98(s, 1H), 7.31(dd, J=2.1, 8.4Hz, 1H), 7.43–7.53(m, 3H), 7.58(dd, J=1.8, 11.1Hz, 1H)
IR(KBr) 3600–2800(br), 1711, 1609, 1533, 1493, 1464, 1390, 1212, 1181, 1162, 1052, 1027 cm$^{-1}$

I-1173 mp 141–143° C.
$^1$H NMR(CDCl$_3$) δ 1.75(d, J=0.9Hz, 3H), 1.78(d, J=0.9

TABLE 232-continued

| | |
|---|---|
| | Hz, 3H), 2.99(s, 6H), 3.50(s, 3H), 3.74(s, 3H), 3.78(d, J=6.6Hz, 2H), 3.93(br, 1H), 5.35–5.40(m, 1H), 5.86(s, 1H), 6.44(s, 1H), 6.74–6.86(m, 3H), 7.30–7.38(m, 4H)<br>IR(KBr) 3600–2800(br), 1625, 1611, 1530, 1491, 1458, 1444, 1400, 1348, 1333, 1250, 1217, 1103, 1075 cm$^{-1}$ |
| I-1174 | mp 226–228° C.<br>$^1$H NMR(CDCl$_3$) δ 3.93(s, 3H), 4.95(s, 1H), 5.21(s, 2H), 6.90–6.94(m, 2H), 6.96(s, 1H), 6.97(s, 1H), 7.03(d, J=0.9 Hz, 1H), 7.30–7.49(m, 1H)<br>IR(KBr) 3600–2800(br), 1608, 1589, 1520, 1471, 1446, 1384, 1358, 1270, 1250, 1238, 1210, 1172, 1141, 1093, 1031, 997 cm$^{-1}$ |
| I-1175 | mp 143–145° C.<br>$^1$H NMR(CDCl$_3$) δ 3.21(s, 3H), 3.93(s, 3H), 5.22(s, 2H), 6.97(s, 2H), 7.03(s, 1H), 7.30–7.55(m, 11H)<br>IR(KBr) 3600–2800(br), 1602, 1517, 1468, 1368, 1348, 1248, 1210, 1176, 1151, 1095, 1038, 989 cm$^{-1}$ |

TABLE 233

| | |
|---|---|
| I-1176 | mp 98–100° C.<br>$^1$H NMR(CDCl$_3$) δ 1.76(s, 3H), 1.79(s, 3H), 3.21(s, 3H), 3.91(s, 3H), 4.65(d, J=6.9Hz, 2H), 5.53–5.58(m, 1H), 6.94–7.03(m, 3H), 7.23–7.41(m, 2H), 7.45(s, 1H), 7.49(s, 1H), 7.51–7.56(m, 1H)<br>IR(KBr) 3600–2800(br), 1604, 1583, 1519, 1470, 1449, 1365, 1250, 1202, 1177, 1151, 1095, 1041, 972 cm$^{-1}$ |
| I-1177 | mp 118–120° C.<br>$^1$H NMR(CDCl$_3$) δ 1.76(s, 3H), 1.79(s, 3H), 3.91(s, 3H), 4.64(d, J=6.9Hz, 2H), 5.53–5.58(m, 1H), 6.88–7.02(m, 5H), 7.23–7.37(m, 2H), 7.44(s, 1H), 7.46(s, 1H)<br>IR(KBr) 3600–2800(br), 1626, 1609, 1526, 1490, 1429, 1253, 1187 cm$^{-1}$ |
| I-1178 | mp 161–164° C.<br>$^1$H NMR(CDCl$_3$) δ 3.00(s, 3H), 3.79(s, 3H), 3.80(s, 3H), 6.78–6.83(m, 2H), 6.90(s, 1H), 6.97(s, 1H), 7.47–7.52(m, 2H), 7.71(d, J=1.8Hz, 1H), 8.37(d, J=8.7Hz, 1H), 8.46(br s, 1H)<br>IR(KBr) 3600–2800(br), 1716, 1613, 1532, 1505, 1487, 1463, 1384, 1357, 1280, 1195, 1172, 1059, 1033 cm$^{-1}$ |
| I-1179 | mp 135–137° C.<br>$^1$H NMR(CDCl$_3$) δ 1.74(s, 3H), 1.78(s, 3H), 3.00(s, 6H), 3.78(s, 3H), 3.79(s, 3H), 4.29(d, J=6.6Hz, 1H), 5.35–5.40(m, 1H), 6.71(d, J=8.4Hz, 1H), 6.80–6.83(m, 2H), 6.90(s, 1H), 6.94(s, 1H), 7.38–7.42(m, 1H), 7.48–7.56(m, 3H)<br>IR(KBr) 3600–2800(br), 1612, 1532, 1495, 1460, 1444, 1385, 1365, 1273, 1257, 1203, 1059, 1039, 1029 cm$^{-1}$ |
| I-1180 | $^1$H NMR(CDCl$_3$) δ 1.57(d, J=6.3Hz, 3H), 2.26(s, 3H), 2.28(s, 3H), 5.18(s, 2H), 5.22(q, J=6.3Hz, 1H), 7.02(d, J=8.4 Hz, 1H), 7.12(s, 1H), 7.15(s, 1H), 7.23(d.d, J=8.4 & 2.1Hz, 1H), 7.30–7.51(m, 10H)<br>IR(KBr) 3557, 1605, 1486, 1370, 1235, 1177, 1149, 1078, 1017 cm$^{-1}$ |
| I-1181 | $^1$H NMR(CDCl$_3$) δ 1.66(s, 6H), 2.27(s, 3H), 2.28(s, 3H), 3.20(s, 3H), 4.22(s, 1H), 5.22(s, 2H), 7.06(d, J=8.4Hz, 1H), 7.12(s, 1H), 7.14(s, 1H), 7.23(d.d, J=8.4 & 2.1Hz, 1H), 7.30–7.51(m, 10H)<br>IR(KBr)3544,3441, 1604, 1512, 1485, 1367, 1222, 1173, 1149 cm$^{-1}$ |

TABLE 234

| | |
|---|---|
| I-1182 | $^1$H NMR(CDCl$_3$) δ 1.28(t, J=7.2Hz, 3H), 2.26(s, 3H), 2.28(s, 3H), 2.70(q, J=7.2Hz, 2H), 3.20(s, 3H), 4.73(s, 1H), 6.82(d, J=8.4Hz, 1H), 7.03–7.11(m, 2H), 7.14(s, 1H), 7.15(s, 1H), 7.29–7.46(m, 4H)<br>IR(KBr) 3510, 1605, 1515, 1488, 1369, 1263, 1177, 1147, 1117 cm$^{-1}$ |
| I-1183 | $^1$H NMR(CDCl$_3$) δ 1.29(d, J=6.9Hz, 6H), 2.27(s, 3H), 2.28(s, 3H), 3.20(s, 3H), 3.27(qintet, J=6.9Hz, 1H), 4.76(s, 1H), 6.81(d, J=7.8Hz, 1H), 7.07(d.d, J=7.8 & 2.1Hz, 1H), 7.11(s, 1H), 7.15(s, 1H), 7.20(d, J=2.1Hz, 1H), 7.34(d, J=8.7 Hz, 2H), 7.42(d, J=8.7Hz, 2H),<br>IR(KBr) 3511, 1606, 1484, 1356, 1174, 1151 cm$^{-1}$ |
| I-1184 | $^1$H NMR(CDCl$_3$) δ 1.23(t, J=8.1Hz, 3H), 1.77(s, 3H), 1.82(s, 3H), 2.26(s, 3H), 2.29(s, 3H), 2.70(q, J=8.1Hz, 2H), 3.20(s, 3H), 4.58(d, J=6.6Hz, 2H), 5.48–5.57(m, 1H), 6.90(d, J=7.8Hz, 1H), 7.08–7.13(m, 2H), 7.16(s, 2H), 7.23–7.47(m, 4H)<br>IR(KBr) 1605, 1485, 1369, 1352, 1236, 1201, 1174, 1150, 1133, 1008 cm$^{-1}$ |
| I-1185 | $^1$H NMR(CDCl$_3$) δ 1.23(t, J=7.5Hz, 3H), 1.76(s, 3H), 1.81(s, 3H), 2.27(s, 3H), 2.29(s, 3H), 2.70(q, J=7.5Hz, 2H), 4.57(d, J=6.6Hz, 2H), 4.79(brs, 1H), 5.49–5.58(m, 1H), 6.83–6.92(m, 3H), 7.08–7.19(m, 4H), 7.27(.d, J=8.4Hz, 2H)<br>IR(KBr) 3529, 1608, 1519, 1487, 1241, 1136, 1024 cm$^{-1}$ |
| I-1186 | $^1$H NMR(CDCl$_3$) δ 1.23(d, J=1.8Hz, 6H), 1.76(s, 3H), 1.82(s, 3H), 2.27(s, 3H), 2.29(s, 3H), 3.20(s, 3H), 3.40(quintet, J=1.8Hz, 1H), 4.58(d, J=6.6Hz, 2H), 5.48–5.59(m, 1H), 6.90(d, J=7.8Hz, 1H), 7.10–7.44(m, 8H)<br>IR(KBr)1602, 1468, 1369, 1232, 1174, 1151 cm$^{-1}$ |
| I-1187 | $^1$H NMR(CDCl$_3$) δ 1.24(d, J=6.9Hz, 6H), 1.76(s, 3H), 1.81(s, 3H), 2.27(s, 3H), 2.29(s, 3H), 3.40(quintet, J=6.9Hz, 1H), 4.58(d, J=6.6Hz, 2H), 4.79(broad, s., 1H), 5.50–5.57(m, 1H), 6.84–6.93(m, 3H), 7.09–7.16(m, 3H), 7.00–7.28(m, 3H)<br>IR(KBr) 3265, 1607, 1519, 1486, 1448, 1383, 1232, 1170 cm$^{-1}$ |

TABLE 235

| | |
|---|---|
| I-1188 | $^1$H NMR(CDCl$_3$) δ 1.31(d, J=6.9Hz, 6H), 1.44(s, 3H), 1.67(s, 3H), 2.97(quintet, J=6.9Hz, 1H), 3.78(s, 3H), 3.80(s, 3H), 3.92(s, 3H), 4.20–4.30(broad, 1H), 5.17–5.30(m, 1H), 6.96(s, 1H), 6.99(s, 1H), 7.07–7.35(m, 5H), 7.52(d, J=8.1 Hz, 2H)<br>IR(KBr) 3422, 1601, 1529, 1492, 1462, 1378, 1341, 1257, 1203, 1138, 1028 cm$^{-1}$ |
| I-1189 | $^1$H NMR(CDCl$_3$) δ 2.67(s, 3H), 3.13(s, 3H), 3.57(s, 3H), 3.79(s, 3H), 5.19(s, 2H), 6.84(s, 1H), 7.15(d, J=9.0Hz, 1H), 7.31–7.50(m, 8H), 7.55(d.d, J=12.0 & 1.8Hz, 1H), 8.34–8.41(m, 1H)<br>IR(KBr)3428, 1740, 1601, 1535, 1482, 1366, 1292, 1238, 1177, 1164, 1112, 1079, 1013 cm$^{-1}$ |
| I-1190 | $^1$H NMR(CDCl$_3$) δ 1.48(s, 3H), 1.70(s, 3H), 1.77(s, 3H), 1.81(s,3H), 2.70(s, 3H), 3.24(s, 3H), 3.55(s, 3H), 3.81(s, 3H), 4.09–4.20(m, 1H),4.53–4.68(m, 3H), 5.18–5.30(m, 1H), 5.43–5.54(m, 1H), 6.86(s, 1H), 7.06–7.51(m, 6H)<br>IR(KBr) 1702, 1521, 1482, 1367, 1204, 1177, 1115, 1080 cm$^{-1}$ |
| I-1191 | $^1$H NMR(CDCl$_3$) δ 1.75(s, 3H), 1.78(s, 3H), 1.82(s, 3H), 3.49(s, 3H), 3.74(s, 3H), 3.79(d, J=6.3Hz, 2H), 4.61(d, J=6.6Hz, 2H), 5.32–5.43(m, 1H), 5.49–5.57(m, 1H), 5.68(s, 1H), 5.90(s, 1H), 6.44(s, 1H), 6.74–6.85(m, 1H), 6.95(s, 2H), 7.05(s, 1H), 7.29–7.38(m, 2H)<br>IR(KBr) 3527, 1624, 1530, 1491, 1248, 1221, 1197, 1125, 1105, 1072 cm$^{-1}$ |
| I-1192 | $^1$H NMR(CDCl$_3$) δ 1.75(s, 3H), 1.78(s, 3H), 3.49(s, 3H), 3.73(s, 3H), 3.78(d, J=6.9Hz, 2H), 5.32–5.43(m, 1H), 6.44(s, 1H), 6.73–6.97(m, 4H), 7.25–7.37(m, 2H)<br>IR(KBr)3551,3437,3310, 1607, 1529, 1491, 1463, 1402, 1362, 1269, 1255, 1184, 1099,1070, 1013 cm$^{-1}$ |
| I-1193 | $^1$H NMR(CDCl$_3$) δ 2.28(s, 3H), 2.30(s, 3H), 3.00(s, 6H), 5.16(s, 2H), 5.69(s, 1H), 6.80(d, J=8.7Hz, 2H), 6.84(d.d, J=8.1 & 2.1Hz, 1H), 6.98(.d, J=8.1Hz, 1H), 6.99 (d, J=2.1Hz, 1H), 7.12(s, 1H), 7.13(s, 1H), 7.27(d, J=8.7Hz, 2H), 7.34–7.50(m, 5H)<br>IR(KBr)1605, 1525, 1490, 1417, 1242, 1199, 1127, 1006 cm$^{-1}$ |

TABLE 236

| | |
|---|---|
| I-1194 | mp 174–175° C.<br>$^1$H NMR(CDCl$_3$) δ 3.48(s, 3H), 3.78(s, 3H), 4.41(s, 4H), 5.17(s, 2H), 5.71(s, 1H), 5.88(s, 1H), 6.48(s, 1H), 6.94–7.50 |

TABLE 236-continued

| | |
|---|---|
| | (m, 18H), 7.86(ABq, J=8.4Hz, 4H)<br>IR(KBr) 3463, 3409, 1588, 1519, 1482, 15455, 1417, 1385, 1321, 1285, 1247, 1154, 1112, 1096, 1067, 1015 cm$^{-1}$ |
| I-1195 | mp 165–167° C.<br>$^1$H NMR(CDCl$_3$) δ 2.68(s, 3H), 3.14(s, 3H), 3.56(s, 3H), 3.81(s, 3H), 4.40(s, 4H), 5.20(s, 2H), 6.86(s, 1H), 7.09–7.50 (m, 18H), 7.79(ABq, J=8.1Hz, 4H)<br>IR(KBr) 3434, 2938, 1606, 1596, 1518, 1478, 1455, 1368, 1335, 1293, 1268, 1239, 1174, 1157, 1118, 1079 cm$^{-1}$ |
| I-1196 | mp 176–178° C.<br>$^1$H NMR(CDCl$_3$) δ 1.58(s, 3H), 1.66(s, 3H), 1.77(s, 3H), 1.81(s, 3H), 2.71(s, 3H), 3.24(s, 3H), 3.55(s, 3H), 3.64(m, 2H), 3.80(s, 3H), 4.28(t, J=6.0Hz, 1H), 4.64(d, J=6.9Hz, 2H), 5.10(m, 1H), 5.49(m, 1H), 6.86(s, 1H), 7.10(d, J=8.4 Hz, 1H), 7.35(dd, J=2.1, 8.4Hz, 1H), 7.39(d, J=2.1Hz, 1H), 7.87(ABq, J=8.7Hz, 4H)<br>IR(KBr) 3434, 3321, 2939, 1517, 1477, 1366, 1325, 1292, 1269, 1240, 1176, 1156, 1120, 1077 cm$^{-1}$ |
| I-1197 | mp 180–181° C.<br>$^1$H NMR(DMSO) δ 1.74(s, 3H), 1.77(s, 3H), 2.87(s, 3H), 3.36(s, 3H), 3.51(s, 3H), 3.79(s, 3H), 4.68(d, J=6.6Hz, 2H), 5.48(m, 1H), 7.10(s, 1H), 7.28–7.30(m, 3H), 7.45(bs, 2H), 7.87(ABq, J=8.7Hz, 4H)<br>IR(KBr) 3340, 3238, 2939, 1598, 1518, 1481, 1362, 1333, 1291, 1270, 1239, 1172, 1161, 1120, 1076, 1007 cm$^{-1}$ |
| I-1198 | oil<br>$^1$H NMR(CDCl$_3$) δ 1.45(s, 3H), 1.66(s, 3H), 1.87(s, 3H), 2.24(s, 3H), 2.27(s, 3H), 2.30(s, 3H), 3.84(s, 3H), 3.92(s, 3H), 3.95–4.03(m, 1H), 4.50–4.58(m, 1H), 5.22–5.29(m, 1H), 6.87–6.99(m, 4H), 7.09–7.17(m, 3H), 7.80(s, 1H), 8.34–8.42 (m, 1H)<br>IR(CHCl$_3$) 3673, 3021, 1685, 1639, 1525, 1495, 1406, 1237, 1128, 1037 cm$^{-1}$ |

TABLE 237

| | |
|---|---|
| I-1199 | mp 177–179° C.<br>$^1$H NMR(CDCl$_3$) δ 1.45(s, 6H), 1.66(s, 6H), 1.87(s, 6H), 2.29(s, 6H), 3.85(s, 6H), 3.95–4.04(m, 2H), 4.50–4.59(m, 2H), 5.23–5.29(m, 2H), 6.90–6.95(m, 4H), 7.10–7.15(m, 2H), 7.19(s, 2H)<br>IR(KBr) 2929, 1661, 1492, 1405, 1288, 1214, 1030, 869, 829 cm$^{-1}$ |
| I-1200 | mp 224–226° C.<br>$^1$H NMR(CDCl$_3$) δ 2.88(s, 3H), 3.22(s, 3H), 3.54(s, 3H), 3.78(s, 3H), 6.43(s, 1H), 6.85(s, 1H), 7.01(d, J=8.4Hz, 1H), 7.20(dd, J=2.1, 8.4Hz, 1H), 7.35–7.42(m, 2H), 7.65–7.72(m, 2H), 7.96(d, J=2.1Hz, 1H), 8.96(s, 1H)<br>IR(KBr) 3441, 3370, 3024, 2938, 1729, 1508, 1481, 1365, 1177, 1148, 1085, 884, 798, 524 cm$^{-1}$ |
| I-1201 | powder<br>$^1$H NMR(CDCl$_3$) δ 1.77(s, 3H), 1.82(s, 3H), 2.80(s, 3H), 3.21(s, 3H), 3.56(s, 3H), 3.79(s, 3H), 4.67(d, J=6.6Hz, 2H), 5.46–5.51(m, 1H), 6.84(s, 1H), 7.05(d, J=8.1Hz, 1H), 7.22–7.26(m, 1H), 7.36–7.41(m, 2H), 7.67–7.71(m, 2H), 8.35 (d, J=1.8Hz, 1H), 9.24(s, 1H)<br>IR(KBr) 3385, 2937, 1718, 1532, 1479, 1362, 1175, 1152, 1078, 973, 876, 797, 526 cm$^{-1}$ |
| I-1202 | mp 260–262° C.<br>$^1$H NMR(DMSO) δ 2.27(s, 6H), 3.87(s, 6H), 7.00(dd, J= 1.8, 8.1Hz, 2H), 7.10(d, J=1.8Hz, 2H), 7.21(s, 2H), 7.48(d, J=8.1Hz, 2H), 10.73(s, 2H)<br>IR(KBr) 3392, 3008, 1719, 1600, 1542, 1413, 1297, 1158, 1032, 905, 627 cm$^{-1}$ |
| I-1203 | mp 143–144° C.<br>$^1$H NMR(CDCl$_3$) δ 1.76(s, 3H), 1.82(s, 3H), 3.61(s, 3H), 3.67(s, 3H), 3.73(s, 3H), 3.87(s, 3H), 4.62(d, J=6.9Hz, 2H), 5.50–5.58(m, 1H), 5.66(s, 1H), 6.86–7.02(m, 5H), 7.54 (d, J=9Hz, 2H)<br>IR(KBr) 3494, 2935, 1673, 1609, 1584, 1519, 1479, 1456, 1389, 1284, 1249, 1178, 1109, 1081, 1016, 829, 798 cm$^{-1}$ |

TABLE 238

| | |
|---|---|
| I-124 | mp 90–91° C.<br>$^1$H NMR(CDCl$_3$) δ 1.72(s, 3H), 1.79(s, 3H), 2.26(s, 6H), 4.69(d, J=7.2Hz, 2H), 4.9–5.0(brs, 1H), 5.57(t, J=7.2Hz, 1H), 6.85–7.0(m, 4H), 7.10(d, J=8.7Hz, 2H), 7.23(d, J=8.7 Hz, 2H)<br>IR(KBr) 3253, 3013, 2979, 2928, 1676, 1584, 1521, 1492, 1232, 1034, 950, 848, 825 cm$^{-1}$ |
| I-1205 | mp 131–132° C.<br>$^1$H NMR(CDCl$_3$) δ 1.73(s, 3H), 1.79(s, 3H), 3.43(s, 3H), 3.76(s, 3H), 4.68(d, J=6.9Hz, 2H), 4.9–5.1(brs, 1H), 5.58 (t, J=7.2Hz, 1H), 6.09(brs, 1H), 6.44(s, 1H), 6.92(d, J= 8.4Hz, 2H), 7.0–7.1(m, 2H), 7.52(d, J=8.4Hz, 2H)<br>IR(KBr) 3428, 2951, 2932, 1671, 1611, 1523, 1491, 1402, 1233, 1111, 1077, 1027, 969, 833 cm$^{-1}$ |
| I-1206 | mp 191–192° C.<br>$^1$H NMR(CDCl$_3$) δ 2.15(s, 6H), 3.22(s, 3H), 3.87(s, 3H), 5.18(AB q, J=12.0Hz, 2H), 6.74(dd, J=2.1, 8.1Hz, 1H), 6.78(d, J=2.1Hz, 1H), 6.93(d, J=8.1Hz, 1H), 7.24(s, 1H), 7.30–7.50(m, 9H)<br>IR(KBr) 1528, 1479, 1453, 1364, 1326, 1262, 1243, 1223, 1209, 1200, 1176, 1152, 1137, 963, 870, 846, 754 cm$^{-1}$ |
| I-1207 | mp 108–109° C.<br>$^1$H NMR(CDCl$_3$) δ 1.77(s, 3H), 1.82(d, J=0.6Hz, 3H), 2.27 (s, 3H), 2.28(s, 3H), 4.56(d, J=6.6Hz, 2H), 4.89(m, 1H), 5.54(m, 1H), 6.86–6.92(m, 2H), 6.94–7.00(m, 2H), 7.12(s, 1H), 7.13(s, 1H), 7.22–7.27(m, 2H), 7.27–7.31(m, 2H)<br>IR(KBr) 3349, 1608, 1520, 1488, 1439, 1383, 1287, 1263, 1235, 1175, 999, 979 cm$^{-1}$ |
| I-1208 | mp 194–195° C.<br>$^1$H NMR(CDCl$_3$) δ 2.14(s, 3H), 2.16(s, 3H), 3.87(s, 3H), 4.97(s, 1H), 5.17(AB q, J=12.6Hz, 2H), 6.74(dd, J=2.1, 8.1Hz, 1H), 6.79(d, J=2.1Hz, 1H), 6.88–6.93(m, 2H), 6.93 (d, J=8.1Hz, 2H), 7.17–7.22(m, 2H), 7.24(s, 1H), 7.29–7.49 (m, 5H)<br>IR(KBr) 3408, 1611, 1526, 1479, 1463, 1455, 1382, 1263, 1242, 1225, 1212, 1143, 997, 751 cm$^{-1}$ |

TABLE 239

| | |
|---|---|
| I-1209 | mp 183–184° C.<br>$^1$H NMR(CDCl$_3$) δ 2.03(s, 3H), 2.07(s, 3H), 3.19(s, 3H), 3.80(br s, 2H), 3.89(s, 3H), 5.21(s, 2H), 6.63(s, 1H), 6.77 (dd, J=2.1, 8.1Hz, 1H), 6.83(d, J=2.1Hz, 1H), 7.02(d, J= 8.1Hz, 1H), 7.29–7.52(m, 9H)<br>IR(KBr) 3481, 3391, 1610, 1511, 1482, 1370, 1240, 1212, 1197, 1173, 1153, 1137, 1024, 1007, 870, 844 cm$^{-1}$ |
| I-1210 | mp 133–134° C.<br>$^1$H NMR(CDCl$_3$) δ 1.75(s, 3H), 1.80(s, 3H), 2.16(s, 3H), 2.17(s, 3H), 3.22(s, 3H), 3.85(s, 3H), 4.61(d, J=6.9Hz, 2H), 5.55(m, 1H), 6.74–6.79(m, 2H), 6.92(d, J=8.7Hz, 1H), 7.24(s, 1H), 7.39(s, 4H)<br>IR(KBr) 1529, 1516, 1478, 1371, 1353, 1328, 1263, 1242, 1201, 1176, 1150, 975, 866, 846, 787 cm$^{-1}$ |
| I-1211 | mp 243–244° C.<br>$^1$H NMR(DMSO-d$_6$) δ 1.91(s, 3H), 1.96(s, 3H), 3.77(s, 3H), 4.05(br s, 2H), 5.12(s, 2H), 6.40(s, 1H), 6.71(dd, J=1.8, 8.1 Hz, 1H), 6.77–6.84(m, 3H), 7.06–7.12(m, 2H), 7.16(d, J=8.1 Hz, 1H), 7.32–7.52(m, 5H), 9.38(s, 1H)<br>IR(KBr) 3378, 3289, 1609, 1586, 1518, 1483, 1454, 1402, 1267, 1236, 1207, 1171, 1136, 1024, 853, 835, 816, 753, 730, 695 cm$^{-1}$ |
| I-1212 | mp 195–196° C.<br>$^1$H NMR(CDCl$_3$) δ 1.75(s, 3H), 1.79(s, 3H), 2.15(s, 3H), 2.16(s, 3H), 3.85(s, 3H), 4.61(d, J=6.9Hz, 2H), 4.97(s, 1H), 5.55(m, 1H), 6.76–6.79(m, 2H), 6.89–6.94(m, 3H), 7.18–7.23(m, 2H), 7.24(s, 1H)<br>IR(KBr) 3462, 1611, 1519, 1479, 1459, 1431, 1379, 1271, 1240, 1228, 1211, 1137, 983, 835 cm$^{-1}$ |
| I-1213 | IR(KBr) 3275, 1494, 1462, 1444, 1387, 1371, 1232, 1212, 1183, 1141 cm$^{-1}$ |
| I-124 | mp 106–108° C.<br>$^1$H NMR(CDCl$_3$) δ 2.24(s, 3H), 3.79(s, 3H), 4.72(br, 1H), 5.20(s, 2H), 6.72–7.18(m, 8H), 7.36–7.50(m, 6H)<br>IR(CHCl$_3$) 3596, 1610, 1523, 1493, 1465, 1455, 1388, 1318, 1298, 1262, 1173, 1127, 1038, 834 cm$^{-1}$ |

TABLE 240

| | |
|---|---|
| I-1215 | mp 108–110° C.<br>$^1$H NMR(CDCl$_3$) δ 1.77(s, 3H), 1.82(s, 3H), 2.25(s, 3H), 3.79(s, 3H), 4.63–4.65(d, J=7.2Hz, 2H), 5.56(s, 2H), 6.81 (s, 1H), 6.87–7.18(m, 6H), 7.44–7.47(m, 2H)<br>IR(CHCl$_3$) 3596, 2937, 1610, 1523, 1493, 1465, 1446, 1387, 1297, 1261, 1173, 1125, 1038, 993, 834 cm$^{-1}$ |
| I-1216 | mp 121–122° C.<br>$^1$H NMR(CDCl$_3$) δ 2.24(s, 3H), 3.79(s, 3H), 4.78–4.80(d, J=6.9Hz, 2H), 6.24(t, J=6.9Hz, 1H), 6.80(s, 1H), 6.87–7.19 (m, 6H), 7.43–7.48(m, 2H)<br>IR(CHCl$_3$) 3596, 1612, 1523, 1493, 1464, 1389, 1300, 1259, 1173, 1127, 1038, 886, 834 cm$^{-1}$ |
| I-1217 | mp 163–165° C.<br>$^1$H NMR(CDCl$_3$) δ 2.26(s, 3H), 2.28(s, 3H), 4.78(br s, 1H), 4.78(d, J=6.5Hz, 2H), 5.60(s, 1H) 6.23(t, J=6.5Hz, 1H), 6.83–6.92(m, 4H), 6.99(d, J=2.1Hz, 1H), 7.10(s, 1H), 7.11 (s, 1H), 7.22–7.27(m, 2H)<br>IR(CHCl$_3$) 3597, 3548, 3027, 3010, 1613, 1588, 1522, 1490, 1218, 1208, 1171 cm$^{-1}$ |
| I-1218 | foam<br>$^1$H NMR(CDCl$_3$) δ 2.37(s, 3H), 3.39(s, 3H), 3.73(s, 3H), 5.15(s, 2H), 5.68(s, 1H), 5.92(s, 1H), 6.46(s, 1H), 6.71(dd, J=3.7, 0.7Hz, 1H), 6.96(dd, J=8.4, 2.1Hz, 1H), 7.03(d, J=8.4Hz, 1H), 7.09(d, J=2.1Hz, 1H), 7.26(dd, J=8.6, 0.7Hz, 2H), 7.37–7.45(m, 5H), 7.60(dd, J=8.7, 1.5Hz, 1H), 7.61(d, J=3.7Hz, 1H), 7.78(d, J=1.5Hz, 1H), 7.82(d, J=8.6Hz, 1H), 8.05(d, J=8.7Hz, 1H)<br>IR(KBr) 3476, 1457, 1371, 1254, 1107, 1131, 1107, 1011, 814, 685, 581 cm$^{-1}$ |
| I-1219 | mp 217–219° C.<br>$^1$H NMR(CDCl$_3$) δ 2.37(s, 3H), 2.69(s, 3H), 3.12(s, 3H), 3.47(s, 3H), 3.76(s, 3H), 5.18(s, 2H), 6.71(d, J=3.8Hz, 1H), 6.86(s, 1H), 7.15(d, J=8.4Hz, 1H), 7.26(d, J=8.7Hz, 2H), 7.32–7.48(m, 7H), 7.56(dd, J=8.7, 1.8Hz, 1H), 7.61 (d, J=3.8Hz, 1H), 7.78(d, J=1.8Hz, 1H), 7.82(d, J=8.7 Hz, 1H), 8.05(d, J=8.7Hz, 1H)<br>IR(KBr) 1366, 1174, 1079, 963, 814, 685, 586 cm$^{-1}$ |

TABLE 241

| | |
|---|---|
| I-1220 | mp 208–210° C.<br>$^1$H NMR(CDCl$_3$) δ 2.37(s, 3H), 2.72(s, 3H), 3.23(s, 3H), 3.47(s, 3H), 3.76(s, 3H), 4.63(d, J=6.6Hz, 2H), 5.49(t, J=6.6Hz, 1H), 6.71(d, J=3.8Hz, 1H), 6.86(s, 1H), 7.09(d, J=8.4Hz, 1H), 7.26(d, J=8.3Hz, 2H), 7.35(dd, J=8.4, 2.1Hz, 1H), 7.40(d, J=2.1Hz, 1H), 7.56(dd, J=8.4, 1.7Hz, 1H), 7.61(d, J=3.8Hz, 1H), 7.78(d, J=1.7Hz, 1H), 7.82(d, J=8.3Hz, 2H), 8.05(d, J=8.7Hz, 1H)<br>IR(KBr) 1466, 1445, 1365, 1174, 1116, 1079, 964, 812, 686, 584 cm$^{-1}$ |
| I-1221 | mp 203–205° C.<br>$^1$H NMR(CDCl$_3$) δ 1.76(s, 3H), 1.81(s, 3H), 2.39(s, 3H), 2.69(s, 3H), 2.97(t, J=8.6Hz, 2H), 3.23(s, 3H), 3.50(s, 3H), 3.77(s, 3H), 3.98(t, J=8.6Hz, 2H), 4.63(d, J=6.6Hz, 2H), 5.49(t, J=6.6Hz, 1H), 6.80(s, 1H), 7.08(d, J=8.5Hz, 1H), 7.24–7.28(m, 2H), 7.33(dd, J=8.5, 2.0Hz, 1H), 7.37–7.39(m, 2H), 7.41–7.45(m, 1H), 7.71(d, J=8.4Hz, 1H), 7.73 (d, J=8.1Hz, 2H)<br>IR(KBr) 1474, 1362, 1241, 1166, 1079, 975, 808 cm$^{-1}$ |
| I-1222 | amorphous<br>$^1$H NMR(CDCl$_3$) δ 1.76(s, 3H), 1.82(s, 3H), 2.39(s, 3H), 2.98(t, J=8.4Hz, 2H), 3.43(s, 3H), 3.73(s, 3H), 3.98(t, J=8.4Hz, 2H), 4.61(d, J=6.6Hz, 2H), 5.53(t, J=6.6Hz, 1H), 5.68(s, 1H), 5.86(s, 1H), 6.40(s, 1H), 6.93–6.95(m, 2H), 7.03–7.05(m, 1H), 7.23–7.27(m, 2H), 7.35–7.37(m, 1H), 7.45–7.50(m, 1H), 7.71(d, J=8.4Hz, 1H), 7.74(d, J=8.4 Hz, 2H)<br>IR(KBr) 3457, 1480, 1354, 1244, 1164, 1099, 978, 817 cm$^{-1}$ |
| I-1223 | mp 199–201° C.<br>$^1$H NMR(CDCl$_3$) δ 3.19(s, 3H), 3.72(s, 3H), 3.90(s, 3H), 4.20–4.27(m, 4H), 5.20(s, 2H), 6.53(s, 1H), 6.90–6.99(m, 3H), 7.25–7.65(m, 9H)<br>IR(KBr) 3434, 2938, 1604, 1586, 1522, 1484, 1465, 1432, 1368, 1339, 1326, 1249, 1226, 1203, 1174, 1146, 1136, 1106, 1027 cm$^{-1}$ |

TABLE 242

| | |
|---|---|
| I-1224 | mp 127–129° C.<br>$^1$H NMR(CDCl$_3$) δ 1.57(s, 3H), 1.65(s, 3H), 1.76(s, 3H), 1.82(s, 3H), 3.46(s, 3H), 3.64(m, 2H), 3.76(s, 3H), 4.30(t, J=5.7Hz, 1H), 4.62(d, J=6.9Hz, 2H), 5.10(m, 1H), 5.53 (m, 1H), 5.72(s, 1H), 5.85(s, 1H), 6.47(s, 1H), 6.93(dd, J=1.8, 8.4Hz, 1H), 6.98(d, J=8.4Hz, 1H), 7.05(d, J=1.8Hz, 1H), 7.88(ABq, J=8.7Hz, 4H)<br>IR(KBr) 3478, 3314, 2937, 1585, 1556, 1518, 1501, 1484, 1460, 1417, 1387, 1363, 1328, 1279, 1243, 1228, 1191, 1155, 1129, 1113, 1090, 1068, 1013 cm$^{-1}$ |
| I-1225 | mp 162–164° C.<br>$^1$H NMR(CDCl$_3$) δ 3.19(s, 3H), 3.72(s, 3H), 4.19–4.23(m, 4H), 5.18(s, 2H), 6.52(s, 1H), 7.03–7.64(m, 12H)<br>IR(KBr) 3433, 2933, 1523, 1483, 1463, 1435, 1377, 1360, 1269, 1227, 1172, 1149, 1126, 1096 cm$^{-1}$ |
| I-1226 | mp 188–190° C.<br>$^1$H NMR(DMSO) δ 1.72(s, 3H), 1.75(s, 3H), 3.33(s, 3H), 3.67(s, 3H), 4.55(d, J=6.9Hz, 2H), 5.49(m, 1H), 6.50(s, 1H), 6.66(dd, J=2.1, 8.1Hz, 1H), 6.74(d, J=2.1Hz, 1H), 6.91(d, J=8.1Hz, 1H), 7.42(bs, 2H), 7.85(ABq, J=8.4Hz, 4H), 8.75(bs, 2H)<br>IR(KBr) 3465, 2937, 1588, 1517, 1500, 1483, 1470, 1446, 1415, 1385, 1340, 1308, 1283, 1246, 1224, 1201, 1186, 1168, 1130, 1116, 1091, 1067, 1011 cm$^{-1}$ |
| I-1227 | mp 172–174° C.<br>$^1$H NMR(CDCl$_3$) δ 1.75(s, 3H), 1.78(s, 3H), 3.19(s, 3H), 3.72(s, 3H), 3.87(s, 3H), 4.20–4.27(m, 4H), 4.62(d, J=6.9 Hz, 2H), 5.57(m, 1H), 6.54(s, 1H), 6.96(s, 3H), 7.49(ABq, J=8.7Hz, 4H)<br>IR(KBr) 3433, 2937, 1604, 1582, 1522, 1483, 1465, 1432, 1368, 1340, 1326, 1242, 1226, 1218, 1204, 1174, 1138, 1107 cm$^{-1}$ |

TABLE 243

| | |
|---|---|
| I-1228 | mp 169–175° C.<br>$^1$H NMR(CDCl$_3$) δ −0.07–0.02(m, 2H), 0.34–0.42(m, 2H), 0.98(m, 1H), 2.44(s, 3H), 3.20(s, 3H), 3.47(d, J=7.2Hz, 2H), 3.78(s, 3H), 3.91(s, 3H), 5.22(s, 2H), 6.85(s, 1H), 6.91(dd, J=1.8, 8.1Hz, 1H), 6.976(d, J=1.8Hz, 1H), 6.979 (d, J=8.1Hz, 1H), 7.26–7.73(m, 9H)<br>IR(KBr) 3447, 2934, 1604, 1518, 1480, 1390, 1362, 1240, 1227, 1175, 1140, 1081 cm$^{-1}$ |
| I-1229 | mp 172–174° C.<br>$^1$H NMR(CDCl$_3$) δ 1.74(s, 3H), 1.78(s, 3H), 3.71(s, 3H), 3.87(s, 3H), 4.20–4.25(m, 4H), 4.62(d, J=6.3Hz, 2H), 4.94 (bs, 1H), 5.57(m, 1H), 6.55(s, 1H), 6.89–7.50(m, 7H)<br>IR(KBr) 3410, 2933, 1611, 1522, 1484, 1462, 1422, 1371, 1264, 1238, 1224, 1173, 1134, 1103 cm$^{-1}$ |
| I-1230 | mp 149–151° C.<br>$^1$H NMR(CDCl$_3$) δ 1.75(s, 3H), 1.81(s, 3H), 3.45(s, 3H), 3.75(s, 3H), 3.87(s, 3H), 4.61(d, J=6.6Hz, 2H), 5.54–5.58 (m, 1H), 5.69(s, 1H), 5.91(s, 1H), 6.46(s, 1H), 6.93–7.06(m, 5H), 7.58(d, J=8.7Hz, 2H)<br>IR(KBr) 3501, 2939, 1680, 1609, 1582, 1520, 1487, 1458, 1397, 1284, 1246, 1191, 1179, 1115, 1067, 1015, 940, 822, 794 cm$^{-1}$ |
| I-1231 | mp 151–152° C.<br>$^1$H NMR(CDCl$_3$) δ 1.77(d, J=0.6Hz, 3H), 1.81(d, J=0.6 Hz, 3H), 2.04(s, 3H), 2.08(s, 3H), 3.20(s, 3H), 3.77(br s, 2H), 3.86(s, 3H), 4.65(d, J=6.6Hz, 2H), 5.58(m, 1H), 6.04 (s, 1H), 6.81(dd, J=2.1, 8.7Hz, 1H), 6.81(d, J=2.1Hz, 1H), 7.01(d, J=8.7Hz, 1H), 7.30–7.36(m, 2H), 7.38–7.43 (m, 2H)<br>IR(KBr) 3484, 3393, 2934, 1608, 1511, 1482, 1371, 1239, 1213, 1197, 1173, 1153, 1138, 989, 973, 871, 844, 791 cm$^{-1}$ |

TABLE 244

I-1232 mp 198–199° C.
$^1$H NMR (DMSO-d$_6$) δ 1.72 (s, 3H), 1.77 (s, 3H), 1.91 (s, 3H), 1.95 (s, 3H), 3.75 (s, 3H), 4.04 (s, 2H), 4.55 (d, J = 6.9 Hz, 2H), 5.48 (m, 1H), 6.40 (s, 1H), 6.69 (dd, J = 1.8, 8.1 Hz, 1H), 6.75 (d, J = 1.8 Hz, 1H), 6.77–6.83 (m, 2H), 7.05–7.11 (m, 3H), 9.39 (s, 1H)
IR (KBr) 3375, 3287, 2913, 1609, 1587, 1578, 1518, 1484, 1434, 1403, 1270, 1235, 1207, 1171, 1136, 1032, 1009, 863, 853, 816, 749 cm$^{-1}$

I-1233 mp 198–199° C.
$^1$H NMR (CDCl$_3$) δ 1.77 (s, 3H), 1.80 (s, 3H), 1.91 (s, 3H), 2.11 (s, 3H), 2.13 (s, 3H), 3.20 (s, 3H), 3.84 (s, 3H), 4.64 (d, J = 6.6 Hz, 2H), 5.58 (m, 1H), 6.46 (s, 1H), 6.69–6.74 (m, 2H), 6.96 (d, J = 8.4 Hz, 1H), 7.11 (s, 1H), 7.32–7.38 (m, 2H), 7.40–7.46 (m, 2H)
IR (KBr) 1651, 1513, 1470, 1448, 1414, 1368, 1330, 1267, 1241, 1214, 1199, 1175, 970, 869 cm$^{-1}$

I-1232 mp 193–194° C.
$^1$H NMR (CDCl$_3$) δ 1.77 (s, 3H), 1.80 (d, J = 0.6 Hz, 3H), 1.94 (s, 3H), 2.11 (s, 3H), 2.13 (s, 3H), 3.84 (s, 3H), 4.64 (d, J = 6.6 Hz, 2H), 5.58 (m, 1H), 6.58 (s, 1H), 6.70–6.75 (m, 2H), 6.85–6.93 (m, 2H), 6.96 (d, J = 8.4 Hz, 1H), 7.13 (s, 1H), 7.19–7.24 (m, 2H)
IR (KBr) 3271, 1654, 1611, 1517, 1467, 1448, 1370, 1289, 1262, 1240, 1213, 1177, 1136, 835 cm$^{-1}$

I-1235 mp 114–115° C.
$^1$H NMR (CDCl$_3$) δ 1.77 (s, 3H), 1.81 (s, 3H), 2.27 (s, 6H), 3.91 (s, 3H), 4.63 (d, J = 6.6 Hz, 2H), 5.56 (m, 1H), 5.61 (s, 1H), 6.86 (dd, J = 2.1, 8.4 Hz, 1H), 6.86 (d, J = 2.1 Hz, 1H), 6.97 (d, J = 8.4 Hz, 1H), 7.02–7.14 (m, 5H)
IR (KBr) 3410, 1597, 1521, 1470, 1449, 1415, 1382, 1297, 1276, 1261, 1220, 1122, 1052, 983, 862 cm$^{-1}$

TABLE 245

I-1236 powder
$^1$H NMR (CDCl$_3$) δ 3.22 (s, 3H), 3.38 (s, 3H), 3.46 (s, 3H), 3.92 (s, 3H), 5.22 (s, 2H), 5.76 (s, 1H), 6.97–7.09 (m, 3H), 7.32–7.51 (m, 9H)
IR (KBr) 3448, 2935, 1516, 1455, 1394, 1366, 1352, 1246, 1148, 1076, 1015, 972, 881, 699, 541, 524 cm$^{-1}$ I-1237 mp 169–172° C.
$^1$H NMR (CDCl$_3$) δ 2.49 (s, 3H), 3.21 (s, 3H), 3.47 (s, 3H), 3.50 (s, 3H), 3.92 (s, 3H), 5.23 (s, 2H), 6.95–7.04 (m, 3H), 7.31–7.49 (m, 9H)
IR (KBr) 3009, 2932, 1518, 1459, 1370, 1362, 1250, 1176, 1151, 872, 809, 542, 527 cm$^{-1}$ I-1238 mp 182–184° C.
$^1$H NMR (CDCl$_3$) δ 2.67 (s, 3H), 3.21 (s, 3H), 3.48 (s, 3H), 3.50 (s, 3H), 3.93 (s, 3H), 5.77 (s, 1H), 6.98–7.06 (m, 3H), 7.38–7.51 (m, 4H)
IR (KBr) 3548, 3502, 2938, 1602, 1519, 1389, 1364, 1176, 1159, 1012, 963, 875, 521 cm$^{-1}$ I-1239 mp 132–135° C.
$^1$H NMR (CDCl$_3$) δ 1.77 (s, 3H), 1.80 (s, 3H), 2.62 (s, 3H), 3.21 (s, 3H), 3.48 (s, 3H), 3.51 (s, 3H), 3.90 (s, 3H), 4.64 (d, J = 6.6 Hz, 2H), 5.51–5.58 (m, 1H), 6.97–7.04 (m, 3H), 7.37–7.51 (m, 4H)
IR (KBr) 2936, 1518, 1464, 1375, 1362, 1246, 1175, 1153, 1013, 968, 872, 805, 529 cm$^{-1}$ I-1240 mp 169–172° C.
$^1$H NMR (CDCl$_3$) δ 1.76 (s, 3H), 1.80 (s, 3H), 3.38 (s, 3H), 3.47 (s, 3H), 3.89 (s, 3H), 4.65 (d, J = 6.6 Hz, 2H), 5.06 (s, 1H), 5.54–5.61 (m, 1H), 5.83 (s, 1H), 6.92–7.00 (m, 3H), 7.05–7.09 (m, 2H), 7.28–7.33 (m, 2H)
IR (KBr) 3458, 2935, 1611, 1520, 1458, 1392, 1244, 1222, 1015, 828, 803 cm$^{-1}$

TABLE 246

I-1241 mp 170–173° C.
$^1$H NMR (CDCl$_3$) δ 1.73 (s, 3H), 1.79 (s, 3H), 2.55–3.00 (m, 3H), 3.21 (s, 3H), 3.22–3.80 (m, 6H), 4.55–4.63 (m, 2H), 5.41–5.47 (m, 1H), 6.83 (s, 1H), 7.03–7.70 (m, 8H)
IR (KBr) 2938, 1686, 1516, 1481, 1378, 1235, 1235, 1179, 1152, 1081, 847, 799, 675, 527 cm$^{-1}$

I-1242 mp 117–118° C.
$^1$H NMR (CDCl$_3$) δ 1.77 (s, 3H)1.81 (d, J = 0.6 Hz, 3H), 2.11 (s, 3H), 2.19 (s, 3H), 3.38 (s, 3H), 4.64 (d, J = 6.9 Hz, 2H), 4.75 (br s, 1H), 5.54–5.90 (m, 1H), 6.86–6.91 (m, 2H), 6.93 (s, 1H), 7.10–7.69 (m, 3H), 7.20–7.25 (m, 2H)
IR (CHCl$_3$) 3596, 3010, 2934, 1675, 1519, 1473, 1262, 1172, 1098 cm$^{-1}$

I-1243 foam
$^1$H NMR (CDCl$_3$) δ 3.43 (s, 3H), 3.72 (s, 3H), 5.03 (s, 2H), 6.43 (s, 1H), 6.93 (dd, J = 8.4, 2.1 Hz, 1H), 6.94 (d, J = 8.7 Hz, 2H), 7.09 (d, J = 8.4 Hz, 1H), 7.11 (d, J = 2.1 Hz, 1H), 7.29 (ddd, J = 7.8, 4.8, 1.5 Hz, 1H), 7.49 (brd, J = 7.8 Hz, 1H), 7.53 (d, J = 8.7 Hz, 2H), 7.70 (ddd, J = 7.8, 7.8, 1.5 Hz, 1H), 8.61 (brd, J = 4.8 Hz, 1H)
IR (KBr) 3432, 1611, 1588, 1562, 1523, 1488, 1467, 1226, 1114, 1071, 1015, 939, 824, 778, 758 cm$^{-1}$ I-1244 foam
$^1$H NMR (CDCl$_3$) δ 3.45 (s, 3H), 3.75 (s, 3H), 5.01 (s, 2H), 6.45 (s, 1H), 6.92 (d, J = 8.7 Hz, 2H), 6.99 (dd, J = 8.4, 2.1 Hz, 1H), 7.10 (d, J = 2.1 Hz, 1H), 7.14 (d, J = 8.4 Hz, 1H), 7.30 ~ 7.36 (m, 3H), 7.46 ~ 7.49 (m, 2H), 7.54 (d, J = 8.7 Hz, 2H)
IR (KBr) 3433, 1612, 1589, 1523, 1489, 1403, 1224, 1192, 1113, 1070, 1013, 938, 813, 758 cm$^{-1}$ I-1245 foam
$^1$H NMR (CDCl$_3$) δ 3.45 (s, 3H), 3.75 (s, 3H), 5.01 (s, 2H), 6.45 (s, 1H), 6.92 (d, J = 8.7 Hz, 2H), 6.99 (dd, J = 5.1, 3.6 Hz, 1H), 6.99 (dd, J = 8.4, 2.1 Hz, 1H), 7.10 (d, J = 2.1 Hz, 1H), 7.11 (d, J = 8.4 Hz, 1H), 7.27 (dd, J = 3.6, 1.0 Hz, 1H), 7.29 (dd, J = 5.1, 1.0 Hz, 1H), 7.54 (d, J = 8.7 Hz, 2H)
IR (KBr) 3433, 1612, 1589, 1523, 1488, 1403, 1241, 1224, 1192, 1113, 1070, 1011, 826 cm$^{-1}$

TABLE 247

I-1246 foam
$^1$H NMR (CDCl$_3$) δ 3.45 (s, 3H), 3.75 (s, 3H), 4.93 (s, 2H), 5.70 (d, J = 1.5 Hz, 1H), 5.75 (d, J = 1.5 Hz, 1H), 6.45 (s, 1H), 6.92 (d, J = 8.7 Hz, 2H), 6.99 (dd, J = 8.4, 2.1 Hz, 1H), 7.05 (d, J = 8.4 Hz, 1H), 7.10 (d, J = 2.1 Hz, 1H), 7.54 (d, J = 8.7 Hz, 2H)
IR (KBr) 3432, 1611, 1590, 1523, 1489, 1403, 1224, 1193, 1113, 1071, 1010, 938, 826 cm$^{-1}$ I-1247 foam
$^1$H NMR (CDCl$_3$) δ 3.45 (s, 3H), 3.75 (s, 3H), 5.53 (d, J = 10.5 Hz, 1H), 5.69 (d, J = 16.5 Hz, 1H), 6.11 (ddd, J = 16.5, 10.5, 6.3 Hz, 1H), 6.44 (d, J = 6.3 Hz, 1H), 6.45 (s, 1H), 6.88 (d, J = 8.4 Hz, 2H), 6.91 ~ 6.93 (m, 2H), 6.92 (d, J = 8.7 Hz, 2H), 7.53 (d, J = 8.7 Hz, 2H)
IR (KBr) 3433, 1611, 1592, 1522, 1485, 1403, 1226, 1106, 1059, 814 cm$^{-1}$ I-1248 foam
$^1$H NMR (CDCl$_3$) δ 1.16 (t, J = 7.5 Hz, 3H), 2.26 (tq, J = 2.1, 7.5 Hz, 2H), 3.45 (s, 3H), 3.75 (s, 3H), 4.76 (t, J = 2.1 Hz, 2H), 6.45 (s, 1H), 6.91 (d, J = 8.7 Hz, 2H), 6.96 (dd, J = 2.1, 8.4 Hz, 1H), 7.06 (d, J = 8.4 Hz, 1H), 7.07 (d, J = 2.1 Hz, 1H), 7.53 (d, J = 8.7 Hz, 2H)
IR (KBr) 3434, 2230, 1612, 1590, 1523, 1479, 1225, 1113, 1070, 1005, 938, 815 cm$^{-1}$ I-1249 foam
$^1$H NMR (CDCl$_3$) δ 3.38 (s, 3H), 3.67 (s, 3H), 5.12 (s, 2H), 6.43 (s, 1H), 6.56 (d, J = 3.3 Hz, 1H), 6.79 (dd, J = 2.1, 8.1 Hz, 1H), 6.84 (d, J = 8.7 Hz, 2H), 6.87 (d, J = 2.1 Hz, 1H), 7.02 (d, J = 3.3 Hz, 1H), 7.02 (d, J = 8.1 Hz, 1H), 7.45 (d, J = 8.7 Hz, 2H)
IR (KBr) 3431, 1698, 1611, 1523, 1489, 1405, 1246, 1114, 1071, 1012, 816, 786 cm$^{-1}$

TABLE 247-continued

I-1250  $^1$H NMR (CDCl$_3$) δ 3.38 (s, 3H), 3.67 (s, 3H), 4.66 (tt, J = 2.7, 6.9 Hz, 2H), 4.90 (tt, J = 2.7, 6.9 Hz, 2H), 5.43 (tt, J = 6.9, 6.9 Hz, 1H), 6.45 (s, 1H), 6.92 (d, J = 8.7 Hz, 2H), 6.96 (br.s, 2H), 7.07 (s, 1H), 7.53 (d, J = 8.7 Hz, 2H)
IR (KBr) 3430, 1955, 1612, 1589, 1522, 1489, 1404, 1248, 1113, 1070, 1008, 938, 845, 825 cm$^{-1}$

TABLE 248

I-1251  foam
  $^1$H NMR (CDCl$_3$) δ 1.69 (dd, J = 3.3, 6.9 Hz, 3H), 3.46 (s, 3H), 3.74 (s, 3H), 4.63 (dd, J = 2.4, 6.3 Hz, 2H), 5.28 (m, 1H), 5.33 (m, 1H), 6.45 (s, 1H), 6.92 (d, J = 8.7 Hz, 2H), 6.95 (d, J = 1.5 Hz, 1H), 6.96 (br.s, 1H), 7.06 (d, J = 1.5 Hz, 1H), 7.52 (d, J = 8.7 Hz, 2H)
  IR (KBr) 3436, 2933, 1968, 1612, 1587, 1523, 1489, 1464, 1404, 1112, 1071, 1011, 998, 824 cm$^{-1}$ I-1252  foam
  $^1$H NMR (CDCl$_3$) δ 1.02 (t, J = 7.2 Hz, 3H), 2.05 (ddq, J = 3.3, 6.3, 7.2 Hz, 2H), 3.46 (s, 3H), 3.74 (s, 3H), 4.64 (dd, J = 2.4, 6.0 Hz, 2H), 5.40 (m, 2H), 6.45 (s, 1H), 6.91 (d, J = 8.7 Hz, 2H), 6.94 (d, J = 2.1, 8.4 Hz, 1H), 6.97 (d, J = 8.4 Hz, 1H), 7.06 (d, J = 2.1 Hz, 1H), 7.54 (d, J = 8.7 Hz, 2H)
  IR (KBr) 3479, 2960, 2933, 1964, 1612, 1582, 1522, 1489, 1403, 1242, 1113, 1072, 1011, 999, 944, 872 cm$^{-1}$ I-1253  foam
  $^1$H NMR (CDCl$_3$) δ 1.03 (d, J = 6.6 Hz, 6H), 2.34 (m, 1H), 3.46 (s, 3H), 3.74 (s, 3H), 4.63 (dd, J = 2.7, 6.3 Hz, 2H), 5.33 (m, 1H), 5.44 (m, 1H), 6.45 (s, 1H), 6.92 (d, J = 8.7 Hz, 2H), 6.93 (d, J = 1.8, 7.8 Hz, 1H), 6.97 (d, J = 7.8 Hz, 1H), 7.06 (d, J = 1.8 Hz, 1H), 7.53 (d, J = 8.7 Hz, 2H)
  IR (KBr) 3434, 2958, 1960, 1612, 1589, 1523, 1489, 1226, 1113, 1071, 1011, 939, 825 cm$^{-1}$ I-124  foam
  $^1$H NMR (CDCl$_3$) δ 2.62 (d, J = 2.4 Hz, 1H), 3.45 (s, 3H), 3.75 (s, 3H), 4.18 (dd, J = 7.2, 11.4 Hz, 1H), 4.38 (dd, J = 2.4, 11.4 Hz, 1H), 4.94 (ddd, J = 2.4, 2.4, 7.2 Hz, 1H), 6.44 (s, 1H), 6.92 (d, J = 8.7 Hz, 2H), 6.98 (d, J = 8.4 Hz, 1H), 7.01 (d, J = 1.8, 8.4 Hz, 1H), 7.08 (d, J = 1.8 Hz, 1H), 7.52 (d, J = 8.7 Hz, 2H)
  IR (KBr) 3434, 3283, 2127, 1612, 1586, 15323, 1487, 1226, 1115, 1069, 1007, 943, 825 cm$^{-1}$

TABLE 249

I-1255  mp 148–150° C.
  $^1$H NMR (CDCl$_3$) δ 2.99 (s, 6H), 3.75–3.80 (br, 2H), 3.75 (s, 3H), 3.77 (s, 3H), 6.45–6.53 (m, 2H), 6.79–6.83 (m, 2H), 6.88 (s, 1H), 6.95 (s, 1H), 7.17–7.23 (m, 1H), 7.48–7.51 (m, 2H)
  IR (KBr) 3600–2800(br), 1630, 1609, 1530, 1492, 1461, 1444, 1388, 1331, 1209, 1165, 1125, 1050, 1028 cm$^{-1}$

I-1256  mp 209–212° C.
  $^1$H NMR (CDCl$_3$) δ 3.00 (s, 6H), 3.11 (s, 3H), 3.76 (s, 3H), 3.79 (s, 3H), 6.66 (br s, 1H), 6.78–6.83 (m, 2H), 6.87 (s, 1H), 6.98 (s, 1H), 7.02 (dd, J = 2.4, 8.4 Hz, 1H), 7.10 (d, J = 2.4, 10.8 Hz, 1H), 7.39–7.52 (m, 3H)
  IR (KBr) 3600–2800(br), 1627, 1609, 1530, 1494, 1463, 1390, 1325, 1213, 1154, 1127, 1052, 1028, 984 cm$^{-1}$

I-1257  mp 198–200° C.
  $^1$H NMR (CDCl$_3$) δ 1.43 (t, J = 7.5 Hz, 3H), 3.00 (s, 3H), 3.19–3.26 (m, 2H), 3.76 (s, 3H), 3.79 (s, 3H), 6.69 (br s, 1H), 6.79–6.85 (m, 2H), 6.86 (s, 1H), 6.97 (s, 1H), 7.01 (dd, J = 2.4, 8.4 Hz, 1H), 7.09 (dd, J = 2.4, 10.8 Hz, 1H), 7.37–7.53 (m, 3H)
  IR (KBr) 3600–2800(br), 1611, 1530, 1492, 1495, 1445, 1389, 1355, 1325, 1207, 1163, 1141, 1122, 1051, 1025, 981 cm$^{-1}$

I-1258  IR (KBr) 1612, 1526, 1490, 1444, 1349, 1301, 1196, 1129.1038 cm$^{-1}$
  mp 102–103° C.
  $^1$H NMR (CDCl$_3$) δ 2.27 (s, 3H), 2.31 (s, 3H), 3.00 (s, 6H), 4.78 (d, J = 6.6 Hz, 2H), 6.24 (t, J = 6.6 Hz, 1H), 6.80 (d, J = 8.4 Hz, 2H), 6.96–7.16 (m, 5H), 7.26 (d, J = 8.4 Hz, 2H)

TABLE 249-continued

I-1259  mp 114–115° C.
  $^1$H NMR (CDCl$_3$) δ 1.75 (s, 3H), 1.79 (s, 3H), 3.61 (s, 3H), 3.65 (s, 3H), 3.74 (s, 3H), 3.87 (s, 3H), 3.88 (s, 3H), 4.63 (d, J = 6.9 Hz, 2H), 5.54–5.62 (m, 1H), 6.68 (s, 1H), 6.94–7.03 (m, 5H), 7.54 (d, J = 9.0 Hz, 2H)
  IR (KBr) 3433, 2932, 1682, 1605, 1580, 1519, 1465, 1439, 1389, 1290, 1253, 1237, 1186, 1140, 1109, 1089, 1039, 1029, 992, 833 cm$^{-1}$

TABLE 250

I-1260  mp 163–165° C.
  $^1$H NMR (CDCl$_3$) δ 1.76 (s, 3H), 1.81 (s, 3H), 3.19 (s, 3H), 3.72 (s, 3H), 4.20–4.26 (m, 4H), 4.62 (d, J = 6.6 Hz, 2H), 5.55 (m, 1H), 6.53 (s, 1H), 7.00–7.20 (m, 3H), 7.49 (ABq, J = 8.1 Hz, 4H)
  IR (KBr) 3433, 2933, 1523, 1483, 1463, 1433, 1371, 1359, 1340, 1299, 1266, 1227, 1220, 1172, 1149, 1127, 1098 cm$^{-1}$

I-1261  mp 135–137° C.
  $^1$H NMR (CDCl$_3$) δ −0.03–0.03 (m, 2H), 0.36–0.42 (m, 2H), 1.00 (m, 1H), 1.75 (s, 3H), 1.79 (s, 3H), 2.56 (s, 3H), 3.20 (s, 3H), 3.48 (d, J = 4.8 Hz, 2H), 3.78 (s, 3H), 3.88 (s, 3H), 4.63 (d, J = 6.9 Hz, 2H), 5.54 (m, 1H), 6.86 (s, 1H), 6.95–6.97 (m, 3H), 7.55 (ABq, J = 8.7 Hz, 4H)
  IR (KBr) 3433, 2936, 1604, 1519, 1481, 1467, 1369, 1336, 1245, 1231, 1201, 1177, 1153, 1081 cm$^{-1}$

I-1262  mp 181–182° C.
  $^1$H NMR (CDCl$_3$) δ 1.76 (s, 3H), 1.80 (s, 3H), 3.72 (s, 3H), 4.19–4.26 (m, 4H), 4.62 (d, J = 6.9 Hz, 2H), 4.91 (bs, 1H), 5.55 (m, 1H), 6.53 (s, 1H), 6.89–7.49 (m, 7H)
  IR (KBr) 3404, 1612, 1523, 1485, 1462, 1434, 1373, 1266, 1227, 1212, 1116, 1101 cm$^{-1}$

I-1263  mp 80–82° C.
  $^1$H NMR (CDCl$_3$) δ −0.05–0.09 (m, 2H), 0.44–0.51 (m, 2H), 1.04 (m., 1H), 1.74 (s, 3H), 1.78 (s, 3H), 3.33 (d, J = 4.8 Hz, 2H), 3.75 (s, 3H), 3.88 (s, 3H), 4.63 (d, J = 6.6 Hz, 2H), 4.98 (s, 1H), 5.57 (m, 1H), 6.15 (s, 1H), 6.46 (s, 1H), 6.89–7.03 (m, 5H), 7.52–7.56 (m, 2H)
  IR (KBr) 3374, 1614, 1523, 1490, 1465, 1446, 1391, 1267, 1235, 1172, 1113, 1073 cm$^{-1}$

I-1264  mp 112–113° C.
  $^1$H NMR (CDCl$_3$) δ 2.19 (s, 3H), 2.28 (s, 3H), 3.91 (s, 3H), 5.20 (s, 2H), 6.84–6.86 (m, 1H), 6.92–6.97 (m, 2H), 7.09 (s, 1H), 7.16 (s, 1H), 7.31–7.43 (m, 5H), 7.47–7.49 (m, 2H), 7.60 (d, J = 10.2 Hz, 1H), 8.01 (brs, 1H)
  IR(KBr) 3421, 3303, 2935, 1711, 1519, 1490, 1365, 1231, 1198, 1178, 1134, 1009, 864 cm$^{-1}$

TABLE 251

I-1265  mp 85–86° C.
  $^1$H NMR (CDCl$_3$) δ 2.85 (s, 3H), 3.32 (s, 3H), 3.82 (s, 3H), 3.96 (s, 3H), 5.38 (s, 2H), 7.04 (s, 1H), 7.22 (s, 1H), 7.25 (d, J = 8.4 Hz, 1H), 7.35 (d, J = 8.4 Hz, 1H), 7.48–7.67 (m, 7H), 8.45 (brs, 1H)
  IR(KBr) 3432, 2938, 1740, 1608, 1517, 1483, 1396, 1366, 1271, 1179, 1111, 1080, 832, 810, 698 cm$^{-1}$ I-1266  mp 79–80° C.
  $^1$H NMR (CDCl$_3$) δ 2.14 (s, 3H), 3.50 (s, 3H), 4.95 (brs, 1H), 5.22 (s, 2H), 5.88 (brs, 1H), 6.81 (s, 1H), 6.94 (d, J = 8.1 Hz, 2H), 7.02–7.14 (m, 3H), 7.37–7.56 (m, 7H)
  IR(KBr) 3409, 2933, 1612, 1522, 1488, 1454, 1400, 1266, 1229, 1199, 1162, 1007, 834, 696 cm$^{-1}$ I-1267  mp 87–88° C.
  $^1$H NMR (CDCl$_3$) δ 2.13 (s, 3H), 2.59 (s, 3H), 3.20 (s, 3H), 3.55 (s, 3H), 5.22 (s, 2H), 6.99–7.17 (m, 5H), 7.34–7.48 (m, 6H), 7.67 (d, J = 8.4 Hz, 2H)
  IR(KBr) 3428, 2931, 1612, 1522, 1488, 1454, 1400, 1266, 1230, 1163, 1007, 835 cm$^{-1}$

TABLE 251-continued

I-1268 mp 76–77° C.
$^1$H NMR (CDCl$_3$) δ 1.72 (s, 3H), 1.77 (s, 6H), 1.81 (s, 3H), 2.69 (s, 3H), 3.24 (s, 3H), 3.61 (s, 3H), 3.79 (s, 3H), 4.12–4.20 (m, 1H), 4.55–4.61 (m, 1H), 4.64 (d, J = 6.6 Hz, 2H), 5.25 (t, J = 7.5 Hz, 1H), 5.50 (t, J = 6.4 Hz, 1H), 6.85 (s, 1H), 7.05–7.11 (m, 2H), 7.34–7.40 (m, 3H)
IR(KBr) 3423, 2939, 1707, 1521, 1484, 1367, 1241, 1178, 1079, 1034, 972, 799, 521 cm$^{-1}$

I-1269 mp 73–74° C.
$^1$H NMR (CDCl$_3$) δ 2.17 (s, 3H), 2.28 (s, 3H), 5.16 (s, 2H), 5.71 (brs, 1H), 6.83 (d, J = 8.1 Hz, 1H), 6.97–7.00 (m, 2H), 7.08 (s, 1H), 7.15 (s, 1H), 7.32–7.33 (m, 2H), 7.36–7.45 (m, 5H), 7.60 (d, J = 10.5 Hz, 1H), 8.05 (brs, 1H)
IR(KBr) 3410, 2923, 1718, 1606, 1540, 1521, 1489, 1424, 1282, 1179, 976, 728 cm$^{-1}$

TABLE 252

I-1270 mp 65–67° C.
$^1$H NMR (CDCl$_3$) δ 1.77 (s, 3H), 1.81 (s, 3H), 2.14 (s, 3H), 2.72 (s, 3H), 3.20 (s, 3H), 3.56 (s, 3H), 4.64 (d, J = 6.9 Hz, 2H), 5.53 (t, J = 6.6 Hz, 1H), 7.01–7.11 (m, 3H), 7.18 (s, 1H), 7.37 (d, J = 8.7 Hz, 2H), 7.67 (d, J = 8.7 Hz, 2H),..
IR(KBr) 3434, 2938, 1519, 1478, 1365, 1267, 1176, 1151, 968, 871, 799, 524 cm$^{-1}$

I-1271 mp 99–100° C.
$^1$H NMR (CDCl$_3$) δ 1.76 (s, 6H), 1.79 (s, 3H), 1.81 (s, 3H), 3.52 (s, 3H), 3.72 (s, 3H), 4.61 (d, J = 7.2 Hz, 2H), 5.36 (t, J = 6.6 Hz, 1H), 5.53 (t, J = 5.7 Hz, 1H), 5.69 (brs, 1H), 5.81 (brs, 1H), 6.43 (s, 1H), 6.46–6.52 (m, 1H), 6.95 (s, 2H), 7.05 (s, 1H), 7.10–7.16 (m, 1H)
IR(KBr) 3496, 3407, 2933, 1638, 1535, 1493, 1098, 1000 cm$^{-1}$ I-1272 mp 75–76° C.
$^1$H NMR (CDCl$_3$) δ 2.17 (s, 3H), 2.28 (s, 3H), 3.12 (s, 3H), 5.18 (s, 2H), 7.09–7.14 (m, 4H), 7.26–7.47 (m, 8H), 7.61 (d, J = 11.4 Hz, 1H), 8.00 (brs, 1H)
IR(KBr) 3330, 2927, 1731, 1607, 1541, 1521, 1488, 1364, 1290, 1169, 1105, 975, 878, 811 cm$^{-1}$ I-1273 mp 112–113° C.
$^1$H NMR (CDCl$_3$) δ 1.76 (s, 3H), 1.81 (s, 3H), 2.11 (s, 3H), 3.47 (s, 3H), 4.64 (d, J = 6.6 Hz, 2H), 4.83 (brs, 1H), 5.56 (t, J = 7.2 Hz, 1H), 5.84 (brs, 1H), 6.78 (s, 1H), 6.91 (d, J = 8.7 Hz, 2H), 7.02–7.10 (m, 3H), 7.51 (d, J = 8.4 Hz, 2H),..
IR(KBr) 3498, 2978, 1613, 1522, 1487, 1453, 1302, 1204, 1232, 1196, 987, 812 cm$^{-1}$ I-1274 oil
$^1$H NMR (CDCl$_3$) δ 1.73 (s, 3H), 1.76 (s, 3H), 1.77 (s, 3H), 1.79 (s, 3H), 2.22 (s, 3H), 2.27 (s, 3H), 3.73 (d, J = 6.0 Hz, 2H), 3.88 (s, 3H), 4.63 (d, J = 6.6 Hz, 2H), 5.36 (t, J = 6.0 Hz, 1H), 5.57 (t, J = 6.6 Hz, 1H), 6.40–6.51 (m, 2H), 6.87–6.95 (m, 3H), 7.05–7.14 (m, 3H)
IR(CHCl$_3$) 3021, 2934, 1628, 1523, 1492, 1235, 1219, 1139 cm$^{-1}$

TABLE 253

I-1275 mp 64–65° C.
$^1$H NMR (CDCl$_3$) δ 1.74 (s, 3H), 1.77 (s, 6H), 1.82 (s, 3H), 2.16 (s, 3H), 2.29 (s, 3H), 3.23 (s, 3H), 4.36 (d, J = 7.5 Hz, 2H), 4.64 (d, J = 6.3 Hz, 2H), 5.28 (t, J = 8.4 Hz, 1H), 5.51 (t, J = 6.3 Hz, 1H), 7.01–7.16 (m, 6H), 7.24–7.35 (m, 2H)
IR(KBr) 3422, 2926, 1698, 1519, 1489, 1367, 1209, 1170, 962, 807 cm$^{-1}$

I-1276 oil
$^1$H NMR (CDCl$_3$) δ 2.21 (s, 3H), 2.26 (s, 3H), 3.95 (d, J = 6.6 Hz, 2H), 4.28 (brs, 1H), 4.78 (d, J = 6.0 Hz, 2H), 6.05 (t, J = 6.3 Hz, 1H), 6.24 (t, J = 6.0 Hz, 1H), 6.36–6.49 (m, 2H), 6.97–7.15 (m, 6H)
IR(CHCl$_3$) 3446, 3009, 1628, 1525, 1492, 1274, 1224, 1130, 883 cm$^{-1}$

TABLE 253-continued

I-1277 mp 64–65° C.
$^1$H NMR (CDCl$_3$) δ 1.76 (s, 3H), 1.80 (s, 6H), 1.85 (s, 3H), 2.23 (s, 3H), 2.30 (s, 3H), 3.74 (d, J = 6.3 Hz, 2H), 4.64 (d, J = 6.0 Hz, 2H), 5.38 (t, J = 6.6 Hz, 1H), 5.55 (t, J = 6.9 Hz, 1H), 5.73 (brs, 1H), 6.41–6.50 (m, 2H), 6.84–7.15 (m, 6H)
IR(KBr) 3354, 2971, 1627, 1522, 1490, 1274, 1200, 1128, 990, 843 cm$^{-1}$ I-1278 mp 153–154° C.
$^1$H NMR (CDCl$_3$) δ 1.77 (s, 3H), 1.82 (s, 3H), 1.95 (s, 12H), 4.64 (d, J = 6.9 Hz, 2H), 4.78 (s, 1H), 5.57 (t, J = 6.9 Hz, 1H), 6.85 (ddd, J = 8.3, 2.1, 1.2 Hz, 1H), 6.90 (d, J = 8.6 Hz, 2H), 6.92 (dd, J = 12.0, 2.1 Hz, 1H), 7.04 (d, J = 8.6 Hz, 2H), 7.04 (t, J = 8.3 Hz, 1H),
IR (KBr) 3433, 1514, 1293, 1262, 1242, 1112, 984 cm$^{-1}$ I-1279 mp 115–117° C.
$^1$H NMR (CDCl$_3$) δ 1.76 (s, 3H), 1.81 (s, 3H), 2.23 (s, 3H), 3.21 (s, 3H), 3.81 (s, 3H), 4.63 (d, J = 6.6 Hz, 2H), 5.55 (t, J = 6.6 Hz, 1H), 6.81 (s, 1H), 7.02 (t, J = 8.6 Hz, 1H), 7.20 (s, 1H), 7.24–7.28 (m, 1H), 7.33–7.44 (m, 3H)
IR (KBr) 3434, 1522, 1492, 1337, 1218, 1200, 1148, 979, 876 cm$^{-1}$

TABLE 254

I-1280 mp 88–90° C.
$^1$H NMR (CDCl$_3$) δ 1.76 (s, 3H), 1.80 (s, 3H), 2.24 (s, 3H), 3.80 (s, 3H), 4.63 (d, J = 6.7 Hz, 2H), 4.88 (br s, 1H), 5.55 (t, J = 6.7 Hz, 1H), 6.83 (s, 1H), 6.90 (d, J = 8.7 Hz, 2H), 7.01 (t, J = 8.6 Hz, 1H), 7.18 (s, 1H), 7.24–7.28 (m, 3H), 7.36 (dd, J = 12.9, 2.1 Hz, 1H)
IR (KBr) 3400, 1523, 1493, 1263, 1217, 1128, 977, 836 cm$^{-1}$

I-1281 mp 158–159° C.
$^1$H NMR (CDCl$_3$) δ 1.76 (s, 3H), 1.80 (d, J = 0.3 Hz, 3H), 2.10 (s, 3H), 2.34 (s, 3H), 2.50 (s, 3H), 3.87 (s, 3H), 4.63 (d, J = 6.9 Hz, 2H), 5.14 (s, 1H), 5.55 (m, 1H), 5.88 (s, 1H), 6.77–6.82 (m, 2H), 6.85–6.91 (m, 2H), 6.98 (d, J = 8.1 Hz, 1H), 7.13 (s, 1H), 7.18–7.24 (m, 2H)
IR (KBr) 3465, 1610, 1516, 1473, 1382, 1322, 1307, 1266, 1240, 1213, 1179, 1168, 1147, 1100, 982, 836 cm$^{-1}$

I-1282 mp 85–86° C.
$^1$H NMR (CDCl$_3$) δ 0.99 (d, J = 6.2 Hz, 6H), 1.71–1.98 (m, 3H), 2.27 (s, 3H), 2.29 (s, 3H), 3.20 (s, 3H), 3.88 (s, 3H), 4.10 (t, J = 6.8 Hz, 2H), 6.88 (d, J = 2.0, 8.6 Hz, 1H), 6.88 (d, J = 2.0 Hz, 1H), 6.95 (d, J = 8.6 Hz, 1H), 7.30–7.46 (m, 4H)
IR (KBr) 1519, 1488, 1375, 1255, 1243, 1214, 1204, 1173, 1154, 1134, 867, 850, 792 cm$^{-1}$

I-1283 mp 117–118° C.
$^1$H NMR (CDCl$_3$) δ 0.99 (d, J = 6.3 Hz, 6H), 1.75–1.94 (m, 3H), 2.27 (s, 3H), 2.28 (s, 3H), 3.88 (s, 3H), 4.10 (t, J = 6.6 Hz, 2H), 4.91 (s, 1H), 6.86–6.91 (m, 4H), 6.94 (d, J = 8.7 Hz, 1H), 7.12 (s, 1H), 7.15 (m, 1H), 7.22–7.27 (m, 2H)
IR (KBr) 3438, 1611, 1522, 1490, 1475, 1464, 1446, 1256, 1242, 1212, 1180, 1171, 1137, 1032, 834, 818 cm$^{-1}$

I-1284 mp 156–157° C.
$^1$H NMR (CDCl$_3$) δ 3.46 (s, 3H), 3.76 (s, 3H), 3.89 (s, 3H), 4.78 (d, J = 6.3 Hz, 2H), 4.99 (s, 1H), 5.96 (s, 1H), 6.25 (t, J = 6.3 Hz, 1H), 6.47 (s, 1H), 6.90–6.95 (m, 2H), 6.93 (d, J = 7.8 Hz, 1H), 7.04 (dd, J = 2.1, 7.8 Hz, 1H), 7.04 (d, J = 2.1 Hz, 1H), 7.51–7.57 (m, 2H)
IR (KBr) 3455, 1612, 1522, 1487, 1456, 1396, 1269, 1234, 1223, 1209, 1173, 1140, 1115, 1024, 885, 825, 813 cm$^{-1}$

TABLE 255

I-1285 mp 84–85° C.
$^1$H NMR (CDCl$_3$) δ 1.00 (d, J = 6.6 Hz, 6H), 1.71–1.96 (m, 3H), 2.27 (s, 6H), 4.11 (t, J = 6.9 Hz, 2H), 4.80 (br s, 1H), 6.86–6.92 (m, 2H), 6.97–7.14 (m, 5H), 7.22–7.27 (m, 2H)
IR (KBr) 3389, 1523, 1491, 1476, 1427, 1301, 1276, 1233, 1196, 1168, 1126, 836, 815 cm$^{-1}$

TABLE 255-continued

I-1286  mp 152–153° C.
¹H NMR (CDCl₃) δ 1.76 (s, 3H), 1.80 (d, J = 0.6 Hz, 3H), 2.12 (s, 3H), 2.20 (s, 3H), 3.39 (s, 3H), 3.87 (s, 3H), 4.64 (d, J = 6.3 Hz, 2H), 4.79 (br s, 1H), 5.56–5.61 (m, 1H), 6.82–6.97 (m, 6H), 7.21–7.26 (m, 2H)
IR (CHCl₃) 3596, 3440, 3011, 2935, 1676, 1612, 1588, 1518, 1473, 1449, 1259, 1238, 1173 cm⁻¹

I-1287  mp 123–125° C.
¹H NMR (CDCl₃) δ −0.01–0.08 (m, 2H), 0.44–0.50 (m, 2H), 1.01 (m, 1H), 3.21 (s, 3H), 3.34 (d, J = 7.5 Hz, 2H), 3.75 (s, 3H), 3.91 (s, 3H), 5.21 (s, 2H), 6.08 (s, 1H), 6.45 (s, 1H), 6.97–7.04 (m. 3H), 7.26–7.72 (m, 9H)

I-1288  mp 177–178° C.
¹H NMR (CDCl₃) δ 0.27 (t, J = 4.8 Hz, 1H), 0.60 (dd, J = 4.8, 8.7 Hz, 1H), 1.13 (s, 3H), 1.17 (s, 3H), 1.13–1.22 (m, 1H), 3.46 (s, 3H), 3.75 (s, 3H), 3.80 (s, 3H), 4.00 (dd, J = 7.8, 10.5 Hz, 1H), 4.12 (dd, J = 6.6, 10.5 Hz, 1H), 4.95 (bs, 1H), 5.91 (s, 1H), 6.46 (s, 1H), 6.91–7.02 (m, 5H), 7.52–7.56 (m, 2H)
IR (KBr) 3479, 3434, 3389, 2940, 1614, 1589, 1523, 1490, 1466, 1395, 1361, 1319, 1271, 1238, 1218, 1174, 1137, 1117, 1072, 1011 cm⁻¹

I-1289  mp 153–155° C.
¹H NMR (CDCl₃) δ 1.76 (s, 3H), 1.80 (s, 3H), 2.25 (s, 3H), 3.80 (s, 3H), 3.89 (s, 3H), 4.63–4.65 (d, J = 6.6 Hz, 2H), 4.80 (br, 1H), 5.57 (m, 1H), 6.86–6.97 (m, 6H), 7.18 (s, 1H), 7.45–7.48 (m, 2H)
IR (CHCl₃) 3596, 1609, 1523, 1493, 1464, 1387, 1256, 1173, 1138, 1042, 1032, 997, 834 cm⁻¹

TABLE 256

I-1290  mp 150–152° C.
¹H NMR (CDCl₃) δ 2.25 (s, 3H), 3.80 (s, 3H), 3.90 (s, 3H), 4.74–4.80 (m, 3H), 6.26 (t, J = 6.0 Hz, 1H), 6.85–6.92 (m, 6H), 7.19 (s, 1H), 7.45–7.48 (m, 2H)
IR (CHCl₃) 3596, 2958, 2938, 1609, 1523, 1493, 1464, 1389, 1328, 1257, 1173, 1140, 1102, 1030, 886, 854, 834 cm⁻¹

I-1291  mp 117–118° C.
¹H NMR (CDCl₃) δ 1.76 (s, 3H), 1.79 (s, 3H), 2.28 (s, 3H), 2.31 (s, 3H), 3.01 (s, 6H), 3.88 (s, 3H), 4.63 (d, J = 6.6 Hz, 2H), 5.53–5.60 (m, 1H), 6.76–6.96 (m, 5H), 7.15 (s, 2H), 7.28 (d, J = 8.7 Hz, 2H)
IR (KBr) 1611, 1529, 1490, 1447, 1359, 1322, 1239, 1214, 1193, 1135, 1038, cm⁻¹

I-1292  mp 116–118° C.
¹H NMR (CDCl₃) 2.24 (s, 3H), 3.81 (s, 3H), 4.77 (d, J = 6.3 Hz, 2H), 4.90 (br s, 1H), 6.23 (t, J = 6.3 Hz, 1H), 6.83 (s, 1H), 6.90 (d, J = 8.7 Hz, 2H), 6.99 (t, J = 8.6 Hz, 1H), 7.17 (s, 1H), 7.25 (d, J = 8.7 Hz, 2H), 7.27 (ddd, J = 8.6, 2.1, 1.2 Hz, 1H), 7.37 (dd, J = 12.6, 2.1 Hz, 1H)
IR (KBr) 3596, 1731, 1613, 1523, 1493, 1259, 1130, 1033, 885 cm⁻¹

I-1293  mp 151–154° C.
¹H NMR (CDCl₃) δ 2.23 (s, 3H), 3.21 (s, 3H), 3.80 (s, 3H), 3.93 (s, 3H), 5.20 (s, 2H), 6.81 (s, 1H), 6.95 (d, J = 8.4 Hz, 1H), 7.05 (dd, J = 8.4, 2.1 Hz, 1H), 7.15 (d, J = 2.1 Hz, 1H), 7.21 (s, 1H), 7.30–7.50 (m, 9H)
IR (KBr) 1490, 1361, 1243, 1148, 1032, 876 cm⁻¹

I-1294  mp 119–121° C.
¹H NMR (CDCl₃) δ 1.76 (s, 3H), 1.79 (s, 3H), 2.24 (s, 3H), 3.21 (s, 3H), 3.80 (s, 3H), 3.91 (s, 3H), 4.63 (d, J = 6.5 Hz, 2H), 5.56 (t, J = 6.5 Hz, 1H), 6.82 (s, 1H), 6.94 (d, J = 8.4 Hz, 2H), 7.10 (dd, J = 8.4, 1.5 Hz, 1H), 7.13 (d, J = 1.5 Hz, 1H), 7.23 (s, 1H), 7.36 (d, J = 8.3 Hz, 2H), 7.43 (d, J = 8.3 Hz, 2H)
IR (KBr) 1519, 1490, 1364, 1156, 1031, 971, 858 cm⁻¹

TABLE 257

I-1295  mp 135–137° C.
¹H NMR (CDCl₃) δ 1.75 (s, 3H), 1.78 (s, 3H), 2.25 (s, 3H), 3.80 (s, 3H), 3.90 (s, 3H), 4.63 (d, J = 6.7 Hz, 2H), 4.95 (s, 1H), 5.56 (t, J = 6.7 Hz, 1H), 6.84 (d, J = 8.7 Hz, 2H), 6.94 (d, J = 8.3 Hz, 1H), 7.10 (dd, J = 8.3, 2.1 Hz, 1H), 7.13 (d, J = 2.1 Hz, 1H), 7.21 (s, 1H), 7.26 (d, J = 8.7 Hz, 2H)
IR (KBr) 3423, 1609, 1523, 1493, 1258, 1219, 1142, 1033, 834 cm⁻¹

I-1296  mp 140–141° C.
¹H NMR (CDCl₃) δ 1.46 (t, J = 6.9 Hz, 3H), 3.46 (s, 3H), 3.75 (s, 3H), 4.13 (q, J = 6.9 Hz, 2H), 4.77 (d, J = 6.0 Hz, 2H), 5.05 (s, 1H), 5.95 (s, 1H), 6.25 (t, J = 6.0 Hz, 1H), 6.47 (s, 1H), 6.90–6.97 (m, 3H), 7.01–7.06 (m, 2H), 7.50–7.57 (m, 2H)
IR (KBr) 3463, 3433, 1613, 1521, 1491, 1259, 1400, 1267, 1235, 1204, 1167, 1136, 1112, 1097, 1076, 1019, 993, 882, 824, 811 cm⁻¹

I-1297  mp 204–205° C.
¹H NMR (DMSO-d₆) δ 2.21 (s, 3H), 2.22 (s, 3H), 2.87 (s, 3H), 3.02 (s, 3H), 4.96 (s, 2H), 6.80–6.86 (m, 2H), 7.05–7.11 (m, 4H), 7.13–7.19 (m, 2H), 7.20–7.27 (m, 1H)
IR (KBr) 3153, 1644, 1590, 1522, 1487, 1437, 1314, 1264, 1231, 1197, 1127, 1067, 833 cm⁻¹

I-1298  mp 155–158° C.
¹H NMR (CDCl₃) δ 3.21 (s, 3H), 3.45 (s, 3H), 3.75 (s, 3H), 4.42 (s, 4H), 5.93 (s, 1H), 6.44 (s, 1H), 6.90–6.96 (m, 1H), 7.06–7.11 (m, 1H), 7.19–7.39 (m, 13H), 7.67–7.72 (m, 2H)
IR (KBr) 3445, 2940, 1615, 1521, 1483, 1367, 1149, 875, 707, 546, 526 cm⁻¹

I-1299  mp 174–175° C.
¹H NMR (CDCl₃) δ 2.15 (s, 3H), 3.20 (s, 3H), 3.53 (s, 3H), 3.78 (s, 3H), 4.40 (s, 4H), 6.82 (s, 1H), 6.91–7.01 (m, 2H), 7.11–7.39 (m, 13H), 7.65–7.70 (m, 2H)
IR (KBr) 3028, 2936, 1618, 1520, 1482, 1365, 1176, 1151, 1079, 871, 798, 698, 527 cm⁻¹

TABLE 258

I-1300  mp 218–221° C.
¹H NMR (CDCl₃) δ 2.69 (s, 3H), 3.21 (s, 3H), 3.55 (s, 3H), 3.77 (s, 3H), 6.83 (s, 1H), 6.86–6.93 (m, 1H), 7.02–7.15 (m, 2H), 7.35–7.41 (m, 2H), 7.64–7.71 (m, 2H)
IR (KBr) 3435, 3389, 2940, 1635, 1525, 1362, 1175, 1152, 1076, 962, 874, 802, 527 cm⁻¹

I-1301  mp 209–211° C.
¹H NMR (CDCl₃) δ 2.91 (s, 3H), 3.22 (s, 3H), 3.54 (s, 3H), 3.78 (s, 3H), 6.86 (s, 1H), 7.26–7.33 (m, 2H), 7.37–7.42 (m, 2H), 7.64–7.71 (m, 2H), 8.15 (s, 1H), 8.34–8.41 (m, 1H)
IR (KBr) 3336, 2943, 1736, 1539, 1480, 1356, 1174, 1151, 1077, 881, 799, 523, 507 cm⁻¹

I-1302  powder
¹H NMR (CDCl₃) δ 1.50 (s, 3H), 1.71 (s, 3H), 2.78 (s, 3H), 3.23 (s, 3H), 3.55 (s, 3H), 3.78 (s, 3H), 4.11–4.20 (m, 1H), 4.54–4.63 (m, 1H), 5.20–5.28 (m, 1H), 6.87 (s, 1H), 7.25–7.31 (m, 3H), 7.37–7.42 (m, 2H), 7.66–7.72 (m, 2H)
IR (KBr) 2941, 1702, 1482, 1369, 1203, 1176, 1152, 1080, 964, 873, 797, 525 cm⁻¹

I-1303  mp 133–136° C.
¹H NMR (CDCl₃) δ 1.73 (s, 3H), 1.77 (s, 3H), 3.45 (s, 3H), 3.74–3.78 (m, 5H), 4.96 (s, 1H), 5.34–5.42 (m, 1H), 5.94 (s, 1H), 6.45 (s, 1H), 6.75–6.81 (m, 1H), 6.89–6.95 (m, 2H), 7.10–7.18 (m, 2H), 7.51–7.56 (m, 2H)
IR (KBr) 3401, 2935, 1626, 1614, 1527, 1490, 1402, 1267, 1223, 1113, 1071, 1005, 829, 589 cm⁻¹

I-1304  mp 170–171° C.
¹H NMR (CDCl₃) δ 2.11 (s, 3H), 3.47 (s, 3H), 4.40 (s, 4H), 4.91 (s, 1H), 5.81 (s, 1H), 6.77 (s, 1H), 6.86–7.08 (m, 5H), 7.22–7.33 (m, 10H), 7.48–7.53 (m, 2H)
IR (KBr) 3483, 3029, 1612, 1523, 1489, 1453, 1400, 1265, 1215, 834, 749, 698, 494, 526 cm⁻¹

TABLE 259

I-1305  mp 166–168° C.
¹H NMR (CDCl₃) δ 2.15 (s, 3H), 2.17 (s, 3H), 3.19 (s, 3H), 4.21–4.59 (m, 4H), 6.84–7.05 (m, 3H), 7.14–7.15 (m, 1H), 7.20–7.38 (m, 12H), 7.63–7.69 (m, 2H)

TABLE 259-continued

| | |
|---|---|
| | IR (KBr) 3028, 2938, 1519, 1476, 1454, 1363, 1174, 1151, 969, 873, 801, 700, 525 cm$^{-1}$ |
| I-1306 | mp 210–212° C.<br>$^1$H NMR (CDCl$_3$) δ 2.11 (s, 3H), 2.90 (s, 3H), 3.44 (s, 3H), 3.52 (s, 3H), 6.82–7.02 (m, 3H), 7.30 (s, 1H), 7.44–7.49 (m, 2H), 7.65–7.71 (m, 2H)<br>IR (KBr) 3401, 2850, 1632, 1478, 1365, 1177, 1151, 967, 877, 800, 526 cm$^{-1}$ |
| I-1307 | mp 171–173° C.<br>$^1$H NMR (CDCl$_3$) δ 2.13 (s, 3H), 2.95 (s, 3H), 3.22 (s, 3H), 3.55 (s, 3H), 7.17–7.22 (m, 3H), 7.35–7.41 (m, 2H), 7.64–7.69 (m, 2H), 8.17 (s, 1H), 8.37–8.43 (m, 1H)<br>IR (KBr) 3431, 3034, 2942, 1741, 1538, 1478, 1364, 1291, 1152, 971, 870, 801, 525 cm$^{-1}$ |
| I-1308 | powder<br>$^1$H NMR (CDCl$_3$) δ 1.47 (s, 3H), 1.70 (s, 3H), 2.11 (s, 3H), 2.67–3.15 (m, 3H), 3.22 (s, 3H), 3.56 (s, 3H), 4.13–4.22 (m, 1H), 4.54–4.63 (m, 1H), 5.21–5.28 (m, 1H), 7.09–7.42 (m, 6H), 7.63–7.71 (m, 2H)<br>IR (CHCl$_3$) 2940, 1700, 1519, 1478, 1372, 1175, 1151, 968 cm$^{-1}$ |
| I-1309 | mp 139–141° C.<br>$^1$H NMR (CDCl$_3$) δ 1.74 (s, 3H), 1.78 (s, 3H), 2.13 (s, 3H), 3.48 (s, 3H), 3.77 (d, J = 6.6 Hz, 2H), 4.70–5.20 (br s, 1H), 5.35–5.42 (m, 1H), 5.77 (s, 1H), 6.77–6.83 (m, 2H), 6.88–6.99 (m, 4H), 7.48–7.54 (m, 2H)<br>IR (KBr) 3525, 3377, 2931, 1625, 1526, 1488, 1222, 1164, 1011, 833 cm$^{-1}$ |

TABLE 260

| | |
|---|---|
| I-1310 | mp 177–179° C.<br>$^1$H NMR (CDCl$_3$) δ 1.76 (s, 3H), 1.81 (s, 3H), 3.20 (t, J = 8.4 Hz, 2H), 3.21 (t, J = 8.4 Hz, 2H), 4.521 (d, J = 7.2 Hz, 2H), 4.523 (t, J = 8.4 Hz, 2H), 4.90 (brs, 1H), 5.53 (t, J = 6.8 Hz, 1H), 6.71 (s, 1H), 6.89 (d, J = 8.4 Hz, 2H), 6.98 (d, J = 8.7 Hz, 2H), 7.41 (d, J = 8.7 Hz, 2H), 7.45 (d, J = 9.0 Hz, 2H)<br>IR (KBr) 3389, 2971, 2911, 1611, 1525, 1394, 1238, 1175, 997, 828 cm$^{-1}$ |
| I-1311 | mp 175–177° C.<br>$^1$H NMR (CDCl$_3$) δ 3.20 (t, J = 8.3 Hz, 4H), 4.53 (t, J = 8.4 Hz, 4H), 4.70 (d, J = 6.3 Hz, 2H), 4.88 (brs, 1H), 6.19 (t, J = 6.2 Hz, 1H), 6.89 (d, J = 8.7 Hz, 2H), 6.96 (d, J = 9.0 Hz, 2H), 7.41 (d, J = 9.0 Hz, 2H), 7.47 (d, J = 8.7 Hz, 2H)<br>IR (KBr) 3409, 3269, 2934, 2901, 1524, 1480, 1395, 1235, 1223, 1003, 881, 817 cm$^{-1}$ |
| I-1312 | mp 186–187° C.<br>$^1$H NMR (CDCl$_3$) δ 2.06 (s, 3H), 2.16 (s, 3H), 4.72 (s, 1H), 4.80 (d, J = 6.3 Hz, 2H), 4.83 (s, 1H), 6.25 (t, J = 6.3 Hz, 1H), 6.76 (s, 1H), 6.86–6.92 (m, 2H), 7.03–7.13 (m, 3H), 7.21–7.26 (m, 2H)<br>IR (CHCl$_3$) 3689, 3598, 3551, 3024, 3008, 1732, 1614, 1520, 1487, 1260, 1223 cm$^{-1}$ |
| I-1313 | mp 201° C.<br>$^1$H NMR (CDCl$_3$) δ 2.08 (s, 3H), 2.17 (s, 3H), 3.88 (s, 3H), 4.80 (d, J = 6.3 Hz, 2H), 4.90 (br s, 1H), 4.99 (s, 1H), 6.26 (t, J = 6.3 Hz, 1H), 6.77 (s, 1H), 6.85–6.92 (m, 4H), 7.01 (d, J = 6.9 Hz, 1H), 7.22–7.27 (m, 2H)<br>IR (CHCl$_3$) 3688, 3598, 3538, 3024, 3014, 2938, 1731, 1631, 1520, 1488, 1240, 1172 cm$^{-1}$ |
| I-1314 | mp 132–134° C.<br>$^1$H NMR (CDCl$_3$) δ 2.12 (s, 3H), 2.29 (s, 3H), 3.00 (s, 6H), 3.74 (br, 2H), 6.62 (dd, J = 2.4, 8.1 Hz, 1H), 6.77–6.82 (m, 3H), 7.01–7.05 (m, 2H), 7.12 (s, 1H), 7.26–7.31 (m, 2H)<br>IR (KBr) 3600–2800(br), 1610, 1523, 1483, 1443, 1325, 1297 cm$^{-1}$ |

TABLE 261

| | |
|---|---|
| I-1315 | mp 123–125° C.<br>$^1$H NMR (CDCl$_3$) δ 2.13 (s, 3H), 2.29 (m, 4H), 3.00 (s, 6H), 3.98 (br, 3H), 6.63 (dd, J = 2.4, 8.1 Hz, 1H), 6.77–6.81 (m, 3H), 7.02 (s, 1H), 7.09–7.13 (m, 2H), 7.25–7.32 (m, 2H)<br>IR (KBr) 3600–2800(br), 1609, 1525, 1488, 1443, 1356, 1232, 1194 cm$^{-1}$ |
| I-1316 | mp 125–127° C.<br>$^1$H NMR (CDCl$_3$) δ 2.10 (s, 3H), 2.31 (s, 3H), 3.01 (s, 6H), 6.77–6.84 (m, 2H), 7.00 (s, 1H), 7.15 (s, 1H), 7.27–7.33 (m, 3H), 7.52 (dd, J = 3.0, 12.9 Hz, 1H), 7.09 (d, J = 3.0 Hz, 1H), 7.95 (br s, 1H)<br>IR (KBr) 3600–2800(br), 1707, 1611, 1528, 1484, 1350, 1279, 1229, 1196, 1154 cm$^{-1}$ |
| I-1317 | mp 94–95° C.<br>$^1$H NMR (CDCl$_3$) δ 1.77 (s, 3H), 1.81 (s, 3H), 2.26 (s, 6H), 4.63 (d, J = 6.6 Hz, 2H), 5.51–5.60 (m, 1H), 6.01 (s, 2H), 6.78–6.89 (m, 3H), 6.97–7.15 (m, 5H) |
| I-1318 | $^1$H NMR (CDCl$_3$) δ 1.77 (s, 3H), 1.82 (s, 3H), 2.29 (s, 6H), 4.64 (d, J = 6.3 Hz, 2H), 5.53–5.60 (m, 1H), 6.99–7.21 (m, 5H), .7.33–7.39 (m, 2H), 7.49 (d.d, J = 5.4 & 0.3 Hz, 1H), 7.80 (s, 1H), 7.92 (d, J = 8.1 Hz, 1H) |
| I-1319 | mp188–189° C.<br>$^1$H NMR (CDCl$_3$) δ 1.31 (t, J = 7.5 Hz, 3H), 2.26 (s, 3H), 2.29 (s, 3H), 2.68 (q, J = 7.5 Hz, 2H), 5.17 (s, 2H), 5.70 (brs, 1H), 6.83 (d, J = 6.8 Hz, 1H), 6.98–7.00 (m, 2H), 7.13 (d, J = 9.0 Hz, 2H), 7.26–7.30 (m, 2H), 7.38–7.48 (m, 5H), 7.78 (brs, 1H), 7.86 (d, J = 8.7 Hz, 1H)<br>IR(KBr) 3444, 3269, 1710, 1533, 1487, 1269, 1244, 1199, 1174, 744, 697 cm$^{-1}$ |
| I-1320 | mp157–159° C.<br>$^1$H NMR (CDCl$_3$) δ 1.30 (t, J = 7.6 Hz, 3H), 2.27 (s, 3H), 2.28 (s, 3H), 2.68 (q, J = 7.2 Hz, 2H), 3.91 (s, 3H), 5.21 (s, 2H), 6.81–6.97 (m, 3H), 7.14 (d, J = 7.6 Hz, 2H), 7.25–7.51 (m, 7H), 7.79 (brs, 1H), 7.86 (d, J = 8.8 Hz, 1H)<br>IR(KBr) 3434, 3260, 1707, 1519, 1501, 1488, 1260, 1241, 1213, 1172, 744, 697 cm$^{-1}$ |

TABLE 262

| | |
|---|---|
| I-1321 | mp186–187° C.<br>$^1$H NMR (CDCl$_3$) δ 1.30 (t, J = 8.4 Hz, 3H), 2.26 (s, 3H), 2.27 (s, 3H), 2.68 (q, J = 7.5 Hz, 2H), 5.20 (s, 2H), 7.04–7.14 (m, 6H), 7.26–7.50 (m, 6H), 7.79 (brs, 1H), 7.86 (d, J = 8.7 Hz, 1H)<br>IR(KBr) 3436, 3266, 1709, 1536, 1521, 1487, 1267, 1199, 1176, 744, 697 cm$^{-1}$ |
| I-1322 | mp136–137° C.<br>$^1$H NMR (CDCl$_3$) δ 1.32 (t, J = 7.5 Hz, 3H), 2.28 (s, 3H), 2.30 (s, 3H), 2.70 (q, J = 7.5 Hz, 2H), 3.13 (s, 3H), 5.19 (s, 2H), 7.12–7.15 (m, 3H), 7.26–7.29 (m, 3H), 7.37–7.50 (m, 5H), 7.80 (brs, 1H), 7.87 (d, J = 9.0 Hz, 1H)<br>IR(KBr) 3435, 1725, 1536, 1486, 1363, 1292, 1266, 1179, 1163, 1108, 7970, 895, 811, 525 cm$^{-1}$ |
| I-1323 | mp150–151° C.<br>$^1$H NMR (CDCl$_3$) δ 2.18 (s, 3H), 2.27 (s, 3H), 5.20 (s, 2H), 7.04–7.14 (m, 6H), 7.26–7.50 (m, 6H), 7.60 (d, J = 12.0 Hz, 1H), 7.94 (brs, 1H)<br>IR(KBr) 3421, 3302, 1712, 1523, 1490, 1422, 1299, 1274, 1205, 1176, 1132, 743, 697 cm$^{-1}$ |
| I-1324 | mp83–84° C.<br>$^1$H NMR (CDCl$_3$) δ 1.30 (t, J = 7.6 Hz, 3H), 1.77 (s, 3H), 1.78 (s, 3H), 1.81 (s, 6H), 2.31 (s, 3H), 2.34 (s, 3H), 2.56 (q, J = 7.6 Hz, 2H), 3.80 (d, J = 6.4 Hz, 2H), 3.90 (s, 3H), 4.65 (d, J = 6.2 Hz, 2H), 5.44 (d, J = 6.2 Hz, 2H), 5.44 (t, J = 5.2 Hz, 1H), 5.59 (t, J = 5.4 Hz, 1H), 6.73 (d, J = 8.0 Hz, 1H), 6.92–6.94 (m, 3H), 7.12–7.20 (m, 4H)<br>IR(KBr) 3428, 3374, 2964, 1607, 1519, 1494, 1458, 1311, 1256, 1239, 1139, 1036, 1002, 855, 820 cm$^{-1}$ |
| I-1325 | mp113–114° C.<br>$^1$H NMR (CDCl$_3$) δ 1.30 (t, J = 7.4 Hz, 3H), 1.76 (s, 3H), 1.78 (s, 3H), 1.80 (s, 3H), 1.84 (s, 3H), 2.30 (s, 3H), 2.32 (s, 3H), 2.55 (q, J = 7.6 Hz, 2H), 3.79 (d, J = 6.6 Hz, 2H), 4.63 (d, J = 6.6 Hz, 2H), 5.43 (t, J = 5.6 Hz, 1H), 5.55 (t, J = 6.6 Hz, 1H), 5.73 (brs, 1H), 6.72 (d, J = 8.0 Hz, 1H), 6.83–6.98 (m, 3H), 7.11–7.19 (m, 4H)<br>IR(KBr) 3413, 3298, 2965, 2924, 1518, 1494, 1435, 1242, 1127, 1013, 883 cm$^{-1}$ |

TABLE 263

I-1326 mp 81–82° C.
$^1$H NMR (CDCl$_3$) δ 1.29 (t, J = 7.4 Hz, 3H), 1.74 (s, 3H), 1.77 (s, 3H), 1.78 (s, 3H), 1.81 (s, 3H), 2.27 (s, 3H), 2.31 (s, 3H), 2.54 (q, J = 7.2 Hz, 2H), 3.79 (d, J = 7.2 Hz, 2H), 4.63 (d, J = 6.6 Hz, 2H), 5.42 (t, J = 6.4 Hz, 1H), 5.55 (t, J = 6.6 Hz, 1H), 6.71 (d, J = 8.0 Hz, 1H), 7.04–7.19 (m, 7H)
IR(KBr) 3413, 2969, 2912, 2856, 1613, 1520, 1492, 1295, 1261, 1127, 1004, 881, 813 cm$^{-1}$

I-1327 mp 94–95° C.
$^1$H NMR (CDCl$_3$) δ 1.74 (s, 3H), 1.77 (s, 6H), 1.81 (s, 3H), 2.21 (s, 3H), 2.26 (s, 3H), 3.72 (d, J = 6.9 Hz, 2H), 4.63 (d, J = 6.3 Hz, 2H), 5.35 (t, J = 6.9 Hz, 1H), 5.55 (t, J = 6.9 Hz, 1H), 6.37–6.48 (m, 2H), 7.01–7.13 (m, 6H)
IR(KBr) 3423, 2967, 2918, 1627, 1525, 1488, 1296, 1267, 1129, 981, 837, 805 cm$^{-1}$

I-1328 mp 178–180° C. (decomp.)
$^1$H NMR (DMSO-d$_6$) δ 3.30 (s, 3H), 3.64 (s, 3H), 4.45 (s, 2H), 5.65 (s, 2H), 6.39 (s, 1H), 6.65 (dd, J = 8.4, 2.1 Hz, 1H), 6.74 (d, J = 2.1 Hz, 1H), 6.84 (d, J = 8.7 Hz, 2H), 6.99 (d, J = 8.4 Hz, 1H), 7.43 (d, J = 8.7 Hz, 2H), 9.26 (s, 1H)
IR (Nujol) 3487, 3382, 1696, 1670, 1591, 1523, 1491, 1458, 1243, 1202, 1114, 1077, 1013, 937, 811 cm$^{-1}$ I-1329 mp 205–210° C. (decomp.)
$^1$H NMR (DMSO-d$_6$) δ 3.34 (s, 3H), 3.44 (s, 3H), 3.67 (s, 3H), 4.93 (s, 2H), 6.43 (s, 1H), 6.76 (dd, J = 8.4, 2.1 Hz, 1H), 6.85 (d, J = 2.1 Hz, 1H), 6.86 (d, J = 8.7 Hz, 2H), 7.04 (d, J = 8.4 Hz, 1H), 7.46 (d, J = 8.7 Hz, 2H)
IR (Nujol) 3388, 3333, 3270, 1671, 1614, 1579, 1556, 1523, 1443, 1223, 1172, 1121, 1033, 922, 813 cm$^{-1}$ I-1330 mp 185–187° C.
$^1$H NMR (CDCl$_3$) δ 1.79 (t, J = 2.6 Hz, 3H), 2.69 (m, 2H), 2.75 (s, 3H), 3.21 (s, 3H), 3.29 (s, 3H), 3.56 (s, 3H), 3.77 (s, 3H), 4.17 (t, J = 6.6 Hz, 2H), 6.84 (s, 1H), 7.08 (d, J = 9.0 Hz, 1H), 7.36 (dd, J = 9.0, 2.1 Hz, 1H), 7.38 (d, J = 8.7 Hz, 2H), 7.40 (d, J = 2.1 Hz, 1H), 7.68 (d, J = 8.7 Hz, 2H)
IR (Nujol) 1604, 1520, 1480, 1175, 1151, 1081, 1012, 971, 948, 878, 840, 807 cm$^{-1}$

TABLE 264

I-1331 foam
$^1$H NMR (CDCl$_3$) δ 1.81 (t, J = 2.4 Hz, 3H), 2.65 (m, 2H), 3.45 (s, 3H), 3.74 (s, 3H), 4.16 (t, J = 6.6 Hz, 2H), 6.45 (s, 1H), 6.92 (d, J = 8.7 Hz, 2H), 6.95 (m, 2H), 7.07 (brs, 1H), 7.07 (d, J = 8.7 Hz, 2H)
IR (Nujol) 3427, 1612, 1586, 1523, 1489, 1251, 1224, 1113, 1071, 1012 cm$^{-1}$ I-1332 foam
$^1$H NMR (CDCl$_3$) δ 3.45 (s, 3H), 3.75 (s, 3H), 4.16 (m, 2H), 4.76 (m, 2H), 5.89~6.02 (m, 2H), 6.45 (s, 1H), 6.92 (d, J = 8.7 Hz, 2H), 6.96 (m, 2H), 7.09 (brs, 1H), 7.53 (d, J = 8.7 Hz, 2H)
IR (Nujol) 3433, 1612, 1588, 1523, 1489, 1286, 1248, 1224, 1175, 1113, 1070, 1011 cm$^{-1}$ I-1333 foam
$^1$H NMR (CDCl$_3$) δ 3.45 (s, 3H), 3.74 (s, 3H), 4.11 (m, 2H), 4.67 (m, 2H), 5.96–6.12 (m, 2H), 6.45 (s, 1H), 6.92 (d, J = 8.7 Hz, 2H), 6.92 (d, J = 8.4 Hz, 1H), 6.96 (dd, J = 8.4, 2.1 Hz, 1H), 7.08 (d, J = 2.1 Hz, 1H), 7.53 (d, J = 8.7 Hz, 2H)
IR (Nujol) 3434, 1612, 1588, 1523, 1489, 1285, 1248, 1224, 1174, 1112, 1070, 1011 cm$^{-1}$ I-1334 foam
$^1$H NMR (CDCl$_3$) δ 1.95 (s, 3H), 3.45 (s, 3H), 3.75 (s, 3H), 4.11 (m, 2H), 4.68 (d, J = 6.9 Hz, 2H), 5.75 (d, J = 6.9 Hz, 1H), 6.45 (s, 1H), 6.91 (d, J = 8.7 Hz, 2H), 6.96 (s, 2H), 7.08 (s, 1H), 7.53 (d, J = 8.7 Hz, 2H)
IR (KBr) 3390, 1612, 1585, 1523, 1491, 1225, 1072, 1003, 822 cm$^{-1}$ I-1335 m.p 179–180° C.
$^1$H NMR (CDCl$_3$) δ 1.88 (s, 3H), 3.45 (s, 3H), 3.75 (s, 3H), 4.07 (s, 2H), 4.69 (d, J = 6.6 Hz, 2H), 5.89 (d, J = 6.6 Hz, 1H), 6.45 (s, 1H), 6.91 (d, J = 8.7 Hz, 2H), 6.92 (d, J = 8.4 Hz, 1H), 6.96 (m, 1H), 7.07 (d, J = 1.8 Hz, 1H), 7.53 (d, J = 8.7 Hz, 2H)
IR (KBr) 3392, 1609, 1584, 1523, 1492, 1226, 1116, 1072, 1002, 813, 782 cm$^{-1}$

TABLE 265

I-136 foam
$^1$H NMR (CD3OD) δ 3.38 (s, 3H), 3.67 (s, 3H), 3.88 (dd, J = 7.8, 9.9 Hz, 1H), 4.10 (dd, J = 3.6, 9.9 Hz, 1H), 4.51 (m, 1H), 5.25 (dt, J = 10.5, 1.5 Hz, 1H), 5.44 (dt, J = 17.4, 1.5 Hz, 1H), 6.00 (ddd, J = 5.4, 10.5, 17.4 Hz, 1H), 6.43 (s, 1H), 6.79 (dd, J = 1.8, 8.4 Hz, 1H), 6.85 (d, J = 8.7 Hz, 2H), 6.86 (d, J = 1.8 Hz, 1H), 6.92 (d, J = 8.4 Hz, 1H), 7.45 (d, J = 8.7 Hz, 2H)
IR (KBr) 3399, 2934, 1612, 1588, 1523, 1489, 1254, 1114, 1071, 1012, 939, 816 cm$^{-1}$ I-1337 foam
$^1$H NMR (CDCl$_3$) δ 3.45 (s, 3H), 3.75 (s, 3H), 4.20 (t, J = 2.1 Hz, 2H), 4.84 (t, J = 2.1 Hz, 2H), 6.45 (s, 1H), 6.92 (d, J = 8.7 Hz, 2H), 6.98 (dd, J = 2.1, 8.4 Hz, 1H), 7.04 (d, J = 8.4 Hz, 1H), 7.09 (d, J = 2.1 Hz, 1H), 7.45 (d, J = 8.7 Hz, 2H)
IR (KBr) 3431, 1612, 1589, 1523, 1489, 1404, 1224, 1113, 1070, 1011, 939, 826 cm$^{-1}$ I-1338 foam
$^1$H NMR (CD3OD) δ 3.38 (s, 3H), 3.67 (s, 3H), 4.25 (d, J = 21.0 Hz, 2H), 4.84 (d, J = 7.5 Hz, 2H), 5.58 (dt, J = 19.5, 7.5 Hz, 1H), 6.43 (s, 1H), 6.79 (dd, J = 2.1, 8.4 Hz, 1H), 6.84 (d, J = 8.7 Hz, 2H), 6.86 (d, J = 2.1 Hz, 1H), 6.96 (d, J = 8.4 Hz, 1H), 7.45 (d, J = 8.7 Hz, 2H)
IR (KBr) 3409, 1701, 1612, 1591, 1523, 1489, 1404, 1246, 1113, 1071, 1010, 939, 816 cm$^{-1}$ I-1339 foam
$^1$H NMR (CDCl$_3$) δ 3.44 (s, 3H), 3.74 (s, 3H), 4.21 (d, J = 21.3 Hz, 2H), 4.66 (dd, J = 1.8, 7.5 Hz, 2H), 5.70 (dt, J = 16.5, 7.5 Hz, 1H), 6.45 (s, 1H), 6.95 (d, J = 8.7 Hz, 2H), 6.96 (d, J = 8.4 Hz, 1H), 6.98 (dd, J = 1.5, 8.4 Hz, 1H), 7.09 (d, J = 1.5 Hz, 1H), 7.51 (d, J = 8.7 Hz, 2H)
IR (KBr) 3411, 1698, 1611, 1588, 1522, 1488, 1223, 1112, 1070, 1011, 939, 825 cm$^{-1}$ I-1340 mp 171–172° C.
$^1$H NMR (CDCl$_3$) δ 1.50 (s, 3H), 1.67 (s, 3H), 1.96 (s, 3H), 3.45 (s, 3H), 3.77 (s, 3H), 4.13–4.49 (m, 2H), 5.23–5.30 (m, 1H), 5.59 (s, 1H), 6.13 (s, 1H), 6.47 (s, 1H), 6.92–6.98 (m, 2H), 7.18–7.35 (m, 3H), 7.50–7.57 (m, 2H)
IR (KBr) 3390, 3140, 2935, 1640, 1523, 1401, 1240, 1119, 1070, 835, 820 cm$^{-1}$

TABLE 266

I-1341 mp 216–218° C.
$^1$H NMR (CDCl$_3$ + CD3OD) δ 1.46 (s, 3H), 1.67 (s, 3H), 1.95 (s, 3H), 2.10 (s, 3H), 3.46 (s, 3H), 4.16–4.47 (m, 2H), 5.21–5.28 (m, 1H), 6.79 (s, 1H), 6.88–6.95 (m, 2H), 7.11–7.27 (m, 3H), 7.45–7.52 (m, 2H)
IR (KBr) 3337, 3099, 2928, 1637, 1608, 1587, 1521, 1444, 1409, 1261, 1232, 1161, 836, 769, 592, 540 cm$^{-1}$

I-1342 mp 103–105° C.
$^1$H NMR (CDCl$_3$) δ 1.15 (d, J = 6.8 Hz, 6H), 2.26 (s, 3H), 3.08 (sept, J = 6.8 Hz, 1H), 4.94 (s, 1H), 5.20 (s, 2H), 6.88 (d, J = 8.7 Hz, 2H), 7.04–7.07 (m, 3H), 7.12–7.18 (m, 1H), 7.18 (s, 1H), 7.20 (d, J = 8.7 Hz, 2H), 7.32–7.51 (m, 5H)
IR (KBr) 3429, 1522, 1490, 1262, 1227, 1128, 1011, 833 cm$^{-1}$ I-1343 mp 115–117° C.
$^1$H NMR (CDCl$_3$) δ 1.15 (d, J = 6.6 Hz, 6H), 1.77 (s, 3H), 1.82 (s, 3H), 2.27 (s, 3H), 3.08 (sept, J = 6.8 Hz, 1H), 4.64 (d, J = 6.9 Hz, 2H), 4.86 (s, 1H), 5.56 (t, J = 6.9 Hz, 1H), 6.89 (d, J = 8.6 Hz, 2H), 7.03 (d, J = 8.4 Hz, 1H), 7.05–7.19 (m, 3H), 7.19 (s, 1H), 7.21 (d, J = 8.6 Hz, 2H)
IR (KBr) 3524, 1611, 1523, 1489, 1260, 1228, 1200, 1128, 836 cm$^{-1}$ I-1344 mp 119–120° C.
$^1$H NMR (CDCl$_3$) δ 1.15 (d, J = 6.9 Hz, 6H), 2.26 (s, 3H), 3.08 (sept, J = 6.8 Hz, 1H), 4.79 (d, J = 6.3 Hz, 2H), 4.85 (s, 1H), 6.25 (t, J = 6.3 Hz, 1H), 6.89 (d, J = 8.7 Hz, 2H), 7.01 (t, J = 8.4 Hz, 1H), 7.07–7.12 (m, 2H), 7.15 (dd, J = 12.0, 2.1 Hz, 1H), 7.18 (s, 1H), 7.20 (d, J = 8.7 Hz, 2H)
IR (KBr) 3425, 1610, 1523, 1488, 1300, 1263, 1300, 1263, 1227, 1134, 1038, 896 cm$^{-1}$ I-1345 mp 109–110° C.
$^1$H NMR (CDCl$_3$) δ 1.34 (d, J = 6.9 Hz, 3H), 2.24 (s, 3H), 4.00

TABLE 266-continued (q, J = 6.9 Hz, 2H), 4.77–4.79 (m, 3H), 6.24 (t, J = 6.3 Hz, 1H), 6.86–6.90 (m, 2H), 6.98–7.19 (m, 4H), 7.47–7.50 (m, 2H)
IR (CHCl₃) 3596, 2927, 1612, 1523, 1493, 1476, 1388, 1299, 1259, 1173, 1127, 1049, 885, 834 cm⁻¹

TABLE 267

I-1346 mp 114–116° C.
¹H NMR (CDCl₃) δ 1.33 (d, J = 6.9 Hz, 3H), 1.77 (s, 3H), 1.81 (s, 3H), 2.24 (s, 3H), 4.00 (q, J = 6.9 Hz, 2H), 4.63 (m, 2H), 4.73 (br, 1H), 5.56 (m, 1H), 6.81 (s, 1H), 6.86–6.90 (m, 2H), 7.00–7.19 (m, 4H), 7.47–4.51 (m, 2H)
IR (CHCl₃) 3596, 2929, 2877, 1610, 1523, 1493, 1476, 1386, 1329, 1316, 1297, 1261, 1173, 1125, 1048, 992, 834 cm⁻¹
I-1347 mp 144–146° C.
¹H NMR (CDCl₃) δ 3.20 (s, 3H), 3.40 (s, 3H), 3.75 (s, 3H), 4.74 (s, 2H), 5.19 (s, 2H), 6.44 (s, 1H), 7.05–7.62 (m, 12H)
IR (KBr) 3437, 1614, 1579, 1520, 1488, 1465, 1453, 1436, 1414, 1393, 1364, 1346, 1299, 1270, 1235, 1198, 1175, 1149, 1129, 1114, 1085, 1063 cm⁻¹
I-1348 mp 156–159° C.
¹H NMR (CDCl₃) δ 2.48 (s, 3H), 3.05 (s, 3H), 3.20 (s, 3H), 3.78 (s, 3H), 4.83 (s, 2H), 5.21 (s, 2H), 6.84 (s, 1H), 7.02–7.67 (m, 12H)
IR (KBr) 3430, 2940, 1607, 1522, 1481, 1452, 1419, 1389, 1365, 1294, 1273, 1230, 1200, 1176, 1151, 1132, 1080, 1011 cm⁻¹
I-1349 mp 155–156° C.
¹H NMR (CDCl₃) δ 1.15 (t, J = 6.9 Hz, 3H), 3.60 (q, J = 6.9 Hz, 2H), 3.75 (s, 3H), 3.90 (s, 3H), 4.93 (bs, 1H), 5.20 (s, 2H), 5.98 (s, 1H), 6.46 (s, 1H), 6.90–7.05 (m, 5H), 7.26–7.56 (m, 7H)
IR (KBr) 3409, 2938, 1613, 1522, 1438, 1416, 1396, 1382, 1360, 1268, 1232, 1211, 1169, 1131, 1113, 1078, 1022, 1006 cm⁻¹
I-1350 mp 58–60° C.
¹H NMR (DMSO-d₆) δ 1.71 (s, 6H), 2.21 (s, 3H), 2.22 (s, 3H), 3.71–3.75 (m, 2H), 5.11 (br s, 2H), 5.25–5.29 (m, 1H), 5.50–5.53 (m, 1H), 6.60–6.63 (m, 2H), 6.66–6.73 (m, 1H), 6.95–7.05 (m, 6H)
IR (KBr) 3600–2800(br), 1623, 1527, 1492, 1454, 1428, 1331, 1269, 1257, 1184, 1116 cm⁻¹

TABLE 268

I-1351 mp 140–142° C. (dec.)
¹H NMR (CDCl₃) δ 2.33 (s, 3H), 4.93 (s, 1H), 5.19 (s, 2H), 6.89 (d, J = 8.7 Hz, 2H), 7.06 (t, J = 8.6 Hz, 1H), 7.23 (d, J = 8.7 Hz, 2H), 7.24–7.50 (m, 10H)
IR (KBr) 3400, 1609, 1529, 1490, 1269, 1243, 1005, 807, 745 cm⁻¹
I-1352 mp 114–116° C.
¹H NMR (CDCl₃) δ 1.77 (s, 3H), 1.81 (s, 3H), 2.33 (s, 3H), 4.63 (d, J = 6.9 Hz, 2H), 4.89 (s, 1H), 5.54 (t, J = 6.9 Hz, 1H), 6.89 (d, J = 8.6 Hz, 2H), 7.04 (t, J = 8.6 Hz, 1H), 7.23 (d, J = 8.6 Hz, 2H), 7.25–7.43 (m, 5H)
IR (KBr) 3368, 1609, 1526, 1490, 1271, 1241, 1131, 991, 827, 811 cm⁻¹
I-1353 mp 78–79° C.
¹H NMR (CDCl₃) δ 1.77 (s, 3H), 1.82 (s, 3H), 2.24 (s, 3H), 2.27 (s, 3H), 4.64 (d, J = 6.6 Hz, 2H), 5.51–5.59 (m, 1H), 6.98–7.20 (m, 7H), .7.28–7.36 (m, 2H)

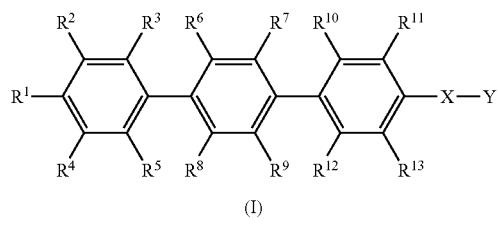

(I)

| No. | R¹ | R² | R³ | R⁴ | R⁵ | R⁶ | R⁷ | R⁸ | R⁹ | R¹⁰ | R¹¹ | R¹² | R¹³ | X | Y |
|---|---|---|---|---|---|---|---|---|---|---|---|---|---|---|---|
| I-1354 | OH | H | H | H | H | H | OMe | OMe | OH | H | H | H | OMs | O | —CH₂CH═CMe₂ |
| I-1355 | OH | H | H | H | H | H | OMe | OMe | OH | H | H | H | OMs | O | —(CH₂)₂CH═CMe₂ |
| I-1356 | OH | H | H | H | H | H | OMe | OMe | OH | H | H | H | OMs | O | —CH₂CH═CCl₂ |
| I-1357 | OH | H | H | H | H | H | OMe | OMe | OH | H | H | H | OMs | O | —CH₂C≡CMe |
| I-1358 | OH | H | H | H | H | H | OMe | OMe | OH | H | H | H | OMs | O | —CH₂C₆H₄-4-Me |
| I-1359 | OH | H | H | H | H | H | OMe | OMe | OH | H | H | H | COOH | O | —(CH₂)₂CH═CMe₂ |
| I-1360 | OH | H | H | H | H | H | OMe | OMe | OH | H | H | H | COOH | O | —CH₂CH═CCl₂ |
| I-1361 | OH | H | H | H | H | H | OMe | OMe | OH | H | H | H | COOH | O | —CH₂C≡CMe |
| I-1362 | OH | H | H | H | H | H | OMe | OMe | OH | H | H | H | COOH | O | —CH₂C₆H₄-4-Me |
| I-1363 | OH | H | H | H | H | H | OMe | OMe | OH | H | H | H | CH₂OH | O | —(CH₂)₂CH═CMe₂ |
| I-1364 | OH | H | H | H | H | H | OMe | OMe | OH | H | H | H | CH₂OH | O | —CH₂CH═CCl₂ |
| I-1365 | OH | H | H | H | H | H | OMe | OMe | OH | H | H | H | CH₂OH | O | —CH₂C≡CMe |
| I-1366 | OH | H | H | H | H | H | OMe | OMe | OH | H | H | H | CH₂OH | O | —CH₂C₆H₄-4-Me |
| I-1367 | OH | H | H | H | H | H | OMe | OMe | OH | H | H | H | F | O | —(CH₂)₂CH═CMe₂ |
| I-1368 | OH | H | H | H | H | H | OMe | OMe | OH | H | H | H | F | O | —CH₂CH═CCl₂ |
| I-1369 | OH | H | H | H | H | H | OMe | OMe | OH | H | H | H | F | O | —CH₂C≡CMe |

TABLE 270

| | | | | | | | | | | | | | | | |
|---|---|---|---|---|---|---|---|---|---|---|---|---|---|---|---|
| I-1370 | OH | H | H | H | H | H | OMe | OMe | OH | H | H | H | F | O | —CH$_2$C$_6$H$_4$-4-Me |
| I-1371 | OH | H | H | H | H | H | OMe | OMe | COOH | H | H | H | OH | O | —CH$_2$CH=CCl$_2$ |
| I-1372 | OH | H | H | H | H | H | OMe | OMe | COOH | H | H | H | OH | O | —CH$_2$C≡CMe |
| I-1373 | OH | H | H | H | H | H | OMe | OMe | COOH | H | H | H | OMs | O | —CH$_2$CH=CMe$_2$ |
| I-1374 | OH | H | H | H | H | H | OMe | OMe | COOH | H | H | H | OMs | O | —(CH$_2$)$_2$CH=CMe$_2$ |
| I-1375 | OH | H | H | H | H | H | OMe | OMe | COOH | H | H | H | OMs | O | —CH$_2$CH=CCl$_2$ |
| I-1376 | OH | H | H | H | H | H | OMe | OMe | COOH | H | H | H | OMs | O | —CH$_2$C≡CMe |
| I-1377 | OH | H | H | H | H | H | OMe | OMe | COOH | H | H | H | OMs | O | —CH$_2$C$_6$H$_4$-4-Me |
| I-1378 | OH | H | H | H | H | H | OMe | OMe | COOH | H | H | H | COOH | O | —CH$_2$CH=CMe$_2$ |
| I-1379 | OH | H | H | H | H | H | OMe | OMe | COOH | H | H | H | COOH | O | —(CH$_2$)$_2$CH=CMe$_2$ |
| I-1380 | OH | H | H | H | H | H | OMe | OMe | COOH | H | H | H | COOH | O | —CH$_2$CH=CCl$_2$ |
| I-1381 | OH | H | H | H | H | H | OMe | OMe | COOH | H | H | H | COOH | O | —CH$_2$C≡CMe |
| I-1382 | OH | H | H | H | H | H | OMe | OMe | COOH | H | H | H | COOH | O | —CH$_2$C$_6$H$_4$-4-Me |
| I-1383 | OH | H | H | H | H | H | OMe | OMe | COOH | H | H | H | CH$_2$OH | O | —CH$_2$CH=CMe$_2$ |
| I-1384 | OH | H | H | H | H | H | OMe | OMe | COOH | H | H | H | CH$_2$OH | O | —(CH$_2$)$_2$CH=CMe$_2$ |
| I-1385 | OH | H | H | H | H | H | OMe | OMe | COOH | H | H | H | CH$_2$OH | O | —CH$_2$CH=CCl$_2$ |
| I-1386 | OH | H | H | H | H | H | OMe | OMe | COOH | H | H | H | CH$_2$OH | O | —CH$_2$C≡CMe |
| I-1387 | OH | H | H | H | H | H | OMe | OMe | COOH | H | H | H | CH$_2$OH | O | —CH$_2$C$_6$H$_4$-4-Me |
| I-1388 | OH | H | H | H | H | H | OMe | OMe | COOH | H | H | H | F | O | —CH$_2$CH=CCl$_2$ |
| I-1389 | OH | H | H | H | H | H | OMe | OMe | COOH | H | H | H | F | O | —CH$_2$C≡CMe |
| I-1390 | OH | H | H | H | H | H | OMe | OMe | CH$_2$OH | H | H | H | OH | O | —CH$_2$CH=CMe$_2$ |

TABLE 271

| | | | | | | | | | | | | | | | |
|---|---|---|---|---|---|---|---|---|---|---|---|---|---|---|---|
| I-1391 | OH | H | H | H | H | H | OMe | OMe | CH$_2$OH | H | H | H | OH | O | —(CH$_2$)$_2$CH=CMe$_2$ |
| I-1392 | OH | H | H | H | H | H | OMe | OMe | CH$_2$OH | H | H | H | OH | O | —CH$_2$CH=CCl$_2$ |
| I-1393 | OH | H | H | H | H | H | OMe | OMe | CH$_2$OH | H | H | H | OH | O | —CH$_2$C≡CMe |
| I-1394 | OH | H | H | H | H | H | OMe | OMe | CH$_2$OH | H | H | H | OH | O | —CH$_2$C$_6$H$_4$-4-Me |
| I-1395 | OH | H | H | H | H | H | OMe | OMe | CH$_2$OH | H | H | H | OMs | O | —CH$_2$CH=CMe$_2$ |
| I-1396 | OH | H | H | H | H | H | OMe | OMe | CH$_2$OH | H | H | H | OMs | O | —(CH$_2$)$_2$CH=CMe$_2$ |
| I-1397 | OH | H | H | H | H | H | OMe | OMe | CH$_2$OH | H | H | H | OMs | O | —CH$_2$CH=CCl$_2$ |
| I-1398 | OH | H | H | H | H | H | OMe | OMe | CH$_2$OH | H | H | H | OMs | O | —CH$_2$C≡CMe |
| I-1399 | OH | H | H | H | H | H | OMe | OMe | CH$_2$OH | H | H | H | OMs | O | —CH$_2$C$_6$H$_4$-4-Me |
| I-1400 | OH | H | H | H | H | H | OMe | OMe | CH$_2$OH | H | H | H | COOH | O | —CH$_2$CH=CMe$_2$ |
| I-1401 | OH | H | H | H | H | H | OMe | OMe | CH$_2$OH | H | H | H | COOH | O | —(CH$_2$)$_2$CH=CMe$_2$ |
| I-1402 | OH | H | H | H | H | H | OMe | OMe | CH$_2$OH | H | H | H | COOH | O | —CH$_2$CH=CCl$_2$ |
| I-1403 | OH | H | H | H | H | H | OMe | OMe | CH$_2$OH | H | H | H | COOH | O | —CH$_2$C≡CMe |
| I-1404 | OH | H | H | H | H | H | OMe | OMe | CH$_2$OH | H | H | H | COOH | O | —CH$_2$C$_6$H$_4$-4-Me |
| I-1405 | OH | H | H | H | H | H | OMe | OMe | CH$_2$OH | H | H | H | CH$_2$OH | O | —CH$_2$CH=CMe$_2$ |
| I-1406 | OH | H | H | H | H | H | OMe | OMe | CH$_2$OH | H | H | H | CH$_2$OH | O | —CH$_2$CH=CCl$_2$ |
| I-1407 | OH | H | H | H | H | H | OMe | OMe | CH$_2$OH | H | H | H | CH$_2$OH | O | —CH$_2$C≡CMe |
| I-1408 | OH | H | H | H | H | H | OMe | OMe | CH$_2$OH | H | H | H | CH$_2$OH | O | —CH$_2$C$_6$H$_4$-4-Me |
| I-1409 | OH | H | H | H | H | H | OMe | OMe | CH$_2$OH | H | H | H | F | O | —CH$_2$CH=CMe$_2$ |
| I-1410 | OH | H | H | H | H | H | OMe | OMe | CH$_2$OH | H | H | H | F | O | —(CH$_2$)$_2$CH=CMe$_2$ |
| I-1411 | OH | H | H | H | H | H | OMe | OMe | CH$_2$OH | H | H | H | F | O | —CH$_2$CH=CCl$_2$ |

TABLE 272

| | | | | | | | | | | | | | | | |
|---|---|---|---|---|---|---|---|---|---|---|---|---|---|---|---|
| I-1412 | OH | H | H | H | H | H | OMe | OMe | CH$_2$OH | H | H | H | F | O | —CH$_2$C≡CMe |
| I-1413 | OH | H | H | H | H | H | OMe | OMe | CH$_2$OH | H | H | H | F | O | —CH$_2$C$_6$H$_4$-4-Me |
| I-1414 | OH | H | H | H | H | H | OMe | OMe | Me | H | H | H | OH | O | —CH$_2$CH=CCl$_2$ |
| I-1415 | OH | H | H | H | H | H | OMe | OMe | Me | H | H | H | OH | O | —CH$_2$C≡CMe |
| I-1416 | OH | H | H | H | H | H | OMe | OMe | Me | H | H | H | OMs | O | —CH$_2$CH=CMe$_2$ |
| I-1417 | OH | H | H | H | H | H | OMe | OMe | Me | H | H | H | OMs | O | —(CH$_2$)$_2$CH=CMe$_2$ |
| I-1418 | OH | H | H | H | H | H | OMe | OMe | Me | H | H | H | OMs | O | —CH$_2$CH=CCl$_2$ |
| I-1419 | OH | H | H | H | H | H | OMe | OMe | Me | H | H | H | OMs | O | —CH$_2$C≡CMe |
| I-1420 | OH | H | H | H | H | H | OMe | OMe | Me | H | H | H | OMs | O | —CH$_2$C$_6$H$_4$-4-Me |
| I-1421 | OH | H | H | H | H | H | OMe | OMe | Me | H | H | H | COOH | O | —CH$_2$CH=CMe$_2$ |
| I-1422 | OH | H | H | H | H | H | OMe | OMe | Me | H | H | H | COOH | O | —(CH$_2$)$_2$CH=CMe$_2$ |
| I-1423 | OH | H | H | H | H | H | OMe | OMe | Me | H | H | H | COOH | O | —CH$_2$CH=CCl$_2$ |
| I-1424 | OH | H | H | H | H | H | OMe | OMe | Me | H | H | H | COOH | O | —CH$_2$C≡CMe |
| I-1425 | OH | H | H | H | H | H | OMe | OMe | Me | H | H | H | COOH | O | —CH$_2$C$_6$H$_4$-4-Me |
| I-1426 | OH | H | H | H | H | H | OMe | OMe | Me | H | H | H | CH$_2$OH | O | —CH$_2$CH=CMe$_2$ |
| I-1427 | OH | H | H | H | H | H | OMe | OMe | Me | H | H | H | CH$_2$OH | O | —(CH$_2$)$_2$CH=CCl$_2$ |
| I-1428 | OH | H | H | H | H | H | OMe | OMe | Me | H | H | H | CH$_2$OH | O | —CH$_2$CH=CCl$_2$ |
| I-1429 | OH | H | H | H | H | H | OMe | OMe | Me | H | H | H | CH$_2$OH | O | —CH$_2$C≡CMe |
| I-1430 | OH | H | H | H | H | H | OMe | OMe | Me | H | H | H | CH$_2$OH | O | —CH$_2$C$_6$H$_4$-4-Me |
| I-1431 | OH | H | H | H | H | H | OMe | OMe | Me | H | H | H | F | O | —CH$_2$CH=CMe$_2$ |
| I-1432 | OH | H | H | H | H | H | OMe | OMe | Me | H | H | H | F | O | —(CH$_2$)$_2$CH=CMe$_2$ |

TABLE 273

| | | | | | | | | | | | | | | | |
|---|---|---|---|---|---|---|---|---|---|---|---|---|---|---|---|
| I-1433 | OH | H | H | H | H | H | OMe | OMe | Me | H | H | H | F | O | —CH$_2$CH=CCl$_2$ |
| I-1434 | OH | H | H | H | H | H | OMe | OMe | Me | H | H | H | F | O | —CH$_2$C≡CMe |
| I-1435 | OH | H | H | H | H | H | OMe | OMe | Me | H | H | H | F | O | —CH$_2$C$_6$H$_4$-4-Me |
| I-1436 | OH | H | H | H | H | H | OMe | OMe | H | H | H | H | OH | O | —CH$_2$CH=CCl$_2$ |
| I-1437 | OH | H | H | H | H | H | OMe | OMe | H | H | H | H | OH | O | —CH$_2$C≡CMe |
| I-1438 | OH | H | H | H | H | H | OMe | OMe | H | H | H | H | OH | O | —CH$_2$C$_6$H$_4$-4-Me |
| I-1439 | OH | H | H | H | H | H | OMe | OMe | H | H | H | H | OMs | O | —(CH$_2$)$_2$CH=CMe$_2$ |
| I-1440 | OH | H | H | H | H | H | OMe | OMe | H | H | H | H | OMs | O | —CH$_2$CH=CCl$_2$ |
| I-1441 | OH | H | H | H | H | H | OMe | OMe | H | H | H | H | OMs | O | —CH$_2$C≡CMe |
| I-1442 | OH | H | H | H | H | H | OMe | OMe | H | H | H | H | OMs | O | —CH$_2$C$_6$H$_4$-4-Me |
| I-1443 | OH | H | H | H | H | H | OMe | OMe | H | H | H | H | COOH | O | —CH$_2$CH=CMe$_2$ |
| I-1444 | OH | H | H | H | H | H | OMe | OMe | H | H | H | H | COOH | O | —(CH$_2$)$_2$CH=CMe$_2$ |
| I-1445 | OH | H | H | H | H | H | OMe | OMe | H | H | H | H | COOH | O | —CH$_2$CH=CCl$_2$ |
| I-1446 | OH | H | H | H | H | H | OMe | OMe | H | H | H | H | COOH | O | —CH$_2$C≡CMe |
| I-1447 | OH | H | H | H | H | H | OMe | OMe | H | H | H | H | COOH | O | —CH$_2$C$_6$H$_4$-4-Me |
| I-1448 | OH | H | H | H | H | H | OMe | OMe | H | H | H | H | CH$_2$OH | O | —CH$_2$CH=CMe$_2$ |
| I-1449 | OH | H | H | H | H | H | OMe | OMe | H | H | H | H | CH$_2$OH | O | —(CH$_2$)$_2$CH=CMe$_2$ |
| I-1450 | OH | H | H | H | H | H | OMe | OMe | H | H | H | H | CH$_2$OH | O | —CH$_2$CH=CCl$_2$ |
| I-1451 | OH | H | H | H | H | H | OMe | OMe | H | H | H | H | CH$_2$OH | O | —CH$_2$C≡CMe |
| I-1452 | OH | H | H | H | H | H | OMe | OMe | H | H | H | H | CH$_2$OH | O | —CH$_2$C$_6$H$_4$-4-Me |
| I-1453 | OH | H | H | H | H | H | OMe | OMe | H | H | H | H | F | O | —(CH$_2$)$_2$CH=CMe$_2$ |

TABLE 274

| | | | | | | | | | | | | | | | |
|---|---|---|---|---|---|---|---|---|---|---|---|---|---|---|---|
| I-1454 | OH | H | H | H | H | H | OMe | OMe | H | H | H | H | F | O | —CH$_2$CH=CCl$_2$ |
| I-1455 | OH | H | H | H | H | H | OMe | OMe | H | H | H | H | F | O | —CH$_2$C≡CMe |
| I-1456 | OH | H | H | H | H | H | OMe | OMe | H | H | H | H | F | O | —CH$_2$C$_6$H$_4$-4-Me |
| I-1457 | OH | H | H | H | H | F | OMe | OMe | OH | H | H | H | OH | O | —(CH$_2$)$_2$CH=CMe$_2$ |
| I-1458 | OH | H | H | H | H | F | OMe | OMe | OH | H | H | H | OH | O | —CH$_2$CH=CCl$_2$ |
| I-1459 | OH | H | H | H | H | F | OMe | OMe | OH | H | H | H | OH | O | —CH$_2$C≡CMe |
| I-1460 | OH | H | H | H | H | F | OMe | OMe | OH | H | H | H | OH | O | —CH$_2$C$_6$H$_4$-4-Me |
| I-1461 | OH | H | H | H | H | F | OMe | OMe | OH | H | H | H | OMs | O | —CH$_2$CH=CMe$_2$ |
| I-1462 | OH | H | H | H | H | F | OMe | OMe | OH | H | H | H | OMs | O | —(CH$_2$)$_2$CH=CMe$_2$ |
| I-1463 | OH | H | H | H | H | F | OMe | OMe | OH | H | H | H | OMs | O | —CH$_2$CH=CCl$_2$ |
| I-1464 | OH | H | H | H | H | F | OMe | OMe | OH | H | H | H | OMs | O | —CH$_2$C≡CMe |
| I-1465 | OH | H | H | H | H | F | OMe | OMe | OH | H | H | H | OMs | O | —CH$_2$C$_6$H$_4$-4-Me |
| I-1466 | OH | H | H | H | H | F | OMe | OMe | OH | H | H | H | COOH | O | —CH$_2$CH=CMe$_2$ |
| I-1467 | OH | H | H | H | H | F | OMe | OMe | OH | H | H | H | COOH | O | —(CH$_2$)$_2$CH=CMe$_2$ |
| I-1468 | OH | H | H | H | H | F | OMe | OMe | OH | H | H | H | COOH | O | —CH$_2$CH=CCl$_2$ |
| I-1469 | OH | H | H | H | H | F | OMe | OMe | OH | H | H | H | COOH | O | —CH$_2$C≡CMe |
| I-1470 | OH | H | H | H | H | F | OMe | OMe | OH | H | H | H | COOH | O | —CH$_2$C$_6$H$_4$-4-Me |
| I-1471 | OH | H | H | H | H | F | OMe | OMe | OH | H | H | H | CH$_2$OH | O | —CH$_2$CH=CMe$_2$ |
| I-1472 | OH | H | H | H | H | F | OMe | OMe | OH | H | H | H | CH$_2$OH | O | —(CH$_2$)$_2$CH=CMe$_2$ |
| I-1473 | OH | H | H | H | H | F | OMe | OMe | OH | H | H | H | CH$_2$OH | O | —CH$_2$CH=CCl$_2$ |
| I-1474 | OH | H | H | H | H | F | OMe | OMe | OH | H | H | H | CH$_2$OH | O | —CH$_2$C≡CMe |

TABLE 275

| | | | | | | | | | | | | | | | |
|---|---|---|---|---|---|---|---|---|---|---|---|---|---|---|---|
| I-1475 | OH | H | H | H | H | F | OMe | OMe | OH | H | H | H | CH$_2$OH | O | —CH$_2$C$_6$H$_4$-4-Me |
| I-1476 | OH | H | H | H | H | F | OMe | OMe | OH | H | H | H | F | O | —CH$_2$CH=CMe$_2$ |
| I-1477 | OH | H | H | H | H | F | OMe | OMe | OH | H | H | H | F | O | —(CH$_2$)$_2$CH=CMe$_2$ |
| I-1478 | OH | H | H | H | H | F | OMe | OMe | OH | H | H | H | F | O | —CH$_2$CH=CCl$_2$ |
| I-1479 | OH | H | H | H | H | F | OMe | OMe | OH | H | H | H | F | O | —CH$_2$C≡CMe |
| I-1480 | OH | H | H | H | H | F | OMe | OMe | OH | H | H | H | F | O | —CH$_2$C$_6$H$_4$-4-Me |
| I-1481 | OMs | H | H | H | H | H | OMe | OMe | OH | H | H | H | OH | O | —CH$_2$CH=CMe$_2$ |
| I-1482 | OMs | H | H | H | H | H | OMe | OMe | OH | H | H | H | OH | O | —(CH$_2$)$_2$CH=CMe$_2$ |
| I-1483 | OMs | H | H | H | H | H | OMe | OMe | OH | H | H | H | OH | O | —CH$_2$CH=CCl$_2$ |
| I-1484 | OMs | H | H | H | H | H | OMe | OMe | OH | H | H | H | OH | O | —CH$_2$C≡CMe |
| I-1485 | OMs | H | H | H | H | H | OMe | OMe | OH | H | H | H | OH | O | —CH$_2$C$_6$H$_4$-4-Me |
| I-1486 | OMs | H | H | H | H | H | OMe | OMe | OH | H | H | H | OMs | O | —CH$_2$CH=CMe$_2$ |
| I-1487 | OMs | H | H | H | H | H | OMe | OMe | OH | H | H | H | OMs | O | —(CH$_2$)$_2$CH=CMe$_2$ |
| I-1488 | OMs | H | H | H | H | H | OMe | OMe | OH | H | H | H | OMs | O | —CH$_2$CH=CCl$_2$ |
| I-1489 | OMs | H | H | H | H | H | OMe | OMe | OH | H | H | H | OMs | O | —CH$_2$C≡CMe |
| I-1490 | OMs | H | H | H | H | H | OMe | OMe | OH | H | H | H | OMs | O | —CH$_2$C$_6$H$_4$-4-Me |
| I-1491 | OMs | H | H | H | H | H | OMe | OMe | OH | H | H | H | COOH | O | —CH$_2$CH=CMe$_2$ |
| I-1492 | OMs | H | H | H | H | H | OMe | OMe | OH | H | H | H | COOH | O | —(CH$_2$)$_2$CH=CMe$_2$ |

TABLE 275-continued

| | | | | | | | | | | | | | | | |
|---|---|---|---|---|---|---|---|---|---|---|---|---|---|---|---|
| I-1493 | OMs | H | H | H | H | H | OMe | OMe | OH | H | H | H | COOH | O | —CH$_2$CH=CCl$_2$ |
| I-1494 | OMs | H | H | H | H | H | OMe | OMe | OH | H | H | H | COOH | O | —CH$_2$C≡CMe |
| I-1495 | OMs | H | H | H | H | H | OMe | OMe | OH | H | H | H | COOH | O | —CH$_2$C$_6$H$_4$-4-Me |

TABLE 276

| | | | | | | | | | | | | | | | |
|---|---|---|---|---|---|---|---|---|---|---|---|---|---|---|---|
| I-1496 | OMs | H | H | H | H | H | OMe | OMe | OH | H | H | H | CH$_2$OH | O | —CH$_2$CH=CMe$_2$ |
| I-1497 | OMs | H | H | H | H | H | OMe | OMe | OH | H | H | H | CH$_2$OH | O | —(CH$_2$)$_2$CH=CMe$_2$ |
| I-1498 | OMs | H | H | H | H | H | OMe | OMe | OH | H | H | H | CH$_2$OH | O | —CH$_2$CH=CCl$_2$ |
| I-1499 | OMs | H | H | H | H | H | OMe | OMe | OH | H | H | H | CH$_2$OH | O | —CH$_2$C≡CMe |
| I-1500 | OMs | H | H | H | H | H | OMe | OMe | OH | H | H | H | CH$_2$OH | O | —CH$_2$C$_6$H$_4$-4-Me |
| I-1501 | OMs | H | H | H | H | H | OMe | OMe | OH | H | H | H | F | O | —CH$_2$CH=CMe$_2$ |
| I-1502 | OMs | H | H | H | H | H | OMe | OMe | OH | H | H | H | F | O | —(CH$_2$)$_2$CH=CMe$_2$ |
| I-1503 | OMs | H | H | H | H | H | OMe | OMe | OH | H | H | H | F | O | —CH$_2$CH=CCl$_2$ |
| I-154 | OMs | H | H | H | H | H | OMe | OMe | OH | H | H | H | F | O | —CH$_2$C≡CMe |
| I-1505 | OMs | H | H | H | H | H | OMe | OMe | OH | H | H | H | F | O | —CH$_2$C$_6$H$_4$-4-Me |
| I-1506 | OMs | H | H | H | H | H | OMe | OMe | COOH | H | H | H | OH | O | —CH$_2$CH=CMe$_2$ |
| I-1507 | OMs | H | H | H | H | H | OMe | OMe | COOH | H | H | H | OH | O | —(CH$_2$)$_2$CH=CMe$_2$ |
| I-1508 | OMs | H | H | H | H | H | OMe | OMe | COOH | H | H | H | OH | O | —CH$_2$CH=CCl$_2$ |
| I-1509 | OMs | H | H | H | H | H | OMe | OMe | COOH | H | H | H | OH | O | —CH$_2$C≡CMe |
| I-1510 | OMs | H | H | H | H | H | OMe | OMe | COOH | H | H | H | OH | O | —CH$_2$C$_6$H$_4$-4-Me |
| I-1511 | OMs | H | H | H | H | H | OMe | OMe | COOH | H | H | H | OMs | O | —CH$_2$CH=CMe$_2$ |
| I-1512 | OMs | H | H | H | H | H | OMe | OMe | COOH | H | H | H | OMs | O | —(CH$_2$)$_2$CH=CMe$_2$ |
| I-1513 | OMs | H | H | H | H | H | OMe | OMe | COOH | H | H | H | OMs | O | —CH$_2$CH=CCl$_2$ |
| I-1514 | OMs | H | H | H | H | H | OMe | OMe | COOH | H | H | H | OMs | O | —CH$_2$C≡CMe |
| I-1515 | OMs | H | H | H | H | H | OMe | OMe | COOH | H | H | H | OMs | O | —CH$_2$C$_6$H$_4$-4-Me |
| I-1516 | OMs | H | H | H | H | H | OMe | OMe | COOH | H | H | H | COOH | O | —CH$_2$CH=CMe$_2$ |

TABLE 277

| | | | | | | | | | | | | | | | |
|---|---|---|---|---|---|---|---|---|---|---|---|---|---|---|---|
| I-1517 | OMs | H | H | H | H | H | OMe | OMe | COOH | H | H | H | COOH | O | —(CH$_2$)$_2$CH=CMe$_2$ |
| I-1518 | OMs | H | H | H | H | H | OMe | OMe | COOH | H | H | H | COOH | O | —CH$_2$CH=CCl$_2$ |
| I-1519 | OMs | H | H | H | H | H | OMe | OMe | COOH | H | H | H | COOH | O | —CH$_2$C≡CMe |
| I-1520 | OMs | H | H | H | H | H | OMe | OMe | COOH | H | H | H | COOH | O | —CH$_2$C$_6$H$_4$-4-Me |
| I-1521 | OMs | H | H | H | H | H | OMe | OMe | COOH | H | H | H | CH$_2$OH | O | —CH$_2$CH=CMe$_2$ |
| I-1522 | OMs | H | H | H | H | H | OMe | OMe | COOH | H | H | H | CH$_2$OH | O | —(CH$_2$)$_2$CH=CMe$_2$ |
| I-1523 | OMs | H | H | H | H | H | OMe | OMe | COOH | H | H | H | CH$_2$OH | O | —CH$_2$CH=CCl$_2$ |
| I-1524 | OMs | H | H | H | H | H | OMe | OMe | COOH | H | H | H | CH$_2$OH | O | —CH$_2$C≡CMe |
| I-1525 | OMs | H | H | H | H | H | OMe | OMe | COOH | H | H | H | CH$_2$OH | O | —CH$_2$C$_6$H$_4$-4-Me |
| I-1526 | OMs | H | H | H | H | H | OMe | OMe | COOH | H | H | H | F | O | —CH$_2$CH=CMe$_2$ |
| I-1527 | OMs | H | H | H | H | H | OMe | OMe | COOH | H | H | H | F | O | —(CH$_2$)$_2$CH=CMe$_2$ |
| I-1528 | OMs | H | H | H | H | H | OMe | OMe | COOH | H | H | H | F | O | —CH$_2$CH=CCl$_2$ |
| I-1529 | OMs | H | H | H | H | H | OMe | OMe | COOH | H | H | H | F | O | —CH$_2$C≡CMe |
| I-1530 | OMs | H | H | H | H | H | OMe | OMe | COOH | H | H | H | F | O | —CH$_2$C$_6$H$_4$-4-Me |
| I-1531 | OMs | H | H | H | H | H | OMe | OMe | CH$_2$OH | H | H | H | OH | O | —(CH$_2$)$_2$CH=CMe$_2$ |
| I-1532 | OMs | H | H | H | H | H | OMe | OMe | CH$_2$OH | H | H | H | OH | O | —CH$_2$CH=CCl$_2$ |
| I-1533 | OMs | H | H | H | H | H | OMe | OMe | CH$_2$OH | H | H | H | OH | O | —CH$_2$C≡CMe |
| I-1534 | OMs | H | H | H | H | H | OMe | OMe | CH$_2$OH | H | H | H | OH | O | —CH$_2$C$_6$H$_4$-4-Me |
| I-1535 | OMs | H | H | H | H | H | OMe | OMe | CH$_2$OH | H | H | H | OMs | O | —(CH$_2$)$_2$CH=CMe$_2$ |
| I-1536 | OMs | H | H | H | H | H | OMe | OMe | CH$_2$OH | H | H | H | OMs | O | —CH$_2$CH=CCl$_2$ |
| I-1537 | OMs | H | H | H | H | H | OMe | OMe | CH$_2$OH | H | H | H | OMs | O | —CH$_2$C≡CMe |

TABLE 278

| | | | | | | | | | | | | | | | |
|---|---|---|---|---|---|---|---|---|---|---|---|---|---|---|---|
| I-1538 | OMs | H | H | H | H | H | OMe | OMe | CH$_2$OH | H | H | H | OMs | O | —CH$_2$C$_6$H$_4$-4-Me |
| I-1539 | OMs | H | H | H | H | H | OMe | OMe | CH$_2$OH | H | H | H | COOH | O | —CH$_2$CH=CMe$_2$ |
| I-1540 | OMs | H | H | H | H | H | OMe | OMe | CH$_2$OH | H | H | H | COOH | O | —(CH$_2$)$_2$CH=CMe$_2$ |
| I-1541 | OMs | H | H | H | H | H | OMe | OMe | CH$_2$OH | H | H | H | COOH | O | —CH$_2$CH=CCl$_2$ |
| I-1542 | OMs | H | H | H | H | H | OMe | OMe | CH$_2$OH | H | H | H | COOH | O | —CH$_2$C≡CMe |
| I-1543 | OMs | H | H | H | H | H | OMe | OMe | CH$_2$OH | H | H | H | COOH | O | —CH$_2$C$_6$H$_4$-4-Me |
| I-1544 | OMs | H | H | H | H | H | OMe | OMe | CH$_2$OH | H | H | H | CH$_2$OH | O | —(CH$_2$)$_2$CH=CMe$_2$ |
| I-1545 | OMs | H | H | H | H | H | OMe | OMe | CH$_2$OH | H | H | H | CH$_2$OH | O | —CH$_2$CH=CCl$_2$ |
| I-1546 | OMs | H | H | H | H | H | OMe | OMe | CH$_2$OH | H | H | H | CH$_2$OH | O | —CH$_2$C≡CMe |

TABLE 278-continued

| | | | | | | | | | | | | | | | |
|---|---|---|---|---|---|---|---|---|---|---|---|---|---|---|---|
| I-1547 | OMs | H | H | H | H | H | OMe | OMe | CH$_2$OH | H | H | H | CH$_2$OH | O | —CH$_2$C$_6$H$_4$-4-Me |
| I-1548 | OMs | H | H | H | H | H | OMe | OMe | CH$_2$OH | H | H | H | F | O | —CH$_2$CH═CMe$_2$ |
| I-1549 | OMs | H | H | H | H | H | OMe | OMe | CH$_2$OH | H | H | H | F | O | —(CH$_2$)$_2$CH═CMe$_2$ |
| I-1550 | OMs | H | H | H | H | H | OMe | OMe | CH$_2$OH | H | H | H | F | O | —CH$_2$CH═CCl$_2$ |
| I-1551 | OMs | H | H | H | H | H | OMe | OMe | CH$_2$OH | H | H | H | F | O | —CH$_2$C≡CMe |
| I-1552 | OMs | H | H | H | H | H | OMe | OMe | CH$_2$OH | H | H | H | F | O | —CH$_2$C$_6$H$_4$-4-Me |
| I-1553 | OMs | H | H | H | H | H | OMe | OMe | Me | H | H | H | OH | O | —CH$_2$CH═CMe$_2$ |
| I-1554 | OMs | H | H | H | H | H | OMe | OMe | Me | H | H | H | OH | O | —(CH$_2$)$_2$CH═CMe$_2$ |
| I-1555 | OMs | H | H | H | H | H | OMe | OMe | Me | H | H | H | OH | O | —CH$_2$CH═CCl$_2$ |
| I-1556 | OMs | H | H | H | H | H | OMe | OMe | Me | H | H | H | OH | O | —CH$_2$C≡CMe |
| I-1557 | OMs | H | H | H | H | H | OMe | OMe | Me | H | H | H | OH | O | —CH$_2$C$_6$H$_4$-4-Me |
| I-1558 | OMs | H | H | H | H | H | OMe | OMe | Me | H | H | H | OMs | O | —CH$_2$CH═CMe$_2$ |

TABLE 279

| | | | | | | | | | | | | | | | |
|---|---|---|---|---|---|---|---|---|---|---|---|---|---|---|---|
| I-1559 | OMs | H | H | H | H | H | OMe | OMe | Me | H | H | H | OMs | O | —CH$_2$CH═CCl$_2$ |
| I-1560 | OMs | H | H | H | H | H | OMe | OMe | Me | H | H | H | OMs | O | —CH$_2$C≡CMe |
| I-1561 | OMs | H | H | H | H | H | OMe | OMe | Me | H | H | H | COOH | O | —CH$_2$CH═CMe$_2$ |
| I-1562 | OMs | H | H | H | H | H | OMe | OMe | Me | H | H | H | COOH | O | —(CH$_2$)$_2$CH═CMe$_2$ |
| I-1563 | OMs | H | H | H | H | H | OMe | OMe | Me | H | H | H | COOH | O | —CH$_2$CH═CCl$_2$ |
| I-1564 | OMs | H | H | H | H | H | OMe | OMe | Me | H | H | H | COOH | O | —CH$_2$C≡CMe |
| I-1565 | OMs | H | H | H | H | H | OMe | OMe | Me | H | H | H | COOH | O | —CH$_2$C$_6$H$_4$-4-Me |
| I-1566 | OMs | H | H | H | H | H | OMe | OMe | Me | H | H | H | CH$_2$OH | O | —CH$_2$CH═CMe$_2$ |
| I-1567 | OMs | H | H | H | H | H | OMe | OMe | Me | H | H | H | CH$_2$OH | O | —(CH$_2$)$_2$CH═CMe$_2$ |
| I-1568 | OMs | H | H | H | H | H | OMe | OMe | Me | H | H | H | CH$_2$OH | O | —CH$_2$CH═CCl$_2$ |
| I-1569 | OMs | H | H | H | H | H | OMe | OMe | Me | H | H | H | CH$_2$OH | O | —CH$_2$C≡CMe |
| I-1570 | OMs | H | H | H | H | H | OMe | OMe | Me | H | H | H | CH$_2$OH | O | —CH$_2$C$_6$H$_4$-4-Me |
| I-1571 | OMs | H | H | H | H | H | OMe | OMe | Me | H | H | H | F | O | —CH$_2$CH═CMe$_2$ |
| I-1572 | OMs | H | H | H | H | H | OMe | OMe | Me | H | H | H | F | O | —(CH$_2$)$_2$CH═CMe$_2$ |
| I-1573 | OMs | H | H | H | H | H | OMe | OMe | Me | H | H | H | F | O | —CH$_2$CH═CCl$_2$ |
| I-1574 | OMs | H | H | H | H | H | OMe | OMe | Me | H | H | H | F | O | —CH$_2$C≡CMe |
| I-1575 | OMs | H | H | H | H | H | OMe | OMe | Me | H | H | H | F | O | —CH$_2$C$_6$H$_4$-4-Me |
| I-1576 | OMs | H | H | H | H | H | OMe | OMe | H | H | H | H | OH | O | —CH$_2$CH═CMe$_2$ |
| I-1577 | OMs | H | H | H | H | H | OMe | OMe | H | H | H | H | OH | O | —(CH$_2$)$_2$CH═CMe$_2$ |
| I-1578 | OMs | H | H | H | H | H | OMe | OMe | H | H | H | H | OH | O | —CH$_2$CH═CCl$_2$ |
| I-1579 | OMs | H | H | H | H | H | OMe | OMe | H | H | H | H | OH | O | —CH$_2$C≡CMe |

TABLE 280

| | | | | | | | | | | | | | | | |
|---|---|---|---|---|---|---|---|---|---|---|---|---|---|---|---|
| I-1580 | OMs | H | H | H | H | H | OMe | OMe | H | H | H | H | OH | O | —CH$_2$C$_6$H$_4$-4-Me |
| I-1581 | OMs | H | H | H | H | H | OMe | OMe | H | H | H | H | OMs | O | —CH$_2$CH═CCl$_2$ |
| I-1582 | OMs | H | H | H | H | H | OMe | OMe | H | H | H | H | OMs | O | —CH$_2$C≡CMe |
| I-1583 | OMs | H | H | H | H | H | OMe | OMe | H | H | H | H | COOH | O | —CH$_2$CH═CMe$_2$ |
| I-1584 | OMs | H | H | H | H | H | OMe | OMe | H | H | H | H | COOH | O | —(CH$_2$)$_2$CH═CMe$_2$ |
| I-1585 | OMs | H | H | H | H | H | OMe | OMe | H | H | H | H | COOH | O | —CH$_2$CH═CCl$_2$ |
| I-1586 | OMs | H | H | H | H | H | OMe | OMe | H | H | H | H | COOH | O | —CH$_2$C≡CMe |
| I-1587 | OMs | H | H | H | H | H | OMe | OMe | H | H | H | H | COOH | O | —CH$_2$C$_6$H$_4$-4-Me |
| I-1588 | OMs | H | H | H | H | H | OMe | OMe | H | H | H | H | CH$_2$OH | O | —CH$_2$CH═CMe$_2$ |
| I-1589 | OMs | H | H | H | H | H | OMe | OMe | H | H | H | H | CH$_2$OH | O | —(CH$_2$)$_2$CH═CMe$_2$ |
| I-1590 | OMs | H | H | H | H | H | OMe | OMe | H | H | H | H | CH$_2$OH | O | —CH$_2$CH═CCl$_2$ |
| I-1591 | OMs | H | H | H | H | H | OMe | OMe | H | H | H | H | CH$_2$OH | O | —CH$_2$C≡CMe |
| I-1592 | OMs | H | H | H | H | H | OMe | OMe | H | H | H | H | CH$_2$OH | O | —CH$_2$C$_6$H$_4$-4-Me |
| I-1593 | OMs | H | H | H | H | H | OMe | OMe | H | H | H | H | F | O | —(CH$_2$)$_2$CH═CMe$_2$ |
| I-1594 | OMs | H | H | H | H | H | OMe | OMe | H | H | H | H | F | O | —CH$_2$CH═CCl$_2$ |
| I-1595 | OMs | H | H | H | H | H | OMe | OMe | H | H | H | H | F | O | —CH$_2$C≡CMe |
| I-1596 | OMs | H | H | H | H | F | OMe | OMe | OH | H | H | H | OH | O | —CH$_2$CH═CMe$_2$ |
| I-1597 | OMs | H | H | H | H | F | OMe | OMe | OH | H | H | H | OH | O | —(CH$_2$)$_2$CH═CMe$_2$ |
| I-1598 | OMs | H | H | H | H | F | OMe | OMe | OH | H | H | H | OH | O | —CH$_2$CH═CCl$_2$ |
| I-1599 | OMs | H | H | H | H | F | OMe | OMe | OH | H | H | H | OH | O | —CH$_2$C≡CMe |
| I-1600 | OMs | H | H | H | H | F | OMe | OMe | OH | H | H | H | OH | O | —CH$_2$C$_6$H$_4$-4-Me |

TABLE 281

| | | | | | | | | | | | | | | | |
|---|---|---|---|---|---|---|---|---|---|---|---|---|---|---|---|
| I-1601 | OMs | H | H | H | H | F | OMe | OMe | OH | H | H | H | OMs | O | —CH$_2$CH=CMe$_2$ |
| I-1602 | OMs | H | H | H | H | F | OMe | OMe | OH | H | H | H | OMs | O | —(CH$_2$)$_2$CH=CMe$_2$ |
| I-1603 | OMs | H | H | H | H | F | OMe | OMe | OH | H | H | H | OMs | O | —CH$_2$CH=CCl$_2$ |
| I-1604 | OMs | H | H | H | H | F | OMe | OMe | OH | H | H | H | OMs | O | —CH$_2$C≡CMe |
| I-1605 | OMs | H | H | H | H | F | OMe | OMe | OH | H | H | H | OMs | O | —CH$_2$C$_6$H$_4$-4-Me |
| I-1606 | OMs | H | H | H | H | F | OMe | OMe | OH | H | H | H | COOH | O | —CH$_2$CH=CMe$_2$ |
| I-1607 | OMs | H | H | H | H | F | OMe | OMe | OH | H | H | H | COOH | O | —(CH$_2$)$_2$CH=CMe$_2$ |
| I-1608 | OMs | H | H | H | H | F | OMe | OMe | OH | H | H | H | COOH | O | —CH$_2$CH=CCl$_2$ |
| I-1609 | OMs | H | H | H | H | F | OMe | OMe | OH | H | H | H | COOH | O | —CH$_2$C≡CMe |
| I-1610 | OMs | H | H | H | H | F | OMe | OMe | OH | H | H | H | COOH | O | —CH$_2$C$_6$H$_4$-4-Me |
| I-1611 | OMs | H | H | H | H | F | OMe | OMe | OH | H | H | H | CH$_2$OH | O | —CH$_2$CH=CMe$_2$ |
| I-1612 | OMs | H | H | H | H | F | OMe | OMe | OH | H | H | H | CH$_2$OH | O | —(CH$_2$)$_2$CH=CMe$_2$ |
| I-1613 | OMs | H | H | H | H | F | OMe | OMe | OH | H | H | H | CH$_2$OH | O | —CH$_2$CH=CCl$_2$ |
| I-1614 | OMs | H | H | H | H | F | OMe | OMe | OH | H | H | H | CH$_2$OH | O | —CH$_2$C≡CMe |
| I-1615 | OMs | H | H | H | H | F | OMe | OMe | OH | H | H | H | CH$_2$OH | O | —CH$_2$C$_6$H$_4$-4-Me |
| I-1616 | OMs | H | H | H | H | F | OMe | OMe | OH | H | H | H | F | O | —CH$_2$CH=CMe$_2$ |
| I-1617 | OMs | H | H | H | H | F | OMe | OMe | OH | H | H | H | F | O | —(CH$_2$)$_2$CH=CMe$_2$ |
| I-1618 | OMs | H | H | H | H | F | OMe | OMe | OH | H | H | H | F | O | —CH$_2$CH=CCl$_2$ |
| I-1619 | OMs | H | H | H | H | F | OMe | OMe | OH | H | H | H | F | O | —CH$_2$C≡CMe |
| I-1620 | OMs | H | H | H | H | F | OMe | OMe | OH | H | H | H | F | O | —CH$_2$C$_6$H$_4$-4-Me |
| I-1621 | F | H | H | H | H | H | OMe | OMe | OH | H | H | H | OH | O | —CH$_2$CH=CCl$_2$ |

TABLE 282

| | | | | | | | | | | | | | | | |
|---|---|---|---|---|---|---|---|---|---|---|---|---|---|---|---|
| I-1622 | F | H | H | H | H | H | OMe | OMe | OH | H | H | H | OH | O | —CH$_2$C≡CMe |
| I-1623 | F | H | H | H | H | H | OMe | OMe | OH | H | H | H | OMs | O | —CH$_2$CH=CCl$_2$ |
| I-1624 | F | H | H | H | H | H | OMe | OMe | OH | H | H | H | OMs | O | —CH$_2$C≡CMe |
| I-1625 | F | H | H | H | H | H | OMe | OMe | OH | H | H | H | COOH | O | —CH$_2$CH=CMe$_2$ |
| I-1626 | F | H | H | H | H | H | OMe | OMe | OH | H | H | H | COOH | O | —(CH$_2$)$_2$CH=CMe$_2$ |
| I-1627 | F | H | H | H | H | H | OMe | OMe | OH | H | H | H | COOH | O | —CH$_2$CH=CCl$_2$ |
| I-1628 | F | H | H | H | H | H | OMe | OMe | OH | H | H | H | COOH | O | —CH$_2$C≡CMe |
| I-1629 | F | H | H | H | H | H | OMe | OMe | OH | H | H | H | COOH | O | —CH$_2$C$_6$H$_4$-4-Me |
| I-1630 | F | H | H | H | H | H | OMe | OMe | OH | H | H | H | CH$_2$OH | O | —CH$_2$CH=CMe$_2$ |
| I-1631 | F | H | H | H | H | H | OMe | OMe | OH | H | H | H | CH$_2$OH | O | —(CH$_2$)$_2$CH=CMe$_2$ |
| I-1632 | F | H | H | H | H | H | OMe | OMe | OH | H | H | H | CH$_2$OH | O | —CH$_2$CH=CCl$_2$ |
| I-1633 | F | H | H | H | H | H | OMe | OMe | OH | H | H | H | CH$_2$OH | O | —CH$_2$C≡CMe |
| I-1634 | F | H | H | H | H | H | OMe | OMe | OH | H | H | H | CH$_2$OH | O | —CH$_2$C$_6$H$_4$-4-Me |
| I-1635 | F | H | H | H | H | H | OMe | OMe | OH | H | H | H | F | O | —CH$_2$CH=CCl$_2$ |
| I-1636 | F | H | H | H | H | H | OMe | OMe | OH | H | H | H | F | O | —CH$_2$C≡CMe |
| I-1637 | F | H | H | H | H | H | OMe | OMe | COOH | H | H | H | OH | O | —CH$_2$CH=CCl$_2$ |
| I-1638 | F | H | H | H | H | H | OMe | OMe | COOH | H | H | H | OH | O | —CH$_2$C≡CMe |
| I-1639 | F | H | H | H | H | H | OMe | OMe | COOH | H | H | H | OMs | O | —CH$_2$CH=CMe$_2$ |
| I-1640 | F | H | H | H | H | H | OMe | OMe | COOH | H | H | H | OMs | O | —(CH$_2$)$_2$CH=CMe$_2$ |
| I-1641 | F | H | H | H | H | H | OMe | OMe | COOH | H | H | H | OMs | O | —CH$_2$CH=CCl$_2$ |
| I-1642 | F | H | H | H | H | H | OMe | OMe | COOH | H | H | H | OMs | O | —CH$_2$C≡CMe |

TABLE 283

| | | | | | | | | | | | | | | | |
|---|---|---|---|---|---|---|---|---|---|---|---|---|---|---|---|
| I-1643 | F | H | H | H | H | H | OMe | OMe | COOH | H | H | H | OMs | O | —CH$_2$C$_6$H$_4$-4-Me |
| I-1644 | F | H | H | H | H | H | OMe | OMe | COOH | H | H | H | COOH | O | —CH$_2$CH=CMe$_2$ |
| I-1645 | F | H | H | H | H | H | OMe | OMe | COOH | H | H | H | COOH | O | —(CH$_2$)$_2$CH=CMe$_2$ |
| I-1646 | F | H | H | H | H | H | OMe | OMe | COOH | H | H | H | COOH | O | —CH$_2$CH=CCl$_2$ |
| I-1647 | F | H | H | H | H | H | OMe | OMe | COOH | H | H | H | COOH | O | —CH$_2$C≡CMe |
| I-1648 | F | H | H | H | H | H | OMe | OMe | COOH | H | H | H | COOH | O | —CH$_2$C$_6$H$_4$-4-Me |
| I-1649 | F | H | H | H | H | H | OMe | OMe | COOH | H | H | H | CH$_2$OH | O | —CH$_2$CH=CMe$_2$ |
| I-1650 | F | H | H | H | H | H | OMe | OMe | COOH | H | H | H | CH$_2$OH | O | —(CH$_2$)$_2$CH=CMe$_2$ |
| I-1651 | F | H | H | H | H | H | OMe | OMe | COOH | H | H | H | CH$_2$OH | O | —CH$_2$CH=CCl$_2$ |
| I-1652 | F | H | H | H | H | H | OMe | OMe | COOH | H | H | H | CH$_2$CH | O | —CH$_2$C≡CMe |
| I-1653 | F | H | H | H | H | H | OMe | OMe | COOH | H | H | H | CH$_2$OH | O | —CH$_2$C$_6$H$_4$-4-Me |
| I-1654 | F | H | H | H | H | H | OMe | OMe | COOH | H | H | H | F | O | —CH$_2$CH=CCl$_2$ |
| I-1655 | F | H | H | H | H | H | OMe | OMe | COOH | H | H | H | F | O | —CH$_2$C≡CMe |
| I-1656 | F | H | H | H | H | H | OMe | OMe | CH$_2$OH | H | H | H | OH | O | —CH$_2$CHC=Me$_2$ |
| I-1657 | F | H | H | H | H | H | OMe | OMe | CH$_2$OH | H | H | H | OH | O | —(CH$_2$)$_2$CH=CMe$_2$ |
| I-1658 | F | H | H | H | H | H | OMe | OMe | CH$_2$OH | H | H | H | OH | O | —CH$_2$CH=CCl$_2$ |
| I-1659 | F | H | H | H | H | H | OMe | OMe | CH$_2$OH | H | H | H | OH | O | —CH$_2$C≡CMe |
| I-1660 | F | H | H | H | H | H | OMe | OMe | CH$_2$OH | H | H | H | OH | O | —CH$_2$C$_6$H$_4$-4-Me |
| I-1661 | F | H | H | H | H | H | OMe | OMe | CH$_2$OH | H | H | H | OMs | O | —CH$_2$CH=CMe$_2$ |
| I-1662 | F | H | H | H | H | H | OMe | OMe | CH$_2$OH | H | H | H | OMs | O | —(CH$_2$)$_2$CH=CMe$_2$ |
| I-1663 | F | H | H | H | H | H | OMe | OMe | CH$_2$OH | H | H | H | OMs | O | —CH$_2$CH=CCl$_2$ |

TABLE 284

| | | | | | | | | | | | | | | | |
|---|---|---|---|---|---|---|---|---|---|---|---|---|---|---|---|
| I-1664 | F | H | H | H | H | H | OMe | OMe | Ch₂OH | H | H | H | OMs | O | —CH₂C≡CMe |
| I-1665 | F | H | H | H | H | H | OMe | OMe | CH₂OH | H | H | H | OMs | O | —CH₂C₆H₄-4-Me |
| I-1666 | F | H | H | H | H | H | OMe | OMe | CH₂OH | H | H | H | COOH | O | —CH₂CH=CMe₂ |
| I-1667 | F | H | H | H | H | H | OMe | OMe | CH₂OH | H | H | H | COOH | O | —(CH₂)₂CH=CMe₂ |
| I-1668 | F | H | H | H | H | H | OMe | OMe | CH₂OH | H | H | H | COOH | O | —CH₂CH=CCl₂ |
| I-1669 | F | H | H | H | H | H | OMe | OMe | CH₂OH | H | H | H | COOH | O | —CH₂C≡CMe |
| I-1670 | F | H | H | H | H | H | OMe | OMe | CH₂OH | H | H | H | COOH | O | —CH₂C₆H₄-4-Me |
| I-1671 | F | H | H | H | H | H | OMe | OMe | CH₂OH | H | H | H | CH₂OH | O | —CH₂CH=CMe₂ |
| I-1672 | F | H | H | H | H | H | OMe | OMe | CH₂OH | H | H | H | CH₂OH | O | —(CH₂)₂CH=CMe₂ |
| I-1673 | F | H | H | H | H | H | OMe | OMe | CH₂OH | H | H | H | CH₂OH | O | —CH₂CH=CCl₂ |
| I-1674 | F | H | H | H | H | H | OMe | OMe | CH₂OH | H | H | H | CH₂OH | O | —CH₂C≡CMe |
| I-1675 | F | H | H | H | H | H | OMe | OMe | CH₂OH | H | H | H | CH₂OH | O | —CH₂C₆H₄-4-Me |
| I-1676 | F | H | H | H | H | H | OMe | OMe | CH₂OH | H | H | H | F | O | —CH₂CH=CMe₂ |
| I-1677 | F | H | H | H | H | H | OMe | OMe | CH₂OH | H | H | H | F | O | —(CH₂)₂CH=CMe₂ |
| I-1678 | F | H | H | H | H | H | OMe | OMe | CH₂OH | H | H | H | F | O | —CH₂CH=CCl₂ |
| I-1679 | F | H | H | H | H | H | OMe | OMe | CH₂OH | H | H | H | F | O | —CH₂C≡CMe |
| I-1680 | F | H | H | H | H | H | OMe | OMe | CH₂OH | H | H | H | F | O | —CH₂C₆H₄-4-Me |
| I-1681 | F | H | H | H | H | H | OMe | OMe | Me | H | H | H | OH | O | —CH₂CH=CMe₂ |
| I-1682 | F | H | H | H | H | H | OMe | OMe | Me | H | H | H | OH | O | —(CH₂)₂CH=CMe₂ |
| I-1683 | F | H | H | H | H | H | OMe | OMe | Me | H | H | H | OH | O | —CH₂CH=CCl₂ |
| I-1684 | F | H | H | H | H | H | OMe | OMe | Me | H | H | H | OH | O | —CH₂C≡CMe |

TABLE 285

| | | | | | | | | | | | | | | | |
|---|---|---|---|---|---|---|---|---|---|---|---|---|---|---|---|
| I-1685 | F | H | H | H | H | H | OMe | OMe | Me | H | H | H | OH | O | —CH₂C₆H₄-4-Me |
| I-1686 | F | H | H | H | H | H | OMe | OMe | Me | H | H | H | OMs | O | —CH₂CH=CMe₂ |
| I-1687 | F | H | H | H | H | H | OMe | OMe | Me | H | H | H | OMs | O | —(CH₂)₂CH=CMe₂ |
| I-1688 | F | H | H | H | H | H | OMe | OMe | Me | H | H | H | OMs | O | —CH₂CH=CCl₂ |
| I-1689 | F | H | H | H | H | H | OMe | OMe | Me | H | H | H | OMs | O | —CH₂C≡CMe |
| I-1690 | F | H | H | H | H | H | OMe | OMe | Me | H | H | H | OMs | O | —CH₂C₆H₄-4-Me |
| I-1691 | F | H | H | H | H | H | OMe | OMe | Me | H | H | H | COOH | O | —CH₂CH=CMe₂ |
| I-1692 | F | H | H | H | H | H | OMe | OMe | Me | H | H | H | COOH | O | —(CH₂)₂CH=CMe₂ |
| I-1693 | F | H | H | H | H | H | OMe | OMe | Me | H | H | H | COOH | O | —CH₂CH=CCl₂ |
| I-1694 | F | H | H | H | H | H | OMe | OMe | Me | H | H | H | COOH | O | —CH₂C≡CMe |
| I-1695 | F | H | H | H | H | H | OMe | OMe | Me | H | H | H | COOH | O | —CH₂C₆H₄-4-Me |
| I-1696 | F | H | H | H | H | H | OMe | OMe | Me | H | H | H | CH₂OH | O | —CH₂CH=CMe₂ |
| I-1697 | F | H | H | H | H | H | OMe | OMe | Me | H | H | H | CH₂OH | O | —(CH₂)₂CH=CMe₂ |
| I-1698 | F | H | H | H | H | H | OMe | OMe | Me | H | H | H | CH₂OH | O | —CH₂CH=CCl₂ |
| I-1699 | F | H | H | H | H | H | OMe | OMe | Me | H | H | H | CH₂OH | O | —CH₂C≡CMe |
| I-1700 | F | H | H | H | H | H | OMe | OMe | Me | H | H | H | CH₂OH | O | —CH₂C₆H₄-4-Me |
| I-1701 | F | H | H | H | H | H | OMe | OMe | Me | H | H | H | F | O | —CH₂CH=CMe₂ |
| I-1702 | F | H | H | H | H | H | OMe | OMe | Me | H | H | H | F | O | —(CH₂)₂CH=CMe₂ |
| I-1703 | F | H | H | H | H | H | OMe | OMe | Me | H | H | H | F | O | —CH₂CH=CCl₂ |
| I-1704 | F | H | H | H | H | H | OMe | OMe | Me | H | H | H | F | O | —CH₂C≡CMe |
| I-1705 | F | H | H | H | H | H | OMe | OMe | Me | H | H | H | F | O | —CH₂C₆H₄-4-Me |

TABLE 286

| | | | | | | | | | | | | | | | |
|---|---|---|---|---|---|---|---|---|---|---|---|---|---|---|---|
| I-1706 | F | H | H | H | H | H | OMe | OMe | H | H | H | H | OH | O | —CH₂CH=CMe₂ |
| I-1707 | F | H | H | H | H | H | OMe | OMe | H | H | H | H | OH | O | —(CH₂)₂CH=CMe₂ |
| I-1708 | F | H | H | H | H | H | OMe | OMe | H | H | H | H | OH | O | —CH₂CH=CCl₂ |
| I-1709 | F | H | H | H | H | H | OMe | OMe | H | H | H | H | OH | O | —CH₂C≡CMe |
| I-1710 | F | H | H | H | H | H | OMe | OMe | H | H | H | H | OH | O | —CH₂C₆H₄-4-Me |
| I-1711 | F | H | H | H | H | H | OMe | OMe | H | H | H | H | OMs | O | —(CH₂)₂CH=CMe₂ |
| I-1712 | F | H | H | H | H | H | OMe | OMe | H | H | H | H | OMs | O | —CH₂CH=CCl₂ |
| I-1713 | F | H | H | H | H | H | OMe | OMe | H | H | H | H | OMs | O | —CH₂C≡CMe |
| I-1714 | F | H | H | H | H | H | OMe | OMe | H | H | H | H | OMs | O | —CH₂C₆H₄-4-Me |
| I-1715 | F | H | H | H | H | H | OMe | OMe | H | H | H | H | COOH | O | —CH₂CH=CMe₂ |
| I-1716 | F | H | H | H | H | H | OMe | OMe | H | H | H | H | COOH | O | —(CH₂)₂CH=CMe₂ |
| I-1717 | F | H | H | H | H | H | OMe | OMe | H | H | H | H | COOH | O | —CH₂CH=CCl₂ |
| I-1718 | F | H | H | H | H | H | OMe | OMe | H | H | H | H | COOH | O | —CH₂C≡CMe |
| I-1719 | F | H | H | H | H | H | OMe | OMe | H | H | H | H | COOH | O | —CH₂C₆H₄-4-Me |
| I-1720 | F | H | H | H | H | H | OMe | OMe | H | H | H | H | CH₂OH | O | —CH₂CH=CMe₂ |
| I-1721 | F | H | H | H | H | H | OMe | OMe | H | H | H | H | CH₂OH | O | —(CH₂)₂CH=CMe₂ |
| I-1722 | F | H | H | H | H | H | OMe | OMe | H | H | H | H | CH₂OH | O | —CH₂CH=CCl₂ |
| I-1723 | F | H | H | H | H | H | OMe | OMe | H | H | H | H | CH₂OH | O | —CH₂C≡CMe |

TABLE 286-continued

| | | | | | | | | | | | | | | | |
|---|---|---|---|---|---|---|---|---|---|---|---|---|---|---|---|
| I-1724 | F | H | H | H | H | H | OMe | OMe | H | H | H | H | CH$_2$OH | O | —CH$_2$C$_6$H$_4$-4-Me |
| I-1725 | F | H | H | H | H | H | OMe | OMe | H | H | H | H | F | O | —CH$_2$CH=CMe$_2$ |
| I-1726 | F | H | H | H | H | H | OMe | OMe | H | H | H | H | F | O | —(CH$_2$)$_2$CH=CMe$_2$ |

TABLE 287

| | | | | | | | | | | | | | | | |
|---|---|---|---|---|---|---|---|---|---|---|---|---|---|---|---|
| 1-1727 | F | H | H | H | H | H | OMe | OMe | H | H | H | H | F | O | —CH$_2$CH=CCl$_2$ |
| 1-1728 | F | H | H | H | H | H | OMe | OMe | H | H | H | H | F | O | —CH$_2$C≡CMe |
| 1-1729 | F | H | H | H | H | H | OMe | OMe | H | H | H | H | F | O | —CH$_2$C$_6$H$_4$-4-Me |
| 1-1730 | F | H | H | H | H | F | OMe | OMe | OH | H | H | H | OH | O | —(CH$_2$)$_2$CH=CMe$_2$ |
| 1-1731 | F | H | H | H | H | F | OMe | OMe | OH | H | H | H | OH | O | —CH$_2$CH=CCl$_2$ |
| 1-1732 | F | H | H | H | H | F | OMe | OMe | OH | H | H | H | OH | O | —CH$_2$C≡CMe |
| 1-1733 | F | H | H | H | H | F | OMe | OMe | OH | H | H | H | OH | O | —CH$_2$C$_6$H$_4$-4-Me |
| 1-1734 | F | H | H | H | H | F | OMe | OMe | OH | H | H | H | OMs | O | —CH$_2$CH=CMe$_2$ |
| 1-1735 | F | H | H | H | H | F | OMe | OMe | OH | H | H | H | OMs | O | —(CH$_2$)$_2$CH=CMe$_2$ |
| 1-1736 | F | H | H | H | H | F | OMe | OMe | OH | H | H | H | OMs | O | —CH$_2$CH=CCl$_2$ |
| 1-1737 | F | H | H | H | H | F | OMe | OMe | OH | H | H | H | OMs | O | —CH$_2$C≡CMe |
| 1-1738 | F | H | H | H | H | F | OMe | OMe | OH | H | H | H | OMs | O | —CH$_2$C$_6$H$_4$-4-Me |
| 1-1739 | F | H | H | H | H | F | OMe | OMe | OH | H | H | H | COOH | O | —CH$_2$CH=CMe$_2$ |
| 1-1740 | F | H | H | H | H | F | OMe | OMe | OH | H | H | H | COOH | O | —(CH$_2$)$_2$CH=CMe$_2$ |
| 1-1741 | F | H | H | H | H | F | OMe | OMe | OH | H | H | H | COOH | O | —CH$_2$CH=CCl$_2$ |
| 1-1742 | F | H | H | H | H | F | OMe | OMe | OH | H | H | H | COOH | O | —CH$_2$C≡CMe |
| 1-1743 | F | H | H | H | H | F | OMe | OMe | OH | H | H | H | COOH | O | —CH$_2$C$_6$H$_4$-4-Me |
| 1-1744 | F | H | H | H | H | F | OMe | OMe | OH | H | H | H | CH$_2$OH | O | —CH$_2$CH=CMe$_2$ |
| 1-1745 | F | H | H | H | H | F | OMe | OMe | OH | H | H | H | CH$_2$OH | O | —(CH$_2$)$_2$CH=CMe$_2$ |
| 1-1746 | F | H | H | H | H | F | OMe | OMe | OH | H | H | H | CH$_2$OH | O | —CH$_2$CH=CCl$_2$ |
| 1-1747 | F | H | H | H | H | F | OMe | OMe | OH | H | H | H | CH$_2$OH | O | —CH$_2$C≡CMe |

TABLE 288

| | | | | | | | | | | | | | | | |
|---|---|---|---|---|---|---|---|---|---|---|---|---|---|---|---|
| 1-1748 | F | | H | H | H | H | F | OMe | OMe | OH | H | H | H | CH$_2$OH | O | —CH$_2$C$_6$H$_4$-4-Me |
| 1-1749 | F | | H | H | H | H | F | OMe | OMe | OH | H | H | H | F | O | —CH$_2$CH=CMe$_2$ |
| 1-1750 | F | | H | H | H | H | F | OMe | OMe | OH | H | H | H | F | O | —(CH$_2$)$_2$CH=CMe$_2$ |
| 1-1751 | F | | H | H | H | H | F | OMe | OMe | OH | H | H | H | F | O | —CH$_2$CH=CCl$_2$ |
| 1-1752 | F | | H | H | H | H | F | OMe | OMe | OH | H | H | H | F | O | —CH$_2$C≡CMe |
| 1-1753 | F | | H | H | H | H | F | OMe | OMe | OH | H | H | H | F | O | —CH$_2$C$_6$H$_4$-4-Me |
| 1-1754 | —OCH$_2$O— * | H | H | * | H | H | OMe | OMe | OH | H | H | H | OH | O | —CH$_2$CH=CMe$_2$ |
| 1-1755 | —OCH$_2$O— * | H | H | * | H | H | OMe | OMe | OH | H | H | H | OH | O | —(CH$_2$)$_2$CH=CMe$_2$ |
| 1-1756 | —OCH$_2$O— * | H | H | * | H | H | OMe | OMe | OH | H | H | H | OH | O | —CH$_2$CH=CCl$_2$ |
| 1-1757 | —OCH$_2$O— * | H | H | * | H | H | OMe | OMe | OH | H | H | H | OH | O | —CH$_2$C≡CMe |
| 1-1758 | —OCH$_2$O— * | H | H | * | H | H | OMe | OMe | OH | H | H | H | OH | O | —CH$_2$C$_6$H$_4$-4-Me |
| 1-1759 | —OCH$_2$O— * | H | H | * | H | H | OMe | OMe | OH | H | H | H | OMs | O | —CH$_2$CH=CMe$_2$ |
| 1-1760 | —OCH$_2$O— * | H | H | * | H | H | OMe | OMe | OH | H | H | H | OMs | O | —(CH$_2$)$_2$CH=CMe$_2$ |
| 1-1761 | —OCH$_2$O— * | H | H | * | H | H | OMe | OMe | OH | H | H | H | OMs | O | —CH$_2$CH=CCl$_2$ |
| 1-1762 | —OCH$_2$O— * | H | H | * | H | H | OMe | OMe | OH | H | H | H | OMs | O | —CH$_2$C≡CMe |
| 1-1763 | —OCH$_2$O— * | H | H | * | H | H | OMe | OMe | OH | H | H | H | OMs | O | —CH$_2$C$_6$H$_4$-4-Me |
| 1-1764 | —OCH$_2$O— * | H | H | * | H | H | OMe | OMe | OH | H | H | H | COOH | O | —CH$_2$CH=CMe$_2$ |
| 1-1765 | —OCH$_2$O— * | H | H | * | H | H | OMe | OMe | OH | H | H | H | COOH | O | —(CH$_2$)$_2$CH=CMe$_2$ |
| 1-1766 | —OCH$_2$O— * | H | H | * | H | H | OMe | OMe | OH | H | H | H | COOH | O | —CH$_2$CH=CCl$_2$ |
| 1-1767 | —OCH$_2$O— * | H | H | * | H | H | OMe | OMe | OH | H | H | H | COOH | O | —CH$_2$C≡CMe |
| 1-1768 | —OCH$_2$O— * | H | H | * | H | H | OMe | OMe | OH | H | H | H | COOH | O | —CH$_2$C$_6$H$_4$-4-Me |

TABLE 289

| | | | | | | | | | | | | | | | |
|---|---|---|---|---|---|---|---|---|---|---|---|---|---|---|---|
| 1-1768 | —OCH$_2$O— * | H | H | * | H | H | OMe | OMe | OH | H | H | H | CH$_2$OH | O | —CH$_2$CH=CMe$_2$ |
| 1-1769 | —OCH$_2$O— * | H | H | * | H | H | OMe | OMe | OH | H | H | H | CH$_2$OH | O | —(CH$_2$)$_2$CH=CMe$_2$ |
| 1-1770 | —OCH$_2$O— * | H | H | * | H | H | OMe | OMe | OH | H | H | H | CH$_2$OH | O | —CH$_2$CH=CCl$_2$ |
| 1-1771 | —OCH$_2$O— * | H | H | * | H | H | OMe | OMe | OH | H | H | H | CH$_2$OH | O | —CH$_2$C≡CMe |
| 1-1772 | —OCH$_2$O— * | H | H | * | H | H | OMe | OMe | OH | H | H | H | CH$_2$OH | O | —CH$_2$C$_6$H$_4$-4-Me |
| 1-1773 | —OCH$_2$O— * | H | H | * | H | H | OMe | OMe | OH | H | H | H | F | O | —CH$_2$CH=CMe$_2$ |
| 1-1774 | —OCH$_2$O— * | H | H | * | H | H | OMe | OMe | OH | H | H | H | F | O | —(CH$_2$)$_2$CH=CMe$_2$ |
| 1-1775 | —OCH$_2$O— * | H | H | * | H | H | OMe | OMe | OH | H | H | H | F | O | —CH$_2$CH=CCl$_2$ |
| 1-1776 | —OCH$_2$O— * | H | H | * | H | H | OMe | OMe | OH | H | H | H | F | O | —CH$_2$C≡CMe |

TABLE 289-continued

| | | | | | | | | | | | | | | | |
|---|---|---|---|---|---|---|---|---|---|---|---|---|---|---|---|
| 1-1777 | —OCH$_2$O—* | H | H | * | H | H | OMe | OMe | OH | H | H | H | F | O | —CH$_2$C$_6$H$_4$-4-Me |
| 1-1778 | —OCH$_2$O—* | H | H | * | H | H | OMe | OMe | COOH | H | H | H | OH | O | —CH$_2$CH=CMe$_2$ |
| 1-1779 | —OCH$_2$O—* | H | H | * | H | H | OMe | OMe | COOH | H | H | H | OH | O | —(CH$_2$)$_2$CH=CMe$_2$ |
| 1-1780 | —OCH$_2$O—* | H | H | * | H | H | OMe | OMe | COOH | H | H | H | OH | O | —CH$_2$CH=CCl$_2$ |
| 1-1781 | —OCH$_2$O—* | H | H | * | H | H | OMe | OMe | COOH | H | H | H | OH | O | —CH$_2$C≡CMe |
| 1.1782 | —OCH$_2$O—* | H | H | * | H | H | OMe | OMe | COOH | H | H | H | OH | O | —CH$_2$C$_6$H$_4$-4-Me |
| 1-1783 | —OCH$_2$O—* | H | H | * | H | H | OMe | OMe | COOH | H | H | H | OMs | O | —CH$_2$CH=CMe$_2$ |
| 1-1784 | —OCH$_2$O—* | H | H | * | H | H | OMe | OMe | COOH | H | H | H | OMs | O | —(CH$_2$)$_2$CH=CMe$_2$ |
| 1-1785 | —OCH$_2$O—* | H | H | * | H | H | OMe | OMe | COOH | H | H | H | OMs | O | —CH$_2$CH=CCl$_2$ |
| 1-1786 | —OCH$_2$O—* | H | H | * | H | H | OMe | OMe | COOH | H | H | H | OMs | O | —CH$_2$C≡CMe |
| 1-1787 | —OCH$_2$O—* | H | H | * | H | H | OMe | OMe | COOH | H | H | H | OMs | O | —CH$_2$C$_6$H$_4$-4-Me |
| 1-1788 | —OCH$_2$O—* | H | H | * | H | H | OMe | OMe | COOH | H | H | H | COOH | O | —CH$_2$CH=CMe$_2$ |

TABLE 290

| | | | | | | | | | | | | | | | |
|---|---|---|---|---|---|---|---|---|---|---|---|---|---|---|---|
| 1-1789 | —OCH$_2$O—* | H | H | * | H | H | OMe | OMe | COOH | H | H | H | COOH | O | —(CH$_2$)$_2$CH=CMe$_2$ |
| 1-1790 | —OCH$_2$O—* | H | H | * | H | H | OMe | OMe | COOH | H | H | H | COOH | O | —CH$_2$CH=CCl$_2$ |
| 1-1791 | —OCH$_2$O—* | H | H | * | H | H | OMe | OMe | COOH | H | H | H | COOH | O | —CH$_2$C≡CMe |
| 1-1792 | —OCH$_2$O—* | H | H | * | H | H | OMe | OMe | COOH | H | H | H | COOH | O | —CH$_2$C$_6$H$_4$-4-Me |
| 1-1793 | —OCH$_2$O—* | H | H | * | H | H | OMe | OMe | COOH | H | H | H | CH$_2$OH | O | —CH$_2$CH=CMe$_2$ |
| 1-1794 | —OCH$_2$O—* | H | H | * | H | H | OMe | OMe | COOH | H | H | H | CH$_2$OH | O | —(CH$_2$)$_2$CH=CMe$_2$ |
| 1-1795 | —OCH$_2$O—* | H | H | * | H | H | OMe | OMe | COOH | H | H | H | CH$_2$OH | O | —CH$_2$CH=CCl$_2$ |
| 1-1796 | —OCH$_2$O—* | H | H | * | H | H | OMe | OMe | COOH | H | H | H | CH$_2$OH | O | —CH$_2$C≡CMe |
| 1-1797 | —OCH$_2$O—* | H | H | * | H | H | OMe | OMe | COOH | H | H | H | CH$_2$OH | O | —CH$_2$C$_6$H$_4$-4-Me |
| 1-1798 | —OCH$_2$O—* | H | H | * | H | H | OMe | OMe | COOH | H | H | H | F | O | —CH$_2$CH=CMe$_2$ |
| 1-1799 | —OCH$_2$O—* | H | H | * | H | H | OMe | OMe | COOH | H | H | H | F | O | —(CH$_2$)$_2$CH=CMe$_2$ |
| 1-1800 | —OCH$_2$O—* | H | H | * | H | H | OMe | OMe | COOH | H | H | H | F | O | —CH$_2$CH=CCl$_2$ |
| 1-1801 | —OCH$_2$O—* | H | H | * | H | H | OMe | OMe | COOH | H | H | H | F | O | —CH$_2$C≡CMe |
| 1-1802 | —OCH$_2$O—* | H | H | * | H | H | OMe | OMe | COOH | H | H | H | F | O | —CH$_2$C$_6$H$_4$-4-Me |
| 1-1803 | —OCH$_2$O—* | H | H | * | H | H | OMe | OMe | CH$_2$OH | H | H | H | OH | O | —CH$_2$CH=CMe$_2$ |
| 1-1804 | —OCH$_2$O—* | H | H | * | H | H | OMe | OMe | CH$_2$OH | H | H | H | OH | O | —(CH$_2$)$_2$CH=CMe$_2$ |
| 1-1805 | —OCH$_2$O—* | H | H | * | H | H | OMe | OMe | CH$_2$OH | H | H | H | OH | O | —CH$_2$CH=CCl$_2$ |
| 1-1806 | —OCH$_2$O—* | H | H | * | H | H | OMe | OMe | CH$_2$OH | H | H | H | OH | O | —CH$_2$C≡CMe |
| 1-1807 | —OCH$_2$O—* | H | H | * | H | H | OMe | OMe | CH$_2$OH | H | H | H | OH | O | —CH$_2$C$_6$H$_4$-4-Me |
| 1-1808 | —OCH$_2$O—* | H | H | * | H | H | OMe | OMe | CH$_2$OH | H | H | H | OMs | O | —CH$_2$CH=CMe$_2$ |
| 1-1809 | —OCH$_2$O—* | H | H | * | H | H | OMe | OMe | CH$_2$OH | H | H | H | OMs | O | —(CH$_2$)$_2$CH=CMe$_2$ |

TABLE 291

| | | | | | | | | | | | | | | | |
|---|---|---|---|---|---|---|---|---|---|---|---|---|---|---|---|
| 1-1810 | —OCH$_2$O—* | H | H | * | H | H | OMe | OMe | CH$_2$OH | H | H | H | OMs | O | —CH$_2$CH≡CCl$_2$ |
| 1-1811 | —OCH$_2$O—* | H | H | * | H | H | OMe | OMe | CH$_2$OH | H | H | H | OMs | O | —CH$_2$C≡CMe |
| 1-1812 | —OCH$_2$O—* | H | H | * | H | H | OMe | OMe | CH$_2$OH | H | H | H | OMs | O | —CH$_2$C$_6$H$_4$-4-Me |
| 1-1813 | —OCH$_2$O—* | H | H | * | H | H | OMe | OMe | CH$_2$OH | H | H | H | COOH | O | —CH$_2$CH=CMe$_2$ |
| 1-1814 | —OCH$_2$O—* | H | H | * | H | H | OMe | OMe | CH$_2$OH | H | H | H | COOH | O | —(CH$_2$)$_2$CH=CMe$_2$ |
| 1-1815 | —OCH$_2$O—* | H | H | * | H | H | OMe | OMe | CH$_2$OH | H | H | H | COOH | O | —CH$_2$CH=CCl$_2$ |
| 1-1816 | —OCH$_2$O—* | H | H | * | H | H | OMe | OMe | CH$_2$OH | H | H | H | COOH | O | —CH$_2$C≡CMe |
| 1-1817 | —OCH$_2$O—* | H | H | * | H | H | OMe | OMe | CH$_2$OH | H | H | H | COOH | O | —CH$_2$C$_6$H$_4$-4-Me |
| 1-1818 | —OCH$_2$O—* | H | H | * | H | H | OMe | OMe | CH$_2$OH | H | H | H | CH$_2$OH | O | —CH$_2$CH=CMe$_2$ |
| 1-1819 | —OCH$_2$O—* | H | H | * | H | H | OMe | OMe | CH$_2$OH | H | H | H | CH$_2$OH | O | —(CH$_2$)$_2$CH=CMe$_2$ |
| 1-1820 | —OCH$_2$O—* | H | H | * | H | H | OMe | OMe | CH$_2$OH | H | H | H | CH$_2$OH | O | —CH$_2$CH=CCl$_2$ |
| 1-1821 | —OCH$_2$O—* | H | H | * | H | H | OMe | OMe | CH$_2$OH | H | H | H | CH$_2$OH | O | —CH$_2$C≡CMe |
| 1-1822 | —OCH$_2$O—* | H | H | * | H | H | OMe | OMe | CH$_2$OH | H | H | H | CH$_2$OH | O | —CH$_2$C$_6$H$_4$-4-Me |
| 1-1823 | —OCH$_2$O—* | H | H | * | H | H | OMe | OMe | CH$_2$OH | H | H | H | F | O | —CH$_2$CH=CMe$_2$ |
| 1-1824 | —OCH$_2$O—* | H | H | * | H | H | OMe | OMe | CH$_2$OH | H | H | H | F | O | —(CH$_2$)$_2$CH=CMe$_2$ |
| 1-1825 | —OCH$_2$O—* | H | H | * | H | H | OMe | OMe | CH$_2$OH | H | H | H | F | O | —CH$_2$CH=CCl$_2$ |
| 1-1826 | —OCH$_2$O—* | H | H | * | H | H | OMe | OMe | CH$_2$OH | H | H | H | F | O | —CH$_2$C≡CMe |
| 1-1827 | —OCH$_2$O—* | H | H | * | H | H | OMe | OMe | CH$_2$OH | H | H | H | F | O | —CH$_2$C$_6$H$_4$-4-Me |
| 1-1828 | —OCH$_2$O—* | H | H | * | H | H | OMe | OMe | Me | H | H | H | OH | O | —CH$_2$CH=CMe$_2$ |
| 1-1829 | —OCH$_2$O—* | H | H | * | H | H | OMe | OMe | Me | H | H | H | OH | O | —(CH$_2$)$_2$CH=CMe$_2$ |
| 1-1830 | —OCH$_2$O—* | H | H | * | H | H | OMe | OMe | Me | H | H | H | OH | O | —CH$_2$CH=CCl$_2$ |

TABLE 292

| | | | | | | | | | | | | | | | |
|---|---|---|---|---|---|---|---|---|---|---|---|---|---|---|---|
| 1-1831 | —OCH$_2$O—* | H | H | * | H | H | OMe | OMe | Me | H | H | H | OH | O | —CH$_2$C≡CMe |
| 1-1832 | —OCH$_2$O—* | H | H | * | H | H | OMe | OMe | Me | H | H | H | OH | O | —CH$_2$C$_6$H$_4$-4-Me |
| 1-1833 | —OCH$_2$O—* | H | H | * | H | H | OMe | OMe | Me | H | H | H | OMs | O | —CH$_2$CH=CMe$_2$ |
| 1-1834 | —OCH$_2$O—* | H | H | * | H | H | OMe | OMe | Me | H | H | H | OMs | O | —(CH$_2$)$_2$CH=CMe$_2$ |
| 1-1835 | —OCH$_2$O—* | H | H | * | H | H | OMe | OMe | Me | H | H | H | OMs | O | —CH$_2$CH=CCl$_2$ |
| 1-1836 | —OCH$_2$O—* | H | H | * | H | H | OMe | OMe | Me | H | H | H | OMs | O | —CH$_2$C≡CMe |
| 1-1837 | —OCH$_2$O—* | H | H | * | H | H | OMe | OMe | Me | H | H | H | OMs | O | —CH$_2$C$_6$H$_4$-4-Me |
| 1-1838 | —OCH$_2$O—* | H | H | * | H | H | OMe | OMe | Me | H | H | H | COOH | O | —CH$_2$CH=CMe$_2$ |
| 1-1839 | —OCH$_2$O—* | H | H | * | H | H | OMe | OMe | Me | H | H | H | COOH | O | —(CH$_2$)$_2$CH=CMe$_2$ |
| 1-1840 | —OCH$_2$O—* | H | H | * | H | H | OMe | OMe | Me | H | H | H | COOH | O | —CH$_2$CH=CCl$_2$ |
| 1-1841 | —OCH$_2$O—* | H | H | * | H | H | OMe | OMe | Me | H | H | H | COOH | O | —CH$_2$C≡CMe |
| 1-1842 | —OCH$_2$O—* | H | H | * | H | H | OMe | OMe | Me | H | H | H | COOH | O | —CH$_2$C$_6$H$_4$-4-Me |
| 1-1843 | —OCH$_2$O—* | H | H | * | H | H | OMe | OMe | Me | H | H | H | CH$_2$OH | O | —CH$_2$CH=CMe$_2$ |
| 1-1844 | —OCH$_2$O—* | H | H | * | H | H | OMe | OMe | Me | H | H | H | CH$_2$OH | O | —(CH$_2$)$_2$CH=CMe$_2$ |
| 1-1845 | —OCH$_2$O—* | H | H | * | H | H | OMe | OMe | Me | H | H | H | CH$_2$OH | O | —CH$_2$CH=CCl$_2$ |
| 1-1846 | —OCH$_2$O—* | H | H | * | H | H | OMe | OMe | Me | H | H | H | CH$_2$OH | O | —CH$_2$C≡CMe |
| 1-1847 | —OCH$_2$O—* | H | H | * | H | H | OMe | OMe | Me | H | H | H | CH$_2$OH | O | —CH$_2$C$_6$H$_4$-4-Me |
| 1-1848 | —OCH$_2$O—* | H | H | * | H | H | OMe | OMe | Me | H | H | H | F | O | —CH$_2$CH=CMe$_2$ |
| 1-1849 | —OCH$_2$O—* | H | H | * | H | H | OMe | OMe | Me | H | H | H | F | O | —(CH$_2$)$_2$CH=CMe$_2$ |
| 1-1850 | —OCH$_2$O—* | H | H | * | H | H | OMe | OMe | Me | H | H | H | F | O | —CH$_2$CH=CCl$_2$ |
| 1-1851 | —OCH$_2$O—* | H | H | * | H | H | OMe | OMe | Me | H | H | H | F | O | —CH$_2$C≡CMe |

TABLE 293

| | | | | | | | | | | | | | | | |
|---|---|---|---|---|---|---|---|---|---|---|---|---|---|---|---|
| 1-1852 | —OCH$_2$O—* | H | H | * | H | H | OMe | OMe | Me | H | H | H | F | O | —CH$_2$C$_6$H$_4$-4-Me |
| 1-1853 | —OCH$_2$O—* | H | H | * | H | H | OMe | OMe | H | H | H | H | OH | O | —CH$_2$CH=CMe$_2$ |
| 1-1854 | —OCH$_2$O—* | H | H | * | H | H | OMe | OMe | H | H | H | H | OH | O | —(CH$_2$)$_2$CH=CMe$_2$ |
| 1-1855 | —OCH$_2$O—* | H | H | * | H | H | OMe | OMe | H | H | H | H | OH | O | —CH$_2$CH=CCl$_2$ |
| 1-1856 | —OCH$_2$O—* | H | H | * | H | H | OMe | OMe | H | H | H | H | OH | O | —CH$_2$C≡CMe |
| 1-1857 | —OCH$_2$O—* | H | H | * | H | H | OMe | OMe | H | H | H | H | OH | O | —CH$_2$C$_6$H$_4$-4-Me |
| 1-1858 | —OCH$_2$O—* | H | H | * | H | H | OMe | OMe | H | H | H | H | OMs | O | —CH$_2$CH=CMe$_2$ |
| 1-1859 | —OCH$_2$O—* | H | H | * | H | H | OMe | OMe | H | H | H | H | OMs | O | —(CH$_2$)$_2$CH=CMe$_2$ |
| 1-1860 | —OCH$_2$O—* | H | H | * | H | H | OMe | OMe | H | H | H | H | OMs | O | —CH$_2$CH=CCl$_2$ |
| 1-1861 | —OCH$_2$O—* | H | H | * | H | H | OMe | OMe | H | H | H | H | OMs | O | —CH$_2$C≡CMe |
| 1-1862 | —OCH$_2$O—* | H | H | * | H | H | OMe | OMe | H | H | H | H | OMs | O | —CH$_2$C$_6$H$_4$-4-Me |
| 1-1863 | —OCH$_2$O—* | H | H | * | H | H | OMe | OMe | H | H | H | H | COOH | O | —CH$_2$CH=CMe$_2$ |
| 1-1864 | —OCH$_2$O—* | H | H | * | H | H | OMe | OMe | H | H | H | H | COOH | O | —(CH$_2$)$_2$CH=CMe$_2$ |
| 1-1865 | —OCH$_2$O—* | H | H | * | H | H | OMe | OMe | H | H | H | H | COOH | O | —CH$_2$CH=CCl$_2$ |
| 1-1866 | —OCH$_2$O—* | H | H | * | H | H | OMe | OMe | H | H | H | H | COOH | O | —CH$_2$C≡CMe |
| 1-1867 | —OCH$_2$O—* | H | H | * | H | H | OMe | OMe | H | H | H | H | COOH | O | —CH$_2$C$_6$H$_4$-4-Me |
| 1-1868 | —OCH$_2$O—* | H | H | * | H | H | OMe | OMe | H | H | H | H | CH$_2$OH | O | —CH$_2$CH=CMe$_2$ |
| 1-1869 | —OCH$_2$O—* | H | H | * | H | H | OMe | OMe | H | H | H | H | CH$_2$OH | O | —(CH$_2$)$_2$CH=CMe$_2$ |
| 1-1870 | —OCH$_2$O—* | H | H | * | H | H | OMe | OMe | H | H | H | H | CH$_2$OH | O | —CH$_2$CH=CCl$_2$ |
| 1-1871 | —OCH$_2$O—* | H | H | * | H | H | OMe | OMe | H | H | H | H | CH$_2$OH | O | —CH$_2$C≡CMe |
| 1-1872 | —OCH$_2$O—* | H | H | * | H | H | OMe | OMe | H | H | H | H | CH$_2$OH | O | —CH$_2$C$_6$H$_4$-4-Me |

TABLE 294

| | | | | | | | | | | | | | | | |
|---|---|---|---|---|---|---|---|---|---|---|---|---|---|---|---|
| 1-1873 | —OCH$_2$O—* | H | H | * | H | H | OMe | OMe | H | H | H | H | F | O | —CH$_2$CH=CMe$_2$ |
| 1-1874 | —OCH$_2$O—* | H | H | * | H | H | OMe | OMe | H | H | H | H | F | O | —(CH$_2$)$_2$CH=CMe$_2$ |
| 1-1875 | —OCH$_2$O—* | H | H | * | H | H | OMe | OMe | H | H | H | H | F | O | —CH$_2$CH=CCl$_2$ |
| 1-1876 | —OCH$_2$O—* | H | H | * | H | H | OMe | OMe | H | H | H | H | F | O | —CH$_2$C≡CMe |
| 1-1877 | —OCH$_2$O—* | H | H | * | H | H | OMe | OMe | H | H | H | H | F | O | —CH$_2$C$_6$H$_4$-4-Me |
| 1-1878 | —OCH$_2$O—* | H | H | * | H | F | OMe | OMe | OH | H | H | H | OH | O | —CH$_2$CH=CMe$_2$ |
| 1-1879 | —OCH$_2$O—* | H | H | * | H | F | OMe | OMe | OH | H | H | H | OH | O | —(CH$_2$)$_2$CH=CMe$_2$ |
| 1-1880 | —OCH$_2$O—* | H | H | * | H | F | OMe | OMe | OH | H | H | H | OH | O | —CH$_2$CH=CCl$_2$ |
| 1-1881 | —OCH$_2$O—* | H | H | * | H | F | OMe | OMe | OH | H | H | H | OH | O | —CH$_2$C≡CMe |
| 1-1882 | —OCH$_2$O—* | H | H | * | H | F | OMe | OMe | OH | H | H | H | OH | O | —CH$_2$C$_6$H$_4$-4-Me |
| 1-1883 | —OCH$_2$O—* | H | H | * | H | F | OMe | OMe | OH | H | H | H | OMs | O | —CH$_2$CH=CMe$_2$ |
| 1-1884 | —OCH$_2$O—* | H | H | * | H | F | OMe | OMe | OH | H | H | H | OMs | O | —(CH$_2$)$_2$CH=CMe$_2$ |
| 1-1885 | —OCH$_2$O—* | H | H | * | H | F | OMe | OMe | OH | H | H | H | OMs | O | —CH$_2$CH=CCl$_2$ |
| 1-1886 | —OCH$_2$O—* | H | H | * | H | F | OMe | OMe | OH | H | H | H | OMs | O | —CH$_2$C≡CMe |
| 1-1887 | —OCH$_2$O—* | H | H | * | H | F | OMe | OMe | OH | H | H | H | OMs | O | —CH$_2$C$_6$H$_4$-4-Me |
| 1-1888 | —OCH$_2$O—* | H | H | * | H | F | OMe | OMe | OH | H | H | H | COOH | O | —CH$_2$CH=CMe$_2$ |
| 1-1889 | —OCH$_2$O—* | H | H | * | H | F | OMe | OMe | OH | H | H | H | COOH | O | —(CH$_2$)$_2$CH=CMe$_2$ |
| 1-1890 | —OCH$_2$O—* | H | H | * | H | F | OMe | OMe | OH | H | H | H | COOH | O | —CH$_2$CH=CCl$_2$ |
| 1-1891 | —OCH$_2$O—* | H | H | * | H | F | OMe | OMe | OH | H | H | H | COOH | O | —CH$_2$C≡CMe |
| 1-1892 | —OCH$_2$O—* | H | H | * | H | F | OMe | OMe | OH | H | H | H | COOH | O | —CH$_2$C$_6$H$_4$-4-Me |
| 1-1893 | —OCH$_2$O—* | H | H | * | H | F | OMe | OMe | OH | H | H | H | CH$_2$OH | O | —CH$_2$CH=CMe$_2$ |

TABLE 295

| | | | | | | | | | | | | | | | | |
|---|---|---|---|---|---|---|---|---|---|---|---|---|---|---|---|---|
| 1-1894 | —OCH$_2$O— | * | H | H | * | H | F | OMe | OMe | OH | H | H | H | CH$_2$OH | O | —(CH$_2$)$_2$CH=CMe$_2$ |
| 1-1895 | —OCH$_2$O— | * | H | H | * | H | F | OMe | OMe | OH | H | H | H | CH$_2$OH | O | —CH$_2$CH=CCl$_2$ |
| 1-1896 | —OCH$_2$O— | * | H | H | * | H | F | OMe | OMe | OH | H | H | H | CH$_2$OH | O | —CH$_2$C≡CMe |
| 1-1897 | —OCH$_2$O— | * | H | H | * | H | F | OMe | OMe | OH | H | H | H | CH$_2$OH | O | —CH$_2$C$_6$H$_4$-4-Me |
| 1-1898 | —OCH$_2$O— | * | H | H | * | H | F | OMe | OMe | OH | H | H | H | F | O | —CH$_2$CH=CMe$_2$ |
| 1-1899 | —OCH$_2$O— | * | H | H | * | H | F | OMe | OMe | OH | H | H | H | F | O | —(CH$_2$)$_2$CH=CMe$_2$ |
| 1-1900 | —OCH$_2$O— | * | H | H | * | H | F | OMe | OMe | OH | H | H | H | F | O | —CH$_2$CH=CCl$_2$ |
| 1-1901 | —OCH$_2$O— | * | H | H | * | H | F | OMe | OMe | OH | H | H | H | F | O | —CH$_2$C≡CMe |
| 1-1902 | —OCH$_2$O— | * | H | H | * | H | F | OMe | OMe | OH | H | H | H | F | O | —CH$_2$C$_6$H$_4$-4-Me |
| 1-1903 | NMe$_2$ | | H | H | H | H | H | OMe | OMe | OH | H | H | H | OH | O | —(CH$_2$)$_2$CH=CMe$_2$ |
| 1-1904 | NMe$_2$ | | H | H | H | H | H | OMe | OMe | OH | H | H | H | OH | O | —CH$_2$CH=CCl$_2$ |
| 1-1905 | NMe$_2$ | | H | H | H | H | H | OMe | OMe | OH | H | H | H | OH | O | —CH$_2$C≡CMe |
| 1-1906 | NMe$_2$ | | H | H | H | H | H | OMe | OMe | OH | H | H | H | OMs | O | —CH$_2$CH=CMe$_2$ |
| 1-1907 | NMe$_2$ | | H | H | H | H | H | OMe | OMe | OH | H | H | H | OMs | O | —(CH$_2$)$_2$CH=CMe$_2$ |
| 1-1908 | NMe$_2$ | | H | H | H | H | H | OMe | OMe | OH | H | H | H | OMs | O | —CH$_2$CH=CCl$_2$ |
| 1-1909 | NMe$_2$ | | H | H | H | H | H | OMe | OMe | OH | H | H | H | OMs | O | —CH$_2$C≡CMe |
| 1-1910 | NMe$_2$ | | H | H | H | H | H | OMe | OMe | OH | H | H | H | OMs | O | —CH$_2$C$_6$H$_4$-4-Me |
| 1-1911 | NMe$_2$ | | H | H | H | H | H | OMe | OMe | OH | H | H | H | COOH | O | —CH$_2$CH=CMe$_2$ |
| 1-1912 | NMe$_2$ | | H | H | H | H | H | OMe | OMe | OH | H | H | H | COOH | O | —(CH$_2$)$_2$CH=CMe$_2$ |
| 1-1913 | NMe$_2$ | | H | H | H | H | H | OMe | OMe | OH | H | H | H | COOH | O | —CH$_2$CH=CCl$_2$ |
| 1-1914 | NMe$_2$ | | H | H | H | H | H | OMe | OMe | OH | H | H | H | COOH | O | —CH$_2$C≡CMe |

TABLE 296

| | | | | | | | | | | | | | | | |
|---|---|---|---|---|---|---|---|---|---|---|---|---|---|---|---|
| 1-1915 | NMe$_2$ | H | H | H | H | H | OMe | OMe | OH | H | H | H | COOH | O | —CH$_2$C$_6$H$_4$-4-Me |
| 1-1916 | NMe$_2$ | H | H | H | H | H | OMe | OMe | OH | H | H | H | CH$_2$OH | O | —CH$_2$CH=CMe$_2$ |
| 1-1917 | NMe$_2$ | H | H | H | H | H | OMe | OMe | OH | H | H | H | CH$_2$OH | O | —(CH$_2$)$_2$CH=CMe$_2$ |
| 1-1918 | NMe$_2$ | H | H | H | H | H | OMe | OMe | OH | H | H | H | CH$_2$OH | O | —CH$_2$CH=CCl$_2$ |
| 1-1919 | NMe$_2$ | H | H | H | H | H | OMe | OMe | OH | H | H | H | CH$_2$OH | O | —CH$_2$C≡CMe |
| 1-1920 | NMe$_2$ | H | H | H | H | H | OMe | OMe | OH | H | H | H | CH$_2$OH | O | —CH$_2$C$_6$H$_4$-4-Me |
| 1-1921 | NMe$_2$ | H | H | H | H | H | OMe | OMe | OH | H | H | H | F | O | —CH$_2$CH=CMe$_2$ |
| 1-1922 | NMe$_2$ | H | H | H | H | H | OMe | OMe | OH | H | H | H | F | O | —(CH$_2$)$_2$CH=CMe$_2$ |
| 1-1923 | NMe$_2$ | H | H | H | H | H | OMe | OMe | OH | H | H | H | F | O | —CH$_2$CH=CCl$_2$ |
| 1-1924 | NMe$_2$ | H | H | H | H | H | OMe | OMe | OH | H | H | H | F | O | —CH$_2$C≡CMe |
| 1-1925 | NMe$_2$ | H | H | H | H | H | OMe | OMe | OH | H | H | H | F | O | —CH$_2$C$_6$H$_4$-4-Me |
| 1-1926 | NMe$_2$ | H | H | H | H | H | OMe | OMe | COOH | H | H | H | OH | O | —CH$_2$CH=CMe$_2$ |
| 1-1927 | NMe$_2$ | H | H | H | H | H | OMe | OMe | COOH | H | H | H | OH | O | —(CH$_2$)$_2$CH=CMe$_2$ |
| 1-1928 | NMe$_2$ | H | H | H | H | H | OMe | OMe | COOH | H | H | H | OH | O | —CH$_2$CH=CCl$_2$ |
| 1-1929 | NMe$_2$ | H | H | H | H | H | OMe | OMe | COOH | H | H | H | OH | O | —CH$_2$C≡CMe |
| 1-1930 | NMe$_2$ | H | H | H | H | H | OMe | OMe | COOH | H | H | H | OH | O | —CH$_2$C$_6$H$_4$-4-Me |
| 1-1931 | NMe$_2$ | H | H | H | H | H | OMe | OMe | COOH | H | H | H | OMs | O | —CH$_2$CH=CMe$_2$ |
| 1-1932 | NMe$_2$ | H | H | H | H | H | OMe | OMe | COOH | H | H | H | OMs | O | —(CH$_2$)$_2$CH=CMe$_2$ |
| 1-1933 | NMe$_2$ | H | H | H | H | H | OMe | OMe | COOH | H | H | H | OMs | O | —CH$_2$CH=CCl$_2$ |
| 1-1934 | NMe$_2$ | H | H | H | H | H | OMe | OMe | COOH | H | H | H | OMs | O | —CH$_2$C≡CMe |
| 1-1935 | NMe$_2$ | H | H | H | H | H | OMe | OMe | COOH | H | H | H | OMs | O | —CH$_2$C$_6$H$_4$-4-Me |

TABLE 297

| | | | | | | | | | | | | | | | |
|---|---|---|---|---|---|---|---|---|---|---|---|---|---|---|---|
| 1-1936 | NMe$_2$ | H | H | H | H | H | OMe | OMe | COOH | H | H | H | COOH | O | —CH$_2$CH=CMe$_2$ |
| 1-1937 | NMe$_2$ | H | H | H | H | H | OMe | OMe | COOH | H | H | H | COOH | O | —(CH$_2$)$_2$CH=CMe$_2$ |
| 1-1938 | NMe$_2$ | H | H | H | H | H | OMe | OMe | COOH | H | H | H | COOH | O | —CH$_2$CH=CCl$_2$ |
| 1-199 | NMe$_2$ | H | H | H | H | H | OMe | OMe | COOH | H | H | H | COOH | O | —CH$_2$C≡CMe |
| 1-190 | NMe$_2$ | H | H | H | H | H | OMe | OMe | COOH | H | H | H | COOH | O | —CH$_2$C$_6$H$_4$-4-Me |
| 1-1941 | NMe$_2$ | H | H | H | H | H | OMe | OMe | COOH | H | H | H | CH$_2$OH | O | —CH$_2$CH=CMe$_2$ |
| 1-1942 | NMe$_2$ | H | H | H | H | H | OMe | OMe | COOH | H | H | H | CH$_2$OH | O | —(CH$_2$)$_2$CH=CMe$_2$ |
| 1-1943 | NMe$_2$ | H | H | H | H | H | OMe | OMe | COOH | H | H | H | CH$_2$OH | O | —CH$_2$CH=CCl$_2$ |
| 1-1944 | NMe$_2$ | H | H | H | H | H | OMe | OMe | COOH | H | H | H | CH$_2$CH | O | —CH$_2$C≡CMe |
| 1-1945 | NMe$_2$ | H | H | H | H | H | OMe | OMe | COOH | H | H | H | CH$_2$OH | O | —CH$_2$C$_6$H$_4$-4-Me |
| 1-1946 | NMe$_2$ | H | H | H | H | H | OMe | OMe | COOH | H | H | H | F | O | —CH$_2$CH=CMe$_2$ |
| 1-1947 | NMe$_2$ | H | H | H | H | H | OMe | OMe | COOH | H | H | H | F | O | —(CH$_2$)$_2$CH=CMe$_2$ |
| 1-1948 | NMe$_2$ | H | H | H | H | H | OMe | OMe | COOH | H | H | H | F | O | —CH$_2$CH=CCl$_2$ |
| 1-1949 | NMe$_2$ | H | H | H | H | H | OMe | OMe | COOH | H | H | H | F | O | —CH$_2$C≡CMe |
| 1-1950 | NMe$_2$ | H | H | H | H | H | OMe | OMe | COOH | H | H | H | F | O | —CH$_2$C$_6$H$_4$-4-Me |
| 1-1951 | NMe$_2$ | H | H | H | H | H | OMe | OMe | CH$_2$OH | H | H | H | OH | O | —CH$_2$CH=CMe$_2$ |
| 1-1952 | NMe$_2$ | H | H | H | H | H | OMe | OMe | CH$_2$CH | H | H | H | OH | O | —(CH$_2$)$_2$CH=CMe$_2$ |
| 1-1953 | NMe$_2$ | H | H | H | H | H | OMe | OMe | CH$_2$CH | H | H | H | OH | O | —CH$_2$CH=CCl$_2$ |

TABLE 297-continued

| | | | | | | | | | | | | | | | |
|---|---|---|---|---|---|---|---|---|---|---|---|---|---|---|---|
| 1-1954 | NMe$_2$ | H | H | H | H | H | OMe | OMe | CH$_2$OH | H | H | H | OH | O | —CH$_2$C≡CMe |
| 1-1955 | NMe$_2$ | H | H | H | H | H | OMe | OMe | CH$_2$OH | H | H | H | OH | O | —CH$_2$C$_6$H$_4$-4-Me |
| 1-1956 | NMe$_2$ | H | H | H | H | H | OMe | OMe | CH$_2$CH | H | H | H | OMs | O | —CH$_2$CH=CMe$_2$ |

TABLE 298

| | | | | | | | | | | | | | | | |
|---|---|---|---|---|---|---|---|---|---|---|---|---|---|---|---|
| 1-1957 | NMe$_2$ | H | H | H | H | H | OMe | OMe | CH$_2$OH | H | H | H | OMs | O | —(CH$_2$)$_2$CH=CMe$_2$ |
| 1-1958 | NMe$_2$ | H | H | H | H | H | OMe | OMe | CH$_2$OH | H | H | H | OMs | O | —CH$_2$CH=CCl$_2$ |
| 1-1959 | NMe$_2$ | H | H | H | H | H | OMe | OMe | CH$_2$OH | H | H | H | OMs | O | —CH$_2$C≡CMe |
| 1-1960 | NMe$_2$ | H | H | H | H | H | OMe | OMe | CH$_2$OH | H | H | H | OMs | O | —CH$_2$C$_6$H$_4$-4-Me |
| 1-1961 | NMe$_2$ | H | H | H | H | H | OMe | OMe | CH$_2$OH | H | H | H | COOH | O | —CH$_2$CH=CMe$_2$ |
| 1-1962 | NMe$_2$ | H | H | H | H | H | OMe | OMe | CH$_2$OH | H | H | H | COOH | O | —(CH$_2$)$_2$CH=CMe$_2$ |
| 1-1963 | NMe$_2$ | H | H | H | H | H | OMe | OMe | CH$_2$OH | H | H | H | COOH | O | —CH$_2$CH=CCl$_2$ |
| 1-1964 | NMe$_2$ | H | H | H | H | H | OMe | OMe | CH$_2$OH | H | H | H | COOH | O | —CH$_2$C≡CMe |
| 1-1965 | NMe$_2$ | H | H | H | H | H | OMe | OMe | CH$_2$OH | H | H | H | COOH | O | —CH$_2$C$_6$H$_4$-4-Me |
| 1-1966 | NMe$_2$ | H | H | H | H | H | OMe | OMe | CH$_2$OH | H | H | H | CH$_2$OH | O | —CH$_2$CH=CMe$_2$ |
| 1-1967 | NMe$_2$ | H | H | H | H | H | OMe | OMe | CH$_2$OH | H | H | H | CH$_2$OH | O | —(CH$_2$)$_2$CH=CMe$_2$ |
| 1-198 | NMe$_2$ | H | H | H | H | H | OMe | OMe | CH$_2$OH | H | H | H | CH$_2$OH | O | —CH$_2$CH=CCl$_2$ |
| 1-1969 | NMe$_2$ | H | H | H | H | H | OMe | OMe | CH$_2$OH | H | H | H | CH$_2$OH | O | —CH$_2$C≡CMe |
| 1-1970 | NMe$_2$ | H | H | H | H | H | OMe | OMe | CH$_2$OH | H | H | H | CH$_2$OH | O | —CH$_2$C$_6$H$_4$-4-Me |
| 1-1971 | NMe$_2$ | H | H | H | H | H | OMe | OMe | CH$_2$OH | H | H | H | F | O | —CH$_2$CH=CMe$_2$ |
| 1-1972 | NMe$_2$ | H | H | H | H | H | OMe | OMe | CH$_2$OH | H | H | H | F | O | —(CH$_2$)$_2$CH=CMe$_2$ |
| 1-1973 | NMe$_2$ | H | H | H | H | H | OMe | OMe | CH$_2$OH | H | H | H | F | O | —CH$_2$CH=CCl$_2$ |
| 1-1974 | NMe$_2$ | H | H | H | H | H | OMe | OMe | CH$_2$OH | H | H | H | F | O | —CH$_2$C≡CMe |
| 1-1975 | NMe$_2$ | H | H | H | H | H | OMe | OMe | CH$_2$OH | H | H | H | F | O | —CH$_2$C$_6$H$_4$-4-Me |
| 1-1976 | NMe$_2$ | H | H | H | H | H | OMe | OMe | Me | H | H | H | OH | O | —CH$_2$CH=CMe$_2$ |
| 1-1977 | NMe$_2$ | H | H | H | H | H | OMe | OMe | Me | H | H | H | OH | O | —(CH$_2$)$_2$CH=CMe$_2$ |

TABLE 299

| | | | | | | | | | | | | | | | |
|---|---|---|---|---|---|---|---|---|---|---|---|---|---|---|---|
| 1-1978 | NMe$_2$ | H | H | H | H | H | OMe | OMe | Me | H | H | H | OH | O | —CH$_2$CH=CCl$_2$ |
| 1-1979 | NMe$_2$ | H | H | H | H | H | OMe | OMe | Me | H | H | H | OH | O | —CH$_2$C≡CMe |
| 1-1980 | NMe$_2$ | H | H | H | H | H | OMe | OMe | Me | H | H | H | OH | O | —CH$_2$C$_6$H$_4$-4-Me |
| 1-1981 | NMe$_2$ | H | H | H | H | H | OMe | OMe | Me | H | H | H | OMs | O | —CH$_2$CH=CMe$_2$ |
| 1-1982 | NMe$_2$ | H | H | H | H | H | OMe | OMe | Me | H | H | H | OMs | O | —(CH$_2$)$_2$CH=CMe$_2$ |
| 1-1983 | NMe$_2$ | H | H | H | H | H | OMe | OMe | Me | H | H | H | OMs | O | —CH$_2$CH=CCl$_2$ |
| 1-1984 | NMe$_2$ | H | H | H | H | H | OMe | OMe | Me | H | H | H | OMs | O | —CH$_2$C≡CMe |
| 1-1985 | NMe$_2$ | H | H | H | H | H | OMe | OMe | Me | H | H | H | OMs | O | —CH$_2$C$_6$H$_4$-4-Me |
| 1-1986 | NMe$_2$ | H | H | H | H | H | OMe | OMe | Me | H | H | H | COOH | O | —CH$_2$CH=CMe$_2$ |
| 1-1987 | NMe$_2$ | H | H | H | H | H | OMe | OMe | Me | H | H | H | COOH | O | —(CH$_2$)$_2$CH=CMe$_2$ |
| 1-1988 | NMe$_2$ | H | H | H | H | H | OMe | OMe | Me | H | H | H | COOH | O | —CH$_2$CH=CCl$_2$ |
| 1-1989 | NMe$_2$ | H | H | H | H | H | OMe | OMe | Me | H | H | H | COOH | O | —CH$_2$C≡CMe |
| 1-1990 | NMe$_2$ | H | H | H | H | H | OMe | OMe | Me | H | H | H | COOH | O | —CH$_2$C$_6$H$_4$-4-Me |
| 1-1991 | NMe$_2$ | H | H | H | H | H | OMe | OMe | Me | H | H | H | CH$_2$OH | O | —CH$_2$CH=CMe$_2$ |
| 1-1992 | NMe$_2$ | H | H | H | H | H | OMe | OMe | Me | H | H | H | CH$_2$OH | O | —(CH$_2$)$_2$CH=CMe$_2$ |
| 1-1993 | NMe$_2$ | H | H | H | H | H | OMe | OMe | Me | H | H | H | CH$_2$OH | O | —CH$_2$CH=CCl$_2$ |
| 1-1994 | NMe$_2$ | H | H | H | H | H | OMe | OMe | Me | H | H | H | CH$_2$OH | O | —CH$_2$C≡CMe |
| 1-1995 | NMe$_2$ | H | H | H | H | H | OMe | OMe | Me | H | H | H | CH$_2$OH | O | —CH$_2$C$_6$H$_4$-4-Me |
| 1-1996 | NMe$_2$ | H | H | H | H | H | OMe | OMe | Me | H | H | H | F | O | —CH$_2$CH=CMe$_2$ |
| 1-1997 | NMe$_2$ | H | H | H | H | H | OMe | OMe | Me | H | H | H | F | O | —(CH$_2$)$_2$CH=CMe$_2$ |
| 1-1998 | NMe$_2$ | H | H | H | H | H | OMe | OMe | Me | H | H | H | F | O | —CH$_2$CH=CCl$_2$ |

TABLE 300

| | | | | | | | | | | | | | | | |
|---|---|---|---|---|---|---|---|---|---|---|---|---|---|---|---|
| 1-1999 | NMe$_2$ | H | H | H | H | H | OMe | OMe | Me | H | H | H | F | O | —CH$_2$C≡CMe |
| 1-2000 | NMe$_2$ | H | H | H | H | H | OMe | OMe | Me | H | H | H | F | O | —CH$_2$C$_6$H$_4$-4-Me |
| 1-2001 | NMe$_2$ | H | H | H | H | H | OMe | OMe | H | H | H | H | OH | O | —CH$_2$CH=CMe$_2$ |
| 1-2002 | NMe$_2$ | H | H | H | H | H | OMe | OMe | H | H | H | H | OH | O | —(CH$_2$)$_2$CH=CMe$_2$ |
| 1-2003 | NMe$_2$ | H | H | H | H | H | OMe | OMe | H | H | H | H | OH | O | —CH$_2$CH=CCl$_2$ |
| 1-204 | NMe$_2$ | H | H | H | H | H | OMe | OMe | H | H | H | H | OH | O | —CH$_2$C≡CMe |
| 1-2005 | NMe$_2$ | H | H | H | H | H | OMe | OMe | H | H | H | H | OH | O | —CH$_2$C$_6$H$_4$-4-Me |
| 1-2006 | NMe$_2$ | H | H | H | H | H | OMe | OMe | H | H | H | H | OMs | O | —CH$_2$CH=CMe$_2$ |
| 1-2007 | NMe$_2$ | H | H | H | H | H | OMe | OMe | H | H | H | H | OMs | O | —(CH$_2$)$_2$CH=CMe$_2$ |

TABLE 300-continued

| | | | | | | | | | | | | | | | |
|---|---|---|---|---|---|---|---|---|---|---|---|---|---|---|---|
| 1-2008 | NMe$_2$ | H | H | H | H | H | OMe | OMe | H | H | H | H | OMs | O | —CH$_2$CH=CCl$_2$ |
| 1-2009 | NMe$_2$ | H | H | H | H | H | OMe | OMe | H | H | H | H | OMs | O | —CH$_2$C≡CMe |
| 1-2010 | NMe$_2$ | H | H | H | H | H | OMe | OMe | H | H | H | H | OMs | O | —CH$_2$C$_6$H$_4$-4-Me |
| 1-2011 | NMe$_2$ | H | H | H | H | H | OMe | OMe | H | H | H | H | COOH | O | —CH$_2$CH=CMe$_2$ |
| 1-2012 | NMe$_2$ | H | H | H | H | H | OMe | OMe | H | H | H | H | COOH | O | —(CH$_2$)$_2$CH=CMe$_2$ |
| 1-2013 | NMe$_2$ | H | H | H | H | H | OMe | OMe | H | H | H | H | COOH | O | —CH$_2$CH=CCl$_2$ |
| 1-2014 | NMe$_2$ | H | H | H | H | H | OMe | OMe | H | H | H | H | COOH | O | —CH$_2$C≡CMe |
| 1-2015 | NMe$_2$ | H | H | H | H | H | OMe | OMe | H | H | H | H | COOH | O | —CH$_2$C$_6$H$_4$-4-Me |
| 1-2016 | NMe$_2$ | H | H | H | H | H | OMe | OMe | H | H | H | H | CH$_2$OH | O | —CH$_2$CH=CMe$_2$ |
| 1-2017 | NMe$_2$ | H | H | H | H | H | OMe | OMe | H | H | H | H | CH$_2$OH | O | —(CH$_2$)$_2$CH=CMe$_2$ |
| 1-2018 | NMe$_2$ | H | H | H | H | H | OMe | OMe | H | H | H | H | CH$_2$OH | O | —CH$_2$CH=CCl$_2$ |
| 1-2019 | NMe$_2$ | H | H | H | H | H | OMe | OMe | H | H | H | H | CH$_2$OH | O | —CH$_2$C≡CMe |

TABLE 301

| | | | | | | | | | | | | | | | |
|---|---|---|---|---|---|---|---|---|---|---|---|---|---|---|---|
| 1-2020 | NMe$_2$ | H | H | H | H | H | OMe | OMe | H | H | H | H | CH$_2$OH | O | —CH$_2$C$_6$H$_4$-4-Me |
| 1-2021 | NMe$_2$ | H | H | H | H | H | OMe | OMe | H | H | H | H | F | O | —CH$_2$CH=CMe$_2$ |
| 1-2022 | NMe$_2$ | H | H | H | H | H | OMe | OMe | H | H | H | H | F | O | —(CH$_2$)$_2$CH=CMe$_2$ |
| 1-2023 | NMe$_2$ | H | H | H | H | H | OMe | OMe | H | H | H | H | F | O | —CH$_2$CH=CCl$_2$ |
| 1-2024 | NMe$_2$ | H | H | H | H | H | OMe | OMe | H | H | H | H | F | O | —CH$_2$C≡CMe |
| 1-2025 | NMe$_2$ | H | H | H | H | H | OMe | OMe | H | H | H | H | F | O | —CH$_2$C$_6$H$_4$-4-Me |
| 1-2026 | NMe$_2$ | H | H | H | H | F | OMe | OMe | OH | H | H | H | OH | O | —CH$_2$CH=CMe$_2$ |
| 1-2027 | NMe$_2$ | H | H | H | H | F | OMe | OMe | OH | H | H | H | OH | O | —(CH$_2$)$_2$CH=CMe$_2$ |
| 1-2028 | NMe$_2$ | H | H | H | H | F | OMe | OMe | OH | H | H | H | OH | O | —CH$_2$CH=CCl$_2$ |
| 1-2029 | NMe$_2$ | H | H | H | H | F | OMe | OMe | OH | H | H | H | OH | O | —CH$_2$C≡CMe |
| 1-2030 | NMe$_2$ | H | H | H | H | F | OMe | OMe | OH | H | H | H | OH | O | —CH$_2$C$_6$H$_4$-4-Me |
| 1-2031 | NMe$_2$ | H | H | H | H | F | OMe | OMe | OH | H | H | H | OMs | O | —CH$_2$CH=CMe$_2$ |
| 1-2032 | NMe$_2$ | H | H | H | H | F | OMe | OMe | OH | H | H | H | OMs | O | —(CH$_2$)$_2$CH=CMe$_2$ |
| 1-2033 | NMe$_2$ | H | H | H | H | F | OMe | OMe | OH | H | H | H | OMs | O | —CH$_2$CH=CCl$_2$ |
| 1-2034 | NMe$_2$ | H | H | H | H | F | OMe | OMe | OH | H | H | H | OMs | O | —CH$_2$C≡CMe |
| 1-2035 | NMe$_2$ | H | H | H | H | F | OMe | OMe | OH | H | H | H | OMs | O | —CH$_2$C$_6$H$_4$-4-Me |
| 1-2036 | NMe$_2$ | H | H | H | H | F | OMe | OMe | OH | H | H | H | COOH | O | —CH$_2$CH=CMe$_2$ |
| 1-2037 | NMe$_2$ | H | H | H | H | F | OMe | OMe | OH | H | H | H | COOH | O | —(CH$_2$)$_2$CH=CMe$_2$ |
| 1-2038 | NMe$_2$ | H | H | H | H | F | OMe | OMe | OH | H | H | H | COOH | O | —CH$_2$CH=CCl$_2$ |
| 1-2039 | NMe$_2$ | H | H | H | H | F | OMe | OMe | OH | H | H | H | COOH | O | —CH$_2$C≡CMe |
| 1-2040 | NMe$_2$ | H | H | H | H | F | OMe | OMe | OH | H | H | H | COOH | O | —CH$_2$C$_6$H$_4$-4-Me |

TABLE 302

| | | | | | | | | | | | | | | | |
|---|---|---|---|---|---|---|---|---|---|---|---|---|---|---|---|
| I-2041 | NMe$_2$ | H | H | H | H | F | OMe | OMe | OH | H | H | H | CH$_2$OH | O | —CH$_2$CH=CMe$_2$ |
| I-2042 | NMe$_2$ | H | H | H | H | F | OMe | OMe | OH | H | H | H | CH$_2$OH | O | —(CH$_2$)$_2$CH=CMe$_2$ |
| I-2043 | NMe$_2$ | H | H | H | H | F | OMe | OMe | OH | H | H | H | CH$_2$OH | O | —CH$_2$CH=CCl$_2$ |
| I-2044 | NMe$_2$ | H | H | H | H | F | OMe | OMe | OH | H | H | H | CH$_2$OH | O | —CH$_2$C≡CMe |
| I-2045 | NMe$_2$ | H | H | H | H | F | OMe | OMe | OH | H | H | H | CH$_2$OH | O | —CH$_2$C$_6$H$_4$-4-Me |
| I-2046 | NMe$_2$ | H | H | H | H | F | OMe | OMe | OH | H | H | H | F | O | —CH$_2$CH=CMe$_2$ |
| I-2047 | NMe$_2$ | H | H | H | H | F | OMe | OMe | OH | H | H | H | F | O | —(CH$_2$)$_2$CH=CMe$_2$ |
| I-2048 | NMe$_2$ | H | H | H | H | F | OMe | OMe | OH | H | H | H | F | O | —CH$_2$CH=CCl$_2$ |
| I-2049 | NMe$_2$ | H | H | H | H | F | OMe | OMe | OH | H | H | H | F | O | —CH$_2$C≡CMe |
| I-2050 | NMe$_2$ | H | H | H | H | F | OMe | OMe | OH | H | H | H | F | O | —CH$_2$C$_6$H$_4$-4-Me |
| I-2051 | COOH | H | H | H | H | H | OMe | OMe | OH | H | H | H | OH | O | —(CH$_2$)$_2$CH=CMe$_2$ |
| I-2052 | COOH | H | H | H | H | H | OMe | OMe | OH | H | H | H | OH | O | —CH$_2$CH=CCl$_2$ |
| I-2053 | COOH | H | H | H | H | H | OMe | OMe | OH | H | H | H | OH | O | —CH$_2$C≡CMe |
| I-2054 | COOH | H | H | H | H | H | OMe | OMe | OH | H | H | H | OMs | O | —CH$_2$CH=CMe$_2$ |
| I-2055 | COOH | H | H | H | H | H | OMe | OMe | OH | H | H | H | OMs | O | —(CH$_2$)$_2$CH=CMe$_2$ |
| I-2056 | COOH | H | H | H | H | H | OMe | OMe | OH | H | H | H | OMs | O | —CH$_2$CH=CCl$_2$ |
| I-2057 | COOH | H | H | H | H | H | OMe | OMe | OH | H | H | H | OMs | O | —CH$_2$C≡CMe |
| I-2058 | COOH | H | H | H | H | H | OMe | OMe | OH | H | H | H | OMs | O | —CH$_2$C$_6$H$_4$-4-Me |
| I-2059 | COOH | H | H | H | H | H | OMe | OMe | OH | H | H | H | COOH | O | —CH$_2$CH=CMe$_2$ |
| I-2060 | COOH | H | H | H | H | H | OMe | OMe | OH | H | H | H | COOH | O | —(CH$_2$)$_2$CH=CMe$_2$ |
| I-2061 | COOH | H | H | H | H | H | OMe | OMe | OH | H | H | H | COOH | O | —CH$_2$CH=CCl$_2$ |

TABLE 303

| | | | | | | | | | | | | | | | |
|---|---|---|---|---|---|---|---|---|---|---|---|---|---|---|---|
| I-2062 | COOH | H | H | H | H | H | OMe | OMe | OH | H | H | H | COOH | O | —CH$_2$C≡CMe |
| I-2063 | COOH | H | H | H | H | H | OMe | OMe | OH | H | H | H | COOH | O | —CH$_2$C$_6$H$_4$-4-Me |
| I-2064 | COOH | H | H | H | H | H | OMe | OMe | OH | H | H | H | CH$_2$OH | O | —CH$_2$CH=CMe$_2$ |
| I-2065 | COOH | H | H | H | H | H | OMe | OMe | OH | H | H | H | CH$_2$OH | O | —(CH$_2$)$_2$CH=CMe$_2$ |
| I-2066 | COOH | H | H | H | H | H | OMe | OMe | OH | H | H | H | CH$_2$OH | O | —CH$_2$CH=CCl$_2$ |
| I-2067 | COOH | H | H | H | H | H | OMe | OMe | OH | H | H | H | CH$_2$OH | O | —CH$_2$C≡CMe |
| I-2068 | COOH | H | H | H | H | H | OMe | OMe | OH | H | H | H | CH$_2$OH | O | —CH$_2$C$_6$H$_4$-4-Me |
| I-2069 | COOH | H | H | H | H | H | OMe | OMe | OH | H | H | H | F | O | —CH$_2$CH=CMe$_2$ |
| I-2070 | COOH | H | H | H | H | H | OMe | OMe | OH | H | H | H | F | O | —(CH$_2$)$_2$CH=CMe$_2$ |
| I-2071 | COOH | H | H | H | H | H | OMe | OMe | OH | H | H | H | F | O | —CH$_2$CH=CCl$_2$ |
| I-2072 | COOH | H | H | H | H | H | OMe | OMe | OH | H | H | H | F | O | —CH$_2$C≡CMe |
| I-2073 | COOH | H | H | H | H | H | OMe | OMe | OH | H | H | H | F | O | —CH$_2$C$_6$H$_4$-4-Me |
| I-2074 | COOH | H | H | H | H | H | OMe | OMe | COOH | H | H | H | OH | O | —CH$_2$CH=CMe$_2$ |
| I-2075 | COOH | H | H | H | H | H | OMe | OMe | COOH | H | H | H | OH | O | —(CH$_2$)$_2$CH=CMe$_2$ |
| I-2076 | COOH | H | H | H | H | H | OMe | OMe | COOH | H | H | H | OH | O | —CH$_2$CH=CCl$_2$ |
| I-2077 | COOH | H | H | H | H | H | OMe | OMe | COOH | H | H | H | OH | O | —CH$_2$C≡CMe |
| I-2078 | COOH | H | H | H | H | H | OMe | OMe | COOH | H | H | H | OH | O | —CH$_2$C$_6$H$_4$-4-Me |
| I-2079 | COOH | H | H | H | H | H | OMe | OMe | COOH | H | H | H | OMs | O | —CH$_2$CH=CMe$_2$ |
| I-2080 | COOH | H | H | H | H | H | OMe | OMe | COOH | H | H | H | OMs | O | —(CH$_2$)$_2$CH=CMe$_2$ |
| I-2081 | COOH | H | H | H | H | H | OMe | OMe | COOH | H | H | H | OMs | O | —CH$_2$CH=CCl$_2$ |
| I-2082 | COOH | H | H | H | H | H | OMe | OMe | COOH | H | H | H | OMs | O | —CH$_2$C≡CMe |

TABLE 304

| | | | | | | | | | | | | | | | |
|---|---|---|---|---|---|---|---|---|---|---|---|---|---|---|---|
| I-2083 | COOH | H | H | H | H | H | OMe | OMe | COOH | H | H | H | OMs | O | —CH$_2$C$_6$H$_4$-4-Me |
| I-2084 | COOH | H | H | H | H | H | OMe | OMe | COOH | H | H | H | COOH | O | —CH$_2$CH=CMe$_2$ |
| I-2085 | COOH | H | H | H | H | H | OMe | OMe | COOH | H | H | H | COOH | O | —(CH$_2$)$_2$CH=CMe$_2$ |
| I-2086 | COOH | H | H | H | H | H | OMe | OMe | COOH | H | H | H | COOH | O | —CH$_2$CH=CCl$_2$ |
| I-2087 | COOH | H | H | H | H | H | OMe | OMe | COOH | H | H | H | COOH | O | —CH$_2$C≡CMe |
| I-2088 | COOH | H | H | H | H | H | OMe | OMe | COOH | H | H | H | COOH | O | —CH$_2$C$_6$H$_4$-4-Me |
| I-2089 | COOH | H | H | H | H | H | OMe | OMe | COOH | H | H | H | CH$_2$OH | O | —CH$_2$CH=CMe$_2$ |
| I-2090 | COOH | H | H | H | H | H | OMe | OMe | COOH | H | H | H | CH$_2$OH | O | —(CH$_2$)$_2$CH=CMe$_2$ |
| I-2091 | COOH | H | H | H | H | H | OMe | OMe | COOH | H | H | H | CH$_2$OH | O | —CH$_2$CH=CCl$_2$ |
| I-2092 | COOH | H | H | H | H | H | OMe | OMe | COOH | H | H | H | CH$_2$OH | O | —CH$_2$C≡CMe |
| I-2093 | COOH | H | H | H | H | H | OMe | OMe | COOH | H | H | H | CH$_2$OH | O | —CH$_2$C$_6$H$_4$-4-Me |
| I-2094 | COOH | H | H | H | H | H | OMe | OMe | COOH | H | H | H | F | O | —CH$_2$CH=CMe$_2$ |
| I-2095 | COOH | H | H | H | H | H | OMe | OMe | COOH | H | H | H | F | O | —(CH$_2$)$_2$CH=CMe$_2$ |
| I-2096 | COOH | H | H | H | H | H | OMe | OMe | COOH | H | H | H | F | O | —CH$_2$CH=CCl$_2$ |
| I-2097 | COOH | H | H | H | H | H | OMe | OMe | COOH | H | H | H | F | O | —CH$_2$C≡CMe |
| I-2098 | COOH | H | H | H | H | H | OMe | OMe | COOH | H | H | H | F | O | —CH$_2$C$_6$H$_4$-4-Me |
| I-2099 | COOH | H | H | H | H | H | OMe | OMe | CH$_2$OH | H | H | H | OH | O | —CH$_2$CH=CMe$_2$ |
| I-2100 | COOH | H | H | H | H | H | OMe | OMe | CH$_2$OH | H | H | H | OH | O | —(CH$_2$)$_2$CH=CMe$_2$ |
| I-2101 | COOH | H | H | H | H | H | OMe | OMe | CH$_2$OH | H | H | H | OH | O | —CH$_2$CH=CCl$_2$ |
| I-2102 | COOH | H | H | H | H | H | OMe | OMe | CH$_2$OH | H | H | H | OH | O | —CH$_2$C≡CMe |
| I-2103 | COOH | H | H | H | H | H | OMe | OMe | CH$_2$OH | H | H | H | OH | O | —CH$_2$C$_6$H$_4$-4-Me |

TABLE 305

| | | | | | | | | | | | | | | | |
|---|---|---|---|---|---|---|---|---|---|---|---|---|---|---|---|
| I-2104 | COOH | H | H | H | H | H | OMe | OMe | CH$_2$OH | H | H | H | OMs | O | —CH$_2$CH=CMe$_2$ |
| I-2105 | COOH | H | H | H | H | H | OMe | OMe | CH$_2$OH | H | H | H | OMs | O | —(CH$_2$)$_2$CH=CMe$_2$ |
| I-2106 | COOH | H | H | H | H | H | OMe | OMe | CH$_2$OH | H | H | H | OMs | O | —CH$_2$CH=CCl$_2$ |
| I-2107 | COOH | H | H | H | H | H | OMe | OMe | CH$_2$OH | H | H | H | OMs | O | —CH$_2$C≡CMe |
| I-2108 | COOH | H | H | H | H | H | OMe | OMe | CH$_2$OH | H | H | H | OMs | O | —CH$_2$C$_6$H$_4$-4-Me |
| I-2109 | COOH | H | H | H | H | H | OMe | OMe | CH$_2$OH | H | H | H | COOH | O | —CH$_2$CH=CMe$_2$ |
| I-2110 | COOH | H | H | H | H | H | OMe | OMe | CH$_2$OH | H | H | H | COOH | O | —(CH$_2$)$_2$CH=CMe$_2$ |
| I-2111 | COOH | H | H | H | H | H | OMe | OMe | CH$_2$OH | H | H | H | COOH | O | —CH$_2$CH=CCl$_2$ |
| I-2112 | COOH | H | H | H | H | H | OMe | OMe | CH$_2$OH | H | H | H | COOH | O | —CH$_2$C≡CMe |
| I-2113 | COOH | H | H | H | H | H | OMe | OMe | CH$_2$OH | H | H | H | COOH | O | —CH$_2$C$_6$H$_4$-4-Me |
| I-2114 | COOH | H | H | H | H | H | OMe | OMe | CH$_2$OH | H | H | H | CH$_2$OH | O | —CH$_2$CH=CMe$_2$ |
| I-2115 | COOH | H | H | H | H | H | OMe | OMe | CH$_2$OH | H | H | H | CH$_2$OH | O | —(CH$_2$)$_2$CH=CMe$_2$ |
| I-2116 | COOH | H | H | H | H | H | OMe | OMe | CH$_2$OH | H | H | H | CH$_2$OH | O | —CH$_2$CH=CCl$_2$ |
| I-2117 | COOH | H | H | H | H | H | OMe | OMe | CH$_2$OH | H | H | H | CH$_2$OH | O | —CH$_2$C≡CMe |
| I-2118 | COOH | H | H | H | H | H | OMe | OMe | CH$_2$OH | H | H | H | CH$_2$OH | O | —CH$_2$C$_6$H$_4$-4-Me |
| I-2119 | COOH | H | H | H | H | H | OMe | OMe | CH$_2$OH | H | H | H | F | O | —CH$_2$CH=CMe$_2$ |
| I-2120 | COOH | H | H | H | H | H | OMe | OMe | CH$_2$OH | H | H | H | F | O | —(CH$_2$)$_2$CH=CMe$_2$ |
| I-2121 | COOH | H | H | H | H | H | OMe | OMe | CH$_2$OH | H | H | H | F | O | —CH$_2$CH=CCl$_2$ |
| I-2122 | COOH | H | H | H | H | H | OMe | OMe | CH$_2$OH | H | H | H | F | O | —CH$_2$C≡CMe |
| I-2123 | COOH | H | H | H | H | H | OMe | OMe | CH$_2$OH | H | H | H | F | O | —CH$_2$C$_6$H$_4$-4-Me |
| I-2124 | COOH | H | H | H | H | H | OMe | OMe | Me | H | H | H | OH | O | —CH$_2$CH=CMe$_2$ |

TABLE 306

| | | | | | | | | | | | | | | | |
|---|---|---|---|---|---|---|---|---|---|---|---|---|---|---|---|
| I-2125 | COOH | H | H | H | H | H | OMe | OMe | Me | H | H | H | OH | O | —(CH$_2$)$_2$CH=CMe$_2$ |
| I-2126 | COOH | H | H | H | H | H | OMe | OMe | Me | H | H | H | OH | O | —CH$_2$CH=CCl$_2$ |
| I-2127 | COOH | H | H | H | H | H | OMe | OMe | Me | H | H | H | OH | O | —CH$_2$C≡CMe |
| I-2128 | COOH | H | H | H | H | H | OMe | OMe | Me | H | H | H | OH | O | —CH$_2$C$_6$H$_4$-4-Me |
| I-2129 | COOH | H | H | H | H | H | OMe | OMe | Me | H | H | H | OMs | O | —CH$_2$CH=CMe$_2$ |
| I-2130 | COOH | H | H | H | H | H | OMe | OMe | Me | H | H | H | OMs | O | —(CH$_2$)$_2$CH=CMe$_2$ |
| I-2131 | COOH | H | H | H | H | H | OMe | OMe | Me | H | H | H | OMs | O | —CH$_2$CH=CCl$_2$ |
| I-2132 | COOH | H | H | H | H | H | OMe | OMe | Me | H | H | H | OMs | O | —CH$_2$C≡CMe |
| I-2133 | COOH | H | H | H | H | H | OMe | OMe | Me | H | H | H | OMs | O | —CH$_2$C$_6$H$_4$-4-Me |
| I-2134 | COOH | H | H | H | H | H | OMe | OMe | Me | H | H | H | COOH | O | —CH$_2$CH=CMe$_2$ |
| I-2135 | COOH | H | H | H | H | H | OMe | OMe | Me | H | H | H | COOH | O | —(CH$_2$)$_2$CH=CMe$_2$ |
| I-2136 | COOH | H | H | H | H | H | OMe | OMe | Me | H | H | H | COOH | O | —CH$_2$CH=CCl$_2$ |
| I-2137 | COOH | H | H | H | H | H | OMe | OMe | Me | H | H | H | COOH | O | —CH$_2$C≡CMe |
| I-2138 | COOH | H | H | H | H | H | OMe | OMe | Me | H | H | H | COOH | O | —CH$_2$C$_6$H$_4$-4-Me |
| I-2139 | COOH | H | H | H | H | H | OMe | OMe | Me | H | H | H | CH$_2$OH | O | —CH$_2$CH=CMe$_2$ |
| I-2140 | COOH | H | H | H | H | H | OMe | OMe | Me | H | H | H | CH$_2$OH | O | —(CH$_2$)$_2$CH=CMe$_2$ |
| I-2141 | COOH | H | H | H | H | H | OMe | OMe | Me | H | H | H | CH$_2$OH | O | —CH$_2$CH=CCl$_2$ |
| I-2142 | COOH | H | H | H | H | H | OMe | OMe | Me | H | H | H | CH$_2$OH | O | —CH$_2$C≡CMe |
| I-2143 | COOH | H | H | H | H | H | OMe | OMe | Me | H | H | H | CH$_2$OH | O | —CH$_2$C$_6$H$_4$-4-Me |
| I-2144 | COOH | H | H | H | H | H | OMe | OMe | Me | H | H | H | F | O | —CH$_2$CH=CMe$_2$ |
| I-2145 | COOH | H | H | H | H | H | OMe | OMe | Me | H | H | H | F | O | —(CH$_2$)$_2$CH=CMe$_2$ |

TABLE 307

| | | | | | | | | | | | | | | | |
|---|---|---|---|---|---|---|---|---|---|---|---|---|---|---|---|
| I-2146 | COOH | H | H | H | H | H | OMe | OMe | Me | H | H | H | F | O | —CH$_2$CH=CCl$_2$ |
| I-2147 | COOH | H | H | H | H | H | OMe | OMe | Me | H | H | H | F | O | —CH$_2$C≡CMe |
| I-2148 | COOH | H | H | H | H | H | OMe | OMe | Me | H | H | H | F | O | —CH$_2$C$_6$H$_4$-4-Me |
| I-2149 | COOH | H | H | H | H | H | OMe | OMe | H | H | H | H | OH | O | —CH$_2$CH=CMe$_2$ |
| I-2150 | COOH | H | H | H | H | H | OMe | OMe | H | H | H | H | OH | O | —(CH$_2$)$_2$CH=CMe$_2$ |
| I-2151 | COOH | H | H | H | H | H | OMe | OMe | H | H | H | H | OH | O | —CH$_2$CH=CCl$_2$ |
| I-2152 | COOH | H | H | H | H | H | OMe | OMe | H | H | H | H | OH | O | —CH$_2$C≡CMe |
| I-2153 | COOH | H | H | H | H | H | OMe | OMe | H | H | H | H | OH | O | —CH$_2$C$_6$H$_4$-4-Me |
| I-2154 | COOH | H | H | H | H | H | OMe | OMe | H | H | H | H | OMs | O | —CH$_2$CH=CMe$_2$ |
| I-2155 | COOH | H | H | H | H | H | OMe | OMe | H | H | H | H | OMs | O | —(CH$_2$)$_2$CH=CMe$_2$ |
| I-2156 | COOH | H | H | H | H | H | OMe | OMe | H | H | H | H | OMs | O | —CH$_2$CH=CCl$_2$ |
| I-2157 | COOH | H | H | H | H | H | OMe | OMe | H | H | H | H | OMs | O | —CH$_2$C≡CMe |
| I-2158 | COOH | H | H | H | H | H | OMe | OMe | H | H | H | H | OMs | O | —CH$_2$C$_6$H$_4$-4-Me |
| I-2159 | COOH | H | H | H | H | H | OMe | OMe | H | H | H | H | COOH | O | —CH$_2$CH=CMe$_2$ |
| I-2160 | COOH | H | H | H | H | H | OMe | OMe | H | H | H | H | COOH | O | —(CH$_2$)$_2$CH=CMe$_2$ |
| I-2161 | COOH | H | H | H | H | H | OMe | OMe | H | H | H | H | COOH | O | —CH$_2$CH=CCl$_2$ |
| I-2162 | COOH | H | H | H | H | H | OMe | OMe | H | H | H | H | COOH | O | —CH$_2$C≡CMe |
| I-2163 | COOH | H | H | H | H | H | OMe | OMe | H | H | H | H | COOH | O | —CH$_2$C$_6$H$_4$-4-Me |
| I-2164 | COOH | H | H | H | H | H | OMe | OMe | H | H | H | H | CH$_2$OH | O | —CH$_2$CH=CMe$_2$ |
| I-2165 | COOH | H | H | H | H | H | OMe | OMe | H | H | H | H | CH$_2$OH | O | —(CH$_2$)$_2$CH=CMe$_2$ |
| I-2166 | COOH | H | H | H | H | H | OMe | OMe | H | H | H | H | CH$_2$OH | O | —CH$_2$CH=CCl$_2$ |

TABLE 308

| | | | | | | | | | | | | | | | |
|---|---|---|---|---|---|---|---|---|---|---|---|---|---|---|---|
| I-2167 | COOH | H | H | H | H | H | OMe | OMe | H | H | H | H | CH$_2$OH | O | —CH$_2$C≡CMe |
| I-2168 | COOH | H | H | H | H | H | OMe | OMe | H | H | H | H | CH$_2$OH | O | —CH$_2$C$_6$H$_4$-4-Me |
| I-2169 | COOH | H | H | H | H | H | OMe | OMe | H | H | H | H | F | O | —CH$_2$CH=CMe$_2$ |
| I-2170 | COOH | H | H | H | H | H | OMe | OMe | H | H | H | H | F | O | —(CH$_2$)$_2$CH=CMe$_2$ |
| I-2171 | COOH | H | H | H | H | H | OMe | OMe | H | H | H | H | F | O | —CH$_2$CH=CCl$_2$ |
| I-2172 | COOH | H | H | H | H | H | OMe | OMe | H | H | H | H | F | O | —CH$_2$C≡CMe |
| I-2173 | COOH | H | H | H | H | H | OMe | OMe | H | H | H | H | F | O | —CH$_2$C$_6$H$_4$-4-Me |
| I-2174 | COOH | H | H | H | H | F | OMe | OMe | OH | H | H | H | OH | O | —CH$_2$CH=CMe$_2$ |
| I-2175 | COOH | H | H | H | H | F | OMe | OMe | OH | H | H | H | OH | O | —(CH$_2$)$_2$CH=CMe$_2$ |
| I-2176 | COOH | H | H | H | H | F | OMe | OMe | OH | H | H | H | OH | O | —CH$_2$CH=CCl$_2$ |
| I-2177 | COOH | H | H | H | H | F | OMe | OMe | OH | H | H | H | OH | O | —CH$_2$C≡CMe |
| I-2178 | COOH | H | H | H | H | F | OMe | OMe | OH | H | H | H | OH | O | —CH$_2$C$_6$H$_4$-4-Me |
| I-2179 | COOH | H | H | H | H | F | OMe | OMe | OH | H | H | H | OMs | O | —CH$_2$CH=CMe$_2$ |
| I-2180 | COOH | H | H | H | H | F | OMe | OMe | OH | H | H | H | OMs | O | —(CH$_2$)$_2$CH=CMe$_2$ |
| I-2181 | COOH | H | H | H | H | F | OMe | OMe | OH | H | H | H | OMs | O | —CH$_2$CH=CCl$_2$ |
| I-2182 | COOH | H | H | H | H | F | OMe | OMe | OH | H | H | H | OMs | O | —CH$_2$C≡CMe |
| I-2183 | COOH | H | H | H | H | F | OMe | OMe | OH | H | H | H | OMs | O | —CH$_2$C$_6$H$_4$-4-Me |
| I-2184 | COOH | H | H | H | H | F | OMe | OMe | OH | H | H | H | COOH | O | —CH$_2$CH=CMe$_2$ |

TABLE 308-continued

| | | | | | | | | | | | | | | | |
|---|---|---|---|---|---|---|---|---|---|---|---|---|---|---|---|
| I-2185 | COOH | H | H | H | H | F | OMe | OMe | OH | H | H | H | COOH | O | —(CH$_2$)$_2$CH=CMe$_2$ |
| I-2186 | COOH | H | H | H | H | F | OMe | OMe | OH | H | H | H | COOH | O | —CH$_2$CH=CCl$_2$ |
| I-2187 | COOH | H | H | H | H | F | OMe | OMe | OH | H | H | H | COOH | O | —CH$_2$C≡CMe |

TABLE 309

| | | | | | | | | | | | | | | | |
|---|---|---|---|---|---|---|---|---|---|---|---|---|---|---|---|
| I-2188 | COOH | H | H | H | H | F | OMe | OMe | OH | H | H | H | COOH | O | —CH$_2$C$_6$H$_4$-4-Me |
| I-2189 | COOH | H | H | H | H | F | OMe | OMe | OH | H | H | H | CH$_2$OH | O | —CH$_2$CH=CMe$_2$ |
| I-2190 | COOH | H | H | H | H | F | OMe | OMe | OH | H | H | H | CH$_2$OH | O | —(CH$_2$)$_2$CH=CMe$_2$ |
| I-2191 | COOH | H | H | H | H | F | OMe | OMe | OH | H | H | H | CH$_2$OH | O | —CH$_2$CH=CCl$_2$ |
| I-2192 | COOH | H | H | H | H | F | OMe | OMe | OH | H | H | H | CH$_2$OH | O | —CH$_2$C≡CMe |
| I-2193 | COOH | H | H | H | H | F | OMe | OMe | OH | H | H | H | CH$_2$OH | O | —CH$_2$C$_6$H$_4$-4-Me |
| I-2194 | COOH | H | H | H | H | F | OMe | OMe | OH | H | H | H | F | O | —CH$_2$CH=CMe$_2$ |
| I-2195 | COOH | H | H | H | H | F | OMe | OMe | OH | H | H | H | F | O | —(CH$_2$)$_2$CH=CMe$_2$ |
| I-2196 | COOH | H | H | H | H | F | OMe | OMe | OH | H | H | H | F | O | —CH$_2$CH=CCl$_2$ |
| I-2197 | COOH | H | H | H | H | F | OMe | OMe | OH | H | H | H | F | O | —CH$_2$C≡CMe |
| I-2198 | COOH | H | H | H | H | F | OMe | OMe | OH | H | H | H | F | O | —CH$_2$C$_6$H$_4$-4-Me |
| I-2199 | NO$_2$ | H | H | H | H | H | OMe | OMe | H | H | H | H | OMs | O | —(CH$_2$)$_2$CH=CMe$_2$ |
| I-2200 | OMs | NO$_2$ | H | H | H | H | OMe | OMe | H | H | H | H | OMs | O | —(CH$_2$)$_2$CH=CMe$_2$ |
| I-2201 | OMs | H | H | H | H | H | OMe | OMe | H | NO$_2$ | H | H | OMs | O | —(CH$_2$)$_2$CH=CMe$_2$ |
| I-2202 | CN | H | H | H | H | H | OMe | OMe | H | H | H | H | OMs | O | —(CH$_2$)$_2$CH=CMe$_2$ |
| I-2203 | OMs | CN | H | H | H | H | OMe | OMe | H | H | H | H | OMs | O | —(CH$_2$)$_2$CH=CMe$_2$ |
| I-2204 | OH | H | H | H | H | H | OMe | OMe | OMs | H | H | H | OH | O | —CH$_2$CH=CMe$_2$ |
| I-2205 | OH | H | H | H | H | H | OMe | OMe | OMs | H | H | H | OH | O | —CH$_2$C$_6$H$_5$ |
| I-2206 | OH | H | H | H | H | H | OMe | OMe | OMs | H | H | H | NH$_2$ | O | —CH$_2$CH=CMe$_2$ |
| I-2207 | OH | H | H | H | H | H | OMe | OMe | OMs | H | H | H | NH$_2$ | O | —CH$_2$C$_6$H$_5$ |
| I-2208 | OH | H | H | H | H | H | OMe | OEt | OH | H | H | H | OH | O | —CH$_2$C$_6$H$_5$ |

TABLE 310

| | | | | | | | | | | | | | | | |
|---|---|---|---|---|---|---|---|---|---|---|---|---|---|---|---|
| I-2209 | OH | H | H | H | H | H | OMe | OEt | OH | H | H | H | NH$_2$ | O | —CH$_2$CH=CMe$_2$ |
| I-2210 | OH | H | H | H | H | H | Me | Me | H | H | H | H | OH | O | —CH$_2$C$_6$H$_5$ |
| I-2211 | OH | H | H | H | H | H | Me | Me | H | H | H | H | NH$_2$ | O | —CH$_2$CH=CMe$_2$ |
| I-2212 | OH | H | H | H | H | H | Me | Me | H | H | H | H | NH$_2$ | O | —CH$_2$C$_6$H$_5$ |
| I-2213 | OH | H | H | H | H | H | OMe | OMe | NH$_2$ | H | H | H | OH | O | —CH$_2$CH=CMe$_2$ |
| I-2214 | OH | H | H | H | H | H | OMe | OMe | NH$_2$ | H | H | H | NH$_2$ | O | —CH$_2$CH=CMe$_2$ |
| I-2215 | OH | H | H | H | H | H | OMe | OMe | NH$_2$ | H | H | H | NH$_2$ | O | —CH$_2$C$_6$H$_5$ |
| I-2216 | OH | H | H | H | H | H | OMe | OMe | OH | H | H | H | OH | O | —CH$_2$CH=CMe$_2$ |
| I-2217 | OH | H | H | H | H | H | OMe | OMe | OH | H | H | H | OH | O | —CH$_2$C$_6$H$_5$ |
| I-2218 | OH | H | H | H | H | H | OMe | OMe | OH | H | H | H | NH$_2$ | O | —CH$_2$CH=CMe$_2$ |
| I-2219 | OH | H | H | H | H | H | OMe | OMe | OH | H | H | H | NH$_2$ | O | —CH$_2$C$_6$H$_5$ |
| I-2220 | OMs | H | H | H | H | H | OMe | OMe | OMs | H | H | H | OH | O | —CH$_2$CH=CMe$_2$ |
| I-2221 | OMs | H | H | H | H | H | OMe | OMe | OMs | H | H | H | OH | O | —CH$_2$C$_6$H$_5$ |
| I-2222 | OMs | H | H | H | H | H | OMe | OMe | OMs | H | H | H | NH$_2$ | O | —CH$_2$CH=CMe$_2$ |
| I-2223 | OMs | H | H | H | H | H | OMe | OMe | OMs | H | H | H | NH$_2$ | O | —CH$_2$C$_6$H$_5$ |
| I-2224 | OMs | H | H | H | H | H | OMe | OEt | OH | H | H | H | OH | O | —CH$_2$CH=CMe$_2$ |
| I-2225 | OMs | H | H | H | H | H | OMe | OEt | OH | H | H | H | OH | O | —CH$_2$C$_6$H$_5$ |
| I-2226 | OMs | H | H | H | H | H | OMe | OEt | OH | H | H | H | NH$_2$ | O | —CH$_2$CH=CMe$_2$ |
| I-2227 | OMs | H | H | H | H | H | OMe | OEt | OH | H | H | H | NH$_2$ | O | —CH$_2$C$_6$H$_5$ |
| I-2228 | OMs | H | H | H | H | H | Me | Me | H | H | H | H | OH | O | —CH$_2$CH=CMe$_2$ |
| I-2229 | OMs | H | H | H | H | H | Me | Me | H | H | H | H | OH | O | —CH$_2$C$_6$H$_5$ |

TABLE 311

| | | | | | | | | | | | | | | | |
|---|---|---|---|---|---|---|---|---|---|---|---|---|---|---|---|
| I-2230 | OMs | H | H | H | H | H | Me | Me | H | H | H | H | NH$_2$ | O | —CH$_2$CH=CMe$_2$ |
| I-2231 | OMs | H | H | H | H | H | Me | Me | H | H | H | H | NH$_2$ | O | —CH$_2$C$_6$H$_5$ |
| I-2232 | OMs | H | H | H | H | H | OMe | OMe | NH$_2$ | H | H | H | OH | O | —CH$_2$CH=CMe$_2$ |
| I-2233 | OMs | H | H | H | H | H | OMe | OMe | NH$_2$ | H | H | H | NH$_2$ | O | —CH$_2$CH=CMe$_2$ |
| I-2234 | OMs | H | H | H | H | H | OMe | OMe | NH$_2$ | H | H | H | NH$_2$ | O | —CH$_2$C$_6$H$_5$ |
| I-2235 | OMs | H | H | H | H | H | OMe | OMe | OH | H | H | H | OH | O | —CH$_2$CH=CMe$_2$ |
| I-2236 | OMs | H | H | H | H | H | OMe | OMe | OH | H | H | H | OH | O | —CH$_2$C$_6$H$_5$ |
| I-2237 | OMs | H | H | H | H | H | OMe | OMe | OH | H | H | H | NH$_2$ | O | —CH$_2$CH=CMe$_2$ |
| I-2238 | OMs | H | H | H | H | H | OMe | OMe | OH | H | H | H | NH$_2$ | O | —CH$_2$C$_6$H$_5$ |

TABLE 311-continued

| | | | | | | | | | | | | | | | |
|---|---|---|---|---|---|---|---|---|---|---|---|---|---|---|---|
| I-2239 | CF$_3$ | H | H | H | H | H | OMe | OMe | OMs | H | H | H | OH | O | —CH$_2$CH=CMe$_2$ |
| I-2240 | CF$_3$ | H | H | H | H | H | OMe | OMe | OMs | H | H | H | OH | O | —CH$_2$C$_6$H$_5$ |
| I-2241 | CF$_3$ | H | H | H | H | H | OMe | OMe | OMs | H | H | H | NH$_2$ | O | —CH$_2$CH=CMe$_2$ |
| I-2242 | CF$_3$ | H | H | H | H | H | OMe | OMe | OMs | H | H | H | NH$_2$ | O | —CH$_2$C$_6$H$_5$ |
| I-2243 | CF$_3$ | H | H | H | H | H | OMe | OEt | OH | H | H | H | OH | O | —CH$_2$CH=CMe$_2$ |
| I-2244 | CF$_3$ | H | H | H | H | H | OMe | OEt | OH | H | H | H | OH | O | —CH$_2$C$_6$H$_5$ |
| I-2245 | CF$_3$ | H | H | H | H | H | OMe | OEt | OH | H | H | H | NH$_2$ | O | —CH$_2$CH=CMe$_2$ |
| I-2246 | CF$_3$ | H | H | H | H | H | OMe | OEt | OH | H | H | H | NH$_2$ | O | —CH$_2$C$_6$H$_5$ |
| I-2247 | CF$_3$ | H | H | H | H | H | Me | Me | H | H | H | H | OH | O | —CH$_2$CH=CMe$_2$ |
| I-2248 | CF$_3$ | H | H | H | H | H | Me | Me | H | H | H | H | OH | O | —CH$_2$C$_6$H$_5$ |
| I-2249 | CF$_3$ | H | H | H | H | H | Me | Me | H | H | H | H | NH$_2$ | O | —CH$_2$CH=CMe$_2$ |
| I-2250 | CF$_3$ | H | H | H | H | H | Me | Me | H | H | H | H | NH$_2$ | O | —CH$_2$C$_6$H$_5$ |

TABLE 312

| | | | | | | | | | | | | | | | |
|---|---|---|---|---|---|---|---|---|---|---|---|---|---|---|---|
| I-2251 | CF$_3$ | H | H | H | H | H | OMe | OMe | NH$_2$ | H | H | H | OH | O | —CH$_2$CH=CMe$_2$ |
| I-2252 | CF$_3$ | H | H | H | H | H | OMe | OMe | NH$_2$ | H | H | H | OH | O | —CH$_2$C$_6$H$_5$ |
| I-2253 | CF$_3$ | H | H | H | H | H | OMe | OMe | NH$_2$ | H | H | H | NH$_2$ | O | —CH$_2$CH=CMe$_2$ |
| I-2254 | CF$_3$ | H | H | H | H | H | OMe | OMe | NH$_2$ | H | H | H | NH$_2$ | O | —CH$_2$C$_6$H$_5$ |
| I-2255 | CF$_3$ | H | H | H | H | H | OMe | OMe | OH | H | H | H | OH | O | —CH$_2$CH=CMe$_2$ |
| I-2256 | CF$_3$ | H | H | H | H | H | OMe | OMe | OH | H | H | H | OH | O | —CH$_2$C$_6$H$_5$ |
| I-2257 | CF$_3$ | H | H | H | H | H | OMe | OMe | OH | H | H | H | NH$_2$ | O | —CH$_2$CH=CMe$_2$ |
| I-2258 | CF$_3$ | H | H | H | H | H | OMe | OMe | OH | H | H | H | NH$_2$ | O | —CH$_2$C$_6$H$_5$ |
| I-2259 | NH$_2$ | H | H | H | H | H | OMe | OMe | OMs | H | H | H | OH | O | —CH$_2$CH=CMe$_2$ |
| I-2260 | NH$_2$ | H | H | H | H | H | OMe | OMe | OMs | H | H | H | OH | O | —CH$_2$C$_6$H$_5$ |
| I-2261 | NH$_2$ | H | H | H | H | H | OMe | OMe | OMs | H | H | H | NH$_2$ | O | —CH$_2$CH=CMe$_2$ |
| I-2262 | NH$_2$ | H | H | H | H | H | OMe | OMe | OMs | H | H | H | NH$_2$ | O | —CH$_2$C$_6$H$_5$ |
| I-2263 | NH$_2$ | H | H | H | H | H | OMe | OEt | OH | H | H | H | OH | O | —CH$_2$CH=CMe$_2$ |
| I-2264 | NH$_2$ | H | H | H | H | H | OMe | OEt | OH | H | H | H | OH | O | —CH$_2$C$_6$H$_5$ |
| I-2265 | NH$_2$ | H | H | H | H | H | OMe | OEt | OH | H | H | H | NH$_2$ | O | —CH$_2$CH=CMe$_2$ |
| I-2266 | NH$_2$ | H | H | H | H | H | OMe | OEt | OH | H | H | H | NH$_2$ | O | —CH$_2$C$_6$H$_5$ |
| I-2267 | NH$_2$ | H | H | H | H | H | Me | Me | H | H | H | H | OH | O | —CH$_2$CH=CMe$_2$ |
| I-2268 | NH$_2$ | H | H | H | H | H | Me | Me | H | H | H | H | OH | O | —CH$_2$C$_6$H$_5$ |
| I-2269 | NH$_2$ | H | H | H | H | H | Me | Me | H | H | H | H | NH$_2$ | O | —CH$_2$CH=CMe$_2$ |
| I-2270 | NH$_2$ | H | H | H | H | H | Me | Me | H | H | H | H | NH$_2$ | O | —CH$_2$C$_6$H$_5$ |
| I-2271 | NH$_2$ | H | H | H | H | H | OMe | OMe | NH$_2$ | H | H | H | OH | O | —CH$_2$CH=CMe$_2$ |

TABLE 313

| | | | | | | | | | | | | | | | |
|---|---|---|---|---|---|---|---|---|---|---|---|---|---|---|---|
| I-2272 | NH$_2$ | H | H | H | H | H | OMe | OMe | NH$_2$ | H | H | H | OH | O | —CH$_2$C$_6$H$_5$ |
| I-2273 | NH$_2$ | H | H | H | H | H | OMe | OMe | NH$_2$ | H | H | H | NH$_2$ | O | —CH$_2$CH=CMe$_2$ |
| I-2274 | NH$_2$ | H | H | H | H | H | OMe | OMe | NH$_2$ | H | H | H | NH$_2$ | O | —CH$_2$C$_6$H$_5$ |
| I-2275 | NH$_2$ | H | H | H | H | H | OMe | OMe | OH | H | H | H | OH | O | —CH$_2$CH=CMe$_2$ |
| I-2276 | NH$_2$ | H | H | H | H | H | OMe | OMe | OH | H | H | H | OH | O | —CH$_2$C$_6$H$_5$ |
| I-2277 | NH$_2$ | H | H | H | H | H | OMe | OMe | OH | H | H | H | NH$_2$ | O | —CH$_2$CH=CMe$_2$ |
| I-2278 | NH$_2$ | H | H | H | H | H | OMe | OMe | OH | H | H | H | NH$_2$ | O | —CH$_2$C$_6$H$_5$ |
| I-2279 | —NHCH$_2$CH=CMe$_2$ | H | F | H | H | Me | Me | Me | H | H | H | H | OMe | NH | —CH$_2$CH=CMe$_2$ |
| I-2280 | —NHCH$_2$CH=CMe$_2$ | H | F | H | H | Me | Me | Me | H | H | H | H | OMe | NH | —(CH$_2$)$_2$CHMe$_2$ |
| I-2281 | —NHCH$_2$CH=CMe$_2$ | H | F | H | H | Me | Me | Me | H | H | H | H | OMe | NMe | Me |
| I-2282 | —NHCH$_2$CH=CMe$_2$ | H | F | H | H | Me | Me | Me | H | H | H | H | OMe | O | —CH$_2$CH=CMe$_2$ |
| I-2283 | —NHCH$_2$CH=CMe$_2$ | H | F | H | H | Me | Me | Me | H | H | H | H | OMe | O | —CH$_2$CH=CCl$_2$ |
| I-2284 | —NHCH$_2$CH=CMe$_2$ | H | F | H | H | Me | Me | Me | H | H | H | F | H | NH | —CH$_2$CH=CMe$_2$ |
| I-2285 | —NHCH$_2$CH=CMe$_2$ | H | F | H | H | Me | Me | Me | H | H | H | F | H | NH | —(CH$_2$)$_2$CHMe$_2$ |
| I-2286 | —NHCH$_2$CH=CMe$_2$ | H | F | H | H | Me | Me | Me | H | H | H | F | H | NMe | Me |
| I-2287 | —NHCH$_2$CH=CMe$_2$ | H | F | H | H | Me | Me | Me | H | H | H | F | H | O | —CH$_2$CH=CMe$_2$ |
| I-2288 | —NHCH$_2$CH=CMe$_2$ | H | F | H | H | Me | Me | Me | H | H | H | F | H | O | —CH$_2$CH=CCl$_2$ |
| I-2289 | —NHCH$_2$CH=CMe$_2$ | H | F | H | H | Me | Me | Me | H | H | H | H | OEt | NH | —CH$_2$CH=CMe$_2$ |
| I-2290 | —NHCH$_2$CH=CMe$_2$ | H | F | H | H | Me | Me | Me | H | H | H | H | OEt | NH | —(CH$_2$)$_2$CHMe$_2$ |
| I-2291 | —NHCH$_2$CH=CMe$_2$ | H | F | H | H | Me | Me | Me | H | H | H | H | OEt | NMe | Me |
| I-2292 | —NHCH$_2$CH=CMe$_2$ | H | F | H | H | Me | Me | Me | H | H | H | H | OEt | O | —CH$_2$CH=CMe$_2$ |

TABLE 314

| ID | R | | | | | | | | | | | | | | |
|---|---|---|---|---|---|---|---|---|---|---|---|---|---|---|---|
| I-2293 | —NHCH$_2$CH=CMe$_2$ | H | F | H | H | Me | Me | Me | H | H | H | H | OEt | O | —CH$_2$CH=CCl$_2$ |
| I-2294 | —NHCH$_2$CH=CMe$_2$ | H | F | H | H | H | Me | OMe | OH | H | H | H | OMe | NH | —CH$_2$CH=CMe$_2$ |
| I-2295 | —NHCH$_2$CH=CMe$_2$ | H | F | H | H | H | Me | OMe | OH | H | H | H | OMe | NH | —(CH$_2$)$_2$CHMe$_2$ |
| I-2296 | —NHCH$_2$CH=CMe$_2$ | H | F | H | H | H | Me | OMe | OH | H | H | H | OMe | NMe | Me |
| I-2297 | —NHCH$_2$CH=CMe$_2$ | H | F | H | H | H | Me | OMe | OH | H | H | H | OMe | O | —CH$_2$CH=CMe$_2$ |
| I-2298 | —NHCH$_2$CH=CMe$_2$ | H | F | H | H | H | Me | OMe | OH | H | H | H | OMe | O | —CH$_2$CH=CCl$_2$ |
| I-2299 | —NHCH$_2$CH=CMe$_2$ | H | F | H | H | H | Me | OMe | OH | H | H | F | H | NH | —CH$_2$CH=CMe$_2$ |
| I-2300 | —NHCH$_2$CH=CMe$_2$ | H | F | H | H | H | Me | OMe | OH | H | H | F | H | NH | —(CH$_2$)$_2$CHMe$_2$ |
| I-2301 | —NHCH$_2$CH=CMe$_2$ | H | F | H | H | H | Me | OMe | OH | H | H | F | H | NMe | Me |
| I-2302 | —NHCH$_2$CH=CMe$_2$ | H | F | H | H | H | Me | OMe | OH | H | H | F | H | O | —CH$_2$CH=CMe$_2$ |
| I-2303 | —NHCH$_2$CH=CMe$_2$ | H | F | H | H | H | Me | OMe | OH | H | H | F | H | O | —CH$_2$CH=CCl$_2$ |
| I-2304 | —NHCH$_2$CH=CMe$_2$ | H | F | H | H | H | Me | OMe | OH | H | H | H | OEt | NH | —CH$_2$CH=CMe$_2$ |
| I-2305 | —NHCH$_2$CH=CMe$_2$ | H | F | H | H | H | Me | OMe | OH | H | H | H | OEt | NH | —(CH$_2$)$_2$CHMe$_2$ |
| I-2306 | —NHCH$_2$CH=CMe$_2$ | H | F | H | H | H | Me | OMe | OH | H | H | H | OEt | NMe | Me |
| I-2307 | —NHCH$_2$CH=CMe$_2$ | H | F | H | H | H | Me | OMe | OH | H | H | H | OEt | O | —CH$_2$CH=CMe$_2$ |
| I-2308 | —NHCH$_2$CH=CMe$_2$ | H | F | H | H | H | Me | OMe | OH | H | H | H | OEt | O | —CH$_2$CH=CCl$_2$ |
| I-2309 | —NHCH$_2$CH=CMe$_2$ | H | F | H | H | Me | H | Me | OH | H | H | H | OMe | NH | —CH$_2$CH=CMe$_2$ |
| I-2330 | —NHCH$_2$CH=CMe$_2$ | H | F | H | H | Me | H | Me | OH | H | H | H | OMe | NH | —(CH$_2$)$_2$CHMe$_2$ |
| I-2331 | —NHCH$_2$CH=CMe$_2$ | H | F | H | H | Me | H | Me | OH | H | H | H | OMe | NMe | Me |
| I-2332 | —NHCH$_2$CH=CMe$_2$ | H | F | H | H | Me | H | Me | OH | H | H | H | OMe | O | —CH$_2$CH=CMe$_2$ |
| I-2333 | —NHCH$_2$CH=CMe$_2$ | H | F | H | H | Me | H | Me | OH | H | H | H | OMe | O | —CH$_2$CH=CCl$_2$ |

TABLE 315

| ID | R | | | | | | | | | | | | | | |
|---|---|---|---|---|---|---|---|---|---|---|---|---|---|---|---|
| I-2334 | —NHCH$_2$CH=CMe$_2$ | H | F | H | H | Me | H | Me | OH | H | H | F | H | NH | —CH$_2$CH=CMe$_2$ |
| I-2335 | —NHCH$_2$CH=CMe$_2$ | H | F | H | H | Me | H | Me | OH | H | H | F | H | NH | —(CH$_2$)$_2$CHMe$_2$ |
| I-2336 | —NHCH$_2$CH=CMe$_2$ | H | F | H | H | Me | H | Me | OH | H | H | F | H | NMe | Me |
| I-2337 | —NHCH$_2$CH=CMe$_2$ | H | F | H | H | Me | H | Me | OH | H | H | F | H | O | —CH$_2$CH=CMe$_2$ |
| I-2338 | —NHCH$_2$CH=CMe$_2$ | H | F | H | H | Me | H | Me | OH | H | H | F | H | O | —CH$_2$CH=CCl$_2$ |
| I-2339 | —NHCH$_2$CH=CMe$_2$ | H | F | H | H | Me | H | Me | OH | H | H | H | OEt | NH | —CH$_2$CH=CMe$_2$ |
| I-2340 | —NHCH$_2$CH=CMe$_2$ | H | F | H | H | Me | H | Me | OH | H | H | H | OEt | NH | —(CH$_2$)$_2$CHMe$_2$ |
| I-2341 | —NHCH$_2$CH=CMe$_2$ | H | F | H | H | Me | H | Me | OH | H | H | H | OEt | NMe | Me |
| I-2342 | —NHCH$_2$CH=CMe$_2$ | H | F | H | H | Me | H | Me | OH | H | H | H | OEt | O | —CH$_2$CH=CMe$_2$ |
| I-2343 | —NHCH$_2$CH=CMe$_2$ | H | F | H | H | Me | H | Me | OH | H | H | H | OEt | O | —CH$_2$CH=CCl$_2$ |
| I-2344 | —NHCH$_2$CH=CMe$_2$ | H | F | H | H | H | Me | Me | Me | H | H | H | OMe | NH | —CH$_2$CH=CMe$_2$ |
| I-2345 | —NHCH$_2$CH=CMe$_2$ | H | F | H | H | H | Me | Me | Me | H | H | H | OMe | NH | —(CH$_2$)$_2$CHMe$_2$ |
| I-2346 | —NHCH$_2$CH=CMe$_2$ | H | F | H | H | H | Me | Me | Me | H | H | H | OMe | NMe | Me |
| I-2347 | —NHCH$_2$CH=CMe$_2$ | H | F | H | H | H | Me | Me | Me | H | H | H | OMe | O | —CH$_2$CH=CMe$_2$ |
| I-2348 | —NHCH$_2$CH=CMe$_2$ | H | F | H | H | H | Me | Me | Me | H | H | H | OMe | O | —CH$_2$CH=CCl$_2$ |
| I-2349 | —NHCH$_2$CH=CMe$_2$ | H | F | H | H | H | Me | Me | Me | H | H | F | H | NH | —CH$_2$CH=CMe$_2$ |
| I-2350 | —NHCH$_2$CH=CMe$_2$ | H | F | H | H | H | Me | Me | Me | H | H | F | H | NH | —(CH$_2$)$_2$CHMe$_2$ |
| I-2351 | —NHCH$_2$CH=CMe$_2$ | H | F | H | H | H | Me | Me | Me | H | H | F | H | NMe | Me |
| I-2352 | —NHCH$_2$CH=CMe$_2$ | H | F | H | H | H | Me | Me | Me | H | H | F | H | O | —CH$_2$CH=CMe$_2$ |
| I-2353 | —NHCH$_2$CH=CMe$_2$ | H | F | H | H | H | Me | Me | Me | H | H | F | H | O | —CH$_2$CH=CCl$_2$ |
| I-2354 | —NHCH$_2$CH=CMe$_2$ | H | F | H | H | H | Me | Me | Me | H | H | H | OEt | NH | —CH$_2$CH=CMe$_2$ |

TABLE 316

| ID | R | | | | | | | | | | | | | | |
|---|---|---|---|---|---|---|---|---|---|---|---|---|---|---|---|
| I-2355 | —NHCH$_2$CH=CMe$_2$ | H | F | H | H | H | Me | Me | Me | H | H | H | OEt | NH | —(CH$_2$)$_2$CHMe$_2$ |
| I-2356 | —NHCH$_2$CH=CMe$_2$ | H | F | H | H | H | Me | Me | Me | H | H | H | OEt | NMe | Me |
| I-2357 | —NHCH$_2$CH=CMe$_2$ | H | F | H | H | H | Me | Me | Me | H | H | H | OEt | O | —CH$_2$CH=CMe$_2$ |
| I-2358 | —NHCH$_2$CH=CMe$_2$ | H | F | H | H | H | Me | Me | Me | H | H | H | OEt | O | —CH$_2$CH=CCl$_2$ |
| I-2359 | —NHCH$_2$CH=CMe$_2$ | H | F | H | H | H | OMe | OEt | OH | H | H | H | OMe | NH | —CH$_2$CH=CMe$_2$ |
| I-2360 | —NHCH$_2$CH=CMe$_2$ | H | F | H | H | H | OMe | OEt | OH | H | H | H | OMe | NH | —(CH$_2$)$_2$CHMe$_2$ |
| I-2361 | —NHCH$_2$CH=CMe$_2$ | H | F | H | H | H | OMe | OEt | OH | H | H | H | OMe | NMe | Me |
| I-2362 | —NHCH$_2$CH=CMe$_2$ | H | F | H | H | H | OMe | OEt | OH | H | H | H | OMe | O | —CH$_2$CH=CMe$_2$ |
| I-2363 | —NHCH$_2$CH=CMe$_2$ | H | F | H | H | H | OMe | OEt | OH | H | H | H | OMe | O | —CH$_2$CH=CCl$_2$ |
| I-2364 | —NHCH$_2$CH=CMe$_2$ | H | F | H | H | H | OMe | OEt | OH | H | H | F | H | NH | —CH$_2$CH=CMe$_2$ |
| I-2365 | —NHCH$_2$CH=CMe$_2$ | H | F | H | H | H | OMe | OEt | OH | H | H | F | H | NH | —(CH$_2$)$_2$CHMe$_2$ |
| I-2366 | —NHCH$_2$CH=CMe$_2$ | H | F | H | H | H | OMe | OEt | OH | H | H | F | H | NMe | Me |
| I-2367 | —NHCH$_2$CH=CMe$_2$ | H | F | H | H | H | OMe | OEt | OH | H | H | F | H | O | —CH$_2$CH=CMe$_2$ |
| I-2368 | —NHCH$_2$CH=CMe$_2$ | H | F | H | H | H | OMe | OEt | OH | H | H | F | H | O | —CH$_2$CH=CCl$_2$ |
| I-2369 | —NHCH$_2$CH=CMe$_2$ | H | F | H | H | H | OMe | OEt | OH | H | H | H | OEt | NH | —CH$_2$CH=CMe$_2$ |
| I-2370 | —NHCH$_2$CH=CMe$_2$ | H | F | H | H | H | OMe | OEt | OH | H | H | H | OEt | NH | —(CH$_2$)$_2$CHMe$_2$ |
| I-2371 | —NHCH$_2$CH=CMe$_2$ | H | F | H | H | H | OMe | OEt | OH | H | H | H | OEt | NMe | Me |
| I-2372 | —NHCH$_2$CH=CMe$_2$ | H | F | H | H | H | OMe | OEt | OH | H | H | H | OEt | O | —CH$_2$CH=CMe$_2$ |
| I-2373 | —NHCH$_2$CH=CMe$_2$ | H | F | H | H | H | OMe | OEt | OH | H | H | H | OEt | O | —CH$_2$CH=CCl$_2$ |
| I-2374 | —NH$_2$ | H | F | H | H | Me | Me | Me | H | H | H | H | OMe | NH | —CH$_2$CH=CMe$_2$ |
| I-2375 | —NH$_2$ | H | F | H | H | Me | Me | Me | H | H | H | H | OMe | NH | —(CH$_2$)$_2$CHMe$_2$ |

TABLE 317

| | | | | | | | | | | | | | | | |
|---|---|---|---|---|---|---|---|---|---|---|---|---|---|---|---|
| I-2376 | —NH$_2$ | H | F | H | H | Me | Me | Me | H | H | H | H | OMe | NMe | Me |
| I-2377 | —NH$_2$ | H | F | H | H | Me | Me | Me | H | H | H | H | OMe | O | —CH$_2$CH=CMe$_2$ |
| I-2378 | —NH$_2$ | H | F | H | H | Me | Me | Me | H | H | H | H | OMe | O | —CH$_2$CH=CCl$_2$ |
| I-2379 | —NH$_2$ | H | F | H | H | Me | Me | Me | H | H | F | H | NH | —CH$_2$CH=CMe$_2$ | |
| I-2380 | —NH$_2$ | H | F | H | H | Me | Me | Me | H | H | F | H | NH | —(CH$_2$)$_2$CHMe$_2$ | |
| I-2381 | —NH$_2$ | H | F | H | H | Me | Me | Me | H | H | F | H | NMe | Me | |
| I-2382 | —NH$_2$ | H | F | H | H | Me | Me | Me | H | H | F | H | O | —CH$_2$CH=CMe$_2$ | |
| I-2383 | —NH$_2$ | H | F | H | H | Me | Me | Me | H | H | F | H | O | —CH$_2$CH=CCl$_2$ | |
| I-2384 | —NH$_2$ | H | F | H | H | Me | Me | Me | H | H | H | H | OEt | NH | —CH$_2$CH=CMe$_2$ |
| I-2385 | —NH$_2$ | H | F | H | H | Me | Me | Me | H | H | H | H | OEt | NH | —(CH$_2$)$_2$CHMe$_2$ |
| I-2386 | —NH$_2$ | H | F | H | H | Me | Me | Me | H | H | H | H | OEt | NMe | Me |
| I-2387 | —NH$_2$ | H | F | H | H | Me | Me | Me | H | H | H | H | OEt | O | —CH$_2$CH=CMe$_2$ |
| I-2388 | —NH$_2$ | H | F | H | H | Me | Me | Me | H | H | H | H | OEt | O | —CH$_2$CH=CCl$_2$ |
| I-2389 | —NH$_2$ | H | F | H | H | H | Me | OMe | OH | H | H | H | OMe | NH | —CH$_2$CH=CMe$_2$ |
| I-2390 | —NH$_2$ | H | F | H | H | H | Me | OMe | OH | H | H | H | OMe | NH | —(CH$_2$)$_2$CHMe$_2$ |
| I-2391 | —NH$_2$ | H | F | H | H | H | Me | OMe | OH | H | H | H | OMe | NMe | Me |
| I-2392 | —NH$_2$ | H | F | H | H | H | Me | OMe | OH | H | H | H | OMe | O | —CH$_2$CH=CMe$_2$ |
| I-2393 | —NH$_2$ | H | F | H | H | H | Me | OMe | OH | H | H | H | OMe | O | —CH$_2$CH=CCl$_2$ |
| I-2394 | —NH$_2$ | H | F | H | H | H | Me | OMe | OH | H | H | F | H | NH | —CH$_2$CH=CMe$_2$ |
| I-2395 | —NH$_2$ | H | F | H | H | H | Me | OMe | OH | H | H | F | H | NH | —(CH$_2$)$_2$CHMe$_2$ |
| I-2396 | —NH$_2$ | H | F | H | H | H | Me | OMe | OH | H | H | F | H | NMe | Me |

TABLE 318

| | | | | | | | | | | | | | | | |
|---|---|---|---|---|---|---|---|---|---|---|---|---|---|---|---|
| I-2397 | —NH$_2$ | H | F | H | H | H | Me | OMe | OH | H | H | F | H | O | —CH$_2$CH=CMe$_2$ |
| I-2398 | —NH$_2$ | H | F | H | H | H | Me | OMe | OH | H | H | F | H | O | —CH$_2$CH=CCl$_2$ |
| I-2399 | —NH$_2$ | H | F | H | H | H | Me | OMe | OH | H | H | H | OEt | NH | —CH$_2$CH=CMe$_2$ |
| I-2400 | —NH$_2$ | H | F | H | H | H | Me | OMe | OH | H | H | H | OEt | NH | —(CH$_2$)$_2$CHMe$_2$ |
| I-2301 | —NH$_2$ | H | F | H | H | H | Me | OMe | OH | H | H | H | OEt | NMe | Me |
| I-2302 | —NH$_2$ | H | F | H | H | H | Me | OMe | OH | H | H | H | OEt | O | —CH$_2$CH=CMe$_2$ |
| I-2303 | —NH$_2$ | H | F | H | H | H | Me | OMe | OH | H | H | H | OEt | O | —CH$_2$CH=CCl$_2$ |
| I-2304 | —NH$_2$ | H | F | H | H | Me | H | Me | OH | H | H | H | OMe | NH | —CH$_2$CH=CMe$_2$ |
| I-2305 | —NH$_2$ | H | F | H | H | Me | H | Me | OH | H | H | H | OMe | NH | —(CH$_2$)$_2$CHMe$_2$ |
| I-2306 | —NH$_2$ | H | F | H | H | Me | H | Me | OH | H | H | H | OMe | NMe | Me |
| I-237 | —NH$_2$ | H | F | H | H | Me | H | Me | OH | H | H | H | OMe | O | —CH$_2$CH=CMe$_2$ |
| I-2308 | —NH$_2$ | H | F | H | H | Me | H | Me | OH | H | H | H | OMe | O | —CH$_2$CH=CCl$_2$ |
| I-2309 | —NH$_2$ | H | F | H | H | Me | H | Me | OH | H | H | F | H | NH | —CH$_2$CH=CMe$_2$ |
| I-2310 | —NH$_2$ | H | F | H | H | Me | H | Me | OH | H | H | F | H | NH | —(CH$_2$)$_2$CHMe$_2$ |
| I-2311 | —NH$_2$ | H | F | H | H | Me | H | Me | OH | H | H | F | H | NMe | Me |
| I-2312 | —NH$_2$ | H | F | H | H | Me | H | Me | OH | H | H | F | H | O | —CH$_2$CH=CMe$_2$ |
| I-2313 | —NH$_2$ | H | F | H | H | Me | H | Me | OH | H | H | F | H | O | —CH$_2$CH=CCl$_2$ |
| I-2314 | —NH$_2$ | H | F | H | H | Me | H | Me | OH | H | H | H | OEt | NH | —CH$_2$CH=CMe$_2$ |
| I-2315 | —NH$_2$ | H | F | H | H | Me | H | Me | OH | H | H | H | OEt | NH | —(CH$_2$)$_2$CHMe$_2$ |
| I-236 | —NH$_2$ | H | F | H | H | Me | H | Me | OH | H | H | H | OEt | NMe | Me |
| I-237 | —NH$_2$ | H | F | H | H | Me | H | Me | OH | H | H | H | OEt | O | —CH$_2$CH=CMe$_2$ |

TABLE 319

| | | | | | | | | | | | | | | | |
|---|---|---|---|---|---|---|---|---|---|---|---|---|---|---|---|
| I-2318 | —NH$_2$ | H | F | H | H | Me | H | Me | OH | H | H | H | OEt | O | —CH$_2$CH=CCl$_2$ |
| I-2319 | —NH$_2$ | H | F | H | H | H | Me | Me | Me | H | H | H | OMe | NH | —CH$_2$CH=CMe$_2$ |
| I-230 | —NH$_2$ | H | F | H | H | H | Me | Me | Me | H | H | H | OMe | NH | —(CH$_2$)$_2$CHMe$_2$ |
| I-2321 | —NH$_2$ | H | F | H | H | H | Me | Me | Me | H | H | H | OMe | NMe | Me |
| I-2322 | —NH$_2$ | H | F | H | H | H | Me | Me | Me | H | H | H | OMe | O | —CH$_2$CH=CMe$_2$ |
| I-2323 | —NH$_2$ | H | F | H | H | H | Me | Me | Me | H | H | H | OMe | O | —CH$_2$CH=CCl$_2$ |
| I-2324 | —NH$_2$ | H | F | H | H | H | Me | Me | Me | H | H | F | H | NH | —CH$_2$CH=CMe$_2$ |
| I-2325 | —NH$_2$ | H | F | H | H | H | Me | Me | Me | H | H | F | H | NH | —(CH$_2$)$_2$CHMe$_2$ |
| I-236 | —NH$_2$ | H | F | H | H | H | Me | Me | Me | H | H | F | H | NMe | Me |
| I-2327 | —NH$_2$ | H | F | H | H | H | Me | Me | Me | H | H | F | H | O | —CH$_2$CH=CMe$_2$ |
| I-2328 | —NH$_2$ | H | F | H | H | H | Me | Me | Me | H | H | F | H | O | —CH$_2$CH=CCl$_2$ |
| I-2329 | —NH$_2$ | H | F | H | H | H | Me | Me | Me | H | H | H | OEt | NH | —CH$_2$CH=CMe$_2$ |
| I-2330 | —NH$_2$ | H | F | H | H | H | Me | Me | Me | H | H | H | OEt | NH | —(CH$_2$)$_2$CHMe$_2$ |
| I-2331 | —NH$_2$ | H | F | H | H | H | Me | Me | Me | H | H | H | OEt | NMe | Me |
| I-2332 | —NH$_2$ | H | F | H | H | H | Me | Me | Me | H | H | H | OEt | O | —CH$_2$CH=CMe$_2$ |
| I-2333 | —NH$_2$ | H | F | H | H | H | Me | Me | Me | H | H | H | OEt | O | —CH$_2$CH=CCl$_2$ |
| I-2334 | —NH$_2$ | H | F | H | H | H | OMe | OEt | OH | H | H | H | OMe | NH | —CH$_2$CH=CMe$_2$ |
| I-2335 | —NH$_2$ | H | F | H | H | H | OMe | OEt | OH | H | H | H | OMe | NH | —(CH$_2$)$_2$CHMe$_2$ |

TABLE 319-continued

| | | | | | | | | | | | | | | | |
|---|---|---|---|---|---|---|---|---|---|---|---|---|---|---|---|
| I-2336 | —NH$_2$ | H | F | H | H | H | OMe | OEt | OH | H | H | H | OMe | NMe | Me |
| I-2337 | —NH$_2$ | H | F | H | H | H | OMe | OEt | OH | H | H | H | OMe | O | —CH$_2$CH=CMe$_2$ |
| I-2338 | —NH$_2$ | H | F | H | H | H | OMe | OEt | OH | H | H | H | OMe | O | —CH$_2$CH=CCl$_2$ |

TABLE 320

| | | | | | | | | | | | | | | | |
|---|---|---|---|---|---|---|---|---|---|---|---|---|---|---|---|
| I-2339 | —NH$_2$ | H | F | H | H | H | OMe | OEt | OH | H | H | F | H | NH | —CH$_2$CH=CMe$_2$ |
| I-2340 | —NH$_2$ | H | F | H | H | H | OMe | OEt | OH | H | H | F | H | NH | —(CH$_2$)$_2$CHMe$_2$ |
| I-2341 | —NH$_2$ | H | F | H | H | H | OMe | OEt | OH | H | H | F | H | NMe | Me |
| I-2342 | —NH$_2$ | H | F | H | H | H | OMe | OEt | OH | H | H | F | H | O | —CH$_2$CH=CMe$_2$ |
| I-2343 | —NH$_2$ | H | F | H | H | H | OMe | OEt | OH | H | H | F | H | O | —CH$_2$CH=CCl$_2$ |
| I-2344 | —NH$_2$ | H | F | H | H | H | OMe | OEt | OH | H | H | H | OEt | NH | —CH$_2$CH=CMe$_2$ |
| I-2345 | —NH$_2$ | H | F | H | H | H | OMe | OEt | OH | H | H | H | OEt | NH | —(CH$_2$)$_2$CHMe$_2$ |
| I-2346 | —NH$_2$ | H | F | H | H | H | OMe | OEt | OH | H | H | H | OEt | NMe | Me |
| I-2347 | —NH$_2$ | H | F | H | H | H | OMe | OEt | OH | H | H | H | OEt | O | —CH$_2$CH=CMe$_2$ |
| I-2348 | —NH$_2$ | H | F | H | H | H | OMe | OEt | OH | H | H | H | OEt | O | —CH$_2$CH=CCl$_2$ |
| I-2349 | —NHCH$_2$CH=CMe$_2$ | H | H | H | H | Me | Me | Me | H | H | H | H | OMe | NH | —CH$_2$CH=CMe$_2$ |
| I-2350 | —NHCH$_2$CH=CMe$_2$ | H | H | H | H | Me | Me | Me | H | H | H | H | OMe | NH | —(CH$_2$)$_2$CHMe$_2$ |
| I-2351 | —NHCH$_2$CH=CMe$_2$ | H | H | H | H | Me | Me | Me | H | H | H | H | OMe | NMe | Me |
| I-2352 | —NHCH$_2$CH=CMe$_2$ | H | H | H | H | Me | Me | Me | H | H | H | H | OMe | O | —CH$_2$CH=CMe$_2$ |
| I-2353 | —NHCH$_2$CH=CMe$_2$ | H | H | H | H | Me | Me | Me | H | H | H | H | OMe | O | —CH$_2$CH=CCl$_2$ |
| I-2354 | —NHCH$_2$CH=CMe$_2$ | H | H | H | H | Me | Me | Me | H | H | H | F | H | NH | —CH$_2$CH=CMe$_2$ |
| I-2355 | —NHCH$_2$CH=CMe$_2$ | H | H | H | H | Me | Me | Me | H | H | H | F | H | NH | —(CH$_2$)$_2$CHMe$_2$ |
| I-2356 | —NHCH$_2$CH=CMe$_2$ | H | H | H | H | Me | Me | Me | H | H | H | F | H | NMe | Me |
| I-2357 | —NHCH$_2$CH=CMe$_2$ | H | H | H | H | Me | Me | Me | H | H | H | F | H | O | —CH$_2$CH=CMe$_2$ |
| I-238 | —NHCH$_2$CH=CMe$_2$ | H | H | H | H | Me | Me | Me | H | H | H | F | H | O | —CH$_2$CH=CCl$_2$ |
| I-2359 | —NHCH$_2$CH=CMe$_2$ | H | H | H | H | Me | Me | Me | H | H | H | H | OEt | NH | —CH$_2$CH=CMe$_2$ |

TABLE 321

| | | | | | | | | | | | | | | | |
|---|---|---|---|---|---|---|---|---|---|---|---|---|---|---|---|
| I-2360 | —NHCH$_2$CH=CMe$_2$ | H | H | H | H | Me | Me | Me | H | H | H | H | OEt | NH | —(CH$_2$)$_2$CHMe$_2$ |
| I-2361 | —NHCH$_2$CH=CMe$_2$ | H | H | H | H | Me | Me | Me | H | H | H | H | OEt | NMe | Me |
| I-2362 | —NHCH$_2$CH=CMe$_2$ | H | H | H | H | Me | Me | Me | H | H | H | H | OEt | O | —CH$_2$CH=CMe$_2$ |
| I-2363 | —NHCH$_2$CH=CMe$_2$ | H | H | H | H | Me | Me | Me | H | H | H | H | OEt | O | —CH$_2$CH=CCl$_2$ |
| I-2364 | —NHCH$_2$CH=CMe$_2$ | H | H | H | H | H | Me | OMe | OH | H | H | H | OMe | NH | —CH$_2$CH=CMe$_2$ |
| I-2365 | —NHCH$_2$CH=CMe$_2$ | H | H | H | H | H | Me | OMe | OH | H | H | H | OMe | NH | —(CH$_2$)$_2$CHMe$_2$ |
| I-2366 | —NHCH$_2$CH=CMe$_2$ | H | H | H | H | H | Me | OMe | OH | H | H | H | OMe | NMe | Me |
| I-2367 | —NHCH$_2$CH=CMe$_2$ | H | H | H | H | H | Me | OMe | OH | H | H | H | OMe | O | —CH$_2$CH=CMe$_2$ |
| I-2368 | —NHCH$_2$CH=CMe$_2$ | H | H | H | H | H | Me | OMe | OH | H | H | H | OMe | O | —CH$_2$CH=CCl$_2$ |
| I-2369 | —NHCH$_2$CH=CMe$_2$ | H | H | H | H | H | Me | OMe | OH | H | H | F | H | NH | —CH$_2$CH=CMe$_2$ |
| I-2370 | —NHCH$_2$CH=CMe$_2$ | H | H | H | H | H | Me | OMe | OH | H | H | F | H | NH | —(CH$_2$)$_2$CHMe$_2$ |
| I-2371 | —NHCH$_2$CH=CMe$_2$ | H | H | H | H | H | Me | OMe | OH | H | H | F | H | NMe | Me |
| I-2372 | —NHCH$_2$CH=CMe$_2$ | H | H | H | H | H | Me | OMe | OH | H | H | F | H | O | —CH$_2$CH=CMe$_2$ |
| I-2373 | —NHCH$_2$CH=CMe$_2$ | H | H | H | H | H | Me | OMe | OH | H | H | F | H | O | —CH$_2$CH=CCl$_2$ |
| I-2374 | —NHCH$_2$CH=CMe$_2$ | H | H | H | H | H | Me | OMe | OH | H | H | H | OEt | NH | —CH$_2$CH=CMe$_2$ |
| I-2375 | —NHCH$_2$CH=CMe$_2$ | H | H | H | H | H | Me | OMe | OH | H | H | H | OEt | NH | —(CH$_2$)$_2$CHMe$_2$ |
| I-2376 | —NHCH$_2$CH=CMe$_2$ | H | H | H | H | H | Me | OMe | OH | H | H | H | OEt | NMe | Me |
| I-2377 | —NHCH$_2$CH=CMe$_2$ | H | H | H | H | H | Me | OMe | OH | H | H | H | OEt | O | —CH$_2$CH=CMe$_2$ |
| I-2378 | —NHCH$_2$CH=CMe$_2$ | H | H | H | H | H | Me | OMe | OH | H | H | H | OEt | O | —CH$_2$CH=CCl$_2$ |
| I-2379 | —NHCH$_2$CH=CMe$_2$ | H | H | H | H | Me | H | Me | OH | H | H | H | OMe | NH | —CH$_2$CH=CMe$_2$ |
| I-2380 | —NHCH$_2$CH=CMe$_2$ | H | H | H | H | Me | H | Me | OH | H | H | H | OMe | NH | —(CH$_2$)$_2$CHMe$_2$ |

TABLE 322

| | | | | | | | | | | | | | | | |
|---|---|---|---|---|---|---|---|---|---|---|---|---|---|---|---|
| I-2381 | —NHCH$_2$CH=CMe$_2$ | H | H | H | H | Me | H | Me | OH | H | H | H | OMe | NMe | Me |
| I-2382 | —NHCH$_2$CH=CMe$_2$ | H | H | H | H | Me | H | Me | OH | H | H | H | OMe | O | —CH$_2$CH=CMe$_2$ |
| I-2383 | —NHCH$_2$CH=CMe$_2$ | H | H | H | H | Me | H | Me | OH | H | H | H | OMe | O | —CH$_2$CH=CCl$_2$ |
| I-2384 | —NHCH$_2$CH=CMe$_2$ | H | H | H | H | Me | H | Me | OH | H | H | F | H | NH | —CH$_2$CH=CMe$_2$ |
| I-2385 | —NHCH$_2$CH=CMe$_2$ | H | H | H | H | Me | H | Me | OH | H | H | F | H | NH | —(CH$_2$)$_2$CHMe$_2$ |
| I-236 | —NHCH$_2$CH=CMe$_2$ | H | H | H | H | Me | H | Me | OH | H | H | F | H | NMe | Me |
| I-2387 | —NHCH$_2$CH=CMe$_2$ | H | H | H | H | Me | H | Me | OH | H | H | F | H | O | —CH$_2$CH=CMe$_2$ |
| I-2388 | —NHCH$_2$CH=CMe$_2$ | H | H | H | H | Me | H | Me | OH | H | H | F | H | O | —CH$_2$CH=CCl$_2$ |
| I-2389 | —NHCH$_2$CH=CMe$_2$ | H | H | H | H | Me | H | Me | OH | H | H | H | OEt | NH | —CH$_2$CH=CMe$_2$ |

TABLE 322-continued

| ID | R1 | | | | | | | | | | | | | | |
|---|---|---|---|---|---|---|---|---|---|---|---|---|---|---|---|
| I-2390 | —NHCH₂CH=CMe₂ | H | H | H | H | Me | H | Me | OH | H | H | H | OEt | NH | —(CH₂)₂CHMe₂ |
| I-2391 | —NHCH₂CH=CMe₂ | H | H | H | H | Me | H | Me | OH | H | H | H | OEt | NMe | Me |
| I-2392 | —NHCH₂CH=CMe₂ | H | H | H | H | Me | H | Me | OH | H | H | H | OEt | O | —CH₂CH=CMe₂ |
| I-2393 | —NHCH₂CH=CMe₂ | H | H | H | H | Me | H | Me | OH | H | H | H | OEt | O | —CH₂CH=CCl₂ |
| I-2394 | —NHCH₂CH=CMe₂ | H | H | H | H | H | Me | Me | Me | H | H | H | OMe | NH | —CH₂CH=CMe₂ |
| I-2395 | —NHCH₂CH=CMe₂ | H | H | H | H | H | Me | Me | Me | H | H | H | OMe | NH | —(CH₂)₂CHMe₂ |
| I-2396 | —NHCH₂CH=CMe₂ | H | H | H | H | H | Me | Me | Me | H | H | H | OMe | NMe | Me |
| I-2397 | —NHCH₂CH=CMe₂ | H | H | H | H | H | Me | Me | Me | H | H | H | OMe | O | —CH₂CH=CMe₂ |
| I-2398 | —NHCH₂CH=CMe₂ | H | H | H | H | H | Me | Me | Me | H | H | H | OMe | O | —CH₂CH=CCl₂ |
| I-2399 | —NHCH₂CH=CMe₂ | H | H | H | H | H | Me | Me | Me | H | H | F | H | NH | —CH₂CH=CMe₂ |
| I-2400 | —NHCH₂CH=CMe₂ | H | H | H | H | H | Me | Me | Me | H | H | F | H | NH | —(CH₂)₂CHMe₂ |
| I-2401 | —NHCH₂CH=CMe₂ | H | H | H | H | H | Me | Me | Me | H | H | F | H | NMe | Me |

TABLE 323

| ID | R1 | | | | | | | | | | | | | | |
|---|---|---|---|---|---|---|---|---|---|---|---|---|---|---|---|
| I-2402 | —NHCH₂CH=CMe₂ | H | H | H | H | H | Me | Me | Me | H | H | F | H | O | —CH₂CH=CMe₂ |
| I-2403 | —NHCH₂CH=CMe₂ | H | H | H | H | H | Me | Me | Me | H | H | F | H | O | —CH₂CH=CCl₂ |
| I-2404 | —NHCH₂CH=CMe₂ | H | H | H | H | H | Me | Me | Me | H | H | H | OEt | NH | —CH₂CH=CMe₂ |
| I-2405 | —NHCH₂CH=CMe₂ | H | H | H | H | H | Me | Me | Me | H | H | H | OEt | NH | —(CH₂)₂CHMe₂ |
| I-2406 | —NHCH₂CH=CMe₂ | H | H | H | H | H | Me | Me | Me | H | H | H | OEt | NMe | Me |
| I-2407 | —NHCH₂CH=CMe₂ | H | H | H | H | H | Me | Me | Me | H | H | H | OEt | O | —CH₂CH=CMe₂ |
| I-2408 | —NHCH₂CH=CMe₂ | H | H | H | H | H | Me | Me | Me | H | H | H | OEt | O | —CH₂CH=CCl₂ |
| I-2409 | —NHCH₂CH=CMe₂ | H | H | H | H | H | OMe | OEt | OH | H | H | H | OMe | NH | —CH₂CH=CMe₂ |
| I-2410 | —NHCH₂CH=CMe₂ | H | H | H | H | H | OMe | OEt | OH | H | H | H | OMe | NH | —(CH₂)₂CHMe₂ |
| I-2411 | —NHCH₂CH=CMe₂ | H | H | H | H | H | OMe | OEt | OH | H | H | H | OMe | NMe | Me |
| I-2412 | —NHCH₂CH=CMe₂ | H | H | H | H | H | OMe | OEt | OH | H | H | H | OMe | O | —CH₂CH=CMe₂ |
| I-2413 | —NHCH₂CH=CMe₂ | H | H | H | H | H | OMe | OEt | OH | H | H | H | OMe | O | —CH₂CH=CCl₂ |
| I-2414 | —NHCH₂CH=CMe₂ | H | H | H | H | H | OMe | OEt | OH | H | H | F | H | NH | —CH₂CH=CMe₂ |
| I-2415 | —NHCH₂CH=CMe₂ | H | H | H | H | H | OMe | OEt | OH | H | H | F | H | NH | —(CH₂)₂CHMe₂ |
| I-2416 | —NHCH₂CH=CMe₂ | H | H | H | H | H | OMe | OEt | OH | H | H | F | H | NMe | Me |
| I-2417 | —NHCH₂CH=CMe₂ | H | H | H | H | H | OMe | OEt | OH | H | H | F | H | O | —CH₂CH=CMe₂ |
| I-2418 | —NHCH₂CH=CMe₂ | H | H | H | H | H | OMe | OEt | OH | H | H | F | H | O | —CH₂CH=CCl₂ |
| I-2419 | —NHCH₂CH=CMe₂ | H | H | H | H | H | OMe | OEt | OH | H | H | H | OEt | NH | —CH₂CH=CMe₂ |
| I-2420 | —NHCH₂CH=CMe₂ | H | H | H | H | H | OMe | OEt | OH | H | H | H | OEt | NH | —(CH₂)₂CHMe₂ |
| I-2421 | —NHCH₂CH=CMe₂ | H | H | H | H | H | OMe | OEt | OH | H | H | H | OEt | NMe | Me |
| I-2422 | —NHCH₂CH=CMe₂ | H | H | H | H | H | OMe | OEt | OH | H | H | H | OEt | O | —CH₂CH=CMe₂ |

TABLE 324

| ID | R1 | | | | | | | | | | | | | | |
|---|---|---|---|---|---|---|---|---|---|---|---|---|---|---|---|
| I-2423 | —NHCH₂CH=CMe₂ | H | H | H | H | H | OMe | OEt | OH | H | H | H | OEt | O | —CH₂CH=CCl₂ |
| I-2424 | —OMe | H | H | H | H | Me | Me | Me | H | H | H | H | OMe | NH | —CH₂CH=CMe₂ |
| I-2425 | —OMe | H | H | H | H | Me | Me | Me | H | H | H | H | OMe | NH | —(CH₂)₂CHMe₂ |
| I-2426 | —OMe | H | H | H | H | Me | Me | Me | H | H | H | H | OMe | NMe | Me |
| I-2427 | —OMe | H | H | H | H | Me | Me | Me | H | H | H | H | OMe | O | —CH₂CH=CMe₂ |
| I-2428 | —OMe | H | H | H | H | Me | Me | Me | H | H | H | H | OMe | O | —CH₂CH=CCl₂ |
| I-2429 | —OMe | H | H | H | H | Me | Me | Me | H | H | F | H | NH | —CH₂CH=CMe₂ | |
| I-2430 | —OMe | H | H | H | H | Me | Me | Me | H | H | F | H | NH | —(CH₂)₂CHMe₂ | |
| I-2431 | —OMe | H | H | H | H | Me | Me | Me | H | H | F | H | NMe | Me | |
| I-2432 | —OMe | H | H | H | H | Me | Me | Me | H | H | F | H | O | —CH₂CH=CMe₂ | |
| I-2433 | —OMe | H | H | H | H | Me | Me | Me | H | H | F | H | O | —CH₂CH=CCl₂ | |
| I-2434 | —OMe | H | H | H | H | Me | Me | Me | H | H | H | OEt | NH | —CH₂CH=CMe₂ | |
| I-2435 | —OMe | H | H | H | H | Me | Me | Me | H | H | H | OEt | NH | —(CH₂)₂CHMe₂ | |
| I-2436 | —OMe | H | H | H | H | Me | Me | Me | H | H | H | OEt | NMe | Me | |
| I-2437 | —OMe | H | H | H | H | Me | Me | Me | H | H | H | OEt | O | —CH₂CH=CMe₂ | |
| I-2438 | —OMe | H | H | H | H | Me | Me | Me | H | H | H | OEt | O | —CH₂CH=CCl₂ | |
| I-2439 | —OMe | H | H | H | H | H | Me | OMe | OH | H | H | H | OMe | NH | —CH₂CH=CMe₂ |
| I-2440 | —OMe | H | H | H | H | H | Me | OMe | OH | H | H | H | OMe | NH | —(CH₂)₂CHMe₂ |
| I-2441 | —OMe | H | H | H | H | H | Me | OMe | OH | H | H | H | OMe | NMe | Me |
| I-2442 | —OMe | H | H | H | H | H | Me | OMe | OH | H | H | H | OMe | O | —CH₂CH=CMe₂ |
| I-2443 | —OMe | H | H | H | H | H | Me | OMe | OH | H | H | H | OMe | O | —CH₂CH=CCl₂ |

TABLE 325

| | | | | | | | | | | | | | | | |
|---|---|---|---|---|---|---|---|---|---|---|---|---|---|---|---|
| I-2444 | —OMe | H | H | H | H | H | Me | OMe | OH | H | H | F | H | NH | —CH₂CH=CMe₂ |
| I-2445 | —OMe | H | H | H | H | H | Me | OMe | OH | H | H | F | H | NH | —(CH₂)₂CHMe₂ |
| I-2446 | —OMe | H | H | H | H | H | Me | OMe | OH | H | H | F | H | NMe | Me |
| I-2447 | —OMe | H | H | H | H | H | Me | OMe | OH | H | H | F | H | O | —CH₂CH=CMe₂ |
| I-2448 | —OMe | H | H | H | H | H | Me | OMe | OH | H | H | F | H | O | —CH₂CH=CCl₂ |
| I-2449 | —OMe | H | H | H | H | H | Me | OMe | OH | H | H | H | OEt | NH | —CH₂CH=CMe₂ |
| I-2450 | —OMe | H | H | H | H | H | Me | OMe | OH | H | H | H | OEt | NH | —(CH₂)₂CHMe₂ |
| I-2451 | —OMe | H | H | H | H | H | Me | OMe | OH | H | H | H | OEt | NMe | Me |
| I-2452 | —OMe | H | H | H | H | H | Me | OMe | OH | H | H | H | OEt | O | —CH₂CH=CMe₂ |
| I-2453 | —OMe | H | H | H | H | H | Me | OMe | OH | H | H | H | OEt | O | —CH₂CH=CCl₂ |
| I-2454 | —OMe | H | H | H | H | Me | H | Me | OH | H | H | H | OMe | NH | —CH₂CH=Me₂ |
| I-2455 | —OMe | H | H | H | H | Me | H | Me | OH | H | H | H | OMe | NH | —(CH₂)₂CHMe₂ |
| I-2456 | —OMe | H | H | H | H | Me | H | Me | OH | H | H | H | OMe | NMe | Me |
| I-2457 | —OMe | H | H | H | H | Me | H | Me | OH | H | H | H | OMe | O | —CH₂CH=CMe₂ |
| I-2458 | —OMe | H | H | H | H | Me | H | Me | OH | H | H | H | OMe | O | —CH₂CH=CCl₂ |
| I-2459 | —OMe | H | H | H | H | Me | H | Me | OH | H | H | F | H | NH | —CH₂CH=CMe₂ |
| I-2460 | —OMe | H | H | H | H | Me | H | Me | OH | H | H | F | H | NH | —(CH₂)₂CHMe₂ |
| I-2461 | —OMe | H | H | H | H | Me | H | Me | OH | H | H | F | H | NMe | Me |
| I-2462 | —OMe | H | H | H | H | Me | H | Me | OH | H | H | F | H | O | —CH₂CH=CMe₂ |
| I-2463 | —OMe | H | H | H | H | Me | H | Me | OH | H | H | F | H | O | —CH₂CH=CCl₂ |
| I-2464 | —OMe | H | H | H | H | Me | H | Me | OH | H | H | H | OEt | NH | —CH₂CH=CMe₂ |

TABLE 326

| | | | | | | | | | | | | | | | |
|---|---|---|---|---|---|---|---|---|---|---|---|---|---|---|---|
| I-2465 | —OMe | H | H | H | H | Me | H | Me | OH | H | H | H | OEt | NH | —(CH₂)₂CHMe₂ |
| I-2466 | —OMe | H | H | H | H | Me | H | Me | OH | H | H | H | OEt | NMe | Me |
| I-2467 | —OMe | H | H | H | H | Me | H | Me | OH | H | H | H | OEt | O | —CH₂CH=CMe₂ |
| I-2468 | —OMe | H | H | H | H | Me | H | Me | OH | H | H | H | OEt | O | —CH₂CH=CCl₂ |
| I-2469 | —OMe | H | H | H | H | H | Me | Me | Me | H | H | H | OMe | NH | —CH₂CH=CMe₂ |
| I-2470 | —OMe | H | H | H | H | H | Me | Me | Me | H | H | H | OMe | NH | —(CH₂)₂CHMe₂ |
| I-2471 | —OMe | H | H | H | H | H | Me | Me | Me | H | H | H | OMe | NMe | Me |
| I-2472 | —OMe | H | H | H | H | H | Me | Me | Me | H | H | H | OMe | O | —CH₂CH=CMe₂ |
| I-2473 | —OMe | H | H | H | H | H | Me | Me | Me | H | H | H | OMe | O | —CH₂CH=CCl₂ |
| I-2474 | —OMe | H | H | H | H | H | Me | Me | Me | H | H | F | H | NH | —CH₂CH=CMe₂ |
| I-2475 | —OMe | H | H | H | H | H | Me | Me | Me | H | H | F | H | NH | —(CH₂)₂CHMe₂ |
| I-2476 | —OMe | H | H | H | H | H | Me | Me | Me | H | H | F | H | NMe | Me |
| I-2477 | —OMe | H | H | H | H | H | Me | Me | Me | H | H | F | H | O | —CH₂CH=CMe₂ |
| I-2478 | —OMe | H | H | H | H | H | Me | Me | Me | H | H | F | H | O | —CH₂CH=CCl₂ |
| I-2479 | —OMe | H | H | H | H | H | Me | Me | Me | H | H | H | OEt | NH | —CH₂CH=CMe₂ |
| I-2480 | —OMe | H | H | H | H | H | Me | Me | Me | H | H | H | OEt | NH | —(CH₂)₂CHMe₂ |
| I-2481 | —OMe | H | H | H | H | H | Me | Me | Me | H | H | H | OEt | NMe | Me |
| I-2482 | —OMe | H | H | H | H | H | Me | Me | Me | H | H | H | OEt | O | —CH₂CH=CMe₂ |
| I-2483 | —OMe | H | H | H | H | H | Me | Me | Me | H | H | H | OEt | O | —CH₂CH=CCl₂ |
| I-2484 | —OMe | H | H | H | H | H | OMe | OEt | OH | H | H | H | OMe | NH | —CH₂CH=CMe₂ |
| I-2485 | —OMe | H | H | H | H | H | OMe | OEt | OH | H | H | H | OMe | NH | —(CH₂)₂CHMe₂ |

TABLE 327

| | | | | | | | | | | | | | | | |
|---|---|---|---|---|---|---|---|---|---|---|---|---|---|---|---|
| I-2486 | —OMe | H | H | H | H | H | OMe | OEt | OH | H | H | H | OMe | NMe | Me |
| I-2487 | —OMe | H | H | H | H | H | OMe | OEt | OH | H | H | H | OMe | O | —CH₂CH=CMe₂ |
| I-2488 | —OMe | H | H | H | H | H | OMe | OEt | OH | H | H | H | OMe | O | —CH₂CH=CCl₂ |
| I-2489 | —OMe | H | H | H | H | H | OMe | OEt | OH | H | H | F | H | NH | —CH₂CH=CMe₂ |
| I-2490 | —OMe | H | H | H | H | H | OMe | OEt | OH | H | H | F | H | NH | —(CH₂)₂CHMe₂ |
| I-2491 | —OMe | H | H | H | H | H | OMe | OEt | OH | H | H | F | H | NMe | Me |
| I-2492 | —OMe | H | H | H | H | H | OMe | OEt | OH | H | H | F | H | O | —CH₂CH=CMe₂ |
| I-2493 | —OMe | H | H | H | H | H | OMe | OEt | OH | H | H | F | H | O | —CH₂CH=CCl₂ |
| I-2494 | —OMe | H | H | H | H | H | OMe | OEt | OH | H | H | H | OEt | NH | —CH₂CH=CMe₂ |
| I-2495 | —OMe | H | H | H | H | H | OMe | OEt | OH | H | H | H | OEt | NH | —(CH₂)₂CHMe₂ |
| I-2496 | —OMe | H | H | H | H | H | OMe | OEt | OH | H | H | H | OEt | NMe | Me |
| I-2497 | —OMe | H | H | H | H | H | OMe | OEt | OH | H | H | H | OEt | O | —CH₂CH=CMe₂ |
| I-2498 | —OMe | H | H | H | H | H | OMe | OEt | OH | H | H | H | OEt | O | —CH₂CH=CCl₂ |

In the above tables, "—OCH$_2$O—*" and "*" mean that they taken together form a ring.

Experiment 1 Suppressive Effect on a Mitogenic Activity of Mouse Splenocytes In Vitro In 96-well microtiter plate 5×10$^5$ C3H/HeN mouse splenocytes suspended in 0.1 ml of 10% fetal bovine serum-fortified RPMI 1640 medium containing 2 mM of sodium bicarbonate, 50 units/ml of penicillin, 50 μg/ml of streptomycin and 5×10$^{-5}$ M of 2-mercaptoethanol were added. Then, 5 μg/ml of Concanavalin A (Con A) or 10 μg/ml of lipopolysaccharide (LPS) as a mitogen and the compound of a pre-determined concentration of the present invention were added to each well so that a final volume of each well reached 0.2 ml. Each compound of the present invention was dissolved in dimethylsulfoxide (DMSO) and diluted with the above RPMI 1640 medium to adjust the final concentration of 100 ng/ml or less. The splenocytes in the 96-well microtiter plate were cultivated at 37° C. for 3 days in an incubator keeping the humidity 100%, carbon dioxide 5% and air 95%. Then, 25 μl of 6 mg/ml MTT [3-(4,5-dimethylthiazol-2-yl)-2,5-diphenyltetrazolium bromide] (Sigma) was added to the each well and cultivated at 37° C. for 4 hours under the same conditions. After the cultivation, 50 μl of 0.02 N hydrochloric acid in 20% sodium dodecyl sulfate (SDS) was added to formazan generated and left at 37° C. for 24 hours for dissolving formazan. An absorption intensity (OD) of formazan generated in proportion to the number of living cells was measured with an immunoreader (InterMed) equipped with a 570 nm filter (The Journal of Immunological Method, 65, 55-63, 1983). The 50% inhibitory concentration of a cell proliferation (IC 50) was calculated from a correlation between the concentration of the compound of the present invention and the absorption intensity.

Experiment 2 Anti-Proliferative Activity on EL4 Cells

In 96-well microtiter plate 4×10$^4$/0.1 ml of mouse thymoma strain EL4 cells were added and 0.1 ml of the compound of the present invention was added to the mixture so that the concentration was in the range of 0-5,000 ng/ml. After the cultivation for 3 days, the IC$_{50}$ was calculated by the MTT method as described in Experiment 1.

The results are shown in Tables 328–329.

TABLE 328

| Compound | ConA IC$_{50}$ (ng/ml) | LPS IC$_{50}$ (ng/ml) | EL-4 IC$_{50}$ (ng/ml) |
|---|---|---|---|
| I-1 | 0.86 | 1.92 | 8.56 |
| I-9 | <20 | <20 | <20 |
| I-12 | 1.3 | 2.8 | 46.2 |
| I-22 | 5.62 | 4.26 | 6.2 |
| I-35 | 19.5 | 39.4 | 140 |
| I-40 | 6.1 | 16.5 | 37.4 |
| I-41 | 0.73 | 1.74 | 4.89 |
| I-46 | 10.6 | 23.9 | 67.5 |
| I-49 | 8.89 | 16.2 | 31.7 |
| I-50 | 3.83 | 9.2 | 11.9 |
| I-51 | 6.6 | 14.7 | 70.0 |
| I-59 | 8.5 | 22.4 | 140 |
| I-62 | 29.2 | 25 | 23.4 |
| I-63 | 13 | 27 | 16 |
| I-66 | 0.22 | 0.35 | 0.48 |
| I-71 | 4.56 | 14.2 | 31.2 |
| I-101 | 0.8 | 0.5 | 1.8 |
| I-103 | 3.4 | 3.7 | 4.6 |
| I-104 | 3.0 | 3.1 | 4.8 |
| I-106 | 0.6 | 0.4 | 2.7 |
| I-107 | 0.6 | 0.7 | 12 |

TABLE 328-continued

| Compound | ConA IC$_{50}$ (ng/ml) | LPS IC$_{50}$ (ng/ml) | EL-4 IC$_{50}$ (ng/ml) |
|---|---|---|---|
| I-121 | 0.8 | 1.2 | 0.8 |
| I-163 | <20 | <20 | <20 |
| I-173 | <20 | <20 | <20 |
| I-175 | <20 | 29.4 | <20 |
| I-187 | 12.0 | 25.1 | 36.2 |
| I-211 | <20 | <20 | <20 |
| I-248 | <10 | <10 | 312 |
| I-250 | <10 | <10 | 88.3 |
| I-251 | <10 | <10 | 97.4 |
| I-255 | <20 | <20 | <20 |
| I-256 | <20 | 28.7 | 310 |
| I-275 | 6.34 | 13.5 | 100 |
| I-276 | 1.8 | 3.1 | 200 |
| I-299 | 5.53 | 7.85 | 13.6 |
| I-301 | 7.06 | 11.0 | 15.8 |
| I-360 | <20 | <20 | 99.8 |
| I-361 | <20 | <20 | 124 |
| I-418 | 255 | 497 | >10000 |
| I-427 | 255 | 497 | >10000 |
| I-457 | <20 | <20 | 205 |
| I-466 | <20 | <20 | 46 |
| I-484 | 14.7 | 32.2 | 91.4 |
| I-513 | 6.89 | 11.1 | 61.8 |
| I-525 | 0.76 | 1.11 | 5.0 |
| I-639 | 4.59 | 6.25 | 50 |
| I-661 | 0.67 | 1.28 | 50 |
| I-739 | 18.8 | 20.7 | 430 |
| I-742 | 10 | 20 | 45.2 |
| I-758 | 6.78 | 9.63 | 55.1 |
| I-773 | 8.45 | 12.6 | 92.9 |
| I-797 | 1.75 | 3.71 | 26.5 |
| I-834 | 36 | 46 | 226 |
| I-839 | 1.48 | 1.87 | 20.7 |
| I-840 | 5.31 | 6.94 | 31.9 |
| I-878 | 14.1 | 27.4 | 194 |
| I-880 | 23.0 | 41.1 | 105 |
| I-892 | <0.2 | <0.2 | 1.41 |
| I-893 | 0.49 | 1.05 | 7.06 |

TABLE 329

| Compound | ConA IC$_{50}$ (ng/ml) | LPS IC$_{50}$ (ng/ml) | EL-4 IC$_{50}$ (ng/ml) |
|---|---|---|---|
| I-907 | 23.4 | 44.5 | 82.7 |
| I-908 | 0.45 | 0.86 | 3.50 |
| I-909 | <20 | <20 | 20 |
| I-931 | 2.93 | 5.76 | 4.37 |
| I-934 | 16.1 | 22.2 | 52.7 |
| I-943 | 2.97 | 4.89 | 46.8 |
| I-962 | 12.1 | 16.3 | 20.4 |
| I-970 | <20 | <20 | 50.3 |
| I-976 | 17.7 | 34.2 | 330 |
| I-981 | 14.9 | 27.1 | >100 |
| I-982 | 2.0 | 3.75 | 55.3 |
| I-988 | 0.2 | 0.31 | 1.23 |
| I-993 | 5.10 | 7.54 | 13.8 |
| I-995 | 20.9 | 25.2 | 49.2 |
| I-1006 | 8.66 | 12.3 | 33.0 |
| I-1007 | 8.05 | 10.4 | 13.1 |
| I-1017 | 9.74 | 16.7 | 72.9 |
| I-1031 | <20 | 21.2 | 41.7 |
| I-1040 | 1.80 | 5.31 | 1.85 |
| I-1043 | 2.19 | 3.27 | 9.70 |
| I-1058 | 21.2 | 30.2 | 48.8 |
| I-1066 | 3.91 | 4.87 | 20.6 |
| I-1095 | 6.90 | 9.57 | 34.2 |
| I-1103 | 4.7 | 6.9 | 31.4 |
| I-1107 | 5.8 | 9.1 | 34.1 |
| I-1115 | <20 | <20 | <20 |
| I-1121 | 3.12 | 9.0 | 18.6 |

TABLE 329-continued

| Compound | ConA IC$_{50}$ (ng/ml) | LPS IC$_{50}$ (ng/ml) | EL-4 IC$_{50}$ (ng/ml) |
|---|---|---|---|
| I-1123 | 0.80 | 2.00 | 3.9 |
| I-1124 | 94 | 272 | >10000 |
| I-1126 | 79 | 234 | >10000 |
| I-1127 | 44 | 111 | 412 |
| I-1128 | 5.00 | 11.4 | 26.0 |
| I-1135 | 1.00 | 2.70 | 11.7 |
| I-1160 | 10.6 | 14.1 | 97.4 |
| I-1161 | 2.4 | 4.2 | 33.2 |
| I-1162 | 0.65 | 1.95 | 30.9 |
| I-1167 | 0.08 | 0.23 | 8.1 |
| I-1168 | 0.26 | 0.54 | 12.5 |
| I-1171 | 0.63 | 0.64 | 27.5 |
| I-1172 | 13.1 | 19.4 | >100 |
| I-1173 | 16.4 | 31.1 | >100 |
| I-1177 | 12.2 | 20.8 | 47.2 |
| I-1191 | 0.16 | 0.66 | 22.8 |
| I-1193 | 1.46 | 5.3 | 50 |
| I-1203 | 14.1 | >100 | 43.5 |
| I-1212 | 12.87 | 24.2 | 85.0 |
| I-1217 | <20 | <20 | <20 |
| I-1227 | 197 | 423 | >10000 |
| I-1229 | 5.95 | 8.05 | 20.4 |
| I-1230 | 12.0 | 15.3 | 5.22 |
| I-1232 | 3.77 | 4.93 | 15.1 |
| I-1240 | 2.50 | 3.34 | 11.8 |
| I-1248 | 25.9 | 36.8 | 118 |
| I-1250 | 0.68 | 1.35 | 2.90 |
| I-1251 | 6.30 | 10.7 | 27.8 |
| I-1263 | <20 | <20 | 29.8 |
| I-1271 | 0.10 | 0.32 | 1.66 |
| I-1274 | 0.33 | 1.38 | 1.44 |
| I-1276 | <20 | 31.3 | 105 |
| I-1277 | <20 | <20 | <20 |
| I-1278 | <20 | <20 | 41.7 |
| I-1284 | <20 | <20 | <20 |
| I-1286 | <20 | <20 | <20 |
| I-1289 | <20 | <20 | <20 |
| I-1290 | <20 | <20 | 27.3 |
| I-1295 | <20 | <20 | <20 |
| I-1296 | <20 | <20 | 39.7 |

As shown in the above, the compound of the present invention has immunosuppressive and anti-allergic effects.

Experiment 3 Suppressive Effect on the Antibody Production Against Bovine γ Globulin (BGG)

On an immunizing day and 7 days after, 50 μg of BGG was subcutaneously inoculated to backs of BALB/c mice (male, 6-8 weeks old) for inducing an immune reaction. After the compound of the present invention was dissolved or suspended in N, N-dimethylacetoamide, the mixture was diluted with miglyol 812 neutral oil. A proper volume of the compound was orally administered (p.o.) to mice every day from the next day of the immunizing. A two hundredth weight to body weight of miglyol was administered to mice in a control group. After 21 days, blood was drawn from each mouse and a serum was separated. BGG-specific IgE in a serum was measured by the sandwich ELISA method using a BGG-coating plate. The suppressive rate of IgE production was calculated from the dilution rate of the serum which has the same absorption intensity as that of the control group for judging the effect of the compound of the present invention. The results are shown in Table 330.

TABLE 330

| Compound | Dose (mg/kg) | Suppressive rate of antigen-specific IgE (%) |
|---|---|---|
| I-525 | 100 | >95 |
| I-915 | 100 | >99 |
| I-892 | 5 | >99 |
| I-963 | 50 | >99 |
| I-1031 | 100 | >99 |
| I-1093 | 100 | >99 |

Experiment 4 Suppressive Effect on the IgE Production Against Ovalbumin (OVA)

1) Animals

BALB/c mice (female, 8-10 weeks old) and Wistar rats (female, 8-10 weeks old) which were bought from Japan SLC, Inc. (Shizuoka) were used.

2) Immunizing Method

BALB/c mice were immunized by an intraperitoneal administration of 0.2 ml suspension of 2 μg of ovalbumin (OVA) and 2 mg of aluminium hydroxide gel in physiological saline. After 10 days, blood was drawn from hearts, sera were separated and stocked at −40° C. till the measurement of an IgE antibody titer.

3) Compounds

After the compound of the present invention was dissolved or suspended in N, N-dimethylacetoamide, the mixture was diluted 20 times with miglyol 812 neutral oil. The obtained solution was orally administered to mice at 0.1 ml per mouse. The administration was continued for 10 days from the immunizing day to the day before drawing blood. IPD-1151-T (a compound described in Jpn. Pharmacol. (1993) 61, 31–39) and a compound No. 36 (a compound 36 described in J. Med. Chem. (1997) 40: 395–407) were examined as controls by the same method.

4) Measurement of Anti-OVA IgE Antibody Titer (PCA Titer)

The samples 2-fold diluted with physiological saline were prepared from the obtained mouse serum and each 50 μl of the solution was intradermally injected to backs of Wistar rats which previously hair cut. After 24 hours, a passive cutaneous anaphylaxis reaction (PCA) was induced by an intravenous injection of 0.5 ml of physiological saline containing 1 mg of OVA and 5 mg of Evans' blue dye. After 30 minutes, the rats were sacrified and the highest dilution rate of the serum giving bluing with a diameter of more than 5 mm was recorded as the PCA titer. For example, when a serum is positive for the PCA reaction till 27 times dilution, the anti-OVA IgE antibody titer of the mouse is defined as 7. The results are shown in Table 331.

TABLE 331

| Compound | Dose (mg/kg) | PCA Titer |
|---|---|---|
| I-484 | 40 | <0 |
| I-839 | 40 | 2.4** |
| I-851 | 40 | 1.8** |
| I-892 | 40 | <0 |
| I-893 | 40 | 2.5** |
| I-908 | 40 | 3.4** |
| I-915 | 40 | <0 |
| I-925 | 40 | 1** |
| I-928 | 40 | <0 |

TABLE 331-continued

| Compound | Dose (mg/kg) | PCA Titer |
|---|---|---|
| I-948 | 40 | 2.6** |
| I-957 | 40 | 4.5** |
| I-962 | 40 | <0 |
| I-963 | 40 | 3.6** |
| I-988 | 40 | 0.8** |
| I-1031 | 40 | 4.4** |
| I-1043 | 40 | 4.8** |
| I-1066 | 40 | <0 |
| I-1072 | 40 | 0.8** |
| I-1095 | 40 | <0 |
| I-1123 | 40 | 2.4** |
| I-1135 | 40 | 4.8** |
| I-1167 | 40 | 4.4** |
| I-1171 | 40 | <0 |
| I-1177 | 40 | 3.6** |
| I-1229 | 40 | <0 |
| I-1232 | 40 | 1.8** |
| I-1242 | 40 | 2.8** |
| I-1258 | 40 | 1.2** |
| I-1271 | 40 | <0 |
| IPD-1151-T | 50 | 9.8 |
| No.36 | 10 | 10.4 |

**P < 0.01 vs vehicle

The PCA titers of mice in a group to which any compound was not administered were 9–12.

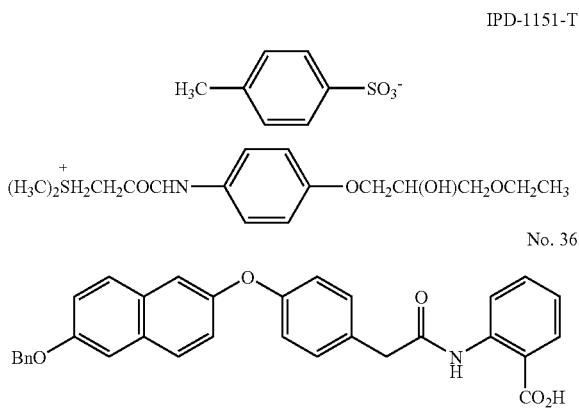

As shown in the above, the compound of the present invention has a suppressive effect on the antibody production.

Experiment 5 Suppressive Effect on the Antibody Production of Human Lymphocytes

1. Experimental Method

1) Human Peripheral Blood

Human peripheral blood was drawn from healthy male adults by plastic syringes filled with heparin (final concentration 1.5%). Lymphocytes were collected immediately after blood was drawn.

2) Medium

RPMI medium (Nissui Pharmaceutical Co., Ltd.) containing 10% fetal bovine serum (HyClone Lab.) inactivated at 56° C. for 30 minutes, penicillin (100 units/ml) and streptomycin (100 µg/ml) (GIBCO) was used.

3) Compounds

After the compound (I-839) of the present invention was dissolved in dimethylsulfoxide (Nakaraitesk) at 2 µg/ml, the solution was diluted with the medium to adjust a final concentration to be 0.01 µg/ml –10 µg/ml. The compound No. 36 was examined as a control by the same method.

4) Human Lymphocytes

Human peripheral blood was stratified in a tube filled with Ficoll-Hypaque mixture solution (Dainippon Pharmaceutical Co., Ltd. (Osaka), Mono-poly resolving medium) at the same volume and centrifuged at 300×g at 15° C. for 30 minutes to obtain a lymphocytes layer. After the collected cell suspension was washed with sterile Hanks' solution (Nissui Pharmaceutical Co., Ltd.) by centrifugation, sterile distilled water was added to the suspension. After 30 seconds, twice-concentrated Hanks' solution of which amount is equal to the water was added for removal of contaminating erythrocytes. Lymphocytes which were filtered by a nylon mesh and washed by centrifugation were used for experiments as human lymphocytes.

5) Induction of the IgE Antibody Production by Stimulation of B Cells

In 96-well cultivating plate (Sumitomo bakelite) the lymphocytes were inoculated $2 \times 10^5$ cells per well, and the compound, anti-human CD 40 antigen (Pharmingen, 2 µg/ml), human recombinant interleukin-4 (IL-4) (Genzyme, 0.1 µg/ml) and human recombinant interleukin-10 (IL-10) (Genzyme, 0.2 µg/ml) were added and cultivated at 37° C. under 5% of $CO_2$ (0.2 ml/well). After the cultivation for 10 days, the amount of antibody in a supernatant was quantified by ELISA method.

6) Quantification of the IgE Antibody

A commercial kit MESACUP IgE test (Medical & Biological Laboratories Co., Ltd.) was used for the quantification of the IgE. The experiment followed an instruction manual and was carried out in triplicate to calculate the average.

7) Quantification of the IgG and IgM Antibodies

ELISA method was used for the quantification. In 96-well plate (Nunc) 50 µl of 1 µg/ml F(ab')$_2$ Goat Anti-human IgG +A +M (H+ L) (ZYMED Laboratories) was added and the plate was coated at 4° C. overnight. The plate was washed twice with 0.05% Tween/PBS (PBST) solution and 100 µl of 0.5% gelatin/PBST was added for blocking at room temperature for 2 hours. After washing three times with PBST, 100 µl of a sample diluted with PBS or 100 µl of human Plasma IgG standard solution or IgM standard solution (BioPur AG, Switzerland) of a pre-determined concentration was added and incubated at room temperature for 1 hour. After washing three times with PBST, 100 µl of a peroxydase-labeled anti-human IgG antibody or anti-human IgM antibody (Southern Biotechnology, Birmingham) which was diluted two thousandth with PBS was added and incubated at room temperature for 1 hour. After washing four times with PBST, 100 µl of a substrate, o-phenylenediamine dihydrochloride, was added for color development. After 30 minutes, the reaction was terminated by addition of 50 µl of 2 N HCl, and the absorption at 492 nm was measured with a microplate reader and the amount of the IgG and IgM was calculated from a standard curve of a standard solution.

2. Results

Figure 2:
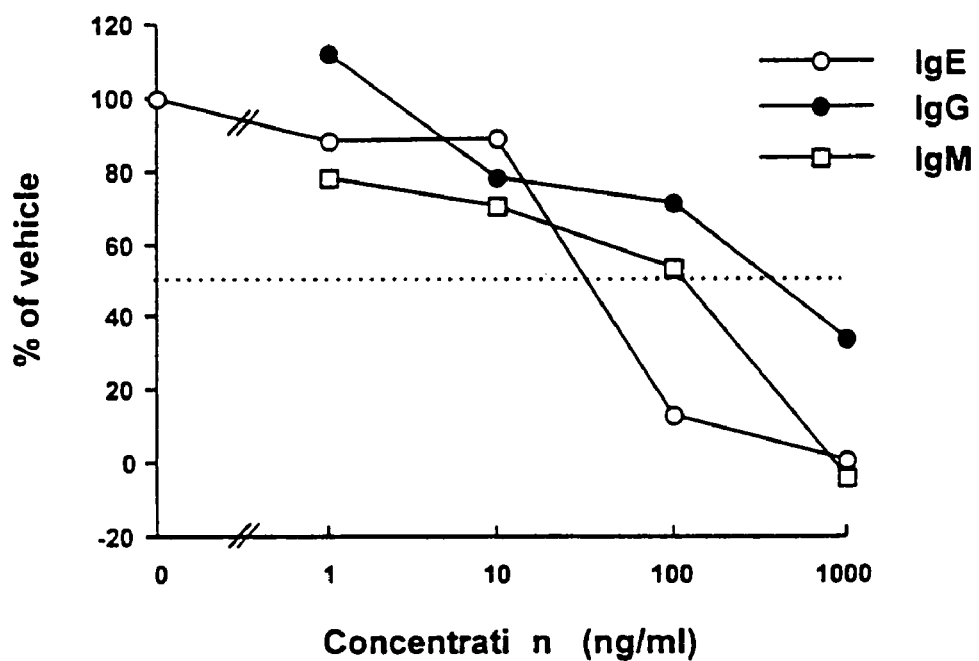
FIG. 2 shows an antibody production-suppressive effect on human peripheral lymphocytes of the compound No. 36. The ordinate represents a percentage of the amount of antibodies to that of antibodies which are produced in the absence of the compound. The abscissa represents a concentration of the compound.

The results are shown in FIGS. 1 and 2. The compound (I-839) of the present invention has a selective suppressive effect on the IgE antibody production and the intensity was 2,000 times or more of that of the IgG production and 30,000 times or more of that of the IgM. The suppressive effects of the typical compounds on the antibody production are shown in Table 332.

TABLE 332

| Compound | IC$_{50}$ (ng/ml) | | |
|---|---|---|---|
| | IgE | IgG | IgM |
| I-839 | <0.00001 | 0.027 | 0.37 |
| I-892 | <0.00001 | <0.00001 | >1 |
| I-121 | <0.0001 | <0.0001 | >1 |
| I-988 | <0.00001 | <0.00001 | >1 |
| I-893 | <0.00001 | <0.0001 | >1 |

Experiment 6 Suppressive Effect on Antibody Production of Mouse Spleen Lymphocytes 1. Experimental Method 1) Animals BALB/c (nu/nu) mice were bought from Japan SLC, Inc. (Shizuoka) and 7 weeks old-male mice were used.

2) Medium

RPMI medium (Nissui Pharmaceutical Co., Ltd.) containing 10% fetal bovine serum (HyClone Lab.) inactivated at 56° C. for 30 minutes, penicillin (100 units/ml) and streptomycin (100 μg/ml) (GIBCO) was used for experiments.

3) Compounds

Each of the compounds was dissolved in dimethylsulfoxide (Nakaraitesk) at 2 μg/ml and diluted with the medium to adjust a final concentration to 0.1 μg/ml –10 μg/ml.

4) Mouse Spleen Lymphocytes

A spleen of mouse was taken out and put in a cultivating schale which was filled with Hanks' solution. The spleen was crushed and the cells were pushed out from the organ and filtered through a metal mesh (200 mesh). After the collected cell suspension was washed by centrifugation with sterile Hanks' solution (Nissui Pharmaceutical Co., Ltd.), sterile distilled water was added. After 30 seconds, an equal amount of twice-concentrated Hanks' solution was added for removal of contaminating erythrocytes. The cell suspension, filtered by a nylon mesh and washed by centrifugation, were used as mouse spleen lymphocytes for experiments.

5) Induction of the IgE Antibody Production by the B Cell Stimulation

In 96-well cultivating plate (Sumitomo Bakelite Company Limited) mouse spleen lymphocytes were inoculated 2×10$^5$ cells per well. The compound of the present invention, lipopolysaccharide (DIFCO Lab., 2 μg/ml) and mouse recombinant interleukin-4 (IL-4) (Genzyme, 50 ng/ml) were added to the well and cultivated at 37° C. under 5% CO$_2$ (0.2 ml/well). After the cultivation for 10 days, the amount of the antibody in a supernatant was quantified by ELISA method.

6) Quantification of the IgE Antibody

A commercial mouse IgE EIA kit (Yamasa Shoyu Co., Ltd.) was used for the quantification of the IgE. The experiment followed an instruction manual and was carried out in triplicate to calculate the average.

7) Quantification of the IgG1, IgG2a and IgM Antibodies

In 96-well plate 50 μl of 10 μg/ml Goat Anti-Mouse Ig (IgM+G+A, H+ L) (Southern Biotechnology, Birmingham) was added and the plate was coated at 4° C. overnight. After the plate was washed twice with a PBST solution, 100 μl of 0.5% gelatin/PBST was added and the plate was blocked at room temperature for 2 hours. After washing three times with PBST, 100 μl of culture supernatant which was diluted with PBS or 100 μl of an antibody standard solution (Mouse IgG1 standard, Mouse IgG2a standard, Mouse IgM standard, BETHYL Laboratories) of a pre-determined concentration was added and incubated for 1 hour. After washing three times with PBST, 100 μl of diluted solution of alkalinephosphatase-labeled anti-mouse IgG1, IgG2a or IgM antibody (Southern Biotechnology, Birmingham) was added and incubated at room temperature for 1 hour. After washing four times with PBST, a substrate, p-nitrophenyl phosphate disodium, was added, and after 30 minutes-incubation period, after 5 N—NaOH was added to stop the reaction. The absorption at 405 nm was measured with a microplate reader, and the amount of the antibody was calculated from the standard curve. For the dilution of the mouse sample and the standard solution was used 10% FCS/PBS.

2. Results

Figure 3:
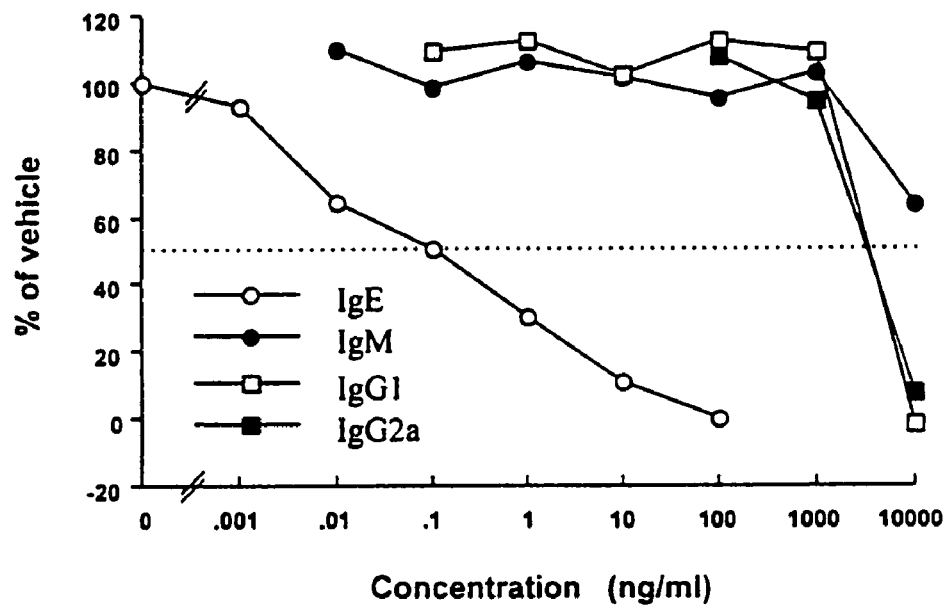
FIG. 3 shows an antibody production-suppressive effect on mouse spleen lymphocytes of the compound (I-967) of the present invention. The ordinate represents a percentage of the amount of antibodies to that of antibodies which are produced in the absence of the compound. The abscissa represents a concentration of the compound.

The results are shown in FIG. 3. The figure shows that the compound (I-967) has a suppressive effect on the IgG1, IgG2a and IgM antibodies production only at 1000 ng/ml or more but has a dose-dependent suppressive effect on the IgE production at 0.01 ng/ml or more. In Table 333 the suppressive effects of the representative compounds on the IgE, IgM, IgG1 and IgG2a production are shown.

TABLE 333

| Compound | IC$_{50}$ (ng/ml) | | | |
|---|---|---|---|---|
| | IgE | IgG1 | IgG2a | IgM |
| I-73 | 0.044 | 2600 | 4900 | 4200 |
| I-963 | 0.00026 | 510 | 3600 | 3500 |
| I-967 | 0.1 | 3500 | 3600 | >10000 |

Experiment 7 Suppressive Effect on Bronchial Inflammatory Cell Infiltration by Inhalation of Antigen 1. Experimental Method 1) Animals BALB/c mice bought from Japan SLC, Inc. (Shizuoka) (female, 8-11 weeks old) were used for experiments.

2) Sensitizing and Challenge of Antigen

For immunizing, 0.2 ml of a suspension of 2 μg of ovalbumin (OVA; Grade V, SIGMA) and 2 mg of aluminium hydroxide gel in physiological saline was intraperitoneally injected. After 2 weeks, 0.2 ml of a solution of 2 μg of OVA in physiological saline was intraperitoneally injected for a booster. After 1 week, each of mice was put in a nebulizing container (an airtight polycarbonate container, 24.5 cm in inner diameter and 20 cm in effective inner height, equipped with 12 cylindrical tubes of 4.8 cm in inner diameter and 12 cm in height) and made inhale a solution of 5% ovalbumin (Grade III, SIGMA) in physiological saline for 20 minutes with an ultrasonic neblizer (Omron Tateisi Elec-Tronics co., NE-U12) for the challenge of antigen.

3) Administration of the Compound of the Present Invention

The compound (I-963) of the present invention was dissolved in N, N-dimethylacetoamide (Nakaraitesk) and diluted one twentieth with miglyol 812 neutral oil (Mitsuba Trading Co., Ltd.) and the solution was orally administered to mice at 40 mg/kg. The administration was continued for 9 days from the booster day to the day before bronchoalveolar lavage.

4) Broncho-Alveolar Lavage (BAL)

After 48 hours of the challenge of antigen, the mice were exsanguinated from hearts under ether anesthetic, and the trachea was then cannulated. 0.3 ml of PBS were injected into the lungs and collected, and reinjected four times more (total 1.5 ml).

5) Measurement of the Total Cell Number in BAL Solution and Classification of Inflammatory Cells After calculation of the total cell number by coloring of a part of BAL solution with Türk solution, cells in BAL solution were put on a slide glass with cytospin (SHANDON) for May-Grünwald-Giemsa (MERCK) staining. Under a microscope, 500 cells were classified to a macrophage, an eosinophil, a neutrophil and a lymphocyte and a proportion of each type of the cells was calculated. The number of each type of the cells was calculated by a multiplication of its proportion and the total cell number.

2. Results

Figure 4:
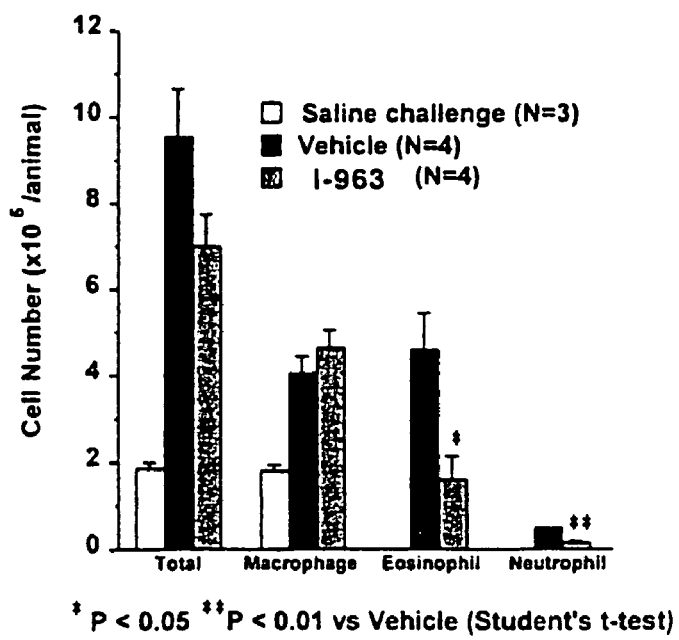
FIG. 4 shows a suppressive effect of the compound (I-963) of the present invention for an infiltration of inflammatory cells to irrigation water of pulmonary alveolus by an antigen stimulation on mice. The ordinate represents the number of inflammatory cells and the abscissa represents the number of total inflammatory cells, the number of macrophages, the number of eosinophils and the number of neutrophils. The white column represents a group inhaling saline instead of ovalbumin, the black column represents a group inhaling an antigen to cause inflammation and without administration of any compound of the present invention, and the gray column represents a group inhaling an antigen to cause inflammation with administration of the compound of the present invention.

The results are shown in FIG. 4. As shown in the figure, the compound (I-963) of the present invention significantly suppresses increasing number of eosinophils and neutrophils by the challenge of antigen.

Experiment 8 Suppressive Effect on the Cytokine Production of a Mouse T Cell Strain EL-4

In 48-well plate were added $2\times10^5$ mouse T cell strain EL-4 which were suspended in 0.2 ml of 1% fetal bovine serum-added RPMI 1640 medium (2 mM of sodium bicarbonate, 50 units/ml of penicillin, 50 µg/ml of streptomycin and $5\times10^{-5}$ M of 2-mercaptoethanol were added) and the compound of the present invention of a predetermined concentration. TPA was added as a cell stimulater at a final concentration of 10 ng/ml to adjust a final volume of each well to 0.4 ml. Each compound of the present invention was dissolved in DMSO and diluted with the above RPMI 1640 medium, and then for added at a final concentration of 100 ng/ml or less. The cells in the 48-well plate were cultivated in an incubator keeping the humidity 100%, carbon dioxide 5% and air 95% at 37° C. for 24 hours to collect a supernatant of each well. The amount of IL-2, IL-4 and IL-5 released in the medium of each well were measured with the ELISA kit (Amersham K. K.) to be taken as an index of the cytokine production of the cells. TPA free group (-TPA) was used as a control. The results are shown in Table 334.

TABLE 334

| Compound | $IC_{50}$ (ng/ml) | | |
|---|---|---|---|
| | IL-2 | IL-4 | IL-5 |
| I-4 | >500 | 14 | 120 |
| I-37 | >500 | 7 | 110 |
| I-39 | 1300 | 7 | 130 |
| I-70 | >2000 | 0.2 | 1000 |
| I-73 | 500 | 20 | 15 |
| I-83 | >10000 | 140 | 1000 |
| I-128 | >10000 | 140 | 450 |
| I-148 | >10000 | 100 | 11000 |
| I-157 | >10000 | 170 | >10000 |
| I-189 | >10000 | 100 | 10000 |
| I-190 | >100 | 7 | 10 |
| I-202 | >2000 | <20 | <20 |
| I-209 | >200 | 14 | 12 |
| I-213 | >1000 | 25 | 23 |
| I-218 | >1000 | 4.8 | 30 |
| I-220 | >1000 | 150 | 720 |
| I-223 | 1000 | 16 | 45 |
| I-226 | 880 | 17 | 300 |
| I-228 | >1000 | 21 | 30 |
| I-229 | >1000 | 42 | 80 |
| I-230 | >1000 | 13 | 20 |
| I-231 | >500 | 9.6 | 9.2 |
| I-233 | >1000 | 12 | 3.8 |

TABLE 334-continued

| Compound | $IC_{50}$ (ng/ml) | | |
|---|---|---|---|
| | IL-2 | IL-4 | IL-5 |
| I-237 | >100 | 17 | 100 |
| I-238 | >1000 | 35 | >1000 |
| I-239 | >1000 | 54 | 900 |
| I-242 | >1000 | 100 | 880 |
| I-243 | >500 | 63 | >550 |
| I-279 | >1000 | 38 | 90 |
| I-282 | >500 | <5 | 130 |
| I-292 | >1000 | 72 | 600 |
| I-296 | >1000 | 70 | 47 |
| I-301 | 500 | <10 | 120 |
| I-302 | >1000 | 25 | 280 |
| I-305 | >1000 | 10 | 340 |
| I-307 | >1000 | 52 | 23 |
| I-309 | >500 | 29 | 10 |
| I-318 | >1000 | 68 | 58 |
| I-323 | >1000 | 230 | 24 |
| I-368 | >1000 | 72 | 380 |
| I-375 | >1000 | 200 | >1000 |
| I-379 | >1000 | 88 | >1000 |
| I-386 | >1000 | 68 | 40 |
| I-387 | >1000 | 75 | 40 |
| I-390 | >1000 | 200 | 160 |
| I-392 | >1000 | 50 | >1000 |
| I-395 | >1000 | 1–10 | >1000 |
| I-403 | >1000 | 13 | >1000 |
| I-720 | >500 | 6 | 110 |

Formulation Example 1

| | |
|---|---|
| The compound of the present invention | 15 mg |
| Starch | 15 mg |
| Lactose | 15 mg |
| Crystalline cellulose | 19 mg |
| Polyvinyl alcohol | 3 mg |
| Distilled water | 30 ml |
| Calcium stearate | 3 mg |

After all of the above ingredients except for calcium stearate were uniformly mixed, the mixture was crushed and granulated, and dried to obtain a suitable size of granules. After calcium stearate was added to the granules, tablets were formed by compression molding.

INDUSTRIAL APPLICABILITY

As indicated in the above experiments, the compound of the present invention has a potent immunosuppressive and/or anti-allergic activity. The compound of the present invention and a substance which has the same activity as the compound of the present invention are very useful for a selective suppressor of the IgE production, an immunosuppressive agent and/or an anti-allergic agent.

What is claimed is:

1. A compound of the formula (I):

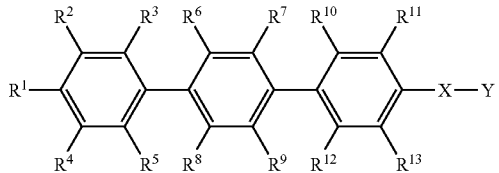

wherein $R^1$, $R^2$, $R^3$, $R^4$, $R^5$, $R^6$, $R^7$, $R^8$, $R^9$, $R^{10}$, $R^{11}$, $R^{12}$ and $R^{13}$ are each independently hydrogen, hydroxy, halogen, carboxy, optionally substituted lower alkyl, optionally substituted lower alkoxy, optionally substituted lower alkenyl, optionally substituted lower alkenyloxy, optionally substituted lower alkylthio, optionally substituted lower alkoxycarbonyl, optionally substituted acyloxy, optionally substituted lower alkylsulfonyl, optionally substituted lower alkylsulfonyloxy, optionally substituted lower alkylsulfinyl, nitro, cyano, formyl, optionally substituted amino, optionally substituted carbamoyl, optionally substituted sulfamoyl or optionally substituted heterocyclyl, X is —O—, —CH$_2$—, —NR$^{14}$— wherein R$^{14}$ is hydrogen, optionally substituted lower alkyl, optionally substituted lower alkenyl or acetyl, or —S(O)$_p$— wherein p is an integer of 0 to 2, Y is optionally substituted lower alkyl, optionally substituted lower alkenyl, optionally substituted lower alkynyl, optionally substituted acyl, optionally substituted cycloalkyl, optionally substituted cycloalkenyl, optionally substituted aryl or optionally substituted heterocyclyl, and Y may optionally be substituted lower alkoxy when X is —CH$_2$— and may optionally be substituted lower alkoxycarbonyl, optionally substituted lower alkylsulfonyl or optionally substituted arylsulfonyl when X is —O— or —NR$^{14}$—, $R^1$ and $R^4$, $R^1$ and $R^2$, $R^2$ and $R^3$, $R^4$ and $R^5$, $R^6$ and $R^7$, $R^8$ and $R^9$, $R^{10}$ and $R^{11}$, $R^{12}$ and $R^{13}$, $R^1$ and —X—Y, or $R^{13}$ and —X—Y taken together may form a 5- or 6-membered ring which may contain one or more of O, S or NR$^{15}$ wherein R$^{15}$ is hydrogen, optionally substituted lower alkyl, optionally substituted lower alkenyl, optionally substituted arylsulfonyl and which may optionally be substituted, excluding compounds wherein one or more of $R^6$, $R^7$, $R^8$ and $R^9$ are halogen and the others are hydrogen, compounds wherein all of $R^6$, $R^7$, $R^8$ and $R^9$ are halogen and compounds wherein all of $R^2$–$R^{13}$ are each independently selected from the group consisting of hydrogen, halogen and cyano, provided that $R^1$ is not hydrogen, fluorine, optionally substituted lower alkyl or optionally substituted lower alkoxy, all of $R^2$, $R^3$, $R^4$, $R^5$ and $R^{12}$ are hydrogen, or $R^{13}$ is not hydrogen or halogen when $R^6$, $R^7$, $R^8$ and $R^9$ are all simultaneously hydrogen, and further provided that $R^1$ is not methyl or acetyloxy, $R^{13}$ is not hydrogen, optionally substituted lower alkoxycarbonyl or optionally substituted carbamoyl, or —X—Y is not methoxy when at least one of $R^6$, $R^7$, $R^8$ and $R^9$ is a substituent other than hydrogen, and excluding a compound of the formula (I'):

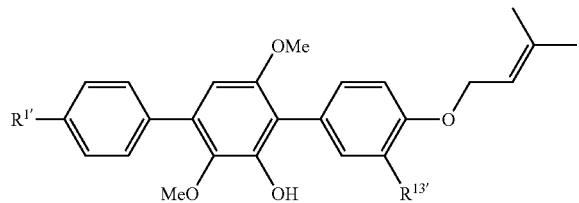

wherein $R^{1'}$ is hydrogen or hydroxy and $R^{13'}$ is hydroxy or methoxy;

or a pharmaceutically acceptable salt thereof.

2. The compound claimed in claim 1, wherein $R^1$ is hydrogen, hydroxy, halogen, carboxy, optionally substituted lower alkyl, optionally substituted lower alkoxy, optionally substituted lower alkenyloxy, optionally substituted lower alkylthio, optionally substituted lower alkoxycarbonyl, optionally substituted lower alkylsulfonyloxy, lower alkylsulfonyl, formyl, optionally substituted amino, lower alkylsulfinyl, acyloxy, nitro, cyano, optionally substituted sulfamoyl or heterocyclyl, $R^2$ is hydrogen, hydroxy, halogen, optionally substituted lower alkyl or optionally substituted lower alkylsulfonyloxy, $R^3$ is hydrogen, hydroxy, halogen or optionally substituted lower alkoxy, $R^4$ is hydrogen, optionally substituted lower alkyl, halogen, optionally substituted lower alkoxy, nitro or optionally substituted amino, $R^5$ is hydrogen, optionally substituted lower alkoxy, lower alkoxycarbonyl or carboxy, $R^6$ is hydrogen, halogen, optionally substituted lower alkyl, carboxy, lower alkoxycarbonyl, nitro, formyl, amino or lower alkylsulfonyloxy, $R^7$ and $R^8$ are each independently hydrogen, halogen, optionally substituted lower alkyl, optionally substituted lower alkoxy, formyl or optionally substituted amino, $R^9$ is hydrogen, hydroxy, carboxy, optionally substituted lower alkyl, optionally substituted lower alkoxy, optionally substituted lower alkenyl, optionally substituted lower alkoxycarbonyl, optionally substituted lower alkylsulfonyloxy, formyl, optionally substituted carbamoyl or optionally substituted amino, $R^{10}$ is hydrogen or lower alkoxy, $R^{11}$ is hydrogen, halogen, optionally substituted lower alkyl, carboxy, lower alkoxycarbonyl, optionally substituted lower alkylsulfonyloxy, formyl, nitro or amino, $R^{12}$ is hydrogen, $R^{13}$ is hydroxy, halogen, carboxy, optionally substituted lower alkyl, optionally substituted lower alkoxy, optionally substituted lower alkenyloxy, optionally substituted acyloxy, optionally substituted lower alkylsulfonyloxy, formyl, nitro or optionally substituted amino, Y is optionally substituted lower alkyl, optionally substituted lower alkenyl, optionally substituted lower alkynyl, optionally substituted acyl or optionally substituted cycloalkenyl and Y may be optionally substituted lower alkoxycarbonyl, optionally substituted lower alkylsulfonyl or optionally substituted arylsulfonyl when X is —O— or —NR$^{14}$—, and $R^1$ and $R^2$, $R^1$ and $R^4$, $R^8$ and $R^9$, $R^{11}$ and —X—Y, or $R^1$ and —X—Y taken together may form a 5- or 6-membered ring which contains one or more of O or $NR^{15}$ wherein $R^{15}$ is the same as defined in claim 1 and which may optionally be substituted;
or a pharmaceutically acceptable salt thereof.

3. A pharmaceutical composition comprising a compound or a pharmaceutically acceptable salt thereof, and a pharmaceutically acceptable excipient,
wherein the compound is of the formula (I):

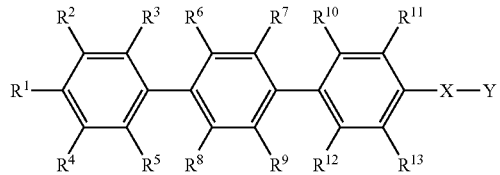

(I)

wherein $R^1$, $R^2$, $R^3$, $R^4$, $R^5$, $R^6$, $R^7$, $R^8$, $R^9$, $R^{10}$, $R^{11}$, $R^{12}$ and $R^{13}$ are each independently hydrogen, hydroxy, halogen, carboxy, optionally substituted lower alkyl, optionally substituted lower alkoxy, optionally substituted lower alkenyl, optionally substituted lower alkenyloxy, optionally substituted lower alkylthio, optionally substituted lower alkoxycarbonyl, optionally substituted acyloxy, optionally substituted lower alkylsulfonyl, optionally substituted lower alkylsulfonyloxy, optionally substituted lower alkylsulfinyl, nitro, cyano, formyl, optionally substituted amino, optionally substituted carbamoyl, optionally substituted sulfamoyl or optionally substituted heterocyclyl, X is —O—, —CH₂—, —$NR^{14}$— wherein $R^{14}$ is hydrogen, optionally substituted lower alkyl, optionally substituted lower alkenyl or acetyl, or —S(O)p— wherein p is an integer of 0 to 2, Y is optionally substituted lower alkyl, optionally substituted lower alkenyl, optionally substituted lower alkynyl, optionally substituted acyl, optionally substituted cycloalkyl, optionally substituted cycloalkenyl, optionally substituted aryl or optionally substituted heterocyclyl, and Y may optionally be substituted lower alkoxy when X is —CH₂— and may optionally be substituted lower alkoxycarbonyl, optionally substituted lower alkylsulfonyl or optionally substituted arylsulfonyl when X is —O— or —$NR^{14}$—, $R^1$ and $R^4$, $R^1$ and $R^2$, $R^2$ and $R^3$, $R^4$ and $R^5$, $R^6$ and $R^7$, $R^8$ and $R^9$, $R^{10}$ and $R^{11}$, $R^{12}$ and $R^{13}$, $R^{11}$ and —X—Y, or $R^{13}$ and —X—Y taken together may form a 5- or 6-membered ring which may contain one or more of O, S or $NR^{15}$ wherein $R^{15}$ is hydrogen, optionally substituted lower alkyl, optionally substituted lower alkenyl, optionally substituted arylsulfonyl and which may optionally be substituted, excluding compounds wherein one or more of $R^6$, $R^7$, $R^8$ and $R^9$ are halogen and the others are hydrogen, compounds wherein all of $R^6$, $R^7$, $R^8$ and $R^9$ are halogen and compounds wherein all of $R^2$–$R^{13}$ are hydrogen, halogen or cyano, provided that $R^1$ is not hydrogen, fluorine, optionally substituted lower alkyl or optionally substituted lower alkoxy, all of $R^2$, $R^3$, $R^4$, $R^5$ and $R^{12}$ are hydrogen, or $R^{13}$ is not hydrogen or halogen when $R^6$, $R^7$, $R^8$ and $R^9$ are all simultaneously hydrogen, and further provided that $R^1$ is not methyl or acetyloxy, $R^{13}$ is not hydrogen, optionally substituted lower alkoxycarbonyl or optionally substituted carbamoyl, or —X—Y is not methoxy when at least one of $R^6$, $R^7$, $R^8$ and $R^9$ is a substituent other than hydrogen, and excluding a compound of the formula (I'):

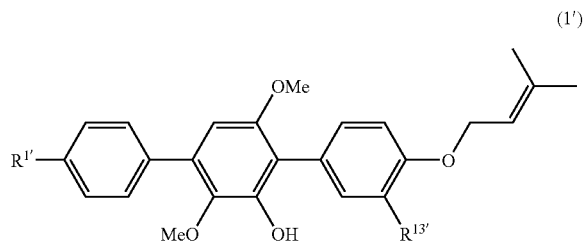

(1')

wherein $R^1$ is hydrogen or hydroxy and $R^{13'}$ is hydroxy or methoxy.

4. An immunosuppressive composition comprising a compound of the formula (I"):

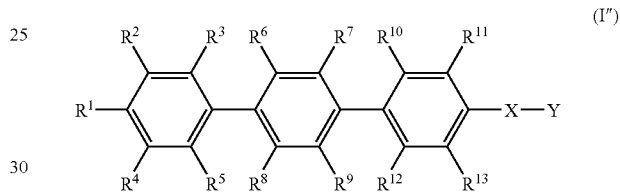

(I")

wherein $R^1$, $R^2$, $R^3$, $R^4$, $R^5$, $R^6$, $R^7$, $R^8$, $R^9$, $R^{10}$, $R^1$, $R^{12}$ and $R^{13}$ are each independently hydrogen, hydroxy, halogen, carboxy, optionally substituted lower alkyl optionally substituted, lower alkoxy, optionally substituted lower alkenyl, optionally substituted lower alkenyloxy, optionally substituted lower alkylthio, optionally substituted lower alkoxycarbonyl, optionally substituted acyloxy, optionally substituted lower alkylsulfonyl, optionally substituted lower alkylsulfonyloxy, optionally substituted lower alkylsulfinyl, nitro, cyano, formyl, optionally substituted amino, optionally substituted carbamoyl, optionally substituted sulfamoyl or optionally substituted heterocyclyl, X is —O—, —CH₂—, —$NR^{14}$— wherein $R^{14}$ is hydrogen, optionally substituted lower alkyl, optionally substituted lower alkenyl or acetyl, or —S(O)$_p$— wherein p is an integer of 0 to 2, Y is optionally substituted lower alkyl, optionally substituted lower alkenyl, optionally substituted lower alkynyl, optionally substituted acyl, optionally substituted cycloalkyl, optionally substituted cycloalkenyl, optionally substituted aryl or optionally substituted heterocyclyl, and Y may optionally be substituted lower alkoxy when X is —CH₂— and may optionally be substituted lower alkoxycarbonyl, optionally substituted lower alkylsulfonyl or optionally substituted arylsulfonyl when X is —O— or —$NR^{14}$—, $R^1$ and $R^4$, $R^1$ and $R^2$, $R^2$ and $R^3$, $R^4$ and $R^5$, $R^6$ and $R^7$, $R^8$ and $R^9$, $R^{10}$ and $R^{11}$, $R^{12}$ and $R^{13}$, $R^{11}$ and —X—Y, or $R^{13}$ and —X—Y taken together may form a 5- or 6-membered ring which may contain one or more of O, S or $NR^{15}$ wherein $R^{15}$ is hydrogen, optionally substituted lower alkyl, optionally substituted lower alkenyl or optionally substituted arylsulfonyl and which may optionally be substituted, excluding a compound of the formula (I'):

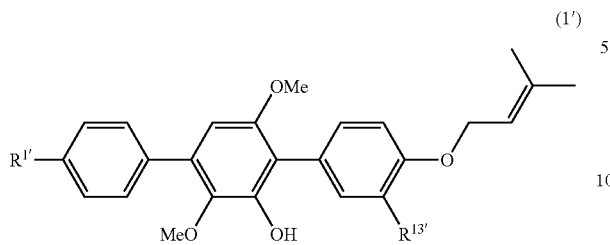

wherein $R^{1'}$ is hydrogen or hydroxy and $R^{13'}$ is hydroxy or methoxy; or a pharmaceutically acceptable salt or hydrate thereof, and
a pharmaceutically acceptable excipient.

5. A process for producing a compound of the formula (I) or a pharmaceutically acceptable salt thereof:

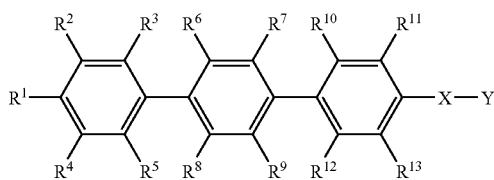

wherein $R^1$, $R^2$, $R^3$, $R^4$, $R^5$, $R^6$, $R^7$, $R^8$, $R^9$, $R^{10}$, $R^{11}$, $R^{12}$ and $R^{13}$ are each independently hydrogen, hydroxy, halogen, carboxy, optionally substituted lower alkyl, optionally substituted lower alkoxy, optionally substituted lower alkenyl, optionally substituted lower alkenyloxy, optionally substituted lower alkylthio, optionally substituted lower alkoxycarbonyl, optionally substituted acyloxy, optionally substituted lower alkylsulfonyl, optionally substituted lower alkylsulfonyloxy, optionally substituted lower alkylsulfinyl, nitro, cyano, formyl, optionally substituted amino, optionally substituted carbamoyl, optionally substituted sulfamoyl or optionally substituted heterocyclyl, X is —O—, —CH$_2$—, —NR$^{14}$— wherein R$^{14}$ is hydrogen, optionally substituted lower alkyl, optionally substituted lower alkenyl or acetyl, or —S(O)$_p$— wherein p is an integer of 0 to 2, Y is optionally substituted lower alkyl, optionally substituted lower alkenyl, optionally substituted lower alkynyl, optionally substituted acyl, optionally substituted cycloalkyl, optionally substituted cycloalkenyl, optionally substituted aryl or optionally substituted heterocyclyl, and Y may optionally be substituted lower alkoxy when X is —CH$_2$— and may optionally be substituted lower alkoxycarbonyl, optionally substituted lower alkylsulfonyl or optionally substituted arylsulfonyl when X is —O— or —NR$^{14}$—, R$^1$ and R$^4$, R$^1$ and R$^2$, R$^2$ and R$^3$, R$^4$ and R$^5$, R$^6$ and R$^7$, R$^8$ and R$^9$, R$^{10}$ and R$^{11}$ R$^{12}$ and R$^{13}$, R$^{11}$ and —X—Y, or R$^{13}$ and —X—Y taken together may form a 5- or 6-membered ring which may contain one or more of O, S or NR$^{15}$ wherein R$^{15}$ is hydrogen, optionally substituted lower alkyl, optionally substituted lower alkenyl, optionally substituted arylsulfonyl and which may optionally be substituted, excluding compounds wherein one or more of R$^6$, R$^7$, R$^8$ and R$^9$ are halogen and the others are hydrogen, compounds wherein all of R$^6$, R$^7$, R$^8$ and R$^9$ are halogen and compounds wherein all of R$^2$–R$^{13}$ are hydrogen, halogen or cyano, provided that R$^1$ is not hydrogen, fluorine, optionally substituted lower alkyl or optionally substituted lower alkoxy, all of R$^2$, R$^3$, R$^4$, R$^5$ and R$^{12}$ are hydrogen, or R$^{13}$ is not hydrogen or halogen when R$^6$, R$^7$, R$^8$ and R$^9$ are all simultaneously hydrogen, and further provided that R$^1$ is not methyl or acetyloxy, R$^{13}$ is not hydrogen, optionally substituted lower alkoxycarbonyl or optionally substituted carbamoyl, or —X—Y is not methoxy when at least one of R$^6$, R$^7$, R$^8$ and R$^9$ is a substituent other than hydrogen, and excluding a compound of the formula (I'):

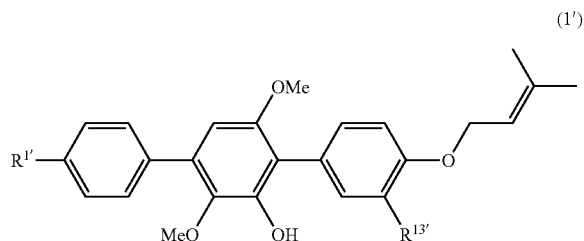

wherein $R^{1'}$ is hydrogen or hydroxy and $R^{13'}$ is hydroxy or methoxy;

said process comprising reacting a compound of the formula (II):

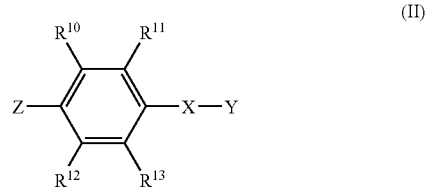

with a compound of the formula (III):

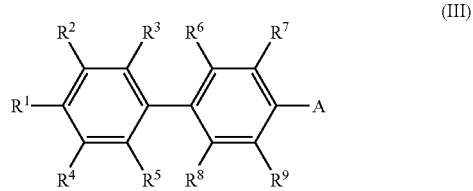

wherein, in the formulas (II) and (III), R$^1$, R$^2$, R$^3$, R$^4$, R$^5$, R$^6$, R$^7$, R$^8$, R$^9$, R$^{10}$, R$^{11}$, R$^{12}$ and R$^{13}$ are each described above; either of A and Z is dihydroxyborane, di(lower)alkoxyborane, di(lower)alkylborane,

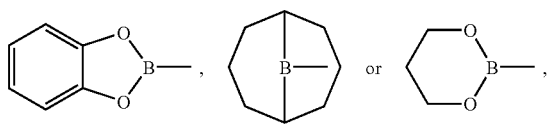

and the other is halogen or —OSO$_2$(C$_q$F$_{2q+1}$)— wherein q is an integer of 1 to 4, or reacting a compound of the formula (II'):

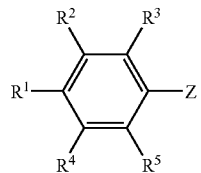

with a compound of the formula (III'):

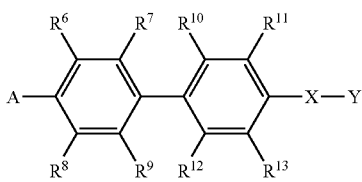

wherein, in the formulas (II') and (III'), R$^1$–R$^{13}$, X and Y are the same as defined above and A and Z are the same as defined in the above formulas (II) and (III).

6. The process for producing the compound of the formula (I) according to claim 5 or the pharmaceutically acceptable salt or hydrate thereof, comprising the reaction of a compound of the formula (IV):

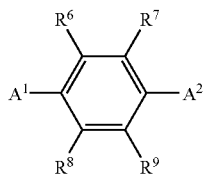

with a compound of the formula (V):

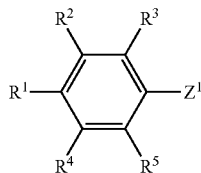

wherein, in the formulas (IV) and (V), R$^1$, R$^2$ R$^3$, R$^4$, R$^5$, R$^6$, R$^7$, R$^8$ and R$^9$ are each independently hydrogen, hydroxy, halogen, carboxy, optionally substituted lower alkyl, optionally substituted lower alkoxy, optionally substituted lower alkenyl, optionally substituted lower alkenyloxy, optionally substituted lower alkylthio, optionally substituted lower alkoxycarbonyl, optionally substituted acyloxy, optionally substituted lower alkylsulfonyl, optionally substituted lower alkylsulfonyloxy, optionally substituted lower alkylsulfinyl, nitro, cyano, formyl, optionally substituted amino, optionally substituted carbamoyl, optionally substituted sulfamoyl or optionally substituted heterocyclyl, Z$^1$ is defined the same as for Z in the formula (II), A$^1$ and A$^2$ are each independently defined the same as for A in the formula (III), and the reactivity of A$^1$ is higher than or equal to that of A$^2$, followed by the reaction with a compound of the formula (VI):

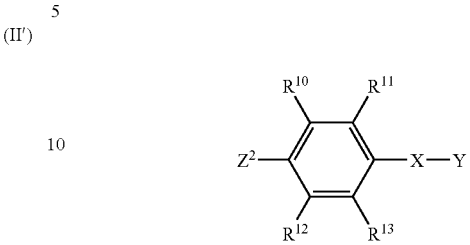

wherein R$^{10}$—R$^{13}$, are as defined for R$^6$–R$^9$ above, X is —O—, —CH$_2$—, NR$^{14}$— wherein R$^{14}$ is hydrogen, optionally substituted lower alkyl, optionally substituted lower alkenyl or acetyl, or —S(O)$_p$—wherein p is an integer of 0 to 2, Y is optionally substituted lower alkyl, optionally substituted lower alkenyl, optionally substituted lower alkynyl, optionally substituted acyl, optionally substituted cycloalkyl, optionally substituted cycloalkenyl, optionally substituted aryl or optionally substituted heterocyclyl, and Y may optionally be substituted lower alkoxy when X is —CH$_2$— and may optionally be substituted lower alkoxycarbonyl, optionally substituted lower alkylsulfonyl or optionally substituted arylsulfonyl when X is —O— or —NR$^{14}$, R$^1$ and R$^4$, R$^1$ and R$^2$, R$^2$ and R$^3$, R$^4$ and R$^5$, R$^6$ and R$^7$, R$^8$ and R$^9$, R$^{10}$ and R$^{11}$, R$^{12}$ and R$^{13}$, R and —X—Y, or R$^{13}$ and —X—Y taken together may form a 5- or 6-membered ring which may contain one or more of O, S or NR$^{15}$ wherein R$^{15}$ is hydrogen, optionally substituted lower alkyl, optionally substituted lower alkenyl, optionally substituted arylsulfonyl, and which may optionally be substituted, and Z$^2$ is the same as Z$^1$ defined in the above formula (II).

7. The process for producing the compound of the formula (I) according to claim 5 or the pharmaceutically acceptable salt thereof, said process comprising:

the reaction of a compound of the formula (IV'):

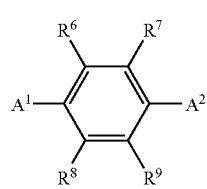

wherein, R$^6$, R$^7$, R$^8$ and R$^9$ are each independently hydrogen, hydroxy, halogen, carboxy, optionally substituted lower alkyl, optionally substituted lower alkoxy, optionally substituted lower alkenyl, optionally substituted lower alkenyloxy, optionally substituted lower alkylthio, optionally substituted lower alkoxycarbonyl, optionally substituted acyloxy, optionally substituted lower alkylsulfonyl, optionally substituted lower alkylsulfonyloxy, optionally substituted lower alkylsulfinyl, nitro, cyano, formyl, optionally substituted amino, optionally substituted carbamoyl, optionally substituted sulfamoyl or optionally substituted heterocyclyl, A$^1$ and A$^2$ are each independently defined the same as A in the formula (III), and the reactivity of A$^2$ is higher than or equal to that of A$^1$, with a compound of the formula (VI),

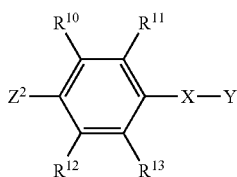

(VI)

wherein $R^{10}-R^{13}$, are as defined for $R^6-R^9$ above, X is —O—, —CH$_2$—, NR$^{14}$— wherein R$^{14}$ is hydrogen, optionally substituted lower alkyl, optionally substituted lower alkenyl or acetyl, or S(O)$_p$-S(O)$_p$- wherein p is an integer of 0 to 2, Y is optionally substituted lower alkyl, optionally substituted lower alkenyl, optionally substituted lower alkynyl, optionally substituted acyl, optionally substituted cycloalkyl, optionally substituted cycloalkenyl, optionally substituted aryl or optionally substituted heterocyclyl, and Y may optionally be substituted lower alkoxy when X is —CH$_2$— and may optionally be substituted lower alkoxycarbonyl, optionally substituted lower alkylsulfonyl or optionally substituted arylsulfonyl when X is —O— or —NR$^{14}$, R$^1$ and R$^4$, R$^1$ and R$^2$, R$^2$ and R$^3$, R$^4$ and R$^5$, R$^6$ and R$^7$, R$^8$ and R$^9$, R$^{10}$ and R$^{11}$, R$^2$ and R$^{13}$, R$^{11}$ and —X—Y, or R$^{13}$ and —X—Y taken together may form a 5- or 6-membered ring which may contain one or more of O, S or NR$^{15}$ wherein R$^{15}$ is hydrogen, optionally substituted lower alkyl, optionally substituted lower alkenyl, optionally substituted arylsulfonyl, and which may optionally be substituted, and Z$^2$ is defined the same as Z in formula (II), followed by the reaction with a compound of the formula (V)

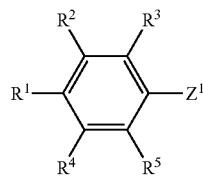

(V)

wherein $R^1-R^5$ are as defined for $R^6-R^9$ above, $Z^1$ is defined the same as for Z in the formula (II).

8. A compound of the formula (I):

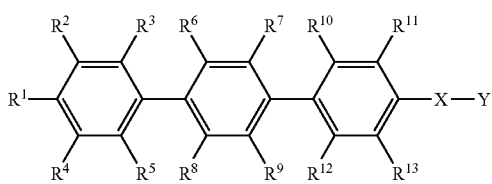

(I)

wherein R$^1$ is hydrogen, halogen, optionally substituted lower alkenyloxy, optionally substituted lower alkylsulfonyloxy, optionally substituted amino or optionally substituted sulfamoyl, R$^2$ is hydrogen, halogen or lower alkyl having 1 to 3 carbon atoms, R$^3$ is hydrogen or halogen, R$^4$ is hydrogen, lower alkyl, lower alkoxy or halogen, R$^5$ is hydrogen, lower alkoxycarbonyl or carboxy, R$^6$ is hydrogen, lower alkyl or halogen, R$^7$ is hydrogen, lower alkyl or lower alkoxy, R$^8$ is hydrogen, lower alkyl or lower alkoxy, R$^9$ is hydrogen, hydroxy, carboxy, optionally substituted lower alkyl, optionally substituted lower alkoxy, optionally substituted lower alkenyl, optionally substituted lower alkoxycarbonyl, optionally substituted lower alkylsulfonyloxy, formyl, optionally substituted carbamoyl or optionally substituted amino, R$^{10}$ is hydrogen, R$^{11}$ is hydrogen or halogen, R$^{12}$ is hydrogen, R$^{13}$ is hydrogen, hydroxy, halogen, carboxy, optionally substituted lower alkyl, optionally substituted lower alkoxy, optionally substituted acyloxy, optionally substituted lower alkylsulfonyloxy, formyl or optionally substituted amino, X is —O—, —NH—, —NMe- or —SO$_2$—, Y is lower alkyl optionally substituted with lower alkoxycarbonyl, aryl, lower alkylaryl, halogenoaryl, lower alkoxyaryl, heterocyclyl or acyl; or lower alkenyl optionally substituted with hydroxy, halogen or aryl, and R$^1$ and R$^4$ or R$^8$ and R$^9$ taken together may form a 5- or 6-membered ring which contains one or more of 0, excluding compounds wherein one or more of R$^6$, R$^7$, R$^8$ and R$^9$ are halogen and the others are hydrogen and compounds wherein all of R$^2$—R$^{13}$ are hydrogen, provided that R$^1$ is not hydrogen or fluorine, all of R$^2$, R$^3$, R$^4$, R$^5$ and R$^{12}$ are hydrogen, or R$^{13}$ is not hydrogen or halogen when R$^6$, R$^7$, R$^8$ and R$^9$ are an simultaneously hydrogen, and further provided that R$^3$ is not hydrogen or —X—Y is not methoxy when at least one of R$^6$, R$^7$, R$^8$ and R$^9$ is a substituent other than hydrogen, and excluding a compound of the formula (I'):

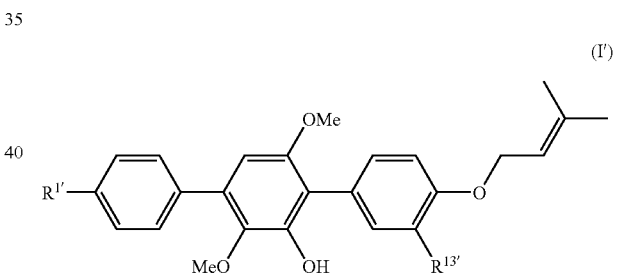

(I')

wherein R$^{1'}$, is hydrogen or hydroxy and R$^{13}$ is hydroxy or methoxy; or a pharmaceutically acceptable salt thereof.

9. A compound of the formula (I):

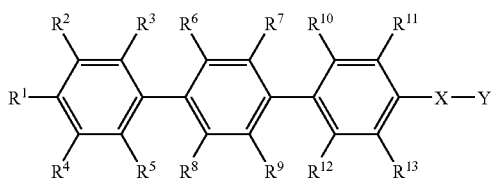

(I)

wherein R$^1$ is hydrogen, hydroxy, halogen, optionally substituted lower alkoxy, optionally substituted alkenyloxy, optionally substituted lower alkylsulfonyloxy, optionally substituted amino or optionally substituted sulfamoyl, R$^2$ is hydrogen, halogen or lower alkyl having 1 to 3 carbon atoms, R$^3$ is hydrogen or halogen, $R^4$ is hydrogen, lower alkyl, lower alkoxy or halogen,
$R^5$ is hydrogen, lower alkoxycarbonyl or carboxy,
$R^6$ is hydrogen, lower alkyl or halogen,
$R^7$ is hydrogen, lower alkyl or lower alkoxy,
$R^8$ is hydrogen, lower alkyl or lower alkoxy,
$R^9$ is hydrogen, hydroxy, carboxy, optionally substituted lower alkyl, optionally substituted lower alkoxy, optionally substituted lower alkenyl, optionally substituted lower alkoxycarbonyl, optionally substituted lower alkylsulfonyloxy, formyl, optionally substituted carbamoyl or optionally substituted amino,
$R^{10}$ is hydrogen,
$R^{11}$ is hydrogen or halogen,
$R^{12}$ is hydrogen,
$R^{13}$ is hydrogen, hydroxy, halogen, carboxy, optionally substituted lower alkyl, optionally substituted lower alkoxy, optionally substituted acyloxy, optionally substituted lower alkylsulfonyloxy, formyl or optionally substituted amino,
X is —O—, —NH—, —NMe- or —SO$_2$—,
Y is lower alkyl optionally substituted with aryl; or lower alkenyl,
and $R^1$ and $R^4$ or $R^8$ and $R^9$ taken together may form a 5- or 6-membered ring which contains one or more of O, excluding compounds wherein one or more of $R^6$, $R^7$, $R^8$ and $R^9$ are halogen and the others are hydrogen and compounds wherein all of $R^2$–$R^{13}$ are hydrogen, provided that $R^1$ is not hydrogen, fluorine or optionally substituted lower alkoxy, all of $R^2$, $R^3$, $R^4$, $R^5$ and $R^{12}$ are hydrogen, or $R^{13}$ is not hydrogen or halogen when $R^6$, $R^7$, $R^8$ and $R^9$ are all simultaneously hydrogen, and further provided that $R^{13}$ is not hydrogen or —X—Y is not methoxy when at least one of $R^6$, $R^7$, $R^8$ and $R^9$ is a substituent other than hydrogen, and excluding a compound of the formula (I'):

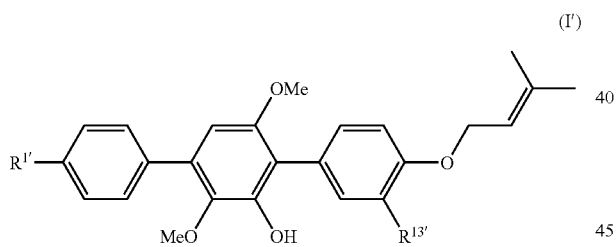

wherein $R^{1'}$ is hydrogen or hydroxy and $R^{13'}$ is hydroxy or methoxy; or a pharmaceutically acceptable salt or hydrate thereof.

10. The compound, pharmaceutically acceptable salt thereof claimed in claim 9, wherein Y is methylbutenyl.

11. The compound pharmaceutically acceptable salt thereof claimed in claim 9, wherein —X—Y is —OCH$_2$CH=CMe$_2$, or —OCH$_2$C$_6$H$_5$.

12. A compound of the formula (I):

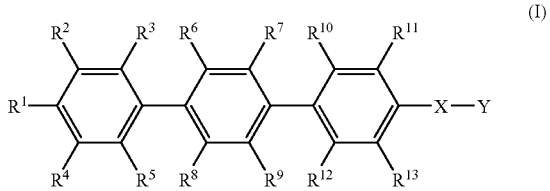

wherein $R^1$, $R^2$, $R^1$, $R^4$, $R^5$, $R^6$, $R^7$, $R^1$, $R^9$, $R^{10}$, $R^{11}$, $R^{12}$ and $R^{13}$ are each independently hydrogen, hydroxy, halogen, carboxy, optionally substituted lower alkyl, optionally substituted lower alkoxy, optionally substituted lower alkenyl, optionally substituted lower alkenyloxy, optionally substituted lower alkylthio, optionally substituted lower alkoxycarbonyl, optionally substituted acyloxy, optionally substituted lower alkylsulfonyl, optionally substituted lower alkylsulfonyloxy, optionally substituted lower alkylsulfinyl, nitro, cyano, formyl, optionally substituted amino, optionally substituted carbamoyl, optionally substituted sulfamoyl or optionally substituted heterocyclyl, X is —O—, —CH$_2$—, —NR$^{14}$— wherein $R^{14}$ is hydrogen, optionally substituted lower alkyl, optionally substituted lower alkenyl or acetyl, or —S(O)$_p$— wherein p is an integer of 0 to 2, Y is optionally substituted lower alkyl, optionally substituted lower alkenyl, optionally substituted lower alkynyl, optionally substituted acyl, optionally substituted cycloalkyl, optionally substituted cycloalkenyl, optionally substituted aryl or optionally substituted heterocyclyl, and Y may be optionally substituted lower alkoxy when X is —CH$_2$— and may be optionally substituted lower alkoxycarbonyl, optionally substituted lower alkylsulfonyl or optionally substituted arylsulfonyl when X is —O— or —NR$^{14}$—, $R^1$ and $R^4$, $R^1$ and $R^2$, $R^2$ and $R^3$, $R^4$ and $R^5$, $R^6$ and $R^7$, $R^8$ and $R^9$, $R^{10}$ and $R^{11}$, $R^{12}$ and $R^{13}$, $R^{11}$ and —X—Y, or $R^{13}$ and —X—Y taken together may form a 5- or 6-membered ring which may contain one or more of O, S or NR$^5$ wherein $R^{15}$ is hydrogen, optionally substituted lower alkyl, optionally substituted lower alkenyl, optionally substituted arylsulfonyl and which may optionally be substituted, excluding compounds wherein one or more of $R^6$, $R^7$, $R^8$ and $R^9$ are halogen and the others are hydrogen, compounds wherein all of $R^6$, $R^7$, $R^1$ and $R^9$ are halogen and compounds wherein all of $R^2$–$R^{13}$ are hydrogen, halogen or cyano, provided that $R^1$ is not hydrogen, fluorine, optionally substituted lower alkyl or optionally substituted lower alkoxy, all of $R^2$, $R^3$, $R^4$, $R^1$ and $R^{12}$ are hydrogen, and $R^{13}$ is not hydrogen or halogen when $R^6$, $R^7$, $R^8$ and $R^9$ are all simultaneously hydrogen, and further provided that $R^1$ is not methyl or acetyloxy, $R^{13}$ is not hydrogen, optionally substituted lower alkoxycarbonyl or optionally substituted carbamoyl, and —X—Y is not methoxy when at least one of $R^6$, $R^7$, $R^8$ and $R^9$ is a substituent other than hydrogen, and excluding a compound of the formula (I'):

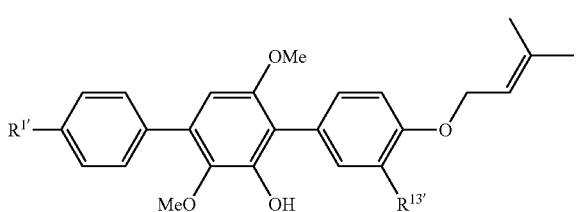

wherein $R^{1'}$ is hydrogen or hydroxy and $R^{13}$ is hydroxy or methoxy; or a pharmaceutically acceptable salt thereof.

13. A pharmaceutical composition comprising the compound or the pharmaceutically acceptable salt thereof according to claim 8, 9, 10, 11 or 12, and a pharmaceutically acceptable excipient.

14. A process for producing the compound of the formula (I) according to claim 8, 9, 10, 11 or 12, or the pharmaceutically acceptable salt thereof, said process comprising:
reacting a compound of the formula (IV)

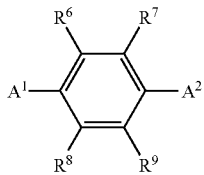

with a compound of the formula (V):

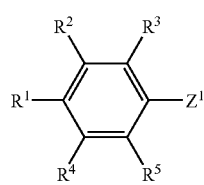

wherein, in the formulas (IV) and (V),
R¹ is hydrogen, halogen, optionally substituted lower alkenyloxy, optionally substituted lower alkylsulfonyloxy, optionally substituted amino or optionally substituted sulfamoyl,
R² is hydrogen, halogen or lower alkyl having 1 to 3 carbon atoms,
R³ is hydrogen or halogen,
R⁴ is hydrogen, lower alkyl, lower alkoxy or halogen,
R⁵ is hydrogen, lower alkoxycarbonyl or carboxy,
R⁶ is hydrogen, lower alkyl or halogen,
R⁷ is hydrogen, lower alkyl or lower alkoxy,
R⁸ is hydrogen, lower alkyl or lower alkoxy,
R⁹ is hydrogen, hydroxy, carboxy, optionally substituted lower alkyl, optionally substituted lower alkoxy, optionally substituted lower alkenyl, optionally substituted lower alkoxycarbonyl, optionally substituted lower alkylsulfonyloxy, formyl, optionally substituted carbamoyl or optionally substituted amino,
Z¹, A¹ and A² are each independently dihydroxyborane, di(lower)alkoxyborane, di(lower)alkylborane,

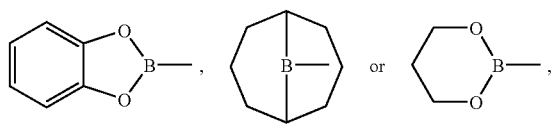

and the other is halogen or —OSO₂(C$^q$F$_{2q+1}$)— wherein q is an integer of 1 to 4, and the reactivity of A¹ is higher than or equal to that of A²,
followed by the reaction with a compound of the formula (VI):

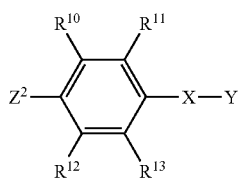

wherein R¹⁰ is hydrogen,
R¹¹ is hydrogen or halogen,
R¹² is hydrogen,

R¹³ is hydrogen, hydroxy, halogen, carboxy, optionally substituted lower alkyl, optionally substituted lower alkoxy, optionally substituted acyloxy, optionally substituted lower alkylsulfonyloxy, formyl or optionally substituted amino,
X is —O—, —NH—, —NMe- or —SO₂—,
Y is lower alkyl optionally substituted with lower alkoxycarbonyl, aryl, lower alkylaryl, halogenoaryl, lower alkoxyaryl, heterocyclyl or acyl; or lower alkenyl optionally substituted with hydroxy, halogen or aryl,
and excluding compounds wherein one or more of R⁶, R⁷, R⁸ and R⁹ are halogen and the others are hydrogen and compounds wherein all of R²—R are hydrogen,
provided that R¹ is not hydrogen or fluorine, all of R², R³, R⁴, R⁵ and R¹² are hydrogen, or R¹³ is not hydrogen or halogen when R⁶, R⁷, R⁸ and R⁹ are an simultaneously hydrogen,
and further provided that R³ is not hydrogen or —X—Y is not methoxy when at least one of R⁶, R⁷, R⁸ and R⁹ is a substituent other than hydrogen, and excluding a product compound of the formula (I'):

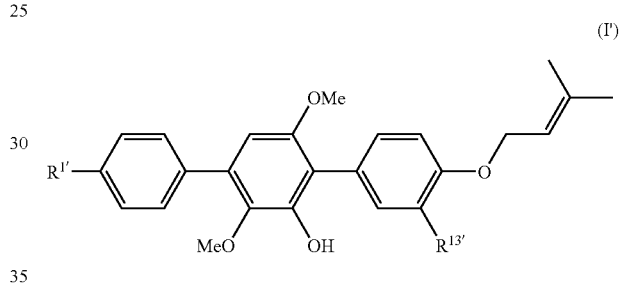

wherein R¹', is hydrogen or hydroxy and R¹³' is hydroxy or methoxy, pharmaceutically acceptable salt, thereof.

15. A process for producing the compound of the formula (I), according to claim 8, 9, 10, 11 or 12, or the pharmaceutically acceptable salt or hydrate thereof, said process comprising:
reacting a compound of the formula (IV')

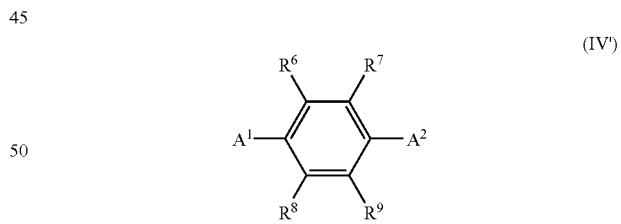

wherein
R⁶ is hydrogen, lower alkyl or halogen,
R⁷ is hydrogen, lower alkyl or lower alkoxy,
R⁸ is hydrogen, lower alkyl or lower alkoxy,
R⁹ is hydrogen, hydroxy, carboxy, optionally substituted lower alkyl, optionally substituted lower alkoxy, optionally substituted lower alkenyl, optionally substituted lower alkoxycarbonyl, optionally substituted lower alkylsulfonyloxy, formyl, optionally substituted carbamoyl or optionally substituted amino,
wherein A¹ and A² are each independently dihydroxyborane, di(lower)alkoxyborane, di(lower)alkylborane,

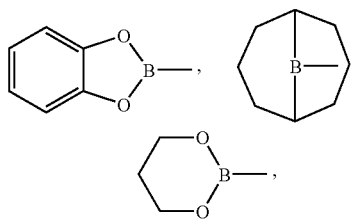

and the other is halogen or —OSO$_2$(C$_q$F$_{2q+1}$)— wherein q is an integer of 1 to 4, and the reactivity of A$^1$ is higher than or equal to that of A$^2$, and the reactivity of A$^1$ is higher than or equal to that of A$^2$ with a compound of the formula (VI)

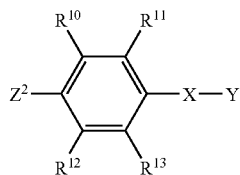

(VI)

wherein R$^{10}$–R$^{13}$ are as defined for R$^6$–R$^9$ above,
X is —O—, —NH—, —NMe- or —SO$_2$—,
Y is lower alkyl optionally substituted with lower alkoxycarbonyl, aryl, lower alkylaryl, halogenoaryl, lower alkoxyaryl, heterocyclyl or acyl; or lower alkenyl optionally substituted with hydroxy, halogen or aryl,
wherein Z$^2$ is dihydroxyborane, di(lower)alkoxyborane, di(lower)alkylborane,

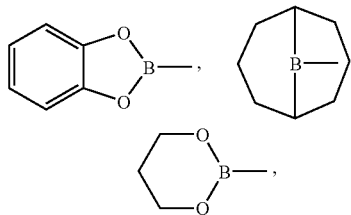

and the other is halogen or —OSO$_2$(C$_q$F$_{2q+1}$)— wherein q is an integer of 1 to 4, followed by the reaction with a compound of the formula (V)

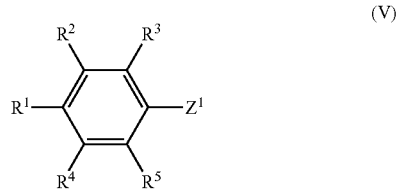

(V)

wherein R$^1$–R$^5$ are as defined for R$^6$–R$^9$ above, Z$^1$ is defined the same as for Z$^2$ above, and excluding compounds wherein one or more of R$^6$, R$^7$, R$^8$ and R$^9$ are halogen and the others are hydrogen and compounds wherein all of R$^2$–R$^{13}$ are hydrogen, provided that R$^1$ is not hydrogen or fluorine, all of R$^2$, R$^3$, R$^4$, R$^5$ and R$^{12}$ are hydrogen, or R$^{13}$ is not hydrogen or halogen when R$^6$, R$^7$, R$^8$ and R$^9$ are an simultaneously hydrogen, and further provided that R$^{13}$ is not hydrogen or —X—Y is not methoxy when at least one of R$^6$, R$^7$, R$^8$ and R$^9$ is a substituent other than hydrogen, and excluding a product compound of the formula (I'):

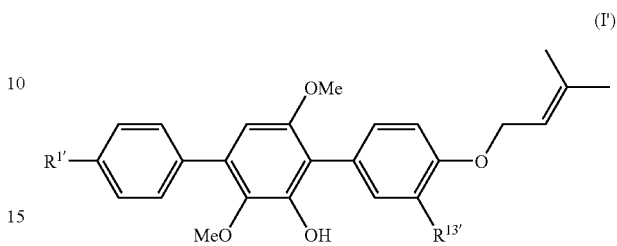

(I')

wherein R$^{1'}$, is hydrogen or hydroxy and R$^{13'}$ is hydroxy or methoxy, pharmaceutically acceptable salt thereof.

16. A compound of the formula (I):

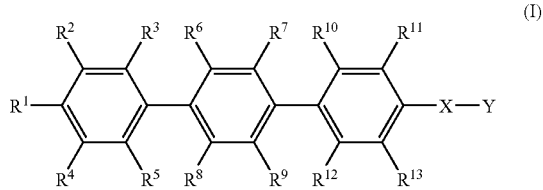

(I)

wherein R$^1$, R$^2$, R$^3$, R$^4$, R$^5$, R$^6$, R$^7$, R$^8$, R$^9$, R$^{10}$, R$^1$, R$^{12}$ and R$^{13}$ are each independently hydrogen, hydroxy, carboxy, optionally substituted lower alkoxy, optionally substituted lower alkenyl, optionally substituted lower alkenyloxy, optionally substituted lower alkylthio, optionally substituted lower alkoxycarbonyl, optionally substituted acyloxy, optionally substituted lower alkylsulfonyl, optionally substituted lower alkylsulfonyloxy, optionally substituted lower alkylsulfinyl, nitro, formyl, optionally substituted amino, optionally substituted carbamoyl, optionally substituted sulfamoyl or optionally substituted heterocyclyl, X is —O—, —CH$_2$—, —NR$^{14}$— wherein R$^{14}$ is hydrogen, optionally substituted lower alkyl, optionally substituted lower alkenyl or acetyl, or —S(O)$_p$— wherein p is an integer of 0 to 2, Y is optionally substituted lower alkyl, optionally substituted lower alkenyl, optionally substituted lower alkynyl, optionally substituted acyl, optionally substituted cycloalkyl, optionally substituted cycloalkenyl, optionally substituted aryl or optionally substituted heterocyclyl, and Y may optionally be substituted lower alkoxy when X is —CH$_2$— and may optionally be substituted lower alkoxycarbonyl, optionally substituted lower alkylsulfonyl or optionally substituted arylsulfonyl when X is —O— or —NR$^{14}$—, R$^1$ and R$^4$, R$^1$ and R$^2$, R$^2$ and R$^3$, R$^4$ and R$^5$, R$^6$ and R$^7$, R$^8$ and R$^9$, R$^{10}$ and R$^{111}$, R$^{12}$ and R$^{13}$, R$^{11}$ and —X—Y, or R$^{13}$ and —X—Y taken together may form a 5- or 6-membered ring which may contain one or more of O, S or NR$^{15}$ wherein R$^{15}$ is hydrogen, optionally substituted lower alkyl, optionally substituted lower alkenyl, optionally substituted arylsulfonyl and which may optionally be substituted, excluding compounds wherein all of R$^2$–R$^{1\ 3}$ are hydrogen, provided that R$^1$ is not hydrogen or optionally substituted lower alkoxy, all of R$^2$, R$^3$, R$^4$, R$^5$ and R$^{12}$ are hydrogen, or $R^{13}$ is not hydrogen when $R^6$, $R^7$, $R^8$ and $R^9$ are all simultaneously hydrogen, and further provided that $R^1$ is not acetyloxy, $R^{13}$ is not hydrogen, optionally substituted lower alkoxycarbonyl or optionally substituted carbamoyl, or —X—Y is not methoxy when at least one of $R^6$, $R^7$, $R^8$ and $R^9$ is a substituent other than hydrogen, and excluding a compound of the formula (I'):

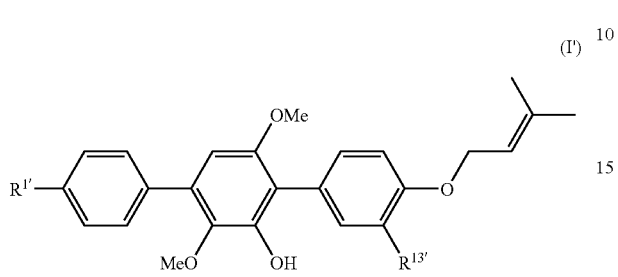

(I')

wherein $R^{1'}$ is hydrogen or hydroxy and $R^{13'}$ is hydroxy or methoxy; or a pharmaceutically acceptable salt thereof.

17. An immunosuppressive composition comprising a compound of the formula (I"):

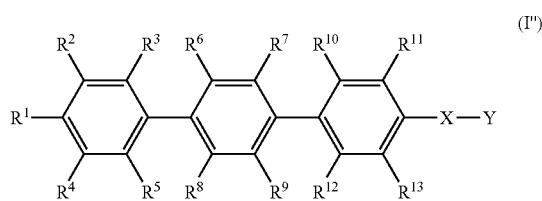

(I")

wherein $R^1, R^2, R^3, R^4, R^5, R^6, R^7, R^8, R^9, R^{10}, R^{11}, R^{12}$ and $R^{13}$ are each independently hydrogen, hydroxy, carboxy, optionally substituted lower alkoxy, optionally substituted lower alkenyl, optionally substituted lower alkenyloxy, optionally substituted lower alkylthio, optionally substituted lower alkoxycarbonyl, optionally substituted acyloxy, optionally substituted lower alkylsulfonyl, optionally substituted lower alkylsulfonyloxy, optionally substituted lower alkylsulfinyl, nitro, formyl, optionally substituted amino, optionally substituted carbamoyl, optionally substituted sulfamoyl or optionally substituted heterocyclyl, X is —O—, —CH$_2$—, —NR$^{14}$— wherein $R^{14}$ is hydrogen, optionally substituted lower alkyl, optionally substituted lower alkenyl or acetyl, or —S(O)$_p$— wherein p is an integer of 0 to 2, Y is optionally substituted lower alkyl, optionally substituted lower alkenyl, optionally substituted lower alkynyl, optionally substituted acyl, optionally substituted cycloalkyl, optionally substituted cycloalkenyl, optionally substituted aryl or optionally substituted heterocyclyl, and Y may optionally be substituted lower alkoxy when X is —CH$_2$— and may optionally be substituted lower alkoxycarbonyl, optionally substituted lower alkylsulfonyl or optionally substituted arylsulfonyl when X is —O— or —NR$^{14}$—, $R^1$ and $R^4$, $R^1$ and $R^2$, $R^2$ and $R^3$, $R^4$ and $R^5$, $R^6$ and $R^7$, $R^8$ and $R^9$, $R^{10}$ and $R^{11}$, $R^{12}$ and $R^{13}$, $R^{11}$ and —X—Y, or $R^{13}$ and —X—Y taken together may form a 5- or 6-membered ring which may contain one or more of O, S or NR$^{15}$ wherein $R^{15}$ is hydrogen, optionally substituted lower alkyl, optionally substituted lower alkenyl or optionally substituted arylsulfonyl and which may optionally be substituted, excluding a compound of the formula (I'):

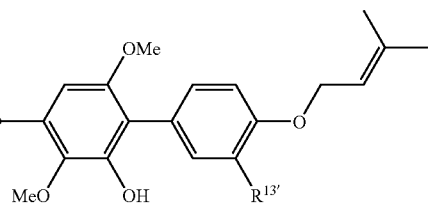

(I')

wherein $R^{1'}$ is hydrogen or hydroxy and $R^{13'}$ is hydroxy or methoxy; or a pharmaceutically acceptable salt thereof, and a pharmaceutically acceptable excipient.

18. The compound or immunosuppressive composition as claimed in any one of claims 1, 4, 8, 9, and 12, wherein at least two of $R^6$, $R^7$, $R^8$ and $R^9$, are each independently selected from the group consisting of hydroxy, carboxy, optionally substituted lower alkyl, optionally substituted lower alkoxy, optionally substituted lower alkenyl, optionally substituted lower alkenyloxy, optionally substituted lower alkylthio, optionally substituted lower alkoxycarbonyl, optionally substituted acyloxy, optionally substituted lower alkylsulfonyl, optionally substituted lower alkylsulfonyloxy, optionally substituted lower alkylsulfinyl, nitro, cyano, formyl, optionally substituted amino, optionally substituted carbamoyl, optionally substituted sulfamoyl and optionally substituted heterocyclyl.

19. The compound claimed in claim 18, wherein at least one of $R^6$, $R^7$, $R^8$ and $R^9$ is a hydrogen, optionally substituted lower alkoxy or optionally substituted lower alkyl.

20. A compound of the formula (I):

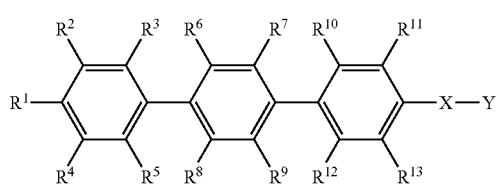

(I)

wherein $R^1, R^2, R^3, R^4, R^5, R^6, R^7, R^8, R^9, R^{10}, R^{11}, R^{12}$ and $R^{13}$ are each independently hydrogen, hydroxy, halogen, carboxy, optionally substituted lower alkyl, optionally substituted lower alkoxy, optionally substituted lower alkenyl, optionally substituted lower alkenyloxy, optionally substituted lower alkylthio, optionally substituted lower alkoxycarbonyl, optionally substituted acyloxy, optionally substituted lower alkylsulfonyl, optionally substituted lower alkylsulfonyloxy, optionally substituted lower alkylsulfinyl, nitro, cyano, formyl, optionally substituted amino, optionally substituted carbamoyl, optionally substituted sulfamoyl or optionally substituted heterocyclyl, X is —O—, —CH$_2$—, —NR$^{14}$— wherein $R^{14}$ is hydrogen, optionally substituted lower alkyl, optionally substituted lower alkenyl or acetyl, or —S(O)p— wherein p is an integer of 0 to 2, Y is optionally substituted lower alkyl, optionally substituted lower alkenyl, optionally substituted lower alkynyl, optionally substituted acyl, optionally substituted cycloalkyl, optionally substituted cycloalkenyl, optionally substituted aryl or optionally substituted heterocyclyl, and Y may optionally be substituted lower alkoxy when X is —CH$_2$— and may optionally be substituted lower alkoxycarbonyl, optionally substituted lower alkylsulfonyl or optionally substituted arylsulfonyl when X is —O— or —NR$^{14}$—, $R^1$ and $R^4$, $R^1$ and $R^2$, $R^2$ and $R^3$, $R^4$ and $R^5$, $R^6$ and $R^7$, $R^8$ and $R^9$, $R^{10}$ and $R^1$ $R^{12}$ and $R^{13}$, $R^{11}$ and —X—Y, or $R^{13}$ and —X—Y taken together may form a 5- or 6-membered ring which may contain one or more of O, S or NR$^{15}$ wherein R$^{15}$ is hydrogen, optionally substituted lower alkyl, optionally substituted lower alkenyl, optionally substituted arylsulfonyl and which may optionally be substituted, excluding compounds wherein one or more of $R^6$, $R^7$, $R^8$ and $R^9$ are halogen and the others are hydrogen, compounds wherein all of $R^6$, $R^7$, $R^8$ and $R^9$ are halogen and compounds wherein all of $R^2$–$R^{13}$ are hydrogen, halogen or cyano, provided that $R^1$ is not hydrogen, fluorine, optionally substituted lower alkyl or optionally substituted lower alkoxy, all of $R^2$, $R^3$, $R^4$, $R^5$ and $R^{12}$ are hydrogen, or $R^{13}$ is not hydrogen or halogen when $R^6$, $R^7$, $R^8$ and $R^9$ are all simultaneously hydrogen, and further provided that $R^1$ is not methyl or acetyloxy, $R^{13}$ is not hydrogen, optionally substituted lower alkoxycarbonyl or optionally substituted carbamoyl, or —X—Y is not methoxy when at least one of $R^6$, $R^7$, $R^8$ and $R^9$ is a substituent other than hydrogen, and excluding a compound of the formula (I'):

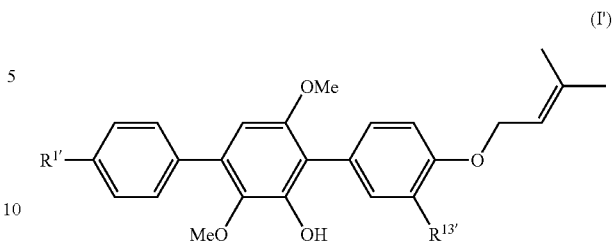

wherein $R^{1'}$ is hydrogen or hydroxy and $R^{13'}$ is hydroxy or methoxy; or a pharmaceutically acceptable salt thereof.

21. A method of suppressing the production of IgE comprising administering to an individual in need thereof an effective amount of the compound of claim 1.

22. A method of suppressing the production of IgE comprising administering to an individual in need thereof an effective amount of the compound of claim 2.

23. A method of suppressing the production of IgE comprising administering to an individual in need thereof an effective amount of the compound of claim 8.

24. A method of suppressing the production of IgE comprising administering to an individual in need thereof an effective amount of the compound of claim 9.

25. A method of suppressing the production of IgE comprising administering to an individual in need thereof an effective amount of the compound of claim 10.

26. A method of suppressing the production of IgE comprising administering to an individual in need thereof an effective amount of the compound of claim 11.

27. A method of suppressing the production of IgE comprising administering to an individual in need thereof an effective amount of the compound of claim 12.

* * * * *